(12) United States Patent
Baloglu et al.

(10) Patent No.: US 11,008,309 B2
(45) Date of Patent: *May 18, 2021

(54) SUBSTITUTED BENZOFURANYL AND BENZOXAZOLYL COMPOUNDS AND USES THEREOF

(71) Applicant: Karyopharm Therapeutics Inc., Newton, MA (US)

(72) Inventors: Erkan Baloglu, Stoneham, MA (US); Sharon Shacham, Newton, MA (US); William Senapedis, Millis, MA (US); Dilara McCauley, Arlington, MA (US); Yosef Landesman, Brookline, MA (US); Gali Golan, Mesilat Zion (IL); Ori Kalid, Pardes Hanna (IL); Sharon Shechter, Andover, MA (US)

(73) Assignee: Karyopharm Therapeutics Inc., Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/507,927

(22) Filed: Jul. 10, 2019

(65) Prior Publication Data

US 2020/0102292 A1 Apr. 2, 2020

Related U.S. Application Data

(63) Continuation of application No. 15/831,111, filed on Dec. 4, 2017, now Pat. No. 10,399,963, which is a continuation of application No. 14/902,202, filed as application No. PCT/US2014/045479 on Jul. 3, 2014, now Pat. No. 9,856,241.

(60) Provisional application No. 61/842,856, filed on Jul. 3, 2013, provisional application No. 61/879,070, filed on Sep. 17, 2013, provisional application No. 61/904,843, filed on Nov. 15, 2013, provisional application No. 61/975,171, filed on Apr. 4, 2014.

(51) Int. Cl.
| | |
|---|---|
| *C07D 405/14* | (2006.01) |
| *C07D 405/12* | (2006.01) |
| *C07D 409/14* | (2006.01) |
| *C07D 413/12* | (2006.01) |
| *C07D 417/12* | (2006.01) |
| *C07D 307/81* | (2006.01) |
| *C07D 413/14* | (2006.01) |
| *C07D 491/048* | (2006.01) |
| *C07D 491/08* | (2006.01) |

(52) U.S. Cl.
CPC ......... *C07D 405/14* (2013.01); *C07D 307/81* (2013.01); *C07D 405/12* (2013.01); *C07D 409/14* (2013.01); *C07D 413/12* (2013.01); *C07D 413/14* (2013.01); *C07D 417/12* (2013.01); *C07D 491/048* (2013.01); *C07D 491/08* (2013.01)

(58) Field of Classification Search
CPC .......................... C07D 405/12; C07D 405/14
USPC .......................................................... 514/210
See application file for complete search history.

(56) References Cited

U.S. PATENT DOCUMENTS

| | | | |
|---|---|---|---|
| 5,229,386 A | 7/1993 | Takasugi et al. | |
| 8,173,677 B2 | 5/2012 | Roulston et al. | |
| 8,450,302 B2 | 5/2013 | Ciufolini et al. | |
| 8,912,184 B1 | 12/2014 | Fleischer et al. | |
| 9,856,241 B2* | 1/2018 | Baloglu | C07D 413/14 |
| 9,938,258 B2* | 4/2018 | Baloglu | C07D 405/14 |
| 9,994,558 B2* | 6/2018 | Baloglu | C07D 401/14 |
| 10,363,247 B2* | 7/2019 | Baloglu | A61P 17/02 |
| 10,399,963 B2* | 9/2019 | Baloglu | C07D 405/14 |
| 2004/0186114 A1 | 9/2004 | Cirillo et al. | |
| 2008/0020413 A1 | 1/2008 | Tong et al. | |
| 2012/0053170 A1 | 3/2012 | Arigon et al. | |

(Continued)

FOREIGN PATENT DOCUMENTS

| | | |
|---|---|---|
| EP | 1627873 A1 | 2/2006 |
| EP | 1798224 A1 | 6/2007 |

(Continued)

OTHER PUBLICATIONS

A. Aboud et al., 15 Molecular Cancer Therapeutics, 2119-2129 (2016) (Year: 2016).*

(Continued)

*Primary Examiner* — Tracy Vivlemore
*Assistant Examiner* — Ebenezer O Sackey
(74) *Attorney, Agent, or Firm* — Foley Hoag LLP

(57) ABSTRACT

The invention generally relates to substituted benzofuranyl and substituted benzoxazolyl compounds, and more particularly to a compound represented by Structural Formula A:

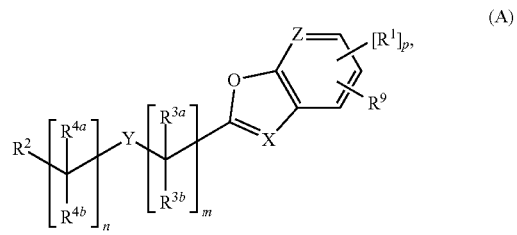

or a pharmaceutically acceptable salt thereof, wherein the variables are as defined and described herein. The invention also includes the synthesis and use of a compound of Structural Formula A, or a pharmaceutically acceptable salt or composition thereof, e.g., in the treatment of cancer (e.g., mantle cell lymphoma), and other diseases and disorders.

20 Claims, 8 Drawing Sheets

(56) References Cited

U.S. PATENT DOCUMENTS

| | | | |
|---|---|---|---|
| 2012/0329786 A1 | 12/2012 | Willardsen et al. | |
| 2013/0317027 A1 | 11/2013 | Willardsen et al. | |
| 2016/0221994 A1 | 8/2016 | Baloglu et al. | |
| 2017/0096417 A1 | 4/2017 | Baloglu et al. | |
| 2017/0369470 A1 | 12/2017 | Baloglu et al. | |
| 2018/0235948 A1 | 8/2018 | Baloglu et al. | |
| 2018/0244660 A1 | 8/2018 | Baloglu et al. | |
| 2019/0002448 A1* | 1/2019 | Baloglu | C07D 405/14 |
| 2020/0102292 A1 | 4/2020 | Baloglu et al. | |

FOREIGN PATENT DOCUMENTS

| | | |
|---|---|---|
| WO | WO-9509159 A1 | 4/1995 |
| WO | WO-97/48397 A1 | 12/1997 |
| WO | WO-97/48696 A1 | 12/1997 |
| WO | WO-99/53920 A1 | 10/1999 |
| WO | WO-03/008365 A2 | 1/2003 |
| WO | WO-03/080054 A1 | 10/2003 |
| WO | WO-2006/106326 A1 | 10/2006 |
| WO | WO-2006/116136 A1 | 11/2006 |
| WO | WO-2008/025857 A2 | 3/2008 |
| WO | WO-2008/026018 A1 | 3/2008 |
| WO | WO-2008/152097 A1 | 12/2008 |
| WO | WO-2009/072004 A2 | 6/2009 |
| WO | WO-2009/109610 A1 | 9/2009 |
| WO | WO-2011/109441 A1 | 9/2011 |
| WO | WO-2012/150952 A1 | 11/2012 |
| WO | WO-2012/177782 A1 | 12/2012 |
| WO | WO-2013/082150 A1 | 6/2013 |
| WO | WO-2014/074715 A1 | 5/2014 |
| WO | WO-2014/085607 A1 | 6/2014 |
| WO | WO-2014/111871 A1 | 7/2014 |
| WO | WO-2015/003166 A1 | 1/2015 |
| WO | WO-2015/042414 A1 | 3/2015 |
| WO | WO-2015/054060 A1 | 4/2015 |
| WO | WO-2016/100515 A1 | 6/2016 |
| WO | WO-2017/031204 A1 | 2/2017 |
| WO | WO-2017/031213 A1 | 2/2017 |
| WO | WO-2017/031323 A1 | 2/2017 |
| WO | WO-2017/117406 A1 | 7/2017 |
| WO | WO-2017/117447 A1 | 7/2017 |

OTHER PUBLICATIONS

V. Hwang et al., 92 Kidney International, 922-933 (2017) (Year: 2017).*
Z. Wang et al., 19 Drug Discovery Today, 145-150 (2014) (Year: 2014).*
U.K. Marelli et al., 3 Frontiers in Oncology, 1-12 (2013) (Year: 2013).*
Eswaran et al., 33 Trends in Biochemical Sciences, 394-403 (2008) (Year: 2008).*
C. Guo et al., 55, Journal of Medicinal Chemistry, 4728-4739 (2012) (Year: 2012).*
P. Kreis et al., 21 Cellular Signaling, 384-393 (2009) (Year: 2009).*
Q-L Ma et al., Cellular Logistics, 2159-2799 (2012) (Year: 2012).*
P. Wu et al., 36 Trends in Pharmacological Sciences, 422-439 (2015) (Year: 2015).*
A. Kooistra et al., Kinase-Centric Computational Drug Development, In 50 Annual Reports in Medicinal Chemistry, 197-236 (2017) (Year: 2017).*
P. Chène, 13 Drug Discovery Today, (2008) (Year: 2008).*
Notice of Allowance and Fees Due for U.S. Appl. No. 15/753,897, "(S,E)-3-(6-Aminopyridin-3-Yl)-N-((5-(4-(3-Fluoro-3-Methylpyrrolidine-1-Carbonyl)Phenyl)-7-(4-Fluorophenyl)Benzofuran-2-Yl)Methyl)Acrylamide for the Treatment of Cancer," dated Mar. 15, 2019.
Notice of Allowance and Fees Due for U.S. Appl. No. 16/066,547, "Substituted Benzofuranyl and Benzoxazolyl Compounds and Uses Thereof" dated May 20, 2019.
Notice of Allowance for U.S. Appl. No. 14/647,662, "Substituted 2,3-Dihydrobenzofuranyl Compounds and Uses Thereof," dated Nov. 24, 2017.
Notice of Allowance for U.S. Appl. No. 15/023,269, "Multicyclic Compounds and Methods of Using Same," dated Feb. 5, 2018.
Notice of Allowance for U.S. Appl. No. 14/902,202, "Substituted Benzofuranyl and Benzoxazolyl Compounds and Uses Thereof," dated Aug. 29, 2017.
Notice of Allowance for U.S. Appl. No. 15/752,542, "3-(Pyridin-3-yl)-Acrylamide and N-(Pyridin-3-yl)-Acrylamide Derivatives and Their Use as PAK or NAMPT Modulators," dated Jun. 6, 2019.
Notice of Allowance for U.S. Appl. No. 15/831,111, "Substituted Benzofuranyl and Benzoxazolyl Compounds and Uses Thereof," dated Apr. 12, 2019.
Restriction Requirement for U.S. Appl. No. 15/536,398, "Multicyclic Compounds and Methods of Using Same," dated Jul. 31, 2018.
Bhatia et al., "Autoimmunity and autoimmune disease," Principles of Medical Biology: Immunobiology, 6:239-263, 244 (1996).
Busso et al., "Pharmacological inhibition of nicotinamide phosphoribosyltransferase/visfatin enzymatic activity identifies a new inflammatory pathway linked to NAD," PLoS One, 3(5):e2267 (2008).
Cea et al., "Intracellular NAD+ depletion induces autophagic death in multiple myeloma cells," Autophagy, 9.3:410-412 (2013).
Cheng et al., "Visfatin promotes osteosarcoma cell migration and invasion via induction of epithelial-mesenchymal transition," Oncology Reports, 34:987-994 (2015).
Dahl et al., "Visfatin/NAMPT: A multifaceted molecule with diverse roles in physiology and pathophysiology," Annu Rev Nutr, 32:229-243 (2012).
Database Registry Chemical Abstracts, Database Accession No. 1025224-12-7, CAS Registry No. 1025224-12-7 (Jun. 4, 2008).
Database Registry Chemical Abstracts, Database Accession No. 1025516-17-9, CAS Registry No. 1025516-17-9 (Jun. 5, 2008).
Database Registry Chemical Abstracts, Database Accession No. 1060535-75-2; CAS Registry Nos. 1060535-75-2; 1060530-87-1; 1060527-21-0; 1060504-54-2; 1060421-07-9; 1060400-89-6 (Oct. 13, 2008).
Database Registry Chemical Abstracts, Database Accession No. 1065636-94-3; CAS Registry No. 1065636 94-3 (Oct. 24, 2008).
Database Registry Chemical Abstracts, Database Accession No. 1067037-85-7; CAS Registry No. 1067037-85-7 (Oct. 27, 2008).
Database Registry Chemical Abstracts, Database Accession No. 1067055-04-2; CAS Registry No. 1067055-04-2 (Oct. 28, 2008).
Database Registry Chemical Abstracts, Database Accession No. 1069903-74-7; CAS Registry Nos. 1069646-70-3; 1069796-77-5; 1069605-79-3 (Nov. 2, 2008).
Database Registry Chemical Abstracts, Database Accession No. 1070271-09-8; CAS Registry No. 1070271-09-08 (Nov. 3, 2008).
Database Registry Chemical Abstracts, Database Accession No. 1110694-76-2, CAS Registry No. 1110694-76-2 (Feb. 23, 2009).
Database Registry Chemical Abstracts, Database Accession No. 1110698-05-9, CAS Registry No. 1110698-05-9 (Feb. 23, 2009).
Database Registry Chemical Abstracts, Database Accession No. 1110699-54-1, CAS Registry No. 1110699-54-1 (Feb. 23, 2009).
Database Registry Chemical Abstracts, Database Accession No. 1110699-68-7, CAS Registry No. 1110699-68-7 (Feb. 23, 2009).
Database Registry Chemical Abstracts, Database Accession No. 1110701-07-9, CAS Registry No. 1110701-07-9 (Feb. 23, 2009).
Database Registry Chemical Abstracts, Database Accession No. 1110701-73-9, CAS Registry No. 1110701-73-9 (Feb. 23, 2009).
Database Registry Chemical Abstracts, Database Accession No. 1110705-13-9, CAS Registry No. 1110705-13-9 (Feb. 23, 2009).
Database Registry Chemical Abstracts, Database Accession No. 1110707-61-3, CAS Registry No. 1110707-61-3 (Feb. 23, 2009).
Database Registry Chemical Abstracts, Database Accession No. 1110708-07-0, CAS Registry No. 1110708-07-0 (Feb. 23, 2009).
Database Registry Chemical Abstracts, Database Accession No. 1110708-69-4, CAS Registry No. 1110708-69-4 (Feb. 23, 2009).
Eswaran et al., "UnPAKing the class differences among p21-activated kinases," Trends Biochem Sci, 33(8): 394-403 (2008).
Galli et al., "Medicinal chemistry of nicotinamide phosphoribosyltransferase (NAMPT) inhibitors," J Med Chem, 56:6279-96 (2013).
Giannetti et al., "Fragment-Based Identification of Amides Derived from trans-2-(Pyridin-3-yl) cyclopropanecarboxylic Acid as Potent

(56) References Cited

OTHER PUBLICATIONS

Inhibitors of Human Nicotinamide Phosphoribosyltransferase (NAMPT)," J Med Chem, 57(3): 770-792 (2014).
Girouard et al., "Neurovascular coupling in the normal brain and in hypertension, stroke, and Alzheimer disease," J Appl Physiol, 100(1): 328-335, 332 (2006).
Guo et al., "Discovery of pyrroloaminopyrazoles as novel PAK inhibitors," J Med Chem, 55(10): 4728-4739 (2012).
Hayter et al., "Updated assessment of the prevalence, spectrum and case definition of autoimmune disease," Autoimmun Rev, 11(10): 754-765, 756 (2012).
Houtkooper et al., "Exploring the therapeutic space around NAD+," J Cell Biol, 199(2):205-9 (2012).
International Preliminary Report on Patentability for International Application No. PCT/US14/045479 dated Jan. 5, 2016.
International Preliminary Report on Patentability for International Application No. PCT/US2013/072264 dated Jun. 2, 2015.
International Preliminary Report on Patentability for International Application No. PCT/US2015/066098 dated Jun. 20, 2017.
International Preliminary Report on Patentability for International Application No. PCT/US2016/047337 dated Feb. 20, 2018.
International Preliminary Report on Patentability for International Application No. PCT/US2016/047358 dated Feb. 20, 2018.
International Preliminary Report on Patentability for International Application No. PCT/US2016/047566 dated Feb. 20, 2018.
International Preliminary Report on Patentability for International Application No. PCT/US2016/069241 dated Jul. 3, 2018.
International Preliminary Report on Patentability for International Application No. PCT/US2016/069303 dated Jul. 3, 2018.
International Preliminary Report on Patentability for International Application No. PCT/US2014/056580, "Multicyclic Compounds and Methods of Using Same," dated Mar. 22, 2016.
International Search Report and Written Opinion for International Application No. PCT/US2016/047337 dated Oct. 6, 2016.
International Search Report and Written Opinion for International Application No. PCT/US2016/047566, "Substituted Benzofuranyl Compounds and Uses Thereof," dated Oct. 4, 2016.
International Search Report and Written Opinion for International Application No. PCT/US2016/069241 dated Mar. 16, 2017.
International Search Report and Written Opinion for International Application No. PCT/US2015/066098, "Cyclic Compounds and Uses Thereof," dated Mar. 16, 2016.
International Search Report and Written Opinion for International Application No. PCT/US2016/047358, "Cyclic Compounds and Uses Thereof," dated Oct. 26, 2016.
International Search Report and Written Opinion for International Patent Application No. PCT/US2016/069303 dated May 26, 2017.
International Search Report for International Application No. PCT/US2013/072264, "Substituted 2,3-Dihydrobenzofuranyl Compounds and Uses Thereof"; dated May 16, 2014.
International Search Report for International Application No. PCT/US2014/045479, "Substituted Benzofuranyl and Benzoxazolyl Compounds and Uses Thereof"; dated Oct. 27, 2014.
International Search Report for International Application No. PCT/US2014/056580, "Multicyclic Compounds and Methods of Using Same"; dated Nov. 27, 2014.
Kreis et al., "PAK signalling in neuronal physiology," Cell Signal, 21: 384-393 (2009).
Ma et al., "PAK in Alzheimer disease, Huntington disease and X-linked mental retardation," Cell Logist, 2(2): 2159-2799 (2012).
Marelli et al., "Tumor targeting via integrin ligands," Front Oncol, 3: 1-12 (2013).
Minden, "PAK4-6 in cancer and neuronal development," Cellular Logistics, 22:95-104 (2012).
Nahimana et al., "The NAD biosynthesis inhibitor APO866 has potent antitumor activity against hematologic malignancies," Blood, 113(14):3276-3266 (2009).
O'Brien, "Vascular cognitive impairment," Lancet Neurol, 2(2): 89-98, 96 (2003).
Olesen et al., "Expression patterns of nicotinamide phosphoribosyltransferase and nicotinic acid phosphoribosyltransferase in human malignant lymphomas," APMIS, 119:296-303 (2011).
Rane et al., "P21 activated kinases Structure, Regulation, and Functions," Small GTPases, e28003-1-e28003-13 (2014).
Sampath et al., "Inhibition of nicotinamide phosphoribosyltransferase (NAMPT) as a therapeutic strategy in cancer," Pharmacol Therapeut, 151:16-31 (2014).
Shah et al., "Current approaches in the treatment of Alzheimer's disease," Biomed & Pharmacother, 62: 199-207 (2008).
Shu et al., "PAK4 confers the malignance of cervical cancers and contributes to the cisplatin-resistance in cervical cancer cells via PI3K/AKT pathway," Diagnostic Pathology, 10(177)1-9 (2015).
Taglieri et al., "P21-activated kinase in inflammatory and cardiovascular disease," Cellular Signaling, 26:2060-2069 (2014).
Tan et al., "Pharmacological inhibition of nicotinamide phosphoribosyltransferase (NAMPT), an enzyme essential for NAD+ biosynthesis, in human cancer cells," The Journal of Biological Chemistry, 288(5):3500-3511 (2013).
Wang et al., "Mathematical modeling in cancer drug discovery," Drug Discov Today, 19(2): 145-150 (2014).
Written Opinion for International Application No. PCT/US14/045479 dated Oct. 27, 2014.
Written Opinion for International Application No. PCT/US14/056580 dated Nov. 27, 2014.
Written Opinion of International Application No. PCT/US2013/072264, "Substituted 2,3-Dihydrobenzofuranyl Compounds and Uses Thereof"; dated May 16, 2014.
Yin et al., "Intrinsic directionality of migrating vascular smooth muscle cells is regulated by NAD+ biosynthesis," J Cell Sci, 125:5770-80 (2012).
Zhang et al., "Nicotinamide Phosphoribosyltransferase in Human Diseases," J Bioanal Biomed, 1-26 (2011).

\* cited by examiner

SUBSTITUTED BENZOFURANYL AND BENZOXAZOLYL COMPOUNDS AND USES THEREOF

RELATED APPLICATIONS

This application is a continuation of U.S. application Ser. No. 15/831,111, filed on Dec. 4, 2017, which is a continuation of U.S. application Ser. No. 14/902,202 (now U.S. Pat. No. 9,856,241), filed on Dec. 30, 2015, which is the U.S. National Stage of International Application No. PCT/US/2014/045479, filed on Jul. 3, 2014, published in English, which claims the benefit of U.S. Provisional Application No. 61/842,856, filed on Jul. 3, 2013, U.S. Provisional Application No. 61/879,070, filed on Sep. 17, 2013, U.S. Provisional Application No. 61/904,843, filed on Nov. 15, 2013, and U.S. Provisional Application No. 61/975,171, filed on Apr. 4, 2014. The entire teachings of these applications are incorporated herein by reference.

BACKGROUND OF THE INVENTION

Cancer remains a disease for which existing treatments are insufficient. For example, of the approximately 66,360 new cases of non-Hodgkin lymphoma in the United States each year, about 6% of the cases involve mantle cell lymphoma (MCL). Treatments for MCL include combination therapies, chemotherapy and stem cell transplantation. Like many cancers, although treatments for MCL have improved, relapses remain common, and treatment resistance is observed.

There is a clear need for additional drug-like compounds that are effective for the treatment of cancer, such as non-Hodgkin lymphoma.

SUMMARY OF THE INVENTION

The present invention relates to substituted benzofuranyl and benzoxazolyl compounds, or pharmaceutically acceptable salts or compositions thereof, useful as anti-cancer agents. In one embodiment of the invention, the substituted benzofuranyl compounds are represented by Structural Formula (A):

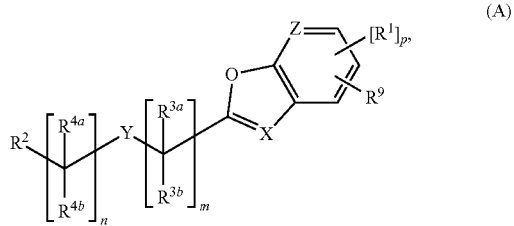

(A)

or a pharmaceutically acceptable salt thereof, wherein each variable is as defined and described herein.

Another embodiment of the invention is a composition comprising a compound of the invention, or a pharmaceutically acceptable salt thereof, and a pharmaceutically acceptable carrier.

Yet another embodiment of the invention is a method for treating cancer in a subject in need thereof, the method comprising administering to a subject in need thereof a therapeutically effective amount of a compound of the invention, or a pharmaceutically acceptable salt thereof, or a composition comprising a compound of the invention, or a pharmaceutically acceptable salt thereof.

Without being bound by a particular theory, it is believed that the compounds described herein can modulate (e.g., inhibit) one or more p21-activated kinases (PAK), for example, one or more of PAKs 1-6. More specifically, and without being bound by a particular theory, it is believed that the compounds described herein can bind to one or more PAKs and function as allosteric modulators of one or more PAKs. For example, the compounds described herein may exert their modulatory effect(s) on one or more PAKs by binding to and destabilizing one or more PAKs or contributing to the degradation of one or more PAKs, thereby modulating (e.g., inhibiting) the effect of one or more PAKs on one or more proteins downstream of the one or more PAKs, for example, growth signaling proteins such as Akt, ERK1/2, p90RSK, β-catenin, cofilin, p21 and cyclin D1.

In a particular embodiment, one or more of the Group I PAKs (e.g., PAK1, PAK2, PAK3) is inhibited. For example, PAK1 is inhibited, PAK2 is inhibited, PAK3 is inhibited or a combination of PAK1, PAK2 and PAK3, such as PAK1 and PAK2, PAK1 and PAK3, PAK2 and PAK3, or PAK1, PAK2 and PAK3 is inhibited. In a particular embodiment, one or more of the group II PAKs (e.g., PAK4, PAK5, PAK6) is inhibited. For example, PAK4 is inhibited, PAK5 is inhibited, PAK6 is inhibited or a combination of PAK4, PAK5 and PAK6, such as PAK4 and PAK5, PAK4 and PAK6, PAK5 and PAK6 or PAK4, PAK5 and PAK6 is inhibited. Therefore, the compounds described herein can be useful for treating PAK-mediated disorders.

As such, in another embodiment, the invention is a method of treating a PAK-mediated disorder in a subject in need thereof, comprising administering to the subject in need thereof a therapeutically effective amount of a compound of the invention, or a pharmaceutically acceptable salt thereof, or a pharmaceutical composition comprising a compound of the invention, or a pharmaceutically acceptable salt thereof.

Another embodiment of the invention is use of a compound of the invention for treating cancer or a PAK-mediated disorder in a subject.

Another embodiment of the invention is use of a compound of the invention for the manufacture of a medicament for treating cancer or a PAK-mediated disorder in a subject.

Compounds of the present invention, and pharmaceutically acceptable salts and/or compositions thereof, are useful for treating a variety of cancers, such as lymphoma and, more specifically, mantle cell lymphoma.

BRIEF DESCRIPTION OF THE DRAWINGS

The foregoing will be apparent from the following more particular description of example embodiments of the invention.

DETAILED DESCRIPTION OF THE INVENTION

Figure 1:
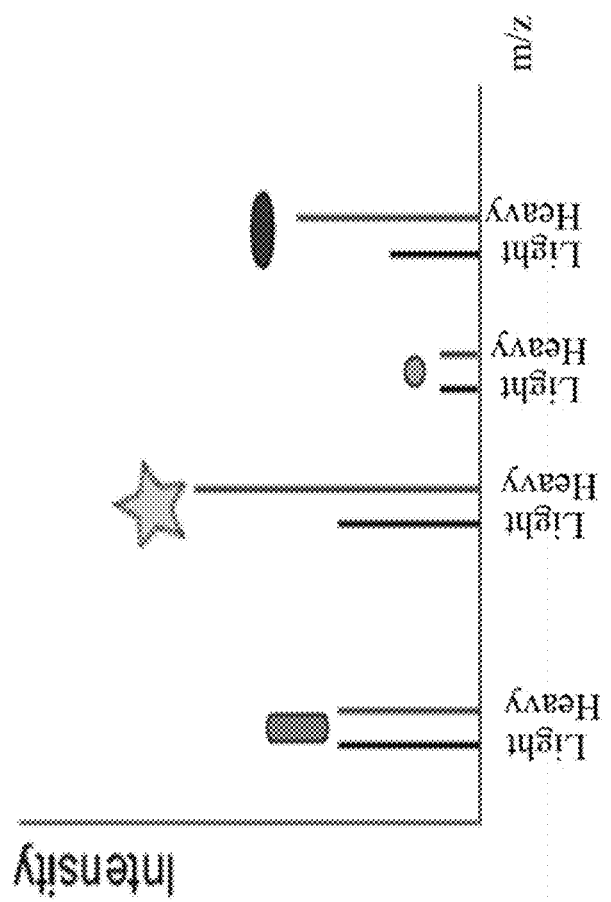
FIG. 1 is a schematic representation of a SILAC experiment and shows the experimental design.
Figure 1:
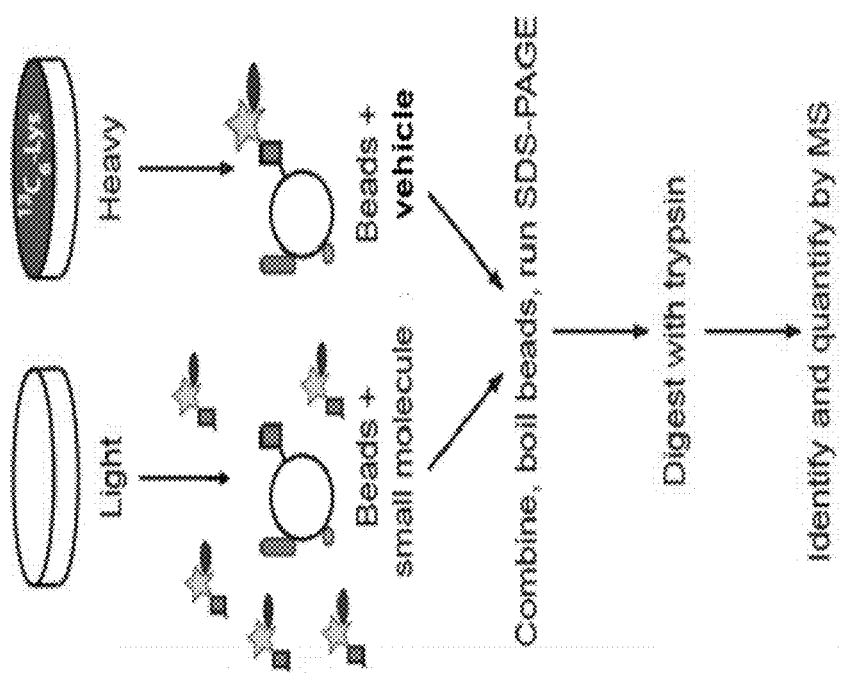

A description of example embodiments of the invention follows.

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

Compounds of the present invention may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers or enantiomers, with all possible isomers and mixtures thereof, including optical isomers, being included in the present invention.

"Aliphatic" means an optionally substituted, saturated or unsaturated, branched or straight-chain monovalent hydrocarbon radical having the specified number of carbon atoms.

"Alkyl" means an optionally substituted saturated aliphatic branched or straight-chain monovalent hydrocarbon radical having the specified number of carbon atoms. Thus, "($C_1$-$C_4$) alkyl" means a radical having from 1-4 carbon atoms in a linear or branched arrangement. "($C_1$-$C_4$)alkyl" includes methyl, ethyl, propyl, isopropyl, n-butyl and tert-butyl.

"Alkylene" means an optionally substituted saturated aliphatic branched or straight-chain divalent hydrocarbon radical having the specified number of carbon atoms. Thus, "($C_1$-$C_4$)alkylene" means a divalent saturated aliphatic radical having from 1-4 carbon atoms in a linear arrangement, e.g., —[($CH_2$)$_n$]—, where n is an integer from 1 to 4. "($C_1$-$C_4$)alkylene" includes methylene, ethylene, propylene, and butylene. Alternatively, "($C_1$-$C_4$)alkylene" means a divalent saturated radical having from 1-4 carbon atoms in a branched arrangement, for example: —[($CH_2CH(CH_3$)($CH_2$)]—, and the like.

"Amino" means —$NH_2$.

As used herein, the term "dialkylamino" means (alkyl)$_2$-N—, wherein the alkyl groups, which may be the same or different, are as herein defined. Particular dialkylamino groups are (($C_1$-$C_4$)alkyl)$_2$-N—, wherein the alkyl groups may be the same or different. Exemplary dialkylamino groups include dimethylamino, diethylamino and methylethylamino.

As used herein, the term "monoalkylamino" means a radical of the formula alkyl-NH, wherein the alkyl group is as herein defined. In one aspect, a monoalkylamino is a ($C_1$-$C_6$) alkyl-amino-. Exemplary monoalkylamino groups include methylamino and ethylamino.

"Aryl" or "aromatic" means an aromatic carbocyclic ring system. An aryl moiety can be monocyclic, fused bicyclic, or polycyclic. In one embodiment, "aryl" is a 6-15 membered monocylic or polycyclic system. Aryl systems include, but are not limited to, phenyl, naphthalenyl, fluorenyl, indenyl, azulenyl, and anthracenyl.

Monocyclic aryls are aromatic rings having the specified number of carbon atoms.

A fused bicyclic aryl has two rings which have two adjacent ring atoms in common. The first ring is a monocyclic aryl and the second ring is a monocyclic carbocyclyl or a monocyclic heterocyclyl.

Polycyclic aryls have more than two rings (e.g., three rings resulting in a tricyclic ring system) and adjacent rings have at least two ring atoms in common. The first ring is a monocyclic aryl and the remaining ring structures are monocyclic carbocyclyls or monocyclic heterocyclyls. Polycyclic ring systems include fused ring systems. A fused polycyclic ring system has at least two rings that have two adjacent ring atoms in common.

"Carbocyclyl" means a cyclic group with only ring carbon atoms. "Carbocyclyl" includes 3-15 membered saturated, partially saturated or unsaturated aliphatic cyclic hydrocarbon rings or 6-15 membered aryl rings. A carbocyclyl moiety can be monocyclic, fused bicyclic, bridged bicyclic, spiro bicyclic, or polycyclic.

Monocyclic carbocyclyls are saturated or unsaturated aliphatic cyclic hydrocarbon rings or aromatic hydrocarbon rings having the specified number of carbon atoms. Monocyclic carbocyclyls include cycloalkyl, cycloalkenyl, cycloalkynyl and phenyl.

A fused bicyclic carbocyclyl has two rings which have two adjacent ring atoms in common. The first ring is a monocyclic carbocyclyl and the second ring is a monocyclic carbocyclyl or a monocyclic heterocyclyl.

A bridged bicyclic carbocyclyl has two rings which have three or more adjacent ring atoms in common. The first ring is a monocyclic carbocyclyl and the second ring is a monocyclic carbocyclyl or a monocyclic heterocyclyl.

A spiro bicyclic carbocyclyl has two rings which have only one ring atom in common. The first ring is a monocyclic carbocyclyl and the second ring is a monocyclic carbocyclyl or a monocyclic heterocyclyl.

Polycyclic carbocyclyls have more than two rings (e.g., three rings resulting in a tricyclic ring system) and adjacent rings have at least one ring atom in common. The first ring is a monocyclic carbocyclyl and the remaining ring structures are monocyclic carbocyclyls or monocyclic heterocyclyls. Polycyclic ring systems include fused, bridged and spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common.

"Cycloalkyl" means a saturated aliphatic cyclic hydrocarbon ring. Thus, "$C_3$-$C_7$ cycloalkyl" means a hydrocarbon radical of a (3-7 membered) saturated aliphatic cyclic hydrocarbon ring. A $C_3$-$C_7$ cycloalkyl includes, but is not limited to cyclopropyl, cyclobutyl, cyclopentyl, cyclohexyl and cycloheptyl.

"Hetero" refers to the replacement of at least one carbon atom member in a ring system with at least one heteroatom selected from N, S, and O. "Hetero" also refers to the replacement of at least one carbon atom member in an acyclic system. In some embodiments, a hetero ring system may have 1, 2, 3 or 4 carbon atom members replaced by a heteroatom.

"Heteroatom" refers to an atom other than carbon. Examples of heteroatoms include nitrogen, oxygen and sulfur.

"Heterocyclyl" means a cyclic 4-15 membered saturated or unsaturated aliphatic or aromatic ring wherein one or more carbon atoms in the ring are independently replaced with a heteroatom. When a heteroatom is S, it can be optionally mono- or di-oxygenated (i.e., —S(O)— or —S(O)$_2$—). The heterocyclyl can be monocyclic, fused bicyclic, bridged bicyclic, spiro bicyclic or polycyclic.

"Saturated heterocyclyl" means an aliphatic heterocyclyl group without any degree of unsaturation (i.e., no double bond or triple bond). It can be monocyclic, fused bicyclic, bridged bicyclic, spiro bicyclic or polycyclic.

Examples of monocyclic saturated heterocyclyls include, but are not limited to, azetidine, pyrrolidine, piperidine, piperazine, azepane, hexahydropyrimidine, tetrahydrofuran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, isothiazolidine 1,1-dioxide.

A fused bicyclic heterocyclyl has two rings which have two adjacent ring atoms in common. The first ring is a monocyclic heterocyclyl and the second ring is a monocyclic carbocycle (such as a cycloalkyl or phenyl) or a monocyclic heterocyclyl. For example, the second ring is a ($C_3$-$C_6$)cycloalkyl, such as cyclopropyl, cyclobutyl, cyclopentyl and cyclohexyl. Alternatively, the second ring is phenyl. Examples of fused bicyclic heterocyclyls include, but are not limited to, octahydrocyclopenta[c]pyrrolyl, indoline, isoindoline, 2,3-dihydro-1H-benzo[d]imidazole, 2,3-dihydrobenzo[d]oxazole, 2,3-dihydrobenzo[d]thiazole, octahydrobenzo[d]oxazole, octahydro-1H-benzo[d]imidazole, octahydrobenzo[d]thiazole, octahydrocyclopenta[c]pyrrole, 3-azabicyclo[3.1.0]hexane, and 3-azabicyclo[3.2.0]heptane.

A spiro bicyclic heterocyclyl has two rings which have only one ring atom in common. The first ring is a monocyclic heterocyclyl and the second ring is a monocyclic carbocycle (such as a cycloalkyl or saturated heterocyclyl) or a monocyclic heterocyclyl. For example, the second ring is a ($C_3$-$C_6$)cycloalkyl. Alternatively, the second ring is a ($C_3$-$C_6$) saturated heterocyclyl. Examples of spiro bicyclic heterocyclyls include, but are not limited to, azaspiro[4.4]nonane, 7-azaspiro[4.4]nonane, azasprio[4.5]decane, 8-azaspiro[4.5]decane, azaspiro[5.5]undecane, 3-azaspiro[5.5]undecane and 3,9-diazaspiro[5.5]undecane. Further examples of spiro bicyclic heterocyclyls include 2-oxa-6-azaspiro[3.3]heptane, 1-oxa-6-azaspiro[3.3]heptane and 2-azaspiro[3.3]heptane.

A bridged bicyclic heterocyclyl has two rings which have three or more adjacent ring atoms in common. The first ring is a monocyclic heterocyclyl and the other ring is a monocyclic carbocycle (such as a cycloalkyl or phenyl) or a monocyclic heterocyclyl. Examples of bridged bicyclic heterocyclyls include, but are not limited to, azabicyclo[3.3.1]nonane, 3-azabicyclo[3.3.1]nonane, azabicyclo[3.2.1]octane, 3-azabicyclo[3.2.1]octane, 6-azabicyclo[3.2.1]octane and azabicyclo[2.2.2]octane, 2-azabicyclo[2.2.2]octane. Further examples of bridged bicyclic heterocyclyls include 6-oxa-3-azabicyclo[3.1.1]heptane, 3-azabicyclo[3.1.0]hexane, 8-oxa-3-azabicyclo[3.2.1]octane and 2-oxa-5-azabicyclo[2.2.1]heptane.

Polycyclic heterocyclyls have more than two rings, one of which is a heterocyclyl (e.g., three rings resulting in a tricyclic ring system) and adjacent rings having at least one ring atom in common. Polycyclic ring systems include fused, bridged and spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common.

"Heteroaryl" or "heteroaromatic ring" means a 5-15 membered monovalent heteroaromatic ring radical. A heteroaryl moiety can be monocyclic, fused bicyclic, or polycyclic. In one embodiment, a heteroaryl contains 1, 2, 3 or 4 heteroatoms independently selected from N, O, and S. Heteroaryls include, but are not limited to, furan, oxazole, thiophene, 1,2,3-triazole, 1,2,4-triazine, 1,2,4-triazole, 1,2,5-thiadiazole 1,1-dioxide, 1,2,5-thiadiazole 1-oxide, 1,2,5-thiadiazole, 1,3,4-oxadiazole, 1,3,4-thiadiazole, 1,3,5-triazine, imidazole, isothiazole, isoxazole, pyrazole, pyridazine, pyridine, pyridine-N-oxide, pyrazine, pyrimidine, pyrrole, tetrazole, and thiazole. Bicyclic heteroaryl rings include, but are not limited to, bicyclo[4.4.0] and bicyclo[4.3.0] fused ring systems such as indolizine, indole, isoindole, indazole, benzimidazole, benzthiazole, purine, quinoline, isoquinoline, cinnoline, phthalazine, quinazoline, quinoxaline, 1,8-naphthyridine, and pteridine.

Monocyclic heteroaryls are heteroaromatic rings having the specified number of carbon atoms.

A fused bicyclic heteroaryl has two rings which have two adjacent ring atoms in common. The first ring is a monocyclic heteroaryl and the second ring is a monocyclic carbocyclyl or a monocyclic heterocyclyl.

Polycyclic heteroaryls have more than two rings (e.g., three rings resulting in a tricyclic ring system) and adjacent rings have at least two ring atoms in common. The first ring is a monocyclic heteroaryl and the remaining ring structures are monocyclic carbocyclyls or monocyclic heterocyclyls. Polycyclic ring systems include fused ring systems. A fused polycyclic ring system has at least two rings that have two adjacent ring atoms in common.

"Halogen" and "halo" are used interchangeably herein and each refers to fluorine, chlorine, bromine, or iodine.

"Chloro" means —Cl.

"Fluoro" means —F.

"Cyano" means —CN.

"Sulfonate" means —SO$_2$H.

"Alkoxy" means an alkyl radical attached through an oxygen linking atom. "(C$_1$-C$_6$)alkoxy" includes methoxy, ethoxy, propoxy, butoxy, pentoxy and hexoxy.

"Thioalkoxy" means an alkyl radical attached through a sulfur linking atom.

"Haloalkyl" include mono, poly, and perhaloalkyl groups, where each halogen is independently selected from fluorine, chlorine, and bromine.

It is understood that substituents and substitution patterns on the compounds of the invention can be selected by one of ordinary skill in the art to provide compounds that are chemically stable and that can be readily synthesized by techniques known in the art, as well as those methods set forth below. In general, the term "substituted," whether preceded by the term "optionally" or not, means that one or more hydrogens of the designated moiety are replaced with a suitable substituent. Unless otherwise indicated, an "optionally substituted group" can have a suitable substituent at each substitutable position of the group and, when more than one position in any given structure may be substituted with more than one substituent selected from a specified group, the substituent can be either the same or different at every position. Alternatively, an "optionally substituted group" can be unsubstituted.

Combinations of substituents envisioned by this invention are preferably those that result in the formation of stable or chemically feasible compounds. If a substituent is itself substituted with more than one group, it is understood that these multiple groups can be on the same carbon atom or on different carbon atoms, as long as a stable structure results. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable atom, for example, a substitutable carbon atom, of an "optionally substituted group" are independently halogen; haloalkyl; —(CH$_2$)$_{0-4}$R$^\circ$; —(CH$_2$)$_{0-4}$OR$^\circ$; —O—(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$ or halo (e.g., fluoro, chloro, bromo or iodo); —CH=CHPh, which may be substituted with R$^\circ$; —(CH$_2$)$_{0-4}$O(CH$_2$)$_{0-1}$-pyridyl which may be substituted with R$^\circ$; —CH(OH)R$^\circ$(e.g., 3,5-dimethylisoxazol-4-yl, 4-fluorophenyl); —CH(CH$_3$)R$^\circ$ (e.g., 4,4-difluoropiperidin-1-yl); —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; N(R$^\circ$)C(S)R$^\circ$; —(CH$_2$)$_{0-4}$N(R$^\circ$)C(O)NR$^\circ{}_2$; —(CH$_2$)$_{0-4}$OC(O)NR$^\circ{}_2$; —N(R$^\circ$)C(S)NR$^\circ{}_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ{}_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ{}_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NR$^\circ{}_2$; —(CH$_2$)$_{0-4}$C(O)NR$^\circ{}_2$; —C(S)NR$^\circ{}_2$; —C(O)NR$^\circ$NR$^\circ{}_2$; —C(S)SR$^\circ$; —SC(S)SR$^\circ$, —(CH$_2$)$_{0-4}$OC(O)NR$^\circ{}_2$; —C(O)N(OR$^\circ$)R$^\circ$; —C(O)C(O)R$^\circ$; —C(O)C(O)NR$^\circ{}_2$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ{}_2$; —(CH$_2$)$_{0-4}$S(O)R$^\circ$; —N(R$^\circ$)S(O)$_2$NR$^\circ{}_2$; —N(R$^\circ$)S(O)$_2$R$^\circ$; —N(OR$^\circ$)R$^\circ$; —C(NH)NR$^\circ{}_2$; —P(O)$_2$R$^\circ$; —P(O)R$^\circ{}_2$; —OP(O)R$^\circ{}_2$; —OP(O)(OR$^\circ$)$_2$; SiR$^\circ{}_3$; —(C$_{1-4}$ straight or branched alkylene)O—N(R$^\circ$)$_2$; or —(C$_{1-4}$ straight or branched alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered carbocyclyl or heterocyclyl, or, notwithstanding the definition above, two independent occurrences of R$^\circ$, taken together with their intervening atom(s), form a 3-12-membered carbocyclyl or heterocyclyl, which may be substituted as defined below.

In some embodiments, suitable monovalent substituents on a substitutable atom, for example, a substitutable carbon atom, of an "optionally substituted group" are independently halogen; haloalkyl; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ{}_2$; —N(R$^\circ$)C(S)NR$^\circ{}_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ{}_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ{}_3$; —(CH$_2$)$_{0-4}$OC(O)R$^\circ$; —OC(O)(CH$_2$)$_{0-4}$SR—, SC(S)SR$^\circ$;

—(CH$_2$)$_{0-4}$SC(O)R$^\circ$; —(CH$_2$)$_{0-4}$C(O)NR$^\circ{}_2$; —(CH$_2$)$_{0-4}$C(O)NR$^\circ{}_2$; —C(S)NR$^\circ{}_2$; —C(O)NR$^\circ$NR$^\circ{}_2$; —C(S)SR$^\circ$; —SC(S)SR$^\circ$, —(CH$_2$)$_{0-4}$OC(O)NR$^\circ{}_2$; —C(O)N(OR)R$^\circ$; —C(O)C(O)R$^\circ$; —C(O)C(O)NR$^\circ{}_2$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ{}_2$; —(CH$_2$)$_{0-4}$S(O)R$^\circ$; —N(R$^\circ$)S(O)$_2$NR$^\circ{}_2$; —N(R$^\circ$)S(O)$_2$R$^\circ$; —N(OR$^\circ$)R$^\circ$; —C(NH)NR$^\circ{}_2$; —P(O)$_2$R$^\circ$; —P(O)R$^\circ{}_2$; —OP(O)R$^\circ{}_2$; —OP(O)(OR$^\circ$)$_2$; SiR$^\circ{}_3$; —(C$_{1-4}$ straight or branched alkylene)O—N(R$^\circ$)$_2$; or —(C$_{1-4}$ straight or branched alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered carbocyclyl or heterocyclyl, or, notwithstanding the definition above, two independent occurrences of R$^\circ$, taken together with their intervening atom(s), form a 3-12-membered carbocyclyl or heterocyclyl, which may be substituted as defined below.

Suitable monovalent substituents on R$^\circ$ (or the ring formed by taking two independent occurrences of R$^\circ$ together with their intervening atoms), are independently halogen, haloalkyl, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet{}_3$, —OSiR$^\bullet{}_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur. Suitable divalent substituents on a saturated carbon atom of R$^\circ$ include =O and =S.

"Heteroaryl substituent," as used herein, refers to a substituent on a heteroaryl group. Such substituents include the suitable monovalent substituents for a substitutable atom, as described above. Preferred heteroaryl substituents include halogen; —(CH$_2$)$_{0-4}$R$^\circ$; —(CH$_2$)$_{0-4}$OR$^\circ$; —O(CH$_2$)$_{0-4}$R$^\circ$, —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —NO$_2$; —CN; —N$_3$; or —(CH$_2$)$_{0-4}$N(R$^\circ$)$_2$, wherein each R$^\circ$ is defined above and may be substituted as defined above. Particularly preferred heteroaryl substituents include hydrogen, halogen; (C$_1$-C$_4$) alkyl; (C$_1$-C$_4$)haloalkyl; (C$_1$-C$_4$)alkoxy; (C$_1$-C$_4$)thioalkoxy; —NO$_2$; —CN; —N$_3$; or —N(R$^\circ$)$_2$, wherein each R$^\circ$ is defined above and may be substituted as defined above.

Suitable divalent substituents on a saturated carbon atom of an "optionally substituted group" include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, and —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, and —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted group" include —R$^\dagger$, —NR$^\dagger{}_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger{}_2$, —C(S)NR$^\dagger{}_2$, —C(NH)NR$^\dagger{}_2$, and —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^\dagger$, taken together with their intervening atom(s) form an unsubstituted 3-12-membered saturated, partially unsaturated, or aryl monocyclic or bicyclic ring having 0-4 heteroatoms independently selected from nitrogen, oxygen, and sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds of this invention include salts derived from suitable inorganic and organic acids and bases that are compatible with the treatment of patients.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable acid addition salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In some embodiments, exemplary inorganic acids which form suitable salts include, but are not limited thereto, hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms.

In some embodiments, acid addition salts of the compounds of formula I are most suitably formed from pharmaceutically acceptable acids, and include, for example, those formed with inorganic acids, e.g., hydrochloric, sulfuric or phosphoric acids and organic acids e.g. succinic, maleic, acetic or fumaric acid.

Other non-pharmaceutically acceptable salts, e.g., oxalates can be used, for example, in the isolation of compounds of formula I for laboratory use, or for subsequent conversion to a pharmaceutically acceptable acid addition salt. Also included within the scope of the invention are base addition salts (such as sodium, potassium and ammonium salts), solvates and hydrates of compounds of the invention. The conversion of a given compound salt to a desired compound salt is achieved by applying standard techniques, well known to one skilled in the art.

A "pharmaceutically acceptable basic addition salt" is any non-toxic organic or inorganic base addition salt of the acid compounds represented by formula I, or any of its intermediates. Illustrative inorganic bases which form suitable salts include, but are not limited thereto, lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

Salts derived from appropriate bases include alkali metal, alkaline earth metal, ammonium and N+(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxyl, sulfate, phosphate, nitrate, lower alkyl sulfonate and aryl sulfonate.

Pharmaceutically acceptable salts include (C$_1$-C$_6$)alkylhalide salts. A (C$_1$-C$_6$)alkylhalide salt of a compound described herein can be formed, for example, by treating a compound of Formula II (e.g., wherein q is 0) with a (C$_1$-C$_6$)alkylhalide salt, thereby alkylating a nitrogen atom (e.g., the nitrogen atom beta to the group —[C(R$^{4a}$)(R$^{4b}$)]$_n$— in Formula II) and forming a (C$_1$-C$_6$)alkylhalide salt of a compound of Formula II. Examples of (C$_1$-C$_6$) alkylhalide salts include methyl iodide and ethyl iodide.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds produced by the replacement of a hydrogen with deuterium or tritium, or of a carbon with a $^{13}$C- or $^{14}$C-enriched carbon are within the scope of this invention. Such compounds are useful, for example, as analytical tools, as probes in biological assays, or as therapeutic agents in accordance with the present invention. For example, in the case of variable R$^1$, the (C$_1$-C$_4$)alkyl or the —O—(C$_1$-C$_4$)alkyl can be suitably deuterated (e.g., —CD$_3$, —OCD$_3$).

The term "stereoisomers" is a general term for all isomers of an individual molecule that differ only in the orientation of their atoms in space. It includes mirror image isomers (enantiomers), geometric (cis/trans) isomers and isomers of compounds with more than one chiral center that are not mirror images of one another (diastereomers).

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of being administered to a patient. One example of such a carrier is pharmaceutically acceptable oil typically used for parenteral administration. Pharmaceutically acceptable carriers are well known in the art.

When introducing elements disclosed herein, the articles "a," "an," "the," and "said" are intended to mean that there are one or more of the elements. The terms "comprising," "having" and "including" are intended to be open-ended and mean that there may be additional elements other than the listed elements.

Compounds of the Invention

A first embodiment of the invention is a compound represented by Structural Formula A:

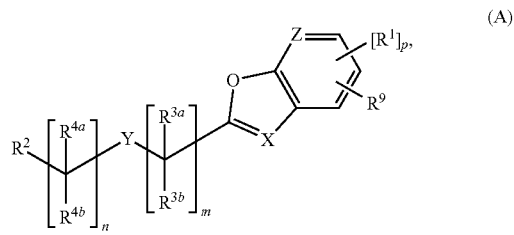

(A)

or a pharmaceutically acceptable salt thereof, wherein:
X is —C(R$^{30}$)— or —N—;
R$^{30}$ is hydrogen, deuterium, (C$_1$-C$_4$)alkyl or halo;
Y is selected from —C(R$^8$)═C(R$^6$)—R$^5$—N(R$^7$)—* and —N(R$^7$)—R$^5$—C(R$^6$)═C(R$^8$)—*, wherein "*" represents a portion of Y directly adjacent to —[C(R$^{3a}$)(R$^{3b}$)]$_m$—;

R$^5$ is selected from —C(O)—, —C(S)— and —S(O)$_2$—;

R$^6$ is selected from hydrogen, CN, and (C$_1$-C$_4$)alkyl;

R$^7$ is selected from hydrogen, (C$_1$-C$_4$)alkyl and (C$_3$-C$_6$)cycloalkyl; and R$^8$ is selected from hydrogen and (C$_1$-C$_4$)alkyl;

Z is —C(H)— or —N—;

each R$^1$ is independently selected from carbocyclyl, heterocyclyl, halo, halo(C$_1$-C$_4$)alkyl, (C$_1$-C$_4$)alkyl, —O—(C$_1$-C$_4$)alkyl, —O-halo(C$_1$-C$_4$)alkyl, cyano, sulfonate, and —S(O)$_{0-2}$(C$_1$-C$_4$)alkyl;

R$^2$ is heteroaryl or aryl;

each of R$^{3a}$ and R$^{3b}$, if present, is independently selected from hydrogen and (C$_1$-C$_4$)alkyl;

each of R$^{4a}$ and R$^{4b}$, if present, is independently selected from hydrogen, (C$_1$-C$_4$)alkyl, and (C$_3$-C$_6$)cycloalkyl;

R$^9$ is carbocyclyl or heterocyclyl;

m is 0, 1 or 2;

n is 0 or 1; and p is 0, 1, 2 or 3 when Z is —C(H)— and 0, 1 or 2 when Z is —N—, wherein:

each aryl, heteroaryl, carbocyclyl, heterocyclyl, alkyl or cycloalkyl is optionally and independently substituted.

In a first aspect of the first embodiment, R$^2$ is optionally substituted and is selected from pyridinyl, isoxazolyl, thiazolyl, pyridazinyl, and phenyl. The values for the remaining variables are as described in the first embodiment.

In a second aspect of the first embodiment, R$^2$ is selected from 6-aminopyridin-3-yl, 6-trifluoromethylpyridin-3-yl, 6-chloropyridin-3-yl, pyridin-3-yl, pyridin-2-yl, pyridin-4-yl, 3,5-dimethylisoxazol-4-yl, thiazol-4-yl, pyridazin-3-yl, 4-aminophenyl and 6-(dimethylamino)pyridin-3-yl. The values for the remaining variables are as described in the first embodiment, or first aspect thereof.

In a third aspect of the first embodiment, each of R$^{4a}$ and R$^{4b}$, if present, is hydrogen. The values for the remaining variables are as described in the first embodiment, or the first or second aspect thereof.

In a fourth aspect of the first embodiment, n is 0. The values for the remaining variables are as described in the first embodiment, or first through third aspects thereof.

In a fifth aspect of the first embodiment, Y is —C(R$^8$)=C(R$^6$)—R$^5$—N(R$^7$)—*. The values for the remaining variables are as described in the first embodiment, or first through fourth aspects thereof.

In a sixth aspect of the first embodiment, Y is —CH=CH—C(O)—NH—*. The values for the remaining variables are as described in the first embodiment, or first through fifth aspects thereof.

In a seventh aspect of the first embodiment, m is 1 or 2. The values for the remaining variables are as described in the first embodiment, or first through sixth aspects thereof.

In an eighth aspect of the first embodiment, m is 1. The values for the remaining variables are as described in the first embodiment, or first through ninth aspects thereof.

In a ninth aspect of the first embodiment, each of R$^{3a}$ and R$^{3b}$, if present, is independently selected from hydrogen and methyl. The values for the remaining variables are as described in the first embodiment, or first through eighth aspects thereof.

In a tenth aspect of the first embodiment, each of R$^{3a}$ and R$^{3b}$, if present, is hydrogen. The values for the remaining variables are as described in the first embodiment, or first through ninth aspects thereof.

In an eleventh aspect of the first embodiment, X is —C(H)—. The values for the remaining variables are as described in the first embodiment, or first through tenth aspects thereof.

In a twelfth aspect of the first embodiment, X is —N—. The values for the remaining variables are as described in the first embodiment, or first through eleventh aspects thereof.

In a thirteenth aspect of the first embodiment, p is 0 or 1. The values for the remaining variables are as described in the first embodiment, or first through twelfth aspects thereof.

In a fourteenth aspect of the first embodiment, p is 1. The values for the remaining variables are as described in the first embodiment, or first through thirteenth aspects thereof.

In a fifteenth aspect of the first embodiment, each R$^1$ is independently selected from halo, halo(C$_1$-C$_4$)alkyl, optionally substituted (C$_1$-C$_4$)alkyl and optionally substituted —O—(C$_1$-C$_4$)alkyl. The values for the remaining variables are as described in the first embodiment, or first through fourteenth aspects thereof.

In a sixteenth aspect of the first embodiment, R$^9$ is optionally and independently substituted with 1, 2 or 3 substituents and is phenyl or a 5-6-membered heteroaryl having 1, 2 or 3 heteroatoms independently selected from nitrogen, oxygen and sulfur. The values for the remaining variables are as described in the first embodiment, or first through fifteenth aspects thereof.

In a seventeenth aspect of the first embodiment, Y is —NH—C(O)—CH=CH—* or —CH=CH—C(O)—NH—*. The values for the remaining variables are as described in the first embodiment, or first through sixteenth aspects thereof.

In an eighteenth aspect of the first embodiment, R$^9$ is:

phenyl or a 6-membered heteroaryl having 1, 2 or 3 heteroatoms independently selected from nitrogen, oxygen and sulfur;

substituted at the meta or para position relative to its attachment point with one substituent selected from —C(O)(C$_1$-C$_4$)alkyl; —C(O)(C$_0$-C$_1$ alkylene)NR$^{11}$R$^{12}$, wherein R$^{11}$ and R$^{12}$ are taken together with the nitrogen atom to which they are commonly attached to form an optionally substituted (C$_3$-C$_7$)heterocyclyl; —S(O)$_2$NR$^{11}$R$^{12}$ wherein R$^{11}$ and R$^{12}$ are taken together with the nitrogen atom to which they are commonly attached to form an optionally substituted (C$_3$-C$_7$)heterocyclyl; and —C(O)NHNHR$^{12}$, wherein R$^{12}$ is an optionally substituted (C$_5$-C$_6$)heteroaryl; and further optionally substituted with 1 or 2 substituents independently selected from halogen, (C$_1$-C$_4$)alkyl and (C$_1$-C$_4$)haloalkyl.

The values for the remaining variables are as defined in the first embodiment, or first through seventeenth aspects thereof.

In a nineteenth aspect of the first embodiment, the compound is represented by Structural Formula I:

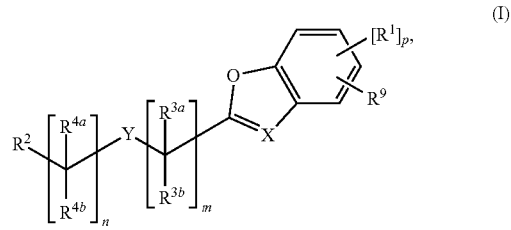

(I)

or a pharmaceutically acceptable salt thereof, wherein:
X is —C(H)— or —N—;
Y is selected from —C(R$^8$)═C(R$^6$)—R$^5$—N(R$^7$)—* and —N(R$^7$)—R$^5$—C(R$^6$)═C(R$^8$)—*, wherein
"*" represents a portion of Y directly adjacent to —[C(R$^{3a}$)(R$^{3b}$)]$_m$—;
R$^5$ is selected from —C(O)— and —S(O)$_2$—;
R$^6$ is selected from hydrogen, CN, and (C$_1$-C$_4$)alkyl;
R$^7$ and R$^8$ are each independently selected from hydrogen and (C$_1$-C$_4$)alkyl;
each R$^1$ is independently selected from carbocyclyl, heterocyclyl, halo (e.g., fluoro, chloro, bromo, iodo), halo (C$_1$-C$_4$)alkyl, (C$_1$-C$_4$)alkyl, —O—(C$_1$-C$_4$)alkyl, cyano, sulfonate, and —S(O)$_{0-2}$(C$_1$-C$_4$)alkyl;
R$^2$ is heteroaryl or aryl;
each of R$^{3a}$ and R$^{3b}$, if present, is independently selected from hydrogen and (C$_1$-C$_4$)alkyl;
each of R$^{4a}$ and R$^{4b}$, if present, is independently selected from hydrogen, (C$_1$-C$_4$)alkyl, and (C$_3$-C$_6$)cycloalkyl;
R$^9$ is carbocyclyl or heterocyclyl;
m is 0, 1 or 2; n is 0 or 1; and
p is 0, 1, 2 or 3, wherein:
each aryl, heteroaryl, carbocyclyl, heterocyclyl, alkyl or cycloalkyl is optionally and independently substituted. Alternative values for the variables are as defined in the first embodiment, or first through eighteenth aspects thereof.

In a twentieth aspect of the first embodiment, R$^2$ is optionally substituted phenyl or optionally substituted C$_5$-C$_6$ heteroaryl having 1, 2 or 3 heteroatoms independently selected from nitrogen, oxygen and sulfur. The values for the remaining variables are as described in the first embodiment, or first through nineteenth aspects thereof.

In a twenty-first aspect of the first embodiment, R$^2$ is optionally substituted with 1, 2 or 3 substituents independently selected from amino, halogen, C$_1$-C$_4$ alkyl and C$_1$-C$_4$ haloalkyl. The values for the variables are as described in the first embodiment, or first through twentieth aspects thereof.

In a twenty-second aspect of the first embodiment, R$^9$ is substituted with one or more substituents independently selected from halogen, (C$_1$-C$_4$)alkyl, (C$_1$-C$_4$)haloalkyl, —C(O)(C$_1$-C$_4$)alkyl, —C(O)(C$_0$-C$_4$ alkylene)NR$^{11}$R$^{12}$, —S(O)$_2$NR$^{11}$R$^{12}$ and —C(O)NR$^{13}$NR$^{11}$R$^{12}$, wherein:
R$^{11}$ and R$^{12}$ are each independently hydrogen, optionally substituted C$_1$-C$_4$ alkyl, optionally substituted carbocyclyl, or optionally substituted heterocyclyl; or
R$^{11}$ and R$^{12}$ are taken together with the nitrogen atom to which they are commonly attached to form an optionally substituted heterocyclyl; and
R$^{13}$ is hydrogen or optionally substituted (C$_1$-C$_4$)alkyl.
The values for the remaining variables (i.e., variables other than R$^{11}$, R$^{12}$ and R$^{13}$) and optional substituents for the remaining variables (i.e., variables other than R$^9$) are as described in the first embodiment, or first through twenty-first aspects thereof.

In a twenty-third aspect of the first embodiment, R$^9$ is substituted with 1, 2 or 3 substituents independently selected from halogen; (C$_1$-C$_4$)alkyl; (C$_1$-C$_4$)haloalkyl; —C(O)(C$_1$-C$_4$)alkyl; —C(O)(C$_0$-C$_1$ alkylene)NR$^{11}$R$^{12}$, wherein R$^{11}$ and R$^{12}$ are taken together with the nitrogen atom to which they are commonly attached to form an optionally substituted (C$_3$-C$_7$)heterocyclyl; —S(O)$_2$NR$^{11}$R$^{12}$, wherein R$^{11}$ and R$^{12}$ are taken together with the nitrogen atom to which they are commonly attached to form an optionally substituted (C$_3$-C$_7$)heterocyclyl; and —C(O)NHNHR$^{12}$, wherein R$^{12}$ is an optionally substituted (C$_5$-C$_6$)heteroaryl. The values for the remaining variables (i.e., variables other than R$^{11}$ and R$^{12}$) and optional substituents for the remaining variables (i.e., variables other than R$^9$) are as described in the first embodiment, or first through twenty-second aspects thereof.

In a twenty-fourth aspect of the first embodiment, R$^9$ is substituted with one substituent selected from —C(O)(C$_1$-C$_4$)alkyl; —C(O)(C$_0$-C$_1$ alkylene)NR$^{11}$R$^{12}$, wherein R$^{11}$ and R$^{12}$ are taken together with the nitrogen atom to which they are commonly attached to form an optionally substituted (C$_3$-C$_7$)heterocyclyl; —S(O)$_2$NR$^{11}$R$^{12}$, wherein R$^{11}$ and R$^{12}$ are taken together with the nitrogen atom to which they are commonly attached to form an optionally substituted (C$_3$-C$_7$)heterocyclyl; and —C(O)NHNHR$^{12}$, wherein R$^{12}$ is an optionally substituted (C$_5$-C$_6$)heteroaryl; and is further optionally substituted with 1 or 2 substituents independently selected from halogen, optionally substituted (C$_1$-C$_4$)alkyl and (C$_1$-C$_4$)haloalkyl. The values for the remaining variables (i.e., variables other than R$^{11}$ and R$^{12}$) and optional substituents for the remaining variables (i.e., variables other than R$^9$) are as described in the first embodiment, or first through twenty-third aspects thereof.

In a twenty-fifth aspect of the first embodiment, the heterocyclyl formed by R$^{11}$ and R$^{12}$ taken together with the nitrogen atom to which they are commonly attached is optionally substituted with 1, 2, 3 or 4 substituents independently selected from halo, hydroxyl, halo(C$_1$-C$_3$)alkyl, (C$_1$-C$_3$)alkyl and (C$_1$-C$_3$)alkoxy. Values for the variables and optional substituents for the remaining variables (i.e., variables other than R$^{11}$ and R$^{12}$) are as defined in the first embodiment, or first through twenty-fourth aspects thereof.

A second embodiment of the invention is a compound represented by Structural Formula B:

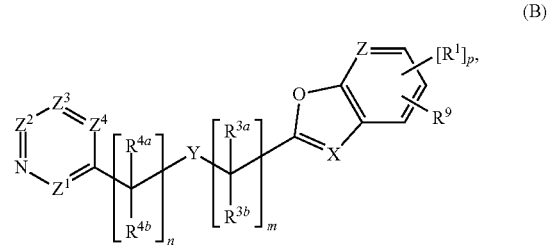

(B)

or a pharmaceutically acceptable salt thereof, wherein:
Z is —N— or —C(H)—; and
each of Z$^1$, Z$^2$, Z$^3$ and Z$^4$ is independently selected from N and C(R$^{10}$), wherein: no more than one of Z$^1$, Z$^2$, Z$^3$ and Z$^4$ is nitrogen, and
each R$^{10}$ is independently hydrogen or a suitable heteroaryl substituent.

Values and alternative values and optional substituents for the remaining variables in Structural Formula B are as defined in the first embodiment, or any aspect thereof.

In a first aspect of the second embodiment, the portion of the compound in Structural Formula II represented by

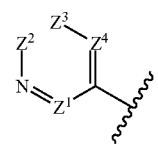

is selected from:

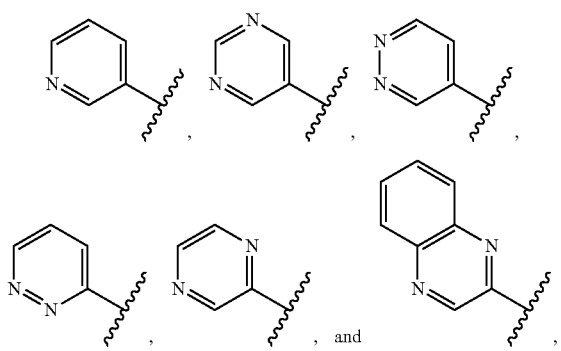

and is optionally further substituted. The values and optional substituents for the remaining variables are as described in the first embodiment, or any aspect thereof, or the second embodiment.

In a second aspect of the second embodiment, the portion of the compound in Structural Formula II represented by

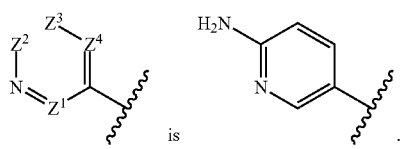

The values and optional substituents for the remaining variables are as described in the first embodiment, or any aspect thereof, or the second embodiment, or first aspect thereof.

In a third aspect of the second embodiment, the compound is represented by Structural Formula II:

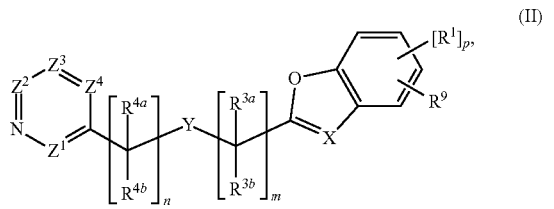

or a pharmaceutically acceptable salt thereof. Values and alternative values and optional substituents for the variables in Structural Formula II are as described in the first embodiment, or any aspect thereof, or the second embodiment, or first or second aspect thereof.

In a fourth aspect of the second embodiment, each $R^{10}$ is independently hydrogen, amino, halogen, $C_1$-$C_4$ alkyl or $C_1$-$C_4$ haloalkyl. The values and optional substituents for the remaining variables are as described in the first embodiment, or any aspect thereof, or the second embodiment, or first through third aspects thereof.

A third embodiment of the invention is a compound represented by Structural Formula III or IV:

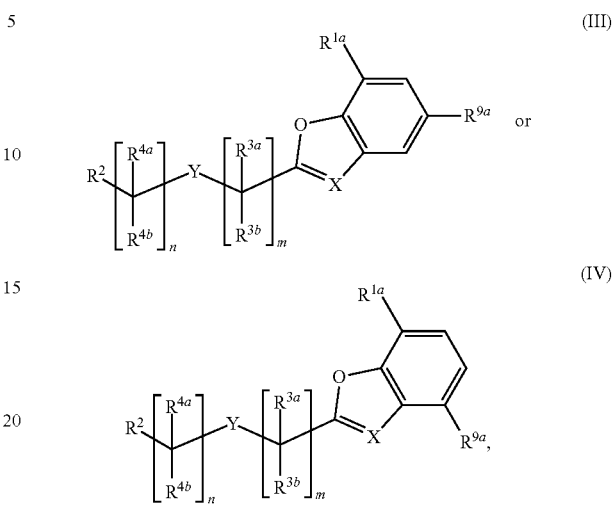

or a pharmaceutically acceptable salt thereof, wherein:
$R^{1a}$ is selected from hydrogen, halogen, halo($C_1$-$C_4$) alkyl, ($C_1$-$C_4$)alkyl, —O—($C_1$-$C_4$)alkyl, —O-halo($C_1$-$C_4$)alkyl, ($C_3$-$C_{12}$)carbocyclyl and ($C_3$-$C_{12}$)heterocyclyl, wherein each alkyl, carbocyclyl and heterocyclyl is optionally and independently substituted; and
$R^{9a}$ is optionally substituted aryl or optionally substituted heteroaryl.

Values and alternative values for the remaining variables in Structural Formulas III and IV and optional substituents for all the variables in Structural Formulas III and IV are as defined in the first or second embodiment, or any aspect of the foregoing.

In a first aspect of the third embodiment, $R^{1a}$ is selected from hydrogen, fluoro, chloro, —$CF_3$, —$CHF_2$, —$OCH_3$ and —$C(CH_3)_3$. The values and optional substituents for the remaining variables are as defined in the first or second embodiment, or any aspect of the foregoing, or the third embodiment.

In a second aspect of the third embodiment, $R^{1a}$ is selected from fluoro, chloro, —$CF_3$ and —$CHF_2$. The values and optional substituents for the remaining variables are as defined in the first or second embodiment, or any aspect of the foregoing, or the third embodiment, or first aspect thereof.

In a third aspect of the third embodiment, $R^{1a}$ is chloro or —$CF_3$. The values and optional substituents for the remaining variables are as defined in the first or second embodiment, or any aspect of the foregoing, or the third embodiment, or first or second aspect thereof.

In a fourth aspect of the third embodiment, $R^{9a}$ is optionally and independently substituted with 1, 2 or 3 substituents and is phenyl or a 5-6-membered heteroaryl having 1, 2 or 3 heteroatoms independently selected from nitrogen, oxygen and sulfur. The values and optional substituents for the remaining variables are as defined in the first or second embodiment, or any aspect of the foregoing, or the third embodiment, or first through third aspects thereof.

In a fifth aspect of the third embodiment, $R^{9a}$ is substituted with one or more substituents independently selected from halogen, ($C_1$-$C_4$)alkyl, ($C_1$-$C_4$)haloalkyl, —C(O)($C_1$-

C$_4$)alkyl, —C(O)(C$_0$-C$_4$ alkylene)NR$^{11}$R$^{12}$, —S(O)$_2$NR$^{11}$R$^{12}$ and —C(O)NR$^{13}$NR$^{11}$R$^{12}$, wherein:
R$^{11}$ and R$^{12}$ are each independently hydrogen, optionally substituted C$_1$-C$_4$ alkyl, optionally substituted carbocyclyl, or optionally substituted heterocyclyl; or
R$^{11}$ and R$^{12}$ are taken together with the nitrogen atom to which they are commonly attached to form an optionally substituted heterocyclyl; and
R$^{13}$ is hydrogen or optionally substituted (C$_1$-C$_4$)alkyl.
The values for the remaining variables (i.e., variables other than R$^{11}$, R$^{12}$ and R$^{13}$) and optional substituents for the remaining variables (i.e., variables other than R$^{9a}$) are as defined in the first or second embodiment, or any aspect of the foregoing, or the third embodiment, or first through fourth aspects thereof.

In a sixth aspect of the third embodiment, R$^{9a}$ is substituted with 1, 2 or 3 substituents independently selected from halogen; (C$_1$-C$_4$)alkyl; (C$_1$-C$_4$)haloalkyl; —C(O)(C$_1$-C$_4$)alkyl; —C(O)(C$_0$-C$_1$ alkylene)NR$^{11}$R$^{12}$, wherein R$^{11}$ and R$^{12}$ are taken together with the nitrogen atom to which they are commonly attached to form an optionally substituted (C$_3$-C$_7$)heterocyclyl; —S(O)$_2$NR$^{11}$R$^{12}$, wherein R$^{11}$ and R$^{12}$ are taken together with the nitrogen atom to which they are commonly attached to form an optionally substituted (C$_3$-C$_7$)heterocyclyl; and —C(O)NHNHR$^{12}$, wherein R$^{12}$ is an optionally substituted (C$_5$-C$_6$)heteroaryl. The values for the remaining variables (i.e., variables other than R$^{11}$ and R$^{12}$) and optional substituents for the remaining variables (i.e., variables other than R$^{9a}$) are as defined in the first or second embodiment, or any aspect of the foregoing, or the third embodiment, or the first through fifth aspects thereof.

In a seventh aspect of the third embodiment, R$^{9a}$ is substituted with one substituent selected from —C(O)(C$_1$-C$_4$)alkyl; —C(O)(C$_0$-C$_1$ alkylene)NR$^{11}$R$^{12}$, wherein R$^{11}$ and R$^{12}$ are taken together with the nitrogen atom to which they are commonly attached to form an optionally substituted (C$_3$-C$_7$)heterocyclyl; —S(O)$_2$NR$^{11}$R$^{12}$, wherein R$^{11}$ and R$^{12}$ are taken together with the nitrogen atom to which they are commonly attached to form an optionally substituted (C$_3$-C$_7$)heterocyclyl; and —C(O)NHNHR$^{12}$, wherein R$^{12}$ is an optionally substituted (C$_5$-C$_6$)heteroaryl; and is further optionally substituted with 1 or 2 substituents independently selected from halogen, (C$_1$-C$_4$)alkyl and (C$_1$-C$_4$) haloalkyl. The values for the remaining variables (i.e., variables other than R$^{11}$ and R$^{12}$) and optional substituents for the remaining variables (i.e., variables other than R$^{9a}$) are as defined in the first or second embodiment, or any aspect of the foregoing, or the third embodiment, or the first through sixth aspects thereof.

In an eighth aspect of the third embodiment, R$^{9a}$ is:
phenyl or a 6-membered heteroaryl having 1, 2 or 3 heteroatoms independently selected from nitrogen, oxygen and sulfur;
substituted at the meta or para position relative to its attachment point with one substituent selected from —C(O)(C$_1$-C$_4$)alkyl; —C(O)(C$_0$-C$_1$ alkylene)NR$^{11}$R$^{12}$, wherein R$^{11}$ and R$^{12}$ are taken together with the nitrogen atom to which they are commonly attached to form an optionally substituted (C$_3$-C$_7$)heterocyclyl; —S(O)$_2$NR$^{11}$R$^{12}$ wherein R$^{11}$ and R$^{12}$ are taken together with the nitrogen atom to which they are commonly attached to form an optionally substituted (C$_3$-C$_7$)heterocyclyl; and —C(O)NHNHR$^{12}$, wherein R$^{12}$ is an optionally substituted (C$_5$-C$_6$)heteroaryl; and further optionally substituted with 1 or 2 substituents independently selected from halogen, (C$_1$-C$_4$)alkyl and (C$_1$-C$_4$)haloalkyl.

The values and optional substituents for the remaining variables (i.e., variables other than R$^{9a}$R$^{11}$ and R$^{12}$) and optional substituents for the remaining variables (i.e., variables other than R$^{9a}$) are as defined in the first or second embodiment, or any aspect of the foregoing, or the third embodiment, or first through seventh aspects thereof.

In a ninth aspect of the third embodiment, R$^{9a}$ is selected from 4-(morpholinosulfonyl)phenyl, 5-(5-(morpholine-4-carbonyl)pyridin-2-yl, 4-(morpholine-4-carbonyl)phenyl, 3-(morpholine-4-carbonyl)phenyl, 5-acetylthiophen-2-yl, 4-(2-(pyrazin-2-yl)hydrazine-1-carbonyl)phenyl, 4-(2-morpholinoacetyl)phenyl, 4-(3,3-difluoroazetidine-1-carbonyl) phenyl), 4-(3-methylmorpholine-4-carbonyl)phenyl, 4-(3,3-dimethylmorpholine-4-carbonyl)phenyl, 4-(2,2-dimethylmorpholine-4-carbonyl)phenyl, 4-(2-(pyridin-2-yl) hydrazine-1-carbonyl)phenyl, 4-(3-fluoropyrrolidine-1-carbonyl)phenyl, 4-(3-fluoroazetidine-1-carbonyl)phenyl, 4-(3,3-dimethylazetidine-1-carbonyl)phenyl, 4-((3-fluoropyrrolidin-1-yl)sulfonyl)phenyl, 4-((3-fluoroazetidin-1-yl) sulfonyl)phenyl, 5-(morpholine-4-carbonyl)pyridin-3-yl, 5-fluoro-6-(morpholine-4-carbonyl)pyridin-3-yl, 4-(2-morpholino-2-oxoacetyl)phenyl, 2-(morpholine-4-carbonyl)pyrimidin-5-yl, 2,5-difluoro-4-(morpholine-4-carbonyl)phenyl, 2,3-difluoro-4-(morpholine-4-carbonyl)phenyl, 3-fluoro-4-(morpholine-4-carbonyl)phenyl, 6-(morpholine-4-carbonyl)pyridazin-3-yl, 4-(2-morpholino-2-oxoethyl) phenyl, 4-aminocarbonylphenyl, 2-methyl-1-oxoisoindolin-5-yl)benzofuran-2-yl, and 2-methyl-1,3-dioxoisoindolin-5-yl. The values and optional substituents for the remaining variables are as defined in the first or second embodiment, or any aspect of the foregoing, or the third embodiment, or first through eighth aspects thereof.

In a tenth aspect of the third embodiment:
R$^{1a}$ is selected from hydrogen, halogen, halo(C$_1$-C$_4$)alkyl, optionally substituted (C$_1$-C$_4$)alkyl, and optionally substituted —O—(C$_1$-C$_4$)alkyl; and
R$^{9a}$ is optionally substituted aryl or optionally substituted heteroaryl. The values for the remaining variables and optional substituents for all the variables are as defined in the first or second embodiment, or any aspect of the foregoing, or the third embodiment, or first through ninth aspects thereof.

In an eleventh aspect of the third embodiment:
R$^{1a}$ is selected from optionally substituted (C$_3$-C$_{12}$)carbocyclyl and optionally substituted (C$_3$-C$_{12}$)heterocyclyl; and
R$^{9a}$ is optionally substituted aryl or optionally substituted heteroaryl. The values for the remaining variables and optional substituents for all the variables are as defined in the first or second embodiment, or any aspect of the foregoing, or the third embodiment, or first through tenth aspects thereof.

In a twelfth aspect of the third embodiment, R$^{1a}$ is selected from optionally substituted (C$_6$-C$_{12}$)aryl and optionally substituted (C$_5$-C$_{12}$)heteroaryl. The values for the remaining variables and optional substituents for all the variables are as defined in the first or second embodiment, or any aspect of the foregoing, or the third embodiment, or first through eleventh aspects thereof.

In a thirteenth aspect of the third embodiment, R$^{1a}$ is selected from optionally substituted phenyl and optionally substituted (C$_6$)heteroaryl. The values for the remaining variables and optional substituents for all the variables are as defined in the first or second embodiment, or any aspect of the foregoing, or the third embodiment, or first through twelfth aspects thereof.

In a fourteenth aspect of the third embodiment, the compound is represented by Structural Formula III, or a pharmaceutically acceptable salt thereof. Values and alternative values and optional substituents for the variables in Structural Formula III are as defined in the first or second embodiment, or any aspect of the foregoing, or the third embodiment, or first through thirteenth aspects thereof.

In a fifteenth aspect of the third embodiment, the compound is represented by Structural Formula IV, or a pharmaceutically acceptable salt thereof. Values and alternative values and optional substituents for the variables in Structural Formula IV are as defined in the first or second embodiment, or any aspect of the foregoing, or the third embodiment, or first through thirteenth aspects thereof.

In a sixteenth aspect of the third embodiment:
$R^{1a}$ is selected from hydrogen, halogen, halo($C_1$-$C_4$)alkyl, ($C_1$-$C_4$)alkyl, —O—($C_1$-$C_4$)alkyl, ($C_3$-$C_{12}$)carbocyclyl and ($C_3$-$C_{12}$)heterocyclyl, wherein each alkyl, carbocyclyl and heterocyclyl is optionally and independently substituted; and
$R^{9a}$ is optionally substituted aryl or optionally substituted heteroaryl. The values for the remaining variables and optional substituents for all the variables are as defined in the first or second embodiment, or any aspect of the foregoing, or the third embodiment, or first through fifteenth aspects thereof.

In a seventeenth aspect of the third embodiment, $R^{9a}$ is:
phenyl or a 6-membered heteroaryl having 1, 2 or 3 heteroatoms independently selected from nitrogen, oxygen and sulfur;
substituted at the meta or para position relative to its attachment point with one substituent selected from —C(O)($C_1$-$C_4$)alkyl; —C(O)($C_0$-$C_1$ alkylene)NR$^{11}$R$^{12}$, wherein $R^{11}$ and $R^{12}$ are taken together with the nitrogen atom to which they are commonly attached to form an optionally substituted ($C_3$-$C_7$)heterocyclyl; —S(O)$_2$NR$^{11}$R$^{12}$, wherein $R^{11}$ and $R^{12}$ are taken together with the nitrogen atom to which they are commonly attached to form an optionally substituted ($C_3$-$C_7$)heterocyclyl; and —C(O)NHNHR$^{12}$, wherein $R^{12}$ is an optionally substituted ($C_5$-$C_6$)heteroaryl; and
further optionally substituted with 1 or 2 substituents independently selected from halogen, ($C_1$-$C_4$)alkyl and ($C_1$-$C_4$)haloalkyl.

The values for the remaining variables (i.e., variables other than $R^{9a}$, $R^{11}$ and $R^{12}$) and optional substituents for the remaining variables (i.e., variables other than $R^{9a}$) are as defined in the first or second embodiment, or any aspect of the foregoing, or the third embodiment, or first through sixteenth aspects thereof.

In an eighteenth aspect of the third embodiment, the heterocyclyl formed by $R^{11}$ and $R^{12}$ taken together with the nitrogen atom to which they are commonly attached is optionally substituted with 1, 2, 3 or 4 (preferably, 1 or 2) substituents independently selected from halo, hydroxyl, halo($C_1$-$C_3$)alkyl, ($C_1$-$C_3$)alkyl and ($C_1$-$C_3$)alkoxy. Values for all the variables and optional substituents for the remaining variables (i.e., variables other than $R^{11}$ and $R^{12}$) are as defined in the first or second embodiment, or any aspect of the foregoing, or the third embodiment, or first through seventeenth aspects thereof.

In a nineteenth aspect of the third embodiment, the heterocyclyl formed by $R^{11}$ and $R^{12}$ taken together with the nitrogen atom to which they are commonly attached is optionally substituted with 1 or 2 substituents independently selected from halo (e.g., fluoro), ($C_1$-$C_3$)alkyl, halo($C_1$-$C_3$)alkyl (e.g., trifluoromethyl), hydroxy, ($C_1$-$C_3$)alkoxy (e.g., methoxy) and halo($C_1$-$C_3$)alkoxy (e.g., trifluoromethoxy). Values for all the variables and optional substituents for the remaining variables (i.e., variables other than $R^{11}$ and $R^{12}$) are as defined in the first or second embodiment, or any aspect of the foregoing, or the third embodiment, or first through eighteenth aspects thereof.

In a twentieth aspect of the third embodiment, the carbocyclyl or heterocyclyl of $R^{1a}$ is optionally substituted with 1, 2 or 3 substituents independently selected from halo (e.g., fluoro, chloro), cyano, ($C_1$-$C_3$)alkyl, halo($C_1$-$C_3$)alkyl (e.g., trifluoromethyl), hydroxy, ($C_1$-$C_3$)alkoxy (e.g., methoxy) and halo($C_1$-$C_3$)alkoxy (e.g., trifluoromethoxy). Values for all the variables and optional substituents for the remaining variables (i.e., variables other than $R^{1a}$) are as defined in the first or second embodiment, or any aspect of the foregoing, or the third embodiment, or first through nineteenth aspects thereof.

A fourth embodiment of the invention is a compound represented by Structural Formula V or VI:

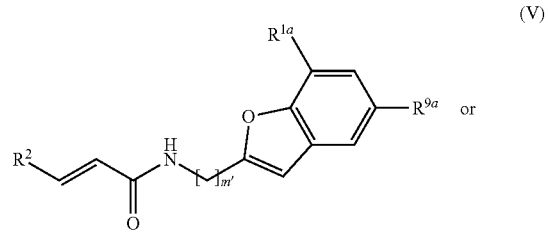

(V)

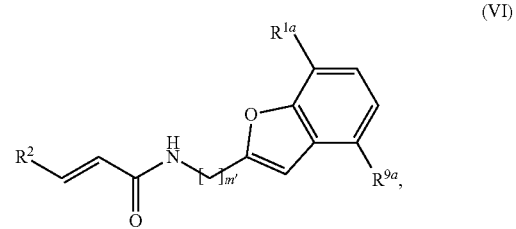

(VI)

or a pharmaceutically acceptable salt thereof, wherein m' is 1 or 2. Values and alternative values and optional substituents for the remaining variables are as described in the first through third embodiments, or any aspect of the foregoing.

In a first aspect of the fourth embodiment, $R^{1a}$ is selected from fluoro, chloro, —CF$_3$, —CHF$_2$, —C(CH$_3$)$_3$ and —OCH$_3$; and $R^{9a}$ is optionally and independently substituted with 1, 2 or 3 substituents and is phenyl or a 5-6-membered heteroaryl having 1, 2 or 3 heteroatoms independently selected from nitrogen, oxygen and sulfur. The values for the remaining variables (i.e., variables other than $R^{1a}$ and $R^{9a}$) and optional substituents for all the variables are as defined in the first through third embodiments, or any aspect of the foregoing, or the fourth embodiment.

In a second aspect of the fourth embodiment, $R^{9a}$ is:
phenyl or a 6-membered heteroaryl having 1, 2 or 3 heteroatoms independently selected from nitrogen, oxygen and sulfur;
substituted at the meta or para position relative to its attachment point with one substituent selected from —C(O)($C_1$-$C_4$)alkyl; —C(O)($C_0$-$C_1$ alkylene)NR$^{11}$R$^{12}$, wherein $R^{11}$ and $R^{12}$ are taken together with the nitrogen atom to which they are commonly attached to form an optionally substituted ($C_3$-$C_7$)heterocyclyl; —S(O)$_2$NR$^{11}$R$^{12}$ wherein $R^{11}$ and $R^{12}$ are taken together with the nitrogen atom to which they are commonly attached to form an optionally substituted ($C_3$-$C_7$)heterocyclyl; and —C(O)NHNHR$^{12}$, wherein R$^{12}$ is an optionally substituted ($C_5$-$C_6$)heteroaryl; and further optionally substituted with 1 or 2 substituents independently selected from halogen, ($C_1$-$C_4$)alkyl and ($C_1$-$C_4$)haloalkyl.

The values for the remaining variables (i.e., variables other than R$^{9a}$, R$^{11}$ and R$^{12}$) and optional substituents for the remaining variables (i.e., variables other than R$^{9a}$) are as defined in the first through third embodiments, or any aspect of the foregoing, or the fourth embodiment, or first aspect thereof.

In a third aspect of the fourth embodiment, R$^2$ is optionally substituted pyridinyl. The values for the remaining variables and optional substituents for all the variables are as defined in the first through third embodiments, or any aspect of the foregoing, or the fourth embodiment, or first or second aspect thereof.

In a fourth aspect of the fourth embodiment, R$^{9a}$ is selected from 4-(morpholinosulfonyl)phenyl, 5-(5-(morpholine-4-carbonyl)pyridin-2-yl, 4-(morpholine-4-carbonyl)phenyl, 3-(morpholine-4-carbonyl)phenyl, 5-acetylthiophen-2-yl, 4-(2-(pyrazin-2-yl)hydrazine-1-carbonyl)phenyl, 4-(2-morpholinoacetyl)phenyl, 4-(3,3-difluoroazetidine-1-carbonyl)phenyl, 4-(3-methylmorpholine-4-carbonyl)phenyl, 4-(3,3-dimethylmorpholine-4-carbonyl)phenyl, 4-(2,2-dimethylmorpholine-4-carbonyl)phenyl, 4-(2-(pyridin-2-yl)hydrazine-1-carbonyl)phenyl, 4-(3-fluoropyrrolidine-1-carbonyl)phenyl, 4-(3-fluoroazetidine-1-carbonyl)phenyl, 4-(3,3-dimethylazetidine-1-carbonyl)phenyl, 4-((3-fluoropyrrolidin-1-yl)sulfonyl)phenyl, 4-((3-fluoroazetidin-1-yl)sulfonyl)phenyl, 5-(morpholine-4-carbonyl)pyridin-3-yl, 5-fluoro-6-(morpholine-4-carbonyl)pyridin-3-yl, 4-(2-morpholino-2-oxoacetyl)phenyl, 2-(morpholine-4-carbonyl)pyrimidin-5-yl, 2,5-difluoro-4-(morpholine-4-carbonyl)phenyl, 2,3-difluoro-4-(morpholine-4-carbonyl)phenyl, 3-fluoro-4-(morpholine-4-carbonyl)phenyl, 6-(morpholine-4-carbonyl)pyridazin-3-yl, and 4-(2-morpholino-2-oxoethyl)phenyl. The values and optional substituents for the remaining variables are as defined in the first through third embodiments, or any aspect of the foregoing, or the fourth embodiment, or first through third aspects thereof.

In a fifth aspect of the fourth embodiment, m' is 1. The values and optional substituents for the remaining variables are as defined in the first through third embodiments, or any aspect of the foregoing, or the fourth embodiment, or first through fourth aspects thereof.

In a sixth aspect of the fourth embodiment, R$^2$ is selected from 6-aminopyridin-3-yl, pyridin-3-yl, pyridin-2-yl, 3,5-dimethylisoxazol-4-yl, and thiazol-4-yl. The values and optional substituents for the remaining variables are as defined in the first through third embodiments, or any aspect of the foregoing, or the fourth embodiment, or first through fifth aspects thereof.

In a seventh aspect of the fourth embodiment, the compound is represented by Structural Formula V, or a pharmaceutically acceptable salt thereof. Values and alternative values and optional substituents for the variables in Structural Formula V are as defined in the first through third embodiments, or any aspect of the foregoing, or the fourth embodiment, or first through sixth aspects thereof.

In an eighth aspect of the fourth embodiment, the compound is represented by Structural Formula VI, or a pharmaceutically acceptable salt thereof. Values and alternative values and optional substituents for the variables in Structural Formula VI are as defined in the first through third embodiments, or any aspect of the foregoing, or the fourth embodiment, or first through seventh aspects thereof.

In a ninth aspect of the fourth embodiment, R$^{1a}$ is selected from fluoro, chloro, —CF$_3$, —CHF$_2$, —C(CH$_3$)$_3$, —OCH$_3$ and —OCF$_3$; and R$^{9a}$ is optionally and independently substituted with 1, 2 or 3 substituents and is phenyl or a 5-6-membered heteroaryl having 1, 2 or 3 heteroatoms independently selected from nitrogen, oxygen and sulfur. The values for the remaining variables (i.e., variables other than R$^{1a}$ and R$^{9a}$) and optional substituents for all the variables are as defined in the first through third embodiments, or any aspect of the foregoing, or the fourth embodiment, or first through eighth aspects thereof.

In a tenth aspect of the fourth embodiment:
m' is 1 or 2;
R$^{1a}$ is halogen, halo($C_1$-$C_4$)alkyl (e.g., trifluoromethyl), ($C_1$-$C_4$)alkyl, —O—($C_1$-$C_4$)alkyl (e.g., methoxy), —O-halo($C_1$-$C_4$)alkyl (e.g., trifluoromethoxy), optionally substituted ($C_5$-$C_{12}$)aryl or optionally substituted ($C_5$-$C_{12}$) heteroaryl; and
R$^{9a}$ is optionally and independently substituted with 1, 2 or 3 substituents and is phenyl or a 5-6-membered heteroaryl having 1, 2 or 3 heteroatoms independently selected from nitrogen, oxygen and sulfur. The values for the remaining variables (i.e., variables other than m', R$^{1a}$, and R$^{9a}$) and optional substituents for all the variables are as defined in the first through third embodiments, or any aspect of the foregoing, or the fourth embodiment, or first through ninth aspects thereof.

In an eleventh aspect of the fourth embodiment, R$^{9a}$ is substituted with one or more substituents independently selected from halogen, ($C_1$-$C_4$)alkyl, ($C_1$-$C_4$)haloalkyl, —C(O)($C_1$-$C_4$)alkyl, —C(O)($C_0$-$C_4$ alkylene)NR$^{11}$R$^{12}$, —S(O)$_2$NR$^{11}$R$^{12}$ and —C(O)NR$^{13}$NR$^{11}$R$^{12}$, wherein:
R$^{11}$ and R$^{12}$ are each independently hydrogen, optionally substituted $C_1$-$C_4$ alkyl, optionally substituted carbocyclyl, or optionally substituted heterocyclyl; or
R$^{11}$ and R$^{12}$ are taken together with the nitrogen atom to which they are commonly attached to form an optionally substituted heterocyclyl; and
R$^{13}$ is hydrogen or optionally substituted ($C_1$-$C_4$)alkyl.

Values for the remaining variables (i.e., variables other than R$^{11}$, R$^{12}$ and R$^{13}$) and optional substituents for the remaining variables (i.e., variables other than R$^{9a}$) are as defined in the first through third embodiments, or any aspect of the foregoing, or the fourth embodiment, or first through tenth aspects thereof.

In a twelfth aspect of the fourth embodiment, R$^{9a}$ is substituted with 1, 2 or 3 substituents independently selected from halogen; ($C_1$-$C_4$)alkyl; ($C_1$-$C_4$)haloalkyl; —C(O)($C_1$-$C_4$)alkyl; —C(O)($C_1$-$C_1$ alkylene)NR$^{11}$R$^{12}$, wherein R$^{11}$ and R$^{12}$ are taken together with the nitrogen atom to which they are commonly attached to form an optionally substituted ($C_3$-$C_7$)heterocyclyl; —S(O)$_2$NR$^{11}$R$^{12}$, wherein R$^{11}$ and R$^{12}$ are taken together with the nitrogen atom to which they are commonly attached to form an optionally substituted ($C_3$-$C_7$)heterocyclyl; and —C(O)NHNHR$^{12}$, wherein R$^{12}$ is an optionally substituted ($C_5$-$C_6$)heteroaryl. Values for the remaining variables (i.e., variables other than R$^{11}$ and R$^{12}$) and optional substituents for the remaining variables (i.e., variables other than R$^{9a}$) are as defined in the first through third embodiments, or any aspect of the foregoing, or the fourth embodiment, or first through eleventh aspects thereof.

In a thirteenth aspect of the fourth embodiment, R$^{9a}$ is substituted with one substituent selected from —C(O)($C_1$-$C_4$)alkyl; —C(O)($C_0$-$C_1$ alkylene)NR$^{11}$R$^{12}$, wherein R$^{11}$ and $R^{12}$ are taken together with the nitrogen atom to which they are commonly attached to form an optionally substituted $(C_3-C_7)$heterocyclyl; —S(O)$_2$NR$^{11}$R$^{12}$, wherein $R^{11}$ and $R^{12}$ are taken together with the nitrogen atom to which they are commonly attached to form an optionally substituted $(C_3-C_7)$heterocyclyl; and —C(O)NHNHR$^{12}$, wherein $R^{12}$ is an optionally substituted $(C_5-C_6)$heteroaryl; and is further optionally substituted with 1 or 2 substituents independently selected from halogen, optionally substituted $(C_1-C_4)$alkyl and $(C_1-C_4)$haloalkyl. Values for the remaining variables (i.e., variables other than $R^{11}$ and $R^{12}$) and optional substituents for the remaining variables (i.e., variables other than $R^{9a}$) are as defined in the first through third embodiments, or any aspect of the foregoing, or the fourth embodiment, or first through twelfth aspects thereof.

In a fourteenth aspect of the fourth embodiment, the heterocyclyl formed by $R^{11}$ and $R^{12}$ taken together with the nitrogen atom to which they are commonly attached is optionally substituted with 1, 2, 3 or 4 substituents independently selected from halo, hydroxyl, halo($C_1-C_3$)alkyl, ($C_1-C_3$)alkyl and ($C_1-C_3$)alkoxy. Values for all the variables and optional substituents for the remaining variables (i.e., variables other than $R^{11}$ and $R^{12}$) are as defined in the first through third embodiments, or any aspect of the foregoing, or the fourth embodiment, or first through thirteenth aspects thereof.

In a fifteenth aspect of the fourth embodiment, the heterocyclyl formed by $R^{11}$ and $R^{12}$ taken together with the nitrogen atom to which they are commonly attached is optionally substituted with 1 or 2 substituents independently selected from halo (e.g., fluoro), ($C_1-C_3$)alkyl, halo($C_1-C_3$)alkyl (e.g., trifluoromethyl), hydroxy, ($C_1-C_3$)alkoxy (e.g., methoxy) and halo($C_1-C_3$)alkoxy (e.g., trifluoromethoxy). Values for all the variables and optional substituents for the remaining variables (i.e., variables other than $R^{11}$ and $R^{12}$) are as defined in the first through third embodiments, or any aspect of the foregoing, or the fourth embodiment, or first through thirteenth aspects thereof.

A fifth embodiment of the invention is a compound represented by Structural Formula VII or VIII:

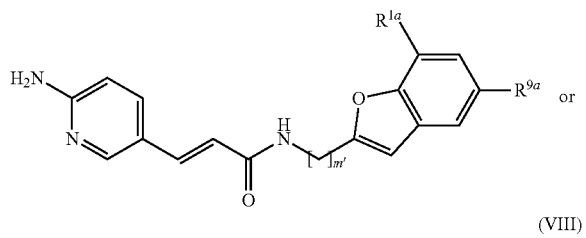

(VII)

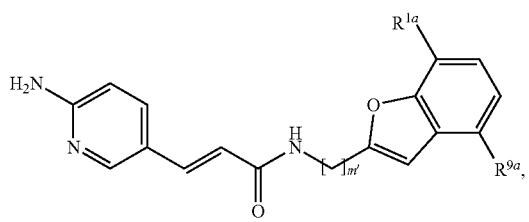

(VIII)

or a pharmaceutically acceptable salt thereof. Values and alternative values and optional substituents for the variables in Structural Formulas VII and VIII are as described in the first through fourth embodiments, or any aspect of the foregoing.

In a first aspect of the fifth embodiment, $R^{1a}$ is selected from chloro, —CF$_3$, and —OCH$_3$. The values and optional substituents for the remaining variables are as defined in the first through fourth embodiments, or any aspect of the foregoing, or the fifth embodiment.

In a second aspect of the fifth embodiment, $R^{9a}$ is selected from 4-(morpholinosulfonyl)phenyl, 5-(5-(morpholine-4-carbonyl)pyridin-2-yl, 4-(morpholine-4-carbonyl)phenyl, and 3-(morpholine-4-carbonyl)phenyl. The values and optional substituents for the remaining variables are as defined in the first through fourth embodiments, or any aspect of the foregoing, or the fifth embodiment, or first aspect thereof.

In a third aspect of the fifth embodiment, the compound is represented by Structural Formula VII, or a pharmaceutically acceptable salt thereof. Values and alternative values and optional substituents for the variables in Structural Formula VII are as defined in the first through fourth embodiments, or any aspect of the foregoing, or the fifth embodiment, or first or second aspect thereof.

In a fourth aspect of the fifth embodiment, the compound is represented by Structural Formula VIII, or a pharmaceutically acceptable salt thereof. Values and alternative values and optional substituents for the variables in Structural Formula VIII are as defined in the first through fourth embodiments, or any aspect of the foregoing, or the fifth embodiment, or first or second aspect thereof.

A sixth embodiment of the invention is a compound represented by Structural Formula VII:

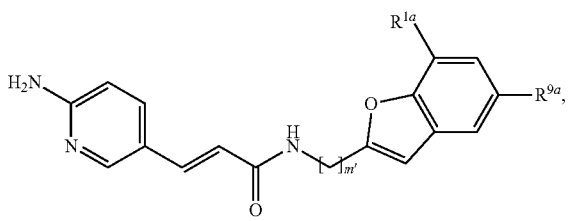

(VII)

or a pharmaceutically acceptable salt thereof, wherein:
m' is 1 or 2;
$R^{1a}$ is halogen, halo($C_1-C_4$)alkyl (e.g., trifluoromethyl), ($C_1-C_4$)alkyl, —O—($C_1-C_4$)alkyl (e.g., methoxy), —O-halo($C_1-C_4$)alkyl (e.g., trifluoromethoxy), optionally substituted ($C_5-C_{12}$)aryl or optionally substituted ($C_5-C_{12}$)heteroaryl; and
$R^{9a}$ is optionally and independently substituted with 1, 2 or 3 substituents and is phenyl or a 5-6-membered heteroaryl having 1, 2 or 3 heteroatoms independently selected from nitrogen, oxygen and sulfur. Optional substituents for variables $R^{1a}$ and $R^{9a}$ are as defined in the first through fifth embodiments, or any aspect of the foregoing.

In a first aspect of the sixth embodiment, $R^{1a}$ is an optionally substituted $C_6$ aryl or an optionally substituted ($C_5-C_6$)heteroaryl. The values for the remaining variables (i.e., variables other than $R^{1a}$) and optional substituents for all the variables are as defined in the first through fifth embodiments, or any aspect of the foregoing, or the sixth embodiment.

In a second aspect of the sixth embodiment, $R^{1a}$ is an optionally substituted phenyl. The values for the remaining variables (i.e., variables other than $R^{1a}$) and optional substituents for all the variables are as defined in the first through fifth embodiments, or any aspect of the foregoing, or the sixth embodiment, or first aspect thereof.

In a third aspect of the sixth embodiment, $R^{1a}$ is an optionally substituted $C_{5-6}$ heteroaryl. The values for the remaining variables (i.e., variables other than $R^{1a}$) and optional substituents for all the variables are as defined in the first through fifth embodiments, or any aspect of the foregoing, or the sixth embodiment, or first or second aspect thereof.

In a fourth aspect of the sixth embodiment, $R^{1a}$ is optionally substituted pyridine. The values for the remaining variables (i.e., variables other than $R^{1a}$) and optional substituents for all the variables are as defined in the first through fifth embodiments, or any aspect of the foregoing, or the sixth embodiment, or first through third aspects thereof.

In a fifth aspect of the sixth embodiment, m' is 1. The values and optional substituents for the remaining variables are as defined in the first through fifth embodiments, or any aspect of the foregoing, or the sixth embodiment, or first through fourth aspects thereof.

In a sixth aspect of the sixth embodiment, $R^{1a}$ is halogen, halo($C_1$-$C_4$)alkyl (e.g., trifluoromethyl), ($C_1$-$C_4$)alkyl, —O—($C_1$-$C_4$)alkyl (e.g., methoxy) or —O-halo($C_1$-$C_4$)alkyl (e.g., trifluoromethoxy). The values and optional substituents for the remaining variables are as defined in the first through fifth embodiments, or any aspect of the foregoing, or the sixth embodiment, or first through fifth aspects thereof.

In a seventh aspect of the sixth embodiment, $R^{1a}$ is optionally substituted ($C_5$-$C_{12}$)aryl or optionally substituted ($C_5$-$C_{12}$)heteroaryl. The values for the remaining variables (i.e., variables other than $R^{1a}$) and optional substituents for all the variables are as defined in the first through fifth embodiments, or any aspect of the foregoing, or the sixth embodiment, or first through sixth aspects thereof.

In an eighth aspect of the sixth embodiment, the aryl or heteroaryl (e.g., ($C_5$-$C_{12}$)aryl, ($C_5$-$C_{12}$)heteroaryl, ($C_5$-$C_6$) heteroaryl, phenyl, pyridinyl) of $R^{1a}$ is optionally substituted with 1, 2 or 3 substituents independently selected from halo (e.g., fluoro, chloro), cyano, ($C_1$-$C_3$)alkyl, halo($C_1$-$C_3$)alkyl (e.g., trifluoromethyl), hydroxy, ($C_1$-$C_3$)alkoxy (e.g., methoxy) and halo($C_1$-$C_3$)alkoxy (e.g., trifluoromethoxy). Values for all the variables and optional substituents for the remaining variables (i.e., variables other than Ria) are as defined in the first through fifth embodiments, or any aspect of the foregoing, or the sixth embodiment, or first through seventh aspects thereof.

A seventh embodiment of the invention is a compound represented by Structural Formula IX:

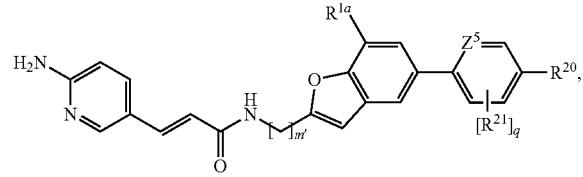

(IX)

or a pharmaceutically acceptable salt thereof, wherein:
m' is 1 or 2;
$R^{1a}$ is halogen, halo($C_1$-$C_4$)alkyl (e.g., trifluoromethyl), ($C_1$-$C_4$)alkyl, —O—($C_1$-$C_4$)alkyl (e.g., methoxy), —O-halo ($C_1$-$C_4$)alkyl (e.g., trifluoromethoxy), optionally substituted ($C_5$-$C_{15}$)aryl or optionally substituted ($C_5$-$C_{15}$) heteroaryl;

$Z^5$ is —N— or —C(H)—;

$R^{20}$ is ($C_1$-$C_4$)alkyl, ($C_1$-$C_4$)haloalkyl, —O—($C_0$-$C_4$ alkylene)carbocyclyl, —O—($C_0$-$C_4$ alkylene)heterocyclyl, —C(H)(OH)-carbocyclyl, —C(H)(OH)-heterocyclyl, —C(H)($CH_3$)-carbocyclyl, —C(H)($CH_3$)-heterocyclyl, —C(O)($C_1$-$C_4$)alkyl, —C(S)($C_1$-$C_4$)alkyl, —C(O)($C_0$-$C_4$ alkylene)$NR^{11}R^{12}$, —C(S)($C_0$-$C_4$ alkylene)$NR^{11}R^{12}$, —S(O)$_2$($C_1$-$C_4$)alkyl, —S(O)$_2NR^{11}R^{12}$ or —C(O) $NR^{13}NR^{11}R^{12}$, wherein:

$R^{11}$ and $R^{12}$ are each independently hydrogen, optionally substituted $C_1$-$C_4$ alkyl, optionally substituted carbocyclyl, or optionally substituted heterocyclyl; or $R^{11}$ and $R^{12}$ are taken together with the nitrogen atom to which they are commonly attached to form an optionally substituted heterocyclyl; and $R^{13}$ is hydrogen or optionally substituted ($C_1$-$C_4$)alkyl;

each $R^{21}$, if present, is independently halo; and q is 0, 1, 2, 3 or 4 if $Z^5$ is —C(H)— and 0, 1 or 3 if $Z^5$ is —N—. Alternative values and optional substituents for the variables in Structural Formula IX are as described in the first through sixth embodiments, or any aspect of the foregoing.

In a first aspect of the seventh embodiment, q is 0, 1 or 2, preferably, 0 or 1. The values and optional substituents for the remaining variables are as defined in the first through sixth embodiments, or any aspect of the foregoing, or the seventh embodiment.

In a second aspect of the seventh embodiment, $R^{21}$, for each occurrence and if present, is fluoro. The values and optional substituents for the remaining variables are as defined in the first through sixth embodiments, or any aspect of the foregoing, or the seventh embodiment, or first aspect thereof.

In a third aspect of the seventh embodiment, $R^{20}$ is —C(O)($C_0$-$C_4$ alkylene)$NR^{11}R^{12}$ or —C(S)($C_0$-$C_4$ alkylene)$NR^{11}R^{12}$, wherein $R^{11}$ and $R^{12}$ are taken together with the nitrogen atom to which they are commonly attached to form an optionally substituted ($C_3$-$C_7$)heterocyclyl having 1 or 2 heteroatoms independently selected from nitrogen, oxygen and sulfur. The values for the remaining variables (i.e., variables other than $R^{20}$, $R^{11}$ and $R^{12}$) and optional substituents for all the variables are as defined in the first through sixth embodiments, or any aspect of the foregoing, or the seventh embodiment, or first or second aspect thereof.

In a fourth aspect of the seventh embodiment, $Z^5$ is —C(H)—. The values and optional substitutents for the remaining variables are as defined in the first through sixth embodiments, or any aspect of the foregoing, or the seventh embodiment, or first through third aspects thereof.

In a fifth aspect of the seventh embodiment, $Z^5$ is —N—. The values and optional substituents for the remaining variables are as defined in the first through sixth embodiments, or any aspect of the foregoing, or the seventh embodiment, or first through fourth aspects thereof.

In a sixth aspect of the seventh embodiment, the compound is represented by Structural Formula X:

(X)

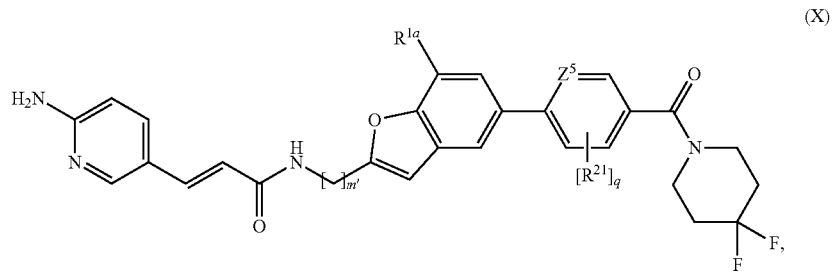

or a pharmaceutically acceptable salt thereof. Values and alternative values and optional substituents for the variables in Structural Formula X are as described in the first through sixth embodiments, or any aspect of the foregoing, or the seventh embodiment, or first through fifth aspects thereof.

An eighth embodiment is a compound represented by Structural Formula XI:

(XI)

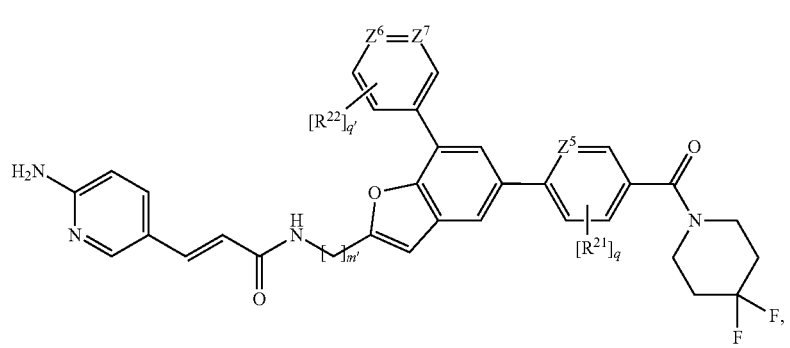

or a pharmaceutically acceptable salt thereof, wherein:
m' is 1 or 2, preferably 1;
$Z^5$ is —N— or —C(H)—;
each of $Z^6$ and $Z^7$ is independently —N— or —C(H)—, preferably —C(H)—, wherein no more than one of $Z^6$ and $Z^7$ is nitrogen;
each $R^{21}$, if present, is independently halo (e.g., fluoro);
each $R^{22}$, if present, is independently halo (e.g., fluoro, chloro), cyano, $(C_1-C_3)$alkyl, halo$(C_1-C_3)$alkyl (e.g., trifluoromethyl), hydroxy, $(C_1-C_3)$alkoxy (e.g., methoxy) or halo$(C_1-C_3)$alkoxy (e.g., trifluoromethoxy), preferably halo;
q is 0, 1, 2, 3 or 4 if $Z^5$ is —C(H)— and 0, 1, 2 or 3 if $Z^5$ is —N—; and
q' is 0, 1, 2 or 3, preferably 0, 1 or 2, more preferably 0 or 1. Values and alternative values for the remaining variables in Structural Formula XI are as described in the first through seventh embodiments, or any aspect of the foregoing.

In a first aspect of the eighth embodiment, $Z^6$ and $Z^7$ are each —C(H)—. The values for the remaining variables are as described in the first through seventh embodiments, or any aspect of the foregoing, or the eighth embodiment.

In a second aspect of the eighth embodiment, $Z^6$ is —N— and $Z^7$ is —C(H)—. The values for the remaining variables are as described in the first through seventh embodiments, or any aspect of the foregoing, or the eighth embodiment, of first aspect thereof.

In a third aspect of the eighth embodiment, $Z^6$ is —C(H)— and $Z^7$ is —N—. The values for the remaining variables are as described in the first through seventh embodiments, or any aspect of the foregoing, or the eighth embodiment, of first or second aspect thereof.

A ninth embodiment is a compound represented by Structural Formula XII:

(XII)

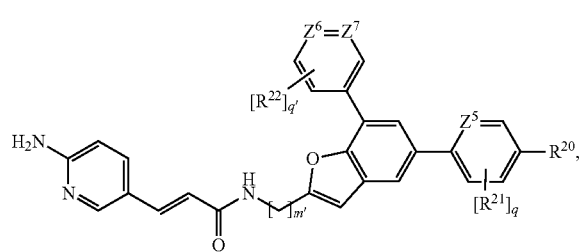

or a pharmaceutically acceptable salt thereof, wherein:
m' is 1 or 2, preferably 1;
$Z^5$ is —N— or —C(H)—;
each of $Z^6$ and $Z^7$ is independently —N— or —C(H)—, preferably —C(H)—, wherein no more than one of $Z^6$ and $Z^7$ is nitrogen;
$R^{20}$ is $(C_1-C_4)$alkyl, $(C_1-C_4)$haloalkyl, —O—$(C_0-C_4$ alkylene)carbocyclyl, —O—$(C_0-C_4$ alkylene)heterocyclyl, —C(H)(OH)-carbocyclyl, —C(H)(OH)-heterocyclyl, —C(H)(CH$_3$)-carbocyclyl, —C(H)(CH$_3$)-heterocyclyl, —C(O)($C_1-C_4$)alkyl, —C(S)($C_1-C_4$)alkyl, —C(O)($C_0-C_4$ alkylene)NR$^{11}$R$^{12}$, —C(S)($C_0-C_4$ alkylene)NR$^{11}$R$^{12}$, —S(O)$_2$(C$_1$-C$_4$)alkyl, —S(O)$_2$NR$^{11}$R$^{12}$ or —C(O)NR$^{13}$NR$^{11}$R$^{12}$, wherein:
- R$^{11}$ and R$^{12}$ are each independently hydrogen, optionally substituted C$_1$-C$_4$ alkyl, optionally substituted carbocyclyl, or optionally substituted heterocyclyl; or
- R$^{11}$ and R$^{12}$ are taken together with the nitrogen atom to which they are commonly attached to form an optionally substituted heterocyclyl; and
- R$^{13}$ is hydrogen or optionally substituted (C$_1$-C$_4$)alkyl;

each R$^{21}$, if present, is independently halo (e.g., fluoro);
each R$^{22}$, if present, is independently halo (e.g., fluoro, chloro), cyano, (C$_1$-C$_3$)alkyl, halo(C$_1$-C$_3$)alkyl (e.g., trifluoromethyl), hydroxy, (C$_1$-C$_3$)alkoxy (e.g., methoxy) or halo(C$_1$-C$_3$)alkoxy (e.g., trifluoromethoxy), preferably halo;
q is 0, 1, 2, 3 or 4 if Z$^5$ is —C(H)— and 0, 1, 2 or 3 if Z$^5$ is —N—; and
q' is 0, 1, 2 or 3, preferably 0, 1 or 2, more preferably 0 or 1. Alternative values and optional substituents for the variables in Structural Formula XII are as described in the first through eighth embodiments, or any aspect of the foregoing.

Exemplary compounds are set forth in Table 1.

Formulation and Administration

Another embodiment of the invention is a composition comprising a compound of the invention, or a pharmaceutically acceptable salt thereof, and a pharmaceutically acceptable carrier, adjuvant, or vehicle. In certain embodiments, a composition of the invention is formulated for administration to a patient in need of the composition. In some embodiments, a composition of the invention is formulated for oral, intravenous, subcutaneous, intraperitoneal or dermatological administration to a patient in need thereof.

The term "patient," as used herein, means an animal. In some embodiments, the animal is a mammal. In certain embodiments, the patient is a veterinary patient (i.e., a non-human mammal patient). In some embodiments, the patient is a dog. In other embodiments, the patient is a human.

"Pharmaceutically or pharmacologically acceptable" includes molecular entities and compositions that do not produce an adverse, allergic or other untoward reaction when administered to an animal, or a human, as appropriate. For human administration, preparations should meet sterility, pyrogenicity, and general safety and purity standards, as required by FDA Office of Biologics standards.

The phrase "pharmaceutically acceptable carrier, adjuvant, or vehicle" refers to a non-toxic carrier, adjuvant, or vehicle that does not destroy the pharmacological activity of the compound with which it is formulated and is nontoxic when administered in doses sufficient to deliver a therapeutic amount of the compound. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or intraperitoneally.

The term "parenteral," as used herein, includes subcutaneous, intracutaneous, intravenous, intramuscular, intraocular, intravitreal, intra-articular, intra-arterial, intra-synovial, intrasternal, intrathecal, intralesional, intrahepatic, intraperitoneal intralesional and intracranial injection or infusion techniques. Preferably, the compositions are administered orally, subcutaneously, intraperitoneally or intravenously.

Pharmaceutically acceptable compositions of this invention can be orally administered in any orally acceptable dosage form including, but not limited to, capsules, tablets, aqueous suspensions, dispersions and solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions and/or emulsions are required for oral use, the active ingredient can be suspended or dissolved in an oily phase and combined with emulsifying and/or suspending agents. If desired, certain sweetening, flavoring or coloring agents may also be added.

In some embodiments, an oral formulation is formulated for immediate release or sustained/delayed release.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders, such as carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium salts, g) wetting agents, such as acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using excipients such as lactose or milk sugar, as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

A compound of the invention can also be in microencapsulated form with one or more excipients, as noted above. In such solid dosage forms, the compound of the invention can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose.

Compositions for oral administration may be designed to protect the active ingredient against degradation as it passes through the alimentary tract, for example, by an outer coating of the formulation on a tablet or capsule.

In another embodiment, a compound of the invention can be provided in an extended (or "delayed" or "sustained") release composition. This delayed-release composition comprises a compound of the invention in combination with a delayed-release component. Such a composition allows targeted release of a provided compound into the lower gastrointestinal tract, for example, into the small intestine, the large intestine, the colon and/or the rectum. In certain embodiments, the delayed-release composition comprising a compound of the invention further comprises an enteric or pH-dependent coating, such as cellulose acetate phthalates and other phthalates (e.g., polyvinyl acetate phthalate, methacrylates (Eudragits)). Alternatively, the delayed-release composition provides controlled release to the small intestine and/or colon by the provision of pH sensitive methacrylate coatings, pH sensitive polymeric microspheres, or polymers which undergo degradation by hydrolysis. The delayed-release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time-dependent hydrogel coatings and/or by acrylic acid linked to azoaromatic bonds coatings.

In certain embodiments, the delayed-release composition of the present invention comprises hypromellose, microcrystalline cellulose, and a lubricant. The mixture of a compound of the invention, hypromellose and microcrystalline cellulose can be formulated into a tablet or capsule for oral administration. In certain embodiments, the mixture is granulated and pressed into tablets.

Alternatively, pharmaceutically acceptable compositions of this invention can be administered in the form of suppositories for rectal administration. These can be prepared by mixing the compound of the invention with a suitable non-irritating excipient that is solid at room temperature but liquid at rectal temperature and, therefore, will melt in the rectum to release the drug. Such materials include cocoa butter, beeswax and polyethylene glycols.

Pharmaceutically acceptable compositions of this invention can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches can also be used.

For other topical applications, the pharmaceutically acceptable compositions of the invention can be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water and penetration enhancers. Alternatively, pharmaceutically acceptable compositions of the invention can be formulated in a suitable lotion or cream containing the active component suspended or dissolved in one or more pharmaceutically acceptable carriers. Alternatively, the pharmaceutical composition can be formulated with a suitable lotion or cream containing the active compound suspended or dissolved in a carrier with suitable emulsifying agents. In some embodiments, suitable carriers include, but are not limited to, mineral oil, sorbitan monostearate, polysorbate 60, cetyl esters wax, cetearyl alcohol, 2-octyldodecanol, benzyl alcohol and water. In other embodiments, suitable carriers include, but are not limited to, mineral oil, sorbitan monostearate, polysorbate 60, cetyl esters wax, cetearyl alcohol, 2-octyldodecanol, benzyl alcohol and water and penetration enhancers.

For ophthalmic use, pharmaceutically acceptable compositions of the invention can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions can be formulated in an ointment such as petrolatum.

Pharmaceutically acceptable compositions of this invention can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions of this invention are formulated for oral administration.

In some embodiments, pharmaceutically acceptable compositions of this invention are formulated for intra-peritoneal administration.

In some embodiments, pharmaceutically acceptable compositions of this invention are formulated for topical administration.

The amount of compounds of the present invention that can be combined with the carrier materials to produce a composition in a single dosage form will vary depending upon the host treated, the particular mode of administration and the activity of the compound employed. Preferably, compositions should be formulated so that a dosage of between 0.01-100 mg/kg body weight/day of the inhibitor can be administered to a patient receiving the composition.

It should also be understood that a specific dosage and treatment regimen for any particular patient will depend upon a variety of factors, including the activity of the specific compound employed, the age, body weight, general health, sex, diet, time of administration, rate of excretion, drug combination, the judgment of the treating physician and the severity of the particular disease being treated. The amount of a compound of the present invention in the composition will also depend upon the particular compound in the composition.

Other pharmaceutically acceptable carriers, adjuvants and vehicles that can be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be advantageously used to enhance delivery of compounds described herein.

The pharmaceutical compositions of this invention are preferably administered by oral administration or by injection. The pharmaceutical compositions of this invention can contain any conventional non-toxic pharmaceutically-acceptable carriers, adjuvants or vehicles. In some cases, the pH of the formulation can be adjusted with pharmaceutically acceptable acids, bases or buffers to enhance the stability of the formulated compound or its delivery form.

The pharmaceutical compositions can be in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agent(s) can be administered separately, as part of a multiple dose regimen, from the compounds of this invention. Alternatively, the additional agent(s) can be part of a single dosage form, mixed together with the compound of this invention in a single composition.

The compounds described herein can, for example, be administered by injection, intravenously, intraarterially, intraocularly, intravitreally, subdermallym, orally, buccally, nasally, transmucosally, topically, in an ophthalmic preparation, or by inhalation, with a dosage ranging from about 0.5 to about 100 mg/kg of body weight or, alternatively, in a dosage ranging from about 1 mg to about 1000 mg/dose, every 4 to 120 hours, or according to the requirements of the particular drug. The methods herein contemplate administration of an effective amount of a compound of the invention, or a composition thereof, to achieve the desired or stated effect. Typically, the pharmaceutical compositions of this invention will be administered from about 1 to about 6 times per day or, alternatively, as a continuous infusion. Such administration can be used as a chronic or acute therapy. The amount of active ingredient that can be combined with a carrier material to produce a single dosage form will vary depending upon the host treated and the particular mode of administration. A typical preparation will contain from about 5% to about 95% active compound (w/w). Alternatively, a preparation can contain from about 20% to about 80% active compound.

Doses lower or higher than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention can be administered, if necessary. Subsequently, the dosage or frequency of administration, or both, can be reduced, as a function of the symptoms, to a level at which the improved condition is retained when the symptoms have been alleviated to the desired level. Patients may, however, require intermittent treatment on a long-term basis upon recurrence of disease symptoms.

Uses of Compounds and Pharmaceutically Acceptable Compositions

As used herein, "PAK-mediated" disorder or condition means any disease or other deleterious condition in which one or more p21-activated kinases (PAK) plays a role. Accordingly, another embodiment of the present invention relates to treating, for example, lessening the severity of, a PAK-mediated disorder or condition. PAK-mediated disorders include cancer, neurodegenerative diseases and immune system diseases. Specific examples of PAK-mediated disorders are set forth in detail below.

P21-activated kinases (PAKs) can be classified into two groups: group I and group II. Group I comprises PAK1, PAK2 and PAK3, and group II comprises PAK4, PAK5 and PAK6. Some embodiments of the invention relate to treating a group I PAK-mediated disorder or condition, for example, a PAK1-mediated disorder or condition, a PAK2-mediated disorder or condition, a PAK3-mediated disorder or condition or a disorder or condition mediated by a combination of PAK1, PAK2, and PAK3, for example, a disorder or condition mediated by PAK1 and PAK2, PAK1 and PAK3, PAK2 and PAK3 or PAK1, PAK2 and PAK3. Other embodiments of the invention relate to treating a group II PAK-mediated disorder or condition, for example, a PAK4-mediated disorder or condition, a PAK5-mediated disorder or condition, a PAK6-mediated disorder or condition or a disorder or condition mediated by a combination of PAK4, PAK5 and PAK6, for example, a disorder or condition mediated by PAK4 and PAK5, PAK4 and PAK6, PAK5 and PAK6 or PAK4, PAK5 and PAK6.

When "PAK" is followed by a numeral, as in "PAK4", the particular PAK isoform corresponding to that numeral is being designated. Thus, as used herein, "PAK4-mediated" disorder or condition means any disease or other deleterious condition in which PAK4 is known to play a role. Accordingly, another embodiment of the present invention relates to treating, for example, lessening the severity of, a PAK4-mediated disorder or condition. PAK4-mediated disorders include cancer, neurodegenerative diseases and immune system diseases. Specific examples of PAK4-mediated disorders are set forth in detail below.

Compounds provided by this invention are also useful as tools, for example, to study PAK modulation in biological and pathological phenomena, to study cancer or for the identification and/or comparative evaluation of PAK modulators. Accordingly, in particular embodiments, the present invention provides a method for studying an effect of a compound described herein, or a salt or composition thereof, on a sample, the method comprising contacting a sample comprising cells in culture or one or more PAKs with the compound, or the salt or composition thereof, and measuring the effect of the compound, or salt or composition thereof, on the cells or the one or more PAKs. For example, the compounds described herein can be used as a standard or control substance in binding assays (e.g., competitive binding assays) to identify or evaluate potential PAK modulators or as a discovery tool to probe the role of PAK modulation in certain disorders or conditions, such as those described herein, including cancer and PAK-mediated disorders or conditions.

Modulation, for example, modulation of one or more PAKs, can be accomplished by ligands, particularly PAK ligands, that act as, for example, agonists, partial agonists, inverse agonists, antagonists or allosteric modulators (e.g., allosteric agonists, positive allosteric modulators, negative allosteric modulators). Agonists act directly to activate a receptor, whereas antagonists act indirectly to block receptor signaling by preventing agonist activity through their association with the receptor. Allosteric modulation occurs when a ligand binds at an allosteric site of a receptor, rather than at an orthosteric binding site. Allosteric modulators can include both positive and negative modulators of orthosteric ligand-mediated activity. Without being bound by a particular theory, it is believed that the compounds described herein can bind to one or more PAKs and function as allosteric modulators.

Compounds and compositions described herein are useful for treating cancer in a subject in need thereof. Thus, in certain embodiments, the present invention provides a method for treating cancer, comprising the step of administering to a patient in need thereof a compound of the present invention, or pharmaceutically acceptable salt or composition thereof. The compounds and compositions described herein can also be administered to cells in culture, e.g., in vitro or ex vivo, or to a subject, e.g., in vivo, to treat, prevent, and/or diagnose a variety of disorders, including those described herein below.

The activity of a compound utilized in this invention as an anti-cancer agent may be assayed in vitro, in vivo or in a cell line. Detailed conditions for assaying a compound utilized in this invention as an anti-cancer agent are set forth in the Exemplification.

As used herein, the term "treat" or "treatment" is defined as the application or administration of a compound, alone or in combination with a second compound, to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, in order to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder). In the case of wound healing, a therapeutically effective amount is an amount that promotes healing of a wound.

As used herein, "promoting wound healing" means treating a subject with a wound and achieving healing, either partially or fully, of the wound. Promoting wound healing can mean, e.g., one or more of the following: promoting epidermal closure; promoting migration of the dermis; promoting dermal closure in the dermis; reducing wound healing complications, e.g., hyperplasia of the epidermis and adhesions; reducing wound dehiscence; and promoting proper scab formation.

As used herein, an amount of a compound effective to treat a disorder, or a "therapeutically effective amount" refers to an amount of the compound which is effective, upon single or multiple dose administration to a subject or a cell, in curing, alleviating, relieving or improving one or more symptoms of a disorder. In the case of wound healing, a therapeutically effective amount is an amount that promotes healing of a wound.

As used herein, an amount of a compound effective to prevent a disorder, or a "prophylactically effective amount" of the compound refers to an amount effective, upon single- or multiple-dose administration to the subject, in preventing or delaying the onset or recurrence of a disorder or one or more symptoms of the disorder.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, cow, pig, etc., and companion animals (dog, cat, horse, etc.).

For example, provided herein are methods of treating various cancers in mammals (including humans and non-humans), comprising administering to a patient in need thereof a compound of the invention, or a pharmaceutically acceptable salt thereof. Such cancers include hematologic malignancies (leukemias, lymphomas, myelomas, myelodysplastic and myeloproliferative syndromes) and solid tumors (carcinomas such as oral, gall bladder, prostate, breast, lung, colon, pancreatic, renal, ovarian as well as soft tissue and osteo-sarcomas, and stromal tumors). Breast cancer (BC) can include basal-like breast cancer (BLBC), triple negative breast cancer (TNBC) and breast cancer that is both BLBC and TNBC. In addition, breast cancer can include invasive or non-invasive ductal or lobular carcinoma, tubular, medullary, mucinous, papillary, cribriform carcinoma of the breast, male breast cancer, recurrent or metastatic breast cancer, phyllodes tumor of the breast and Paget's disease of the nipple. In some embodiments, the present invention provides a method of treating lymphoma, specifically, mantle cell lymphoma.

In some embodiments, the present invention provides a method of treating inflammatory disorders in a patient, comprising administering to the patient a compound of the invention, or a pharmaceutically acceptable salt thereof. Inflammatory disorders treatable by the compounds of this invention include, but are not limited to, multiple sclerosis, rheumatoid arthritis, degenerative joint disease, systemic lupus, systemic sclerosis, vasculitis syndromes (small, medium and large vessel), atherosclerosis, inflammatory bowel disease, irritable bowel syndrome, Crohn's disease, mucous colitis, ulcerative colitis, gastritis, sepsis, psoriasis and other dermatological inflammatory disorders (such as eczema, atopic dermatitis, contact dermatitis, urticaria, scleroderma, and dermatosis with acute inflammatory components, pemphigus, pemphigoid, allergic dermatitis), and urticarial syndromes.

Viral diseases treatable by the compounds of this invention include, but are not limited to, acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster. Viral diseases treatable by the compounds of this invention also include chronic viral infections, including hepatitis B and hepatitis C.

Exemplary ophthalmology disorders include, but are not limited to, macular edema (diabetic and nondiabetic macular edema), aged related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epitheliitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency or cataract.

Neurodegenerative diseases treatable by a compound of Formula I include, but are not limited to, Parkinson's, Alzheimer's, and Huntington's, and Amyotrophic lateral sclerosis (ALS/Lou Gehrig's Disease).

Compounds and compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, polycystic kidney disorder (PKD) and other renal disorders.

Compounds and compositions described herein may also be used to treat disorders related to food intake such as obesity and hyperphagia.

In another embodiment, a compound or composition described herein may be used to treat or prevent allergies and respiratory disorders, including asthma, bronchitis, pulmonary fibrosis, allergic rhinitis, oxygen toxicity, emphysema, chronic bronchitis, acute respiratory distress syndrome, and any chronic obstructive pulmonary disease (COPD).

Other disorders treatable by the compounds and compositions described herein include muscular dystrophy, arthritis, for example, osteoarthritis and rheumatoid arthritis, ankylosing spondilitis, traumatic brain injury, spinal cord injury, sepsis, rheumatic disease, cancer atherosclerosis, type 1 diabetes, type 2 diabetes, leptospiriosis renal disease, glaucoma, retinal disease, ageing, headache, pain, complex regional pain syndrome, cardiac hypertrophy, musclewasting, catabolic disorders, obesity, fetal growth retardation, hypercholesterolemia, heart disease, chronic heart failure, ischemia/reperfusion, stroke, cerebral aneurysm, angina pectoris, pulmonary disease, cystic fibrosis, acid-induced lung injury, pulmonary hypertension, asthma, chronic obstructive pulmonary disease, Sjogren's syndrome, hyaline membrane disease, kidney disease, glomerular disease, alcoholic liver disease, gut diseases, peritoneal endometriosis, skin diseases, nasal sinusitis, mesothelioma, anhidrotic ecodermal dysplasia-ID, behcet's disease, incontinentia pigmenti, tuberculosis, asthma, crohn's disease, colitis, ocular allergy, appendicitis, paget's disease, pancreatitis, periodontitis, endometriosis, inflammatory bowel disease, inflammatory lung disease, silica-induced diseases, sleep apnea, AIDS, HIV-1, autoimmune diseases, antiphospholipid syndrome, lupus, lupus nephritis, familial mediterranean fever, hereditary periodic fever syndrome, psychosocial stress diseases, neuropathological diseases, familial amyloidotic polyneuropathy, inflammatory neuropathy, parkinson's disease, multiple sclerosis, alzheimer's disease, amyotropic lateral sclerosis, huntington's disease, cataracts, or hearing loss.

Yet other disorders treatable by the compounds and compositions described herein include head injury, uveitis, inflammatory pain, allergen induced asthma, non-allergen induced asthma, glomerular nephritis, ulcerative colitis, necrotizing enterocolitis, hyperimmunoglobulinemia D with recurrent fever (HIDS), TNF receptor associated periodic syndrome (TRAPS), cryopyrin-associated periodic syndromes, Muckle-Wells syndrome (urticaria deafness amyloidosis), familial cold urticaria, neonatal onset multisystem inflammatory disease (NOMID), periodic fever, aphthous stomatitis, pharyngitis and adenitis (PFAPA syndrome), Blau syndrome, pyogenic sterile arthritis, pyoderma gangrenosum, acne (PAPA), deficiency of the interleukin-1-receptor antagonist (DIRA), subarachnoid hemorrhage, polycystic kidney disease, transplant, organ transplant, tissue transplant, myelodysplastic syndrome, irritant-induced inflammation, plant irritant-induced inflammation, poison ivy/urushiol oil-induced inflammation, chemical irritant-induced inflammation, bee sting-induced inflammation, insect bite-induced inflammation, sunburn, burns, dermatitis, endotoxemia, lung injury, acute respiratory distress syndrome, alcoholic hepatitis, or kidney injury caused by parasitic infections.

Yet another disorder treatable by the compounds and compositions described herein is schizophrenia.

In further aspects, the present invention provides a use of a compound of the invention, or a pharmaceutically acceptable salt thereof, for the manufacture of a medicament for the treatment of cancer. In some embodiments, the present invention provides a use of a compound of the invention in the manufacture of a medicament for the treatment of any of cancer and/or neoplastic disorders, angiogenesis, autoimmune disorders, inflammatory disorders and/or diseases, epigenetics, hormonal disorders and/or diseases, viral diseases, neurodegenerative disorders and/or diseases, wounds, and ophthamalogic disorders.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders, e.g., tumors arising from prostate, brain, bone, colon, lung, breast, ovarian, and liver origin, hematopoietic neoplastic disorders, e.g., leukemias, lymphomas, myeloma and other malignant plasma cell disorders, and metastatic tumors. Prevalent cancers include: breast, prostate, colon, lung, liver, and pancreatic cancers. Treatment with the compound can be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof, as well as in familial cancer syndromes such as Li Fraumeni Syndrome, Familial Breast-Ovarian Cancer (BRCA1 or BRAC2 mutations) Syndromes, and others. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Exemplary cancers described by the National Cancer Institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Mantle Cell Lymphoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Further exemplary cancers include diffuse large B-cell lymphoma (DLBCL), mantle cell lymphoma (MCL) and serous and endometrioid cancer. Yet a further exemplary cancer is alveolar soft part sarcoma.

Further exemplary cancers include diffuse large B-cell lymphoma (DLBCL) and mantle cell lymphoma (MCL). Yet further exemplary cancers include endocervical cancer, B-cell ALL, T-cell ALL, B- or T-cell lymphoma, mast cell cancer, glioblastoma, neuroblastoma, follicular lymphoma and Richter's syndrome. Yet further exemplary cancers include glioma.

Metastases of the aforementioned cancers can also be treated or prevented in accordance with the methods described herein.

Combination Therapies

In some embodiments, a compound described herein is administered together with an additional "second" therapeutic agent or treatment. The choice of second therapeutic agent may be made from any agent that is typically used in a monotherapy to treat the indicated disease or condition. As used herein, the term "administered together" and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of any of the formulas described herein, an additional therapeutic agent, and a pharmaceutically acceptable carrier, adjuvant, or vehicle.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art. The additional agents may be administered separately, as part of a multiple dose regimen, from the compounds of this invention. Alternatively, those agents may be part of a single dosage form, mixed together with the compounds of this invention in a single composition.

Cancer Combination Therapies

In some embodiments, a compound described herein is administered together with an additional cancer treatment. Exemplary cancer treatments include, for example, chemotherapy, targeted therapies such as antibody therapies, kinase inhibitors, immunotherapy, and hormonal therapy, and anti-angiogenic therapies. Examples of each of these treatments are provided below.

As used herein, the term "combination," "combined," and related terms refer to the simultaneous or sequential administration of therapeutic agents in accordance with this invention. For example, a compound of the present invention can be administered with another therapeutic agent simultaneously or sequentially in separate unit dosage forms or together in a single unit dosage form. Accordingly, the present invention provides a single unit dosage form comprising a compound of the invention, an additional therapeutic agent, and a pharmaceutically acceptable carrier, adjuvant, or vehicle.

The amount of both a compound of the invention and additional therapeutic agent (in those compositions which comprise an additional therapeutic agent as described above) that can be combined with the carrier materials to produce a single dosage form will vary depending upon the host treated and the particular mode of administration. Preferably, compositions of this invention should be formulated so that a dosage of between 0.01-100 mg/kg body weight/day of a compound of the invention can be administered.

Chemotherapy

In some embodiments, a compound described herein is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, topoisomerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, Bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafururacil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

Targeted therapy constitutes the use of agents specific for the deregulated proteins of cancer cells. Small molecule targeted therapy drugs are generally inhibitors of enzymatic domains on mutated, overexpressed, or otherwise critical proteins within a cancer cell. Prominent examples are the tyrosine kinase inhibitors such as axitinib, bosutinib, cediranib, desatinib, erolotinib, imatinib, gefitinib, lapatinib, lestaurtinib, nilotinib, semaxanib, sorafenib, sunitinib, and vandetanib, and also cyclin-dependent kinase inhibitors such as alvocidib and seliciclib. Monoclonal antibody therapy is another strategy in which the therapeutic agent is an antibody which specifically binds to a protein on the surface of the cancer cells. Examples include the anti-HER2/neu antibody trastuzumab (Herceptin®) typically used in breast cancer, and the anti-CD20 antibody rituximab and tositumomab typically used in a variety of B-cell malignancies. Other exemplary antibodies include cetuximab, panitumumab, trastuzumab, alemtuzumab, bevacizumab, edrecolomab, and gemtuzumab. Exemplary fusion proteins include aflibercept and denileukin diftitox. In some embodiments, targeted therapy can be used in combination with a compound described herein, e.g, Gleevec (Vignari and Wang 2001).

Targeted therapy can also involve small peptides as "homing devices" which can bind to cell surface receptors or affected extracellular matrix surrounding a tumor. Radionuclides which are attached to these peptides (e.g., RGDs) eventually kill the cancer cell if the nuclide decays in the vicinity of the cell. An example of such therapy includes BEXXAR®.

Angiogenesis

Compounds and methods described herein may be used to treat or prevent a disease or disorder associated with angiogenesis. Diseases associated with angiogenesis include cancer, cardiovascular disease and macular degeneration.

Angiogenesis is the physiological process involving the growth of new blood vessels from pre-existing vessels. Angiogenesis is a normal and vital process in growth and development, as well as in wound healing and in granulation tissue. However, it is also a fundamental step in the transition of tumors from a dormant state to a malignant one. Angiogenesis may be a target for combating diseases characterized by either poor vascularisation or abnormal vasculature.

Application of specific compounds that may inhibit or induce the creation of new blood vessels in the body may help combat such diseases. The presence of blood vessels where there should be none may affect the mechanical properties of a tissue, increasing the likelihood of failure. The absence of blood vessels in a repairing or otherwise metabolically active tissue may inhibit repair or other essential functions. Several diseases, such as ischemic chronic wounds, are the result of failure or insufficient blood vessel formation and may be treated by a local expansion of blood vessels, thus bringing new nutrients to the site, facilitating repair. Other diseases, such as age-related macular degeneration, may be created by a local expansion of blood vessels, interfering with normal physiological processes.

Vascular endothelial growth factor (VEGF) has been demonstrated to be a major contributor to angiogenesis, increasing the number of capillaries in a given network. Upregulation of VEGF is a major component of the physiological response to exercise and its role in angiogenesis is suspected to be a possible treatment in vascular injuries. In vitro studies clearly demonstrate that VEGF is a potent stimulator of angiogenesis because, in the presence of this growth factor, plated endothelial cells will proliferate and migrate, eventually forming tube structures resembling capillaries.

Tumors induce blood vessel growth (angiogenesis) by secreting various growth factors (e.g., VEGF). Growth factors such as bFGF and VEGF can induce capillary growth into the tumor, which some researchers suspect supply required nutrients, allowing for tumor expansion.

Angiogenesis represents an excellent therapeutic target for the treatment of cardiovascular disease. It is a potent, physiological process that underlies the natural manner in which our bodies respond to a diminution of blood supply to vital organs, namely the production of new collateral vessels to overcome the ischemic insult.

Overexpression of VEGF causes increased permeability in blood vessels in addition to stimulating angiogenesis. In wet macular degeneration, VEGF causes proliferation of capillaries into the retina. Since the increase in angiogenesis also causes edema, blood and other retinal fluids leak into the retina, causing loss of vision.

Anti-angiogenic therapy can include kinase inhibitors targeting vascular endothelial growth factor (VEGF) such as sunitinib, sorafenib, or monoclonal antibodies or receptor "decoys" to VEGF or VEGF receptor including bevacizumab or VEGF-Trap, or thalidomide or its analogs (lenalidomide, pomalidomide), or agents targeting non-VEGF angiogenic targets such as fibroblast growth factor (FGF), angiopoietins, or angiostatin or endostatin.

Epigenetics

Compounds and methods described herein may be used to treat or prevent a disease or disorder associated with epigenetics. Epigenetics is the study of heritable changes in phenotype or gene expression caused by mechanisms other than changes in the underlying DNA sequence. One example of epigenetic changes in eukaryotic biology is the process of cellular differentiation. During morphogenesis, stem cells become the various cell lines of the embryo which in turn become fully differentiated cells. In other words, a single fertilized egg cell changes into the many cell types including neurons, muscle cells, epithelium, blood vessels etc. as it continues to divide. It does so by activating some genes while inhibiting others.

Epigenetic changes are preserved when cells divide. Most epigenetic changes only occur within the course of one individual organism's lifetime, but, if a mutation in the DNA has been caused in sperm or egg cell that results in fertilization, then some epigenetic changes are inherited from one generation to the next. Specific epigenetic processes include paramutation, bookmarking, imprinting, gene silencing, X chromosome inactivation, position effect, reprogramming, transvection, maternal effects, the progress of carcinogenesis, many effects of teratogens, regulation of histone modifications and heterochromatin, and technical limitations affecting parthenogenesis and cloning.

Exemplary diseases associated with epigenetics include ATR-syndrome, fragile X-syndrome, ICF syndrome, Angelman's syndrome, Prader-Wills syndrome, BWS, Rett syndrome, α-thalassaemia, cancer, leukemia, Rubinstein-Taybi syndrome and Coffin-Lowry syndrome.

The first human disease to be linked to epigenetics was cancer. Researchers found that diseased tissue from patients with colorectal cancer had less DNA methylation than normal tissue from the same patients. Because methylated genes are typically turned off, loss of DNA methylation can cause abnormally high gene activation by altering the arrangement of chromatin. On the other hand, too much methylation can undo the work of protective tumor suppressor genes.

DNA methylation occurs at CpG sites, and a majority of CpG cytosines are methylated in mammals. However, there are stretches of DNA near promoter regions that have higher concentrations of CpG sites (known as CpG islands) that are free of methylation in normal cells. These CpG islands become excessively methylated in cancer cells, thereby causing genes that should not be silenced to turn off. This abnormality is the trademark epigenetic change that occurs in tumors and happens early in the development of cancer. Hypermethylation of CpG islands can cause tumors by shutting off tumor-suppressor genes. In fact, these types of changes may be more common in human cancer than DNA sequence mutations.

Furthermore, although epigenetic changes do not alter the sequence of DNA, they can cause mutations. About half of the genes that cause familial or inherited forms of cancer are turned off by methylation. Most of these genes normally suppress tumor formation and help repair DNA, including 06-methylguanine-DNA methyltransferase (MGMT), MLH1 cyclin-dependent kinase inhibitor 2B (CDKN2B), and RASSF1A. For example, hypermethylation of the promoter of MGMT causes the number of G-to-A mutations to increase.

Hypermethylation can also lead to instability of microsatellites, which are repeated sequences of DNA. Microsatellites are common in normal individuals, and they usually consist of repeats of the dinucleotide CA. Too much methylation of the promoter of the DNA repair gene MLH1 can make a microsatellite unstable and lengthen or shorten it. Microsatellite instability has been linked to many cancers, including colorectal, endometrial, ovarian, and gastric cancers.

Fragile X syndrome is the most frequently inherited mental disability, particularly in males. Both sexes can be affected by this condition, but because males only have one X chromosome, one fragile X will impact them more severely. Indeed, fragile X syndrome occurs in approximately 1 in 4,000 males and 1 in 8,000 females. People with this syndrome have severe intellectual disabilities, delayed verbal development, and "autistic-like" behavior.

Fragile X syndrome gets its name from the way the part of the X chromosome that contains the gene abnormality looks under a microscope; it usually appears as if it is hanging by a thread and easily breakable. The syndrome is caused by an abnormality in the FMR1 (fragile X mental retardation 1) gene. People who do not have fragile X syndrome have 6 to 50 repeats of the trinucleotide CGG in their FMR1 gene. However, individuals with over 200 repeats have a full mutation, and they usually show symptoms of the syndrome. Too many CGGs cause the CpG islands at the promoter region of the FMR1 gene to become methylated; normally, they are not. This methylation turns the gene off, stopping the FMR1 gene from producing an important protein called fragile X mental retardation protein. Loss of this specific protein causes fragile X syndrome. Although a lot of attention has been given to the CGG expansion mutation as the cause of fragile X, the epigenetic change associated with FMR1 methylation is the real syndrome culprit.

Fragile X syndrome is not the only disorder associated with mental retardation that involves epigenetic changes. Other such conditions include Rubenstein-Taybi, Coffin-Lowry, Prader-Willi, Angelman, Beckwith-Wiedemann, ATR-X, and Rett syndromes.

Epigenetic therapies include inhibitors of enzymes controlling epigenetic modifications, specifically DNA methyltransferases and histone deacetylases, which have shown promising anti-tumorigenic effects for some malignancies, as well as antisense oligonucloetides and siRNA.

Immunotherapy

In some embodiments, a compound described herein is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, prostate cancer vaccine Provenge, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with a hormonal therapy. The growth of some cancers can be inhibited by providing or blocking certain hormones. Common examples of hormone-sensitive tumors include certain types of breast and prostate cancers, as well as certain types of leukemia which respond to certain retinoids/retinoic acids. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Hormonal therapy agents include the administration of hormone agonists or hormone antagonists and include retinoids/retinoic acid, compounds that inhibit estrogen or testosterone, as well as administration of progestogens.

Inflammation and Autoimmune Disease

The compounds and methods described herein may be used to treat or prevent a disease or disorder associated with inflammation, particularly in humans and other mammals. A compound described herein may be administered prior to the onset of, at, or after the initiation of inflammation. When used prophylactically, the compounds are preferably provided in advance of any inflammatory response or symptom. Administration of the compounds can prevent or attenuate inflammatory responses or symptoms. Exemplary inflammatory conditions include, for example, multiple sclerosis, rheumatoid arthritis, psoriatic arthritis, degenerative joint disease, spondouloarthropathies, other seronegative inflammatory arthridities, polymyalgia rheumatica, various vasculidities (e.g., giant cell arteritis, ANCA+ vasculitis), gouty arthritis, systemic lupus erythematosus, juvenile arthritis, juvenile rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, schleroderma, psoriasis, and dermatosis with acute inflammatory components.

In another embodiment, a compound or method described herein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, a compound or method described herein may be used to treat autoimmune diseases and/or inflammation associated with autoimmune diseases, such as organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

In a particular embodiment, the compounds described herein can be used to treat multiple sclerosis.

Combination Therapy

In certain embodiments, a compound described herein may be administered alone or in combination with other compounds useful for treating or preventing inflammation. Exemplary anti-inflammatory agents include, for example, steroids (e.g., Cortisol, cortisone, fludrocortisone, prednisone, 6[alpha]-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other compound is drotrecogin alfa.

Further examples of anti-inflammatory agents include, for example, aceclofenac, acemetacin, e-acetamidocaproic acid, acetaminophen, acetaminosalol, acetanilide, acetylsalicylic acid, S-adenosylmethionine, alclofenac, alclometasone, alfentanil, algestone, allylprodine, alminoprofen, aloxiprin, alphaprodine, aluminum bis(acetylsalicylate), amcinonide, amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antrafenine, apazone, beclomethasone, bendazac, benorylate, benoxaprofen, benzpiperylon, benzydamine, benzylmorphine, bermoprofen, betamethasone, betamethasone-17-valerate, bezitramide, [alpha]-bisabolol, bromfenac, p-bromoacetanilide, 5-bromosalicylic acid acetate, bromosaligenin, bucetin, bucloxic acid, bucolome, budesonide, bufexamac, bumadizon, buprenorphine, butacetin, butibufen, butorphanol, carbamazepine, carbiphene, caiprofen, carsalam, chlorobutanol, chloroprednisone, chlorthenoxazin, choline salicylate, cinchophen, cinmetacin, ciramadol, clidanac, clobetasol, clocortolone, clometacin, clonitazene, clonixin, clopirac, cloprednol, clove, codeine, codeine methyl bromide, codeine phosphate, codeine sulfate, cortisone, cortivazol, cropropamide, crotethamide, cyclazocine, deflazacort, dehydrotestosterone, desomorphine, desonide, desoximetasone, dexamethasone, dexamethasone-21-isonicotinate, dexoxadrol, dextromoramide, dextropropoxyphene, deoxycorticosterone, dezocine, diampromide, diamorphone, diclofenac, difenamizole, difenpiramide, diflorasone, diflucortolone, diflunisal, difluprednate, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, enoxolone, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, fluazacort, flucloronide, flufenamic acid, flumethasone, flunisolide, flunixin, flunoxaprofen, fluocinolone acetonide, fluocinonide, fluocinolone acetonide, fluocortin butyl, fluocoitolone, fluoresone, fluorometholone, fluperolone, flupirtine, fluprednidene, fluprednisolone, fluproquazone, flurandrenolide, flurbiprofen, fluticasone, formocortal, fosfosal, gentisic acid, glafenine, glucametacin, glycol salicylate, guaiazulene, halcinonide, halobetasol, halometasone, haloprednone, heroin, hydrocodone, hydro cortamate, hydrocortisone, hydrocortisone acetate, hydrocortisone succinate, hydrocortisone hemisuccinate, hydrocortisone 21-lysinate, hydrocortisone cypionate, hydromorphone, hydroxypethidine, ibufenac, ibuprofen, ibuproxam, imidazole salicylate, indomethacin, indoprofen, isofezolac, isoflupredone, isoflupredone acetate, isoladol, isomethadone, isonixin, isoxepac, isoxicam, ketobemidone, ketoprofen, ketorolac, p-lactophenetide, lefetamine, levallorphan, levorphanol, levophenacylmorphan, lofentanil, lonazolac, lomoxicam, loxoprofen, lysine acetylsalicylate, mazipredone, meclofenamic acid, medrysone, mefenamic acid, meloxicam, meperidine, meprednisone, meptazinol, mesalamine, metazocine, methadone, methotrimeprazine, methylprednisolone, methylprednisolone acetate, methylprednisolone sodium succinate, methylprednisolone suleptnate, metiazinic acid, metofoline, metopon, mofebutazone, mofezolac, mometasone, morazone, morphine, morphine hydrochloride, morphine sulfate, morpholine salicylate, myrophine, nabumetone, nalbuphine, nalorphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paramethasone, paranyline, parsalmide, pentazocine, perisoxal, phenacetin, phenadoxone, phenazocine, phenazopyridine hydrochloride, phenocoll, phenoperidine, phenopyrazone, phenomorphan, phenyl acetylsalicylate, phenylbutazone, phenyl salicylate, phenyramidol, piketoprofen, piminodine, pipebuzone, piperylone, pirazolac, piritramide, piroxicam, pirprofen, pranoprofen, prednicarbate, prednisolone, prednisone, prednival, prednylidene, proglumetacin, proheptazine, promedol, propacetamol, properidine, propiram, propoxyphene, propyphenazone, proquazone, protizinic acid, proxazole, ramifenazone, remifentanil, rimazolium metilsulfate, salacetamide, salicin, salicylamide, salicylamide o-acetic acid, salicylic acid, salicylsulfuric acid, salsalate, salverine, simetride, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tixocortol, tolfenamic acid, tolmetin, tramadol, triamcinolone, triamcinolone acetonide, tropesin, viminol, xenbucin, ximoprofen, zaltoprofen and zomepirac.

In one embodiment, a compound described herein may be administered with a selective COX-2 inhibitor for treating or preventing inflammation. Exemplary selective COX-2 inhibitors include, for example, deracoxib, parecoxib, celecoxib, valdecoxib, rofecoxib, etoricoxib, and lumiracoxib.

In some embodiments, a provided compound is administered in combination with an anthracycline or a Topo II inhibitor. In certain embodiments, a provided compound is administered in combination with Doxorubicin (Dox). In certain embodiments, a provided compound is administered in combination with bortezomib (and more broadly including carfilzomib). It was surprisingly found that a provided compound in combination with Dox or bortezomib resulted in a synergystic effect (i.e., more than additive).

Viral Infections

Compounds and methods described herein may be used to treat or prevent a disease or disorder associated with a viral infection, particularly in humans and other mammals. A compound described herein may be administered prior to the onset of, at, or after the initiation of viral infection. When used prophylactically, the compounds are preferably provided in advance of any viral infection or symptom thereof.

Exemplary viral diseases include acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster.

Exemplary viral pathogens include Adenovirus, Coxsackievirus, Dengue virus, Encephalitis Virus, Epstein-Barr virus, Hepatitis A virus, Hepatitis B virus, Hepatitis C virus, Herpes simplex virus type 1, Herpes simplex virus type 2, cytomegalovirus, Human herpesvirus type 8, Human immunodeficiency virus, Influenza virus, measles virus, Mumps virus, Human papillomavirus, Parainfluenza virus, Poliovirus, Rabies virus, Respiratory syncytial virus, Rubella virus, Varicella-zoster virus, West Nile virus, Dungee, and Yellow fever virus. Viral pathogens may also include viruses that cause resistant viral infections.

Antiviral drugs are a class of medications used specifically for treating viral infections. Antiviral action generally falls into one of three mechanisms: interference with the ability of a virus to infiltrate a target cell (e.g., amantadine, rimantadine and pleconaril), inhibition of the synthesis of virus (e.g., nucleoside analogues, e.g., acyclovir and zidovudine (AZT), and inhibition of the release of virus (e.g., zanamivir and oseltamivir).

In some embodiments, the viral pathogen is selected from the group consisting of herpesviridae, flaviviridae, bunyaviridae, arenaviridae, picomaviridae, togaviridae, papovaviridae, poxviridae, respiratory viruses, hepatic viruses, and other viruses.

Exemplary herpesviridae include herpes simplex virus-1; herpes simplex virus-2; cytomegalovirus, for example, human cytomegalovirus; Varicella-Zoster virus; Epstein-Barr virus; herpes virus-6, for example, human herpes virus-6; and herpes virus-8, for example, human herpes virus-8.

Exemplary flaviviridae include Dengue virus, West Nile virus, yellow fever virus, Japanese encephalitis virus, and Powassen virus.

Exemplary bunyaviridae include Rift Valley fever virus, Punta Toro virus, LaCrosse virus, and Marporal virus.

Exemplary arenaviridae include Tacaribe virus, Pinchinde virus, Junin virus, and Lassa fever virus.

Exemplary picomaviridae include polio virus; enterovirus, for example, enterovirus-71; and Coxsackie virus, for example, Coxsackie virus B3.

Exemplary togaviridae include encephalitis virus, for example, Venezuelan equine encephalitis virus, Eastern equine encephalitis virus, and Western equine encephalitis virus; and Chikungunya virus.

Exemplary papoviridae include BK virus, JC virus, and papillomavirus.

Exemplary poxviridae include vaccinia virus, cowpox virus, and monkeypox virus.

Exemplary respiratory viruses include SARS coronavirus; influenza A virus, for dexample, H1N1 virus; and respiratory syncytial virus.

Exemplary hepatic viruses include hepatitis B and hepatitis C viruses.

Exemplary other viruses include adenovirus, for example, adenovirus-5; rabies virus; measles virus; ebola virus; nipah virus; and norovirus.

Ophthalmology

Compounds and methods described herein may be used to treat or prevent an ophthalmology disorder. Exemplary ophthalmology disorders include macular edema (diabetic and nondiabetic macular edema), age related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency and cataract.

Other ophthalmology disorders treatable using the compounds and methods described herein include proliferative vitreoretinopathy and chronic retinal detachment.

Inflammatory eye diseases are also treatable using the compounds and methods described herein.

Neurodegenerative Disease

Neurodegeneration is the umbrella term for the progressive loss of structure or function of neurons, including death of neurons. Many neurodegenerative diseases including Parkinson's, Alzheimer's, and Huntington's occur as a result of neurodegenerative processes. As research progresses, many similarities appear which relate these diseases to one another on a sub-cellular level. Discovering these similarities offers hope for therapeutic advances that could ameliorate many diseases simultaneously. There are many parallels between different neurodegenerative disorders including atypical protein assemblies as well as induced cell death.

Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus.

Huntington's disease causes astrogliosis and loss of medium spiny neurons. Areas of the brain are affected according to their structure and the types of neurons they contain, reducing in size as they cumulatively lose cells. The areas affected are mainly in the striatum, but also the frontal and temporal cortices. The striatum's subthalamic nuclei send control signals to the globus pallidus, which initiates and modulates motion. The weaker signals from subthalamic nuclei thus cause reduced initiation and modulation of movement, resulting in the characteristic movements of the disorder. Exemplary treatments for Huntington's disease include tetrabenazine, neuroleptics, benzodiazepines, amantadine, remacemide, valproic acid, selective serotonin reuptake inhibitors (SSRIs), mirtazapine and antipsychotics.

The mechanism by which the brain cells in Parkinson's are lost may consist of an abnormal accumulation of the protein alpha-synuclein bound to ubiquitin in the damaged cells. The alpha-synuclein-ubiquitin complex cannot be directed to the proteosome. This protein accumulation forms proteinaceous cytoplasmic inclusions called Lewy bodies. The latest research on pathogenesis of disease has shown that the death of dopaminergic neurons by alpha-synuclein is due to a defect in the machinery that transports proteins between two major cellular organelles—the endoplasmic reticulum (ER) and the Golgi apparatus. Certain proteins like Rabl may reverse this defect caused by alpha-synuclein in animal models. Exemplary Parkinson's disease therapies include levodopa, dopamine agonists such as include bromocriptine, pergolide, pramipexole, ropinirole, piribedil, cabergoline, apomorphine and lisuride, dopa decarboxylate inhibitors, MAO-B inhibitors such as selegilene and rasagilene, anticholinergics and amantadine.

Amyotrophic lateral sclerosis (ALS/Lou Gehrig's Disease) is a disease in which motor neurons are selectively targeted for degeneration. Exemplary ALS therapies include riluzole, baclofen, diazepam, trihexyphenidyl and amitriptyline.

Other exemplary neurodegenerative therapeutics include antisense oligonucleotides and stem cells.

Wound Healing

Wounds are a type of condition characterized by cell or tissue damage. Wound healing is a dynamic pathway that optimally leads to restoration of tissue integrity and function. The wound healing process consists of three overlapping phases. The first phase is an inflammatory phase, which is characterized by homeostasis, platelet aggregation and degranulation. Platelets as the first response, release multiple growth factors to recruit immune cells, epithelial cells, and endothelial cells. The inflammatory phase typically occurs over days 0-5. The second stage of wound healing is the proliferative phase during which macrophages and granulocytes invade the wound. Infiltrating fibroblasts begin to produce collagen. The principle characteristics of this phase are epithelialization, angiogenesis, granulation tissue formation and collagen production. The proliferative phase typically occurs over days 3-14. The third phase is the remodeling phase where matrix formation occurs. The fibroblasts, epithelial cells, and endothelial cells continue to produce collagen and collagenase as well as matrix metalloproteases (MMPs) for remodeling. Collagen crosslinking takes place and the wound undergoes contraction. The remodeling phase typically occurs from day 7 to one year.

Compounds and compositions described herein can be used for promoting wound healing (e.g., promoting or accelerating wound closure and/or wound healing, mitigating scar fibrosis of the tissue of and/or around the wound, inhibiting apoptosis of cells surrounding or proximate to the wound). Thus, in certain embodiments, the present invention provides a method for promoting wound healing in a subject, comprising administering to the subject a therapeutically effective amount of a compound (e.g., a CRM1 inhibitor), or pharmaceutically acceptable salt or composition thereof. The method need not achieve complete healing or closure of the wound; it is sufficient for the method to promote any degree of wound closure. In this respect, the method can be employed alone or as an adjunct to other methods for healing wounded tissue.

The compounds and compositions described herein can be used to treat wounds during the inflammatory (or early) phase, during the proliferative (or middle) wound healing phase, and/or during the remodeling (or late) wound healing phase.

In some embodiments, the subject in need of wound healing is a human or an animal, for example, a dog, a cat, a horse, a pig, or a rodent, such as a mouse.

In some embodiments, the compounds and compositions described herein useful for wound healing are administered topically, for example, proximate to the wound site, or systemically.

More specifically, a therapeutically effective amount of a compound or composition described herein can be administered (optionally in combination with other agents) to the wound site by coating the wound or applying a bandage, packing material, stitches, etc., that are coated or treated with the compound or composition described herein. As such, the compounds and compositions described herein can be formulated for topical administration to treat surface wounds. Topical formulations include those for delivery via the mouth (buccal) and to the skin such that a layer of skin (i.e., the epidermis, dermis, and/or subcutaneous layer) is contacted with the compound or composition described herein. Topical delivery systems may be used to administer topical formulations of the compounds and compositions described herein.

Alternatively, the compounds and compositions described herein can be administered at or near the wound site by, for example, injection of a solution, injection of an extended release formulation, or introduction of a biodegradable implant comprising the compound or composition described herein.

The compounds and compositions described herein can be used to treat acute wounds or chronic wounds. A chronic wound results when the normal reparative process is interrupted. Chronic wounds can develop from acute injuries as a result of unrecognized persistent infections or inadequate primary treatment. In most cases however, chronic lesions are the end stage of progressive tissue breakdown owing to venous, arterial, or metabolic vascular disease, pressure sores, radiation damage, or tumors.

In chronic wounds, healing does not occur for a variety of reasons, including improper circulation in diabetic ulcers, significant necrosis, such as in burns, and infections. In these chronic wounds, viability or the recovery phase is often the rate-limiting step. The cells are no longer viable and, thus, initial recovery phase is prolonged by unfavorable wound bed environment.

Chronic wounds include, but are not limited to the following: chronic ischemic skin lesions; scleroderma ulcers; arterial ulcers; diabetic foot ulcers; pressure ulcers; venous ulcers; non-healing lower extremity wounds; ulcers due to inflammatory conditions; and/or long-standing wounds. Other examples of chronic wounds include chronic ulcers, diabetic wounds, wounds caused by diabetic neuropathy, venous insufficiencies, and arterial insufficiencies, and pressure wounds and cold and warm burns. Yet other examples of chronic wounds include chronic ulcers, diabetic wounds, wounds caused by diabetic neuropathy, venous insufficiencies, arterial insufficiencies, and pressure wounds.

Acute wounds include, but are not limited to, post-surgical wounds, lacerations, hemorrhoids and fissures.

In a particular embodiment, the compounds and compositions described herein can be used for diabetic wound healing or accelerating healing of leg and foot ulcers secondary to diabetes or ischemia in a subject.

In one embodiment, the wound is a surface wound. In another embodiment, the wound is a surgical wound (e.g., abdominal or gastrointestinal surgical wound). In a further embodiment, the wound is a burn. In yet another embodiment, the wound is the result of radiation exposure.

The compounds and compositions described herein can also be used for diabetic wound healing, gastrointestinal wound healing, or healing of an adhesion due, for example, to an operation.

The compounds and compositions described herein can also be used to heal wounds that are secondary to another disease. For example, in inflammatory skin diseases, such as psoriasis and dermatitis, there are numerous incidents of skin lesions that are secondary to the disease, and are caused by deep cracking of the skin, or scratching of the skin. The compounds and compositions described herein can be used to heal wounds that are secondary to these diseases, for example, inflammatory skin diseases, such as psoriasis and dermatitis.

In a further embodiment, the wound is an internal wound. In a specific aspect, the internal wound is a chronic wound. In another specific aspect, the wound is a vascular wound. In yet another specific aspect, the internal wound is an ulcer. Examples of internal wounds include, but are not limited to, fistulas and internal wounds associated with cosmetic surgery, internal indications, Crohn's disease, ulcerative colitis, internal surgical sutures and skeletal fixation. Other examples of internal wounds include, but are not limited to, fistulas and internal wounds associated with cosmetic surgery, internal indications, internal surgical sutures and skeletal fixation.

Examples of wounds include, but are not limited to, abrasions, avulsions, blowing wounds (i.e., open pneumothorax), burn wounds, contusions, gunshot wounds, incised wounds, open wounds, penetrating wounds, perforating wounds, puncture wounds, séton wounds, stab wounds, surgical wounds, subcutaneous wounds, diabetic lesions, or tangential wounds. Additional examples of wounds that can be treated by the compounds and compositions described herein include acute conditions or wounds, such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies; trauma-induced injuries including cuts, incisions, excoriations; injuries sustained from accidents; post-surgical injuries, as well as chronic conditions, such as pressure sores, bedsores, conditions related to diabetes and poor circulation, and all types of acne. In addition, the wound can include dermatitis, such as impetigo, intertrigo, folliculitis and eczema, wounds following dental surgery; periodontal disease; wounds following trauma; and tumor-associated wounds. Yet other examples of wounds include animal bites, arterial disease, insect stings and bites, bone infections, compromised skin/muscle grafts, gangrene, skin tears or lacerations, skin aging, surgical incisions, including slow or non-healing surgical wounds, intracerebral hemorrhage, aneurysm, dermal asthenia, and post-operation infections.

In preferred embodiments, the wound is selected from the group consisting of a burn wound, an incised wound, an open wound, a surgical or post surgical wound, a diabetic lesion, a thermal burn, a chemical burn, a radiation burn, a pressure sore, a bedsore, and a condition related to diabetes or poor circulation. In more preferred embodiments, the wound is selected from the group consisting of an incised wound, an open wound, a surgical or post surgical wound, a diabetic lesion, a pressure sore, a bedsore, and a condition or wound related to diabetes or poor circulation.

In some embodiments, the wound is selected from the group consisting of a non-radiation burn wound, an incised wound, an open wound, a surgical or post surgical wound, a diabetic lesion, a thermal burn, a chemical burn, a pressure sore, a bedsore, and a condition related to diabetes or poor circulation. In some embodiments, the wound is selected from the group consisting of an incised wound, an open wound, a surgical or post surgical wound, a diabetic lesion, a pressure sore, a bedsore, and a condition related to diabetes or poor circulation.

The present disclosure also relates to methods and compositions of reducing scar formation during wound healing in a subject. The compounds and compositions described herein can be administered directly to the wound or to cells proximate the wound at an amount effective to reduce scar formation in and/or around the wound. Thus, in some embodiments, a method of reducing scar formation during wound healing in a subject is provided, the method comprising administering to the subject a therapeutically effective amount of a compound described herein (e.g., a CRM1 inhibitor), or a pharmaceutically acceptable salt thereof.

The wound can include any injury to any portion of the body of a subject. According to embodiments, methods are provided to ameliorate, reduce, or decrease the formation of scars in a subject that has suffered a burn injury. According to preferred embodiments, methods are provided to treat, reduce the occurrence of, or reduce the probability of developing hypertrophic scars in a subject that has suffered an acute or chronic wound or injury.

Other Disorders

Compounds and compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, and other renal disorders.

Combination Radiation Therapy

Compounds and compositions described herein are useful as radiosensitizers. Therefore, compounds and compositions described herein can be administered in combination with radiation therapy. Radiation therapy is the medical use of high-energy radiation (e.g., x-rays, gamma rays, charged particles) to shrink tumors and kill malignant cells, and is generally used as part of cancer treatment. Radiation therapy kills malignant cells by damaging their DNA.

Radiation therapy can be delivered to a patient in several ways. For example, radiation can be delivered from an external source, such as a machine outside the patient's body, as in external beam radiation therapy. External beam radiation therapy for the treatment of cancer uses a radiation source that is external to the patient, typically either a radioisotope, such as $^{60}$Co, $^{137}$Cs, or a high energy x-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiating of healthy tissue can be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The irradiation of healthy tissue also can be reduced by tightly collimating the radiation beam to the general cross section of the tumor taken perpendicular to the axis of the radiation beam. Numerous systems exist for producing such a circumferential collimation, some of which use multiple sliding shutters which, piecewise, can generate a radio-opaque mask of arbitrary outline.

For administration of external beam radiation, the amount can be at least about 1 Gray (Gy) fractions at least once every other day to a treatment volume. In a particular embodiment, the radiation is administered in at least about 2 Gray (Gy) fractions at least once per day to a treatment volume. In another particular embodiment, the radiation is administered in at least about 2 Gray (Gy) fractions at least once per day to a treatment volume for five consecutive days per week. In another particular embodiment, radiation is administered in 10 Gy fractions every other day, three times per week to a treatment volume. In another particular embodiment, a total of at least about 20 Gy is administered to a patient in need thereof. In another particular embodiment, at least about 30 Gy is administered to a patient in need thereof. In another particular embodiment, at least about 40 Gy is administered to a patient in need thereof.

Typically, the patient receives external beam therapy four or five times a week. An entire course of treatment usually lasts from one to seven weeks depending on the type of cancer and the goal of treatment. For example, a patient can receive a dose of 2 Gy/day over 30 days.

Internal radiation therapy is localized radiation therapy, meaning the radiation source is placed at the site of the tumor or affected area. Internal radiation therapy can be delivered by placing a radiation source inside or next to the area requiring treatment. Internal radiation therapy is also called brachytherapy. Brachytherapy includes intercavitary treatment and interstitial treatment. In intracavitary treatment, containers that hold radioactive sources are put in or near the tumor. The sources are put into the body cavities. In interstitial treatment, the radioactive sources alone are put into the tumor. These radioactive sources can stay in the patient permanently. Typically, the radioactive sources are removed from the patient after several days. The radioactive sources are in containers.

There are a number of methods for administration of a radiopharmaceutical agent. For example, the radiopharmaceutical agent can be administered by targeted delivery or by systemic delivery of targeted radioactive conjugates, such as a radiolabeled antibody, a radiolabeled peptide and a liposome delivery system. In one particular embodiment of targeted delivery, the radiolabelled pharmaceutical agent can be a radiolabelled antibody. See, for example, Ballangrud A. M., et al. Cancer Res., 2001; 61:2008-2014 and Goldenber, D. M. J. Nucl. Med., 2002; 43(5):693-713, the contents of which are incorporated by reference herein.

In another particular embodiment of targeted delivery, the radiopharmaceutical agent can be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. See, for example, Emfietzoglou D, Kostarelos K, Sgouros G. An analytical dosimetry study for the use of radionuclide-liposome conjugates in internal radiotherapy. J Nucl Med 2001; 42:499-504, the contents of which are incorporated by reference herein.

In yet another particular embodiment of targeted delivery, the radiolabeled pharmaceutical agent can be a radiolabeled peptide. See, for example, Weiner R E, Thakur M L. Radiolabeled peptides in the diagnosis and therapy of oncological diseases. Appl Radiat Isot 2002 November; 57(5): 749-63, the contents of which are incorporated by reference herein.

In addition to targeted delivery, brachytherapy can be used to deliver the radiopharmaceutical agent to the target site. Brachytherapy is a technique that puts the radiation sources as close as possible to the tumor site. Often the source is inserted directly into the tumor. The radioactive sources can be in the form of wires, seeds or rods. Generally, cesium, iridium or iodine are used.

Systemic radiation therapy is another type of radiation therapy and involves the use of radioactive substances in the blood. Systemic radiation therapy is a form of targeted therapy. In systemic radiation therapy, a patient typically ingests or receives an injection of a radioactive substance, such as radioactive iodine or a radioactive substance bound to a monoclonal antibody.

A "radiopharmaceutical agent," as defined herein, refers to a pharmaceutical agent which contains at least one radiation-emitting radioisotope. Radiopharmaceutical agents are routinely used in nuclear medicine for the diagnosis and/or therapy of various diseases. The radiolabelled pharmaceutical agent, for example, a radiolabelled antibody, contains a radioisotope (RI) which serves as the radiation source. As contemplated herein, the term "radioisotope" includes metallic and non-metallic radioisotopes. The radioisotope is chosen based on the medical application of the radiolabeled pharmaceutical agents. When the radioisotope is a metallic radioisotope, a chelator is typically employed to bind the metallic radioisotope to the rest of the molecule. When the radioisotope is a non-metallic radioisotope, the non-metallic radioisotope is typically linked directly, or via a linker, to the rest of the molecule.

As used herein, a "metallic radioisotope" is any suitable metallic radioisotope useful in a therapeutic or diagnostic procedure in vivo or in vitro. Suitable metallic radioisotopes include, but are not limited to: Actinium-225, Antimony-124, Antimony-125, Arsenic-74, Barium-103, Barium-140, Beryllium-7, Bismuth-206, Bismuth-207, Bismuth212, Bismuth213, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-60, Copper-62, Copper-64, Copper-67, Erbium-169, Europium-152, Gallium-64, Gallium-67, Gallium-68, Gadolinium153, Gadolinium-157 Gold-195, Gold-199, Hafnium-175, Hafnium-175-181, Holmium-166, Indium-110, Indium-111, Iridium-192, Iron 55, Iron-59, Krypton85, Lead-203, Lead-210, Lutetium-177, Manganese-54, Mercury-197, Mercury203, Molybdenum-99, Neodymium-147, *Neptunium*-237, Nickel-63, Niobium95, Osmium-185+191, Palladium-103, Palladium-109, Platinum-195m, Praseodymium-143, Promethium-147, Promethium-149, Protactinium-233, Radium-226, Rhenium-186, Rhenium-188, Rubidium-86, Ruthenium-97, Ruthenium-103, Ruthenium-105, Ruthenium-106, Samarium-153, Scandium-44, Scandium-46, Scandium-47, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, Zirconium-89, and Zirconium-95.

As used herein, a "non-metallic radioisotope" is any suitable nonmetallic radioisotope (non-metallic radioisotope) useful in a therapeutic or diagnostic procedure in vivo or in vitro. Suitable non-metallic radioisotopes include, but are not limited to: Iodine-131, Iodine-125, Iodine-123, Phosphorus-32, Astatine-211, Fluorine-18, Carbon-11, Oxygen-15, Bromine-76, and Nitrogen-13.

Identifying the most appropriate isotope for radiotherapy requires weighing a variety of factors. These include tumor uptake and retention, blood clearance, rate of radiation delivery, half-life and specific activity of the radioisotope, and the feasibility of large-scale production of the radioisotope in an economical fashion. The key point for a therapeutic radiopharmaceutical is to deliver the requisite amount of radiation dose to the tumor cells and to achieve a cytotoxic or tumoricidal effect while not causing unmanageable side-effects.

It is preferred that the physical half-life of the therapeutic radioisotope be similar to the biological half-life of the radiopharmaceutical at the tumor site. For example, if the half-life of the radioisotope is too short, much of the decay will have occurred before the radiopharmaceutical has reached maximum target/background ratio. On the other hand, too long a half-life could cause unnecessary radiation dose to normal tissues. Ideally, the radioisotope should have a long enough half-life to attain a minimum dose rate and to irradiate all the cells during the most radiation sensitive phases of the cell cycle. In addition, the half-life of a radioisotope has to be long enough to allow adequate time for manufacturing, release, and transportation.

Other practical considerations in selecting a radioisotope for a given application in tumor therapy are availability and quality. The purity has to be sufficient and reproducible, as trace amounts of impurities can affect the radiolabeling and radiochemical purity of the radiopharmaceutical.

The target receptor sites in tumors are typically limited in number. As such, it is preferred that the radioisotope have high specific activity. The specific activity depends primarily on the production method. Trace metal contaminants must be minimized as they often compete with the radioisotope for the chelator and their metal complexes compete for receptor binding with the radiolabeled chelated agent.

The type of radiation that is suitable for use in the methods of the present invention can vary. For example, radiation can be electromagnetic or particulate in nature. Electromagnetic radiation useful in the practice of this invention includes, but is not limited to, x-rays and gamma rays. Particulate radiation useful in the practice of this invention includes, but is not limited to, electron beams (beta particles), protons beams, neutron beams, alpha particles, and negative pi mesons. The radiation can be delivered using conventional radiological treatment apparatus and methods, and by intraoperative and stereotactic methods. Additional discussion regarding radiation treatments suitable for use in the practice of this invention can be found throughout Steven A. Leibel et al., Textbook of Radiation Oncology (1998) (publ. W. B. Saunders Company), and particularly in Chapters 13 and 14. Radiation can also be delivered by other methods such as targeted delivery, for example by radioactive "seeds," or by systemic delivery of targeted radioactive conjugates. J. Padawer et al., Combined Treatment with Radioestradiol lucanthone in Mouse C3HBA Mammary Adenocarcinoma and with Estradiol lucanthone in an Estrogen Bioassay, Int. J. Radiat. Oncol. Biol. Phys. 7:347-357 (1981). Other radiation delivery methods can be used in the practice of this invention.

For tumor therapy, both at and β-particle emitters have been investigated. Alpha particles are particularly good cytotoxic agents because they dissipate a large amount of energy within one or two cell diameters. The β-particle emitters have relatively long penetration range (2-12 mm in the tissue) depending on the energy level. The long-range penetration is particularly important for solid tumors that have heterogeneous blood flow and/or receptor expression. The β-particle emitters yield a more homogeneous dose distribution even when they are heterogeneously distributed within the target tissue.

In a particular embodiment, therapeutically effective amounts of the compounds and compositions described herein are administered in combination with a therapeutically effective amount of radiation therapy to treat cancer (e.g., lung cancer, such as non-small cell lung cancer). The amount of radiation necessary can be determined by one of skill in the art based on known doses for a particular type of cancer. See, for example, Cancer Medicine 5$^{th}$ ed., Edited by R. C. Bast et al., July 2000, BC Decker.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXEMPLIFICATION

Abbreviations

Ac acetyl
ACN acetonitrile
Boc tert-butoxy carbonyl
CI Chemical ionization
DIPEA N,N-Diisopropyl ethylamine
DMF Dimethylformamide
DMSO dimethylsulfoxide
dppf (diphenylphosphino)ferrocene
EDCI 3-(ethyliminomethyleneamino)-N,N-dimethylpropan-1-amine
EDTA ethylenediamine tetraacetic acid
EI electron impact ionization
equiv(s). equivalent(s)
EtOAc ethyl acetate
EtOH Ethanol
Et Ethyl
g gram(s)
h hour(s)
HATU (Dimethylamino)-N,N-dimethyl(3H-[1,2,3]triazolo[4,5-b]pyridin-3-yloxy)methaniminium hexafluorophosphate
HOBt 1-Hydroxybenzotriazole
LAH lithium aluminum hydride
LCMS liquid chromatography mass spectrometry
LRMS low resolution mass spectrometry
Me methyl
mg milligram(s)
min Minute(s)
mL milliliter(s)
Ms mesityl or mesyl
NMR Nuclear magnetic resonance
PBS phosphate-buffered saline
PEG polyethylene glycol
Ph phenyl
RT, rt, r.t. Room temperature
SDS-PAGE Sodium dodecyl sulfate-polyacrylamide gel electrophoresis
T3P Propylphosphonic anhydride (available from Archimica)
TFA trifluoroacetic acid
THF tetrahydrofuran
$t_R$ Retention time Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994).

Techniques for purification of intermediates and final products include for example, straight and reversed phase chromatography on column or rotating plate, recrystallisation, distillation and liquid-liquid or solid-liquid extraction, which will be readily understood by the one skilled in the art. The definitions of substituents and groups are as in formula I except where defined differently. The term "room temperature" and "ambient temperature" shall mean, unless otherwise specified, a temperature between 16 and 25° C. The term "reflux" shall mean, unless otherwise stated, in reference to an employed solvent a temperature at or above the boiling point of named solvent.

A typical LCMS method used to characterize synthesized compounds is described below:
  Mobile phase: A: water (0.01% TFA); B: CAN (0.01% TFA)
  Gradient: 5% B increase to 100% B within 1.2 min, 100% B for 1.3 min
  Flow Rate: 2.0 mL/min
  Column: SunFire C18, 4.6*50 mm, 3.5 μm
  Column Temperature: 50° C.
  Detection: UV (214, 254 nm) and MS (ESI, Pos mode, 110-1000 amu).
Unless otherwise indicated, retention times reported for synthesized compounds were obtained using this LCMS method.

It is understood that compounds for which a specific synthesis is not shown can be made in accordance with the general procedures disclosed herein.

Example 1. Synthetic Methods

Synthesis of (E)-N-((5-(5-acetylthiophen-2-yl)-7-chlorobenzofuran-2-yl)methyl)-3-(6-aminopyridin-3-yl) acrylamide (500) and (E)-N-((5-(5-acetylthiophen-2-yl)benzofuran-2-yl)methyl)-3-(6-aminopyridin-3-yl)acrylamide (503)

give 5-bromo-3-chloro-2-hydroxybenzaldehyde (2), which was used in the next step without further purification. $^1$H NMR (400 MHz, DMSO-$d_6$) δ 11.22 (s, 1H), 10.12 (s, 1H), 8.00 (s, 1H), 7.84 (s, 1H).

Synthesis of ethyl 5-bromo-7-chlorobenzofuran-2-carboxylate (3)

5-Bromo-3-chloro-2-hydroxybenzaldehyde (2) (13.90 g, 59.03 mmol) was dissolved in DMF at room temperature. Ethyl 2-bromoacetate (10.19 mL, 88.55 mmol) and potassium carbonate (20.40 g, 147.58 mmol) were added and the

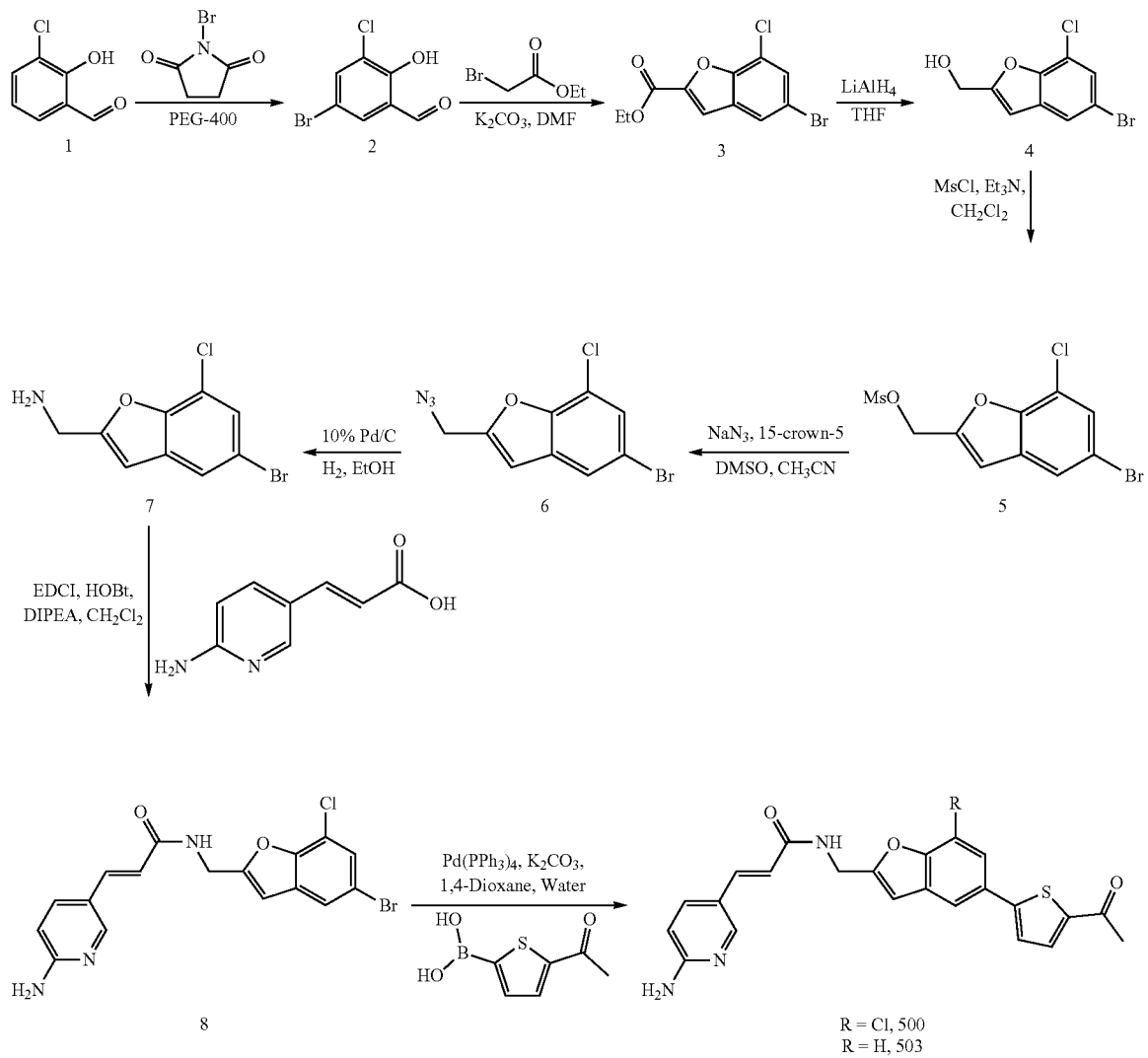

Synthesis of 5-bromo-3-chloro-2-hydroxybenzaldehyde (2)

3-Chloro-2-hydroxybenzaldehyde (1) (10 g, 63.87 mmol) was dissolved in PEG-400 (50 mL) at room temperature. N-Bromosuccinimide (11.94 g, 67.06 mmol) was added to the reaction mixture and stirred for 2 h. The reaction mixture was transferred into iced water and extracted with ethyl acetate (3×500 mL). The combined organic layers were washed with brine and dried over anhydrous $Na_2SO_4$. The organic layer was concentrated under reduced pressure to reaction mixture was heated at 120° C. for 2 h. The reaction mixture was allowed to cool to room temperature, transferred into iced water and extracted with ethyl acetate (3×500 mL). The combined organic layers were washed with brine and dried over anhydrous $Na_2SO_4$. The organic layer was concentrated under reduced pressure to give the crude product, which was purified by silica gel chromatography (0-4% ethyl acetate/n-hexane) to obtain ethyl 5-bromo-7-chlorobenzofuran-2-carboxylate (3). (Yield: 4.40 g, 25%). $^1$H NMR (400 MHz, DMSO-$d_6$) δ 7.71-7.66

(m, 1H), 7.51 (s, 1H), 6.80 (s, 1H), 4.10-4.08 (m, 2H), 1.50-1.49 (m, 3H).

Synthesis of (5-bromo-7-chlorobenzofuran-2-yl) methanol (4)

Ethyl 5-bromo-7-chlorobenzofuran-2-carboxylate (3) (4.80 g, 15.82 mmol) was dissolved in THF (150 mL) at room temperature. The reaction mixture was cooled to −20° C. and 1M lithium aluminum hydride in THF (11 mL, 11 mmol) was added dropwise. The reaction mixture was stirred for 15 min, transferred into iced water and extracted with ethyl acetate (3×250 mL). The combined organic layers were washed with brine and dried over anhydrous $Na_2SO_4$. The organic layer was concentrated under reduced pressure to give crude product which was purified by silica gel chromatography (0-15% ethyl acetate/n-hexane) to obtain (5-bromo-7-chlorobenzofuran-2-yl) methanol (4). (Yield: 3 g, 73%). $^1$H NMR (400 MHz, DMSO-$d_6$) (7.84 (s, 1H), 7.63 (s, 1H), 6.86 (s, 1H), 5.66-5.63 (m, 1H), 4.62 (d, J=4 Hz, 2H). LCMS: m/z 262.5 $[M+H]^+$, $t_R$=2.30 min.

Synthesis of (5-bromo-7-chlorobenzofuran-2-yl) methyl methanesulfonate (5)

(5-Bromo-7-chlorobenzofuran-2-yl) methanol (4) (4 g, 15.29 mmol) was dissolved in dichloromethane (40 mL). The reaction mixture was cooled to 0° C. and triethylamine (3.19 mL, 22.94 mmol) was added dropwise followed by methanesulphonyl chloride (1.44 mL, 18.35 mmol). The reaction mixture was allowed to warm to room temperature and stirred for 4 h. The reaction mixture was transferred into iced water and extracted with dichloromethane (3×250 mL). The combined organic layers were washed with brine, dried over anhydrous $Na_2SO_4$ and concentrated under reduced pressure to give 4.8 g of crude (5-bromo-7-chlorobenzofuran-2-yl) methyl methanesulfonate (5), which was used in the next step without further purification. $^1$H NMR (400 MHz, DMSO-$d_6$) (7.96 (s, 1H), 7.76 (s, 1H), 7.25 (s, 1H), 5.50 (s, 2H), 3.33 (s, 3H). LCMS: m/z 339.56 $[M+H]^+$, $t_R$=2.78 min.

Synthesis of 2-(azidomethyl)-5-bromo-7-chlorobenzofuran (6)

(5-Bromo-7-chlorobenzofuran-2-yl)methyl methanesulfonate (5) (4.8 g, 14.13 mmol) was dissolved in acetonitrile (48 mL) at room temperature. Sodium azide (1.83 g, 28.26 mmol), dimethyl sulfoxide (1.50 mL, 21.20 mmol) and 15-crown-5 (0.48 g, 2.12 mmol) were added to the reaction mixture at room temperature and then the reaction mixture was heated at 90° C. for 30 min. The reaction mixture was then cooled to room temperature, transferred into iced water and extracted with ethyl acetate (3×250 mL). The combined organic layers were washed with brine and dried over anhydrous $Na_2SO_4$. The organic layer was concentrated under reduced pressure to give 4 g of crude 2-(azidomethyl)-5-bromo-7-chlorobenzofuran (6), which was used in the next step without further purification. $^1$H NMR (400 MHz, DMSO-$d_6$) δ 7.91 (s, 1H), 7.70 (s, 1H), 7.07 (s, 1H), 4.75 (s, 2H).

Synthesis of (5-bromo-7-chlorobenzofuran-2-yl) methanamine (7)

2-(Azidomethyl)-5-bromo-7-chlorobenzofuran (6) (4 g, 13.96 mmol) was dissolved in ethanol (40 mL) at room temperature. The reaction mixture was degassed with $N_2$ gas and 10% palladium on carbon (0.8 g) was added. The reaction mixture was purged with $H_2$ gas and stirred for 2 h. The reaction mixture was filtered and washed with dichloromethane (3×100 mL). The combined organic layers were concentrated under reduced pressure to give 3.45 g of crude (5-bromo-7-chlorobenzofuran-2-yl) methanamine (7), which was used in the next step without further purification. $^1$H NMR (400 MHz, DMSO-$d_6$) δ 7.81 (s, 1H), 7.58 (s, 1H), 6.79 (s, 1H), 3.86 (s, 2H), 2.02-1.94 (m, 2H). LCMS: m/z 262.0 $[M+H]^+$, $t_R$=1.80 min.

Synthesis of (E)-3-(6-aminopyridin-3-yl)-N-((5-bromo-7-chlorobenzofuran-2-yl) methyl) acrylamide (8)

General Procedure 1: Amide Coupling

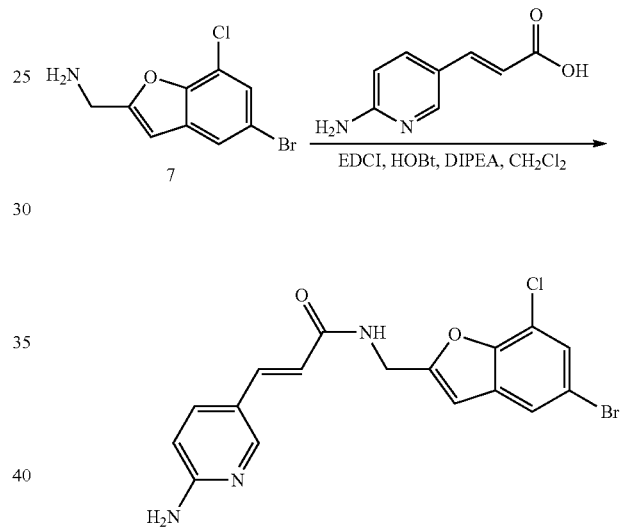

(5-Bromo-7-chlorobenzofuran-2-yl) methanamine (7) (3.45 g, 13.24 mmol) was dissolved in dichloromethane (35 mL). The reaction mixture was cooled to 0° C. and (E)-3-(6-aminopyridin-3-yl) acrylic acid (3.25 g, 19.86 mmol), EDCI (3.04 g, 15.89 mmol) and HOBt (2.14 g, 15.89 mmol) were added followed by DIPEA (6.80 mL, 39.72 mmol). The reaction mixture was allowed to warm to room temperature and stirred for 8 h. The reaction mixture was transferred into iced water and extracted with ethyl acetate (3×250 mL). The combined organic layers were washed with brine, dried over anhydrous $Na_2SO_4$ and concentrated under reduced pressure to give crude product, which was purified by silica gel chromatography (0-5% MeOH in $CH_2Cl_2$) to obtain (E)-3-(6-aminopyridin-3-yl)-N-((5-bromo-7-chlorobenzofuran-2-yl) methyl) acrylamide (8). (Yield: 5.14 g, 95%). $^1$H NMR (400 MHz, DMSO-$d_6$) δ 8.91 (s, 1H), 8.69-8.67 (m, 1H), 8.09 (s, 1H), 7.83 (s, 1H), 7.68-7.63 (m, 2H), 7.35 (d, J=16 Hz, 1H), 6.83 (s, 1H), 6.64 (s, 2H), 6.54-6.52 (m, 1H), 6.43 (d, J=15.6 Hz, 1H), 4.59-4.57 (m, 1H). LCMS: m/z 406.6 $[M+H]^+$, $t_R$=2.04 min.

Synthesis of (E)-N-((5-(5-acetylthiophen-2-yl)-7-chlorobenzofuran-2-yl) methyl)-3-(6-aminopyridin-3-yl) acrylamide (500) and (E)-N-((5-(5-acetylthiophen-2-yl)benzofuran-2-yl)methyl)-3-(6-aminopyridin-3-yl)acrylamide (503)

General Procedure 2: Cross-Coupling

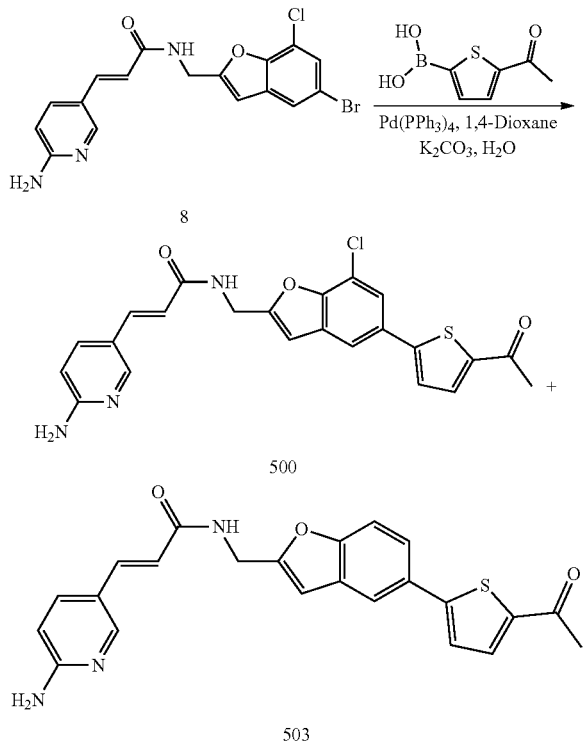

(E)-3-(6-Aminopyridin-3-yl)-N-((5-bromo-7-chlorobenzofuran-2-yl) methyl) acrylamide (8) (0.23 g, 0.56 mmol) was dissolved in 1,4-dioxane (3 mL) at room temperature and degassed with $N_2$ gas for 5 min. Tetrakis(triphenylphosphine)palladium (O) (0.032 g, 0.02 mmol) and 5-acetyl thiophene-2-boronic acid (0.14 g, 0.84 mmol) were added at room temperature and stirred for 5 min. A degassed solution of $K_2CO_3$ (0.12 g, 0.84 mmol) in 0.5 mL of water was added and the reaction mixture was irradiated under microwave for 15 min at 80° C. The reaction mixture was allowed to cool to room temperature, transferred into iced water and extracted with ethyl acetate (3×50 mL). The combined organic layers were washed with brine, dried over anhydrous $Na_2SO_4$ and concentrated under reduced pressure to give the crude product, which was purified by silica gel chromatography (0-6% MeOH in $CH_2Cl_2$) to obtain (E)-N-((5-(5-acetylthiophen-2-yl)-7-chlorobenzofuran-2-yl) methyl)-3-(6-aminopyridin-3-yl) acrylamide (500) and (E)-N-((5-(5-acetylthiophen-2-yl)benzofuran-2-yl)methyl)-3-(6-aminopyridin-3-yl)acrylamide (503).

Data for 500: (Yield: 0.017 g, 6.65%). $^1$H NMR (400 MHz, DMSO-$d_6$) δ 8.66-8.63 (m, 1H), 8.09 (s, 1H), 7.99-7.97 (m, 2H), 7.85 (s, 1H), 7.73 (d, J=4 Hz, 1H), 7.64-7.62 (m, 1H), 7.36 (d, J=15.6 Hz, 1H), 6.90 (s, 1H), 6.49-6.40 (m, 4H), 4.60 (d, J=5.6 Hz, 2H), 2.55-2.50 (m, 3H). LCMS: m/z 452.93 [M+H]$^+$, $t_R$=2.06 min.

Data for 503: (Yield: 0.02 g, 8%). $^1$H NMR (400 MHz, DMSO-$d_6$) δ 8.61-8.58 (m, 1H), 8.08 (d, J=2 Hz, 1H), 8.02 (d, J=1.2 Hz, 1H), 7.95 (d, J=3.6 Hz, 1H), 7.69 (dd, $J_1$=2 Hz, $J_2$=1.6 Hz, 1H), 7.65-7.60 (m, 3H), 7.35 (d, J=16 Hz, 1H), 6.81 (s, 1H), 6.49-6.40 (m, 4H), 4.57 (d, J=5.6 Hz, 2H), 2.55-2.50 (m, 3H). LCMS: m/z 418.48 [M+H]$^+$, $t_R$=1.92 min.

Synthesis of (E)-3-(6-aminopyridin-3-yl)-N-((7-chloro-5-(4-(morpholine-4-carbonyl) phenyl)benzo[d]oxazol-2-yl)methyl)acrylamide (501)

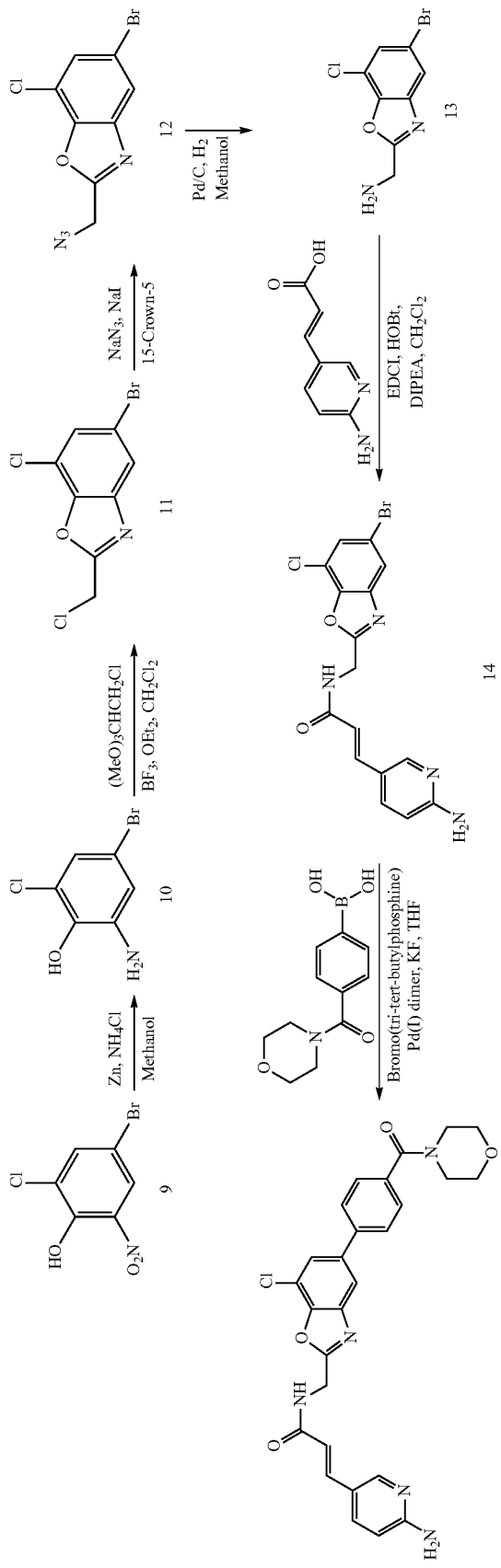

Synthesis of 2-amino-4-bromo-6-chlorophenol (10)

4-Bromo-2-chloro-6-nitrophenol (9) (10 g, 39.61 mmol) was dissolved in methanol (100 mL) at room temperature. Zinc dust (13 g, 198 mmol) was added to the reaction mixture followed by dropwise addition of saturated NH$_4$Cl (100 mL) at room temperature (CAUTION: Exothermic reaction was observed). After completion of addition, the reaction mixture was heated at 50° C. for 1 h. The reaction mixture was allowed to cool to room temperature, filtered and washed with ethyl acetate (3×150 mL). The combined organic layers were washed with brine, dried over anhydrous Na$_2$SO$_4$ and concentrated under reduced pressure to give crude 2-amino-4-bromo-6-chlorophenol (10), which was used in the next step without further purification. $^1$H NMR (400 MHz, DMSO-d$_6$) δ 8.97-8.85 (bs, 1H), 6.71 (s, 1H), 6.68 (s, 1H), 5.57-5.10 (bs, 2H).

Synthesis of 5-bromo-7-chloro-2-(chloromethyl)benzo[d]oxazole (11)

2-Chloro-1,1,1-trimethoxyethane (0.3 mL, 2.04 mmol) was dissolved in dichloromethane (20 mL) at room temperature and cooled to 0° C. Borontrifluoride etherate (0.5 mL, 4.09 mmol) was added dropwise followed by 2-amino-4-bromo-6-chlorophenol (10) (0.5 g, 2.25 mmol). The reaction mixture was allowed to warm to room temperature and stirred for 4 h. The reaction mixture was transferred into saturated NaHCO$_3$ solution and extracted with ethyl acetate (3×20 mL). The combined organic layers were washed with brine, dried over anhydrous Na$_2$SO$_4$ and concentrated under reduced pressure to give crude compound, which was purified by silica gel chromatography (0-20% ethyl acetate/n-hexane) to obtain 5-bromo-7-chloro-2-(chloromethyl)benzo[d]oxazole (11). (Yield: 0.18 g, 19%). $^1$H NMR (400 MHz, CDCl$_3$) (7.82 (s, 1H), 7.58 (s, 1H), 4.78 (s, 2H).

Synthesis of 2-(azidomethyl)-5-bromo-7-chlorobenzo[d]oxazole (12)

5-Bromo-7-chloro-2-(chloromethyl)benzo[d]oxazole (11) (0.1 g, 0.35 mmol) was dissolved in acetonitrile (2 mL) at room temperature. Sodium azide (0.03 g, 0.42 mmol), 15-Crown-5 (0.010 g) and sodium iodide (0.03 g, 0.177 mmol) were added and the reaction mixture was heated at 90° C. for 18 h. The reaction mixture was allowed to cool to room temperature, transferred into iced water and extracted with ethyl acetate (3×20 mL). The combined organic layers were washed with brine, dried over anhydrous Na$_2$SO$_4$ and concentrated under reduced pressure to obtain 0.13 g of crude 2-(azidomethyl)-5-bromo-7-chlorobenzo[d]oxazole (12), which was used in the next step without further purification. $^1$H NMR (400 MHz, DMSO-d$_6$) (8.10 (d, J=1.6 Hz, 1H), 7.86 (d, J=2 Hz, 1H), 4.93 (s, 2H).

Synthesis of (5-bromo-7-chlorobenzo[d]oxazol-2-yl)methanamine (13)

2-(Azidomethyl)-5-bromo-7-chlorobenzo[d]oxazole (12) (0.3 g, 1.04 mmol) was dissolved in methanol (40 mL) at room temperature. The reaction mixture was degassed with N$_2$ gas and 10% palladium on carbon (0.06 g) was added. The reaction mixture was purged with H$_2$ gas and stirred for 2 h. The reaction mixture was filtered and washed with dichloromethane (3×50 mL). The combined organic layers were concentrated under reduced pressure to give crude (5-bromo-7-chlorobenzo[d]oxazol-2-yl) methanamine (13), which was used in the next step without further purification. LCMS: m/z 262.98 [M+H]$^+$, t$_R$=1.71 min.

Synthesis of (E)-3-(6-aminopyridin-3-yl)-N-((5-bromo-7-chlorobenzo[d]oxazol-2-yl)methyl) acrylamide (14)

(5-Bromo-7-chlorobenzo[d]oxazol-2-yl)methanamine (13) (0.5 g, 1.91 mmol) was dissolved in dichloromethane (20 mL) at room temperature. The reaction mixture was cooled to 0° C. and (E)-3-(6-aminopyridin-3-yl) acrylic acid (0.37 g, 2.29 mmol), EDCI (0.43 g, 2.29 mmol) and HOBt (0.31 g, 2.29 mmol) were added, followed by DIPEA (0.65 mL, 3.82 mmol). The reaction mixture was allowed to warm to room temperature and stirred for 8 h. The reaction mixture was transferred into iced water and extracted with ethyl acetate (3×50 mL). The combined organic layers were washed with brine, dried over anhydrous Na$_2$SO$_4$ and concentrated under reduced pressure to give the crude product, which was purified by silica gel chromatography (0-5% MeOH in CH$_2$Cl$_2$) to obtain (E)-3-(6-aminopyridin-3-yl)-N-((5-bromo-7-chlorobenzo[d]oxazol-2-yl)methyl)acryl amide (14). (Yield: 0.14 g, 18%). $^1$H NMR (400 MHz, DMSO-d$_6$) δ 8.80-8.77 (m, 1H), 8.16 (s, 1H), 8.08 (s, 1H), 7.79 (s, 1H), 7.66-7.36 (m, 1H), 7.34 (d, J=16 Hz, 1H), 6.49-6.35 (m, 4H), 4.71 (d, J=5.6 Hz, 2H). LCMS: m/z 409.0 [M+H]$^+$, t$_R$=1.89 min.

Synthesis of (E)-3-(6-aminopyridin-3-yl)-N-((7-chloro-5-(4-(morpholine-4-carbonyl)phenyl) benzo[d]oxazol-2-yl)methyl)acrylamide (501)

(E)-3-(6-Aminopyridin-3-yl)-N-((5-bromo-7-chlorobenzo[d]oxazol-2-yl)methyl)acrylamide (14) (0.02 g, 0.049 mmol) was dissolved in THF (2 mL) at room temperature and degassed with N$_2$ gas for 15 min. Bromo(tri-tert-butylphosphine)Pd(I) dimer (1 mg) and 4-(morpholine-4-carbonyl)phenylboronic acid (0.02 g, 0.073 mmol) and KF (0.01 g, 0.15 mmol) were added at room temperature and stirred for 5 min. The reaction mixture was irradiated under microwave for 30 min at 100° C. The reaction mixture was allowed to cool to room temperature, transferred into iced water and extracted with ethyl acetate (3×20 mL). The combined organic layers were washed with brine, dried over anhydrous Na$_2$SO$_4$ and concentrated under reduced pressure to give crude compound which was purified by silica gel chromatography (0-6% MeOH in CH$_2$Cl$_2$) to obtain (E)-3-(6-aminopyridin-3-yl)-N-((7-chloro-5-(4-(morpholine-4-carbonyl)phenyl)benzo[d]oxazol-2-yl)methyl)acrylamide (501). (Yield: 0.009 g, 36%). $^1$H NMR (400 MHz, DMSO-d$_6$) δ 8.83-8.80 (m, 1H), 8.09 (s, 1H), 8.04 (s, 1H), 7.86-7.83 (m, 3H), 7.67-7.64 (m, 1H), 7.52 (d, J=8.4 Hz, 2H), 7.35 (d, J=16 Hz, 1H), 6.50-6.44 (m, 4H), 4.74 (d, J=6 Hz, 1H), 3.63-3.41 (m, 8H). LCMS: m/z 518.24 [M+H]$^+$, t$_R$=1.82 min.

Synthesis of (E)-3-(6-aminopyridin-3-yl)-N-((7-chloro-5-(4-(morpholine-4-carbonyl) phenyl) benzofuran-2-yl) methyl) acrylamide (502)

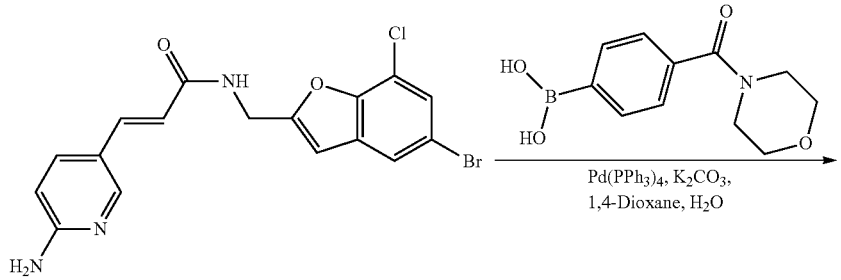

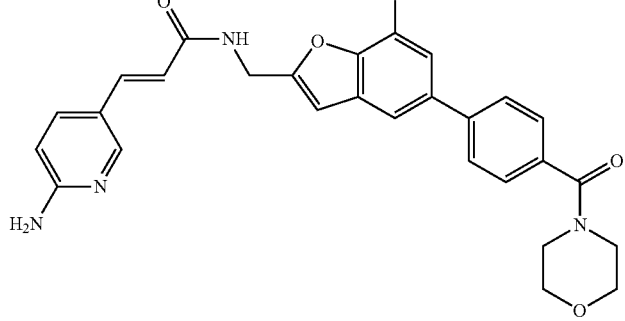

502

(E)-3-(6-Aminopyridin-3-yl)-N-((5-bromo-7-chlorobenzofuran-2-yl)methyl)acrylamide (0.20 g, 0.49 mmol) (8) was dissolved in 1,4-dioxane (3 mL) at room temperature and degassed with $N_2$ gas for 5 min. Tetrakis(triphenylphosphine)palladium (O) (0.028 g, 0.02 mmol) and 4-morpholine-4-carbonylphenylboronic acid (0.17 g, 0.73 mmol) were added at room temperature and stirred for 5 min. A degassed solution of $K_2CO_3$ (0.10 g, 0.73 mmol) in 0.5 mL of water was added and the reaction mixture was irradiated under microwave for 1 h at 80° C. The reaction mixture was allowed to cool to room temperature, transferred into iced water and extracted with ethyl acetate (3×50 mL). The combined organic layers were washed with brine, dried over anhydrous $Na_2SO_4$ and concentrated under reduced pressure to give crude compound, which was purified by silica gel chromatography (0-6% MeOH in $CH_2Cl_2$) to obtain (E)-3-(6-aminopyridin-3-yl)-N-((7-chloro-5-(4-(morpholine-4-carbonyl)phenyl)benzofuran-2-yl)methyl)acrylamide (502). (Yield: 0.12 g, 47%). $^1$H NMR (400 MHz, DMSO-$d_6$) δ 8.66-8.63 (m, 1H), 8.09 (s, 1H), 7.91 (s, 1H), 7.79 (d, J=8.4 Hz, 2H), 7.73 (s, 1H), 7.62 (d, J=11.2 Hz, 1H), 7.51 (d, J=8.4 Hz, 2H), 7.36 (d, J=16 Hz, 1H), 6.90 (s, 1H), 6.49-6.41 (m, 4H), 4.60 (d, J=5.6 Hz, 2H), 3.62 (s, 8H). LCMS: m/z 517.98 [M+H]$^+$, $t_R$=1.88 min.

Synthesis of (E)-3-(6-aminopyridin-3-yl)-N-((7-chloro-5-(4-(morpholinosulfonyl)phenyl) benzofuran-2-yl)methyl)acrylamide (504)

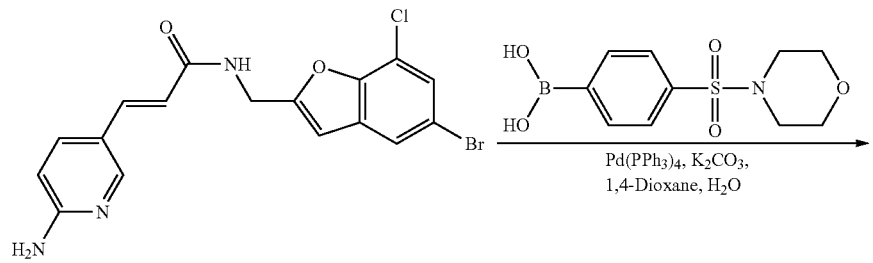

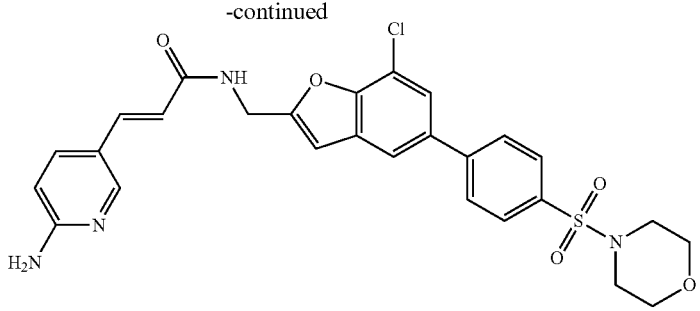

504

(E)-3-(6-Aminopyridin-3-yl)-N-((7-chloro-5-(4-(morpholinosulfonyl)phenyl)benzofuran-2-yl)methyl)acrylamide (504) was synthesized using General Procedure 2. (Yield: 10 mg, 10%). $^1$H NMR (400 MHz, DMSO-$d_6$) δ 8.65 (s, 1H), 8.08 (d, J=4 Hz, 1H), 8.03-7.99 (m, 3H), 7.82 (t, J=2 Hz, 3H), 7.62 (d, J=6 Hz, 1H), 7.35 (d, J=16 Hz, 1H), 6.93 (s, 1H), 6.49 (s, 1H), 6.46 (s, 2H), 6.42 (d, J=16 Hz, 1H), 4.61 (s, 2H), 3.65 (t, J=4.4 Hz, 4H), 2.92 (t, J=4.4 Hz, 4H). LCMS: m/z 553.4 [M+H]$^+$, $t_R$=1.97 min.

Synthesis of (E)-3-(6-aminopyridin-3-yl)-N-((7-chloro-5-(4-(2-(pyrazin-2-yl)hydrazine carbonyl) phenyl)benzofuran-2-yl)methyl)acrylamide (505)

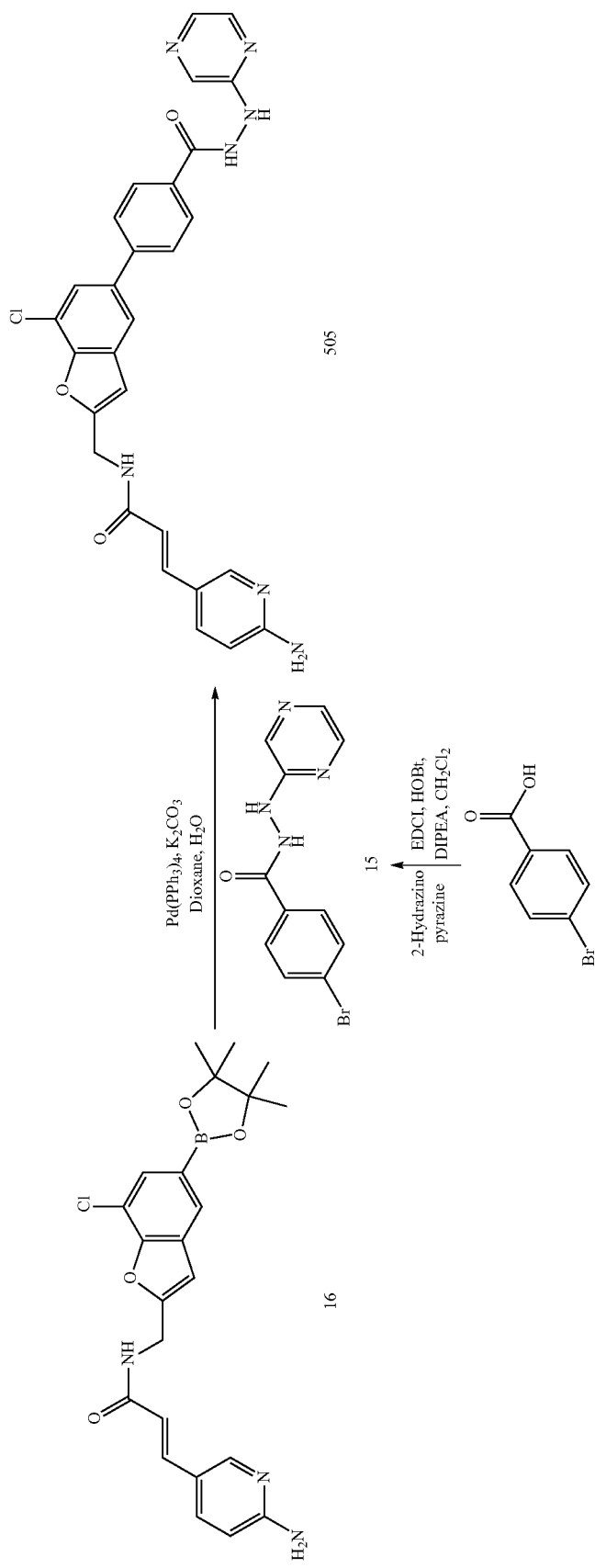

Synthesis of 4-bromo-N'-(pyrazin-2-yl)benzohydrazide (15)

4-Bromobenzoic acid (0.5 g, 2.4 mmol) was dissolved in dichloromethane (20 mL) and cooled to 0° C. 2-Hydrazinylpyrazine (0.32 g, 2.9 mmol), EDCI (0.55 g, 2.9 mmol), HOBt (0.39 g, 2.9 mmol) and DIPEA (0.96 g, 7.4 mmol) were added at 0° C. The reaction mixture was allowed to warm to room temperature and stirred for 4 h. The reaction mixture was transferred into water (100 mL) and extracted with $CH_2Cl_2$ (3×25 mL). The combined organic layers were washed with brine, dried over anhydrous $Na_2SO_4$ and concentrated under reduced pressure to give crude product, which was purified by silica gel chromatography (0-5% MeOH in $CH_2Cl_2$) to obtain 4-bromo-N-(pyrazin-2-yl)benzohydrazide (15). (Yield: 0.15 g, 20%). LCMS: m/z 295.18 [M+2], $t_R$=1.8 min.

Synthesis of (E)-3-(6-aminopyridin-3-yl)-N-((7-chloro-5-(4-(2-(pyrazin-2-yl)hydrazine carbonyl)phenyl)benzofuran-2-yl)methyl)acrylamide (505)

(E)-3-(6-aminopyridin-3-yl)-N-((7-chloro-5-(4,4,5,5-tetramethyl-1,3,2-dioxaborolan-2-yl)benzofuran-2-yl)methyl)acrylamide (16) (0.25 g, 0.55 mmol) was dissolved in 1,4-dioxane (2 mL) at room temperature and degassed using $N_2$ for 5 min. Tetrakis(triphenylphosphine)palladium (0) (31 mg, 20 mol %) and 4-bromo-N-(pyrazin-2-yl)benzohydrazide (0.24 g, 0.82 mmol) were added and stirred for 5 min. A degassed solution of $K_2CO_3$ (0.15 g, 1.1 mmol) in 2 mL of water was added and the reaction mixture was irradiated under microwave for 30 min at 100° C. The reaction mixture was transferred into iced water and extracted with ethyl acetate (3×20 mL). The combined organic layers were washed with brine, dried over anhydrous $Na_2SO_4$, and concentrated under reduced pressure to give crude product, which was purified by chromatography to obtain (E)-3-(6-aminopyridin-3-yl)-N-((7-chloro-5-(4-(2-(pyrazin-2-yl)hydrazine-1-carbonyl)phenyl)benzofuran-2-yl)methyl)acrylamide (505). (Yield: 0.01 g, 4%). $^1$H NMR (400 MHz, DMSO-$d_6$) (10.58 (s, 1H), 9.07 (s, 1H), 8.66 (t, J=5.8 Hz, 1H), 8.16 (s, 1H), 8.10-8.07 (m, 2H), 8.03 (d, J=8.4 Hz, 2H), 7.97 (s, 2H), 7.88 (d, J=8.4 Hz, 2H), 7.78 (s, 1H), 7.61 (dd, $J_1$, $J_2$=2.4 Hz, 1H), 7.36 (d, J=15.6 Hz, 1H), 6.91 (s, 1H), 6.49-6.41 (m, 4H), 4.60 (d, J=5.6 Hz, 2H). LCMS: m/z 540.18 [M+H]$^+$, $t_R$=1.73 min.

Synthesis of (E)-4-(2-((3-(6-aminopyridin-3-yl)acrylamido)methyl)-7-chlorobenzofuran-5-yl)benzamide (506)

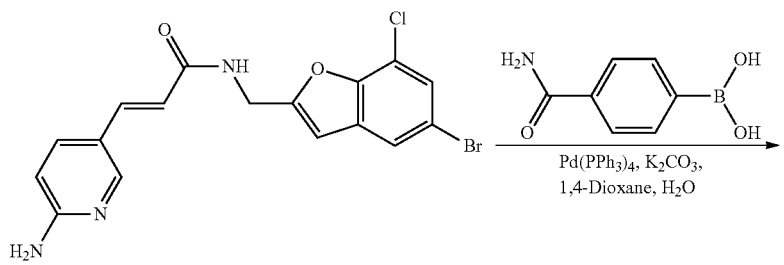

8

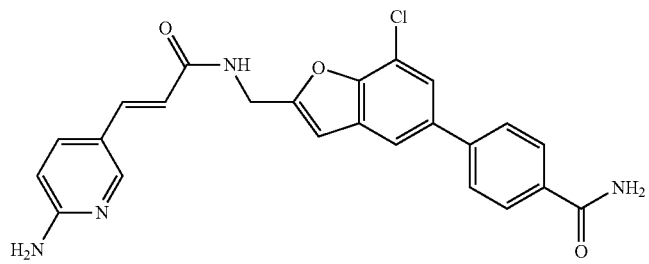

506

(E)-4-(2-((3-(6-aminopyridin-3-yl)acrylamido)methyl)-7-chlorobenzofuran-5-yl)benzamide (506) was synthesized using General Procedure 2. (Yield: 0.12 mg, 12%). $^1$H NMR (400 MHz, DMSO-$d_6$) δ 8.64 (d, J=4 Hz, 1H), 8.08 (d, J=4 Hz, 1H), 8.00-7.94 (m, 3H), 7.83-7.75 (m, 3H), 7.62 (d, J=6 Hz, 1H), 7.42 (s, 1H), 7.35 (d, J=16 Hz, 1H), 6.90 (s, 1H), 6.49 (s, 1H), 6.47 (s, 2H), 6.42 (d, J=16 Hz, 1H), 4.57 (s, 2H). LCMS: m/z 446.99 [M+H]$^+$, $t_R$=4.84 min.

Synthesis of (E)-3-(6-aminopyridin-3-yl)-N-((7-chloro-5-(4-(2-morpholinoacetyl)phenyl) benzofuran-2-yl)methyl)acrylamide (507)

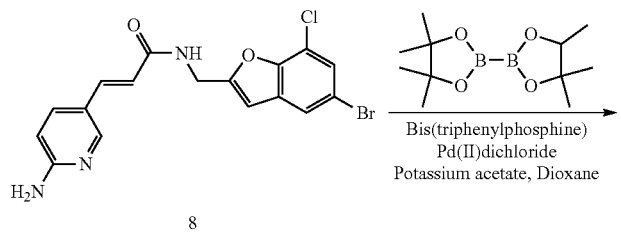 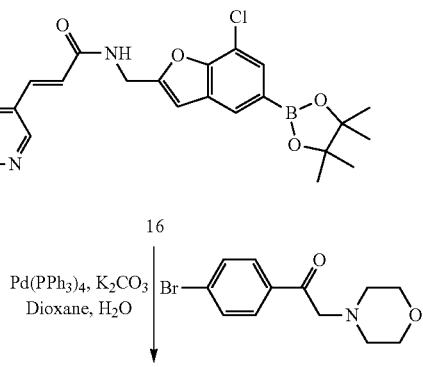

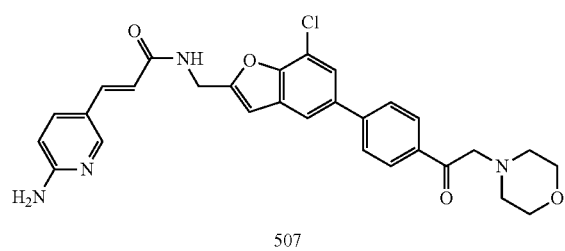

Synthesis of (E)-3-(6-aminopyridin-3-yl)-N-((7-chloro-5-(4,4,5,5-tetramethyl-1,3,2-dioxa borolan-2-yl)benzofuran-2-yl)methyl)acrylamide (16)

(E)-3-(6-Aminopyridin-3-yl)-N-((5-bromo-7-chlorobenzofuran-2-yl)methyl)acrylamide (8) (0.5 g, 1.22 mmol) was dissolved in 1,4-dioxane at room temperature. 4,4,4',4',5,5,5'-heptamethyl-2,2'-bi(1,3,2-dioxaborolane) (0.62 g, 2.44 mmol) and potassium acetate (0.24 g, 2.44 mmol) were added and the reaction mixture was degassed using $N_2$ for 15 min, followed by addition of bis(triphenylphosphine)palladium(II) dichloride (0.08 g, 0.12 mmol). The reaction mixture was irradiated under microwave for 40 min at 100° C. The reaction mixture was allowed to cool to room temperature, transferred into iced water and extracted with ethyl acetate (3×50 mL). The combined organic layers were washed with brine, dried over anhydrous $Na_2SO_4$, and concentrated under reduced pressure to give the crude product, which was purified by silica gel chromatography (0-4% MeOH in $CH_2Cl_2$) to obtain (E)-3-(6-aminopyridin-3-yl)-N-((7-chloro-5-(4,4,5,5-tetramethyl-1,3,2-dioxaborolan-2-yl)benzofuran-2-yl)methyl)acrylamide (16). (Yield: 0.3 g, 55%). $^1$H NMR (400 MHz, DMSO-$d_6$) δ 8.63 (t, J=5.8 Hz, 1H), 8.07 (d, J=2 Hz, 1H), 7.90 (d, J=0.8 Hz, 1H), 7.61 (dd, $J_1$, $J_2$=2.4 Hz, 1H), 7.53 (d, J=0.8 Hz, 1H), 7.34 (d, J=16 Hz, 1H), 6.87 (s, 1H), 6.48-6.39 (m, 4H), 4.58 (d, J=5.6 Hz, 2H), 1.33 (s, 12H).

Synthesis of (E)-3-(6-aminopyridin-3-yl)-N-((7-chloro-5-(4-(2-morpholinoacetyl)phenyl) benzofuran-2-yl)methyl)acrylamide (507)

(E)-3-(6-Aminopyridin-3-yl)-N-((7-chloro-5-(4,4,5,5-tetramethyl-1,3,2-dioxaborolan-2-yl)benzofuran-2-yl)methyl) acrylamide (16) (0.05 g, 0.11 mmol) was dissolved in 1,4-dioxane (2 mL) at room temperature and degassed using $N_2$ for 5 min. Tetrakis(triphenylphosphine) palladium (0) (7 mg, 20 mol %) and 1-(4-bromophenyl)-2-morpholinoethanone (0.47 g, 0.16 mmol) were added at room temperature and stirred for 5 min. A degassed solution of $K_2CO_3$ (0.03 g, 0.22 mmol) in 2 mL of water was added and the reaction mixture was irradiated under microwave for 30 min at 100° C. The reaction mixture was allowed to cool to room temperature, transferred into water and extracted with ethyl acetate (3×50 mL). The combined organic layers were washed with brine, dried over anhydrous $Na_2SO_4$, and concentrated under reduced pressure to give the crude product, which was purified by silica gel chromatography (0-5% MeOH in $CH_2Cl_2$) to obtain (E)-3-(6-aminopyridin-3-yl)-N-((7-chloro-5-(4-(2-morpholinoacetyl)phenyl)benzofuran-2-yl)methyl)acrylamide (507). (Yield: 0.01 g, 10%). $^1$H NMR (400 MHz, DMSO-$d_6$) δ 8.63 (t, J=5.8 Hz, 1H), 8.08 (d, J=4.4 Hz, 3H), 7.96 (d, J=1.6 Hz, 1H), 7.87 (d, J=8.4 Hz, 2H), 7.77 (d, J=1.6 Hz, 1H), 7.61 (dd, $J_1$, $J_2$=2.4 Hz, 1H), 7.34 (d, J=16 Hz, 1H), 6.91 (s, 1H), 6.48-6.40 (m, 4H), 4.61 (d, J=5.6 Hz, 2H), 3.88 (s, 2H) 3.60-3.58 (m, 4H), 3.34-3.32 (m, 4H). LCMS: m/z 531.4 [M+H]$^+$, $t_R$=1.65 min.

Synthesis of (E)-3-(6-aminopyridin-3-yl)-N-((7-chloro-5-(4-(3,3-difluoroazetidine-1-carbonyl)phenyl)benzofuran-2-yl)methyl)acrylamide (508)

fied by silica gel chromatography (10-20% ethyl acetate/petroleum ether) to provide 4-bromo-2-chloro-6-iodophenol (18) (2.3 g, 70.0% yield) as an off-white solid. LCMS: m/z 332.1 [M+H]$^+$, $t_R$=1.92 min.

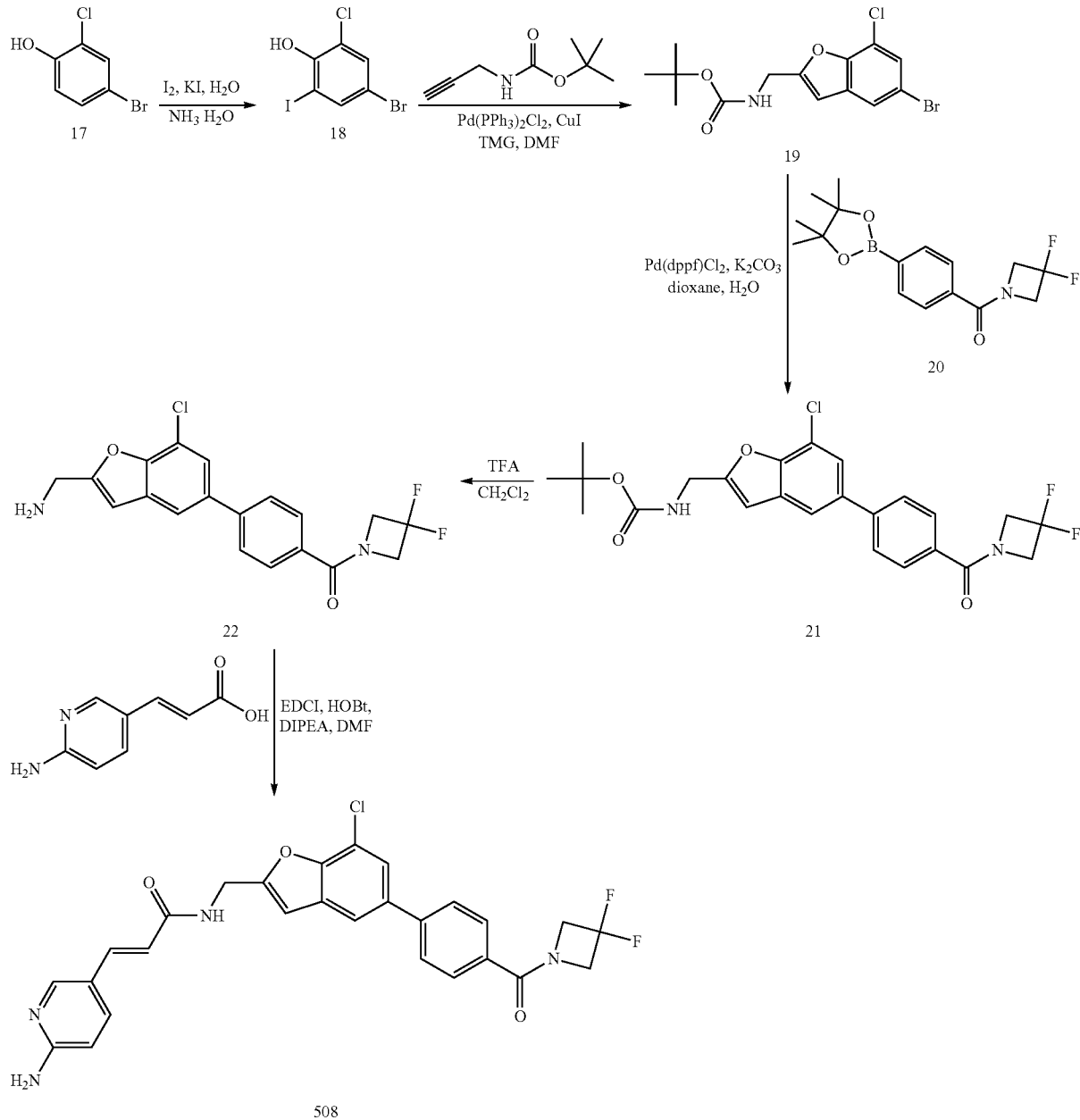

Synthesis of 4-bromo-2-chloro-6-iodophenol (18)

4-Bromo-2-chlorophenol (17) (2.06 g, 10.0 mmol) was dissolved in ammonia (30 mL). KI (0.166 g, 1.0 mmol) in 5 mL of water and iodine (2.54 g, 10.0 mmol) were added at 25° C. and the reaction mixture was stirred at 25° C. for 4 h. The reaction mixture was quenched with water, acidified using concentrated HCl and extracted with ethyl acetate (50 mL×3). The combined organic layers were washed with brine, dried over anhydrous Na$_2$SO$_4$, and concentrated under reduced pressure to obtain crude product, which was puri- Synthesis of tert-butyl (5-bromo-7-chlorobenzofuran-2-yl)methylcarbamate (19)

4-Bromo-2-chloro-6-iodophenol (18) (500 mg, 1.5 mmol) was dissolved in DMF (10 mL). tert-Butyl prop-2-ynylcarbamate (233 mg, 1.5 mmol) and tetramethylguanidine (TMG) (345 mg, 3.0 mmol), CuI (28.8 mg, 0.15 mmol) and Pd(PPh$_3$)$_2$Cl$_2$ (105 mg, 0.15 mmol) were added at 25° C. under nitrogen atmosphere and stirred at 40° C. for 16 h. The reaction mixture was transferred into iced water and extracted with ethyl acetate (50 mL×3). The combined organic layers were washed with brine, dried over anhydrous Na$_2$SO$_4$, and concentrated under reduced pressure to obtain crude product, which was purified by silica gel chromatography (10-20% ethyl acetate/petroleum ether) to provide tert-butyl (5-bromo-7-chlorobenzofuran-2-yl)methylcarbamate (19) (240 mg, 44.4% yield). LCMS: m/z 381.9 [M+Na]$^+$, $t_R$=2.05 min.

Synthesis of tert-butyl (7-chloro-5-(4-(3,3-difluoroazetidine-1-carbonyl) phenyl) benzofuran-2-yl) methylcarbamate (21)

tert-Butyl (7-chloro-5-(4-(3,3-difluoroazetidine-1-carbonyl)phenyl)benzofuran-2-yl)methylcarbamate (21) was synthesized using General Procedure 2. Yield (60%). LCMS: m/z 477.0 [M+H]$^+$, $t_R$=1.91 min.

Synthesis of (4-(2-(aminomethyl)-7-chlorobenzofuran-5-yl) phenyl)(3,3-difluoroazetidin-1-yl) methanone (22)

(4-(2-(Aminomethyl)-7-chlorobenzofuran-5-yl)phenyl)(3,3-difluoroazetidin-1-yl)methanone was synthesized using General Procedure 3 (see below, conversion of 24 to 25). Yield (89%). LCMS: m/z 377.0 [M+H]$^+$, $t_R$=1.36 min.

Synthesis of (E)-3-(6-aminopyridin-3-yl)-N-((7-chloro-5-(4-(3,3-difluoroazetidine-1-carbonyl)phenyl)benzofuran-2-yl)methyl)acrylamide (508)

(E)-3-(6-Aminopyridin-3-yl)-N-((7-chloro-5-(4-(3,3-difluoroazetidine-1-carbonyl)phenyl)benzofuran-2-yl)methyl)acrylamide (508) was synthesized using General Procedure 1. Yield (12%). $^1$H NMR (400 MHz, CD$_3$OD) δ 8.10-7.65 (m, 8H), 7.51-7.36 (m, 2H), 6.95-6.52 (m, 3H), 4.60 (s, 4H), 4.45 (s, 2H). LCMS: m/z 523.1 [M+H]$^+$, $t_R$=1.39 min.

Synthesis of (E)-3-(6-aminopyridin-3-yl)-N-((7-chloro-5-(4-(3,3-difluoroazetidine-1-carbonyl)phenyl)benzo[d]oxazol-2-yl)methyl)acrylamide (509)

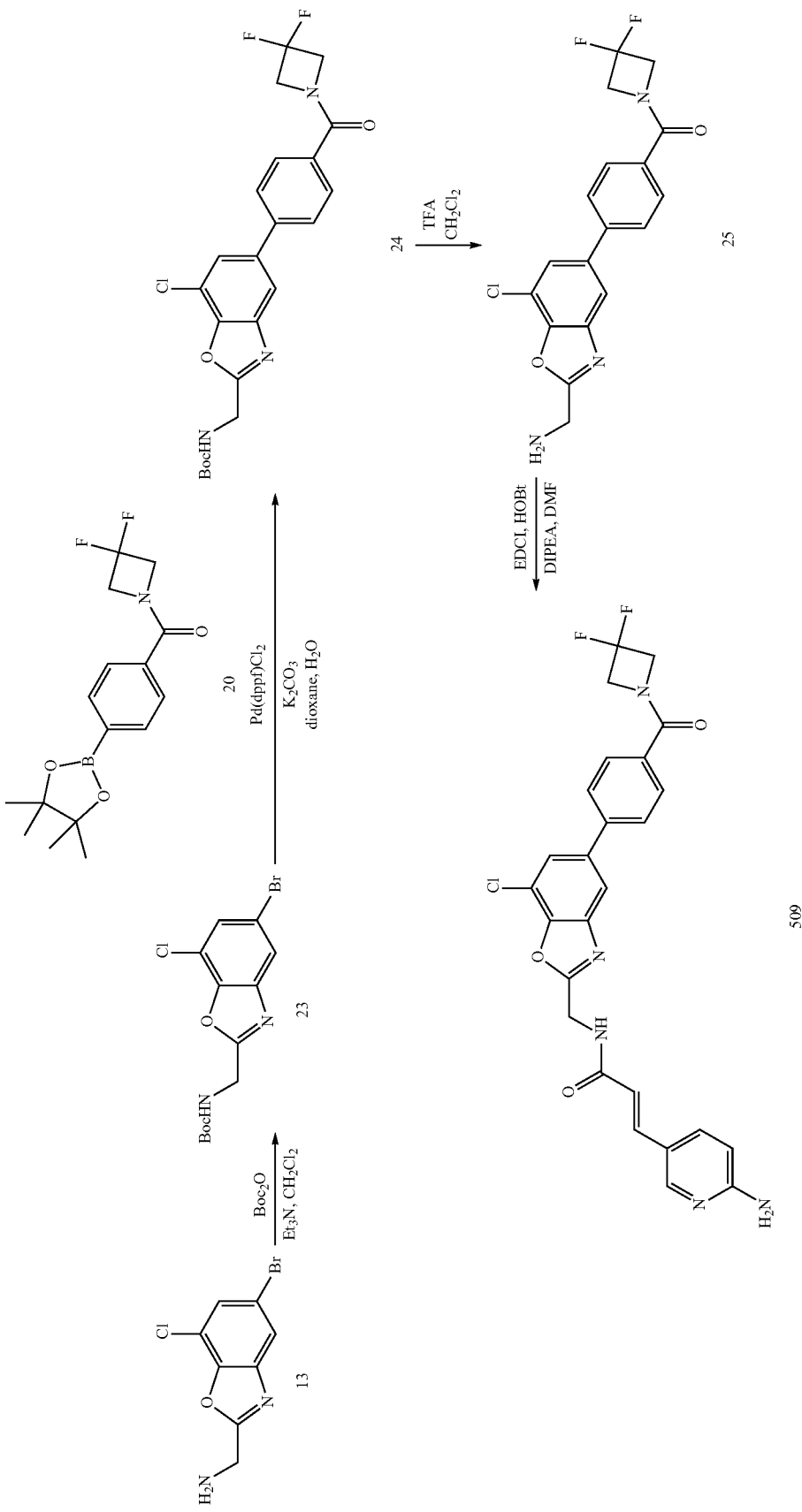

Synthesis of tert-butyl (5-bromo-7-chlorobenzo[d]oxazol-2-yl)methylcarbamate (23)

(5-Bromo-7-chlorobenzo[d]oxazol-2-yl)methanamine (13) (640 mg, 2.46 mmol) was dissolved in dichloromethane (20 mL). Di-tert-butyl dicarbonate (638 mg, 2.95 mmol) and triethylamine (496 mg, 4.92 mmol) were added at 0° C. The reaction mixture was stirred at room temperature for 4 h. The reaction mixture was transferred into iced water and extracted with dichloromethane (50 mL×3). The combined organic layers were washed with brine, dried over anhydrous $Na_2SO_4$, and concentrated under reduced pressure to give crude tert-butyl(5-bromo-7-chlorobenzo[d]oxazol-2-yl)methylcarbamate (23), which was used without further purification in the next step. LCMS: m/z 305.0 [M−55]$^+$, $t_R$=1.87.

Synthesis of tert-butyl (7-chloro-5-(4-(3,3-difluoroazetidine-1-carbonyl)phenyl)benzo[d]oxazol-2-yl)methylcarbamate (24)

A mixture of tert-butyl (5-bromo-7-chlorobenzo[d]oxazol-2-yl)methylcarbamate (23) (310 mg, 0.86 mmol), morpholino(4-(4,4,5,5-tetramethyl-1,3,2-dioxaborolan-2-yl)phenyl)methanone (20) (278 mg, 0.86 mmol), Pd(dppf)Cl$_2$ (63 mg, 0.086 mmol) and $K_2CO_3$ (237 mg, 1.72 mmol) in 15 mL of dioxane and 3 mL of $H_2O$ were stirred at 85° C. under nitrogen atmosphere for 3 h. The reaction mixture was extracted with EtOAc (20 mL×3). The combined organic layers were washed with brine, dried over anhydrous $Na_2SO_4$, and the solvents were removed under reduced pressure to give the crude product, which was purified by silica gel chromatography (20% EtOAc/petroleum ether) to give tert-butyl(7-chloro-5-(4-(3,3-difluoroazetidine-1-carbonyl)phenyl)benzo[d]oxazol-2-yl)methylcarbamate (24) as a yellow solid (yield: 180 mg, 44%). LCMS: m/z 422 [M−55]$^+$; $t_R$=1.77 min.

Synthesis of (4-(2-(aminomethyl)-7-chlorobenzo[d]oxazol-5-yl)phenyl)(3,3-difluoroazetidin-1-yl)methanone (25)

General Procedure 3. Boc Deprotection.

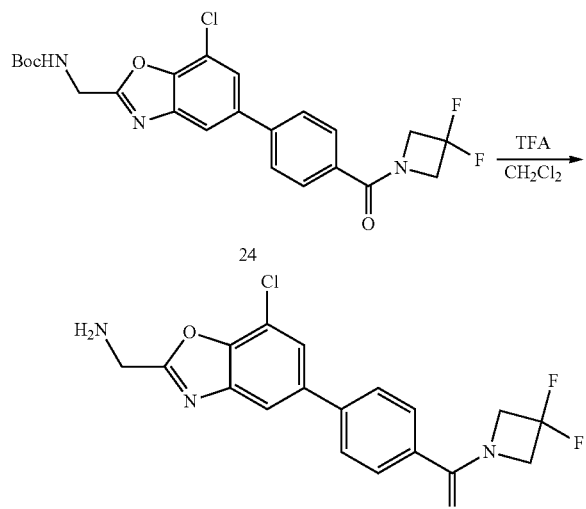

tert-Butyl (7-chloro-5-(4-(3,3-difluoroazetidine-1-carbonyl)phenyl)benzo[d]oxazol-2-yl)methylcarbamate (24) (100 mg, 0.21 mmol) was dissolved in $CH_2Cl_2$ (10 mL). TFA (3 mL) was added at 0° C. The reaction mixture was stirred at room temperature for 2 h, and concentrated under reduced pressure to give crude (4-(2-(aminomethyl)-7-chlorobenzo[d]oxazol-5-yl)phenyl)(3,3-difluoroazetidin-1-yl)methanone (25), which was used without further purification in the next step. Yield (100%). LCMS: m/z 378.1 [M+H]$^+$; $t_R$=1.69 min.

Synthesis of (E)-3-(6-aminopyridin-3-yl)-N-((7-chloro-5-(4-(3,3-difluoroazetidine-1-carbonyl)phenyl)benzo[d]oxazol-2-yl)methyl)acrylamide (509)

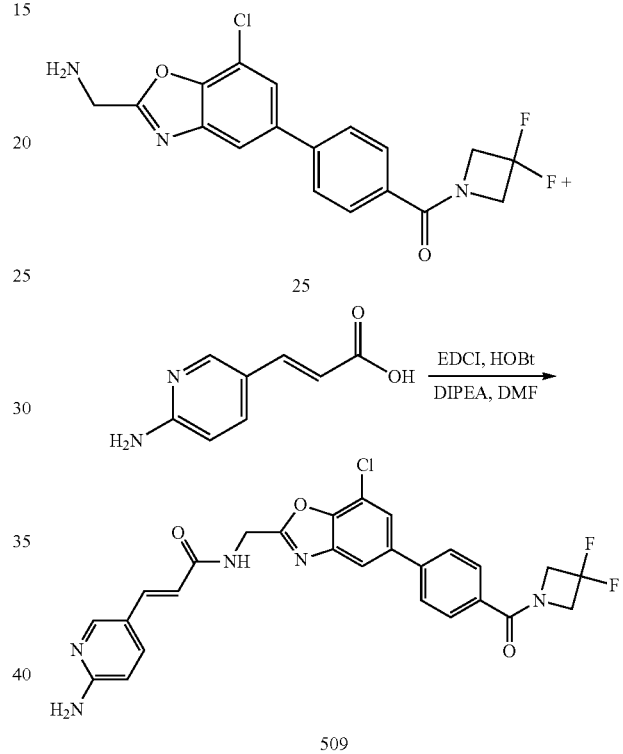

(4-(2-(Aminomethyl)-7-chlorobenzo[d]oxazol-5-yl)phenyl)(3,3-difluoroazetidin-1-yl)methanone (25) (100 mg, 0.265 mmol) was dissolved in DMF (5 mL) and (E)-3-(6-aminopyridin-3-yl)acrylic acid (44 mg, 0.65 mmol) was added at 0° C. EDCl (100 mg, 0.53 mmol) and HOBt (72 mg, 0.53 mmol) were added at 0° C. followed by DIPEA (68 mg, 0.53 mmol) dropwise. The reaction mixture was allowed to warm to room temperature and stirred for 2 h. The reaction mixture was transferred into iced water (20 mL) and extracted with EtOAc (25 mL×3). The combined organic layers were washed with brine, dried over anhydrous $Na_2SO_4$ and concentrated under reduced pressure to give crude product, which was purified by chromatography to afford (E)-3-(6-aminopyridin-3-yl)-N-((7-chloro-5-(4-(3,3-difluoroazetidine-1-carbonyl)phenyl)benzo[d]oxazol-2-yl)methyl)acrylamide (509). Yield (46 mg, 33%). $^1$H NMR (400 MHz, DMSO-d$_6$) δ 8.09-8.08 (m, 1H), 7.92 (d, J=1.5 Hz, 1H), 7.82-7.77 (m, 6H), 7.5 (d, J=15.6 Hz, 1H), 6.63 (d, J=8.9 Hz, 1H), 6.54 (d, J=15.7 Hz, 1H), 4.85-4.83 (m, 4H), 4.63-4.51 (m, 2H). LCMS: m/z 524.2[M+H]$^+$; $t_R$=1.35 min.

Synthesis of (E)-3-(6-aminopyridin-3-yl)-N-((5-(4-(morpholine-4-carbonyl)phenyl)-7-(trifluoromethyl)benzofuran-2-yl)methyl)acrylamide (510)

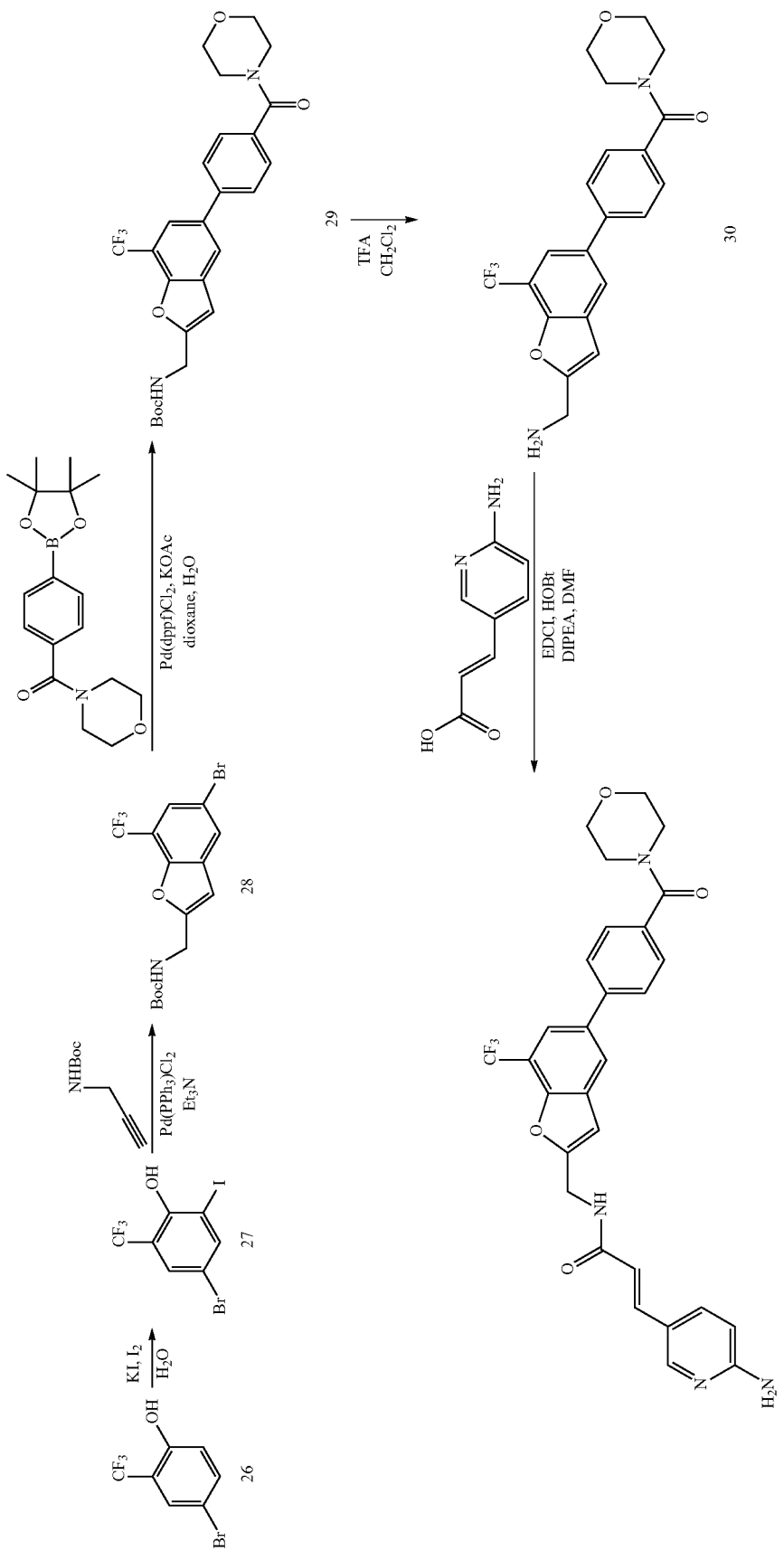

Synthesis of 4-bromo-2-iodo-6-(trifluoromethyl) phenol (27)

A mixture of 4-bromo-2-(trifluoromethyl)phenol (26) (8 g, 33.3 mmol), KI (16 g, 99.9 mmol) and I2 (8.5 g, 33.3 mmol) in 50 mL of $NH_3OH$ and 50 mL of $H_2O$ was stirred at 30° C. for 16 h. HCl was added to the solution to reach a pH of 7. The reaction mixture was extracted with EtOAc (100 mL×3). The combined organic layers were washed with brine, dried over anhydrous $Na_2SO_4$, and concentrated under reduced pressure to give the crude product, which was purified by silica gel chromatography (20% EtOAc/petroleum ether) to give 4-bromo-2-iodo-6-(trifluoromethyl)phenol (27) as a white solid (yield: 8 g, 67%). LCMS: $t_R$=1.53 min.

Synthesis of tert-butyl (5-bromo-7-(trifluoromethyl) benzofuran-2-yl)methylcarbamate (28)

A mixture of 4-bromo-2-iodo-6-(trifluoromethyl)phenol (27) (1 g, 2.7 mmol), tert-butyl prop-2-ynylcarbamate (500 mg, 3.24 mmol), $Pd(PPh_3)Cl_2$ (118 mg, 0.27 mmol) and CuI (51 mg, 0.27 mmol) in 20 mL of triethylamine was stirred at 80° C. under nitrogen atmosphere for 2 h. The reaction mixture was extracted with EtOAc (50 mL×3). The combined organic layers were washed with brine, dried over anhydrous $Na_2SO_4$, and concentrated under reduced pressure to give the crude product, which was purified by silica gel chromatography (20% EtOAc/petroleum ether) to give tert-butyl (5-bromo-7-(trifluoromethyl)benzofuran-2-yl) methylcarbamate (28) as a white solid (yield: 600 mg, 57%). LCMS: m/z 417.9 $[M+Na]^+$; $t_R$=2.04 min.

Synthesis of tert-butyl (5-(4-(morpholine-4-carbonyl)phenyl)-7-(trifluoromethyl)benzofuran-2-yl) methylcarbamate (29)

A mixture of tert-butyl (5-bromo-7-(trifluoromethyl)benzofuran-2-yl)methylcarbamate (28) (200 mg, 0.51 mmol), morpholino(4-(4,4,5,5-tetramethyl-1,3,2-dioxaborolan-2-yl)phenyl)methanone (193 mg, 0.61 mmol), $Pd(dppf)Cl_2$ (38 mg, 0.051 mmol) and KOAc (100 mg, 1.02 mmol) in 8 mL of dioxane and 2 mL of $H_2O$ was stirred at 85° C. under nitrogen atmosphere for 2 h. The mixture was extracted with EtOAc (20 mL×3). The combined organic layers were washed with brine, dried over anhydrous $Na_2SO_4$, and concentrated under reduced pressure to give the crude product, which was purified by silica gel chromatography (40% EtOAc/petroleum ether) to give tert-butyl (5-(4-(morpholine-4-carbonyl)phenyl)-7-(trifluoromethyl)benzofuran-2-yl)methylcarbamate 7 as a white solid. (yield: 150 mg, 47%). LCMS: m/z 505.0 $[M+H]^+$; $t_R$=1.85 min.

Synthesis of (4-(2-(Aminomethyl)-7-(trifluoromethyl)benzofuran-5-yl)phenyl)(morpholino)methanone (30)

tert-Butyl (5-(4-(morpholine-4-carbonyl)phenyl)-7-(trifluoromethyl)benzofuran-2-yl)methylcarbamate 29 (120 mg, 0.24 mmol) was dissolved in $CH_2Cl_2$ (4 mL). TFA (1 mL) was added at 0° C. The reaction mixture was stirred at room temperature for 2 h, and concentrated under reduced pressure to give crude (4-(2-(aminomethyl)-7-(trifluoromethyl) benzofuran-5-yl)phenyl)(morpholino)methanone (30), which was used without further purification in the next step. Yield (100%). LCMS: m/z 405.0$[M+H]^+$; $t_R$=1.316 min.

Synthesis of (E)-3-(6-aminopyridin-3-yl)-N-((5-(4-(morpholine-4-carbonyl)phenyl)-7-(trifluoromethyl) benzofuran-2-yl)methyl)acrylamide (510)

(4-(2-(Aminomethyl)-7-(trifluoromethyl)benzofuran-5-yl)phenyl)(morpholino)methanone (30) (crude product from previous step, 0.24 mmol) was dissolved in DMF (3 mL) and (E)-3-(6-aminopyridin-3-yl)acrylic acid (39 mg, 0.24 mmol). The reaction mixture was cooled to 0° C. EDCI (55 mg, 0.28 mmol) and HOBt (32 mg, 0.24 mmol) were added to this reaction mixture at 0° C. followed by DIPEA (93 mg, 0.72 mmol) dropwise. The reaction mixture was allowed to warm to room temperature and stirred further for 2 h. The reaction mixture was transferred into water (20 mL) and extracted with EtOAc (25 mL×3). The combined organic layers were washed with brine, dried over anhydrous $Na_2SO_4$ and concentrated under reduced pressure to give crude product, which was purified by preparative HPLC to afford (E)-3-(6-aminopyridin-3-yl)-N-((5-(4-(morpholine-4-carbonyl)phenyl)-7-(trifluoromethyl)benzofuran-2-yl) methyl)acrylamide (yield: 68 mg, 52%). $^1H$ NMR (400 MHz, DMSO-$d_6$) δ 8.89 (t, J=5.7 Hz, 1H), 8.25-8.21 (m, 4H), 8.11 (dd, J=2.0 Hz, J=9.2 Hz, 1H), 7.87-7.82 (m, 3H), 7.64 (d, J=8.2 Hz, 1H), 7.44 (d, J=15.8 Hz, 1H), 7.00-6.96 (m, 2H), 6.62 (d, J=15.8 Hz, 1H), 4.64 (d, J=5.7 Hz, 1H), 3.41-3.32 (m, 8H). LCMS: m/z 551.1 $[M+H]^+$; $t_R$=1.423 min.

Synthesis of (E)-3-(6-aminopyridin-3-yl)-N-((7-tert-butyl-5-(4-(morpholine-4-carbonyl)phenyl)benzofuran-2-yl)methyl)acrylamide (511)

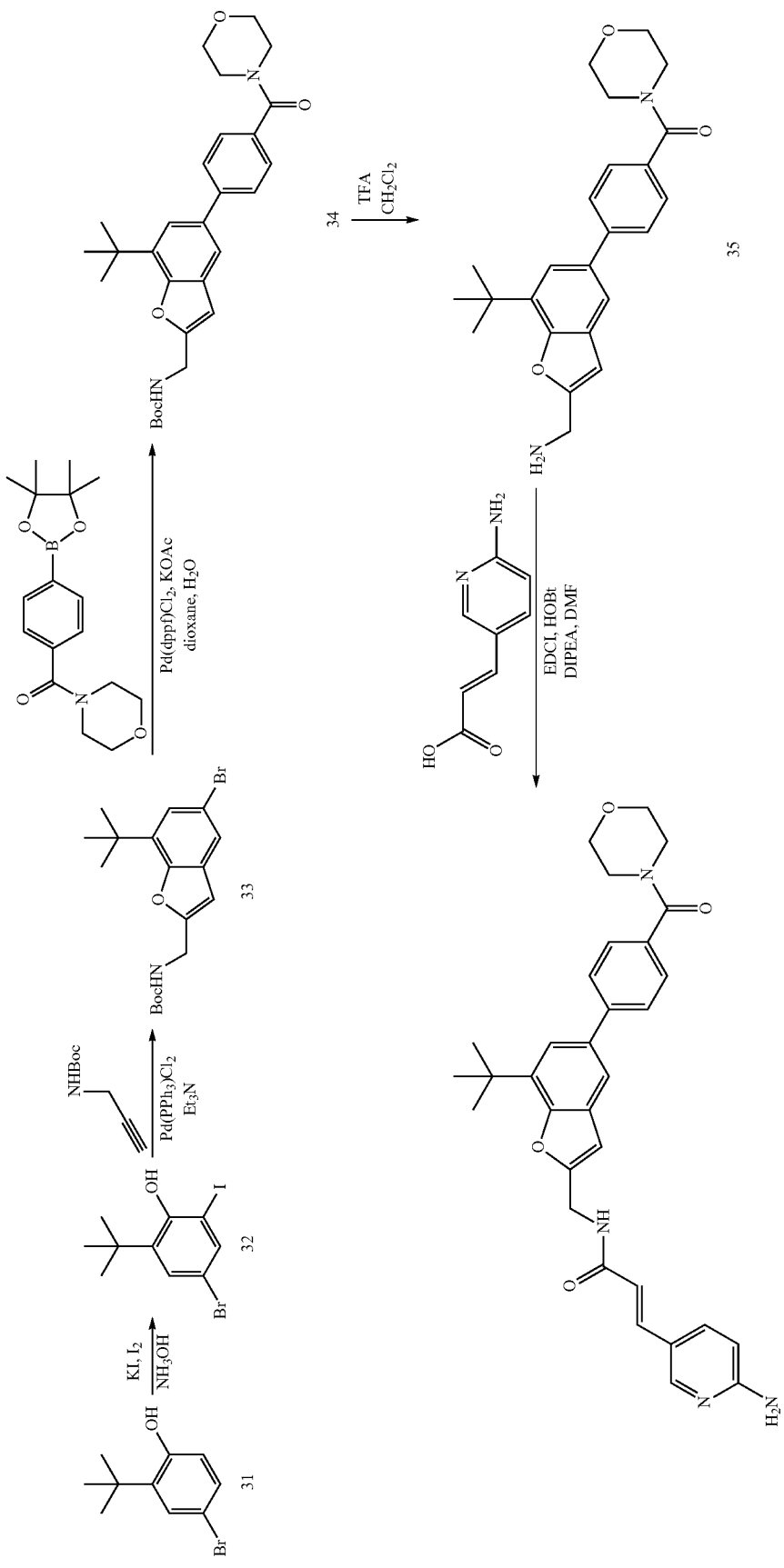

4-Bromo-2-tert-butyl-6-iodophenol (32) was synthesized in accordance with the procedure described above for the conversion of 26 to 27. Yield (37%). $^1$H NMR (400 MHz, CDCl$_3$) δ 7.66 (d, J=2.5 Hz, 1H), 7.36 (d, J 2.2 Hz, 1H), 5.51 (s, 1H), 1.39 (s, 9H).

tert-Butyl (5-bromo-7-tert-butylbenzofuran-2-yl)methylcarbamate (33) was synthesized in accordance with the procedure described above for the conversion of 27 to 28. Yield (27%). LCMS: t$_R$=1.427 min.

tert-Butyl (7-tert-butyl-5-(4-(morpholine-4-carbonyl) phenyl)benzofuran-2-yl)methylcarbamate (35) was synthesized using General Procedure 2. Yield (59%). LCMS: m/z 493.2 [M+H]$^+$; t$_R$=1.945 min.

(4-(2-(Aminomethyl)-7-tert-butylbenzofuran-5-yl)phenyl)(morpholino)methanone 35 was synthesized using General Procedure 3. Yield (100%). LCMS: m/z 393.1 [M+H]$^+$; t$_R$=0.874 min.

((E)-3-(6-Aminopyridin-3-yl)-N-((7-tert-butyl-5-(4-(morpholine-4-carbonyl) phenyl) benzofuran-2-yl)methyl) acrylamide (511) was synthesized using General Procedure 1. Yield (40%). $^1$H NMR (400 MHz, DMSO-d$_6$) δ 8.79 (t, J=6.2 Hz, 1H), 8.21 (s, 1H), 8.15-8.08 (m, 2H), 7.75-7.73 (m, 3H), 7.51-7.44 (m, 3H), 7.37 (d, J=1.8 Hz, 1H), 6.97 (d, J=9.4 Hz, 1H), 6.76 (s, 1H), 6.61 (d, J=16 Hz, 1H), 4.61 (d, J=5.9 Hz, 1H), 3.71-3.40 (m, 8H), 1.50 (s, 9H). LCMS: m/z 539.2 [M+H]$^+$; t$_R$=1.477 min.

Synthesis of (E)-3-(6-aminopyridin-3-yl)-N-(2-(7-chloro-5-(4-(morpholine-4-carbonyl)phenyl)benzofuran-2-yl)propan-2-yl)acrylamide (512)

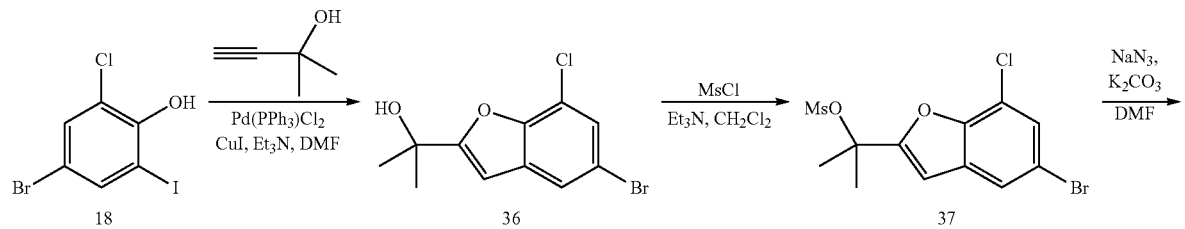

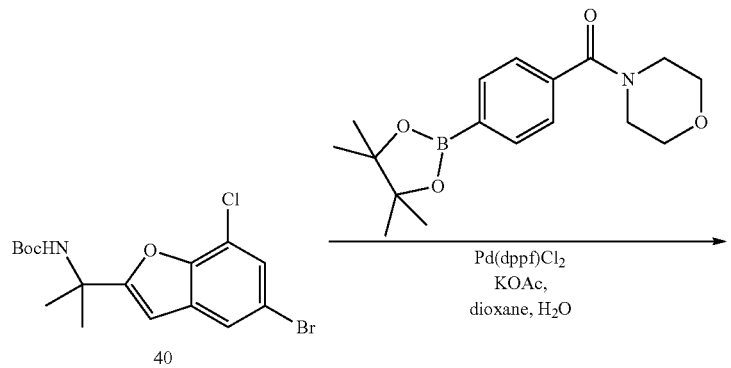

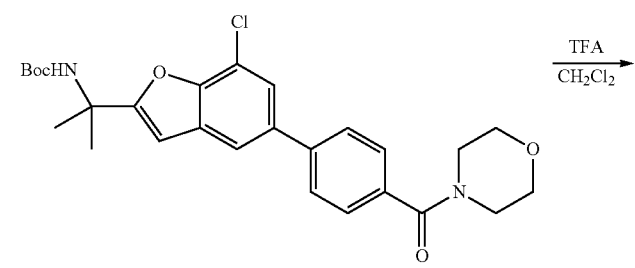

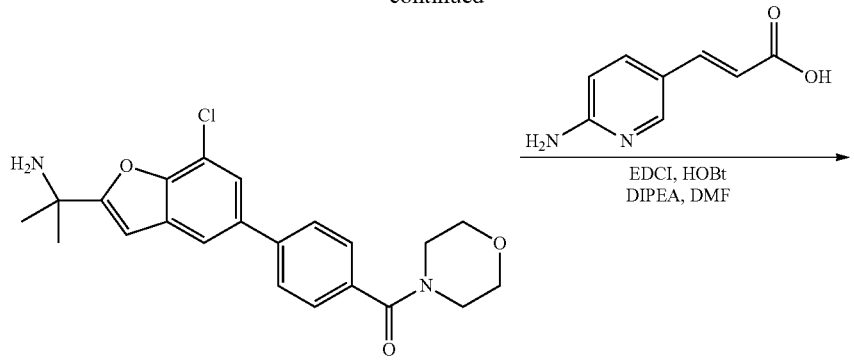

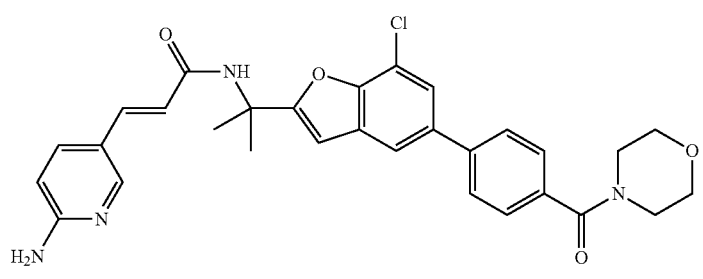

Synthesis of 2-(5-bromo-7-chlorobenzofuran-2-yl)propan-2-ol (36)

2-(5-Bromo-7-chlorobenzofuran-2-yl)propan-2-ol (36) was synthesized was synthesized in accordance with the procedure described above for the conversion of 27 to 28. Yield (71%). LCMS: m/z=271.0 [M-OH]$^+$; $t_R$=1.192 min.

Synthesis of 2-(5-bromo-7-chlorobenzofuran-2-yl)propan-2-yl methanesulfonate (37)

2-(5-Bromo-7-chlorobenzofuran-2-yl)propan-2-ol (36) (500 mg, 1.74 mmol) was dissolved in dichloromethane (15 mL). Methane sulfonyl chloride (299 mg, 2.08 mmol) and triethylamine (263 mg, 2.61 mmol) were added at 0° C. and the reaction mixture was allowed to warm to room temperature and stirred for 4 h. The reaction mixture was transferred into iced water and extracted with dichloromethane (20 mL×3). The combined organic layers were washed with brine, dried over anhydrous Na$_2$SO$_4$, and concentrated under reduced pressure to give crude 2-(5-bromo-7-chlorobenzofuran-2-yl)propan-2-yl methanesulfonate (37), which was used in the next step without further purification. LCMS: m/z 270.9 [M-OMs]$^+$; $t_R$=1.38 min.

Synthesis of 2-(2-azidopropan-2-yl)-5-bromo-7-chlorobenzofuran (38)

2-(5-Bromo-7-chlorobenzofuran-2-yl)propan-2-yl methanesulfonate (37) (crude, 1.74 mmol) was dissolved in DMF (5 mL). Sodium azide (226 mg, 3.48 mmol) was added at room temperature. The reaction mixture was refluxed at 80° C. for 2 h. After cooling to room temperature, the mixture was transferred into iced water, and extracted with ethyl acetate (50 mL×3). The combined organic layers were washed with brine, dried over anhydrous Na$_2$SO$_4$, and concentrated under reduced pressure to give 450 mg crude 2-(2-azidopropan-2-yl)-5-bromo-7-chlorobenzofuran (38), which was used in the next step without further purification. LCMS: m/z 270.9 [M-N$_3$]$^+$; $t_R$=1.37 min.

Synthesis of 2-(5-bromo-7-chlorobenzofuran-2-yl)propan-2-amine (39)

2-(2-Azidopropan-2-yl)-5-bromo-7-chlorobenzofuran (38) (100 mg, 0.32 mmol) was dissolved in methanol (2 mL). Raney Ni (100 mg, wet) was added under hydrogen atmosphere and the mixture was stirred at room temperature for 1 h. The reaction mixture was filtered and the filtrate was concentrated under reduced pressure to give 70 mg of crude 2-(5-bromo-7-chlorobenzofuran-2-yl)propan-2-amine (39), which was used without further purification in the next step. LCMS: m/z 271 [M-NH$_2$]$^+$; $t_R$=0.87 min.

Synthesis of tert-butyl 2-(5-bromo-7-chlorobenzofuran-2-yl)propan-2-ylcarbamate (40)

2-(5-Bromo-7-chlorobenzofuran-2-yl)propan-2-amine (39) (220 mg, 0.77 mmol) was dissolved in dichloromethane (5 mL) and de-tert-butyl dicarbonate (184 mg, 0.847 mmol) was added at 0° C. Triethylamine (116 mg, 1.15 mmol) was added into the reaction mixture and stirred at room temperature for 4 h. The reaction mixture was transferred into iced water and extracted with dichloromethane (50 mL×3). The combined organic layers were washed with brine, dried over anhydrous Na$_2$SO$_4$, and concentrated under reduced pressure to give the crude product, which was purified by chromatography (0-10% ethyl acetate/n-hexane) to give tert-butyl 2-(5-bromo-7-chlorobenzofuran-2-yl)propan-2-ylcarbamate 57. Yield (100 mg, 87%). LCMS: m/z 410.0 [M+Na]$^+$; $t_R$=1.33 mmin.

101

Synthesis of tert-butyl 2-(7-chloro-5-(4-(morpholine-4-carbonyl)phenyl)benzofuran-2-yl)propan-2-ylcarbamate (41)

tert-Butyl 2-(7-chloro-5-(4-(morpholine-4-carbonyl)phenyl)benzofuran-2-yl)propan-2-ylcarbamate (41) was synthesized using General Procedure 2. Yield (78%). LCMS: m/z 499.1 [M+H]$^+$, $t_R$=1.90 min.

Synthesis of (4-(2-(2-aminopropan-2-yl)-7-chlorobenzofuran-5-yl)phenyl)(morpholino)methanone (42)

(4-(2-(2-Aminopropan-2-yl)-7-chlorobenzofuran-5-yl)phenyl)(morpholino)methanone (42) was synthesized using General Procedure 3. Yield (100%). LCMS: m/z 382.0 [M-NH$_2$]$^+$, $t_R$=1.337 min.

102

Synthesis of (E)-3-(6-aminopyridin-3-yl)-N-(2-(7-chloro-5-(4-(morpholine-4-carbonyl)phenyl)benzofuran-2-yl)propan-2-yl)acrylamide (512)

(E)-3-(6-Aminopyridin-3-yl)-N-(2-(7-chloro-5-(4-(morpholine-4-carbonyl)phenyl)benzofuran-2-yl)propan-2-yl)acrylamide (512) was synthesized using General Procedure 1. Yield (11%). $^1$H NMR (400 MHz, DMSO-d$_6$) δ 8.51 (s, 1H), 8.12 (d, J=1.6 Hz, 1H), 7.99 (d, J=9.9 Hz, 2H), 7.87 (d, J=1.6 Hz, 1H), 7.78 (d, J=8.3 Hz, 2H), 7.67 (d, J=1.6 Hz, 1H), 7.52 (d, J=8.3 Hz, 2H), 7.25 (d, J=15.6 Hz, 1H), 6.93 (d, J=9.0 Hz, 1H), 6.84 (s, 1H), 6.61 (d, J=15.8 Hz, 1H), 3.71-3.55 (m, 8H), 1.72 (s, 6H). LCMS: m/z 545.1 [M+H]$^+$, $t_R$=1.498 min.

Synthesis of (E)-3-(6-aminopyridin-3-yl)-N-((7-chloro-5-(2-methyl-1-oxoisoindolin-5-yl)benzofuran-2-yl)methyl)acrylamide (513)

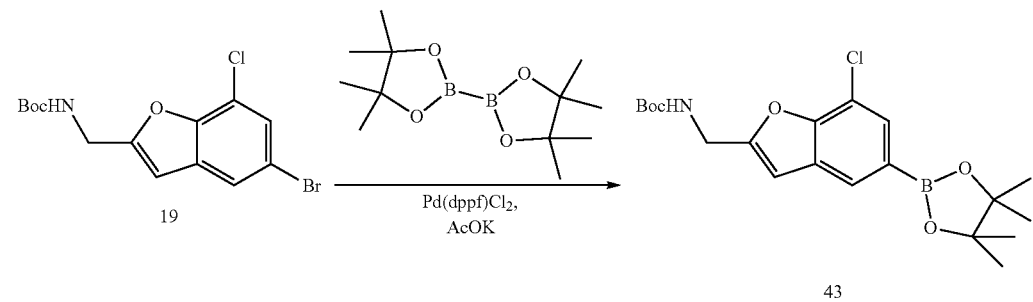

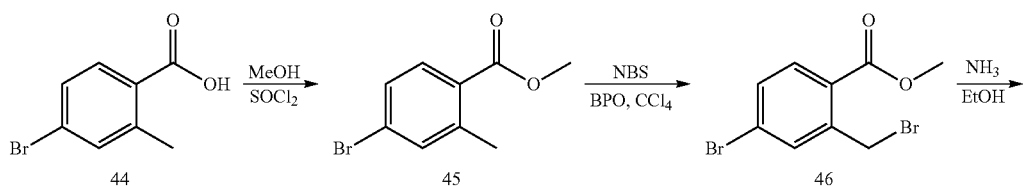

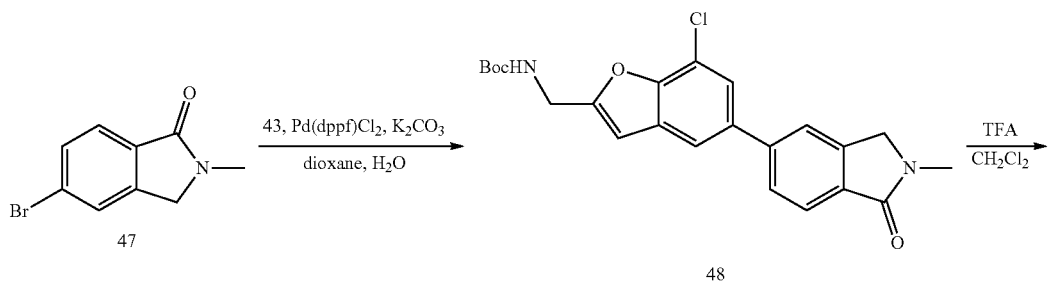

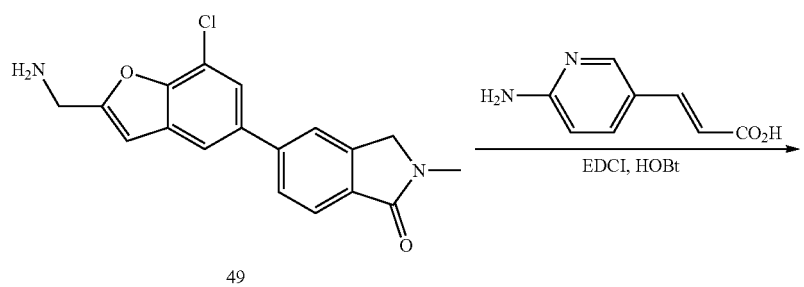

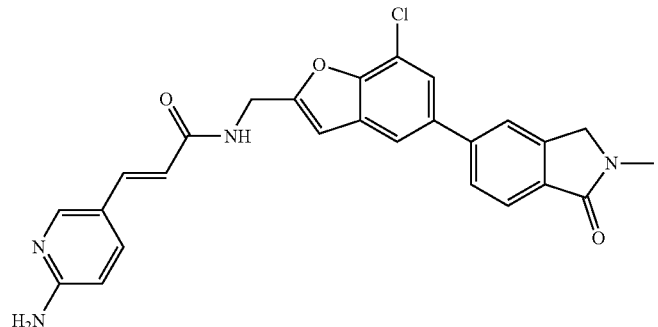

513

Synthesis of tert-butyl ((7-chloro-5-(4,4,5,5-tetramethyl-1,3,2-dioxaborolan-2-yl)benzofuran-2-yl)methyl)carbamate (43)

tert-Butyl ((7-chloro-5-(4,4,5,5-tetramethyl-1,3,2-dioxaborolan-2-yl)benzofuran-2-yl)methyl)carbamate (43) was synthesized in accordance with the procedure described below for the synthesis of (tert-Butyl (5-(4,4,5,5-tetramethyl-1,3,2-dioxaborolan-2-yl)-7-(trifluoromethyl)benzofuran-2-yl)methylcarbamate (60).

Synthesis of methyl 4-bromo-2-methylbenzoate (45)

4-Bromo-2-methylbenzoic acid (44) (2.5 g, 11.6 mmol) was dissolved in methanol (30 mL). $SOCl_2$ (4069 mg, 34.2 mmol) was added at 0° C. After the addition, the mixture was refluxed overnight. The mixture was concentrated to obtain crude methyl 4-bromo-2-methylbenzoate 45, which was used in the next step without further purification. Yield (75.5%). LCMS: m/z 229 [M+H]$^+$, $t_R$=1.91 min.

Synthesis of methyl 4-bromo-2-(bromomethyl)benzoate (46)

A solution of methyl 4-bromo-2-methylbenzoate 45 (2000 mg, 8.77 mmol), N-bromosuccinimide (NBS) (3035 mg, 17.54 mmol), benzoyl peroxide (BPO) (1061 mg, 4.39 mmol) in $CCl_4$ (20 mL) was refluxed overnight under nitrogen atmosphere. After cooling to room temperature, the mixture was washed with brine (20 mL×2) and dried over anhydrous $Na_2SO_4$. The solvent was removed under reduced pressure to give the crude product, which was purified by silica gel chromatography (2-5% EtOAc/petroleum ether) to give methyl 4-bromo-2-(bromomethyl)benzoate 46 as a white solid (yield: 1.8 g, 67%). LCMS: m/z 308.7 [M+H]$^+$; $t_R$=1.88 min.

Synthesis of 5-bromo-2-methylisoindolin-1-one (47)

A solution of 4-bromo-2-(bromomethyl)benzoate 46 (1000 mg, 3.27 mmol) in 30% ammonia in ethanol (10 mL) was heated at reflux overnight. The solvent was removed under reduced pressure and the residue was poured into 10 mL of water and extracted with ethyl acetate (15 mL×3). The combined organic layers were dried over anhydrous $Na_2SO_4$. The solvent was removed under reduced pressure to give the crude product, which was purified by silica gel chromatography (30% EtOAc/petroleum ether) to give 5-bromo-2-methylisoindolin-1-one 47 as a white solid (yield: 400 mg, 54%). LCMS: m/z 226.7 [M+H]$^+$; $t_R$=1.49 min.

Synthesis of tert-butyl (7-chloro-5-(2-methyl-1-oxoisoindolin-5-yl)benzofuran-2-yl)methylcarbamate (48)

tert-Butyl (7-chloro-5-(2-methyl-1-oxoisoindolin-5-yl)benzofuran-2-yl)methylcarbamate (48) was synthesized using General Procedure 2. Yield (79%). LCMS: m/z 427 [M+H]$^+$, $t_R$=1.20 min. Synthesis of 5-(2-(aminomethyl)-7-chlorobenzofuran-5-yl)-2-methylisoindolin-1-one (49): 5-(2-(Aminomethyl)-7-chlorobenzofuran-5-yl)-2-methylisoindolin-1-one (49) was synthesized using General Procedure 3. Yield (70%). LCMS: m/z 327 [M+H]$^+$; $t_R$=1.17 min.

Synthesis of (E)-3-(6-aminopyridin-3-yl)-N-((7-chloro-5-(2-methyl-1-oxoisoindolin-5-yl)benzofuran-2-yl)methyl)acrylamide (513)

(E)-3-(6-Aminopyridin-3-yl)-N-((7-chloro-5-(2-methyl-1-oxoisoindolin-5-yl)benzofuran-2-yl)methyl)acrylamide (513) was synthesized using General Procedure 1. Yield (13.8%). $^1$H NMR (400 MHz, DMSO-d$_6$) δ 8.67-8.64 (t, J=5.6 Hz, 1H), 8.08 (s, 1H), 7.94-7.93 (m, 2H), 7.82-7.61 (m, 5H), 7.36 (d, J=15.6 Hz, 1H), 6.91 (s, 1H), 6.49-6.41 (m, 3H), 4.61-4.52 (m, 4H), 3.10 (s, 3H). LCMS: m/z 473.7 [M+H]$^+$; $t_R$=1.55 min.

Synthesis of (E)-3-(6-aminopyridin-3-yl)-N-((7-chloro-5-(2-methyl-1,3-dioxoisoindolin-5-yl)benzofuran-2-yl)methyl)acrylamide (514)
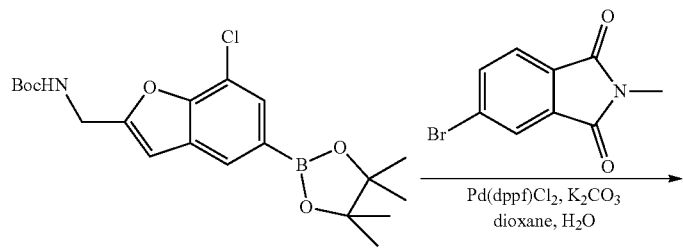
43
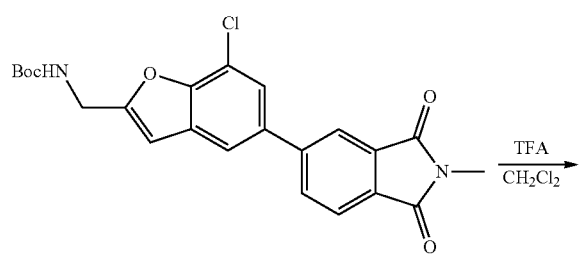
50
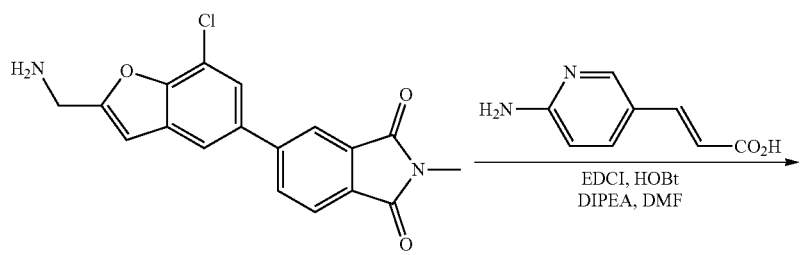
51
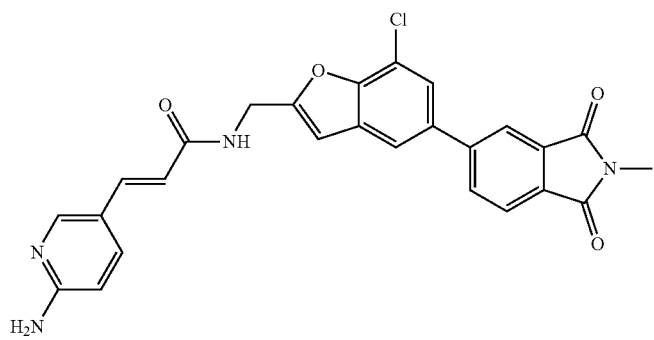
514 tert-Butyl(7-chloro-5-(2-methyl-1,3-dioxoisoindolin-5-yl)benzofuran-2-yl)methylcarbamate (50) was synthesized using General Procedure 2. Yield (63%). LCMS: m/z 463.7 [M+Na]$^+$, $t_R$=1.90 min.

5-(2-(Aminomethyl)-7-chlorobenzofuran-5-yl)-2-methylisoindoline-1,3-dione (51) was synthesized using General Procedure 3. Yield (65%). LCMS: m/z 324 [M-NH$_2$]$^+$; $t_R$=1.22 min.

(E)-3-(6-Aminopyridin-3-yl)-N-((7-chloro-5-(2-methyl-1,3-dioxoisoindolin-5-yl)benzofuran-2-yl)methyl)acrylamide (514) was synthesized using General Procedure 1. Yield (35%). $^1$H NMR (400 MHz, DMSO-d$_6$) δ 8.66-8.34 (t, J=5.6 Hz, 1H), 8.17-8.05 (m, 4H), 7.94-7.87 (m, 2H), 7.62 (d, J=8.8 Hz, 1H), 7.36 (d, J=15.6 Hz, 1H), 6.91 (s, 1H), 6.49-6.41 (m, 3H), 4.61 (d, J=5.6 Hz, 2H), 3.07 (s, 3H). LCMS: m/z 488.7 [M+H]$^+$; $t_R$=1.79 min.

Synthesis of (S,E)-3-(6-aminopyridin-3-yl)-N-((7-chloro-5-(4-(3-methylmorpholine-4-carbonyl)phenyl)benzofuran-2-yl)methyl)acrylamide (515)

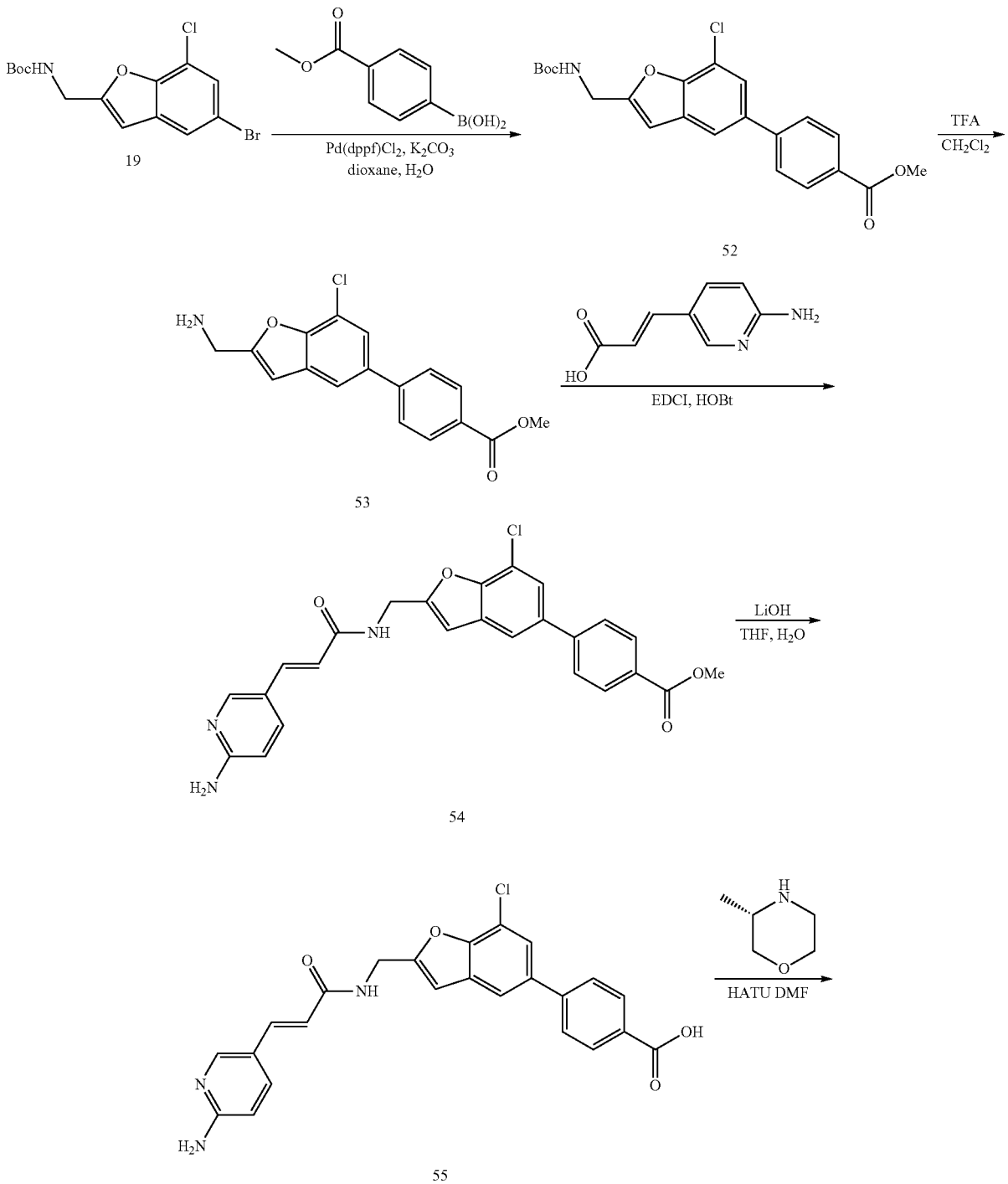

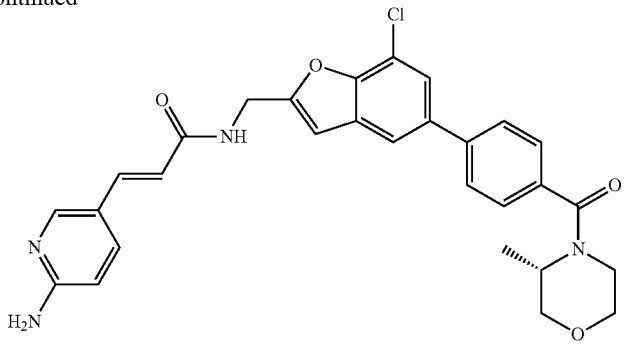

515

Methyl 4-(2-((tert-butoxycarbonylamino)methyl)-7-chlorobenzofuran-5-yl)benzoate (52)

Methyl 4-(2-((tert-butoxycarbonylamino)methyl)-7-chlorobenzofuran-5-yl)benzoate (52) was synthesized using General Procedure 2. Yield (60%). LCMS: m/z: 438 [M+Na]$^+$, $t_R$=1.95 min.

Methyl 4-(2-(aminomethyl)-7-chlorobenzofuran-5-yl)benzoate (53)

Methyl 4-(2-(aminomethyl)-7-chlorobenzofuran-5-yl)benzoate (53) was synthesized using General Procedure 3. Yield (79%). LCMS: m/z: 299 [M-NH$_2$]$^+$; $t_R$=1.01 min.

(E)-Methyl 4-(2-((3-(6-aminopyridin-3-yl)acrylamido)methyl)-7-chlorobenzofuran-5-yl)benzoate (54)

(E)-Methyl 4-(2-((3-(6-aminopyridin-3-yl)acrylamido)methyl)-7-chlorobenzofuran-5-yl)benzoate (54) was synthesized using General Procedure 1. Yield (47.8%). LCMS: m/z: 462.7 [M+H]$^+$; $t_R$=1.35 min.

(E)-4-(2-((3-(6-Aminopyridin-3-yl)acrylamido)methyl)-7-chlorobenzofuran-5-yl)benzoic acid (55)

(E)-Methyl 4-(2-((3-(6-aminopyridin-3-yl)acrylamido)methyl)-7-chlorobenzofuran-5-yl)benzoate (54) (350 mg, 0.759 mmol) was dissolved in 5 mL THF and 5 mL H$_2$O. LiOH (64 mg, 1.52 mmol) was added at 0° C. Then reaction mixture was stirred at room temperature for 4 h. The reaction mixture was transferred into water and neutralized with dilute HCl (1N, until pH 3). The mixture was extracted with ethyl acetate (50 mL×3). The combined organic layers were washed with brine, dried over anhydrous Na$_2$SO$_4$ and concentrated under reduced pressure to obtain (E)-4-(2-((3-(6-aminopyridin-3-yl)acrylamido)methyl)-7-chlorobenzofuran-5-yl)benzoic acid (55). Yield (300 mg, 88%). LCMS: m/z: 447.7 [M+H]$^+$; $t_R$=1.29 min.

Synthesis of (S,E)-3-(6-aminopyridin-3-yl)-N-((7-chloro-5-(4-(3-methylmorpholine-4-carbonyl)phenyl)benzofuran-2-yl)methyl)acrylamide (515)

(E)-4-(2-((3-(6-Aminopyridin-3-yl)acrylamido)methyl)-7-chlorobenzofuran-5-yl)benzoic acid (55) (60 mg, 0.134 mmol) was dissolved in DMF (2 mL) and (S)-2-methylmorpholine (16 mg, 0.161 mmol) was added at 0° C. HATU (102 mg, 0.268 mmol) was added to this reaction mixture at 0° C. The reaction mixture was allowed to warm to room temperature and stirred overnight. The mixture was directly purified by chromatography to afford (S,E)-3-(6-aminopyridin-3-yl)-N-((7-chloro-5-(4-(3-methylmorpholine-4-carbonyl)phenyl)benzofuran-2-yl)methyl)acrylamide (515). Yield (12 mg, 14%). $^1$H NMR (400 MHz, MeOD-d$_6$) δ 8.65 (s, 1H), 8.08-7.34 (m, 9H), 6.89 (s, 1H), 6.41 (s, 4H), 4.60 (s, 2H), 3.81-3.35 (m, 7H), 1.25 (s, 3H). LCMS: m/z 531.2 [M+H]$^+$; $t_R$=1.72 min.

Synthesis of (R,E)-3-(6-aminopyridin-3-yl)-N-((7-chloro-5-(4-(3-methylmorpholine-4-carbonyl)phenyl)benzofuran-2-yl)methyl)acrylamide (516)

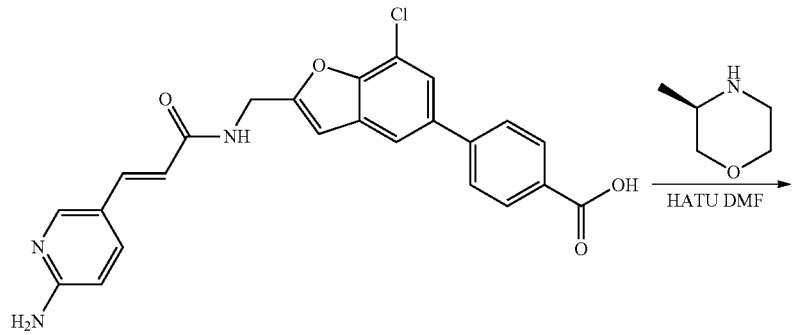

55

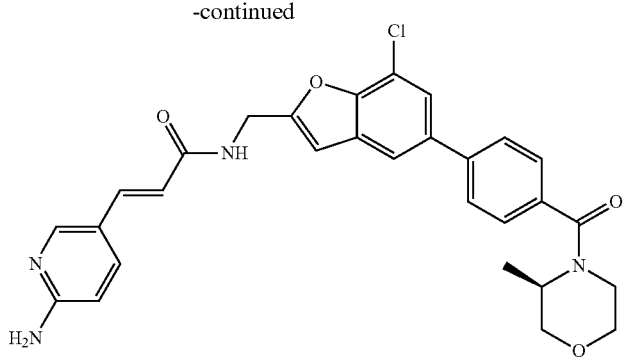

516

(R,E)-3-(6-Aminopyridin-3-yl)-N-((7-chloro-5-(4-(3-methylmorpholine-4-carbonyl)phenyl)benzofuran-2-yl)methyl)acrylamide (516) was synthesized in accordance with the procedure described above for the synthesis of (S,E)-3-(6-aminopyridin-3-yl)-N-((7-chloro-5-(4-(3-methylmorpholine-4-carbonyl)phenyl)benzofuran-2-yl)methyl)acrylamide (515). Yield (17%). $^1$H NMR (400 MHz, DMSO-$d_6$) δ 8.64 (t, J=4.8 Hz, 1H), 8.08 (s, 1H), 7.90 (s, 1H), 7.80-7.72 (m, 4H), 7.62 (d, J=8.8 Hz, 1H), 7.48 (d, J=8.0 Hz, 2H), 7.35 (d, J=15.6 Hz, 1H), 6.90 (s, 1H), 6.49-6.41 (m, 4H), 4.60 (d, J=5.2 Hz, 1H), 3.80-3.31 (m, 7H), 1.27 (d, J=7.20 Hz, 3H). LCMS: m/z 531.2 [M+H]$^+$; $t_R$=1.74 min.

Synthesis of (E)-3-(6-aminopyridin-3-yl)-N-((5-(4-(3,3-dimethylmorpholine-4-carbonyl)phenyl)-7-(trifluoromethyl)benzofuran-2-yl)methyl)acrylamide (517)

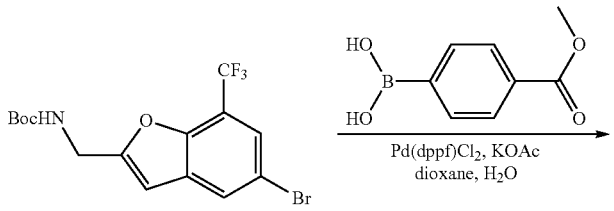

28

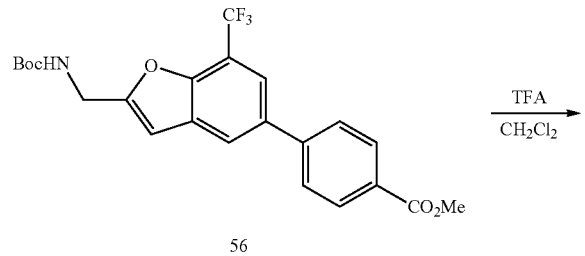

56

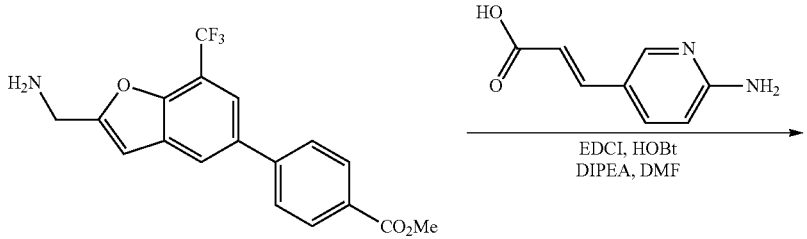

57

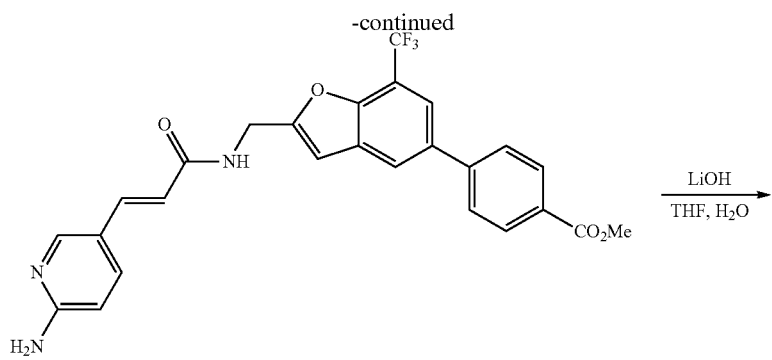

58

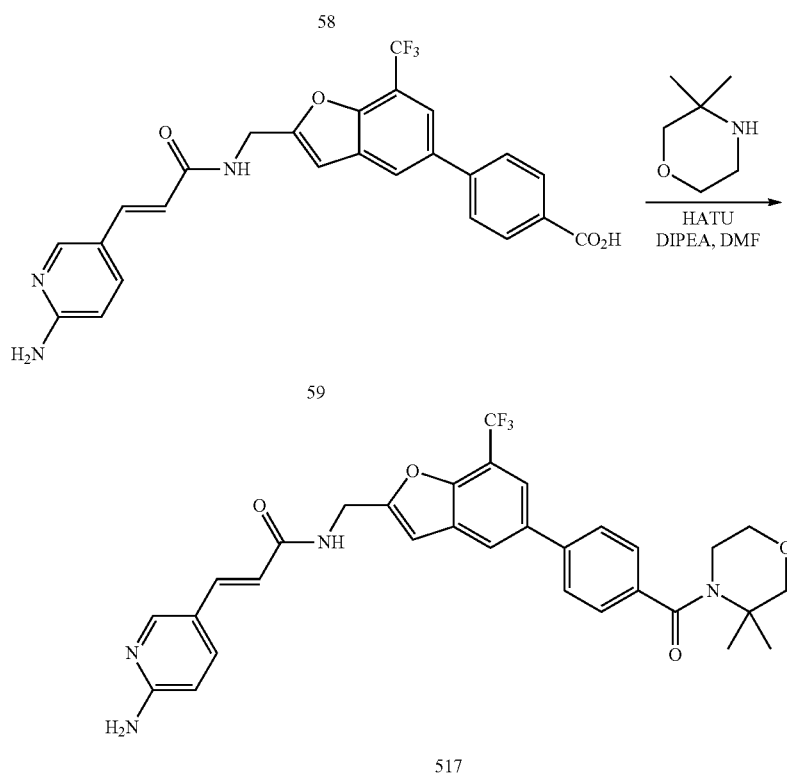

Synthesis of methyl 4-(2-((tert-butoxycarbonylamino)methyl)-7-(trifluoromethyl)benzofuran-5-yl)benzoate (56)

A mixture of tert-butyl (5-bromo-7-(trifluoromethyl)benzofuran-2-yl)methylcarbamate (28) (3.5 g, 8.9 mmol), 4-(methoxycarbonyl)phenylboronic acid (2.0 g, 10.7 mmol), Pd(dppf)Cl$_2$ (679 mg, 0.89 mmol) and KOAc (1.8 g, 17.8 mmol) in 20 mL of dioxane and 1 mL of H$_2$O was stirred at 85° C. under nitrogen atmosphere for 2 h. The mixture was extracted with EtOAc (20 mL×3). The combined organic layers were washed with brine and dried over anhydrous Na$_2$SO$_4$, and the solvents were removed under reduced pressure to give the crude product, which was purified by silica gel chromatography (40% EtOAc/petroleum ether) to give methyl 4-(2-((tert-butoxycarbonylamino)methyl)-7-(trifluoromethyl)benzofuran-5-yl)benzoate (56) as a white solid. Yield (2.5 g, 63%). LCMS: m/z 472.0 [M+Na]$^+$, t$_R$=2.03 min.

Synthesis of methyl 4-(2-(aminomethyl)-7-(trifluoromethyl)benzofuran-5-yl)benzoate (57)

Methyl 4-(2-((tert-butoxycarbonylamino)methyl)-7-(trifluoromethyl)benzofuran-5-yl)benzoate (56) (2.4 g, 5.5 mmol) was dissolved in CH$_2$Cl$_2$ (20 mL). TFA (6 mL) was added at 0° C. The reaction mixture was stirred at room temperature for 2 h, and concentrated under reduced pressure to give crude methyl 4-(2-(aminomethyl)-7-(trifluoromethyl)benzofuran-5-yl)benzoate (57), which was used without further purification in the next step. Yield (100%). LCMS: m/z 367.0 [M+H]$^+$; t$_R$=0.71 min. Yield (100%). LCMS: m/z 333.0 [M-NH$_2$]$^+$, t$_R$=1.49 min.

Synthesis of (E)-methyl 4-(2-((3-(6-aminopyridin-3-yl)acrylamido)methyl)-7-(trifluoromethyl)benzofuran-5-yl)benzoate (58)

The crude methyl 4-(2-(aminomethyl)-7-(trifluoromethyl)benzofuran-5-yl)benzoate (57) (crude mixture from previous step, 5.5 mmol) was dissolved in DMF (20 mL) and (E)-3-(6-aminopyridin-3-yl)acrylic acid (918 mg, 5.6 mmol) was added at 0° C. EDCI (1.3 g, 6.7 mmol) and HOBt (756 mg, 5.6 mmol) were added to this reaction mixture at 0° C. followed by DIPEA (2.2 g, 16.8 mmol) dropwise. The reaction mixture was allowed to warm to room temperature and stirred for 4 h. The crude mixture was purified by preparative-HPLC without workup to afford (E)-methyl 4-(2-((3-(6-aminopyridin-3-yl)acrylamido)methyl)-7-(trifluoromethyl)benzofuran-5-yl)benzoate (58). Yield (1.5 g, 55%). LCMS: m/z 496.0 [M+H]$^+$, $t_R$=0.99 min.

Synthesis of (E)-4-(2-((3-(6-aminopyridin-3-yl)acrylamido)methyl)-7-(trifluoromethyl)benzofuran-5-yl)benzoic acid (59)

(E)-Methyl 4-(2-((3-(6-aminopyridin-3-yl)acrylamido)methyl)-7-(trifluoromethyl)benzofuran-5-yl)benzoate 5 (1.0 g, 2 mmol) was dissolved in THF (4 mL), LiOH (169 mg, 4 mmol) and water (1 mL) was added to this mixture. The mixture was stirred at room temperature for 8 h, then 1N HCl solution was added and the pH adjusted to pH 6. (E)-4-(2-((3-(6-Aminopyridin-3-yl)acrylamido)methyl)-7-(trifluoromethyl)benzofuran-5-yl)benzoic acid (59) was collected by filtration. Yield (600 mg, 83%). LCMS: m/z 482.0 [M+H]$^+$, $t_R$=1.29 min.

Synthesis of (E)-3-(6-aminopyridin-3-yl)-N-((5-(4-(3,3-dimethylmorpholine-4-carbonyl)phenyl)-7-(trifluoromethyl)benzofuran-2-yl)methyl)acrylamide (517)

(E)-4-(2-((3-(6-Aminopyridin-3-yl)acrylamido)methyl)-7-(trifluoromethyl)benzofuran-5-yl)benzoic acid (59) (60 mg, 0.12 mmol) was dissolved in DMF (2 mL) and 3,3-dimethylmorpholine (14 mg, 0.12 mmol) was added at 0° C. HATU (57 mg, 0.15 mmol) was added to this reaction mixture at 0° C. followed by DIPEA (31 mg, 0.24 mmol) dropwise. The reaction mixture was allowed to warm to room temperature and stirred further for 4 h. The reaction mixture was transferred into water (20 mL) and extracted with EtOAc (25 mL×3). The combined organic layers were washed with brine, dried over anhydrous Na$_2$SO$_4$ and concentrated under reduced pressure to give crude product, which was purified by preparative-HPLC to afford (517). (Yield: 20 mg, 27%). $^1$H NMR (400 MHz, CD$_3$OD) δ 8.19 (dd, J=2 Hz, J=9.2 Hz, 1H), 8.18 (s, 1H), 8.05 (d, J=1.6 Hz, 1H), 7.80-7.75 (m, 3H), 7.56 (d, J=8 Hz, 2H), 7.49 (d, J=15.6 Hz, 1H), 7.05 (d, J=9.2 Hz, 1H), 6.93 (s, 1H), 6.65 (d, J=15.6 Hz, 1H), 4.73 (s, 2H), 3.78 (t, J=4.8 Hz, 2H), 3.52 (s, 2H), 3.46 (t, J=5.2 Hz, 2H), 1.54 (s, 6H). LCMS: m/z 579.3 [M+H]$^+$; $t_R$=1.85 min.

Synthesis of (E)-3-(6-aminopyridin-3-yl)-N-((5-(4-(2-(pyridin-2-yl)hydrazinecarbonyl)phenyl)-7-(trifluoromethyl)benzofuran-2-yl)methyl)acrylamide (518)

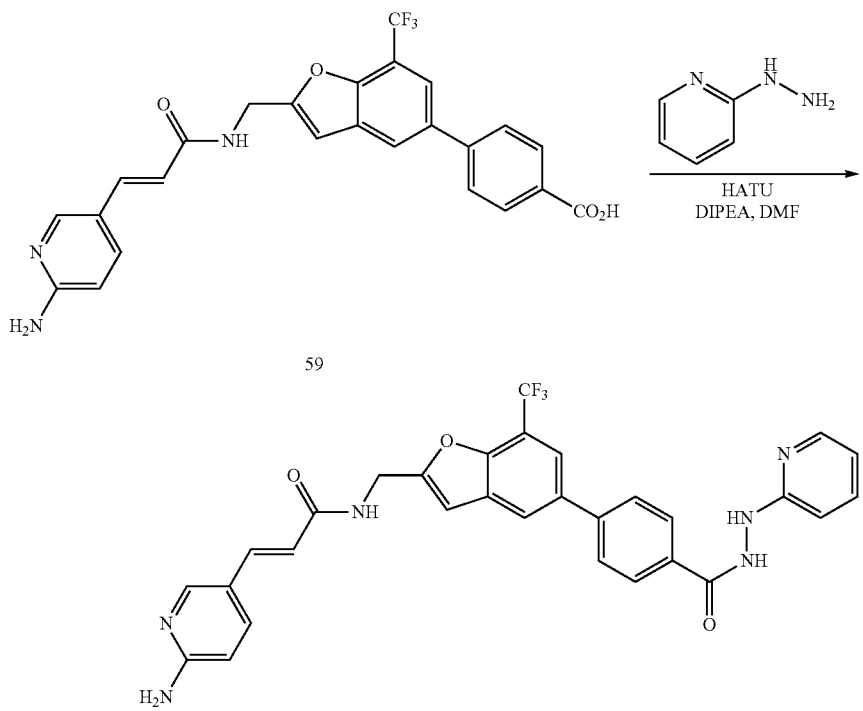

(E)-3-(6-Aminopyridin-3-yl)-N-((5-(4-(2-(pyridin-2-yl)hydrazinecarbonyl)phenyl)-7-(trifluoromethyl)benzofuran-2-yl)methyl)acrylamide (518) was synthesized according to General Procedure 1 using the indicated reagents. Yield (31%). $^1$H NMR (400 MHz, CD$_3$OD) δ 8.16 (s, 1H), 8.09-8.06 (m, 4H), 7.85-7.83 (m, 3H), 7.76 (dd, J=2.4 Hz, J=8.8 Hz, 1H), 7.66-7.62 (m, 1H), 7.50 (d, J=15.6 Hz, 1H), 6.94-6.83 (m, 3H), 6.62-6.47 (m, 2H), 4.73 (s, 2H). LCMS: m/z 573.3 [M+H]$^+$; $t_R$=1.70 min.

Synthesis of (E)-3-(6-aminopyridin-3-yl)-N-((5-(4-(2-(pyrazin-2-yl)hydrazinecarbonyl)phenyl)-7-(trifluoromethyl)benzofuran-2-yl)methyl)acrylamide (519)

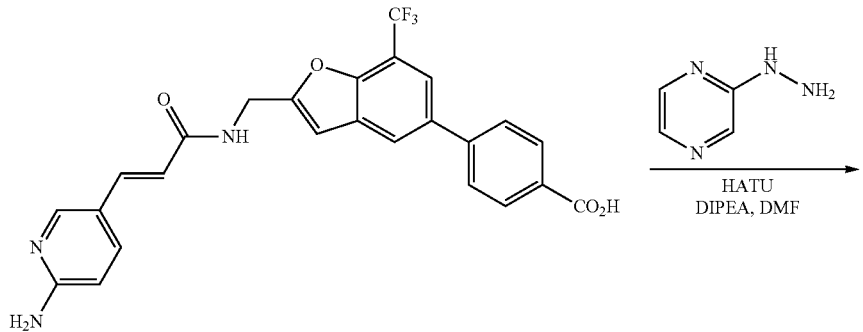

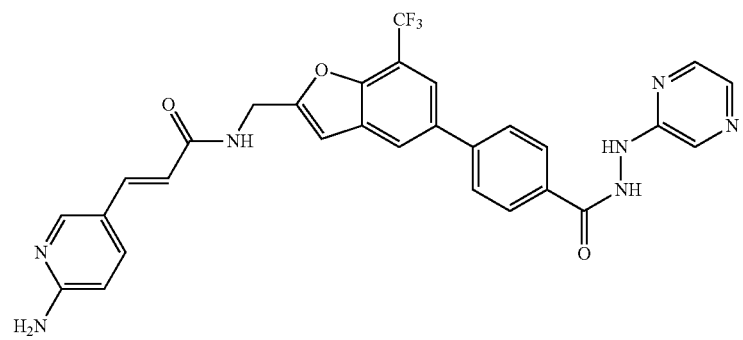

(E)-3-(6-Aminopyridin-3-yl)-N-((5-(4-(2-(pyrazin-2-yl)hydrazinecarbonyl)phenyl)-7-(trifluoromethyl)benzofuran-2-yl)methyl)acrylamide (519) was synthesized according to General Procedure I using the indicated reagents. Yield (9.8%). $^1$H NMR (400 MHz, CD$_3$OD) δ 8.16 (s, 2H), 8.12-8.06 (m, 4H), 7.96 (d, J=2.8 Hz, 1H), 7.87-7.77 (m, 3H), 7.76 (dd, J=2.4 Hz, J=8.8 Hz, 1H), 7.50 (d, J=15.6 Hz, 1H), 6.92 (d, J=14 Hz, 1H), 6.61 (d, J=8.4 Hz, 1H), 6.49 (d, J=15.6 Hz, 1H), 4.73 (s, 2H). LCMS: m/z 574.2 [M+H]$^+$; t$_R$=1.63 min.

Synthesis of (E)-3-(6-aminopyridin-3-yl)-N-((5-(4-(3,3-difluoroazetidine-1-carbonyl)phenyl)-7-(trifluoromethyl)benzofuran-2-yl)methyl)acrylamide (520)

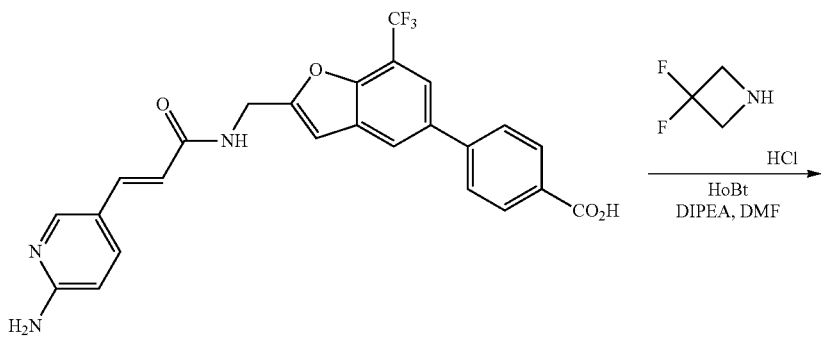

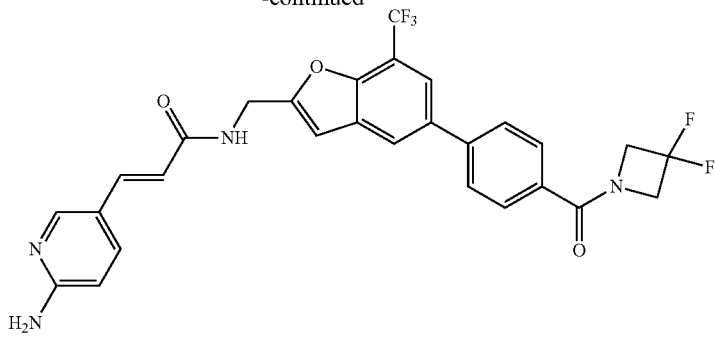
520
(E)-3-(6-Aminopyridin-3-yl)-N-((5-(4-(3,3-difluoroazetidine-1-carbonyl)phenyl)-7-(trifluoromethyl)benzofuran-2-yl)methyl)acrylamide (520) was synthesized using General Procedure 1. Yield (32%). $^1$H NMR (400 MHz, CD$_3$OD) δ 8.14 (s, 1H), 8.07 (s, 1H), 7.82-7.74 (m, 7H), 7.50 (d, J=16 Hz, 1H), 6.93 (s, 1H), 6.61 (d, J=8.8 Hz, 1H), 6.49 (d, J=16 Hz, 1H), 4.72-4.59 (m, 6H). LCMS: m/z 557.2 [M+H]$^+$; t$_R$=1.80 min.
Synthesis of (E)-3-(6-aminopyridin-3-yl)-N-((5-(5-(morpholine-4-carbonyl)pyridin-2-yl)-7-(trifluoromethyl)benzofuran-2-yl)methyl)acrylamide (521)
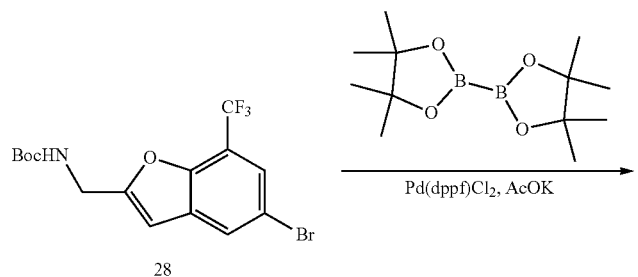
28
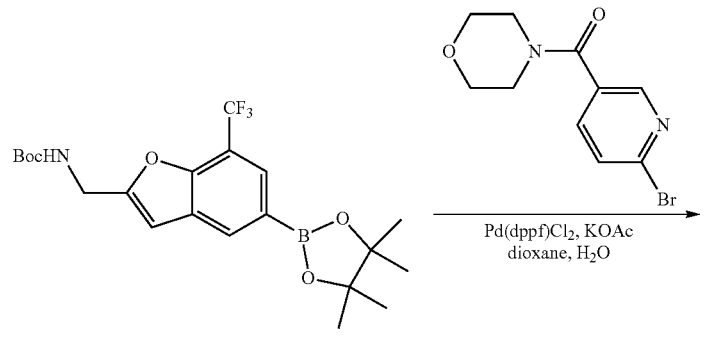
60
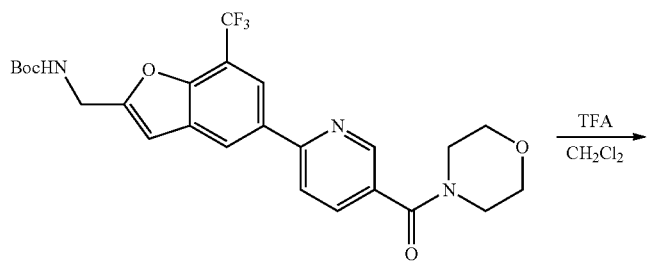
61

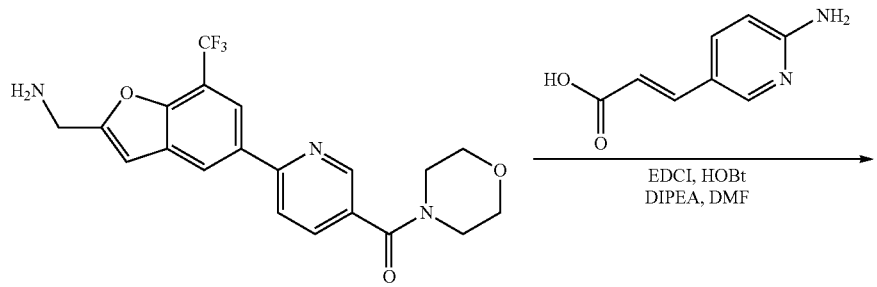

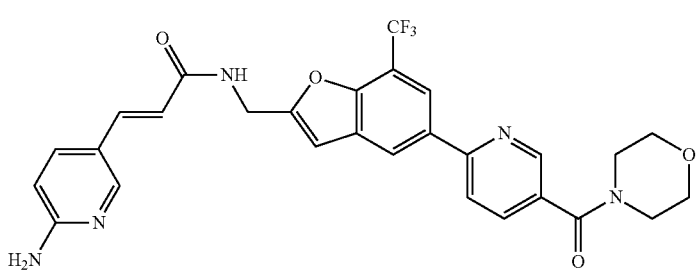

Synthesis of (tert-butyl (5-(4,4,5,5-tetramethyl-1,3,2-dioxaborolan-2-yl)-7-(trifluoromethyl)benzofuran-2-yl)methylcarbamate (60)

A mixture of tert-butyl (5-bromo-7-(trifluoromethyl)benzofuran-2-yl)methyl)carbamate (28) (1.0 g, 2.5 mmol), 4,4,4',4',5,5,5',5'-octamethyl-2,2'-bi(1,3,2-dioxaborolane) (839 mg, 3 mmol), Pd(dppf)Cl$_2$ (184 mg, 0.25 mmol) and AcOK (485 mg, 5 mmol) in 20 mL of dioxane was stirred at 90° C. under nitrogen atmosphere for 4 hours. After cooling to room temperature, the mixture was filtered and the filtrate was concentrated under reduced pressure to give the crude product, which was purified by silica gel chromatography (10% EtOAc/petroleum ether) to give tert-butyl (5-(4,4,5,5-tetramethyl-1,3,2-dioxaborolan-2-yl)-7-(trifluoromethyl) benzofuran-2-yl)methylcarbamate (60) as a white solid (yield: 1.0 g, 89%). LCMS: m/z 386.0 [M-55]$^+$, $t_R$=2.17 min.

Synthesis of tert-butyl (5-(5-(morpholine-4-carbonyl)pyridin-2-yl)-7-(trifluoromethyl)benzofuran-2-yl)methylcarbamate (61)

tert-Butyl (5-(5-(morpholine-4-carbonyl)pyridin-2-yl)-7-(trifluoromethyl)benzofuran-2-yl)methylcarbamate (61) was synthesized using General Procedure 2. Yield (40%). LCMS: m/z 506.2 [M+H]$^+$, $t_R$=1.127 min.

Synthesis of (6-(2-(aminomethyl)-7-(trifluoromethyl)benzofuran-5-yl)pyridin-3-yl)(morpholino)methanone (62)

(6-(2-(Aminomethyl)-7-(trifluoromethyl)benzofuran-5-yl)pyridin-3-yl)(morpholino)methanone (62) was synthesized using General Procedure 3. Yield (100%). LCMS: m/z 406.0 [M+H]$^+$, $t_R$=1.13 min.

Synthesis of (E)-3-(6-aminopyridin-3-yl)-N-((5-(5-(morpholine-4-carbonyl)pyridin-2-yl)-7-(trifluoromethyl)benzofuran-2-yl)methyl)acrylamide (521)

(E)-3-(6-Aminopyridin-3-yl)-N-((5-(5-(morpholine-4-carbonyl)pyridin-2-yl)-7-(trifluoromethyl)benzofuran-2-yl)methyl)acrylamide (521) was synthesized using General Procedure 1. Yield (5%). $^1$H NMR (400 MHz, MeOD) δ 8.77-8.76 (m, 1H), 8.54 (s, 1H), 8.35 (s, 1H), 8.11-8.07 (m, 2H), 8.01-7.99 (m, 1H), 7.76 (dd, J=2.2 Hz, J=8.7 Hz, 1H), 7.50 (d, J=16.0 Hz, 1H), 6.97 (s, 1H), 6.62 (d, J=8.9 Hz, 1H), 6.49 (d, J=15.6 Hz, 1H), 4.73 (s, 2H), 3.81-3.71 (m, 8H). LCMS: m/z 552.2 [M+H]$^+$, $t_R$=1.65 min.

Synthesis of (R,E)-3-(6-aminopyridin-3-yl)-N-((5-(4-(3-fluoropyrrolidine-1-carbonyl)phenyl)-7-(trifluoromethyl)benzofuran-2-yl)methyl)acrylamide (522)

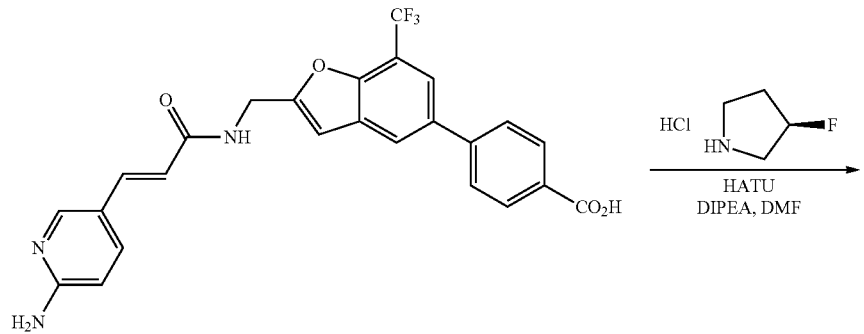

59

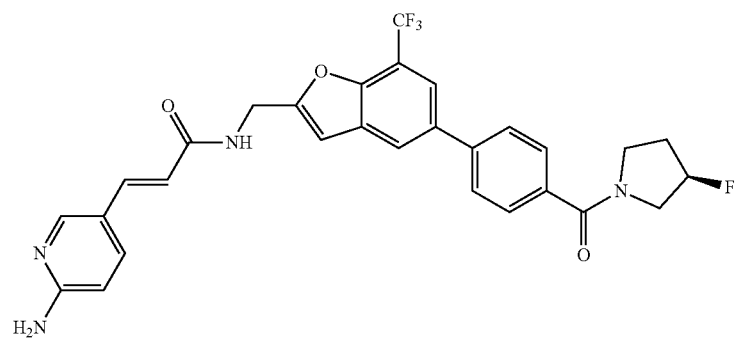

522

(R,E)-3-(6-Aminopyridin-3-yl)-N-((5-(4-(3-fluoropyrrolidine-1-carbonyl)phenyl)-7-(trifluoromethyl)benzofuran-2-yl)methyl)acrylamide (522) was synthesized according to General Procedure 1 using the indicated reagents. Yield (15%). $^1$H NMR (400 MHz, CD$_3$OD) δ 8.06 (d, J=12 Hz, 2H), 7.78-7.64 (m, 6H), 7.48 (d, J=15.6 Hz, 1H), 6.89 (s, 1H), 6.59 (d, J=8.8 Hz, 1H), 6.47 (d, J=15.6 Hz, 1H), 5.44-5.31 (m, 1H), 4.70 (s, 2H), 3.90-3.67 (m, 4H), 2.29-2.04 (m, 2H). LCMS: m/z 553.3 [M+H]$^+$; $t_R$=1.76 min.

Synthesis of (R,E)-3-(6-aminopyridin-3-yl)-N-((7-chloro-5-(4-(3-fluoropyrrolidine-1-carbonyl)phenyl)benzofuran-2-yl)methyl)acrylamide (523)

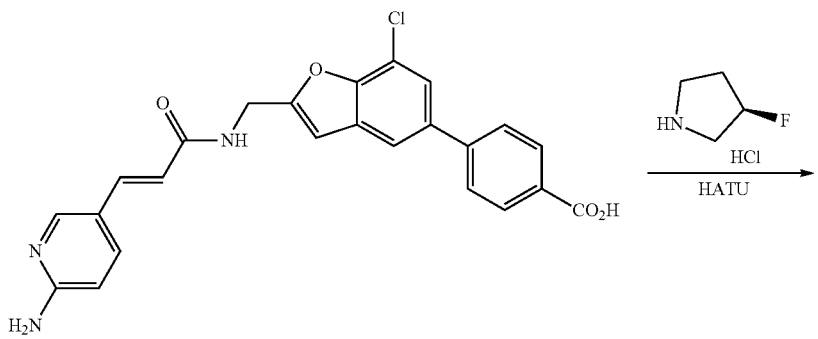

55

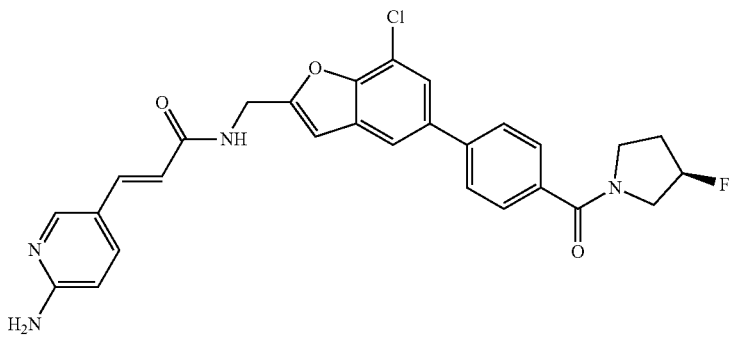

523

(R,E)-3-(6-Aminopyridin-3-yl)-N-((7-chloro-5-(4-(3-fluoropyrrolidine-1-carbonyl)phenyl)benzofuran-2-yl)methyl)acrylamide (523) was synthesized according to General Procedure 1 using the indicated reagents. Yield (11%). $^1$H NMR (400 MHz, MeOD-d$_6$) δ 8.15 (dd, J=2.0 Hz, J=9.2 Hz, 1H), 8.06 (s, 1H), 7.81-7.76 (m, 3H), 7.69-7.63 (m, 3H), 7.50 (d, J=15.6 Hz, 1H), 6.99 (d, J=9.2 Hz, 1H), 6.89 (s, 1H), 6.63 (d, J=15.6 Hz, 1H), 4.72 (s, 2H), 3.92-3.78 (m, 4H), 2.33-2.178 (m, 2H). LCMS: m/z 519.7 [M+H]$^+$; t$_R$=1.61 min.

Synthesis of (E)-3-(6-aminopyridin-3-yl)-N-((5-(4-(3-fluoroazetidine-1-carbonyl)phenyl)-7-(trifluoromethyl)benzofuran-2-yl)methyl)acrylamide (524)

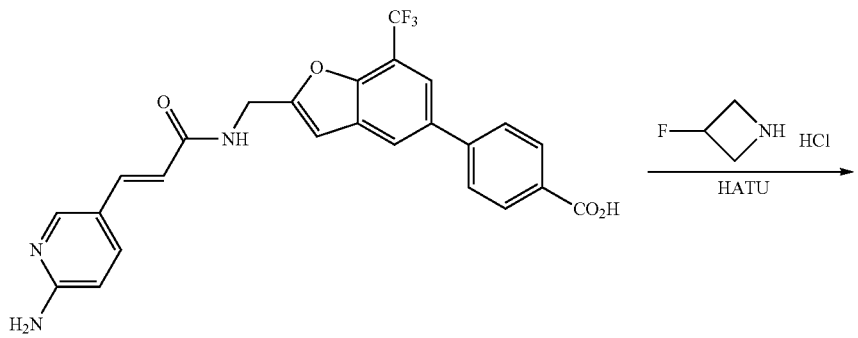

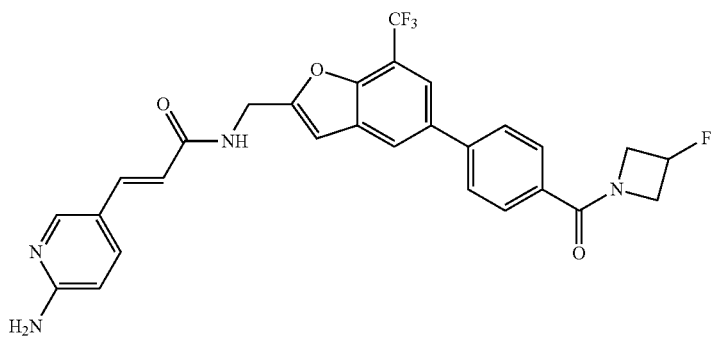

524

(E)-3-(6-Aminopyridin-3-yl)-N-((5-(4-(3-fluoroazetidine-1-carbonyl)phenyl)-7-(trifluoromethyl)benzofuran-2-yl)methyl)acrylamide (524) was synthesized according to General Procedure 1 using the indicated reagents. Yield (34%). ¹H NMR (400 MHz, CD₃OD) δ 8.12 (d, J=0.8 Hz, 1H), 8.06 (d, J=2.4 Hz, 1H), 7.81-7.73 (m, 6H), 7.49 (d, J=15.6 Hz, 1H), 6.92 (s, 1H), 6.61 (d, J=8.4 Hz, 1H), 6.48 (d, J=15.6 Hz, 1H), 5.52-5.34 (m, 1H), 4.84 (s, 2H), 4.72-4.23 (m, 4H). LCMS: m/z 539.3 [M+H]⁺; $t_R$=1.75 min.

Synthesis of (S,E)-3-(6-aminopyridin-3-yl)-N-((5-(4-(3-fluoropyrrolidine-1-carbonyl)phenyl)-7-(trifluoromethyl)benzofuran-2-yl)methyl)acrylamide (525)

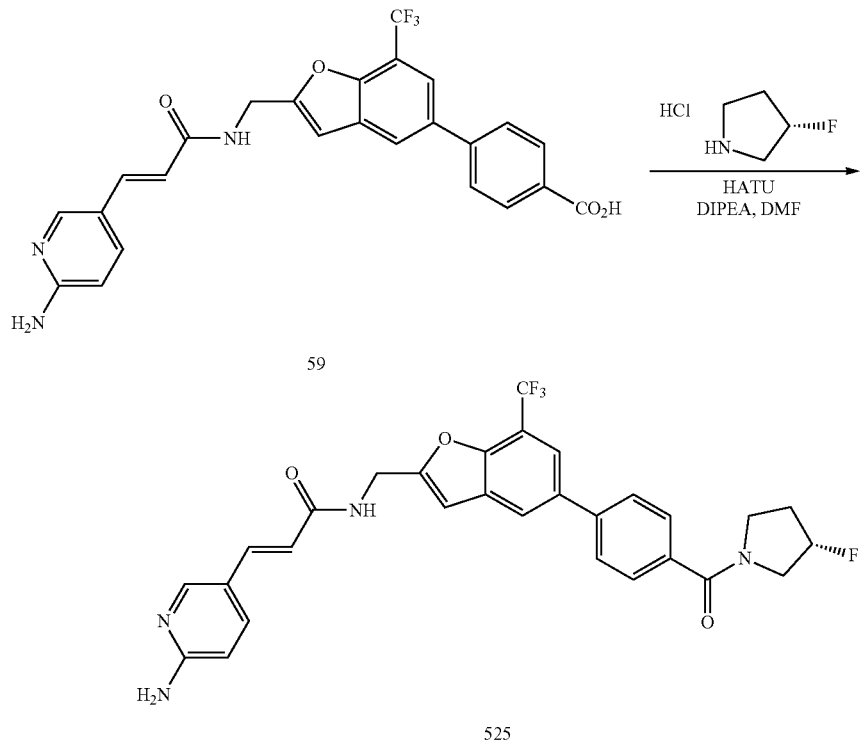

(S,E)-3-(6-Aminopyridin-3-yl)-N-((5-(4-(3-fluoropyrrolidine-1-carbonyl)phenyl)-7-(trifluoromethyl)benzofuran-2-yl)methyl)acrylamide (525) was synthesized according to General Procedure 1 using the indicated reagents. Yield (17%). ¹H NMR (400 MHz, CD₃OD) δ 8.10-8.05 (m, 2H), 7.80-7.65 (m, 6H), 7.49 (d, J=15.6 Hz, 1H), 6.91 (s, 1H), 6.60 (d, J=8.8 Hz, 1H), 6.48 (d, J=15.6 Hz, 1H), 5.45-5.32 (m, 1H), 4.88 (s, 2H), 3.91-3.65 (m, 4H), 2.28-2.05 (m, 2H). LCMS: m/z 553.3 [M+H]⁺; $t_R$=1.76 min.

Synthesis of (E)-3-(6-aminopyridin-3-yl)-N-((5-(4-(3,3-dimethylazetidine-1-carbonyl)phenyl)-7-(trifluoromethyl)benzofuran-2-yl)methyl)acrylamide (526)

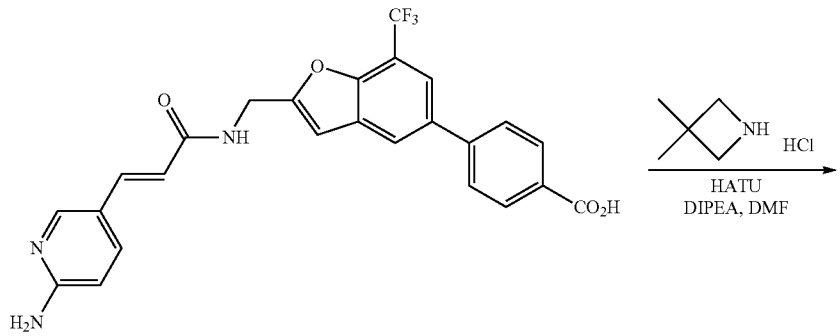

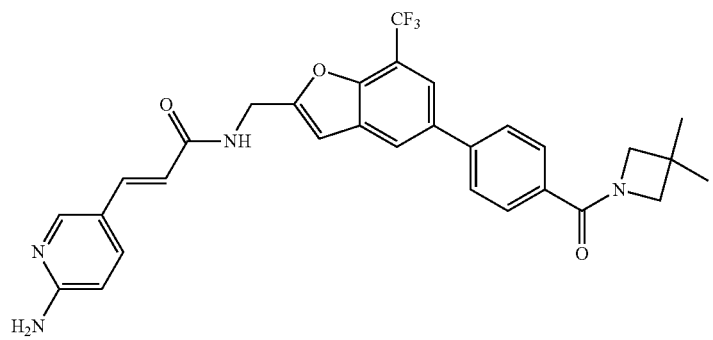

526

(E)-3-(6-Aminopyridin-3-yl)-N-((5-(4-(3,3-dimethylazetidine-1-carbonyl)phenyl)-7-(trifluoromethyl)benzofuran-2-yl)methyl)acrylamide (526) was synthesized according to General Procedure 1 using the indicated reagents. Yield (28%). $^1$H NMR (400 MHz, CD$_3$OD) δ 8.66 (s, 1H), 8.24 (s, 1H), 8.08 (d, J=1.6 Hz, 1H), 7.86-7.73 (m, 5H), 7.62 (dd, J=2 Hz, J=8.8 Hz, 1H), 7.35 (d, J=16 Hz, 1H), 6.94 (s, 1H), 6.49-6.41 (m, 3H) 4.61 (d, J=3.6 Hz, 2H), 4.05-4.02 (m, 3H), 3.75 (s, 2H), 1.25 (s, 6H). LCMS: m/z 549.3 [M+H]$^+$; $t_R$=1.87 min.

Synthesis of (R,E)-3-(6-aminopyridin-3-yl)-N-((7-chloro-5-(4-(3-fluoropyrrolidin-1-ylsulfonyl)phenyl)benzofuran-2-yl)methyl)acrylamide (527)

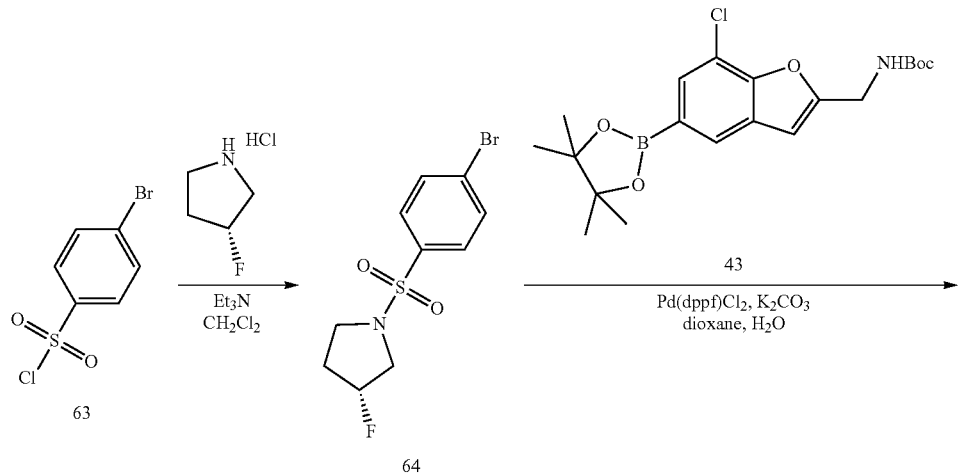

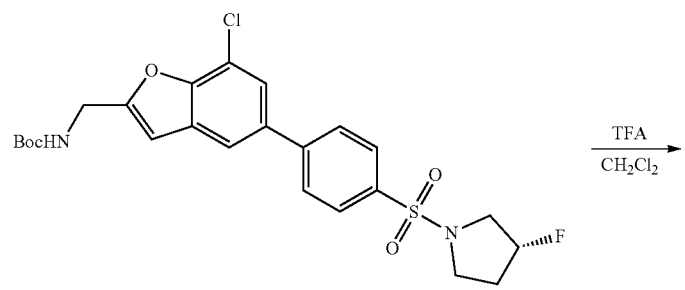

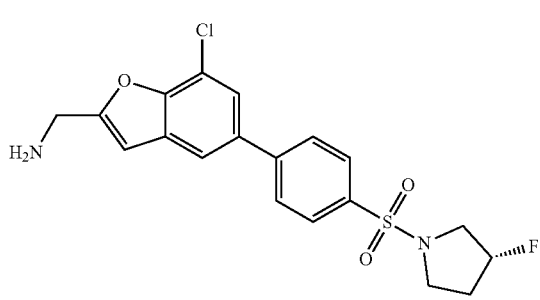
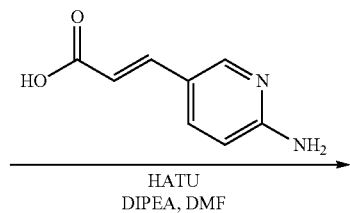

66

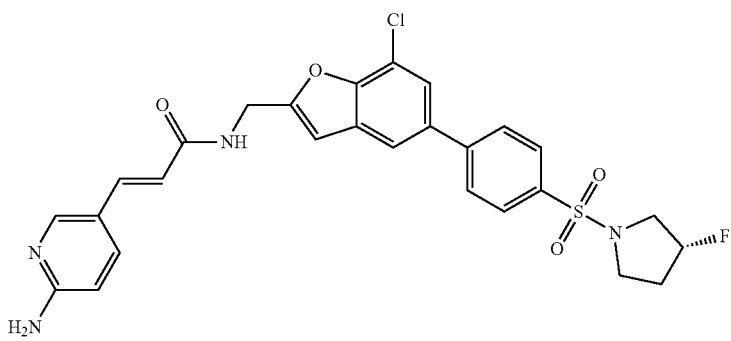

527

Synthesis of (R)-1-(4-bromophenylsulfonyl)-3-fluoropyrrolidine (64)

(R)-3-Fluoropyrrolidine hydrochloride (125 mg, 1 mmol) was dissolved in 10 mL $CH_2Cl_2$. The mixture was cooled to 0° C. and to this mixture were added $Et_3N$ (202 mg, 2 mmol) and 4-bromobenzene-1-sulfonyl chloride (63) (255 mg, 1 mmol). The resulting mixture was allowed to warm to room temperature and stirred for 1 h. The mixture was washed with $H_2O$ (10 mL×2), dried over anhydrous $Na_2SO_4$ and concentrated to give 308 mg of (R)-1-(4-bromophenylsulfonyl)-3-fluoropyrrolidine (64) (100% yield) as a white solid. LCMS: m/z 307.9 [M+H]$^+$; $t_R$=1.74 min.

Synthesis of (R)-tert-butyl (7-chloro-5-(4-(3-fluoropyrrolidin-1-ylsulfonyl)phenyl)benzofuran-2-yl)methylcarbamate (65)

(R)-tert-Butyl (7-chloro-5-(4-(3-fluoropyrrolidin-1-ylsulfonyl)phenyl)benzofuran-2-yl)methylcarbamate (65) was synthesized using General Procedure 2. Yield (68%). LCMS: m/z 509.2 [M+H]$^+$; $t_R$=2.10 min.

Synthesis of (R)-(7-chloro-5-(4-(3-fluoropyrrolidin-1-ylsulfonyl)phenyl)benzofuran-2-yl)methanamine (66)

(R)-(7-Chloro-5-(4-(3-fluoropyrrolidin-1-ylsulfonyl)phenyl)benzofuran-2-yl)methanamine (66) was synthesized using General Procedure 3. Yield (100%). LCMS: m/z 409.2 [M+H]$^+$; $t_R$=1.83 min.

Synthesis of (R,E)-3-(6-aminopyridin-3-yl)-N-((7-chloro-5-(4-(3-fluoropyrrolidin-1-ylsulfonyl)phenyl)benzofuran-2-yl)methyl)acrylamide (527)

(R,E)-3-(6-Aminopyridin-3-yl)-N-((7-chloro-5-(4-(3-fluoropyrrolidin-1-ylsulfonyl)phenyl)benzofuran-2-yl)methyl)acrylamide (527) was synthesized using General Procedure 1. Yield (15%). $^1$H NMR (400 MHz, $CD_3OD$) δ 8.84 (t, J=5.6 Hz, 1H), 8.19 (s, 1H), 8.19-7.88 (m, 8H), 7.79 (d, J=1.6 Hz, 1H), 7.43 (d, J=13.2 Hz, 1H), 6.96-6.93 (m, 2H), 6.59 (d, J=15.6 Hz, 1H), 5.29-5.16 (m, 1H), 4.62 (d, J=5.6 Hz, 2H), 3.25-3.15 (m, 4H), 2.08-2.01 (m, 2H). LCMS: m/z 555.1 [M+H]$^+$; $t_R$=1.70 min.

Synthesis of (S,E)-3-(6-aminopyridin-3-yl)-N-((7-chloro-5-(4-(3-fluoropyrrolidine-1-carbonyl)phenyl)benzofuran-2-yl)methyl)acrylamide (528)

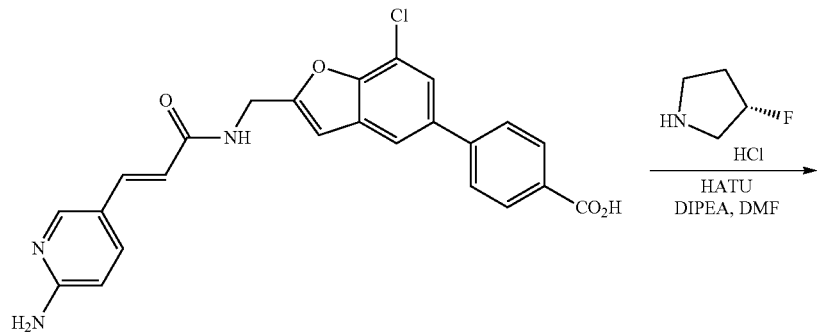

55

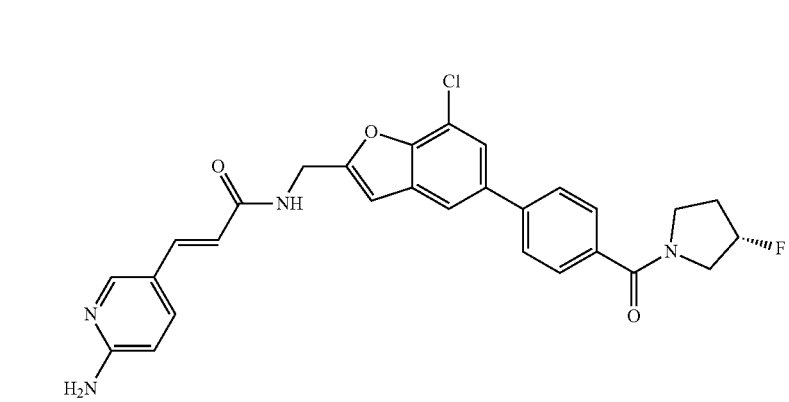

528

(S,E)-3-(6-Aminopyridin-3-yl)-N-((7-chloro-5-(4-(3-fluoropyrrolidine-1-carbonyl)phenyl)benzofuran-2-yl)methyl)acrylamide (528) was synthesized according to General Procedure 1 using the indicated reagents. Yield (26%). $^{1}$H NMR (400 MHz, DMSO-$d_6$) δ 8.64 (t, J=5.6 Hz, 1H), 8.08 (d, J=2.4 Hz, 1H), 7.92 (d, J=1.6 Hz, 1H), 7.79 (d, J=8.4 Hz, 2H), 7.73 (d, J=1.6 Hz, 1H), 7.67-7.61 (m, 3H), 7.36 (d, J=15.6 Hz, 1H), 6.90 (s, 1H), 6.49-6.41 (m, 4H), 4.60 (d, J=6.0 Hz, 2H), 3.79-3.56 (m, 4H), 2.16-2.03 (m, 2H). LCMS: m/z 519.7 [M+H]$^+$; $t_R$=1.63 min.

Synthesis of (E)-3-(6-aminopyridin-3-yl)-N-((7-chloro-5-(4-(3,3-dimethylazetidine-1-carbonyl)phenyl)benzofuran-2-yl)methyl)acrylamide (529)

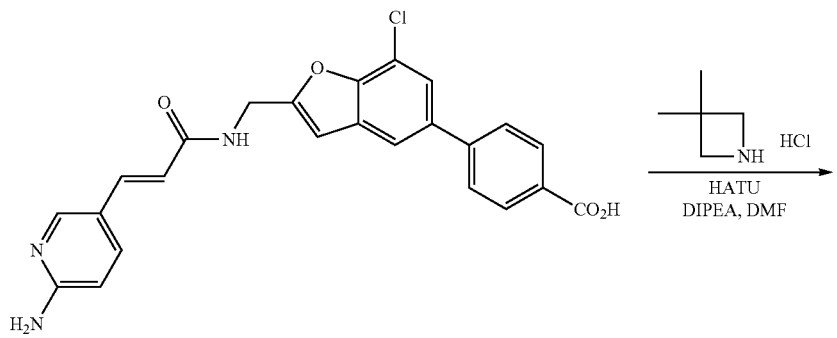

55

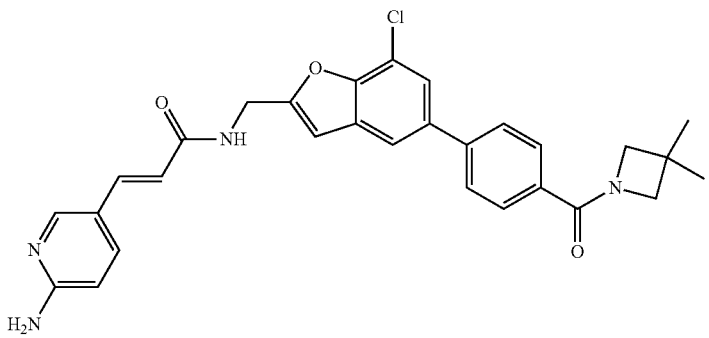

529

(E)-3-(6-Aminopyridin-3-yl)-N-((7-chloro-5-(4-(3,3-dimethylazetidine-1-carbonyl)phenyl)benzofuran-2-yl)methyl)acrylamide (529) was synthesized according to General Procedure 1 using the indicated reagents. Yield (25%). $^1$H NMR (400 MHz, DMSO-d$_6$) δ 8.64 (t, J=5.6 Hz, 1H), 8.08 (d, J=2.4 Hz, 1H), 7.91 (d, J=1.6 Hz, 1H), 7.80-7.60 (m, 6H), 7.35 (d, J=15.6 Hz, 1H), 6.90 (s, 1H), 6.49-6.40 (m, 4H), 4.60 (d, J=5.6 Hz, 2H), 4.03 (s, 2H), 3.75 (s, 2H), 1.26 (s, 6H). LCMS: m/z 515.7 [M+H]$^+$; t$_R$=1.74 min.

Synthesis of (E)-3-(6-aminopyridin-3-yl)-N-((5-(4-(2,2-dimethylmorpholine-4-carbonyl)phenyl)-7-(trifluoromethyl)benzofuran-2-yl)methyl)acrylamide (530)

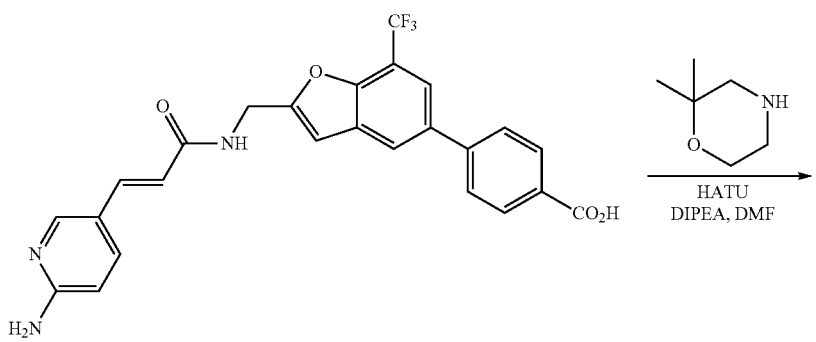

59

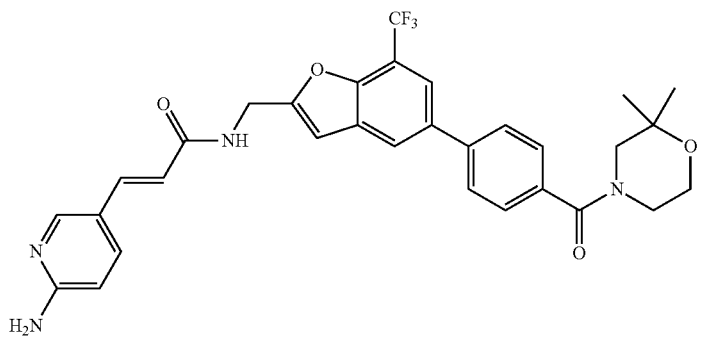

530

(E)-3-(6-Aminopyridin-3-yl)-N-((5-(4-(2,2-dimethylmorpholine-4-carbonyl)phenyl)-7-(trifluoromethyl)benzofuran-2-yl)methyl)acrylamide (530) was synthesized according to General Procedure 1 using the indicated reagents. Yield (27%). $^1$H NMR (400 MHz, CD$_3$OD) δ 8.11 (s, 1H), 8.06 (d, J=2.4 Hz, 1H), 7.80-7.73 (m, 4H), 7.56 (s, 2H), 7.49 (d, J=15.6 Hz, 1H), 6.92 (s, 1H), 6.61 (d, J=8.8 Hz, 1H), 6.48 (d, J=15.6 Hz, 1H), 4.72 (s, 2H), 4.63 (s, 2H), 3.82-3.49 (m, 4H), 1.31-1.16 (s, 6H). LCMS: m/z 579.2 [M+H]$^+$; $t_R$=1.68 min.

Synthesis of (E)-3-(6-aminopyridin-3-yl)-N-((5-(4-(morpholinosulfonyl)phenyl)-7-(trifluoromethyl)benzofuran-2-yl)methyl)acrylamide (531)

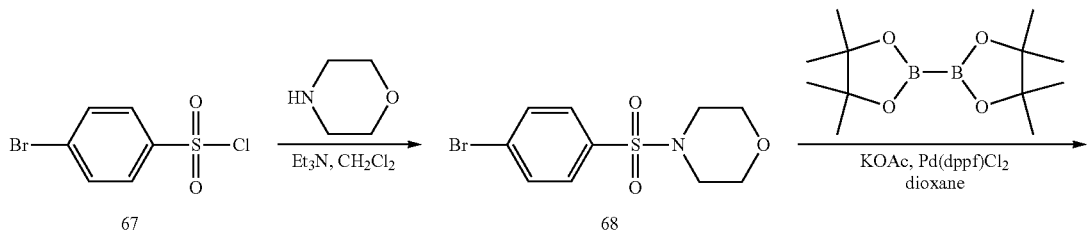

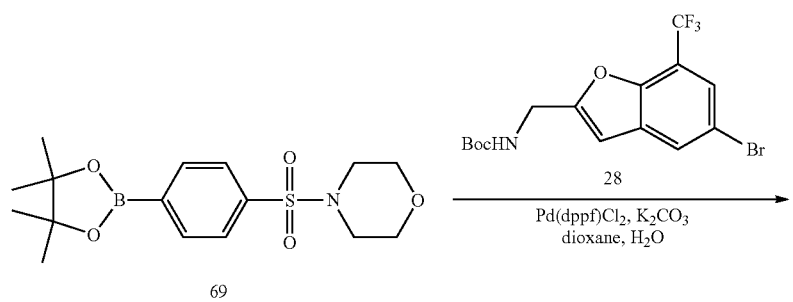

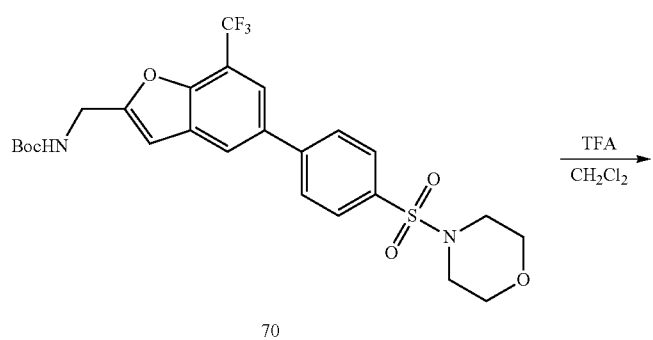

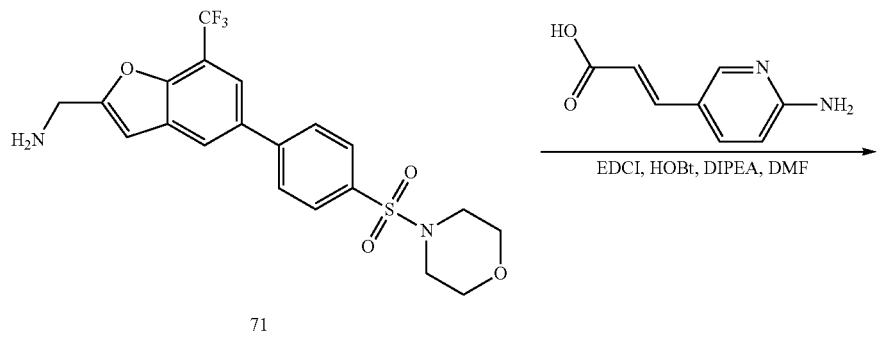

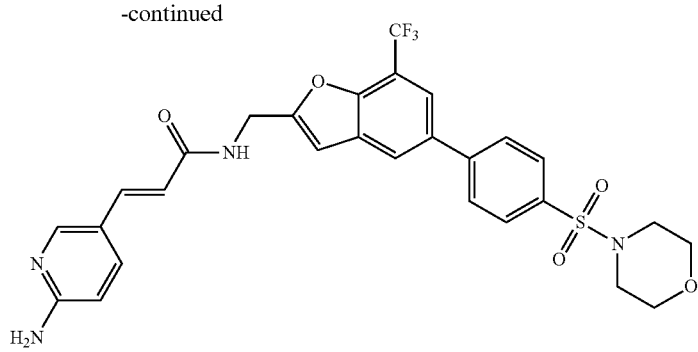

531

Synthesis of 4-(4-bromophenylsulfonyl)morpholine (68)

4-(4-Bromophenylsulfonyl)morpholine (68) was synthesized in accordance with the procedure described above for the synthesis of (R)-1-(4-bromophenylsulfonyl)-3-fluoropyrrolidine (64). Yield (100%). LCMS: m/z 306.0 [M+H]$^+$, t$_R$=1.06 min.

Synthesis of 4-(4-(4,4,5,5-tetramethyl-1,3,2-dioxaborolan-2-yl)phenylsulfonyl)morpholine (69)

A mixture of 4-(4-bromophenylsulfonyl)morpholine (68) 6.0 g, 19.7 mmol), 4,4,4',4',5,5,5',5'-octamethyl-2,2'-bi(1,3, 2-dioxaborolane) (5.0 g, 19.7 mmol), Pd(dppf)Cl$_2$ (1.6 g, 1.97 mmol) and AcOK (3.8 g, 39.4 mmol) in 100 mL of dioxane was stirred at 90° C. under nitrogen atmosphere for 2 hours. After cooling to room temperature, the mixture was filtered and the filtrate was concentrated under reduced pressure to give the crude product, which was purified by silica gel chromatography (10% EtOAc/petroleum ether) to give 5.2 g of 4-(4-(4,4,5,5-tetramethyl-1,3,2-dioxaborolan-2-yl)phenylsulfonyl)morpholine (69) as a yellowish solid (yield: 75%). LCMS: m/z 354.0 [M+H]$^+$, t$_R$=1.89 min.

Synthesis of tert-butyl (5-(4-(morpholinosulfonyl)phenyl)-7-(trifluoromethyl)benzofuran-2-yl)methylcarbamate (70)

tert-Butyl (5-(4-(morpholinosulfonyl)phenyl)-7-(trifluoromethyl)benzofuran-2-yl)methylcarbamate (70) was synthesized using General Procedure 2. Yield (47%). LCMS: m/z 541.0 [M+H]$^+$; t$_R$=1.97 min.

Synthesis of (5-(4-(morpholinosulfonyl)phenyl)-7-(trifluoromethyl)benzofuran-2-yl)methanamine (71)

(5-(4-(Morpholinosulfonyl)phenyl)-7-(trifluoromethyl)benzofuran-2-yl)methanamine (71) was synthesized using General Procedure 3. Yield (88%). LCMS: m/z 441.1 [M+H]$^+$; t$_R$=1.29 min.

Synthesis of (E)-3-(6-aminopyridin-3-yl)-N-((5-(4-(morpholinosulfonyl)phenyl)-7-(trifluoromethyl)benzofuran-2-yl)methyl)acrylamide (531)

(E)-3-(6-Aminopyridin-3-yl)-N-((5-(4-(morpholinosulfonyl)phenyl)-7-(trifluoromethyl)benzofuran-2-yl)methyl)acrylamide (531) was synthesized using General Procedure 1. Yield (77%). $^1$H NMR (400 MHz, CD$_3$OD) δ 8.06-7.95 (m, 5H), 7.85-7.36 (m, 5H), 6.83-6.35 (m, 3H), 4.61 (s, 2H), 3.63-6.22 (m, 4H), 2.92-2.90 (m, 4H). LCMS: m/z 587.0 [M+H]$^+$; t$_R$=1.47 min.

Synthesis of (E)-3-(6-aminopyridin-3-yl)-N-(2-(7-chloro-5-(4-(morpholine-4-carbonyl)phenyl)benzofuran-2-yl)ethyl)acrylamide (532)

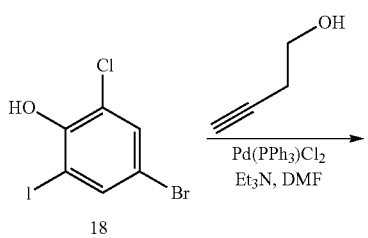

18

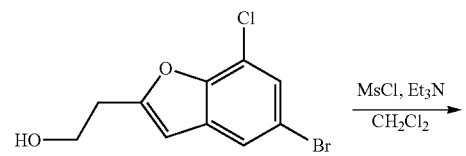

72

-continued
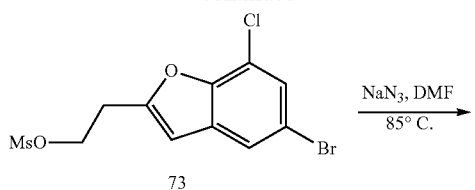
73
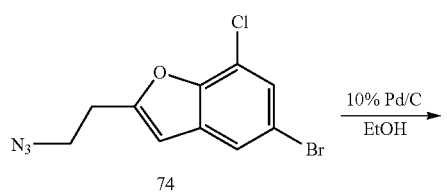
74
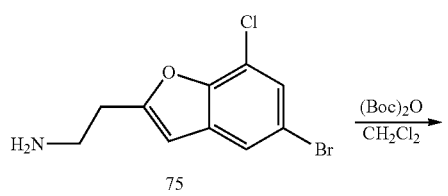
75
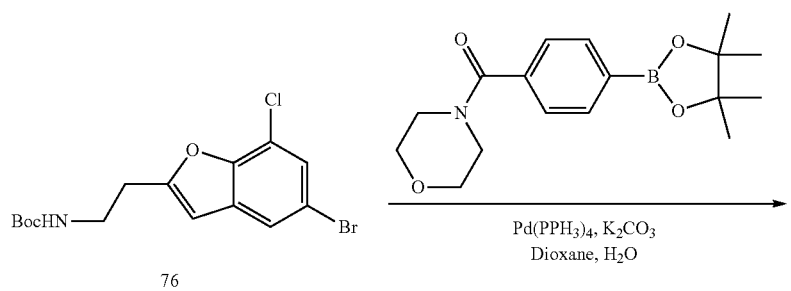
76
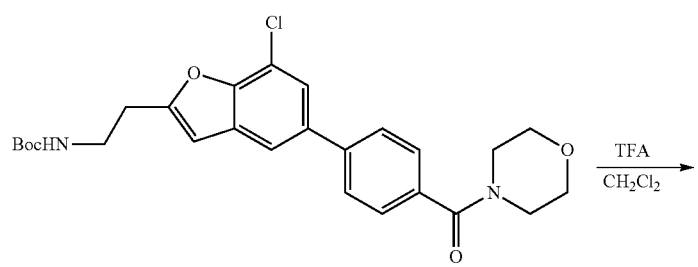
77
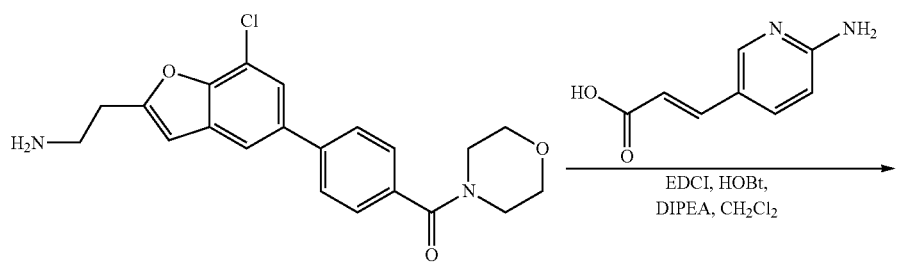
78

-continued

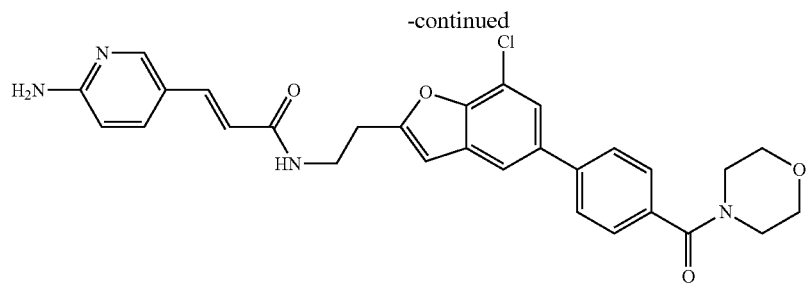

532

Synthesis of 2-(5-bromo-7-chlorobenzofuran-2-yl)ethanol (72)

A mixture of 4-bromo-2-iodo-6-(trifluoromethyl)phenol (18) (6.8 g, 20.48 mmol), tert-butyl prop-2-ynylcarbamate (1.48 g, 20.48 mmol), Pd(PPh$_3$)Cl$_2$ (710 mg, 1.02 mmol) and CuI (503 mg, 2.66 mmol) in 20 mL of Et$_3$N was stirred at 80° C. under nitrogen atmosphere for 4 h. The mixture was extracted with EtOAc (50 mL×3). The combined organic layers were washed with brine, dried over anhydrous Na$_2$SO$_4$, and the solvents were removed under reduced pressure to give the crude product, which was purified by silica gel chromatography (10% EtOAc/petroleum ether) to give 2.8 g of 2-(5-bromo-7-chlorobenzofuran-2-yl)ethanol (72) as a white solid (yield: 50%). LCMS: m/z 256.8 [M-17]$^+$; t$_R$=1.79 min.

Synthesis of 2-(5-bromo-7-chlorobenzofuran-2-yl)ethyl methanesulfonate (73)

2-(5-Bromo-7-chlorobenzofuran-2-yl)ethanol (72) (500 mg, 1.83 mmol) was dissolved in dichloromethane (8 mL). Methane sulfonyl chloride (416 mg, 3.66 mmol) and triethylamine (370 mg, 3.66 mmol) were added at 0° C. The reaction mixture was allowed to warm to room temperature and stirred for 4 h. The reaction mixture was transferred into iced water and extracted with dichloromethane (20 mL×3). The combined organic layers were washed with brine, dried over anhydrous Na$_2$SO$_4$, and concentrated under reduced pressure to give 600 mg crude 2-(5-bromo-7-chlorobenzofuran-2-yl)ethyl methanesulfonate 92, which was used in the next step without further purification. LCMS: m/z 376 [M+Na]$^+$, t$_R$=1.85 min.

Synthesis of 2-(2-azidoethyl)-5-bromo-7-chlorobenzofuran (74)

2-(5-Bromo-7-chlorobenzofuran-2-yl)ethyl methanesulfonate (73) (600 mg, 1.71 mmol) was dissolved in DMF (10 mL). Sodium azide (222 mg, 3.42 mmol) was added at room temperature. The reaction mixture was stirred at 80° C. for 8 h. After cooling to room temperature, the mixture was transferred into iced water and extracted with ethyl acetate (30 mL×3). The combined organic layers were washed with brine, dried over anhydrous Na$_2$SO$_4$, and concentrated under reduced pressure to give 600 mg of the crude product, which was purified by chromatography (0-10% ethyl acetate/n-hexane) to obtain 2-(2-azidoethyl)-5-bromo-7-chlorobenzofuran 93 (yield: 400 mg, 80%). LCMS: m/z 300 [M+H]$^+$, t$_R$=1.96 min.

Synthesis of 2-(5-bromo-7-chlorobenzofuran-2-yl)ethanamine (75)

2-(2-Azidoethyl)-5-bromo-7-chlorobenzofuran (74) (100 mg, 0.34 mmol) was dissolved in ethanol (8 mL). 10% Pd/C (50% wet (10 mg)) was added and the reaction flask was purged with hydrogen gas. The mixture was stirred at room temperature for 1 h. The reaction mixture was filtered and the filtrate was concentrated under reduced pressure to give 60 mg of the crude 2-(5-bromo-7-chlorobenzofuran-2-yl) ethanamine (75), which was used without further purification in the next step. LCMS: m/z 274 [M+H]$^+$, t$_R$=1.32 min.

Synthesis of tert-butyl 2-(5-bromo-7-chlorobenzofuran-2-yl)ethylcarbamate (76)

(2-(5-Bromo-7-chlorobenzofuran-2-yl)ethanamine (75) (250 mg, 0.92 mmol) was dissolved in dichloromethane (10 mL) and di-tert-butyl dicarbonate (400 mg, 1.84 mmol) was added at 0° C. Then triethylamine (185 mg, 1.84 mmol) was added and the reaction mixture was stirred at room temperature for 4 h. The reaction mixture was transferred into iced water and extracted with dichloromethane (15 mL×3). The combined organic layers were washed with brine, dried over anhydrous Na$_2$SO$_4$, and concentrated under reduced pressure to give 300 mg crude tert-butyl 2-(5-bromo-7-chlorobenzofuran-2-yl)ethylcarbamate (76), which was used without further purification in the next step. LCMS: m/z 395 [M+Na]$^+$, t$_R$=2.11.

Synthesis of tert-butyl 2-(7-chloro-5-(4-(morpholine-4-carbonyl)phenyl)benzofuran-2-yl)ethylcarbamate (77)

tert-Butyl 2-(7-chloro-5-(4-(morpholine-4-carbonyl)phenyl)benzofuran-2-yl)ethylcarbamate (77) was synthesized using General Procedure 2. Yield (77%). LCMS: m/z 485 [M+H]$^+$, t$_R$=2.02.

Synthesis of (4-(2-(2-aminoethyl)-7-chlorobenzofuran-5-yl)phenyl)(morpholino)methanone (78)

((4-(2-(2-aminoethyl)-7-chlorobenzofuran-5-yl)phenyl)(morpholino)methanone (78) was synthesized using General Procedure 3. Yield (72%), LCMS: m/z 385 [M+H]$^+$, t$_R$=1.28.

Synthesis of (E)-3-(6-aminopyridin-3-yl)-N-(2-(7-chloro-5-(4-(morpholine-4-carbonyl)phenyl)benzofuran-2-yl)ethyl)acrylamide (532)

(E)-3-(6-Aminopyridin-3-yl)-N-(2-(7-chloro-5-(4-(morpholine-4carbonyl)phenyl)benzofuran-2-yl)ethyl)acrylamide (532) was synthesized using General Procedure 1. Yield (47%). ¹H NMR (400 MHz, DMSO-d$_6$) δ 8.14 (t, J=5.6 Hz, 1H), 8.05 (d, J=2.0 Hz, 1H), 7.86 (d, J=1.6 Hz, 1H), 7.78 (d, J=8.4 Hz, 2H), 7.67 (d, J=1.6 Hz, 1H), 7.58 (dd, J=2.4 Hz, J=8.8 Hz, 1H), 7.50 (d, J=8.4 Hz, 2H), 7.28 (d, J=15.6 Hz, 1H), 6.84 (s, 1H), 6.46-6.30 (m, 4H), 3.60-3.55 (m, 8H), 3.04 (t, J=5.6 Hz, 2H). LCMS: m/z: 531.7 [M+H]⁺; t$_R$=1.71 min.
Synthesis of (E)-3-(6-aminopyridin-3-yl)-N-((7-chloro-5-(4-(3-fluoroazetidin-1-ylsulfonyl)phenyl)benzofuran-2-yl)methyl)acrylamide (533)
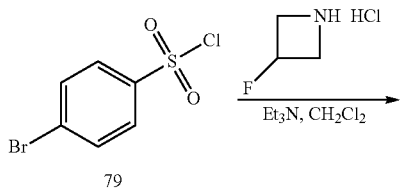
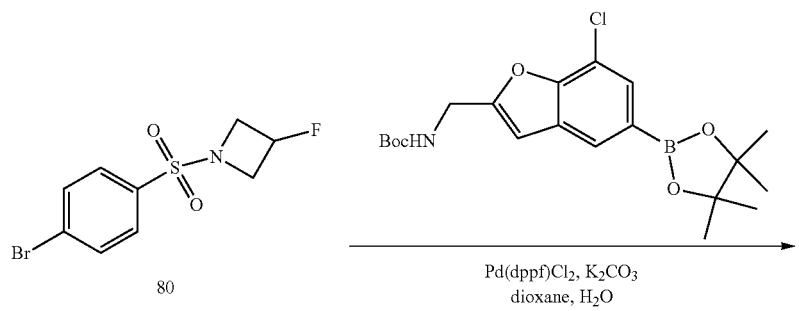
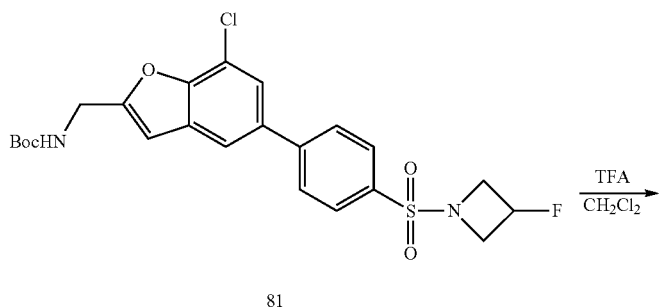
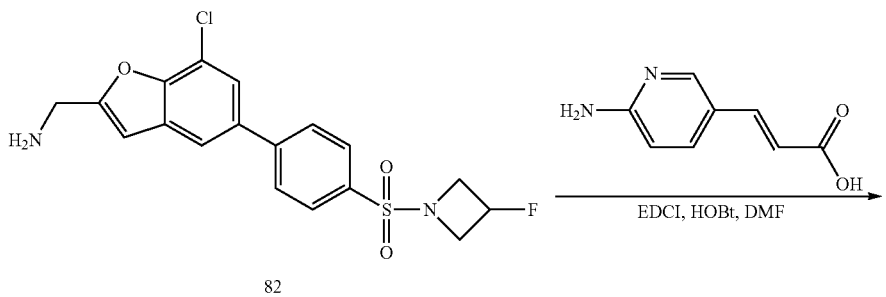

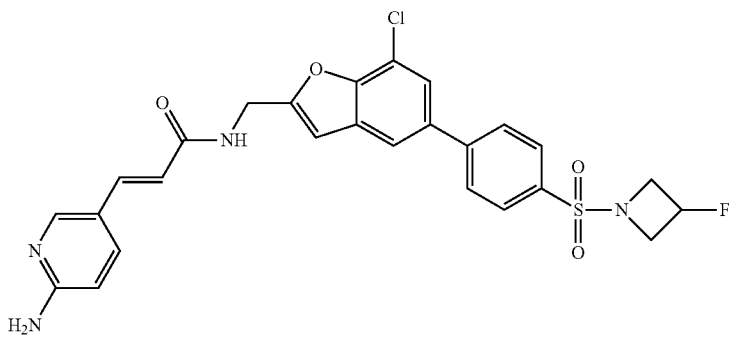

533

Synthesis of 1-(4-bromophenylsulfonyl)-3-fluoroazetidine (80)

1-(4-Bromophenylsulfonyl)-3-fluoroazetidine (80) was synthesized in accordance with the procedure described above for the synthesis of (R)-1-(4-bromophenylsulfonyl)-3-fluoropyrrolidine (64). Yield (90%). LCMS: m/z 294.0 [M+H]$^+$, $t_R$=1.08 min.

Synthesis of tert-butyl (7-chloro-5-(4-(3-fluoroazetidin-1-ylsulfonyl)phenyl)benzofuran-2-yl)methylcarbamate (81)

tert-Butyl (7-chloro-5-(4-(3-fluoroazetidin-1-ylsulfonyl)phenyl)benzofuran-2-yl)methylcarbamate (81) was synthesized using General Procedure 2. Yield (73%). LCMS: m/z 517.0 [M+Na]$^+$, $t_R$=1.82 min.

Synthesis of (7-chloro-5-(4-(3-fluoroazetidin-1-ylsulfonyl)phenyl)benzofuran-2-yl)methanamine (82)

(7-Chloro-5-(4-(3-fluoroazetidin-1-ylsulfonyl)phenyl)benzofuran-2-yl)methanamine (82) was synthesized using General Procedure 3. Yield (100%). LCMS: m/z 395.1 [M+H]$^+$, $t_R$=1.28 min.

Synthesis of (E)-3-(6-aminopyridin-3-yl)-N-((7-chloro-5-(4-(3-fluoroazetidin-1 ylsulfonyl)phenyl)benzofuran-2-yl)methyl)acrylamide (533)

(E)-3-(6-Aminopyridin-3-yl)-1-((7-chloro-5-(4-(3-fluoroazetidin-1 ylsulfonyl)phenyl)benzofuran-2-yl)methyl)acrylamide (533) was synthesized using General Procedure 1. Yield (35%). $^1$H NMR (400 MHz, CD$_3$OD) δ 8.18 (dd, J=9.6 Hz J=2 Hz, 1H), 8.07 (d, J=1.6 Hz, 1H), 7.97 (s, 4H), 7.89 (d, J=1.6 Hz, 1H), 7.72 (d, J=1.6 Hz, 1H), 7.51 (d, J=15.6 Hz, 1H), 7.04 (d, J=9.6 Hz, 1H), 6.92 (s, 1H), 6.65 (d, J=15.6 Hz, 1H), 5.25-5.22 (m, 1H), 5.11-5.08 (m, 1H), 4.73 (s, 2H), 4.18-4.09 (m, 2H), 3.91-3.82 (m, 2H). LCMS: m/z 541.0 [M+H]$^+$, $t_R$=1.48 min.

Synthesis of (E)-3-(6-aminopyridin-3-yl)-N-((7-chloro-5-(5-(morpholine-4-carbonyl)pyridin-3-yl)benzofuran-2-yl)methyl)acrylamide (534)

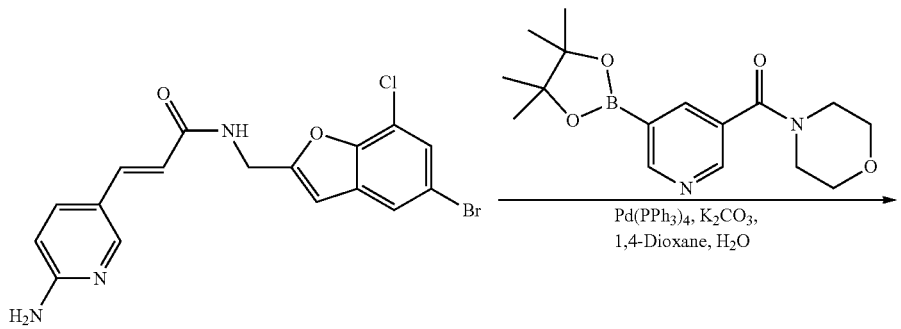

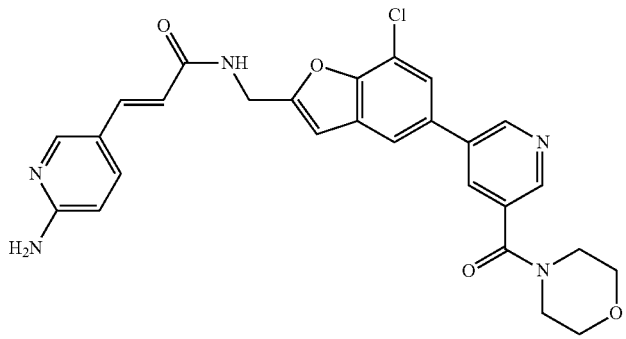

534

(E)-3-(6-Aminopyridin-3-yl)-N-((7-chloro-5-(5-(morpholine-4-carbonyl)pyridin-3-yl)benzofuran-2-yl)methyl)acrylamide (534) was synthesized using General Procedure 2. (Yield: 0.06 g, 22%). $^1$H NMR (400 MHz, DMSO-d$_6$) δ 9.02 (d, J=4 Hz, 1H), 8.67-8.62 (m, 2H), 8.18 (t, J=2 Hz, 1H), 8.09 (d, J=4 Hz, 1H), 8.01 (s, 1H), 7.84 (d, J=4 Hz, 1H), 7.62 (dd, J$_1$, J$_2$=4 Hz, 1H), 7.35 (d, J=16 Hz, 1H), 6.91 (s, 1H), 6.49 (s, 1H), 6.46 (s, 2H), 6.42 (d, J=16 Hz, 1H), 4.61 (d, J=8 Hz, 2H), 3.68 (s, 4H), 3.58 (s, 2H), 3.41 (s, 2H). LCMS: m/z 518.4 [M+H]$^+$, t$_R$=1.70 min.

Synthesis of (E)-N-((7-chloro-5-(4-(morpholine-4-carbonyl)phenyl)benzofuran-2-yl) methyl)-3-(pyridin-4-yl)acrylamide (535)

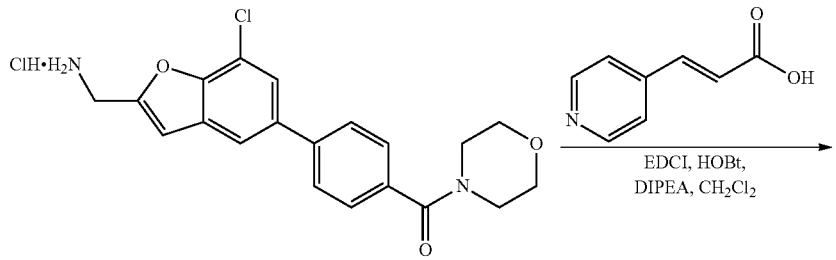

84

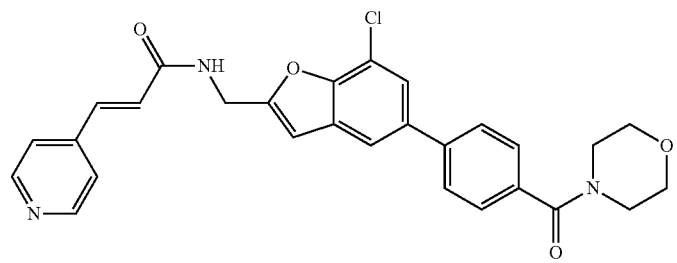

535

(E)-N-((7-Chloro-5-(4-(morpholine-4-carbonyl)phenyl)benzofuran-2-yl)methyl)-3-(pyridin-4-yl)acrylamide (535) was synthesized using General Procedure 1. (Yield: 0.01 g, 37%). $^1$H NMR (400 MHz, DMSO-d$_6$) δ 9.01 (t, J=6.0 Hz, 1H), 8.62 (d, J=6 Hz, 2H), 7.92 (d, J=1.6 Hz, 1H), 7.80 (s, 1H), 7.78 (s, 1H), 7.73 (d, J=1.6 Hz, 1H), 7.56-7.47 (m, 5H), 6.95-6.91 (m, 2H), 4.65 (s, 1H), 4.64 (s, 1H), 3.62-3.38 (m, 8H). LCMS: m/z 502.63 [M+H]$^+$, t$_R$=1.90 min.

Synthesis of (E)-N-((7-chloro-5-(4-(morpholine-4-carbonyl)phenyl)benzofuran-2-yl) methyl)-3-(6-(trifluoromethyl)pyridin-3-yl)acrylamide (536)

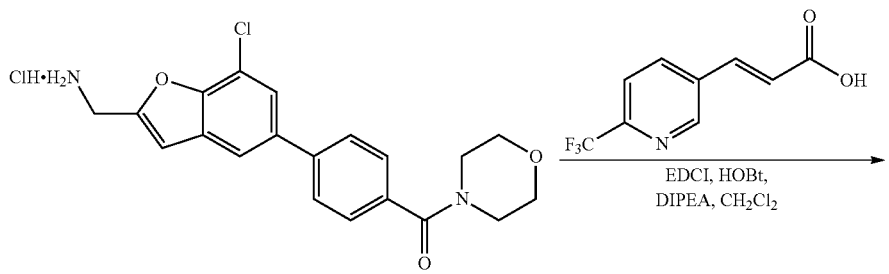

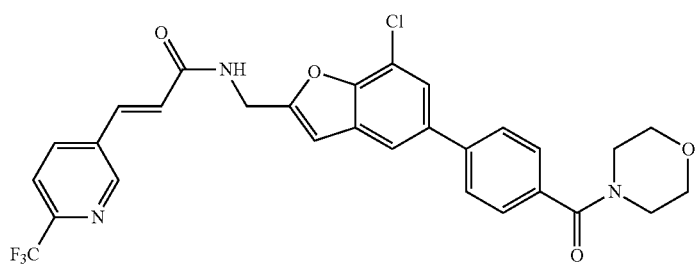

536

(E)-N-((7-Chloro-5-(4-(morpholine-4-carbonyl)phenyl)benzofuran-2-yl)methyl)-3-(6-(trifluoromethyl)pyridin-3-yl)acrylamide (536) was synthesized using General Procedure 1. (Yield: 0.02 g, 13%). $^1$H NMR (400 MHz, DMSO-d$_6$) δ 9.03-8.99 (m, 2H), 8.31-8.28 (m, 1H), 7.97 (d, J=8.4 Hz, 1H), 7.92 (d, J=1.6 Hz, 1H), 7.80 (s, 1H), 7.78 (s, 1H), 7.73 (d, J=1.6 Hz, 1H), 7.52 (s, 1H), 7.50 (s, 1H), 6.98-6.94 (m, 2H), 4.66 (s, 1H), 4.65 (s, 1H), 3.76-3.62 (m, 8H). LCMS: m/z 570.39 [M+H]$^+$, t$_R$=2.32 min.

Synthesis of (E)-N-((7-chloro-5-(4-(morpholine-4-carbonyl)phenyl)benzofuran-2-yl) methyl)-3-(6-chloropyridin-3-yl)acrylamide (537)

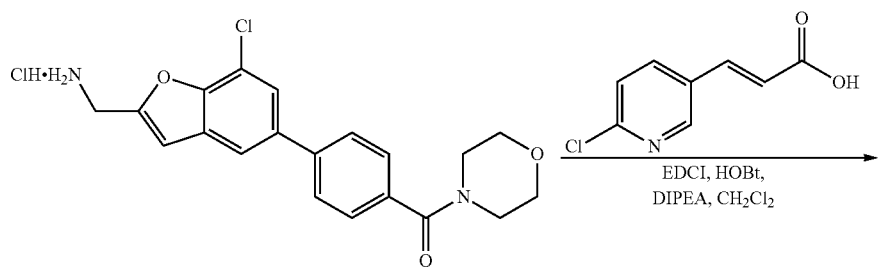

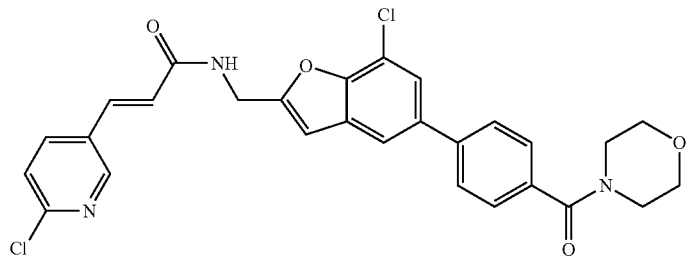
537
(E)-N-((7-Chloro-5-(4-(morpholine-4-carbonyl)phenyl)benzofuran-2-yl)methyl)-3-(6-chloropyridin-3-yl)acrylamide (537) was synthesized using General Procedure 1. (Yield: 0.01 g, 7%). $^1$H NMR (400 MHz, DMSO-$d_6$) δ 8.93 (t, J=5.6 Hz, 1H), 8.64 (d, J=2.4 Hz, 1H), 8.09 (dd, Jr, $J_2$=2.4 Hz, 1H), 7.92 (d, J=1.6 Hz, 1H), 7.81 (s, 1H), 7.78 (s, 1H), 7.73 (d, J=1.6 Hz, 1H), 7.60-7.51 (m, 4H), 6.94 (s, 1H), 6.83 (d, J=16 Hz, 1H), 4.64 (d, J=5.6 Hz, 2H), 3.63-3.16 (m, 8H). LCMS: m/z 536.20 [M]$^+$, $t_R$=2.22 min.
Synthesis of ((E)-N-((7-chloro-5-(4-(morpholine-4-carbonyl)phenyl)benzofuran-2-yl)methyl)-3-(pyridin-3-yl)acrylamide (538)
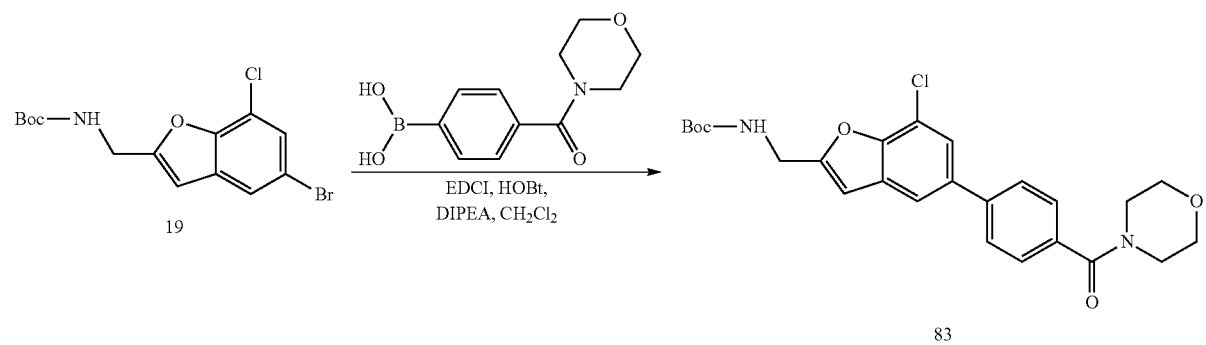
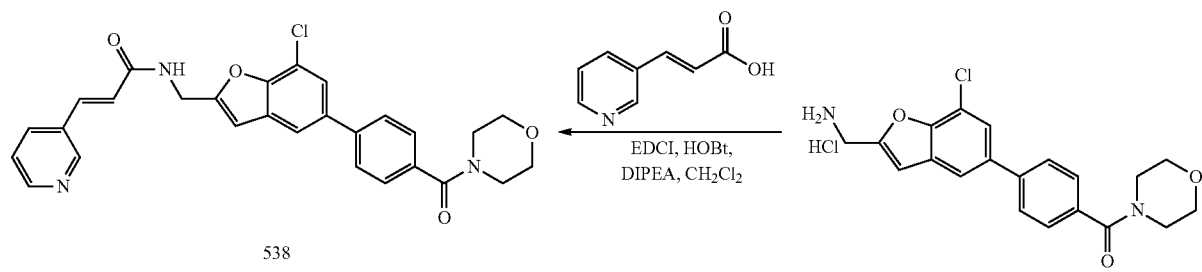

Synthesis of tert-butyl (7-chloro-5-(4-(morpholine-4-carbonyl)phenyl)benzofuran-2-yl) methylcarbamate (83)

tert-Butyl (5-bromo-7-chlorobenzofuran-2-yl)methylcarbamate (19) (0.85 g, 2.35 mmol) was dissolved in 1,4-dioxane (8 mL) at room temperature and degassed with $N_2$ gas for 5 min. Tetrakis(triphenylphosphine)palladium (O) (0.25 g, 0.21 mmol) and 4-(morpholine-4-carbonyl) phenylboronic acid (0.83 g, 3.55 mmol) were added at room temperature and stirred for 5 min. A degassed solution of $K_2CO_3$ (0.65 g, 4.71 mmol) in water (2 mL) was added and the reaction mixture was irradiated under microwave for 30 min at 90° C. The reaction mixture was transferred into iced water and extracted with ethyl acetate (3×50 mL). The combined organic layers were washed with brine, dried over anhydrous $Na_2SO_4$ and concentrated under reduced pressure to give crude compound, which was purified by silica gel chromatography (0-90% ethyl acetate/n-hexane) to obtain tert-butyl (7-chloro-5-(4-(morpholine-4-carbonyl)phenyl) benzofuran-2-yl)methylcarbamate (83). (Yield: 0.50 g, 45%). $^1$H NMR (400 MHz, DMSO-$d_6$) δ 7.91 (s, 1H), 7.80 (s, 1H), 7.78 (s, 1H), 7.10 (d, J=1.6 Hz, 1H), 7.54-7.50 (m, 2H), 6.83 (s, 1H), 4.34 (s, 1H), 4.33 (s, 1H), 3.42-3.37 (m, 8H), 1.42 (s, 9H).

Synthesis of (4-(2-(aminomethyl)-7-chlorobenzofuran-5-yl)phenyl)(morpholino)methanone hydrochloride (84)

tert-Butyl(7-chloro-5-(4-(morpholine-4-carbonyl)phenyl) benzofuran-2-yl)methylcarbamate (83) (0.5 g, 1.06 mmol) was dissolved in dichloromethane (15 mL) at room temperature. The reaction mixture was cooled to 0° C. and HCl in dioxane (5 mL) was added dropwise. The reaction mixture was slowly allowed to warm to room temperature and stirred for 18 h. The reaction mixture was concentrated under reduce pressure and the crude product was crystallized with diethyl ether and dried under reduced pressure to obtain (4-(2-(aminomethyl)-7-chlorobenzofuran-5-yl)phenyl) (morpholino)methanone hydrochloride (84). (Yield: 0.33 g, 85%). $^1$H NMR (400 MHz, DMSO-$d_6$) (8.72 (bs, 3H), 8.03 (d, J=1.6 Hz, 1H), 7.83-7.80 (m, 3H), 7.55 (s, 1H), 7.51 (s, 1H), 7.21 (s, 1H), 4.35 (s, 2H), 3.63-3.41 (m, 8H).

Synthesis of (E)-N-((7-chloro-5-(4-(morpholine-4-carbonyl)phenyl)benzofuran-2-yl) methyl)-3-(pyridin-3-yl)acrylamide (538)

(4-(2-(Aminomethyl)-7-chlorobenzofuran-5-yl)phenyl) (morpholino)methanonehydrochloride (84) (0.1 g, 0.26 mmol) was dissolved in dichloromethane (10 mL) at room temperature. The reaction mixture was cooled to 0° C. and (E)-3-(pyridin-3-yl) acrylic acid (0.06 g, 0.40 mmol), EDCI (0.077 g, 0.40 mmol) and HOBt (0.054 g, 0.4 mmol) were added, followed by DIPEA (0.05 mL, 0.53 mmol). The reaction mixture was allowed to warm to room temperature and stirred for 3 h. The reaction mixture was transferred into iced water and extracted with ethyl acetate (3×25 mL). The combined organic layers were washed with brine, dried over anhydrous $Na_2SO_4$ and concentrated under reduced pressure to give crude product, which was purified by silica gel chromatography (0-5% MeOH in $CH_2Cl_2$) to obtain (E)-N-((7-chloro-5-(4-(morpholine-4-carbonyl)phenyl)benzofuran-2-yl)methyl)-3-(pyridin-3-yl)acrylamide (538). (Yield: 0.01 g, 7%). $^1$H NMR (400 MHz, DMSO-$d_6$) δ 8.92 (t, J=5.6 Hz, 1H), 8.79 (d, J=1.6 Hz, 1H), 8.57 (dd, $J_1$=1.6 Hz, $J_2$=1.2 Hz, 1H), 8.03-7.92 (m, 1H), 7.92 (d, J=1.6 Hz, 1H), 7.80 (s, 1H), 7.78 (s, 1H), 7.73 (d, J=1.6 Hz, 1H), 7.54 (s, 1H), 7.53-7.44 (m, 3H), 6.94 (s, 1H), 6.83 (d, J=15.6 Hz, 1H), 4.65 (s, 1H), 4.63 (s, 1H), 3.63-3.49 (m, 8H). LCMS: m/z 502.63 [M+H]$^+$, $t_R$=1.96 min.

Synthesis of (E)-N-((7-chloro-5-(4-(morpholine-4-carbonyl)phenyl)benzofuran-2-yl)methyl)-3-(pyridin-2-yl)acrylamide (539)

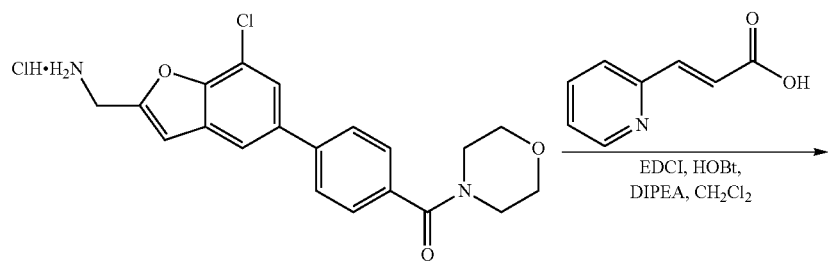

84

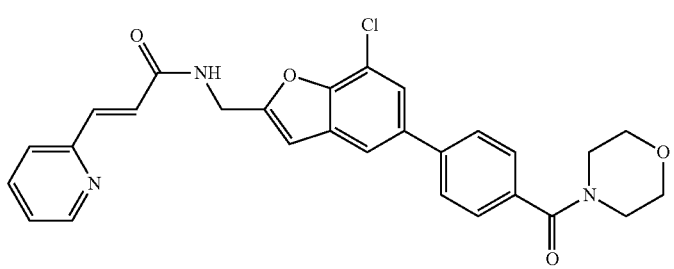

539

(E)-N-((7-Chloro-5-(4-(morpholine-4-carbonyl)phenyl) benzofuran-2-yl)methyl)-3-(pyridin-2-yl)acrylamide (539) was synthesized using General Procedure 1. (Yield: 0.015 g, 11%). $^1$H NMR (400 MHz, DMSO-$d_6$) δ 9.02 (t, J=5.8 Hz, 1H), 8.63 (d, J=3.6 Hz, 1H), 7.91 (d, J=1.6 Hz, 1H), 7.87-7.78 (m, 3H), 7.73 (d, J=1.6 Hz, 1H), 7.61 (d, J=7.6 Hz, 1H), 7.55-7.50 (m, 3H), 7.39-7.36 (m, 1H), 7.16 (d, J=15.6 Hz, 1H), 6.93 (s, 1H), 4.65 (s, 1H), 4.64 (s, 1H), 3.62-3.38 (m, 8H). LCMS: m/z 502.38 [M+H]$^+$, $t_R$=2.06 min.

Synthesis of (E)-N-((7-chloro-5-(4-(morpholine-4-carbonyl)phenyl)benzofuran-2-yl)methyl)-3-(pyridazin-3-yl)acrylamide (540)

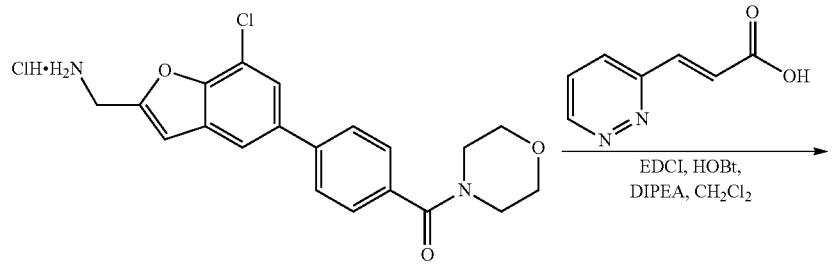

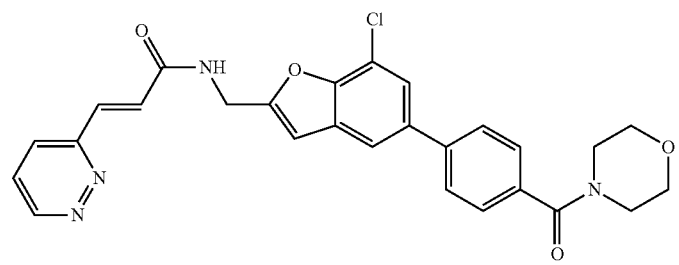

(E)-N-((7-Chloro-5-(4-(morpholine-4-carbonyl)phenyl) benzofuran-2-yl)methyl)-3-(pyridazin-3-yl)acrylamide (540) was synthesized using General Procedure 1. (Yield: 0.02 g, 13%). $^1$H NMR (400 MHz, DMSO-$d_6$) δ 9.20 (dd, $J_1$, $J_2$=1.6 Hz, 1H), 9.15 (t, J=11.2 Hz, 1H), 7.99-7.91 (m, 3H), 7.81-7.76 (m, 4H), 7.52 (s, 1H), 7.50 (s, 1H), 7.29 (d, J=16 Hz, 1H), 6.96 (s, 1H), 4.68 (s, 1H), 4.66 (s, 1H), 3.62-3.35 (m, 8H). LCMS: m/z 503.43 [M+H]$^+$, $t_R$=1.94 min.

Synthesis of (E)-N-((7-chloro-5-(4-(morpholine-4-carbonyl)phenyl)benzofuran-2-yl) methyl)-3-(3,5-dimethylisoxazol-4-yl)acrylamide (541)

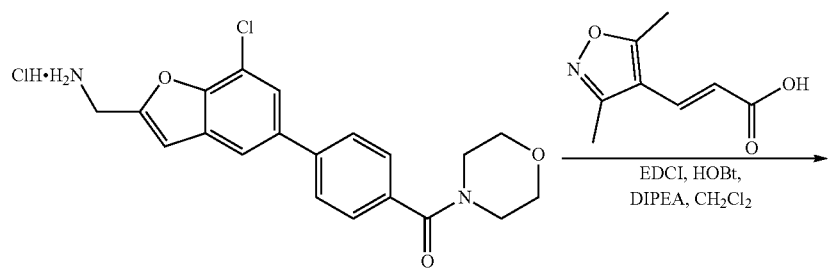

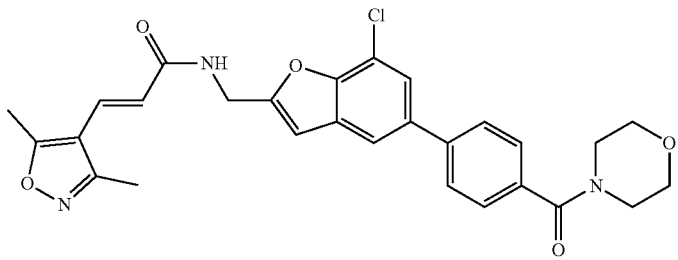
541
(E)-N-((7-Chloro-5-(4-(morpholine-4-carbonyl)phenyl)benzofuran-2-yl)methyl)-3-(3,5-dimethylisoxazol-4-yl)acrylamide (541) was synthesized using General Procedure 1. (Yield: 0.012 g, 9%). $^1$H NMR (400 MHz, DMSO-$d_6$) δ 8.83 (t, J=11.6 Hz, 1H), 7.92 (d, J=1.6 Hz, 1H), 7.81 (s, 1H), 7.79 (s, 1H), 7.74 (d, J=1.6 Hz, 1H), 7.52 (d, J=8.4 Hz, 2H), 7.28 (d, J=16.4 Hz, 1H), 6.94 (s, 1H), 6.51 (d, J=16 Hz, 1H), 4.63 (d, J=5.6 Hz, 2H), 3.63-3.35 (m, 8H), 2.49 (s, 3H), 2.34 (s, 3H). LCMS: m/z 520.4 [M+H]$^+$, $t_R$=2.19 min.
Synthesis of (E)-N-((7-chloro-5-(4-(morpholine-4-carbonyl)phenyl)benzofuran-2-yl) methyl)-3-(thiazol-2-yl)acrylamide (542)
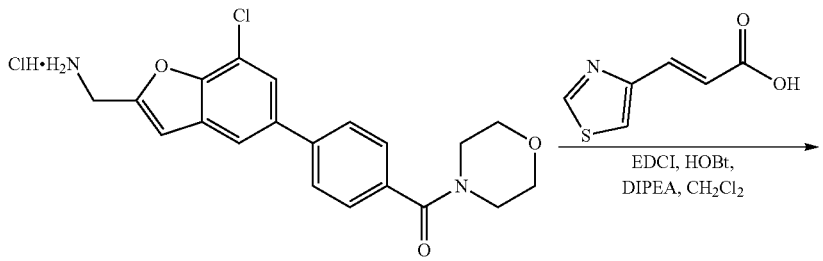
84
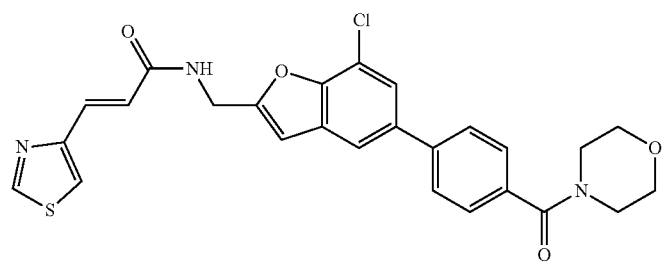
542

(E)-N-((7-Chloro-5-(4-(morpholine-4-carbonyl)phenyl)benzofuran-2-yl)methyl)-3-(thiazol-2-yl)acrylamide (542) was synthesized using General Procedure 1. (Yield: 0.02 g, 15%). $^1$H NMR (400 MHz, DMSO-$d_6$) δ 9.18 (d, J=1.2 Hz, 1H), 8.96 (t, J=10.4 Hz, 1H), 8.02 (d, J=2 Hz, 1H), 7.92 (d, J=1.6 Hz, 1H), 7.81 (s, 1H), 7.78 (s, 1H), 7.73 (d, J=1.6 Hz, 1H), 7.54-7.51 (m, 3H), 6.94 (d, J=14.4 Hz, 2H), 4.63 (d, J=5.6 Hz, 2H), 3.63-3.35 (m, 8H). LCMS: m/z 508.33 [M+H]$^+$, $t_R$=2.07 min.

Synthesis of (E)-3-(6-aminopyridin-3-yl)-N-((7-chloro-5-(3-(morpholine-4-carbonyl) phenyl)benzofuran-2-yl)methyl)acrylamide (543)

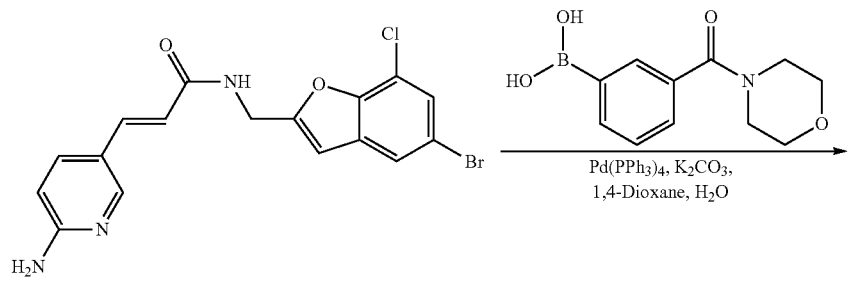

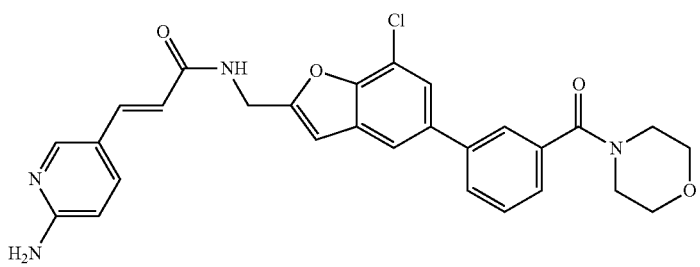

543

(E)-3-(6-Aminopyridin-3-yl)-N-((7-chloro-5-(3-(morpholine-4-carbonyl)phenyl)benzofuran-2-yl)methyl)acrylamide (543) was synthesized using General Procedure 2. (Yield: 0.05 g, 20%). $^1$H NMR (400 MHz, DMSO-$d_6$) δ 8.65 (t, J=6 Hz, 1H), 8.08 (d, J=4 Hz, 1H), 7.91 (d, J=4 Hz, 1H), 7.80 (dd, $J_1$, $J_2$=4 Hz, 1H), 7.72 (d, J=4 Hz, 2H), 7.61 (dd, $J_1$, $J_2$=4 Hz, 1H), 7.54 (t, J=8 Hz, 1H), 7.39 (d, J=8 Hz, 1H), 7.35 (d, J=16 Hz, 1H), 6.89 (s, 1H), 6.47 (d, J=8 Hz, 1H), 6.45 (s, 2H), 6.42 (d, J=16 Hz, 1H), 4.60 (d, J=4 Hz, 2H), 3.65-3.38 (m, 8H). LCMS: m/z 517.63 [M+H]$^+$, $t_R$=1.84 min.

Synthesis of (E)-3-(6-aminopyridin-3-yl)-N-((7-chloro-5-(5-fluoro-6-(morpholine-4-carbonyl)pyridin-3-yl)benzofuran-2-yl)methyl)acrylamide (544)

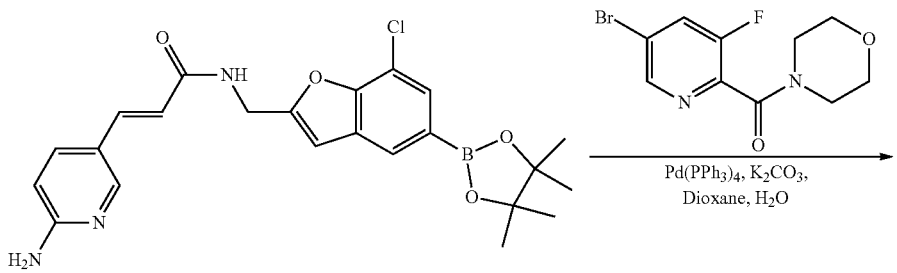

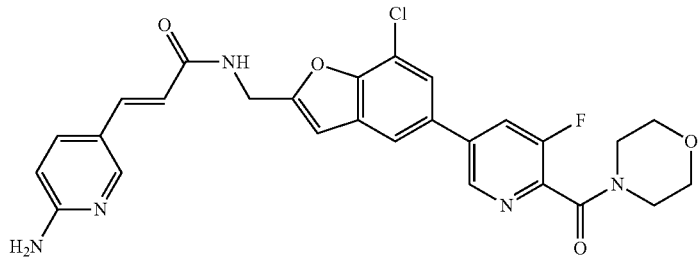

544

(E)-3-(6-Aminopyridin-3-yl)-N-((7-chloro-5-(5-fluoro-6-(morpholine-4-carbonyl)pyridin-3-yl)benzofuran-2-yl)methyl)acrylamide (544) was synthesized using General Procedure 2. (Yield: 0.02 g, 18%). $^1$H NMR (400 MHz, DMSO-$d_6$) δ 8.88 (t, J=4 Hz, 1H), 8.66 (t, J=4 Hz, 1H), 8.30 (dd $J_1$, $J_2$=4 Hz, 1H), 8.09 (s, 1H), 8.06 (s, 1H), 7.90 (s, 1H), 7.63 (dd, $J_1$, $J_2$=2 Hz, 1H), 7.36 (d, J=16 Hz, 1H), 6.92 (s, 1H), 6.51 (d, J=4 Hz, 1H), 6.49 (s, 2H), 6.43 (d, J=16 Hz, 1H), 4.61 (d, J=4 Hz, 2H), 3.69-3.29 (m, 8H). LCMS: m/z 536.43 [M+H]$^+$, $t_R$=1.77 min.

Synthesis of (E)-3-(6-aminopyridin-3-yl)-N-((7-chloro-5-(4-(2-morpholino-2-oxoacetyl) phenyl)benzofuran-2-yl)methyl)acrylamide (545)

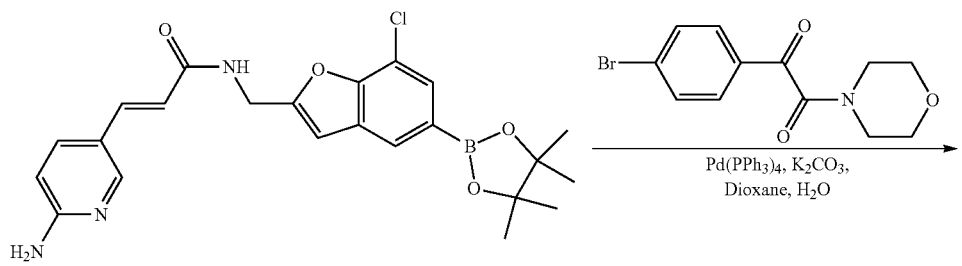

16

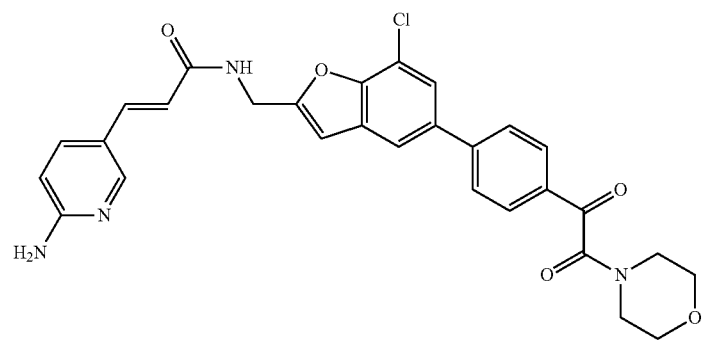

545

(E)-3-(6-Aminopyridin-3-yl)-N-((7-chloro-5-(4-(2-morpholino-2-oxoacetyl)phenyl)benzofuran-2-yl)methyl)acrylamide (545) was synthesized using General Procedure 2. (Yield: 0.02 g, 12%). $^1$H NMR (400 MHz, DMSO-d$_6$) δ 8.65 (t, J=5.8 Hz, 1H), 8.09 (d, J=2 Hz, 1H), 8.01-7.96 (m, 5H), 7.81 (d, J=1.6 Hz, 1H), 7.62 (dd, J$_1$=2.0 Hz, J$_2$=2.4 Hz, 1H), 7.35 (d, J=15.6 Hz, 1H), 6.93 (s, 1H), 6.49-6.40 (m, 4H), 4.61 (d, J=5.6 Hz, 2H), 3.73-3.67 (m, 4H), 3.56-3.54 (m, 2H), 3.34-3.32 (m, 2H). LCMS: m/z 545.29 [M+H]$^+$, t$_R$=1.87 min.

Synthesis of (E)-3-(6-aminopyridin-3-yl)-N-((7-chloro-5-(2-(morpholine-4-carbonyl) pyrimidin-5-yl)benzofuran-2-yl)methyl)acrylamide (546)

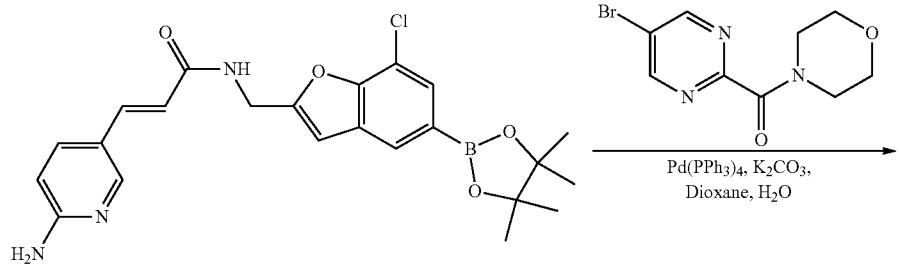

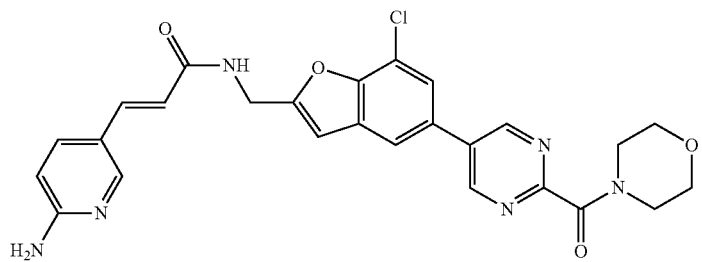

546

(E)-3-(6-Aminopyridin-3-yl)-N-((7-chloro-5-(2-(morpholine-4-carbonyl)pyrimidin-5-yl)benzofuran-2-yl) methyl)acrylamide (546) was synthesized using General Procedure 2. (Yield: 0.03 g, 17%), $^1$H NMR (400 MHz, DMSO-d$_6$) δ 9.28 (s, 2H), 8.66 (s, 1H), 8.08 (d, J=4 Hz, 2H), 7.94 (d, J=4 Hz, 1H), 7.64-7.61 (m, 1H), 7.36 (d, J=16 Hz, 1H), 6.94 (s, 1H), 6.48 (d, J=8 Hz, 1H), 6.46 (s, 2H), 6.43 (d, J=16 Hz, 1H), 4.59 (d, J=4 Hz, 2H), 3.67 (s, 4H), 3.54 (t, J=4 Hz, 2H), 3.25 (t, J=4 Hz, 2H). LCMS: m/z 519.03 [M+H]$^+$, t$_R$=1.69 min.

Synthesis of (E)-3-(6-aminopyridin-3-yl)-N-((7-chloro-5-(2,5-difluoro-4-(morpholine-4-carbonyl) phenyl)benzofuran-2-yl)methyl)acrylamide (547)

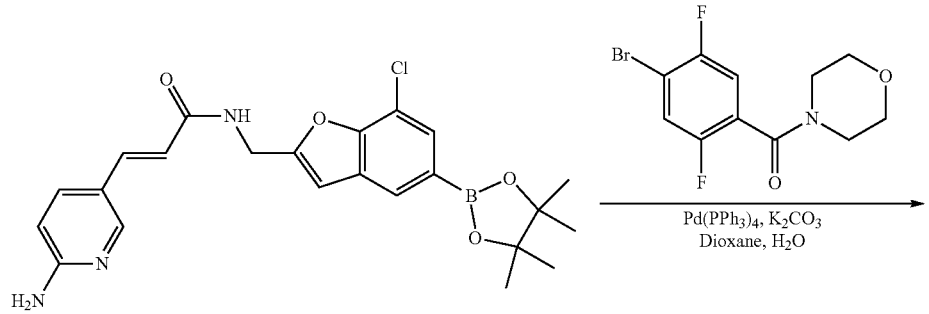

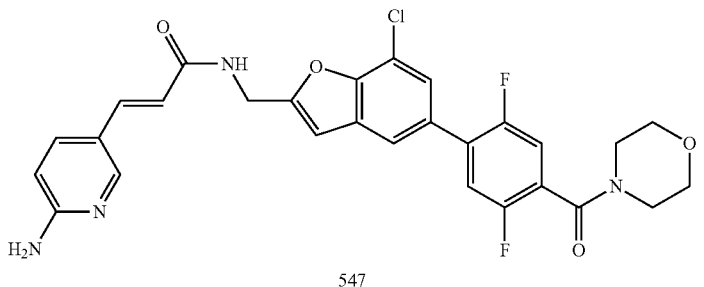

547

(E)-3-(6-Aminopyridin-3-yl)-N-((7-chloro-5-(2,5-difluoro-4-(morpholine-4-carbonyl)phenyl)benzofuran-2-yl)methyl)acrylamide (547) was synthesized using General Procedure 2. (Yield: 0.02 g, 11%), $^1$H NMR (400 MHz, DMSO-d$_6$) δ 8.65 (t, J=4 Hz, 1H), 8.08 (s, 1H), 7.82 (s, 1H), 7.65-7.62 (m, 3H), 7.51-7.48 (m, 1H), 7.36 (d, J=16 Hz, 1H), 6.92 (s, 1H), 6.48 (d, J=8 Hz, 1H), 6.46 (s, 2H), 6.43 (d, J=16 Hz, 1H), 4.61 (d, J=5.2 Hz, 2H), 3.66 (s, 4H), 3.57 (s, 2H), 3.34 (s, 2H). LCMS: m/z 553.39 [M+H]$^+$, t$_R$=1.89 min.

Synthesis of (E)-3-(6-aminopyridin-3-yl)-N-((7-chloro-5-(2,3-difluoro-4-(morpholine-4-carbonyl)phenyl)benzofuran-2-yl)methyl)acrylamide (548)

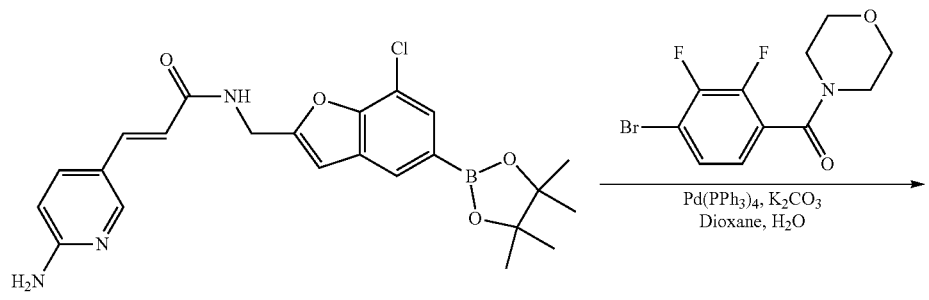

16

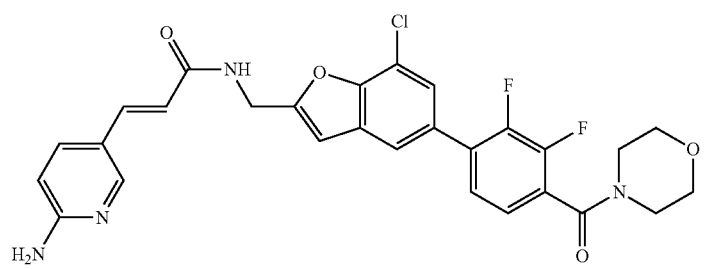

548

(E)-3-(6-Aminopyridin-3-yl)-N-((7-chloro-5-(2,3-difluoro-4-(morpholine-4-carbonyl)phenyl)benzofuran-2-yl)methyl)acrylamide (548) was synthesized using General Procedure 2. (Yield: 0.02 g, 11%). $^1$H NMR (400 MHz, DMSO-$d_6$) δ 8.65 (t, J=5.8 Hz, 1H), 8.08 (s, 1H), 7.81 (s, 1H), 7.63-7.61 (m, 2H), 7.51-7.48 (m, 1H), 7.37-7.32 (m, 2H), 6.93 (s, 1H), 6.49-6.40 (m, 4H), 4.61 (d, J=5.6 Hz, 2H), 3.67 (s, 4H) 3.56-3.55 (m, 2H), 3.34-3.32 (m, 2H). LCMS: m/z 554.21 [M+H]$^+$, $t_R$=1.86 min.

Synthesis of (E)-3-(6-aminopyridin-3-yl)-N-((7-chloro-5-(3-fluoro-4-(morpholine-4-carbonyl)phenyl)benzofuran-2-yl)methyl)acrylamide (549)

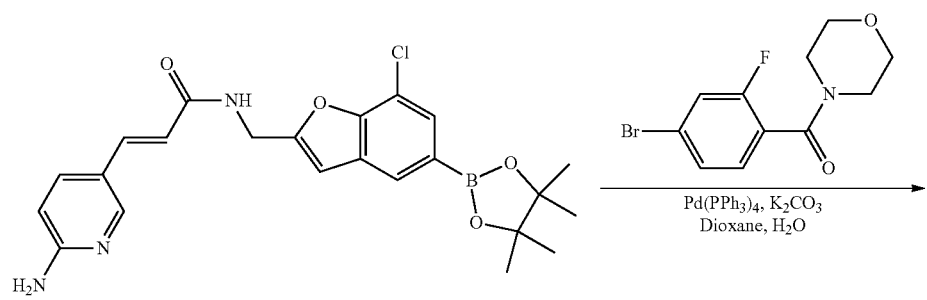

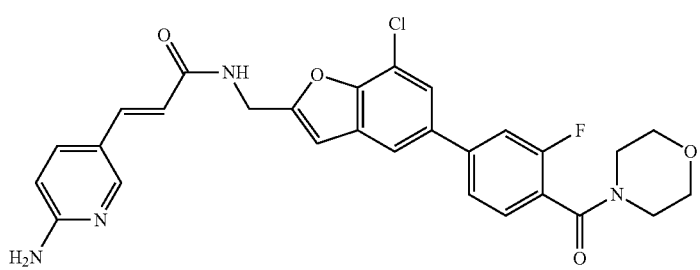

(E)-3-(6-Aminopyridin-3-yl)-N-((7-chloro-5-(3-fluoro-4-(morpholine-4-carbonyl)phenyl)benzofuran-2-yl)methyl)acrylamide (549) was synthesized using General Procedure 2. (Yield: 0.02 g, 12%). $^1$H NMR (400 MHz, DMSO-$d_6$) δ 8.64 (t, J=6.0 Hz, 1H), 8.08 (d, J=1.6 Hz, 1H), 7.96 (d, J=1.6 Hz, 1H), 7.79 (d, J=1.6 Hz, 1H), 7.73-7.61 (m, 3H), 7.61-7.49 (m, 1H), 7.35 (d, J=15.6 Hz, 1H), 6.90 (s, 1H), 6.49-6.40 (m, 4H), 4.61 (d, J=5.2 Hz, 2H), 3.67 (s, 4H), 3.56-3.54 (m, 2H), 3.30-3.28 (m, 2H). LCMS: m/z 535.13 [M+H]$^+$, $t_R$=1.85 min.

Synthesis of (E)-3-(4-aminophenyl)-N-((7-chloro-5-(4-(morpholine-4-carbonyl) phenyl) benzofuran-2-yl)methyl)acylamide (550)

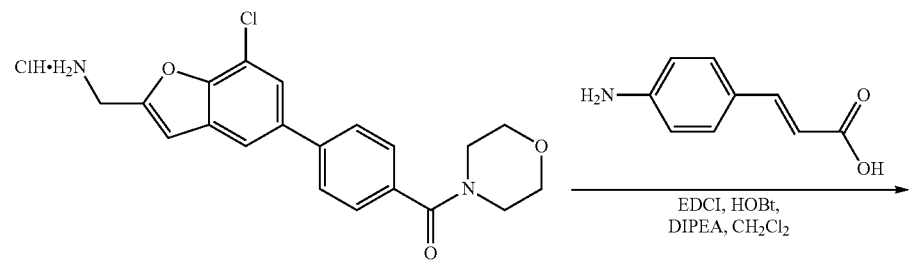

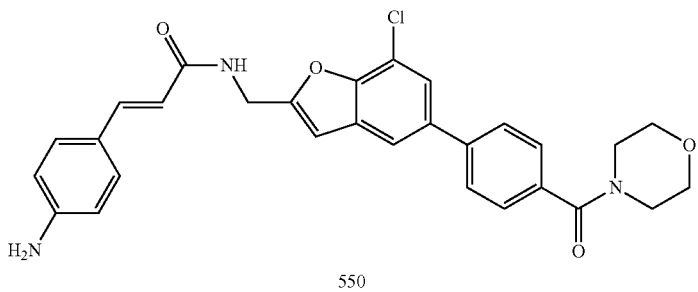

550

(E)-3-(4-Aminophenyl)-N-((7-chloro-5-(4-(morpholine-4-carbonyl)phenyl)benzofuran-2-yl)methyl)acrylamide (550) was synthesized using General Procedure 1. (Yield: 0.012 g, 9%). $^1$H NMR (400 MHz, DMSO-d$_6$) δ 8.58 (t, J=5.8 Hz, 1H), 7.90 (d, J=1.6 Hz, 1H), 7.79 (d, J=8.0 Hz, 2H), 7.72 (d, J=1.6 Hz, 1H), 7.51 (d, J=8.0 Hz, 2H), 7.33 (d, J=15.6 Hz, 1H), 7.25 (d, J=8.4 Hz, 2H), 6.89 (s, 1H), 6.56 (d, J=8.8 Hz, 2H), 6.36 (d, J=15.6 Hz, 1H), 5.61 (s, 2H), 4.59 (d, J=5.6 Hz, 2H), 3.68-3.41 (m, 8H). LCMS: m/z 516.18 [M+H]$^+$, t$_R$=2.08 min.

Synthesis of (E)-N-((7-chloro-5-(4-(morpholine-4-carbonyl)phenyl)benzofuran-2-yl) methyl)-3-(6-(dimethylamino)pyridin-3-yl)acrylamide (551)

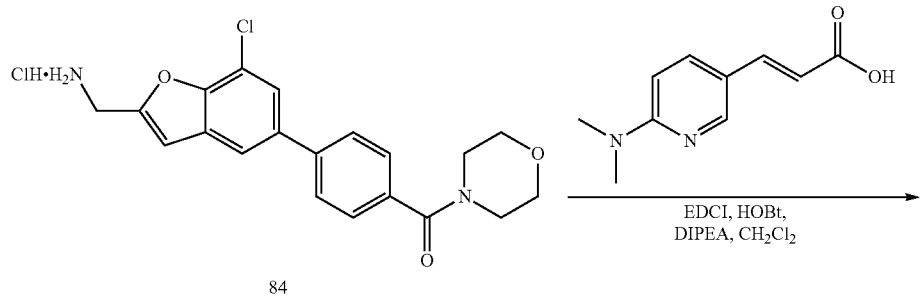

84     EDCI, HOBt, DIPEA, CH$_2$Cl$_2$

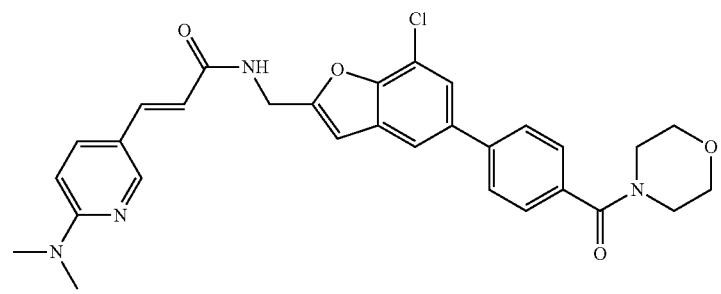

551

(E)-N-((7-Chloro-5-(4-(morpholine-4-carbonyl)phenyl)benzofuran-2-yl)methyl)-3-(6-(dimethylamino)pyridin-3-yl)acrylamide (551) was synthesized using General Procedure 1. (Yield: 0.02 g, 14%). $^1$H NMR (400 MHz, DMSO-$d_6$) δ 8.66 (t, J=5.8 Hz, 1H), 8.26 (d, J=2.4 Hz, 1H), 7.91 (d, J=1.6 Hz, 1H), 7.81 (s, 1H), 7.78 (s, 1H), 7.75-7.72 (m, 2H), 7.51 (d, J=8.4 Hz, 2H), 7.40 (d, J=8.4 Hz, 1H), 6.91 (s, 1H), 7.71 (d, J=9.2 Hz, 1H), 6.48 (d, J=15.6 Hz, 1H), 4.61 (d, J=5.2 Hz, 2H), 3.62-3.47 (m, 8H), 3.02 (s, 6H). LCMS: m/z 545.44 [M]$^+$, $t_R$=1.90 min.

Synthesis of (E)-3-(6-aminopyridin-3-yl)-N-((7-chloro-5-(6-(morpholine-4-carbonyl)pyridazin-3-yl)benzofuran-2-yl)methyl)acrylamide (552)

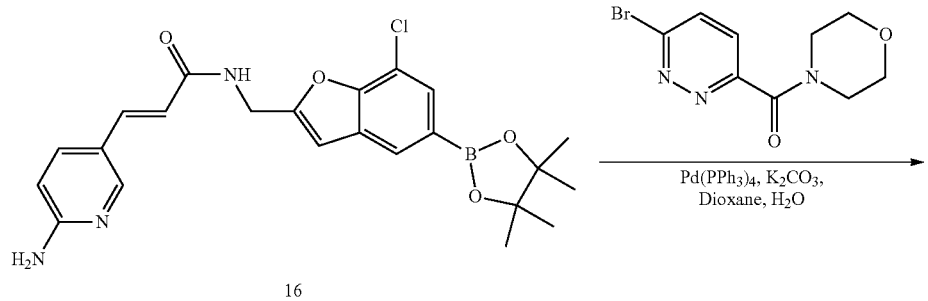

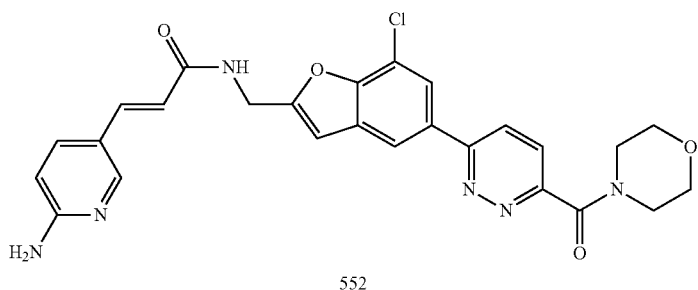

(E)-3-(6-Aminopyridin-3-yl)-N-((7-chloro-5-(6-(morpholine-4-carbonyl)pyridazin-3-yl)benzofuran-2-yl)methyl)acrylamide (552) was synthesized using General Procedure 2. (Yield: 0.012 g, 7%). $^1$H NMR (400 MHz, DMSO-$d_6$) δ 8.67 (t, J=5.2 Hz, 1H), 8.47 (s, 1H), 8.26 (s, 1H), 8.09 (s, 1H), 8.00 (d, J=9.2 Hz, 1H), 7.60 (m, 2H), 7.36 (d, J=16 Hz, 1H), 6.99 (s, 1H), 6.50 (s, 1H), 6.47 (s, 2H), 6.43 (d, J=16 Hz, 1H), 4.61 (d, J=4.8 Hz, 2H), 3.73 (s, 4H), 3.62 (d, J=4 Hz, 2H), 3.53 (d, J=4 Hz, 2H). LCMS: m/z 519.28 [M+H]$^+$, $t_R$=1.69 min.

Synthesis of (E)-3-(6-aminopyridin-3-yl)-N-((7-chloro-5-(4-(2-morpholino-2-oxoethyl) phenyl)benzofuran-2-yl)methyl)acrylamide (553)

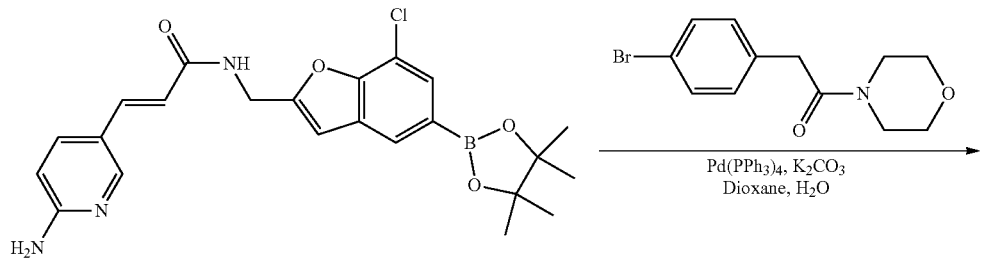

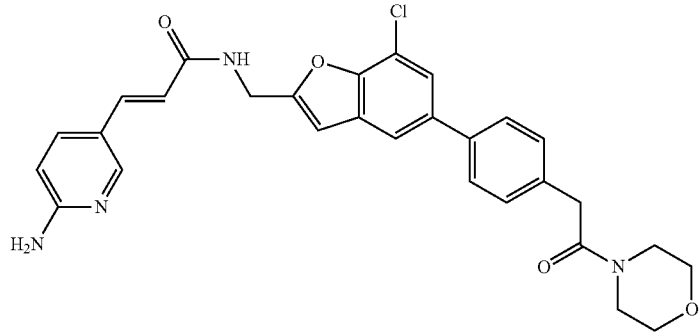
553
(E)-3-(6-Aminopyridin-3-yl)-N-((7-chloro-5-(4-(2-morpholino-2-oxoethyl)phenyl)benzofuran-2-yl)methyl)acrylamide (553) was synthesized using General Procedure 2. (Yield: 0.01 g, 4%). $^1$H NMR (400 MHz, DMSO-$d_6$) δ 8.63 (t, J=5.8 Hz, 1H), 8.08 (d, J=1.6 Hz, 1H), 7.85 (d, J=1.6 Hz, 1H), 7.66-7.60 (m, 4H), 7.37-7.31 (m, 3H), 6.88 (s, 1H), 6.49-6.40 (m, 4H), 4.60 (d, J=5.2 Hz, 2H), 3.77 (s, 2H), 3.55-3.51 (m, 4H), 3.48-3.30 (m, 4H). LCMS: m/z 531.28 [M]$^+$, $t_R$=1.87 min.
Synthesis of (E)-3-(6-aminopyridin-3-yl)-N-((7-methoxy-4-(morpholinesulfonyl)phenyl) benzofuran-2-yl)methyl)acrylamide (554)

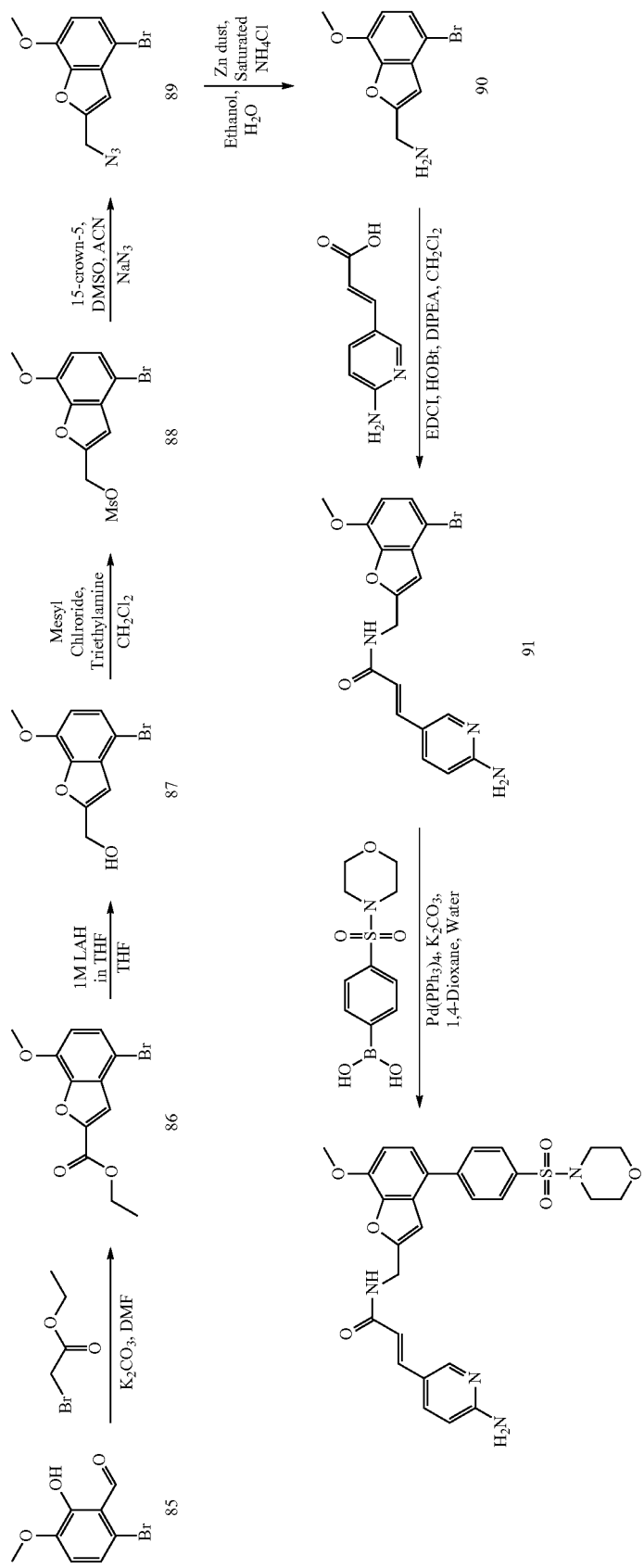

Synthesis of ethyl 4-bromo-7-methoxybenzofuran-2-carboxylate (86)

6-Bromo-2-hydroxy-3-methoxybenzaldehyde (85) (10 g, 43.2 mmol) was dissolved in DMF (100 mL) at room temperature. $K_2CO_3$ (14.92 g, 108.0 mmol) and ethyl bromoacetate (7.47 mL, 64.9 mmol) were added and the reaction mixture was heated at 100° C. for 6 h. The reaction mixture was allowed to cool to room temperature, transferred into iced water and extracted with ethyl acetate (3×200 mL). The combined organic layers were washed with brine solution, dried over anhydrous $Na_2SO_4$ and concentrated under reduced pressure to give crude product, which was purified by silica gel chromatography (0-5% ethyl acetate in hexane) to obtain ethyl 4-bromo-7-methoxybenzofuran-2-carboxylate (86). (Yield: 6.7 g, 52%). $^1H$ NMR (400 MHz, $CDCl_3$) δ 7.54 (s, 1H), 7.49 (d, J=8 Hz, 1H), 7.09 (d, J=8.4 Hz, 1H), 4.34-4.40 (m, 2H), 3.96 (s, 3H), 1.36-1.33 (m, 3H). LCMS: m/z 299.12 $[M]^+$, $t_R$=2.7$^2$ min.

Synthesis of (4-bromo-7-methoxybenzofuran-2-yl)methanol (87)

Ethyl 4-bromo-7-methoxybenzofuran-2-carboxylate (86) (1.7 g, 5.6 mmol) was dissolved in THF (40 mL) at room temperature. The reaction mixture was cooled to 0° C. and 1 M LAH in THF (3.9 mL, 0.02 mmol) was added dropwise at the same temperature and stirred for 15 min. The reaction mixture was transferred into iced water and extracted with ethyl acetate (3×100 mL). The combined organic layers were washed with brine solution, dried over anhydrous $Na_2SO_4$ and concentrated under reduced pressure to give crude product, which was crystallized using n-pentane to obtain (4-bromo-7-methoxybenzofuran-2-yl) methanol (87). (Yield: 1.40 g, 97%). $^1H$ NMR (400 MHz, DMSO-$d_6$) (7.35 (d, J 8.8 Hz, 1H), 6.89 (d, J 8.4 Hz, 1H), 6.88 (s, 1H), 5.59-5.56 (m, 1H), 4.58 (d, J 6.4 Hz, 2H), 3.92 (s, 3H).

Synthesis of Synthesis of (4-bromo-7-methoxybenzofuran-2-yl)methyl methanesulfonate (88)

(4-Bromo-7-methoxybenzofuran-2-yl)methanol (87) (1.48 g, 5.7 mmol) was dissolved in dichloromethane (20 mL) at room temperature. The reaction mixture was cooled to 0° C. and methane sulphonyl chloride (0.54 mL, 6.9 mmol) was added dropwise followed by addition of triethylamine (1.19 mL, 8.5 mmol). The reaction mixture was allowed to warm to room temperature and stirred for 2 h. The reaction mixture was transferred into iced water and extracted with $CH_2Cl_2$ (3×100 mL). The combined organic layers were washed with brine, dried over anhydrous $Na_2SO_4$ and concentrated under reduced pressure to obtain crude (4-bromo-7-methoxybenzofuran-2-yl) methyl methanesulfonate (88), which was used in the next step without further purification.

Synthesis of 2-(azidomethyl)-4-bromo-7-methoxybenzofuran (89)

(4-Bromo-7-methoxybenzofuran-2-yl)methyl methanesulfonate (88) (1.55 g, 4.6 mmol) was dissolved in acetonitrile (ACN) (20 mL) at room temperature. Sodium azide (0.60 g, 9.2 mmol), DMSO (0.48 mL, 6.9 mmol) and 15-crown-5 (0.15 g, 0.70 mmol) were added to the reaction mixture, which was heated at 95° C. for 30 min. The reaction mixture was allowed to cool to room temperature, transferred into iced water and extracted with ethyl acetate (3×100 mL). The combined organic layers were washed with brine solution, dried over anhydrous $Na_2SO_4$ and concentrated under reduced pressure to give crude 2-(azidomethyl)-4-bromo-7-methoxybenzofuran (89), which was used in the next step without further purification.

Synthesis of (4-bromo-7-methoxybenzofuran-2-yl)methanamine (90)

2-(Azidomethyl)-4-bromo-7-methoxybenzofuran (89) (1.4 g, 4.96 mmol) was dissolved in ethanol (15 mL) and water (7 mL) at room temperature. Ammonium chloride (0.618 g, 115.6 mmol) and zinc dust (0.42 g, 6.50 mmol) were added to the reaction mixture, which was heated at 90° C. for 1 h. The reaction mixture was allowed to cool to room temperature, transferred into ethyl acetate (20 mL with 0.2 mL ammonia solution). The reaction mixture was filtered through Celite and the filtrate was concentrated under reduced pressure to give crude (4-bromo-7-methoxybenzofuran-2-yl)methanamine (90), which was used in the next step without further purification. $^1H$ NMR (400 MHz, DMSO-$d_6$) δ 7.32 (d, J=8.4 Hz 1H), 6.85 (d, J=8.4 Hz, 1H), 6.63 (s, 1H), 3.93 (s, 3H), 3.80 (s, 2H).

Synthesis of (E)-3-(6-aminopyridin-3-yl)-N-((4-bromo-7-tert-butyl-2,3-dihydrobenzofuran-2-yl)methyl)acrylamide (91)

(4-Bromo-7-methoxybenzofuran-2-yl)methanamine (90) (1.05 g, 4.09 mmol) was dissolved in dichloromethane (10 mL) at room temperature. (E)-3-(6-aminopyridin-3-yl) acrylic acid (1.00 g, 6.14 mmol), EDCI (0.94 g, 4.91 mmol), HOBt (0.66 g, 4.91 mmol) and DIPEA (2.1 mL, 12.2 mmol) were added at 0° C. The reaction mixture was allowed to warm to room temperature and stirred for 2 h, transferred into iced water and extracted with $CH_2Cl_2$ (3×50 mL). The combined organic layers were washed with brine solution, dried over anhydrous $Na_2SO_4$ and concentrated under reduced pressure to give crude product, which was purified by silica gel column chromatography (0-3% MeOH in $CH_2Cl_2$) to obtain (E)-3-(6-aminopyridin-3-yl)-N-((4-bromo-7-methoxybenzofuran-2-yl)methyl)acrylamide (91) (Yield: 1.5 g, 91%)$^1H$ NMR (400 MHz, DMSO-$d_6$) δ 8.63 (t, J=5.8 Hz, 1H), 8.08 (d, J=2 Hz, 1H), 7.65 (dd, $J_1$=2.4 Hz, $J_2$=2 Hz, 1H), 7.36 (d, J=8.8 Hz, 1H), 7.33 (s, 1H), 6.90 (d, J=8.8 Hz, 1H), 6.66 (s, 1H), 6.60 (bs, 2H), 6.52 (d, J=8.8 Hz, 1H), 6.43 (d, J=16 Hz, 1H), 4.54 (d, J=5.6 Hz, 2H), 3.89 (s, 3H). LCMS m/z 403.24 $[M+H]^+$, $t_R$=1.87 min.

Synthesis of (E)-3-(6-aminopyridin-3-yl)-N-((7-methoxy-4-(4-(morpholinesulfonyl)phenyl) benzofuran-2-yl)methyl)acrylamide (554)

(E)-3-(6-Aminopyridin-3-yl)-N-((4-bromo-7-methoxybenzofuran-2-yl)methyl)acrylamide (91) (0.3 g, 0.74 mmol) was dissolved in 1,4-dioxane (5 mL) at room temperature. (4-(Morpholinesulfonyl)phenyl)boronic acid (0.30 g, 1.11 mmol) and a degassed solution of $K_2CO_3$ (0.20 g, 1.48 mmol) in 1 mL of water were added at room temperature and degassed using $N_2$ for 10 min. Tetrakis(triphenylphosphine) palladium (O) (0.04 g, 0.03 mmol) was added and the reaction mixture was irradiated under microwave for 1 h at 80° C. The reaction mixture was allowed to cool to room temperature, transferred into iced water and extracted with ethyl acetate (3×50 mL). The combined organic layers were washed with brine, dried over anhydrous Na$_2$SO$_4$ and concentrated under reduced pressure to give crude compound, which was purified by preparative HPLC to obtain (E)-3-(6-aminopyridin-3-yl)-N-((7-methoxy-4-(4-(morpholinosulfonyl)phenyl)benzofuran-2-yl)methyl)acrylamide (554). (Yield: 0.18 g, 44%). $^1$H NMR (400 MHz, DMSO-d$_6$) δ 8.57 (t, J=5.8 Hz, 1H), 8.06 (d, J=2.2 Hz, 1H), 7.88-7.82 (m, 4H), 7.60 (dd, J$_1$=2.4 Hz, J$_2$=2 Hz 1H), 7.42 (d, J 8 Hz, 1H), 7.33 (d, J=15.6 Hz, 1H), 7.08 (d, J=8.4 Hz, 1H), 6.95 (s, 1H), 6.47-6.38 (m, 4H), 4.53 (d, J=5.6 Hz, 2H), 3.98 (s, 3H), 3.66 (t, J=8.8 Hz, 4H), 2.93 (t, J=4.4 Hz, 4H). LCMS: m/z 549.61 [M+H]$^+$, t$_R$=1.90 min.

Synthesis of (E)-3-(6-aminopyridin-3-yl)-N-((7-chloro-5-(4-(3,3-dimethylazetidin-1-ylsulfonyl)phenyl)benzofuran-2-yl)methyl)acrylamide (555)

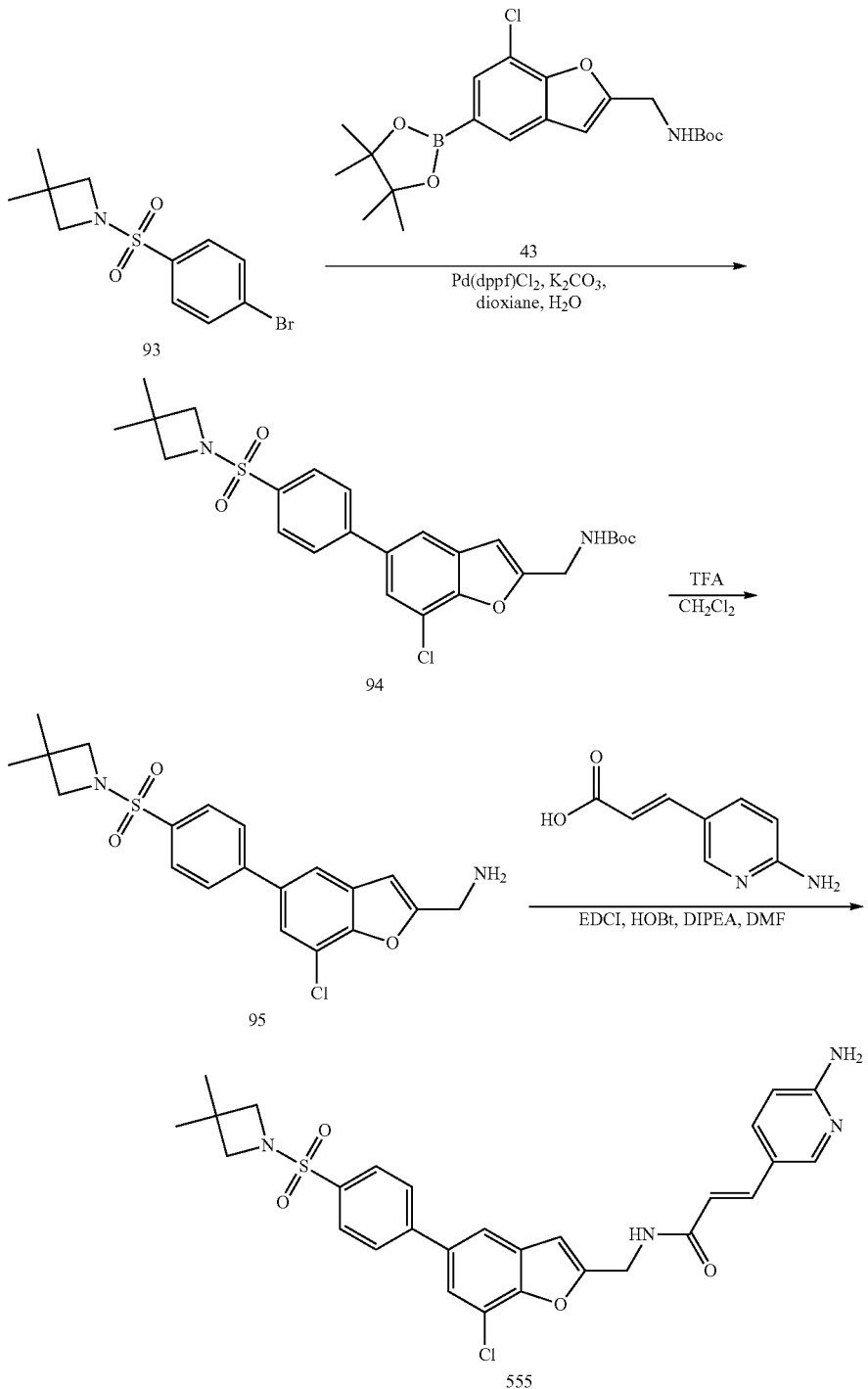

183

Synthesis of tert-butyl (7-chloro-5-(4-(3,3-dimethyl-azetidin-1-ylsulfonyl)phenyl)benzofuran-2-yl)methylcarbamate (94)

tert-Butyl (7-chloro-5-(4-(3,3-dimethylazetidin-1-ylsulfonyl)phenyl)benzofuran-2-yl)methylcarbamate (94) was synthesized using General Procedure 2. Yield (64%). LCMS: m/z 505.1 [M+H]$^+$; $t_R$=1.30 min.

Synthesis of (7-chloro-5-(4-(3,3-dimethylazetidin-1-ylsulfonyl)phenyl)benzofuran-2-yl)methanamine (95)

(7-chloro-5-(4-(3,3-dimethylazetidin-1-ylsulfonyl)phenyl)benzofuran-2-yl)methanamine (95) was synthesized using General Procedure 3. Yield (100%). LCMS: m/z 405.1 [M+H]$^+$; $t_R$=0.95 min.

184

Synthesis of (E)-3-(6-aminopyridin-3-yl)-N-((7-chloro-5-(4-(3,3-dimethylazetidin-1-ylsulfonyl)phenyl)benzofuran-2-yl)methyl)acrylamide (555)

(E)-3-(6-Aminopyridin-3-yl)-N-((7-chloro-5-(4-(3,3-dimethylazetidin-1-ylsulfonyl)phenyl)benzofuran-2-yl)methyl)acrylamide (555) was synthesized using General Procedure 1. Yield (31%). $^1$H NMR (400 MHz, CD$_3$OD) (8.07 (s, 1H), 7.97-7.88 (m, 5H), 7.76-7.74 (m, 1H), 7.69 (s, 1H), 7.50 (d, J=16 Hz, 1H), 6.89 (s, 1H), 6.60 (d, J=9 Hz, 1H), 6.48 (d, J=16 Hz, 1H), 4.71 (s, 2H), 3.50 (s, 4H), 1.07 (s, 6H). LCMS: m/z 551.2 [M+H]$^+$; $t_R$=1.92 min.

Synthesis of (E)-4-(2-((3-(6-aminopyridin-3-yl)acrylamido)methyl)-7-chlorobenzofuran-5-yl)phenyl morpholine-4-carboxylate (556)

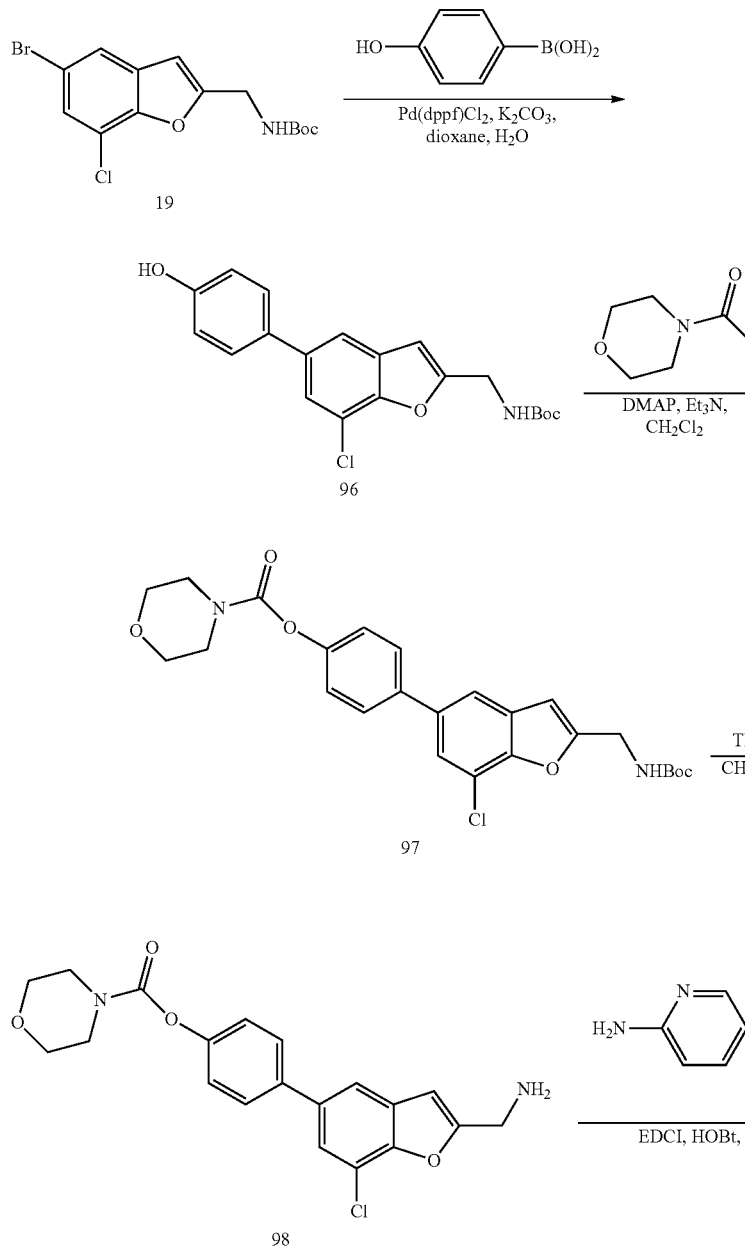

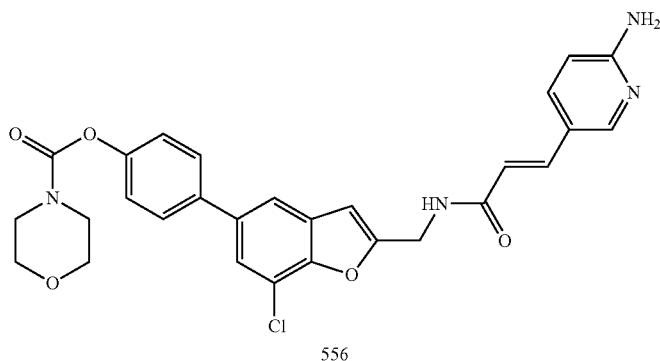

556

Synthesis of tert-butyl (7-chloro-5-(4-hydroxyphenyl)benzofuran-2-yl)methylcarbamate (96)

tert-butyl (7-chloro-5-(4-hydroxyphenyl)benzofuran-2-yl)methylcarbamate (96) was synthesized using General Procedure 2. Yield (92%). LCMS: m/z 396.0 [M+Na]$^+$; $t_R$=1.88 min.

Synthesis of 4-(2-((tert-butoxycarbonylamino)methyl)-7-chlorobenzofuran-5-yl)phenyl morpholine-4-carboxylate (97)

tert-Butyl (7-chloro-5-(4-hydroxyphenyl)benzofuran-2-yl)methylcarbamate (96) (311 mg, 0.83 mmol) was dissolved in 20 mL of CH$_2$Cl$_2$. N,N-dimethylpyridin-4-amine (97 mg, 0.83 mmol), Et$_3$N (167 mg, 1.66 mmol), and morpholine-4-carbonyl chloride (148 mg, 1 mmol) were added successively. The reaction mixture was stirred at room temperature for 1 h, quenched with water (20 mL), extracted with CH$_2$Cl$_2$ (20 mL×2). The combined organic solvents were washed with brine (20 mL), dried over anhydrous Na$_2$SO$_4$, and concentrated to dryness to give 298 mg of 4-(2-((tert-butoxycarbonylamino)methyl)-7-chlorobenzofuran-5-yl)phenyl morpholine-4-carboxylate (97), which was used directly without further purification. Yield (74%). LCMS: m/z 487.0 [M+H]$^+$; $t_R$=1.98 min.

Synthesis of 4-(2-(aminomethyl)-7-chlorobenzofuran-5-yl)phenyl morpholine-4-carboxylate (98)

4-(2-(aminomethyl)-7-chlorobenzofuran-5-yl)phenyl morpholine-4-carboxylate (98) was synthesized using General Procedure 3. Yield (100%). LCMS: m/z 387.0 [M+H]$^+$; $t_R$=1.29 min.

Synthesis of (E)-4-(2-((3-(6-aminopyridin-3-yl)acrylamido)methyl)-7-chlorobenzofuran-5-yl)phenyl morpholine-4-carboxylate (556)

(E)-4-(2-((3-(6-aminopyridin-3-yl)acrylamido)methyl)-7-chlorobenzofuran-5-yl)phenyl morpholine-4-carboxylate (556) was synthesized using General Procedure 1. Yield (51%). $^1$H NMR (400 MHz, CD$_3$OD) δ 6.69-6.59 (m, 1H), 8.05 (d, J=2 Hz, 1H), 7.75-7.45 (m, 5H), 7.29-7.20 (m, 2H), 7.04 (d, J=9 Hz, 1H), 6.86 (s, 1H), 6.65 (d, J=16 Hz, 1H), 4.71 (s, 2H), 3.82-3.52 (m, 8H). LCMS: m/z 533.2 [M+H]$^+$; $t_R$=1.31 min.

Synthesis of (E)-3-(6-aminopyridin-3-yl)-N-((7-(difluoromethyl)-5-(4-(morpholine-4-carbonyl)phenyl)benzofuran-2-yl)methyl)acrylamide (557)

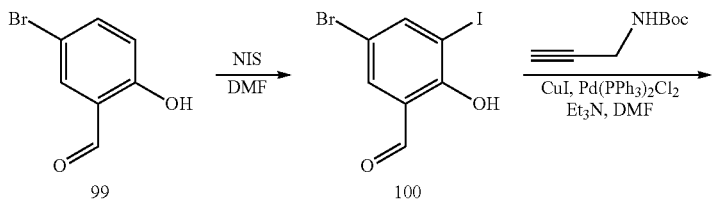

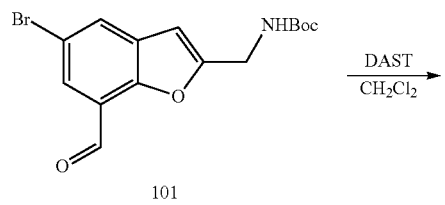

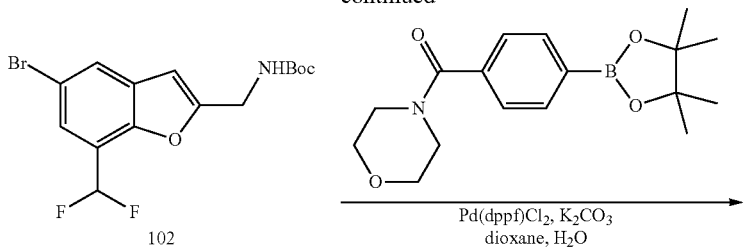

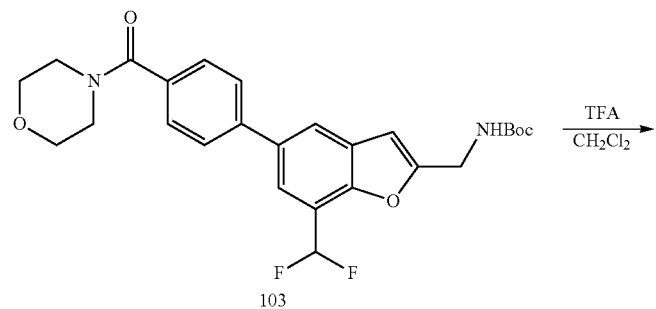

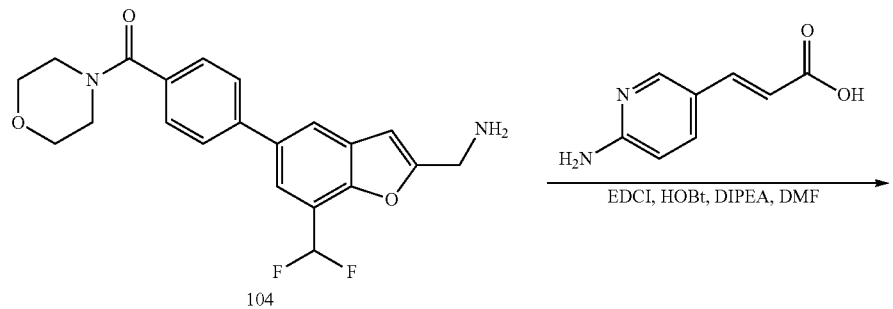

Synthesis of 5-bromo-2-hydroxy-3-iodobenzaldehyde (100)

5-Bromo-2-hydroxybenzaldehyde (99) (10 g, 50 mmol) was dissolved in DMF (100 mL). NIS (11 g, 50 mmol) was added at room temperature and the reaction mixture was stirred for 48 h. The reaction mixture was transferred into iced water and extracted with ethyl acetate (100 mL×3). The combined organic layers were washed with brine, dried over anhydrous $Na_2SO_4$, and concentrated under reduced pressure to give 14 g of 5-bromo-2-hydroxy-3-iodobenzaldehyde (100), which was used in next step without further purification (85% yield). LCMS: $t_R$=1.93 min.

Synthesis of tert-butyl (5-bromo-7-formylbenzofuran-2-yl)methylcarbamate (101)

A mixture of 5-bromo-2-hydroxy-3-iodobenzaldehyde (100) (3.3 g, 10 mmol), tert-butyl prop-2-ynylcarbamate (1.6 g, 10 mmol), $Pd(PPh_3)_2Cl_2$ (700 mg, 1 mmol) and CuI (191 mg, 1 mmol) in 3 mL of $Et_3N$ and 20 mL of DMF was degassed and heated at 80° C. under nitrogen atmosphere for 2 h. After cooling down to room temperature, the reaction mixture was diluted with 20 mL of water, extracted with EtOAc (50 mL×3). The combined organic layers were washed with brine, dried over anhydrous $Na_2SO_4$, and concentrated under reduced pressure to give the crude product, which was purified by silica gel chromatography (20% EtOAc/petroleum ether) to give 2.2 g of tert-butyl (5-bromo-7-formylbenzofuran-2-yl) methylcarbamate (101) as a yellow solid (yield: 63%). LCMS: m/z 378.0 [M+H]$^+$; $t_R$=1.18 min.

Synthesis of tert-butyl (5-bromo-7-(difluoromethyl) benzofuran-2-yl)methylcarbamate (102)

tert-Butyl (5-bromo-7-formylbenzofuran-2-yl) methylcarbamate (101) (353 mg, 1 mmol) was dissolved in dichloromethane (10 mL). DAST (386 mg, 2.4 mmol) was added at 0° C. (ice bath). The reaction mixture was allowed to warm to room temperature where it was stirred for 2 h. The reaction mixture was transferred into iced water and extracted with dichloromethane (20 mL×3). The combined organic layers were washed with brine, dried over anhydrous $Na_2SO_4$, and concentrated under reduced pressure to give the crude product, which was purified by silica gel chromatography (15% EtOAc/petroleum ether) to give 200 mg of tert-butyl (5-bromo-7-(difluoromethyl)benzofuran-2-yl) methylcarbamate (102) (53% yield). LCMS: m/z 375.9 [M+H]$^+$, $t_R$=1.89 min.

Synthesis of tert-butyl (7-(difluoromethyl)-5-(4-(morpholine-4-carbonyl)phenyl)benzofuran-2-yl) methylcarbamate (103)

tert-Butyl (5-bromo-7-(difluoromethyl)benzofuran-2-yl) methylcarbamate (102) (375 mg, 1 mmol) and morpholino (4-(4,4,5,5-tetramethyl-1,3,2-dioxaborolan-2-yl)phenyl) methanone (317 mg, 1 mmol) was dissolved in dioxane (10 mL) and degassed for 5 min. Pd(dppf)Cl$_2$ (82 mg, 0.1 mmol), K$_2$CO$_3$ (276 mg, 2 mmol) and 1 mL of water were added. The reaction mixture was heated at 90° C. for 2 h. The reaction mixture was transferred into water (20 mL), extracted with ethyl acetate (20 mL×3). The combined organic layers were washed with brine, dried over anhydrous Na$_2$SO$_4$, concentrated and purified by chromatography (10-20% ethyl acetate/petroleum) to give tert-butyl (7-(difluoromethyl)-5-(4-(morpholine-4-carbonyl)phenyl)benzofuran-2-yl)methylcarbamate 103 (200 mg, 41% yield) as yellowish solid. LCMS: m/z 487.2 [M+1]$^+$, $t_R$=1.73 min.

Synthesis of (4-(2-(aminomethyl)-7-(difluoromethyl)benzofuran-5-yl)phenyl)(morpholino)methanone (104)

tert-Butyl (7-(difluoromethyl)-5-(4-(morpholine-4-carbonyl)phenyl)benzo-furan-2-yl)methylcarbamate (103) (200 mg, 0.41 mmol) was dissolved in CH$_2$Cl$_2$ (6 mL). TFA (1 mL) was added at 0° C. (ice bath). The reaction mixture was allowed to warm to room temperature and stirred for 2 h. The reaction mixture was concentrated under reduced pressure to give the crude (4-(2-(aminomethyl)-7-(difluoromethyl)benzofuran-5-yl)phenyl)(morpholino)methanone (104), which was used in the next step without further purification. (120 mg, 76% yield). LCMS: m/z 387.2 [M+H]$^+$; $t_R$=1.20 min.

Synthesis of (E)-3-(6-aminopyridin-3-yl)-N-((7-(difluoromethyl)-5-(4-(morpholine-4-carbonyl)phenyl)benzofuran-2-yl)methyl)acrylamide (557)

(4-(2-(Aminomethyl)-7-(difluoromethyl)benzofuran-5-yl)phenyl)(morpholino)methanone (104) (120 mg, 0.31 mmol) was dissolved in DMF (5 mL) and (E)-3-(6-aminopyridin-3-yl)acrylic acid (51 mg, 0.31 mmol) was added at 0° C. EDCI (60 mg, 0.31 mmol) and HOBt hydrate (42 mg, 0.31 mmol) were added followed by DIPEA (80 mg, 0.62 mmol) dropwise. The reaction mixture was allowed to warm to room temperature and stirred further for 1 h. The reaction mixture was purified by Prep-HPLC without work up to afford (E)-3-(6-aminopyridin-3-yl)-N-((7-(difluoromethyl)-5-(4-(morpholine-4-carbonyl)phenyl)benzofuran-2-yl) methyl)acrylamide (557) as white solid (80 mg, 49% yield). $^1$H NMR (400 MHz, DMSO-d$_6$) δ 8.90 (t, J=6 Hz, 1H), 8.46-8.19 (m, 2H), 8.15-8.09 (m, 2H), 7.84-7.76 (m, 3H), 7.58-7.37 (m, 4H), 7.01 (d, J=9 Hz, 1H), 6.91 (s, 1H), 6.64 (d, J=16 Hz, 1H), 4.63 (d, J=5 Hz, 2H), 3.68-3.43 (m, 9H). LCMS: m/z 533.3 [M+H]$^+$; $t_R$=1.29 min.

Synthesis of (E)-3-(2-((3-(6-aminopyridin-3-yl)acrylamido)methyl)-7-(trifluoromethyl)benzofuran-5-yl) phenyl morpholine-4-carboxylate (558)

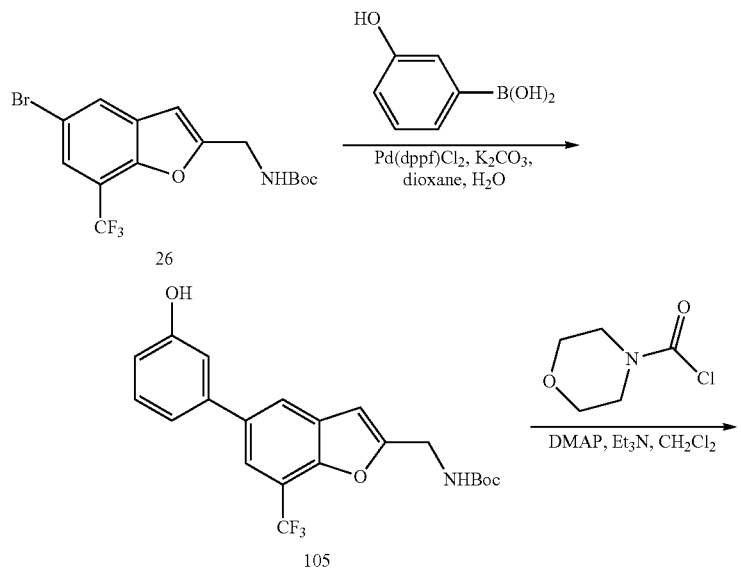

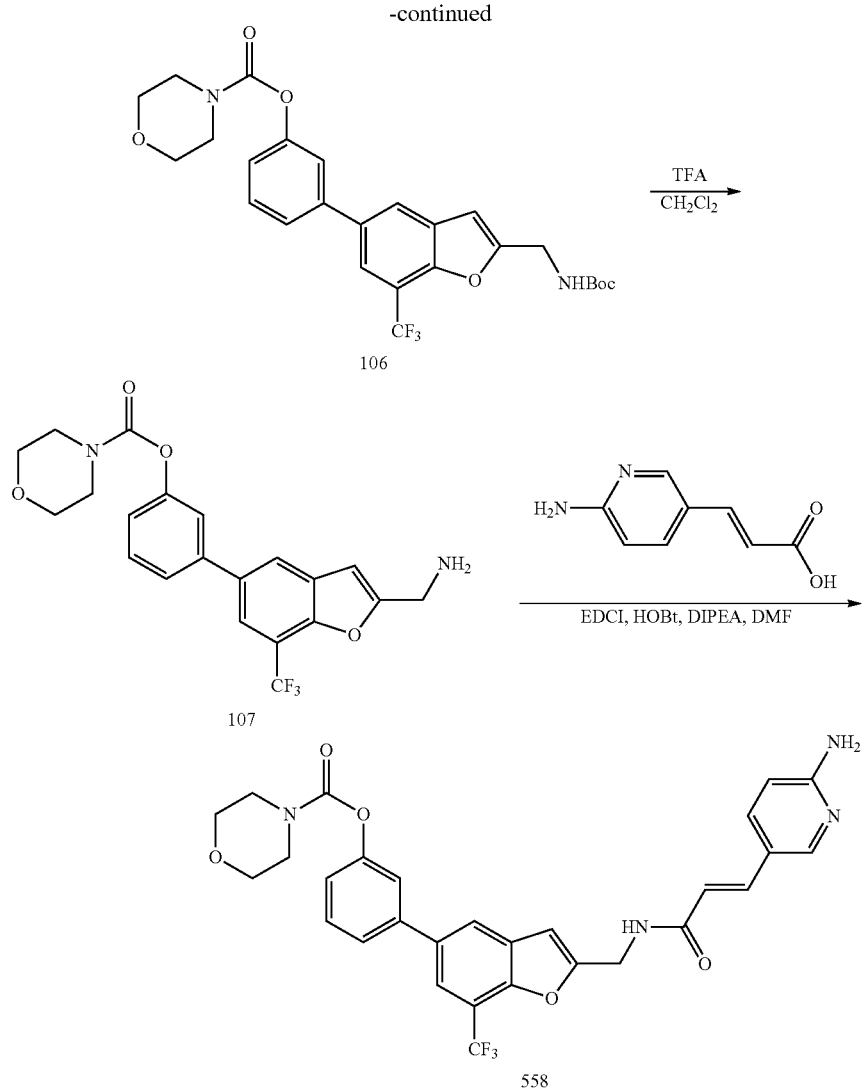

Synthesis of tert-Butyl (5-(3-hydroxyphenyl)-7-(trifluoromethyl)benzofuran-2-yl)methylcarbamate (105)

tert-Butyl (5-(3-hydroxyphenyl)-7-(trifluoromethyl)benzofuran-2-yl)methylcarbamate (105) was synthesized using General Procedure 2. Yield (96%). LCMS: m/z 430.1 [M+Na]$^+$; t$_R$=1.80 min.

Synthesis of 3-(2-((tert-butoxycarbonylamino)methyl)-7-(trifluoromethyl)benzofuran-5-yl)phenyl morpholine-4-carboxylate (106)

tert-Butyl (5-(3-hydroxyphenyl)-7-(trifluoromethyl)benzofuran-2-yl)methylcarbamate (105) (268 mg, 0.66 mmol) was dissolved in 20 mL of CH$_2$Cl$_2$. N,N-dimethylpyridin-4-amine (80 mg, 0.66 mmol), Et$_3$N (132 mg, 1.32 mmol), and morpholine-4-carbonyl chloride (196 mg, 1.31 mmol) were added successively. The reaction mixture was stirred at room temperature for 1 h, quenched with water (20 mL), extracted with CH$_2$Cl$_2$ (20 mL×2). The combined organic solvents were washed with brine (20 mL), dried over anhydrous Na$_2$SO$_4$, and concentrated to dryness to give 279 mg of 3-(2-((tert-butoxycarbonylamino)methyl)-7-(trifluoromethyl)benzofuran-5-yl)phenyl morpholine-4-carboxylate (106), which was used directly without further purification. Yield (82%). LCMS: m/z 521.1 [M+H]$^+$; t$_R$=1.26 min.

Synthesis of 3-(2-(aminomethyl)-7-(trifluoromethyl)benzofuran-5-yl)phenyl morpholine-4-carboxylate (107)

3-(2-(aminomethyl)-7-(trifluoromethyl)benzofuran-5-yl)phenyl morpholine-4-carboxylate (107) was synthesized using General Procedure 3. Yield (100%). LCMS: m/z 421.3 [M+H]$^+$; t$_R$=1.27 min.

Synthesis of (E)-3-(2-((3-(6-aminopyridin-3-yl)acrylamido)methyl)-7-(trifluoromethyl)benzofuran-5-yl)phenyl morpholine-4-carboxylate (558)

(E)-3-(2-((3-(6-aminopyridin-3-yl)acrylamido)methyl)-7-(trifluoromethyl)benzofuran-5-yl)phenyl morpholine-4-carboxylate (558) was synthesized using General Procedure 1. Yield (60%). $^1$H NMR (400 MHz, CD$_3$OD) δ 8.20 (d, J=9 Hz, 1H), 8.07 (d, J=13 Hz, 2H), 7.79 (s, 1H), 7.60-7.43 (m, 4H), 7.18 (d, J=8 Hz, 1H), 7.05 (d, J=9 Hz, 1H), 6.93 (s, 1H), 6.66 (d, J=16 Hz, 1H), 4.73 (s, 2H), 3.80-3.55 (m, 8H). LCMS: m/z 567.2 [M+H]$^+$; $t_R$=1.35 min.

Synthesis of (E)-3-(6-aminopyridin-3-yl)-N-((7-(4-(morpholine-4-carbonyl)phenyl)benzofuran-2-yl)methyl)acrylamide (559)

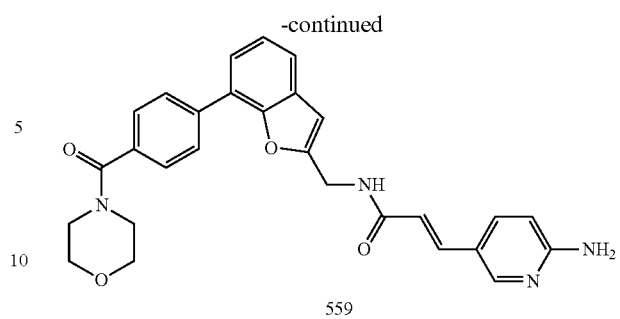

559

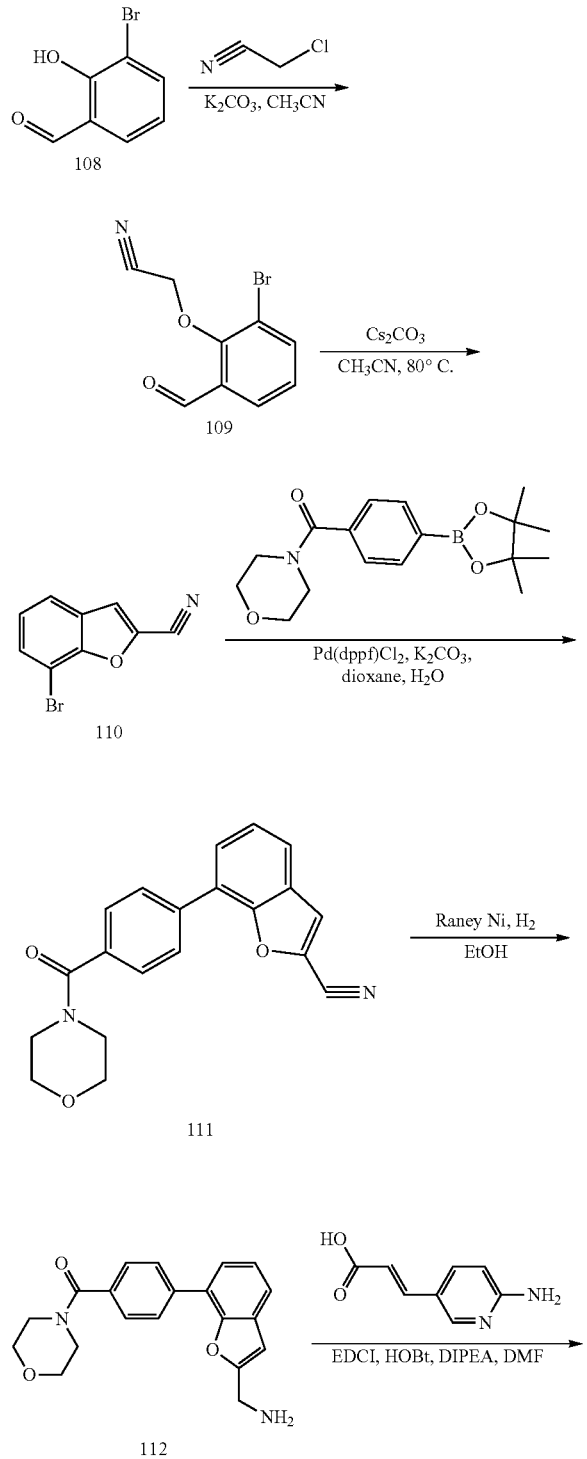

Synthesis of 2-(2-Bromo-6-formylphenoxy)acetonitrile (109)

3-bromo-2-hydroxybenzaldehyde (108) (1.2 g, 6 mmol) was dissolved in 30 mL of CH$_3$CN. 2-Chloroacetonitrile (450 mg, 6 mmol) and K$_2$CO$_3$ (1.66 g, 12 mmol) were added. The reaction mixture was stirred at room temperature for 16 h. After completion, 30 mL of H$_2$O was added to this mixture. The mixture was extracted with EtOAc (40 mL X 3). The combined organic phases were washed with brine (20 mL), dried over anhydrous Na$_2$SO$_4$, concentrated, and purified by silica gel chromatography (10% ethyl acetate/petroleum ether) to give 1.28 g of 2-(2-bromo-6-formylphenoxy)acetonitrile (109). Yield (91%). LCMS: m/z 239.9 [M+H]$^+$; $t_R$=1.56 min.

Synthesis of 7-Bromobenzofuran-2-carbonitrile (110)

2-(2-Bromo-6-formylphenoxy)acetonitrile (109) was dissolved in CH$_3$CN. Cs$_2$CO$_3$ (5.7 g, 17.6 mmol) was added. The reaction mixture was stirred at 80° C. for 16 h. After cooling to room temperature, 30 mL of H$_2$O was added, the reaction mixture was extracted with EtOAc (40 mL×3). The combined organic solvents were washed with brine (20 mL), dried over anhydrous Na$_2$SO$_4$, concentrated and purified by silica gel chromatography (10% ethyl acetate/petroleum ether) to give 210 mg of 7-bromobenzofuran-2-carbonitrile (110). Yield (11%). LCMS: $t_R$=1.78 min.

Synthesis of 7-(4-(Morpholine-4-carbonyl)phenyl)benzofuran-2-carbonitrile (111)

A mixture of morpholino(4-(4,4,5,5-tetramethyl-1,3,2-dioxaborolan-2-yl)phenyl)methanone (301 mg, 0.95 mmol), 7-bromobenzofuran-2-carbonitrile (110) (210 mg, 0.95 mmol), Pd(dppf)Cl$_2$ (73 mg, 0.1 mmol) and K$_2$CO$_3$ (262 mg, 1.95 mmol) in 10 mL of dioxane and 2 mL of H$_2$O was stirred at 90° C. under nitrogen atmosphere for 3 h. The mixture was extracted with EtOAc (10 mL×3). The combined organic layers were washed with brine, dried over anhydrous Na$_2$SO$_4$, and the solvents were removed under reduced pressure to give the crude product, which was purified by silica gel chromatography (30% EtOAc/petroleum ether) to give 185 mg of 7-(4-(morpholine-4-carbonyl)phenyl)benzofuran-2-carbonitrile (111). Yield (58%). LCMS: m/z 333.1 [M+H]$^+$; $t_R$=1.62 min.

Synthesis of (4-(2-(Aminomethyl)benzofuran-7-yl)phenyl)(morpholino)methanone (112)

7-(4-(Morpholine-4-carbonyl)phenyl)benzofuran-2-carbonitrile (111) (154 mg, 0.46 mmol) was dissolved in 15 mL of EtOH. 100 mg of Raney Ni was added. The mixture was stirred under H₂ atmosphere for 20 min. The mixture was filtered, the filtrate was concentrated and purified by Prep-TLC (50% EtOAc/petroleum ether) to give 132 mg of (4-(2-(aminomethyl)benzofuran-7-yl)phenyl)(morpholino)methanone (112). Yield (85%). LCMS: m/z 337.2 [M+H]⁺; $t_R$=0.83 min.

Synthesis of (E)-3-(6-aminopyridin-3-yl)-N-((7-(4-(morpholine-4-carbonyl)phenyl)benzofuran-2-yl)methyl)acrylamide (559)

(4-(2-(aminomethyl)benzofuran-7-yl)phenyl)(morpholino)methanone (112; 100 mg, 0.3 mmol) was dissolved in DMF (5 mL) and (E)-3-(6-aminopyridin-3-yl)acrylic acid (49 mg, 0.3 mmol) was added at 0° C. EDCI (84 mg, 0.44 mmol) and HOBt (59 mg, 0.44 mmol) were added to this reaction mixture at 0° C. followed by DIPEA (77 mg, 0.6 mmol) dropwise. The reaction mixture was allowed to warm to room temperature and stirred further for 4 h. The reaction mixture was transferred into water (20 mL) and extracted with EtOAc (25 mL×3). The combined organic layers were washed with brine, dried over anhydrous Na₂SO₄ and concentrated under reduced pressure to give crude product which was purified by Prep-HPLC to afford (E)-3-(6-aminopyridin-3-yl)-N-((7-(4-(morpholine-4-carbonyl)phenyl)benzofuran-2-yl)methyl)acrylamide (559) (43 mg, yield: 30%). ¹H NMR (400 MHz, CD₃OD) δ 8.22-8.18 (m, 1H), 8.07-7.99 (m, 3H), 7.61-7.46 (m, 5H), 7.38-7.32 (m, 1H), 7.05 (d, J=9 Hz, 1H), 6.82 (s, 1H), 6.63 (d, J=16 Hz, 1H), 4.71 (s, 2H), 3.83-3.53 (m, 8H). LCMS: m/z 483.1 [M+H]⁺; $t_R$=1.22 min.

Synthesis of (E)-3-(6-aminopyridin-3-yl)-N-((7-chloro-5-(5-(morpholine-4-carbonyl)pyridin-2-yl)benzofuran-2-yl)methyl)acrylamide (560)

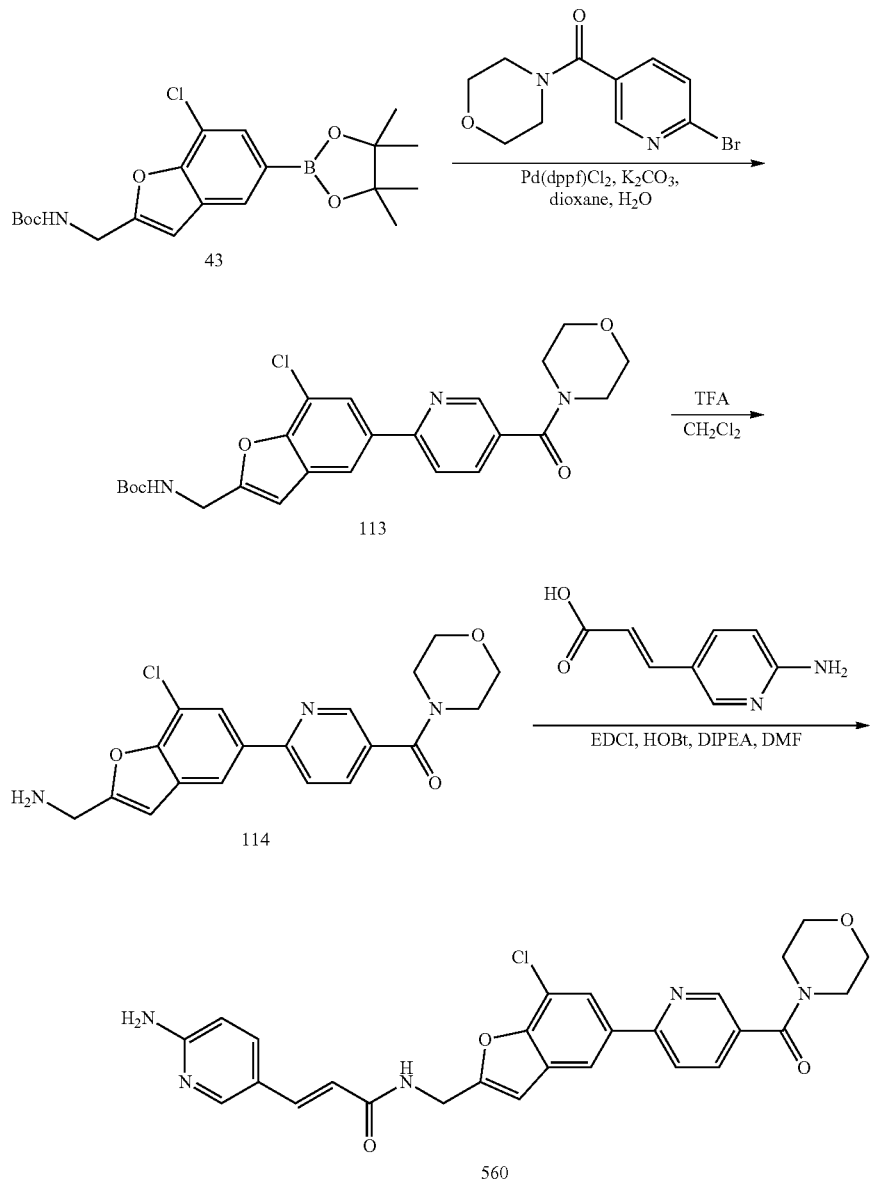

Synthesis of tert-Butyl (7-chloro-5-(5-(morpholine-4-carbonyl)pyridin-2-yl)benzofuran-2-yl)methylcarbamate (113)

tert-Butyl (7-chloro-5-(5-(morpholine-4-carbonyl)pyridin-2-yl)benzofuran-2-yl)methylcarbamate (113) was synthesized using General Procedure 2. Yield (69%). LCMS: m/z: 472.0 [M+H]$^+$, $t_R$=1.70 min.

Synthesis of (6-(2-(Aminomethyl)-7-chlorobenzofuran-5-yl)pyridin-3-yl)(morpholino)methanone (114)

(6-(2-(Aminomethyl)-7-chlorobenzofuran-5-yl)pyridin-3-yl)(morpholino)methanone (114) was synthesized using General Procedure 3. Yield (100%). LCMS: m/z: 372.0 [M+H]$^+$, $t_R$=0.78 min.

Synthesis of (E)-3-(6-aminopyridin-3-yl)-N-((7-chloro-5-(5-(morpholine-4-carbonyl)pyridin-2-yl)benzofuran-2-yl)methyl)acrylamide (560)

(E)-3-(6-aminopyridin-3-yl)-N-((7-chloro-5-(5-(morpholine-4-carbonyl)pyridin-2-yl)benzofuran-2-yl)methyl)acrylamide (560) was synthesized using General Procedure 1. Yield (69%). $^1$H NMR (400 MHz, DMSO-d$_6$) δ 8.85 (t, J=6 Hz, 1H), 8.72 (d, J=2 Hz, 1H), 8.37 (d, J=2 Hz, 1H), 8.27-7.92 (m, 7H), 7.44 (d, J=16 Hz, 1H), 7.01-6.93 (m, 2H), 6.60 (d, J=16 Hz, 1H), 4.63 (d, J=6 Hz, 2H), 3.78-3.36 (m, 8H). LCMS: m/z 518.2 [M+H]$^+$; $t_R$=1.26 min.

Synthesis of (E)-3-(6-aminopyridin-3-yl)-N-((5-(4-(4-methylpiperazine-1-carbonyl)phenyl)-7-(trifluoromethyl)benzofuran-2-yl)methyl)acrylamide (561)

General Procedure 4: Amide Coupling Using HATU.

(E)-4-(2-((3-(6-aminopyridin-3-yl)acrylamido)methyl)-7-(trifluoromethyl)benzofuran-5-yl)benzoic acid (59) (60 mg, 0.12 mmol) was dissolved in DMF (2 mL) and 1-methylpiperazine (12 mg, 0.12 mmol) was added at 0° C. HATU (68 mg, 0.18 mmol) were added to this reaction mixture at 0° C. followed by DIPEA (31 mg, 0.24 mmol) dropwise. The reaction mixture was allowed to warm to room temperature and stirred for 4 h. The reaction mixture was transferred into water (20 mL) and extracted with EtOAc (25 mL×3). The combined organic layers were washed with brine, dried over anhydrous Na$_2$SO$_4$ and concentrated under reduced pressure to give crude product which was purified by Prep-HPLC to afford (E)-3-(6-aminopyridin-3-yl)-N-((5-(4-(4-methylpiperazine-1-carbonyl)phenyl)-7-(trifluoromethyl)benzofuran-2-yl)methyl)acrylamide (561). Yield (9%). $^1$H NMR (400 MHz, CD$_3$OD) δ 8.03-7.93 (m, 3H), 7.73-7.61 (m, 5H), 7.49-7.35 (m, 4H), 6.81 (s, 1H), 6.50 (d, J=9 Hz, 1H), 6.37 (d, J=16 Hz, 1H), 4.61 (s, 2H), 3.77-3.38 (m, 4H), 2.51-2.30 (m, 4H). LCMS: m/z 564.3 [M+H]$^+$; $t_R$=1.71 min.

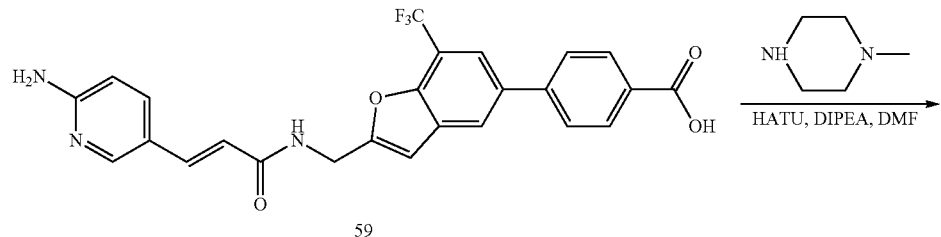

59

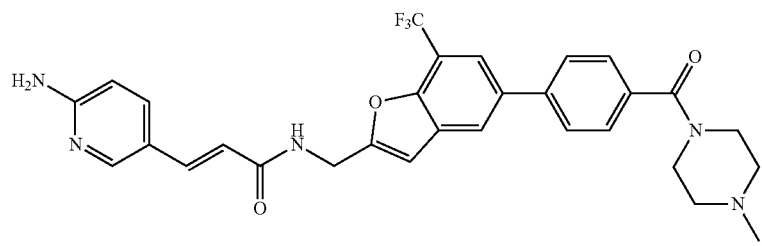

561

Synthesis of (E)-3-(6-aminopyridin-3-yl)-N-((7-chloro-5-(4-fluoro-3-(morpholine-4-carbonyl)phenyl)benzofuran-2-yl)methyl)acrylamide (562)

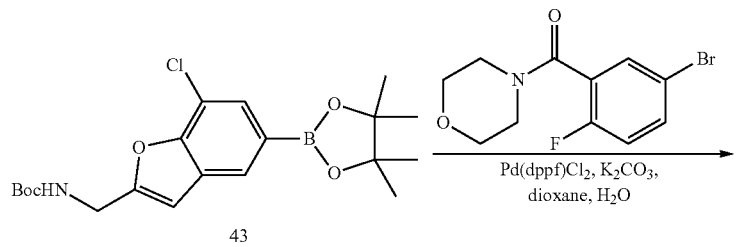

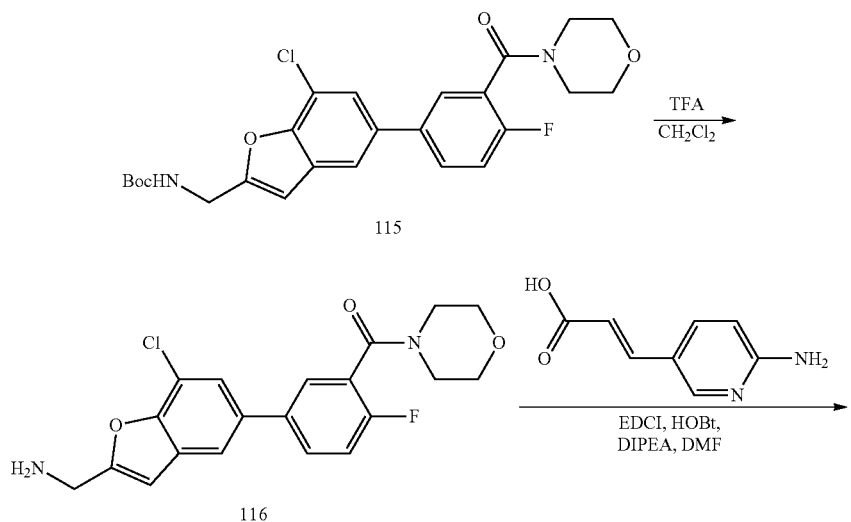

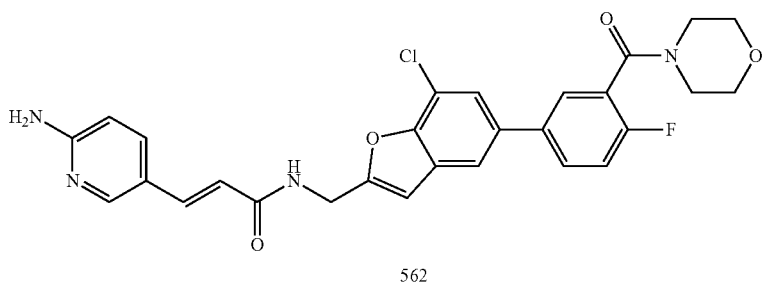

Synthesis of tert-Butyl (7-chloro-5-(4-fluoro-3-(morpholine-4-carbonyl)phenyl)benzofuran-2-yl)methylcarbamate (115)

tert-Butyl (7-chloro-5-(4-fluoro-3-(morpholine-4-carbonyl)phenyl)benzofuran-2-yl)methylcarbamate (115) was synthesized using General Procedure 2. Yield (60%). LCMS: m/z: 489.1 [M+H]$^+$, $t_R$=1.72 min.

Synthesis of (5-(2-(aminomethyl)-7-chlorobenzofuran-5-yl)-2-fluorophenyl)(morpholino)methanone (116)

(5-(2-(aminomethyl)-7-chlorobenzofuran-5-yl)-2-fluorophenyl)(morpholino)methanone (116) was synthesized using General Procedure 3. Yield (100%). LCMS: $t_R$=1.26 min.

Synthesis of (E)-3-(6-aminopyridin-3-yl)-N-((7-chloro-5-(4-fluoro-3-(morpholine-4-carbonyl)phenyl)benzofuran-2-yl)methyl)acrylamide (562)

(E)-3-(6-aminopyridin-3-yl)-N-((7-chloro-5-(4-fluoro-3-(morpholine-4-carbonyl)phenyl)benzofuran-2-yl)methyl)acrylamide (562) was synthesized using General Procedure 1. Yield (23%). $^1$H NMR (400 MHz, CD$_3$OD) δ 8.15-8.06 (m, 1H), 7.93 (s, 1H), 7.70-7.34 (m, 5H), 7.25-7.16 (m, 1H), 6.95 (d, J=9 Hz, 1H), 6.75 (s, 1H), 6.54 (d, J=16 Hz, 1H), 4.60 (s, 2H), 3.75-3.52 (m, 6H), 3.36-3.29 (m, 2H). LCMS: m/z 535.2 [M+H]$^+$; $t_R$=1.73 min.

Synthesis of (E)-3-(6-aminopyridin-3-yl)-N-((5-(4-fluoro-3-(morpholine-4-carbonyl)phenyl)-7-(trifluoromethyl)benzofuran-2-yl)methyl)acrylamide (563)

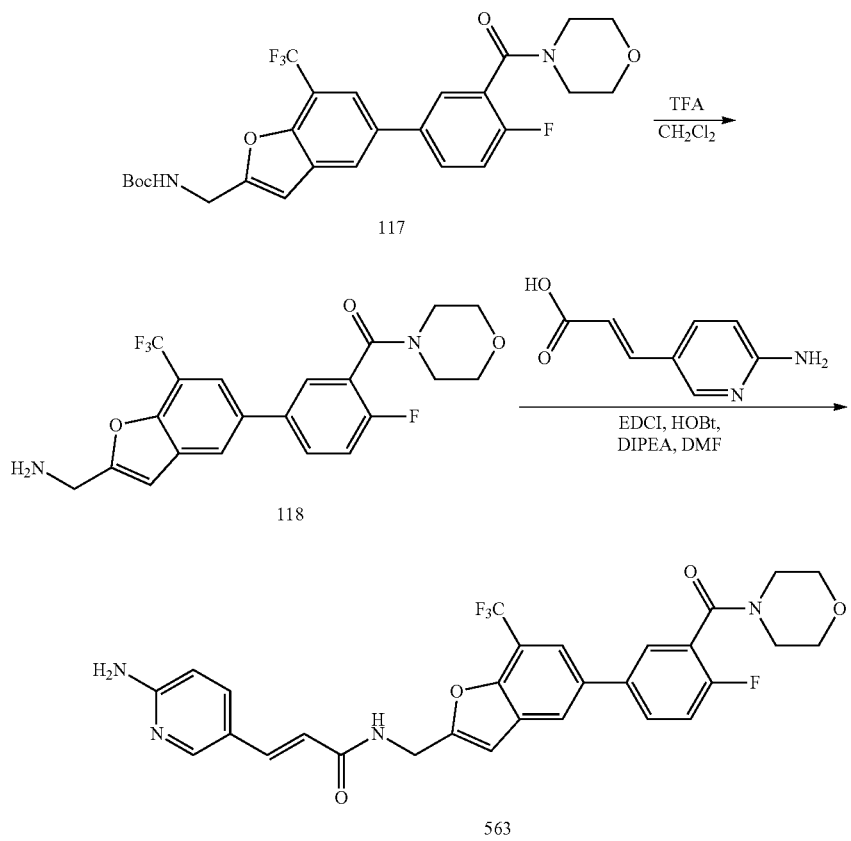

Synthesis of tert-Butyl (5-(4-fluoro-3-(morpholine-4-carbonyl)phenyl)-7-(trifluoromethyl)benzofuran-2-yl)methylcarbamate (117)

tert-Butyl (5-(4-fluoro-3-(morpholine-4-carbonyl)phenyl)-7-(trifluoromethyl)benzofuran-2-yl)methylcarbamate (117) was synthesized using General Procedure 2. Yield (70%). LCMS: m/z: 523.2 [M+H]$^+$, $t_R$=1.91 min.

Synthesis of (5-(2-(aminomethyl)-7-(trifluoromethyl)benzofuran-5-yl)-2-fluorophenyl)(morpholino)methanone (118)

(5-(2-(aminomethyl)-7-(trifluoromethyl)benzofuran-5-yl)-2-fluorophenyl)(morpholino)methanone (118) was synthesized using General Procedure 3. Yield (100%). LCMS: m/z: 423.0 [M+H]$^+$, $t_R$=0.90 min.

Synthesis of (E)-3-(6-aminopyridin-3-yl)-N-((5-(4-fluoro-3-(morpholine-4-carbonyl)phenyl)-7-(trifluoromethyl)benzofuran-2-yl)methyl)acrylamide (563)

(E)-3-(6-aminopyridin-3-yl)-N-((5-(4-fluoro-3-(morpholine-4-carbonyl)phenyl)-7-(trifluoromethyl)benzofuran-2-yl)methyl)acrylamide (563) was synthesized using General Procedure 1. Yield (23%). $^1$H NMR (400 MHz, CD$_3$OD) δ 8.06 (s, 2H), 7.85-7.69 (m, 4H), 7.49 (d, J=16 Hz, 1H), 7.38-7.30 (m, 1H), 6.91 (s, 1H), 6.61 (d, J=9 Hz, 1H), 6.48 (d, J=16 Hz, 1H), 4.71 (s, 2H), 3.86-3.75 (m, 4H), 3.70-3.65 (m, 2H), 3.47-3.40 (m, 2H). LCMS: m/z 569.2 [M+H]$^+$, $t_R$=1.66 min.

Synthesis of (E)-3-(6-aminopyridin-3-yl)-N-((5-(4-(piperazine-1-carbonyl)phenyl)-7-(trifluoromethyl)benzofuran-2-yl)methyl)acrylamide (564)

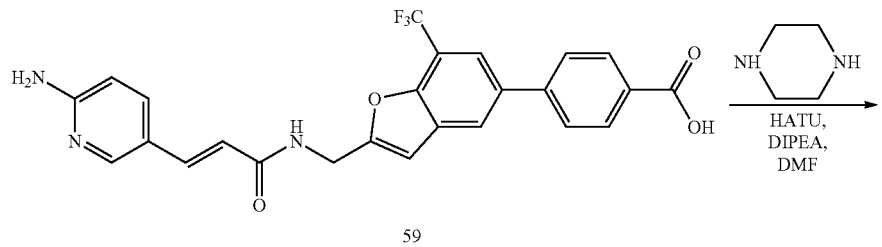

Synthesis of (E)-3-(6-aminopyridin-3-yl)-N-((5-(4-(piperazine-1-carbonyl)phenyl)-7-(trifluoromethyl)benzofuran-2-yl)methyl)acrylamide (564)

(E)-3-(6-aminopyridin-3-yl)-N-((5-(4-(piperazine-1-carbonyl)phenyl)-7-(trifluoromethyl)benzofuran-2-yl)methyl)acrylamide (564) was synthesized using general procedure 4. Yield (9%). $^1$H NMR (400 MHz, CD$_3$OD) δ 8.02-7.94 (m, 2H), 7.72-7.61 (m, 4H), 7.47-7.35 (m, 3H), 6.81 (s, 1H), 6.50 (d, J=9 Hz, 1H), 6.37 (d, J=16 Hz, 1H), 4.60 (s, 2H), 3.70-3.61 (m, 2H), 3.44-3.32 (m, 2H), 2.87-2.64 (m, 4H). LCMS: m/z 550.2 [M+H]$^+$, $t_R$=1.51 min. 4.

Synthesis of (E)-3-(6-aminopyridin-3-yl)-N-((5-(5-(4-methylpiperazine-1-carbonyl)pyridin-2-yl)-7-(trifluoromethyl)benzofuran-2-yl)methyl)acrylamide (565)

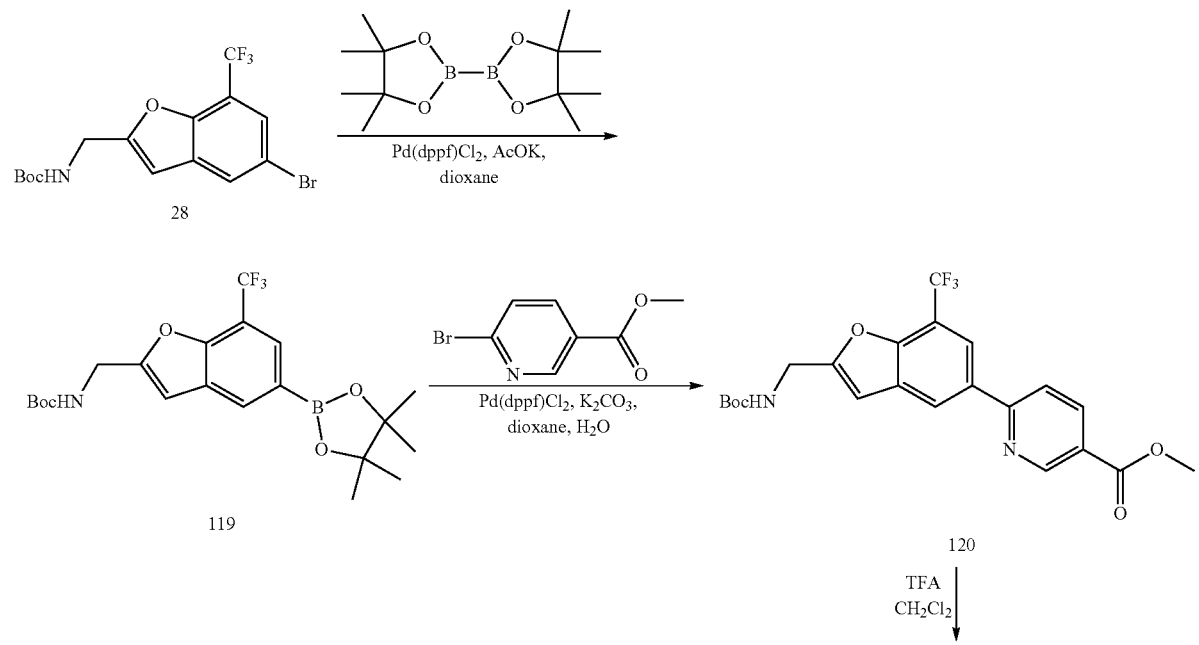

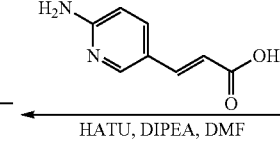
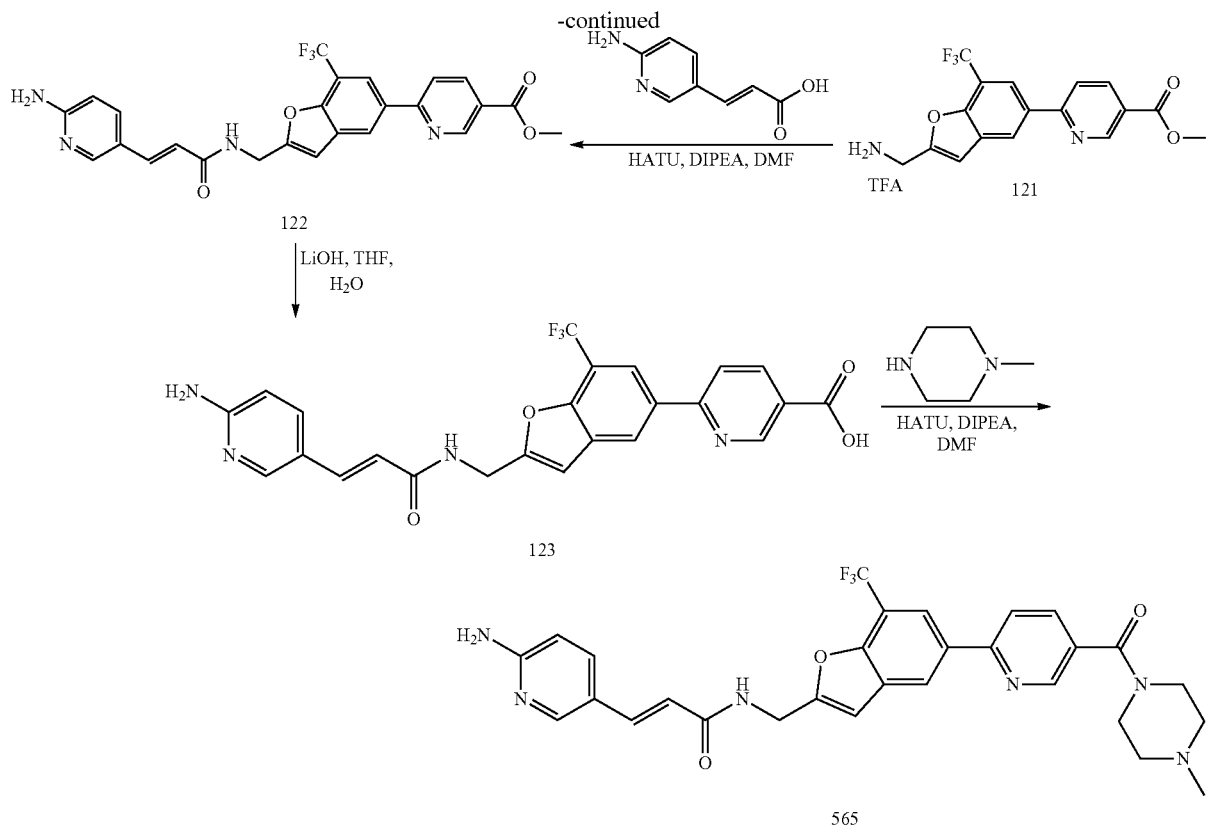

Synthesis of tert-butyl (5-(4,4,5,5-tetramethyl-1,3,2-dioxaborolan-2-yl)-7-(trifluoromethyl)benzofuran-2-yl)methylcarbamate (119)

tert-Butyl (5-bromo-7-(trifluoromethyl)benzofuran-2-yl)methylcarbamate (28) (140 g, 356 mmol), 4,4,4',4',5,5,5',5'-octamethyl-2,2'-bi(1,3,2-dioxaborolane) (100 g, 392 mmol), Pd(dppf)Cl$_2$ (30 g, 36 mmol), and potassium acetate (70 g, 712 mmol) were added in 1.5 L of dioxane and degassed. The reaction mixture was heated at 100° C. under nitrogen atmosphere for 6 h. After cooling down to room temperature, the reaction mixture was filtered. The filtrate was concentrated under reduced pressure to give the crude product, which was purified by silica gel chromatography (5-20% EtOAc/petroleum ether) to yield 143 g of tert-butyl (5-(4,4,5,5-tetramethyl-1,3,2-dioxaborolan-2-yl)-7-(trifluoromethyl)benzofuran-2-yl)methylcarbamate (119) as a yellow solid (90% yield). $^1$H NMR (400 MHz, CDCl$_3$) δ 8.10 (s, 1H), 7.88 (s, 1H), 6.59 (s, 1H), 4.97 (s, 1H), 4.42 (d, J=5 Hz, 2H), 1.40 (s, 9H), 1.30 (s, 12H). LCMS: m/z 464.1 [M+Na]$^+$, t$_R$=2.05 min.

Synthesis of methyl 6-(2-((tert-butoxycarbonylamino)methyl)-7-(trifluoromethyl)benzofuran-5-yl)nicotinate (120)

A mixture of tert-butyl (5-(4,4,5,5-tetramethyl-1,3,2-dioxaborolan-2-yl)-7-(trifluoromethyl)benzofuran-2-yl)methylcarbamate (119) (2.4 g, 5.52 mmol), methyl 6-bromonicotinate (1 g, 4.6 mmol), Pd(dppf)Cl$_2$ (337 mg, 0.46 mmol) and K$_2$CO$_3$ (1.26 g, 9.2 mmol) in 20 mL of dioxane and 4 mL of H$_2$O was stirred at 85° C. under nitrogen atmosphere for 2 h. The mixture was extracted with EtOAc (20 mL×3). The combined organic layers were washed with brine, dried over anhydrous Na$_2$SO$_4$, and concentrated under reduced pressure to give the crude product, which was purified by silica gel chromatography (40% EtOAc/petroleum ether) to give 2 g of methyl 6-(2-(((tert-butoxycarbonylamino)methyl)-7-(trifluoromethyl)benzofuran-5-yl)nicotinate (120) as a yellow solid. Yield (96%). LCMS: m/z 451.1 [M+H]$^+$, t$_R$=1.88 min.

Synthesis of methyl 6-(2-(aminomethyl)-7-(trifluoromethyl)benzofuran-5-yl)nicotinate (121)

Methyl 6-(2-((tert-butoxycarbonylamino)methyl)-7-(trifluoromethyl)benzofuran-5-yl)nicotinate (120) (2 g, 4.4 mmol) was dissolved in CH$_2$Cl$_2$ (20 mL). TFA (6 mL) was added at 0° C. The reaction mixture was stirred at room temperature for 2 h, and concentrated under reduced pressure to give the crude methyl 6-(2-(aminomethyl)-7-(trifluoromethyl)benzofuran-5-yl)nicotinate (121), which was used without further purification in the next step. Yield (100%). LCMS: m/z 351.0 [M+H]$^+$; t$_R$=0.89 min.

Synthesis of (E)-methyl 6-(2-((3-(6-aminopyridin-3-yl)acrylamido)methyl)-7-(trifluoromethyl)benzofuran-5-yl)nicotinate (122)

The crude methyl 6-(2-(aminomethyl)-7-(trifluoromethyl)benzofuran-5-yl)nicotinate (121) (crude mixture from previous step, 4.4 mmol) was dissolved in DMF (8 mL) and (E)-3-(6-aminopyridin-3-yl)acrylic acid (722 mg, 4.4 mmol) was added at 0° C. HATU (2.5 g, 6.6 mmol) was added to this reaction mixture at 0° C. followed by DIPEA (1.13 g, 8.8 mmol) dropwise. The reaction mixture was allowed to warm to room temperature and stirred for 4 h. The crude mixture was purified by Prep-HPLC without workup to afford 800 mg of (E)-methyl 6-(2-((3-(6-aminopyridin-3-yl)acrylamido)methyl)-7-(trifluoromethyl)benzofuran-5-yl)nicotinate (122). Yield (36%). LCMS: m/z 497.1 [M+H]$^+$, $t_R$=1.38 min.

Synthesis of (E)-6-(2-((3-(6-aminopyridin-3-yl)acrylamido)methyl)-7-(trifluoromethyl)benzofuran-5-yl) nicotinic acid (123)

(E)-methyl 6-(2-((3-(6-aminopyridin-3-yl)acrylamido)methyl)-7-(trifluoromethyl)benzofuran-5-yl)nicotinate (122) (800 mg, 1.6 mmol) was dissolved in THF (10 mL). LiOH (98 mg, 2.4 mmol) and water (2 mL) were added to this mixture. The mixture was stirred at room temperature for 8 h, 1N HCl solution was added and adjusted to pH~6.700 mg of (E)-6-(2-((3-(6-aminopyridin-3-yl)acrylamido)methyl)-7-(trifluoromethyl)benzofuran-5-yl)nicotinic acid (123) was collected by filtration and dried in vacuum. Yield (90%). LCMS: m/z 483.1 [M+H]$^+$, $t_R$=1.34 min.

Synthesis of (E)-3-(6-aminopyridin-3-yl)-N-((5-(5-(4-methylpiperazine-1-carbonyl)pyridin-2-yl)-7-(trifluoromethyl)benzofuran-2-yl)methyl)acrylamide (565)

(E)-3-(6-aminopyridin-3-yl)-N-((5-(5-(4-methylpiperazine-1-carbonyl)pyridin-2-yl)-7-(trifluoromethyl)benzofuran-2-yl)methyl)acrylamide (565) was synthesized using the indicated reagents according to general procedure 4. (10 mg; Yield: 14%). $^1$H NMR (400 MHz, CD$_3$OD) δ 8.74-8.73 (m, 1H), 8.49 (d, J=1 Hz, 1H), 8.31 (s, 1H), 8.07-8.06 (m, 2H), 7.98-7.95 (m, 1H), 7.75-7.72 (m, 1H), 7.49 (d, J=16 Hz, 1H), 6.94 (s, 1H), 6.60 (d, J=9 Hz, 1H), 6.48 (d, J=16 Hz, 1H), 4.72 (s, 2H), 3.83 (s, 2H), 3.57 (s, 2H), 2.56-2.49 (m, 4H), 2.35 (s, 3H). LCMS: m/z 565.2 [M+H]$^+$; $t_R$=1.53 min.

Synthesis of (E)-3-(6-aminopyridin-3-yl)-N-((5-(4-(4,4-difluoropiperidine-1-carbonyl)phenyl)-7-(trifluoromethyl)benzofuran-2-yl)methyl)acrylamide (566)

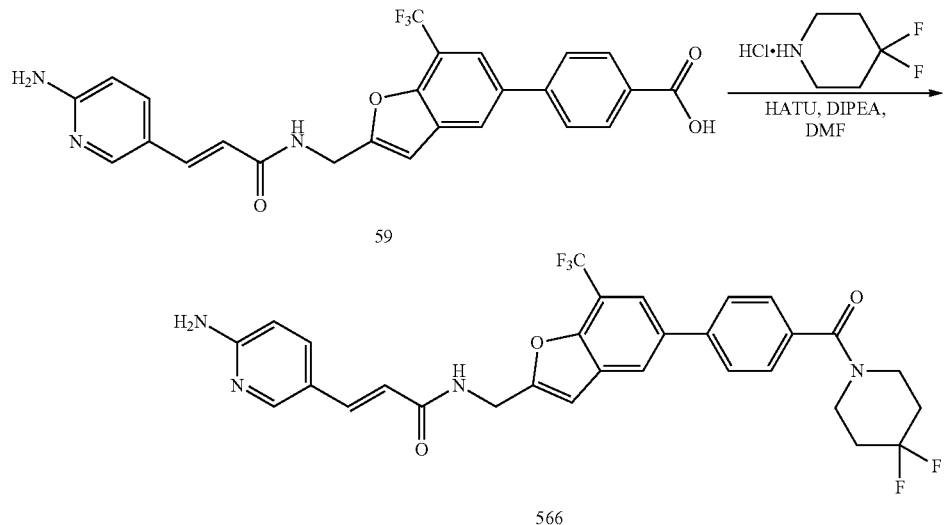

(E)-3-(6-aminopyridin-3-yl)-N-((5-(4-(4,4-difluoropiperidine-1-carbonyl)phenyl)-7-(trifluoromethyl)benzofuran-2-yl)methyl)acrylamide (566) was synthesized using the indicate reagents according to general procedure 4. Yield (77%). $^1$H NMR (400 MHz, CDCl$_3$) δ 8.24-8.18 (m, 1H), 7.87 (s, 1H), 7.76-7.47 (m, 7H), 6.80 (s, 1H), 6.49 (d, J=8 Hz, 1H), 6.34-6.20 (m, 2H), 4.77 (d, J=6 Hz, 2H), 4.71 (s, 2H), 3.98-3.49 (m, 4H), 2.15-1.92 (m, 4H). LCMS: m/z 585.3 [M+H]$^+$; $t_R$=1.81 min.

Synthesis of (E)-3-(6-aminopyridin-3-yl)-N-((5-(4-(4-fluoropiperidine-1-carbonyl)phenyl)-7-(trifluoromethyl)benzofuran-2-yl)methyl)acrylamide (567)

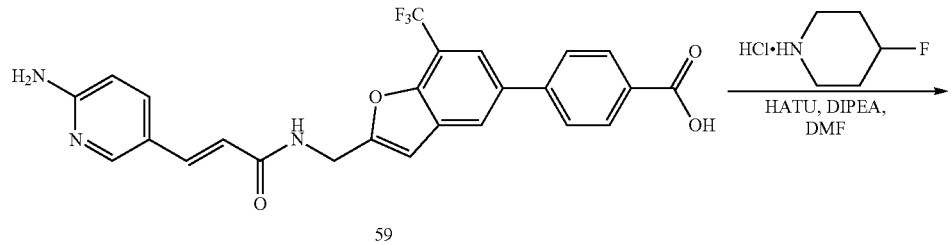

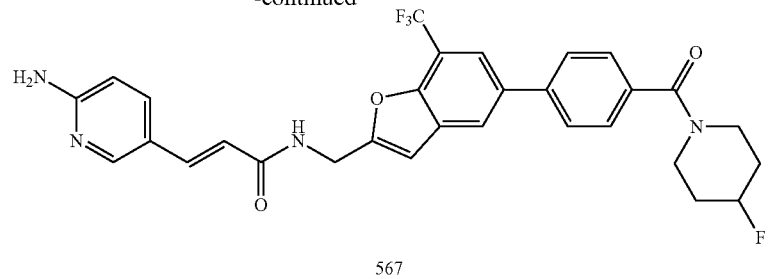

567

(E)-3-(6-aminopyridin-3-yl)-N-((5-(4-(4-fluoropiperidine-1-carbonyl)phenyl)-7-(trifluoromethyl)benzofuran-2-yl)methyl)acrylamide (567) was synthesized using the indicated reagents according to general procedure 4. Yield (55%). $^1$H NMR (400 MHz, DMSO-d$_6$) δ 8.66 (t, J=6 Hz, 1H), 8.25 (s, 1H), 8.09 (d, J=2 Hz, 1H), 7.87-7.82 (m, 3H), 7.64-7.61 (m, 1H), 7.53 (d, J=8 Hz, 2H), 7.36 (d, J=16 Hz, 1H), 6.95 (s, 1H), 6.49-6.41 (m, 4H), 5.00-4.85 (m, 1H), 4.02 (d, J=6 Hz, 2H), 3.68-3.47 (m, 4H), 1.96-1.75 (m, 4H). LCMS: m/z 567.2 [M+H]$^+$; t$_R$=1.70 min.

Synthesis of (E)-3-(6-aminopyridin-3-yl)-N-((7-(4-fluorophenyl)-5-(5-(morpholine-4-carbonyl)pyridin-2-yl)benzofuran-2-yl)methyl)acrylamide (568)

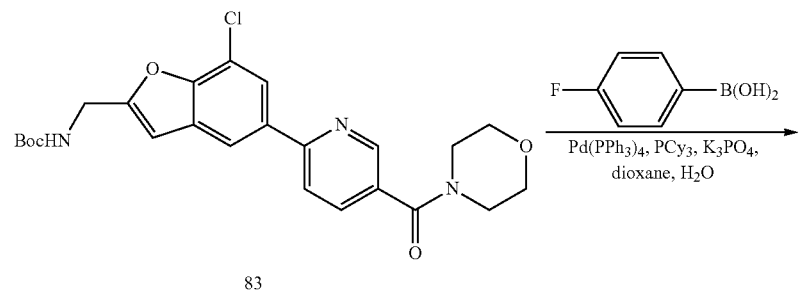

83

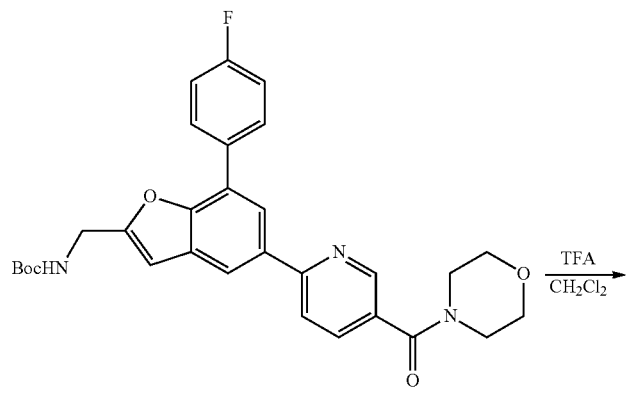

124

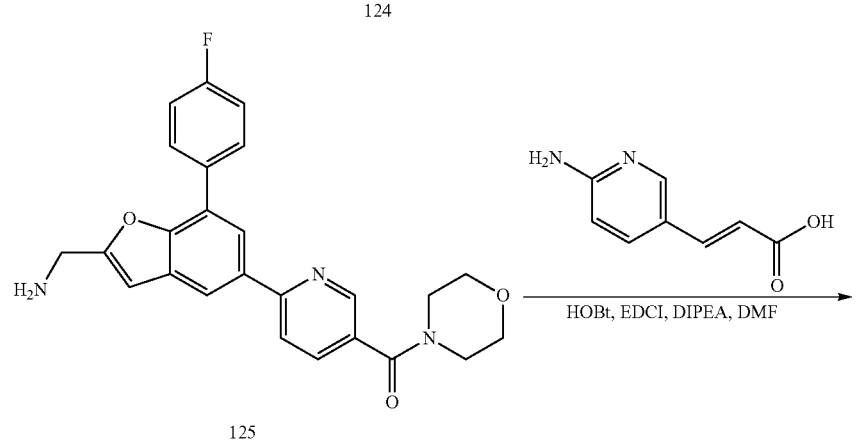

125

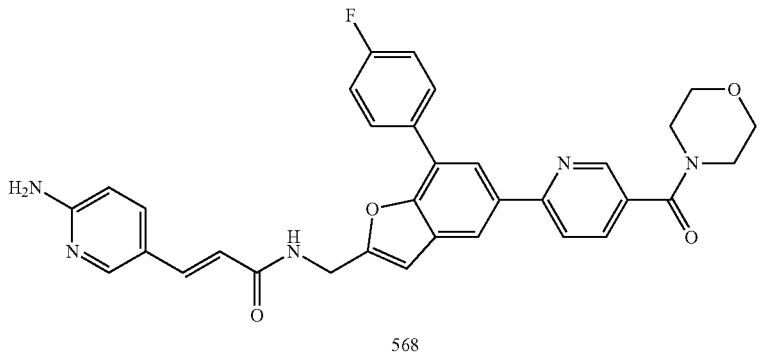

568

Synthesis of tert-butyl (7-(4-fluorophenyl)-5-(5-(morpholine-4-carbonyl)pyridin-2-yl)benzofuran-2-yl)methylcarbamate (124)

tert-Butyl (7-chloro-5-(5-(morpholine-4-carbonyl)pyridin-2-yl)benzofuran-2-yl)methylcarbamate (83) (140 mg, 0.3 mmol), 4-fluorophenylboronic acid (125 mg, 0.9 mmol), Pd(PPh$_3$)$_4$ (35 mg, 0.03 mmol), tricyclohexylphosphine (17 mg, 0.06 mmol) and K$_3$PO$_4$ (201 mg, 0.9 mmol) were added to 10 mL of dioxane and 1 mL of water. The reaction mixture was degassed and heated at 130° C. under nitrogen atmosphere for 12 h. The reaction mixture was cooled down to room temperature, poured into 5 mL of water, extracted with EtOAc (10 mL×3). The combined organic layers were washed with brine, dried over anhydrous Na$_2$SO$_4$, concentrated under reduced pressure to give the crude product which was purified by silica gel chromatography (50% EtOAc/petroleum ether) to give tert-butyl (7-(4-fluorophenyl)-5-(5-(morpholine-4-carbonyl)pyridin-2-yl)benzofuran-2-yl)methylcarbamate (124) as white solid (100 mg, 63% yield). LCMS: m/z 532.1 [M+H]$^+$; t$_R$=1.78 min.

Synthesis of (6-(2-(aminomethyl)-7-(4-fluorophenyl)benzofuran-5-yl)pyridin-3-yl)(morpholino)methanone (125)

tert-Butyl (7-(4-fluorophenyl)-5-(5-(morpholine-4-carbonyl)pyridin-2-yl)benzofuran-2-yl)methylcarbamate (124) (110 mg, 0.21 mmol) was dissolved in CH$_2$Cl$_2$ (5 mL). TFA (1 mL) was added dropwise at 0° C. The reaction mixture was stirred at room temperature for 4 h. The reaction mixture was concentrated under reduced pressure to give (6-(2-(aminomethyl)-7-(4-fluorophenyl)benzofuran-5-yl)pyridin-3-yl)(morpholino)methanone (125), which was used without further purification in the next step (80 mg, 89% yield). LCMS: m/z 432.1 [M+H]$^+$; t$_R$=0.87 min.

Synthesis of (E)-3-(6-aminopyridin-3-yl)-N-((7-(4-fluorophenyl)-5-(5-(morpholine-4-carbonyl)pyridin-2-yl)benzofuran-2-yl)methyl)acrylamide (568)

(6-(2-(Aminomethyl)-7-(4-fluorophenyl) benzofuran-5-yl)pyridin-3-yl)(morpholino)methanone (125) (80 mg, 0.2 mmol), (E)-3-(6-aminopyridin-3-yl)acrylic acid (35 mg, 0.2 mmol), HOBt hydrate (40 mg, 0.3 mmol), EDCI (55 mg, 0.3 mmol) and DIPEA (74 mg, 0.6 mmol) were added in DMF (6 mL) at room temperature. The reaction mixture was stirred at room temperature for 12 h. The reaction mixture was diluted with water (10 mL), extracted with EtOAc (10 mL×3). The combined organic layers were washed with brine, dried over anhydrous Na$_2$SO$_4$, concentrated under reduced pressure to give the crude product which was purified by Pre-HPLC to give (E)-3-(6-aminopyridin-3-yl)-N-((7-(4-fluorophenyl)-5-(5-(morpholine-4-carbonyl)pyridin-2-yl)benzofuran-2-yl)methyl)acrylamide (568) (36 mg, 34% yield) as white solid. $^1$H NMR (400 MHz, DMSO-d$_6$) δ 8.82 (s, 1H), 8.73 (s, 1H), 8.38 (s, 1H), 8.26-7.94 (m, 9H), 7.50-7.36 (m, 3H), 7.01-6.91 (m, 2H), 6.60 (d, J=16 Hz, 1H), 4.62 (d, J=5 Hz, 2H), 3.94-3.42 (m, 8H). LCMS: m/z 578.2 [M+H]$^+$, t$_R$=1.32 min.

Synthesis of (E)-3-(6-aminopyridin-3-yl)-N-((5-(5-(3,3-dimethylmorpholine-4-carbonyl)pyridin-2-yl)-7-(trifluoromethyl)benzofuran-2-yl)methyl)acrylamide (569)

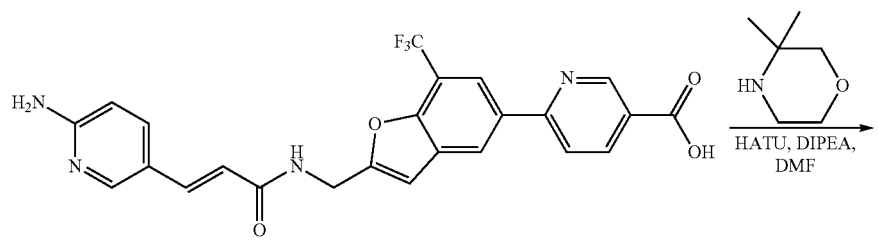

123

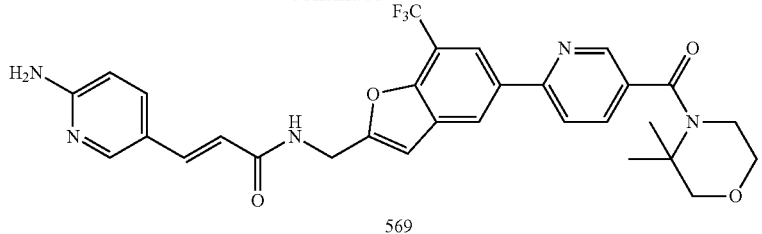

(E)-3-(6-aminopyridin-3-yl)-N-((5-(5-(3,3-dimethylmorpholine-4-carbonyl)pyridin-2-yl)-7-(trifluoromethyl)benzofuran-2-yl)methyl)acrylamide (569) was synthesized using the indicated reagents according to general procedure 4. Yield (49%). $^1$H NMR (400 MHz, DMSO-$d_6$) δ 8.73-8.66 (m, 3H), 8.38 (s, 1H), 8.18 (d, J=8 Hz, 1H), 8.08 (s, 1H), 7.98-7.95 (m, 1H), 7.63-7.61 (m, 1H), 7.36 (d, J=16 Hz, 1H), 7.00 (s, 1H), 6.48-6.41 (m, 4H), 4.62 (d, J=6 Hz, 2H), 3.71-3.69 (m, 2H), 3.44 (s, 2H), 3.33 (s, 2H), 1.44 (s, 6H). LCMS: m z 580.0 [M+H]$^+$; $t_R$=1.37 min.

Synthesis of (S,E)-3-(6-aminopyridin-3-yl)-N-((5-(5-(3-fluoropyrrolidine-1-carbonyl)pyridin-2-yl)-7-(trifluoromethyl)benzofuran-2-yl)methyl)acrylamide (570)

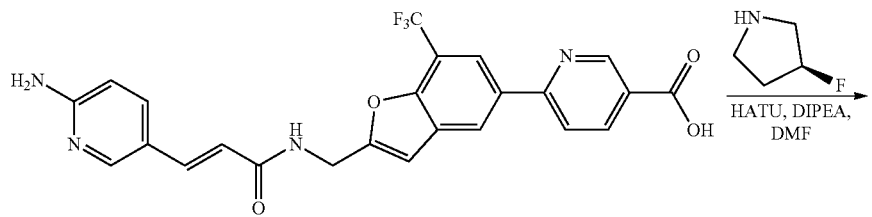

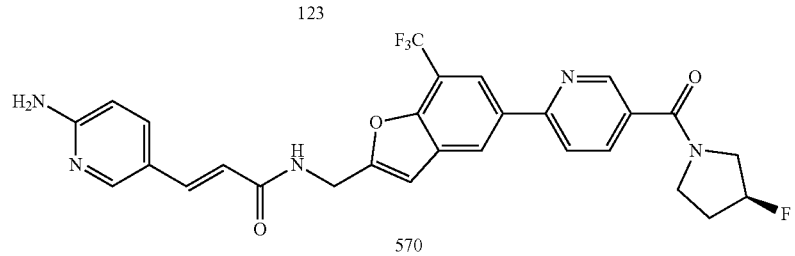

(S,E)-3-(6-aminopyridin-3-yl)-N-((5-(5-(3-fluoropyrrolidine-1-carbonyl)pyridin-2-yl)-7-(trifluoromethyl)benzofuran-2-yl)methyl)acrylamide (570) was synthesized using the indicate reagents according to general procedure 4. Yield (22%). $^1$H NMR (400 MHz, DMSO-$d_6$) δ 8.89-8.85 (m, 1H), 8.70-8.65 (m, 2H), 8.40 (s, 1H), 8.22-8.08 (m, 3H), 7.64-7.61 (m, 1H), 7.36 (d, J=16 Hz, 1H), 7.00 (s, 1H), 6.49-6.41 (m, 4H), 5.48-5.29 (m, 1H), 4.62 (d, J=6 Hz, 2H), 3.80-3.60 (m, 4H), 2.19-2.17 (m, 2H). LCMS: m/z 554.2 [M+H]$^+$; $t_R$=1.31 min.

Synthesis of (E)-3-(6-aminopyridin-3-yl)-N-((5-(4-(4-hydroxy-4-methylpiperidine-1-carbonyl)phenyl)-7-(trifluoromethyl)benzofuran-2-yl)methyl)acrylamide (571)

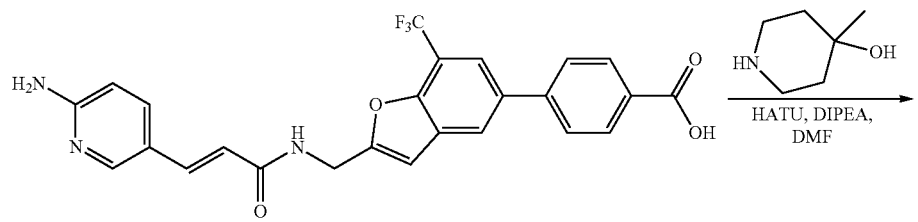

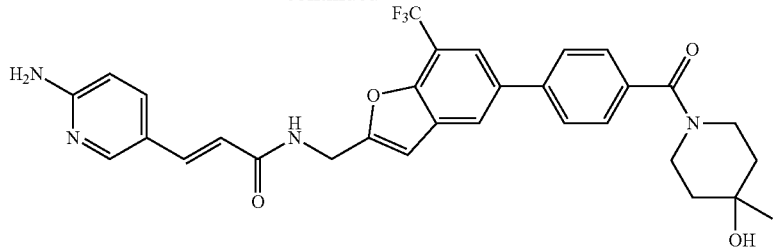

571

(E)-3-(6-aminopyridin-3-yl)-N-((5-(4-(4-hydroxy-4-methylpiperidine-1-carbonyl)phenyl)-7-(trifluoromethyl)benzofuran-2-yl)methyl)acrylamide (571) was synthesized using the indicated reagents according to general procedure 4. Yield (45%). $^1$H NMR (400 MHz, CD$_3$OD) δ 7.98-7.94 (m, 2H), 7.68-7.62 (m, 4H), 7.43-7.36 (m, 3H), 6.80 (s, 1H), 6.49 (d, J=5 Hz, 1H), 6.37 (d, J=16 Hz, 1H), 4.67-4.51 (m, 2H), 4.17-4.14 (m, 1H), 3.43-3.21 (m, 3H), 1.60-1.47 (m, 4H), 1.17 (s, 3H). LCMS: m/z 579.3 [M+H]$^+$; t$_R$=1.69 min.

Synthesis of (E)-3-(6-aminopyridin-3-yl)-N-((5-(4-(3,3-dimethylpiperazine-1-carbonyl)phenyl)-7-(trifluoromethyl)benzofuran-2-yl)methyl)acrylamide (572)

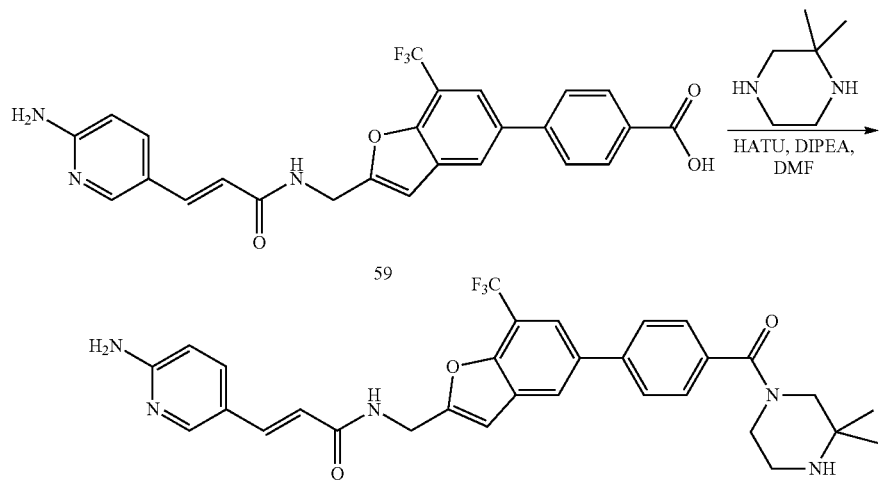

(E)-3-(6-aminopyridin-3-yl)-N-((5-(4-(3,3-dimethylpiperazine-1-carbonyl)phenyl)-7-(trifluoromethyl)benzofuran-2-yl)methyl)acrylamide (572) was synthesized using the indicated reagents according to general procedure 4. Yield (52%). $^1$H NMR (400 MHz, CD$_3$OD) δ 8.11 (s, 1H), 8.06 (d, J=2 Hz, 1H), 7.80-7.74 (m, 4H), 7.54-7.48 (m, 3H), 6.92 (s, 1H), 6.61 (d, J=9 Hz, 1H), 6.49 (d, J=4 Hz, 1H), 4.72-4.64 (m, 4H), 3.74-3.45 (m, 2H), 2.85-2.76 (m, 2H), 1.23 (s, 3H), 1.06 (s, 3H). LCMS: m/z 578.3 [M+H]$^+$; t$_R$=1.63 min.

Synthesis of (E)-N-((5-(4-(1,4-diazepane-1-carbonyl)phenyl)-7-(trifluoromethyl)benzofuran-2-yl)methyl)-3-(6-aminopyridin-3-yl)acrylamide (573)

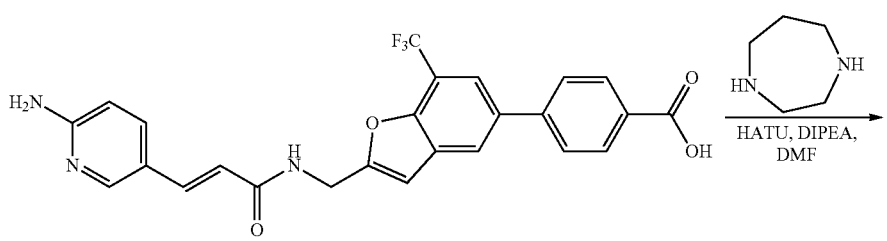

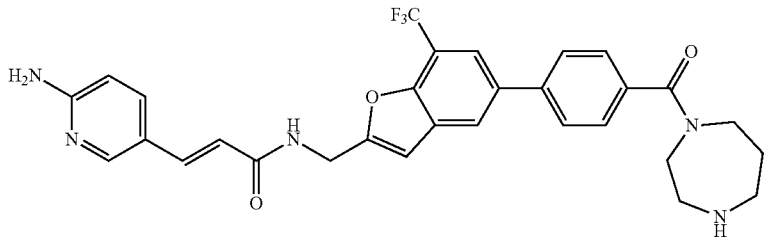

573

(E)-N-((5-(4-(1,4-diazepane-1-carbonyl)phenyl)-7-(trifluoromethyl)benzofuran-2-yl)methyl)-3-(6-aminopyridin-3-yl)acrylamide (573) was synthesized using the indicated reagents according to general procedure 4. Yield (24%). $^1$H NMR (400 MHz, CD$_3$OD) δ 8.12-8.04 (m, 2H), 7.84-7.74 (m, 4H), 7.61-7.46 (m, 3H), 6.92 (s, 1H), 6.61 (d, J=9 Hz, 1H), 6.49 (d, J=16 Hz, 1H), 4.72 (s, 2H), 3.87-3.77 (m, 2H), 3.63-3.53 (m, 2H), 3.13-2.87 (m, 4H), 2.00-1.78 (m, 2H). LCMS: m/z 564.2 [M+H]$^+$, t$_R$=1.19 min.

Synthesis of (E)-N-((5-(4-(1,4-oxazepane-4-carbonyl)phenyl)-7-(trifluoromethyl)benzofuran-2-yl)methyl)-3-(6-aminopyridin-3-yl)acrylamide (574)

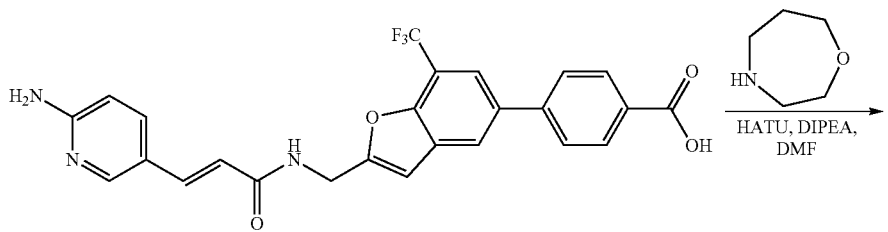

59

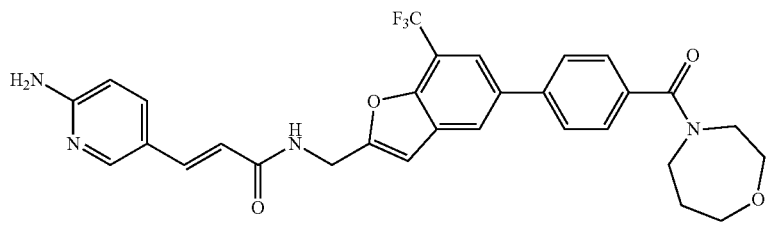

574

(E)-N-((5-(4-(1,4-oxazepane-4-carbonyl)phenyl)-7-(trifluoromethyl)benzofuran-2-yl)methyl)-3-(6-aminopyridin-3-yl)acrylamide (574) was synthesized using the indicated reagents according to general procedure 4. Yield (51%). ¹H NMR (400 MHz, DMSO-d$_6$) δ 8.69 (t, J=6.0 Hz, 1H), 8.25 (s, 1H), 8.08 (d, J=2 Hz, 1H), 7.86-7.81 (m, 3H), 7.65-7.63 (m, 1H), 7.51 (d, J=8 Hz, 2H), 7.36 (d, J=16 Hz, 1H), 6.95 (s, 1H), 6.50-6.41 (m, 4H), 4.61 (d, J=5 Hz, 2H), 3.75-3.59 (m, 8H), 1.91-1.73 (m, 2H). LCMS: m/z 565.2 [M+H]⁺; t$_R$=1.62 min.

Synthesis of (E)-3-(6-aminopyridin-3-yl)-N-((5-(4-(2,2-dimethylpiperazine-1-carbonyl)phenyl)-7-(trifluoromethyl)benzofuran-2-yl)methyl)acrylamide (575)

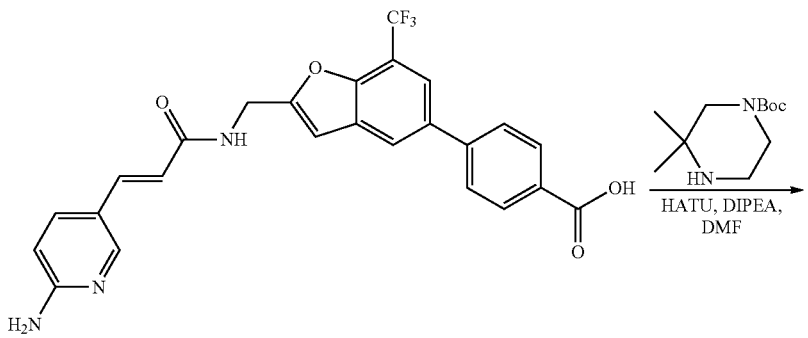

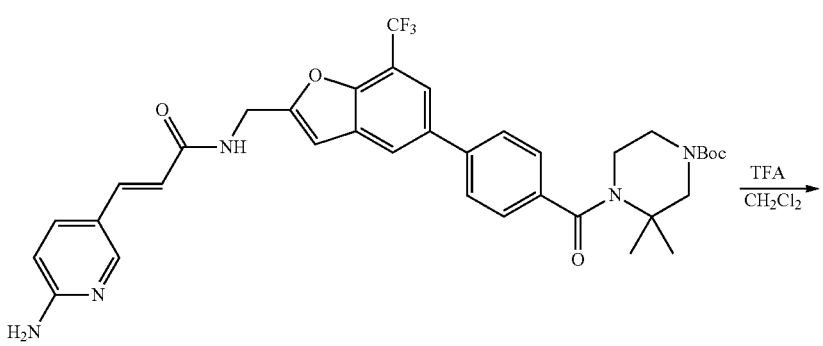

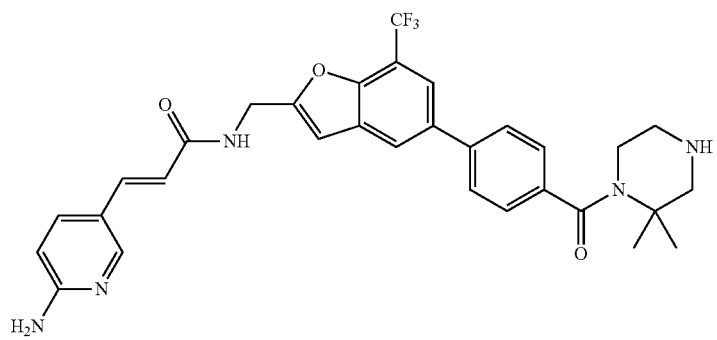

Synthesis of (E)-tert-Butyl 4-(4-(2-((3-(6-amino-pyridin-3-yl)acrylamido)methyl)-7-(trifluoromethyl)benzofuran-5-yl)benzoyl)-3,3-dimethylpiperazine-1-carboxylate (126)

(E)-tert-Butyl 4-(4-(2-((3-(6-aminopyridin-3-yl)acrylamido)methyl)-7-(trifluoromethyl)benzofuran-5-yl)benzoyl)-3,3-dimethylpiperazine-1-carboxylate (126) was synthesized using General Procedure 4. Yield (35%). LCMS: m/z 678.3 [M+H]$^+$; $t_R$=1.86 min.

Synthesis of (E)-3-(6-aminopyridin-3-yl)-N-((5-(4-(2,2-dimethylpiperazine-1-carbonyl)phenyl)-7-(trifluoromethyl)benzofuran-2-yl)methyl)acrylamide (575)

(E)-3-(6-aminopyridin-3-yl)-N-((5-(4-(2,2-dimethylpiperazine-1-carbonyl)phenyl)-7-(trifluoromethyl)benzofuran-2-yl)methyl)acrylamide (575) was synthesized using the indicated reagents according to general procedure 3. Yield (14%). $^1$H NMR (400 MHz, DMSO-d$_6$) δ 8.77 (t, J=6 Hz, 1H), 8.26-8.08 (m, 3H), 7.86-7.92 (m, 2H), 7.50 (d, J=8 Hz, 1H), 6.94 (s, 1H), 6.55-6.31 (m, 5H), 5.80 (d, J=13 Hz, 1H), 4.62-4.56 (m, 2H), 3.20-3.17 (m, 4H), 2.76-2.74 (m, 2H), 2.62 (s, 2H), 1.44 (s, 6H). LCMS: m/z 578.3 [M+H]$^+$, $t_R$=1.59 min.

Synthesis of (E)-3-(6-aminopyridin-3-yl)-N-((7-chloro-5-(4-(4-methylpiperazine-1-carbonyl)phenyl)benzofuran-2-yl)methyl)acrylamide (576)

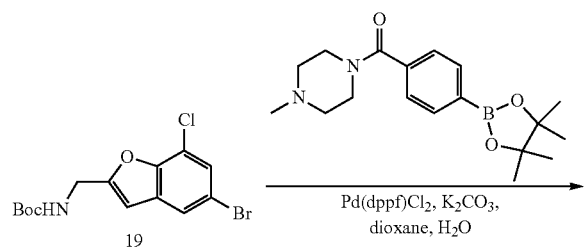

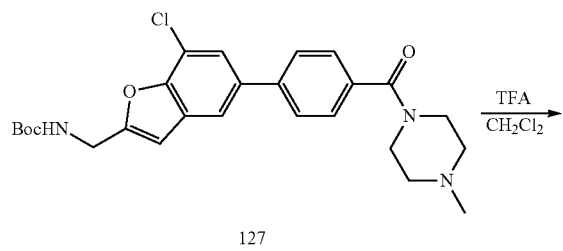

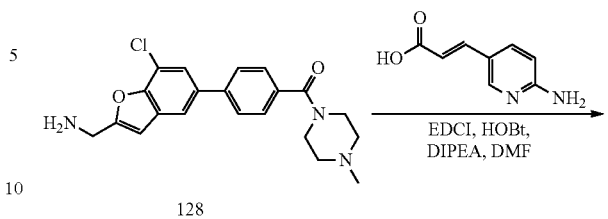

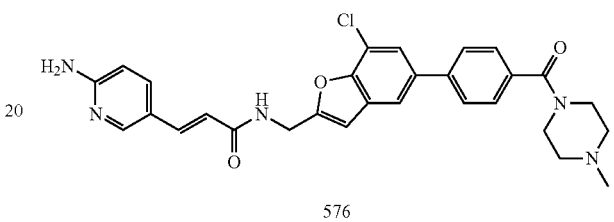

Synthesis of tert-Butyl (7-chloro-5-(4-(4-methylpiperazine-1-carbonyl)phenyl)benzofuran-2-yl)methylcarbamate (127)

tert-Butyl (7-chloro-5-(4-(4-methylpiperazine-1-carbonyl)phenyl)benzofuran-2-yl)methylcarbamate (127) was synthesized using the indicated reagents according to General Procedure 2. Yield (87%). LCMS: m/z 484.1 [M+H]$^+$; $t_R$=1.39 min.

Synthesis of (4-(2-(Aminomethyl)-7-chlorobenzofuran-5-yl)phenyl)(4-methylpiperazin-1-yl)methanone (128)

(4-(2-(Aminomethyl)-7-chlorobenzofuran-5-yl)phenyl)(4-methylpiperazin-1-yl)methanone (128) was synthesized using the indicated reagents according to General Procedure 3. Yield (100%). LCMS: m/z 385.2 [M+H]$^+$; $t_R$=1.54 min.

Synthesis of (E)-3-(6-aminopyridin-3-yl)-N-((7-chloro-5-(4-(4-methylpiperazine-1-carbonyl)phenyl)benzofuran-2-yl)methyl)acrylamide (576)

(E)-3-(6-aminopyridin-3-yl)-N-((7-chloro-5-(4-(4-methylpiperazine-1-carbonyl)phenyl)benzofuran-2-yl)methyl)acrylamide (576) was synthesized using the indicated reagents according to General Procedure 1. Yield (100%). $^1$H NMR (400 MHz, DMSO-d$_6$) δ 8.64 (t, J=6 Hz, 1H), 8.08-7.61 (m, 6H), 7.48 (d, J=8.0 Hz, 2H), 7.36 (d, J=16 Hz, 1H), 6.90 (s, 1H), 6.49-6.41 (m, 4H), 4.61-4.59 (m, 2H), 3.78-3.54 (m, 4H), 2.34-2.33 (m, 4H), 2.20 (s, 3H). LCMS: m/z 530.2 [M+H]$^+$; $t_R$=1.54 min.

Synthesis of (S,E)-3-(6-aminopyridin-3-yl)-N-((5-(5-(3-fluoropyrrolidine-1-carbonyl)pyridin-2-yl)-7-(trifluoromethyl)benzofuran-2-yl)methyl)acrylamide (577)

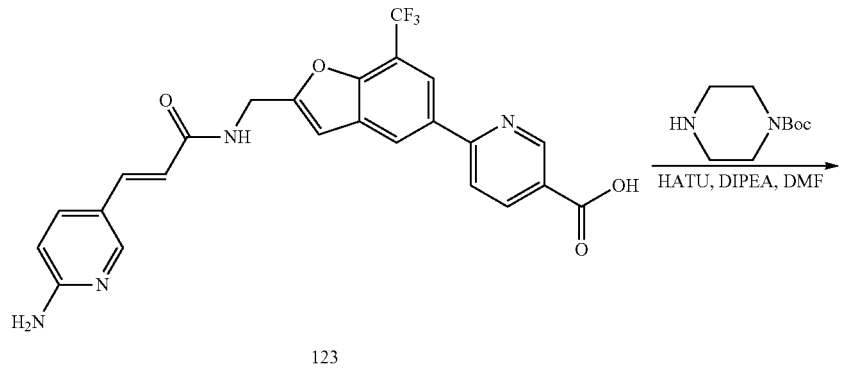

123

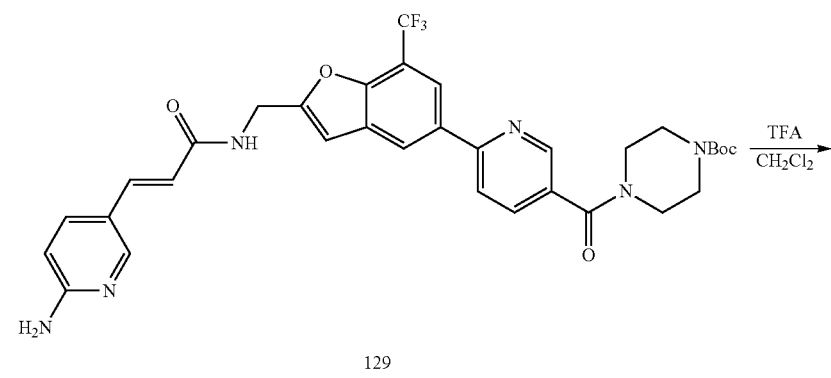

129

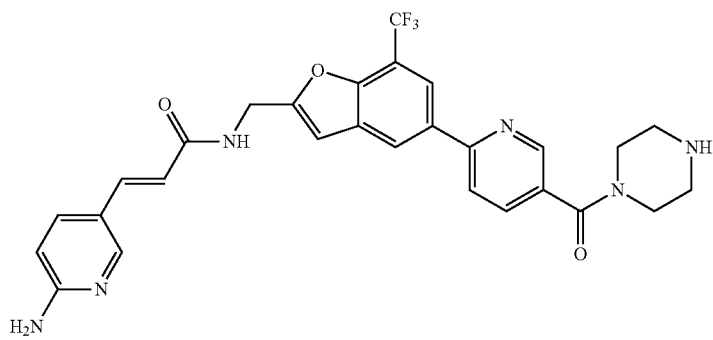

577

Synthesis of (E)-tert-Butyl 4-(6-(2-((3-(6-aminopyridin-3-yl)acrylamido)methyl)-7-(trifluoromethyl)benzofuran-5-yl)nicotinoyl)piperazine-1-carboxylate (129)

(E)-tert-Butyl 4-(6-(2-((3-(6-aminopyridin-3-yl)acrylamido)methyl)-7-(trifluoromethyl)benzofuran-5-yl)nicotinoyl)piperazine-1-carboxylate (136) was synthesized using the indicated reagents according to General Procedure 4. (52% yield). LCMS: m/z 651.2 [M+H]$^+$; $t_R$=1.73 min.

Synthesis of (E)-3-(6-aminopyridin-3-yl)-N-((5-(5-(piperazine-1-carbonyl)pyridin-2-yl)-7-(trifluoromethyl)benzofuran-2-yl)methyl)acrylamide (577)

(E)-3-(6-aminopyridin-3-yl)-N-((5-(5-(piperazine-1-carbonyl)pyridin-2-yl)-7-(trifluoromethyl)benzofuran-2-yl)methyl)acrylamide (577) was synthesized using the indicated reagents according to General Procedure 3. Yield (50%). $^1$H NMR (400 MHz, CD$_3$OD) δ 8.74 (s, 1H), 8.53 (s, 1H), 8.34 (s, 1H), 8.10-7.93 (m, 4H), 7.50 (d, J=16 Hz, 1H), 6.95 (d, J=13 Hz, 1H), 6.66-6.51 (m, 1H), 6.47-6.37 (m, 1H), 4.73-4.67 (m, 2H), 3.79-3.50 (m, 4H), 2.94-2.86 (m, 4H). LCMS: m/z 551.2 [M+H]$^+$; $t_R$=1.45 min.

Synthesis of (E)-3-(6-aminopyridin-3-yl)-N-((7-chloro-5-(5-((3,5-dimethylisoxazol-4-yl)(hydroxy)methyl)thiophen-2-yl)benzofuran-2-yl)methyl)acrylamide (578)

anhydrous Na$_2$SO$_4$, concentrated and purified by silica gel chromatography (10%-20% EtOAc/petroleum ether) to give 455 mg of (5-bromothiophen-2-yl)(3,5-dimethylisoxazol-4-yl)methanol (131) as yellow oil (yield: 8%). LCMS: m/z 290.0 [M+H]$^+$; t$_R$=1.66 min.

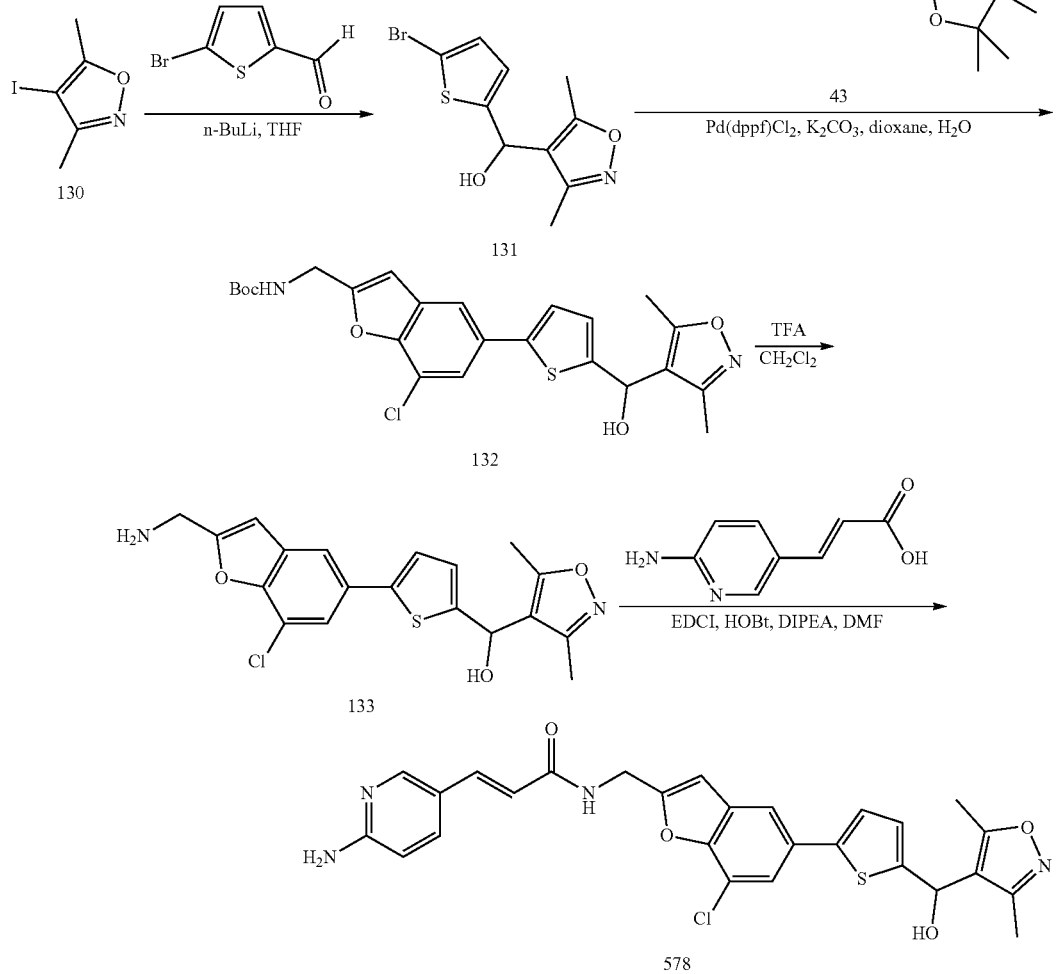

Synthesis of (5-bromothiophen-2-yl)(3,5-dimethylisoxazol-4-yl)methanol (131)

4-Iodo-3,5-dimethylisoxazole (130) (3.35 g, 15 mmol) was dissolved in 45 mL of THF. The mixture was degassed and cooled to −78° C. n-BuLi (6.6 mL, 16.5 mmol, 2.5 N in hexanes) was added slowly. After stirring for 1 h at −78° C., 5-bromothiophene-2-carbaldehyde (3.15 g, 16.5 mmol) was added. The mixture was stirred at −78° C. for additional 1 h, and then allowed to warm up to 0° C. slowly. 10 mL of NH$_4$Cl aqueous solution was added to quench the reaction and the mixture was extracted with EtOAc (35 mL×3). The combined organic layers were washed with brine, dried over Synthesis of tert-butyl (7-chloro-5-(5-((3,5-dimethylisoxazol-4-yl)(hydroxy)methyl)thiophen-2-yl)benzofuran-2-yl)methylcarbamate (132)

(5-Bromothiophen-2-yl)(3,5-dimethylisoxazol-4-yl)methanol (131) (160 mg, 0.55 mmol) and tert-butyl (7-chloro-5-(4,4,5,5-tetramethyl-1,3,2-dioxaborolan-2-yl)benzofuran-2-yl)methylcarbamate (203 mg, 0.5 mmol) was dissolved in dioxane (6 mL) and degassed. Pd(dppf)Cl$_2$ (40 mg, 0.05 mmol), K$_2$CO$_3$ (138 mg, 1 mmol) and 0.6 mL of water were added. The reaction mixture was heated at 100° C. for 2 h. The reaction mixture was transferred into water and extracted with ethyl acetate (20 mL×3). The combined organic layers were washed with brine, dried over anhydrous Na$_2$SO$_4$, and concentrated under reduced pressure to give the crude product which was purified by chromatography (20-30% ethyl acetate/petroleum ether) to give tert-butyl (7-chloro-5-(5-((3,5-dimethylisoxazol-4-yl)(hydroxy)methyl)thiophen-2-yl)benzofuran-2-yl)methylcarbamate (132) (160 mg, 66% yield) as yellowish solid. LCMS: m/z 489.1 [M+H]$^+$, $t_R$=1.85 min.

Synthesis of (5-(2-(aminomethyl)-7-chlorobenzofuran-5-yl)thiophen-2-yl)(3,5-dimethylisoxazol-4-yl)methanol (133)

tert-Butyl (7-chloro-5-(5-((3,5-dimethylisoxazol-4-yl)(hydroxy)methyl)thiophen-2-yl)benzofuran-2-yl)methylcarbamate (132) (80 mg, 0.16 mmol) was dissolved in CH$_2$Cl$_2$ (4 mL). TFA (1 mL) was added at 0° C. (ice bath). The reaction mixture was allowed to warm to room temperature and stirred for 1 h. The reaction mixture was concentrated under reduced pressure to give the crude (5-(2-(aminomethyl)-7-chlorobenzofuran-5-yl)thiophen-2-yl)(3,5-dimethylisoxazol-4-yl)methanol (133), which was used in the next step without further purification. (80 mg, Yield: 100%). LCMS: m/z 371.1 [M+H]$^+$; $t_R$=1.38 min.

Synthesis of (E)-3-(6-aminopyridin-3-yl)-N-((7-chloro-5-(5-((3,5-dimethylisoxazol-4-yl)(hydroxy)methyl)thiophen-2-yl)benzofuran-2-yl)methyl)acrylamide (578)

(5-(2-(Aminomethyl)-7-chlorobenzofuran-5-yl)thiophen-2-yl)(3,5-dimethylisoxazol-4-yl)methanol (133) (80 mg, 0.16 mmol) was dissolved in DMF (3 mL) and (E)-3-(6-aminopyridin-3-yl)acrylic acid (32 mg, 0.19 mmol) was added at 0° C. EDCI (37 mg, 0.19 mmol) and HOBt (26 mg, 0.19 mmol) were added to this reaction mixture at 0° C. followed by DIPEA (41 mg, 0.32 mmol) dropwise. The reaction mixture was allowed to warm to room temperature and stirred for 18 h. The crude mixture was purified by Prep-HPLC to afford (E)-3-(6-aminopyridin-3-yl)-N-((7-chloro-5-(5-((3,5-dimethylisoxazol-4-yl)(hydroxy)methyl)thiophen-2-yl)benzofuran-2-yl)methyl)acrylamide (578) (6 mg, 7% yield). $^1$H NMR (400 MHz, CD$_3$OD) δ 8.07 (d, J=2 Hz, 1H), 7.78-7.72 (m, 2H), 7.57-7.48 (m, 2H), 7.27 (d, J=4 Hz, 1H), 6.88 (m, 1H), 6.81 (s, 1H), 6.61 (d, J=9 Hz, 1H), 6.48 (d, J=16 Hz, 1H), 6.00 (s, 1H), 4.68 (s, 2H), 2.43 (s, 3H), 2.21 (s, 3H). LCMS: m/z 535.0[M+H]$^+$, $t_R$=1.64 min.

Synthesis of (E)-3-(6-aminopyridin-3-yl)-N-((5-(5-fluoro-6-(morpholine-4-carbonyl)pyridin-2-yl)-7-(trifluoromethyl)benzofuran-2-yl)methyl)acrylamide (579)

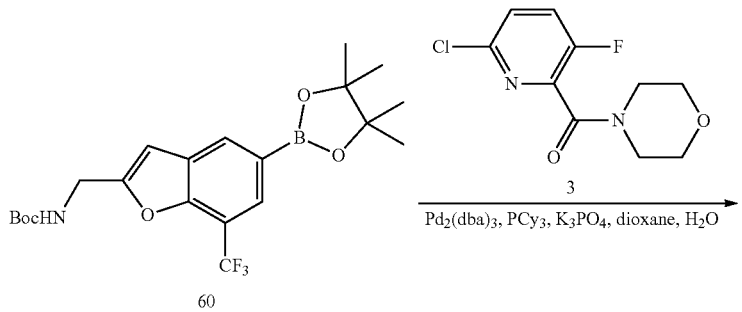

60

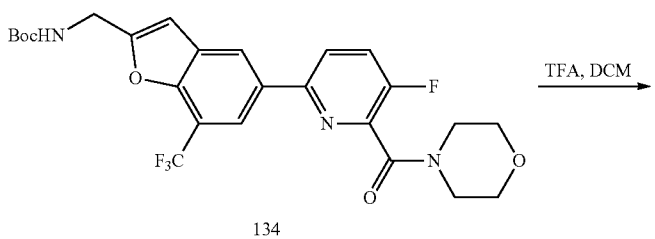

134

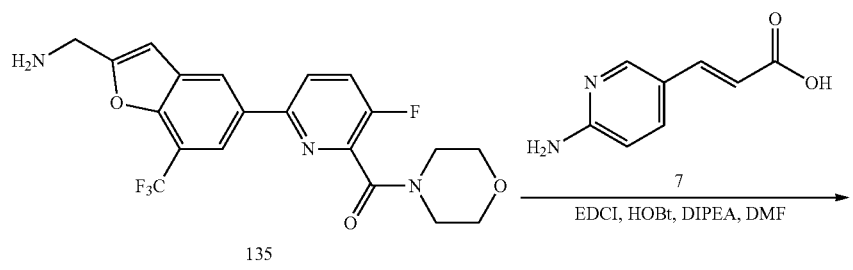

135

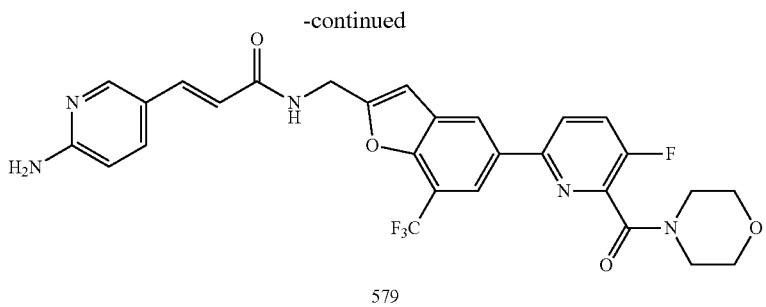

579

Synthesis of tert-butyl (5-(5-fluoro-6-(morpholine-4-carbonyl)pyridin-2-yl)-7-(trifluoromethyl)benzofuran-2-yl)methylcarbamate (134)

(5-(5-fluoro-6-(morpholine-4-carbonyl)pyridin-2-yl)-7-(trifluoromethyl)benzofuran-2-yl)methylcarbamate (134) was synthesized using the indicated reagents according to General Procedure 2. Yield: 68%. LCMS: m/z 524.2 [M+H]$^+$; t$_R$=1.78 min.

Synthesis of (6-(2-(aminomethyl)-7-(trifluoromethyl)benzofuran-5-yl)-3-fluoropyridin-2-yl)(morpholino)methanone (135)

(6-(2-(aminomethyl)-7-(trifluoromethyl)benzofuran-5-yl)-3-fluoropyridin-2-yl)(morpholino)methanone (135) was synthesized using the indicated reagents according to General Procedure 3. Yield: 75%. LCMS: m/z 424.0 [M+H]$^+$; t$_R$=1.22 min.

Synthesis of (E)-3-(6-aminopyridin-3-yl)-N-((5-(5-fluoro-6-(morpholine-4-carbonyl)pyridin-2-yl)-7-(trifluoromethyl)benzofuran-2-yl)methyl)acrylamide (579)

(E)-3-(6-aminopyridin-3-yl)-N-((5-(5-fluoro-6-(morpholine-4-carbonyl)pyridin-2-yl)-7-(trifluoromethyl)benzofuran-2-yl)methyl)acrylamide (579) was synthesized using the indicated reagents according to General Procedure 1. Yield: 38%. $^1$H NMR (400 MHz, DMSO-d$_6$) δ 8.86 (t, J=6 Hz, 1H), 8.61 (s, 1H), 8.34-7.98 (m, 7H), 7.44 (d, J=16 Hz, 1H), 7.02 (s, 1H), 6.94 (d, J=9 Hz, 1H), 6.60 (d, J=16 Hz, 1H), 4.64 (d, J=6 Hz, 2H), 3.75-3.56 (m, 8H). LCMS: m/z 570.2 [M+H]$^+$, t$_R$=1.32 min.

Synthesis of (E)-3-(6-aminopyridin-3-yl)-N-((5-(5-fluoro-4-(morpholine-4-carbonyl)pyridin-2-yl)-7-(trifluoromethyl)benzofuran-2-yl)methyl)acrylamide (580)

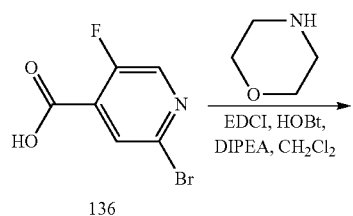

136

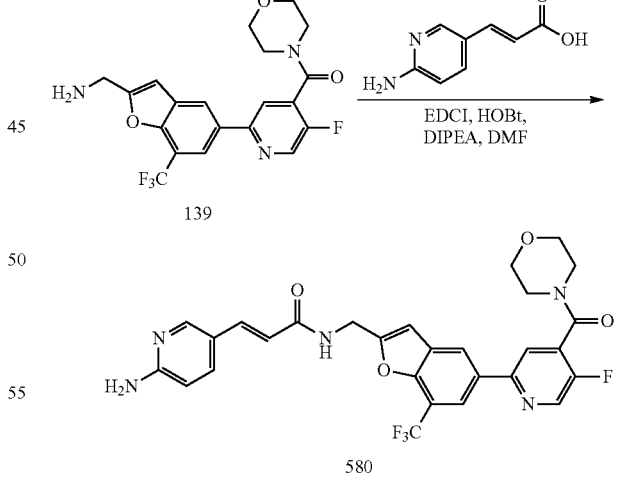

Synthesis of (2-bromo-5-fluoropyridin-4-yl)(morpholino)methanone (137)

2-Bromo-5-fluoroisonicotinic acid (136) (1.0 g, 4.6 mmol) was dissolved in DCM (20 mL) and morpholine (0.4 g, 4.6 mmol) was added at 0° C. EDCI (1.3 g, 6.8 mmol) and HOBt hydrate (0.9 g, 6.8 mmol) were added to this reaction mixture followed by DIPEA (1.2 g, 9.0 mmol) dropwise. The reaction mixture was allowed to warm to room temperature and stirred further for 4 h. The reaction mixture was washed with water (10 mL), brine, dried over Na$_2$SO$_4$, concentrated under reduced pressure to give the crude product, which was purified by silica gel chromatography (15% EtOAc/petroleum ether) to give 1.2 g of (2-bromo-5-fluoropyridin-4-yl)(morpholino)methanone (137). Yield (90%). LCMS: m/z 289.0 [M+H]$^+$, $t_R$=1.50 min Synthesis of tert-butyl (5-(5-fluoro-4-(morpholine-4-carbonyl)pyridin-2-yl)-7-(trifluoromethyl)benzofuran-2-yl)methylcarbamate (138)

A mixture of (2-bromo-5-fluoropyridin-4-yl)(morpholino)methanone (137) (100 mg, 0.34 mmol), tert-butyl (7-(trifluoromethyl)benzofuran-2-yl)methylcarbamate (60) (150 mg, 0.34 mmol), Pd(dppf)Cl$_2$ (25 mg, 0.034 mmol) and K$_2$CO$_3$ (94 mg, 0.68 mmol) in 5 mL of dioxane and 1 mL of H$_2$O was degassed. The reaction mixture was heated at 85° C. under nitrogen atmosphere for 2 h. After cooling down to room temperature, the reaction mixture was poured into iced water (10 mL), extracted with EtOAc (20 mL×3). The combined organic layers were washed with brine, dried over anhydrous Na$_2$SO$_4$, and concentrated under reduced pressure to give the crude product, which was purified by prep-TLC (30% EtOAc/petroleum ether) to give 124 mg of tert-butyl (5-(5-fluoro-4-(morpholine-4-carbonyl)pyridin-2-yl)-7-(trifluoromethyl)benzofuran-2-yl)methylcarbamate (138) as a white solid. Yield (70%). LCMS: m/z 524.2 [M+H]$^+$, $t_R$=1.89 min.

Synthesis of (2-(2-(aminomethyl)-7-(trifluoromethyl)benzofuran-5-yl)-5-fluoropyridin-4-yl)(morpholino)methanone (139)

tert-Butyl (5-(5-fluoro-4-(morpholine-4-carbonyl)pyridin-2-yl)-7-(trifluoromethyl)benzofuran-2-yl)methylcarbamate (138) (90 mg, 0.17 mmol) was dissolved in CH$_2$Cl$_2$ (5 mL). TFA (1 mL) was added at 0° C. (ice bath). The reaction mixture was allowed to warm to room temperature and stirred for 2 h. The reaction mixture was concentrated under reduced pressure to give 75 mg of the crude (2-(2-(aminomethyl)-7-(trifluoromethyl)benzofuran-5-yl)-5-fluoropyridin-4-yl)(morpholino)methanone (139), which was used without further purification in the next step. Yield (100%). LCMS: m/z 424.0 [M+H]$^+$; $t_R$=1.63 min.

Synthesis of (E)-3-(6-aminopyridin-3-yl)-N-((5-(5-fluoro-4-(morpholine-4-carbonyl)pyridin-2-yl)-7-(trifluoromethyl)benzofuran-2-yl)methyl)acrylamide (580)

(2-(2-(Aminomethyl)-7-(trifluoromethyl)benzofuran-5-yl)-5-fluoropyridin-4-yl)(morpholino)methanone (139) (75 mg, 0.17 mmol) was dissolved in DMF (5 mL) and (E)-3-(6-aminopyridin-3-yl)acrylic acid (31 mg, 0.19 mmol) was added at 0° C. (ice bath). EDCI (54 mg, 0.28 mmol) and HOBt hydrate (38 mg, 0.28 mmol) were added to this reaction mixture at 0° C. followed by DIPEA (49 mg, 0.38 mmol) dropwise. The reaction mixture was allowed to warm to room temperature and stirred further for 4 h. The crude mixture was purified by Prep-HPLC without workup to afford 23 mg of (E)-3-(6-aminopyridin-3-yl)-N-((5-(5-fluoro-4-(morpholine-4-carbonyl)pyridin-2-yl)-7-(trifluoromethyl)benzofuran-2-yl)methyl)acrylamide (580). Yield (20%). $^1$H NMR (400 MHz, CD$_3$OD) δ 8.57 (s, 1H), 8.38 (s, 1H), 8.19 (s, 1H), 7.99-7.94 (m, 2H), 7.64 (d, J=9 Hz, 1H), 7.38 (d, J=16 Hz, 1H), 6.83 (s, 1H), 6.50 (d, J=9 Hz, 1H), 6.37 (d, J=16 Hz, 1H), 4.61 (s, 2H), 3.75-3.66 (m, 4H), 3.59-3.55 (m, 2H), 3.34-3.30 (m, 2H). LCMS: m/z 570.2 [M+H]$^+$, $t_R$=1.63 min.

Synthesis of (E)-3-(6-aminopyridin-3-yl)-N-((7-chloro-5-(5-fluoro-6-(morpholine-4-carbonyl)pyridin-2-yl)benzofuran-2-yl)methyl)acrylamide (581)

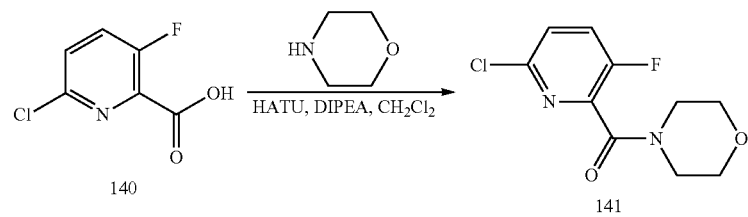

140

141

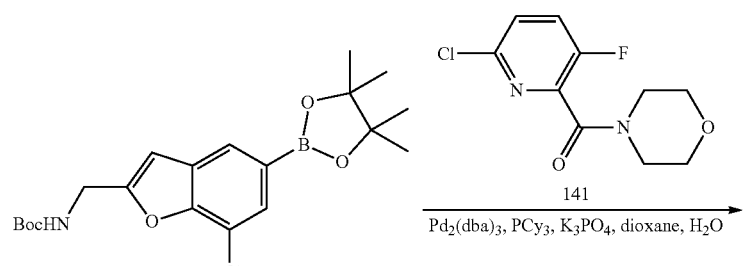

141

-continued

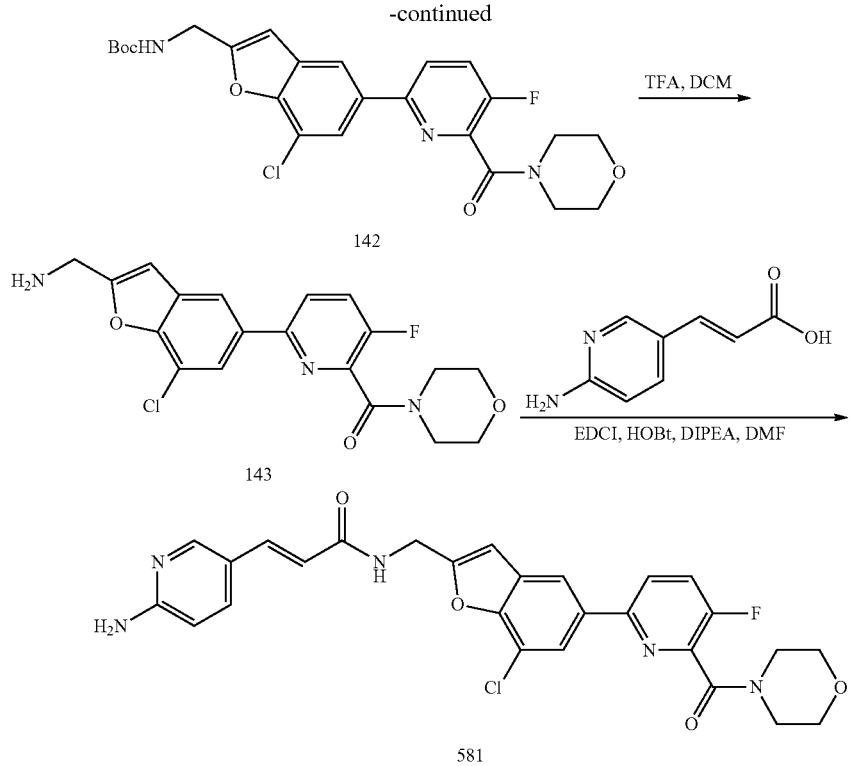

Synthesis of (6-chloro-3-fluoropyridin-2-yl)(morpholino)methanone (141)

6-Chloro-3-fluoropicolinic acid (140) (700 mg, 4.0 mmol) was dissolved in DCM (20 mL). Morpholine (348 mg, 4.0 mmol), HATU (1.5 g, 4.0 mmol) and DIPEA (774 mg, 6.0 mmol) were added at room temperature. The reaction mixture was stirred at room temperature for 16 h. The reaction mixture was washed with water (20 mL), brine, dried over anhydrous $Na_2SO_4$ and concentrated under reduced pressure to give 694 mg of (6-chloro-3-fluoropyridin-2-yl)(morpholino)methanone (141) as white solid, which was used in the next step without further purification. Yield (60%). LCMS: m/z 245.1 [M+H]$^+$; $t_R$=1.56 min.

Synthesis of tert-butyl (7-chloro-5-(5-fluoro-6-(morpholine-4-carbonyl)pyridin-2-yl)benzofuran-2-yl)methylcarbamate (142)

A mixture of tert-butyl (7-chloro-5-(4,4,5,5-tetramethyl-1,3,2-dioxaborolan-2-yl)benzofuran-2-yl)methylcarbamate (43) (322 mg, 0.79 mmol), (6-chloro-3-fluoropyridin-2-yl)(morpholino)methanone (141) (193 mg, 0.79 mmol), $Pd_2(dba)_3$ (56 mg, 0.08 mmol), $PCy_3$ (45 mg, 0.16 mmol) and $K_3PO_4$ (335 mg, 1.58 mmol) in 8 mL of dioxane and 2 mL of $H_2O$ was degassed. The reaction mixture was heated at 100° C. under nitrogen atmosphere for 2 h. After cooling down to room temperature, the reaction mixture was filtered and the filtrate was concentrated under reduced pressure to give the crude product, which was purified by silica gel chromatography (25% EtOAc/petroleum ether) to give 160 mg of tert-butyl (7-chloro-5-(5-fluoro-6-(morpholine-4-carbonyl)pyridin-2-yl)benzofuran-2-yl)methylcarbamate (142) as an oil. Yield (70%). LCMS: m/z 490.2 [M+H]$^+$, $t_R$=1.85 min.

Synthesis of (6-(2-(aminomethyl)-7-chlorobenzofuran-5-yl)-3-fluoropyridin-2-yl)(morpholino)methanone (143)

tert-Butyl (7-chloro-5-(5-fluoro-6-(morpholine-4-carbonyl)pyridin-2-yl)benzofuran-2-yl)methylcarbamate (142) (160 mg, 0.33 mmol) was dissolved in $CH_2Cl_2$ (5 mL). TFA (0.5 mL) was added at 0° C. (ice bath). The reaction mixture was allowed to warm to room temperature and stirred for 2 h. The reaction mixture was concentrated under reduced pressure to give crude (6-(2-(aminomethyl)-7-chlorobenzofuran-5-yl)-3-fluoropyridin-2-yl)(morpholino)methanone (143), which was used without further purification in the next step. Yield (130 mg, 100%). LCMS: m/z 390.0 [M+H]$^+$; $t_R$=1.29 min.

Synthesis of (E)-3-(6-aminopyridin-3-yl)-N-((7-chloro-5-(5-fluoro-6-(morpholine-4-carbonyl)pyridin-2-yl)benzofuran-2-yl)methyl)acrylamide (581)

(6-(2-(Aminomethyl)-7-chlorobenzofuran-5-yl)-3-fluoropyridin-2-yl)(morpholino)methanone (143) (370 mg, 0.95 mmol) was dissolved in DMF (8 mL) and (E)-3-(6-aminopyridin-3-yl)acrylic acid (7; 156 mg, 0.95 mmol) was added at 0° C. (ice bath). EDCI (274 mg, 1.42 mmol) and HOBt hydrate (192 mg, 1.42 mmol) were added to this reaction mixture followed by DIPEA (245 mg, 1.9 mmol) dropwise. The reaction mixture was allowed to warm to room temperature and stirred for 2 h. The reaction mixture was poured into water (30 mL) and extracted with EtOAc (30 mL×3). The combined organic layers were washed with brine, dried over anhydrous $Na_2SO_4$, and concentrated under reduced pressure to give the crude product, which was purified by pre-HPLC to give 33 mg of (E)-3-(6-aminopyridin-3-yl)-N-((7-chloro-5-(5-fluoro-6-(morpholine-4-carbonyl)pyridin-2- yl)benzofuran-2-yl)methyl)acrylamide (581) as white solid. Yield (83%). $^1$H NMR (400 MHz, DMSO-d$_6$) δ 8.84 (t, J=6 Hz, 1H), 8.31-7.94 (m, 8H), 7.43 (d, J=16 Hz, 1H), 6.97 (s, 1H), 6.93 (d, J=9 Hz, 1H), 6.59 (d, J=16 Hz, 1H), 4.63 (d, J=6 Hz, 2H), 3.71 (s, 4H), 3.60-3.56 (m, 2H), 3.35-3.32 (m, 2H). LCMS: m/z 536.2 [M+H]$^+$, t$_R$=1.21 min.

Synthesis of (E)-N-(4-(2-((3-(6-aminopyridin-3-yl)acrylamido)methyl)-7-chlorobenzofuran-5-yl)phenyl)morpholine-4-carboxamide (582)

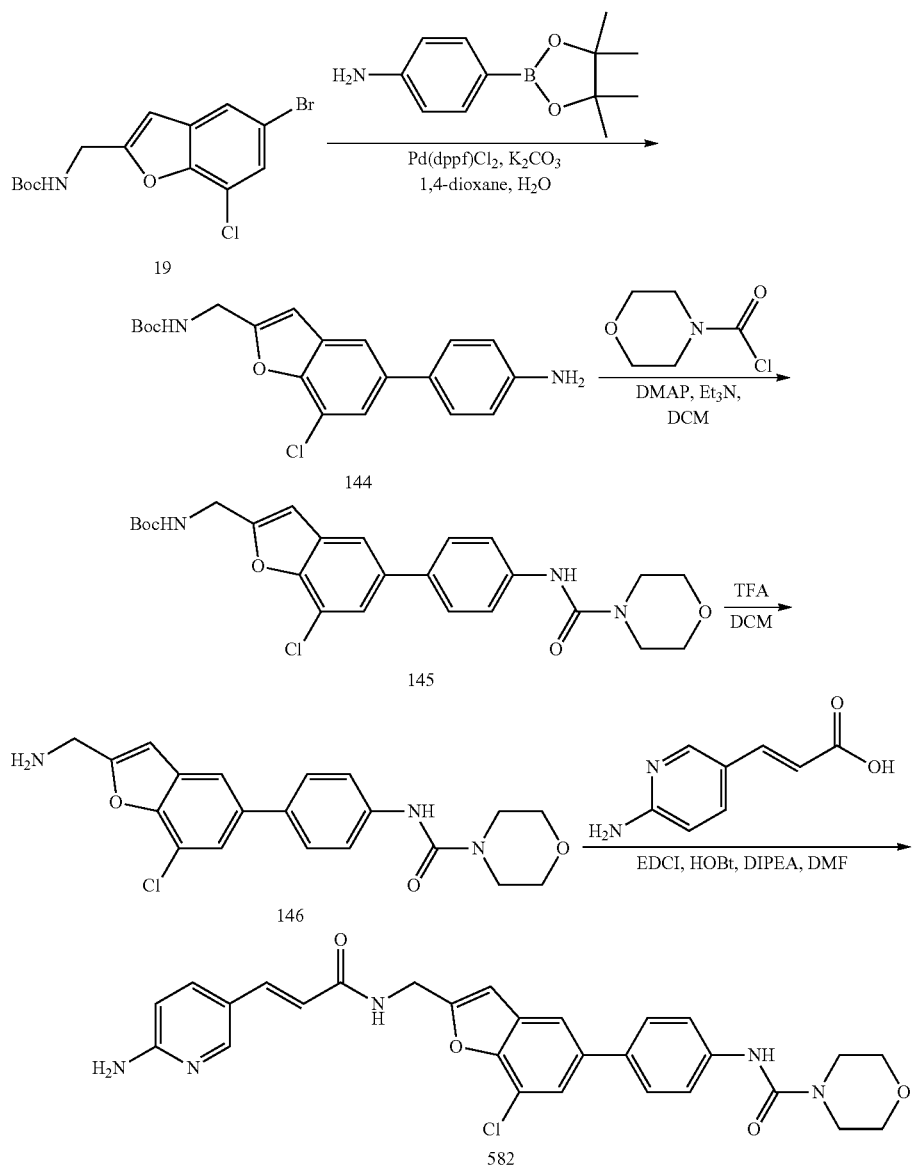

Synthesis of tert-butyl (5-(4-aminophenyl)-7-chlorobenzofuran-2-yl)methylcarbamate (144)

A mixture of tert-butyl (5-bromo-7-chlorobenzofuran-2-yl)methylcarbamate (19) (360 mg, 1 mmol), 4-(4,4,5,5-tetramethyl-1,3,2-dioxaborolan-2-yl)benzenamine (219 mg, 1 mmol), Pd(dppf)Cl$_2$ (82 mg, 0.1 mmol) and K$_2$CO$_3$ (276 mg, 2 mmol) in 10 mL of dioxane and 1 mL of H$_2$O was degassed. The reaction mixture was heated at 100° C. under nitrogen atmosphere for 1 h. After cooling down to room temperature, the mixture was poured into iced water (10 mL), extracted with EtOAc (30 mL×3). The combined organic layers were washed with brine, dried over anhydrous Na$_2$SO$_4$, and concentrated under reduced pressure to give the crude product, which was purified by silica gel chromatography (25% EtOAc/petroleum ether) to give 300 mg of tert-butyl (5-(4-aminophenyl)-7-chlorobenzofuran-2-yl) methylcarbamate (144) as yellow solid. Yield: (81%). LCMS: m/z 373.1 [M+H]$^+$, t$_R$=1.66 min.

Synthesis of tert-butyl (7-chloro-5-(4-(morpholine-4-carboxamido)phenyl)benzofuran-2-yl)methylcarbamate (145)

A mixture of tert-butyl (5-(4-aminophenyl)-7-chlorobenzofuran-2-yl)methylcarbamate (144) (300 mg, 0.8 mmol)

was dissolved in 15 mL of CH$_2$Cl$_2$. Morpholine-4-carbonyl chloride (120 mg, 0.8 mmol), DMAP (98 mg, 0.8 mmol) and Et$_3$N (162 mg, 1.6 mmol) were added at room temperature. The reaction mixture was refluxed for 48 h. After cooling down to room temperature, the reaction mixture was washed with H$_2$O (15 mL), brine, dried over anhydrous Na$_2$SO$_4$ and concentrated under reduced pressure to give the crude product, which was purified by silica gel chromatography (50% EtOAc/petroleum ether) to give 280 mg of tert-butyl (7-chloro-5-(4-(morpholine-4-carboxamido)phenyl)benzofuran-2-yl)methylcarbamate (145) as yellow solid. Yield: (72%). LCMS: m/z 486.2 [M+H]$^+$, t$_R$=2.30 min.

Synthesis of N-(4-(2-(aminomethyl)-7-chlorobenzofuran-5-yl)phenyl)morpholine-4-carboxamide (146)

tert-Butyl (7-chloro-5-(4-(morpholine-4-carboxamido)phenyl)benzofuran-2-yl)methylcarbamate (145) (280 mg, 0.58 mmol) was dissolved in CH$_2$Cl$_2$ (10 mL). TFA (1 mL) was added at 0° C. (ice bath). The reaction mixture was allowed to warm to room temperature and stirred for 1 h. The reaction mixture was concentrated under reduced pressure to give 230 mg of the crude N-(4-(2-(aminomethyl)-7-chlorobenzofuran-5-yl)phenyl)morpholine-4-carboxamide (146), which was used without further purification in the next step. Yield: (100%). LCMS: m/z 386.1 [M+H]$^+$; t$_R$=1.22 min.

Synthesis of (E)-N-(4-(2-((3-(6-aminopyridin-3-yl)acrylamido)methyl)-7-chlorobenzofuran-5-yl)phenyl)morpholine-4-carboxamide (582)

N-(4-(2-(aminomethyl)-7-chlorobenzofuran-5-yl)phenyl)morpholine-4-carboxamide (146) (220 mg, 0.57 mmol) was dissolved in DMF (8 mL) and (E)-3-(6-aminopyridin-3-yl)acrylic acid (94 mg, 0.57 mmol) was added at 0° C. (ice bath). EDCI (163 mg, 0.85 mmol) and HOBt hydrate (115 mg, 0.85 mmol) were added to this reaction mixture followed by DIPEA (147 mg, 1.14 mmol) dropwise. The reaction mixture was allowed to warm to room temperature and stirred for 2 h. The mixture was poured into water (20 mL) and extracted with EtOAc (30 mL×3). The combined organic layers were washed with brine, dried over anhydrous Na$_2$SO$_4$, and concentrated under reduced pressure to give the crude product, which was purified by prep-HPLC to give 53 mg of (E)-N-(4-(2-((3-(6-aminopyridin-3-yl)acrylamido)methyl)-7-chlorobenzofuran-5-yl)phenyl)morpholine-4-carboxamide (582) white solid. Yield: (17%). $^1$H NMR (400 MHz, DMSO-d$_6$) δ 8.85 (t, J=6 Hz, 1H), 8.67 (s, 1H), 8.35-8.06 (m, 4H), 7.81 (s, 1H), 7.67-7.56 (m, 5H), 7.44 (d, J=16 Hz, 1H), 6.99 (d, J=9 Hz, 1H), 6.88 (s, 1H), 6.61 (d, J=16 Hz, 1H), 4.61 (d, J=6 Hz, 2H), 3.67-3.58 (m, 4H), 3.48-3.41 (m, 4H). LCMS: m/z 532.2 [M+H]$^+$, t$_R$=1.23 min.

Synthesis of (E)-3-(6-aminopyridin-3-yl)-N-((7-chloro-5-(5-(morpholine-4-carbonyl)pyrimidin-2-yl)benzofuran-2-yl)methyl)acrylamide (583)

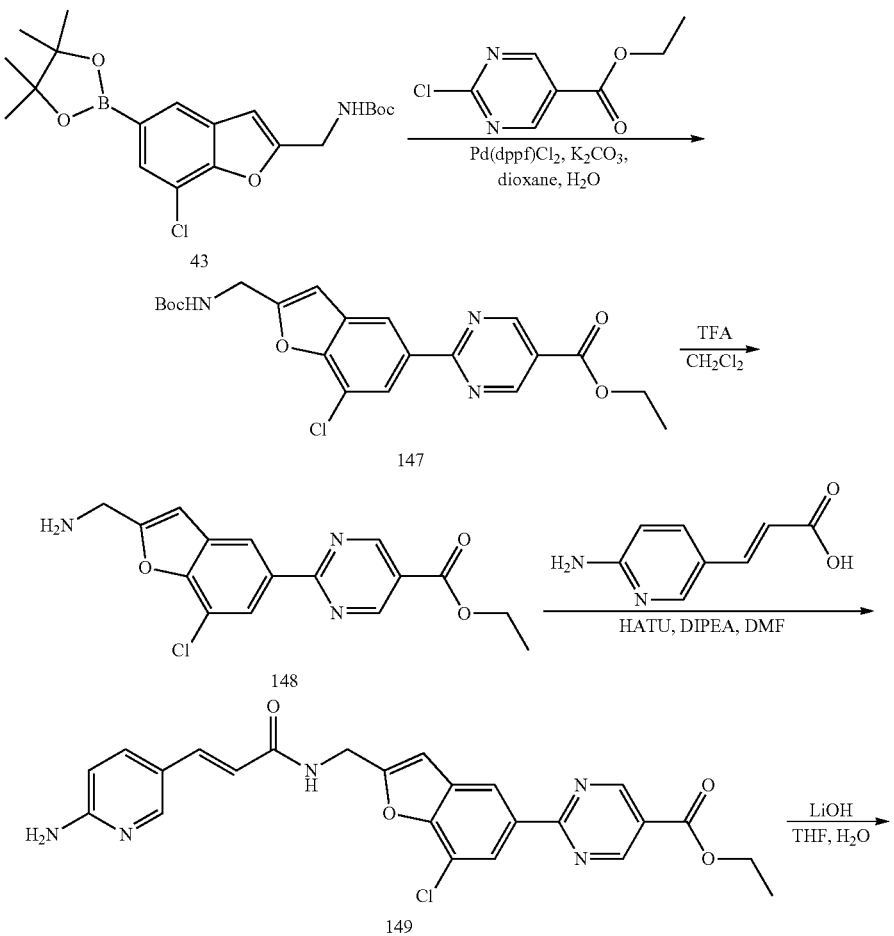

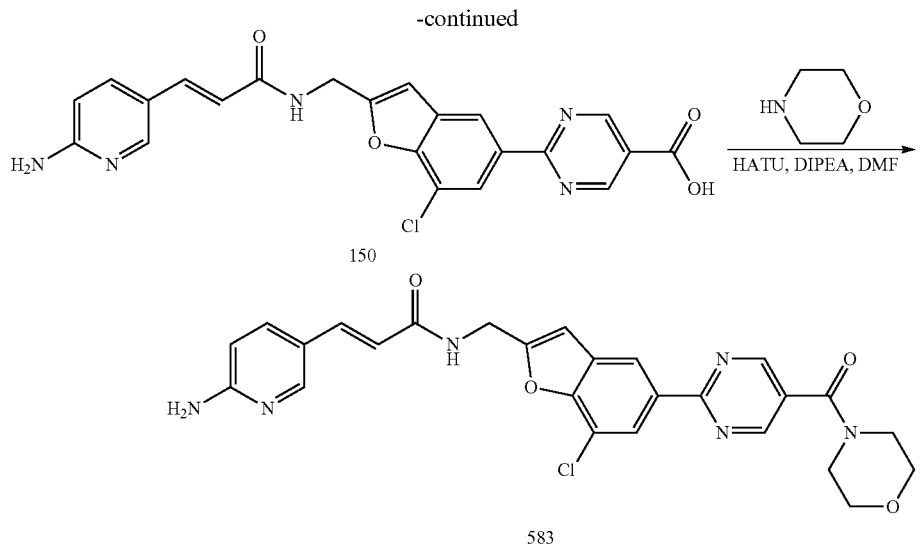

Synthesis of ethyl 2-(2-((tert-butoxycarbonylamino)methyl)-7-chlorobenzofuran-5-yl)pyrimidine-5-carboxylate (147)

tert-Butyl (7-chloro-5-(4,4,5,5-tetramethyl-1,3,2-dioxaborolan-2-yl)benzofuran-2-yl)methylcarbamate (43) (1.2 g, 2.9 mmol), ethyl 2-chloropyrimidine-5-carboxylate (460 mg, 2.5 mmol), Pd(dppf)Cl$_2$ (190 mg, 0.25 mmol) and K$_2$CO$_3$ (680 mg, 4.9 mmol) were added in a mixture of dioxane (10 mL) and H$_2$O (1 mL) and degassed. The reaction mixture was heated at 90° C. under nitrogen atmosphere for 2 h. The reaction mixture was cooled down to room temperature, diluted with iced water (50 mL), extracted with EtOAc (50 mL×3). The combined organic layers were washed with brine, dried over anhydrous Na$_2$SO$_4$, concentrated under reduced pressure to give the crude product, which was purified by silica gel chromatography (20% EtOAc/petroleum ether) to give 370 mg of ethyl 2-(2-((tert-butoxycarbonylamino)methyl)-7-chlorobenzofuran-5-yl)pyrimidine-5-carboxylate (147) as white solid. Yield (35%). LCMS: m/z 432.1 [M+H]$^+$, t$_R$=2.02 min.

Synthesis of ethyl 2-(2-(aminomethyl)-7-chlorobenzofuran-5-yl)pyrimidine-5-carboxylate (148)

Ethyl 2-(2-((tert-butoxycarbonylamino)methyl)-7-chlorobenzofuran-5-yl)pyrimidine-5-carboxylate (147) (370 mg, 0.86 mmol) was dissolved in CH$_2$Cl$_2$ (5 mL). TFA (0.5 mL) was added at 0° C. (ice bath). The reaction mixture was allowed to warm to room temperature and stirred for 1 h. The reaction mixture was concentrated under reduced pressure to give the crude ethyl 2-(2-(aminomethyl)-7-chlorobenzofuran-5-yl)pyrimidine-5-carboxylate (148), which was used without further purification in the next step. Yield (290 mg, 100%). LCMS: m/z 332.0 [M+H]$^+$; t$_R$=1.98 min.

Synthesis of (E)-ethyl 2-(2-((3-(6-aminopyridin-3-yl)acrylamido)methyl)-7-chlorobenzofuran-5-yl)pyrimidine-5-carboxylate (149)

Ethyl 2-(2-(aminomethyl)-7-chlorobenzofuran-5-yl)pyrimidine-5-carboxylate (148) (150 mg, 0.34 mmol) was dissolved in DMF (5 mL) and (E)-3-(6-aminopyridin-3-yl)acrylic acid (55 mg, 0.34 mmol) was added at 0° C. (ice bath). HATU (155 mg, 0.41 mmol) was added followed by DIPEA (87 mg, 0.68 mmol) dropwise. The reaction mixture was allowed to warm to room temperature and stirred for 2 h. The reaction mixture was poured into an iced-water (10 mL), extracted with EtOAc (20 mL×3). The combined organic layers were washed with brine, dried over anhydrous Na$_2$SO$_4$, concentrated under reduced pressure to give the crude product, which was purified by silica gel chromatography (50% EtOAc/petroleum ether) to afford 120 mg of (E)-ethyl 2-(2-((3-(6-aminopyridin-3-yl)acrylamido)methyl)-7-chlorobenzofuran-5-yl)pyrimidine-5-carboxylate (149). Yield (75%). LCMS: m/z 478.2 [M+H]$^+$, t$_R$=1.92 min.

Synthesis of (E)-2-(2-((3-(6-aminopyridin-3-yl)acrylamido)methyl)-7-chlorobenzofuran-5-yl)pyrimidine-5-carboxylic acid (150)

(E)-ethyl 2-(2-((3-(6-aminopyridin-3-yl)acrylamido)methyl)-7-chlorobenzofuran-5-yl)pyrimidine-5-carboxylate (149) (120 mg, 0.25 mmol) was dissolved in THF (4 mL). LiOH (32 mg, 0.75 mmol) and water (1 mL) were added at room temperature. The reaction mixture was stirred at room temperature for 2 h. The reaction mixture was cooled down to 0° C. (ice bath), 2N HCl aqueous solution was added and adjusted to pH=6. The mixture was extracted with EtOAc (20 mL×3). The combined organic layers were washed with brine, dried over anhydrous Na$_2$SO$_4$, concentrated under reduced pressure to afford 100 mg of (E)-2-(2-((3-(6-aminopyridin-3-yl)acrylamido)methyl)-7-chlorobenzofuran-5-yl)pyrimidine-5-carboxylic acid (150). Yield (89%). LCMS: m/z 450.1 [M+H]$^+$, t$_R$=1.28 min.

Synthesis of (E)-3-(6-aminopyridin-3-yl)-N-((7-chloro-5-(5-(morpholine-4-carbonyl)pyrimidin-2-yl)benzofuran-2-yl)methyl)acrylamide (583)

(E)-2-(2-((3-(6-aminopyridin-3-yl)acrylamido)methyl)-7-chlorobenzofuran-5-yl)pyrimidine-5-carboxylic acid (150) (50 mg, 0.11 mmol) was dissolved in DMF (3 mL). Morpholine (10 mg, 0.11 mmol), HATU (84 mg, 0.22 mmol) and DIPEA (28 mg, 0.22 mmol) were added at room temperature. The reaction mixture was stirred at room temperature further for 2 h. 15 mL of EtOAc and 10 mL of H₂O were added. The organic phase was separated and the aqueous phase was extracted with EtOAc (15 mL×2). The combined organic phases were washed with brine (10 mL), dried over anhydrous Na₂SO₄, concentrated and purified by Prep-HPLC to afford 15 mg of (E)-3-(6-aminopyridin-3-yl)-N-((7-chloro-5-(5-(morpholine-4-carbonyl)pyrimidin-2-yl)benzofuran-2-yl)methyl)acrylamide (583). Yield (26%). ¹H NMR (400 MHz, DMSO-d₆) δ 9.02-8.97 (m, 2H), 8.65 (t, J=4 Hz, 2H), 8.39 (d, J=2 Hz, 1H), 8.08 (d, J=2 Hz, 1H), 7.64-7.59 (m, 1H), 7.36 (d, J=16 Hz, 1H), 7.01 (s, 1H), 6.50-6.39 (m, 4H), 4.61 (d, J=6 Hz, 2H), 3.73-3.43 (m, 8H). LCMS: m/z 519.2 [M+H]⁺, $t_R$=1.62 min.

Synthesis of (E)-3-(6-aminopyridin-3-yl)-N-((7-chloro-5-(5-(4-methylpiperazine-1-carbonyl)pyridin-2-yl)benzofuran-2-yl)methyl)acrylamide (584)

Synthesis of (6-bromopyridin-3-yl)(4-methylpiperazin-1-yl)methanone (152)

6-Bromonicotinic acid (151) (500 mg, 2.5 mmol) was dissolved in CH₂Cl₂ (15 mL) and 1-methylpiperazine (274 mg, 2.7 mmol) was added at 0° C. EDCI (573 mg, 3 mmol) and HOBt (402 mg, 3 mmol) were added to this reaction mixture at 0° C. followed by DIPEA (642 mg, 5 mmol) dropwise. The reaction mixture was allowed to warm to room temperature and stirred for 2 h. The reaction mixture was transferred into water (20 mL) and extracted with CH₂Cl₂ (30 mL×3). The combined organic layers were washed with brine, dried over anhydrous Na₂SO₄ and concentrated under reduced pressure to give (6-bromopyridin-3-yl)(4-methylpiperazin-1-yl)methanone (152). Yield (400 mg, 52%). LCMS: m/z 285.1 M+H]⁺; $t_R$=1.35 min.

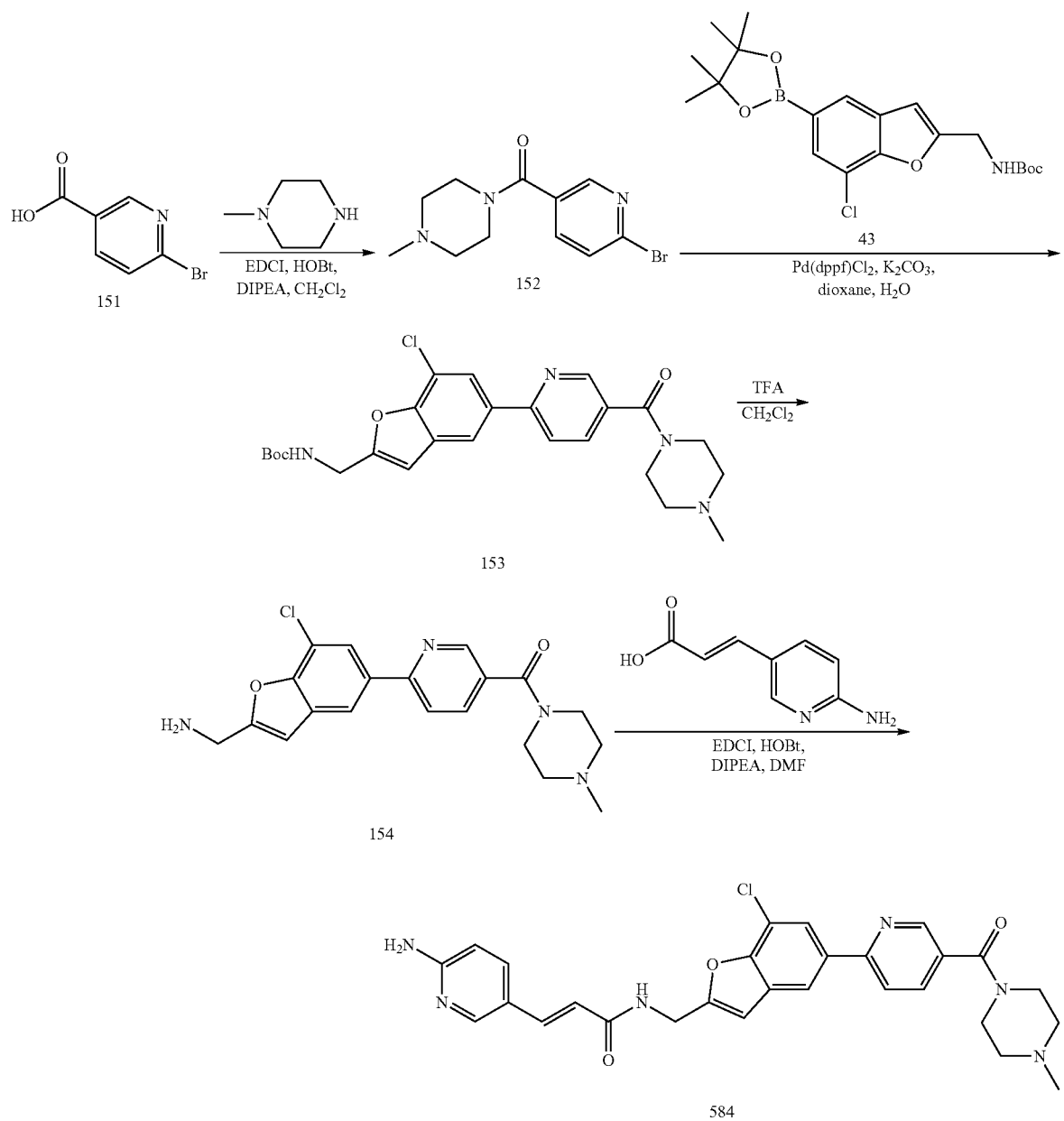

Synthesis of tert-butyl (7-chloro-5-(5-(4-methylpiperazine-1-carbonyl)pyridin-2-yl)benzofuran-2-yl)methylcarbamate (153)

tert-Butyl (7-chloro-5-(5-(4-methylpiperazine-1-carbonyl)pyridin-2-yl)benzofuran-2-yl)methylcarbamate (153) was synthesized using the indicated reagents according to General Procedure 2. Yield (47%). LCMS: m/z 485.2 [M+H]$^+$; t$_R$=1.26 min.

Synthesis of (6-(2-(aminomethyl)-7-chlorobenzofuran-5-yl)pyridin-3-yl)(4-methylpiperazin-1-yl)methanone (154)

(6-(2-(aminomethyl)-7-chlorobenzofuran-5-yl)pyridin-3-yl)(4-methylpiperazin-1-yl)methanone (154) was synthesized using the indicated reagents according to General Procedure 3. Yield (100%). LCMS: m/z 385.1 [M+H]$^+$; t$_R$=1.45 min.

Synthesis of (E)-3-(6-aminopyridin-3-yl)-N-((7-chloro-5-(5-(4-methylpiperazine-1-carbonyl)pyridin-2-yl)benzofuran-2-yl)methyl)acrylamide (584)

(E)-3-(6-Aminopyridin-3-yl)-N-((7-chloro-5-(5-(4-methylpiperazine-1-carbonyl)pyridin-2-yl)benzofuran-2-yl)methyl)acrylamide (584) was synthesized using the indicated reagents according to General Procedure 1. Yield (52%). $^1$H NMR (400 MHz, DMSO-d$_6$) δ 8.72-8.64 (m, 2H), 8.35 (s, 1H), 8.19-8.07 (m, 3H), 7.97-7.90 (m, 1H), 7.66-7.60 (m, 1H), 7.36 (d, J=16 Hz, 1H), 6.95 (s, 1H), 6.51-6.39 (m, 4H), 4.60 (d, J=6 Hz, 2H), 3.64 (s, 4H), 2.41-2.29 (m, 4H), 2.20 (s, 3H). LCMS: m/z 531.2 [M+H]$^+$, t$_R$=1.05 min

Synthesis of (E)-3-(6-aminopyridin-3-yl)-N-((5-(5-(4,4-difluoropiperidine-1-carbonyl)pyridin-2-yl)-7-(trifluoromethyl)benzofuran-2-yl)methyl)acrylamide (585)

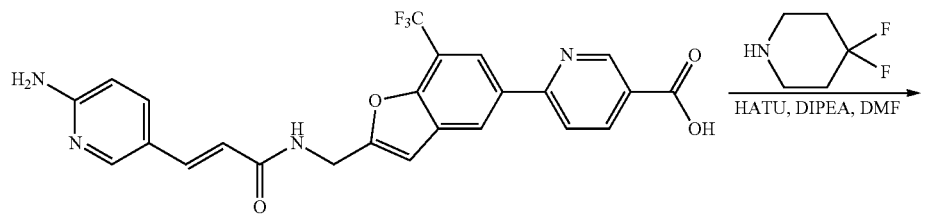

123

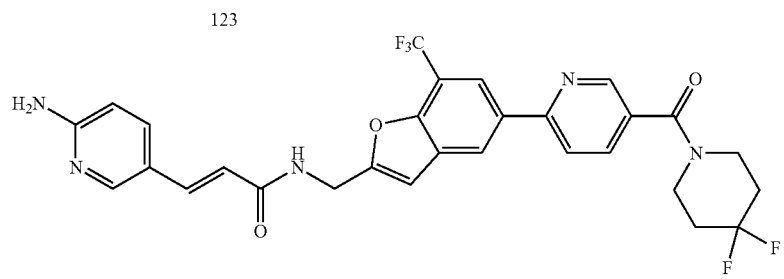

585

(E)-3-(6-aminopyridin-3-yl)-N-((5-(5-(4,4-difluoropiperidine-1-carbonyl)pyridin-2-yl)-7-(trifluoromethyl)benzofuran-2-yl)methyl)acrylamide (585) was synthesized using the indicated reagents according to General Procedure 4. Yield (28%). $^1$H NMR (400 MHz, CD$_3$OD) δ 8.78 (s, 1H), 8.53 (s, 1H), 8.34 (s, 1H), 8.10-8.00 (m, 3H), 7.77-7.74 (m, 1H), 7.50 (d, J=16 Hz, 1H), 6.96 (s, 1H), 6.61 (d, J=9 Hz, 1H), 6.49 (d, J=16 Hz, 1H), 4.73 (s, 2H), 3.91-3.65 (m, 4H), 2.17-2.03 (m, 4H). LCMS: m/z 586.2 [M+H]$^+$; t$_R$=1.81 min.

Synthesis of (E)-3-(6-aminopyridin-3-yl)-N-((7-chloro-5-(5-(piperazine-1-carbonyl)pyrimidin-2-yl)benzofuran-2-yl)methyl)acrylamide (586)

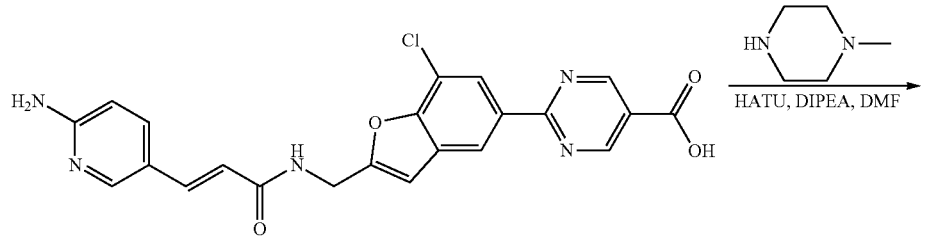

150

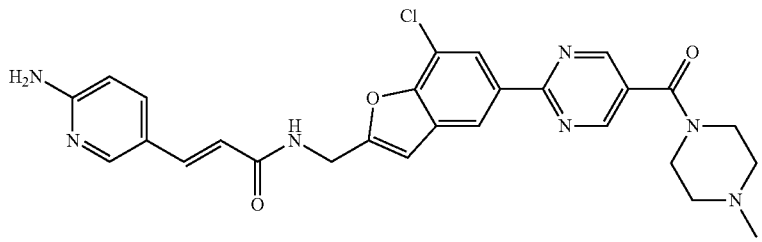

586

(E)-3-(6-Aminopyridin-3-yl)-N-((7-chloro-5-(5-(piperazine-1-carbonyl)pyrimidin-2-yl)benzofuran-2-yl)methyl)acrylamide (586) was synthesized using the indicated reagents according to General Procedure 4. Yield: 17%. $^1$H NMR (400 MHz, DMSO-d$_6$) δ 8.97 (s, 2H), 8.66 (s, 2H), 8.39 (s, 1H), 8.09 (s, 1H), 7.62 (d, J=8 Hz, 1H), 7.36 (d, J=16 Hz, 1H), 7.01 (s, 1H), 6.52-6.38 (m, 4H), 4.61 (d, J=5 Hz, 2H), 3.70-3.60 (m, 2H), 3.49-3.42 (m, 2H), 2.42-2.29 (m, 4H), 2.21 (s, 3H). LCMS: m/z 532.3 [M+H]$^+$, t$_R$=1.61 min.

Synthesis of (E)-3-(6-aminopyridin-3-yl)-N-((5-(4-(3-fluoro-3-methylazetidine-1-carbonyl)phenyl)-7-(trifluoromethyl)benzofuran-2-yl)methyl)acrylamide (587)

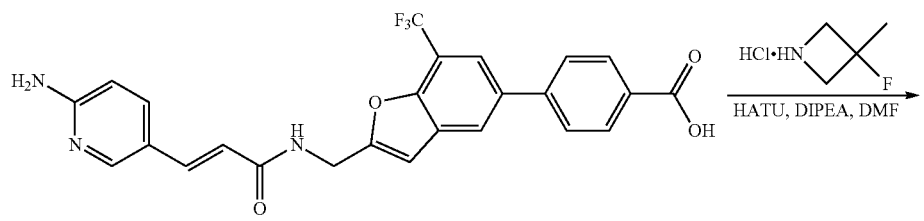

59

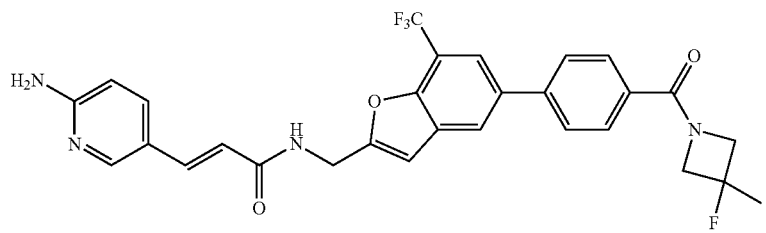

587

(E)-3-(6-Aminopyridin-3-yl)-N-((5-(4-(3-fluoro-3-methylazetidine-1-carbonyl)phenyl)-7-(trifluoromethyl)benzofuran-2-yl)methyl)acrylamide (587) was synthesized using the indicated reagents according to General procedure 4. Yield (18%). $^1$H NMR (400 MHz, DMSO-$d_6$) δ 8.67 (t, J=6 Hz, 1H), 8.26 (s, 1H), 8.08 (s, 1H), 7.91-7.75 (m, 5H), 7.66-7.61 (m, 1H), 7.36 (d, J=16 Hz, 1H), 6.95 (s, 1H), 6.51-6.39 (m, 4H), 4.62 (d, J=6 Hz, 2H), 4.57-4.07 (m, 4H), 1.61 (d, J=22 Hz, 3H). LCMS: m/z 553.2 [M+H]$^+$, $t_R$=1.39 min.

Synthesis of (E)-3-(6-aminopyridin-3-yl)-N-((7-chloro-5-(5-fluoro-4-(morpholine-4-carbonyl)pyridin-2-yl)benzofuran-2-yl)methyl)acrylamide (588)

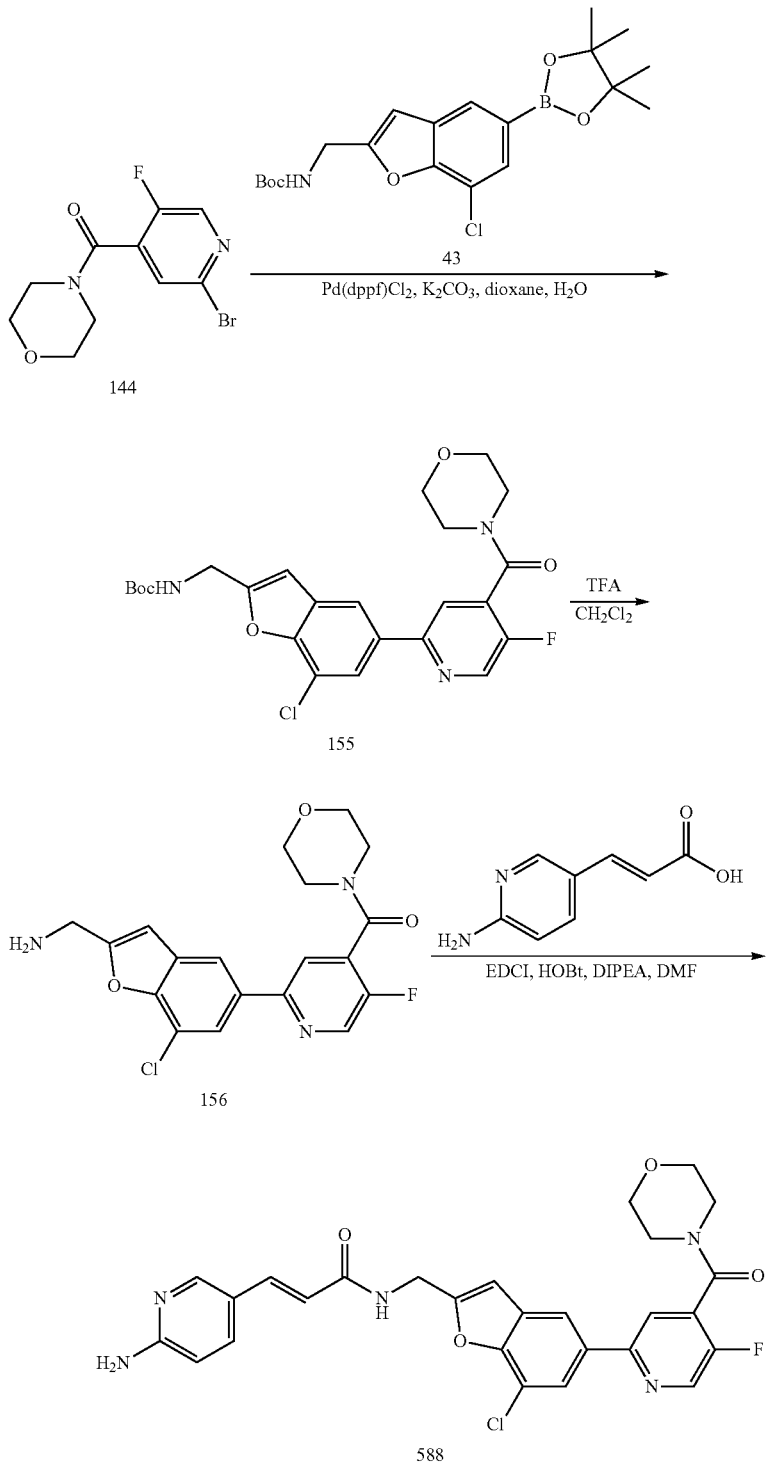

249

Synthesis of tert-butyl (7-chloro-5-(5-fluoro-4-(morpholine-4-carbonyl)pyridin-2-yl)benzofuran-2-yl)methylcarbamate (155)

tert-Butyl (7-chloro-5-(5-fluoro-4-(morpholine-4-carbonyl)pyridin-2-yl)benzofuran-2-yl)methylcarbamate (155) was synthesized using the indicated reagents according to General Procedure 2. Yield: 44%. LCMS: m/z 490.2 [M+H]$^+$, t$_R$=1.85 min.

Synthesis of (2-(2-(aminomethyl)-7-chlorobenzofuran-5-yl)-5-fluoropyridin-4-yl)(morpholino)methanone (156)

(2-(2-(Aminomethyl)-7-chlorobenzofuran-5-yl)-5-fluoropyridin-4-yl)(morpholino)methanone (156) was synthesized using the indicated reagents according to General Procedure 3. Yield: 100%. LCMS: m/z 390.1 [M+H]$^+$; t$_R$=1.30 min.

250

Synthesis of (E)-3-(6-aminopyridin-3-yl)-N-((7-chloro-5-(5-fluoro-4-(morpholine-4-carbonyl)pyridin-2-yl)benzofuran-2-yl)methyl)acrylamide (588)

(E)-3-(6-Aminopyridin-3-yl)-N-((7-chloro-5-(5-fluoro-4-(morpholine-4-carbonyl)pyridin-2-yl)benzofuran-2-yl)methyl)acrylamide (588) was synthesized using the indicated reagents according to General Procedure 1. Yield: 23%. $^1$H NMR (400 MHz, DMSO-d$_6$) δ 8.86 (t, J=6 Hz, 1H), 8.77 (s, 1H), 8.37-8.06 (m, 7H), 7.44 (d, J=16 Hz, 1H), 6.98 (d, J=9 Hz, 1H), 6.95 (s, 1H), 6.61 (d, J=16 Hz, 1H), 4.63 (d, J=6 Hz, 2H), 3.78-3.48 (m, 8H). LCMS: m/z 536.1 [M+H]$^+$, t$_R$=1.28 min.

Synthesis of (E)-3-(6-aminopyridin-3-yl)-N-((7-chloro-5-(5-(piperazine-1-carbonyl)pyridin-2-yl)benzofuran-2-yl)methyl)acrylamide (589)

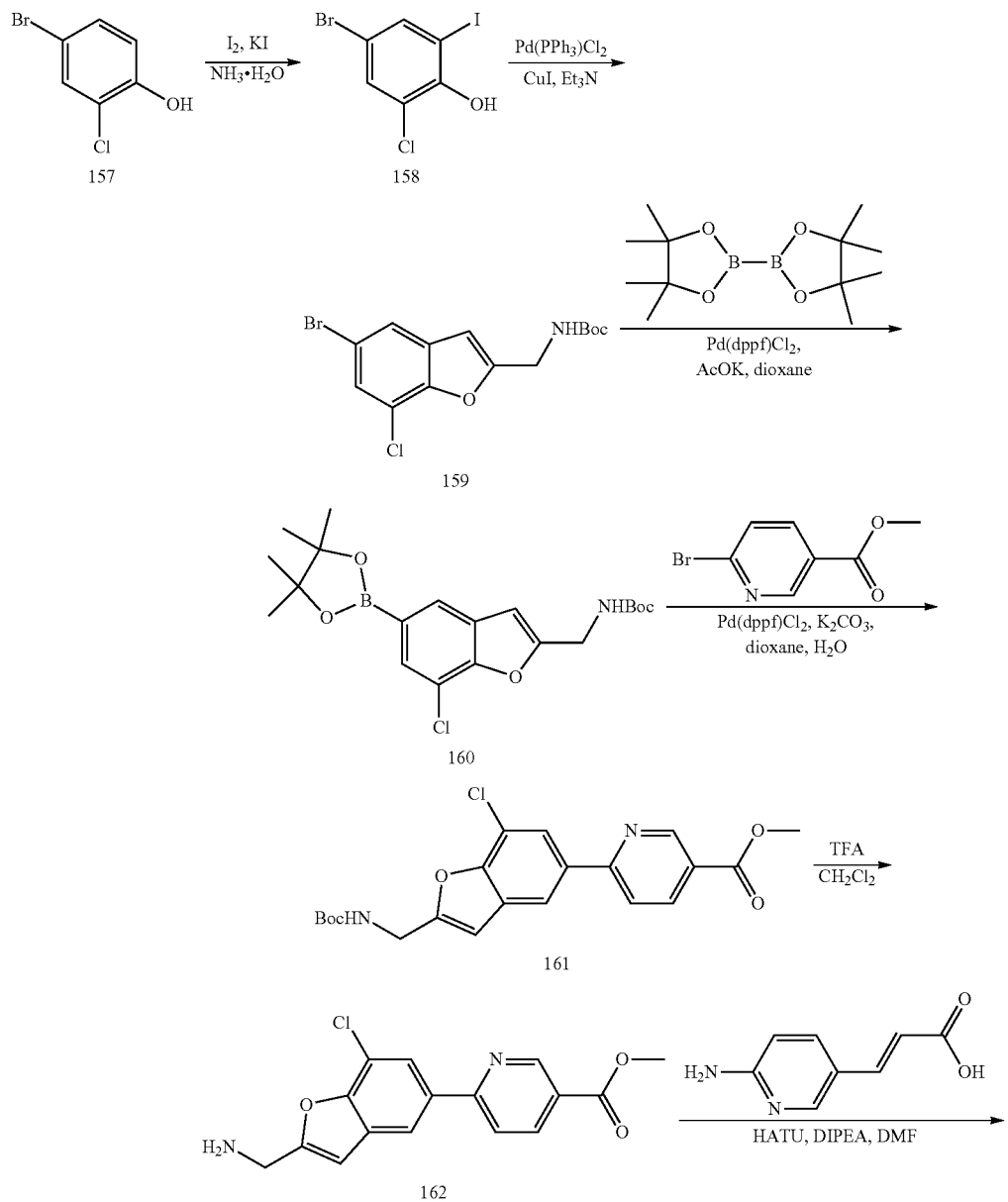

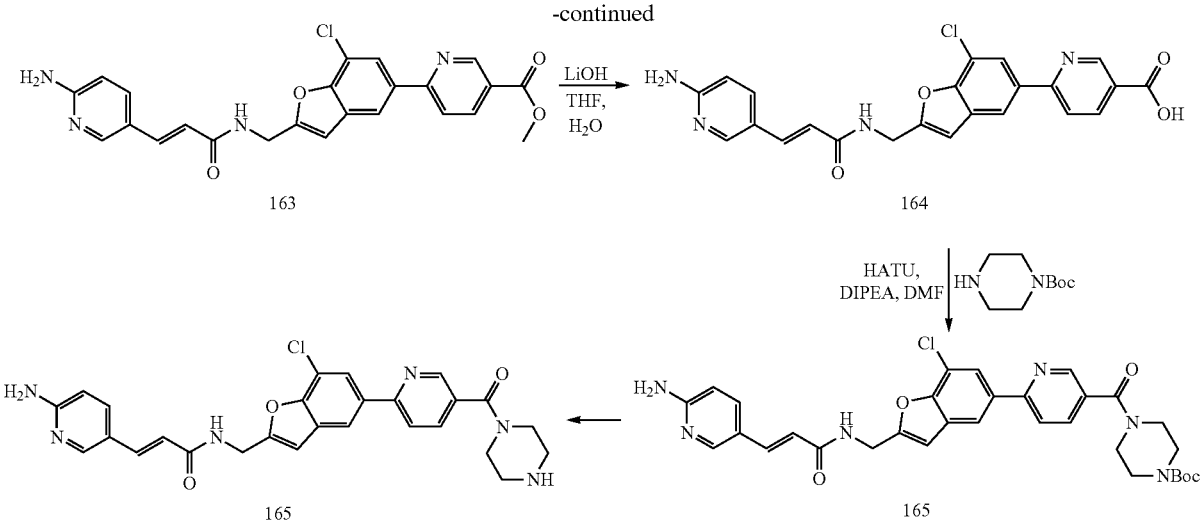

Synthesis of 4-Bromo-2-chloro-6-iodophenol (158)

4-Bromo-2-chloro-6-iodophenol (158) was synthesized using the indicated reagents similar procedure of intermediate (18). Yield (63%).

Synthesis of tert-Butyl (5-bromo-7-chlorobenzofuran-2-yl)methylcarbamate (159)

tert-Butyl (5-bromo-7-chlorobenzofuran-2-yl)methylcarbamate (159) was synthesized using similar procedure of intermediate (19). Yield (75%). LCMS: m/z 306.0 [M-55]$^+$; $t_R$=2.07 min.

Synthesis of tert-Butyl (7-chloro-5-(4,4,5,5-tetramethyl-1,3,2-dioxaborolan-2-yl)benzofuran-2-yl)methylcarbamate (160)

tert-Butyl (7-chloro-5-(4,4,5,5-tetramethyl-1,3,2-dioxaborolan-2-yl)benzofuran-2-yl)methylcarbamate (160) was synthesized using the indicated reagents similar procedure of intermediate (20). Yield (92%). LCMS: m/z 352.1 [M-55]$^+$; $t_R$=2.15 min.

Synthesis of methyl 6-(2-((tert-butoxycarbonylamino)methyl)-7-chlorobenzofuran-5-yl)nicotinate (161)

Methyl 6-(2-((tert-butoxycarbonylamino)methyl)-7-chlorobenzofuran-5-yl)nicotinate (161) was synthesized using the indicated reagents according to General Procedure 2. Yield (96%). LCMS: m/z 417.1 [M+H]$^+$; $t_R$=2.16 min.

Synthesis of methyl 6-(2-(aminomethyl)-7-chlorobenzofuran-5-yl)nicotinate (162)

Methyl 6-(2-(aminomethyl)-7-chlorobenzofuran-5-yl)nicotinate (162) was synthesized using the indicated reagents according to General Procedure 3. Yield (100%). LCMS: m/z 317.1 [M+H]$^+$; $t_R$=1.83 min.

Synthesis of (E)-methyl 6-(2-((3-(6-aminopyridin-3-yl)acrylamido)methyl)-7-chlorobenzofuran-5-yl) nicotinate (163)

(E)-methyl 6-(2-((3-(6-aminopyridin-3-yl)acrylamido)methyl)-7-chlorobenzofuran-5-yl)nicotinate (163) was synthesized using the indicated reagents according to General Procedure 4. Yield (89%). LCMS: m/z 463.1 [M+H]$^+$; $t_R$=1.81 min.

Synthesis of (E)-6-(2-((3-(6-aminopyridin-3-yl)acrylamido)methyl)-7-chlorobenzofuran-5-yl)nicotinic acid (164)

(E)-6-(2-((3-(6-Aminopyridin-3-yl)acrylamido)methyl)-7-chlorobenzofuran-5-yl)nicotinic acid (164) was synthesized using the indicated reagents according to similar procedure of intermediate (55). Yield (78%). LCMS: m/z 449.1 [M+H]$^+$; $t_R$=1.25 min.

Synthesis of (E)-tert-butyl 4-(6-(2-((3-(6-aminopyridin-3-yl)acrylamido)methyl)-7-chlorobenzofuran-5-yl)nicotinoyl)piperazine-1-carboxylate (165)

(E)-tert-Butyl 4-(6-(2-((3-(6-aminopyridin-3-yl)acrylamido)methyl)-7-chlorobenzofuran-5-yl)nicotinoyl)piperazine-1-carboxylate (165) was synthesized using the indicated reagents according to General Procedure 4. Yield (37%). LCMS: m/z 617.2 [M+H]$^+$; $t_R$=1.70 min Synthesis of (E)-3-(6-aminopyridin-3-yl)-N-((7-chloro-5-(5-(piperazine-1-carbonyl)pyridin-2-yl) benzofuran-2-yl)methyl)acrylamide (589)

(E)-3-(6-aminopyridin-3-yl)-N-((7-chloro-5-(5-(piperazine-1-carbonyl)pyridin-2-yl)benzofuran-2-yl)methyl)acrylamide (589) was synthesized using the indicated reagents according to General Procedure 3. Yield (61%). $^1$H NMR (400 MHz, DMSO-d$_6$) δ 8.68-8.62 (m, 2H), 8.36 (s, 1H), 8.17-8.08 (m, 4H), 7.93-7.91 (m, 1H), 7.63-7.60 (m, 1H), 7.35 (d, J=16 Hz, 1H), 6.95 (s, 1H), 6.49-6.40 (m, 4H), 4.60 (d, J=6 Hz, 2H), 3.58-3.56 (m, 2H), 2.76-2.65 (m, 6H). LCMS: m/z 517.2 [M+H]$^+$; $t_R$=1.50 min.

Synthesis of (E)-3-(6-aminopyridin-3-yl)-N-((5-(5-(piperazine-1-carbonyl)pyrimidin-2-yl)-7-(trifluoromethyl)benzofuran-2-yl)methyl)acrylamide (590)
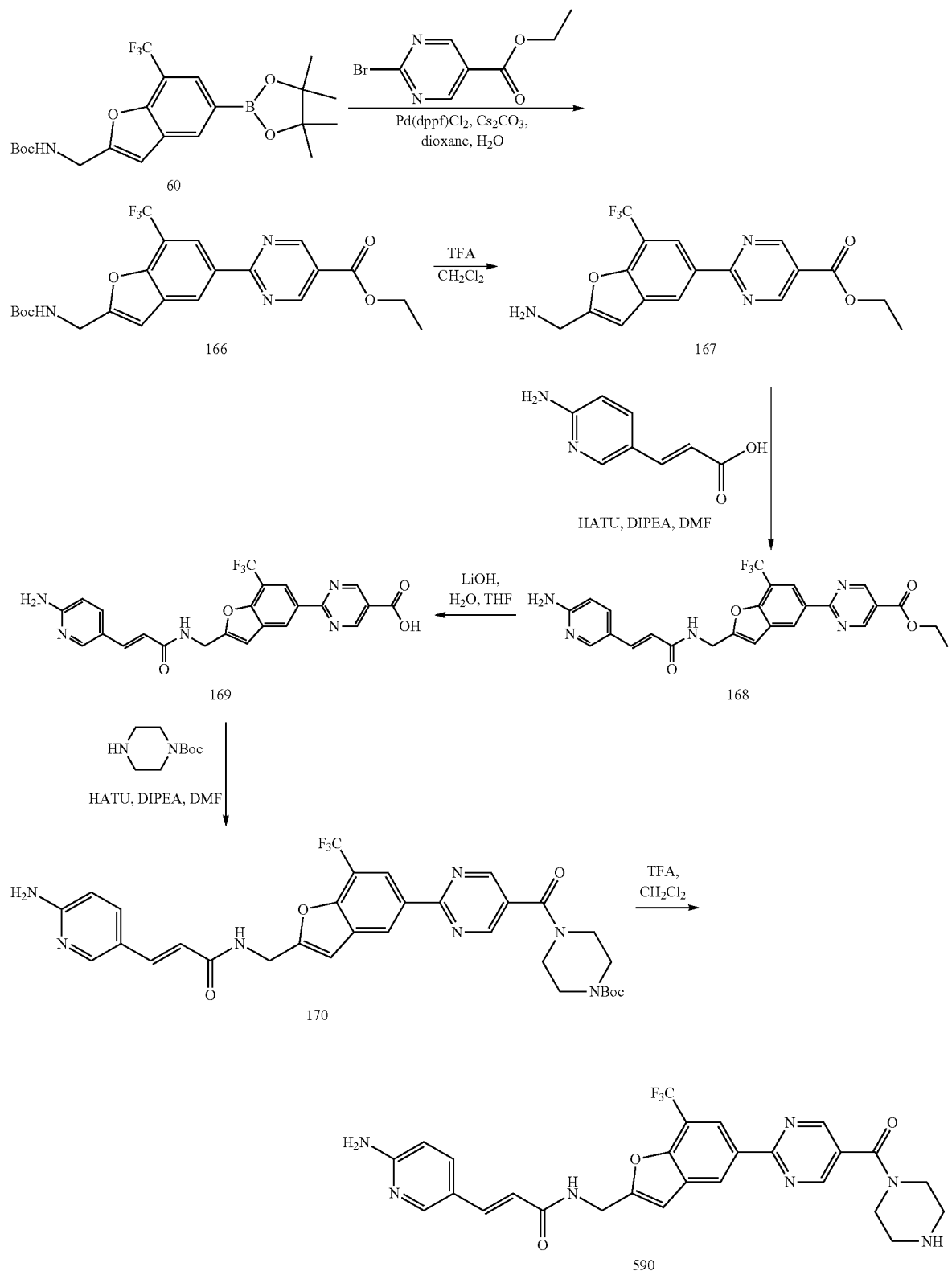

Synthesis of ethyl 2-(2-((tert-butoxycarbonylamino)methyl)-7-(trifluoromethyl)benzofuran-5-yl)pyrimidine-5-carboxylate (166)

tert-Butyl (5-(4,4,5,5-tetramethyl-1,3,2-dioxaborolan-2-yl)-7-(trifluoromethyl)benzofuran-2-yl)methylcarbamate (60) (3.0 g, 6.8 mmol), ethyl 2-chloropyrimidine-5-carboxylate (1.5 g, 38.2 mmol), Pd(dppf)Cl$_2$ (450 mg, 0.6 mmol) and Cs$_2$CO$_3$ (4.4 g, 13.6 mmol) were added in a mixture of dioxane (50 mL) and H$_2$O (5 mL) and degassed. The reaction mixture was heated at 90° C. under nitrogen atmosphere for 2 h. The reaction mixture was cooled down to room temperature, diluted with iced water (50 mL), extracted with EtOAc (50 mL×3). The combined organic layers were washed with brine, dried over anhydrous Na$_2$SO$_4$, concentrated under reduced pressure to give the crude product, which was purified by silica gel chromatography (20% EtOAc/petroleum ether) to give 2.8 g of ethyl 2-(2-((tert-butoxy carbonylamino)methyl)-7-(trifluoromethyl)benzofuran-5-yl)pyrimidine-5-carboxylate (166) as yellow solid. Yield (81%). LCMS: m/z 466.2 [M+H]$^+$, t$_R$=1.97 min.

Synthesis of ethyl 2-(2-(aminomethyl)-7-(trifluoromethyl)benzofuran-5-yl)pyrimidine-5-carboxylate (167)

Ethyl 2-(2-((tert-butoxycarbonylamino)methyl)-7-(trifluoromethyl)benzofuran-5-yl)pyrimidine-5-carboxylate (166) (0.75 g, 1.6 mmol) was dissolved in CH$_2$Cl$_2$ (20 mL). TFA (5 mL) was added at 0° C. (ice bath). The reaction mixture was allowed to warm to room temperature and stirred for 1 h. The reaction mixture was concentrated under reduced pressure to give the crude ethyl 2-(2-(aminomethyl)-7-(trifluoromethyl)benzofuran-5-yl)pyrimidine-5-carboxylate (167), which was used without further purification in the next step Yield (0.6 g, 100%). LCMS: m/z 366.1 [M+H]$^+$; t$_R$=1.31 min.

Synthesis of (E)-ethyl 2-(2-((3-(6-aminopyridin-3-yl)acrylamido)methyl)-7-(trifluoromethyl)benzofuran-5-yl)pyrimidine-5-carboxylate (168)

Ethyl 2-(2-(aminomethyl)-7-(trifluoromethyl)benzofuran-5-yl)pyrimidine-5-carboxylate (167) (0.6 g, 1.6 mmol) was dissolved in DMF (15 mL) and (E)-3-(6-aminopyridin-3-yl)acrylic acid (0.3 g, 1.8 mmol) was added at 0° C. (ice bath). HATU (0.71 g, 1.8 mmol) was added followed by DIPEA (0.4 g, 3.1 mmol) dropwise. The reaction mixture was allowed to warm to room temperature and stirred for 2 h. The reaction mixture was poured into an iced-water (50 mL), extracted with EtOAc (50 mL×3). The combined organic layers were washed with brine, dried over anhydrous Na$_2$SO$_4$, concentrated under reduced pressure to give the crude product, which was purified by silica gel chromatography (50% EtOAc/petroleum ether) to afford 700 mg of (E)-ethyl 2-(2-((3-(6-aminopyridin-3-yl)acrylamido)methyl)-7-(trifluoromethyl)benzofuran-5-yl)pyrimidine-5-carboxylate (168). Yield (88%). LCMS: m/z 512.2 [M+H]$^+$, t$_R$=1.36 min.

Synthesis of (E)-2-(2-((3-(6-aminopyridin-3-yl)acrylamido)methyl)-7-(trifluoromethyl)benzofuran-5-yl)pyrimidine-5-carboxylic acid (169)

(E)-ethyl 2-(2-((3-(6-aminopyridin-3-yl)acrylamido)methyl)-7-(trifluoromethyl)benzofuran-5-yl)pyrimidine-5-carboxylate (168) (630 mg, 1.2 mmol) was dissolved in THF (10 mL). LiOH (150 mg, 3 mmol) and water (2.5 mL) were added at room temperature. The reaction mixture was stirred at room temperature for 2 h. The reaction mixture was cooled down to 0° C. (ice bath), 2N HCl solution was added and adjusted to pH=6. The mixture was extracted with EtOAc (20 mL×3). The combined organic layers were washed with brine, dried over anhydrous Na$_2$SO$_4$, concentrated under reduced pressure to afford 550 mg of (E)-2-(2-((3-(6-aminopyridin-3-yl)acrylamido)methyl)-7-(trifluoromethyl)benzofuran-5-yl)pyrimidine-5-carboxylic acid (169). Yield (92%). LCMS: m/z 484.1 [M+H]$^+$, t$_R$=1.22 min.

Synthesis of (E)-tert-butyl 4-(2-(2-((3-(6-aminopyridin-3-yl)acrylamido)methyl)-7-(trifluoromethyl)benzofuran-5-yl)pyrimidine-5-carbonyl)piperazine-1-carboxylate (170)

(E)-2-(2-((3-(6-aminopyridin-3-yl)acrylamido)methyl)-7-(trifluoromethyl)benzofuran-5-yl)pyrimidine-5-carboxylic acid (169) (20 mg, 0.04 mmol) was dissolved in DMF (3 mL). tert-Butyl piperazine-1-carboxylate (8 mg, 0.04 mmol), HATU (30 mg, 0.08 mmol) and DIPEA (10 mg, 0.08 mmol) were added at room temperature. The reaction mixture was stirred at room temperature for 4 h. The crude mixture was purified by Prep-HPLC without workup to afford 20 mg of (E)-tert-butyl 4-(2-(2-((3-(6-aminopyridin-3-yl)acrylamido)methyl)-7-(trifluoromethyl)benzofuran-5-yl)pyrimidine-5-carbonyl)piperazine-1-carboxylate (170). Yield (60%). LCMS: m/z 652.7 [M+H]$^+$, t$_R$=1.89 min.

Synthesis of (E)-3-(6-aminopyridin-3-yl)-N-((5-(5-(piperazine-1-carbonyl)pyrimidin-2-yl)-7-(trifluoromethyl)benzofuran-2-yl)methyl)acrylamide (590)

(E)-tert-butyl 4-(2-(2-((3-(6-aminopyridin-3-yl)acrylamido)methyl)-7-(trifluoromethyl)benzofuran-5-yl)pyrimidine-5-carbonyl)piperazine-1-carboxylate (170) (20 mg, 0.03 mmol) was dissolved in CH$_2$Cl$_2$ (5 mL). TFA (1 mL) was added at 0° C. (ice bath). The reaction mixture was allowed to warm to room temperature and stirred for 2 h. The reaction mixture was concentrated under reduced pressure to give the crude product, which was purified by Prep-HPLC to afford 18 mg of (E)-3-(6-aminopyridin-3-yl)-N-((5-(5-(piperazine-1-carbonyl)pyrimidin-2-yl)-7-(trifluoromethyl)benzofuran-2-yl)methyl)acrylamide (590) as white solid. (90% yield). $^1$H NMR (400 MHz, DMSO-d$_6$) δ 9.07-8.97 (m, 4H), 8.65-8.67 (m, 3H), 8.10-8.07 (m, 1H), 7.64-7.60 (m, 1H), 7.39-7.32 (m, 1H), 7.07 (s, 1H), 6.50-6.39 (m, 3H), 4.67-4.59 (m, 2H), 3.16-3.09 (m, 4H), 1.35-1.13 (m, 4H). LCMS: m/z 552.2 [M+H]$^+$; t$_R$=1.48 min.

Synthesis of (E)-3-(6-aminopyridin-3-yl)-N-((7-chloro-5-(5-(4,4-difluoropiperidine-1-carbonyl)pyridin-2-yl)benzofuran-2-yl)methyl)acrylamide (591)

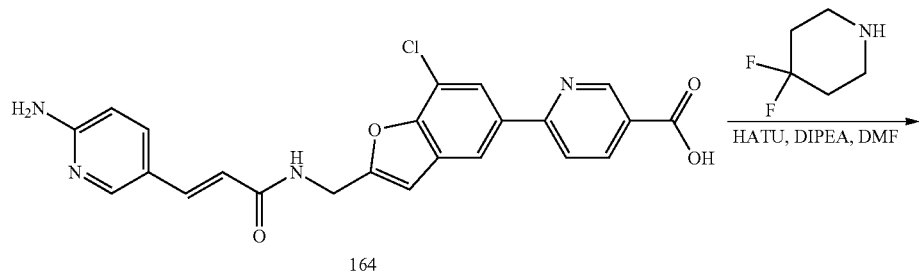

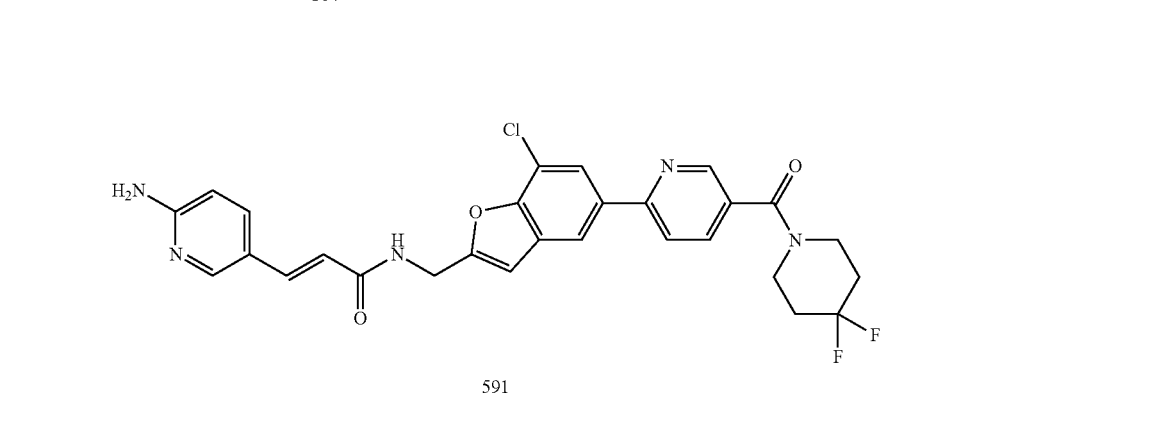

(E)-3-(6-aminopyridin-3-yl)-N-((7-chloro-5-(5-(4,4-difluoropiperidine-1-carbonyl)pyridin-2-yl)benzofuran-2-yl) methyl)acrylamide (591) was synthesized using the indicated reagents according to General Procedure 4. Yield (16%). $^1$H NMR (400 MHz, DMSO-d$_6$) δ 8.75 (s, 1H), 8.66-8.63 (m, 1H), 8.37 (d, J=2 Hz, 1H), 8.17-8.03 (m, 3H), 8.01-7.98 (m, 1H), 7.63-7.61 (m, 1H), 7.36 (d, J=16 Hz, 1H), 6.95 (s, 1H), 6.49-6.41 (m, 4H), 4.61 (d, J=6 Hz, 2H), 3.75-3.49 (m, 4H), 2.08-2.07 (m, 4H). LCMS: m/z 552.2 [M+H]$^+$; t$_R$=1.65 min.

Synthesis of (E)-3-(6-aminopyridin-3-yl)-N-((7-methoxy-5-(4-(morpholine-4-carbonyl)phenyl)benzofuran-2-yl)methyl)acrylamide (592)

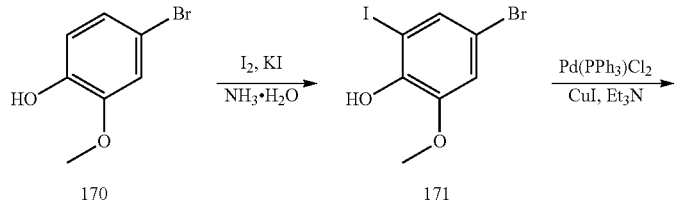

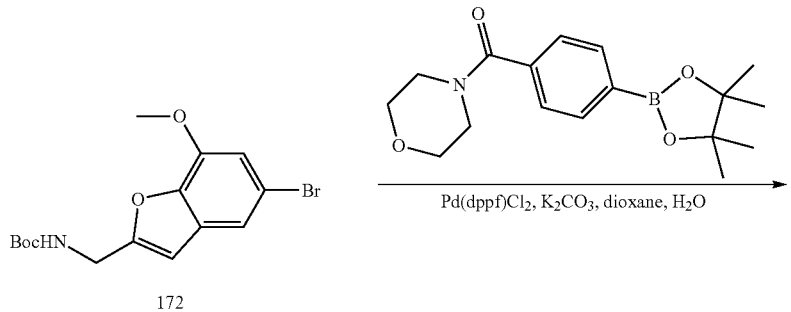

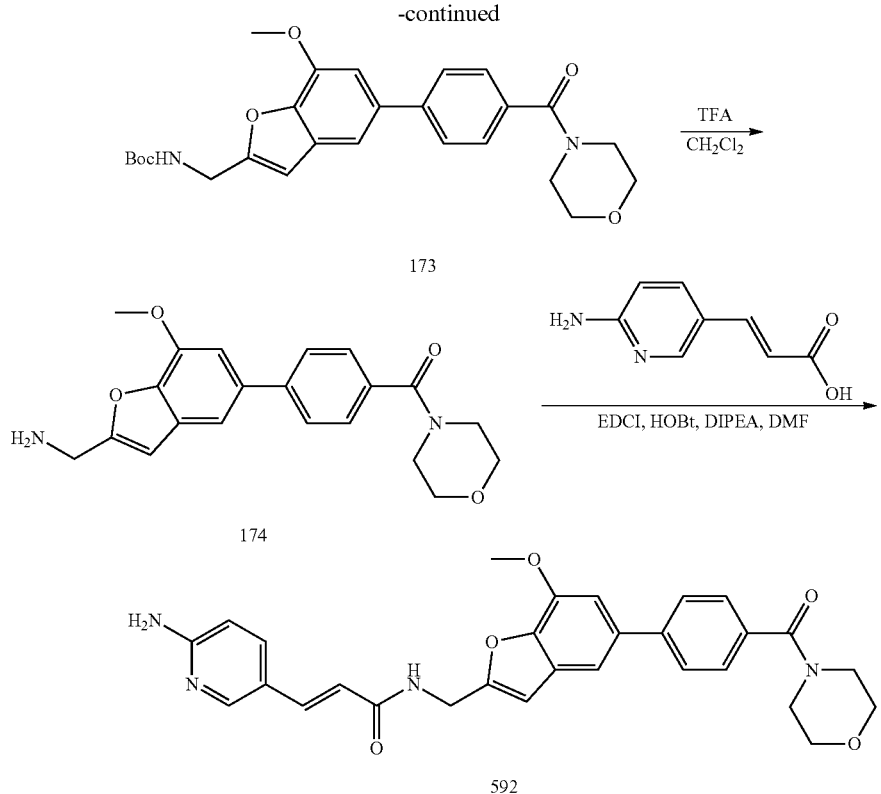

Synthesis of 4-bromo-2-iodo-6-methoxyphenol (171)

4-Bromo-2-methoxyphenol (1; 14.5 g, 71.8 mmol) was dissolved in 500 mL of NH$_4$OH. A solution KI (36.0 g, 220 mmol) and I$_2$ (18.2 g, 71.8 mmol) in 120 mL of H$_2$O was added to this mixture and the reaction mixture was stirred at 30° C. for 4 h. HCl was added to the reaction mixture till pH=7. The mixture was extracted with EtOAc (200 mL×3). The combined organic layers were washed with brine, dried over anhydrous Na$_2$SO$_4$, and concentrated under reduced pressure to give the crude product, which was purified by silica gel chromatography (20% EtOAc/petroleum ether) to give 12.0 g of 4-bromo-2-iodo-6-methoxyphenol (171) as a yellow solid (yield: 52%). LCMS: $t_R$=1.83 min.

Synthesis of tert-butyl (5-bromo-7-methoxybenzofuran-2-yl)methylcarbamate (172)

A mixture of 4-bromo-2-iodo-6-methoxyphenol (171) (12.0 g, 36.6 mmol), tert-butyl prop-2-ynylcarbamate (6.84 g, 44.1 mmol), Pd(PPh$_3$)$_2$Cl$_2$ (1.56 g, 3.66 mmol) and CuI (695 mg, 3.66 mmol) in 100 mL of Et$_3$N was stirred at 80° C. under nitrogen atmosphere for 2 h. After cooling to room temperature, the mixture was poured into iced water and extracted with EtOAc (100 mL×3). The combined organic layers were washed with brine, dried over anhydrous Na$_2$SO$_4$, and concentrated under reduced pressure to give the crude product, which was purified by silica gel chromatography (20% EtOAc/petroleum ether) to give 6.7 g of tert-butyl (5-bromo-7-methoxybenzofuran-2-yl) methylcarbamate (172) as a white solid (yield: 51%). LCMS: m/z 380.0 [M+Na]$^+$, $t_R$=1.92 min.

Synthesis of tert-butyl (7-methoxy-5-(4-(morpholine-4-carbonyl)phenyl)benzofuran-2-yl)methylcarbamate (173)

A mixture of tert-butyl (5-bromo-7-methoxybenzofuran-2-yl) methylcarbamate (172) (200 mg, 0.56 mmol), morpholino(4-(4,4,5,5-tetramethyl-1,3,2-dioxaborolan-2-yl) phenyl)methanone (213 mg, 0.67 mmol), Pd(dppf)Cl$_2$ (44 mg, 0.06 mmol) and K$_2$CO$_3$ (155 g, 1.1 mmol) in 6 mL of dioxane and 0.6 mL of H$_2$O was stirred at 100° C. under nitrogen atmosphere for 2 h. The mixture was extracted with EtOAc (15 mL×3). The combined organic layers were washed with brine, dried over anhydrous Na$_2$SO$_4$, and concentrated under reduced pressure to give the crude product, which was purified by silica gel chromatography (25%-50% EtOAc/petroleum ether) to give 140 mg of tert-butyl (7-methoxy-5-(4-(morpholine-4-carbonyl)phenyl) benzofuran-2-yl)methylcarbamate (173) as a yellow solid. Yield (95%). LCMS: m/z 467.1 [M+H]$^+$, $t_R$=1.68 min.

Synthesis of (4-(2-(aminomethyl)-7-methoxybenzofuran-5-yl)phenyl)(morpholino)methanone (174)

tert-Butyl (7-methoxy-5-(4-(morpholine-4-carbonyl)phenyl)benzofuran-2-yl)methylcarbamate (173) (140 mg, 0.3 mmol) was dissolved in CH$_2$Cl$_2$ (5 mL). TFA (1 mL) was added at 0° C. The reaction mixture was stirred at room temperature for 2 h, and concentrated under reduced pressure to give the crude (4-(2-(aminomethyl)-7-methoxybenzofuran-5-yl)phenyl)(morpholino)methanone (174), which was used without further purification in the next step. Yield (100%). LCMS: m/z 367.2 [M+H]$^+$; $t_R$=1.17 min.

261

Synthesis of (E)-3-(6-aminopyridin-3-yl)-N-((7-methoxy-5-(4-(morpholine-4-carbonyl)phenyl)benzofuran-2-yl)methyl)acrylamide (592)

(4-(2-(Aminomethyl)-7-methoxybenzofuran-5-yl)phenyl)(morpholino)methanone (174) (110 mg, 0.3 mmol) was dissolved in DMF (3 mL) and (E)-3-(6-aminopyridin-3-yl)acrylic acid (74 mg, 0.45 mmol) was added at 0° C. EDCI (86 mg, 0.45 mmol) and HOBt (61 mg, 0.45 mmol) were added to this reaction mixture at 0° C. followed by DIPEA (77 mg, 0.6 mmol) dropwise. The reaction mixture was allowed to warm to room temperature and stirred for 18 h. The crude mixture was purified by Prep-HPLC to afford

262

(E)-3-(6-aminopyridin-3-yl)-N-((7-methoxy-5-(4-(morpholine-4-carbonyl)phenyl)benzofuran-2-yl)methyl)acrylamide (592) (5 mg, yield: 3%). $^1$H NMR (400 MHz, CD$_3$OD) δ 8.18 (d, J=9 Hz, 1H), 8.05 (s, 1H), 7.76 (d, J=8 Hz, 2H), 7.55-7.42 (m, 4H), 7.13 (s, 1H), 7.03 (d, J=9 Hz, 1H), 6.77 (s, 1H), 6.64 (d, J=16 Hz, 1H), 4.68 (s, 2H), 4.06 (s, 3H), 3.82-3.53 (m, 8H). LCMS: m/z 513.2 [M+H]$^+$, $t_R$=1.18 min.

Synthesis of (E)-3-(6-aminopyridin-3-yl)-N-((5-(5-(morpholine-4-carbonyl)pyrimidin-2-yl)-7-(trifluoromethyl)benzofuran-2-yl)methyl)acrylamide (593)

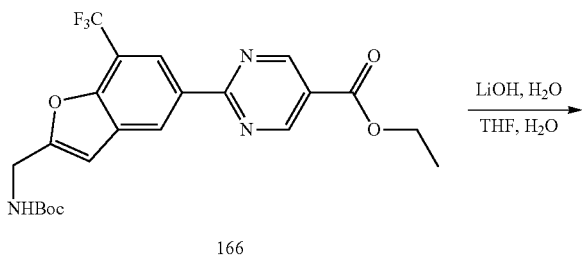

166

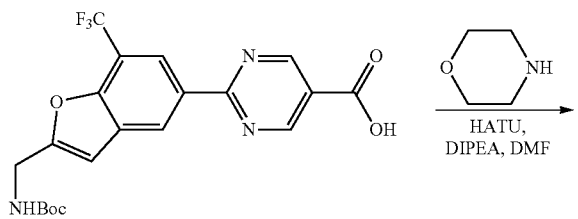

175

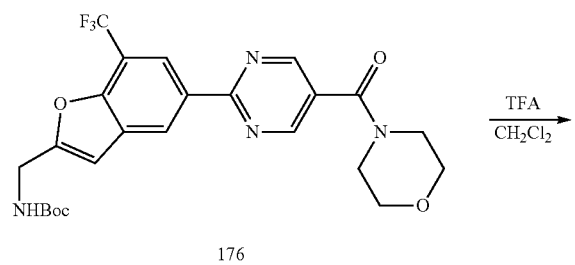

176

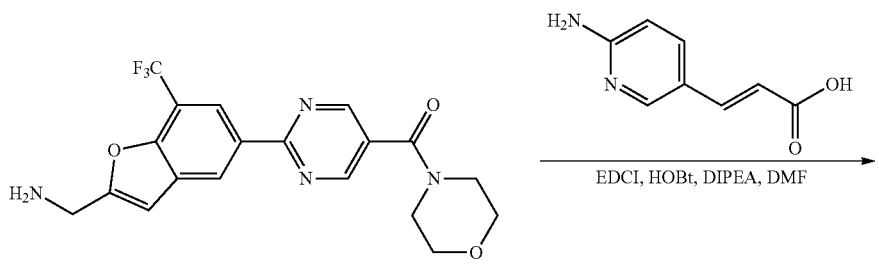

177

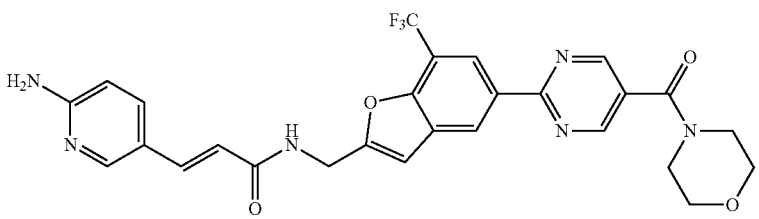

593

Synthesis of 2-(2-((tert-butoxycarbonylamino)methyl)-7-(trifluoromethyl)benzofuran-5-yl)pyrimidine-5-carboxylic acid (175)

Ethyl 2-(2-((tert-butoxycarbonylamino)methyl)-7-(trifluoromethyl)benzofuran-5-yl)pyrimidine-5-carboxylate (166) (300 mg, 0.82 mmol) was dissolved in THF (6 mL), LiOH (103 mg, 2.46 mmol) and water (1.5 mL) was added to this mixture. The reaction mixture was stirred at room temperature for 2 h. 1N HCl solution was added and adjusted to pH=3.250 mg of 2-(2-((tert-butoxycarbonylamino)methyl)-7-(trifluoromethyl)benzofuran-5-yl)pyrimidine-5-carboxylic acid (175) was collected by filtration (90% yield). LCMS: m/z 438.1 [M+H]$^+$; $t_R$=1.3 min.

Synthesis of tert-butyl (5-(5-(morpholine-4-carbonyl)pyrimidin-2-yl)-7-(trifluoromethyl)benzofuran-2-yl)methylcarbamate (176)

2-(2-((tert-Butoxy carbonylamino)methyl)-7-(trifluoromethyl)benzofuran-5-yl)pyrimidine-5-carboxylic acid (175) (200 mg, 0.46 mmol) was dissolved in DMF (3 mL). Morpholine (40 mg, 0.46 mmol), HATU (348 mg, 0.92 mmol) and DIPEA (119 mg, 0.92 mmol)) were added at room temperature. The reaction mixture was stirred at room temperature further for 2 h. 15 mL of EtOAc and 10 mL of H$_2$O were added. The organic phase was separated and the aqueous phase was extracted with EtOAc (15 mL×2). The combined organic phases were washed with brine (10 mL), dried over anhydrous Na$_2$SO$_4$, concentrated and purified by silica gel chromatography (50% EtOAc/petroleum ether) to afford 70 mg of tert-butyl (5-(5-(morpholine-4-carbonyl)pyrimidin-2-yl)-7-(trifluoromethyl)benzofuran-2-yl)methylcarbamate (176). Yield (30%). LCMS: m/z 507.1 [M+H]$^+$, $t_R$=1.84 min.

Synthesis of (2-(2-(aminomethyl)-7-(trifluoromethyl)benzofuran-5-yl)pyrimidin-5-yl)(morpholino)methanone (177)

tert-Butyl (5-(5-(morpholine-4-carbonyl)pyrimidin-2-yl)-7-(trifluoromethyl)benzofuran-2-yl)methylcarbamate (176) (70 mg, 0.14 mmol) was dissolved in CH$_2$Cl$_2$ (5 mL). TFA (1 mL) was added at 0° C. The reaction mixture was allowed to warm to room temperature and stirred for 2 h. The reaction mixture was concentrated under reduced pressure to give crude (2-(2-(aminomethyl)-7-(trifluoromethyl)benzofuran-5-yl)pyrimidin-5-yl)(morpholino)methanone (177), which was used without further purification in the next step (80 mg). Yield (100%). LCMS: m/z 407.1 [M+H]$^+$, $t_R$=1.55 min.

Synthesis of (E)-3-(6-aminopyridin-3-yl)-N-((5-(5-(morpholine-4-carbonyl)pyrimidin-2-yl)-7-(trifluoromethyl)benzofuran-2-yl)methyl)acrylamide (593)

(2-(2-(Aminomethyl)-7-(trifluoromethyl)benzofuran-5-yl)pyrimidin-5-yl)(morpholino)methanone (177) (20 mg, 0.05 mmol) was dissolved in DMF (5 mL) and (E)-3-(6-aminopyridin-3-yl)acrylic acid (9 mg, 0.05 mmol) was added at 0° C. EDCI (14 mg, 0.075 mmol) and HOBt (10 mg, 0.075 mmol) were added to this reaction mixture at 0° C. followed by DIPEA (13 mg, 0.10 mmol) dropwise. The reaction mixture was allowed to warm to room temperature and stirred further for 18 h. The reaction mixture was purified by Prep-HPLC without workup to afford (E)-3-(6-aminopyridin-3-yl)-N-((5-(5-(morpholine-4-carbonyl)pyrimidin-2-yl)-7-(trifluoromethyl)benzofuran-2-yl)methyl)acrylamide (593) (10 mg, yield: 36%). $^1$H NMR (400 MHz, CD$_3$OD) δ 8.88-8.84 (m, 3H), 8.63 (s, 1H), 7.95 (s, 1H), 7.67-7.60 (m, 1H), 7.38 (d, J=16 Hz, 1H), 6.86 (s, 1H), 6.50 (d, J=9 Hz, 1H), 6.37 (d, J=16 Hz, 1H), 4.61 (s, 2H), 3.72-3.46 (m, 8H). LCMS: m/z 553.2 [M+H]$^+$, $t_R$=1.57 min.

Synthesis of (E)-3-(6-aminopyridin-3-yl)-N-((5-(5-(4-methylpiperazine-1-carbonyl)pyrimidin-2-yl)-7-(trifluoromethyl)benzofuran-2-yl)methyl)acrylamide (594)

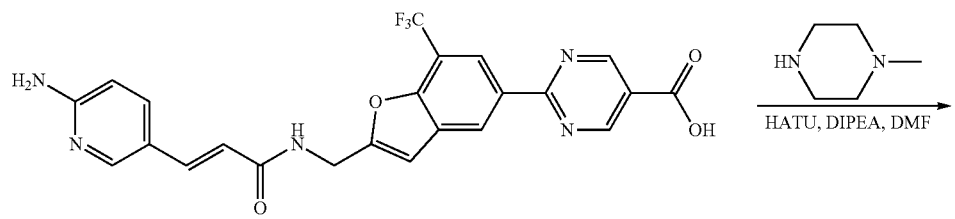

169

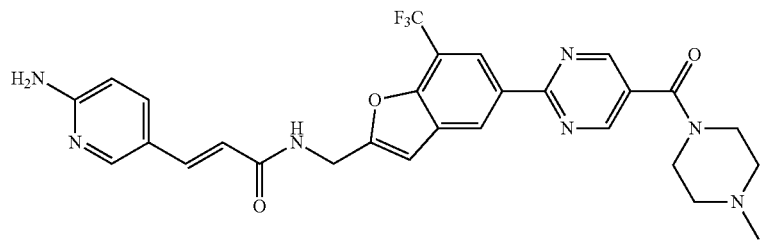

594

(E)-3-(6-aminopyridin-3-yl)-N-((5-(5-(4-methylpiperazine-1-carbonyl)pyrimidin-2-yl)-7-(trifluoromethyl)benzofuran-2-yl)methyl)acrylamide (594) was synthesized using the indicated reagents according to General Procedure 4. Yield (50%). $^1$H NMR (400 MHz, CD$_3$OD) δ 8.84 (s, 3H), 8.62 (s, 1H), 7.95 (s, 1H), 7.67-7.60 (m, 1H), 7.38 (d, J=16 Hz, 1H), 6.85 (s, 1H), 6.49 (d, J=9 Hz, 1H), 6.37 (d, J=16

Hz, 1H), 4.61 (s, 2H), 3.75-3.46 (m, 4H), 2.50-2.36 (m, 4H), 2.25 (s, 3H). LCMS: m/z 566.2 [M+H]⁺, $t_R$=1.55 min.

Synthesis of (E)-3-(6-aminopyridin-3-yl)-N-((5-(4-(piperidine-1-carbonyl)phenyl)-7-(trifluoromethyl)benzofuran-2-yl)methyl)acrylamide (595)

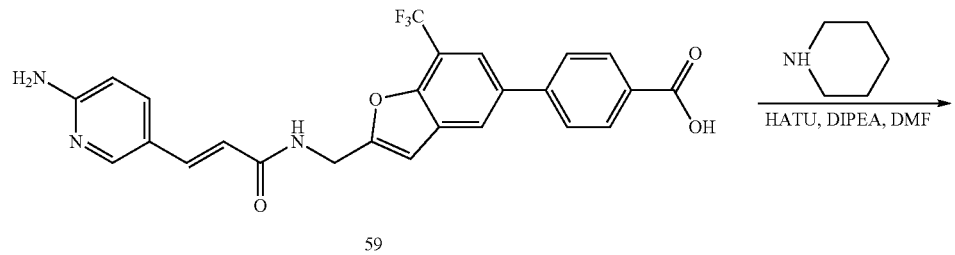

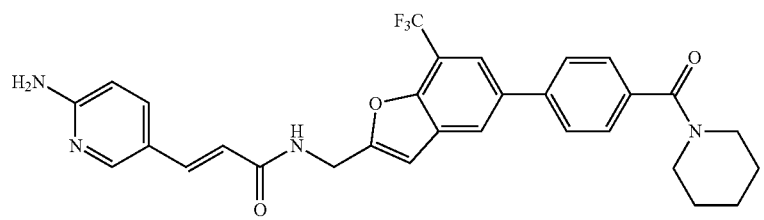

(E)-3-(6-aminopyridin-3-yl)-N-((5-(4-(piperidine-1-carbonyl)phenyl)-7-(trifluoromethyl)benzofuran-2-yl)methyl) acrylamide (595) was synthesized using the indicated reagents according to General Procedure 4. Yield (79%). ¹H NMR (400 MHz, DMSO-$d_6$) δ 8.86 (t, J=6 Hz, 1H), 8.30-7.77 (m, 8H), 7.55-7.39 (m, 3H), 7.01-6.90 (m, 2H), 6.60 (d, J=15.8 Hz, 1H), 4.64 (d, J=6 Hz, 2H), 3.65-3.54 (m, 4H), 1.69-1.45 (m, 6H). LCMS: m/z 549.3 [M+H]⁺; $t_R$=1.33 m Synthesis of (E)-3-(6-aminopyridin-3-yl)-N-((7-chloro-5-(4-(4,4-difluoropiperidine-1-carbonyl)phenyl)benzofuran-2-yl)methyl)acrylamide (596)

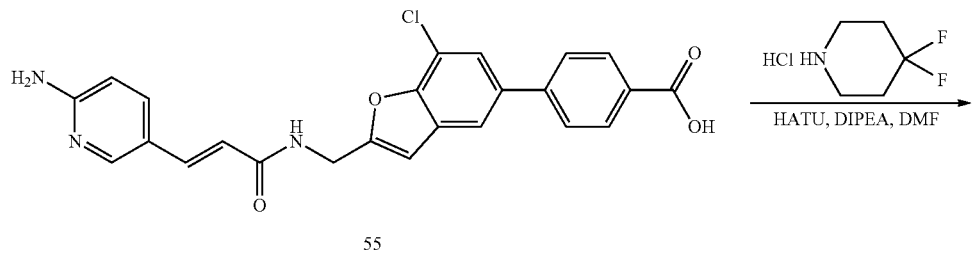

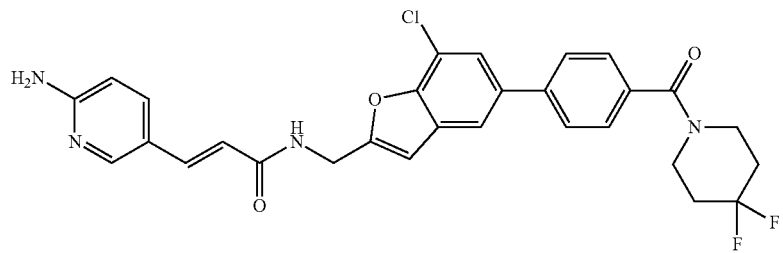

(E)-3-(6-aminopyridin-3-yl)-N-((7-chloro-5-(4-(4,4-difluoropiperidine-1-carbonyl)phenyl)benzofuran-2-yl)methyl)acrylamide (596) was synthesized using the indicated reagents according to General Procedure 4. Yield (37 mg, 43% yield) as white solid. ¹H NMR (400 MHz, DMSO-d₆) δ 8.87 (t, J=6 Hz, 1H), 8.34-8.07 (m, 4H), 7.92 (d, J=2 Hz, 1H), 7.80 (d, J=8 Hz, 2H), 7.74 (d, J=2 Hz, 1H), 7.56 (d, J=8 Hz, 2H), 7.45 (d, J=16 Hz, 1H), 6.99 (d, J=9 Hz, 1H), 6.92 (s, 1H), 6.62 (d, J=16 Hz, 1H), 4.63 (d, J=6 Hz, 2H), 3.82-3.66 (m, 4H), 2.14-1.97 (m, 4H). LCMS: m/z 551.2 [M+H]⁺; $t_R$=1.31 min.

Synthesis of (E)-3-(6-aminopyridin-3-yl)-N-((7-chloro-5-(4-(4-fluoropiperidine-1-carbonyl)phenyl)benzofuran-2-yl)methyl)acrylamide (598)

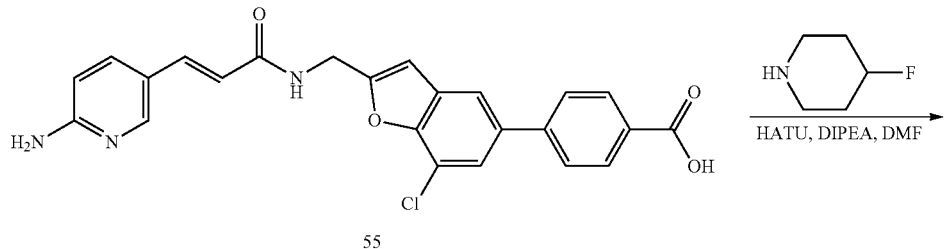

55

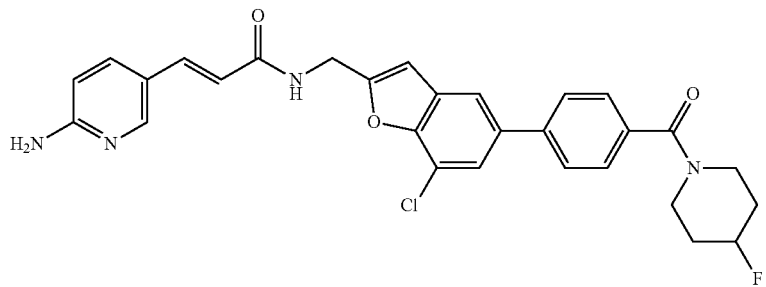

598

(E)-3-(6-aminopyridin-3-yl)-N-((7-chloro-5-(4-(4-fluoropiperidine-1-carbonyl)phenyl)benzofuran-2-yl)methyl)acrylamide (598) was synthesized using the indicated reagents according to General Procedure 4. Yield (32%). ¹H NMR (400 MHz, DMSO-d₆) δ 8.87 (t, J=6 Hz, 1H), 8.36-8.06 (m, 4H), 7.94-7.70 (m, 4H), 7.56-7.40 (m, 3H), 7.03-6.89 (m, 2H), 6.62 (d, J=16 Hz, 1H), 5.04-4.83 (m, 1H), 4.64 (t, J=9 Hz, 2H), 3.75-3.64 (m, 4H), 2.02-1.64 (m, 4H). LCMS: m/z 533.2 [M+H]⁺; $t_R$=1.28 min.

Synthesis of (E)-3-(6-aminopyridin-3-yl)-N-((7-chloro-5-(4-(3-fluoro-3-methylazetidine-1-carbonyl)phenyl)benzofuran-2-yl)methyl)acrylamide (599)

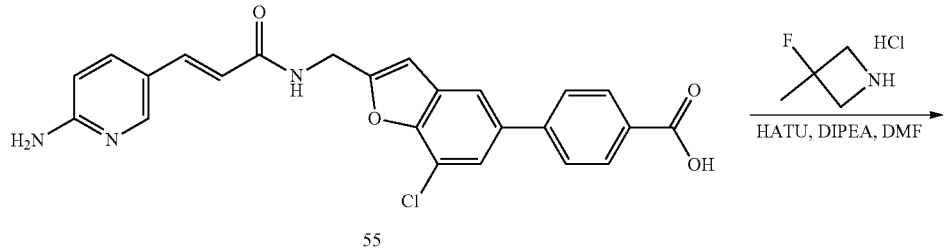

55

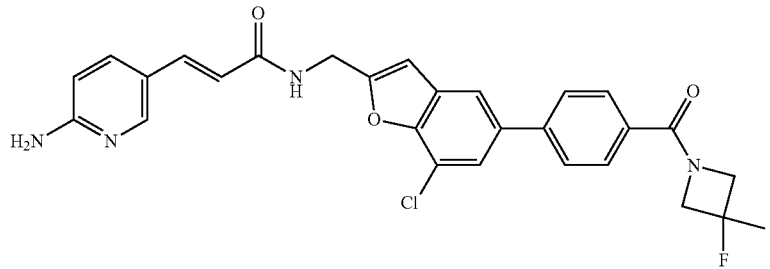

599

(E)-3-(6-aminopyridin-3-yl)-N-((7-chloro-5-(4-(3-fluoro-3-methylazetidine-1-carbonyl)phenyl)benzofuran-2-yl)methyl)acrylamide (599) was synthesized using the indicated reagents according to General Procedure 4. Yield (10%). $^1$H NMR (400 MHz, DMSO-d$_6$) δ 8.65 (t, J=6 Hz, 1H), 8.10-8.08 (m, 1H), 7.96-7.92 (m, 1H), 7.84-7.73 (m, 6H), 7.66-7.59 (m, 1H), 7.39-7.32 (m, 1H), 6.90 (s, 1H), 6.49-6.40 (m, 3H), 4.60 (d, J=6 Hz, 2H), 4.54-4.40 (m, 2H), 4.20-4.11 (m, 2H), 1.61 (d, J=22 Hz, 3H). LCMS: m/z 519.3 [M+H]$^+$, t$_R$=1.65 min.

Synthesis of (E)-3-(6-aminopyridin-3-yl)-N-((7-chloro-5-(4-(piperidine-1-carbonyl)phenyl)benzofuran-2-yl)methyl)acrylamide (600)

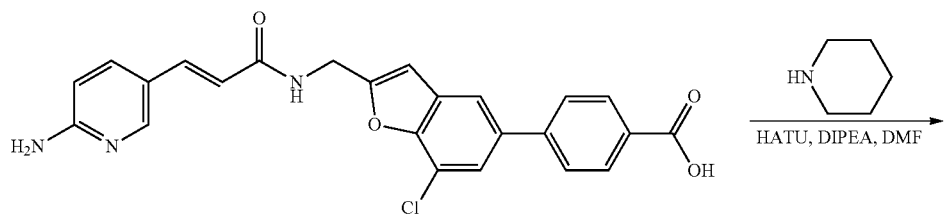

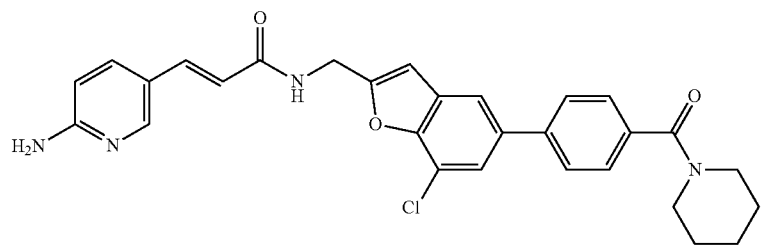

600

(E)-3-(6-aminopyridin-3-yl)-N-((7-chloro-5-(4-(piperidine-1-carbonyl)phenyl)benzofuran-2-yl)methyl)acrylamide (600) was synthesized using the indicated reagents according to General procedure 4. Yield (70%). ¹H NMR (400 MHz, DMSO-d₆) δ 8.84 (t, J=6 Hz, 1H), 8.24-7.97 (m, 4H), 7.91 (d, J=2 Hz, 1H), 7.81-7.70 (m, 3H), 7.50-7.39 (m, 3H), 6.97-6.89 (m, 2H), 6.60 (d, J=16 Hz, 1H), 4.62 (d, J=6 Hz, 2H), 3.64-3.55 (m, 4H), 1.68-1.42 (m, 6H). LCMS: m/z 515.2 [M+H]⁺; t$_R$=1.31 min.

Synthesis of (E)-3-(6-aminopyridin-3-yl)-N-((5-(4-(piperazine-1-carbonyl)phenyl)-7-(trifluoromethyl)benzofuran-2-yl)methyl)acrylamide (601)

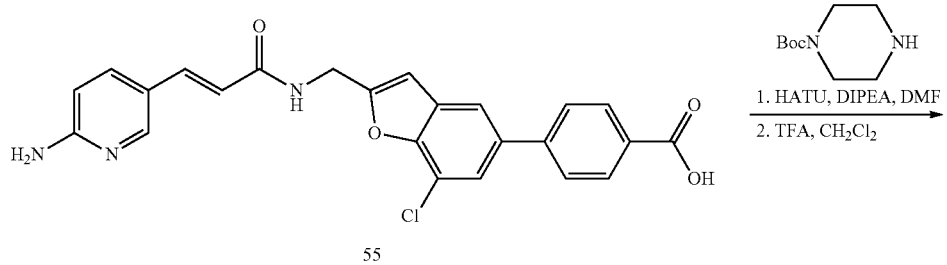

55

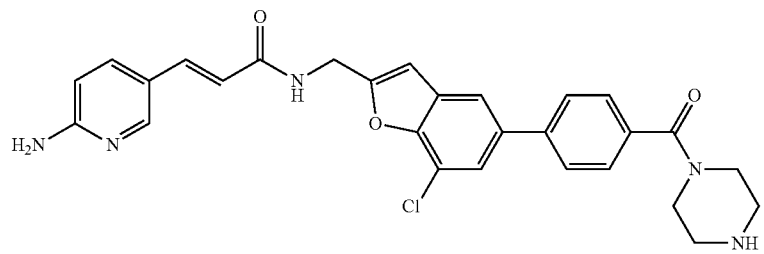

601

(E)-3-(6-aminopyridin-3-yl)-N-((5-(4-(piperazine-1-carbonyl)phenyl)-7-(trifluoromethyl)benzofuran-2-yl)methyl)acrylamide (601) was synthesized using the indicated reagents according to General Procedures 4 and 3. Yield (90%). ¹H NMR (400 MHz, CD₃OD) δ 7.96-7.91 (m, 1H), 7.69-7.61 (m, 4H), 7.50-7.35 (m, 4H), 6.74 (s, 1H), 6.49 (d, J=9 Hz, 1H), 6.37 (d, J=16 Hz, 1H), 4.58 (s, 2H), 3.76-3.34 (m, 4H), 2.92-2.71 (m, 4H). LCMS: m/z 516.3 [M+H]⁺, t$_R$=1.17 min.

Synthesis of (E)-3-(6-aminopyridin-3-yl)-N-((7-chloro-5-(4-(4-hydroxy-4-methylpiperidine-1-carbonyl)phenyl)benzofuran-2-yl)methyl)acrylamide (602)

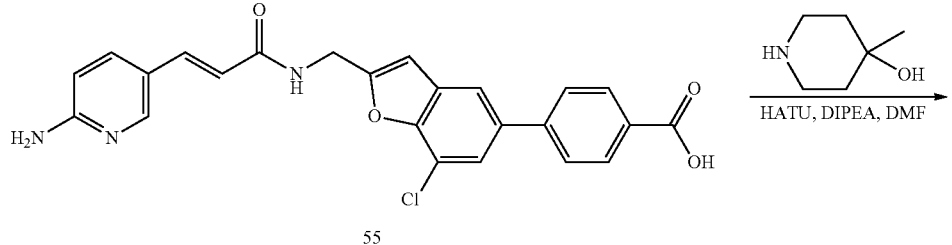

55

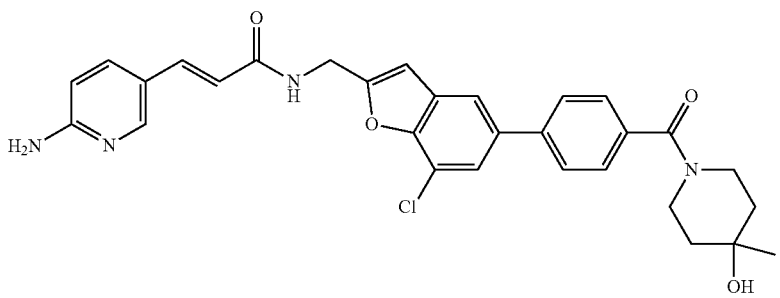

602

(E)-3-(6-aminopyridin-3-yl)-N-((7-chloro-5-(4-(4-hydroxy-4-methylpiperidine-1-carbonyl)phenyl)benzofuran-2-yl)methyl)acrylamide (602) was synthesized according to General Procedure 4. Yield (47%). $^1$H NMR (400 MHz, CD$_3$OD) δ 8.13-8.04 (m, 1H), 7.98-7.90 (m, 1H), 7.72-7.60 (m, 3H), 7.50 (d, J=2 Hz, 1H), 7.44-7.32 (m, 3H), 6.93 (d, J=9 Hz, 1H), 6.76 (s, 1H), 6.54 (d, J=16 Hz, 1H), 4.60 (s, 2H), 4.20-4.10 (m, 1H), 3.49-3.25 (m, 3H), 1.65-1.40 (m, 4H), 1.17 (s, 3H). LCMS: m/z 545.2 [M+H]$^+$; t$_R$=1.21 min.

Synthesis of (E)-3-(6-aminopyridin-3-yl)-N-((5-(4-(3,3-difluoropyrrolidine-1-carbonyl)phenyl)-7-(trifluoromethyl)benzofuran-2-yl)methyl)acrylamide (603)

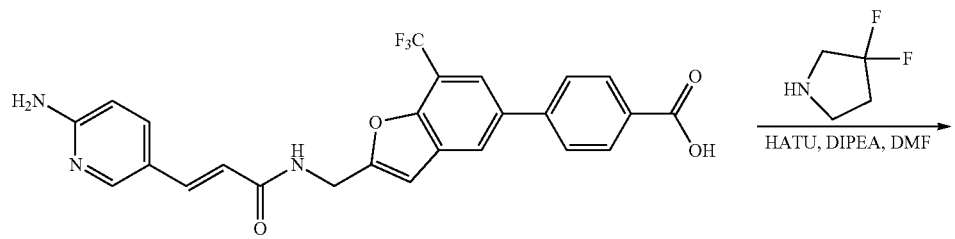

59

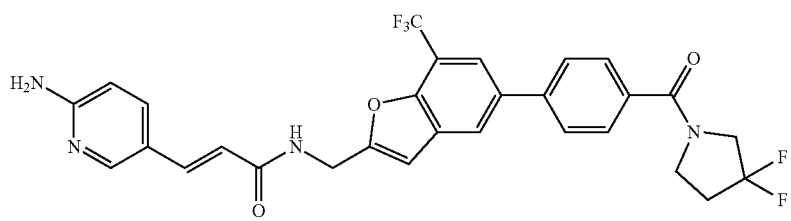

603

(E)-3-(6-aminopyridin-3-yl)-N-((5-(4-(3,3-difluoropyrrolidine-1-carbonyl)phenyl)-7-(trifluoromethyl)benzofuran-2-yl)methyl)acrylamide (603) was synthesized using the indicated reagents according to General Procedure 4. Yield (49%). ¹H NMR (400 MHz, CD₃OD) δ 8.13-7.90 (m, 3H), 7.74-7.52 (m, 5H), 7.38 (d, J=16 Hz, 1H), 6.95 (d, J=9 Hz, 1H), 6.82 (s, 1H), 6.55 (d, J=16 Hz, 1H), 4.61 (s, 2H), 3.94-3.65 (m, 4H), 2.47-2.28 (m, 2H). LCMS: m/z 571.2 [M+H]$^+$; $t_R$=1.32 min.

Synthesis of (E)-3-(6-aminopyridin-3-yl)-N-((5-(4-(4-fluoro-4-methylpiperidine-1-carbonyl)phenyl)-7-(trifluoromethyl)benzofuran-2-yl)methyl)acrylamide (604)

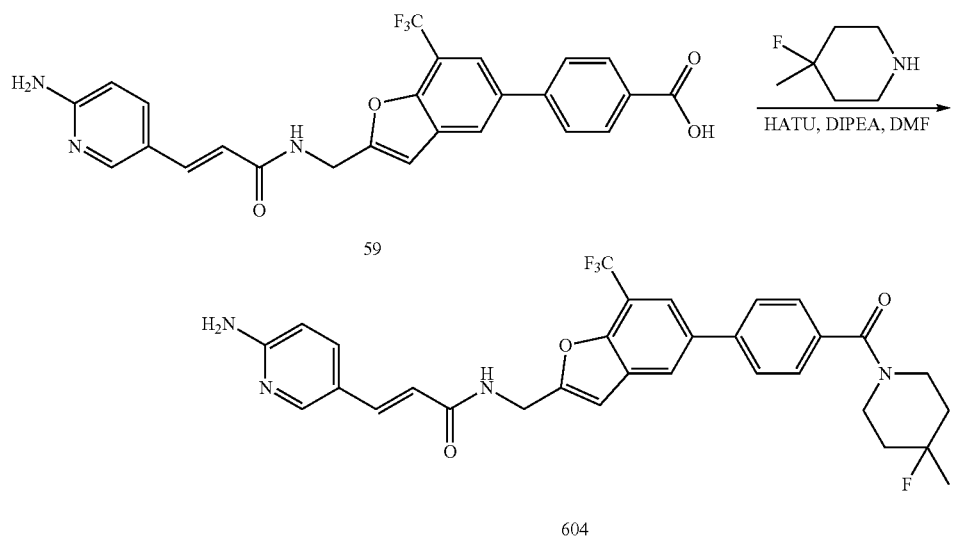

(E)-3-(6-aminopyridin-3-yl)-N-((5-(4-(4-fluoro-4-methylpiperidine-1-carbonyl)phenyl)-7-(trifluoromethyl)benzofuran-2-yl)methyl)acrylamide (604) was synthesized using the indicated reagents according to General Procedure 4. Yield (4%). ¹H NMR (400 MHz, CD₃OD) δ 8.14-7.91 (m, 3H), 7.73-7.62 (m, 3H), 7.52-7.34 (m, 3H), 6.96 (d, J=9 Hz, 1H), 6.82 (s, 1H), 6.55 (d, J=16 Hz, 1H), 4.62 (s, 2H), 4.41-3.27 (m, 4H), 2.09-1.50 (m, 4H), 1.36-1.15 (m, 3H). LCMS: m/z 581.2 [M+H]$^+$; $t_R$=1.07 min.

Synthesis of (E)-3-(6-aminopyridin-3-yl)-N-((7-(trifluoromethyl)-5-(4-(4-(trifluoromethyl)piperidine-1-carbonyl)phenyl)benzofuran-2-yl)methyl)acrylamide (605)

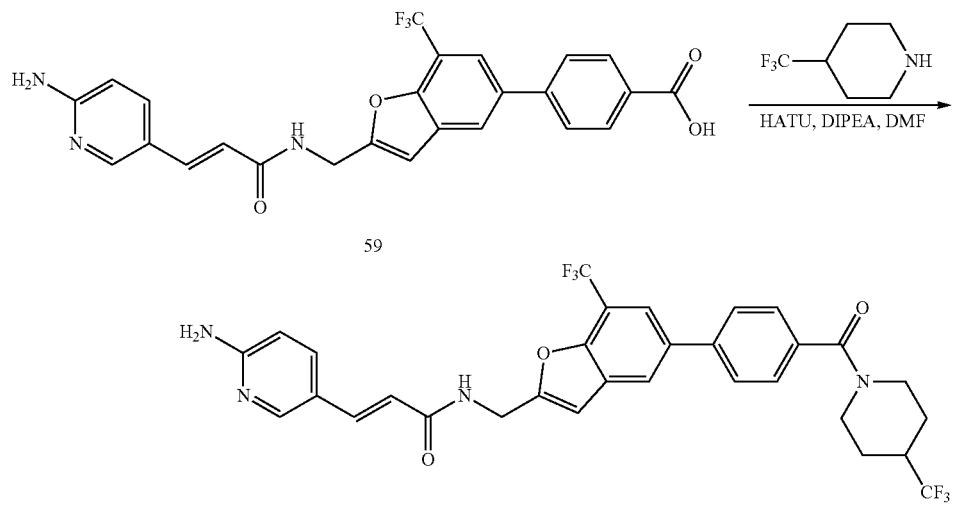

(E)-3-(6-aminopyridin-3-yl)-N-((7-(trifluoromethyl)-5-(4-(4-(trifluoromethyl)piperidine-1-carbonyl)phenyl)benzofuran-2-yl)methyl)acrylamide (605) was synthesized using the indicated reagents according to General Procedure 4. Yield (46%). $^1$H NMR (400 MHz, CD$_3$OD) δ 8.04-7.93 (m, 2H), 7.71-7.62 (m, 4H), 7.48-7.34 (m, 3H), 6.81 (s, 1H), 6.50 (d, J=9 Hz, 1H), 6.37 (d, J=16 Hz, 1H), 4.60 (s, 2H), 4.56-4.47 (m, 1H), 3.88-3.73 (m, 1H), 3.15-3.04 (m, 1H), 2.87-2.73 (m, 1H), 2.52-2.37 (m, 1H), 1.99-1.72 (m, 2H), 1.56-1.35 (m, 2H). LCMS: m/z 617.3 [M+H]$^+$; t$_R$=1.94 min.

Synthesis of (E)-3-(6-aminopyridin-3-yl)-N-((5-(4-(3-hydroxy-3-(trifluoromethyl)pyrrolidine-1-carbonyl)phenyl)-7-(trifluoromethyl)benzofuran-2-yl)methyl)acrylamide (606)

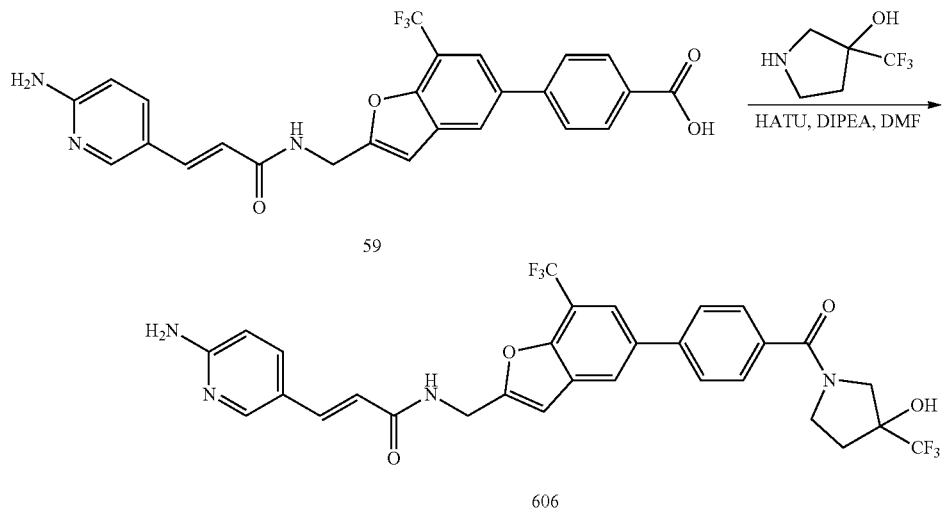

(E)-3-(6-aminopyridin-3-yl)-N-((5-(4-(3-hydroxy-3-(trifluoromethyl)pyrrolidine-1-carbonyl)phenyl)-7-(trifluoromethyl)benzofuran-2-yl)methyl)acrylamide (606) was synthesized using the indicated reagents according to General procedure 4. Yield (42%). %). $^1$H NMR (400 MHz, CD$_3$OD) δ 8.14-7.90 (m, 3H), 7.76-7.53 (m, 5H), 7.38 (d, J=16 Hz, 1H), 6.95 (d, J=9 Hz, 1H), 6.83 (s, 1H), 6.55 (d, J=16 Hz, 1H), 4.62 (s, 2H), 3.87-3.41 (m, 4H), 2.34-1.92 (m, 2H). LCMS: m/z 619.2 [M+H]$^+$; t$_R$=1.30 min.

Synthesis of (E)-3-(6-aminopyridin-3-yl)-N-((5-(4-(4-chloropiperidine-1-carbonyl)phenyl)-7-(trifluoromethyl)benzofuran-2-yl)methyl)acrylamide (607)

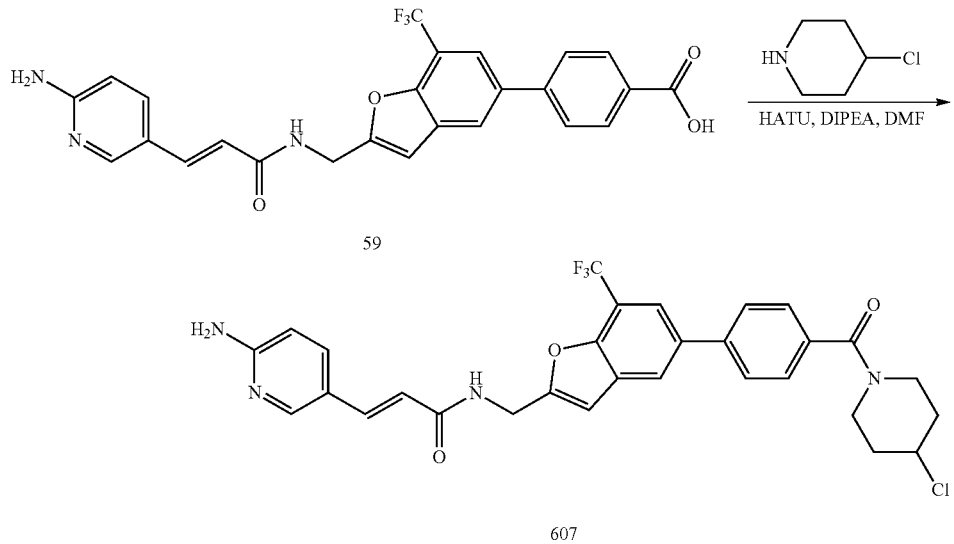

(E)-3-(6-aminopyridin-3-yl)-N-((5-(4-(4-chloropiperidine-1-carbonyl)phenyl)-7-(trifluoromethyl)benzofuran-2-yl)methyl)acrylamide (607) was synthesized using the indicated reagents according to General Procedure 4. Yield (52%). $^1$H NMR (400 MHz, CD$_3$OD) δ 8.10-7.94 (m, 3H), 7.70-7.36 (m, 6H), 6.95-6.53 (m, 3H), 4.62 (s, 2H), 4.32-4.26 (m, 1H), 3.97-3.20 (m, 4H), 2.10-1.70 (m, 4H). LCMS: m/z 583.2 [M+H]$^+$; t$_R$=1.46 min.

Synthesis of (E)-3-(6-aminopyridin-3-yl)-N-((5-(4-(3-fluoro-3-methylpyrrolidine-1-carbonyl)phenyl)-7-(trifluoromethyl)benzofuran-2-yl)methyl)acrylamide (608)

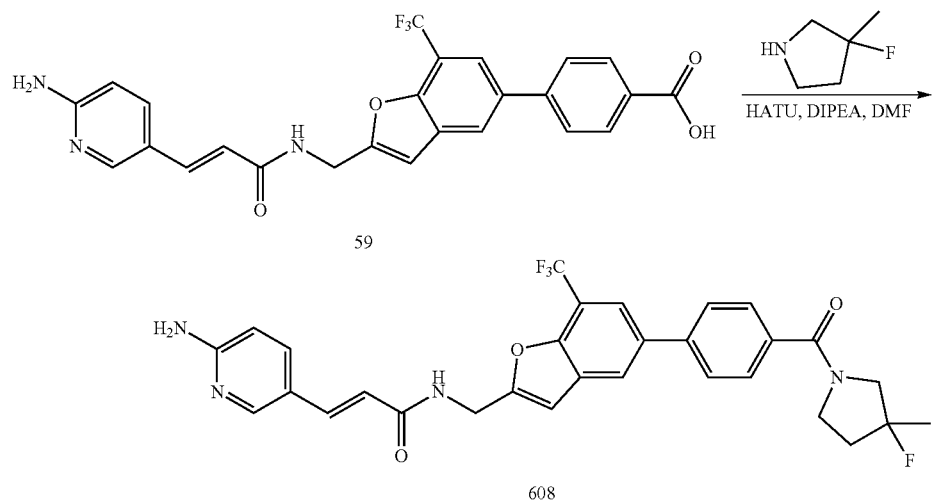

(E)-3-(6-aminopyridin-3-yl)-N-((5-(4-(3-fluoro-3-methylpyrrolidine-1-carbonyl)phenyl)-7-(trifluoromethyl)benzofuran-2-yl)methyl)acrylamide (608) was synthesized using the indicated reagents according to General Procedure 4. Yield (8%). $^1$H NMR (400 MHz, CD$_3$OD) δ 8.03-7.93 (m, 2H), 7.74-7.50 (m, 6H), 7.38 (d, J=16 Hz, 1H), 6.81 (s, 1H), 6.51 (d, J=9 Hz, 1H), 6.38 (d, J=16 Hz, 1H), 4.61 (s, 2H), 3.82-3.48 (m, 4H), 2.21-1.95 (m, 2H), 1.56-1.35 (m, 3H). LCMS: m/z 567.3 [M+H]$^+$; t$_R$=1.83 min.

Synthesis of (E)-3-(6-aminopyridin-3-yl)-N-((5-(4-(4-hydroxy-4-(trifluoromethyl)piperidine-1-carbonyl)phenyl)-7-(trifluoromethyl)benzofuran-2-yl)methyl)acrylamide (609)

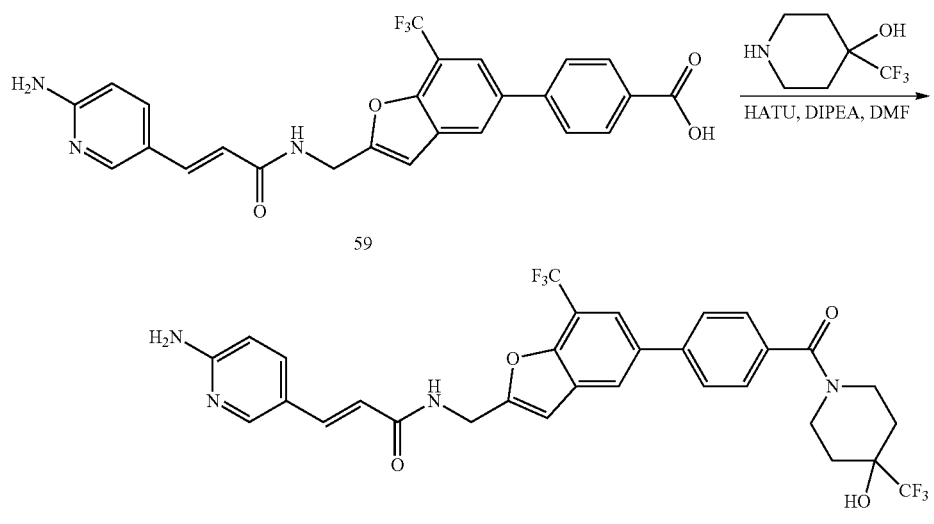

(E)-3-(6-aminopyridin-3-yl)-N-((5-(4-(4-hydroxy-4-(trifluoromethyl)piperidine-1-carbonyl)phenyl)-7-(trifluoromethyl)benzofuran-2-yl)methyl)acrylamide (609) was synthesized using the indicated reagents according to General Procedure 4. Yield (39%). $^{1}$H NMR (400 MHz, DMSO-$d_{6}$) δ 8.73 (t, J=6 Hz, 1H), 8.25 (s, 1H), 8.12 (d, J=2 Hz, 1H), 7.94-7.71 (m, 4H), 7.55 (d, J=8 Hz, 2H), 7.39 (d, J=16 Hz, 1H), 7.03-6.93 (m, 3H), 6.64 (d, J=9 Hz, 1H), 6.49 (d, J=16 Hz, 1H), 6.17 (s, 1H), 4.62 (d, J=5 Hz, 2H), 4.54-4.42 (m, 1H), 3.68-3.52 (m, 1H), 3.23-2.93 (m, 2H), 1.84-1.58 (m, 4H). LCMS: m/z 633.2 [M+H]$^{+}$; $t_{R}$=1.70 min.

Synthesis of (S,E)-3-(6-aminopyridin-3-yl)-N-((5-(4-(3-chloropyrrolidine-1-carbonyl)phenyl)-7-(trifluoromethyl)benzofuran-2-yl)methyl)acrylamide (610)

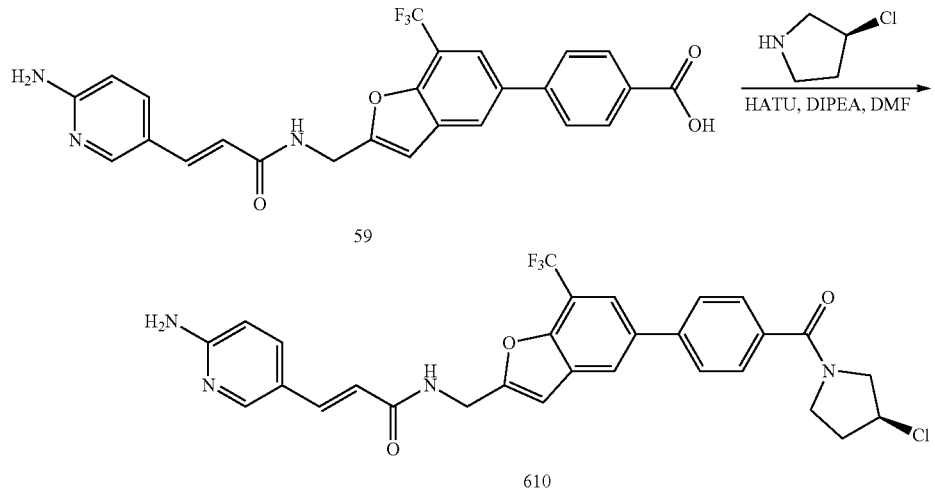

(S,E)-3-(6-aminopyridin-3-yl)-N-((5-(4-(3-chloropyrrolidine-1-carbonyl)phenyl)-7-(trifluoromethyl)benzofuran-2-yl)methyl)acrylamide (610) was synthesized using the indicated reagents according to General Procedure 4. Yield (21%). $^{1}$H NMR (400 MHz, MeOD-$d_{6}$) δ 7.99-7.90 (m, 2H), 7.71-7.49 (m, 6H), 7.36 (d, J=16 Hz, 1H), 6.78 (s, 1H), 6.48 (d, J=9 Hz, 1H), 6.36 (d, J=16 Hz, 1H), 4.68-4.48 (m, 3H), 3.95-3.46 (m, 4H), 2.43-2.07 (m, 2H). LCMS: m/z 569.2 [M+H]$^{+}$; $t_{R}$=1.83 min.

Synthesis of (E)-N-((5-(4-(2-oxa-6-azaspiro[3.3]heptane-6-carbonyl)phenyl)-7-(trifluoromethyl)benzofuran-2-yl)methyl)-3-(6-aminopyridin-3-yl)acrylamide (611)

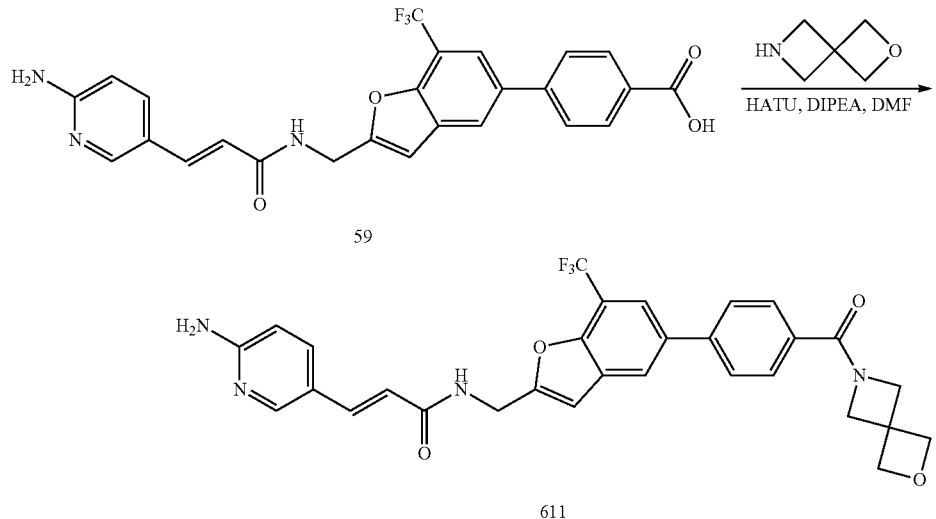

(E)-N-((5-(4-(2-oxa-6-azaspiro[3.3]heptane-6-carbonyl)phenyl)-7-(trifluoromethyl)benzofuran-2-yl)methyl)-3-(6-aminopyridin-3-yl)acrylamide (611) was synthesized using the indicated reagents according to General Procedure 4. Yield: 24%. $^1$H NMR (400 MHz, DMSO-$d_6$) δ 8.90-8.83 (m, 1H), 8.27 (s, 1H), 8.21 (s, 1H), 8.12-8.04 (m, 3H), 7.92-7.81 (m, 3H), 7.73 (d, J=8 Hz, 2H), 7.45 (d, J=16 Hz, 1H), 7.01-6.90 (m, 2H), 6.60 (d, J=16 Hz, 1H), 4.70 (s, 4H), 4.64 (d, J=6 Hz, 2H), 4.53 (s, 2H), 4.24 (s, 2H). LCMS: m/z 563.2 [M+H]$^+$, $t_R$=1.33 min.

Synthesis of (E)-3-(6-aminopyridin-3-yl)-N-((5-(5-(3,3-difluoropyrrolidine-1-carbonyl)pyridin-2-yl)-7-(trifluoromethyl)benzofuran-2-yl)methyl)acrylamide (612)

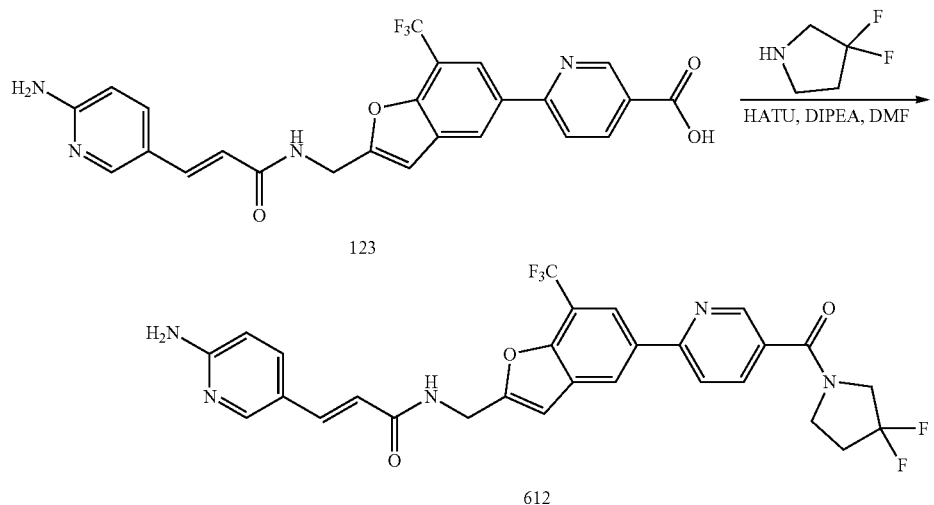

(E)-3-(6-aminopyridin-3-yl)-N-((5-(5-(3,3-difluoropyrrolidine-1-carbonyl)pyridin-2-yl)-7-(trifluoromethyl)benzofuran-2-yl)methyl)acrylamide (612) was synthesized using the indicated reagents according to General Procedure 4. Yield (42%). $^1$H NMR (400 MHz, CD$_3$OD) δ 8.75-8.07 (m, 3H), 7.98-7.92 (m, 4H), 7.39-6.53 (m, 4H), 4.62 (s, 2H), 3.93-3.74 (m, 4H), 2.41-2.37 (m, 2H). LCMS: m/z 572.1 [M+H]$^+$; $t_R$=1.28 min.

Synthesis of (E)-3-(6-aminopyridin-3-yl)-N-((5-(5-(3-hydroxy-3-(trifluoromethyl)pyrrolidine-1-carbonyl)pyridin-2-yl)-7-(trifluoromethyl)benzofuran-2-yl)methyl)acrylamide (613)

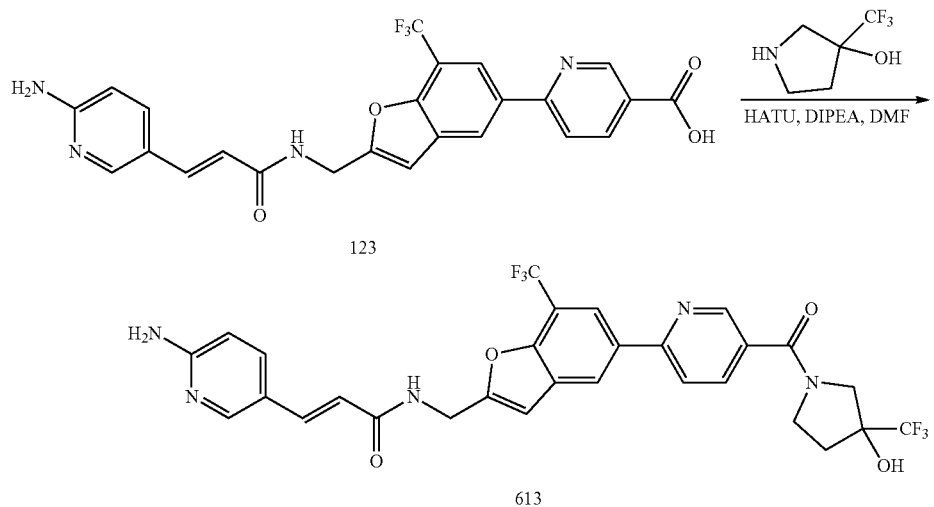

(E)-3-(6-aminopyridin-3-yl)-N-((5-(5-(3-hydroxy-3-(trifluoromethyl)pyrrolidine-1-carbonyl)pyridin-2-yl)-7-(trifluoromethyl)benzofuran-2-yl)methyl)acrylamide (613) was synthesized using the indicated reagents according to General Procedure 4. Yield (48%). $^1$H NMR (400 MHz, CD$_3$OD) δ 8.81-8.71 (m, 1H), 8.41 (s, 1H), 8.24-7.87 (m, 4H), 7.38 (d, J=16 Hz, 1H), 6.95 (d, J=9 Hz, 1H), 6.86 (s, 1H), 6.55 (d, J=16 Hz, 1H), 4.61 (s, 2H), 3.96-3.44 (m, 4H), 2.32-1.94 (m, 2H). LCMS: m/z 620.1 [M+H]$^+$; $t_R$=1.26 min.

Synthesis of (E)-3-(6-aminopyridin-3-yl)-N-((5-(5-(4-chloropiperidine-1-carbonyl)pyridin-2-yl)-7-(trifluoromethyl)benzofuran-2-yl)methyl)acrylamide (614)

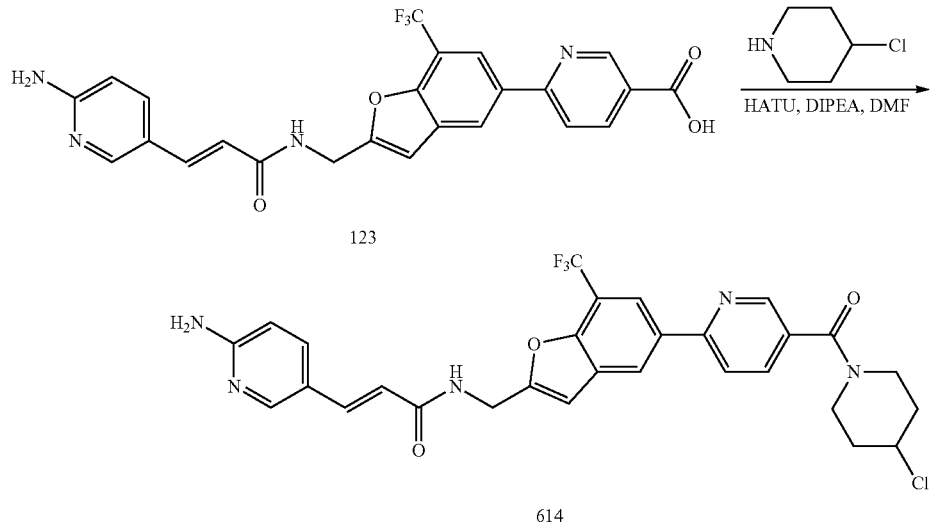

(E)-3-(6-aminopyridin-3-yl)-N-((5-(5-(4-chloropiperidine-1-carbonyl)pyridin-2-yl)-7-(trifluoromethyl)benzofuran-2-yl)methyl)acrylamide (614) was synthesized using the indicated reagents according to General Procedure 4. Yield (33%). $^1$H NMR (400 MHz, CD$_3$OD) δ 8.64-8.09 (m, 4H), 7.98-7.86 (m, 3H), 7.40-6.53 (m, 4H), 4.63 (s, 2H), 4.33-4.28 (m, 1H), 3.96-3.20 (m, 4H), 2.11-1.77 (m, 4H). LCMS: m/z 584.1 [M+H]$^+$; $t_R$=1.40 min.

Synthesis of (E)-3-(6-aminopyridin-3-yl)-N-((7-(trifluoromethyl)-5-(5-(4-(trifluoromethyl)piperidine-1-carbonyl)pyridin-2-yl)benzofuran-2-yl)methyl)acrylamide (615)

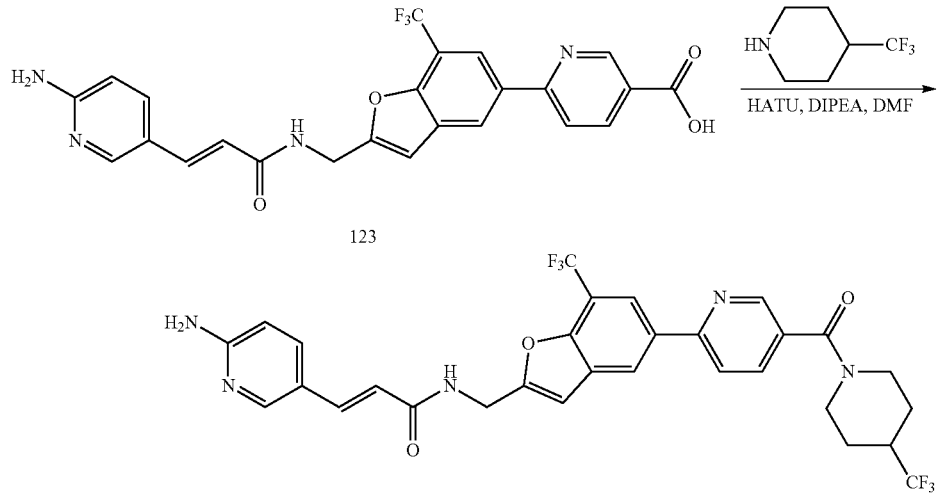

(E)-3-(6-aminopyridin-3-yl)-N-((7-(trifluoromethyl)-5-(5-(4-(trifluoromethyl)piperidine-1-carbonyl)pyridin-2-yl)benzofuran-2-yl)methyl)acrylamide (615) was synthesized using the indicated reagents according to General Procedure 4. Yield (16%). $^1$H NMR (400 MHz, DMSO-$d_6$) δ 8.77-8.61 (m, 3H), 8.39 (s, 1H), 8.20 (d, J=8 Hz, 1H), 8.09 (d, J=2 Hz, 1H), 8.03-7.95 (m, 1H), 7.65-7.59 (m, 1H), 7.36 (d, J=16 Hz, 1H), 7.00 (s, 1H), 6.52-6.39 (m, 4H), 4.69-4.53 (m, 3H), 3.71 (s, 1H), 3.24-3.14 (m, 1H), 2.94-2.60 (m, 2H), 2.00-1.72 (m, 2H), 1.55-1.40 (m, 2H). LCMS: m/z 618.3 [M+H]$^+$; $t_R$=1.87 min.

Synthesis of (E)-3-(6-aminopyridin-3-yl)-N-((5-(5-(4-hydroxy-4-(trifluoromethyl)piperidine-1-carbonyl)pyridin-2-yl)-7-(trifluoromethyl)benzofuran-2-yl)methyl)acrylamide (616)

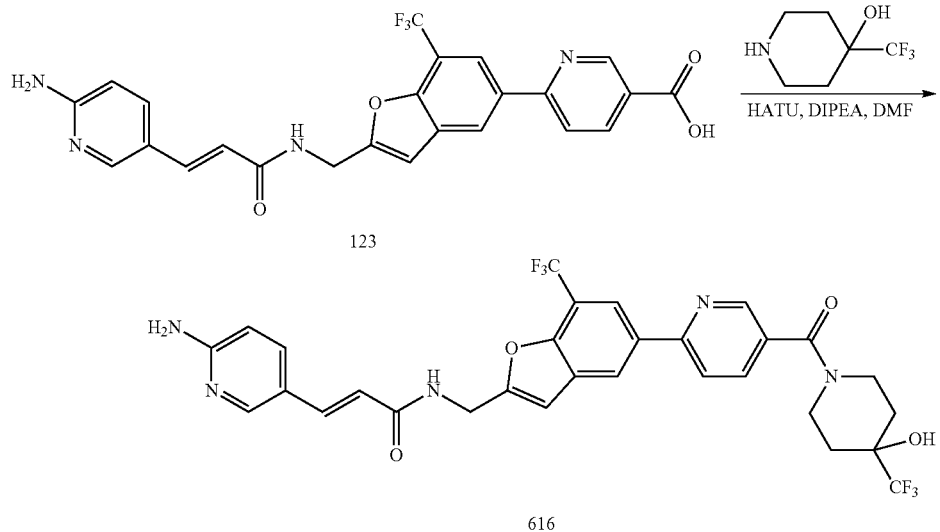

(E)-3-(6-aminopyridin-3-yl)-N-((5-(5-(4-hydroxy-4-(trifluoromethyl)piperidine-1-carbonyl)pyridin-2-yl)-7-(trifluoromethyl)benzofuran-2-yl)methyl)acrylamide (611) was synthesized using the indicated reagents according to General Procedure 4. Yield (23%). $^1$H NMR (400 MHz, DMSO-$d_6$) δ 8.83-8.60 (m, 3H), 8.39 (s, 1H), 8.24-7.97 (m, 3H), 7.66-7.63 (m, 1H), 7.38 (d, J=15.7 Hz, 1H), 7.01 (s, 1H), 6.55-6.39 (m, 4H), 6.21 (s, 1H), 4.70-4.42 (m, 3H), 3.71-3.52 (m, 1H), 3.22-2.94 (m, 2H), 1.89-1.57 (m, 4H). LCMS: m/z 634.2 [M+H]$^+$; $t_R$=1.62 min.

Synthesis of (E)-3-(6-aminopyridin-3-yl)-N-((5-(5-(3-fluoro-3-methylpyrrolidine-1-carbonyl)pyridin-2-yl)-7-(trifluoromethyl)benzofuran-2-yl)methyl)acrylamide (617)

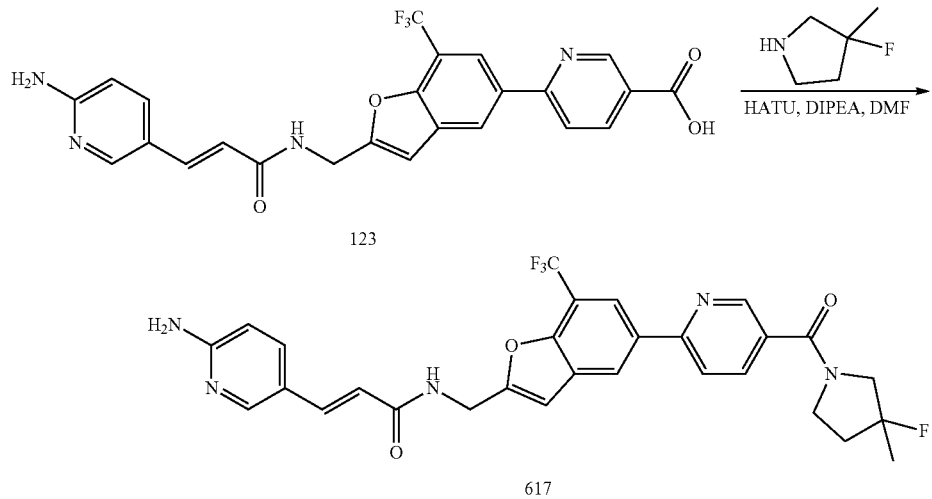

(E)-3-(6-aminopyridin-3-yl)-N-((5-(5-(3-fluoro-3-methylpyrrolidine-1-carbonyl)pyridin-2-yl)-7-(trifluoromethyl)benzofuran-2-yl)methyl)acrylamide (617) was synthesized using the indicated reagents according to General Procedure 4. Yield (14%). ¹H NMR (400 MHz, CD₃OD) δ 8.74 (d, J=8 Hz, 1H), 8.41 (s, 1H), 8.22 (s, 1H), 8.03-7.90 (m, 3H), 7.69-7.61 (m, 1H), 7.38 (d, J=16 Hz, 1H), 6.86-6.82 (m, 1H), 6.51 (d, J=9 Hz, 1H), 6.38 (d, J=16 Hz, 1H), 4.61 (s, 2H), 3.85-3.47 (m, 4H), 2.20-1.94 (m, 2H), 1.55-1.38 (m, 3H). LCMS: m/z 568.2 [M+H]⁺; $t_R$=1.76 min.

Synthesis of (S,E)-3-(6-aminopyridin-3-yl)-N-((5-(5-(3-chloropyrrolidine-1-carbonyl)pyridin-2-yl)-7-(trifluoromethyl)benzofuran-2-yl)methyl)acrylamide (618)

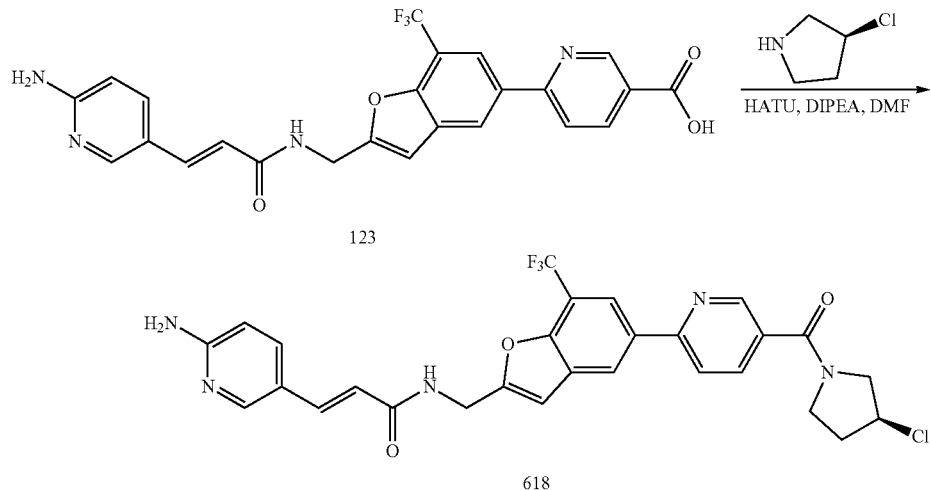

(S,E)-3-(6-aminopyridin-3-yl)-N-((5-(5-(3-chloropyrrolidine-1-carbonyl)pyridin-2-yl)-7-(trifluoromethyl)benzofuran-2-yl)methyl)acrylamide (618) was synthesized using the indicated reagents according to General Procedure 4. Yield (7%). ¹H NMR (400 MHz, CD₃OD) δ 8.75 (d, J=16 Hz, 1H), 8.42 (s, 1H), 8.23 (s, 1H), 8.06-7.91 (m, 3H), 7.68-7.59 (m, 1H), 7.38 (d, J=16 Hz, 1H), 6.85 (s, 1H), 6.50 (d, J=9 Hz, 1H), 6.37 (d, J=16 Hz, 1H), 4.70-4.54 (m, 3H), 4.02-3.56 (m, 4H), 2.45-2.08 (m, 2H). LCMS: m/z 570.2 [M+H]⁺; $t_R$=1.65 min.

Synthesis of (E)-6-(2-((3-(6-aminopyridin-3-yl)acrylamido)methyl)-7-(trifluoromethyl)benzofuran-5-yl)-N-(1-(trifluoromethyl)cyclopropyl)nicotinamide (619)

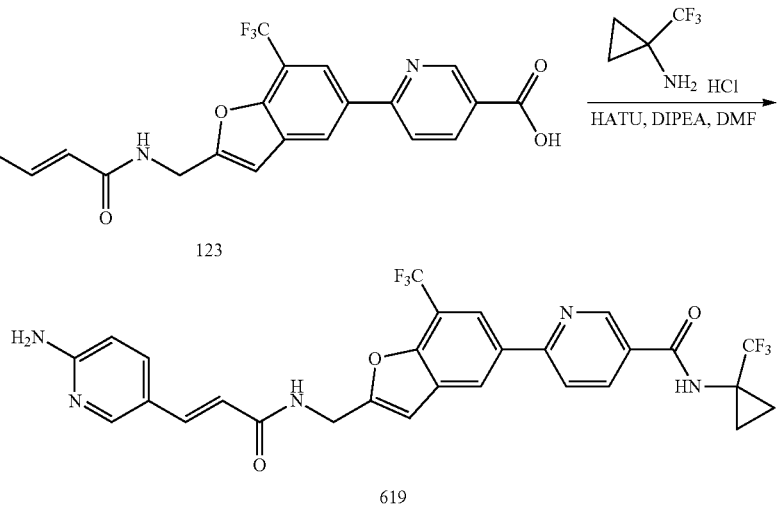

(E)-6-(2-(((3-(6-aminopyridin-3-yl)acrylamido)methyl)-7-(trifluoromethyl)benzofuran-5-yl)-N-(1-(trifluoromethyl)cyclopropyl)nicotinamide (619) was synthesized using the indicated reagents according to General Procedure 4. Yield (28%). ¹H NMR (500 MHz, CD₃OD) δ 9.10 (d, J=2 Hz, 1H), 8.57 (s, 1H), 8.39-8.31 (m, 2H), 8.25 (dd, J=9 Hz, 2 Hz, 1H), 8.12 (d, J=9 Hz, 1H), 8.07 (s, 1H), 7.51 (d, J=16 Hz, 1H), 7.08 (d, J=9 Hz, 1H), 7.00 (s, 1H), 6.67 (d, J=16 Hz, 1H), 4.75 (s, 2H), 1.43 (t, J=7 Hz, 2H), 1.30-1.25 (m, 2H). LCMS: m/z 590.2 [M+H]⁺, $t_R$=1.26 min.

Synthesis of (E)-3-(6-aminopyridin-3-yl)-N-((5-(5-(4-hydroxy-4-methylpiperidine-1-carbonyl)pyridin-2-yl)-7-(trifluoromethyl)benzofuran-2-yl)methyl)acrylamide (620)

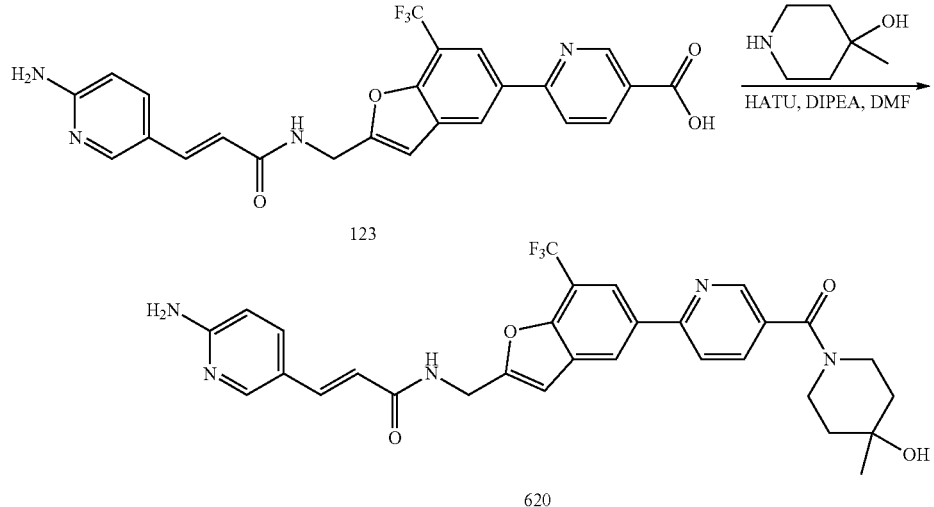

(E)-3-(6-aminopyridin-3-yl)-N-((5-(5-(4-hydroxy-4-methylpiperidine-1-carbonyl)pyridin-2-yl)-7-(trifluoromethyl)benzofuran-2-yl)methyl)acrylamide (620) was synthesized using the indicated reagents according to General Procedure 4. Yield (30%). ¹H NMR (500 MHz, DMSO-d₆) δ 8.88 (t, J=6 Hz, 1H), 8.73-8.67 (m, 2H), 8.39 (s, 1H), 8.25-8.16 (m, 4H), 8.11 (d, J=9 Hz, 1H), 7.99-7.93 (m, 1H), 7.45 (d, J=16 Hz, 1H), 7.02 (s, 1H), 6.99 (d, J=9 Hz, 1H), 6.61 (d, J=16 Hz, 1H), 4.65 (d, J=6 Hz, 2H), 4.17-4.09 (m, 1H), 3.42-3.20 (m, 4H), 1.62-1.39 (m, 4H), 1.17 (s, 3H). LCMS: m/z 580.3 [M+H]⁺, $t_R$=1.26 min.

Synthesis of (E)-3-(6-aminopyridin-3-yl)-N-((5-(5-(3-hydroxy-3-methylazetidine-1-carbonyl)pyridin-2-yl)-7-(trifluoromethyl)benzofuran-2-yl)methyl)acrylamide (621)

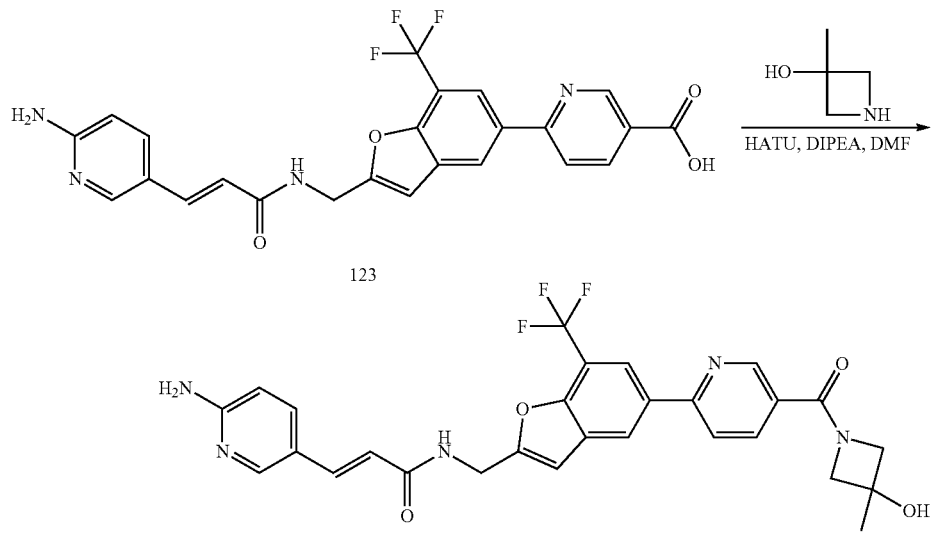

(E)-3-(6-aminopyridin-3-yl)-N-((5-(5-(3-hydroxy-3-methylazetidine-1-carbonyl)pyridin-2-yl)-7-(trifluoromethyl)benzofuran-2-yl)methyl)acrylamide (621) was synthesized using the indicated reagents according to General Procedure 4. Yield (6%). $^1$H NMR (500 MHz, CD$_3$OD) δ 8.95 (s, 1H), 8.54 (s, 1H), 8.35 (s, 1H), 8.27-8.02 (m, 4H), 7.50 (d, J=15 Hz, 1H), 7.11-6.94 (m, 2H), 6.67 (d, J=15 Hz, 1H), 4.75 (s, 2H), 4.40-4.06 (m, 4H), 1.55 (s, 3H). LCMS: m/z 552.2 [M+H]$^+$, t$_R$=1.36 min.

Synthesis of (S,E)-3-(6-aminopyridin-3-yl)-N-((7-(trifluoromethyl)-5-(5-(2-(trifluoromethyl)pyrrolidine-1-carbonyl)pyridin-2-yl)benzofuran-2-yl)methyl)acrylamide (622)

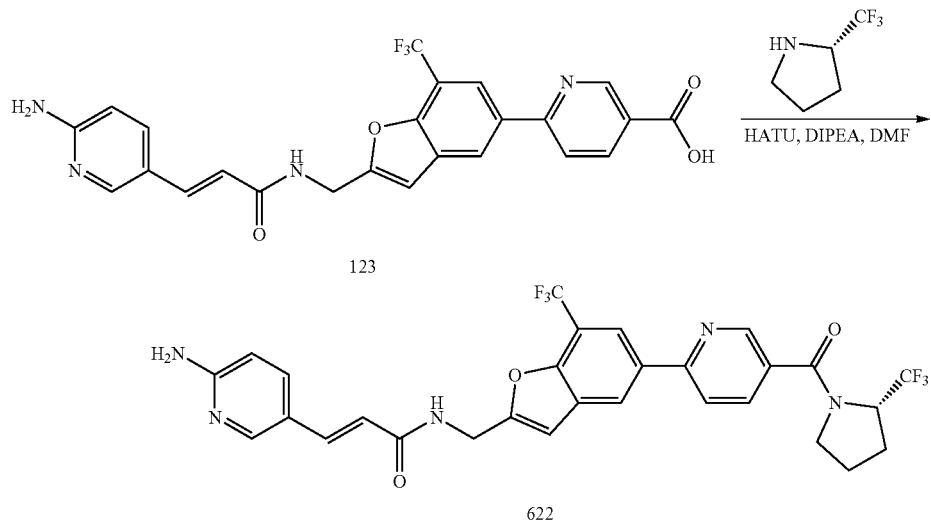

(S,E)-3-(6-aminopyridin-3-yl)-N-((7-(trifluoromethyl)-5-(5-(2-(trifluoromethyl)pyrrolidine-1-carbonyl)pyridin-2-yl)benzofuran-2-yl)methyl)acrylamide (622) was synthesized using the indicated reagents according to General Procedure 4. Yield (40%). $^1$H NMR (500 MHz, DMSO-d$_6$) δ 8.88 (s, 1H), 8.75-8.65 (m, 2H), 8.41 (s, 1H), 8.23 (d, J=8 Hz, 1H), 8.16-8.07 (m, 2H), 7.64 (dd, J=9 Hz, 2 Hz, 1H), 7.38 (d, J=16 Hz, 1H), 7.01 (s, 1H), 6.51-6.42 (m, 4H), 5.17-5.04 (m, 1H), 4.64 (d, J=5 Hz, 2H), 3.77-3.47 (m, 2H), 2.30-2.17 (m, 1H), 2.08-1.85 (m, 3H). LCMS: m/z 604.2 [M+H]$^+$, t$_R$=1.80 min.

Synthesis of (E)-N-((5-(5-(3-azabicyclo[3.1.0]hexane-3-carbonyl)pyridin-2-yl)-7-(trifluoromethyl)benzofuran-2-yl)methyl)-3-(6-aminopyridin-3-yl)acrylamide (623)

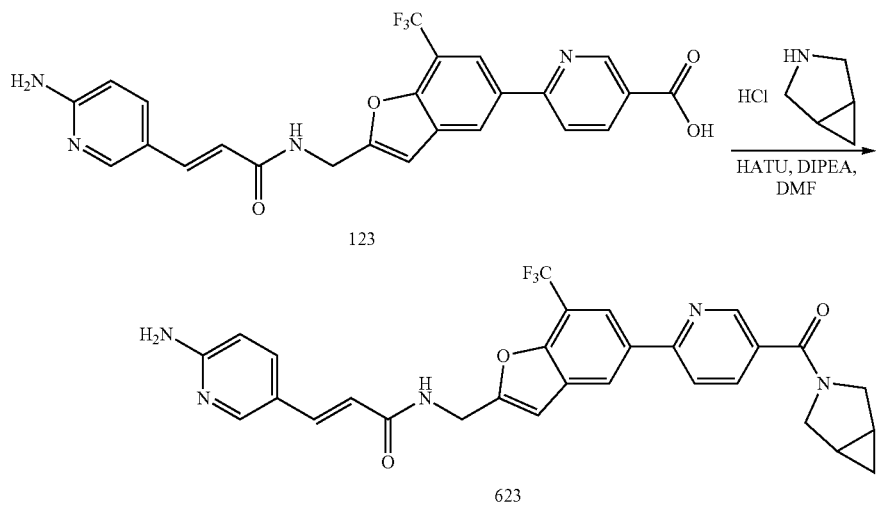

(E)-N-((5-(5-(3-azabicyclo[3.1.0]hexane-3-carbonyl)pyridin-2-yl)-7-(trifluoromethyl)benzofuran-2-yl)methyl)-3-(6-aminopyridin-3-yl)acrylamide (623) was synthesized using the indicate reagents according to General Procedure 4. Yield (8%). ¹H NMR (500 MHz, DMSO-d₆) δ 8.83 (d, J=2 Hz, 1H), 8.77-8.70 (m, 2H), 8.44 (s, 1H), 8.23 (d, J=8 Hz, 1H), 8.14 (d, J=2 Hz, 1H), 8.07 (dd, J=8 Hz, 2 Hz, 1H), 7.68 (dd, J=8 Hz, 2 Hz, 1H), 7.41 (d, J=16 Hz, 1H), 7.05 (s, 1H), 6.56-6.36 (m, 4H), 4.67 (d, J=6 Hz, 2H), 4.00 (d, J=12 Hz, 1H), 3.86-3.78 (m, 1H), 3.51-3.43 (m, 2H), 1.69-1.58 (m, 2H), 0.72 (dd, J=12 Hz, 7 Hz, 1H), 0.25-0.18 (m, 1H). LCMS: m/z 548.3 [M+H]⁺, $t_R$=1.73 min.

Synthesis of (R,E)-3-(6-aminopyridin-3-yl)-N-((7-(trifluoromethyl)-5-(5-(2-(trifluoromethyl)pyrrolidine-1-carbonyl)pyridin-2-yl)benzofuran-2-yl)methyl)acrylamide (624)

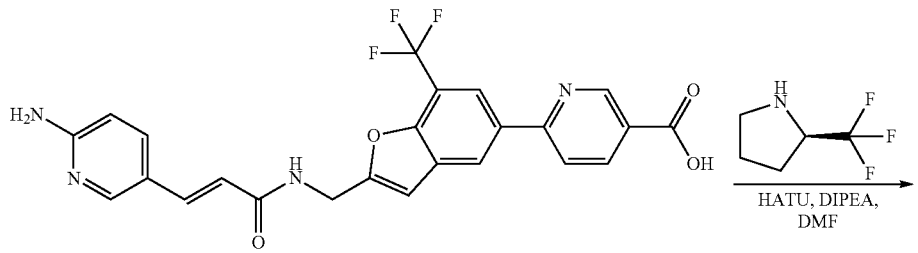

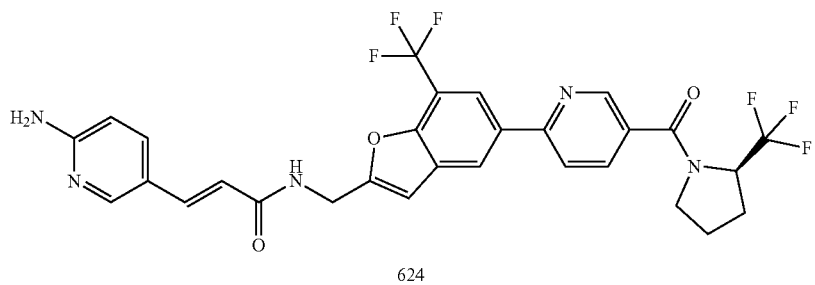

(R,E)-3-(6-aminopyridin-3-yl)-N-((7-(trifluoromethyl)-5-(5-(2-(trifluoromethyl)pyrrolidine-1-carbonyl)pyridin-2-yl)benzofuran-2-yl)methyl)acrylamide (624) was synthesized using the indicated reagents according to General Procedure 4. Yield (17%). ¹H NMR (500 MHz, DMSO-d₆) δ 8.87 (s, 1H), 8.74-8.66 (m, 2H), 8.39 (d, J=16 Hz, 1H), 8.23 (d, J=8 Hz, 1H), 8.15-8.07 (m, 2H), 7.63 (dd, $J_1$=9 Hz, $J_2$ 2 Hz, 1H), 7.37 (d, J=16 Hz, 1H), 7.01 (s, 1H), 6.51-6.40 (m, 4H), 5.17-5.02 (m, 1H), 4.63 (d, J=6 Hz, 2H), 3.77-3.45 (m, 2H), 2.29-2.15 (m, 1H), 2.07-1.84 (m, 3H). LCMS: m/z 604.2 [M+H]⁺, $t_R$=1.39 min.

Synthesis of (E)-N-((5-(5-(2-oxa-6-azaspiro[3.3]heptane-6-carbonyl)pyridin-2-yl)-7-(trifluoromethyl)benzofuran-2-yl)methyl)-3-(6-aminopyridin-3-yl)acrylamide (625)

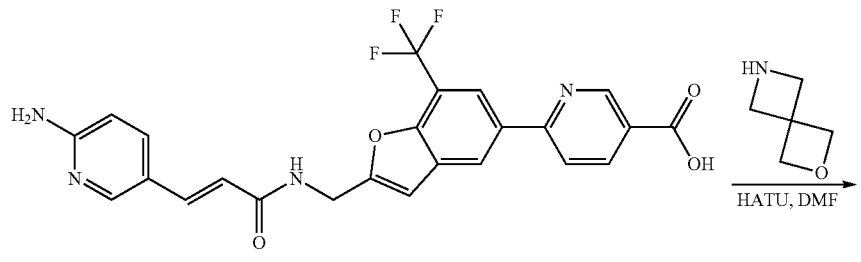

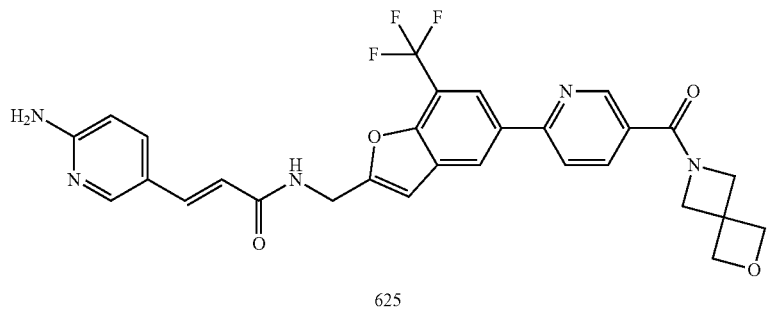

625

(E)-N-((5-(5-(2-oxa-6-azaspiro[3.3]heptane-6-carbonyl)pyridin-2-yl)-7-(trifluoromethyl)benzofuran-2-yl)methyl)-3-(6-aminopyridin-3-yl)acrylamide (625) was synthesized using the indicated reagents according to General procedure 4. Yield (36%). $^1$H NMR (500 MHz, DMSO-$d_6$) δ 8.90 (d, J=2 Hz, 1H), 8.73-8.65 (m, 2H), 8.41 (s, 1H), 8.22 (d, J=8 Hz, 1H), 8.15-8.06 (m, 2H), 7.63 (dd, $J_1$=9 Hz, $J_2$=2 Hz, 1H), 7.36 (d, J=16 Hz, 1H), 7.00 (s, 1H), 6.51-6.40 (m, 4H), 4.70 (q, J=7 Hz, 4H), 4.62 (d, J=6 Hz, 2H), 4.58 (s, 2H), 4.26 (s, 2H). LCMS: m/z 564.2 [M+H]$^+$; $t_R$=1.25 min.

Synthesis of (E)-N-((5-(5-(6-oxa-3-azabicyclo[3.1.1]heptane-3-carbonyl)pyridin-2-yl)-7-(trifluoromethyl)benzofuran-2-yl)methyl)-3-(6-aminopyridin-3-yl)acrylamide (626)

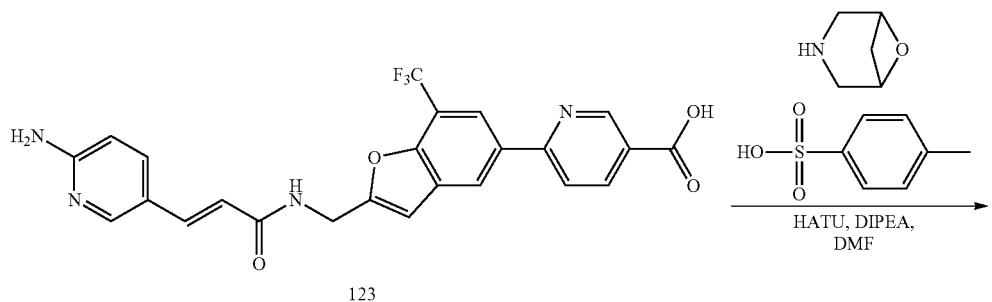

123

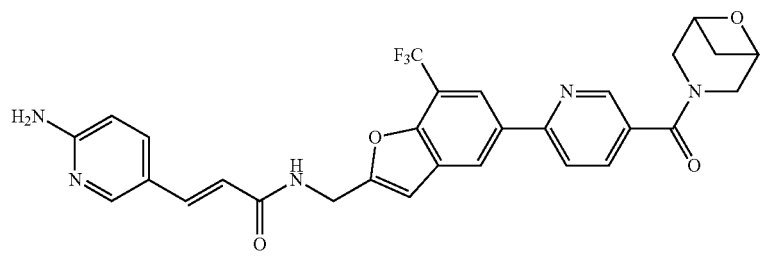

626

(E)-N-((5-(5-(6-oxa-3-azabicyclo[3.1.1]heptane-3-carbonyl)pyridin-2-yl)-7-(trifluoromethyl)benzofuran-2-yl)methyl)-3-(6-aminopyridin-3-yl)acrylamide (626) was synthesized using the indicated reagents according to General Procedure 4. Yield (42%). ¹H NMR (500 MHz, DMSO-$d_6$) δ 8.84 (s, 1H), 8.74-8.65 (m, 2H), 8.40 (s, 1H), 8.21 (d, J=8 Hz, 1H), 8.14-8.06 (m, 2H), 7.63 (d, J=8 Hz, 1H), 7.36 (d, J=16 Hz, 1H), 7.00 (s, 1H), 6.52-6.31 (m, 4H), 4.70-4.47 (m, 4H), 4.04-3.97 (m, 1H), 3.89-3.80 (m, 1H), 3.65-3.53 (m, 2H), 3.34-3.32 (m, 1H), 3.12-3.04 (m, 1H). LCMS: m/z 563.9 [M+H]⁺; $t_R$=1.77 min.

Synthesis of (E)-3-(6-aminopyridin-3-yl)-N-((5-(5-(3-hydroxy-3-methylpyrrolidine-1-carbonyl)pyridin-2-yl)-7-(trifluoromethyl)benzofuran-2-yl)methyl)acrylamide (627)

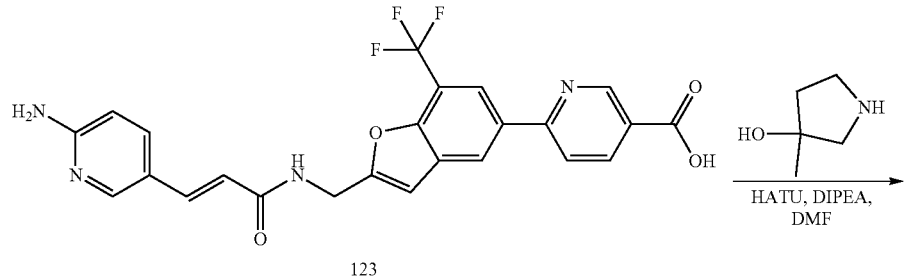

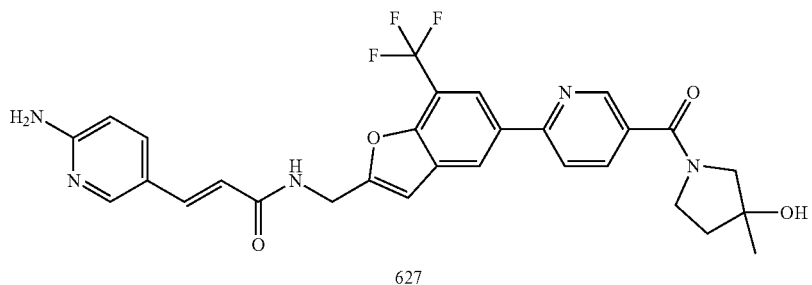

(E)-3-(6-aminopyridin-3-yl)-N-((5-(5-(3-hydroxy-3-methylpyrrolidine-1-carbonyl)pyridin-2-yl)-7-(trifluoromethyl)benzofuran-2-yl)methyl)acrylamide (627) was synthesized using the indicated reagents according to General Procedure 4. Yield (16%). ¹H NMR (500 MHz, CD₃OD) δ 8.77-8.69 (m, 1H), 8.40 (s, 1H), 8.21 (s, 1H), 8.00-7.92 (m, 3H), 7.63 (dd, $J_1$=9 Hz, $J_2$ 2 Hz, 1H), 7.38 (d, J=16 Hz, 1H), 6.84 (s, 1H), 6.49 (d, J=9 Hz, 1H), 6.37 (d, J=16 Hz, 1H), 4.61 (s, 2H), 3.78-3.48 (m, 3H), 3.35 (dd, $J_1$=43 Hz, $J_2$ 12 Hz, 1H), 1.95-1.83 (m, 2H), 1.37-1.27 (m, 3H). LCMS: m/z 566.2 [M+H]⁺; $t_R$=1.23 min.

Synthesis of (E)-3-(6-aminopyridin-3-yl)-N-((5-(5-(3-fluoro-4-methoxypyrrolidine-1-carbonyl)pyridin-2-yl)-7-(trifluoromethyl)benzofuran-2-yl)methyl)acrylamide (628)

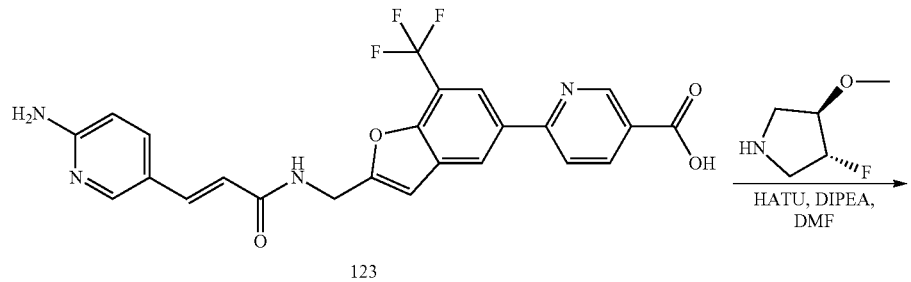

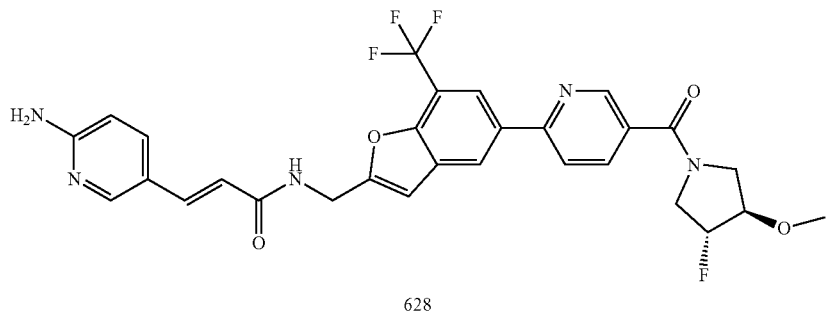

628

(E)-3-(6-aminopyridin-3-yl)-N-((5-(5-(3-fluoro-4-methoxypyrrolidine-1-carbonyl)pyridin-2-yl)-7-(trifluoromethyl)benzofuran-2-yl)methyl)acrylamide (628) was synthesized using the indicated reagents according to General Procedure 4. Yield (50 mg, 17% yield). $^1$H NMR (500 MHz, DMSO-$d_6$) δ 8.93-8.85 (m, 1H), 8.71 (s, 1H), 8.66 (t, J=6 Hz, 1H), 8.41 (s, 1H), 8.24-8.06 (m, 3H), 7.63 (d, J=9 Hz, 1H), 7.37 (d, J=16 Hz, 1H), 7.01 (s, 1H), 6.52-6.39 (m, 4H), 5.28 (dd, $J_1$=50 Hz, $J_2$ 30 Hz, 1H), 4.63 (d, J=5 Hz, 2H), 4.15-3.53 (m, 5H), 3.38 (s, 3H). LCMS: m/z 584.2 [M+H]$^+$; $t_R$=1.32 min.

Synthesis of (E)-6-(2-((3-(6-aminopyridin-3-yl)acrylamido)methyl)-7-(trifluoromethyl)benzofuran-5-yl)-N-(4,4-difluorocyclohexyl)nicotinamide (629)

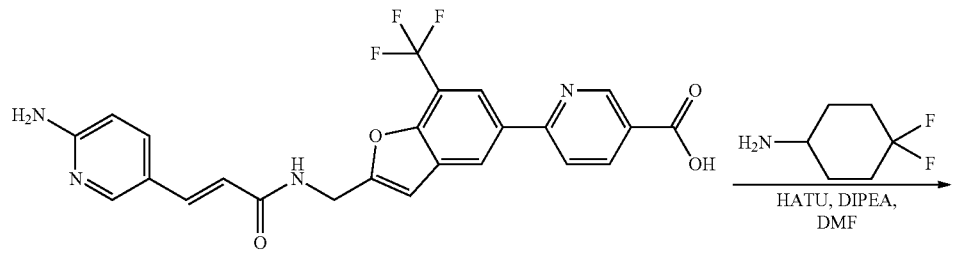

123

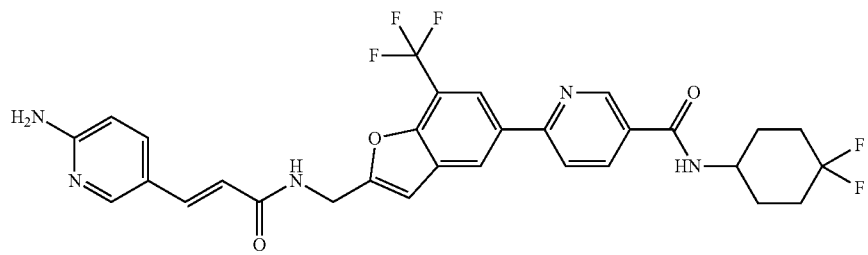

629

(E)-6-(2-((3-(6-aminopyridin-3-yl)acrylamido)methyl)-7-(trifluoromethyl)benzofuran-5-yl)-N-(4,4-difluorocyclohexyl)nicotinamide (629) was synthesized using the indicated reagents according to General Procedure 4. Yield (40%). $^1$H NMR (500 MHz, DMSO-$d_6$) δ 9.10 (d, J=2 Hz, 1H), 8.72 (s, 1H), 8.67 (t, J=6 Hz, 1H), 8.56 (d, J=6 Hz, 1H), 8.40 (s, 1H), 8.33 (dd, J=8 Hz, 2 Hz, 1H), 8.24 (d, J=8 Hz, 1H), 8.09 (d, J=2 Hz, 1H), 7.63 (dd, J=8 Hz, 2 Hz, 1H), 7.36 (d, J=16 Hz, 1H), 7.01 (s, 1H), 6.51-6.39 (m, 4H), 4.63 (d, J=6 Hz, 2H), 4.10-3.99 (m, 1H), 2.15-1.88 (m, 6H), 1.73-1.61 (m, 2H). LCMS: m/z 600.2 [M+H]$^+$; $t_R$=1.74 min.

Synthesis of (E)-6-(2-((3-(6-aminopyridin-3-yl)acrylamido)methyl)-7-(trifluoromethyl)benzofuran-5-yl)-N-(pyridin-3-ylmethyl)nicotinamide (630)

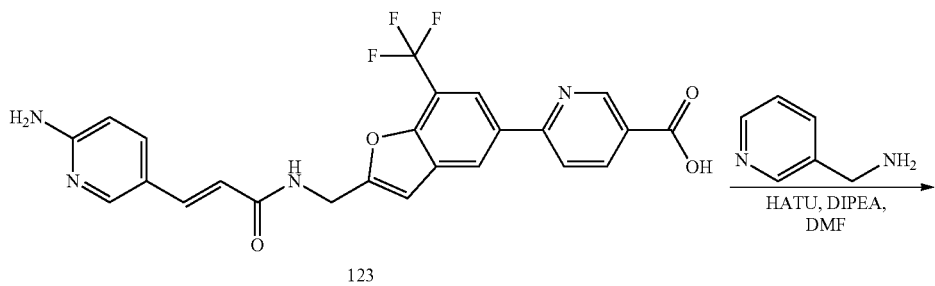

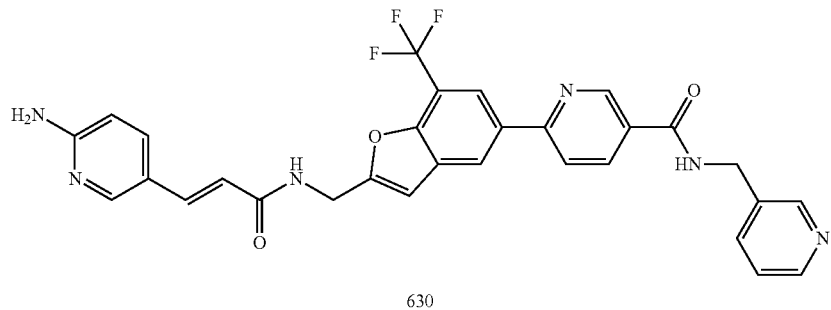

(E)-6-(2-((3-(6-aminopyridin-3-yl)acrylamido)methyl)-7-(trifluoromethyl)benzofuran-5-yl)-N-(pyridin-3-ylmethyl)nicotinamide (630) was synthesized using the indicated reagents according to General Procedure 4. Yield (26%). $^1$H NMR (500 MHz, DMSO-$d_6$) δ 9.48-9.40 (m, 1H), 9.17 (s, 1H), 8.93-8.84 (m, 1H), 8.79-8.70 (m, 2H), 8.68-8.61 (m, 1H), 8.44-8.34 (m, 3H), 8.29-8.18 (m, 3H), 8.15-8.09 (m, 2H), 7.73-7.64 (m, 1H), 7.46 (d, J=16 Hz, 1H), 7.03 (s, 1H), 7.00 (d, J=9 Hz, 1H), 6.62 (d, J=16 Hz, 1H), 4.68-4.58 (m, 4H). LCMS: m/z 573.3 [M+H]$^+$; $t_R$=1.63 min.

Synthesis of (E)-3-(6-aminopyridin-3-yl)-N-((5-(5-(6,6-dimethyl-3-azabicyclo[3.1.0]hexane-3-carbonyl)pyridin-2-yl)-7-(trifluoromethyl)benzofuran-2-yl)methyl)acrylamide (631)

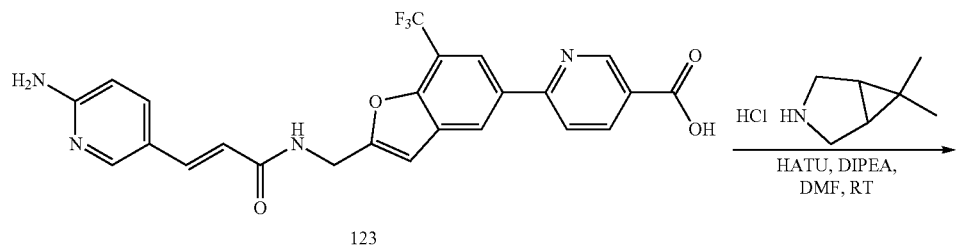

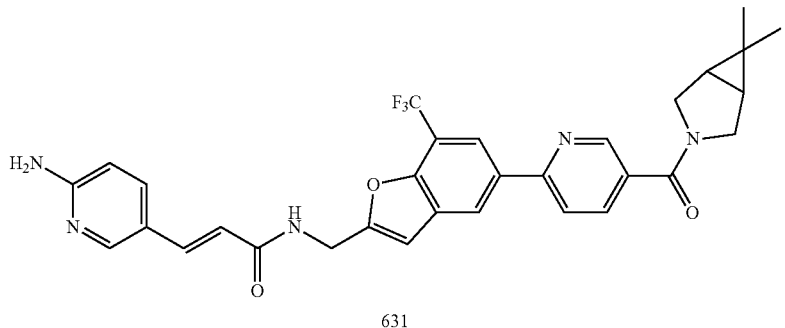

631

(E)-3-(6-aminopyridin-3-yl)-N-((5-(5-(6,6-dimethyl-3-azabicyclo[3.1.0]hexane-3-carbonyl)pyridin-2-yl)-7-(trifluoromethyl)benzofuran-2-yl)methyl)acrylamide (631) was synthesized using the indicated reagents according to General Procedure 4. Yield (35 mg, 38% yield). $^1$H NMR (500 MHz, DMSO-$d_6$) δ 8.79 (d, J=2 Hz, 1H), 8.70-8.63 (m, 2H), 8.39 (s, 1H), 8.18 (d, J=8 Hz, 1H), 8.09 (d, J=2 Hz, 1H), 8.03 (dd, J=8 Hz, 2 Hz, 1H), 7.63 (dd, J=8 Hz, 2 Hz, 1H), 7.37 (d, J=16 Hz, 1H), 7.00 (s, 1H), 6.51-6.40 (m, 4H), 4.63 (d, J=6 Hz, 2H), 3.88-3.82 (m, 1H), 3.69-3.59 (m, 2H), 3.27 (d, J=11 Hz, 1H), 1.50-1.42 (m, 2H), 1.02 (s, 3H), 0.90 (s, 3H). LCMS: m/z 576.3 [M+H]$^+$, $t_R$=1.86 min.

Synthesis of (E)-N-((5-(5-(8-oxa-3-azabicyclo[3.2.1]octane-3-carbonyl)pyridin-2-yl)-7-(trifluoromethyl)benzofuran-2-yl)methyl)-3-(6-aminopyridin-3-yl)acrylamide (632)

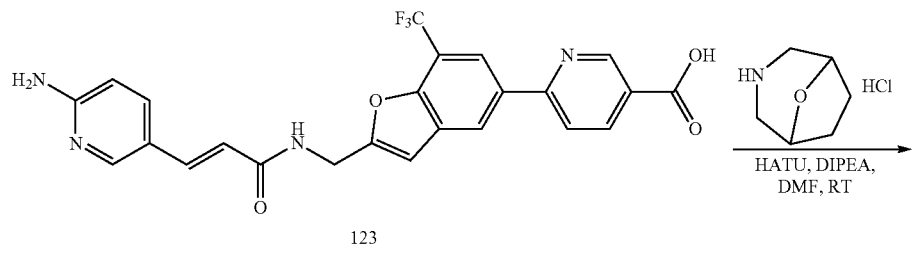

123

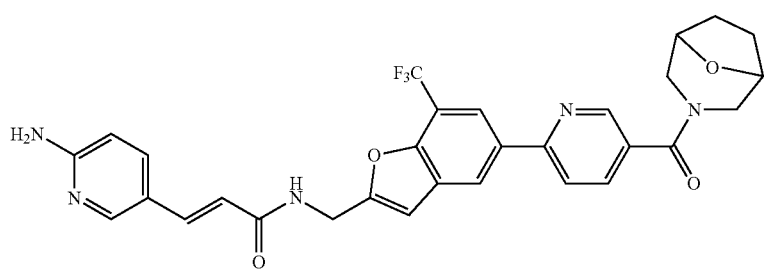

632

(E)-N-((5-(5-(8-oxa-3-azabicyclo[3.2.1]octane-3-carbonyl)pyridin-2-yl)-7-(trifluoromethyl)benzofuran-2-yl)methyl)-3-(6-aminopyridin-3-yl)acrylamide (632) was synthesized using the indicated reagents according to General Procedure 4. Yield (54%). $^1$H NMR (500 MHz, DMSO-$d_6$) δ 8.73 (s, 1H), 8.69 (s, 1H), 8.66 (t, J=6 Hz, 1H), 8.39 (s, 1H), 8.20 (d, J=8 Hz, 1H), 8.09 (s, 1H), 7.98 (d, J=8 Hz, 1H), 7.63 (d, J=9 Hz, 1H), 7.36 (d, J=16 Hz, 1H), 7.00 (s, 1H), 6.50-6.40 (m, 4H), 4.63 (d, J=6 Hz, 2H), 4.46-4.37 (m, 1H), 4.28-4.15 (m, 2H), 3.53-3.43 (m, 1H), 3.30-3.24 (m, 1H), 3.09-2.99 (m, 1H), 1.89-1.60 (m, 4H). LCMS: m/z 578.2 [M+H]$^+$; $t_R$=1.67 min.

Synthesis of (E)-N-((5-(5-(2-oxa-5-azabicyclo[2.2.1]heptane-5-carbonyl)pyridin-2-yl)-7-(trifluoromethyl)benzofuran-2-yl)methyl)-3-(6-aminopyridin-3-yl)acrylamide (633)

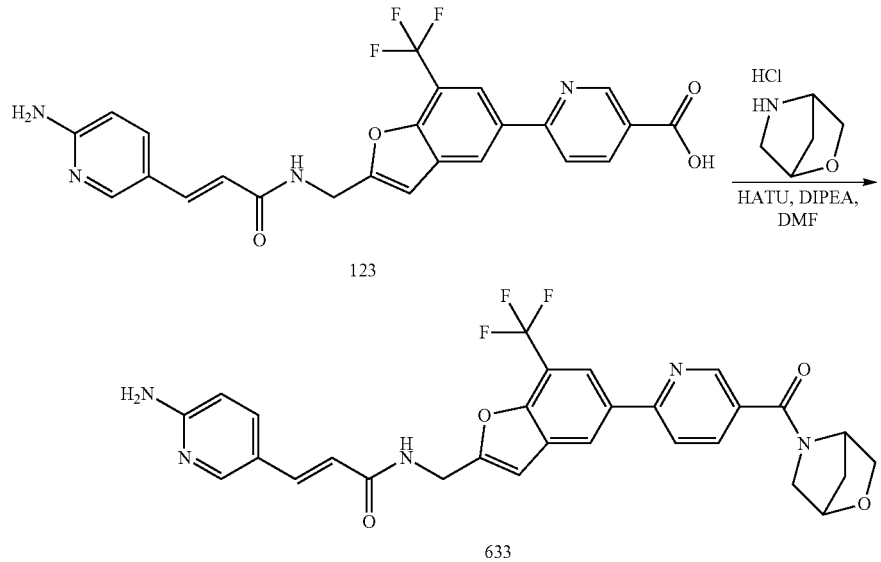

(E)-N-((5-(5-(2-oxa-5-azabicyclo[2.2.1]heptane-5-carbonyl)pyridin-2-yl)-7-(trifluoromethyl)benzofuran-2-yl)methyl)-3-(6-aminopyridin-3-yl)acrylamide (633) was synthesized using the indicated reagents according to General Procedure 4. Yield (9%). $^1$H NMR (500 MHz, DMSO-$d_6$) δ 8.88-8.82 (m, 1H), 8.72-8.64 (m, 2H), 8.41 (d, J=6 Hz, 1H), 8.22 (t, J=9 Hz, 1H), 8.14-8.02 (m, 2H), 7.63 (dd, $J_1$=9 Hz, $J_2$ 2 Hz, 1H), 7.36 (d, J=16 Hz, 1H), 7.01 (s, 1H), 6.53-6.37 (m, 4H), 4.92-4.45 (m, 4H), 4.00-3.52 (m, 4H), 1.98-1.75 (m, 2H). LCMS: m/z 564.3 [M+H]$^+$; $t_R$=1.62 min.

Synthesis of (E)-N-((5-(5-(1-oxa-6-azaspiro[3.3]heptane-6-carbonyl)pyridin-2-yl)-7-(trifluoromethyl)benzofuran-2-yl)methyl)-3-(6-aminopyridin-3-yl)acrylamide (634)

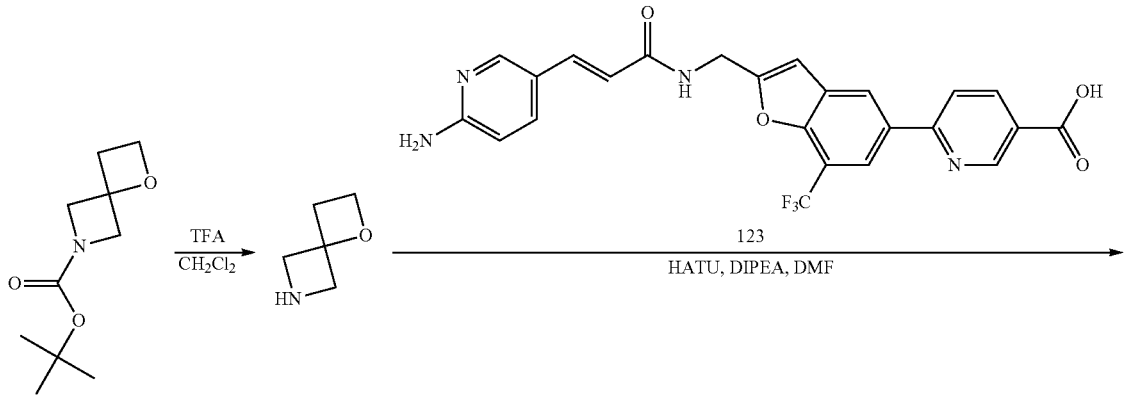

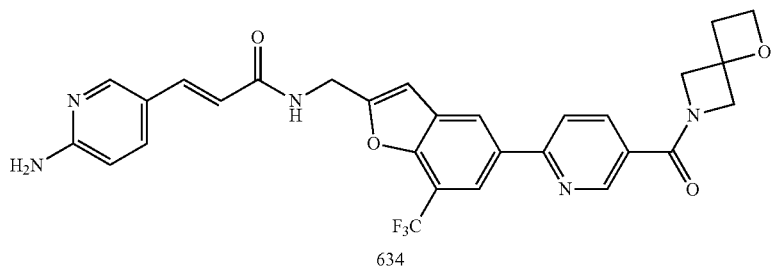

634

(E)-N-((5-(5-(1-oxa-6-azaspiro[3.3]heptane-6-carbonyl)pyridin-2-yl)-7-(trifluoromethyl)benzofuran-2-yl)methyl)-3-(6-aminopyridin-3-yl)acrylamide (634) was synthesized using the indicated reagents according to General Procedures 3 and 4. Yield (21%). $^1$H NMR (400 MHz, DMSO-$d_6$) δ 8.92 (d, J=2 Hz, 1H), 8.71 (s, 1H), 8.67 (t, J=6 Hz, 1H), 8.41 (s, 1H), 8.21 (d, J=8 Hz, 1H), 8.17-8.12 (m, 1H), 8.09 (d, J=2 Hz, 1H), 7.66-7.59 (m, 1H), 7.36 (d, J=16 Hz, 1H), 7.00 (s, 1H), 6.51-6.39 (m, 4H), 4.67-4.54 (m, 4H), 4.47-4.33 (m, 3H), 4.21-4.12 (m, 1H), 2.86 (t, J=8 Hz, 2H). LCMS: m/z 564.3 [M+H]$^+$; $t_R$=1.65 min.

Synthesis of (E)-3-(6-aminopyridin-3-yl)-N-((7-methoxy-5-(4-(morpholinosulfonyl)phenyl)benzofuran-2-yl)methyl)acrylamide (635)

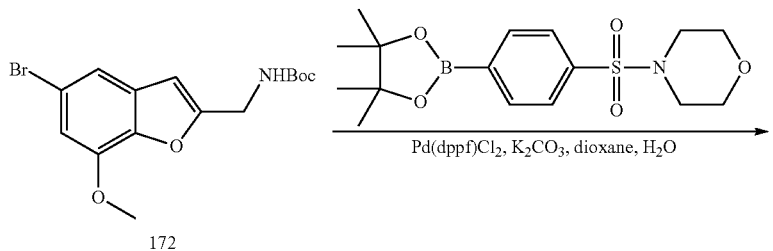

172

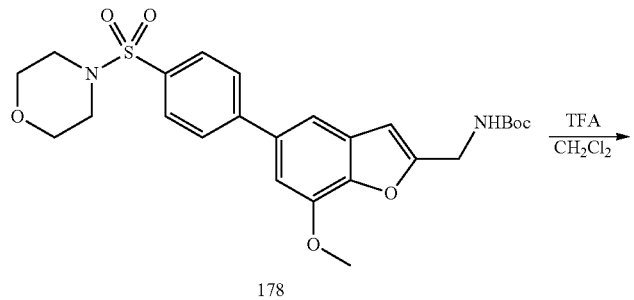

178

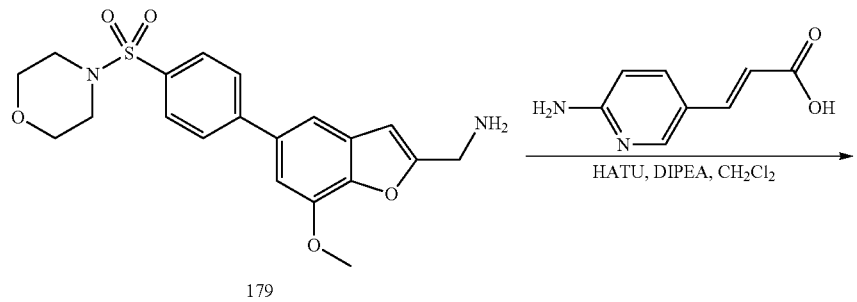

179

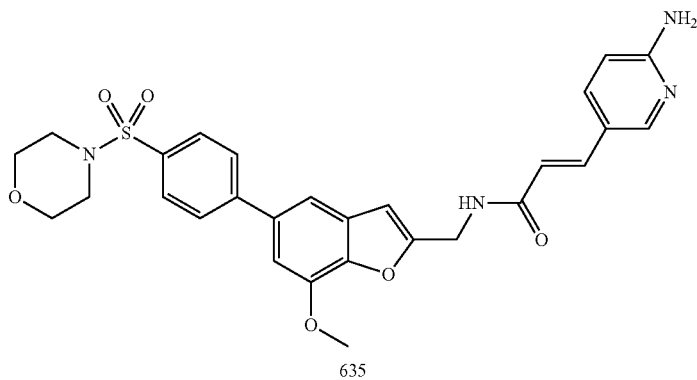

635

Synthesis of tert-butyl (7-methoxy-5-(4-(morpholinosulfonyl)phenyl)benzofuran-2-yl)methylcarbamate (178)

tert-butyl (7-methoxy-5-(4-(morpholinosulfonyl)phenyl) benzofuran-2-yl)methylcarbamate (178) was synthesized using the indicated reagents according to General Procedure 2. Yield (54%). LCMS: m/z 503.1 [M+H]$^+$; $t_R$=1.70 min.

Synthesis of (7-methoxy-5-(4-(morpholinosulfonyl) phenyl)benzofuran-2-yl)methanamine (179)

(7-methoxy-5-(4-(morpholinosulfonyl)phenyl)benzofuran-2-yl)methanamine (179) was synthesized using the indicated reagents according to General Procedure 3. Yield (100%). LCMS: m/z 403.2 [M+H]$^+$; $t_R$=1.10 min.

Synthesis of (E)-3-(6-aminopyridin-3-yl)-N-((7-methoxy-5-(4-(morpholinosulfonyl)phenyl)benzofuran-2-yl)methyl)acrylamide (635)

(E)-3-(6-aminopyridin-3-yl)-N-((7-methoxy-5-(4-(morpholinosulfonyl)phenyl)benzofuran-2-yl)methyl)acrylamide (635) was synthesized using the indicated reagents according to General Procedure 4. Yield (4%). $^1$H NMR (400 MHz, CDCl$_3$) δ 8.22-8.20 (m, 1H), 7.83-7.74 (m, 4H), 7.62-7.52 (m, 3H), 7.36-7.34 (m, 1H), 6.99-6.97 (m, 1H), 6.74 (s, 1H), 6.50 (d, J=8 Hz, 1H), 6.25 (d, J=16 Hz, 1H), 4.75 (d, J=6 Hz, 2H), 4.67 (s, 2H), 4.09 (s, 3H), 3.79-3.76 (m, 4H), 3.07-3.04 (m, 4H). LCMS: m/z 549.2 [M+H]$^+$, $t_R$=1.32 min.

Synthesis of (E)-3-(6-aminopyridin-3-yl)-N-((7-chloro-5-(4-fluoro-3-(morpholinosulfonyl)phenyl) benzofuran-2-yl)methyl)acrylamide (636)

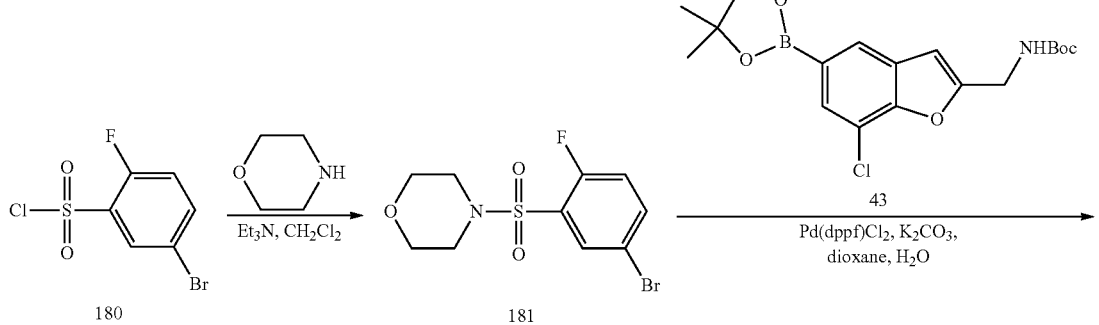

-continued

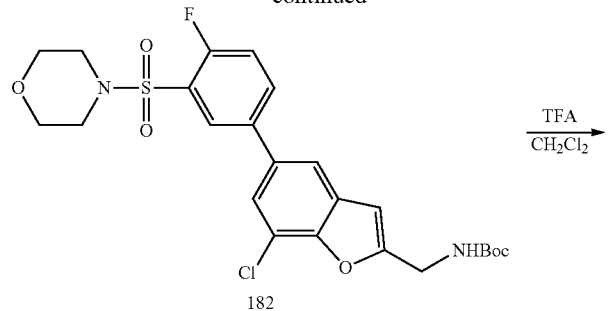
182

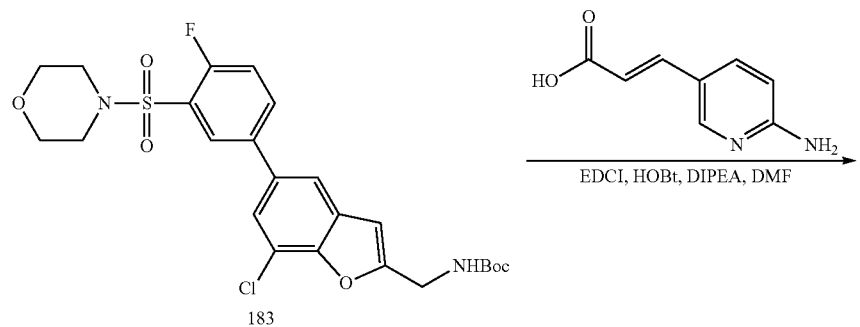
183

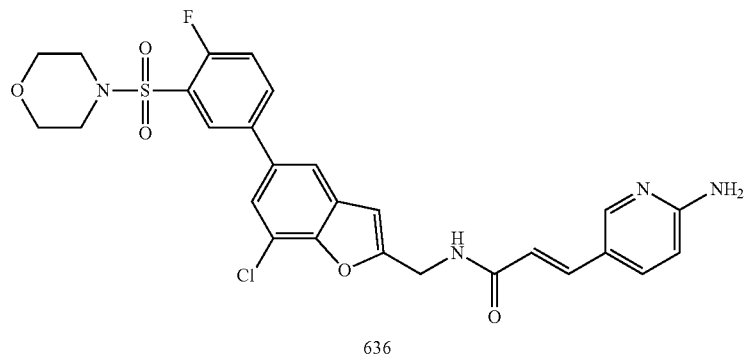
636

Synthesis of 4-(5-Bromo-2-fluorophenylsulfonyl)morpholine (181)

Morpholine (0.64 g, 7.3 mmol) was dissolved in 20 mL of $CH_2Cl_2$. $Et_3N$ (0.74 g, 7.3 mmol) and 5-bromo-2-fluorobenzene-1-sulfonyl chloride (1.0 g, 3.67 mmol) were added at 0° C. The mixture was allowed to warm up to room temperature and stirred for 3 h. The mixture was poured into iced water, extracted with $CH_2Cl_2$ (10 mL×3). The combined organic layers were washed with brine, dried over anhydrous $Na_2SO_4$, and concentrated under reduced pressure to give 4-(5-bromo-2-fluorophenylsulfonyl)morpholine (181) as a white solid (1.18 g, Yield: 100%). LCMS: m/z 324 $[M+H]^+$; $t_R$=1.63 min.

Synthesis of tert-Butyl (7-chloro-5-(4-fluoro-3-(morpholinosulfonyl)phenyl)benzofuran-2-yl)methylcarbamate (182)

tert-Butyl (7-chloro-5-(4-fluoro-3-(morpholinosulfonyl)phenyl)benzofuran-2-yl)methylcarbamate (182) was synthesized using the indicated reagents according to General Procedure 2. Yield (77%). LCMS: m/z 547.1 $[M+Na]^+$; $t_R$=1.78 min.

Synthesis of (7-Chloro-5-(4-fluoro-3-(morpholinosulfonyl)phenyl)benzofuran-2-yl)methanamine (183)

(7-Chloro-5-(4-fluoro-3-(morpholinosulfonyl)phenyl)benzofuran-2-yl)methanamine (183): was synthesized using the indicated reagents according to General Procedure 3. Yield (100%). LCMS: m/z 426.0 $[M+H]^+$; $t_R$=1.72 min.

Synthesis of (E)-3-(6-aminopyridin-3-yl)-N-((7-chloro-5-(4-fluoro-3-(morpholinosulfonyl)phenyl)benzofuran-2-yl)methyl)acrylamide (636)

(E)-3-(6-aminopyridin-3-yl)-N-((7-chloro-5-(4-fluoro-3-(morpholinosulfonyl)phenyl)benzofuran-2-yl)methyl)acrylamide (636): was synthesized using the indicated reagents according to General Procedure 1. Yield (31%). $^1$H NMR (400 MHz, $CD_3OD$) δ 8.08 (d, J=9 Hz, 1H), 7.97-7.81 (m, 3H), 7.64 (s, 1H), 7.48-0.30 (m, 3H), 6.94 (d, J=9 Hz, 1H), 6.76 (s, 1H), 6.54 (d, J=16 Hz, 1H), 4.60 (s, 2H), 3.66-3.58 (m, 4H), 3.12-3.03 (m, 4H). LCMS: m/z 571.1 $[M+H]^+$, $t_R$=1.40 min.

Synthesis of (E)-3-(6-aminopyridin-3-yl)-N-((7-methoxy-5-(4-(piperazine-1-carbonyl)phenyl)benzofuran-2-yl)methyl)acrylamide (637)
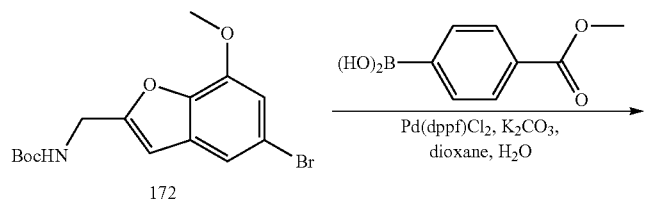
172
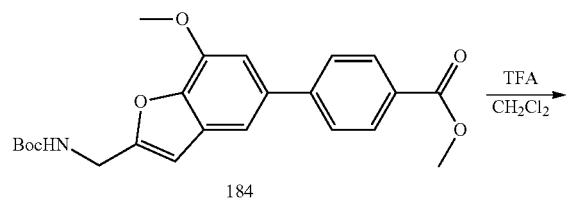
184
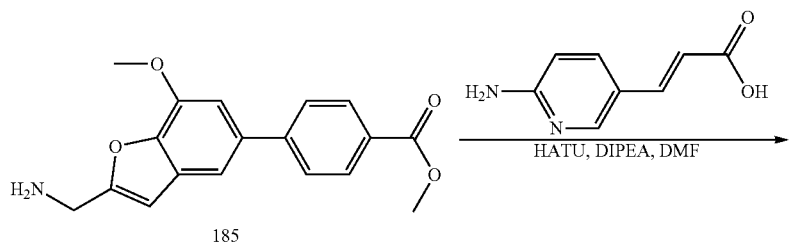
185
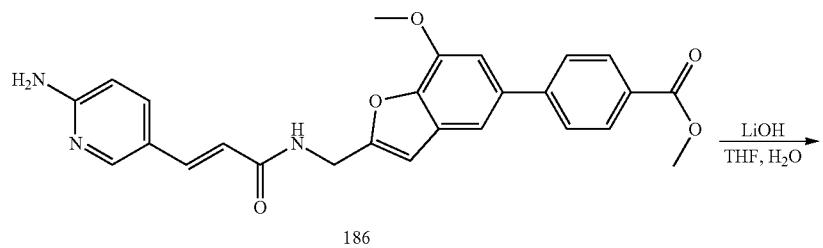
186
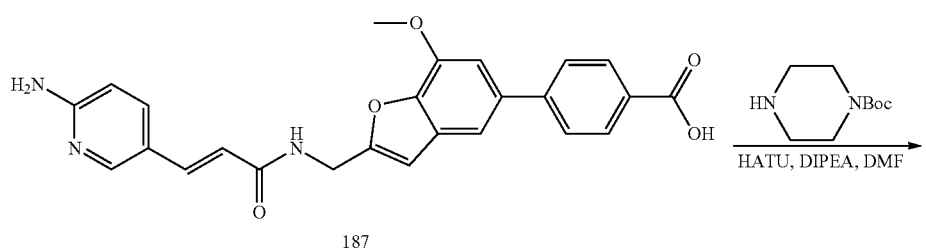
187
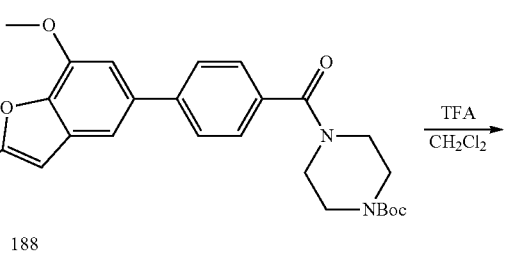
188

-continued

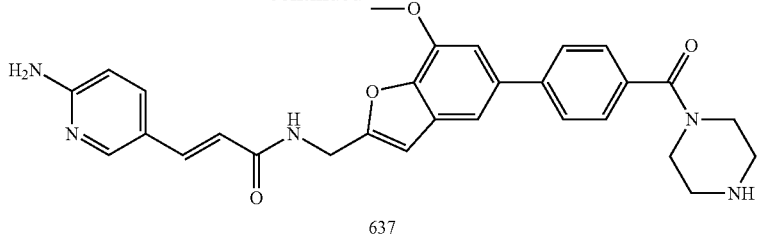

637

Synthesis of methyl 4-(2-((tert-butoxycarbonylamino) methyl)-7-methoxybenzofuran-5-yl) benzoate (184)

A mixture of tert-butyl (5-bromo-7-methoxybenzofuran-2-yl) methylcarbamate (172) (2.0 g, 5.6 mmol), 4-(methoxycarbonyl) phenylboronic acid (1.2 g, 6.7 mmol), Pd(dppf)Cl$_2$ (0.37 g, 0.84 mmol) and K$_2$CO$_3$ (1.56 g, 11.2 mmol) in 40 mL of dioxane and 4 mL of H$_2$O was stirred at 100° C. under nitrogen atmosphere for 2 hours. After cooling to room temperature, the mixture was filtered and the filtrate was concentrated under reduced pressure to give the crude product, which was purified by silica gel chromatography (20% EtOAc/petroleum ether) to give 2.3 g of methyl 4-(2-((tert-butoxycarbonylamino)methyl)-7-methoxybenzofuran-5-yl)benzoate (184) as a yellow solid (yield: 97%). LCMS: m/z 434.1 [M+Na]$^+$, t$_R$=1.79 min.

Synthesis of methyl 4-(2-(aminomethyl)-7-methoxybenzofuran-5-yl)benzoate (185)

Methyl 4-(2-((tert-butoxycarbonylamino)methyl)-7-methoxybenzofuran-5-yl)benzoate (184); (2.3 g, 5.6 mmol) was dissolved in CH$_2$Cl$_2$ (50 mL). TFA (10 mL) was added at 0° C. The reaction mixture was stirred at room temperature for 1 h, and concentrated under reduced pressure to give the crude methyl 4-(2-(aminomethyl)-7-methoxybenzofuran-5-yl)benzoate (185), which was used without further purification in the next step. Yield (100%). LCMS: m/z 334.0 [M+Na]$^+$; t$_R$=1.23 min.

Synthesis of (E)-methyl 4-(2-((3-(6-aminopyridin-3-yl) acrylamido) methyl)-7-methoxybenzofuran-5-yl) benzoate (186)

The crude methyl 4-(2-(aminomethyl)-7-methoxybenzofuran-5-yl)benzoate (185); crude mixture from previous step, 5.6 mmol) was dissolved in DMF (50 mL) and (E)-3-(6-aminopyridin-3-yl)acrylic acid (1.1 g, 6.6 mmol) was added at 0° C. HATU (2.5 g, 6.6 mmol) was added to this reaction mixture at 0° C. followed by DIPEA (1.4 g, 11.2 mmol) dropwise. The reaction mixture was allowed to warm to room temperature and stirred for 2 h. The mixture was extracted with EtOAc (30 mL×3). The combined organic layers were washed with brine, dried over anhydrous Na$_2$SO$_4$, and concentrated under reduced pressure to give 1.64 g crude product, which was used without further purification in the next step. Yield (64%). LCMS: t$_R$=1.30 min.

Synthesis of (E)-4-(2-((3-(6-aminopyridin-3-yl) acrylamido) methyl)-7-methoxybenzofuran-5-yl) benzoic acid (187)

(E)-Methyl 4-(2-((3-(6-aminopyridin-3-yl)acrylamido) methyl)-7-methoxybenzofuran-5-yl)benzoate (186); (200 mg, 0.44 mmol) was dissolved in THF (10 mL). LiOH (30 mg, 1.3 mmol) and water (2.5 mL) were added to this mixture. The mixture was stirred at room temperature for 2 h, 1N HCl solution was added and adjusted to pH=6. 180 mg of (E)-4-(2-((3-(6-aminopyridin-3-yl)acrylamido)methyl)-7-methoxybenzofuran-5-yl)benzoic acid (187) was collected by filtration. Yield (90%). LCMS: m/z 444.3 [M+H]$^+$, t$_R$=1.17 min.

Synthesis of (E)-tert-butyl 4-(4-(2-((3-(6-aminopyridin-3-yl)acrylamido)methyl)-7-methoxybenzofuran-5-yl)benzoyl)piperazine-1-carboxylate (188)

(E)-4-(2-((3-(6-aminopyridin-3-yl)acrylamido)methyl)-7-methoxybenzofuran-5-yl)benzoic acid (187); (180 mg, 0.4 mmol) was dissolved in DMF (10 mL) and tert-butyl piperazine-1-carboxylate (89 mg, 0.48 mmol) was added at 0° C. HATU (180 mg, 0.48 mmol) were added to this reaction mixture at 0° C. followed by DIPEA (31 mg, 0.22 mmol) dropwise. The reaction mixture was allowed to warm to room temperature and stirred for 2 h. The reaction mixture was transferred into water (20 mL) and extracted with EtOAc (10 mL×3). The combined organic layers were washed with brine, dried over anhydrous Na$_2$SO$_4$ and concentrated under reduced pressure to give 200 mg crude product which was used without further purification in the next step. Yield (81%). LCMS: m/z 612.3 [M+H]$^+$, t$_R$=1.33 min.

Synthesis of (E)-3-(6-aminopyridin-3-yl)-N-((7-methoxy-5-(4-(piperazine-1-carbonyl)phenyl)benzofuran-2-yl)methyl)acrylamide (637)

(E)-tert-Butyl 4-(4-(2-((3-(6-aminopyridin-3-yl)acrylamido)methyl)-7-methoxybenzofuran-5-yl)benzoyl)piperazine-1-carboxylate (188); (0.2 g, 0.33 mmol) was dissolved in CH$_2$Cl$_2$ (10 mL). TFA (2 mL) was added at 0° C. The reaction mixture was stirred at room temperature for 1 h, and concentrated under reduced pressure to give the crude product which was purified by Prep-HPLC without workup to afford 16 mg of (E)-3-(6-aminopyridin-3-yl)-N-((7-methoxy-5-(4-(piperazine-1-carbonyl) phenyl) benzofuran-2-yl)methyl)acrylamide (637). Yield (10%). $^1$H NMR (400 MHz, CD$_3$OD) δ 8.07-8.00 (m, 1H), 7.93 (s, 1H), 7.67 (d, J=8 Hz, 2H), 7.47 (d, J=8 Hz, 2H), 7.37 (d, J=16 Hz, 1H), 7.32-7.29 (m, 1H), 7.01 (s, 1H), 6.89 (d, J=9 Hz, 1H), 6.65 (s, 1H), 6.52 (d, J=16 Hz, 1H), 4.56 (s, 2H), 3.94 (s, 3H), 3.90-3.67 (m, 4H), 3.27-3.22 (m, 4H). LCMS: m/z 512.3 [M+H]$^+$, t$_R$=1.06 min.

Synthesis of (E)-3-(6-aminopyridin-3-yl)-N-((7-methoxy-5-(5-(morpholine-4-carbonyl)pyrimidin-2-yl)benzofuran-2-yl)methyl)acrylamide (638)
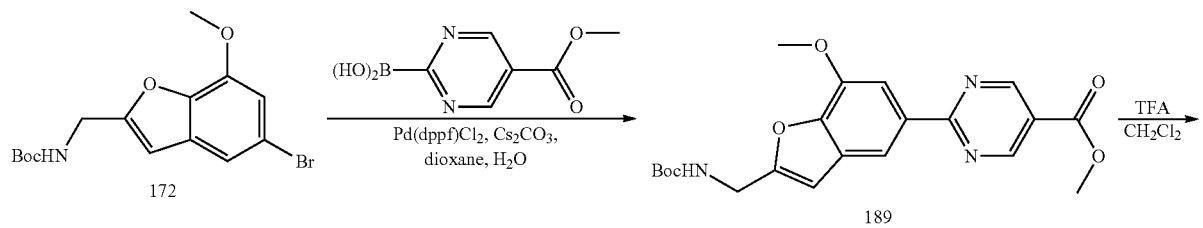
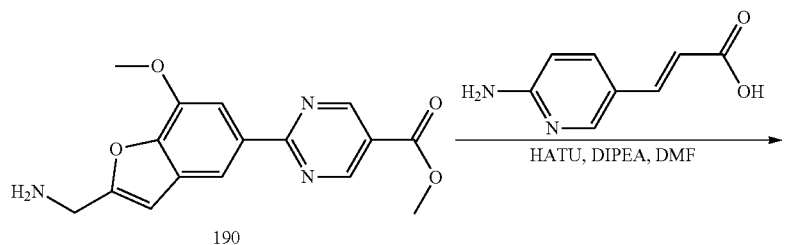
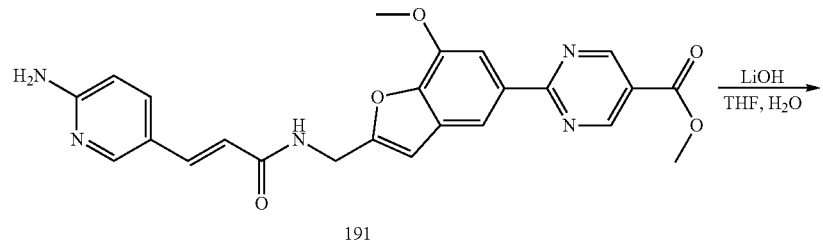
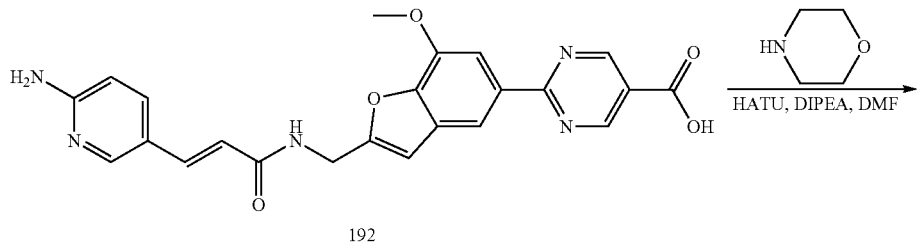
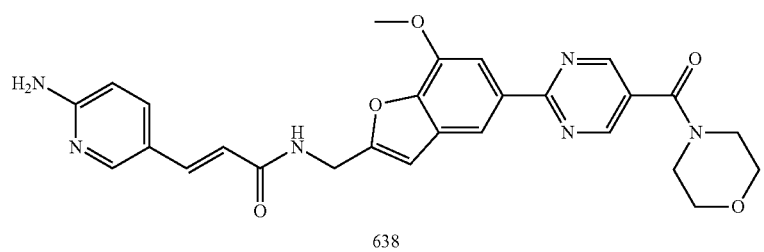

(E)-3-(6-aminopyridin-3-yl)-N-((7-methoxy-5-(5-(morpholine-4-carbonyl)pyrimidin-2-yl)benzofuran-2-yl)methyl)acrylamide (638) was synthesized in a similar fashion as example 637 using the reagents indicated. Yield (10%). $^1$H NMR (400 MHz, CD$_3$OD) δ 8.82 (s, 2H), 8.23 (s, 1H), 8.12-8.05 (m, 1H), 7.97-7.91 (m, 2H), 7.37 (d, J=16 Hz, 1H), 6.94 (d, J=9 Hz, 1H), 6.71 (s, 1H), 6.53 (d, J=16 Hz, 1H), 4.58 (s, 2H), 3.96 (s, 3H), 3.76-3.44 (m, 8H). LCMS: m/z 515.2 [M+H]$^+$, t$_R$=1.14 min.

Synthesis of (E)-3-(6-aminopyridin-3-yl)-N-((7-methoxy-5-(5-(piperazine-1-carbonyl)pyrimidin-2-yl)benzofuran-2-yl)methyl)acrylamide (639)

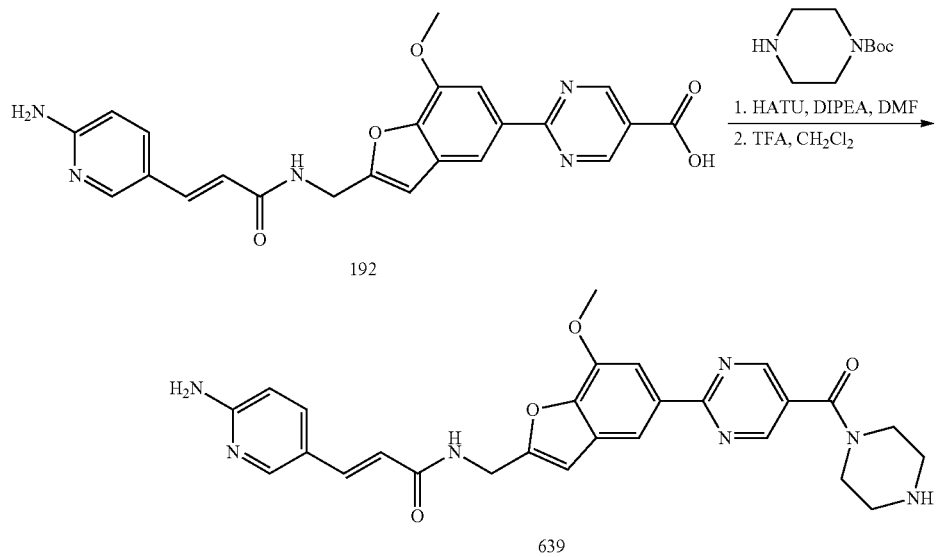

(E)-3-(6-aminopyridin-3-yl)-N-((7-methoxy-5-(5-(piperazine-1-carbonyl)pyrimidin-2-yl)benzofuran-2-yl)methyl)acrylamide (639) was synthesized using the indicated reagents according to General Procedures 2 and 3. Yield (31%). $^1$H NMR (400 MHz, CD$_3$OD) δ 8.83 (s, 2H), 8.19 (s, 1H), 8.08-8.03 (m, 1H), 7.91-7.87 (m, 2H), 7.34 (d, J=16 Hz, 1H), 6.92 (d, J=9 Hz, 1H), 6.69 (s, 1H), 6.52 (d, J=16 Hz, 1H), 4.57 (s, 2H), 3.94 (s, 3H), 3.92-3.76 (m, 4H), 3.31-3.23 (m, 4H). LCMS: m/z 514.2 [M+H]$^+$, t$_R$=1.04 min.

Synthesis of (E)-3-(6-aminopyridin-3-yl)-N-((7-methoxy-5-(5-(morpholine-4-carbonyl)pyridin-2-yl)benzofuran-2-yl)methyl)acrylamide (640)

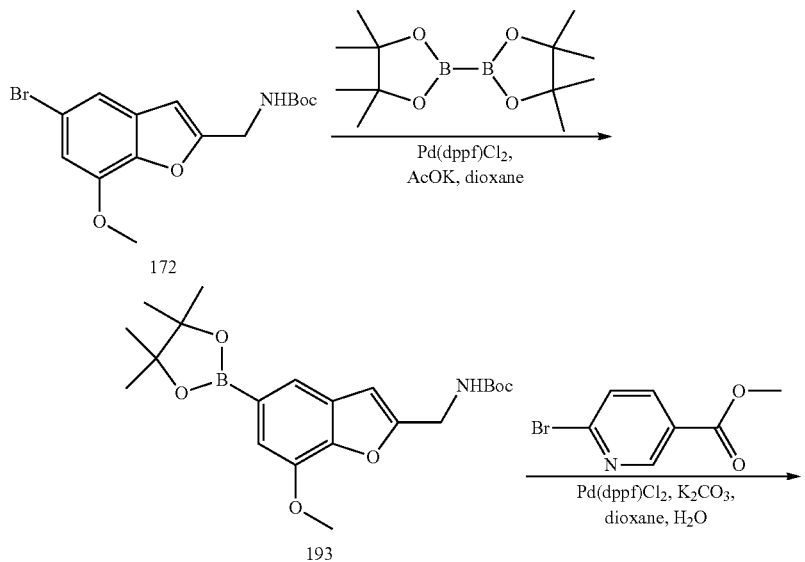

-continued
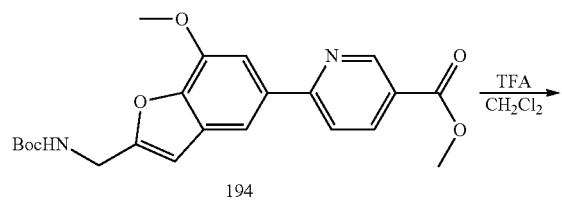
194
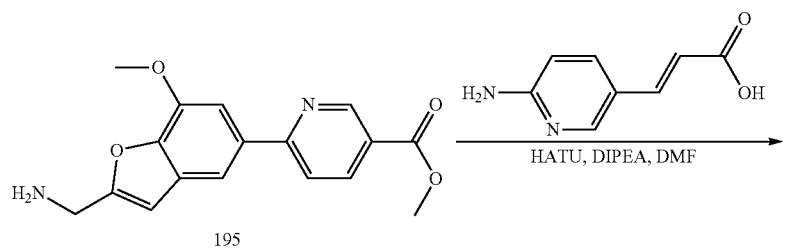
195
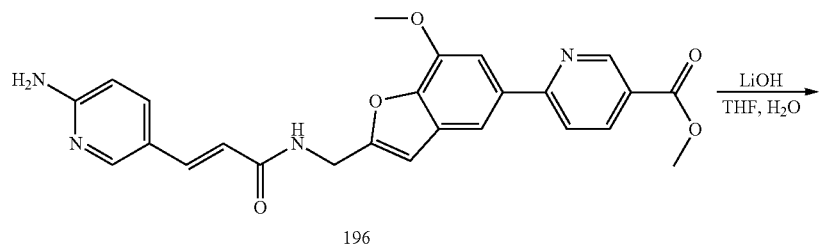
196
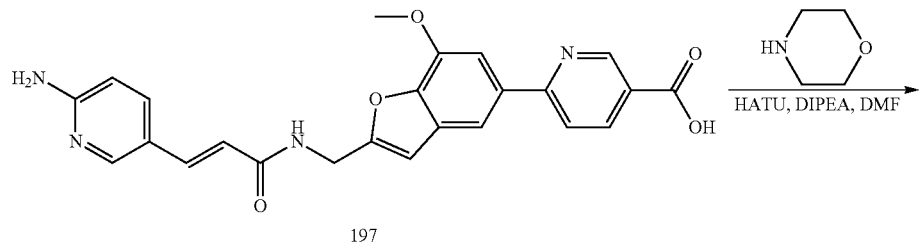
197
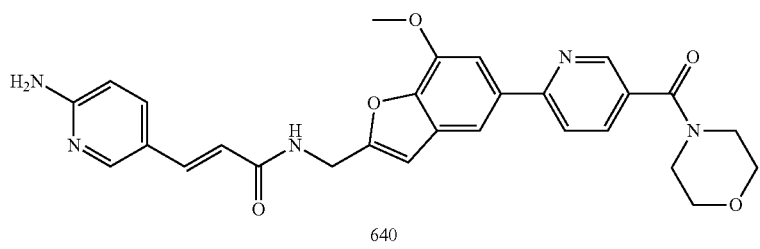
640

(E)-3-(6-aminopyridin-3-yl)-N-((7-methoxy-5-(5-(morpholine-4-carbonyl)pyridin-2-yl)benzofuran-2-yl)methyl)acrylamide (640) was prepared in a similar fashion as example 565 using the indicated reagents. Yield (50%). ¹H NMR (400 MHz, CD₃OD) δ 8.62 (s, 1H), 8.10-7.87 (m, 4H), 7.66 (s, 1H), 7.45 (s, 1H), 7.34 (d, J=16 Hz, 1H), 6.92 (d, J=9 Hz, 1H), 6.68 (s, 1H), 6.51 (d, J=16 Hz, 1H), 4.57 (s, 2H), 3.95 (s, 3H), 3.76-3.39 (m, 8H). LCMS: m/z 514.1 [M+H]⁺, t_R=1.15 min.

Synthesis of (E)-3-(6-aminopyridin-3-yl)-N-((7-methoxy-5-(5-(piperazine-1-carbonyl) pyridin-2-yl) benzofuran-2-yl)methyl)acrylamide (641)

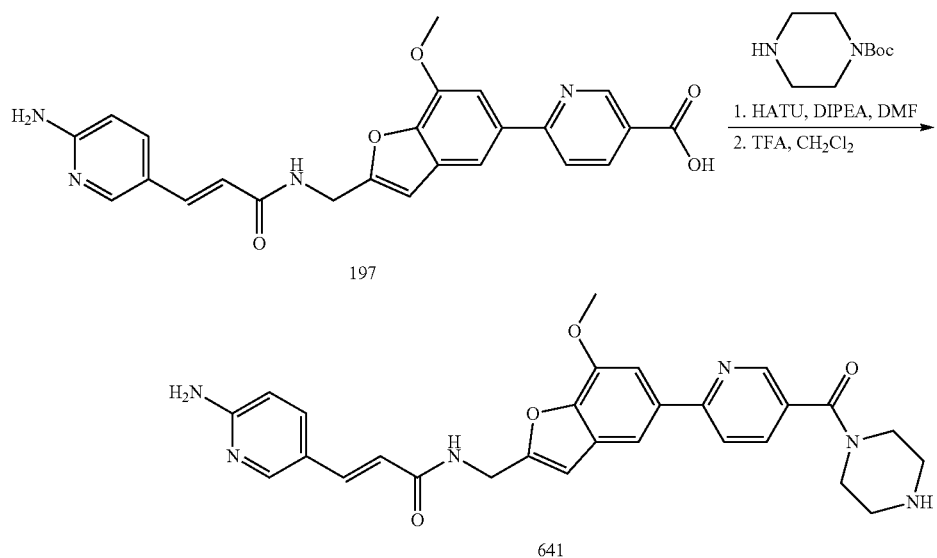

(E)-3-(6-aminopyridin-3-yl)-N-((7-methoxy-5-(5-(piperazine-1-carbonyl) pyridin-2-yl)benzofuran-2-yl)methyl) acrylamide (641) was synthesized using the indicated reagents according to General Procedures 2 and 3. Yield (50%). ¹H NMR (400 MHz, CD₃OD) δ 8.65 (s, 1H), 8.08 (d, J=9 Hz, 1H), 7.96-7.87 (m, 3H), 7.70 (s, 1H), 7.50 (s, 1H), 7.36 (d, J=16 Hz, 1H), 6.94 (d, J=9 Hz, 1H), 6.69 (s, 1H), 6.53 (d, J=16 Hz, 1H), 4.57 (s, 2H), 3.96 (s, 3H), 3.91-3.70 (m, 4H), 3.30-3.22 (m, 4H). LCMS: m/z 513.2 [M+H]⁺, t_R=1.05 min.

Synthesis of (E)-3-(6-aminopyridin-3-yl)-N-((7-chloro-5-(4-(3,3-difluoroazetidin-1-ylsulfonyl)phenyl)benzofuran-2-yl)methyl)acrylamide (642)

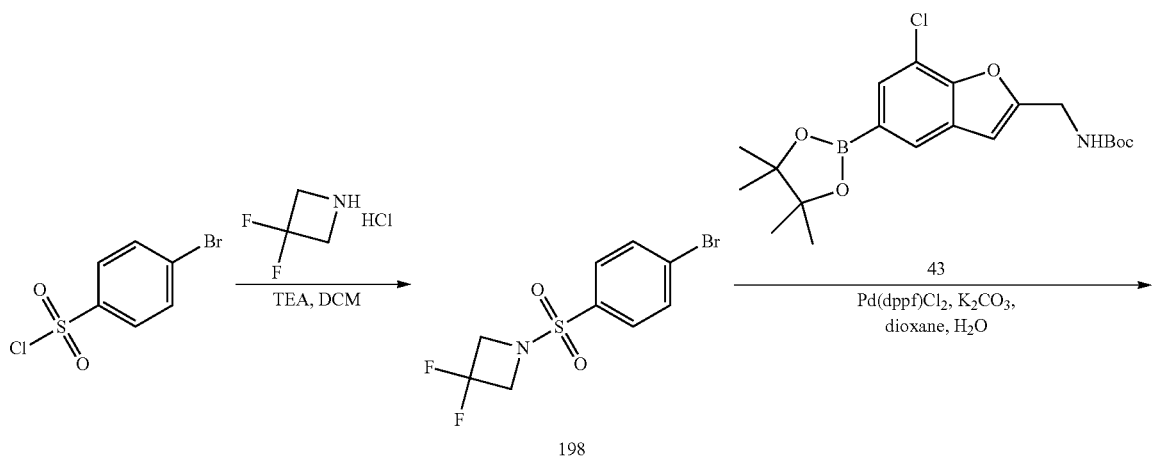

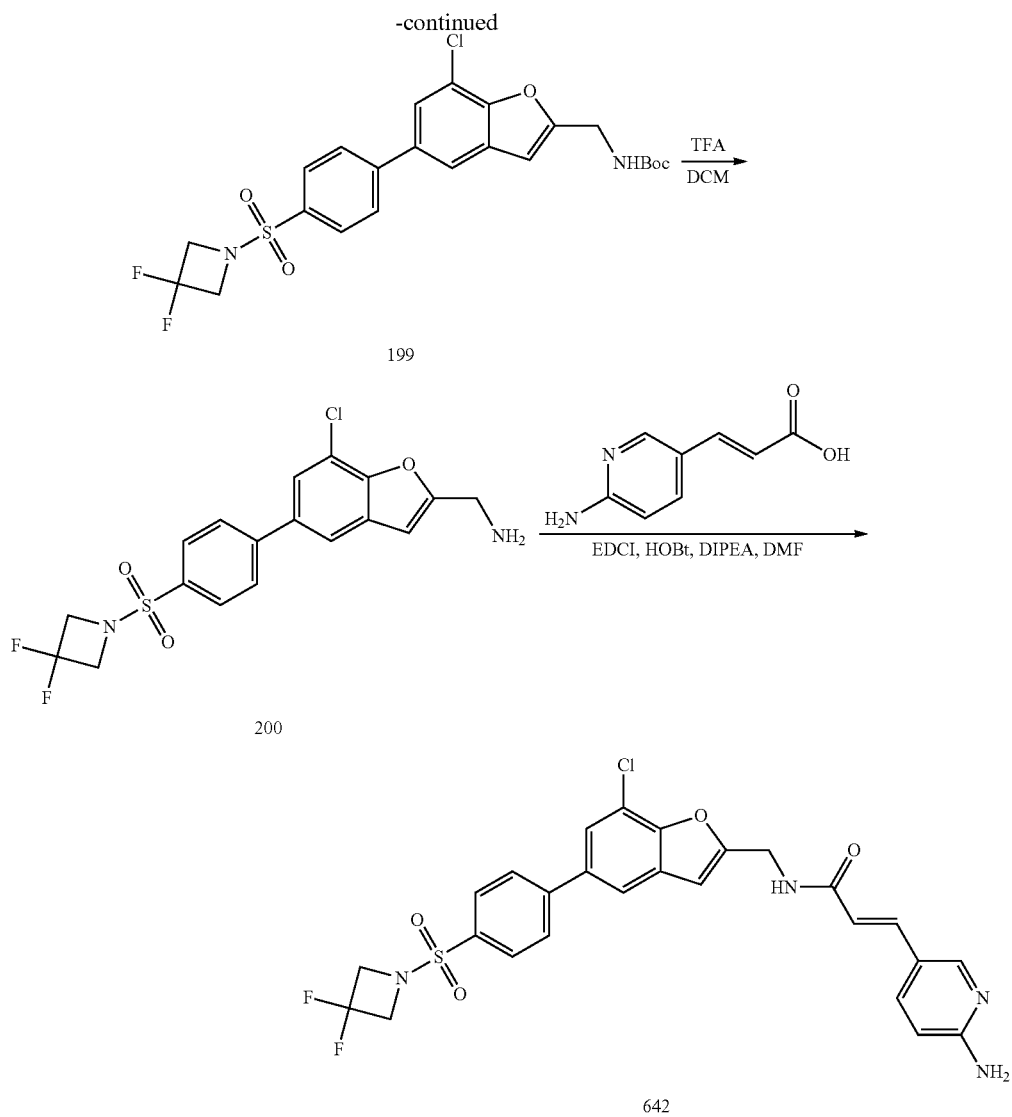

Synthesis of 1-(4-Bromophenylsulfonyl)-3,3-difluoroazetidine (198)

1-(4-Bromophenylsulfonyl)-3,3-difluoroazetidine (198) was synthesized using similar to procedure of intermediate (199). Yield (92%). LCMS: m/z 311.9 [M+H]$^+$, $t_R$=1.85 min.

Synthesis of tert-Butyl (7-chloro-5-(4-(3,3-difluoroazetidin-1-ylsulfonyl)phenyl)benzofuran-2-yl)methylcarbamate (199)

Synthesis of tert-Butyl (7-chloro-5-(4-(3,3-difluoroazetidin-1-ylsulfonyl)phenyl)benzofuran-2-yl)methylcarbamate (199) was synthesized using General Procedure 2. Yield (53%). LCMS: m/z 513.0 [M+H]$^+$, $t_R$=1.98 min.

Synthesis of (7-Chloro-5-(4-(3,3-difluoroazetidin-1-ylsulfonyl)phenyl)benzofuran-2-yl)methanamine (200)

(7-Chloro-5-(4-(3,3-difluoroazetidin-1-ylsulfonyl)phenyl)benzofuran-2-yl)methanamine (200) was synthesized using General Procedure 3. Yield (100%). LCMS: m/z 413.7 [M+H]$^+$, $t_R$=1.29 min.

Synthesis of (E)-3-(6-aminopyridin-3-yl)-N-((7-chloro-5-(4-(3,3-difluoroazetidin-1-ylsulfonyl)phenyl)benzofuran-2-yl)methyl)acrylamide (642)

(E)-3-(6-aminopyridin-3-yl)-N-((7-chloro-5-(4-(3,3-difluoroazetidin-1-ylsulfonyl)phenyl)benzofuran-2-yl)methyl)acrylamide (642) was synthesized using General Procedure 4. Yield (25%). $^1$H NMR (400 MHz, CD$_3$OD) δ 7.95 (s, 1H), 7.91-7.84 (m, 4H), 7.77 (s, 1H), 7.64 (d, J=9 Hz, 1H), 7.58 (s, 1H), 7.38 (d, J=16 Hz, 1H), 6.78 (s, 1H), 6.50 (d, J=9 Hz, 1H), 6.37 (d, J=16 Hz, 1H), 4.60 (s, 2H), 4.13 (t, J=12 Hz, 4H). LCMS: m/z 559.1 [M+H]$^+$, $t_R$=1.85 min.

Synthesis of (S,E)-3-(6-aminopyridin-3-yl)-N-((7-chloro-5-(4-(3-fluoropyrrolidin-1-ylsulfonyl)phenyl)benzofuran-2-yl)methyl)acrylamide (643)
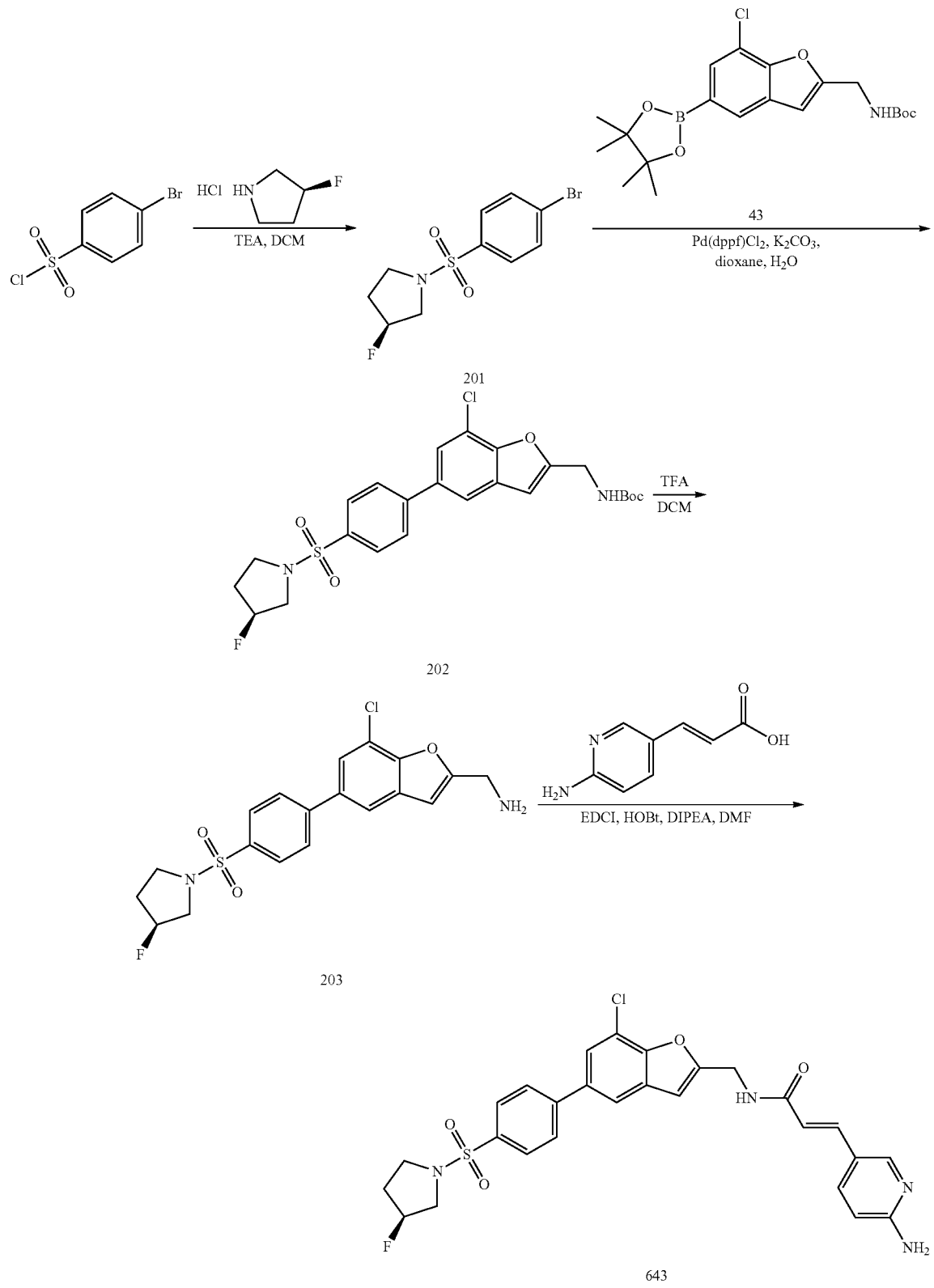

(S,E)-3-(6-aminopyridin-3-yl)-N-((7-chloro-5-(4-(3-fluoropyrrolidin-1-ylsulfonyl)phenyl)benzofuran-2-yl)methyl)acrylamide (643) was synthesized in a similar fashion as example 642 using the indicated reagents. Yield (12%). $^1$H NMR (400 MHz, CD$_3$OD) δ 8.07 (d, J=2 Hz, 1H), 7.97-7.84 (m, 5H), 7.78-7.73 (m, 1H), 7.67 (d, J=2 Hz, 1H), 7.50 (d, J=16 Hz, 1H), 6.88 (s, 1H), 6.62 (d, J=9 Hz, 1H), 6.49 (d, J=16 Hz, 1H), 5.18 (d, J=52 Hz, 1H), 4.71 (s, 2H), 3.65-3.43 (m, 4H), 2.19-1.90 (m, 2H). LCMS: m/z 555.2 [M+H]$^+$, $t_R$=1.81 min.

Synthesis of (E)-3-(6-aminopyridin-3-yl)-N-((5-(4-(3,3-difluoroazetidin-1-ylsulfonyl)phenyl)-7-(trifluoromethyl)benzofuran-2-yl)methyl)acrylamide (644)

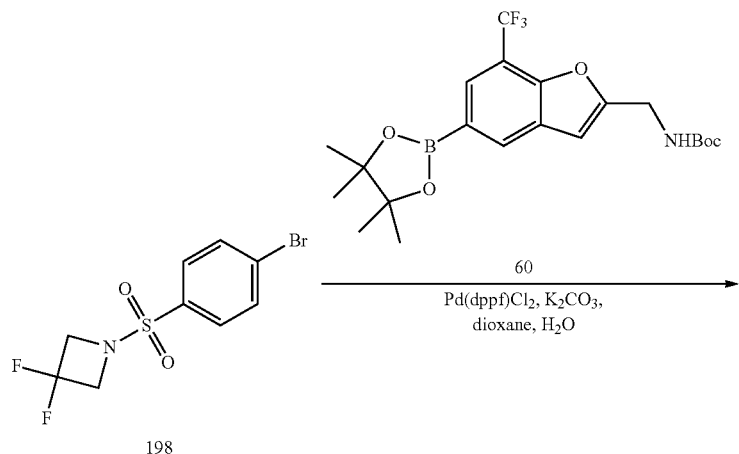

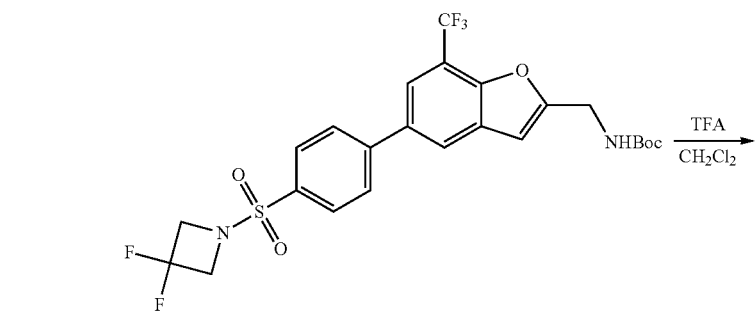

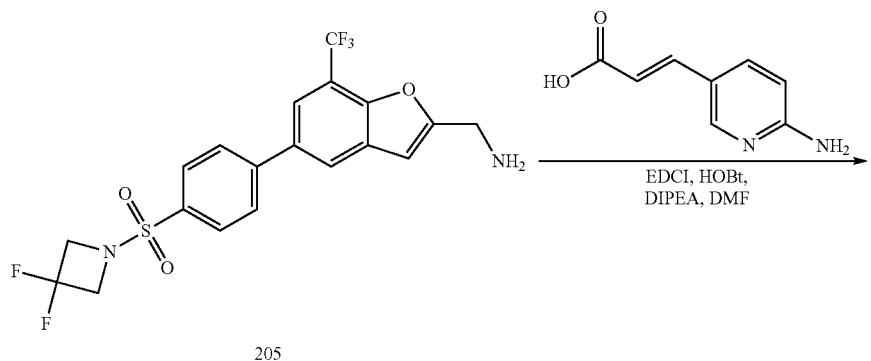

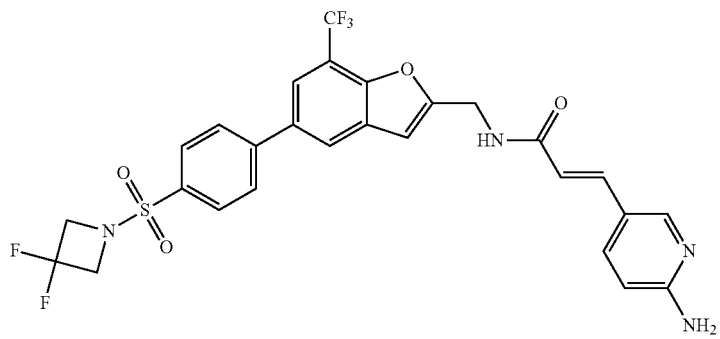

644

(E)-3-(6-aminopyridin-3-yl)-N-((5-(4-(3,3-difluoroazetidin-1-ylsulfonyl)phenyl)-7-(trifluoromethyl)benzofuran-2-yl)methyl)acrylamide (644) was synthesized in a similar fashion as example (643) using the indicated reagents. Yield (27%). $^1$H NMR (400 MHz, CD$_3$OD) δ 8.21 (s, 1H), 8.07-8.06 (m, 5H), 7.89 (s, 1H), 7.77-7.74 (m, 1H), 7.50 (d, J=16 Hz, 1H), 6.95 (s, 1H), 6.62 (d, J=9 Hz, 1H), 6.49 (d, J=16 Hz, 1H), 4.77-4.73 (m, 2H), 4.28-4.22 (m, 4H). LCMS: m/z 593.2 [M+H]$^+$; t$_R$=1.89 min. (E)-3-(6-aminopyridin-3-yl)-N-((5-(5-(3,3-difluoroazetidine-1-carbonyl)pyridin-2-yl)-7-(trifluoromethyl)benzofuran-2-yl)methyl)acrylamide (645).

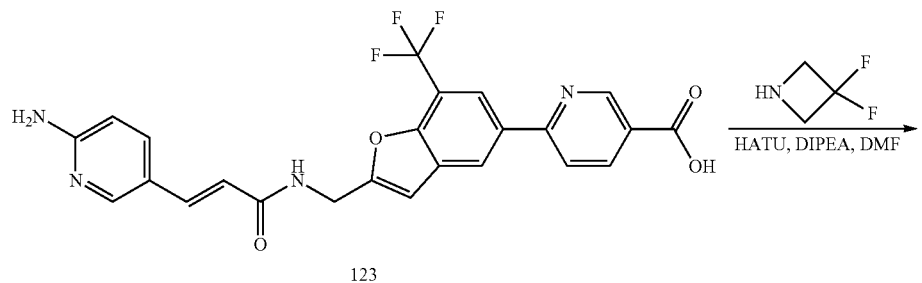

123

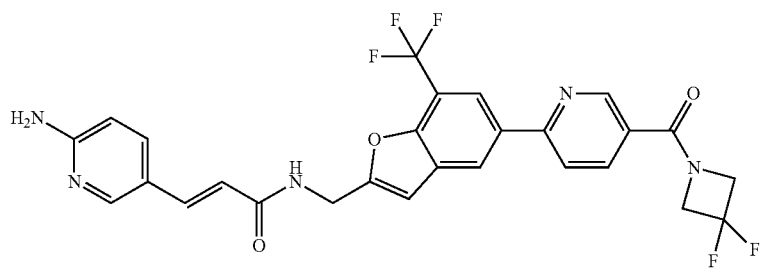

645

(E)-3-(6-aminopyridin-3-yl)-N-((5-(5-(3,3-difluoroazetidine-1-carbonyl)pyridin-2-yl)-7-(trifluoromethyl)benzofuran-2-yl)methyl)acrylamide (645) was synthesized using the indicated reagents according to General Procedure 4. Yield (43%). $^1$H NMR (400 MHz, CD$_3$OD) δ 8.99 (s, 1H), 8.56 (s, 1H), 8.37 (s, 1H), 8.23-8.20 (m, 1H), 8.12-8.07 (m, 2H), 7.77-7.74 (m, 1H), 7.50 (d, J=16 Hz, 1H), 6.97 (s, 1H), 6.61 (d, J=9 Hz, 1H), 6.49 (d, J=16 Hz, 1H), 4.73 (s, 2H), 4.61 (s, 4H). LCMS: m/z 558.2 [M+H]$^+$; $t_R$=1.78 min.

Synthesis of (E)-3-(6-aminopyridin-3-yl)-N-((7-chloro-5-(5-(dimethylamino)pyridin-2-yl)benzofuran-2-yl)methyl)acrylamide (646)

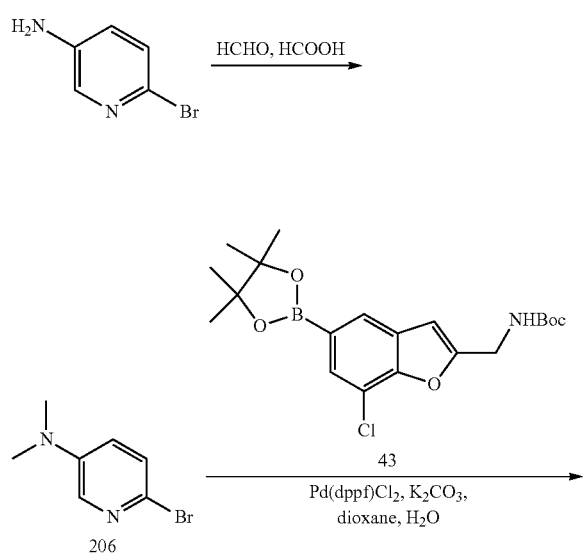

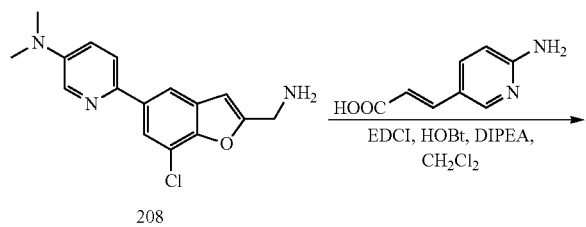

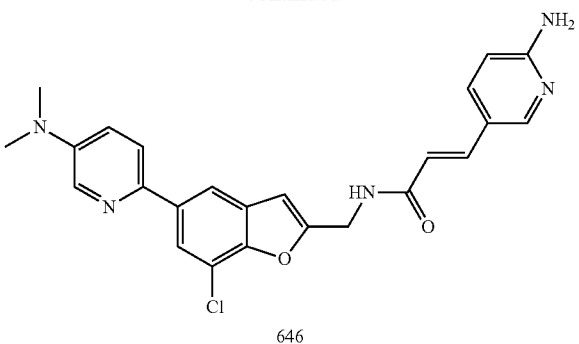

Synthesis of (E)-3-(6-aminopyridin-3-yl)-N-((7-chloro-5-(5-(dimethylamino)pyridin-2-yl)benzofuran-2-yl)methyl)acrylamide (646)

(E)-3-(6-aminopyridin-3-yl)-N-((7-chloro-5-(5-(dimethylamino)pyridin-2-yl)benzofuran-2-yl)methyl)acrylamide (646) in a similar fashion as example (644) using the indicated reagents. $^1$H NMR (400 MHz, DMSO-d$_6$) δ 8.62 (t, J=6 Hz, 1H), 8.21-8.07 (m, 3H), 8.00 (s, 1H), 7.84 (d, J=9 Hz, 1H), 7.65-7.58 (m, 1H), 7.35 (d, J=16 Hz, 1H), 7.22-7.14 (m, 1H), 6.88 (s, 1H), 6.51-6.36 (m, 4H), 4.58 (d, J=6 Hz, 2H), 2.99 (s, 6H). LCMS: m/z 448.2 [M+H]$^+$, $t_R$=1.70 min.

Synthesis of (E)-3-(6-aminopyridin-3-yl)-N-((5-(5-(4-fluorophenyl)-3-methylisoxazol-4-yl)-7-(trifluoromethyl)benzofuran-2-yl)methyl)acrylamide (648)

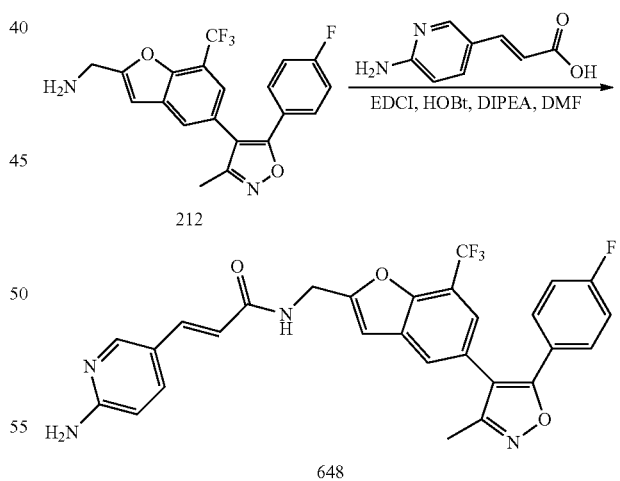

(E)-3-(6-aminopyridin-3-yl)-N-((5-(5-(4-fluorophenyl)-3-methylisoxazol-4-yl)-7-(trifluoromethyl)benzofuran-2-yl)methyl)acrylamide (648) was synthesized using the indicated reagents according to General Procedure 1. Yield: 41%. $^1$H NMR (400 MHz, CD$_3$OD) δ 7.91 (s, 1H), 7.72-7.58 (m, 2H), 7.44-7.31 (m, 4H), 7.03-6.91 (m, 2H), 6.76 (s, 1H), 6.48 (d, J=9 Hz, 1H), 6.41-6.29 (m, 1H), 4.59 (s, 2H), 2.11 (s, 3H). LCMS: m/z 537.2 [M+H]$^+$, $t_R$=1.83 min.

Synthesis of (E)-3-(6-aminopyridin-3-yl)-N-((7-chloro-5-(5-(piperazine-1-carbonyl)pyrimidin-2-yl)benzofuran-2-yl)methyl)acrylamide (649)

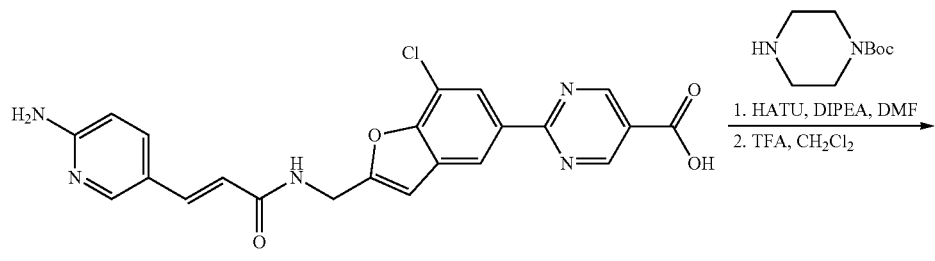

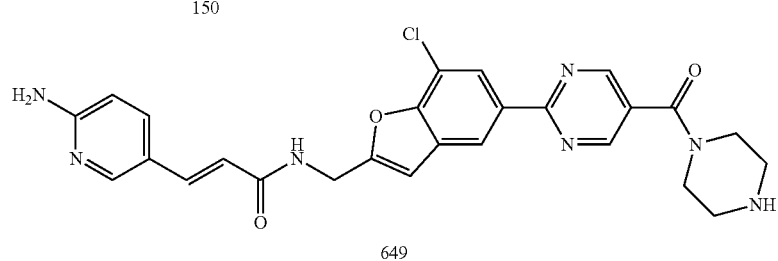

(E)-3-(6-aminopyridin-3-yl)-N-((7-chloro-5-(5-(piperazine-1-carbonyl)pyrimidin-2-yl)benzofuran-2-yl)methyl)acrylamide (649) was synthesized using the indicated reagents according to General Procedures 4 and 3. $^1$H NMR (400 MHz, CD$_3$OD) δ 9.04-8.96 (m, 2H), 8.68 (s, 1H), 8.49 (s, 1H), 8.20 (d, J=9 Hz, 1H), 8.05 (s, 1H), 7.49 (d, J=16 Hz, 1H), 7.05 (d, J=9 Hz, 1H), 6.94 (s, 1H), 6.66 (d, J=16 Hz, 1H), 4.73 (s, 2H), 4.05-3.87 (m, 4H), 3.43-3.34 (m, 4H). LCMS: m/z 518.2 [M+H]$^+$, t$_R$=1.14 min.

Synthesis of (E)-3-(6-aminopyridin-3-yl)-N-((7-chloro-5-(5-(2-hydroxypropan-2-yl)thiophen-2-yl)benzofuran-2-yl)methyl)acrylamide (650)

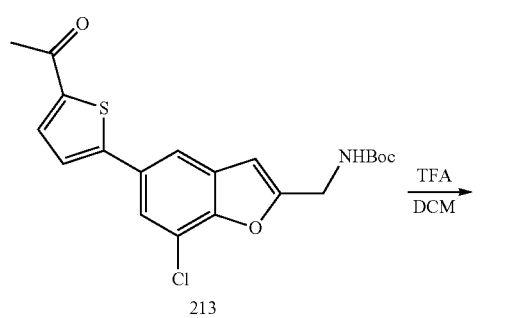

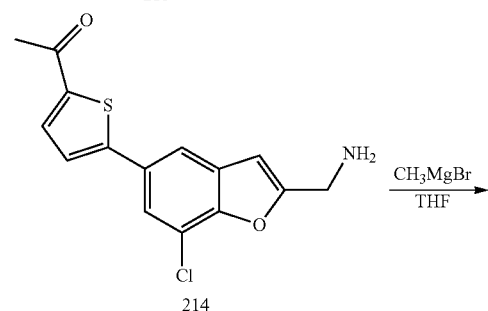

-continued

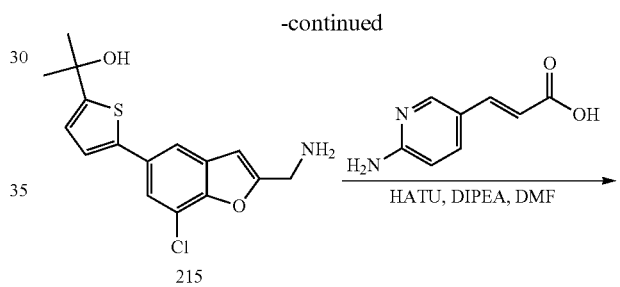

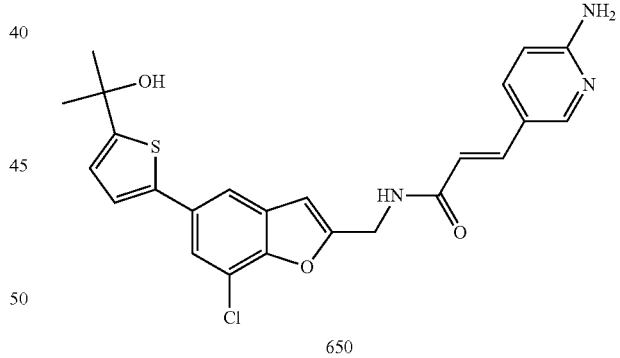

Synthesis of 1-(5-(2-(aminomethyl)-7-chlorobenzofuran-5-yl)thiophen-2-yl)ethanone (214)

tert-Butyl (5-(5-acetylthiophen-2-yl)-7-chlorobenzofuran-2-yl)methylcarbamate (213; 200 mg, 0.49 mmol) was dissolved in CH$_2$Cl$_2$ (5 mL) and TFA (1 mL) was added dropwise at room temperature. The reaction mixture was stirred at room temperature for 2 h. The reaction mixture was concentrated under reduced pressure to give the crude product, which was purified by Prep-TLC (5% MeOH/DCM) to give 120 mg of 1-(5-(2-(aminomethyl)-7-chlorobenzofuran-5-yl)thiophen-2-yl)ethanone (214) (80% yield). LCMS: m/z 306.0 [M+H]$^+$; t$_R$=0.97 min.

Synthesis of 2-(5-(2-(aminomethyl)-7-chlorobenzofuran-5-yl)thiophen-2-yl)propan-2-ol (215)

1-(5-(2-(Aminomethyl)-7-chlorobenzofuran-5-yl)thiophen-2-yl)ethanone (214); (200 mg, 0.65 mmol) was dissolved in THF (10 mL) and CH$_3$MgBr (1.8 mL, 5.2 mmol, 3M in THF) was added dropwise at 0° C. (ice bath). The reaction mixture was allowed to warm to room temperature and stirred for 3 h. The reaction mixture was cooled down to 0° C. (ice bath), sat. NaHCO$_3$ aqueous solution (10 mL) was added to the reaction mixture and extracted with dichloromethane (15 mL×3). The combined organic layers were washed with brine, dried over anhydrous Na$_2$SO$_4$, and concentrated under reduced pressure to give the crude product, which was purified by Prep-HPLC to give 100 mg of 2-(5-(2-(aminomethyl)-7-chlorobenzofuran-5-yl)thiophen-2-yl)propan-2-ol (215) (48% yield). LCMS: m/z 344.9 [M+Na]$^+$; t$_R$=1.34 min.

Synthesis of (E)-3-(6-aminopyridin-3-yl)-N-((7-chloro-5-(5-(2-hydroxypropan-2-yl)thiophen-2-yl)benzofuran-2-yl)methyl)acrylamide (650)

2-(5-(2-(Aminomethyl)-7-chlorobenzofuran-5-yl)thiophen-2-yl)propan-2-ol (215); (100 mg, 0.3 mmol) was dissolved in DMF (2 mL) and (E)-3-(6-aminopyridin-3-yl)acrylic acid (49 mg, 0.3 mmol), HATU (136 mg, 0.36 mmol), DIPEA (77 mg, 0.6 mmol)) were added at room temperature. The reaction mixture was stirred at room temperature for 4 h and purified by Prep-HPLC without work up to give 9 mg of (E)-3-(6-aminopyridin-3-yl)-N-((7-chloro-5-(5-(2-hydroxypropan-2-yl)thiophen-2-yl)benzofuran-2-yl)methyl)acrylamide (650). Yield 6%. $^1$H NMR (400 MHz, CD$_3$OD) δ 8.07 (s, 1H), 7.78-7.69 (m, 2H), 7.58-7.45 (m, 2H), 7.21 (d, J=4 Hz, 1H), 6.94 (d, J=4 Hz, 1H), 6.81 (s, 1H), 6.62 (d, J=9 Hz, 1H), 6.48 (d, J=16 Hz, 1H), 4.68 (s, 2H), 1.65 (s, 6H). LCMS: m/z 468.0 [M+H]$^+$, t$_R$=1.74 min.

Synthesis of (E)-3-(6-aminopyridin-3-yl)-N-((5-(5-(4,4-difluoropiperidine-1-carbonyl)pyridin-2-yl)-7-methoxybenzofuran-2-yl)methyl)acrylamide (651)

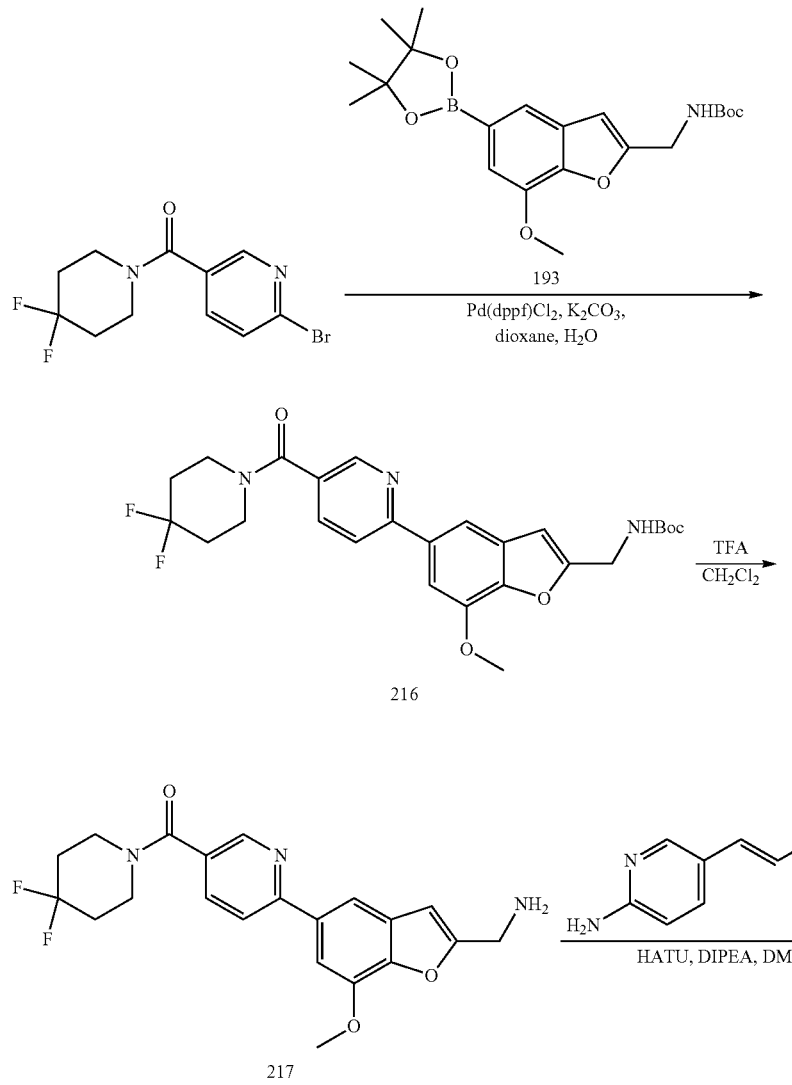

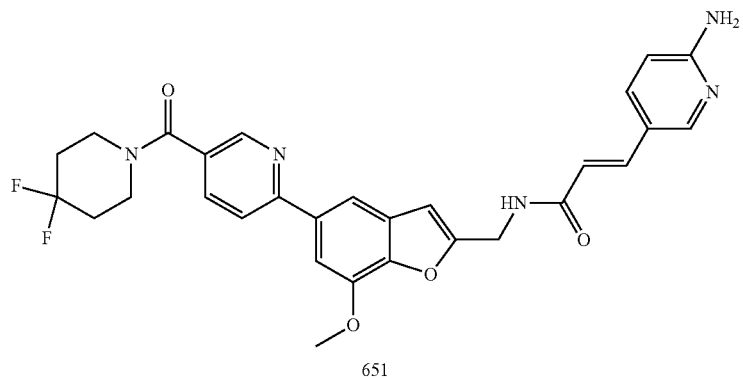

651

(E)-3-(6-aminopyridin-3-yl)-N-((5-(5-(4,4-difluoropiperidine-1-carbonyl)pyridin-2-yl)-7-(trideuteromethoxy)benzofuran-2-yl)methyl)acrylamide (651) was synthesized in a similar fashion as example (640) using the indicated reagents. $^1$H NMR (400 MHz, DMSO-$d_6$) δ 8.77-8.71 (m, 1H), 8.64-8.54 (m, 1H), 8.15-7.92 (m, 4H), 7.70 (s, 1H), 7.65-7.58 (m, 1H), 7.36 (d, J=16 Hz, 1H), 6.82 (s, 1H), 6.49-6.40 (m, 4H), 4.56 (s, 2H), 4.03 (s, 3H), 3.83-3.43 (m, 4H), 2.18-2.00 (m, 4H). LCMS: m/z 548.0 [M+H]$^+$, $t_R$=1.37 min.

Synthesis of (E)-3-(6-aminopyridin-3-yl)-N-((5-(5-(4,4-difluoropiperidine-1-carbonyl)pyrimidin-2-yl)-7-(trifluoromethyl)benzofuran-2-yl)methyl)acrylamide (652)

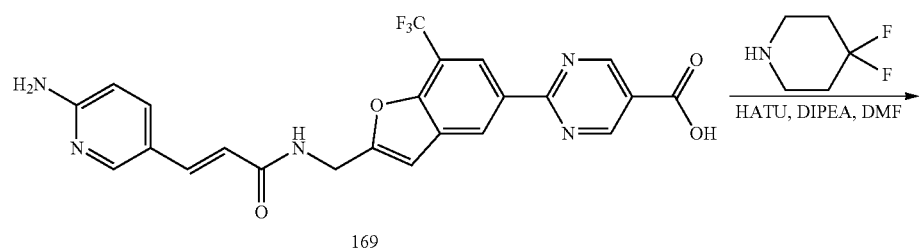

169

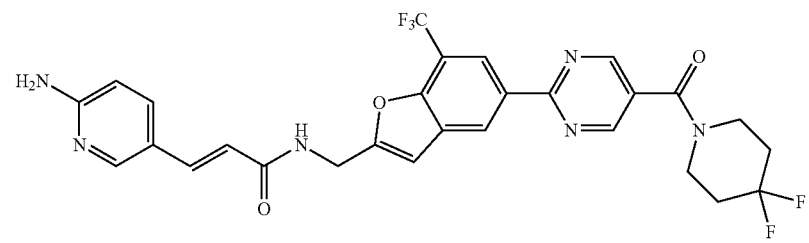

652

(E)-3-(6-aminopyridin-3-yl)-N-((5-(5-(4,4-difluoropiperidine-1-carbonyl)pyrimidin-2-yl)-7-(trifluoromethyl)benzofuran-2-yl)methyl)acrylamide (652) was synthesized using the indicated reagents according to General Procedure 4. Yield 83%. $^1$H NMR (400 MHz, CD$_3$OD) δ 8.91-8.82 (m, 3H), 8.63 (s, 1H), 8.10 (d, J=9 Hz, 1H), 7.97-7.91 (m, 1H), 7.38 (d, J=16 Hz, 1H), 6.95 (d, J=9 Hz, 1H), 6.88 (s, 1H), 6.55 (d, J=16 Hz, 1H), 4.63 (s, 2H), 3.90-3.50 (m, 4H), 2.11-1.94 (m, 4H). LCMS: m/z 587.1 [M+H]$^+$, $t_R$=1.30 min.

Synthesis of (E)-3-(6-aminopyridin-3-yl)-N-((5-(5-(3,3-difluoropyrrolidine-1-carbonyl)pyrimidin-2-yl)-7-(trifluoromethyl)benzofuran-2-yl)methyl)acrylamide (653)

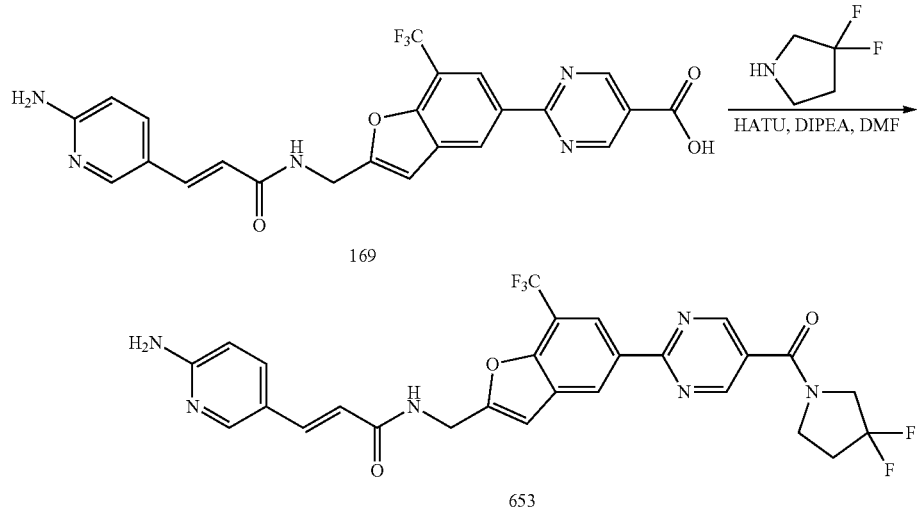

(E)-3-(6-aminopyridin-3-yl)-N-((5-(5-(3,3-difluoropyrrolidine-1-carbonyl)pyrimidin-2-yl)-7-(trifluoromethyl)benzofuran-2-yl)methyl)acrylamide (652) was synthesized using the indicated reagents according to General Procedure 4. Yield 50%. $^1$H NMR (400 MHz, CD$_3$OD) δ 8.84 (s, 3H), 8.62 (s, 1H), 7.95 (s, 1H), 7.67-7.60 (m, 1H), 7.38 (d, J=16 Hz, 1H), 6.85 (s, 1H), 6.49 (d, J=9 Hz, 1H), 6.37 (d, J=16 Hz, 1H), 4.61 (s, 2H), 3.75-3.46 (m, 4H), 2.50-2.36 (m, 4H), 2.25 (s, 3H). LCMS: m/z 566.2 [M+H]$^+$, $t_R$=1.55 min. Chiral resolution of (E)-3-(6-aminopyridin-3-yl)-N-((5-(5-(3-fluoro-3-methylpyrrolidine-1-carbonyl)pyridin-2-yl)-7-(trifluoromethyl)benzofuran-2-yl)methyl)acrylamide (617).

120 mg of Compound 617 was resolved under the following chiral HPLC conditions to afford a crude mixture of cis-trans isomers 654 and 656 and a crude mixture of cis-trans isomers 655 and 657:

Column: AD-H (250*4.6 mm×5 μm)
Mobile Phase: n-hexane (0.1% DEA):EtOH (0.1% DEA) =10:90
Flow: 1.0 mL/minute
Temperature: 40° C.
Wavelengths: 214 nm and 254 nm
Instrument: SHIMADZU.

Cis, single enantiomer 656 was formed during the concentration of trans, single enantiomer 654, and cis, single enantiomer 657 was formed during the concentration of trans, single enantiomer 655. 654 and 656 were subsequently separated from each other via preparative TLC (6% MeOH/CH$_2$Cl$_2$) to give trans (or E), single enantiomer 654 and cis (or Z), single enantiomer 656. 10 mg of 654 and 10 mg of 656 was obtained. 655 and 657 were also separated from each other via preparative TLC (6% MeOH/CH$_2$Cl$_2$) to give trans, single enantiomer 655 and cis, single enantiomer 657. 7 mg of 655 and 11 mg of 657 was obtained.

The absolute configuration of Compounds 654, 655, 656 and 657 has not been determined. Therefore, each of 654, 655, 656 and 657, as used herein in reference to a particular compound, refers to a compound having the indicated analytical data and the indicated retention time in the chiral preparative HPLC method described above for the chiral resolution of Compound 617. The analytical data and retention times for each of Compounds 654, 655, 656 and 657 are indicated below.

(654) ($t_R$=19.46 minutes by chiral preparative HPLC). $^1$H NMR (400 MHz, CD$_3$OD) δ 8.77-8.69 (m, 1H), 8.39 (s, 1H), 8.20 (s, 1H), 8.01-7.89 (m, 3H), 7.65-7.58 (m, 1H), 7.37 (d, J=16 Hz, 1H), 6.82 (s, 1H), 6.48 (d, J=9 Hz, 1H), 6.36 (d, J=16 Hz, 1H), 4.60 (s, 2H), 3.85-3.49 (m, 4H), 2.23-1.92 (m, 2H), 1.55-1.37 (m, 3H). LCMS: m/z 568.2 [M+H]$^+$, $t_R$=1.27 min.

(655) ($t_R$=30.74 minutes by chiral preparative HPLC). $^1$H NMR (400 MHz, CD$_3$OD) δ 8.94-8.78 (m, 1H), 8.52 (s, 1H), 8.34 (s, 1H), 8.13-8.05 (m, 3H), 7.79-7.69 (m, 1H), 7.50 (d, J=16 Hz, 1H), 6.95 (s, 1H), 6.61 (d, J=9 Hz, 1H), 6.49 (d, J=16 Hz, 1H), 4.73 (s, 2H), 3.98-3.60 (m, 4H), 2.31-2.06 (m, 2H), 1.67-1.48 (m, 3H). LCMS: m/z 568.2 [M+H]$^+$, $t_R$=1.31 min.

(657) ($t_R$=7.51 minutes by chiral preparative HPLC). $^1$H NMR (400 MHz, CD$_3$OD) δ 8.76-8.70 (m, 1H), 8.39 (s, 1H), 8.21 (s, 1H), 8.03-7.94 (m, 3H), 7.87-7.79 (m, 1H), 6.81 (s, 1H), 6.51 (d, J=12 Hz, 1H), 6.26 (d, J=9 Hz, 1H), 5.81 (d, J=12 Hz, 1H), 4.54 (s, 2H), 3.86-3.48 (m, 4H), 2.23-1.89 (m, 2H), 1.55-1.35 (m, 3H). LCMS: m/z 568.2 [M+H]$^+$, $t_R$=1.26 min.

(656) ($t_R$=8.16 minutes by chiral preparative HPLC). $^1$H NMR (400 MHz, CD$_3$OD) δ 8.78-8.67 (m, 1H), 8.37 (s, 1H), 8.20 (s, 1H), 8.02-7.89 (m, 3H), 7.86-7.79 (m, 1H), 6.78 (s, 1H), 6.51 (d, J=13 Hz, 1H), 6.26 (d, J=9 Hz, 1H), 5.80 (d, J=13 Hz, 1H), 4.54 (s, 2H), 3.84-3.49 (m, 4H), 2.21-1.91 (m, 2H), 1.55-1.36 (m, 3H). LCMS: m/z 568.2 [M+H]$^+$, $t_R$=1.30 min.

345

(R,E)-3-(6-aminopyridin-3-yl)-N-((5-(5-(3-fluoro-3-methylpyrrolidine-1-carbonyl)pyridin-2-yl)-7-(trifluoromethyl)benzofuran-2-yl)methyl)acrylamide, (R,Z)-3-(6-aminopyridin-3-yl)-N-((5-(5-(3-fluoro-3-methylpyrrolidine-1-carbonyl)pyridin-2-yl)-7-(trifluoromethyl)benzofuran-2-yl)methyl)acrylamide, (S,E)-3-(6-aminopyridin-3-yl)-N-((5-(5-(3-fluoro-3-methylpyrrolidine-1-carbonyl)pyridin-2-yl)-7-(trifluoromethyl)benzofuran-2-yl)methyl)acrylamide and (S,Z)-3-(6-aminopyridin-3-yl)-N-((5-(5-(3-fluoro-3-methylpyrrolidine-1-carbonyl)pyridin-2-yl)-7-(trifluoromethyl)benzofuran-2-yl)methyl)acrylamide can be depicted as follows:

346
-continued

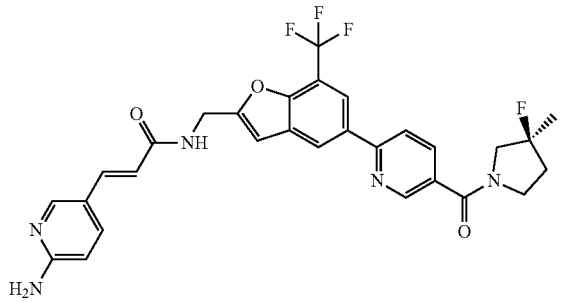

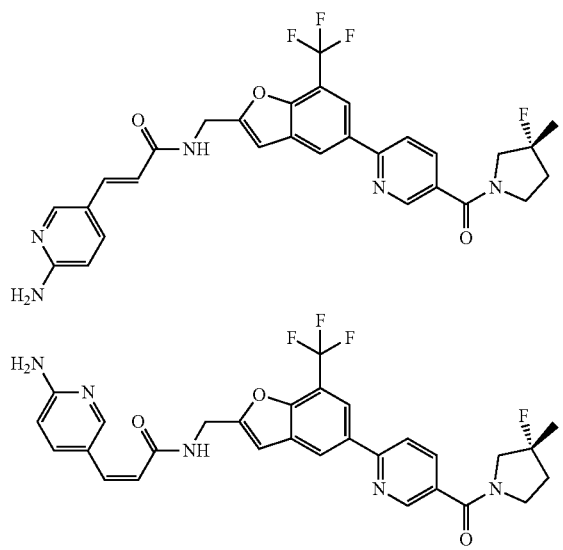

respectively.

Synthesis of (E)-3-(6-aminopyridin-3-yl)-N-((5-(5-(4,4-difluoropiperidine-1-carbonyl)pyridin-2-yl)furo[2,3-b]pyridin-2-yl)methyl)acrylamide (658)

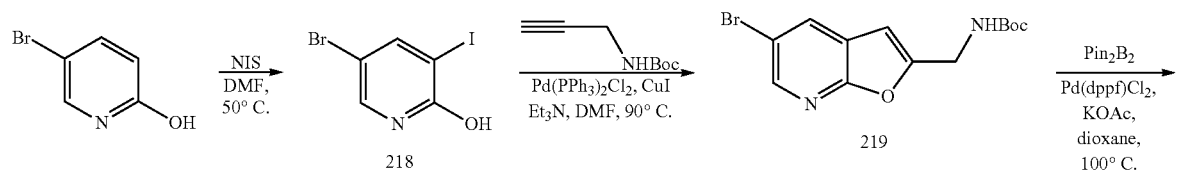

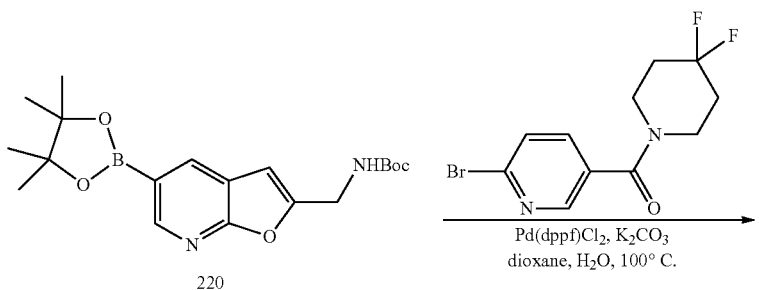

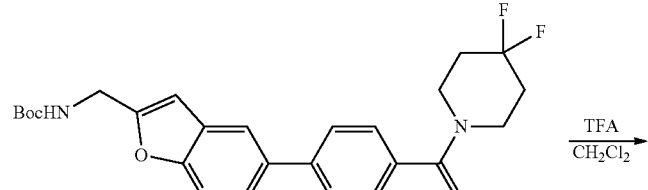

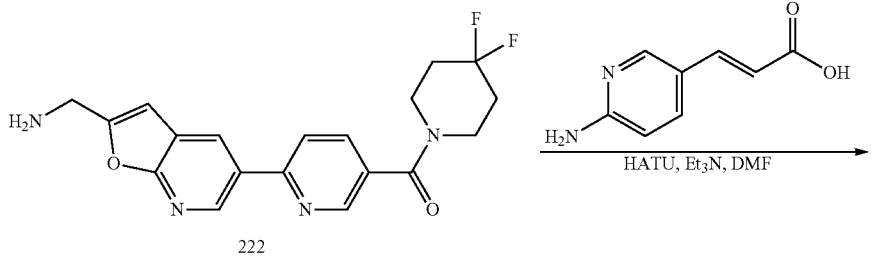
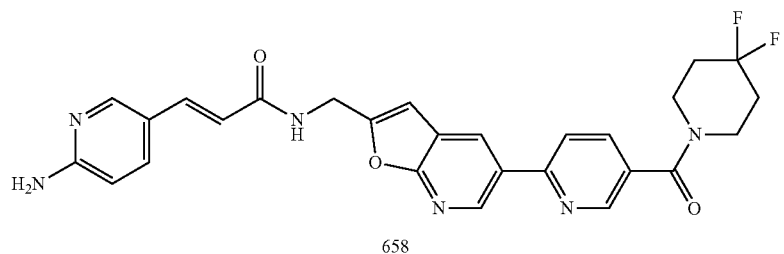

Synthesis of 5-bromo-3-iodopyridin-2-ol (218)

5-Bromopyridin-2-ol (1.74 g, 10 mmol) was dissolved in DMF (40 mL) and NIS (2.7 g, 12 mmol) was added at room temperature. The reaction mixture was heated at 50° C. for 6 h. The reaction mixture was cooled down to room temperature, poured into 50 mL of water, extracted with EtOAc (60 mL×3). The combined organic layers were washed with brine, dried over anhydrous $Na_2SO_4$, and concentrated under reduced pressure to give 5-bromo-3-iodopyridin-2-ol (218) as yellow solid (1.0 g, 33% yield). LCMS: m/z 301.9 $[M+H]^+$; $t_R$=1.34 min.

Synthesis of tert-butyl (5-bromofuro[2,3-b]pyridin-2-yl) methylcarbamate (219)

5-Bromo-3-iodopyridin-2-ol (218); (200 mg, 0.67 mmol), tert-butyl prop-2-ynylcarbamate (104 mg, 0.67 mmol), $Pd(PPh_3)_2Cl_2$ (47 mg, 0.07 mmol), CuI (13 mg, 0.07 mmol), and triethylamine (135 mg, 1.34 mmol) were added in 10 mL of DMF and degassed. The reaction mixture was heated at 90° C. under nitrogen atmosphere for 3 h. After cooling down to room temperature, the reaction mixture was filtered. The filtrate was concentrated under reduced pressure to give the crude product, which was purified by silica gel chromatography (30% EtOAc/petroleum ether) to yield 150 mg of tert-butyl (5-bromofuro[2,3-b]pyridin-2-yl) methylcarbamate (219) as a yellow solid (69% yield). LCMS: m/z 329.0 $[M+H]^+$; $t_R$=1.76 min.

Synthesis of tert-butyl (5-(4,4,5,5-tetramethyl-1,3,2-dioxaborolan-2-yl)furo[2,3-b]pyridin-2-yl)methylcarbamate (220)

tert-Butyl (5-bromofuro[2,3-b]pyridin-2-yl) methylcarbamate (219); (600 mg, 1.8 mmol), 4,4,4',4',5,5,5',5'-octamethyl-2,2'-bi(1,3,2-dioxaborolane) (460 mg, 1.8 mmol), Pd(dppf)Cl₂ (147 mg, 0.18 mmol), and potassium acetate (353 mg, 3.6 mmol) were added in 10 mL of dioxane and degassed. The reaction mixture was heated at 100° C. under nitrogen atmosphere for 2 h. After cooling down to room temperature, the reaction mixture was filtered. The filtrate was concentrated under reduced pressure to give the crude product, which was purified by silica gel chromatography (5-20% EtOAc/petroleum ether) to yield 300 mg of tert-butyl (5-(4,4,5,5-tetramethyl-1,3,2-dioxaborolan-2-yl)furo[2,3-b]pyridin-2-yl)methylcarbamate (220) as a yellow solid (45% yield). LCMS: m/z 375.2 $[M+H]^+$, $t_R$=1.36 min.

Synthesis of tert-butyl (5-(5-(4,4-difluoropiperidine-1-carbonyl)pyridin-2-yl)furo[2,3-b]pyridin-2-yl) methylcarbamate (221)

(6-Bromopyridin-3-yl)(4,4-difluoropiperidin-1-yl)methanone (83 mg, 0.27 mmol), tert-butyl (5-(4,4,5,5-tetramethyl-1,3,2-dioxaborolan-2-yl)furo[2,3-b]pyridin-2-yl)methylcarbamate (220); (100 mg, 0.27 mmol), Pd(dppf)Cl₂ (22 mg, 0.03 mmol), and $K_2CO_3$ (75 mg, 0.54 mmol) were added in a mixture of (10:1) dioxane (10 mL) and water (1 mL) and degassed. The reaction mixture was heated at 100° C. under nitrogen atmosphere for 3 h. The reaction mixture was cooled down to room temperature and filtered. The solids collected were rinsed with ethyl acetate and discarded. The filtrate was concentrated under reduced pressure to give the crude product, which was purified by silica gel chromatography (30% EtOAc/petroleum ether) to yield 100 mg of tert-butyl (5-(5-(4,4-difluoropiperidine-1-carbonyl)pyridin-2-yl)furo[2,3-b]pyridin-2-yl)methylcarbamate (221) as off-white solid (yield 39%). LCMS: m/z 473.2 $[M+H]^+$, $t_R$=1.65 min.

Synthesis of (6-(2-(aminomethyl)furo[2,3-b]pyridin-5-yl)pyridin-3-yl)(4,4-difluoropiperidin-1-yl)methanone (222)

tert-Butyl (5-(5-(4,4-difluoropiperidine-1-carbonyl)pyridin-2-yl)furo[2,3-b]pyridin-2-yl)methylcarbamate (221); (47.2 mg, 0.1 mmol) was dissolved in $CH_2Cl_2$ (5 mL). TFA (1 mL) was added dropwise at 0° C. The reaction mixture was stirred at room temperature for 4 h. The reaction mixture was concentrated under reduced pressure to give (6-(2-(aminomethyl)furo[2,3-b]pyridin-5-yl)pyridin-3-yl)(4,4-difluoropiperidin-1-yl)methanone (222), which was used without further purification in the next step (35 mg, yield 85%). LCMS: m/z 373.2 $[M+H]^+$; $t_R$=1.21 min.

Synthesis of (E)-3-(6-aminopyridin-3-yl)-N-((5-(5-(4,4-difluoropiperidine-1-carbonyl)pyridin-2-yl)furo[2,3-b]pyridin-2-yl)methyl)acrylamide (658)

(6-(2-(Aminomethyl)furo[2,3-b]pyridin-5-yl)pyridin-3-yl)(4,4-difluoropiperidin-1-yl)methanone (222); (37.2 mg, 0.1 mmol), (E)-3-(6-aminopyridin-3-yl)acrylic acid (16.4 mg, 0.1 mmol), HATU (38 mg, 0.1 mmol), and triethylamine (21 mg, 0.2 mmol) were added in DMF (5 mL) at room temperature. The reaction mixture was stirred at room temperature for 16 h. The reaction mixture was diluted with water (10 mL), extracted with EtOAc (20 mL×3). The combined organic layers were washed with brine, dried over anhydrous $Na_2SO_4$, and concentrated under reduced pressure to give the crude product which was purified by Pre-HPLC to give (E)-3-(6-aminopyridin-3-yl)-N-((5-(5-(4,4-difluoropiperidine-1-carbonyl)pyridin-2-yl)furo[2,3-b]pyridin-2-yl)methyl)acrylamide (658) (30 mg, yield 57%). $^1$H NMR (400 MHz, DMSO-$d_6$) δ 9.00 (t, J=2 Hz, 1H), 8.83-7.98 (m, 6H), 7.67-7.31 (m, 1H), 6.90 (s, 1H), 6.58-5.77 (m, 5H), 4.65-4.52 (m, 2H), 3.83-3.48 (m, 4H), 2.18-2.01 (m, 4H). LCMS: m/z 519.2 [M+H]$^+$, $t_R$=1.50 min.

Synthesis of (E)-3-(6-aminopyridin-3-yl)-N-((7-cyclopropyl-5-(5-(4,4-difluoropiperidine-1-carbonyl)pyridin-2-yl)benzofuran-2-yl)methyl)acrylamide (659)

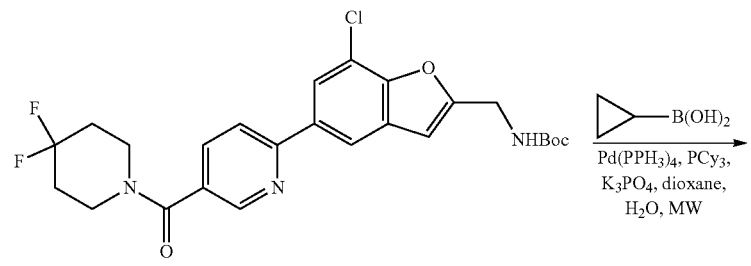

223

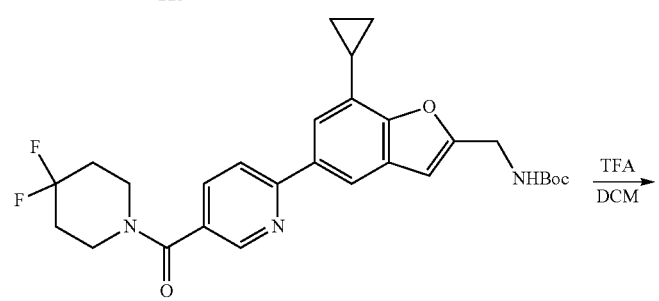

224

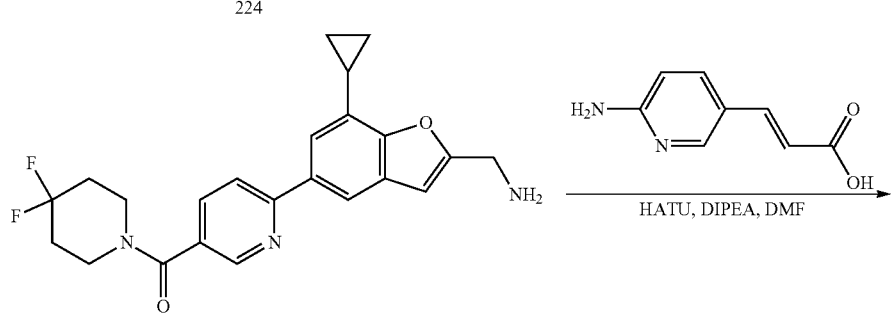

225

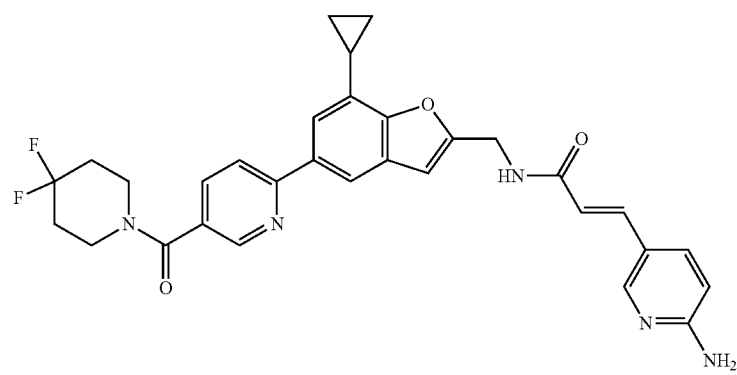

659

Synthesis of tert-butyl (7-cyclopropyl-5-(5-(4,4-difluoropiperidine-1-carbonyl)pyridin-2-yl)benzofuran-2-yl)methylcarbamate (224)

tert-Butyl (7-chloro-5-(5-(4,4-difluoropiperidine-1-carbonyl)pyridin-2-yl)benzofuran-2-yl)methylcarbamate (223); (300 mg, 0.6 mmol), cyclopropylboronic acid (155 mg, 1.8 mmol), Pd(PPh$_3$)$_4$ (70 mg, 0.06 mmol), PCy$_3$ (40 mg, 0.12 mmol), and potassium phosphate (407 mg, 1.8 mmol) were added in a mixture of dioxane (5 mL) and H$_2$O (0.5 mL) and degassed. The reaction mixture was heated at 140° C. under microwave condition for 1 h. After cooling down to room temperature, the reaction mixture was filtered and the filtrate was concentrated under reduced pressure to give the crude product, which was purified by silica gel chromatography (20% EtOAc/petroleum ether) to yield 150 mg of tert-butyl (7-cyclopropyl-5-(5-(4,4-difluoropiperidine-1-carbonyl)pyridin-2-yl)benzofuran-2-yl)methylcarbamate (224) as a white solid (50% yield). LCMS: m/z 512.3 [M+H]$^+$, t$_R$=1.84 min.

Synthesis of (6-(2-(aminomethyl)-7-cyclopropylbenzofuran-5-yl)pyridin-3-yl)(4,4-difluoropiperidin-1-yl)methanone (225)

tert-Butyl (7-cyclopropyl-5-(5-(4,4-difluoropiperidine-1-carbonyl)pyridin-2-yl)benzofuran-2-yl)methylcarbamate (224); (100 mg, 0.2 mmol) was dissolved in CH$_2$Cl$_2$ (12 mL). TFA (2 mL) was added dropwise at 0° C. The reaction mixture was allowed to warm to room temperature and stirred for 1 h. The reaction mixture was concentrated under reduced pressure to give (6-(2-(aminomethyl)-7-cyclopropylbenzofuran-5-yl)pyridin-3-yl)(4,4-difluoropiperidin-1-yl)methanone (225), which was used without further purification in the next step (80 mg, 100% yield). LCMS: m/z 412.2 [M+H]$^+$; t$_R$=1.35 min.

Synthesis of (E)-3-(6-aminopyridin-3-yl)-N-((7-cyclopropyl-5-(5-(4,4-difluoropiperidine-1-carbonyl)pyridin-2-yl)benzofuran-2-yl)methyl)acrylamide (659)

(6-(2-(Aminomethyl)-7-cyclopropylbenzofuran-5-yl)pyridin-3-yl)(4,4-difluoropiperidin-1-yl)methanone (225); (80 mg, 0.19 mmol) was dissolved in DMF (3 mL) and (E)-3-(6-aminopyridin-3-yl)acrylic acid (34 mg, 0.21 mmol) was added at 0° C. HATU (87 mg, 0.23 mmol) was added to this reaction mixture at 0° C. followed by DIPEA (74 mg, 0.57 mmol) dropwise. The reaction mixture was allowed to warm to room temperature and stirred further for 1 h. The reaction mixture was purified by Prep-HPLC to afford 40 mg of (E)-3-(6-aminopyridin-3-yl)-N-((7-cyclopropyl-5-(5-(4,4-difluoropiperidine-1-carbonyl)pyridin-2-yl)benzofuran-2-yl)methyl)acrylamide (659) (38% yield). $^1$H NMR (400 MHz, DMSO-d$_6$) δ 8.81 (t, J=6 Hz, 1H), 8.72 (d, J=2 Hz, 1H), 8.33-8.05 (m, 6H), 7.95 (dd, J$_1$=8 Hz, J$_2$=2 Hz, 1H), 7.62 (d, J=2 Hz, 1H), 7.45 (d, J=16 Hz, 1H), 7.00 (d, J=9 Hz, 1H), 6.82 (s, 1H), 6.62 (d, J=16 Hz, 1H), 4.61 (d, J=5 Hz, 2H), 3.83-3.42 (m, 4H), 2.35-2.27 (m, 1H), 2.16-2.00 (m, 4H), 1.12-0.96 (m, 4H). LCMS: m/z 558.2 [M+H]$^+$, t$_R$=1.32 min.

Synthesis of (E)-3-(6-aminopyridin-3-yl)-N-((5-(5-(4,4-difluoropiperidine-1-carbonyl)pyridin-2-yl)-7-(methoxy-d$_3$)benzofuran-2-yl)methyl)acrylamide (660)

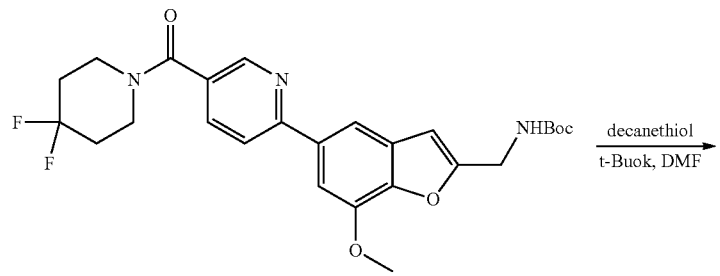

226

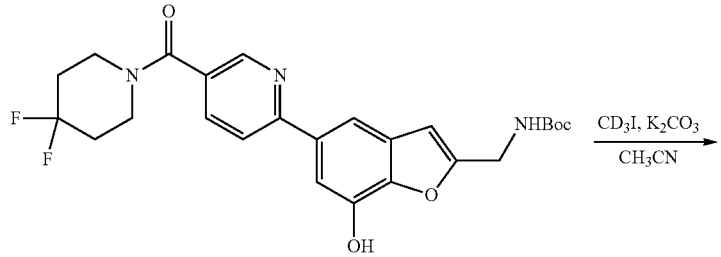

227

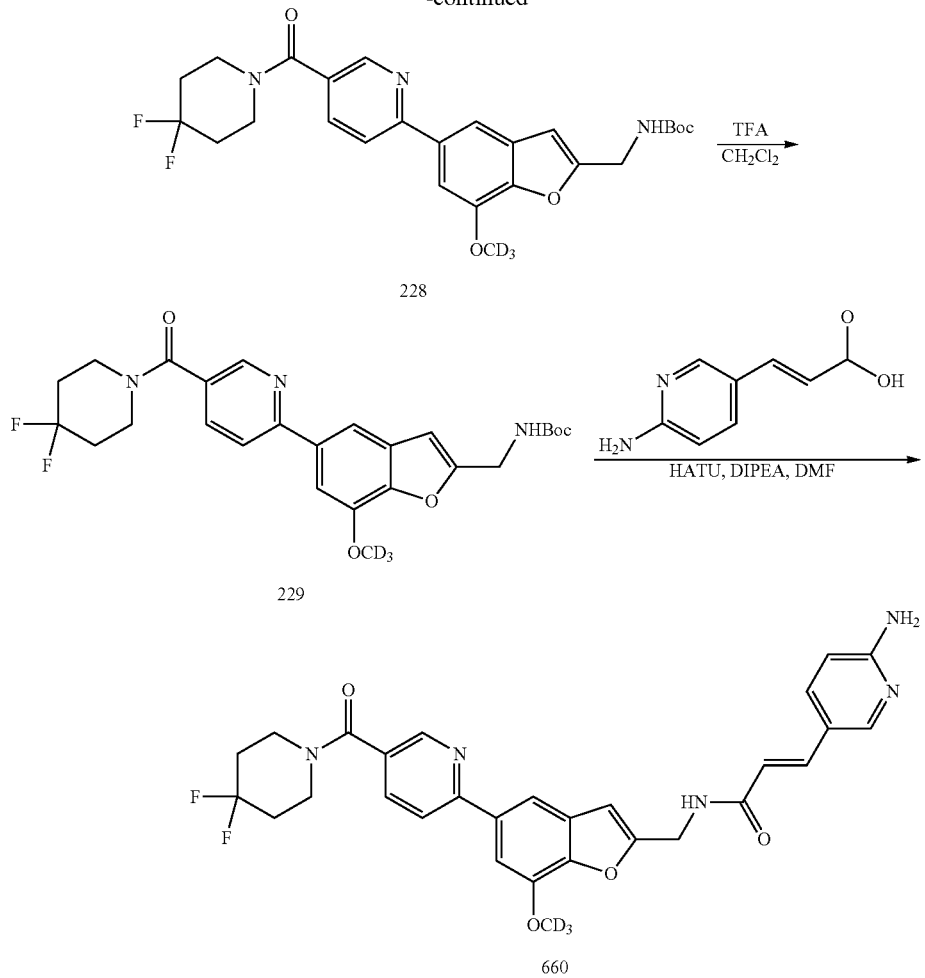

Synthesis of tert-butyl (5-(5-(4,4-difluoropiperidine-1-carbonyl)pyridin-2-yl)-7-hydroxybenzofuran-2-yl)methylcarbamate (227)

tert-Butyl (5-(5-(4,4-difluoropiperidine-1-carbonyl)pyridin-2-yl)-7-methoxybenzofuran-2-yl)methylcarbamate (226); (1 g, 2 mmol) was dissolved in 15 mL of DMF. Decanethiol (521 mg, 3 mmol) and t-BuOK (336 mg, 3 mmol) were added to this mixture. The mixture was heated to 110° C. and stirred for 1.5 h. After cooling to room temperature, the mixture was poured into 20 mL of H$_2$O, and extracted with ethyl acetate (30 mL×3). The combined organic layers were washed with brine, dried over anhydrous Na$_2$SO$_4$, and concentrated under reduced pressure to give the crude product, which was purified by silica gel chromatography (10-20% ethyl acetate/petroleum ether) to afford 300 mg of tert-butyl (5-(5-(4,4-difluoropiperidine-1-carbonyl)pyridin-2-yl)-7-hydroxybenzofuran-2-yl)methylcarbamate (227) (31% yield). LCMS: m/z 488.1 [M+H]$^+$; t$_R$=1.58 min.

Synthesis of tert-butyl (5-(5-(4,4-difluoropiperidine-1-carbonyl)pyridin-2-yl)-7-(trideuteromethoxy)benzofuran-2-yl)methylcarbamate (228)

tert-Butyl (5-(5-(4,4-difluoropiperidine-1-carbonyl)pyridin-2-yl)-7-hydroxybenzofuran-2-yl)methylcarbamate (5; 20 mg, 0.05 mmol) was dissolved in 5 mL of CH$_3$CN. K$_2$CO$_3$, (14 mg, 0.1 mmol) and CD$_3$I (15 mg, 0.1 mmol) were added at room temperature. The mixture was stirred room temperature for 18 h. 3 mL of H$_2$O was added and the mixture was extracted with ethyl acetate (10 mL×3). The combined organic layers were washed with brine, dried over anhydrous Na$_2$SO$_4$, and concentrated under reduced pressure to give the crude product, which was purified by silica gel chromatography (20% ethyl acetate/petroleum ether) to give 10 mg of tert-butyl (5-(5-(4,4-difluoropiperidine-1-carbonyl)pyridin-2-yl)-7-(trideuteromethoxy)benzofuran-2-yl)methylcarbamate (228) (50% yield). LCMS: m/z 505.1 [M+H]$^+$; t$_R$=1.68 min.

Synthesis of (6-(2-(aminomethyl)-7-(trideuteromethoxy)benzofuran-5-yl)pyridin-3-yl)(4,4-difluoropiperidin-1-yl)methanone (229)

tert-Butyl (5-(5-(4,4-difluoropiperidine-1-carbonyl)pyridin-2-yl)-7-(trideuteromethoxy)benzofuran-2-yl)methylcarbamate (228); (100 mg, 0.2 mmol) was dissolved in CH$_2$Cl$_2$ (5 mL) and TFA (1 mL) was added dropwise at room temperature. The reaction mixture was stirred at room temperature for 2 h. The reaction mixture was concentrated under reduced pressure to give the crude product, which was used without further purification in the next step (60 mg, 75% yield). LCMS: m/z 405.2 [M+H]$^+$; t$_R$=1.28 min.

Synthesis of (E)-3-(6-aminopyridin-3-yl)-N-((5-(5-(4,4-difluoropiperidine-1-carbonyl)pyridin-2-yl)-7-(methoxy-d₃)benzofuran-2-yl)methyl)acrylamide (660)

(6-(2-(aminomethyl)-7-(trideuteromethoxy)benzofuran-5-yl)pyridin-3-yl)(4,4-difluoropiperidin-1-yl)methanone (229); (60 mg, 0.15 mmol) was dissolved in DMF (3 mL) and (E)-3-(6-aminopyridin-3-yl)acrylic acid (25 mg, 0.15 mmol), HATU (113 mg, 0.3 mmol), DIPEA (39 mg, 0.3 mmol)) were added at room temperature. The reaction mixture was stirred at room temperature for 18 h. The reaction mixture was purified by Prep-HPLC without work up to give 30 mg of (E)-3-(6-aminopyridin-3-yl)-N-((5-(5-(4,4-difluoropiperidine-1-carbonyl)pyridin-2-yl)-7-(methoxy-d₃)benzofuran-2-yl)methyl)acrylamide (660). Yield (37%). $^1$H NMR (500 MHz, DMSO-d₆) δ 8.83 (s, 1H), 8.74 (s, 1H), 8.49-8.07 (m, 5H), 8.03-7.93 (m, 2H), 7.69 (s, 1H), 7.46 (d, J=16 Hz, 1H), 7.03 (d, J=9 Hz, 1H), 6.84 (s, 1H), 6.61 (d, J=16 Hz, 1H), 4.59 (d, J=5 Hz, 2H), 3.82-3.43 (m, 4H), 2.14-2.02 (m, 4H). LCMS: m/z 551.2 [M+H]⁺, $t_R$=1.82 min.

Synthesis of (E)-3-(6-aminopyridin-3-yl)-N-((5-(5-(6,6-difluoro-2-azaspiro[3.3]heptane-2-carbonyl)pyridin-2-yl)-7-(trifluoromethyl)benzofuran-2-yl)methyl)acrylamide (661)

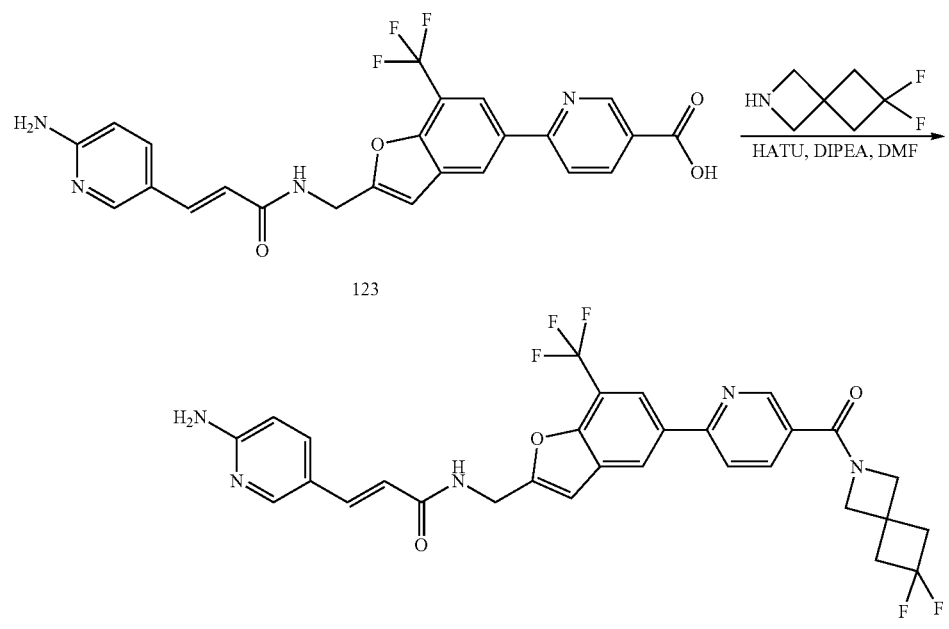

(E)-3-(6-aminopyridin-3-yl)-N-((5-(5-(6,6-difluoro-2-azaspiro[3.3]heptane-2-carbonyl)pyridin-2-yl)-7-(trifluoromethyl)benzofuran-2-yl)methyl)acrylamide (661) was synthesized using the indicated reagents according to General Procedure 4. $^1$H NMR (500 MHz, CD₃OD) δ 8.82 (d, J=2 Hz, 1H), 8.42 (s, 1H), 8.23 (s, 1H), 8.07-8.03 (m, 1H), 7.99-7.93 (m, 2H), 7.66-7.61 (m, 1H), 7.38 (d, J=16 Hz, 1H), 6.84 (s, 1H), 6.49 (d, J=9 Hz, 1H), 6.37 (d, J=16 Hz, 1H), 4.61 (s, 2H), 4.46 (s, 2H), 4.20 (s, 2H), 2.78-2.73 (m, 4H). LCMS: m/z 598.2 [M+H]⁺; $t_R$=1.25 min.

Synthesis of (E)-3-(6-aminopyridin-3-yl)-N-((5-(5-(4,4-difluoropiperidine-1-carbonyl)pyridin-2-yl)-7-(1,3,4-oxadiazol-2-yl)benzofuran-2-yl)methyl)acrylamide (662)

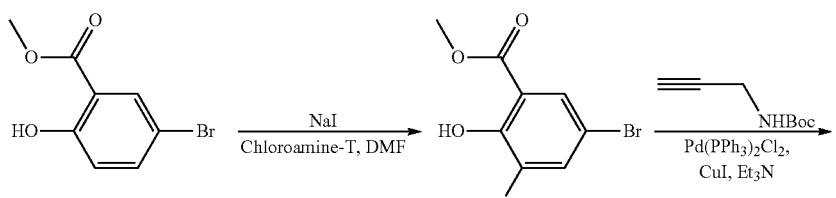

-continued
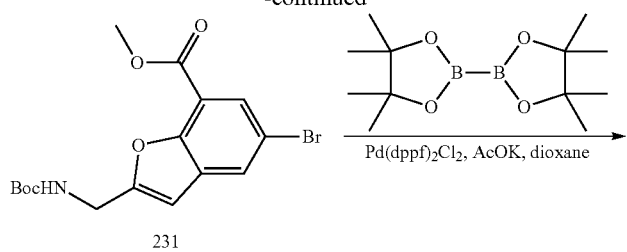
231
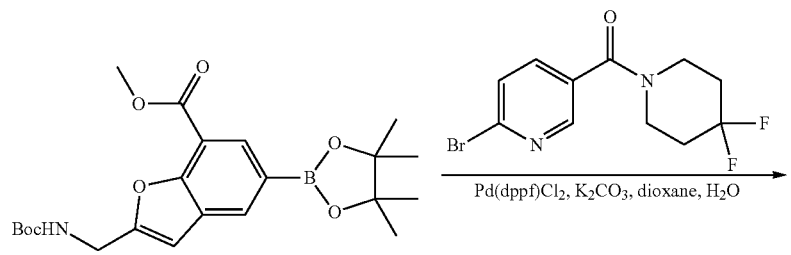
232
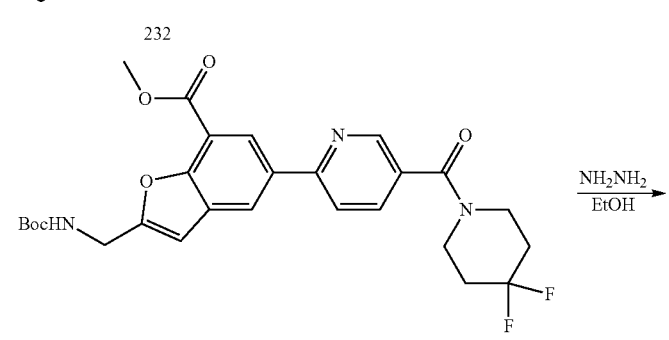
233
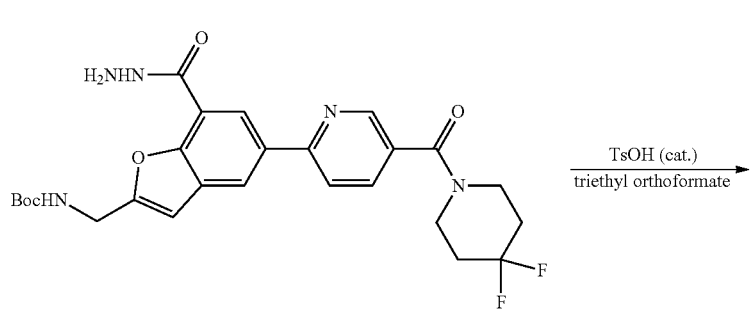
234
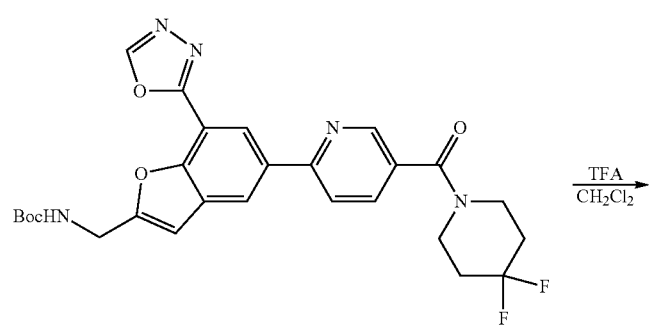
235

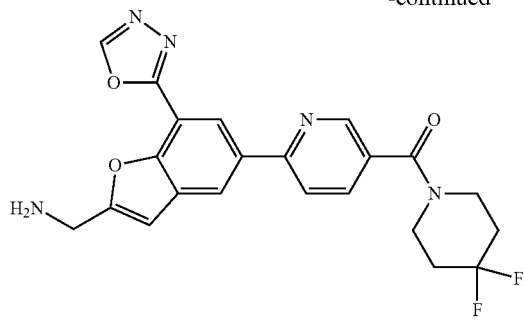
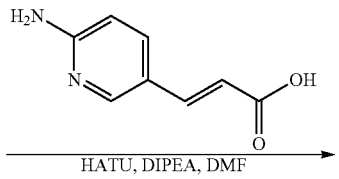

236

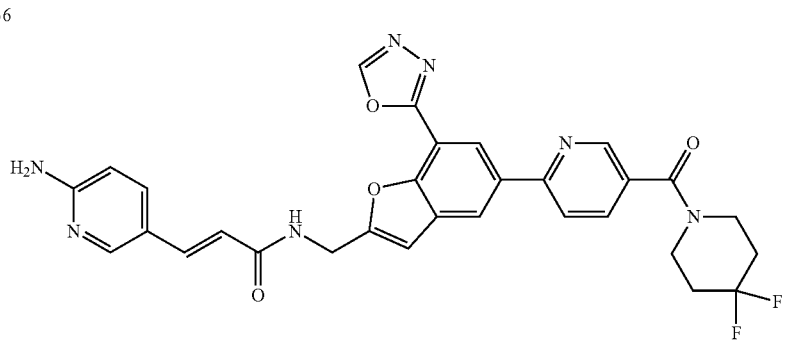

662

Synthesis of methyl 5-bromo-2-hydroxy-3-iodobenzoate (230)

Methyl 5-bromo-2-hydroxybenzoate (10 g, 43.3 mmol) and NaI (7.8 g, 52 mmol) were added to 200 mL of DMF. The mixture was cooled to 0° C. and chloroamine-T hydrate (14.7 g, 52 mmol) was added. The reaction mixture was stirred at 0° C. for 5 h, quenched with 200 mL of H$_2$O, extracted with EtOAc (500 mL×3). The combined organic layers were washed with sat. sodium bisulfite and brine, dried over anhydrous Na$_2$SO$_4$, concentrated under reduced pressure and purified by silica gel chromatography (20% EtOAc/petroleum ether) to give 8.6 g of methyl 5-bromo-2-hydroxy-3-iodobenzoate (230) (55% yield). LCMS: m/z 356.2 [M−55]$^+$; $t_R$=1.95 min.

Synthesis of methyl 5-bromo-2-((tert-butoxycarbonylamino)methyl)benzofuran-7-carboxylate (231)

A mixture of methyl 5-bromo-2-hydroxy-3-iodobenzoate (230) (7.5 g, 21 mmol), tert-butyl prop-2-ynylcarbamate (3.6 g, 23 mmol), Pd(PPh$_3$)$_2$Cl$_2$ (1.5 g, 2.1 mmol), CuI (800 mg, 4.2 mmol) in 80 mL of Et$_3$N was heated at 90° C. under nitrogen atmosphere for 2 h. After cooling down to room temperature, the reaction mixture was filtered and the filtrate was concentrated under reduced pressure to give the crude product, which was purified by silica gel chromatography (33%-59% EtOAc/petroleum ether) to give 6.1 g of methyl 5-bromo-2-((tert-butoxycarbonylamino)methyl)benzofuran-7-carboxylate (231) as a yellowish solid (76% yield). LCMS: m/z 408.0 [M+Na]$^+$; $t_R$=1.82 min.

Synthesis of methyl 2-((tert-butoxycarbonylamino)methyl)-5-(4,4,5,5-tetramethyl-1,3,2-dioxaborolan-2-yl)benzofuran-7-carboxylate (232)

A mixture of methyl 5-bromo-2-((tert-butoxycarbonylamino)methyl)benzofuran-7-carboxylate (231) (5 g, 13 mmol), 4,4,4',4',5,5,5',5'-octamethyl-2,2'-bi(1,3,2-dioxaborolane) (4.6 g, 18 mmol), Pd(dppf)Cl$_2$ (913 mg, 1.3 mmol) and AcOK (2.6 g, 26 mmol) in 50 mL of dioxane was degassed and heated at 100° C. under nitrogen atmosphere for 6 h. After cooling down to room temperature, the reaction mixture was filtered and the filtrate was concentrated under reduced pressure to give the crude product, which was purified by silica gel chromatography (10% EtOAc/petroleum ether) to give 4.65 g of methyl 2-((tert-butoxycarbonylamino)methyl)-5-(4,4,5,5-tetramethyl-1,3,2-dioxaborolan-2-yl)benzofuran-7-carboxylate (232) as a yellow solid (83% yield). LCMS: m/z 453.9 [M+Na]$^+$, $t_R$=2.1$^2$ min.

Synthesis of methyl 2-((tert-butoxycarbonylamino)methyl)-5-(5-(4,4-difluoropiperidine-1-carbonyl)pyridin-2-yl)benzofuran-7-carboxylate (233)

A mixture of (6-bromopyridin-3-yl)(4,4-difluoropiperidin-1-yl)methanone (3.1 g, 10 mmol), methyl 2-((tert-butoxycarbonylamino)methyl)-5-(4,4,5,5-tetramethyl-1,3,2-dioxaborolan-2-yl)benzofuran-7-carboxylate (232) (4.3 g, 10 mmol), Pd(dppf)Cl$_2$ (702 mg, 1 mmol) and K$_2$CO$_3$ (2.8 g, 20 mmol) in 50 mL of dioxane and 5 mL of H$_2$O was degassed. The reaction mixture was heated at 100° C. under nitrogen atmosphere for 6 h, cooled down to room temperature and filtered. The filtrate was concentrated under reduced pressure to remove most of the solvent and 50 mL water was added. The resulting mixture was extracted with EtOAc (30 mL×3). The combined organic layers were washed with brine, dried over anhydrous Na$_2$SO$_4$, and concentrated under reduced pressure to give the crude product, which was purified by silica gel chromatography (50%-70% EtOAc/petroleum ether) to give 3.2 g of methyl 2-((tert-butoxycarbonylamino)methyl)-5-(5-(4,4-difluoropiperidine-1-carbonyl)pyridin-2-yl)benzofuran-7-carboxylate (233) as a yellow solid. (60% yield). LCMS: m/z 530.2 [M+H]+, t_R=1.92 min.

Synthesis of tert-butyl (5-(5-(4,4-difluoropiperidine-1-carbonyl)pyridin-2-yl)-7-(hydrazinecarbonyl)benzofuran-2-yl)methylcarbamate (234)

Methyl 2-((tert-butoxycarbonylamino)methyl)-5-(5-(4,4-difluoropiperidine-1-carbonyl)pyridin-2-yl)benzofuran-7-carboxylate (233); (1 g, 1.9 mmol) was dissolved in 9 mL of EtOH. Hydrazine hydrate (3 mL) was added at room temperature. The reaction mixture was heated at 100° C. for 2 h. After cooling down to room temperature, the precipitate was collected by filtration and dried under reduced pressure to afford 0.81 g of tert-butyl (5-(5-(4,4-difluoropiperidine-1-carbonyl)pyridin-2-yl)-7-(hydrazinecarbonyl)benzofuran-2-yl)methylcarbamate (234). (68% yield). LCMS: m/z 530.2 [M+H]+, t_R=1.71 min.

Synthesis of tert-butyl (5-(5-(4,4-difluoropiperidine-1-carbonyl)pyridin-2-yl)-7-(1,3,4-oxadiazol-2-yl)benzofuran-2-yl)methylcarbamate (235)

tert-Butyl (5-(5-(4,4-difluoropiperidine-1-carbonyl)pyridin-2-yl)-7-(hydrazinecarbonyl)benzofuran-2-yl)methylcarbamate (234); (423 mg, 0.8 mmol) was added to 26 mL of triethyl orthoformate. 4-Methylbenzenesulfonic acid (7 mg, 0.04 mmol) was added. The reaction mixture was heated at 125° C. for 2 h. The solvent was removed under reduced pressure and the residue was purified by silica gel chromatography (50% EtOAc/petroleum ether) to give 215 mg of tert-butyl (5-(5-(4,4-difluoropiperidine-1-carbonyl)pyridin-2-yl)-7-(1,3,4-oxadiazol-2-yl)benzofuran-2-yl)methylcarbamate (235) (50% yield). LCMS: m/z 540.3 [M+H]+, t_R=1.83 min.

Synthesis of (6-(2-(aminomethyl)-7-(1,3,4-oxadiazol-2-yl)benzofuran-5-yl)pyridin-3-yl)(4,4-difluoropiperidin-1-yl)methanone (236)

tert-Butyl (5-(5-(4,4-difluoropiperidine-1-carbonyl)pyridin-2-yl)-7-(1,3,4-oxadiazol-2-yl)benzofuran-2-yl)methylcarbamate (235); (162 mg, 0.3 mmol) was dissolved in CH_2Cl_2 (4 mL). TFA (1 mL) was added at 0° C. (ice bath). The reaction mixture was allowed to warm to room temperature and stirred for 1 h. The reaction mixture was concentrated under reduced pressure to give 167 mg of crude (6-(2-(aminomethyl)-7-(1,3,4-oxadiazol-2-yl)benzofuran-5-yl)pyridin-3-yl)(4,4-difluoropiperidin-1-yl)methanone (236), which was used without further purification in the next step. (100% yield). LCMS: m/z 440.2 [M+H]+; t_R=1.54 min.

Synthesis of (E)-3-(6-aminopyridin-3-yl)-N-((5-(5-(4,4-difluoropiperidine-1-carbonyl)pyridin-2-yl)-7-(1,3,4-oxadiazol-2-yl)benzofuran-2-yl)methyl)acrylamide (662)

(6-(2-(Aminomethyl)-7-(1,3,4-oxadiazol-2-yl)benzofuran-5-yl)pyridin-3-yl)(4,4-difluoropiperidin-1-yl)methanone (236) (167 mg, 0.3 mmol) was dissolved in DMF (4 mL) and (E)-3-(6-aminopyridin-3-yl)acrylic acid (59 mg, 0.36 mmol) was added at 0° C. HATU (148 mg, 0.39 mmol) was added to this reaction mixture at 0° C. followed by DIPEA (77 mg, 0.6 mmol) dropwise. The reaction mixture was allowed to warm to room temperature and stirred for 4 h. 20 mL of EtOAc and 10 mL of water were added to this mixture. The aqueous phase was separated and extracted with EtOAc (15 mL×2). The combined organic layers were washed with brine, dried over anhydrous Na_2SO_4, and concentrated under reduced pressure to give the crude product, which was purified by silica gel chromatography (50% EtOAc/petroleum ether to 5% MeOH/EtOAc) to give 40 mg of (E)-3-(6-aminopyridin-3-yl)-N-((5-(5-(4,4-difluoropiperidine-1-carbonyl)pyridin-2-yl)-7-(1,3,4-oxadiazol-2-yl)benzofuran-2-yl)methyl)acrylamide (662) as a yellow solid (23% yield). $^1$H NMR (500 MHz, CD_3OD) δ 9.20 (s, 1H), 8.80 (d, J=2 Hz, 1H), 8.73 (d, J=2 Hz, 1H), 8.52 (d, J=2 Hz, 1H), 8.11 (d, J=8 Hz, 1H), 8.07-8.02 (m, 2H), 7.77-7.74 (m, 1H), 7.50 (d, J=16 Hz, 1H), 6.97 (s, 1H), 6.61 (d, J=9 Hz, 1H), 6.50 (d, J=16 Hz, 1H), 4.78 (s, 2H), 3.99-3.63 (m, 4H), 2.23-2.05 (m, 4H). LCMS: m/z 586.2 [M+H]+, t_R=1.23 min.

Synthesis of (E)-3-(6-aminopyridin-3-yl)-N-((5-(5-(4,4-difluoropiperidine-1-carbonyl)pyridin-2-yl)-7-(trifluoromethoxy)benzofuran-2-yl)methyl)acrylamide (663)

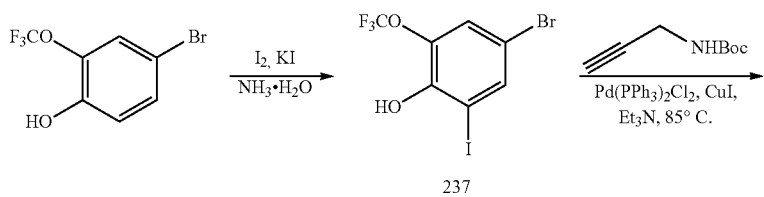

237

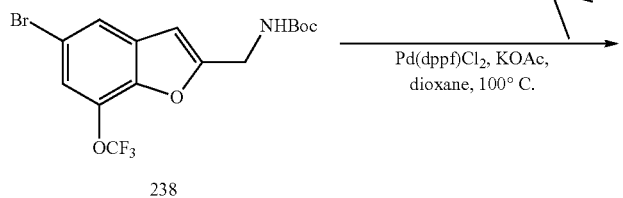

238

-continued

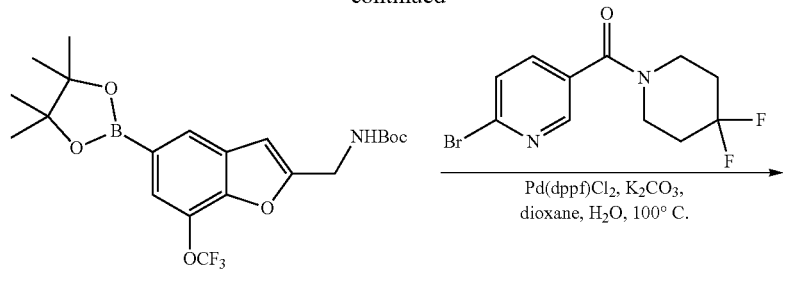

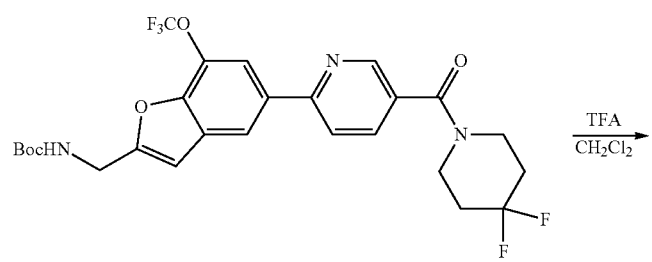

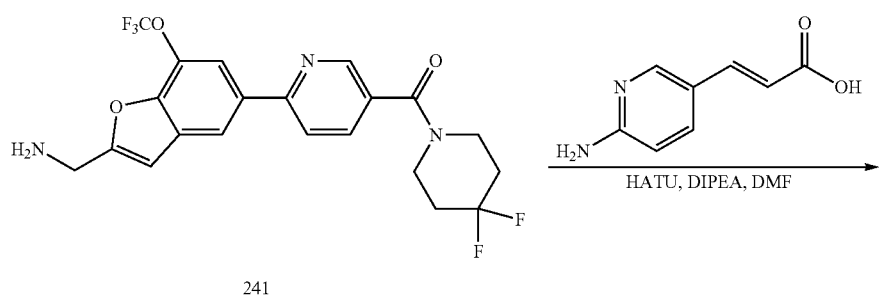

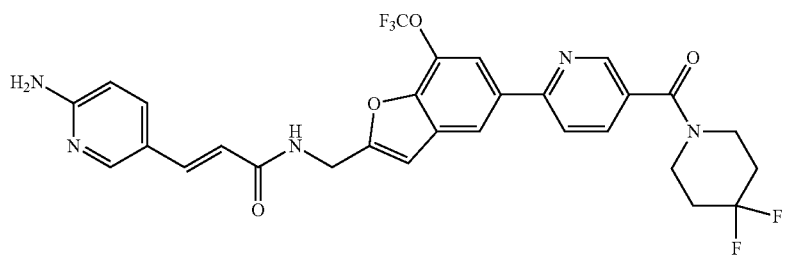

Synthesis of 4-bromo-2-iodo-6-(trifluoromethoxy)phenol (237)

4-Bromo-2-(trifluoromethoxy)phenol (3.2 g, 12 mmol) was dissolved in 100 mL of NH$_4$OH. A solution of KI (6.2 g, 37 mmol) and I2 (3.3 g, 13 mmol) in 50 mL of H$_2$O was added to the reaction mixture and stirred at room temperature up to 5 h. The reaction mixture was cooled down to 0° C. (ice bath), neutralized with HCl (conc.) until pH~6-7; extracted with EtOAc (150 mL×3). The combined organic layers were washed with sat. aq. sodium bisulfite solution, brine, dried over anhydrous Na$_2$SO$_4$, and concentrated under reduced pressure to give 4 g of 4-bromo-2-iodo-6-(trifluoromethoxy)phenol (237) as a yellow solid (85% yield). LCMS: t$_R$=1.79 min.

Synthesis of tert-butyl (5-bromo-7-(trifluoromethoxy)benzofuran-2-yl)methylcarbamate (238)

4-Bromo-2-iodo-6-(trifluoromethoxy)phenol (237) (4 g, 15.7 mmol), tert-butyl prop-2-ynylcarbamate (2.9 g, 18.8 mmol), Pd(PPh$_3$)$_2$Cl$_2$ (0.73 g, 1.6 mmol), CuI (0.6 g, 3.1 mmol) were added in 50 mL of triethylamine and degassed. The reaction mixture was refluxed at 85° C. under nitrogen atmosphere for 2 h. After cooling down to room temperature, the reaction mixture was filtered. The filtrate was concentrated under reduced pressure to give the crude product, which was purified by silica gel chromatography (5% EtOAc/petroleum ether) to yield 3.6 g of tert-butyl (5-bromo-7-(trifluoromethoxy)benzofuran-2-yl)methylcarbamate (238) as a pale yellow solid (82% yield). LCMS: m/z 354.0 [M-55]$^+$, t$_R$=1.88 min.

Synthesis of tert-butyl (5-(4,4,5,5-tetramethyl-1,3,2-dioxaborolan-2-yl)-7-(trifluoromethoxy)benzofuran-2-yl)methylcarbamate (239)

tert-Butyl (5-bromo-7-(trifluoromethoxy)benzofuran-2-yl)methylcarbamate (238) (4.7 g, 11 mmol), 4,4,4',4',5,5,5',5'-octamethyl-2,2'-bi(1,3,2-dioxaborolane) (5.8 g, 22 mmol), Pd(dppf)Cl$_2$ (0.9 g, 1.2 mmol), and potassium acetate (2.3 g, 22 mmol) were added in 50 mL of dioxane and degassed. The reaction mixture was heated at 100° C. under nitrogen atmosphere for 2 h. After cooling down to room temperature, the reaction mixture was filtered. The filtrate was concentrated under reduced pressure to give the crude product, which was purified by silica gel chromatography (10% EtOAc/petroleum ether) to yield 5.1 g of tert-butyl (5-(4,4,5,5-tetramethyl-1,3,2-dioxaborolan-2-yl)-7-(trifluoromethoxy)benzofuran-2-yl)methylcarbamate (239) as a white solid (96% yield). LCMS: m/z 480.2 [M+Na]$^+$, t$_R$=1.93 min.

Synthesis of tert-butyl (5-(5-(4,4-difluoropiperidine-1-carbonyl)pyridin-2-yl)-7-(trifluoromethoxy)benzofuran-2-yl)methylcarbamate (240)

tert-Butyl (5-(4,4,5,5-tetramethyl-1,3,2-dioxaborolan-2-yl)-7-(trifluoromethoxy)benzofuran-2-yl)methylcarbamate (239) (5 g, 11 mmol), (6-bromopyridin-3-yl)(4,4-difluoropiperidin-1-yl)methanone (3.7 g, 12 mmol), Pd(dppf)Cl$_2$ (0.8 g, 1.1 mmol), and K$_2$CO$_3$ (3 g, 22 mmol) were added in a mixture of dioxane (50 mL) and water (5 mL) and degassed. The reaction mixture was heated at 100° C. under nitrogen atmosphere for 5 h. The reaction mixture was cooled down to room temperature, filtered and the filtrate was concentrated under reduced pressure to give the crude product, which was purified by silica gel chromatography (50% EtOAc/petroleum ether) to yield 4.7 g of tert-butyl (5-(5-(4,4-difluoropiperidine-1-carbonyl)pyridin-2-yl)-7-(trifluoromethoxy)benzofuran-2-yl)methylcarbamate (240) as a white solid (yield 78%). LCMS: m/z 556.2 [M+H]$^+$, t$_R$=2.06 min.

Synthesis of (6-(2-(aminomethyl)-7-(trifluoromethoxy)benzofuran-5-yl)pyridin-3-yl)(4,4-difluoropiperidin-1-yl)methanone (241)

tert-Butyl (5-(5-(4,4-difluoropiperidine-1-carbonyl)pyridin-2-yl)-7-(trifluoromethoxy)benzofuran-2-yl)methylcarbamate (240) (3.7 g, 6.7 mmol) was dissolved in CH$_2$Cl$_2$ (30 mL). TFA (3 mL) was added dropwise at room temperature. The reaction mixture was stirred at room temperature for 2 h. The reaction mixture was concentrated under reduced pressure to give the crude (6-(2-(aminomethyl)-7-(trifluoromethoxy)benzofuran-5-yl)pyridin-3-yl)(4,4-difluoropiperidin-1-yl)methanone (241), which was used without further purification in the next step (3 g, 100% yield). LCMS: m/z 456.1 [M+H]$^+$, t$_R$=1.83 min.

Synthesis of (E)-3-(6-aminopyridin-3-yl)-N-((5-(5-(4,4-difluoropiperidine-1-carbonyl)pyridin-2-yl)-7-(trifluoromethoxy)benzofuran-2-yl)methyl)acrylamide (663)

(6-(2-(Aminomethyl)-7-(trifluoromethoxy)benzofuran-5-yl)pyridin-3-yl)(4,4-difluoropiperidin-1-yl)methanone (241) (2.2 g, 4.8 mmol) was dissolved in DMF (40 mL) and (E)-3-(6-aminopyridin-3-yl)acrylic acid (0.9 g, 5.3 mmol) was added at 0° C. HATU (3.7 g, 9.7 mmol) was added to this reaction mixture at 0° C. followed by DIPEA (12 g, 96 mmol) dropwise. The reaction mixture was allowed to warm to room temperature and stirred further for 4 h. The reaction mixture was poured into iced water (100 mL), extracted with EtOAc (100 mL×3). The combined organic layers were washed with brine, dried over Na$_2$SO$_4$, concentrated under reduced pressure to give crude product which was purified by silica gel chromatography (10% MeOH/EtOAc) to afford 1 g of (E)-3-(6-aminopyridin-3-yl)-N-((5-(5-(4,4-difluoropiperidine-1-carbonyl)pyridin-2-yl)-7-(trifluoromethoxy)benzofuran-2-yl)methyl)acrylamide (663) (34% yield). $^1$H NMR (400 MHz, DMSO-d$_6$) δ 8.77 (d, J=2 Hz, 1H), 8.65 (t, J=6 Hz, 1H), 8.43 (d, J=1 Hz, 1H), 8.17 (d, J=8 Hz, 1H), 8.15-8.07 (m, 2H), 8.05-7.99 (m, 1H), 7.66-7.60 (m, 1H), 7.36 (d, J=16 Hz, 1H), 6.97 (s, 1H), 6.52-6.38 (m, 4H), 4.61 (d, J=6 Hz, 2H), 3.83-3.43 (m, 4H), 2.17-2.00 (m, 4H). LCMS: m/z 602.4 [M+H]$^+$; t$_R$=1.80 min.

Synthesis of (E)-3-(6-aminopyridin-3-yl)-N-((5-(5-(4,4-difluoropiperidine-1-carbonyl)pyridin-2-yl)-6-(trifluoromethyl)benzofuran-2-yl)methyl)acrylamide (664)

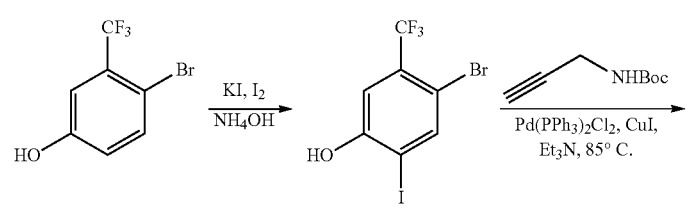

242

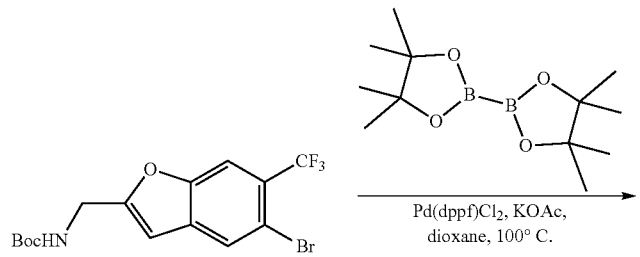

243

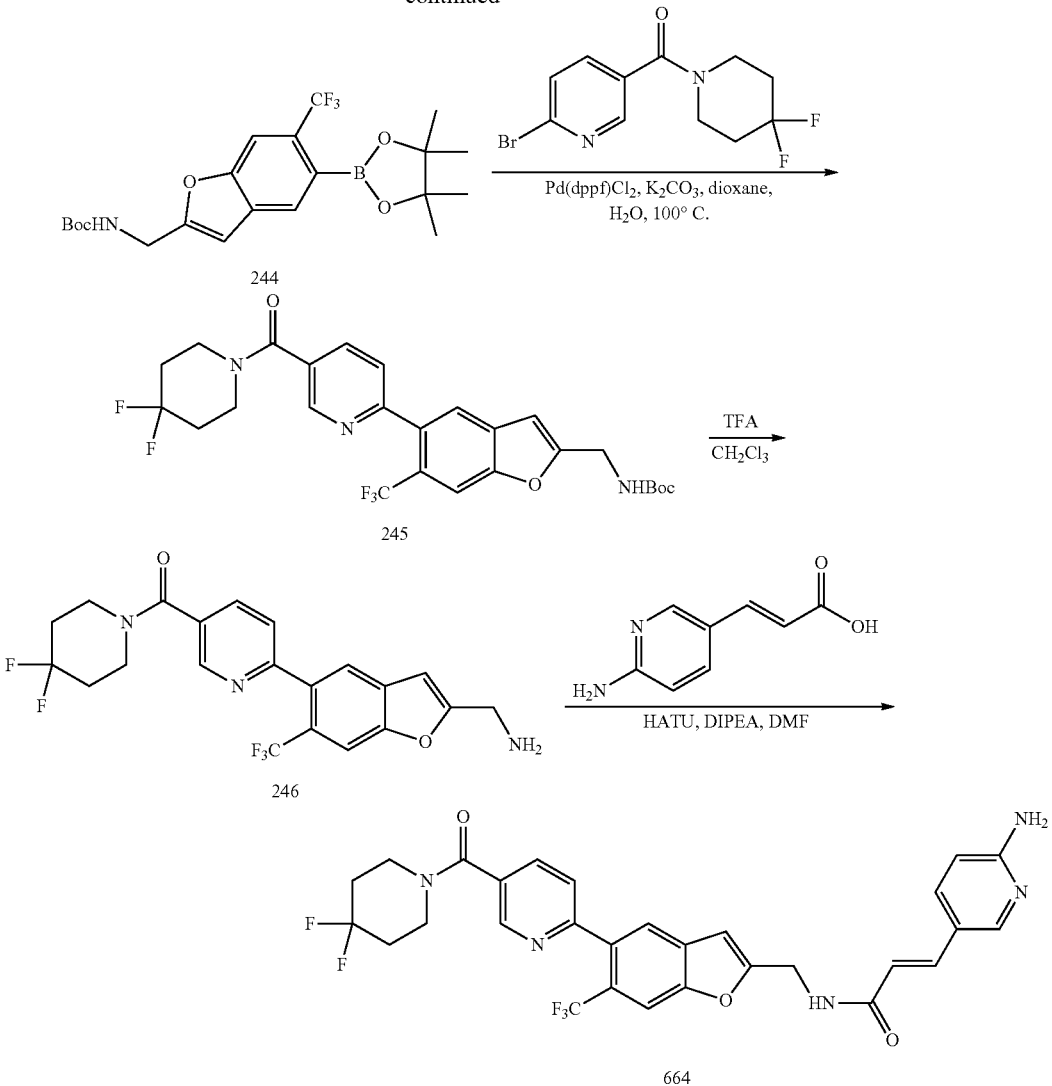

Synthesis of 4-bromo-2-iodo-5-(trifluoromethyl)phenol (242)

4-Bromo-3-(trifluoromethyl)phenol (2 g, 8.3 mmol) was dissolved in 100 mL of NH₄OH. A solution of KI (4.1 g, 25 mmol) and I2 (2.1 g, 8.3 mmol) in 50 mL of H₂O was added to the reaction mixture and stirred at room temperature up to 2 h. The reaction mixture was cooled down to 0° C. (ice bath), neutralized with HCl (conc.) until pH~6-7; extracted with EtOAc (150 mL×3). The combined organic layers were washed with sat. aq. sodium bisulfite solution, brine, dried over anhydrous Na₂SO₄, and concentrated under reduced pressure to give 2.1 g of 4-bromo-2-iodo-5-(trifluoromethyl) phenol (242) as a yellow solid (70% yield). LCMS: $t_R$=1.22 min.

Synthesis of tert-butyl (5-bromo-6-(trifluoromethyl)benzofuran-2-yl)methylcarbamate (243)

4-Bromo-2-iodo-5-(trifluoromethyl)phenol (242) (2.1 g, 5.7 mmol), tert-butyl prop-2-ynylcarbamate (0.93 g, 6 mmol), Pd(PPh₃)₂Cl₂ (0.42 g, 0.6 mmol), CuI (0.1 g, 0.05 mmol) were added in 50 mL of triethylamine and degassed. The reaction mixture was refluxed at 85° C. under nitrogen atmosphere for 2 h. After cooling down to room temperature, the reaction mixture was filtered. The filtrate was concentrated under reduced pressure to give the crude product, which was purified by silica gel chromatography (5% EtOAc/petroleum ether) to yield 2.2 g of tert-butyl (5-bromo-6-(trifluoromethyl)benzofuran-2-yl)methylcarbamate (243) as a pale yellow solid (95% yield). ¹H NMR (400 MHz, CDCl₃) δ 7.85 (s, 1H), 7.79 (s, 1H), 6.60 (s, 1H), 4.47 (d, J=6 Hz, 2H), 1.47 (s, 9H). LCMS: m/z 339.9 [M-55]⁺; $t_R$=1.95 min.

Synthesis of tert-butyl (5-(4,4,5,5-tetramethyl-1,3,2-dioxaborolan-2-yl)-6-(trifluoromethyl)benzofuran-2-yl)methylcarbamate (244)

tert-Butyl (5-bromo-6-(trifluoromethyl)benzofuran-2-yl) methylcarbamate (243) (1 g, 2.5 mmol), 4,4,4',4',5,5,5',5'-octamethyl-2,2'-bi(1,3,2-dioxaborolane) (2.8 g, 11 mmol), Pd(dppf)Cl₂ (0.3 g, 0.42 mmol), and potassium acetate (1.1 g, 11 mmol) were added in 50 mL of dioxane and degassed.

The reaction mixture was heated at 100° C. under nitrogen atmosphere for 2 h. After cooling down to room temperature, the reaction mixture was filtered. The filtrate was concentrated under reduced pressure to give the crude product, which was purified by silica gel chromatography (10% EtOAc/petroleum ether) to yield 240 mg of tert-butyl (5-(4,4,5,5-tetramethyl-1,3,2-dioxaborolan-2-yl)-6-(trifluoromethyl)benzofuran-2-yl)methylcarbamate (244) as a white solid (22% yield). LCMS: $t_R$=2.02 min.

Synthesis of tert-butyl (5-(5-(4,4-difluoropiperidine-1-carbonyl)pyridin-2-yl)-6-(trifluoromethyl)benzofuran-2-yl)methylcarbamate (245)

tert-Butyl (5-(4,4,5,5-tetramethyl-1,3,2-dioxaborolan-2-yl)-6-(trifluoromethyl)benzofuran-2-yl)methylcarbamate (244) (200 mg, 0.45 mmol), (6-bromopyridin-3-yl)(4,4-difluoropiperidin-1-yl)methanone (130 mg, 0.5 mmol), Pd(dppf)Cl$_2$ (48 mg, 0.05 mmol), and K$_2$CO$_3$ (124 mg, 0.9 mmol) were added in a mixture of dioxane (10 mL) and water (1 mL) and degassed. The reaction mixture was heated at 100° C. under nitrogen atmosphere for 5 h. The reaction mixture was cooled down to room temperature, filtered and the filtrate was concentrated under reduced pressure to give the crude product, which was purified by silica gel chromatography (50% EtOAc/petroleum ether) to yield 135 mg of tert-butyl (5-(5-(4,4-difluoropiperidine-1-carbonyl)pyridin-2-yl)-6-(trifluoromethyl)benzofuran-2-yl)methylcarbamate (245) as a white solid (yield 56%). LCMS: m/z 540.2 [M+H]$^+$, $t_R$=1.33 min.

Synthesis of (6-(2-(aminomethyl)-6-(trifluoromethyl)benzofuran-5-yl)pyridin-3-yl)(4,4-difluoropiperidin-1-yl)methanone (246)

tert-Butyl (5-(5-(4,4-difluoropiperidine-1-carbonyl)pyridin-2-yl)-6-(trifluoromethyl)benzofuran-2-yl)methylcarbamate (245) (135 mg, 0.25 mmol) was dissolved in CH$_2$Cl$_2$ (10 mL). TFA (1.5 mL) was added dropwise at room temperature. The reaction mixture was stirred at room temperature for 1 h. The reaction mixture was concentrated under reduced pressure to give the crude (6-(2-(aminomethyl)-6-(trifluoromethyl)benzofuran-5-yl)pyridin-3-yl)(4,4-difluoropiperidin-1-yl)methanone (246), which was used without further purification in the next step (110 mg, 100% yield). LCMS: m/z 440.1 [M+H]$^+$, $t_R$=1.36 min.

Synthesis of (E)-3-(6-aminopyridin-3-yl)-N-((5-(5-(4,4-difluoropiperidine-1-carbonyl)pyridin-2-yl)-6-(trifluoromethyl)benzofuran-2-yl)methyl)acrylamide (664)

(6-(2-(Aminomethyl)-6-(trifluoromethyl)benzofuran-5-yl)pyridin-3-yl)(4,4-difluoropiperidin-1-yl)methanone (246) (50 mg, 0.10 mmol) was dissolved in DMF (3 mL) and (E)-3-(6-aminopyridin-3-yl)acrylic acid (18 mg, 0.10 mmol) was added at 0° C. HATU (46 mg, 0.12 mmol) was added to this reaction mixture at 0° C. followed by DIPEA (65 mg, 0.50 mmol) dropwise. The reaction mixture was allowed to warm to room temperature and stirred further for 1 h. The reaction mixture was purified by Prep-HPLC to afford 15 mg of (E)-3-(6-aminopyridin-3-yl)-N-((5-(5-(4,4-difluoropiperidine-1-carbonyl)pyridin-2-yl)-6-(trifluoromethyl)benzofuran-2-yl)methyl)acrylamide (664) (26% yield). $^1$H NMR (400 MHz, DMSO-d$_6$) δ 8.75-8.71 (m, 1H), 8.68-8.62 (m, 1H), 8.12 (s, 1H), 8.08 (d, J=2 Hz, 1H), 8.02-7.98 (m, 1H), 7.78 (s, 1H), 7.64-7.58 (m, 2H), 7.36 (d, J=16 Hz, 1H), 6.91 (s, 1H), 6.49-6.39 (m, 4H), 4.63 (d, J=6 Hz, 2H), 3.82-3.70 (m, 2H), 3.53-3.44 (m, 2H), 2.19-2.03 (m, 4H). LCMS: m/z 586.2 [M+H]$^+$, $t_R$=1.63 min.

Synthesis of (E)-3-(6-aminopyridin-3-yl)-N-((5-(5-(4,4-difluoropiperidine-1-carbonyl)pyridin-2-yl)-7-(4-fluorophenyl)benzofuran-2-yl)methyl)acrylamide (665)

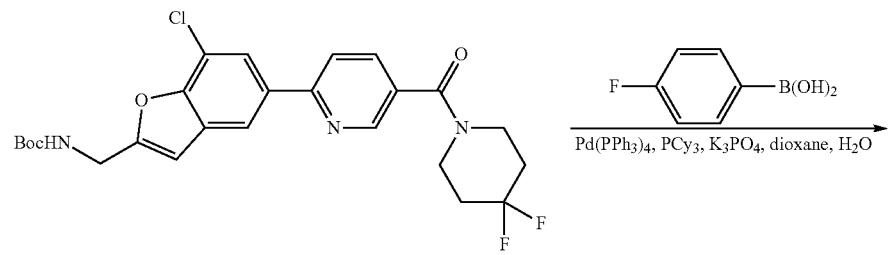

223

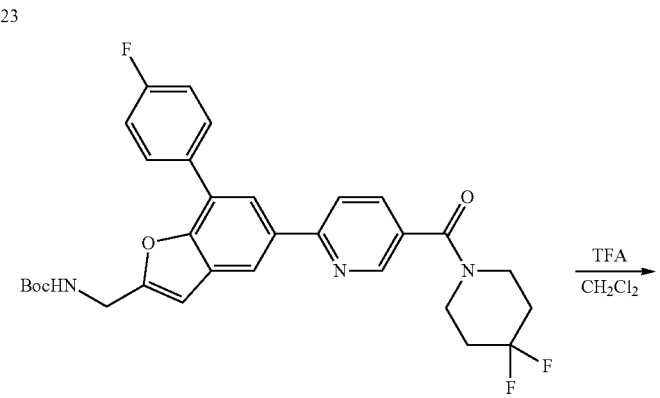

247

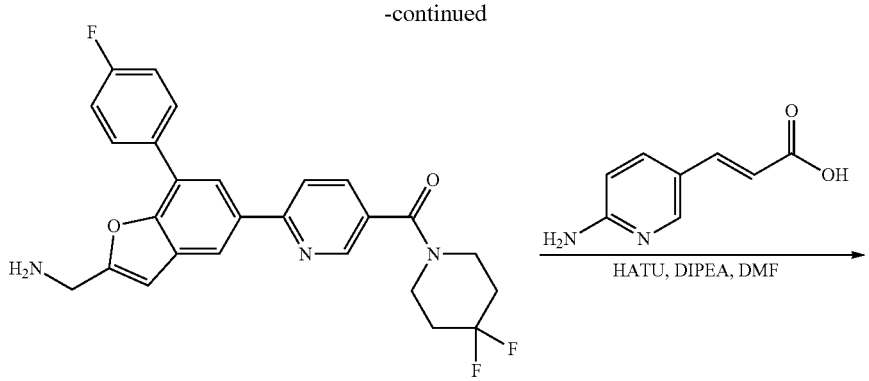

248

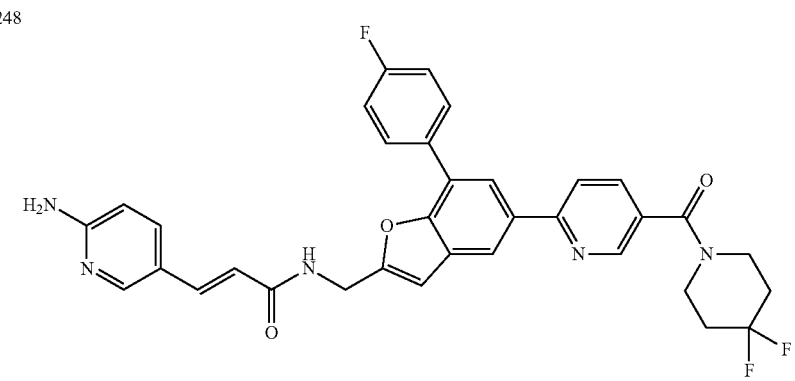

665

(E)-3-(6-aminopyridin-3-yl)-N-((5-(5-(4,4-difluoropiperidine-1-carbonyl)pyridin-2-yl)-7-(4-fluorophenyl)benzofuran-2-yl)methyl)acrylamide (665) was synthesized in a similar fashion as example (659) using the indicated reagents. $^1$H NMR (400 MHz, DMSO-$d_6$) δ 8.86-8.79 (m, 1H), 8.76 (d, J=2 Hz, 1H), 8.38 (d, J=2 Hz, 1H), 8.28-8.16 (m, 3H), 8.08-7.97 (m, 4H), 7.48-7.35 (m, 3H), 7.30-6.89 (m, 4H), 6.64-6.54 (m, 1H), 4.62 (d, J=6 Hz, 2H), 3.82-3.68 (m, 4H), 2.15-2.03 (m, 4H). LCMS: m/z 612.2 [M+H]$^+$; $t_R$=1.44 min.

Synthesis of (E)-3-(6-aminopyridin-3-yl)-N-((5-(5-(4,4-difluoropiperidine-1-carbonyl)pyridin-2-yl)-7-(pyridin-4-yl)benzofuran-2-yl)methyl)acrylamide (666)

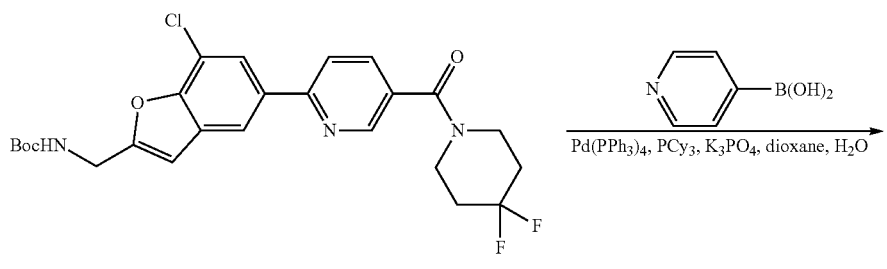

223

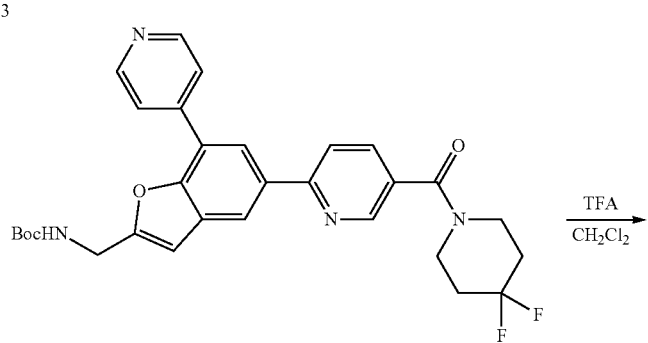

249

-continued

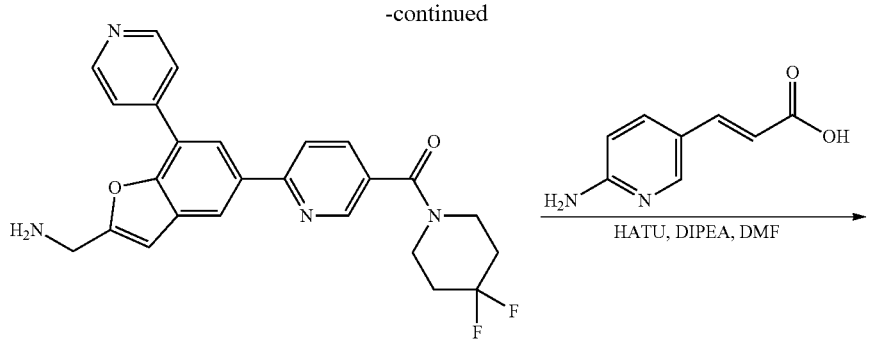

250

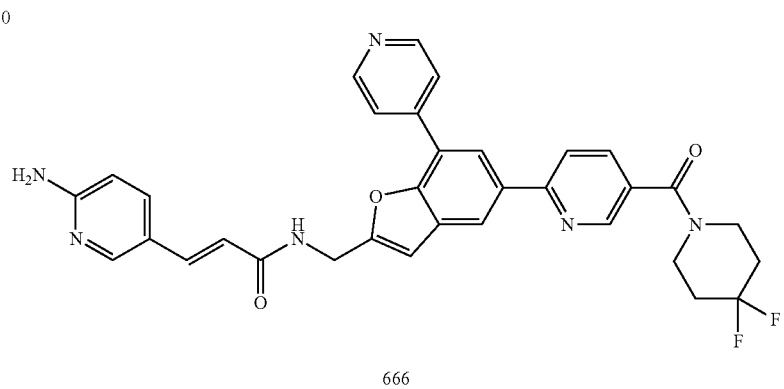

666

(E)-3-(6-aminopyridin-3-yl)-N-((5-(5-(4,4-difluoropiperidine-1-carbonyl)pyridin-2-yl)-7-(pyridin-4-yl)benzofuran-2-yl)methyl)acrylamide (666) was synthesized in a similar fashion as example (659) using the indicated reagents. $^1$H NMR (500 MHz, DMSO-d$_6$) δ 8.91-8.83 (m, 3H), 8.79 (s, 1H), 8.56 (s, 1H), 8.48 (s, 1H), 8.35-8.18 (m, 6H), 8.12 (d, J=8 Hz, 1H), 8.04 (d, J=10 Hz, 1H), 7.48 (d, J=16 Hz, 1H), 7.04-6.96 (m, 2H), 6.62 (d, J=16 Hz, 1H), 4.67 (d, J=6 Hz, 2H), 3.84-3.43 (m, 4H), 2.17-2.02 (m, 4H). LCMS: m z 595.2 [M+H]$^+$, t$_R$=1.65 min.

Synthesis of (E)-3-(6-aminopyridin-3-yl)-N-((5-(5-(4,4-difluoropiperidine-1-carbonothioyl)pyridin-2-yl)-7-(trifluoromethyl)benzofuran-2-yl)methyl)acrylamide (667)

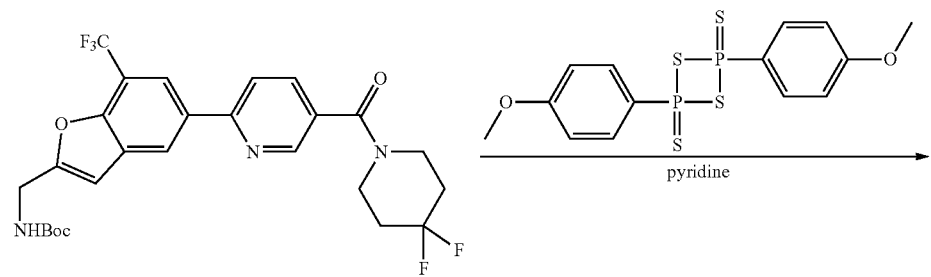

251

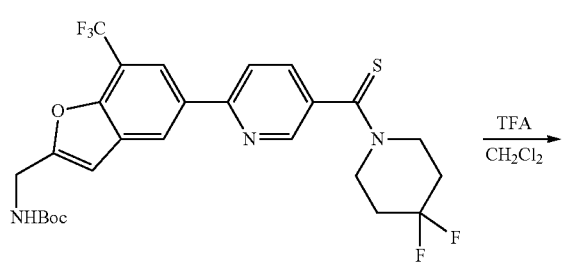

252

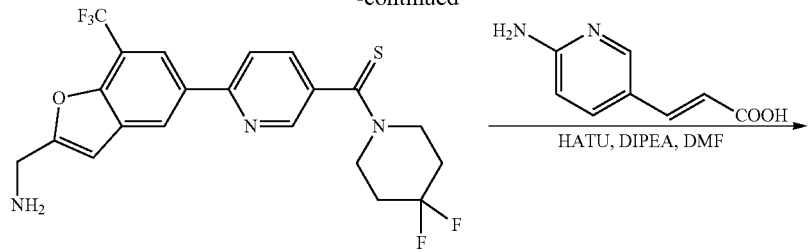

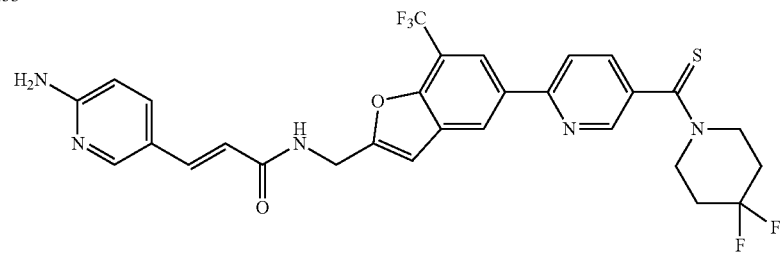

Synthesis of tert-butyl (5-(5-(4,4-difluoropiperidine-1-carbonothioyl)pyridin-2-yl)-7-(trifluoromethyl)benzofuran-2-yl)methylcarbamate (252)

tert-Butyl (5-(5-(4,4-difluoropiperidine-1-carbonyl)pyridin-2-yl)-7-(trifluoromethyl)benzofuran-2-yl)methylcarbamate (251) (200 mg, 0.37 mmol) and Lawesson's reagent (105 mg, 0.26 mmol) were added in 10 mL of pyridine. The reaction mixture was heated at 80° C. for 12 h. After cooling down to room temperature, the reaction mixture was concentrated under reduced pressure to give the crude product, which was purified by Prep-HPLC to afford 55 mg of tert-butyl (5-(5-(4,4-difluoropiperidine-1-carbonothioyl)pyridin-2-yl)-7-(trifluoromethyl)benzofuran-2-yl)methylcarbamate (252) as a pale yellow solid (27% yield).). LCMS: m/z 556.2 [M+H]$^+$; $t_R$=1.82 min.

Synthesis of (6-(2-(aminomethyl)-7-(trifluoromethyl)benzofuran-5-yl)pyridin-3-yl)(4,4-difluoropiperidin-1-yl)methanethione (253)

tert-Butyl (5-(5-(4,4-difluoropiperidine-1-carbonothioyl)pyridin-2-yl)-7-(trifluoromethyl)benzofuran-2-yl)methylcarbamate (252) (55 mg, 0.10 mmol) was dissolved in CH$_2$Cl$_2$ (10 mL). TFA (1.5 mL) was added dropwise at 0° C. The reaction mixture was stirred at room temperature for 1 h. The reaction mixture was concentrated under reduced pressure to give the crude (6-(2-(aminomethyl)-7-(trifluoromethyl)benzofuran-5-yl)pyridin-3-yl)(4,4-difluoropiperidin-1-yl)methanethione (253), which was used without further purification in the next step (45 mg, 100% yield). LCMS: m/z 456.1 [M+H]$^+$; $t_R$=1.37 min.

Synthesis of (E)-3-(6-aminopyridin-3-yl)-N-((5-(5-(4,4-difluoropiperidine-1-carbonothioyl)pyridin-2-yl)-7-(trifluoromethyl)benzofuran-2-yl)methyl)acrylamide (667)

(6-(2-(Aminomethyl)-7-(trifluoromethyl)benzofuran-5-yl)pyridin-3-yl)(4,4-difluoropiperidin-1-yl)methanethione (253); (45 mg, 0.10 mmol) was dissolved in DMF (3 mL) and (Z)-3-(6-aminopyridin-3-yl)acrylic acid (16 mg, 0.10 mmol) was added at 0° C. HATU (46 mg, 0.15 mmol) was added at 0° C. followed by DIPEA (39 mg, 0.30 mmol) dropwise. The reaction mixture was allowed to warm to room temperature and stirred further for 1 h. The reaction mixture was purified by Prep-HPLC without workup to afford 25 mg of (E)-3-(6-aminopyridin-3-yl)-N-((5-(5-(4,4-difluoropiperidine-1-carbonothioyl)pyridin-2-yl)-7-(trifluoromethyl)benzofuran-2-yl)methyl)acrylamide (667) (yield: 42%). $^1$H NMR (500 MHz, DMSO-d$_6$) δ 8.90-8.84 (m, 1H), 8.72-8.66 (m, 2H), 8.38 (s, 1H), 8.20 (s, 1H), 8.17 (d, J=8 Hz, 1H), 8.12-8.05 (m, 1H), 7.93 (dd, J=8 Hz, 2 Hz, 1H), 7.46 (d, J=16 Hz, 1H), 7.02 (s, 1H), 6.95 (d, J=8 Hz, 1H), 6.60 (d, J=16 Hz, 1H), 4.65 (d, J=5 Hz, 2H), 4.48-4.41 (m, 2H), 3.75-3.70 (m, 2H), 2.32-2.11 (m, 4H). LCMS: m/z 602.2 [M+H]$^+$; $t_R$=1.46 min.

Synthesis of (E)-3-(6-aminopyridin-3-yl)-N-((5'-(5-(4,4-difluoropiperidine-1-carbonyl)pyridin-2-yl)-2,7'-bibenzofuran-2'-yl)methyl)acrylamide (668)

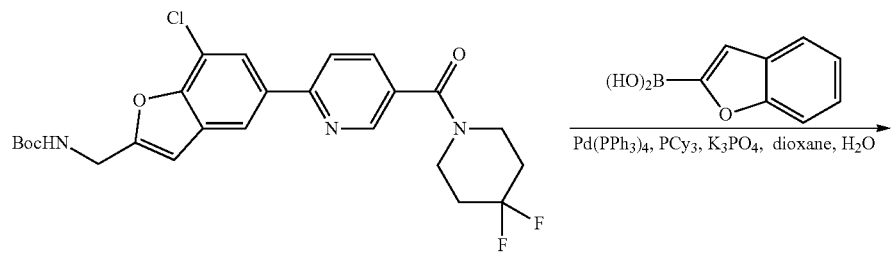

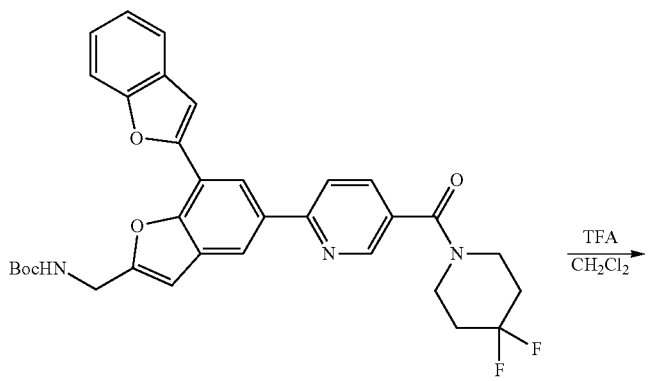
254
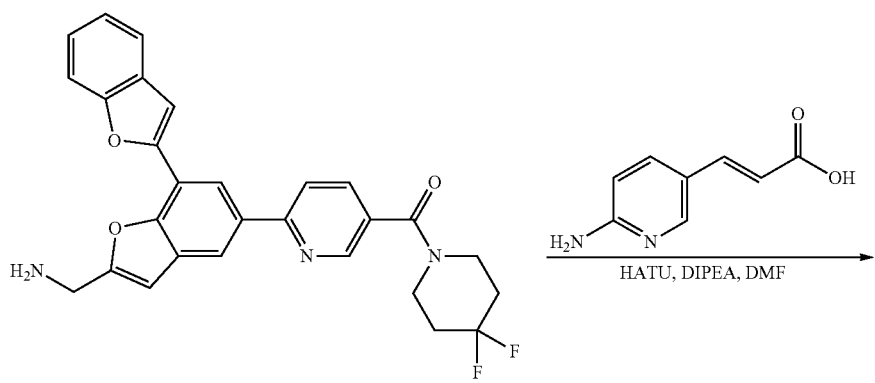
255
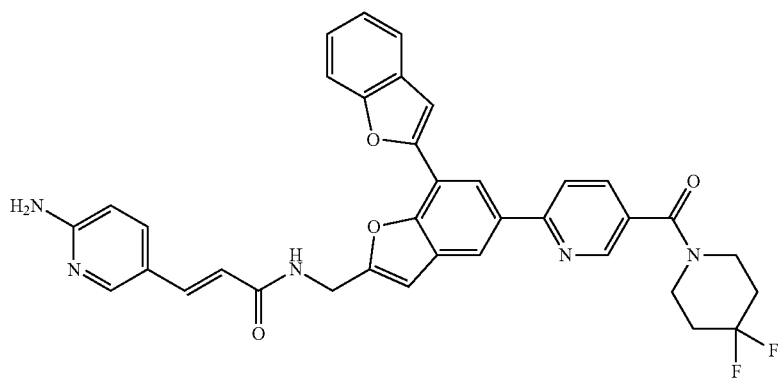
668
(E)-3-(6-aminopyridin-3-yl)-N-((5'-(5-(4,4-difluoropiperidine-1-carbonyl)pyridin-2-yl)-2,7'-bibenzofuran-2'-yl)methyl)acrylamide (668) was synthesized in a similar fashion as example (659) using the indicated reagents. $^1$H NMR (400 MHz, DMSO-$d_6$) δ 8.82 (d, J=2 Hz, 1H), 8.70 (d, J=2 Hz, 2H), 8.43 (d, J=2 Hz, 1H), 8.21 (d, J=8 Hz, 1H), 8.11 (d, J=2 Hz, 1H), 8.03 (dd, J$_1$=8 Hz, J$_2$ 2 Hz, 1H), 7.80-7.74 (m, 3H), 7.64 (dd, J$_1$=8 Hz, J$_2$ 2 Hz, 1H), 7.46-7.29 (m, 3H), 6.97 (s, 1H), 6.51-6.41 (m, 4H), 4.71 (d, J=6 Hz, 2H), 3.86-3.44 (m, 4H), 2.17-2.03 (m, 4H). LCMS: m/z 634.5 [M+H]$^+$; t$_R$=1.86 min.

Synthesis of (E)-3-(6-aminopyridin-3-yl)-N-((5-(5-(4,4-difluoropiperidine-1-carbonyl)pyridin-2-yl)-7-(pyridin-3-yl)benzofuran-2-yl)methyl)acrylamide (669)

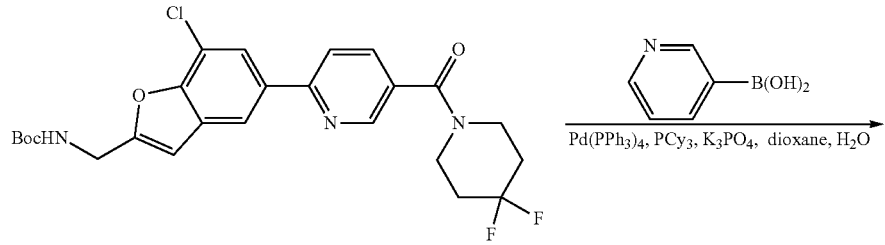

223

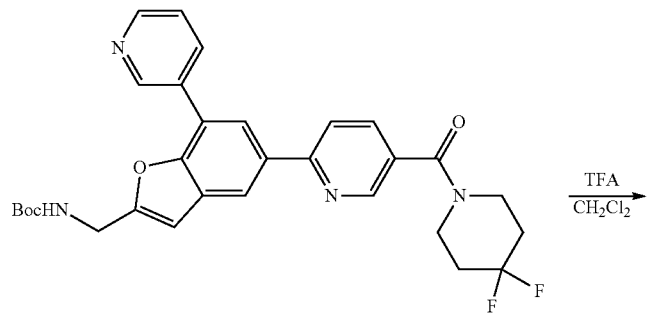

256

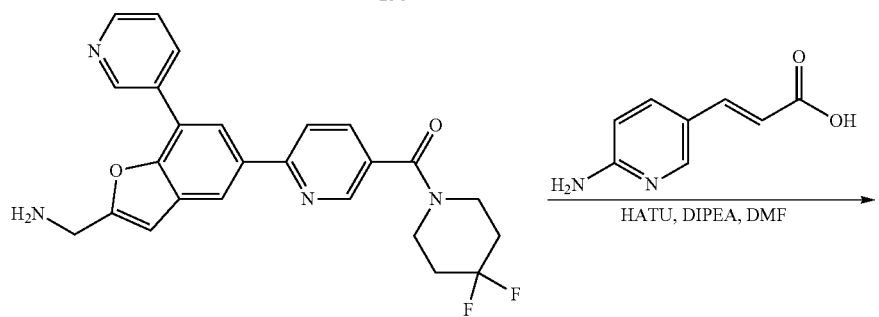

257

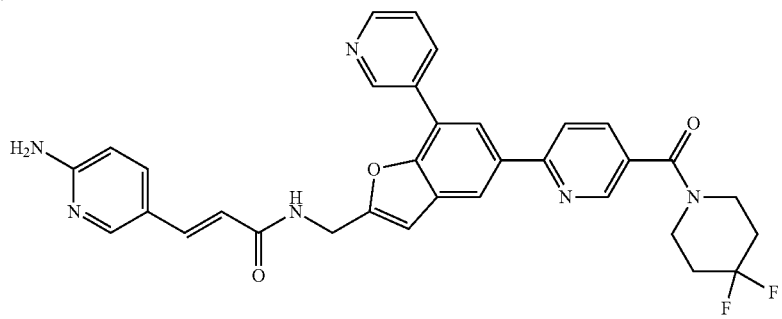

669

(E)-3-(6-aminopyridin-3-yl)-N-((5-(5-(4,4-difluoropiperidine-1-carbonyl)pyridin-2-yl)-7-(pyridin-3-yl)benzofuran-2-yl)methyl)acrylamide (669) was synthesized in a similar fashion as example (659) using the indicated reagents. $^1$H NMR (400 MHz, DMSO-$d_6$) δ 9.24-9.14 (m, 1H), 8.77 (s, 1H), 8.69-8.63 (m, 1H), 8.45 (s, 2H), 8.43-7.95 (m, 6H), 7.66-7.53 (m, 2H), 6.94 (s, 1H), 6.56-6.36 (m, 3H), 6.36-6.26 (m, 1H), 4.64-4.50 (m, 2H), 3.83-3.67 (m, 2H), 3.60-3.46 (m, 2H), 2.15-2.03 (m, 4H). LCMS: m/z 595.6 [M+H]$^+$; $t_R$=1.66 min.

Synthesis of (E)-3-(3-aminoisoquinolin-7-yl)-N-((5-(5-(4,4-difluoropiperidine-1-carbonyl)pyridin-2-yl)-7-(trifluoromethyl)benzofuran-2-yl)methyl)acrylamide (670)
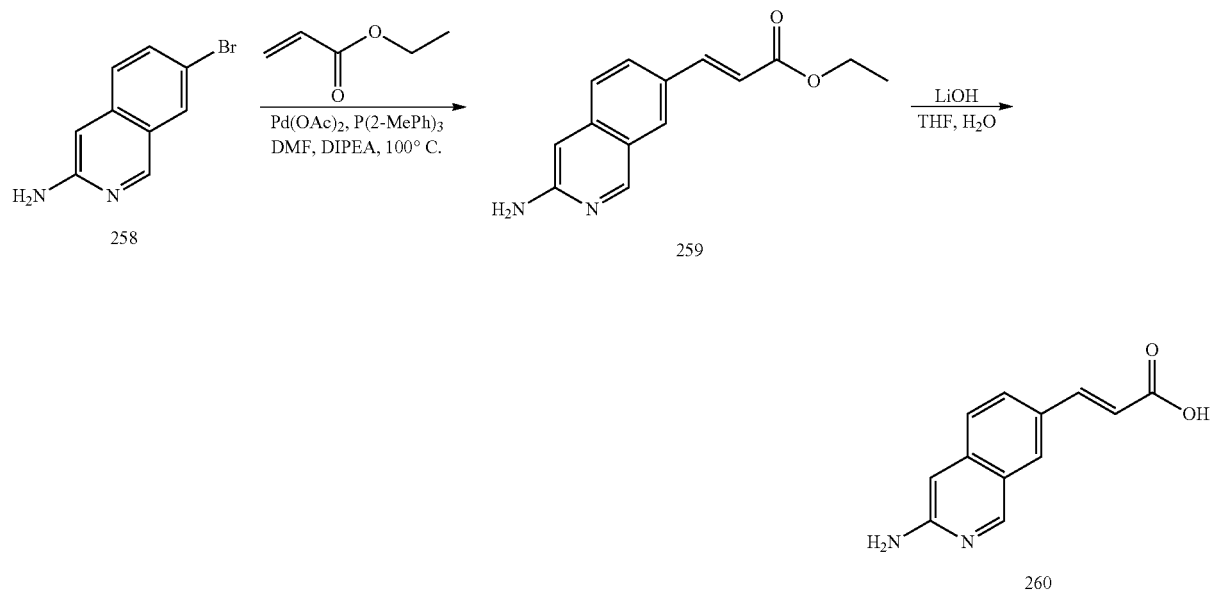
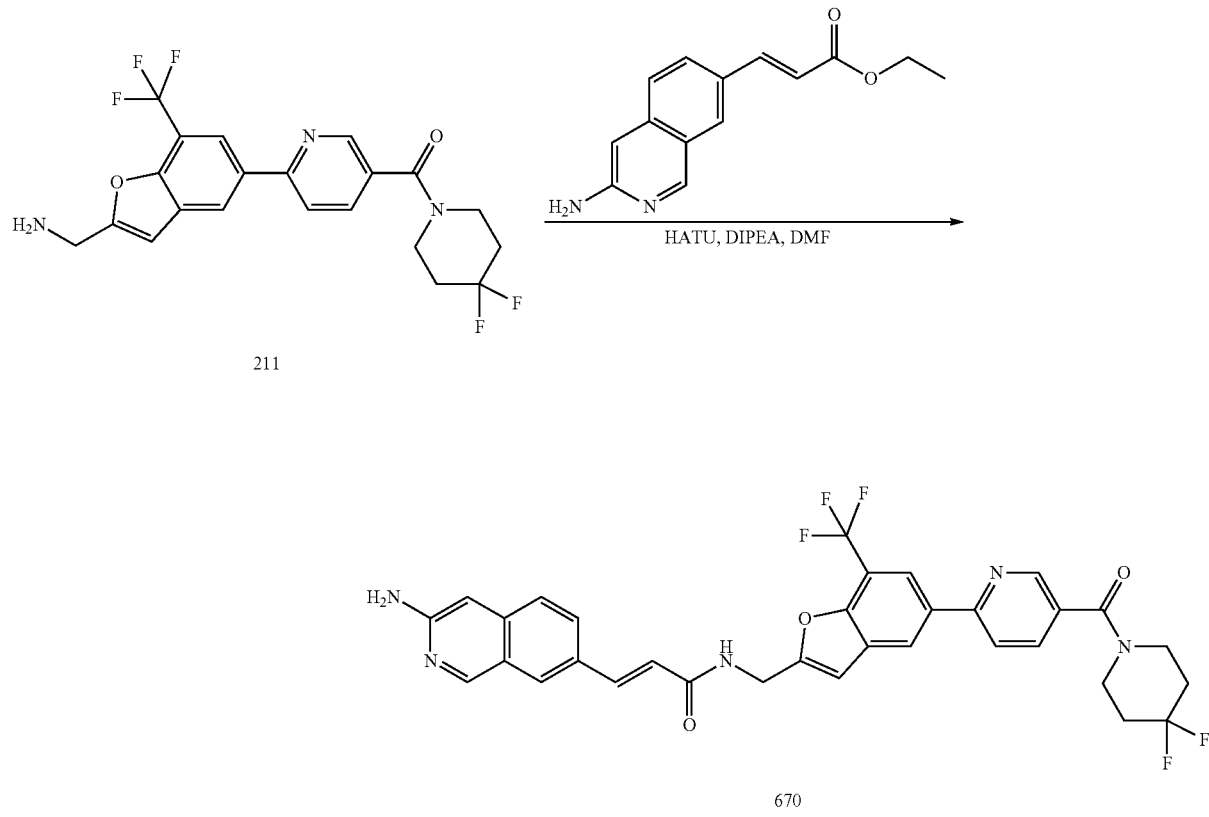

Synthesis of (E)-ethyl 3-(3-aminoisoquinolin-7-yl)acrylate (259)

7-Bromoisoquinolin-3-amine (258) (450 mg, 2.0 mmol), ethyl acrylate (300 mg, 3.0 mmol), Pd(OAc)$_2$ (45 mg, 0.2 mmol), trio-tolylphosphine (122 mg. 0.4 mmol), and DIPEA (516 mg, 4.0 mmol) were added in DMF (4 mL) and degassed. The reaction mixture was heated at 100° C. for 3 h under nitrogen atmosphere. After cooling down to room temperature, the reaction mixture was poured into iced water (20 mL), extracted with EtOAc (100 mL×3). The combined organic layers were washed with brine, dried over anhydrous Na$_2$SO$_4$, concentrated under reduced pressure to give the crude product, which was purified by column chromatography on silica gel (10% EtOAc/petroleum ether) to give (E)-ethyl 3-(3-aminoisoquinolin-7-yl)acrylate (259) as white solid (400 mg, 83% yield). LCMS: m/z 243.2 [M+H]$^+$; t$_R$=1.34 min.

Synthesis of (E)-3-(3-aminoisoquinolin-7-yl)acrylic acid (260)

(E)-ethyl 3-(3-aminoisoquinolin-7-yl)acrylate (259); (400 mg, 1.7 mmol) and LiOH (200 mg, 8.3 mmol) were added in a mixture of THF (10 mL) and H$_2$O (1 mL) at room temperature. The reaction mixture was heated at 70° C. for 3 h. The reaction mixture was concentrated under reduced pressure to remove THF, diluted with water (10 mL), neutralized with 2N HCl until pH=3, extracted with CH$_2$Cl$_2$ (50 mL×3). The combined organic layers were washed with brine, dried over anhydrous Na$_2$SO$_4$, and concentrated under reduced pressure to give 200 mg of (E)-3-(3-aminoisoquinolin-7-yl)acrylic acid (260) as white solid, which was used without further purification in the next step (57% yield). LCMS: m/z 215.1 [M+H]$^+$; t$_R$=1.09 min.

Synthesis of (E)-3-(3-aminoisoquinolin-7-yl)-N-((5-(5-(4,4-difluoropiperidine-1-carbonyl)pyridin-2-yl)-7-(trifluoromethyl)benzofuran-2-yl)methyl)acrylamide (670)

(6-(2-(Aminomethyl)-7-(trifluoromethyl)benzofuran-5-yl)pyridin-3-yl)(4,4-difluoropiperidin-1-yl)methanone (211) (75 mg, 0.17 mmol) was dissolved in DMF (3 mL) and (E)-3-(3-aminoisoquinolin-7-yl)acrylic acid (260) (35 mg, 0.16 mmol) was added at 0° C. HATU (122 mg, 0.32 mmol) was added to this reaction mixture at 0° C. followed by DIPEA (62 mg, 0.48 mmol) dropwise. The reaction mixture was allowed to warm to room temperature and stirred further for 1 h. The reaction mixture was purified by Prep-HPLC to afford 53 mg of (E)-3-(3-aminoisoquinolin-7-yl)-N-((5-(5-(4,4-difluoropiperidine-1-carbonyl)pyridin-2-yl)-7-(trifluoromethyl)benzofuran-2-yl)methyl)acrylamide (670) (52% yield). $^1$H NMR (500 MHz, DMSO-d$_6$) δ 8.93 (s, 1H), 8.88 (s, 1H), 8.81-8.69 (m, 4H), 8.41 (s, 1H), 8.23 (d, J=8 Hz, 1H), 8.06-8.01 (m, 2H), 7.77 (d, J=9 Hz, 1H), 7.65 (d, J=9 Hz, 1H), 7.58 (d, J=16 Hz, 1H), 7.04 (s, 1H), 6.86-6.80 (m, 1H), 6.75 (d, J=16 Hz, 1H), 4.67 (d, J=5 Hz, 2H), 3.81-3.71 (m, 2H), 3.55-3.44 (m, 2H), 2.15-2.03 (m, 4H). LCMS: m/z 636.2 [M+H]$^+$; t$_R$=1.46 min.

Synthesis of (E)-N-((5-(5-(4,4-difluoropiperidine-1-carbonyl)pyridin-2-yl)-7-(trifluoromethyl)benzofuran-2-yl)methyl)-3-(pyridin-3-yl)acrylamide (671)

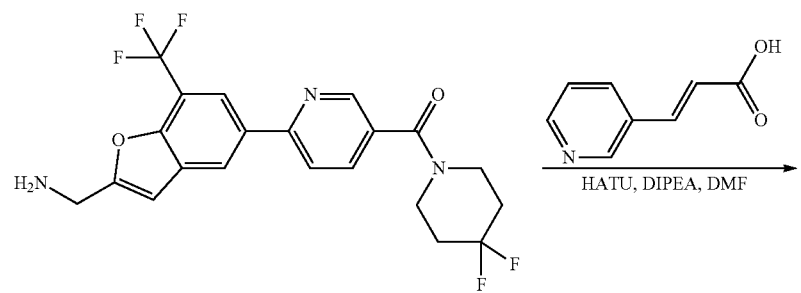

211

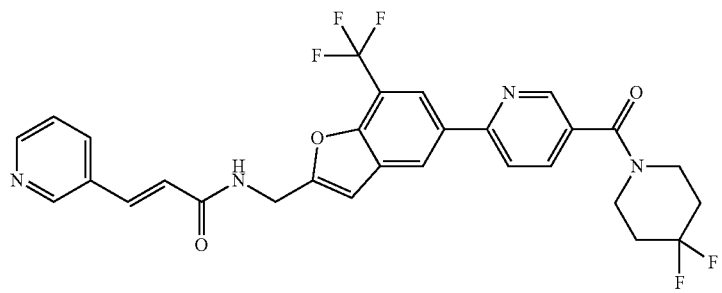

671

(E)-N-((5-(5-(4,4-difluoropiperidine-1-carbonyl)pyridin-2-yl)-7-(trifluoromethyl)benzofuran-2-yl)methyl)-3-(pyridin-3-yl)acrylamide (671) was synthesized using the indicated reagents according to General Procedure 4. Yield: 75%. $^1$H NMR (400 MHz, CD$_3$OD) δ 8.79 (s, 1H), 8.67 (d, J=2 Hz, 1H), 8.56 (d, J=5 Hz, 1H), 8.43 (s, 1H), 8.31 (d, J=8 Hz, 1H), 8.24 (s, 1H), 8.01-7.88 (m, 2H), 7.69-7.62 (m, 1H), 7.58 (d, J=16 Hz, 1H), 6.89 (s, 1H), 6.80 (d, J=16 Hz, 1H), 4.65 (s, 2H), 3.87-3.49 (m, 4H), 2.11-1.91 (m, 4H). LCMS: m/z 571.2 [M+H]$^+$, $t_R$=1.50 min.

Synthesis of (E)-3-(6-aminopyridin-3-yl)-N-((5-(5-(4,4-difluoropiperidine-1-carbonyl)pyridin-2-yl)-7-(isoquinolin-6-yl)benzofuran-2-yl)methyl)acrylamide (672)

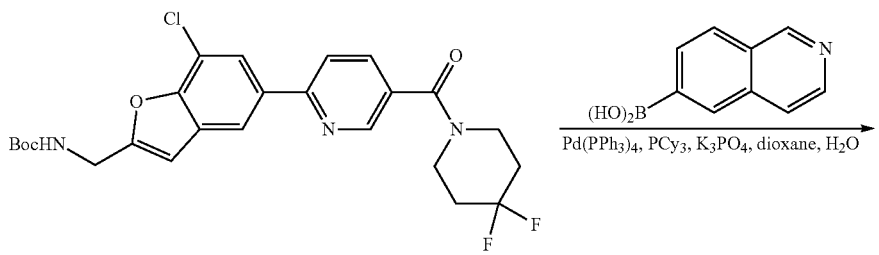

223

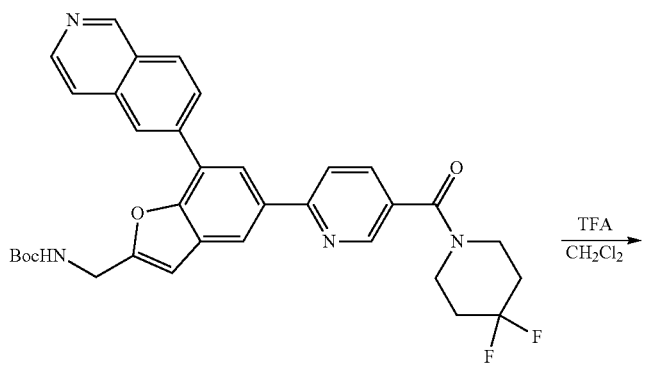

261

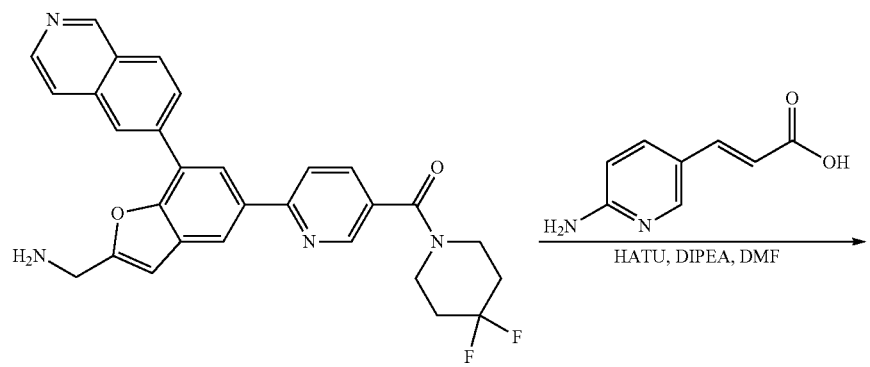

262

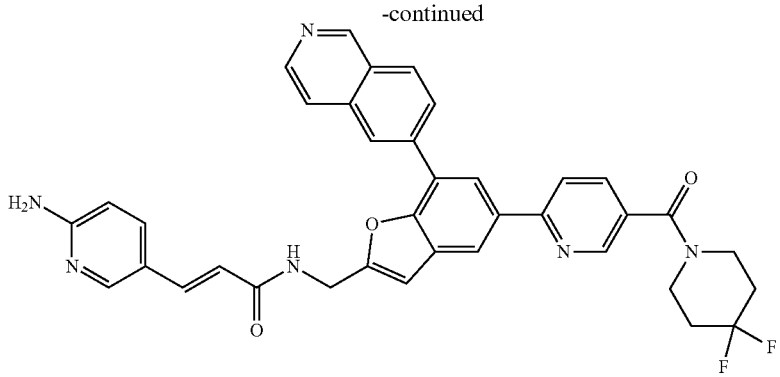

672

(E)-3-(6-aminopyridin-3-yl)-N-((5-(5-(4,4-difluoropiperidine-1-carbonyl)pyridin-2-yl)-7-(isoquinolin-6-yl)benzofuran-2-yl)methyl)acrylamide (672) was synthesized in a similar fashion as example (658). $^1$H NMR (400 MHz, DMSO-d$_6$) δ 9.67-9.59 (m, 1H), 8.89-8.73 (m, 3H), 8.68-8.61 (m, 1H), 8.54-8.42 (m, 5H), 8.30-8.00 (m, 6H), 7.48 (d, J=16 Hz, 1H), 7.02-6.95 (m, 2H), 6.62 (d, J=16 Hz, 1H), 4.68 (d, J=5 Hz, 2H), 3.82-3.46 (m, 4H), 2.18-2.03 (m, 4H). LCMS: m/z 645.3 [M+H]$^+$; t$_R$=1.70 min.

Synthesis of (E)-N-((5-(5-(4,4-difluoropiperidine-1-carbonyl)pyridin-2-yl)-7-(pyridin-3-yl)benzofuran-2-yl)methyl)-3-(pyridin-3-yl)acrylamide (673)

(E)-N-((5-(5-(4,4-difluoropiperidine-1-carbonyl)pyridin-2-yl)-7-(pyridin-3-yl)benzofuran-2-yl)methyl)-3-(pyridin-3-yl)acrylamide (673) was synthesized using the indicated reagents according to General Procedure 4. Yield: 17%. $^1$H NMR (400 MHz, DMSO-d$_6$) δ 9.21 (d, J=2 Hz, 1H), 8.91 (d, J=5 Hz, 1H), 8.81-8.75 (m, 2H), 8.69-8.64 (m, 1H), 8.59-8.53 (m, 1H), 8.46 (d, J=2 Hz, 1H), 8.38 (d, J=8 Hz, 1H), 8.32 (d, J=2 Hz, 1H), 8.26 (d, J=8 Hz, 1H), 8.05-7.96 (m, 2H), 7.63-7.57 (m, 1H), 7.55 (d, J=16 Hz, 1H), 7.49-7.42 (m, 1H), 6.98 (s, 1H), 6.82 (d, J=16 Hz, 1H), 4.65 (d, J=5 Hz, 2H), 3.81-3.46 (m, 4H), 2.17-2.01 (m, 4H). LCMS: m/z 580.2 [M+H]$^+$, t$_R$=1.71 min.

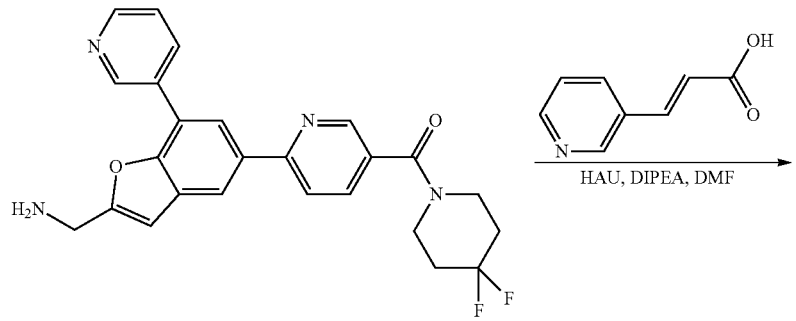

257

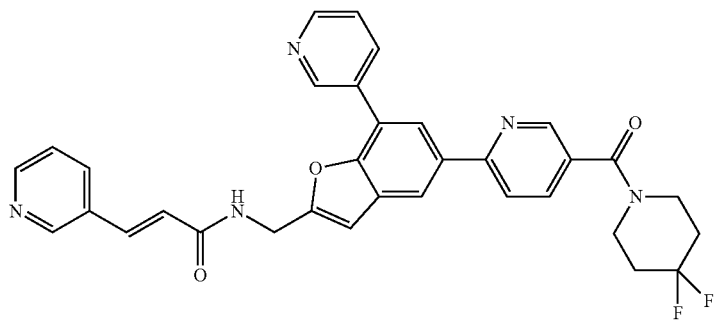

673

Synthesis of (E)-3-(6-aminopyridin-3-yl)-N-((5-(5-(4,4-difluoropiperidine-1-carbonyl)pyridin-2-yl)-7-(pyridin-3-yl)benzofuran-2-yl)methyl)acrylamide (674)

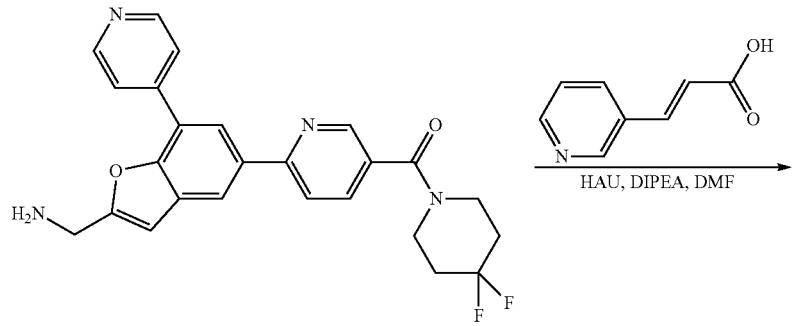

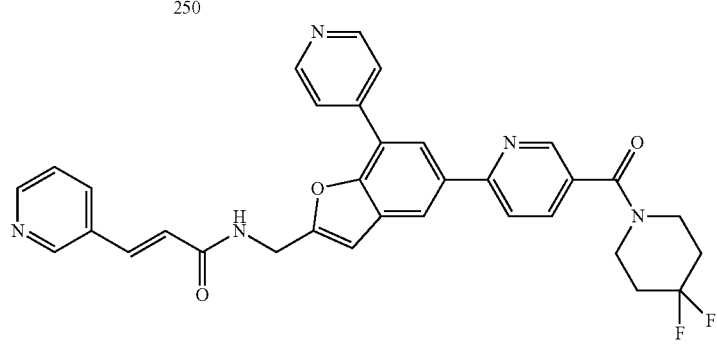

(E)-3-(6-aminopyridin-3-yl)-N-((5-(5-(4,4-difluoropiperidine-1-carbonyl)pyridin-2-yl)-7-(pyridin-3-yl)benzofuran-2-yl)methyl)acrylamide (674) was synthesized using the indicated reagents according to General Procedure 4. Yield: 10%. $^1$H NMR (400 MHz, DMSO-d$_6$) δ 8.94-8.88 (m, 1H), 8.81-8.73 (m, 4H), 8.60-8.47 (m, 2H), 8.40 (s, 1H), 8.26 (d, J=8 Hz, 1H), 8.08-7.96 (m, 4H), 7.56 (d, J=16 Hz, 1H), 7.50-7.41 (m, 1H), 6.99 (s, 1H), 6.83 (d, J=16 Hz, 1H), 4.67 (d, J=6 Hz, 2H), 3.82-3.45 (m, 4H), 2.09 (s, 4H). LCMS: m/z 580.2 [M+H]$^+$, t$_R$=1.70 min.

Synthesis of (E)-3-(6-aminopyridin-3-yl)-N-((5-(5-((4,4-difluoropiperidin-1-yl)methyl)pyridin-2-yl)-7-(trifluoromethyl)benzofuran-2-yl)methyl)acrylamide (675)

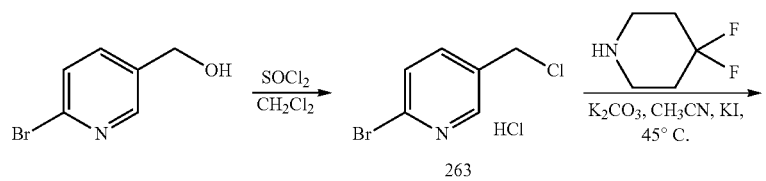

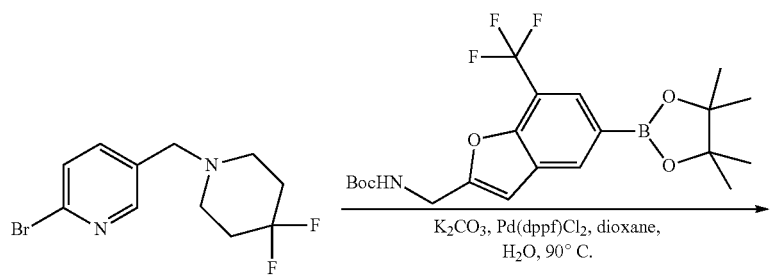

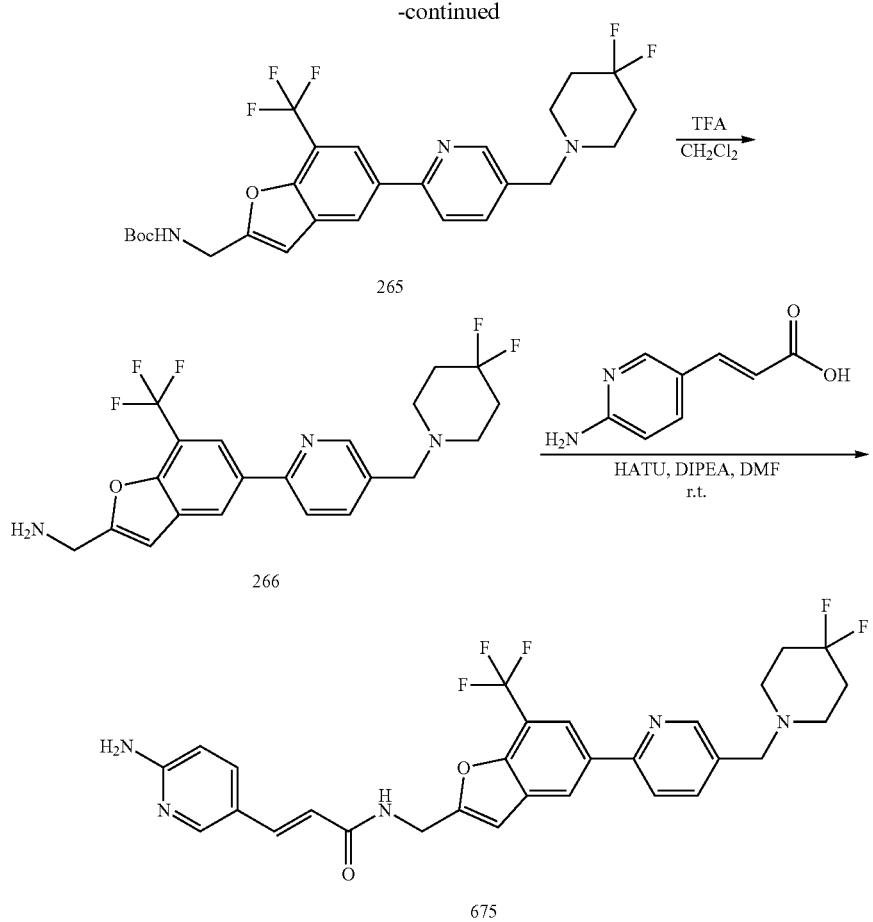

Synthesis of 2-bromo-5-(chloromethyl)pyridine hydrochloride (264)

(6-Bromopyridin-3-yl)methanol (1) (1.0 g, 5.3 mmol) was dissolved in CH$_2$Cl$_2$ (15 mL), SOCl$_2$ (3 mL, 42 mmol) was added dropwise at room temperature. The reaction mixture was stirred at room temperature for 2 h and concentrated under reduced pressure to give 2-bromo-5-(chloromethyl) pyridine hydrochloride (263) as white solid (1.3 g, 98% yield). LCMS: m/z 205.1 [M+H]$^+$; t$_R$=1.78 min.

Synthesis of 2-bromo-5-((4,4-difluoropiperidin-1-yl) methyl)pyridine (264)

2-Bromo-5-(chloromethyl)pyridine hydrochloride (263) (1.3 g, 5.2 mmol), 4,4-difluoro piperidine (692 mg, 5.7 mmol), K$_2$CO$_3$ (3.6 g, 26 mmol) and KI (86 mg, 0.52 mol) were added in CH$_3$CN (15 mL). The reaction mixture was heated at 45° C. for 6 h. LC-MS analysis showed the completion of reaction. After cooling down to room temperature, the reaction mixture was diluted EtOAc (100 mL), washed with H$_2$O (100 mL), brine, dried over anhydrous Na$_2$SO$_4$, concentrated under reduced pressure to give 2-bromo-5-((4,4-difluoropiperidin-1-yl) methyl)pyridine (264) as white solid, which was used in next step without further purification (1.3 g, 85% yield). LCMS: m/z 291.1 [M+H]$^+$; t$_R$=1.77 min.

Synthesis of tert-butyl (5-(5-((4,4-difluoropiperidin-1-yl)methyl)pyridin-2-yl)-7-(trifluoromethyl)benzofuran-2-yl)methylcarbamate (265)

2-Bromo-5-((4,4-difluoropiperidin-1-yl)methyl)pyridine (264) 190 mg, 0.65 mmol), tert-butyl(5-(4,4,5,5-tetramethyl-1,3,2-dioxaborolan-2-yl)-7-(trifluoromethyl)benzofuran-2-yl)methylcarbamate (300 mg, 0.68 mmol), Pd(dppf)Cl$_2$ (48 mg, 0.065 mmol), and K$_2$CO$_3$ (180 mg, 1.3 mmol) were added in a mixture of dioxane (15 mL) and H$_2$O (0.3 mL) and degassed. The reaction mixture was heated at 90° C. under nitrogen atmosphere for 16 h. LC-MS analysis showed the completion of reaction. After cooling down to room temperature, the reaction mixture was diluted with water (20 mL), extracted with EtOAc (50 mL×2). The combined organic layers were washed with brine, dried over anhydrous Na$_2$SO$_4$, concentrated under reduced pressure to give crude product, which was purified by column chromatography on silica gel (30% EtOAc/petroleum ether) to give tert-butyl (5-(5-((4,4-difluoropiperidin-1-yl)methyl)pyridin-2-yl)-7-(trifluoromethyl)benzofuran-2-yl)methylcarbamate (265) as white solid (40 mg, 24% yield). LCMS: m/z 526.1 [M+H]$^+$; t$_R$=1.48 min.

Synthesis of (5-(5-((4,4-difluoropiperidin-1-yl) methyl)pyridin-2-yl)-7-(trifluoromethyl)benzofuran-2-yl)methanamine (266)

tert-Butyl(5-(5-((4,4-difluoropiperidin-1-yl)methyl)pyridin-2-yl)-7-(trifluoromethyl)benzofuran-2-yl)methylcarbamate (264) (40 mg, 0.076 mmol) was dissolved in $CH_2Cl_2$ (3 mL), and TFA (1 mL) was added dropwise at room temperature. The reaction mixture was stirred at room temperature for 1 h. TLC showed the completion of reaction. The reaction mixture was concentrated under reduced pressure to afford (5-(5-((4,4-difluoropiperidin-1-yl)methyl)pyridin-2-yl)-7-(trifluoromethyl)benzofuran-2-yl)methanamine (266), which was used without further purification in the next step (35 mg, 99% yield). LCMS: m/z 426.2 $[M+H]^+$; $t_R$=1.81 min.

Synthesis of (E)-3-(6-aminopyridin-3-yl)-N-((5-(5-((4,4-difluoropiperidin-1-yl)methyl)pyridin-2-yl)-7-(trifluoromethyl)benzofuran-2-yl)methyl)acrylamide (675)

(5-(5-((4,4-Difluoropiperidin-1-yl)methyl)pyridin-2-yl)-7-(trifluoromethyl)benzofuran-2-yl)methanamine (266) (35 mg, 0.076 mmol), (E)-3-(6-aminopyridin-3-yl) acrylic acid (16 mg, 0.1 mmol), HATU (0.11 mol), and DIPEA (59 mg, 0.46 mmol) were added in DMF (2 mL). The reaction mixture was stirred at room temperature for 2 h. The reaction mixture was purified by Prep-HPLC without work up to give (E)-3-(6-aminopyridin-3-yl)-N-((5-(5-((4,4-difluoropiperidin-1-yl)methyl)pyridin-2-yl)-7-(trifluoromethyl)benzofuran-2-yl)methyl)acrylamide (675) as white solid (10 mg, 23% yield). $^1$H NMR (500 MHz, DMSO-$d_6$) δ 8.69-8.60 (m, 3H), 8.34 (s, 1H), 8.11-8.06 (m, 2H), 7.86 (d, J=8 Hz, 1H), 7.63 (d, J=9 Hz, 1H), 7.36 (d, J=16 Hz, 1H), 6.98 (s, 1H), 6.51-6.40 (m, 4H), 4.62 (d, J=6 Hz, 2H), 3.64 (s, 2H), 2.56-2.51 (m, 4H), 2.03-1.92 (n, 4H). LCMS: m/z 572.5 $[M+H]^+$; $t_R$=1.90 min.

Synthesis of (E)-3-(4-amino-3-fluorophenyl)-N-((5-(5-(4,4-difluoropiperidine-1-carbonyl)pyridin-2-yl)-7-(trifluoromethyl)benzofuran-2-yl)methyl)acrylamide (676)

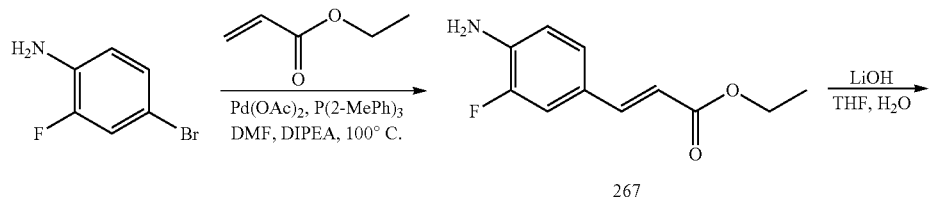

267

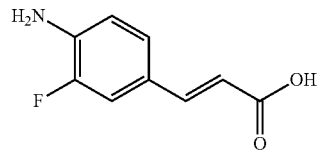

268

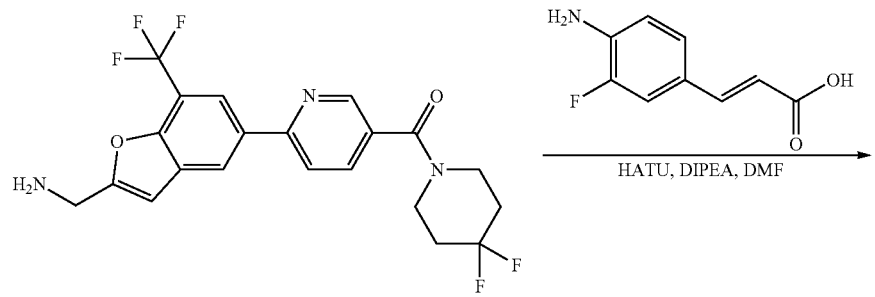

269

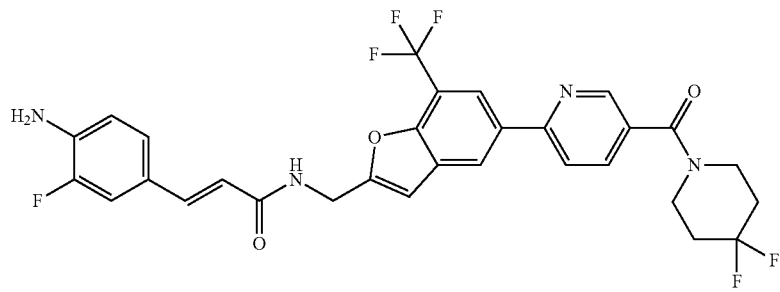

676

Synthesis of (E)-ethyl 3-(4-amino-3-fluorophenyl)acrylate (267)

(E)-ethyl 3-(4-amino-3-fluorophenyl)acrylate (267) was synthesized in a similar fashion as intermediate (259). Yield: 95%. LCMS: m/z 210.2 [M+H]$^+$; $t_R$=1.59 min.

Synthesis of (E)-3-(4-amino-3-fluorophenyl)acrylic acid (268)

(E)-3-(4-amino-3-fluorophenyl)acrylic acid (268) was synthesized in a similar fashion as intermediate (260). Yield: 87%. LCMS: m/z 182.1 [M+H]$^+$; $t_R$=1.30 min.

Synthesis of (E)-3-(4-amino-3-fluorophenyl)-N-((5-(5-(4,4-difluoropiperidine-1-carbonyl)pyridin-2-yl)-7-(trifluoromethyl)benzofuran-2-yl)methyl)acrylamide (676)

(E)-3-(4-amino-3-fluorophenyl)-N-((5-(5-(4,4-difluoropiperidine-1-carbonyl)pyridin-2-yl)-7-(trifluoromethyl)benzofuran-2-yl)methyl)acrylamide (676) was synthesized using the indicated reagents according to General Procedure 4. Yield: 6%. $^1$H NMR (500 MHz, DMSO-d$_6$) δ 8.78 (d, J=2 Hz, 1H), 8.70 (s, 1H), 8.67 (t, J=6 Hz, 1H), 8.39 (s, 1H), 8.22 (d, J=8 Hz, 1H), 8.05-8.01 (m, 1H), 7.34 (d, J=16 Hz, 1H), 7.24 (d, J=11 Hz, 1H), 7.14 (d, J=8 Hz, 1H), 7.00 (s, 1H), 6.75 (t, J=9 Hz, 1H), 6.43 (d, J=16 Hz, 1H), 4.62 (d, J=6 Hz, 2H), 3.80-3.72 (m, 2H), 3.53-3.44 (m, 2H), 2.14-2.04 (m, 4H). LCMS: m/z 603.3 [M+H]$^+$; $t_R$=1.90 min.

Synthesis of (E)-3-(6-aminopyridin-3-yl)-N-((5-(5-(4,4-difluoropiperidine-1-carbonyl)pyridin-2-yl)-3-methyl-7-(trifluoromethyl)benzofuran-2-yl)methyl)acrylamide (677)

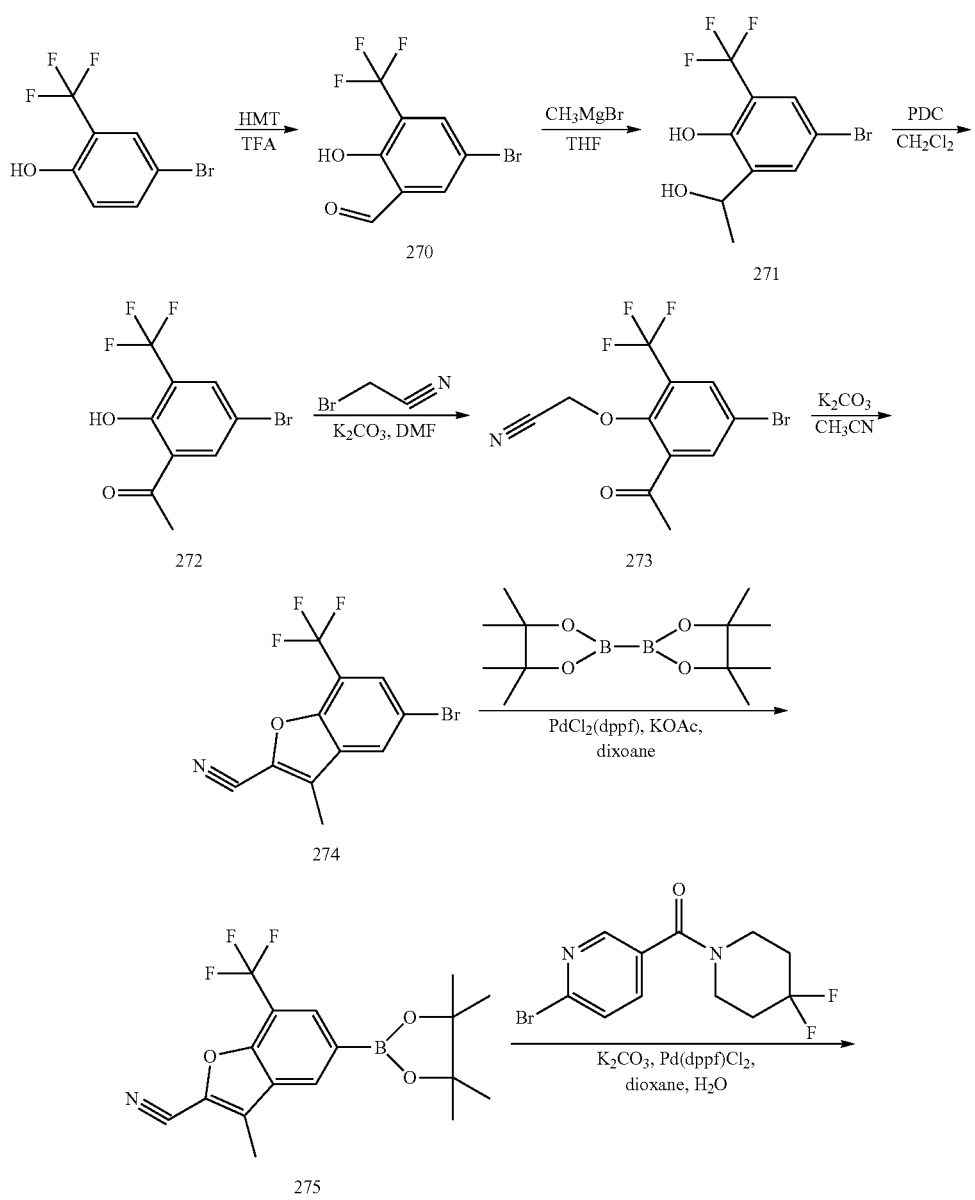

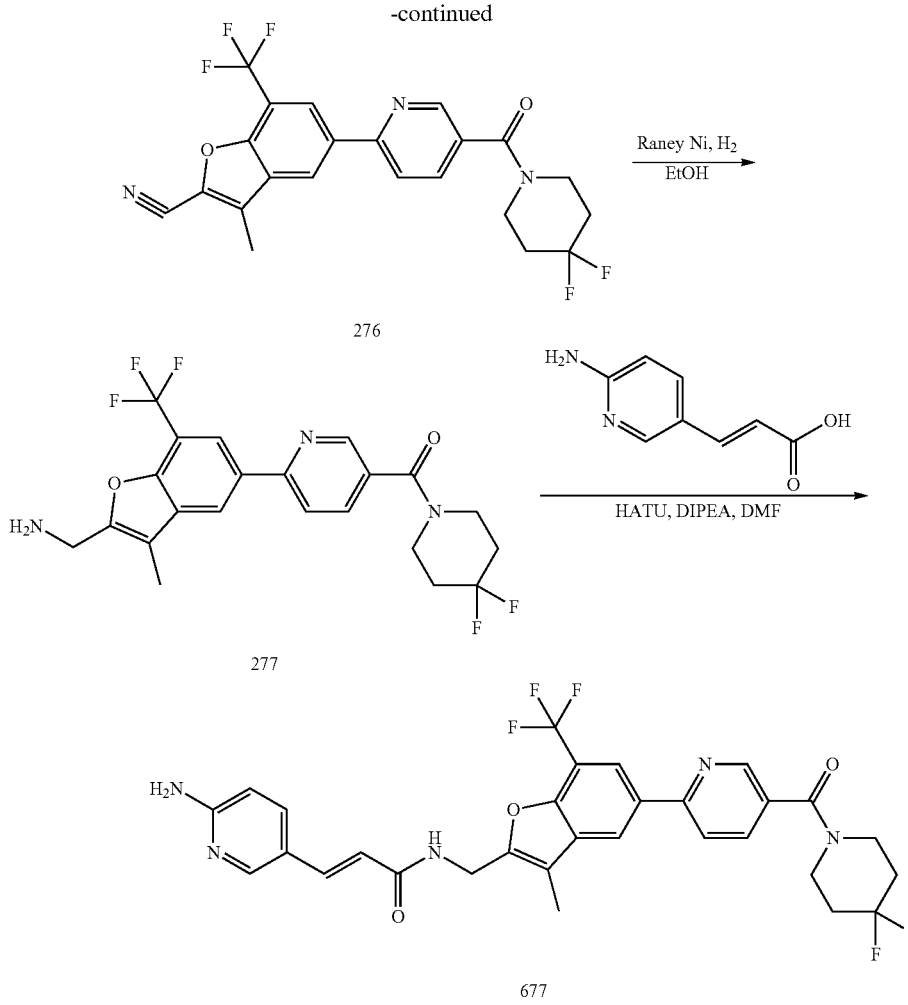

Synthesis of 5-bromo-2-hydroxy-3-(trifluoromethyl)benzaldehyde (270)

4-Bromo-2-(trifluoromethyl)phenol (20 g, 83 mmol) was dissolved in $CF_3CO_2H$ (100 mL), hexamethylenetetramine (23.2 g, 166 mmol) was added in portions over 10 min. The mixture was stirred at 90° C. under nitrogen atmosphere for 18 h. The mixture was cooled to room temperature. $H_2O$ (100 mL) was added followed by 50% $H_2SO_4$ (60 mL), the mixture was stirred for 2 h. $H_2O$ (100 mL) was added, the resulting precipitate was collected by filtration to afford crude 5-bromo-2-hydroxy-3-(trifluoromethyl)benzaldehyde (270) as yellow solid (12.5 g, 56% yield), which was used directly. LCMS: m/z 271.1 $[M+H]^+$; $t_R$=1.58 min.

Synthesis of 4-bromo-2-(1-hydroxyethyl)-6-(trifluoromethyl)phenol (271)

5-Bromo-2-hydroxy-3-(trifluoromethyl)benzaldehyde (270) (12.5 g, 46 mmol) was dissolved in THF (100 mL), $CH_3MgBr$ (38.3 mL, 115 mmol, 3M in diethyl ether) was added dropwise at 0° C. under nitrogen atmosphere. The reaction mixture was stirred at room temperature for 1 h, quenched with $NH_4Cl$ aqueous solution (100 mL), extracted with EtOAc (200 mL×2). The combined organic layers were dried over anhydrous $Na_2SO_4$, filtered, concentrated and purified by silica gel chromatography (6% EtOAc/petroleum ether) to afford 4-bromo-2-(1-hydroxyethyl)-6-(trifluoromethyl)phenol (271) as yellow solid (7.5 g, 57% yield). LCMS: m/z 269.2 $[M-OH]^+$; $t_R$=1.70 min.

Synthesis of 1-(5-bromo-2-hydroxy-3-(trifluoromethyl)phenyl)ethanone (272)

PDC (11.8 g, 315 mmol) was added to a stirred solution of 4-bromo-2-(1-hydroxyethyl)-6-(trifluoromethyl)phenol (271) (6.0 g, 21 mmol) in $CH_2Cl_2$ (260 mL), the mixture was stirred at room temperature for 2 h, and filtered. The filtrate was concentrated and purified by silica gel chromatography (6% EtOAc/petroleum ether) to give 1-(5-bromo-2-hydroxy-3-(trifluoromethyl) phenyl) ethanone (272) as white solid (300 mg, 6% yield). LCMS: m/z 285.0 $[M+H]^+$; $t_R$=1.70 min.

Synthesis of 2-(2-acetyl-4-bromo-6-(trifluoromethyl)phenoxy)acetonitrile (273)

1-(5-Bromo-2-hydroxy-3-(trifluoromethyl) phenyl) ethanone (271); (300 mg, 1.06 mmol) was dissolved in DMF (4 mL). $K_2CO_3$ (293 mg, 2.1 mmol) and 2-bromoacetonitrile (0.1 mL, 1.4 mmol) were added. The mixture was stirred at 40° C. under nitrogen atmosphere for 2 h. The mixture was poured into water (10 mL), extracted with EtOAc (50 mL×2), dried over anhydrous $Na_2SO_4$, concentrated, and purified by silica gel chromatography (6% EtOAc/petroleum ether) to give 2-(2-acetyl-4-bromo-6-(trifluoromethyl)phenoxy) acetonitrile (268) as white solid (150 mg, yield 44%). LCMS: m/z 322.0 $[M+H]^+$; $t_R$=1.66 min.

Synthesis of 5-bromo-3-methyl-7-(trifluoromethyl) benzofuran-2-carbonitrile (274)

2-(2-Acetyl-4-bromo-6-(trifluoromethyl)phenoxy)acetonitrile (273); (150 mg, 0.46 mmol) was dissolved in $CH_3CN$ (4 mL). $K_2CO_3$ (254 mg, 1.84 mmol) was added. The mixture was stirred at 95° C. for 18 h, concentrated, and purified by silica gel chromatography (6% EtOAc/petroleum ether) to give 5-bromo-3-methyl-7-(trifluoromethyl)benzofuran-2-carbonitrile (274) as white solid (60 mg, 43% yield). $^1H$ NMR (500 MHz, DMSO-$d_6$) δ 8.54 (s, 1H), 8.17 (s, 1H), 2.48 (s, 3H).

Synthesis of 3-methyl-5-(4,4,5,5-tetramethyl-1,3,2-dioxaborolan-2-yl)-7-(triflu oromethyl) benzofuran-2-carbonitrile (275)

5-Bromo-3-methyl-7-(trifluoromethyl)benzofuran-2-carbonitrile (274); (60 mg, 0.2 mmol), 4,4,4',4',5,5,5',5'-octamethyl-2,2'-bi(1,3,2-dioxaborolane) (76 mg, 0.3 mmol), Pd(dppf)Cl$_2$ (15 mg, 0.02 mmol), and potassium acetate (39 mg, 0.4 mmol) were added in 3 mL of dioxane and degassed. The reaction mixture was heated at 100° C. under nitrogen atmosphere for 3 h. After cooling down to room temperature, the reaction mixture was filtered. The filtrate was concentrated under reduced pressure to give the crude product, which was purified by silica gel chromatography (20% EtOAc/petroleum ether) to yield 60 mg of 3-methyl-5-(4,4,5,5-tetramethyl-1,3,2-dioxaborolan-2-yl)-7-(trifluoromethyl) benzofuran-2-carbonitrile (275) as white solid (85% yield). LCMS: m/z 352.1 $[M+H]^+$; $t_R$=2.01 min.

Synthesis of 5-(5-(4,4-difluoropiperidine-1-carbonyl)pyridin-2-yl)-3-methyl-7-(trifluoromethyl)benzofuran-2-carbonitrile (276)

3-Methyl-5-(4,4,5,5-tetramethyl-1,3,2-dioxaborolan-2-yl)-7-(trifluoromethyl) benzofuran-2-carbonitrile (275) (60 mg, 0.17 mmol), (6-bromopyridin-3-yl)(4,4-difluoropiperidin-1-yl)methanone (61 mg, 0.2 mmol), Pd(dppf)Cl$_2$ (13 mg, 0.02 mmol), and $K_2CO_3$ (47 mg, 0.34 mmol) were added in a mixture of dioxane (3 mL) and water (0.2 mL) and degassed. The reaction mixture was heated at 100° C. under nitrogen atmosphere for 3 h. The reaction mixture was cooled down to room temperature, filtered and the filtrate was concentrated under reduced pressure to give the crude product, which was purified by silica gel chromatography (10% EtOAc/petroleum ether) to yield 40 mg of 5-(5-(4,4-difluoropiperidine-1-carbonyl)pyridin-2-yl)-3-methyl-7-(trifluoromethyl) benzofuran-2-carbonitrile (276) as white solid (yield 53%). LCMS: m/z 450.1 $[M+H]^+$; $t_R$=1.81 min.

Synthesis of (6-(2-(aminomethyl)-3-methyl-7-(trifluoromethyl)benzofuran-5-yl) pyridin-3-yl)(4,4-difluoropiperidin-1-yl)methadone (277)

A solution of 5-(5-(4,4-difluoropiperidine-1-carbonyl) pyridin-2-yl)-3-methyl-7-(trifluoromethyl) benzofuran-2-carbonitrile (276) (40 mg, 0.09 mmol), Raney Ni (5 mg) in $C_2H_5OH$ (5 mL) was stirred under hydrogen atmosphere at room temperature for 2 h. The mixture was filtered, the filtrate was concentrated to give (6-(2-(amino methyl)-3-methyl-7-(trifluoromethyl)benzofuran-5-yl)pyridin-3-yl)(4,4-difluoropiperidin-1-yl)methadone (277) as white solid (20 mg, yield 50%). LCMS: m/z 454.2 $[M+H]^+$; $t_R$=1.83 min.

Synthesis of (E)-3-(6-aminopyridin-3-yl)-N-((5-(5-(4,4-difluoropiperidine-1-carbonyl)pyridin-2-yl)-3-methyl-7-(trifluoromethyl)benzofuran-2-yl)methyl) acryl amide (677)

(6-(2-(Aminomethyl)-3-methyl-7-(trifluoromethyl)benzofuran-5-yl)pyridin-3-yl) (4,4-difluoropiperidin-1-yl) methadone (277) (20 mg, 0.04 mmol) was dissolved in DMF (3 mL) and (E)-3-(6-aminopyridin-3-yl)acrylic acid (8 mg, 0.05 mmol) was added at 0° C. HATU (23 mg, 0.06 mmol) was added to this reaction mixture at 0° C. followed by DIPEA (8 mg, 0.08 mmol). The reaction mixture was allowed to warm to room temperature and stirred further for 2 h. The reaction mixture was purified by Prep-HPLC without workup to give 5 mg of ((E)-3-(6-aminopyridin-3-yl)-N-((5-(5-(4,4-difluoropiperidine-1-carbonyl)pyridin-2-yl)-3-methyl-7-(trifluoromethyl)benzofuran-2-yl)methyl) acryl amide (677). Yield: 21%. $^1H$ NMR (500 MHz, DMSO-$d_6$) δ 8.83-8.76 (m, 2H), 8.68 (s, 1H), 8.42 (s, 1H), 8.31 (d, J=8 Hz, 1H), 8.17 (s, 1H), 8.07-8.01 (m, 2H), 7.42 (d, J=16 Hz, 1H), 6.93 (d, J=9 Hz, 1H), 6.54 (d, J=16 Hz, 1H), 4.60 (d, J=6 Hz, 2H), 3.80-3.72 (m, 2H), 3.53-3.44 (m, 2H), 2.37 (s, 3H), 2.15-2.03 (m, 4H). LCMS: m/z 600.2 $[M+H]^+$; $t_R$=1.43 min.

Synthesis of (E)-3-(6-aminopyridin-3-yl)-N-((5-(5-(4,4-difluoropiperidine-1-carbonothioyl)pyridin-2-yl)-7-(trifluoromethyl)benzofuran-2-yl)methyl)prop-2-enethioamide (678)

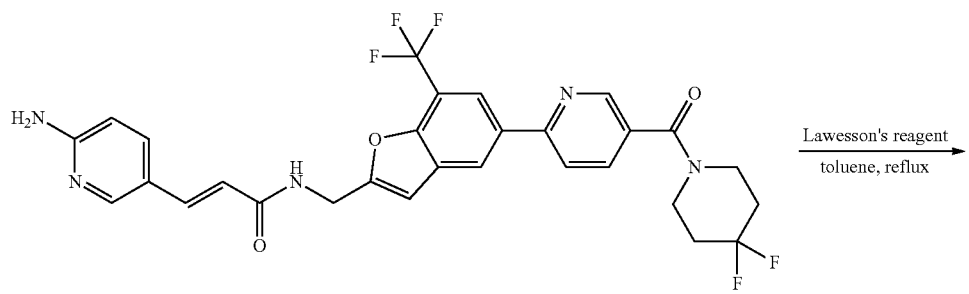

-continued

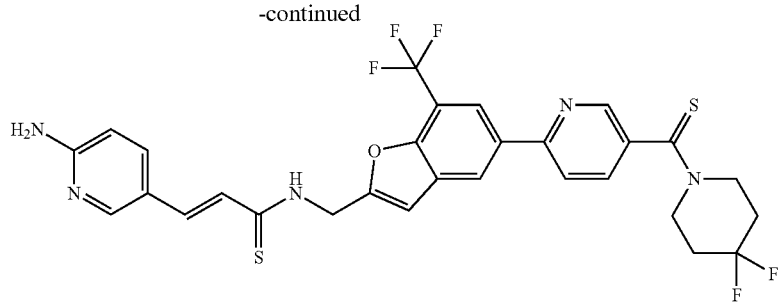

678

(E)-3-(6-aminopyridin-3-yl)-N-((5-(5-(4,4-difluoropiperidine-1-carbonyl)pyridin-2-yl)-7-(trifluoromethyl)benzofuran-2-yl)methyl)acrylamide (585) (293 mg, 0.5 mmol) and Lawesson's reagent (404 mg, 1 mmol) was dissolved in toluene (10 mL). The reaction mixture was heated to reflux for 16 h. The mixture was concentrated under reduced pressure, which was purified by Prep-HPLC to afford 3 mg of (E)-3-(6-aminopyridin-3-yl)-N-((5-(5-(4,4-difluoropiperidine-1-carbonothioyl)pyridin-2-yl)-7-(trifluoromethyl) benzofuran-2-yl)methyl)prop-2-enethioamide (678). Yield: 1%. $^1$H NMR (400 MHz, CD$_3$OD) δ 8.67-7.34 (m, 8H), 7.01-5.97 (m, 3H), 5.20 (s, 2H), 4.55-4.87 (m, 2H), 3.87-3.76 (m, 2H), 2.34-2.01 (m, 2H), 2.12-2.05 (m, 2H). LCMS: m/z 618.2 [M+H]$^+$, $t_R$=2.00 min.

Synthesis of (E)-3-(6-aminopyridin-3-yl)-N-((5-(4-((4,4-difluoropiperidin-1-yl)sulfonyl)phenyl)-7-(trifluoromethyl)benzofuran-2-yl)methyl)acrylamide (679)

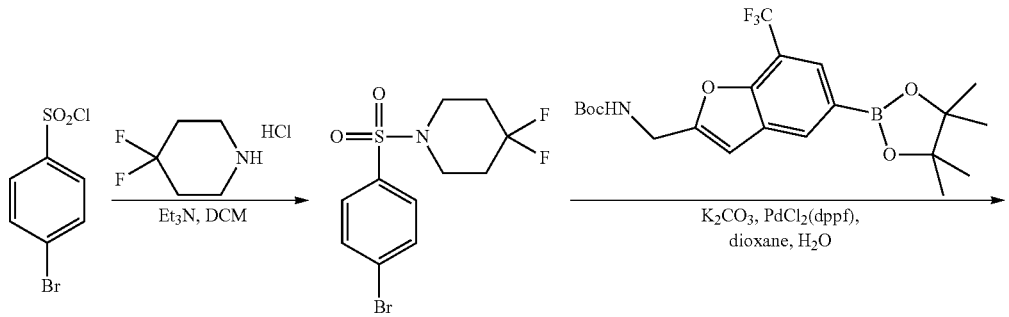

278

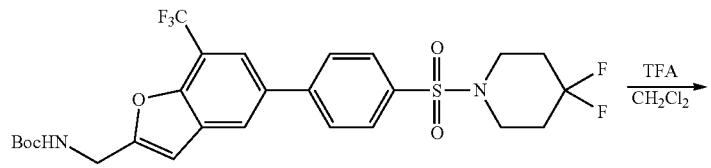

279

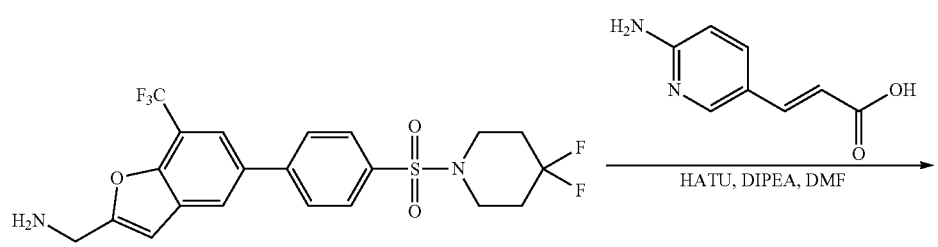

280

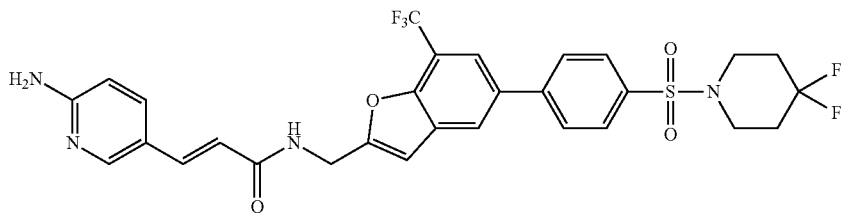

679

Synthesis of 1-(4-bromophenylsulfonyl)-4,4-difluoropiperidine (278)

4-Bromobenzene-1-sulfonyl chloride (2.5 g, 10 mmol) was dissolved in DCM (30 mL) and triethylamine (3 g, 30 mmol) was added. 4,4-Difluoropiperidine hydrochloride (1.8 g, 12 mmol) was added at 0° C. (ice bath). The reaction mixture was allowed to warm to room temperature and stirred for 1 h. The reaction mixture was diluted with DCM (100 mL), washed with water, brine, dried over anhydrous $Na_2SO_4$, and concentrated under reduced pressure to give 2.9 g of 1-(4-bromophenylsulfonyl)-4,4-difluoropiperidine (278), which was used in next step without further purification (87% yield). LCMS: m/z 340.0 [M+H]$^+$, $t_R$=1.73 min.

Synthesis of tert-butyl (5-(4-(4,4-difluoropiperidin-1-ylsulfonyl)phenyl)-7-(trifluoromethyl)benzofuran-2-yl)methylcarbamate (279)

1-(4-Bromophenylsulfonyl)-4,4-difluoropiperidine (278) (1.5 g, 4.4 mmol), tert-butyl (5-(4,4,5,5-tetramethyl-1,3,2-dioxaborolan-2-yl)-7-(trifluoromethyl)benzofuran-2-yl)methylcarbamate (2.1 g, 4.8 mmol), Pd(dppf)Cl$_2$ (0.36 g, 0.44 mmol), and $K_2CO_3$ (1.8 g, 13.2 mmol) were added to a mixture of dioxane (30 mL) and water (6 mL) and degassed. The reaction mixture was heated at 90° C. under nitrogen atmosphere for 6 h. The reaction mixture was cooled down to room temperature, filtered and the filtrate was concentrated under reduced pressure to give the crude product, which was purified by silica gel chromatography (10-30% EtOAc/petroleum ether) to yield 1.5 g of tert-butyl (5-(4-(4,4-difluoropiperidin-1-ylsulfonyl)phenyl)-7-(trifluoromethyl)benzofuran-2-yl)methylcarbamate (279) as a white solid (58% yield). LCMS: m/z 575.1 [M+H]$^+$, $t_R$=1.86 min.

Synthesis of (5-(4-(4,4-difluoropiperidin-1-ylsulfonyl)phenyl)-7-(trifluoromethyl)benzofuran-2-yl)methanamine (280)

tert-Butyl (5-(4-(4,4-difluoropiperidin-1-ylsulfonyl)phenyl)-7-(trifluoromethyl)benzofuran-2-yl)methylcarbamate (279) 1 g, 3.1 mmol) was dissolved in $CH_2Cl_2$ (20 mL). TFA (5 mL) was added dropwise at room temperature. The reaction mixture was stirred at room temperature for 2 h. The reaction mixture was concentrated under reduced pressure to give (5-(4-(4,4-difluoropiperidin-1-ylsulfonyl)phenyl)-7-(trifluoromethyl)benzofuran-2-yl)methanamine (280), which was used without further purification in the next step (580 mg, 70% yield). LCMS: m/z 475.1 [M+H]$^+$, $t_R$=1.44 min.

Synthesis of (E)-3-(6-aminopyridin-3-yl)-N-((5-(4-((4,4-difluoropiperidin-1-yl)sulfonyl)phenyl)-7-(trifluoromethyl)benzofuran-2-yl)methyl)acrylamide (679)

(5-(4-(4,4-Difluoropiperidin-1-ylsulfonyl)phenyl)-7-(trifluoromethyl)benzofuran-2-y)methanamine (280) (250 mg, 0.53 mmol) was dissolved in DMF (4 mL) and (E)-3-(6-aminopyridin-3-yl)acrylic acid (95 mg, 0.58 mmol) was added at 0° C. HATU (222 mg, 0.58 mmol) was added to this reaction mixture at 0° C. followed by DIPEA (205 mg, 1.6 mmol) dropwise. The reaction mixture was allowed to warm to room temperature and stirred further for 2 h. The reaction mixture was purified Prep-HPLC to afford 70 mg of (E)-3-(6-aminopyridin-3-yl)-N-((5-(4-((4,4-difluoropiperidin-1-yl)sulfonyl)phenyl)-7-(trifluoromethyl)benzofuran-2-yl)methyl)acrylamide (679) (21% yield). $^1$H NMR (500 MHz, DMSO-d$_6$) δ 8.88-8.82 (m, 1H), 8.34 (s, 1H), 8.20 (s, 1H), 8.09-7.84 (m, 8H), 7.45 (d, J=16 Hz, 1H), 7.02-6.90 (m, 2H), 6.60 (d, J=16 Hz, 1H), 4.68-4.61 (m, 2H), 3.19-3.07 (m, 4H), 2.16-2.03 (m, 4H). LCMS: m/z 621.2 [M+H]$^+$, $t_R$=1.91 min.

Synthesis of (E)-N-((5-(4-((4,4-difluoropiperidin-1-yl)sulfonyl)phenyl)-7-(trifluoromethyl)benzofuran-2-yl)methyl)-3-(pyridin-3-yl)acrylamide (680)

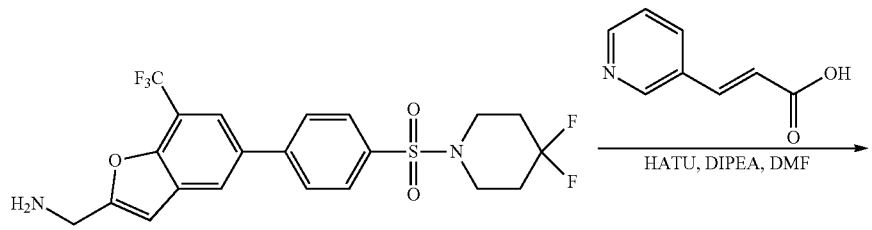

275

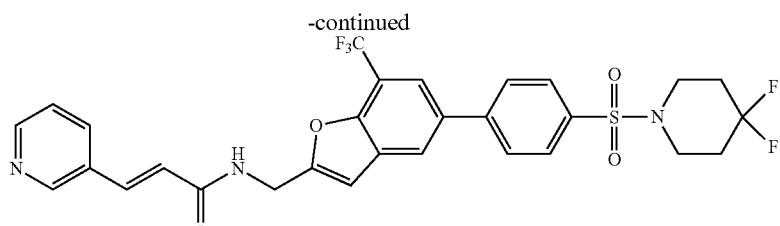

680

(E)-N-((5-(4-((4,4-difluoropiperidin-1-yl)sulfonyl)phenyl)-7-(trifluoromethyl)benzofuran-2-yl)methyl)-3-(pyridin-3-yl)acrylamide (680) was synthesized in a similar fashion as example (677). Yield: 24%. $^1$H NMR (500 MHz, DMSO-$d_6$) δ 8.99-8.94 (m, 1H), 8.86 (s, 1H), 8.68-8.60 (m, 1H), 8.34 (s, 1H), 8.20-8.14 (m, 1H), 8.10-8.03 (m, 2H), 7.97 (s, 1H), 7.92-7.87 (m, 2H), 7.62-7.55 (m, 2H), 7.01 (s, 1H), 6.87 (d, J=16 Hz, 1H), 4.68 (d, J=5 Hz, 2H), 3.18-3.11 (m, 4H), 2.14-2.06 (m, 4H). LCMS: m/z 606.2 [M+H]$^+$, $t_R$=1.96 min.

Synthesis of (E)-3-(6-aminopyridin-3-yl)-N-((5-(5-(4,4-difluoropiperidine-1-carbonyl)pyridin-2-yl)-6,7-difluorobenzofuran-2-yl)methyl)acrylamide (681)

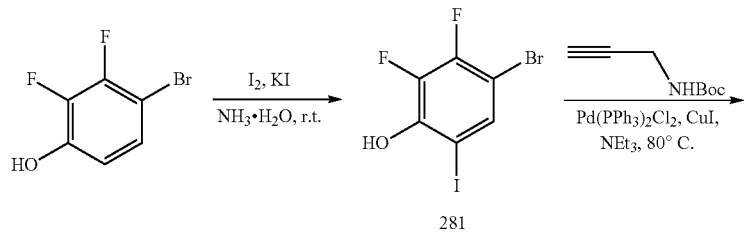

281

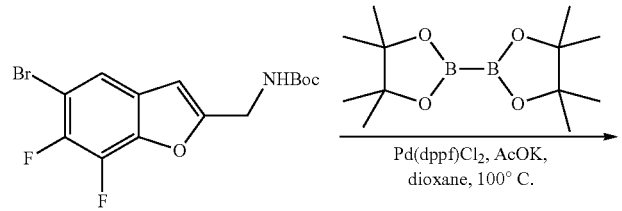

282

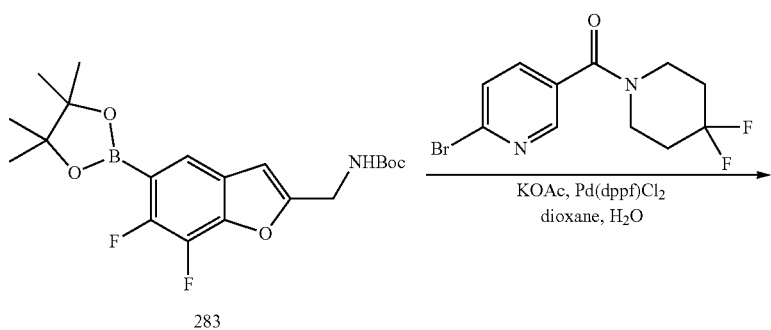

283

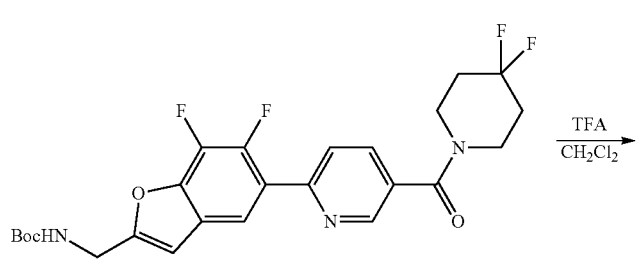

284

-continued

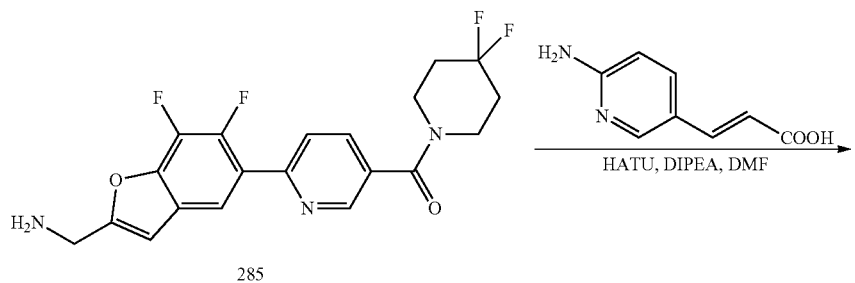
285

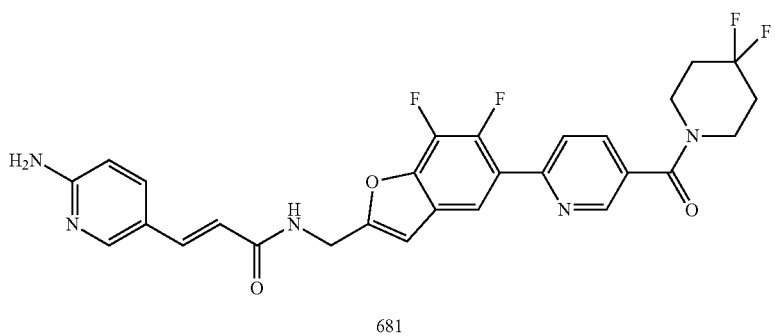
681

Synthesis of 4-bromo-2,3-difluoro-6-iodophenol (281)

4-Bromo-2,3-difluorophenol (2 g, 9.7 mmol) was dissolved in 100 mL of NH₄OH. A solution of KI (4.8 g, 29 mmol) and I2 (2.5 g, 9.7 mmol) in 50 mL of H₂O was added to the reaction mixture and stirred at room temperature up to 1 h. The reaction mixture was cooled down to 0° C. (ice bath), neutralized with HCl (conc.) until pH~6-7; extracted with EtOAc (200 mL×3). The combined organic layers were washed with sat. aq. sodium bisulfite solution, brine, dried over anhydrous Na₂SO₄, and concentrated under reduced pressure to give 2.8 g of 4-bromo-2,3-difluoro-6-iodophenol (281) as a yellow solid (85% yield). LCMS: m/z $t_R$=1.31 min.

Synthesis of tert-butyl (5-bromo-6,7-difluorobenzofuran-2-yl)methylcarbamate (282)

4-Bromo-2,3-difluoro-6-iodophenol (281) (2 g, 5.9 mmol), tert-butyl prop-2-ynylcarbamate (1.1 g, 7.1 mmol), Pd(PPh₃)₂Cl₂ (0.6 g, 0.9 mmol), CuI (0.17 g, 0.9 mmol) were added in 30 mL of triethylamine and degassed. The reaction mixture was refluxed at 80° C. under nitrogen atmosphere for 2 h. After cooling down to room temperature, the reaction mixture was filtered. The filtrate was concentrated under reduced pressure to give the crude product, which was purified by silica gel chromatography (5% EtOAc/petroleum ether) to yield 1.7 g of tert-butyl (5-bromo-6,7-difluorobenzofuran-2-yl)methylcarbamate (282) as a pale yellow solid (80% yield). LCMS: m/z 384.3 [M+Na]⁺, $t_R$=2.13 min.

Synthesis of tert-butyl (6,7-difluoro-5-(4,4,5,5-tetramethyl-1,3,2-dioxaborolan-2-yl)benzofuran-2-yl)methylcarbamate (283)

tert-Butyl (5-bromo-6,7-difluorobenzofuran-2-yl)methylcarbamate (282) (500 mg, 1.4 mmol), 4,4,4',4',5,5,5',5'-octamethyl-2,2'-bi(1,3,2-dioxaborolane) (534 mg, 2.2 mmol), Pd(dppf)Cl₂ (190 mg, 0.2 mmol), and potassium acetate (280 mg, 2.8 mmol) were added in 10 mL of dioxane and degassed. The reaction mixture was heated at 100° C. under nitrogen atmosphere for 2 h. After cooling down to room temperature, the reaction mixture was filtered. The filtrate was concentrated under reduced pressure to give the crude product, which was purified by silica gel chromatography (10% EtOAc/petroleum ether) to yield 0.4 g of tert-butyl (6,7-difluoro-5-(4,4,5,5-tetramethyl-1,3,2-dioxaborolan-2-yl)benzofuran-2-yl)methylcarbamate (283) as a white solid (70% yield). LCMS: m/z $t_R$=1.87 min.

Synthesis of tert-butyl (5-(5-(4,4-difluoropiperidine-1-carbonyl)pyridin-2-yl)-6,7-difluorobenzofuran-2-yl)methylcarbamate (284)

tert-Butyl (6,7-difluoro-5-(4,4,5,5-tetramethyl-1,3,2-dioxaborolan-2-yl)benzofuran-2-yl)methylcarbamate (283) (0.4 g, 0.96 mmol), (6-bromopyridin-3-yl)(4,4-difluoropiperidin-1-yl)methanone (0.29 g, 0.96 mmol), Pd(dppf)Cl₂

(0.11 g, 0.14 mmol), and K₂CO₃ (0.26 g, 1.92 mmol) were added in a mixture of dioxane (10 mL) and water (1 mL) and degassed. The reaction mixture was heated at 100° C. under nitrogen atmosphere for 5 h. The reaction mixture was cooled down to room temperature, filtered and the filtrate was concentrated under reduced pressure to give the crude product, which was purified by silica gel chromatography (50% EtOAc/petroleum ether) to yield 0.38 g of tert-butyl (5-(5-(4,4-difluoropiperidine-1-carbonyl)pyridin-2-yl)-6,7-difluorobenzofuran-2-yl)methylcarbamate (284) as a white solid (yield 80%). LCMS: m/z 508.1 [M+H]⁺, $t_R$=1.96 min.

Synthesis of (6-(2-(aminomethyl)-6,7-difluorobenzofuran-5-yl)pyridin-3-yl)(4,4-difluoropiperidin-1-yl)methanone (285)

tert-Butyl (5-(5-(4,4-difluoropiperidine-1-carbonyl)pyridin-2-yl)-6,7-difluorobenzofuran-2-yl)methylcarbamate (284) (100 mg, 0.2 mmol) was dissolved in CH₂Cl₂ (5 mL). TFA (1 mL) was added dropwise at room temperature. The reaction mixture was stirred at room temperature for 2 h. The reaction mixture was concentrated under reduced pressure to give the crude (6-(2-(aminomethyl)-6,7-difluorobenzofuran-5-yl)pyridin-3-yl)(4,4-difluoropiperidin-1-yl)methanone (285), which was used without further purification in the next step (81 mg, 100% yield). LCMS: m/z 408.1 [M+H]⁺, $t_R$=1.22 min.

Synthesis of (E)-3-(6-aminopyridin-3-yl)-N-((5-(5-(4,4-difluoropiperidine-1-carbonyl)pyridin-2-yl)-6,7-difluorobenzofuran-2-yl)methyl)acrylamide (681)

(6-(2-(Aminomethyl)-6,7-difluorobenzofuran-5-yl)pyridin-3-yl)(4,4-difluoropiperidin-1-yl)methanone (285) (81 mg, 0.2 mmol) was dissolved in DMF (2 mL) and (E)-3-(6-aminopyridin-3-yl)acrylic acid (33 mg, 0.2 mmol) was added at 0° C. HATU (152 mg, 0.4 mmol) was added to this reaction mixture at 0° C. followed by DIPEA (52 mg, 0.4 mmol) dropwise. The reaction mixture was allowed to warm to room temperature and stirred further for 2 h. The reaction mixture was purified by Prep-HPLC to afford 23 mg of (E)-3-(6-aminopyridin-3-yl)-N-((5-(5-(4,4-difluoropiperidine-1-carbonyl)pyridin-2-yl)-6,7-difluorobenzofuran-2-yl)methyl)acrylamide (681) (20% yield). ¹H NMR (500 MHz, DMSO-d₆) δ 8.96-8.76 (m, 2H), 8.32-7.82 (m, 7H), 7.45 (d, J=16 Hz, 1H), 7.08-6.89 (m, 2H), 6.60 (d, J=16 Hz, 1H), 4.68-4.58 (m, 2H), 3.82-3.71 (m, 2H), 3.56-3.42 (m, 2H), 2.15-2.02 (m, 4H). LCMS: m/z 554.2 [M+H]⁺; $t_R$=1.71 min.

Synthesis of (E)-N-((5-(4-(4,4-difluoropiperidine-1-carbonyl)phenyl)-7-(trifluoromethyl)benzofuran-2-yl)methyl)-3-(pyridin-3-yl)acrylamide (682)

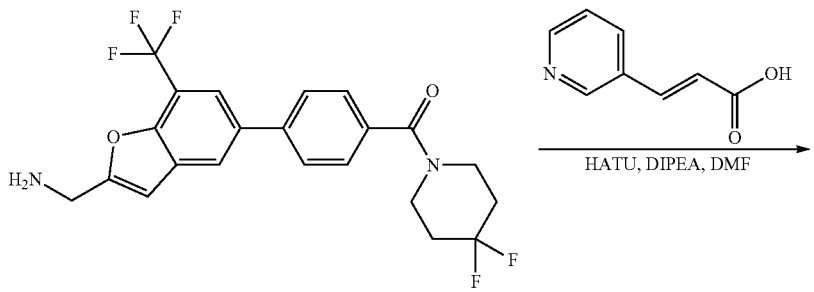

211

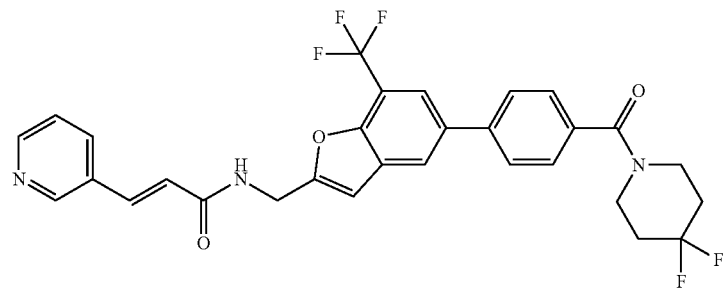

682

411

(E)-N-((5-(4-(4,4-difluoropiperidine-1-carbonyl)phenyl)-7-(trifluoromethyl)benzofuran-2-yl)methyl)-3-(pyridin-3-yl)acrylamide (682) was synthesized using the indicated reagents according to General Procedure 4. Yield: 31%. $^1$H NMR (400 MHz, DMSO-$d_6$) δ 8.94 (t, J=6 Hz, 1H), 8.79 (d, J=2 Hz, 1H), 8.62-8.53 (m, 1H), 8.27 (s, 1H), 8.06-8.00 (m, 1H), 7.91-7.81 (m, 3H), 7.61-7.52 (m, 3H), 7.49-7.43 (m, 1H), 6.99 (s, 1H), 6.84 (d, J=16 Hz, 1H), 4.66 (d, J=6 Hz, 2H), 3.78-3.43 (m, 4H), 2.16-1.96 (m, 4H). LCMS: m/z 569.9 [M+H]$^+$, $t_R$=2.03 min.

412

Synthesis of (E)-3-(6-aminopyridin-3-yl)-N-((5-(4-(4,4-difluoropiperidine-1-carbonyl)-2-fluorophenyl)-7-(trifluoromethyl)benzofuran-2-yl)methyl)acrylamide (683)

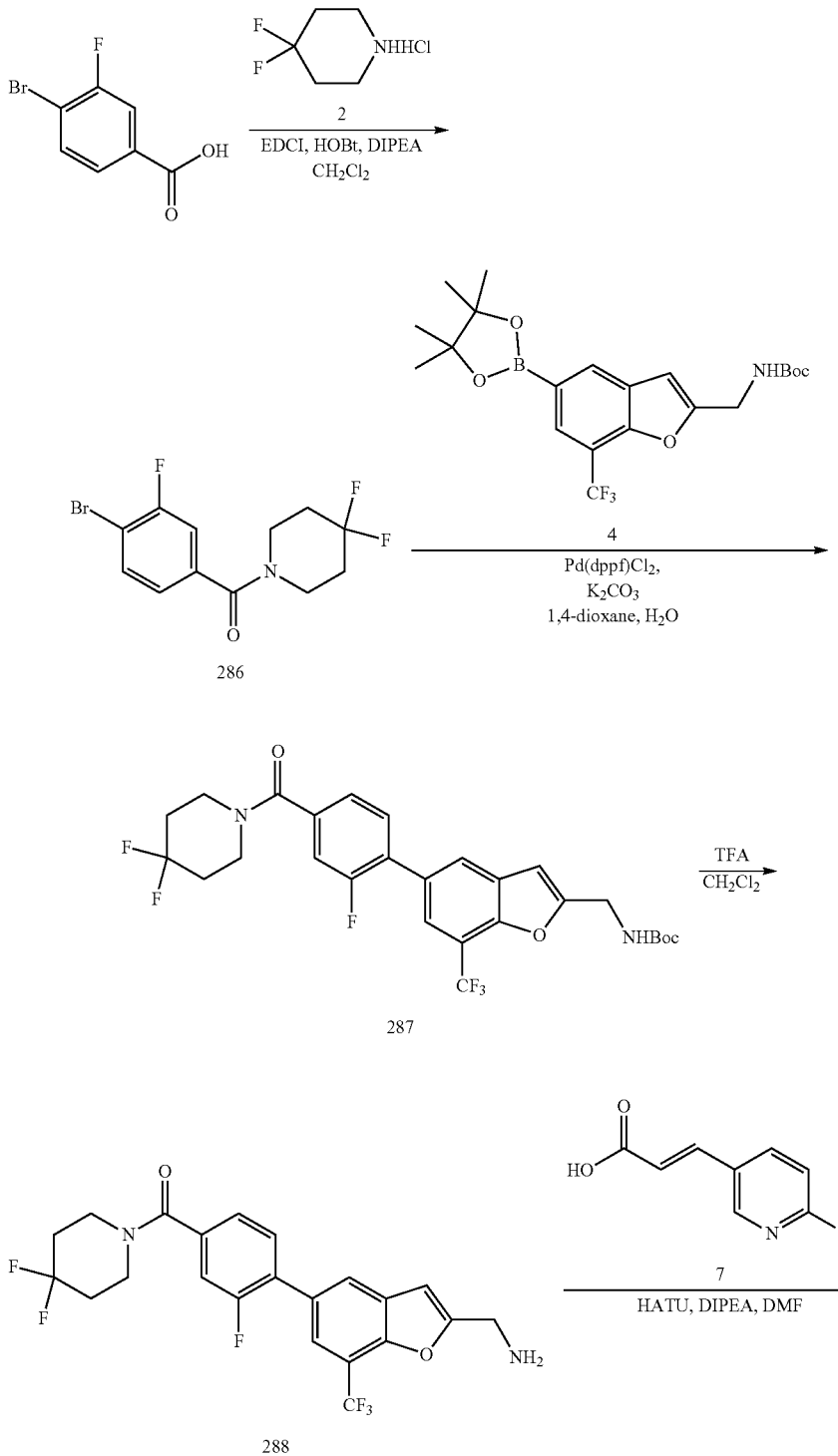

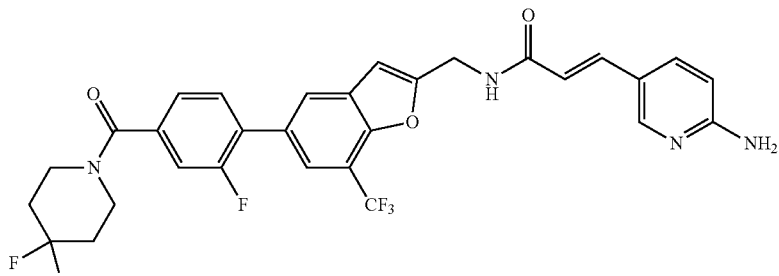

683

(E)-3-(6-aminopyridin-3-yl)-N-((5-(4-(4,4-difluoropiperidine-1-carbonyl)-2-fluorophenyl)-7-(trifluoromethyl)benzofuran-2-yl)methyl)acrylamide (683) was synthesized in a similar fashion as example (538). $^1$H NMR (400 MHz, CD$_3$OD) δ 8.98 (s, 1H), 8.74 (s, 1H), 8.63-8.55 (m, 1H), 8.07 (s, 1H), 7.94-7.86 (m, 1H), 7.78-7.65 (m, 3H), 7.46-7.38 (m, 2H), 7.01-6.91 (m, 2H), 4.78 (s, 2H), 3.98-3.81 (m, 2H), 3.73-3.57 (m, 2H), 2.20-1.99 (m, 4H). LCMS: m/z 603.2 [M+H]$^+$, t$_R$=1.44 min.

Synthesis of (E)-N-((5-(4-(4,4-difluoropiperidine-1-carbonyl)-2-fluorophenyl)-7-(trifluoromethyl)benzofuran-2-yl)methyl)-3-(pyridin-3-yl)acrylamide (684)

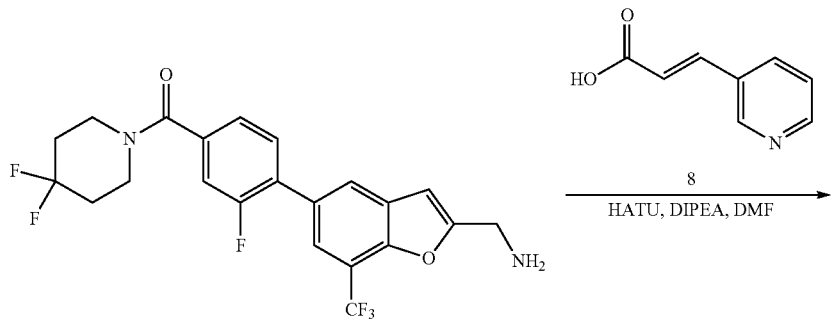

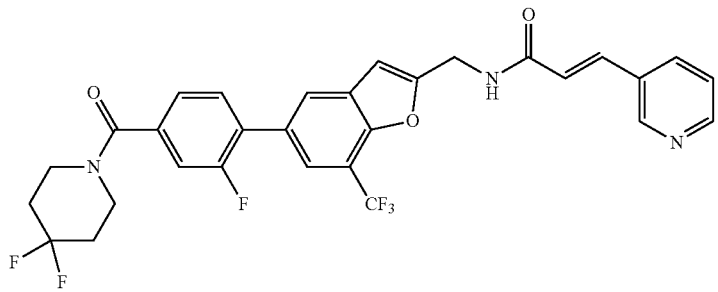

684

415

(E)-N-((5-(4-(4,4-difluoropiperidine-1-carbonyl)-2-fluorophenyl)-7-(trifluoromethyl)benzofuran-2-yl)methyl)-3-(pyridin-3-yl)acrylamide (684) was synthesized using the indicated reagents according to General Procedure 4. Yield: 37%. ¹H NMR (400 MHz, DMSO-d₆) δ 9.02-8.84 (m, 2H), 8.70-8.61 (m, 1H), 8.29-8.12 (m, 2H), 7.79 (s, 1H), 7.72 (t, J=8 Hz, 1H), 7.68-7.55 (m, 2H), 7.50 (d, J=11 Hz, 1H), 7.44-7.38 (m, 1H), 7.01 (s, 1H), 6.92-6.83 (m, 1H), 4.67 (d, J=6 Hz, 2H), 3.82-3.65 (m, 2H), 3.54-3.35 (m, 2H), 2.15-1.99 (m, 4H). LCMS: m/z 588.2 [M+H]⁺, t$_R$=1.58 min.

416

Synthesis of (E)-3-(6-aminopyridin-3-yl)-N-((5-(5-(4,4-difluoropiperidine-1-carbonyl)thiophen-2-yl)-7-(trifluoromethyl)benzofuran-2-yl)methyl)acrylamide (685)

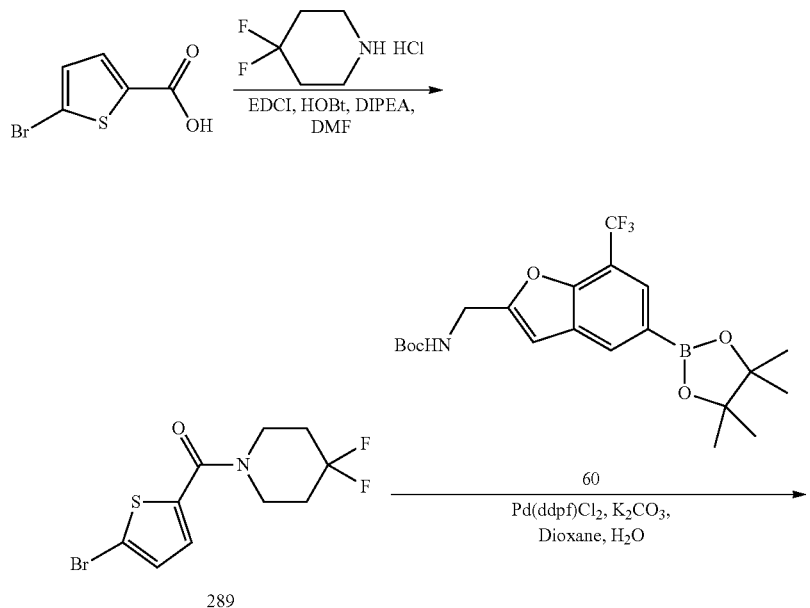

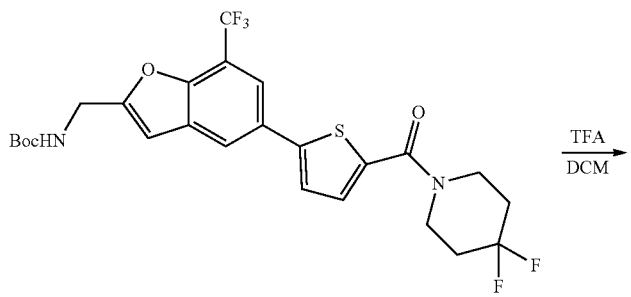

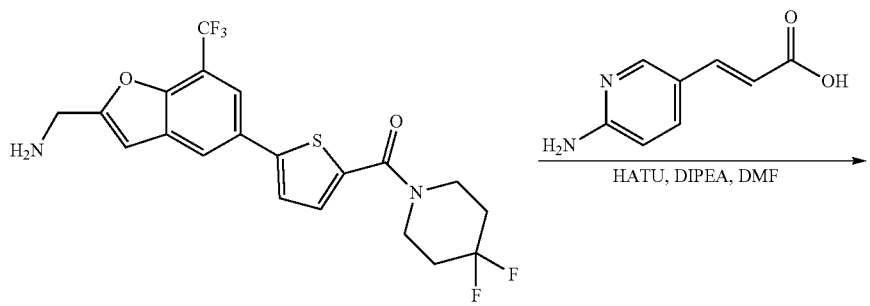

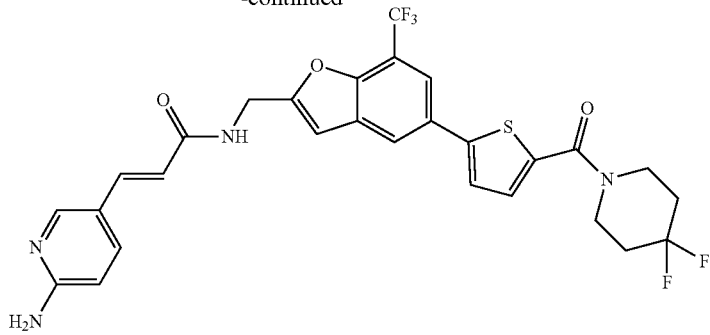

685

(E)-3-(6-aminopyridin-3-yl)-N-((5-(5-(4,4-difluoropiperidine-1-carbonyl)thiophen-2-yl)-7-(trifluoromethyl)benzofuran-2-yl)methyl)acrylamide (685) was synthesized in a similar fashion as example (521). $^1$H NMR (400 MHz, CD$_3$OD) δ 8.15 (s, 1H), 8.07 (s, 1H), 7.83 (s, 1H), 7.76 (d, J=9 Hz, 1H), 7.53-7.45 (m, 3H), 6.91 (s, 1H), 6.61 (d, J=9 Hz, 1H), 6.48 (d, J=16 Hz, 1H), 4.71 (s, 2H), 3.95-3.89 (m, 4H), 2.18-2.07 (m, 4H). LCMS: m/z 591.2 [M+H]$^+$, t$_R$=1.84 min.

Synthesis of (E)-3-(6-aminopyridin-3-yl)-N-((5-(4-(4,4-difluoropiperidine-1-carbonyl)phenyl)-7-(trifluoromethoxy)benzofuran-2-yl)methyl)acrylamide (686)

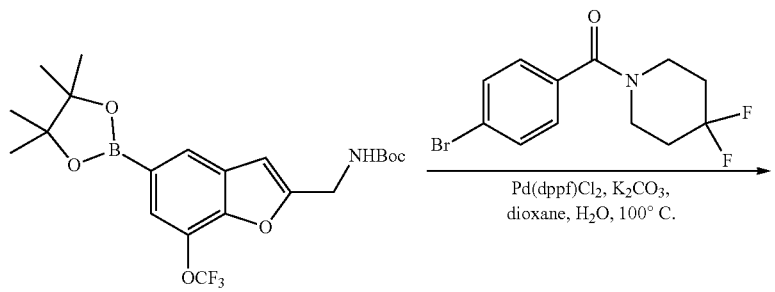

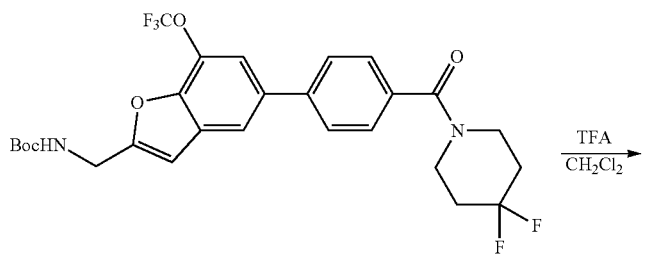

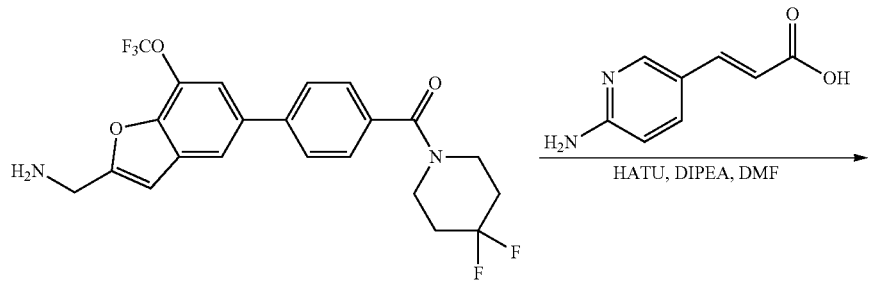

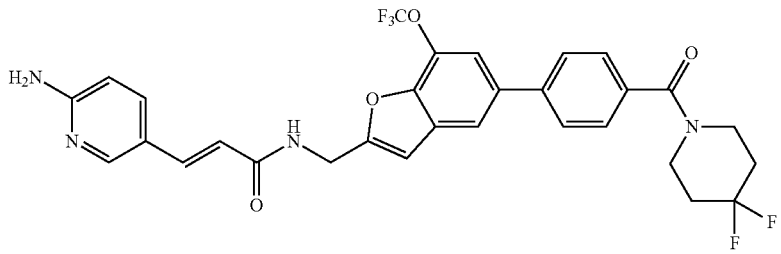

686

(E)-3-(6-aminopyridin-3-yl)-N-((5-(4-(4,4-difluoropiperidine-1-carbonyl)phenyl)-7-(trifluoromethoxy)benzofuran-2-yl)methyl)acrylamide (688) was synthesized in a similar fashion as example (663) using the indicated reagents. $^1$H NMR (400 MHz, DMSO-d$_6$) δ 8.65 (t, J=6 Hz, 1H), 8.08 (d, J=2 Hz, 1H), 7.99 (d, J=2 Hz, 1H), 7.83-7.77 (m, 2H), 7.68-7.54 (m, 4H), 7.35 (d, J=16 Hz, 1H), 6.92 (s, 1H), 6.53-6.31 (m, 4H), 4.60 (d, J=6 Hz, 2H), 3.79-3.42 (m, 4H), 2.13-1.98 (m, 4H). LCMS: m/z 601.3 [M+H]$^+$, t$_R$=1.84 min.

Synthesis of (E)-N-((5-(4-(4,4-difluoropiperidine-1-carbonyl)phenyl)-7-(trifluoromethoxy)benzofuran-2-yl)methyl)-3-(pyridin-3-yl)acrylamide (687)

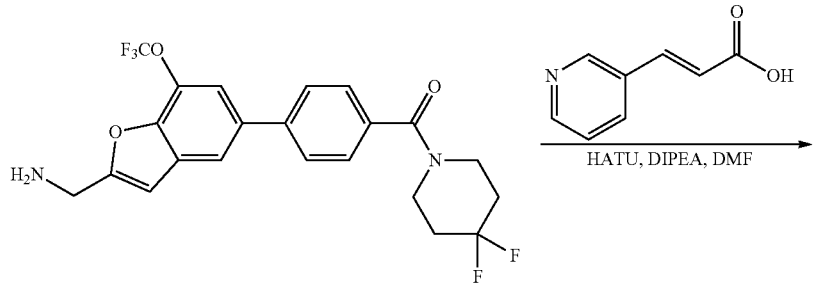

293

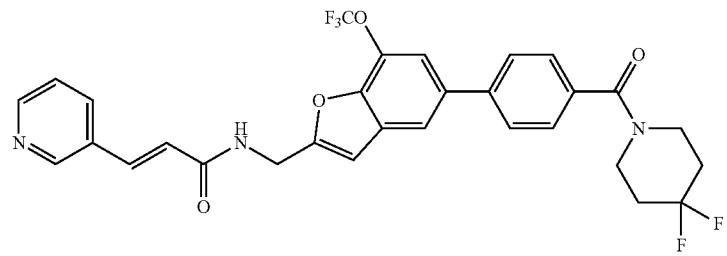

687

(E)-N-((5-(4-(4,4-difluoropiperidine-1-carbonyl)phenyl)-7-(trifluoromethoxy)benzofuran-2-yl)methyl)-3-(pyridin-3-yl)acrylamide (687) was synthesized using the indicated reagent according to General Procedure 4. Yield: 27%. $^1$H NMR (400 MHz, DMSO-$d_6$) δ 8.92 (t, J=6 Hz, 1H), 8.79 (d, J=2 Hz, 1H), 8.60-8.53 (m, 1H), 8.05-7.98 (m, 2H), 7.84-7.77 (m, 2H), 7.67 (s, 1H), 7.60-7.43 (m, 4H), 6.96 (s, 1H), 6.82 (d, J=16 Hz, 1H), 4.64 (d, J=6 Hz, 2H), 3.79-3.41 (m, 4H), 2.14-1.97 (m, 4H). LCMS: m/z 586.2 [M+H]$^+$, $t_R$=1.88 min.

Synthesis of (E)-N-((5-(4-(2-oxa-6-azaspiro[3.3]heptane-6-carbonyl)phenyl)-7-(trifluoromethyl)benzofuran-2-yl)methyl)-3-(pyridin-3-yl)acrylamide (688)

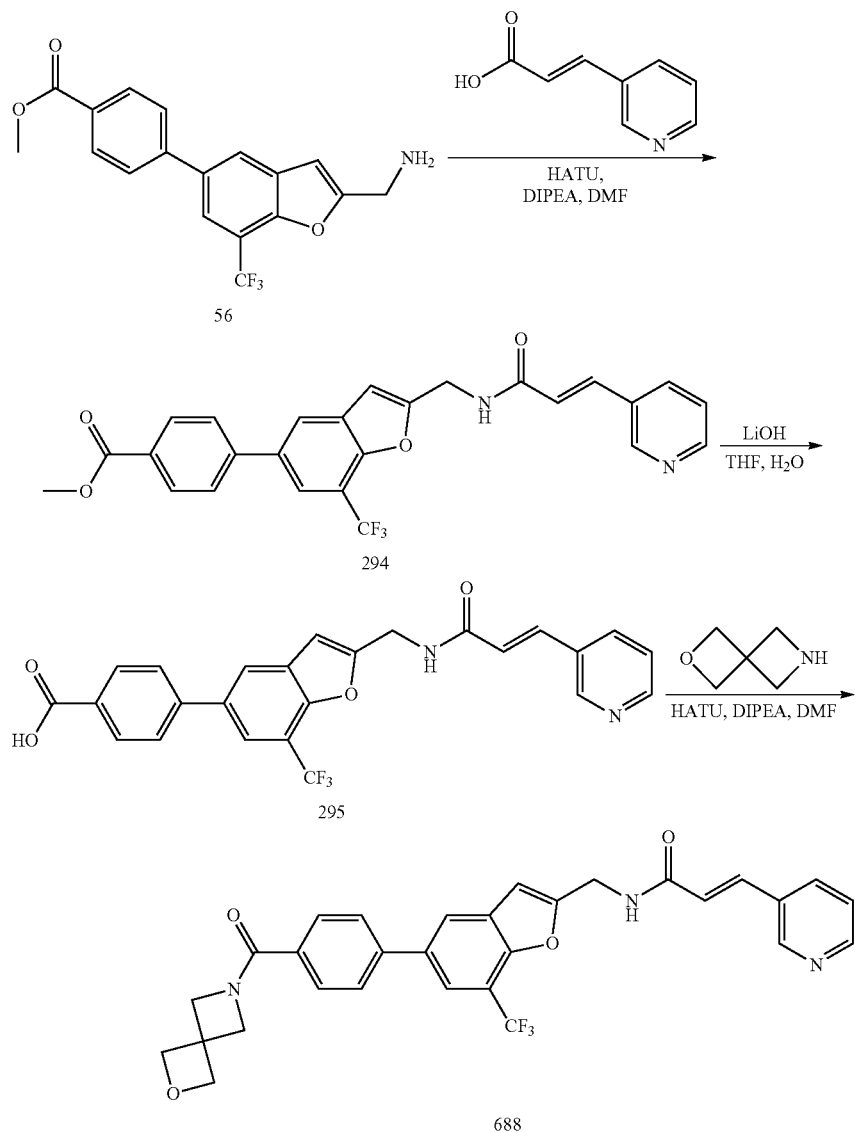

(E)-N-((5-(4-(2-oxa-6-azaspiro[3.3]heptane-6-carbonyl)phenyl)-7-(trifluoromethyl)benzofuran-2-yl)methyl)-3-(pyridin-3-yl)acrylamide (688) was synthesized using the indicated reagents in a similar fashion as example (517). $^1$H NMR (400 MHz, DMSO-$d_6$) δ 9.03-8.85 (m, 2H), 8.66 (s, 1H), 8.30-8.18 (m, 2H), 7.89 (s, 1H), 7.84 (d, J=8 Hz, 2H), 7.73 (d, J=8 Hz, 2H), 7.68-7.55 (m, 2H), 6.99 (s, 1H), 6.89 (d, J=16 Hz, 1H), 4.75-4.63 (m, 6H), 4.53 (s, 2H), 4.24 (s, 2H). LCMS: m/z 548.2 [M+H]$^+$, $t_R$=1.39 min.

Synthesis of (E)-N-((5-(5-(2-oxa-6-azaspiro[3.3]heptane-6-carbonyl)pyridin-2-yl)-7-(trifluoromethyl)benzofuran-2-yl)methyl)-3-(pyridin-3-yl)acrylamide (689)

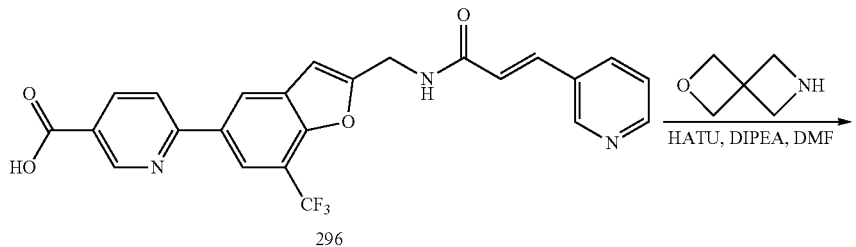

296

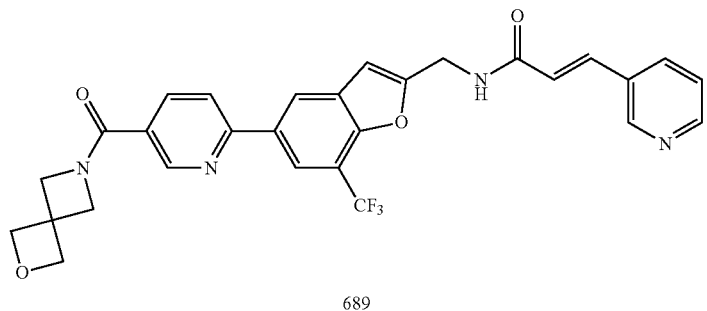

689

(E)-N-((5-(5-(2-oxa-6-azaspiro[3.3]heptane-6-carbonyl)pyridin-2-yl)-7-(trifluoromethyl)benzofuran-2-yl)methyl)-3-(pyridin-3-yl)acrylamide (689) was synthesized using the indicated reagents according to General Procedure 4. Yield (22%). $^1$H NMR (400 MHz, DMSO-$d_6$) δ 8.98-8.88 (m, 2H), 8.79 (d, J=2 Hz, 1H), 8.72 (s, 1H), 8.60-8.53 (m, 1H), 8.41 (s, 1H), 8.22 (d, J=8 Hz, 1H), 8.14-8.10 (m, 1H), 8.02 (d, J=8 Hz, 1H), 7.56 (d, J=16 Hz, 1H), 7.50-7.43 (m, 1H), 7.04 (s, 1H), 6.84 (d, J=16 Hz, 1H), 4.75-4.62 (m, 6H), 4.58 (s, 2H), 4.26 (s, 2H). LCMS: m/z 549.2 [M+H]$^+$, $t_R$=1.61 min.

Synthesis of (E)-3-(6-aminopyridin-3-yl)-N-(2-(5-(5-(4,4-difluoropiperidine-1-carbonyl)pyridin-2-yl)-7-(trifluoromethyl)benzofuran-2-yl)ethyl)acrylamide (690)

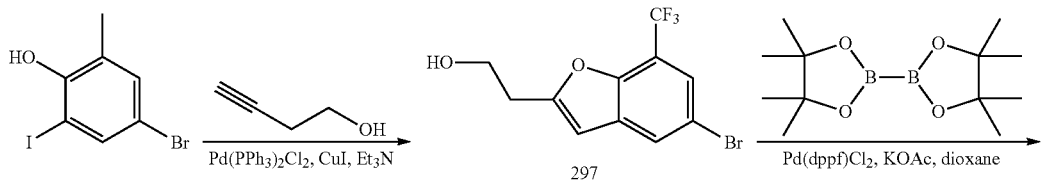

297

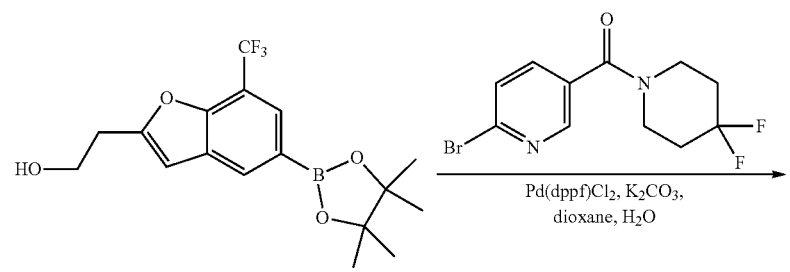

298

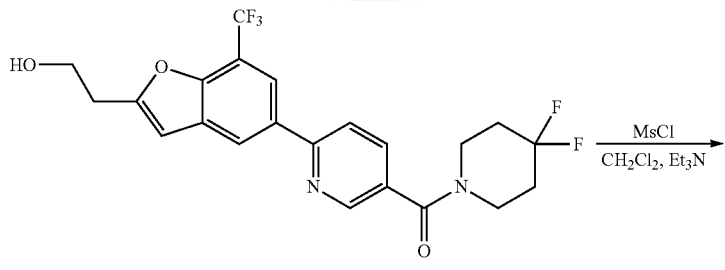
299
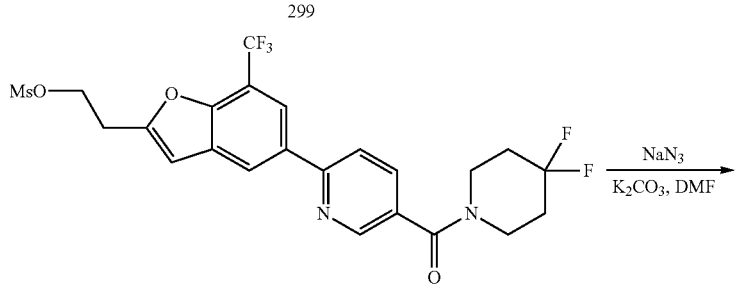
300
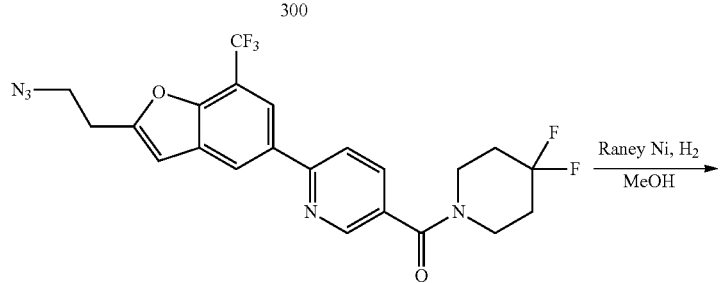
301
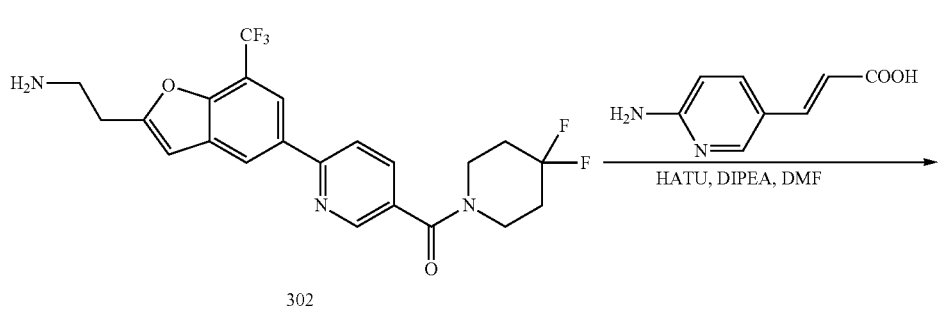
302
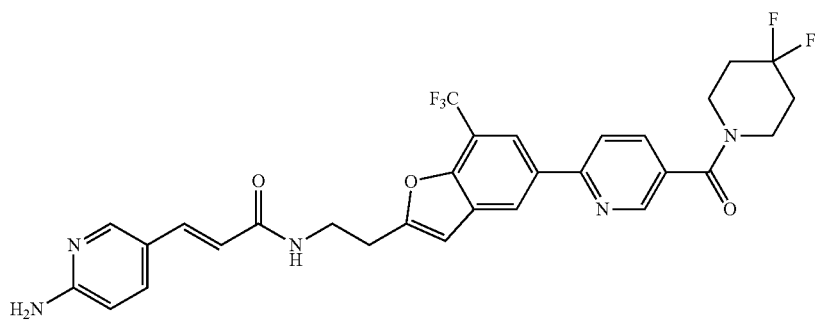
690

Synthesis of 2-(5-bromo-7-(trifluoromethyl)benzofuran-2-yl)ethanol (297)

4-Bromo-2-iodo-6-(trifluoromethyl)phenol (20 g, 55 mmol), but-3-yn-1-ol (3.9 g, 55 mmol), Pd(PPh$_3$)$_2$Cl$_2$ (3.9 g, 5.5 mmol), CuI (1.1 g, 5.5 mmol) were added in 400 mL of triethylamine and degassed. The reaction mixture was refluxed at 80° C. under nitrogen atmosphere for 2 h. After cooling down to room temperature, the reaction mixture was filtered. The filtrate was concentrated under reduced pressure to give the crude product, which was purified by silica gel chromatography (10% EtOAc/petroleum ether) to yield 13.5 g of 2-(5-bromo-7-(trifluoromethyl)benzofuran-2-yl)ethanol (297) as a pale yellow solid (80% yield). LCMS: $t_R$=1.94 min.

Synthesis of 2-(5-(4,4,5,5-tetramethyl-1,3,2-dioxaborolan-2-yl)-7-(trifluoromethyl)benzofuran-2-yl)ethanol (298)

2-(5-Bromo-7-(trifluoromethyl)benzofuran-2-yl)ethanol (297) (10 g, 32.5 mmol), 4,4,4',4',5,5,5',5'-octamethyl-2,2'-bi(1,3,2-dioxaborolane) (12.4 g, 48.8 mmol), Pd(dppf)Cl$_2$ (2.4 g, 3.3 mmol), and potassium acetate (6.4 g, 65 mmol) were added in 200 mL of dioxane and degassed. The reaction mixture was heated at 80° C. under nitrogen atmosphere for 2 h. After cooling down to room temperature, the reaction mixture was filtered. The filtrate was concentrated under reduced pressure to give the crude product, which was purified by silica gel chromatography (10% EtOAc/petroleum ether) to yield 9 g of 2-(5-(4,4,5,5-tetramethyl-1,3,2-dioxaborolan-2-yl)-7-(trifluoromethyl)benzofuran-2-yl)ethanol (298) as a white solid (80% yield). LCMS: m/z 357.1, $t_R$=1.86 min.

Synthesis of (4,4-difluoropiperidin-1-yl)(6-(2-(2-hydroxyethyl)-7-(trifluoromethyl)benzofuran-5-yl)pyridin-3-yl)methanone (299)

2-(5-(4,4,5,5-Tetramethyl-1,3,2-dioxaborolan-2-yl)-7-(trifluoromethyl)benzofuran-2-yl)ethanol (298) (8 g, 22.5 mmol), (6-bromopyridin-3-yl)(4,4-difluoropiperidin-1-yl)methanone (6.9 g, 22.5 mmol), Pd(dppf)Cl$_2$ (1.6 g, 2.3 mmol), and K$_2$CO$_3$ (3.5 g, 25 mmol) were added in a mixture of dioxane (150 mL) and water (15 mL) and degassed. The reaction mixture was heated at 80° C. under nitrogen atmosphere for 2 h. The reaction mixture was cooled down to room temperature, filtered and the filtrate was concentrated under reduced pressure to give the crude product, which was purified by silica gel chromatography (50% EtOAc/petroleum ether) to yield 9 g of (4,4-difluoropiperidin-1-yl)(6-(2-(2-hydroxyethyl)-7-(trifluoromethyl)benzofuran-5-yl)pyridin-3-yl)methanone (299) as a white solid (yield 90%). LCMS: m/z 455.1 [M+H]$^+$, $t_R$=1.82 min.

Synthesis of 2-(5-(5-(4,4-difluoropiperidine-1-carbonyl)pyridin-2-yl)-7-(trifluoromethyl)benzofuran-2-yl)ethyl methanesulfonate (300)

(4,4-Difluoropiperidin-1-yl)(6-(2-(2-hydroxyethyl)-7-(trifluoromethyl)benzofuran-5-yl)pyridin-3-yl)methanone (299); (3 g, 6.6 mmol) was dissolved in DCM (50 mL) and triethylamine (1.3 g, 13.2 mmol) was added. Methanesulfonyl chloride (0.75 g, 6.6 mmol) was added dropwise at 0° C. (ice bath) over 10 min. The reaction mixture was allowed to warm to room temperature and stirred for 1 h. The reaction mixture was diluted with DCM (100 mL), washed with water, brine, dried over anhydrous Na$_2$SO$_4$, and concentrated under reduced pressure to give 3.3 g of 2-(5-(5-(4,4-difluoropiperidine-1-carbonyl)pyridin-2-yl)-7-(trifluoromethyl)benzofuran-2-yl)ethyl methanesulfonate (300), which was used in next step without further purification (95% yield). LCMS: m/z 533.1 [M+H]$^+$, $t_R$=1.67 min.

Synthesis of (6-(2-(2-azidoethyl)-7-(trifluoromethyl)benzofuran-5-yl)pyridin-3-yl)(4,4-difluoropiperidin-1-yl)methanone (301)

2-(5-(5-(4,4-Difluoropiperidine-1-carbonyl)pyridin-2-yl)-7-(trifluoromethyl)benzofuran-2-yl)ethyl methanesulfonate (300; 1 g, 1.9 mmol) was dissolved in 20 mL of DMF. NaN$_3$ (0.4 g, 5.7 mmol) and K$_2$CO$_3$ (0.5 g, 3.7 mmol) were added. The reaction mixture was heated at 60° C. for 2 h, cooled down to room temperature, poured into iced water (50 mL), extracted with EtOAc (50 mL×3), washed with brine (50 mL), dried over Na$_2$SO$_4$, and concentrated under reduced pressure to afford 0.8 g of (6-(2-(2-azidoethyl)-7-(trifluoromethyl)benzofuran-5-yl)pyridin-3-yl)(4,4-difluoropiperidin-1-yl)methanone (301) as yellow solid, which was used without further purification in the next step (90% yield). LCMS: m/z 480.1 [M+H]$^+$; $t_R$=1.80 min.

Synthesis of (6-(2-(2-aminoethyl)-7-(trifluoromethyl)benzofuran-5-yl)pyridin-3-yl)(4,4-difluoropiperidin-1-yl)methanone (302)

(6-(2-(2-Azidoethyl)-7-(trifluoromethyl)benzofuran-5-yl)pyridin-3-yl)(4,4-difluoropiperidin-1-yl)methanone (301; 200 mg, 0.42 mmol) was dissolved in methanol (10 mL). 10% Raney Ni (50% wet) (0.3 g) was added and hydrogen gas was purged at room temperature for 1 h. The reaction mixture was filtered and the filtrate was concentrated under reduced pressure to give 170 mg of (6-(2-(2-aminoethyl)-7-(trifluoromethyl)benzofuran-5-yl)pyridin-3-yl)(4,4-difluoropiperidin-1-yl)methanone (302), which was used without further purification in the next step (90% yield). LCMS: m/z 454.1 [M+H]$^+$; $t_R$=1.33 min.

Synthesis of (E)-3-(6-aminopyridin-3-yl)-N-(2-(5-(5-(4,4-difluoropiperidine-1-carbonyl)pyridin-2-yl)-7-(trifluoromethyl)benzofuran-2-yl)ethyl)acrylamide (690)

(6-(2-(2-Aminoethyl)-7-(trifluoromethyl)benzofuran-5-yl)pyridin-3-yl)(4,4-difluoropiperidin-1-yl)methanone (302; 50 mg, 0.11 mmol) was dissolved in DMF (2 mL) and (E)-3-(6-aminopyridin-3-yl)acrylic acid (18 mg, 0.11 mmol) was added at 0° C. HATU (84 mg, 0.22 mmol) was added to this reaction mixture at 0° C. followed by DIPEA (28 mg, 0.22 mmol) dropwise. The reaction mixture was allowed to warm to room temperature and stirred further for 2 h. The reaction mixture was purified Prep-HPLC to afford 38 mg of (E)-3-(6-aminopyridin-3-yl)-N-(2-(5-(5-(4,4-difluoropiperidine-1-carbonyl)pyridin-2-yl)-7-(trifluoromethyl)benzofuran-2-yl)ethyl)acrylamide (690) (58% yield). $^1$H NMR (400 MHz, CD$_3$OD) δ 8.82-8.76 (m, 1H), 8.50 (s, 1H), 8.30 (s, 1H), 8.19 (d, J=9 Hz, 1H), 8.13-8.00 (m, 3H), 7.43 (d, J=16 Hz, 1H), 7.06 (d, J=9 Hz, 1H), 6.87 (s, 1H), 6.57 (d, J=16 Hz, 1H), 4.00-3.87 (m, 2H), 3.77 (t, J=7 Hz, 2H), 3.71-3.61 (m, 2H), 3.19 (t, J=7 Hz, 2H), 2.21-2.03 (m, 4H). LCMS: m/z 600.1 [M+H]$^+$, $t_R$=1.40 min.

Synthesis of (E)-3-(6-aminopyridin-3-yl)-N-(2-(5-(4-(4,4-difluoropiperidine-1-carbonyl)phenyl)-7-(trifluoromethyl)benzofuran-2-yl)ethyl)acrylamide (691)
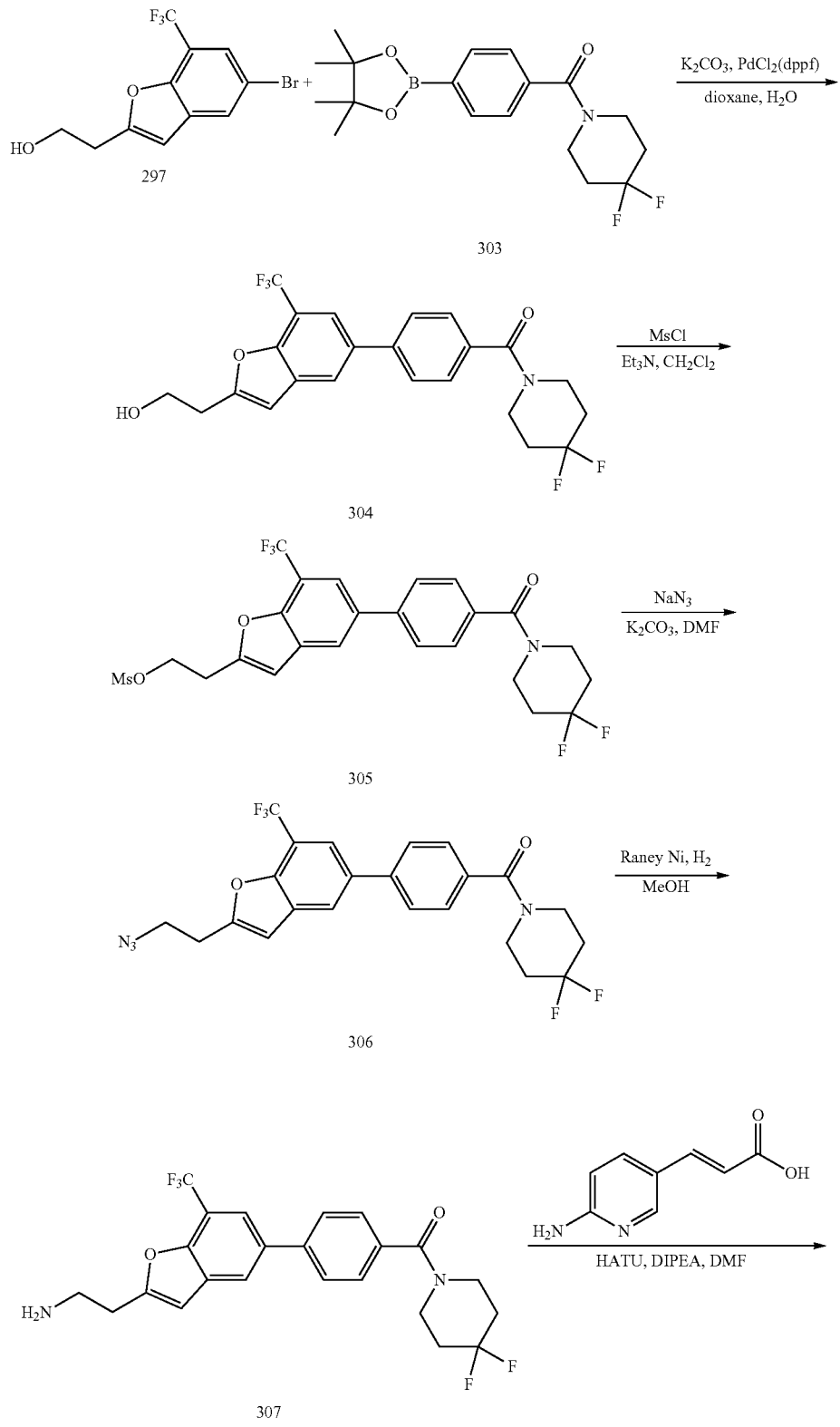

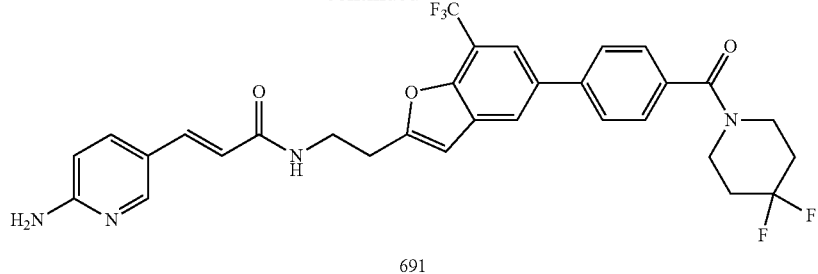

691

(E)-3-(6-aminopyridin-3-yl)-N-(2-(5-(4-(4,4-difluoropiperidine-1-carbonyl)phenyl)-7-(trifluoromethyl)benzofuran-2-yl)ethyl)acrylamide (691) was prepared using the indicated reagents in a similar fashion as example (690). ¹H NMR (400 MHz, DMSO-d₆) δ 8.41-8.15 (m, 5H), 8.09 (d, J=9 Hz, 1H), 7.87-7.79 (m, 3H), 7.58 (d, J=8 Hz, 2H), 7.38 (d, J=16 Hz, 1H), 6.99 (d, J=9 Hz, 1H), 6.91 (s, 1H), 6.51 (d, J=16 Hz, 1H), 3.80-3.45 (m, 6H), 3.08 (t, J=7 Hz, 2H), 2.15-1.98 (m, 4H). LCMS: m/z 599.1 [M+H]⁺, $t_R$=1.47 min.

Synthesis of (E)-3-(6-aminopyridin-3-yl)-N-((7-(4-fluorophenyl)-5-(4-(trifluoromethyl)phenyl)benzofuran-2-yl)methyl)acrylamide (692)

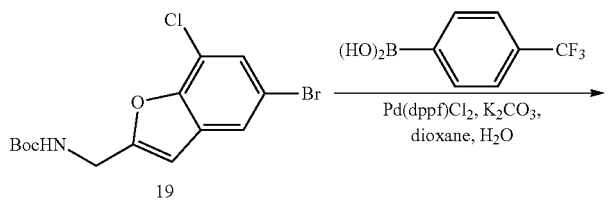

19

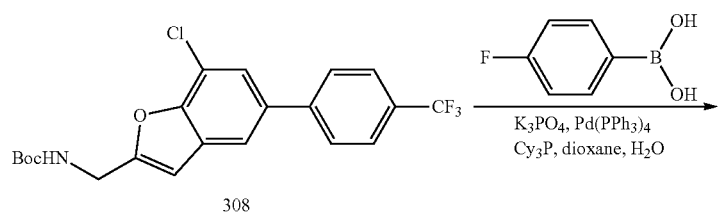

308

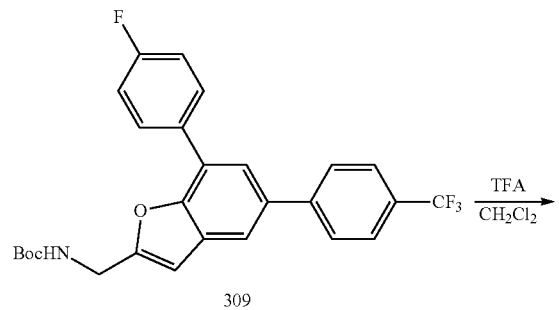

309

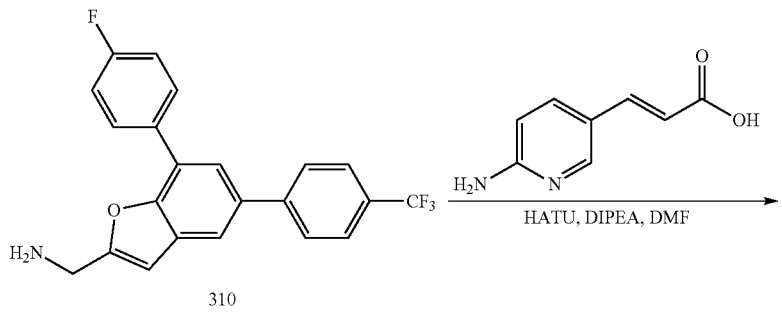

310

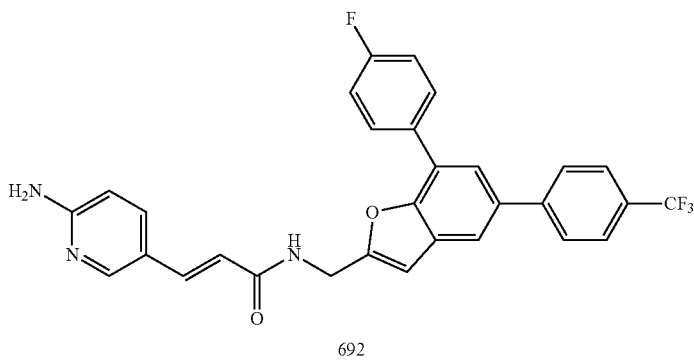

692

Synthesis of tert-Butyl (7-chloro-5-(4-(trifluoromethyl)phenyl)benzofuran-2-yl)methylcarbamate (308)

tert-Butyl (7-chloro-5-(4-(trifluoromethyl)phenyl)benzofuran-2-yl)methylcarbamate (308) was synthesized using General Procedure 2. Yield: 91%. LCMS: m/z 448.1 [M+Na]⁺, $t_R$=1.95 min.

Synthesis of Tert-Butyl (7-(4-fluorophenyl)-5-(4-(trifluoromethyl)phenyl)benzofuran-2-yl)methylcarbamate (309)

tert-Butyl (7-(4-fluorophenyl)-5-(4-(trifluoromethyl)phenyl)benzofuran-2-yl)methylcarbamate (309) was synthesized using the indicated reagents according to General Procedure 2 Yield: 61%. LCMS: m/z 508.1 [M+Na], $t_R$=1.99 min.

Synthesis of (7-(4-Fluorophenyl)-5-(4-(trifluoromethyl)phenyl)benzofuran-2-yl)methanamine (310)

(7-(4-Fluorophenyl)-5-(4-(trifluoromethyl)phenyl)benzofuran-2-yl)methanamine (310) was synthesized using the indicated reagents according to General Procedure 3. Yield: 98%. LCMS: m z 369.0 [M-NH₂]⁺, $t_R$=1.56 min.

Synthesis of (E)-3-(6-aminopyridin-3-yl)-N-((7-(4-fluorophenyl)-5-(4-(trifluoromethyl)phenyl)benzofuran-2-yl)methyl)acrylamide (692)

(E)-3-(6-aminopyridin-3-yl)-N-((7-(4-fluorophenyl)-5-(4-(trifluoromethyl)phenyl)benzofuran-2-yl)methyl)acrylamide (692) was synthesized using the indicated reagents according to General Procedure 4. Yield: 45%. ¹H NMR (400 MHz, DMSO-d₆) δ 8.62 (t, J=6 Hz, 1H), 8.11-7.99 (m, 5H), 7.96 (d, J=2 Hz, 1H), 7.86-7.76 (m, 3H), 7.64-7.58 (m, 1H), 7.44-7.31 (m, 3H), 6.88 (s, 1H), 6.50-6.39 (m, 4H), 4.60 (d, J=6 Hz, 2H). LCMS: m/z 532.2 [M+H]⁺, $t_R$=2.05 min.

Synthesis of (E)-3-(6-aminopyridin-3-yl)-N-((7-(4-fluorophenyl)-5-(4-(methylsulfonyl)phenyl)benzofuran-2-yl)methyl)acrylamide (693)

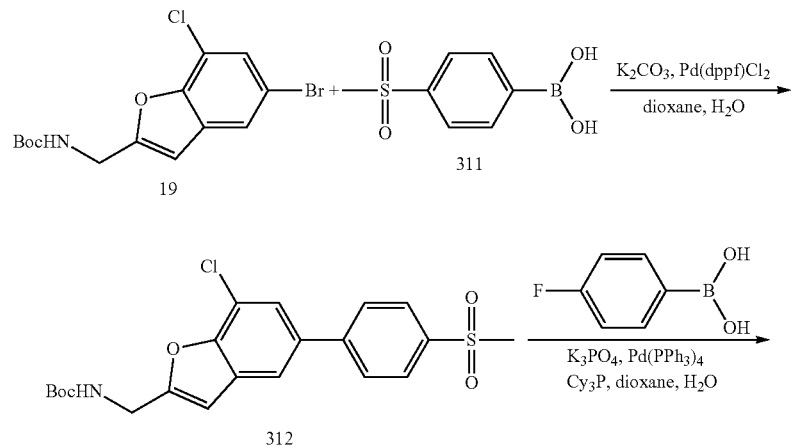

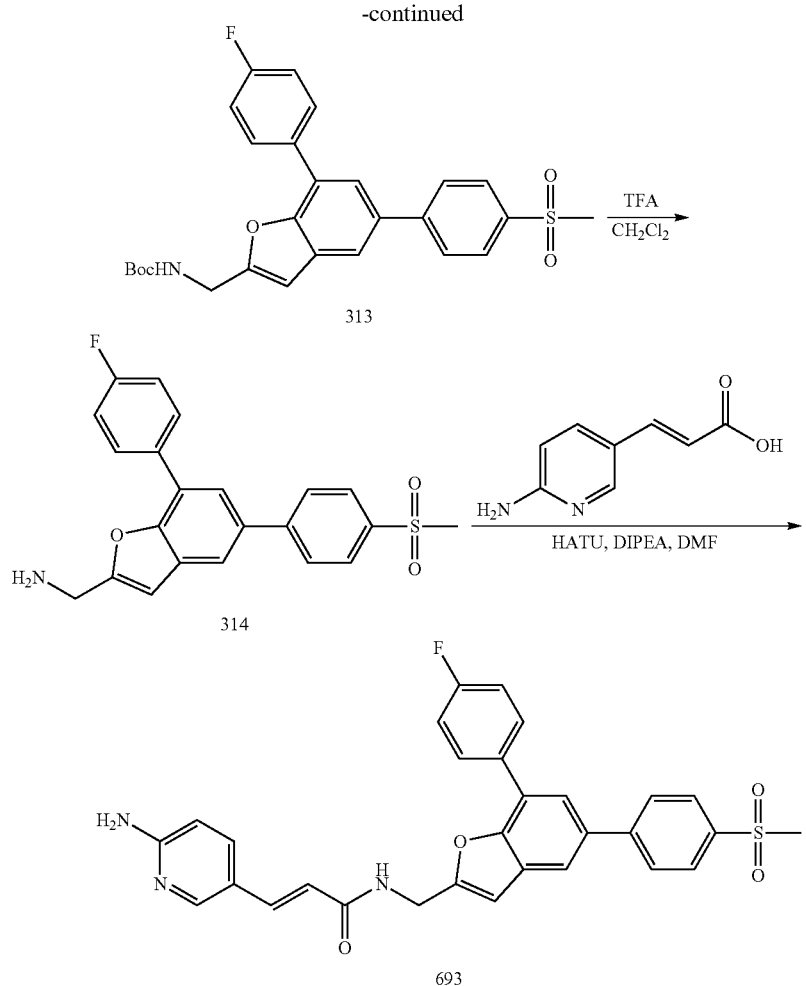

Synthesis of tert-butyl (7-chloro-5-(4-(methylsulfonyl)phenyl)benzofuran-2-yl)methylcarbamate (312)

tert-Butyl (5-bromo-7-chlorobenzofuran-2-yl)methylcarbamate (19, 500 mg, 1.9 mmol), 4-(methylsulfonyl)phenylboronic acid (311, 460 mg, 2.3 mmol), Pd(dppf)Cl$_2$ (163 mg, 0.2 mmol) and K$_2$CO$_3$ (787 mg, 5.7 mmol) were added in a mixture of dioxane (30 mL) and H$_2$O (6 mL). The reaction mixture was stirred at 95° C. under nitrogen atmosphere for 12 h. LCMS showed the reaction was complete. The reaction mixture was cooled down to room temperature, diluted with EtOAc (30 mL), washed with water, brine, dried over anhydrous Na$_2$SO$_4$, and concentrated under reduced pressure to give the crude product, which was purified by silica gel chromatography (0-30% EtOAc/petroleum ether) to give tert-butyl (7-chloro-5-(4-(methylsulfonyl)phenyl)benzofuran-2-yl)methylcarbamate (312), (450 mg, 54% yield) as yellowish solid. LCMS: m/z 458.0 [M+23]$^+$, t$_R$=1.73 min.

Synthesis of tert-butyl (7-(4-fluorophenyl)-5-(4-(methylsulfonyl)phenyl)benzofuran-2-yl)methylcarbamate (313)

tert-Butyl (7-chloro-5-(4-(methylsulfonyl)phenyl)benzofuran-2-yl)methylcarbamate (312, 220 mg, 0.5 mmol), 4-fluorophenylboronic acid (84 mg, 0.6 mmol), Pd(PhP3)$_4$ (58 mg, 0.05 mmol), PCy$_3$ (14 mg, 0.05 mmol) and K$_3$PO$_4$ (320 mg, 1.5 mmol) in a mixture of dioxane (2 mL) and H$_2$O (0.2 mL). The mixture was heated to 140° C. under microwave for 1.5 h. The reaction mixture was cooled down to room temperature, diluted with EtOAc (30 mL), washed with water, brine, dried over anhydrous Na$_2$SO$_4$, and concentrated under reduced pressure to give the crude product, which was purified by silica gel chromatography (0-20% EtOAc/petroleum ether) to give tert-butyl (7-(4-fluorophenyl)-5-(4-(methylsulfonyl)phenyl)benzofuran-2-yl)methylcarbamate (313), (200 mg, 80% yield) as off white solid. LCMS: m/z 518.0 [M+23]$^+$, t$_R$=1.79 min.

Synthesis of (7-(4-fluorophenyl)-5-(4-(methylsulfonyl)phenyl)benzofuran-2-yl)methanamine (314)

tert-Butyl (7-(4-fluorophenyl)-5-(4-(methylsulfonyl)phenyl)benzofuran-2-yl)methylcarbamate (313, 200 mg, 0.4 mmol) was dissolved in CH$_2$Cl$_2$ (20 mL). TFA (4 mL) was added at 0° C. The reaction mixture was stirred at 15° C. for 2 h, and concentrated under reduced pressure to give the crude (7-(4-fluorophenyl)-5-(4-(methylsulfonyl)phenyl)benzofuran-2-yl)methanamine (314), (160 mg, 100% yield), which was used without further purification in the next step. LCMS: m/z 396.1 [M+H]$^+$; t$_R$=1.33 min.

Synthesis of (E)-3-(6-aminopyridin-3-yl)-N-((7-(4-fluorophenyl)-5-(4-(methylsulfonyl)phenyl)benzofuran-2-yl)methyl)acrylamide (693)

(7-(4-Fluorophenyl)-5-(4-(methylsulfonyl)phenyl)benzofuran-2-yl)methanamine (314, 80 mg, 0.20 mmol), (E)-3-(6-aminopyridin-3-yl)acrylic acid (36 mg, 0.22 mmol) and HATU (84 mg, 0.22 mmol) was dissolved in DMF (3 mL) and DIPEA (78 mg, 0.60 mmol) was added slowly. The reaction mixture was stirred at 20° C. for 2 h. The mixture was purified by Pre-HPLC to give (E)-3-(6-aminopyridin-3-yl)-N-((7-(4-fluorophenyl)-5-(4-(methylsulfonyl)phenyl)benzofuran-2-yl)methyl)acrylamide (693) as white solid (40 mg, 37% yield). $^1$H NMR (400 MHz, DMSO-d$_6$) δ 8.81 (t, J=6 Hz, 1H), 8.20 (s, 1H), 8.11-7.96 (m, 10H), 7.82 (d, J=2 Hz, 1H), 7.48-7.36 (m, 3H), 6.94 (d, J=9 Hz, 1H), 6.90 (s, 1H), 6.59 (d, J=16 Hz, 1H), 4.62 (d, J=6 Hz, 2H), 3.28 (s, 3H). LCMS: m/z 542.2 [M+H]$^+$, t$_R$=1.40 min.

Synthesis of (E)-3-(6-aminopyridin-3-yl)-N-((5-(3,5-dimethylisoxazol-4-yl)-7-(4-fluorophenyl)benzofuran-2-yl)methyl)acrylamide (694)

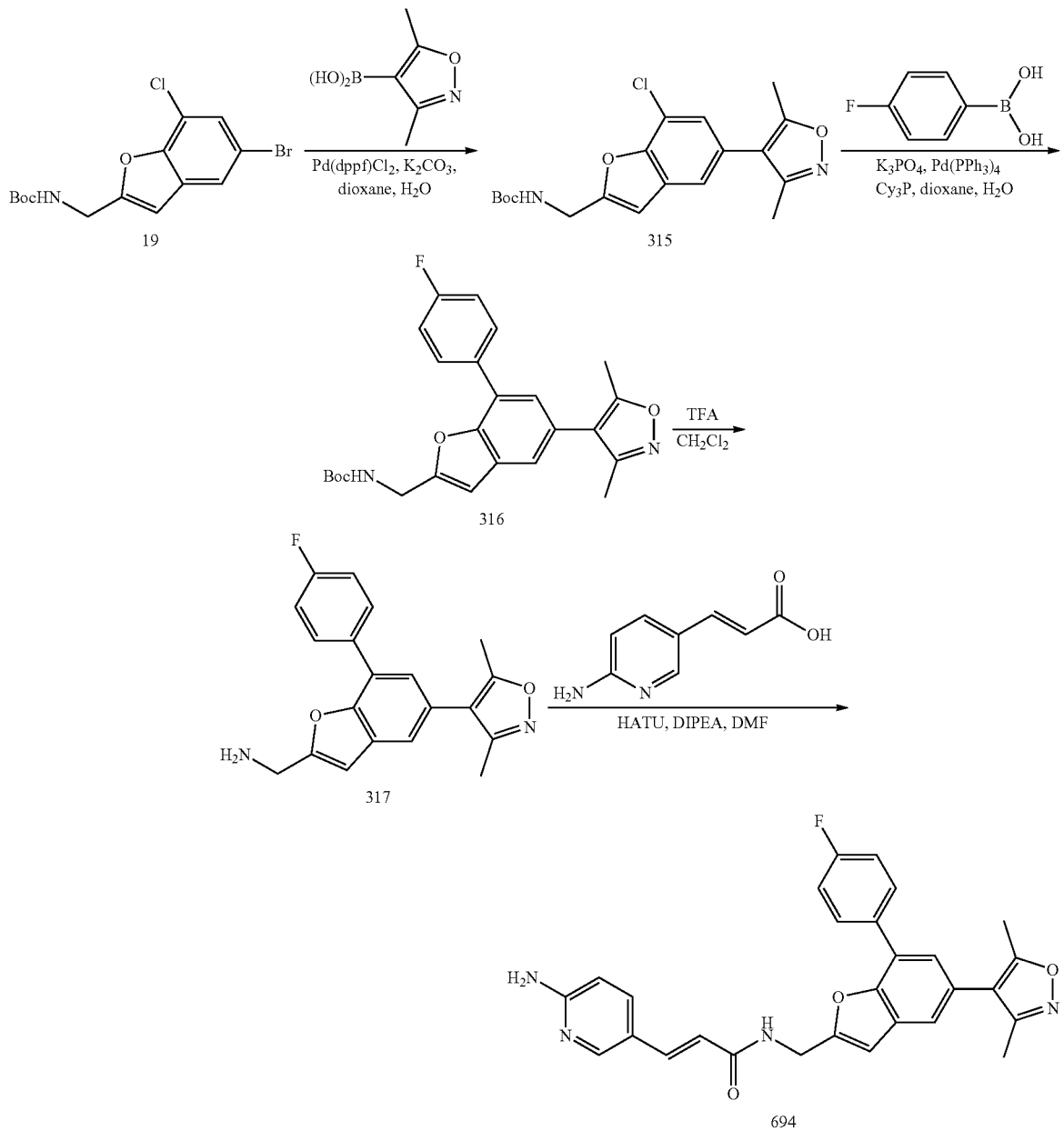

(E)-3-(6-aminopyridin-3-yl)-N-((5-(3,5-dimethylisoxazol-4-yl)-7-(4-fluorophenyl)benzofuran-2-yl)methyl)acrylamide (694) was synthesized using the indicated reagents in a similar fashion as example (693). $^1$H NMR (400 MHz, DMSO-d$_6$) δ 8.07 (s, 1H), 8.01-7.84 (m, 4H), 7.65 (d, J=9 Hz, 1H), 7.57 (s, 1H), 7.46-7.20 (m, 5H), 6.87-6.77 (m, 1H), 6.53-6.37 (m, 2H), 4.57 (s, 2H), 2.41 (s, 3H), 2.24 (s, 3H). LCMS: m/z 483.2 [M+H]$^+$, t$_R$=1.84 min.

Synthesis of (E)-3-(6-aminopyridin-3-yl)-N-((5-(2-(4,4-difluoropiperidine-1-carbonyl)cyclopropyl)-7-(trifluoromethyl)benzofuran-2-yl)methyl)acrylamide (695)
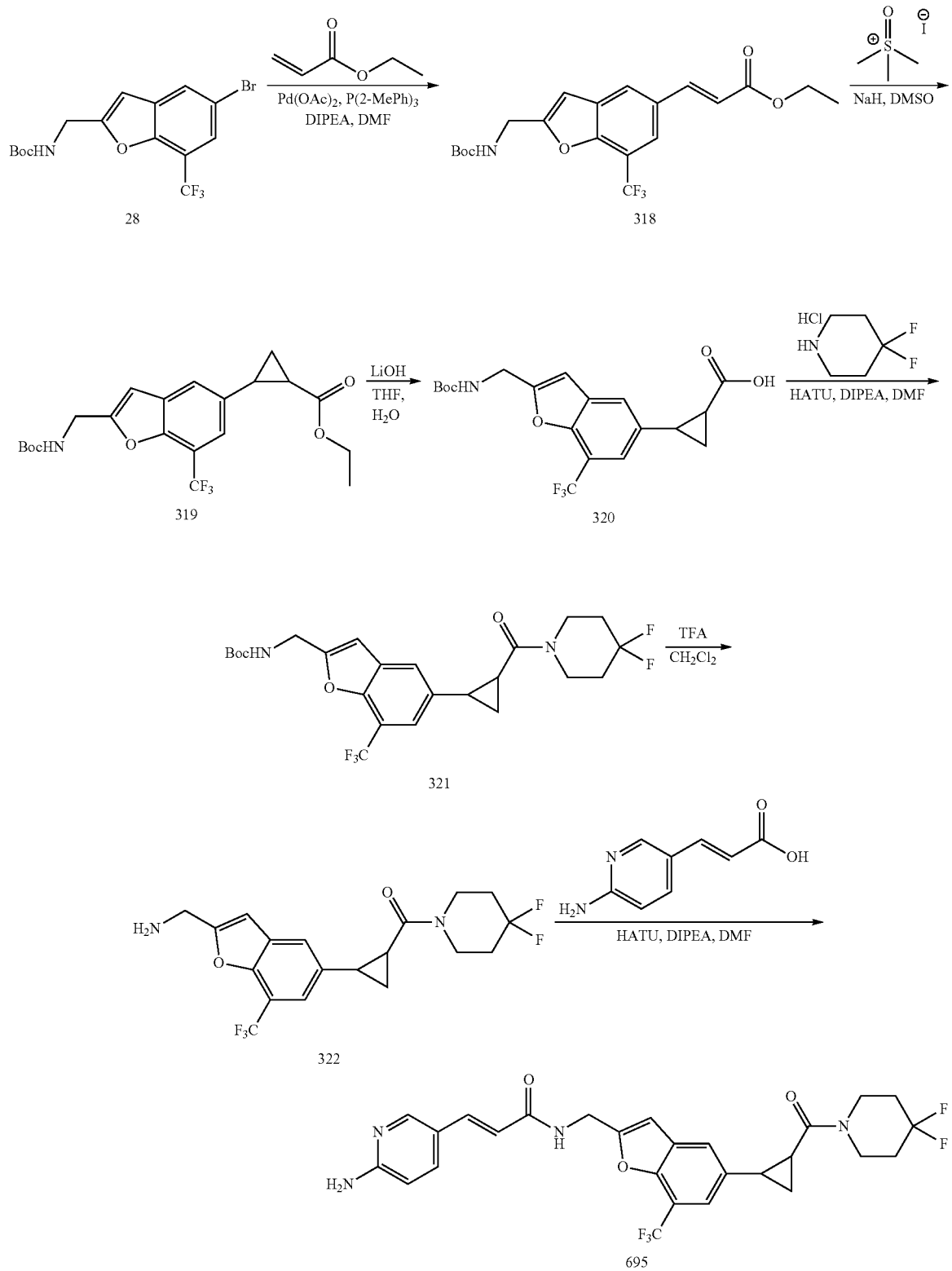

Synthesis of (E)-ethyl 3-(2-((tert-butoxycarbonylamino)methyl)-7-(trifluoromethyl)benzofuran-5-yl)acrylate (318)

A mixture of tert-butyl (5-bromo-7-(trifluoromethyl)benzofuran-2-yl)methylcarbamate (28; 2.0 g, 5.1 mmol), ethyl acrylate (1.02 g, 10.2 mmol), Pd(OAc)$_2$ (228 mg, 1.02 mmol), trio-tolylphosphine (620 mg, 2.04 mmol) and DIPEA (1.32 g, 10.2 mmol) in 30 mL of DMF was stirred at 100° C. under nitrogen atmosphere for 16 h. The mixture was extracted with EtOAc (50 mL×3). The combined organic layers were washed with brine, dried over anhydrous Na$_2$SO$_4$, and concentrated under reduced pressure to give the crude product, which was purified by silica gel chromatography (20% EtOAc/petroleum ether) to give 0.7 g of (E)-ethyl 3-(2-((tert-butoxycarbonylamino)methyl)-7-(trifluoromethyl)benzofuran-5-yl)acrylate (318) as a yellow liquid. Yield: 30%. LCMS: m/z 357.9 [M−55]$^+$, $t_R$=2.29 min.

Synthesis of ethyl 2-(2-((tert-butoxycarbonylamino)methyl)-7-(trifluoromethyl)benzofuran-5yl)cyclopropanecarboxylate (319)

Sodium hydride (20 mg, 0.5 mmol, 60% in mineral oil) was added to a stirred solution of trimethyl sulfoxonium iodide (198 mg, 0.86 mmol) in 10 mL of DMSO at 0° C. The mixture was stirred at 0° C. for one hour. (E)-ethyl 3-(2-((tert-butoxycarbonylamino)methyl)-7-(trifluoromethyl)benzofuran-5-yl)acrylate (318; 206 mg, 0.5 mmol) in 2 mL of DMSO and 2 mL of THF was added to the reaction mixture. After completion of the reaction, 1 N HCl was added and the reaction mixture extracted with ethyl acetate (20 mL×3). The combined organic layers were washed with brine, dried over anhydrous Na$_2$SO$_4$, and concentrated under reduced pressure to give the crude product, which was purified by silica gel chromatography (20% EtOAc/petroleum ether) to give 50 mg of ethyl 2-(2-((tert-butoxycarbonylamino)methyl)-7-(trifluoromethyl)benzofuran-5yl)cyclopropanecarboxylate (319) as a yellow liquid. Yield: 23%. LCMS: m/z 450.1 [M+Na]$^+$, $t_R$=1.71 min.

Synthesis of 2-(2-((tert-butoxycarbonylamino)methyl)-7-(trifluoromethyl)benzofuran-5-yl)cyclopropanecarboxylic acid (320)

Ethyl 2-(2-((tert-butoxycarbonylamino)methyl)-7-(trifluoromethyl)benzofuran-5yl)cyclopropanecarboxylate (319; 150 mg, 0.35 mmol) was dissolved in THF (5 mL). LiOH (30 mg, 0.7 mmol) and water (2 mL) were added to this mixture. The mixture was stirred at room temperature for 16 h, 1N HCl solution was added and adjusted to pH~6. The reaction mixture extracted with ethyl acetate (20 mL×3). The combined organic layers were washed with brine, dried over anhydrous Na$_2$SO$_4$, and concentrated under reduced pressure to give 110 mg of 2-(2-((tert-butoxycarbonylamino) methyl)-7-(trifluoromethyl)benzofuran-5-yl)cyclopropanecarboxylic acid (320) as a yellowish solid. Yield: 79%. LCMS: m/z 422.1 [M+Na]$^+$, $t_R$=1.66 min.

Synthesis of tert-butyl (5-(2-(4,4-difluoropiperidine-1-carbonyl)cyclopropyl)-7-(trifluoromethyl)benzofuran-2-yl)methylcarbamate (321)

2-(2-((tert-butoxycarbonylamino) methyl)-7-(trifluoromethyl)benzofuran-5-yl)cyclopropanecarboxylic acid (320; 40 mg, 0.1 mmol) and 4,4-difluoropiperidine hydrochloride (16 mg, 0.1 mmol) was dissolved in DMF (5 mL) at 0° C. HATU (38 mg, 0.1 mmol) was added to this reaction mixture followed by DIPEA (26 mg, 0.2 mmol). The reaction mixture was stirred for 4 h. The reaction mixture was transferred into water (20 mL) and extracted with ethyl acetate (20 mL×3). The combined organic layers were washed with brine, dried over anhydrous Na$_2$SO$_4$ and concentrated under reduced pressure to give 30 mg of tert-butyl (5-(2-(4,4-difluoropiperidine-1-carbonyl)cyclopropyl)-7-(trifluoromethyl)benzofuran-2-yl)methylcarbamate (321), which was used in next step directly without any purification. Yield: 60%. LCMS: m/z 503.1 [M+H]$^+$, $t_R$=1.77 min.

Synthesis of (2-(2-(aminomethyl)-7-(trifluoromethyl)benzofuran-5-yl)cyclopropyl)(4,4-difluoropiperidin-1-yl)methanone (322)

tert-Butyl (5-(2-(4,4-difluoropiperidine-1-carbonyl)cyclopropyl)-7-(trifluoromethyl)-benzofuran-2-yl)methylcarbamate (321; 50 mg, 0.1 mmol) was dissolved in CH$_2$Cl$_2$ (6 mL). TFA (1 mL) was added at 0° C. The reaction mixture was stirred at room temperature for 2 h, and concentrated under reduced pressure to give 40 mg of (2-(2-(aminomethyl)-7-(trifluoromethyl)benzofuran-5-yl)cyclopropyl)(4,4-difluoropiperidin-1-yl)methanone (322), which was used without further purification in the next step. Yield: 99%. LCMS: m/z 403.1 [M+H]$^+$; $t_R$=1.30 min.

Synthesis of (E)-3-(6-aminopyridin-3-yl)-N-((5-(2-(4,4-difluoropiperidine-1-carbonyl)cyclopropyl)-7-(trifluoromethyl)benzofuran-2-yl)methyl)acrylamide (695)

(2-(2-(Aminomethyl)-7-(trifluoromethyl)benzofuran-5-yl)cyclopropyl)(4,4-difluoropiperidin-1-yl)methanone (322; 40 mg, 0.1 mmol) and (E)-3-(6-aminopyridin-3-yl)acrylic acid (16.4 mg, 0.1 mmol) was dissolved in DMF (5 mL) at 0° C. HATU (38 mg, 0.1 mmol) was added to this reaction mixture at 0° C. followed by DIPEA (26 mg, 0.2 mmol). The reaction mixture was allowed to warm to room temperature and stirred for 4 h. The reaction mixture was transferred into water (20 mL) and extracted with ethyl acetate (20 mL×3). The combined organic layers were washed with brine, dried over anhydrous Na$_2$SO$_4$ and concentrated under reduced pressure to give crude product which was purified by Prep-HPLC to afford 30 mg of (E)-3-(6-aminopyridin-3-yl)-N-((5-(2-(4,4-difluoropiperidine-1-carbonyl)cyclopropyl)-7-(trifluoromethyl)benzofuran-2-yl)methyl) acrylamide (695). Yield: 55%. $^1$H NMR (400 MHz, CD$_3$OD) δ 8.10 (d, J=9 Hz, 1H), 7.94 (s, 1H), 7.54 (s, 1H), 7.37 (d, J=16 Hz, 1H), 7.28 (s, 1H), 6.95 (d, J=9 Hz, 1H), 6.70 (s, 1H), 6.53 (d, J=16 Hz, 1H), 4.57 (s, 2H), 3.78-3.57 (m, 4H), 2.51-2.44 (m, 1H), 2.29-2.22 (m, 1H), 1.98-1.80 (m, 4H), 1.52-1.45 (m, 1H), 1.36-1.28 (m, 1H). LCMS: m/z 549.1 [M+H]$^+$, $t_R$=1.38 min.

Synthesis of (E)-3-(6-aminopyridin-3-yl)-N-((5-(4-(4,4-difluoropiperidine-1-carbonyl)phenyl)-7-(3-fluoropyridin-4-yl)benzofuran-2-yl)methyl)acrylamide (696)
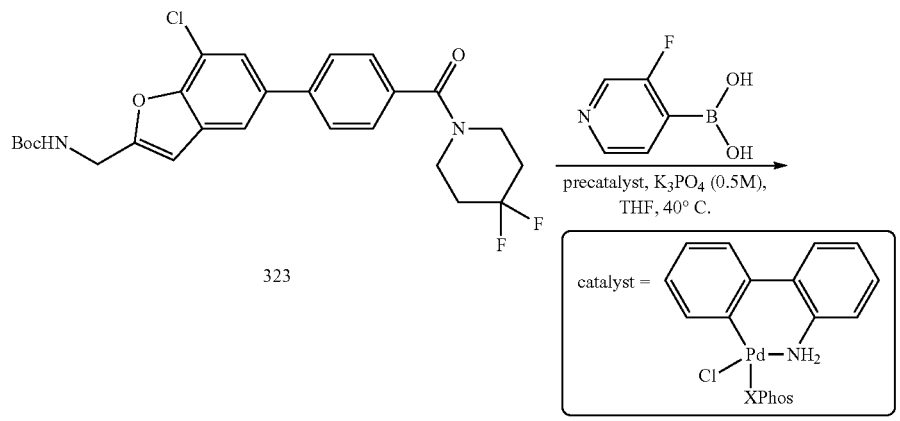
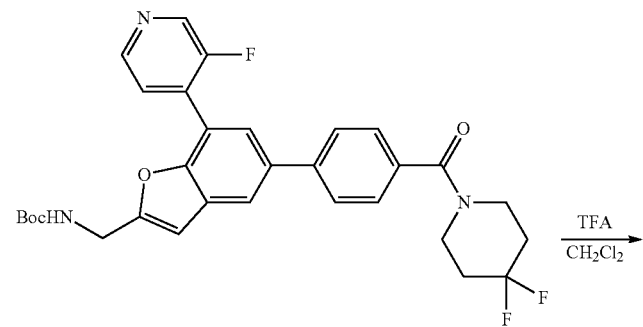
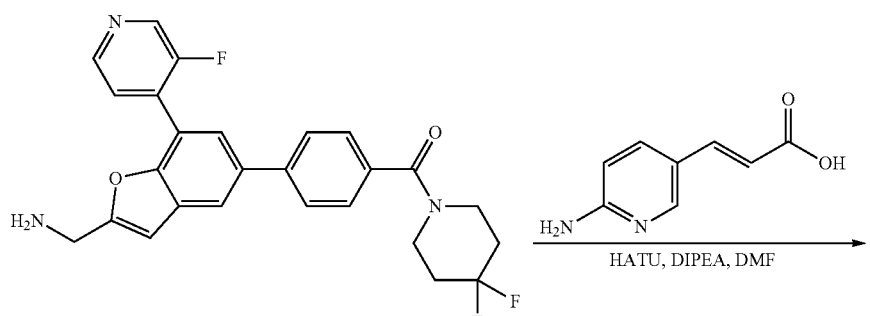
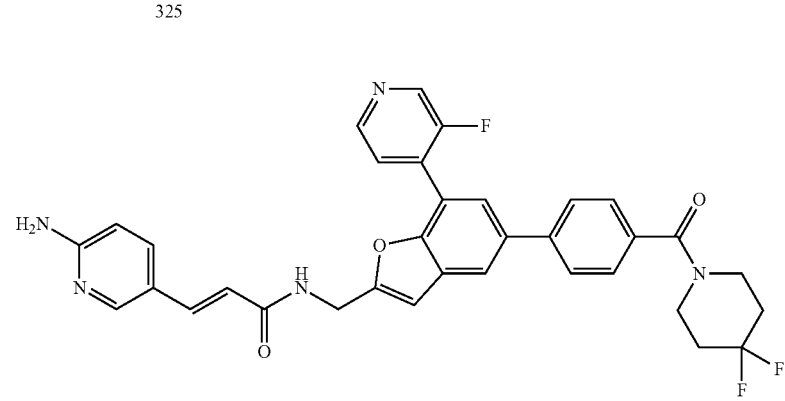

Synthesis of tert-butyl (5-(4-(4,4-difluoropiperidine-1-carbonyl)phenyl)-7-(3-fluoropyridin-4-yl)benzofuran-2-yl)methylcarbamate (324)

tert-Butyl (7-chloro-5-(4-(4,4-difluoropiperidine-1-carbonyl)phenyl)benzofuran-2-yl)methylcarbamate (323; 200 mg, 0.4 mmol), 3-fluoropyridin-4-ylboronic acid (85 mg, 0.6 mmol), catalyst (31 mg, 0.04 mmol) and $K_3PO_4$ (2 mL, 1 mmol, 0.5 M) were added in THF (4 mL) and degassed. The reaction mixture was heated at 40° C. for 2 h. The reaction mixture was concentrated under reduced pressure to give the crude product which was purified by silica gel chromatography (20% EtOAc/petroleum ether) to give tert-butyl (5-(4-(4,4-difluoropiperidine-1-carbonyl)phenyl)-7-(3-fluoropyridin-4-yl)benzofuran-2-yl)methylcarbamate (324) (200 mg, 88% yield). LCMS: m/z 566.2 [M+H]$^+$; $t_R$=1.97 min.

Synthesis of (4-(2-(aminomethyl)-7-(3-fluoropyridin-4-yl)benzofuran-5-yl)phenyl)(4,4-difluoropiperidin-1-yl)methanone (325)

tert-Butyl (5-(4-(4,4-difluoropiperidine-1-carbonyl)phenyl)-7-(3-fluoropyridin-4-yl)benzofuran-2-yl)methylcarbamate (324; 200 mg, 0.35 mmol) was dissolved in $CH_2Cl_2$ (5 mL). TFA (1 mL) was added dropwise at 0° C. (ice bath). The reaction mixture was allowed to warm to room temperature and stirred for 2 h. The reaction mixture was concentrated under reduced pressure to give (4-(2-(aminomethyl)-7-(3-fluoropyridin-4-yl)benzofuran-5-yl)phenyl)(4,4-difluoropiperidin-1-yl)methanone (325), which was used without further purification in the next step (200 mg, 100% yield). LCMS: m/z 466.1 [M+H]$^+$; $t_R$=1.74 min.

Synthesis of (E)-3-(6-aminopyridin-3-yl)-N-((5-(4-(4,4-difluoropiperidine-1-carbonyl)phenyl)-7-(3-fluoropyridin-4-yl)benzofuran-2-yl)methyl)acrylamide (696)

(4-(2-(Aminomethyl)-7-(3-fluoropyridin-4-yl)benzofuran-5-yl)phenyl)(4,4-difluoropiperidin-1-yl)methanone (325; 200 mg, 0.34 mmol) was dissolved in DMF (2 mL). (E)-3-(6-aminopyridin-3-yl)acrylic acid (85 mg, 0.52 mmol), HATU (260 mg, 0.68 mmol), and DIPEA (220 mg, 1.7 mmol) were added at room temperature. The reaction mixture was stirred at room temperature for 1 h. The reaction mixture was purified by Pre-HPLC to give (E)-3-(6-aminopyridin-3-yl)-N-((5-(4-(4,4-difluoropiperidine-1-carbonyl)phenyl)-7-(3-fluoropyridin-4-yl)benzofuran-2-yl)methyl)acrylamide (696) (75 mg, 36% yield) as white solid. $^1$H NMR (400 MHz, DMSO-$d_6$) δ 8.84-8.74 (m, 2H), 8.61 (d, J=5 Hz, 1H), 8.37-8.01 (m, 5H), 7.91-7.73 (m, 4H), 7.60-7.54 (m, 2H), 7.43 (d, J=16 Hz, 1H), 6.99 (d, J=9 Hz, 1H), 6.91 (s, 1H), 6.59 (d, J=16 Hz, 1H), 4.58 (d, J=5 Hz, 2H), 3.78-3.47 (m, 4H), 2.15-1.97 (m, 4H). LCMS: m/z 612.3 [M+H]$^+$; $t_R$=1.38 min.

Synthesis of (E)-3-(6-aminopyridin-3-yl)-N-((5-(4-(4,4-difluoropiperidine-1-carbonyl)phenyl)-7-(2,4,6-trifluorophenyl)benzofuran-2-yl)methyl)acrylamide (697)

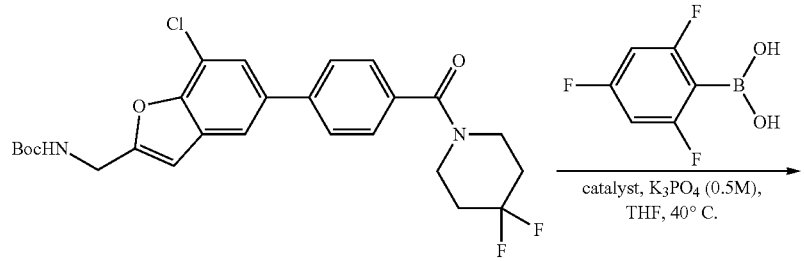

323

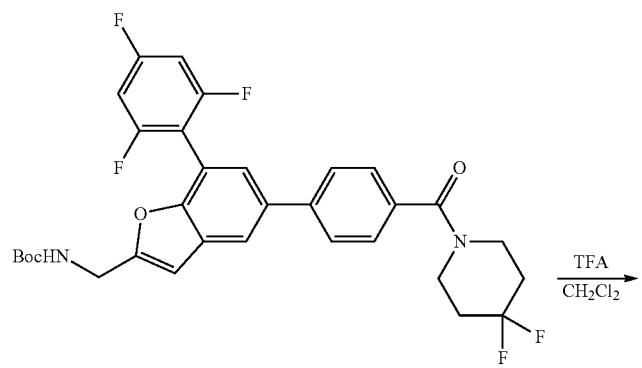

326

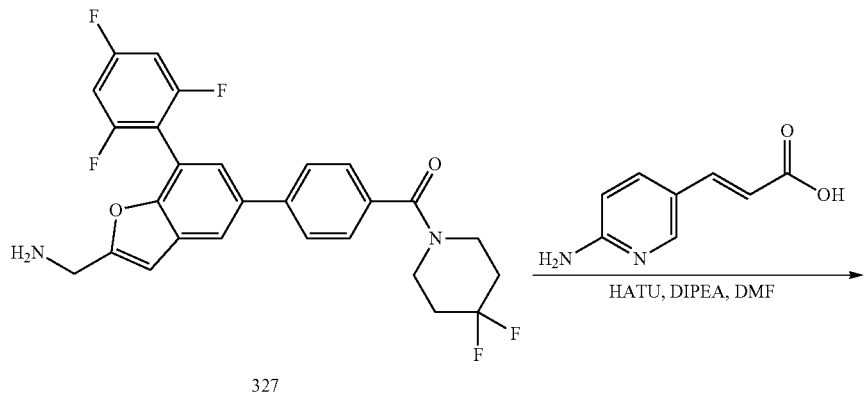

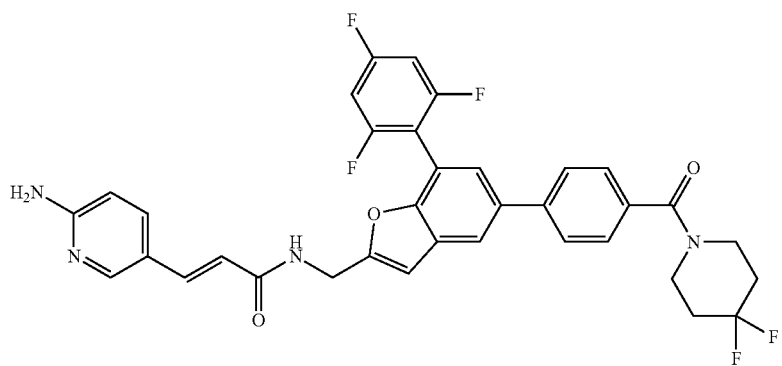

(E)-3-(6-aminopyridin-3-yl)-N-((5-(4-(4,4-difluoropiperidine-1-carbonyl)phenyl)-7-(2,4,6-trifluorophenyl)benzofuran-2-yl)methyl)acrylamide (697) was synthesized using the indicated reagents in a similar fashion as example (696). $^1$H NMR (400 MHz, DMSO-d$_6$) δ 8.62-8.53 (m, 1H), 8.10-8.01 (m, 2H), 7.80 (d, J=8 Hz, 2H), 7.69-7.52 (m, 4H), 7.43 (t, J=9 Hz, 2H), 7.33 (d, J=16 Hz, 1H), 6.86 (s, 1H), 6.50-6.35 (m, 4H), 4.52 (d, J=6 Hz, 2H), 3.77-3.45 (m, 4H), 2.15-1.97 (m, 4H). LCMS: m/z 647.3 [M+H]$^+$; t$_R$=1.86 min.

Synthesis of (E)-3-(6-aminopyridin-3-yl)-N-((7-(5-chloro-2,4-difluorophenyl)-5-(4-(4,4-difluoropiperidine-1-carbonyl)phenyl)benzofuran-2-yl)methyl)acrylamide (698)

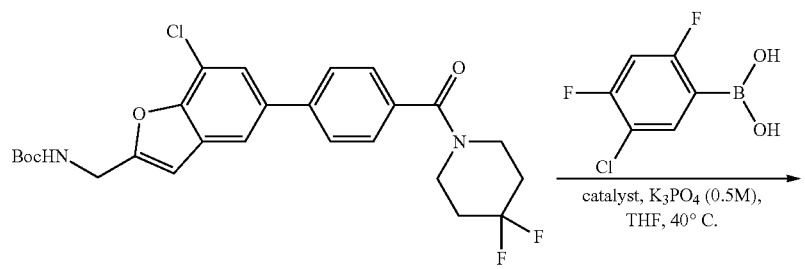

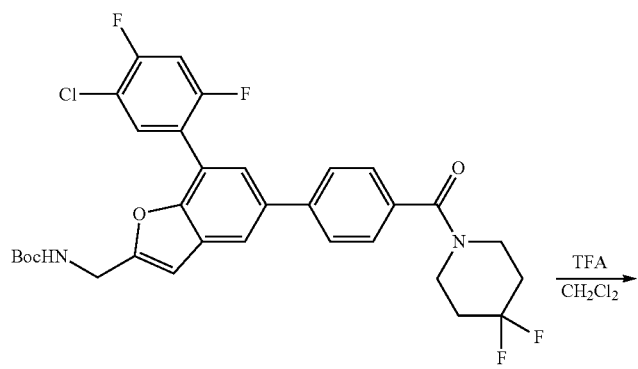
328
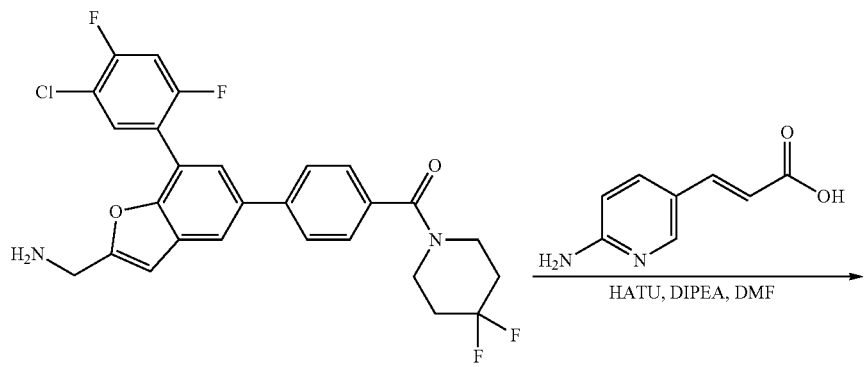
329
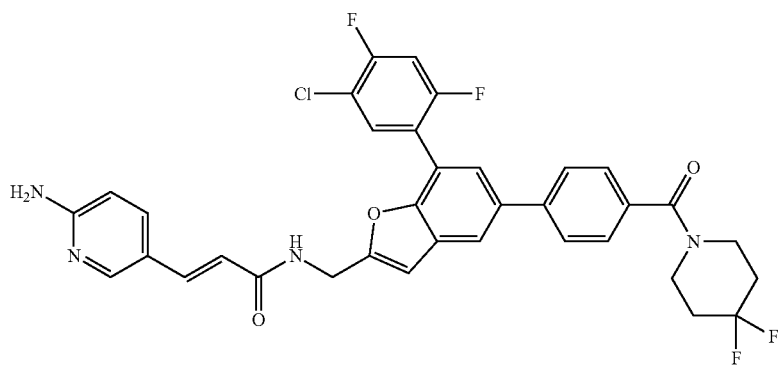
698
(E)-3-(6-aminopyridin-3-yl)-N-((7-(5-chloro-2,4-difluorophenyl)-5-(4-(4,4-difluoropiperidine-1-carbonyl)phenyl)benzofuran-2-yl)methyl)acrylamide (698) was synthesized using the indicated reagents in a similar fashion as example (696). $^1$H NMR (400 MHz, DMSO-d$_6$) δ 8.58 (t, J=5 Hz, 1H), 8.10-7.98 (m, 3H), 7.88-7.81 (m, 2H), 7.76 (t, J=9 Hz, 1H), 7.68 (s, 1H), 7.63-7.52 (m, 3H), 7.34 (d, J=16 Hz, 1H), 6.86 (s, 1H), 6.50-6.36 (m, 4H), 4.54 (d, J=5 Hz, 2H), 3.75-3.46 (m, 4H), 2.14-1.97 (m, 4H). LCMS: m/z 663.2 [M+H]$^+$; t$_R$=1.91 min.

Synthesis of (E)-3-(6-aminopyridin-3-yl)-N-((5'-(4-(4,4-difluoropiperidine-1-carbonyl)phenyl)-2,7'-bibenzofuran-2'-yl)methyl)acrylamide (699)
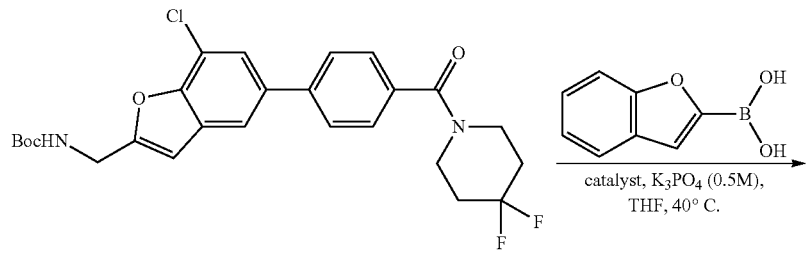
323
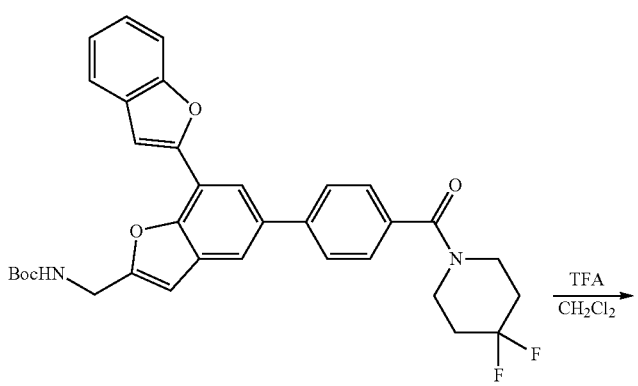
330
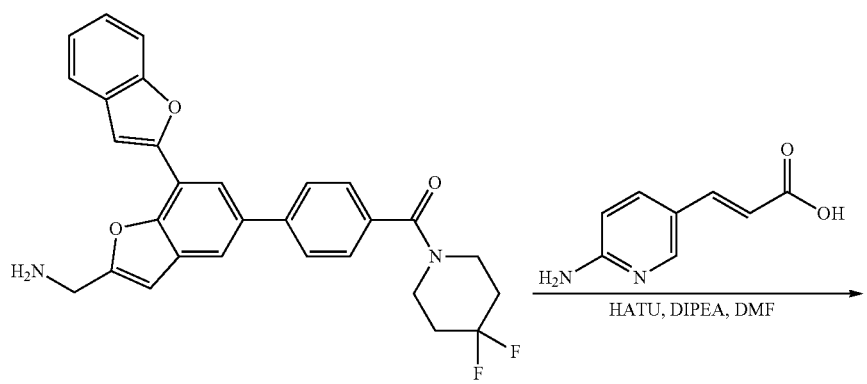
331
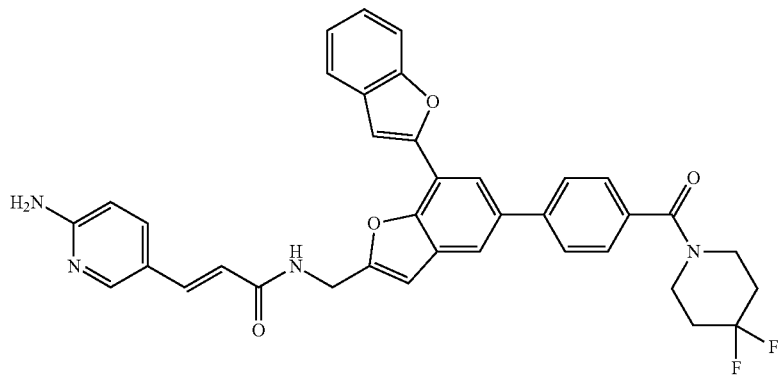
699

(E)-3-(6-aminopyridin-3-yl)-N-((5'-(4-(4,4-difluoropiperidine-1-carbonyl)phenyl)-2,7'-bibenzofuran-2'-yl)methyl)acrylamide (699) was synthesized using the indicated reagents in a similar fashion as example (696). $^1$H NMR (400 MHz, CD$_3$OD) δ 8.20-8.16 (m, 1H), 8.09 (s, 1H), 7.91-7.84 (m, 3H), 7.81-7.75 (m, 1H), 7.74-7.68 (m, 2H), 7.66-7.59 (m, 3H), 7.56 (d, J=16 Hz, 1H), 7.39-7.26 (m, 2H), 6.91 (s, 1H), 6.62 (d, J=9 Hz, 1H), 6.54 (d, J=16 Hz, 1H), 4.82 (s, 2H), 3.96-3.64 (m, 4H), 2.21-2.01 (m, 4H). LCMS: m/z 633.3 [M+H]$^+$; $t_R$=1.94 min.

Synthesis of (E)-3-(6-aminopyridin-3-yl)-N-((7-(3,5-dichlorophenyl)-5-(4-(4,4-difluoropiperidine-1-carbonyl)phenyl)benzofuran-2-yl)methyl)acrylamide (700)

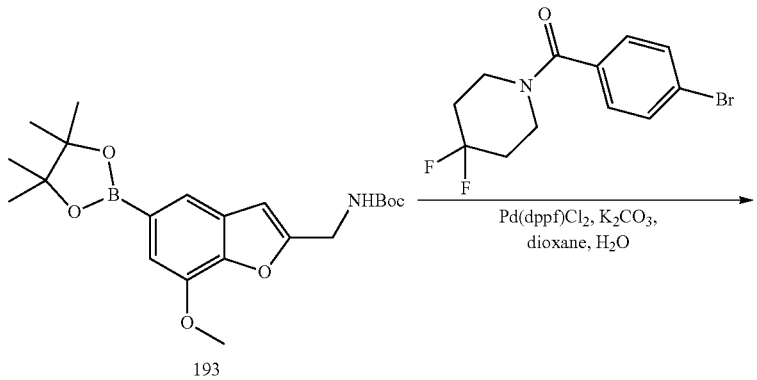

193

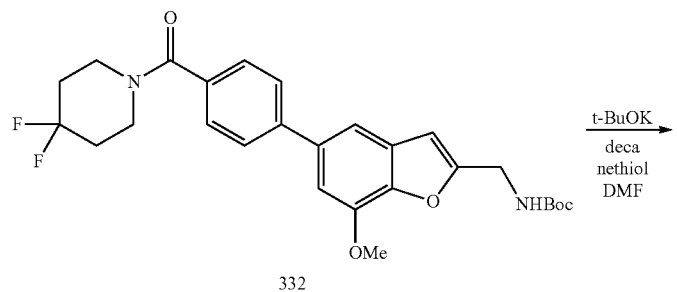

332

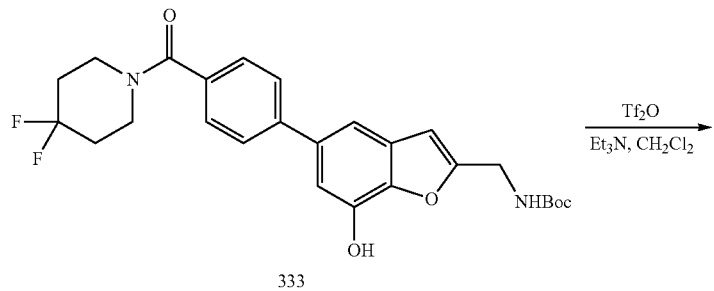

333

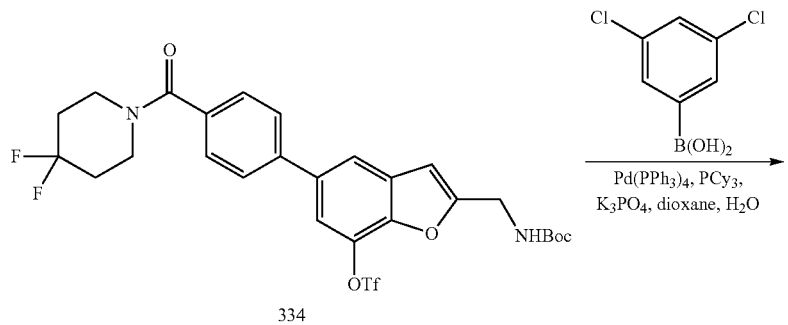

334

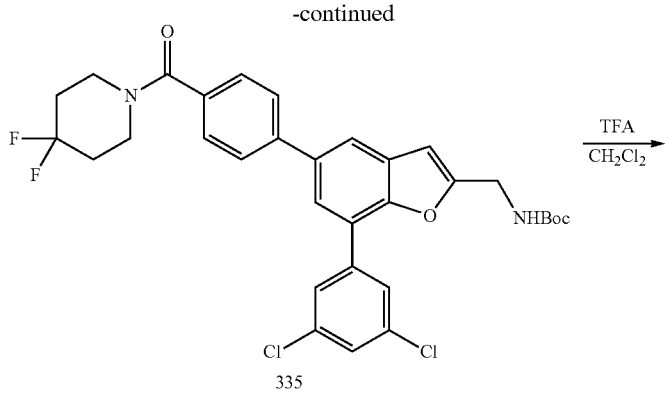

335

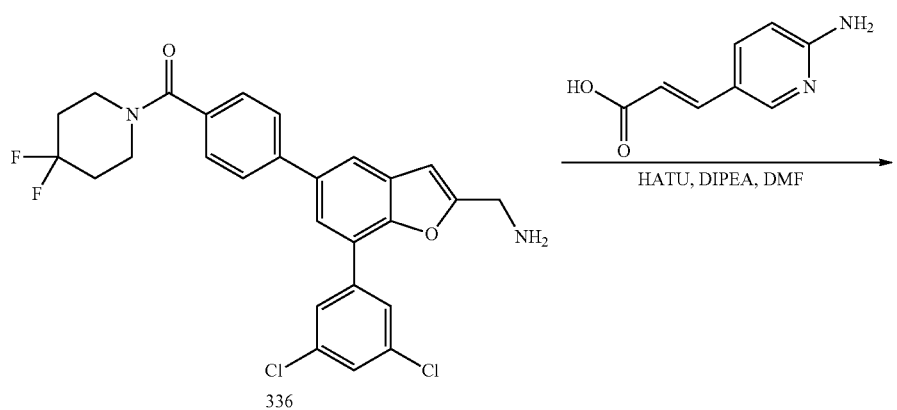

336

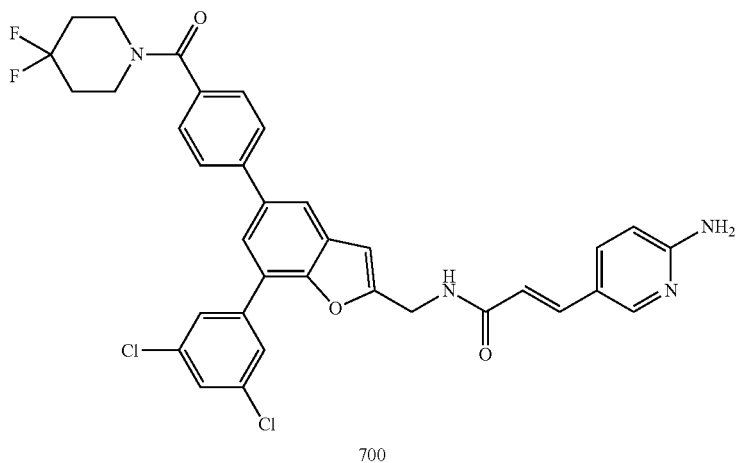

700

Synthesis of tert-butyl (5-(4-(4,4-difluoropiperidine-1-carbonyl)phenyl)-7-methoxybenzofuran-2-yl)methylcarbamate (332)

A mixture of (4-bromophenyl)(4,4-difluoropiperidin-1-yl)methanone (4.1 g, 14.6 mmol), tert-butyl (7-methoxy-5-(4,4,5,5-tetramethyl-1,3,2-dioxaborolan-2-yl)benzofuran-2-yl)methylcarbamate (193; 5 g, 12.4 mmol), Pd(dppf)Cl$_2$ (0.91 g, 1.2 mmol) and K$_2$CO$_3$ (3.4 g, 24.8 mmol) in 50 mL of dioxane and 5 mL of H$_2$O was stirred at 90° C. for 4 h. After cooling down to room temperature, the reaction mixture was transferred into water (50 mL), extracted with ethyl acetate (50 mL×3). The combined organic layers were washed with brine, dried over anhydrous Na$_2$SO$_4$, and concentrated under reduced pressure to give the crude product, which was purified by silica gel chromatography (0-50% ethyl acetate/petroleum ether) to give 1.75 g of tert-butyl (5-(4-(4,4-difluoropiperidine-1-carbonyl)phenyl)-7-methoxybenzofuran-2-yl)methylcarbamate (332) (30% yield). LCMS: m/z 501.1 [M+H]$^+$; t$_R$=1.72 min.

Synthesis of tert-butyl (5-(4-(4,4-difluoropiperidine-1-carbonyl)phenyl)-7-hydroxybenzofuran-2-yl)methylcarbamate (333)

tert-Butyl (5-(4-(4,4-difluoropiperidine-1-carbonyl)phenyl)-7-methoxybenzofuran-2-yl)methylcarbamate (332; 1 g, 2 mmol) was dissolved in 20 mL of DMF. Decanethiol (521 mg, 3 mmol) and t-BuOK (336 mg, 3 mmol) were added to this mixture. The mixture was heated to 110° C. and stirred for 4 h. After cooling to room temperature, the mixture was poured into 20 mL of H$_2$O, and extracted with ethyl acetate (30 mL×3). The combined organic layers were washed with brine, dried over anhydrous Na$_2$SO$_4$, and concentrated under reduced pressure to give the crude product, which was purified by silica gel chromatography (10-20% ethyl acetate/ petroleum ether) to afford 500 mg of tert-butyl (5-(4-(4,4-difluoropiperidine-1-carbonyl)phenyl)-7-hydroxybenzofuran-2-yl)methylcarbamate (333) (31% yield). LCMS: m/z 487.1 [M+H]$^+$; t$_R$=1.63 min.

Synthesis of 2-((tert-butoxycarbonylamino)methyl)-5-(4-(4,4-difluoropiperidine-1-carbonyl)phenyl)benzofuran-7-yl trifluoromethanesulfonate (334)

tert-Butyl (5-(4-(4,4-difluoropiperidine-1-carbonyl)phenyl)-7-hydroxybenzofuran-2-yl)methylcarbamate (333; 500 mg, 1.03 mmol) was dissolved in 20 mL of CH$_2$Cl$_2$. Et$_3$N (312 mg, 3.1 mmol) and Tf$_2$O (348 mg, 1.23 mmol) were added at 0° C. The mixture was stirred at room temperature for 1 h, diluted with 20 mL of H$_2$O, extracted with CH$_2$Cl$_2$ (20 mL×3). The combined organic phases were washed with brine (10 mL), dried over Na$_2$SO$_4$, concentrated and purified by silica gel chromatography (20% ethyl acetate/petroleum ether) to yield 210 mg of 2-((tert-butoxycarbonylamino)methyl)-5-(4-(4,4-difluoropiperidine-1-carbonyl)phenyl)benzofuran-7-yl trifluoromethanesulfonate (334). Yield: 40%. LCMS: m/z 619.1 [M+H]$^+$; t$_R$=1.80 min.

Synthesis of tert-butyl (7-(3,5-dichlorophenyl)-5-(4-(4,4-difluoropiperidine-1-carbonyl)phenyl)benzofuran-2-yl)methylcarbamate (335)

2-((tert-butoxycarbonylamino)methyl)-5-(4-(4,4-difluoropiperidine-1-carbonyl)phenyl)benzofuran-7-yl trifluoromethanesulfonate (334; 40 mg, 0.07 mmol), 3,5-dichlorophenylboronic acid (37 mg, 0.19 mmol), Pd(PPh$_3$)$_4$ (8 mg, 0.007 mmol), tricyclohexylphosphine (5 mg, 0.02 mmol) and K$_3$PO$_4$ (28 mg, 0.13 mmol) were added to a mixture of dioxane (2 mL) and water (0.2 mL) and degassed. The reaction mixture was heated under microwave irradiation at 140° C. for 2 h. The reaction mixture was cooled down to room temperature, poured into 5 mL of water, extracted with EtOAc (10 mL×3). The combined organic layers were washed with brine, dried over anhydrous Na$_2$SO$_4$, concentrated under reduced pressure to give the crude product which was purified by Prep-TLC (50% EtOAc/petroleum ether) to give tert-butyl (7-(3,5-dichlorophenyl)-5-(4-(4,4-difluoropiperidine-1-carbonyl)phenyl)benzofuran-2-yl)methylcarbamate (335) as white solid (30 mg, 75% yield). LCMS: m/z 615.1 [M+H]$^+$; t$_R$=1.93 min.

Synthesis of (4-(2-(aminomethyl)-7-(3,5-dichlorophenyl)benzofuran-5-yl)phenyl)(4,4-difluoropiperidin-1-yl)methanone (336)

tert-Butyl (7-(3,5-dichlorophenyl)-5-(4-(4,4-difluoropiperidine-1-carbonyl)phenyl)benzofuran-2-yl)methylcarbamate (335; 30 mg, 0.05 mmol) was dissolved in CH$_2$Cl$_2$ (5 mL). TFA (1 mL) was added dropwise at 0° C. The reaction mixture was allowed to warm to room temperature and stirred for 1 h. The reaction mixture was concentrated under reduced pressure to give (4-(2-(aminomethyl)-7-(3,5-dichlorophenyl)benzofuran-5-yl)phenyl)(4,4-difluoropiperidin-1-yl)methanone (336), which was used without further purification in the next step (25 mg, 100% yield). LCMS: m/z 515.0 [M+H]$^+$; t$_R$=1.50 min.

Synthesis of (E)-3-(6-aminopyridin-3-yl)-N-((7-(3,5-dichlorophenyl)-5-(4-(4,4-difluoropiperidine-1-carbonyl)phenyl)benzofuran-2-yl)methyl)acrylamide (700)

(4-(2-(Aminomethyl)-7-(3,5-dichlorophenyl)benzofuran-5-yl)phenyl)(4,4-difluoropiperidin-1-yl)methanone (336; 25 mg, 0.05 mmol) was dissolved in DMF (3 mL). (E)-3-(6-aminopyridin-3-yl)acrylic acid (10 mg, 0.06 mmol), HATU (37 mg, 0.1 mmol), and DIPEA (13 mg, 0.1 mmol) were added at room temperature. The reaction mixture was stirred at room temperature for 1 h. The crude mixture was purified by Pre-HPLC to give (E)-3-(6-aminopyridin-3-yl)-N-((7-(3,5-dichlorophenyl)-5-(4-(4,4-difluoropiperidine-1-carbonyl)phenyl)benzofuran-2-yl)methyl)acrylamide (700) (3 mg, 10% yield) as white solid. $^1$H NMR (400 MHz, CD$_3$OD) δ 8.11 (d, J=9 Hz, 1H), 7.94-7.83 (m, 6H), 7.75 (s, 1H), 7.60-7.50 (m, 5H), 6.90 (s, 1H), 6.61 (d, J=16 Hz, 1H), 4.74 (s, 2H), 3.99-3.60 (m, 4H), 2.18-2.01 (m, 4H). LCMS: m/z 661.0 [M+H]$^+$; t$_R$=1.57 min.

Synthesis of (E)-3-(6-aminopyridin-3-yl)-N-((5-(4-(4-fluorophenoxy)phenyl)-7-(4-fluorophenyl)benzofuran-2-yl)methyl)acrylamide (701)

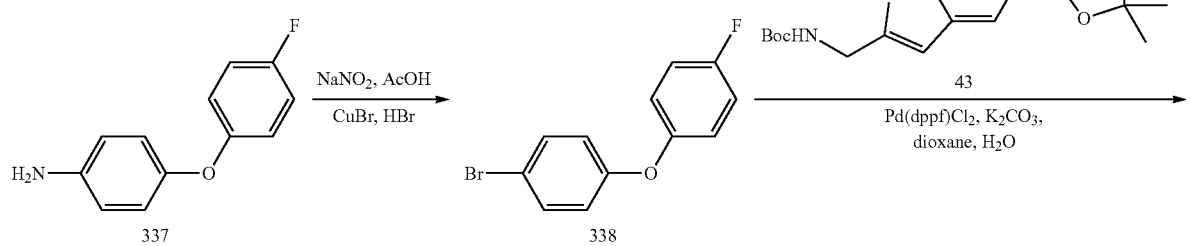

-continued

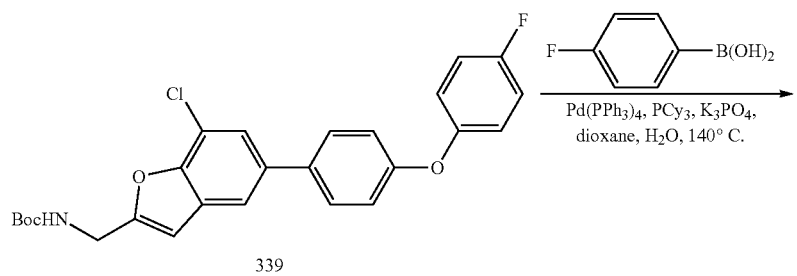

339

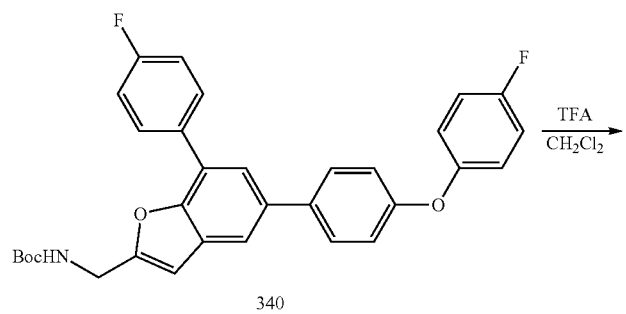

340

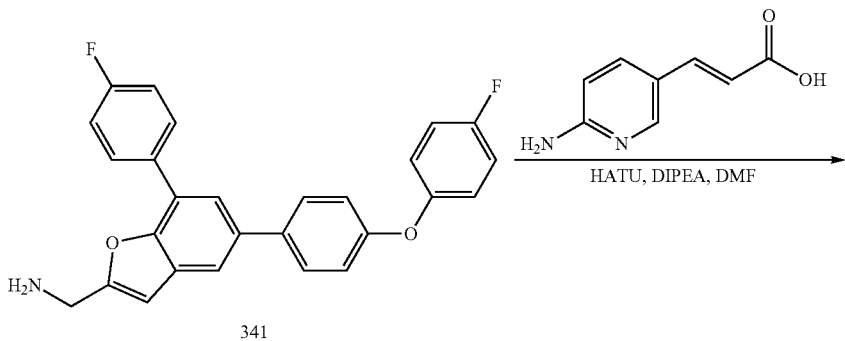

341

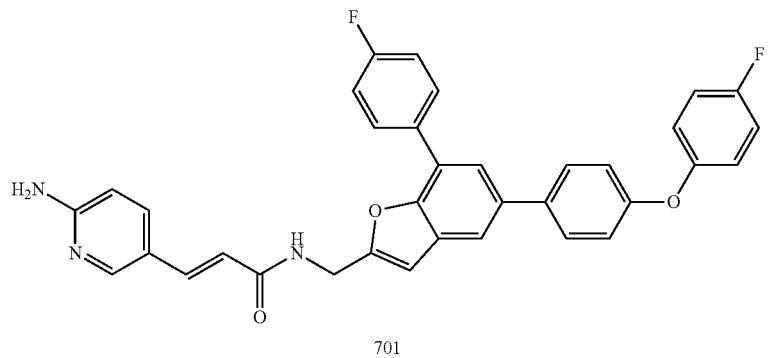

701

Synthesis of 1-bromo-4-(4-fluorophenoxy)benzene (338)

4-(4-Fluorophenoxy)aniline (337; 200 mg, 1 mmol) was dissolved in 10 mL of AcOH, the mixture was cooled to 0° C. and degassed. NaNO$_2$ (76 mg, 1.1 mmol) was added. After stirring for 0.5 h, CuBr (240 mg, 1.5 mmol) and HBr aqueous solution (5 mL) was added. The mixture was stirred at 70° C. for 3 h. After cooling to room temperature, the mixture was diluted with 20 mL of H$_2$O, extracted with EtOAc (20 mL×3). The combined organic layers were washed with brine (10 mL), dried over Na$_2$SO$_4$, concentrated and purified by silica gel chromatography to give 200 mg of 1-bromo-4-(4-fluorophenoxy)benzene (338) as white solid. Yield: 80%. LCMS: $t_R$=1.86 min.

Synthesis of tert-butyl (7-chloro-5-(4-(4-fluorophenoxy)phenyl)benzofuran-2-yl)methylcarbamate (339)

A mixture of 1-bromo-4-(4-fluorophenoxy)benzene (338; 300 mg, 1.12 mmol), tert-butyl (7-chloro-5-(4,4,5,5-tetramethyl-1,3,2-dioxaborolan-2-yl)benzofuran-2-yl)methylcarbamate (456 mg, 1.12 mmol), Pd(dppf)Cl$_2$ (82 mg, 0.12 mmol) and K$_2$CO$_3$ (309 mg, 2.24 mmol) in 10 mL of dioxane and 1 mL of H$_2$O was stirred at 100° C. under nitrogen atmosphere for 2 h. The mixture was extracted with EtOAc (20 mL×3). The combined organic layers were washed with brine, dried over anhydrous Na$_2$SO$_4$, and the solvents were removed under reduced pressure to give the crude product, which was purified by silica gel chromatography (40% EtOAc/petroleum ether) to give 400 mg of tert-butyl (7-chloro-5-(4-(4-fluorophenoxy)phenyl)benzofuran-2-yl)methylcarbamate (339) as a white solid. Yield (80%). LCMS: m/z 490.1 [M+Na]$^+$, $t_R$=2.3 min.

Synthesis of tert-butyl (5-(4-(4-fluorophenoxy)phenyl)-7-(4-fluorophenyl)benzofuran-2-yl)methylcarbamate (340)

tert-Butyl (7-chloro-5-(4-(4-fluorophenoxy)phenyl)benzofuran-2-yl)methylcarbamate (339; 150 mg, 0.32 mmol), 4-fluorophenylboronic acid (90 mg, 0.64 mmol), Pd(PPh$_3$)$_4$ (70 mg, 0.06 mmol), tricyclohexylphosphine (27 mg, 0.1 mmol) and K$_3$PO$_4$ (136 mg, 0.64 mmol) were added to a mixture of dioxane (5 mL) and water (0.5 mL) and degassed. The reaction mixture was heated under microwave irradiation at 140° C. for 2 h. The reaction mixture was cooled down to room temperature, poured into 5 mL of water, extracted with EtOAc (10 mL×3). The combined organic layers were washed with brine, dried over anhydrous Na$_2$SO$_4$, concentrated under reduced pressure to give the crude product which was purified by silica gel chromatography (17-50% EtOAc/petroleum ether) to give tert-butyl (5-(4-(4-fluorophenoxy)phenyl)-7-(4-fluorophenyl)benzofuran-2-yl)methylcarbamate (340) as white solid (130 mg, 80% yield). LCMS: m/z 550.1 [M+H]$^+$; $t_R$=1.99 min.

Synthesis of (5-(4-(4-fluorophenoxy)phenyl)-7-(4-fluorophenyl)benzofuran-2-yl)methanamine (341)

tert-Butyl (5-(4-(4-fluorophenoxy)phenyl)-7-(4-fluorophenyl)benzofuran-2-yl)methylcarbamate (340; 100 mg, 0.19 mmol) was dissolved in CH$_2$Cl$_2$ (5 mL). TFA (2 mL) was added dropwise at 0° C. The reaction mixture was allowed to warm to room temperature and stirred for 4 h. The reaction mixture was concentrated under reduced pressure to give (5-(4-(4-fluorophenoxy)phenyl)-7-(4-fluorophenyl)benzofuran-2-yl)methanamine (341), which was used without further purification in the next step (80 mg, 100% yield). LCMS: m/z 411.0 [M-NH$_2$]$^+$; $t_R$=1.56 min.

Synthesis of (E)-3-(6-aminopyridin-3-yl)-N-((5-(4-(4-fluorophenoxy)phenyl)-7-(4-fluorophenyl)benzofuran-2-yl)methyl)acrylamide (701)

(5-(4-(4-Fluorophenoxy)phenyl)-7-(4-fluorophenyl)benzofuran-2-yl)methanamine (341; 80 mg, 0.19 mmol) was dissolved in DMF (3 mL). (E)-3-(6-aminopyridin-3-yl)acrylic acid (46 mg, 0.28 mmol), HATU (108 mg, 0.28 mmol), and DIPEA (49 mg, 3.8 mmol) were added at room temperature. The reaction mixture was stirred at room temperature for 1 h. The crude mixture was purified by Pre-HPLC without workup to give (E)-3-(6-aminopyridin-3-yl)-N-((5-(4-(4-fluorophenoxy)phenyl)-7-(4-fluorophenyl)benzofuran-2-yl)methyl)acrylamide (701) (5 mg, 5% yield) as yellow solid. $^1$H NMR (400 MHz, CD$_3$OD) δ 8.06 (s, 1H), 8.01-7.89 (m, 2H), 7.80-7.62 (m, 5H), 7.50 (d, J=16.0 Hz, 1H), 7.30-7.02 (m, 8H), 6.83 (s, 1H), 6.61 (d, J=9 Hz, 1H), 6.48 (d, J=16 Hz, 1H), 4.70 (s, 2H). LCMS: m/z 574.2 [M+H]$^+$; $t_R$=2.18 min.

Synthesis of (E)-3-(6-aminopyridin-3-yl)-N-((7-(4-(4,4-difluoropiperidine-1-carbonyl)phenyl)-5-(trifluoromethyl)benzofuran-2-yl)methyl)acrylamide (702)

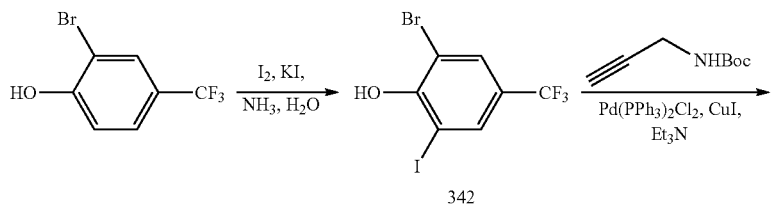

342

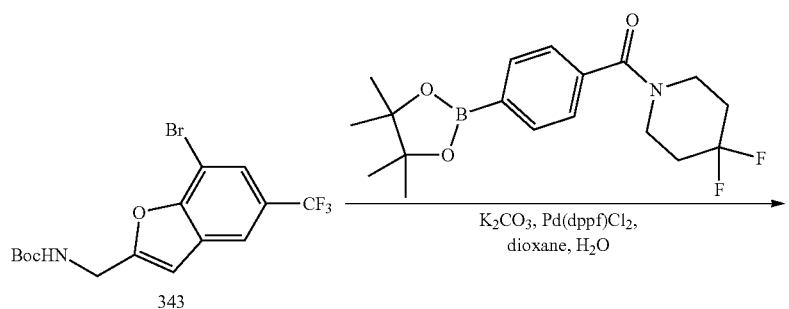

343

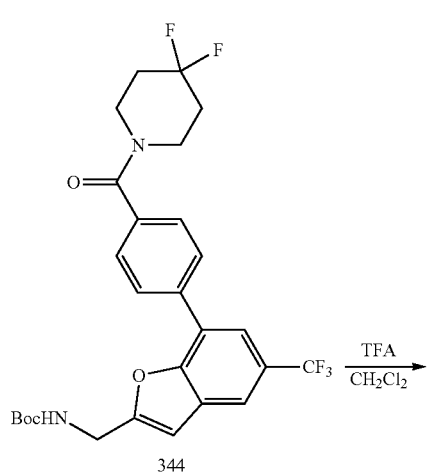
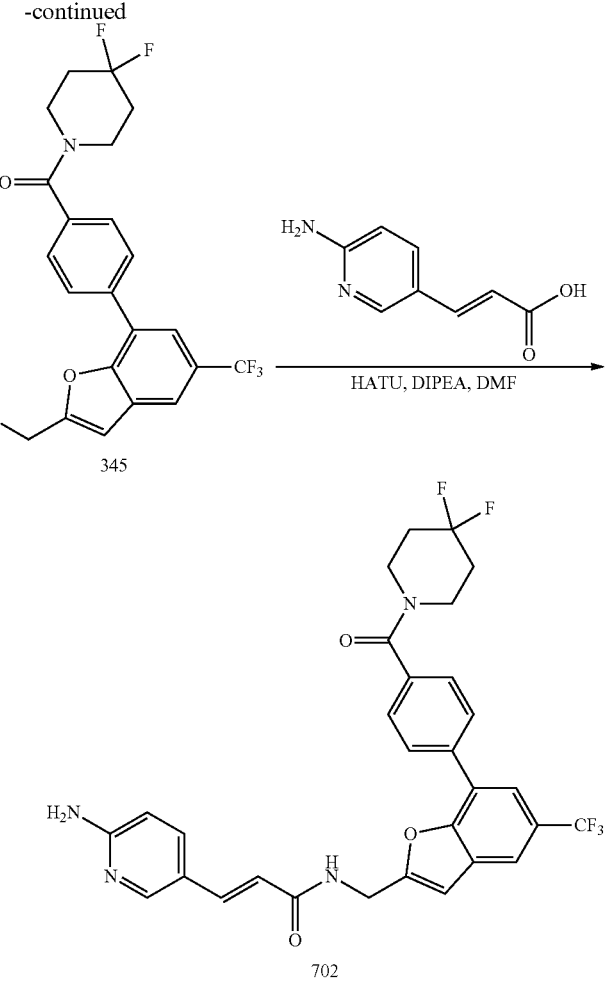

Synthesis of 2-bromo-6-iodo-4-(trifluoromethyl)phenol (342)

2-Bromo-4-(trifluoromethyl)phenol (3 g, 12.4 mmol) was dissolved in 100 mL of NH$_4$OH. A solution of KI (6 g, 37.2 mmol) and I$_2$ (3.2 g, 12.4 mmol) in 200 mL of H$_2$O was added to this mixture and the reaction mixture was stirred at 20° C. for 6 h. The mixture was cooled to 0° C., HCl (conc.) was added to the reaction mixture till pH=7. The mixture was extracted with EtOAc (300 mL×2). The combined organic layers were washed with sat. sodium bisulfite and brine, dried over anhydrous Na$_2$SO$_4$, and concentrated under reduced pressure to give 2-bromo-6-iodo-4-(trifluoromethyl)phenol (342), (4.5 g, 99% yield) as a yellow solid which was used without further purification in the next step. LCMS: t$_R$=1.76 min.

Synthesis of tert-butyl (7-bromo-5-(trifluoromethyl)benzofuran-2-yl)methylcarbamate (343)

A mixture of 2-bromo-6-iodo-4-(trifluoromethyl)phenol (342, 4.5 g, 12.3 mmol), tert-butyl prop-2-ynylcarbamate (2.1 g, 13.5 mmol), Pd(PPh$_3$)$_2$Cl$_2$ (882 mg, 1.2 mmol), and CuI (228 mg, 1.2 mmol) in 100 mL of triethylamine was stirred at 70° C. under nitrogen atmosphere for 2 h. After cooling to room temperature, the mixture was filtered and the filtrate was concentrated under reduced pressure to give the crude product, which was purified by silica gel chromatography (EtOAc/petroleum ether 0-15%) to give tert-butyl (7-bromo-5-(trifluoromethyl)benzofuran-2-yl)methylcarbamate (343), (1.7 g, 35% yield) as orange solid. LCMS: m/z 340 [M-55]$^+$; t$_R$=1.86 min.

Synthesis of tert-butyl (7-(4-(4,4-difluoropiperidine-1-carbonyl)phenyl)-5-(trifluoromethyl)benzofuran-2-yl)methylcarbamate (344)

tert-Butyl (7-bromo-5-(trifluoromethyl)benzofuran-2-yl)methylcarbamate (343, 420 mg, 1.1 mmol), (4,4-difluoropiperidin-1-yl)(4-(4,4,5,5-tetramethyl-1,3,2-dioxaborolan-2-yl)phenyl)methanone (420 mg, 1.2 mmol), Pd(dppf)Cl$_2$ (82 mg, 0.1 mmol) and K$_2$CO$_3$ (455 mg, 3.3 mmol) were added in a mixture of dioxane (20 mL) and H$_2$O (4 mL). The reaction mixture was stirred at 95° C. under nitrogen atmosphere for 16 h. LCMS showed the reaction was complete. The reaction mixture was cooled down to room temperature, diluted with EtOAc (30 mL), washed with water, brine, dried over anhydrous Na$_2$SO$_4$, and concentrated under reduced pressure to give the crude product, which was purified by silica gel chromatography (0-30% EtOAc/petroleum ether) to give tert-butyl (7-(4-(4,4-difluoropiperidine-1-carbonyl)phenyl)-5-(trifluoromethyl)benzofuran-2-yl)methylcarbamate (344), (480 mg, 85% yiled) as white solid. LCMS: m/z 483.1 [M-55]$^+$, t$_R$=1.81 min.

Synthesis of (4-(2-(aminomethyl)-5-(trifluoromethyl)benzofuran-7-yl)phenyl)(4,4-difluoropiperidin-1-yl)methanone (345)

(7-(4-(4,4-Difluoropiperidine-1-carbonyl)phenyl)-5-(trifluoromethyl)benzofuran-2-yl)methylcarbamate (344, 95 mg, 0.18 mmol) was dissolved in CH$_2$Cl$_2$ (10 mL). TFA (1 mL) was added at 0° C. The reaction mixture was stirred at 15° C. for 3 h, and concentrated under reduced pressure to give the crude (4-(2-(aminomethyl)-5-(trifluoromethyl)benzofuran-7-yl)phenyl)(4,4-difluoropiperidin-1-yl)methanone (345), (77 mg, 100% yield), which was used without further purification in the next step. LCMS: m/z 439.1 [M+H]$^+$; t$_R$=1.41 min.

Synthesis of (E)-3-(6-aminopyridin-3-yl)-N-((7-(4-(4,4-difluoropiperidine-1-carbonyl)phenyl)-5-(trifluoromethyl)benzofuran-2-yl)methyl)acrylamide (702)

(4-(2-(Aminomethyl)-5-(trifluoromethyl)benzofuran-7-yl)phenyl)(4,4-difluoropiperidin-1-yl)methanone (345, 95 mg, 0.18 mmol), (E)-3-(6-aminopyridin-3-yl)acrylic acid (33 mg, 0.2 mmol) and HATU (76 mg, 0.2 mmol) was dissolved in DMF (3 mL) and DIPEA (70 mg, 0.54 mmol) was added slowly. The reaction mixture was stirred at 20° C. for 2 h. The mixture was purified by Pre-HPLC to give (E)-3-(6-aminopyridin-3-yl)-N-((7-(4-(4,4-difluoropiperidine-1-carbonyl)phenyl)-5-(trifluoromethyl)benzofuran-2-yl)methyl)acrylamide (702) as white solid (40 mg, 39% yield). $^1$H NMR (400 MHz, DMSO-d$_6$) δ 8.88-8.79 (m, 1H), 8.22-7.96 (m, 7H), 7.83 (s, 1H), 7.63 (d, J=8.1 Hz, 2H), 7.44 (d, J=16 Hz, 1H), 6.98 (s, 1H), 6.93 (d, J=9 Hz, 1H), 6.58 (d, J=16 Hz, 1H), 4.64 (d, J=5 Hz, 2H), 3.89-3.38 (m, 4H), 2.20-1.92 (m, 4H). LCMS: m/z 584.8 [M+H]$^+$, t$_R$=2.02 min.

Synthesis of (E)-3-(6-aminopyridin-3-yl)-N-((5-(5-(4-fluorobenzoyl)pyridin-2-yl)-7-(4-fluorophenyl)benzofuran-2-yl)methyl)acrylamide (703) and (E)-3-(6-aminopyridin-3-yl)-N-((7-(4-fluorophenyl)-5-(5-((4-fluorophenyl)(hydroxy)methyl)pyridin-2-yl)benzofuran-2-yl)methyl)acrylamide (704)

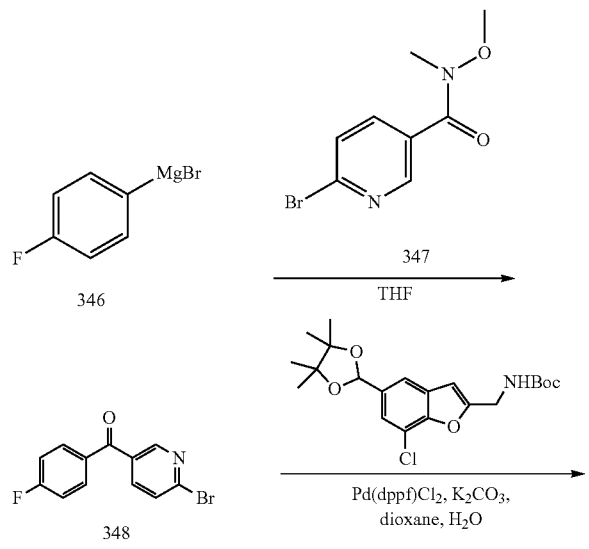

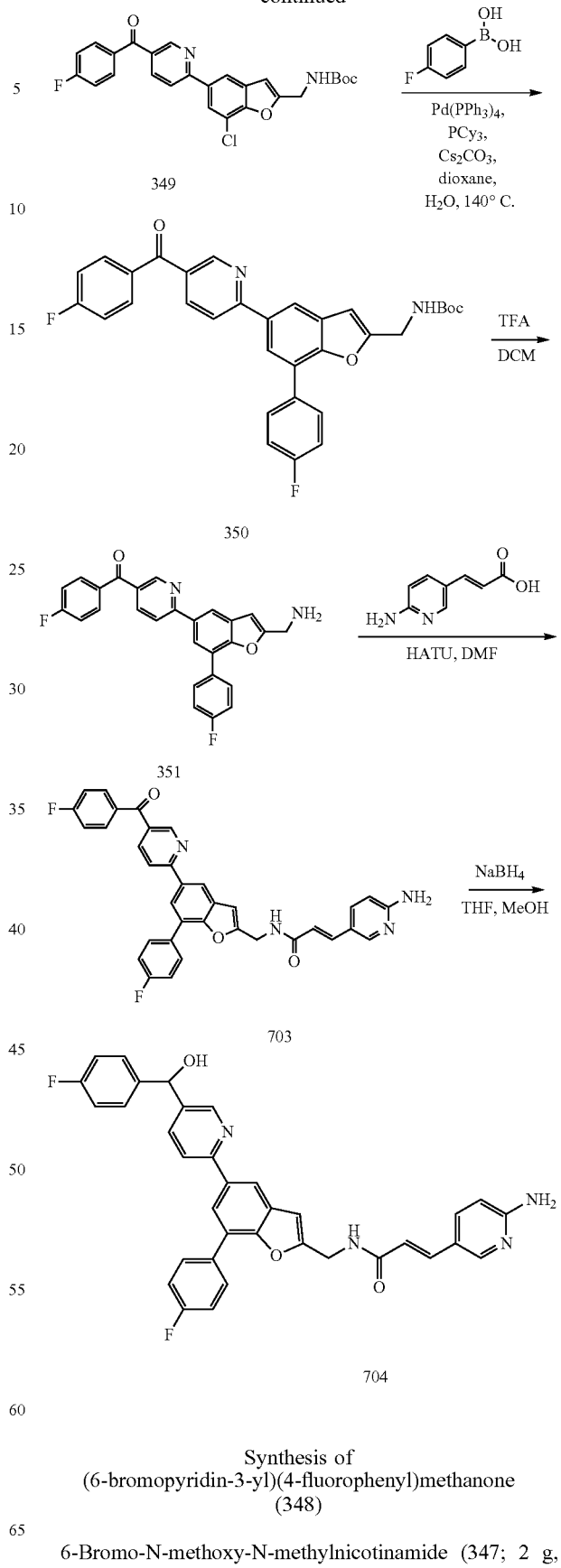

Synthesis of (6-bromopyridin-3-yl)(4-fluorophenyl)methanone (348)

6-Bromo-N-methoxy-N-methylnicotinamide (347; 2 g, 8.1 mmol) was dissolved in THF (10 mL). (4-Fluorophenyl)

magnesium bromide (346; 4.5 mL, 9 mmol, 2 M in THF) was added dropwise over 5 min at 0° C. (ice bath). The reaction mixture was allowed to warm to room temperature and stirred for 1 h. The reaction mixture was quenched with saturated NH$_4$Cl aqueous solution (10 mL), extracted with EtOAc (20 mL×3). The combined organic layers were washed with brine, dried over anhydrous Na$_2$SO$_4$, concentrated under reduced pressure to give the crude product, which was purified by silica gel chromatography (20% EtOAc/petroleum ether) to give 1.7 g of (6-bromopyridin-3-yl)(4-fluorophenyl)methanone (348) as white solid (75% yield). LCMS: m/z 280.1 [M+H]$^+$; $t_R$=1.93 min.

Synthesis of tert-butyl (7-chloro-5-(5-(4-fluorobenzoyl)pyridin-2-yl)benzofuran-2-yl)methylcarbamate (349)

tert-Butyl (7-chloro-5-(4,4,5,5-tetramethyl-1,3,2-dioxaborolan-2-yl)benzofuran-2-yl)methylcarbamate (1.8 g, 4.3 mmol), (6-bromopyridin-3-yl)(4-fluorophenyl)methanone (348; 1 g, 3.6 mmol), Pd(dppf)Cl$_2$ (0.29 g, 0.4 mmol), and K$_2$CO$_3$ (1 g, 7.2 mmol) were added in a mixture of (10:1) dioxane (10 mL) and water (1 mL) and degassed. The reaction mixture was heated at 80° C. under nitrogen atmosphere for 2 h. The reaction mixture was cooled down to room temperature, diluted with water (10 mL), extracted with EtOAc (20 mL×3). The combined organic layers were washed with brine, dried over anhydrous Na$_2$SO$_4$, concentrated under reduced pressure to give 1.4 g of tert-butyl (7-chloro-5-(5-(4-fluorobenzoyl)pyridin-2-yl)benzofuran-2-yl)methylcarbamate (349), which was used in next step without further purification (81% yield). LCMS: m/z 481.1 [M+H]$^+$; $t_R$=1.88 min.

Synthesis of tert-butyl (5-(5-(4-fluorobenzoyl)pyridin-2-yl)-7-(4-fluorophenyl)benzofuran-2-yl)methylcarbamate (350)

tert-Butyl (7-chloro-5-(5-(4-fluorobenzoyl)pyridin-2-yl)benzofuran-2-yl)methylcarbamate (349; 200 mg, 0.42 mmol), 4-fluorophenylboronic acid (175 mg, 1.25 mmol), Pd(PPh$_3$)$_4$ (50 mg, 0.04 mmol), tricyclohexylphosphine (35 mg, 0.08 mmol) and Cs$_2$CO$_3$ (410 mg, 1.25 mmol) were added to a mixture of dioxane (5 mL) and water (0.5 mL) and degassed. The reaction mixture was heated under microwave irradiation at 140° C. for 2 h. The reaction mixture was cooled down to room temperature, poured into 10 mL of water, extracted with EtOAc (20 mL×3). The combined organic layers were washed with brine, dried over anhydrous Na$_2$SO$_4$, concentrated under reduced pressure to give the crude product which was purified by silica gel chromatography (50% EtOAc/petroleum ether) to give tert-butyl (5-(5-(4-fluorobenzoyl)pyridin-2-yl)-7-(4-fluorophenyl)benzofuran-2-yl)methylcarbamate (350) as white solid (120 mg, 54% yield). LCMS: m/z 541.2 [M+H]$^+$; $t_R$=2.21 min.

Synthesis of (6-(2-(aminomethyl)-7-(4-fluorophenyl)benzofuran-5-yl)pyridin-3-yl)(4-fluorophenyl)methanone (351)

tert-Butyl (5-(5-(4-fluorobenzoyl)pyridin-2-yl)-7-(4-fluorophenyl)benzofuran-2-yl)methylcarbamate (350; 120 mg, 0.22 mmol) was dissolved in CH$_2$Cl$_2$ (5 mL). TFA (1 mL) was added dropwise at 0° C. (ice bath). The reaction mixture was allowed to warm to room temperature and stirred for 2 h. The reaction mixture was concentrated under reduced pressure to give (6-(2-(aminomethyl)-7-(4-fluorophenyl)benzofuran-5-yl)pyridin-3-yl)(4-fluorophenyl)methanone (351), which was used without further purification in the next step (70 mg, 72% yield). LCMS: m/z 441.2 [M+H]$^+$; $t_R$=2.21 min.

Synthesis of (E)-3-(6-aminopyridin-3-yl)-N-((5-(5-(4-fluorobenzoyl)pyridin-2-yl)-7-(4-fluorophenyl)benzofuran-2-yl)methyl)acrylamide (703)

(6-(2-(Aminomethyl)-7-(4-fluorophenyl)benzofuran-5-yl)pyridin-3-yl)(4-fluorophenyl)methanone (351; 70 mg, 0.18 mmol) was dissolved in DMF (5 mL). (E)-3-(6-aminopyridin-3-yl)acrylic acid (30 mg, 0.18 mmol) and HATU (116 mg, 0.31 mmol) were added at room temperature. The reaction mixture was stirred at room temperature for 2 h. The reaction mixture was purified by Pre-HPLC to give (E)-3-(6-aminopyridin-3-yl)-N-((5-(5-(4-fluorobenzoyl)pyridin-2-yl)-7-(4-fluorophenyl)benzofuran-2-yl)methyl)acrylamide (703) (60 mg, 57% yield) as white solid. $^1$H NMR (400 MHz, DMSO-d$_6$) δ 8.99 (s, 1H), 8.66-8.59 (m, 1H), 8.46 (s, 1H), 8.37-8.28 (m, 2H), 8.26-8.18 (m, 1H), 8.09 (s, 1H), 8.06-7.91 (m, 4H), 7.62 (d, J=10 Hz, 1H), 7.50-7.33 (m, 6H), 6.94 (s, 1H), 6.51-6.38 (m, 3H), 4.61 (d, J=5 Hz, 2H). LCMS: m/z 587.2 [M+H]$^+$; $t_R$=1.97 min.

Synthesis of (E)-3-(6-aminopyridin-3-yl)-N-((7-(4-fluorophenyl)-5-(5-((4-fluorophenyl)(hydroxy)methyl)pyridin-2-yl)benzofuran-2-yl)methyl)acrylamide (704)

(E)-3-(6-aminopyridin-3-yl)-N-((5-(5-(4-fluorobenzoyl)pyridin-2-yl)-7-(4-fluorophenyl)benzofuran-2-yl)methyl)acrylamide (703; 40 mg, 0.07 mmol) was dissolved in THF (5 mL) and MeOH (5 mL). Sodium borohydride (5 mg, 0.14 mmol) was added at room temperature and stirred for 5 h. The reaction mixture was concentrated under reduced pressure to give the crude product, which was purified by Pre-HPLC to give (E)-3-(6-aminopyridin-3-yl)-N-((7-(4-fluorophenyl)-5-(5-((4-fluorophenyl)(hydroxy)methyl)pyridin-2-yl)benzofuran-2-yl)methyl)acrylamide (704). (5 mg, 12% yield) as white solid. $^1$H NMR (400 MHz, CD$_3$OD) δ 8.62 (s, 1H), 8.12-7.99 (m, 4H), 7.96-7.85 (m, 4H), 7.43-7.34 (m, 3H), 7.16 (t, J=9 Hz, 2H), 7.02 (t, J=9 Hz, 2H), 6.94 (d, J=9 Hz, 1H), 6.81 (s, 1H), 6.53 (d, J=16 Hz, 1H), 5.89 (s, 1H), 4.62 (s, 2H). LCMS: m/z 589.0 [M+H]$^+$; $t_R$=1.44 min.

Synthesis of (E)-3-(6-aminopyridin-3-yl)-N-((5-(4-(4,4-difluoropiperidine-1-carbonothioyl)phenyl)-7-(pyridin-4-yl)benzofuran-2-yl)methyl)acrylamide (705)

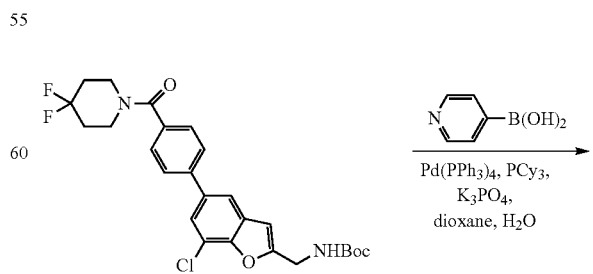

323

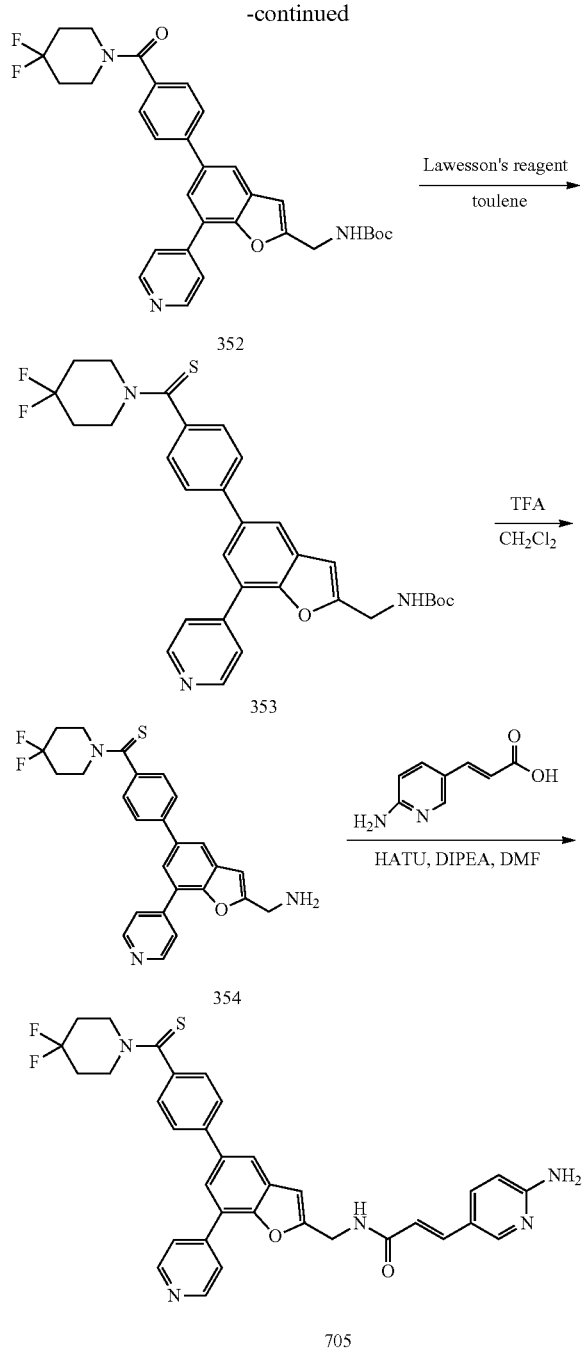

Synthesis of tert-butyl (5-(4-(4,4-difluoropiperidine-1-carbonyl)phenyl)-7-(pyridin-4-yl)benzofuran-2-yl)methylcarbamate (352)

tert-Butyl (7-chloro-5-(4-(4,4-difluoropiperidine-1-carbonyl)phenyl)benzofuran-2-yl)methylcarbamate (323; 250 mg, 0.5 mmol), pyridin-4-ylboronic acid (183 mg, 1.5 mmol), Pd(PPh$_3$)$_4$ (57 mg, 0.05 mmol), tricyclohexylphosphine (42 mg, 0.15 mmol) and K$_3$PO$_4$ (210 mg, 1 mmol) were added to a mixture of dioxane (3 mL) and water (0.3 mL) and degassed. The reaction mixture was heated under microwave irradiation at 140° C. for 2 h. The reaction mixture was cooled down to room temperature, poured into 5 mL of water, extracted with EtOAc (10 mL×3). The combined organic layers were washed with brine, dried over anhydrous Na$_2$SO$_4$, concentrated under reduced pressure to give the crude product which was purified by silica gel chromatography (17-20% EtOAc/petroleum ether) to give tert-butyl (5-(4-(4,4-difluoropiperidine-1-carbonyl)phenyl)-7-(pyridin-4-yl)benzofuran-2-yl)methylcarbamate (352) as white solid (209 mg, 71% yield). LCMS: m/z 548.3 [M+H]$^+$; t$_R$=1.92 min.

Synthesis of tert-butyl (5-(4-(4,4-difluoropiperidine-1-carbonothioyl)phenyl)-7-(pyridin-4-yl)benzofuran-2-yl)methylcarbamate (353)

tert-Butyl (5-(4-(4,4-difluoropiperidine-1-carbonyl)phenyl)-7-(pyridin-4-yl)benzofuran-2-yl)methylcarbamate (352; 209 mg, 0.38 mmol) and Lawesson's reagent (170 mg, 0.42 mmol) were added in 30 mL of toluene. The reaction mixture was heated at 100° C. for 1 h. After cooling down to room temperature, the reaction mixture was concentrated under reduced pressure to give the crude product, which was purified by silica gel chromatography (10-25% EtOAc/petroleum ether) to give 145 mg of tert-butyl (5-(4-(4,4-difluoropiperidine-1-carbonothioyl)phenyl)-7-(pyridin-4-yl)benzofuran-2-yl)methylcarbamate (353) as a yellow solid. Yield: 67%. LCMS: m/z 564.3 [M+H]$^+$; t$_R$=2.04 min.

Synthesis of (4-(2-(aminomethyl)-7-(pyridin-4-yl)benzofuran-5-yl)phenyl)(4,4-difluoropiperidin-1-yl)methanethione (354)

tert-Butyl (5-(4-(4,4-difluoropiperidine-1-carbonothioyl)phenyl)-7-(pyridin-4-yl)benzofuran-2-yl)methylcarbamate (353; 159 mg, 0.28 mmol) was dissolved in CH$_2$Cl$_2$ (10 mL). TFA (2 mL) was added dropwise at 0° C. The reaction mixture was allowed to warm to room temperature and stirred for 4 h. The reaction mixture was concentrated under reduced pressure to give (4-(2-(aminomethyl)-7-(pyridin-4-yl)benzofuran-5-yl)phenyl)(4,4-difluoropiperidin-1-yl)methanethione (354), which was used without further purification in the next step (168 mg, 100% yield). LCMS: m/z 464.2 [M+H]$^+$; t$_R$=1.82 min.

Synthesis of (E)-3-(6-aminopyridin-3-yl)-N-((5-(4-(4,4-difluoropiperidine-1-carbonothioyl)phenyl)-7-(pyridin-4-yl)benzofuran-2-yl)methyl)acrylamide (705)

(4-(2-(Aminomethyl)-7-(pyridin-4-yl)benzofuran-5-yl)phenyl)(4,4-difluoropiperidin-1-yl)methanethione (354; 138 mg, 0.30 mmol) was dissolved in DMF (3 mL). (E)-3-(6-aminopyridin-3-yl)acrylic acid (49 mg, 0.3 mmol), HATU (110 mg, 0.36 mmol), and DIPEA (192 mg, 1.49 mmol) were added at room temperature. The reaction mixture was stirred at room temperature for 1 h. The crude mixture was purified by Pre-HPLC without workup to give (E)-3-(6-aminopyridin-3-yl)-N-((5-(4-(4,4-difluoropiperidine-1-carbonothioyl)phenyl)-7-(pyridin-4-yl)benzofuran-2-yl)methyl)acrylamide (705) (22 mg, 11% yield) as yellow solid. $^1$H NMR (400 MHz, DMSO-d$_6$) δ 8.73 (d, J=6 Hz, 2H), 8.64 (t, J=6 Hz, 1H), 8.11-8.00 (m, 4H), 7.95-7.93 (m, 1H), 7.84 (d, J=8 Hz, 2H), 7.65-7.59 (m, 1H), 7.48 (d, J=8 Hz, 2H), 7.37 (d, J=16 Hz, 1H), 6.89 (s, 1H), 6.52-6.37 (m, 4H), 4.62 (d, J=5 Hz, 2H), 4.51-4.39 (m, 2H), 3.76-3.63 (m, 2H), 2.30-2.06 (m, 4H). LCMS: m/z 610.2 [M+H]$^+$; t$_R$=1.81 min.

471

Synthesis of (E)-3-(6-aminopyridin-3-yl)-N-((7-(2,4-difluorophenyl)-5-(4-(4,4-difluoropiperidine-1-carbonothioyl)phenyl)benzofuran-2-yl)methyl)acrylamide (706)

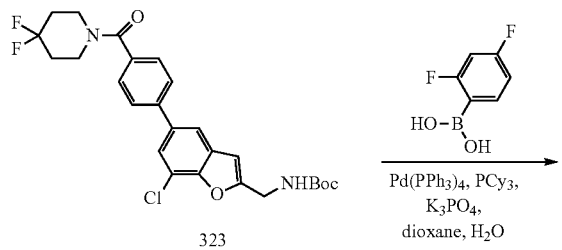

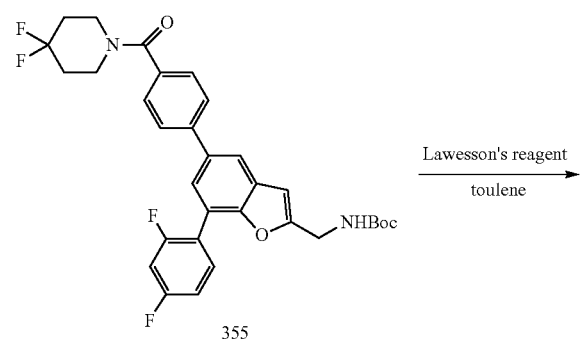

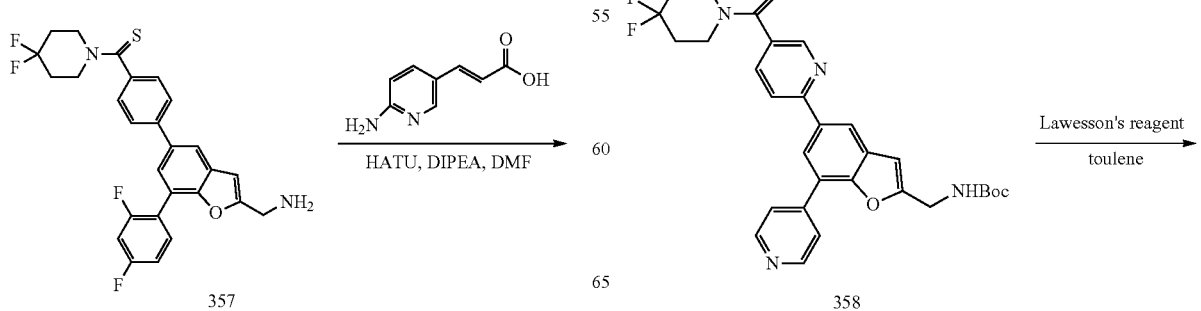

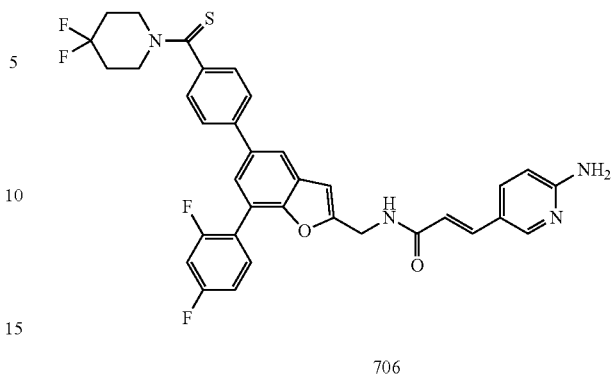

(E)-3-(6-aminopyridin-3-yl)-N-((7-(2,4-difluorophenyl)-5-(4-(4,4-difluoropiperidine-1-carbonothioyl)phenyl)benzofuran-2-yl)methyl)acrylamide (706) was synthesized using the indicated reagents in a similar fashion as example (705). $^1$H NMR (500 MHz, DMSO-$d_6$) δ 8.57 (t, J=6 Hz, 1H), 8.07 (s, 1H), 7.97 (s, 1H), 7.84-7.75 (m, 3H), 7.64-7.57 (m, 2H), 7.51-7.42 (m, 3H), 7.37-7.25 (m, 2H), 6.85 (s, 1H), 6.55-6.34 (m, 4H), 4.59-4.39 (m, 4H), 3.75-3.62 (m, 2H), 2.29-2.05 (m, 4H). LCMS: m/z 645.3 [M+H]$^+$, $t_R$=1.98 min.

Synthesis of (E)-3-(6-aminopyridin-3-yl)-N-((5-(5-(4,4-difluoropiperidine-1-carbonothioyl)pyridin-2-yl)-7-(pyridin-4-yl)benzofuran-2-yl)methyl)acrylamide (707)

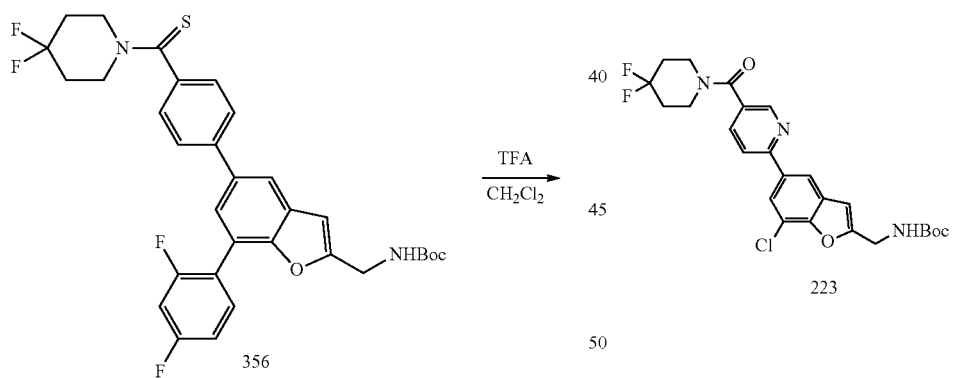

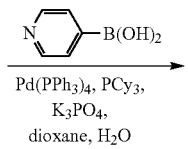

473
-continued

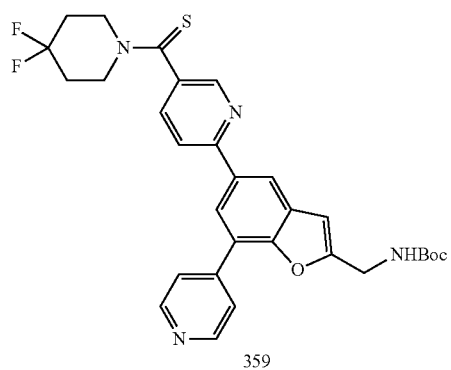

359

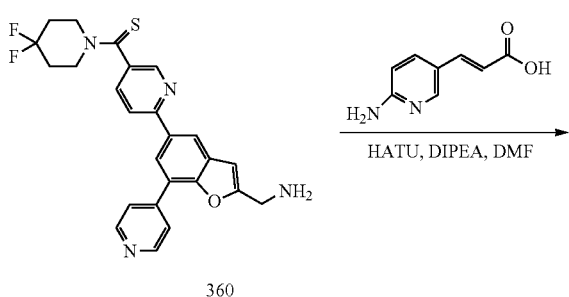

360

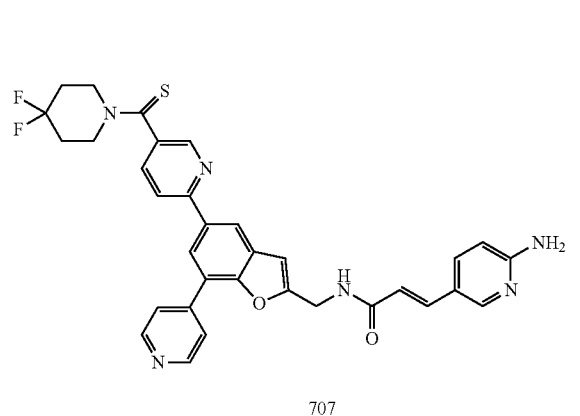

707

(E)-3-(6-aminopyridin-3-yl)-N-((5-(5-(4,4-difluoropiperidine-1-carbonothioyl)pyridin-2-yl)-7-(pyridin-4-yl)benzofuran-2-yl)methyl)acrylamide (707) was synthesized using the indicated reagents in a similar fashion as example (705). $^1$H NMR (400 MHz, CD$_3$OD) δ 8.61-8.54 (m, 3H), 8.26-8.20 (m, 2H), 8.02-7.89 (m, 4H), 7.81-7.76 (m, 1H), 7.67-7.63 (m, 1H), 7.40 (d, J=16 Hz, 1H), 6.82 (s, 1H), 6.51 (d, J=9 Hz, 1H), 6.38 (d, J=16 Hz, 1H), 4.63 (s, 2H), 4.48-4.38 (m, 2H), 3.77-3.70 (m, 2H), 2.23-1.96 (m, 4H). LCMS: m/z 611.3 [M+H]$^+$, t$_R$=1.90 min.

474

Synthesis of (E)-3-(6-aminopyridin-3-yl)-N-((7-(2,4-difluorophenyl)-5-(5-(4,4-difluoropiperidine-1-carbonothioyl)pyridin-2-yl)benzofuran-2-yl)methyl)acrylamide (708)

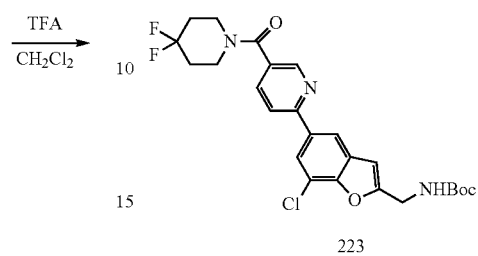 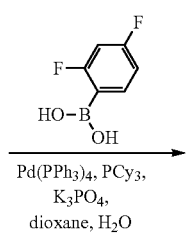

223

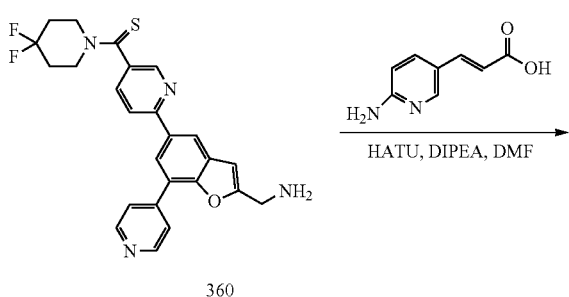

361

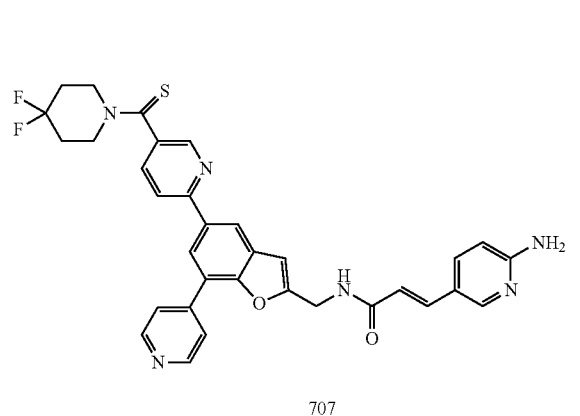

362

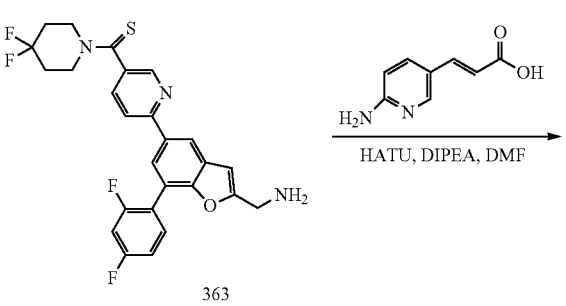

363

475

-continued

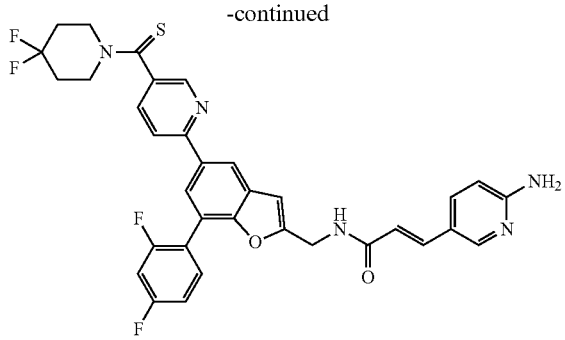

708

(E)-3-(6-aminopyridin-3-yl)-N-((7-(2,4-difluorophenyl)-5-(5-(4,4-difluoropiperidine-1-carbonothioyl)pyridin-2-yl)benzofuran-2-yl)methyl)acrylamide (708) was synthesized using the indicate reagents in a similar fashion as example (706). $^1$H NMR (500 MHz, DMSO-d$_6$) δ 8.66 (s, 1H), 8.58 (s, 1H), 8.42 (s, 1H), 8.14-8.05 (m, 3H), 7.91-7.75 (m, 2H), 7.60 (d, J=8 Hz, 1H), 7.52-7.44 (m, 1H), 7.37-7.26 (m, 2H), 6.90 (s, 1H), 6.51-6.35 (m, 4H), 4.54 (d, J=5 Hz, 2H), 4.47-4.39 (s, 2H), 3.77-3.69 (m, 2H), 2.31-2.11 (m, 4H). LCMS: m/z 646.2 [M+H]$^+$, t$_R$=1.91 min.

Synthesis of (E)-3-(6-aminopyridin-3-yl)-N-((5-(4-(ethylsulfonyl)phenyl)-7-(4-fluorophenyl)benzofuran-2-yl)methyl)acrylamide (709)

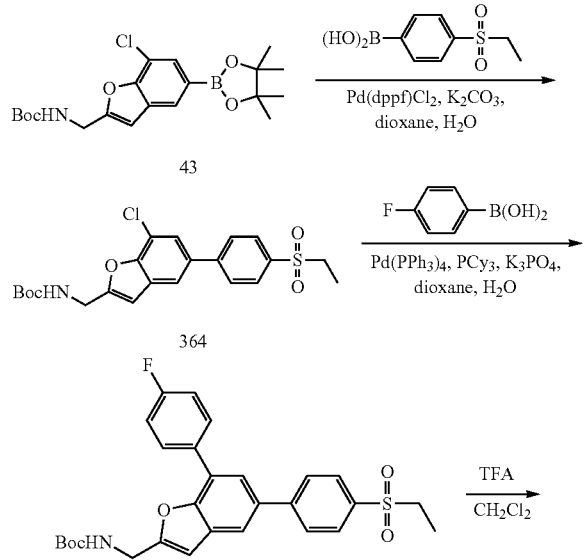

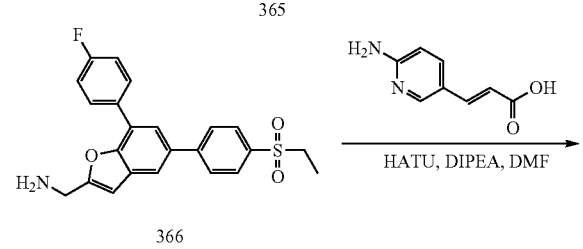

476

-continued

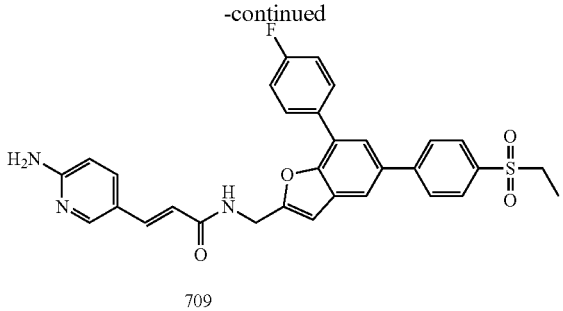

709

Synthesis of tert-butyl (7-chloro-5-(4-(ethylsulfonyl)phenyl)benzofuran-2-yl)methylcarbamate (364)

A mixture of 4-(ethylsulfonyl)phenylboronic acid (300 mg, 1.4 mmol), tert-butyl (7-chloro-5-(4,4,5,5-tetramethyl-1,3,2-dioxaborolan-2-yl)benzofuran-2-yl)methylcarbamate (43) (500 mg, 1.4 mmol), Pd(dppf)Cl$_2$ (100 mg, 0.14 mmol) and K$_2$CO$_3$ (380 mg, 2.8 mmol) in 20 mL of dioxane and 1 mL of H$_2$O was heated at 100° C. under nitrogen atmosphere for 5 h. The reaction mixture was cooled down to room temperature and filtered. The filtrate was concentrated under reduced pressure to give the crude product, which was purified by silica gel chromatography (10% EtOAc/petroleum ether) to give 600 mg of tert-butyl (7-chloro-5-(4-(ethylsulfonyl)phenyl)benzofuran-2-yl)methylcarbamate (364) as white solid. Yield (96%). LCMS: m/z 394.0 [M-55]$^+$, t$_R$=2.01 min.

Synthesis of tert-butyl (5-(4-(ethylsulfonyl)phenyl)-7-(4-fluorophenyl)benzofuran-2-yl)methylcarbamate (365)

tert-Butyl (7-chloro-5-(4-(ethylsulfonyl)phenyl)benzofuran-2-yl)methylcarbamate (364; 200 mg, 0.44 mmol), 4-fluorophenylboronic acid (187 mg, 1.32 mmol), Pd(PPh$_3$)$_4$ (51 mg, 0.05 mmol), tricyclohexylphosphine (25 mg, 0.10 mmol) and K$_3$PO$_4$ (280 mg, 1.32 mmol) were added to a mixture of dioxane (3 mL) and water (0.3 mL) and degassed. The reaction mixture was heated under microwave irradiation at 140° C. for 2 h. The reaction mixture was cooled down to room temperature, poured into 5 mL of water, extracted with EtOAc (10 mL×3). The combined organic layers were washed with brine, dried over anhydrous Na$_2$SO$_4$, concentrated under reduced pressure to give the crude product, which was purified by silica gel chromatography (50% EtOAc/petroleum ether) to give 220 mg of tert-butyl (5-(4-(ethylsulfonyl)phenyl)-7-(4-fluorophenyl)benzofuran-2-yl)methylcarbamate (365) as white solid (98% yield). LCMS: m/z 410.1 [M+H-100]$^+$; t$_R$=2.08 min.

Synthesis of (5-(4-(ethylsulfonyl)phenyl)-7-(4-fluorophenyl)benzofuran-2-yl)methanamine (366)

tert-Butyl (5-(4-(ethylsulfonyl)phenyl)-7-(4-fluorophenyl)benzofuran-2-yl)methylcarbamate (365; 220 mg, 0.43 mmol) was dissolved in CH$_2$Cl$_2$ (5 mL). TFA (5 mL) was added dropwise at 0° C. (ice bath). The reaction mixture was allowed to warm to room temperature and stirred for 1 h. The reaction mixture was concentrated under reduced pressure to give (5-(4-(ethylsulfonyl)phenyl)-7-(4-fluorophenyl)benzofuran-2-yl)methanamine (366), which was used without further purification in the next step (175 mg, 100% yield). LCMS: m/z 410.2 [M+H]⁺; $t_R$=1.86 min.

Synthesis of (E)-3-(6-aminopyridin-3-yl)-N-((5-(4-(ethylsulfonyl)phenyl)-7-(4-fluorophenyl)benzofuran-2-yl)methyl)acrylamide (709)

(5-(4-(Ethylsulfonyl)phenyl)-7-(4-fluorophenyl)benzofuran-2-yl)methanamine (366; 175 mg, 0.43 mmol) was dissolved in DMF (5 mL). (E)-3-(6-aminopyridin-3-yl) acrylic acid (78 mg, 0.48 mmol), HATU (245 mg, 0.64 mmol), and DIPEA (166 mg, 1.30 mmol) were added at room temperature. The reaction mixture was stirred at room temperature for 4 h. The reaction mixture was purified by Pre-HPLC to give (E)-3-(6-aminopyridin-3-yl)-N-((5-(4-(ethylsulfonyl)phenyl)-7-(4-fluorophenyl)benzofuran-2-yl)methyl)acrylamide (709) (120 mg, 50% yield) as white solid. ¹H NMR (400 MHz, CD₃OD) δ 8.20 (d, J=9 Hz, 1H), 8.07-7.93 (m, 7H), 7.88 (d, J=2 Hz, 1H), 7.75 (s, 1H), 7.49 (d, J=16 Hz, 1H), 7.26 (t, J=9 Hz, 2H), 7.05 (d, J=9 Hz, 1H), 6.89 (s, 1H), 6.65 (d, J=16 Hz, 1H), 4.73 (s, 2H), 3.27 (q, J=7 Hz, 2H), 1.28 (t, J=7 Hz, 3H). LCMS: m/z 556.1 [M+H]⁺; $t_R$=1.42 min.

Synthesis of (E)-3-(6-aminopyridin-3-yl)-N-((7-(2,4-difluorophenyl)-5-(5-(4,4-difluoropiperidine-1-carbonyl)pyridin-2-yl)benzofuran-2-yl)methyl)acrylamide (710)

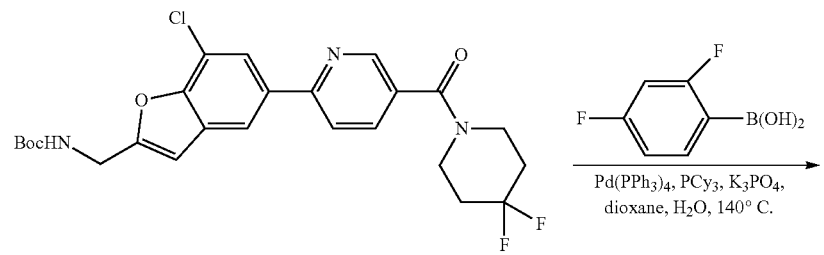

223

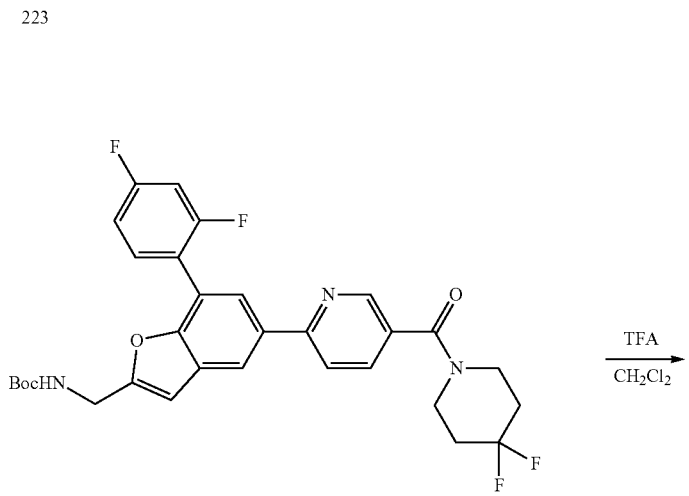

367

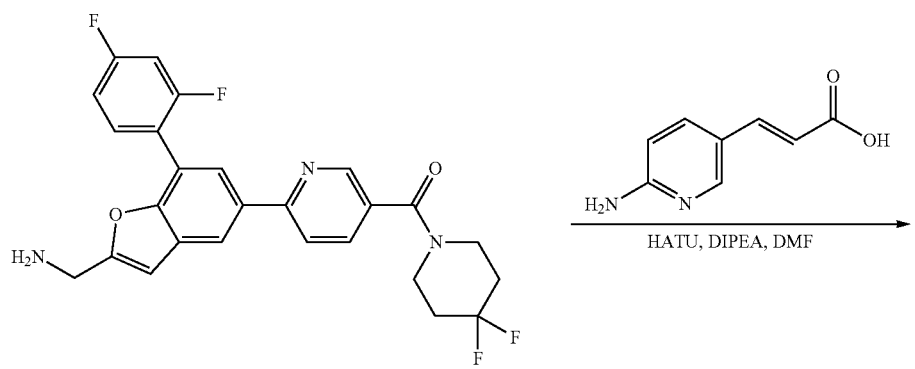

368

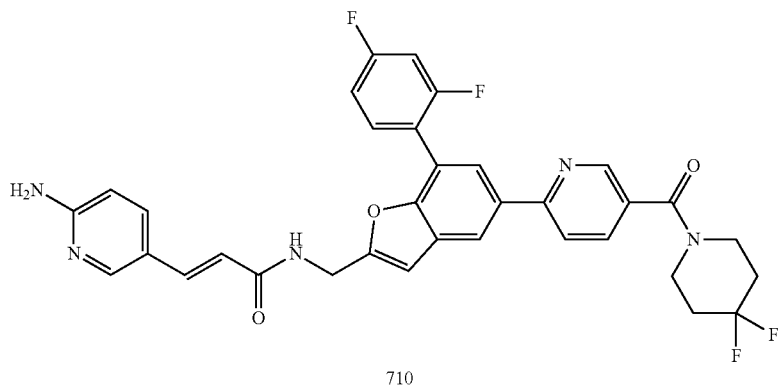

710

(E)-3-(6-aminopyridin-3-yl)-N-((7-(2,4-difluorophenyl)-5-(5-(4,4-difluoropiperidine-1-carbonyl)pyridin-2-yl)benzofuran-2-yl)methyl)acrylamide (710) was synthesized using the indicated reagents in a similar fashion as example (699). $^1$H NMR (400 MHz, DMSO-$d_6$) δ 8.84-8.78 (m, 1H), 8.75 (s, 1H), 8.44 (s, 1H), 8.36-8.08 (m, 6H), 7.99 (d, J=6 Hz, 1H), 7.82-7.73 (m, 1H), 7.53-7.39 (m, 2H), 7.33-7.26 (m, 1H), 7.01 (d, J=10 Hz, 1H), 6.92 (s, 1H), 6.59 (d, J=16 Hz, 1H), 4.57 (d, J=5 Hz, 2H), 3.80-3.44 (m, 4H), 2.15-2.02 (m, 4H). LCMS: m/z 630.2 [M+H]$^+$, $t_R$=1.41 min.

Synthesis of (E)-3-(6-aminopyridin-3-yl)-N-((7-(3-chloro-4-fluorophenyl)-5-(4-(4,4-difluoropiperidine-1-carbonyl)phenyl)benzofuran-2-yl)methyl)acrylamide (711)

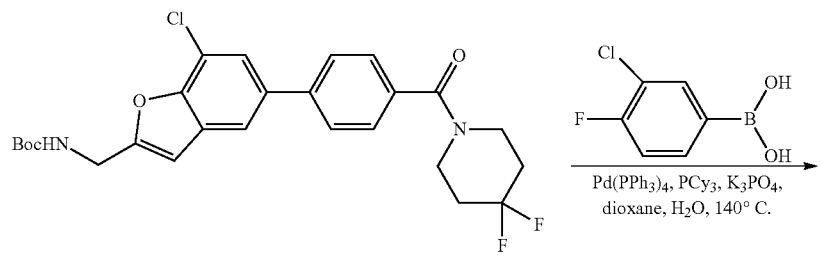

319

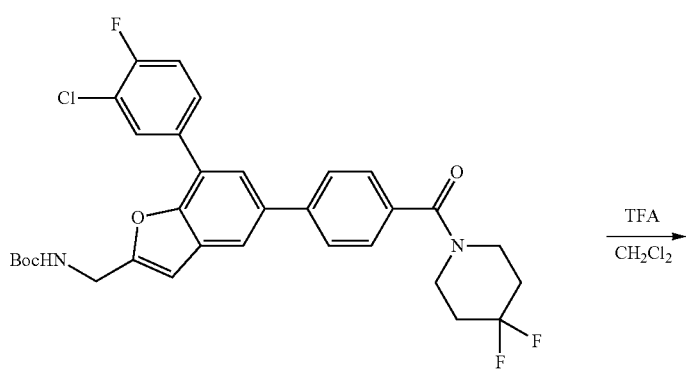

369

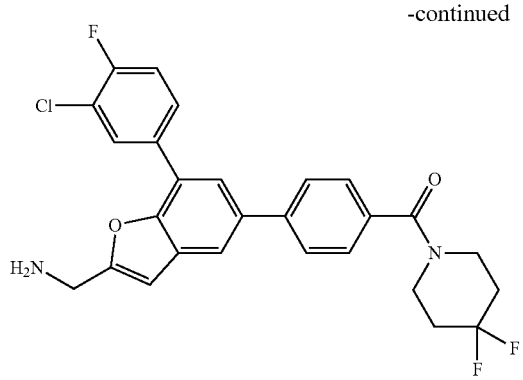

370

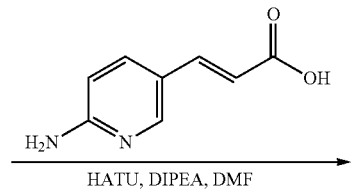

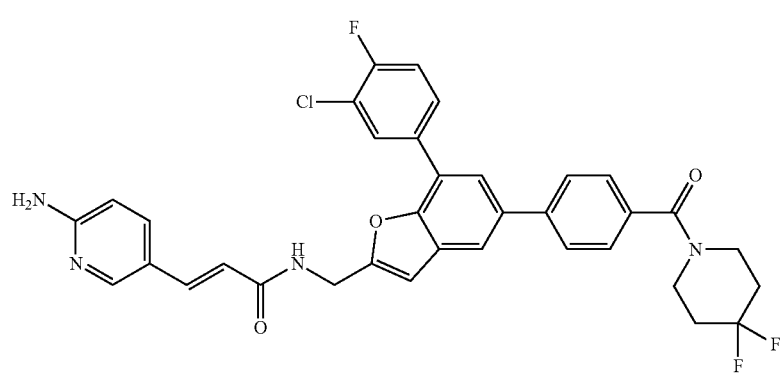

711

(E)-3-(6-aminopyridin-3-yl)-N-((7-(3-chloro-4-fluorophenyl)-5-(4-(4,4-difluoropiperidine-1-carbonyl)phenyl)benzofuran-2-yl)methyl)acrylamide (711) was synthesized using the indicated reagents in a similar fashion as example (699). $^1$H NMR (400 MHz, DMSO-$d_6$) δ 8.61 (t, J=5 Hz, 1H), 8.25-8.20 (m, 1H), 8.11-8.00 (m, 2H), 7.97-7.79 (m, 4H), 7.65-7.52 (m, 4H), 7.36 (d, J=16 Hz, 1H), 6.87 (s, 1H), 6.50-6.38 (m, 4H), 4.60 (d, J=5 Hz, 2H), 3.77-3.42 (m, 4H), 2.14-1.98 (m, 4H). LCMS: m/z 645.3 [M+H]$^+$; $t_R$=1.91 min.

Synthesis of (E)-3-(6-aminopyridin-3-yl)-N-((6-chloro-4-(4-(4,4-difluoropiperidine-1-carbonyl)phenyl)benzofuran-2-yl)methyl)acrylamide (713)

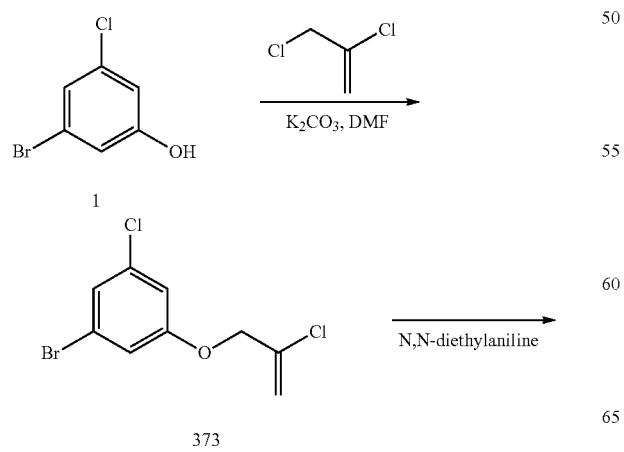

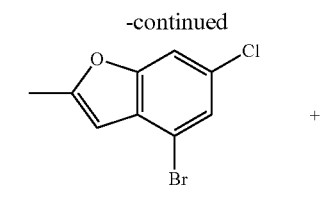

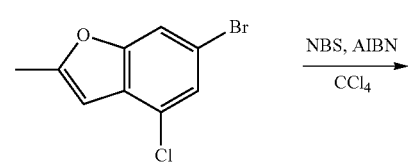

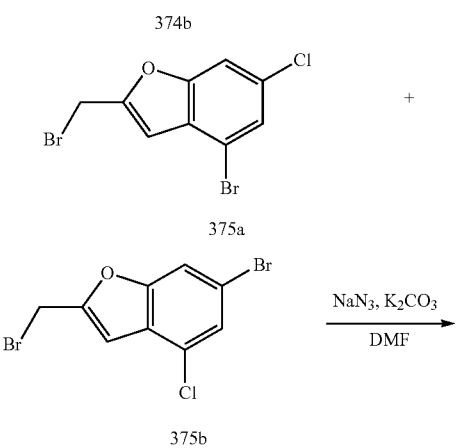

483
-continued

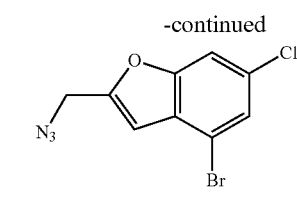
376a

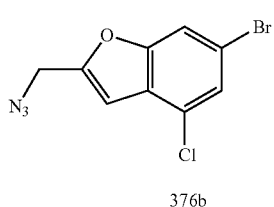
376b

PPh₃
THF, H₂O

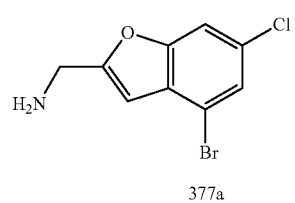
377a

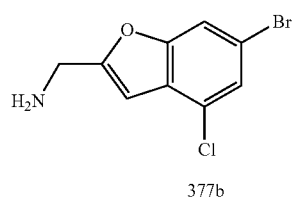
377b (Boc)₂O
Et₃N, CH₂Cl₂

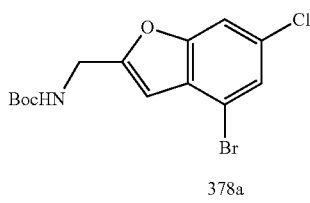
378a

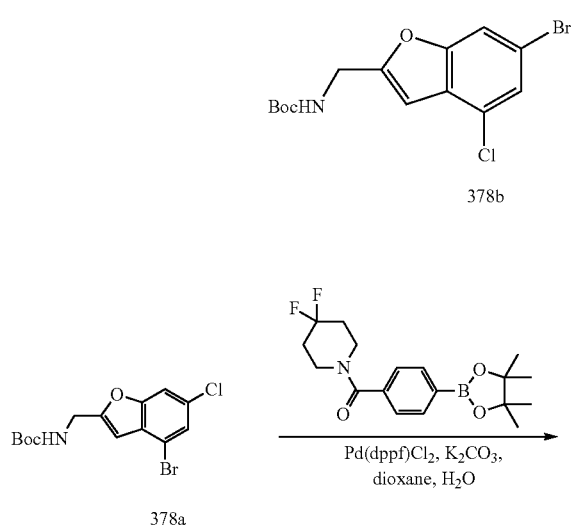

Pd(dppf)Cl₂, K₂CO₃,
dioxane, H₂O

484
-continued

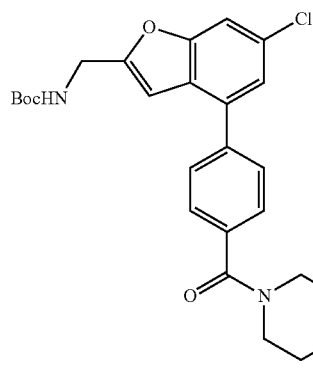
379

TFA
CH₂Cl₂

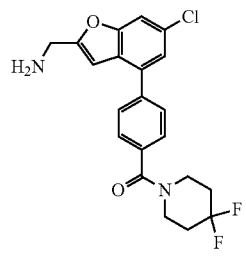
380

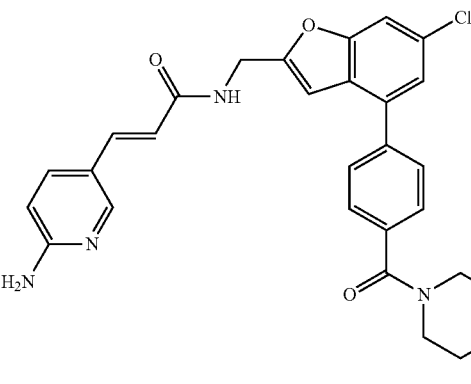

HATU, DIPEA, DMF

713

Synthesis of 1-bromo-3-chloro-5-(2-chloroallyloxy)benzene (373)

3-Bromo-5-chlorophenol (13.4 g, 64.6 mmol) was dissolved in 100 mL of DMF. 2,3-Dichloroprop-1-ene (14.4 g, 129.2 mmol) and K₂CO₃ (17.8 g, 129.2 mmol) were added. The mixture was stirred at 110° C. for 4 h. The mixture was cooled to room temperature, diluted with H₂O (100 mL), extracted with EtOAc (30 mL×3). The combined organic solvents were dried over anhydrous Na₂SO₄, concentrated and purified by silica gel chromatography (petroleum ether) to give 15.5 g of 1-bromo-3-chloro-5-(2-chloroallyloxy) benzene (373) as colorless liquid. Yield (85%). ¹H NMR (400 MHz, CDCl₃) δ 7.17-7.16 (m, 1H), 7.01-7.00 (m, 1H), 6.89-6.88 (m 1H), 5.57-5.56 (m, 1H), 5.50 (s, 1H), 4.57 (s, 2H).

Synthesis of 4-bromo-6-chloro-2-methylbenzofuran (374a) and 6-bromo-4-chloro-2-methylbenzofuran (374b)

1-Bromo-3-chloro-5-(2-chloroallyloxy)benzene (373; 22 g, 78 mmol) was dissolved in 100 mL of N,N-diethylaniline. The mixture was heated to 220° C. for 32 h. After cooling to room temperature, 500 mL of EtOAc was added. The mixture was washed with 2N HCl aqueous solution (200 mL×3), brine (60 mL), dried over anhydrous $Na_2SO_4$, concentrated and purified by silica gel chromatography (petroleum ether) to afford 1.4 g of mixture 4-bromo-6-chloro-2-methylbenzofuran (374a) and 6-bromo-4-chloro-2-methylbenzofuran (374b) as a white solid. Yield (7%). LCMS: $t_R$=2.01 min.

Synthesis of 4-bromo-2-(bromomethyl)-6-chlorobenzofuran (375a) and 6-bromo-2-(bromomethyl)-4-chlorobenzofuran (375b)

4-Bromo-6-chloro-2-methylbenzofuran (374a) and 6-bromo-4-chloro-2-methylbenzofuran (374b) (500 mg, 2 mmol) was dissolved in 20 mL of $CCl_4$. NBS (399 mg, 2.2 mmol) and AIBN (66 mg, 0.4 mmol) were added. The mixture was degassed and stirred for 5 h, cooled to room temperature and filtered, the filtrate was concentrated to give 650 mg of 4-bromo-2-(bromomethyl)-6-chlorobenzofuran (375a) and 6-bromo-2-(bromomethyl)-4-chlorobenzofuran (375b), which was used directly to next step. Yield (98%). LCMS: $t_R$=1.95 min.

Synthesis of 2-(azidomethyl)-4-bromo-6-chlorobenzofuran (376a) and 2-(azidomethyl)-6-bromo-4-chlorobenzofuran (376b)

4-Bromo-2-(bromomethyl)-6-chlorobenzofuran (375a) and 6-bromo-2-(bromomethyl)-4-chlorobenzofuran (375b) (650 mg, 2 mmol) was dissolved in 10 mL of DMF. $NaN_3$ (195 mg, 3 mmol) and $K_2CO_3$ (553 mg, 4 mmol) were added. The mixture was stirred at room temperature for 2 h, diluted with $H_2O$ (20 mL), extracted with EtOAc (10 mL X 3), washed with brine (10 mL), dried over $Na_2SO_4$, concentrated to afford 550 mg of 2-(azidomethyl)-4-bromo-6-chlorobenzofuran (376a) and 2-(azidomethyl)-6-bromo-4-chlorobenzofuran (376b) as yellow solid, which was used directly. Yield (96%). LCMS: $t_R$=1.91 min.

Synthesis of (4-bromo-6-chlorobenzofuran-2-yl)methanamine (377a) and (6-bromo-4-chlorobenzofuran-2-yl)methanamine (377b)

2-(Azidomethyl)-4-bromo-6-chlorobenzofuran (376a) and 2-(azidomethyl)-6-bromo-4-chlorobenzofuran (376b) (500 mg, 1.7 mmol) was dissolved in 20 mL of THF. $PPh_3$ (668 mg, 2.5 mmol) was added. The mixture was stirred at room temperature for 1 h, and $H_2O$ (10 mL) was added. The mixture was stirred at 60° C. for 4 h, cooled to room temperature, concentrated and purified by silica gel chromatography (EtOAc) to afford 360 mg of (4-bromo-6-chlorobenzofuran-2-yl)methanamine (377a) and (6-bromo-4-chlorobenzofuran-2-yl)methanamine (377b). Yield (62%). LCMS: m/z 244.9 $[M-NH_2]^+$; $t_R$=1.27 min.

Synthesis of tert-butyl (4-bromo-6-chlorobenzofuran-2-yl)methylcarbamate (378a) and tert-butyl (6-bromo-4-chlorobenzofuran-2-yl)methylcarbamate (378b)

(4-Bromo-6-chlorobenzofuran-2-yl)methanamine (377a) and (6-bromo-4-chlorobenzofuran-2-yl)methanamine (377b) (310 mg, 1.2 mmol) was dissolved in dichloromethane (15 mL). Di-tert-butyl dicarbonate (523 mg, 2.4 mmol) and triethylamine (364 mg, 3.6 mmol) were added at 0° C. and the reaction mixture was stirred at room temperature for 18 h. The reaction mixture was concentrated and purified by silica gel chromatography (10% ethyl acetate/petroleum ether) to give 360 mg of tert-butyl (4-bromo-6-chlorobenzofuran-2-yl)methylcarbamate (378a) and tert-butyl (6-bromo-4-chlorobenzofuran-2-yl)methylcarbamate (378b) (84% yield). LCMS: m/z 388.9.7 $[M+Na]^+$; $t_R$=1.87 min. The two compounds were separated from each other by chiral HPLC (AD-H column) to give 100 mg of tert-butyl (4-bromo-6-chlorobenzofuran-2-yl)methylcarbamate 374a and 100 mg of tert-butyl (6-bromo-4-chlorobenzofuran-2-yl)methylcarbamate 374b.

Synthesis of tert-butyl (6-chloro-4-(4-(4,4-difluoropiperidine-1-carbonyl)phenyl)benzofuran-2-yl)methylcarbamate (375)

A mixture of tert-butyl (4-bromo-6-chlorobenzofuran-2-yl)methylcarbamate (378a; 50 mg, 0.14 mmol), (4,4-difluoropiperidin-1-yl)(4-(4,4,5,5-tetramethyl-1,3,2-dioxaborolan-2-yl)phenyl)methanone (73 mg, 0.21 mmol), Pd(dppf)$Cl_2$ (10 mg, 0.01 mmol) and $K_2CO_3$ (38 g, 0.28 mmol) in 10 mL of dioxane and 2 mL of $H_2O$ was stirred at 100° C. under nitrogen atmosphere for 2 h. The mixture was concentrated and purified by Prep-TLC (33% EtOAc/petroleum ether) to give 60 mg of tert-butyl (6-chloro-4-(4-(4,4-difluoropiperidine-1-carbonyl)phenyl)benzofuran-2-yl)methylcarbamate (379) as a white solid. Yield (83%). $^1$H NMR (400 MHz, $CD_3OD$) δ 7.72 (d, J=8 Hz, 2H), 7.62 (d, J=8 Hz, 2H), 7.54 (s, 1H), 7.36 (s, 1H), 6.78 (s, 1H), 4.39 (s, 2H), 3.92-3.54 (m, 4H), 2.01-2.20 (m, 4H), 1.47 (s, 9H). LCMS: m/z 449.0 $[M-55]^+$, $t_R$=1.82 min.

Synthesis of (4-(2-(aminomethyl)-6-chlorobenzofuran-4-yl)phenyl)(4,4-difluoropiperidin-1-yl)methanone (380)

tert-Butyl (6-chloro-4-(4-(4,4-difluoropiperidine-1-carbonyl)phenyl)benzofuran-2-yl)methylcarbamate (379; 60 mg, 0.1 mmol) was dissolved in $CH_2Cl_2$ (10 mL). TFA (2 mL) was added at 0° C. The reaction mixture was stirred at room temperature for 2 h, and concentrated under reduced pressure to give 47 mg of (4-(2-(aminomethyl)-6-chlorobenzofuran-4-yl)phenyl)(4,4-difluoropiperidin-1-yl)methanone (380), which was used without further purification in the next step. Yield (98%). LCMS: m/z 405.1 $[M+H]^+$; $t_R$=1.37 min.

Synthesis of (E)-3-(6-aminopyridin-3-yl)-N-((6-chloro-4-(4-(4,4-difluoropiperidine-1-carbonyl)phenyl)benzofuran-2-yl)methyl)acrylamide (713)

(4-(2-(Aminomethyl)-6-chlorobenzofuran-4-yl)phenyl)(4,4-difluoropiperidin-1-yl)methanone (380; 47 mg, 0.1 mmol) was dissolved in DMF (2 mL) and (E)-3-(pyridin-3-yl)acrylic acid (25 mg, 0.15 mmol) was added at 0° C. HATU (57 mg, 0.15 mmol) was added to this reaction mixture at 0° C. followed by DIPEA (38 mg, 0.3 mmol) dropwise. The reaction mixture was allowed to warm to room temperature and stirred further for 1 h. The crude mixture was purified by Prep-HPLC without workup to yield 25 mg of (E)-3-(6-aminopyridin-3-yl)-N-((6-chloro-4-(4-(4,4-difluoropiperidine-1-carbonyl)phenyl)benzofuran-2-yl)methyl)acrylamide (713). Yield (39%). $^1$H NMR (400 MHz, DMSO-d$_6$) δ 8.56 (t, J=6 Hz, 1H), 8.07 (s, 1H), 7.81 (s, 1H), 7.73 (d, J=8 Hz, 2H), 7.64-7.57 (m, 3H), 7.46 (d, J=2 Hz, 1H), 7.33 (d, J=16 Hz, 1H), 6.91 (s, 1H), 6.50-6.34 (m, 4H), 4.58 (d, J=5 Hz, 2H), 3.82-3.44 (m, 4H), 2.19-1.97 (m, 4H). LCMS: m/z 551.2 [M+H]$^+$, t$_R$=1.85 min.
Synthesis of (E)-3-(5-aminopyridin-2-yl)-N-((4-chloro-6-(4-(4,4-difluoropiperidin-1-yl)phenyl)benzofuran-2-yl)methyl)acrylamide (714)
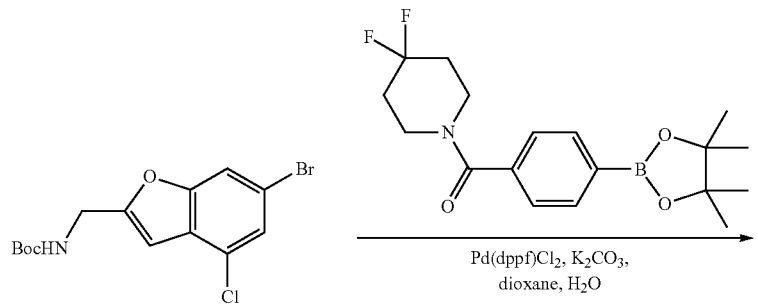
378b
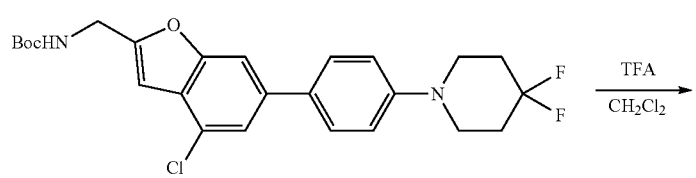
381
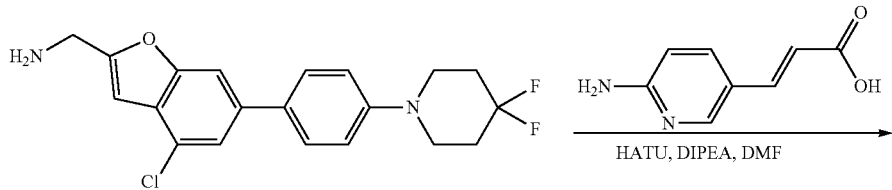
382
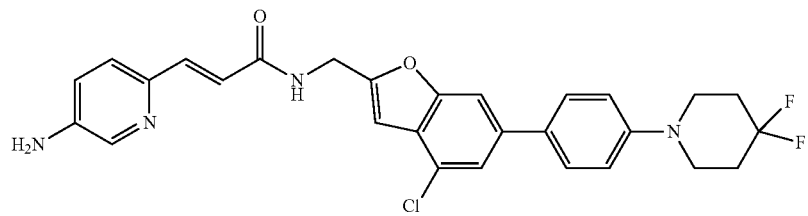
714

(E)-3-(5-aminopyridin-2-yl)-N-((4-chloro-6-(4-(4,4-difluoropiperidin-1-yl)phenyl)benzofuran-2-yl)methyl)acrylamide (714) was synthesized using the indicated reagents in a similar fashion as example (713). Yield (16%). $^1$H NMR (400 MHz, DMSO-$d_6$) δ 8.62 (t, J=5 Hz, 1H), 8.09 (s, 1H), 7.96 (s, 1H), 7.85 (d, J=8 Hz, 2H), 7.71 (s, 1H), 7.66-7.53 (m, 3H), 7.36 (d, J=16 Hz, 1H), 6.83 (s, 1H), 6.55-6.34 (m, 4H), 4.67-4.56 (m, 2H), 3.83-3.39 (m, 4H), 2.20-1.95 (m, 4H). LCMS: m/z 551.2 [M+H]$^+$, $t_R$=1.79 min.

Chiral Resolution of Compound (608).

200 mg of Compound (608) was resolved using the following conditions to afford 27 mg of single enantiomer 715 and 40 mg of single enantiomer 716:

Column: As—H (250*4.6 mm, 5 μM)
Mobile Phase; Hexanes:Methanol (0.1% DEA) (70:30)
Flow: 3 mL/min
Temp: 40° C.
Wavelengths: 214 nm and 254 mm.

Under these chiral HPLC conditions, the retention time for Compound 715 was 5.09 minutes and the retention time for Compound 716 was 5.99 minutes.

The absolute configuration of Compounds 715 and 716 has not been determined. Therefore, 715, as used herein in reference to a particular compound, refers to a compound having the indicated analytical data and a retention time of 5.09 minutes in the chiral HPLC method described above for the chiral resolution of Compound 608. 716, as used herein in reference to a particular compound, refers to a compound having the indicated analytical data and a retention time of 5.99 minutes in the chiral HPLC method described above for the chiral resolution of Compound 608. The analytical data for Compounds 715 and 716 are indicated below.

715: $^1$H NMR (400 MHz, CD$_3$OD) δ 8.12 (s, 1H), 8.07 (s, 1H), 7.84-7.64 (m, 6H), 7.50 (d, J=16 Hz, 1H), 6.93 (s, 1H), 6.62 (d, J=9 Hz, 1H), 6.49 (d, J=16 Hz, 1H), 4.72 (s, 2H), 3.93-3.59 (m, 4H), 2.34-2.01 (m, 2H), 1.67-1.48 (m, 3H). LCMS: m/z 567.3 [M+H]$^+$; $t_R$=1.38 min.

716: $^1$H NMR (400 MHz, CD$_3$OD) δ 8.12 (s, 1H), 8.07 (d, J=2 Hz, 1H), 7.83-7.64 (m, 6H), 7.50 (d, J=16 Hz, 1H), 6.92 (s, 1H), 6.61 (d, J=9 Hz, 1H), 6.49 (d, J=16 Hz, 1H), 4.72 (s, 2H), 3.94-3.60 (m, 4H), 2.35-2.01 (m, 2H), 1.66-1.48 (m, 3H). LCMS: m/z 567.3 [M+H]$^+$; $t_R$=1.38 min.

(R,E)-3-(6-aminopyridin-3-yl)-N-((5-(4-(3-fluoro-3-methylpyrrolidine-1-carbonyl)phenyl)-7-(trifluoromethyl)benzofuran-2-yl)methyl)acrylamide and (S,E)-3-(6-aminopyridin-3-yl)-N-((5-(4-(3-fluoro-3-methylpyrrolidine-1-carbonyl)phenyl)-7-(trifluoromethyl)benzofuran-2-yl)methyl)acrylamide can be depicted as follows:

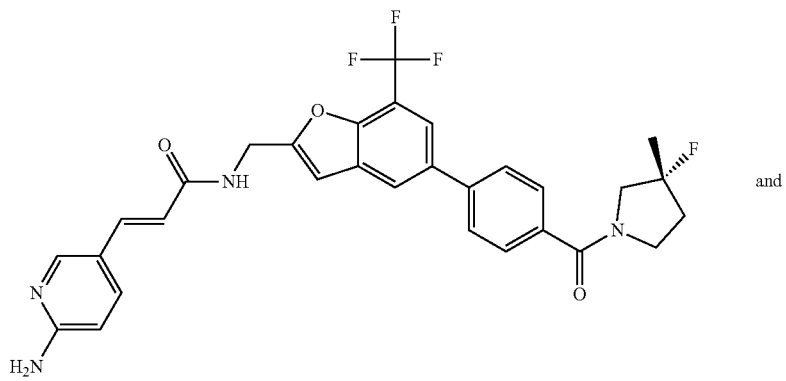

and

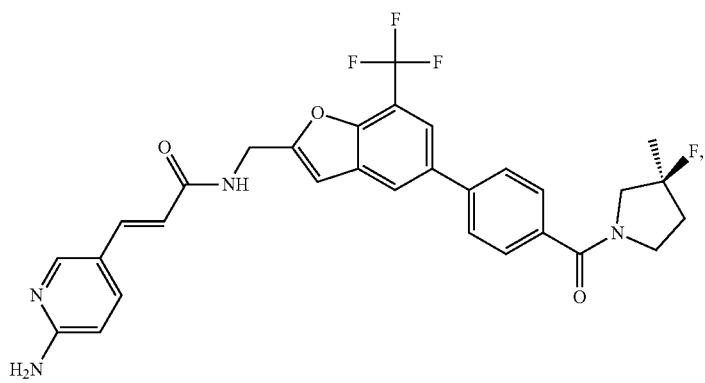

respectively.

491

Synthesis of (E)-3-(6-aminopyridin-3-yl)-N-((5-(3-(morpholine-4-carbonyl)phenyl)-7-(trifluoromethyl)benzofuran-2-yl)methyl)acrylamide (717)

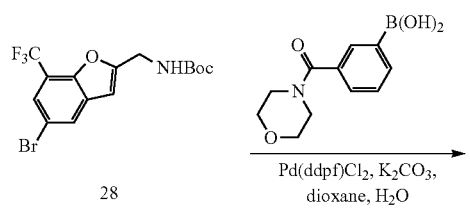

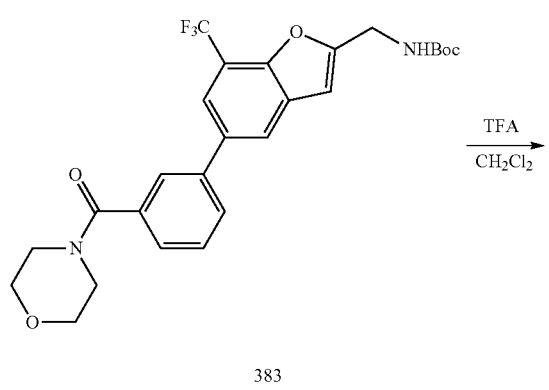

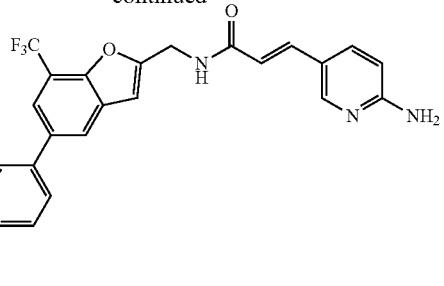

717

Synthesis of tert-butyl (5-(3-(morpholine-4-carbonyl)phenyl)-7-(trifluoromethyl)benzofuran-2-yl)methylcarbamate (383)

tert-butyl (5-(3-(morpholine-4-carbonyl)phenyl)-7-(trifluoromethyl)benzofuran-2-yl)methylcarbamate (383) was synthesized using the indicated reagents according to General Procedure 2. Yield: 67%. LCMS: m/z 504.9 [M+H]$^+$; $t_R$=1.81 min.

Synthesis of (3-(2-(aminomethyl)-7-(trifluoromethyl)benzofuran-5-yl)phenyl)(morpholino)methanone (384)

(3-(2-(aminomethyl)-7-(trifluoromethyl)benzofuran-5-yl)phenyl)(morpholino)methanone (384) ws synthesized using the indicated reagent according to General Procedure 3. Yield (100%). LCMS: m/z 404.8 [M+H]$^+$; $t_R$=1.27 min.

Synthesis of (E)-3-(6-aminopyridin-3-yl)-N-((5-(3-(morpholine-4-carbonyl)phenyl)-7-(trifluoromethyl)benzofuran-2-yl)methyl)acrylamide (717)

(E)-3-(6-aminopyridin-3-yl)-N-((5-(3-(morpholine-4-carbonyl)phenyl)-7-(trifluoromethyl)benzofuran-2-yl)methyl)acrylamide (717) was synthesized using the indicated reagents according to General Procedure 4. (45 mg, yield: 48%). $^1$H NMR (400 MHz, DMSO-d$_6$) δ 8.86-8.83 (m, 1H), 8.26-7.42 (m, 11H), 6.96 (s, 1H), 6.91 (d, J=10 Hz, 1H), 6.58 (d, J=16 Hz, 1H), 4.64 (d, J=6 Hz, 2H), 3.65-3.40 (m, 8H). LCMS: m/z 550.8 [M+H]$^+$, $t_R$=1.35 min.

Synthesis of (E)-3-(6-aminopyridin-3-yl)-N-((6-(5-(4,4-difluoropiperidine-1-carbonyl)pyridin-2-yl)benzofuran-2-yl)methyl)acrylamide (718)

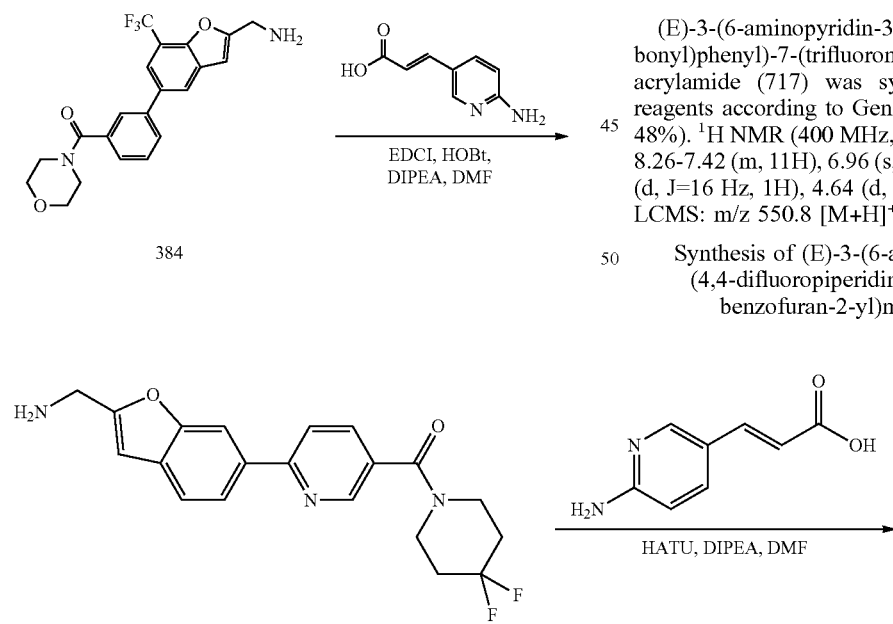

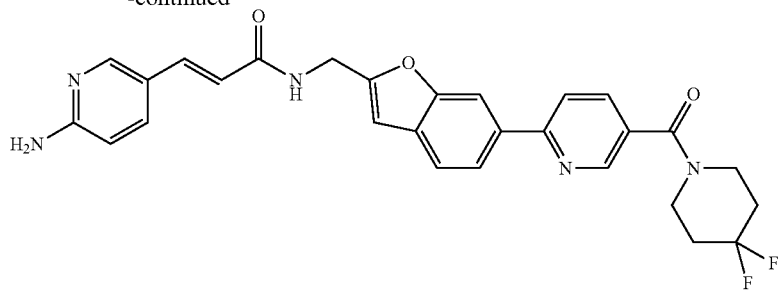

718

(E)-3-(6-Aminopyridin-3-yl)-N-((6-(5-(4,4-difluoropiperidine-1-carbonyl)pyridin-2-yl)benzofuran-2-yl)methyl)acrylamide (718) was synthesized using the indicated reagents according to General Procedure 4. Yield: 46%. $^1$H NMR (400 MHz, DMSO-d$_6$) δ 8.85 (t, J=6 Hz, 1H), 8.75 (s, 1H), 8.41-8.20 (m, 4H), 8.17-8.04 (m, 3H), 7.98 (dd, J=8 Hz, 2 Hz, 1H), 7.71 (d, J=8 Hz, 1H), 7.45 (d, J=16 Hz, 1H), 7.02 (d, J=9 Hz, 1H), 6.83 (s, 1H), 6.62 (d, J=16 Hz, 1H), 4.61 (d, J=5 Hz, 2H), 3.81-3.45 (m, 4H), 2.15-2.02 (m, 4H). LCMS: m/z 518.2 [M+H]$^+$, t$_R$=1.27 min.

Synthesis of (E)-N-((5-(5-(4,4-difluoropiperidine-1-carbonyl)pyridin-2-yl)-7-(4-fluorophenyl)benzofuran-2-yl)methyl)-3-(pyridin-3-yl)acrylamide (719)

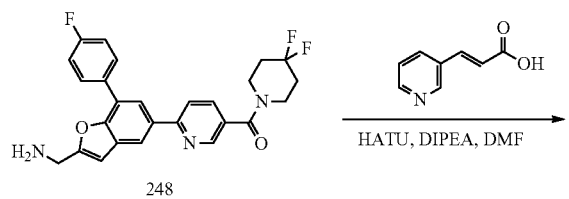

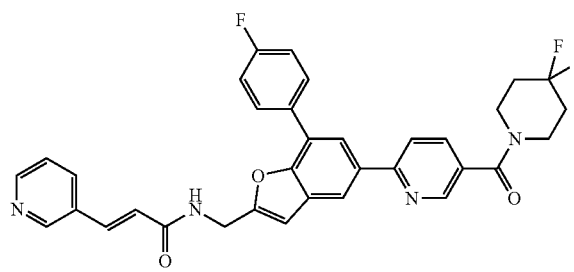

719

(E)-N-((5-(5-(4,4-difluoropiperidine-1-carbonyl)pyridin-2-yl)-7-(4-fluorophenyl)benzofuran-2-yl)methyl)-3-(pyridin-3-yl)acrylamide (719) was synthesized using the indicated reagents according to General Procedure 4. Yield: 18%. $^1$H NMR (400 MHz, DMSO-d$_6$) δ 8.94-8.87 (m, 1H), 8.83 (s, 1H), 8.77 (s, 1H), 8.64-8.56 (m, 1H), 8.39 (s, 1H), 8.27-7.95 (m, 6H), 7.62-7.49 (m, 2H), 7.44-7.35 (m, 2H), 6.95 (s, 1H), 6.84 (d, J=16 Hz, 1H), 4.64 (d, J=5 Hz, 2H), 3.81-3.46 (m, 4H), 2.18-2.01 (m, 4H). LCMS: m/z 597.2 [M+H]$^+$, t$_R$=1.53 min.

Synthesis of (E)-N-((5-(5-(4,4-difluoropiperidine-1-carbonyl)pyridin-2-yl)-7-(3-fluorophenyl)benzofuran-2-yl)methyl)-3-(pyridin-3-yl)acrylamide (720)

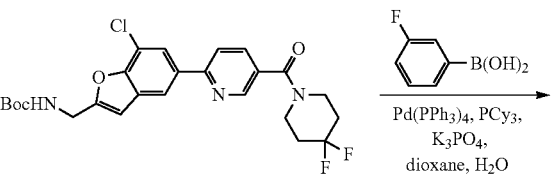

223

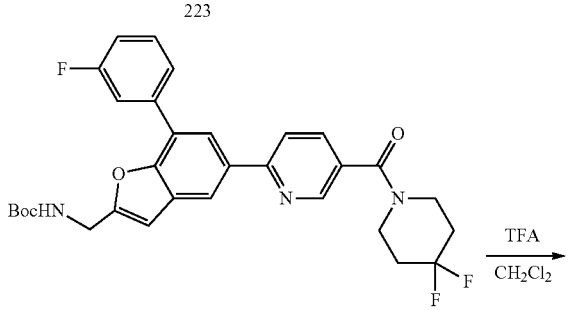

385

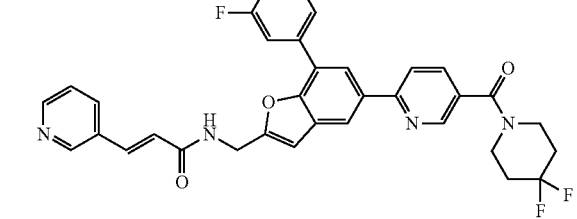

720

495

(E)-N-((5-(5-(4,4-difluoropiperidine-1-carbonyl)pyridin-2-yl)-7-(3-fluorophenyl)benzofuran-2-yl)methyl)-3-(pyridin-3-yl)acrylamide (720) was synthesized using the indicated reagents in a similar fashion as example (699). Yield: 52%. $^1$H NMR (500 MHz, DMSO-$d_6$) δ 8.97-8.90 (m, 1H), 8.90-8.85 (m, 1H), 8.80-8.74 (m, 1H), 8.68-8.62 (m, 1H), 8.44 (s, 1H), 8.32-8.16 (m, 3H), 8.04-7.98 (m, 1H), 7.88-7.80 (m, 2H), 7.65-7.55 (m, 3H), 7.34-7.27 (m, 1H), 6.98 (s, 1H), 6.88 (d, J=16 Hz, 1H), 4.69-4.62 (m, 2H), 3.82-3.45 (m, 4H), 2.16-2.02 (m, 4H). LCMS: m/z 597.2 [M+H]$^+$, $t_R$=1.53 min.

Synthesis of (E)-N-((5'-(5-(4,4-difluoropiperidine-1-carbonyl)pyridin-2-yl)-[2,7'-bibenzofuran]-2'-yl)methyl)-3-(pyridin-3-yl)acrylamide (721)

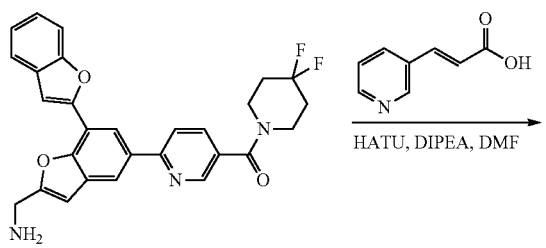

255

496

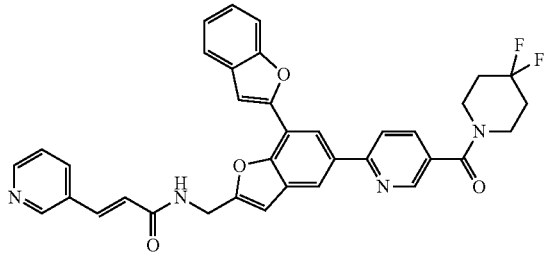

721

(E)-N-((5'-(5-(4,4-difluoropiperidine-1-carbonyl)pyridin-2-yl)-[2,7'-bibenzofuran]-2'-yl)methyl)-3-(pyridin-3-yl)acrylamide (721) was synthesized using the indicated reagents according to General Procedure 4. Yield: 40%. $^1$H NMR (400 MHz, CD$_3$OD) δ 9.02-8.94 (m, 1H), 8.82 (s, 1H), 8.76-8.68 (m, 1H), 8.65 (s, 1H), 8.56 (d, J=8 Hz, 1H), 8.29 (s, 1H), 8.17-8.03 (m, 2H), 7.87 (s, 1H), 7.79-7.68 (m, 3H), 7.63 (d, J=8 Hz, 1H), 7.42-7.27 (m, 2H), 7.04-6.94 (m, 2H), 4.86 (s, 2H), 4.00-3.63 (m, 4H), 2.22-2.05 (m, 4H). LCMS: m/z 619.2 [M+H]$^+$, $t_R$=1.61 min.

Synthesis of (E)-3-(6-aminopyridin-3-yl)-N-((5-(4-(4,4-difluoropiperidine-1-carbonyl)phenyl)-7-(pyridin-4-yl)benzofuran-2-yl)methyl)acrylamide (722)

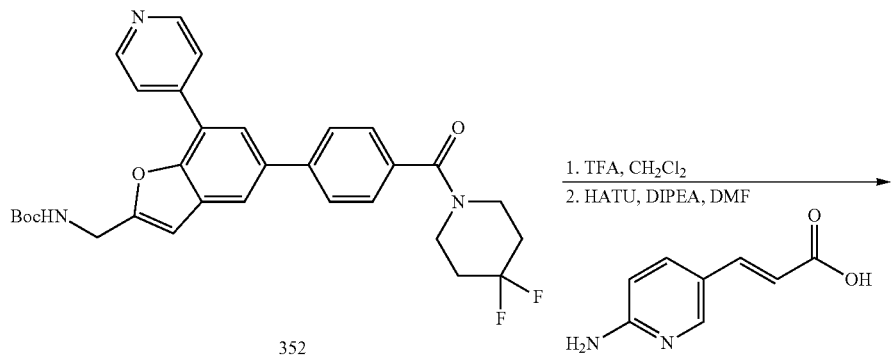

352

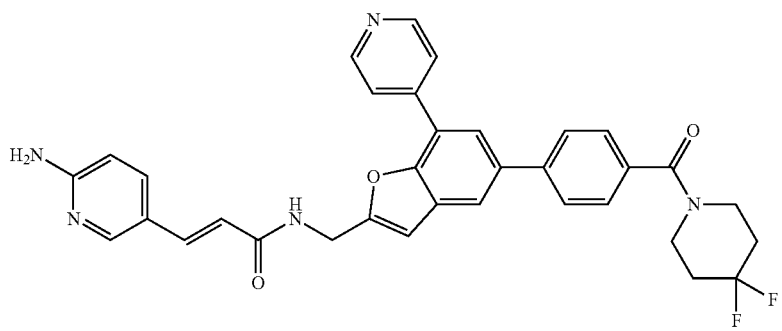

722

(E)-3-(6-aminopyridin-3-yl)-N-((5-(4-(4,4-difluoropiperidine-1-carbonyl)phenyl)-7-(pyridin-4-yl)benzofuran-2-yl)methyl)acrylamide (722) was synthesized using the indicated reagents according to General Procedures 3 and 4. Yield: 40%. ¹H NMR (400 MHz, DMSO-d₆) δ 8.73 (d, J=6 Hz, 2H), 8.63 (t, J=6 Hz, 1H), 8.11-8.01 (m, 4H), 7.96-7.86 (m, 3H), 7.65-7.54 (m, 3H), 7.37 (d, J=16 Hz, 1H), 6.90 (s, 1H), 6.53-6.38 (m, 4H), 4.62 (d, J=5 Hz, 2H), 3.78-3.44 (m, 4H), 2.14-2.01 (m, 4H). LCMS: m/z 594.2 [M+H]⁺, $t_R$=1.68 min.

Synthesis of (E)-N-((5-(4-(4,4-difluoropiperidine-1-carbonyl)phenyl)-7-(pyridin-4-yl)benzofuran-2-yl)methyl)-3-(pyridin-3-yl)acrylamide (723)

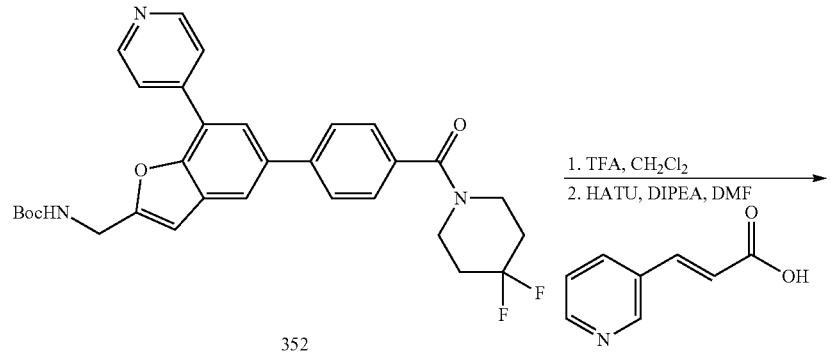

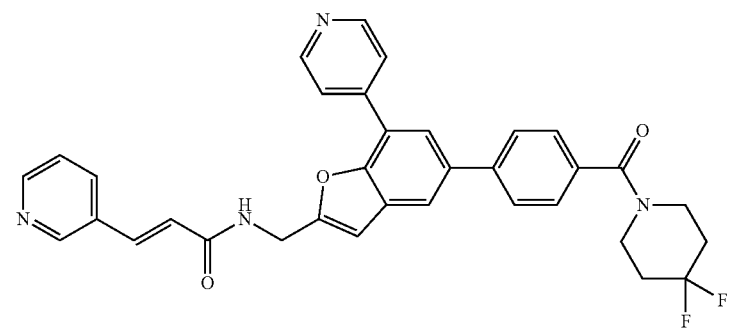

(E)-N-((5-(4-(4,4-difluoropiperidine-1-carbonyl)phenyl)-7-(pyridin-4-yl)benzofuran-2-yl)methyl)-3-(pyridin-3-yl)acrylamide (723) was synthesized using the indicated reagents according to General Procedures 3 and 4. Yield: 48%. ¹H NMR (400 MHz, DMSO-d₆) δ 8.90 (t, J=6 Hz, 1H), 8.82-8.71 (m, 3H), 8.57 (d, J=4 Hz, 1H), 8.09-7.99 (m, 4H), 7.97-7.86 (m, 3H), 7.62-7.52 (m, 3H), 7.49-7.42 (m, 1H), 6.94 (s, 1H), 6.83 (d, J=16 Hz, 1H), 4.66 (d, J=5 Hz, 2H), 3.79-3.43 (m, 4H), 2.14-1.99 (m, 4H). LCMS: m/z 579.2 [M+H]⁺, $t_R$=1.72 min.

Synthesis of (E)-3-(6-aminopyridin-3-yl)-N-((5-(4-(4,4-difluoropiperidine-1-carbonyl)phenyl)-7-(pyridin-3-yl)benzofuran-2-yl)methyl)acrylamide (724)

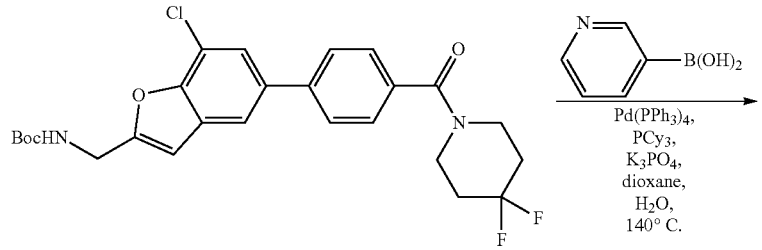

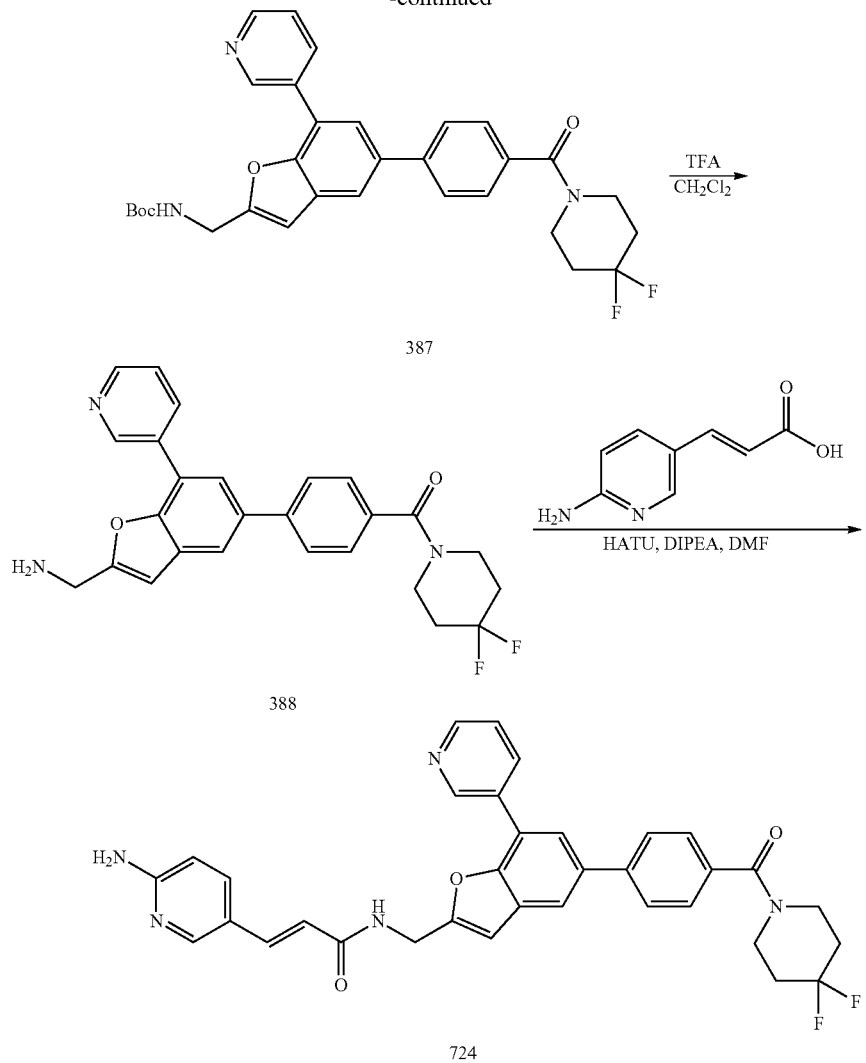

(E)-3-(6-aminopyridin-3-yl)-N-((5-(4-(4,4-difluoropiperidine-1-carbonyl)phenyl)-7-(pyridin-3-yl)benzofuran-2-yl)methyl)acrylamide (724) was synthesized using the indicated reagents in a similar fashion as example (699). $^1$H NMR (400 MHz, DMSO-$d_6$) δ 9.24 (s, 1H), 8.86-8.79 (m, 1H), 8.71-8.65 (m, 1H), 8.50-8.41 (m, 1H), 8.20 (s, 1H), 8.13-8.06 (m, 1H), 8.02-7.98 (m, 1H), 7.93-7.86 (m, 2H), 7.68-7.52 (m, 3H), 7.45 (d, J=16 Hz, 1H), 6.97 (d, J=9 Hz, 1H), 6.91 (s, 1H), 6.59 (d, J=16 Hz, 1H), 4.63 (d, J=5 Hz, 2H), 3.60-3.43 (m, 4H), 2.16-1.98 (m, 4H). LCMS: m/z 594.2 [M+H]$^+$, $t_R$=1.34 min.

Synthesis of (E)-N-((5-(4-(4,4-difluoropiperidine-1-carbonyl)phenyl)-7-(pyridin-3-yl)benzofuran-2-yl)methyl)-3-(pyridin-3-yl)acrylamide (725)

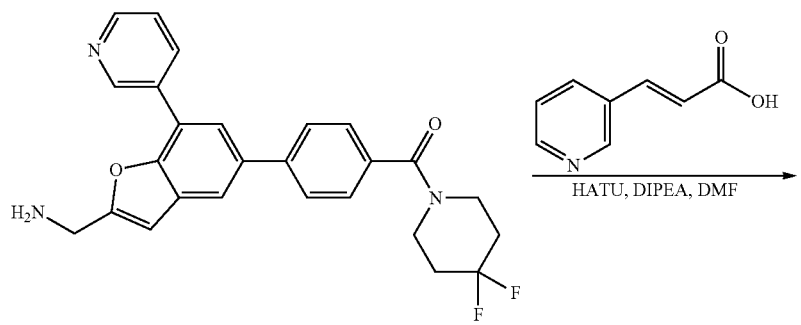

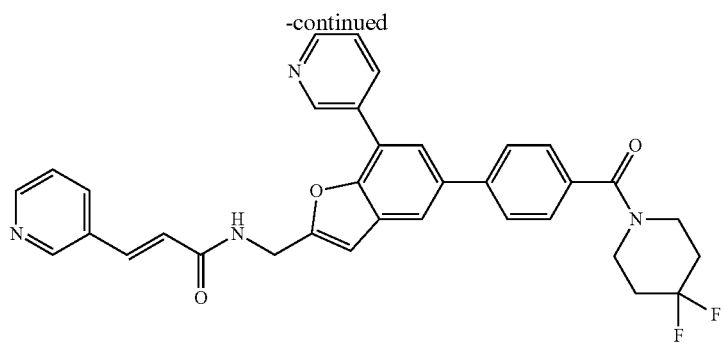

725

(E)-N-((5-(4-(4,4-difluoropiperidine-1-carbonyl)phenyl)-7-(pyridin-3-yl)benzofuran-2-yl)methyl)-3-(pyridin-3-yl)acrylamide (725) was synthesized using the indicated reagents according to General Procedure 4. Yield: 20%. $^1$H NMR (400 MHz, DMSO-$d_6$) δ 9.32 (d, J=2 Hz, 1H), 8.93 (t, J=6 Hz, 1H), 8.90-8.84 (m, 1H), 8.78-8.72 (m, 1H), 8.67-8.60 (m, 2H), 8.21-8.15 (m, 1H), 8.03 (d, J=2 Hz, 1H), 7.96-7.87 (m, 3H), 7.81-7.74 (m, 1H), 7.63-7.54 (m, 4H), 6.95 (s, 1H), 6.86 (d, J=16 Hz, 1H), 4.66 (d, J=6 Hz, 2H), 3.78-3.45 (m, 4H), 2.13-1.99 (m, 4H). LCMS: m/z 579.2 [M+H]$^+$, $t_R$=1.74 min.

Synthesis of (E)-3-(6-aminopyridin-3-yl)-N-((5-(4-(4,4-difluoropiperidine-1-carbonyl)phenyl)-7-(3-fluorophenyl)benzofuran-2-yl)methyl)acrylamide (726)

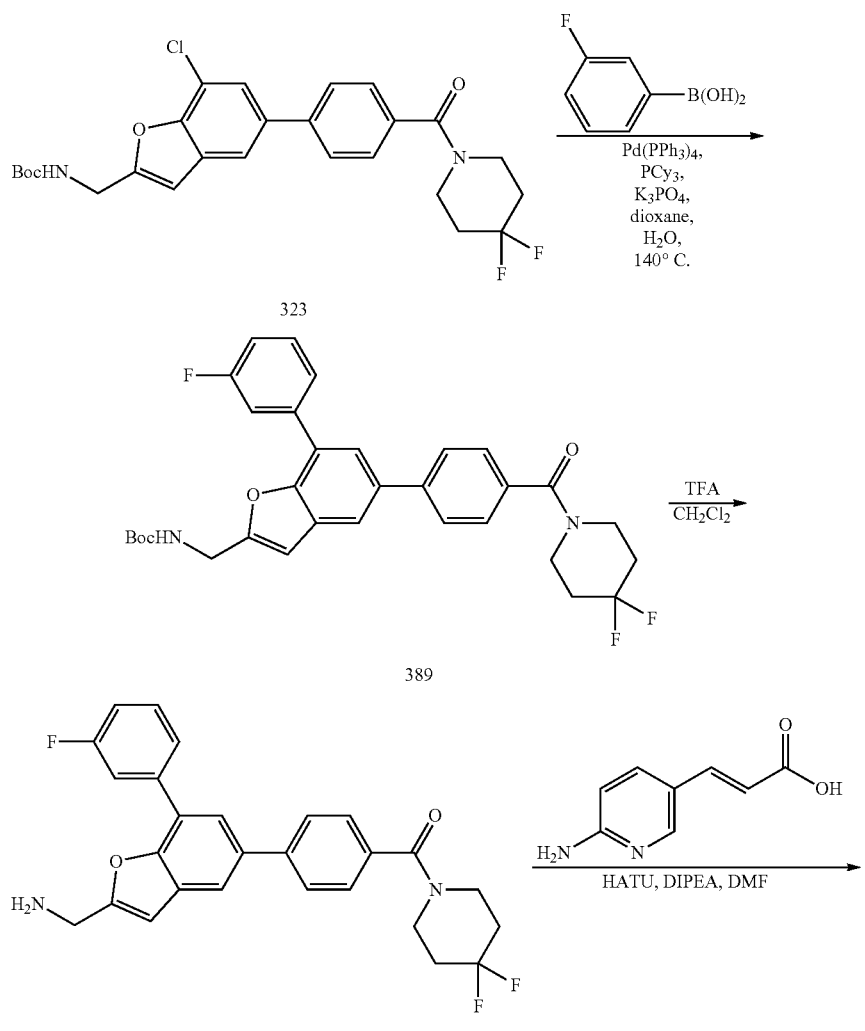

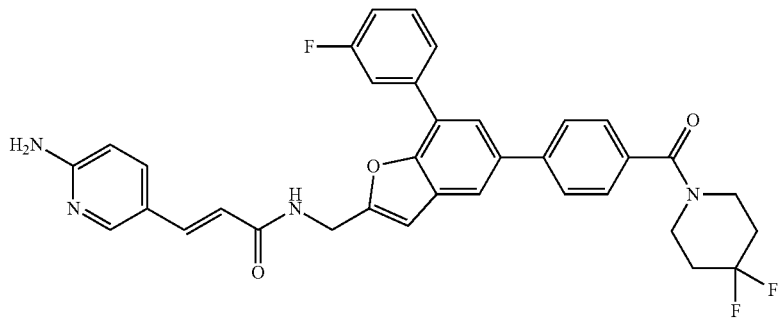

726

(E)-3-(6-aminopyridin-3-yl)-N-((5-(4-(4,4-difluoropiperidine-1-carbonyl)phenyl)-7-(3-fluorophenyl)benzofuran-2-yl)methyl)acrylamide (726) was synthesized using the indicated reagents in a similar fashion as example (699). $^1$H NMR (400 MHz, DMSO-$d_6$) δ 8.81 (t, J=6 Hz, 1H), 8.20 (s, 1H), 8.10-8.03 (m, 1H), 7.96 (d, J=2 Hz, 1H), 7.92-7.81 (m, 6H), 7.63-7.54 (m, 4H), 7.44 (d, J=16 Hz, 1H), 7.33-7.24 (m, 1H), 6.95 (d, J=9 Hz, 1H), 6.89 (s, 1H), 6.59 (d, J=16 Hz, 1H), 4.63 (d, J=6 Hz, 2H), 3.81-3.60 (m, 4H), 2.15-2.01 (m, 4H). LCMS: m/z 611.3 [M+H]$^+$, $t_R$=1.79 min.

Synthesis of (E)-N-((5-(4-(4,4-difluoropiperidine-1-carbonyl)phenyl)-7-(3-fluorophenyl)benzofuran-2-yl)methyl)-3-(pyridin-3-yl)acrylamide (727)

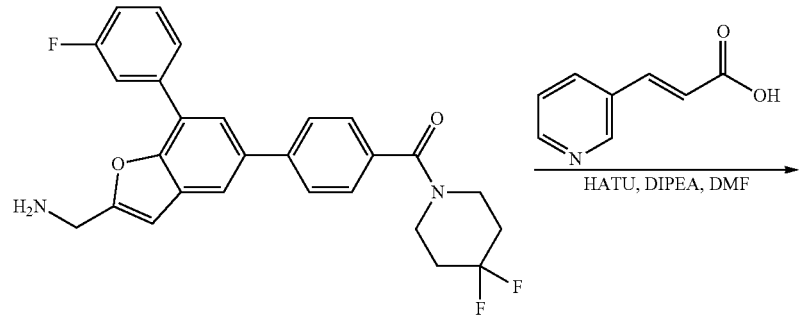

390

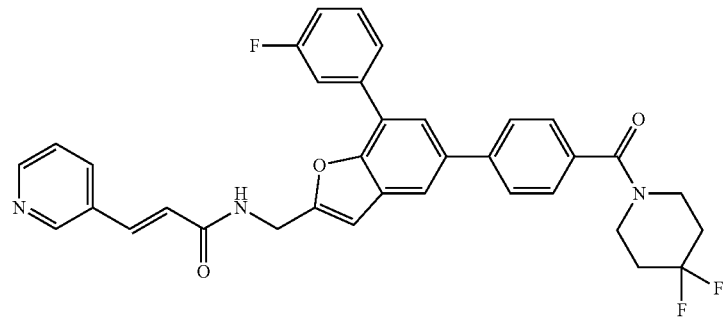

725

(E)-N-((5-(4-(4,4-difluoropiperidine-1-carbonyl)phenyl)-7-(3-fluorophenyl)benzofuran-2-yl)methyl)-3-(pyridin-3-yl)acrylamide (727) was synthesized using the indicated reagents according to General Procedure 4. Yield: 39%. $^1$H NMR (400 MHz, DMSO-$d_6$) δ 8.88 (t, J=6 Hz, 1H), 8.78 (d, J=2 Hz, 1H), 8.59-8.53 (m, 1H), 8.01 (d, J=8 Hz, 1H), 7.96 (d, J=2 Hz, 1H), 7.93-7.81 (m, 5H), 7.63-7.51 (m, 4H), 7.49-7.42 (m, 1H), 7.32-7.25 (m, 1H), 6.91 (s, 1H), 6.82 (d, J=16 Hz, 1H), 4.65 (d, J=6 Hz, 2H), 3.81-3.44 (m, 4H), 2.14-2.00 (m, 4H). LCMS: m/z 596.3 [M+H]$^+$, $t_R$=2.11 min.

Synthesis of (E)-3-(6-aminopyridin-3-yl)-N-((5-(4-(4,4-difluoropiperidine-1-carbonyl)phenyl)-7-(4-fluorophenyl)benzofuran-2-yl)methyl)acrylamide (728)

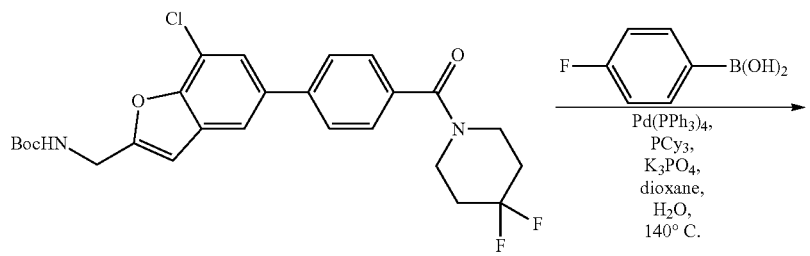

323

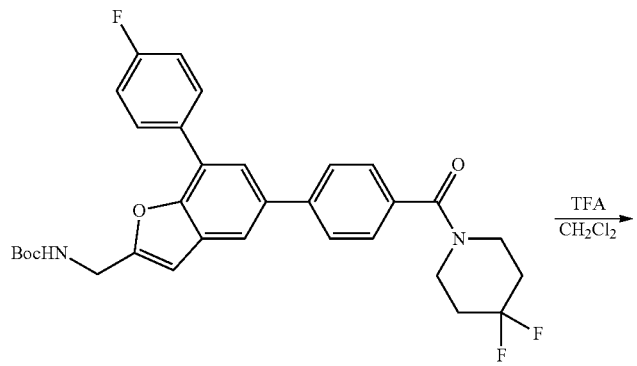

391

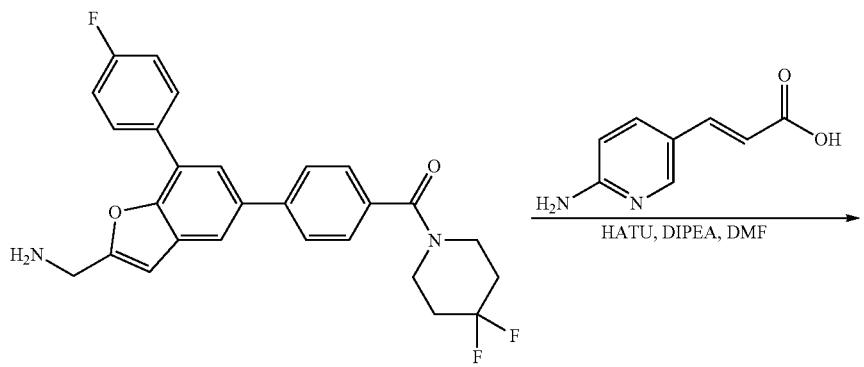

392

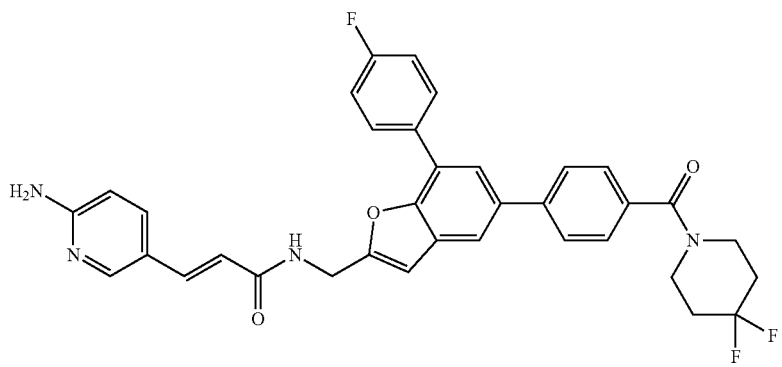

728

(E)-3-(6-aminopyridin-3-yl)-N-((5-(4-(4,4-difluoropiperidine-1-carbonyl)phenyl)-7-(4-fluorophenyl)benzofuran-2-yl)methyl)acrylamide (728) was synthesized using the indicated reagents in a similar fashion as example (699). $^1$H NMR (400 MHz, DMSO-d$_6$) δ 8.83 (t, J=6 Hz, 1H), 8.27-8.15 (m, 2H), 8.13-8.00 (m, 3H), 7.92 (d, J=2 Hz, 1H), 7.87 (d, J=8 Hz, 2H), 7.82-7.71 (m, 2H), 7.61-7.52 (m, 2H), 7.49-7.33 (m, 3H), 6.99 (d, J=9 Hz, 1H), 6.88 (s, 1H), 6.60 (d, J=16 Hz, 1H), 4.62 (d, J=6 Hz, 2H), 3.80-3.40 (m, 4H), 2.14-1.98 (m, 4H). LCMS: m/z 611.3 [M+H]$^+$, t$_R$=1.88 min.

Synthesis of (E)-3-(6-aminopyridin-3-yl)-N-((5-(4-(4,4-difluoropiperidine-1-carbonyl)phenyl)-7-(4-fluorophenyl)benzofuran-2-yl)methyl)acrylamide (729)

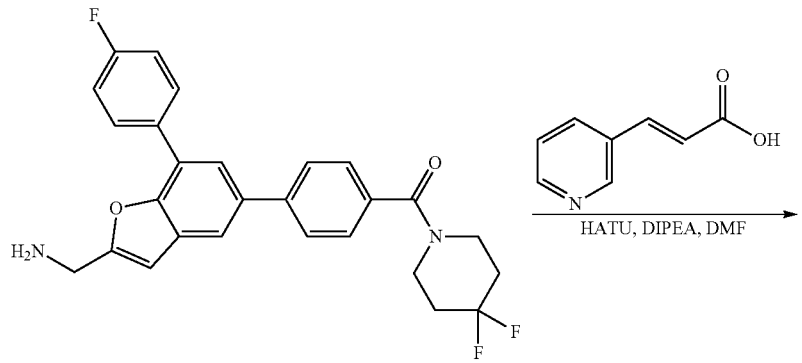

392

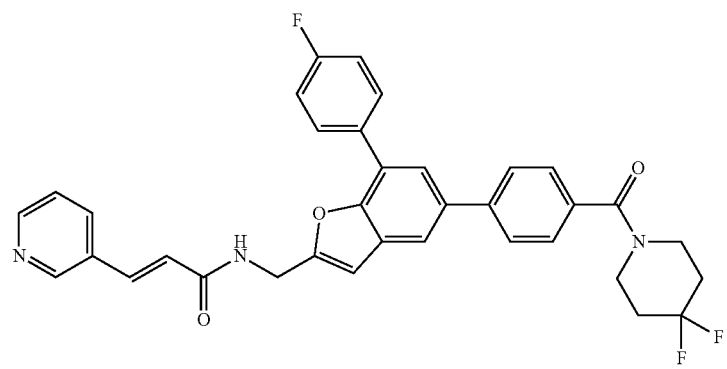

729

(E)-3-(6-aminopyridin-3-yl)-N-((5-(4-(4,4-difluoropiperidine-1-carbonyl)phenyl)-7-(4-fluorophenyl)benzofuran-2-yl)methyl)acrylamide (729) was synthesized using the inciated reagents according to General Procedure 4. Yield: 19%. $^1$H NMR (400 MHz, DMSO-d$_6$) δ 8.88 (t, J=6 Hz, 1H), 8.78 (d, J=2 Hz, 1H), 8.59-8.54 (m, 1H), 8.08-7.98 (m, 3H), 7.93 (d, J=2 Hz, 1H), 7.87 (d, J=8 Hz, 2H), 7.77 (d, J=2 Hz, 1H), 7.60-7.51 (m, 3H), 7.48-7.43 (m, 1H), 7.42-7.34 (m, 2H), 6.90 (s, 1H), 6.82 (d, J=16 Hz, 1H), 4.63 (d, J=5 Hz, 2H), 3.79-3.44 (m, 4H), 2.14-2.01 (m, 4H). LCMS: m/z 596.3 [M+H]$^+$, t$_R$=1.92 min.

Synthesis of (E)-3-(6-aminopyridin-3-yl)-N-((7-(5-chloro-2-methoxyphenyl)-5-(4-(4,4-difluoropiperidine-1-carbonyl)phenyl)benzofuran-2-yl)methyl)acrylamide (730)

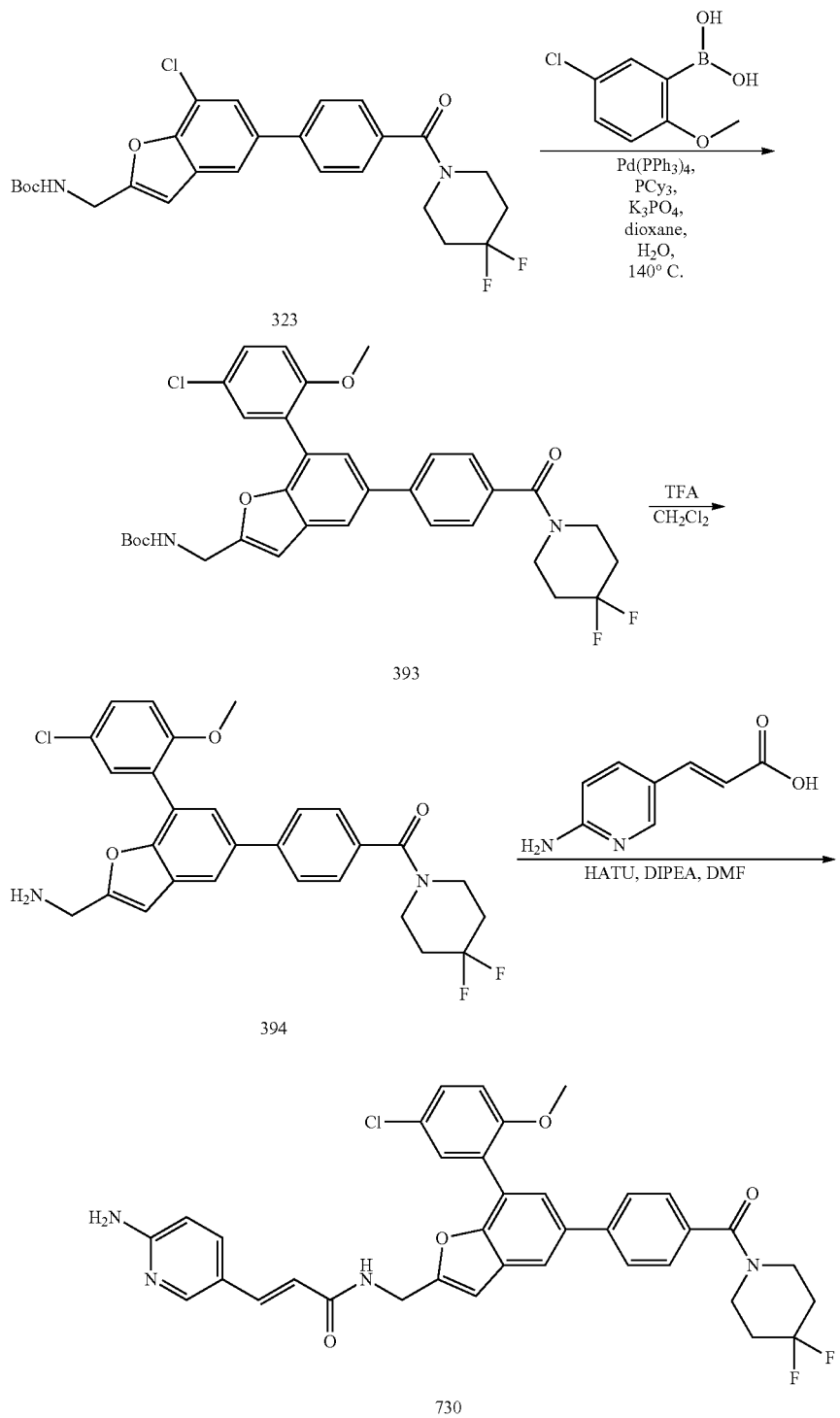

511

(E)-3-(6-aminopyridin-3-yl)-N-((7-(5-chloro-2-methoxyphenyl)-5-(4-(4,4-difluoropiperidine-1-carbonyl)phenyl)benzofuran-2-yl)methyl)acrylamide (730) was synthesized using the indicated reagents in a similar fashion as example (699). $^1$H NMR (400 MHz, DMSO-$d_6$) δ 8.54 (t, J=6 Hz, 1H), 8.07 (d, J=2 Hz, 1H), 7.91 (d, J=2 Hz, 1H), 7.81 (d, J=8 Hz, 2H), 7.62-7.46 (m, 6H), 7.33 (d, J=16 Hz, 1H), 7.22 (d, J=9 Hz, 1H), 6.82 (s, 1H), 6.49-6.36 (m, 4H), 4.52 (d, J=6 Hz, 2H), 3.76 (s, 3H), 3.72-3.44 (m, 4H), 2.13-1.99 (m, 4H). LCMS: m/z 657.3 [M+H]$^+$, $t_R$=1.89 min.

512

Synthesis of (E)-3-(6-aminopyridin-3-yl)-N-((5-(4-(4,4-difluoropiperidine-1-carbonyl)phenyl)-7-(3-(trifluoromethyl)phenyl)benzofuran-2-yl)methyl)acrylamide (731)

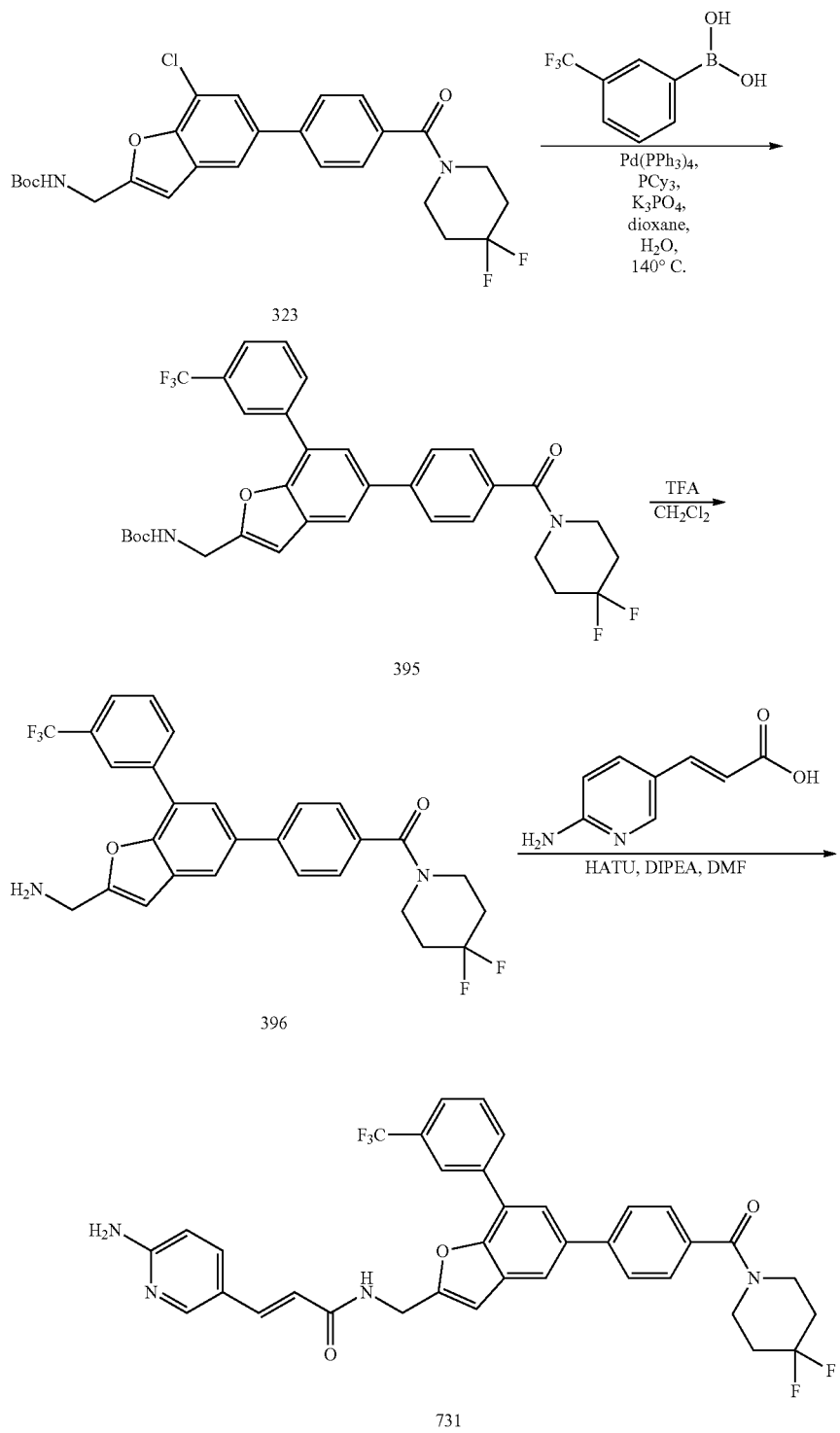

513

(E)-3-(6-aminopyridin-3-yl)-N-((5-(4-(4,4-difluoropiperidine-1-carbonyl)phenyl)-7-(3-(trifluoromethyl)phenyl)benzofuran-2-yl)methyl)acrylamide (731) was synthesized using the indicated reagents in a similar fashion as example (699). $^1$H NMR (400 MHz, DMSO-d$_6$) δ 8.82 (t, J=6 Hz, 1H), 8.34-8.06 (m, 6H), 7.99 (d, J=2 Hz, 1H), 7.93-7.85 (m, 3H), 7.84-7.75 (m, 2H), 7.57 (d, J=8 Hz, 2H), 7.45 (d, J=16 Hz, 1H), 6.99 (d, J=9 Hz, 1H), 6.91 (s, 1H), 6.60 (d, J=16

514

Hz, 1H), 4.63 (d, J=6 Hz, 2H), 3.79-3.42 (m, 4H), 2.14-1.97 (m, 4H). LCMS: m/z 661.2 [M+H]$^+$, t$_R$=1.54 min.

Synthesis of (E)-3-(6-aminopyridin-3-yl)-N-((7-(3-cyanophenyl)-5-(4-(4,4-difluoropiperidine-1-carbonyl)phenyl)benzofuran-2-yl)methyl)acrylamide (732)

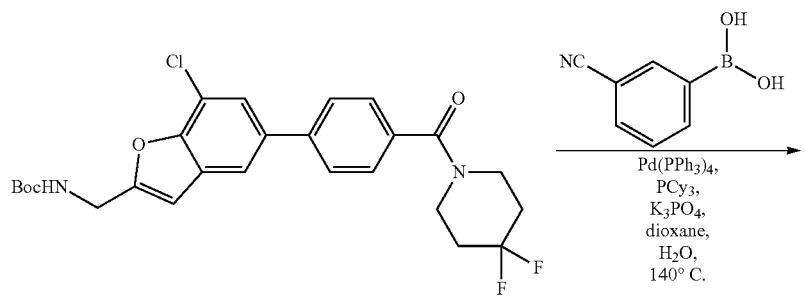

323

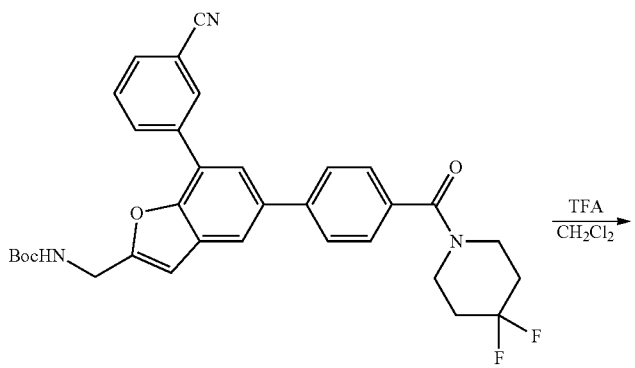

397

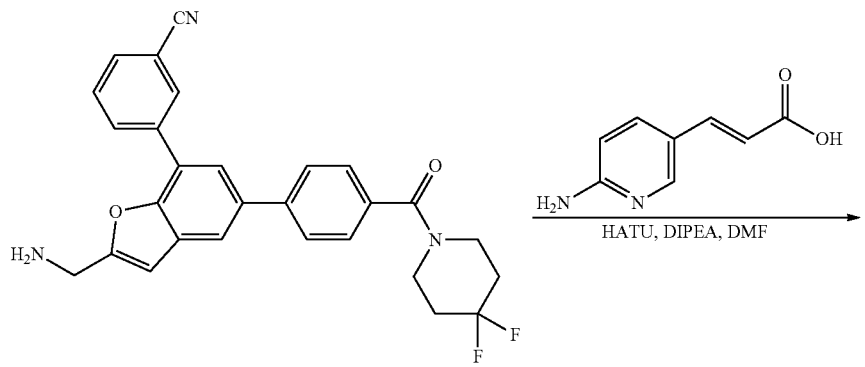

398

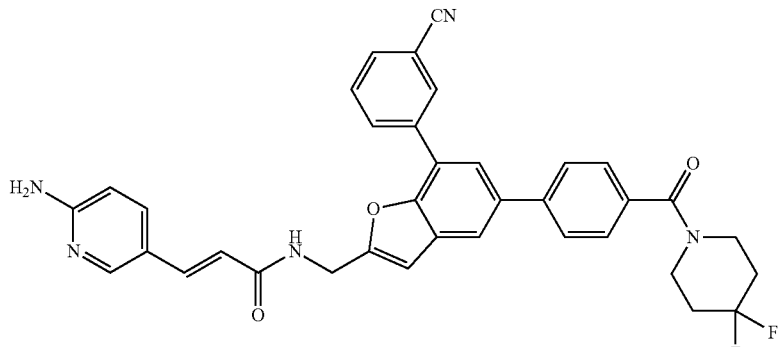
732
(E)-3-(6-aminopyridin-3-yl)-N-((7-(3-cyanophenyl)-5-(4-(4,4-difluoropiperidine-1-carbonyl)phenyl)benzofuran-2-yl)methyl)acrylamide (732). $^1$H NMR (400 MHz, DMSO-$d_6$) δ 8.66-8.59 (m, 1H), 8.48 (s, 1H), 8.38 (d, J=8 Hz, 1H), 8.10-8.06 (m, 1H), 8.01-7.96 (m, 1H), 7.96-7.87 (m, 4H), 7.76 (t, J=8 Hz, 1H), 7.65-7.53 (m, 3H), 7.37 (d, J=16 Hz, 1H), 6.89 (s, 1H), 6.54-6.38 (m, 4H), 4.61 (d, J=5 Hz, 2H), 3.81-3.46 (m, 4H), 2.16-1.99 (m, 4H). LCMS: m/z 618.2 [M+H]$^+$, $t_R$=1.81 min.
Synthesis of (E)-3-(6-aminopyridin-3-yl)-N-((5-(4-(4,4-difluoropiperidine-1-carbonyl)phenyl)-7-(4-(trifluoromethyl)phenyl)benzofuran-2-yl)methyl)acrylamide (733)
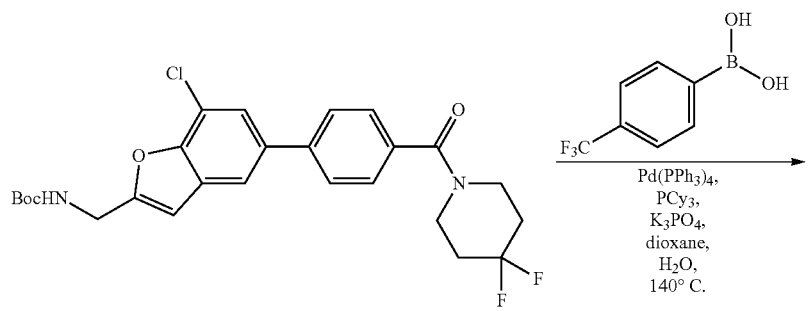
323
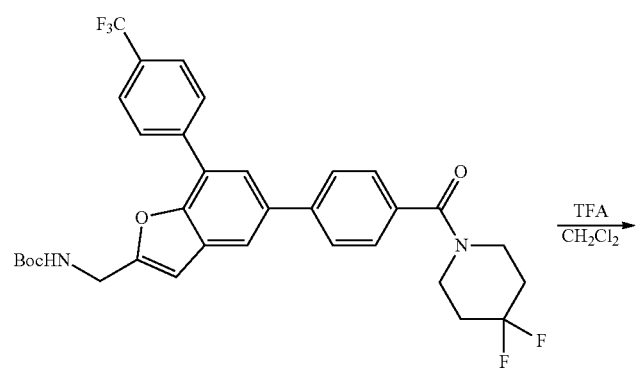
399

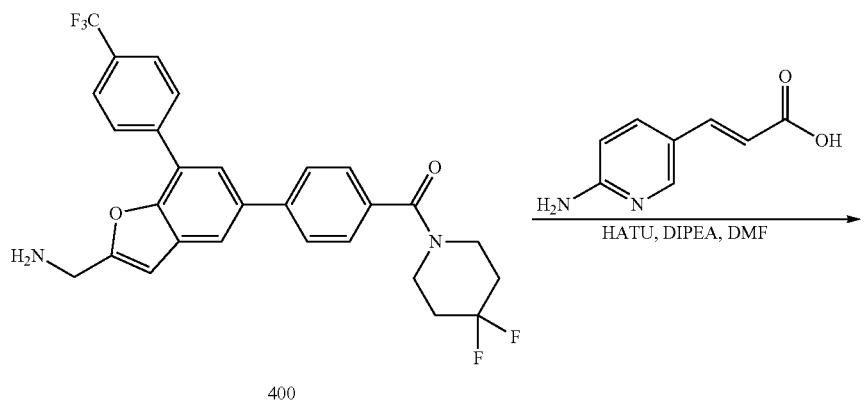

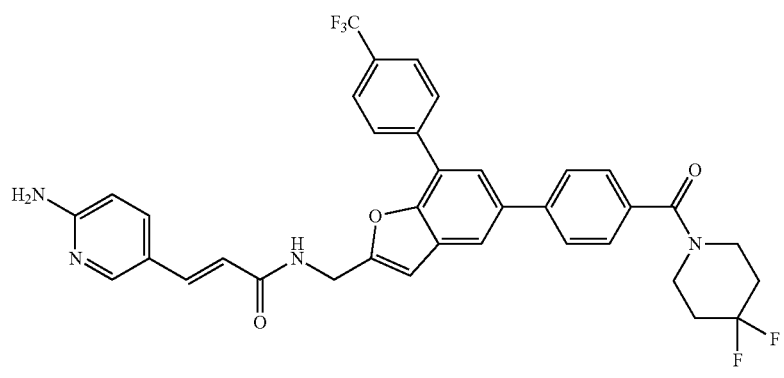

(E)-3-(6-aminopyridin-3-yl)-N-((5-(4-(4,4-difluoropiperidine-1-carbonyl)phenyl)-7-(4-(trifluoromethyl)phenyl)benzofuran-2-yl)methyl)acrylamide (733) was synthesized using the indicated reagents in a similar fashion as example (699). $^1$H NMR (400 MHz, DMSO-$d_6$) δ 8.61 (t, J=6 Hz, 1H), 8.26-8.18 (m, 2H), 8.08 (s, 1H), 7.99 (s, 1H), 7.95-7.83 (m, 5H), 7.64-7.53 (m, 3H), 7.36 (d, J=16 Hz, 1H), 6.89 (s, 1H), 6.49-6.30 (m, 4H), 4.60 (d, J=5 Hz, 2H), 3.80-3.43 (m, 4H), 2.13-1.99 (m, 4H). LCMS: m/z 661.3 [M+H]$^+$, $t_R$=1.93 min.

Synthesis of (E)-3-(6-aminopyridin-3-yl)-N-((7-(3,5-difluorophenyl)-5-(4-(4,4-difluoropiperidine-1-carbonyl)phenyl)benzofuran-2-yl)methyl)acrylamide (734)

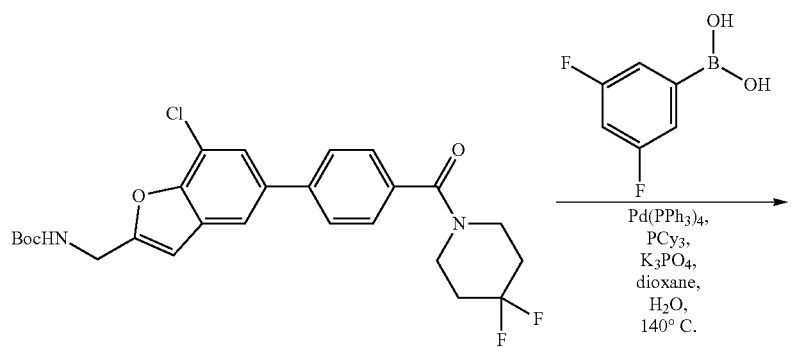

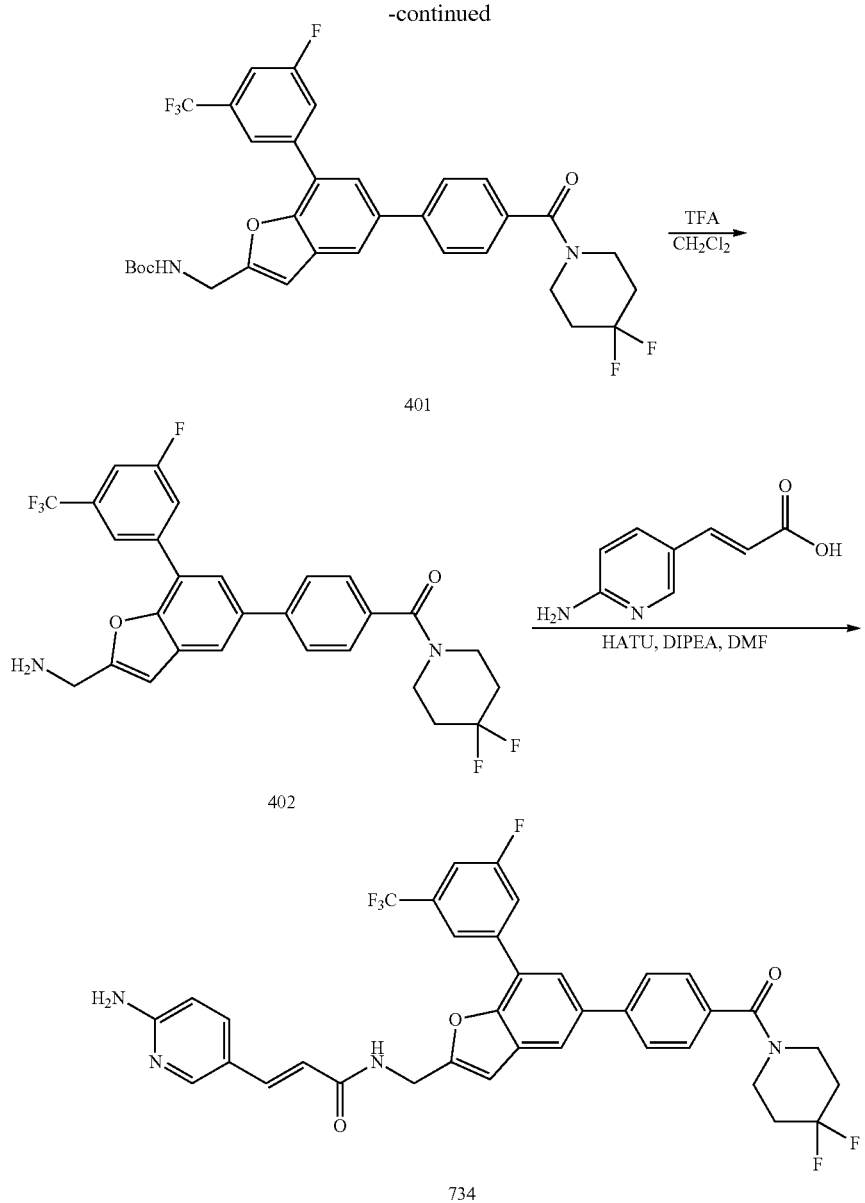
(E)-3-(6-aminopyridin-3-yl)-N-((7-(3,5-difluorophenyl)-5-(4-(4,4-difluoropiperidine-1-carbonyl)phenyl)benzofuran-2-yl)methyl)acrylamide (734) was synthesized using the indicated reagents in a similar fashion as example (699). $^1$H NMR (400 MHz, DMSO-$d_6$) δ 8.63 (t, J=5 Hz, 1H), 8.08 (s, 1H), 7.99 (s, 1H), 7.94-7.87 (m, 3H), 7.84-7.77 (m, 2H), 7.65-7.53 (m, 3H), 7.41-7.29 (m, 2H), 6.92-6.85 (m, 1H), 6.50-6.32 (m, 4H), 4.62 (d, J=5 Hz, 2H), 3.80-3.44 (m, 4H), 2.15-2.01 (m, 4H). LCMS: m/z 629.3 [M+H]$^+$, $t_R$=1.89 min.

Synthesis of (E)-3-(6-aminopyridin-3-yl)-N-((5-(4-(4,4-difluoropiperidine-1-carbonyl)phenyl)-7-(6-fluoropyridin-3-yl)benzofuran-2-yl)methyl)acrylamide (735)
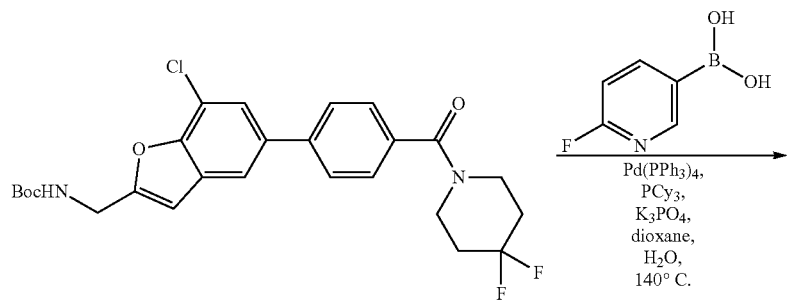
323
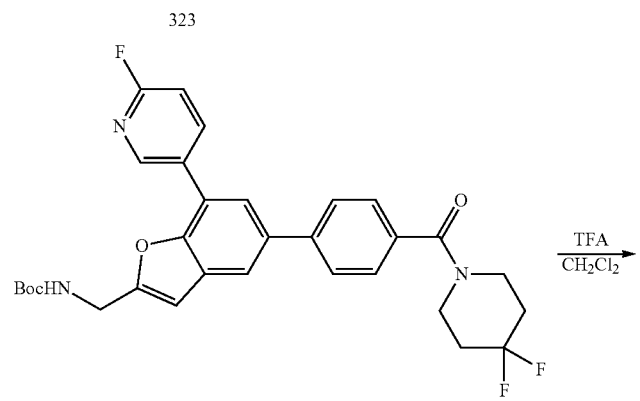
403
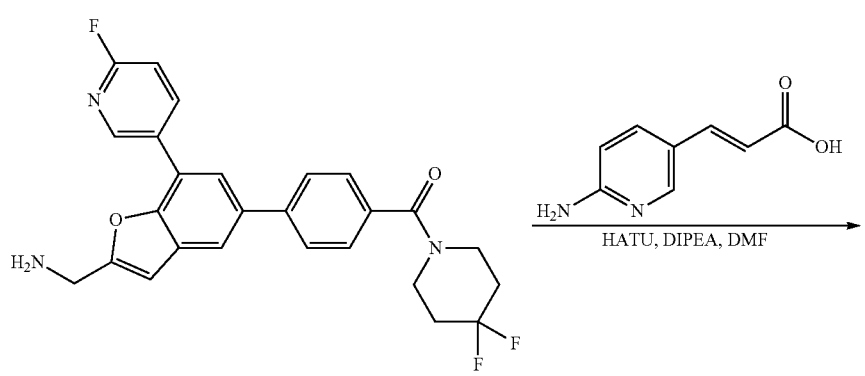
404
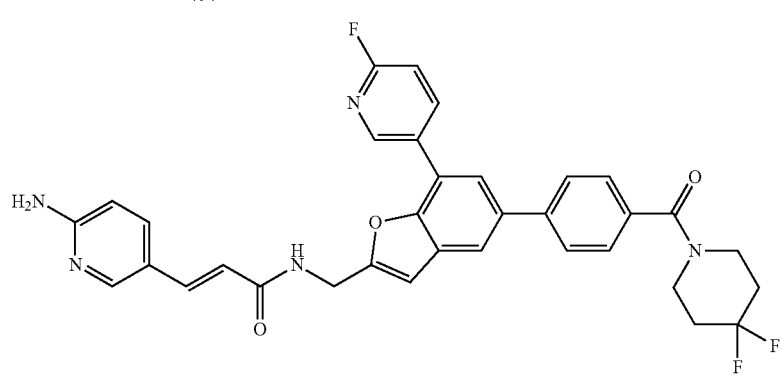
735

523

(E)-3-(6-aminopyridin-3-yl)-N-((5-(4-(4,4-difluoropiperidine-1-carbonyl)phenyl)-7-(6-fluoropyridin-3-yl)benzofuran-2-yl)methyl)acrylamide (735) was synthesized using the indicated reagents in a similar fashion as example (699).
$^1$H NMR (400 MHz, DMSO-$d_6$) δ 8.90 (d, J=2 Hz, 1H), 8.84 (t, J=5 Hz, 1H), 8.65-8.58 (m, 1H), 8.23-8.03 (m, 4H), 7.99 (d, J=2 Hz, 1H), 7.93-7.86 (m, 3H), 7.60-7.54 (m, 2H), 7.48-7.37 (m, 2H), 6.96 (d, J=9 Hz, 1H), 6.91 (s, 1H), 6.59

524

(d, J=16 Hz, 1H), 4.63 (d, J=5 Hz, 2H), 3.80-3.45 (m, 4H), 2.15-1.99 (m, 4H). LCMS: m/z 612.3 [M+H]$^+$, $t_R$=1.78 min.

Synthesis of (E)-3-(6-aminopyridin-3-yl)-N-((7-(2,4-difluorophenyl)-5-(4-(4,4-difluoropiperidine-1-carbonyl)phenyl)benzofuran-2-yl)methyl)acrylamide (736)

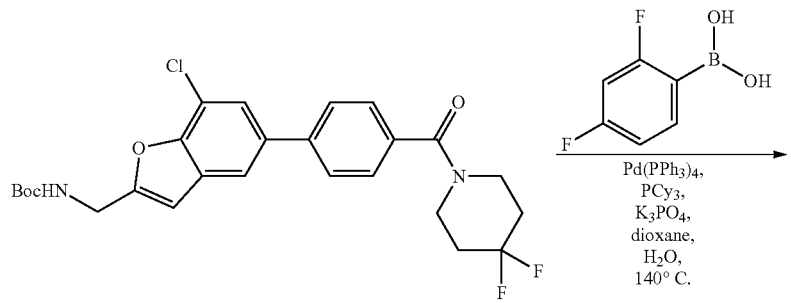

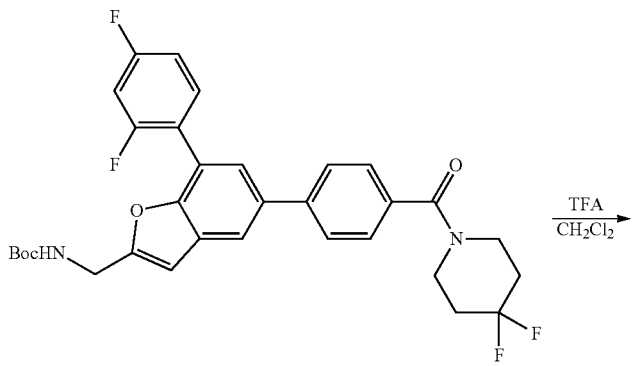

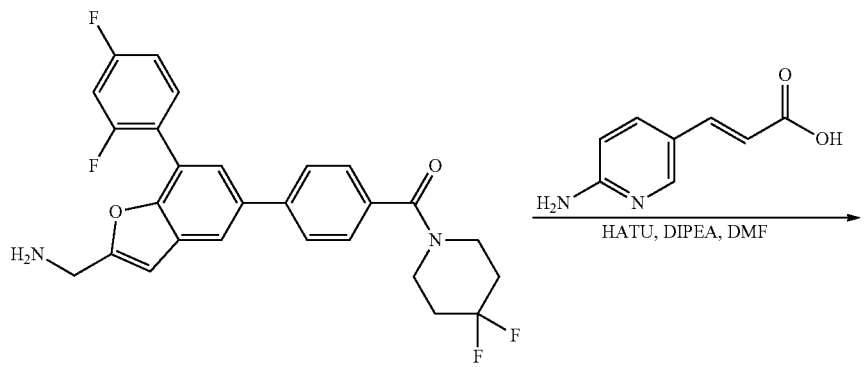

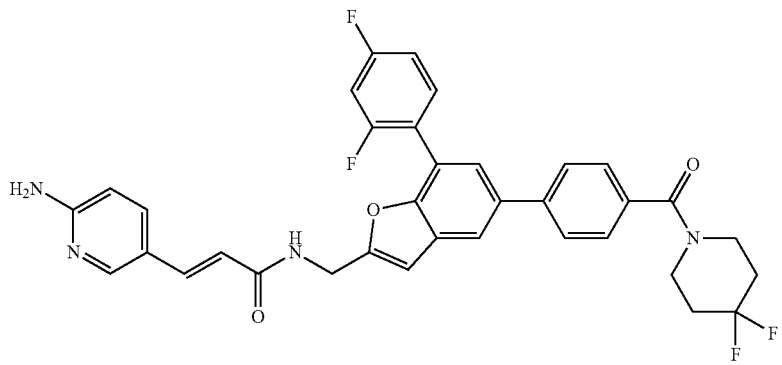

736

(E)-3-(6-aminopyridin-3-yl)-N-((7-(2,4-difluorophenyl)-5-(4-(4,4-difluoropiperidine-1-carbonyl)phenyl)benzofuran-2-yl)methyl)acrylamide (736) was synthesized using the indicated reagents in a similar fashion as example (699). $^1$H NMR (400 MHz, DMSO-d$_6$) δ 8.63-8.57 (m, 1H), 8.07 (s, 1H), 7.98 (s, 1H), 7.85-7.76 (m, 3H), 7.64-7.43 (m, 5H), 7.37-7.25 (m, 2H), 6.85 (s, 1H), 6.50-6.36 (m, 4H), 4.53 (d, J=6 Hz, 2H), 3.80-3.43 (m, 4H), 2.13-1.98 (m, 4H). LCMS: m/z 628.9 [M+H]$^+$, t$_R$=2.02 min.

Synthesis of (E)-3-(6-aminopyridin-3-yl)-N-((7-(3,4-difluorophenyl)-5-(4-(4,4-difluoropiperidine-1-carbonyl)phenyl)benzofuran-2-yl)methyl)acrylamide (737)

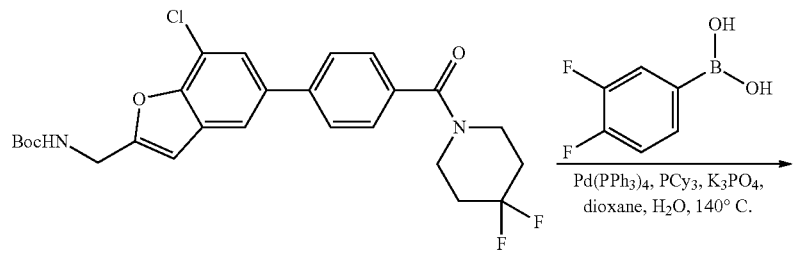

323

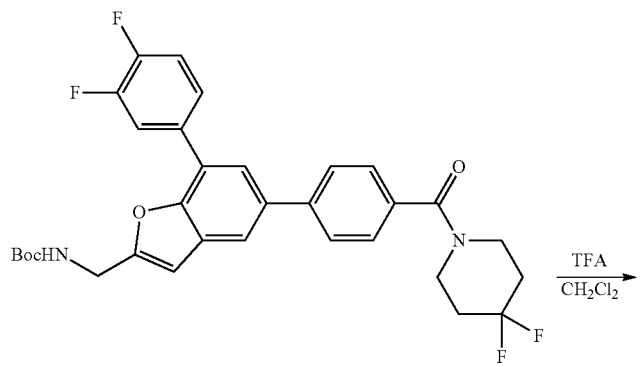

407

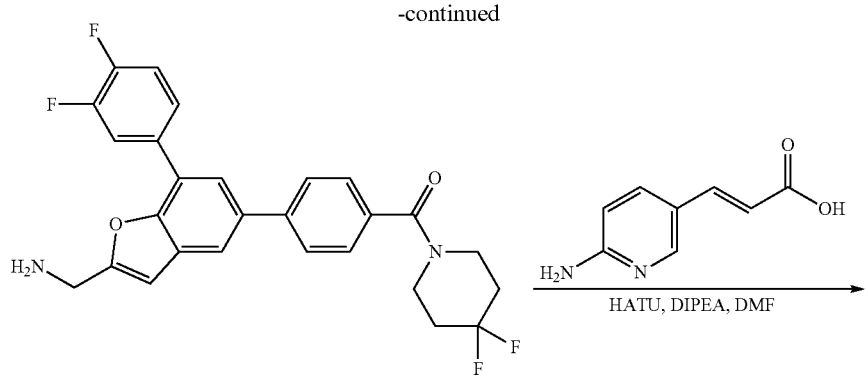

408

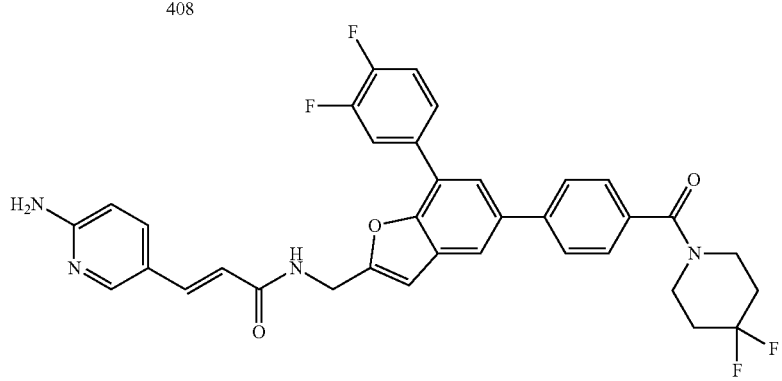

737

(E)-3-(6-Aminopyridin-3-yl)-N-((7-(3,4-difluorophenyl)-5-(4-(4,4-difluoropiperidine-1-carbonyl)phenyl)benzofuran-2-yl)methyl)acrylamide (737) was synthesized using the indicated reagents in a similar fashion as example (699). $^1$H NMR (400 MHz, DMSO-d$_6$) δ 8.62 (t, J=6 Hz, 1H), 8.15-8.06 (m, 2H), 7.97-7.79 (m, 5H), 7.65-7.53 (m, 4H), 7.36 (d, J=16 Hz, 1H), 6.87 (s, 1H), 6.50-6.39 (m, 4H), 4.61 (d, J=6 Hz, 2H), 3.80-3.42 (m, 4H), 2.16-1.96 (m, 4H). LCMS: m/z 629.3 [M+H]$^+$, t$_R$=1.88 min.

Synthesis of (E)-3-(6-aminopyridin-3-yl)-N-((7-(2-chloro-4-fluorophenyl)-5-(4-(4,4-difluoropiperidine-1-carbonyl)phenyl)benzofuran-2-yl)methyl)acrylamide (738)

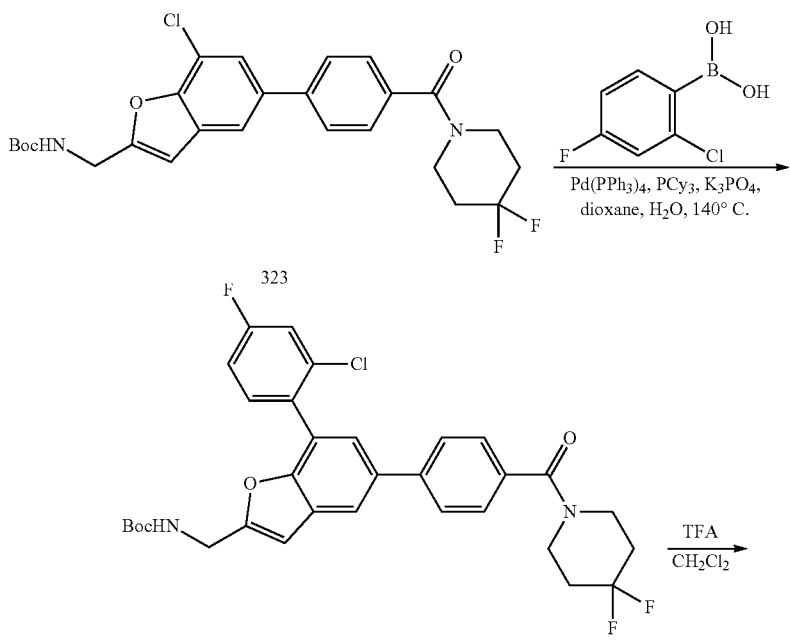

409

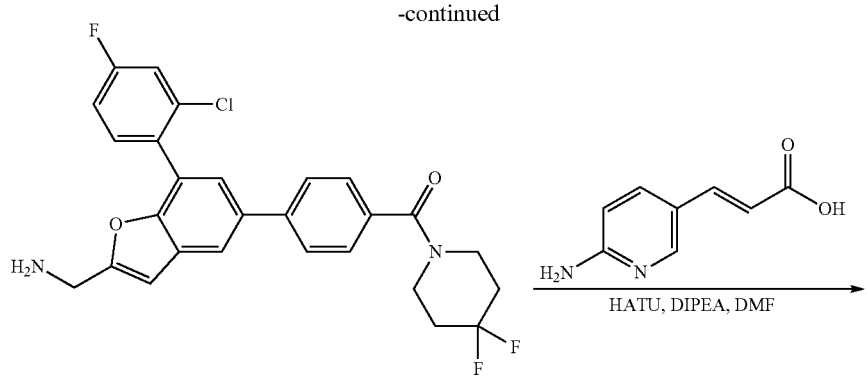

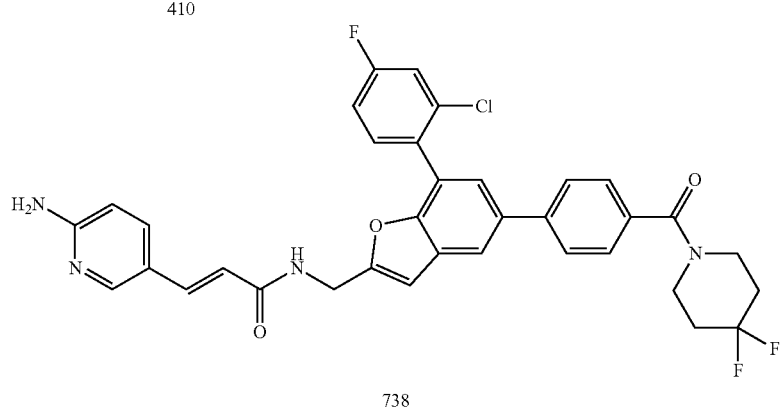

(E)-3-(6-aminopyridin-3-yl)-N-((7-(2-chloro-4-fluorophenyl)-5-(4-(4,4-difluoropiperidine-1-carbonyl)phenyl)benzofuran-2-yl)methyl)acrylamide (738) was synthesized using the indicated reagents in a similar fashion as example (699). $^1$H NMR (400 MHz, CD$_3$OD) δ 8.08 (d, J=9 Hz, 1H), 7.92 (s, 1H), 7.79 (s, 1H), 7.73-7.65 (m, 2H), 7.51-7.42 (m, 3H), 7.42-7.27 (m, 3H), 7.16-7.08 (m, 1H), 6.94 (d, J=9 Hz, 1H), 6.76 (s, 1H), 6.50 (d, J=16 Hz, 1H), 4.53 (s, 2H), 3.85-3.45 (m, 4H), 2.09-1.84 (m, 4H). LCMS: m/z 645.2 [M+H]$^+$, t$_R$=1.50 min.

Synthesis of (E)-3-(6-aminopyridin-3-yl)-N-((7-(4-chloro-2-fluorophenyl)-5-(4-(4,4-difluoropiperidine-1-carbonyl)phenyl)benzofuran-2-yl)methyl)acrylamide (739)

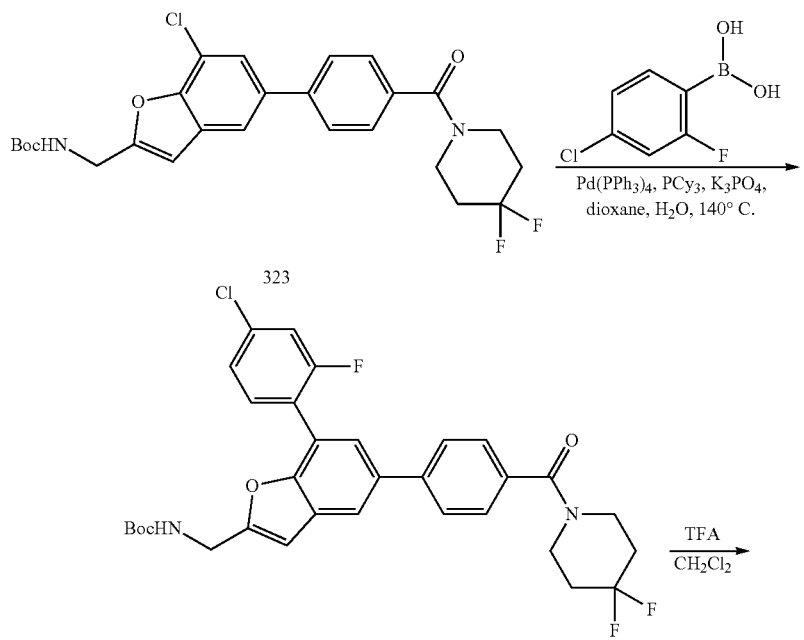

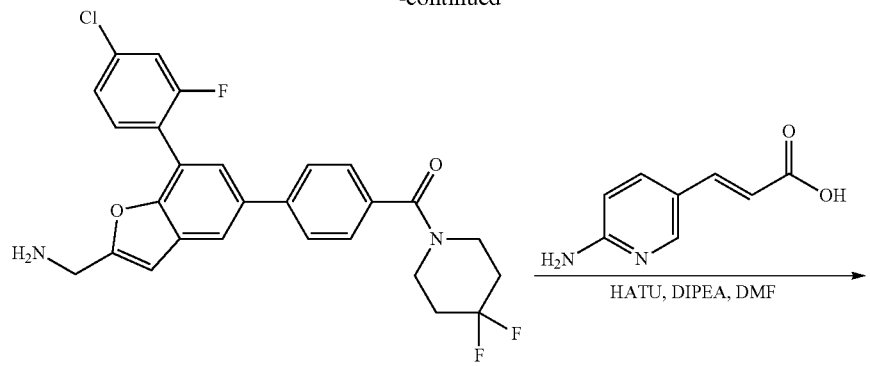

412

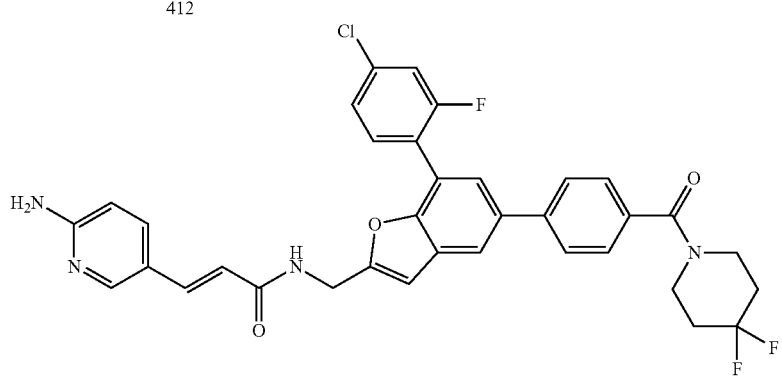

739

(E)-3-(6-aminopyridin-3-yl)-N-((7-(4-chloro-2-fluorophenyl)-5-(4-(4,4-difluoropiperidine-1-carbonyl)phenyl)benzofuran-2-yl)methyl)acrylamide (739) was synthesized using the indicated reagents in a similar fashion as example (699). $^1$H NMR (400 MHz, CD$_3$OD) δ 8.21 (d, J=9 Hz, 1H), 8.05 (s, 1H), 7.91 (d, J=2 Hz, 1H), 7.84-7.55 (m, 9H), 7.47 (d, J=16 Hz, 1H), 7.42-7.35 (m, 2H), 7.07 (d, J=9 Hz, 1H), 6.88 (s, 1H), 6.63 (d, J=16 Hz, 1H), 4.68 (s, 2H), 3.94-3.60 (m, 4H), 2.19-1.97 (m, 4H). LCMS: m/z 645.3 [M+H]$^+$, $t_R$=1.92 min.

Synthesis of (E)-3-(6-aminopyridin-3-yl)-N-((7-(2,5-difluorophenyl)-5-(4-(4,4-difluoropiperidine-1-carbonyl)phenyl)benzofuran-2-yl)methyl)acrylamide (740)

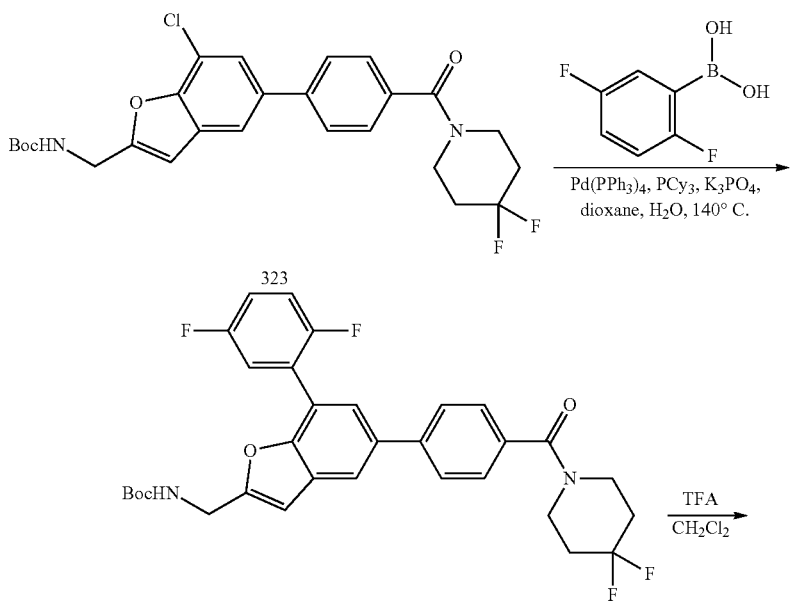

413

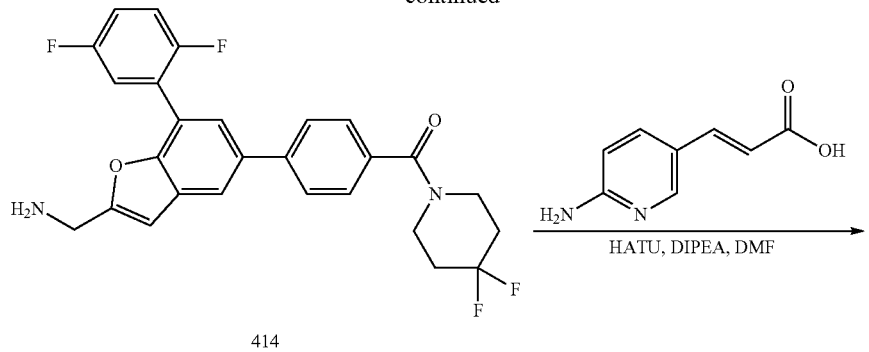

414

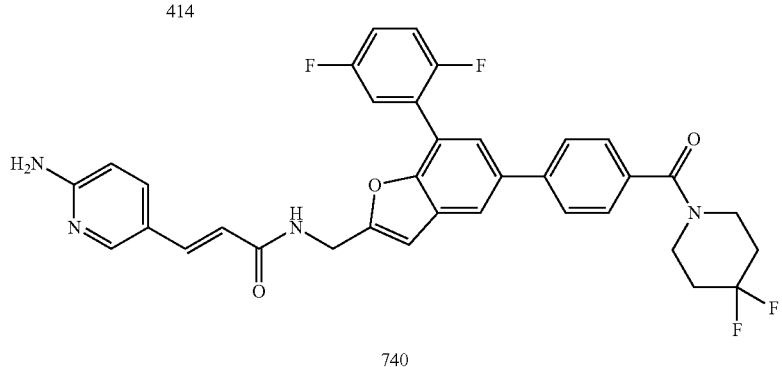

740

(E)-3-(6-aminopyridin-3-yl)-N-((7-(2,5-difluorophenyl)-5-(4-(4,4-difluoropiperidine-1-carbonyl)phenyl)benzofuran-2-yl)methyl)acrylamide (740) was synthesized using the indicated reagents in a similar fashion as example (699). $^1$H NMR (400 MHz, DMSO-d$_6$) δ $^1$H NMR (400 MHz, DMSO) δ 8.59 (t, J=6 Hz, 1H), 8.09-7.97 (m, 2H), 7.87-7.82 (m, 2H), 7.72-7.28 (m, 8H), 6.86 (s, 1H), 6.56-6.31 (m, 4H), 4.60-4.49 (m, 2H), 3.84-3.41 (m, 4H), 2.18-1.94 (m, 4H). LCMS: m/z 629.3 [M+H]$^+$, t$_R$=1.88 min.

Synthesis of (E)-3-(6-aminopyridin-3-yl)-N-((7-(3-chlorophenyl)-5-(4-(4,4-difluoropiperidine-1-carbonyl)phenyl)benzofuran-2-yl)methyl)acrylamide (741)

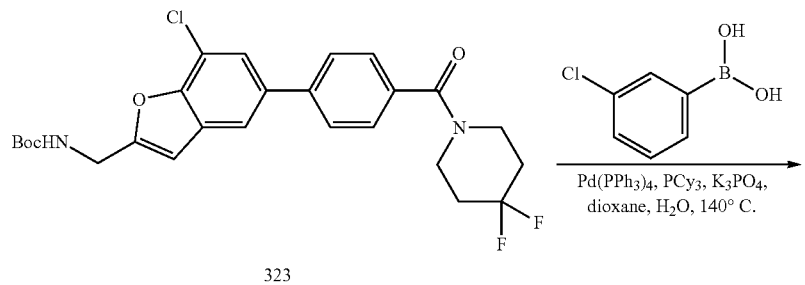

323

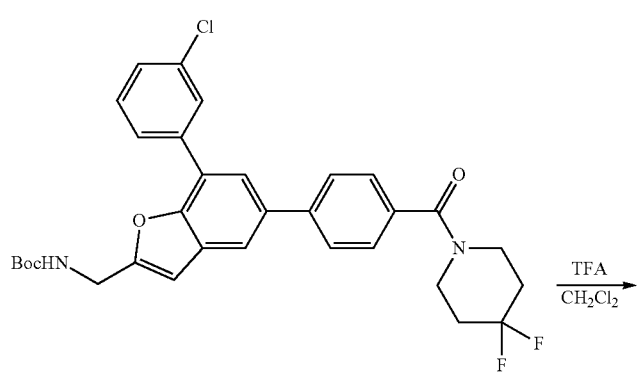

415

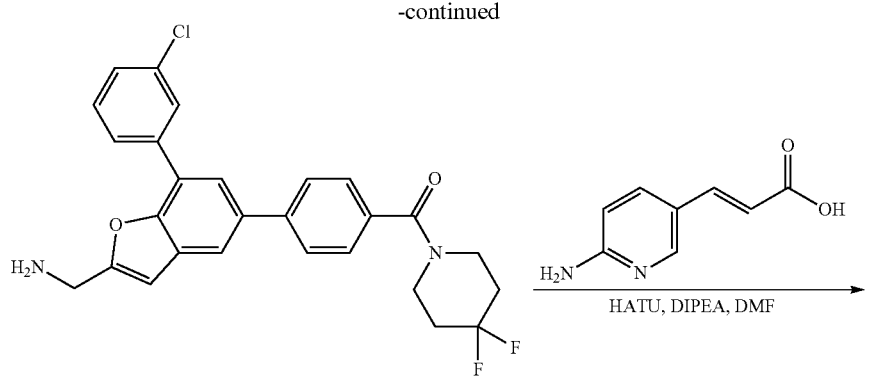

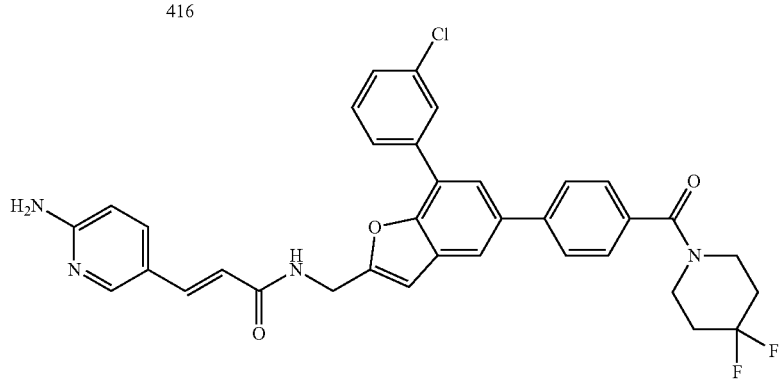

741

(E)-3-(6-aminopyridin-3-yl)-N-((7-(3-chlorophenyl)-5-(4-(4,4-difluoropiperidine-1-carbonyl)phenyl)benzofuran-2-yl)methyl)acrylamide (741) was synthesized using the indicated reagents in a similar fashion as example (699). $^1$H NMR (400 MHz, DMSO-$d_6$) δ 8.65-8.56 (m, 1H), 8.13-7.77 (m, 7H), 7.70-7.48 (m, 5H), 7.36 (d, J=16 Hz, 1H), 6.87 (s, 1H), 6.56-6.36 (m, 4H), 4.70-4.48 (m, 2H), 3.84-3.40 (m, 4H), 2.18-1.96 (m, 4H). LCMS: m/z 627.1 [M+H]$^+$, $t_R$=1.91 min.

Synthesis of (E)-3-(6-aminopyridin-3-yl)-N-((7-(4-chlorophenyl)-5-(4-(4,4-difluoropiperidine-1-carbonyl)phenyl)benzofuran-2-yl)methyl)acrylamide (742)

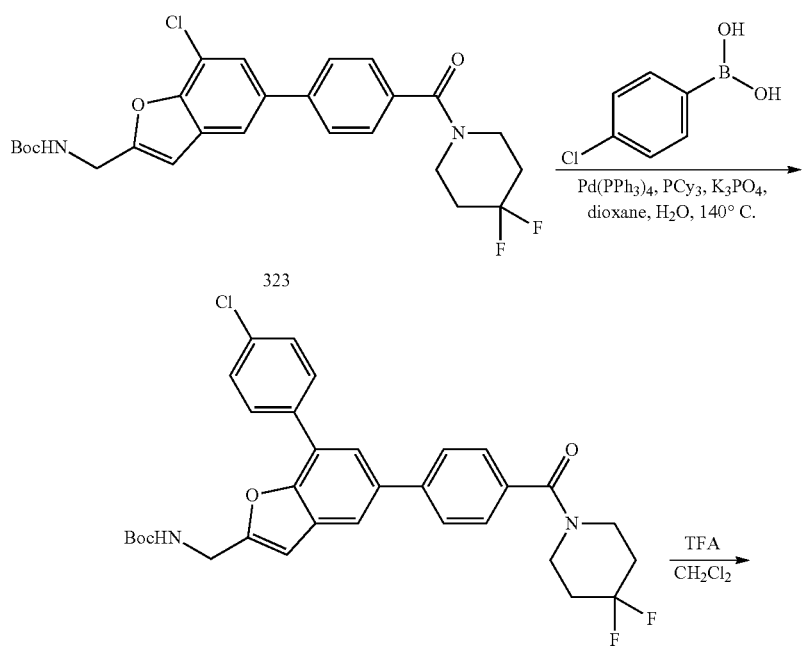

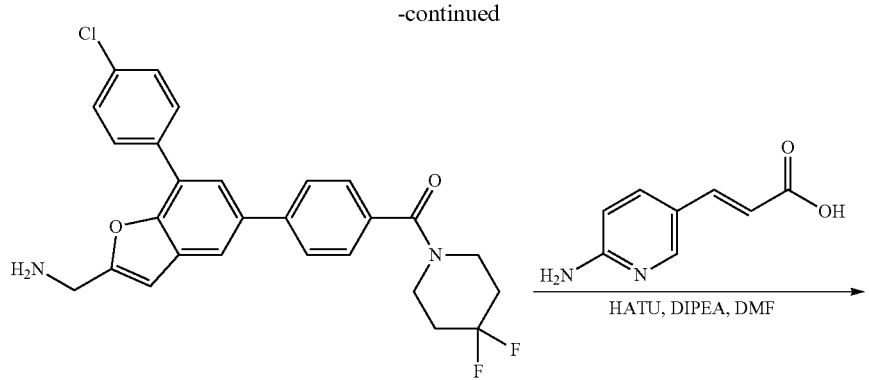

418

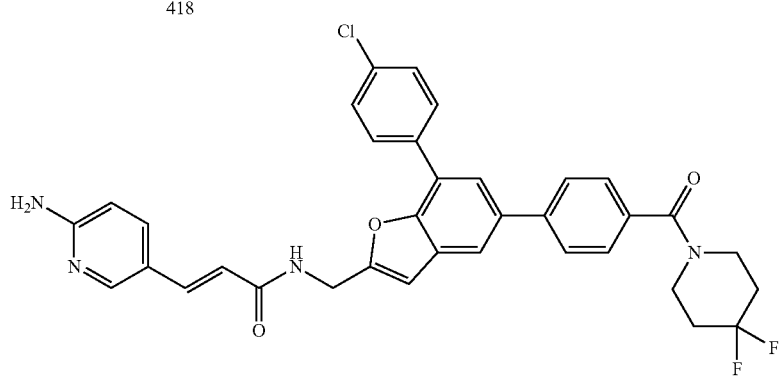

742

(E)-3-(6-aminopyridin-3-yl)-N-((7-(4-chlorophenyl)-5-(4-(4,4-difluoropiperidine-1-carbonyl)phenyl)benzofuran-2-yl)methyl)acrylamide (742) was synthesized using the indicated reagents in a similar fashion as example (699). $^1$H NMR (400 MHz, DMSO-$d_6$) δ 8.66-8.58 (m, 1H), 8.13-7.51 (m, 12H), 7.36 (d, J=16 Hz, 1H), 6.87 (s, 1H), 6.57-6.31 (m, 4H), 4.68-4.51 (m, 2H), 3.85-3.42 (m, 4H), 2.19-1.96 (m, 4H). LCMS: m/z 627.2 [M+H]$^+$, $t_R$=1.94 min.

Synthesis of (E)-3-(6-aminopyridin-3-yl)-N-((5-(4-(4,4-difluoropiperidine-1-carbonyl)phenyl)-7-(6-fluoro-4-methylpyridin-3-yl)benzofuran-2-yl)methyl)acrylamide (743)

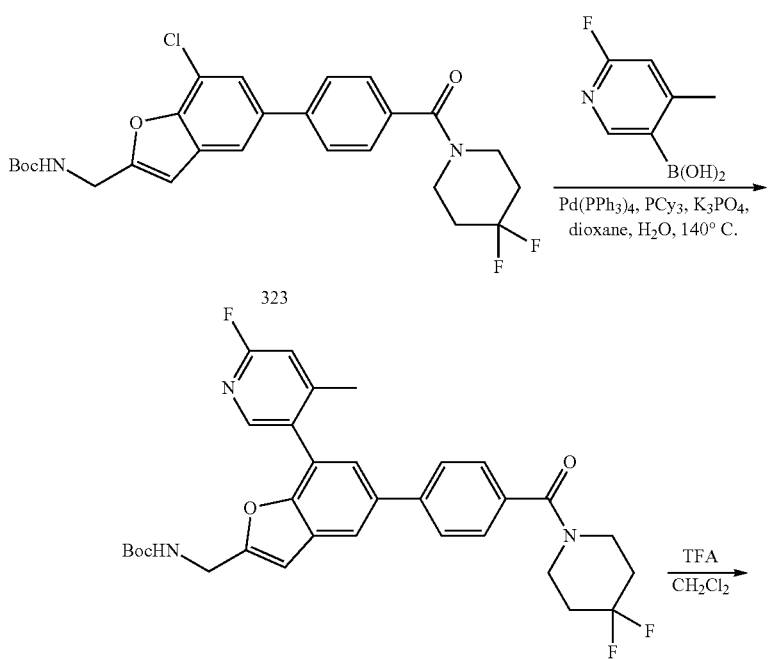

419

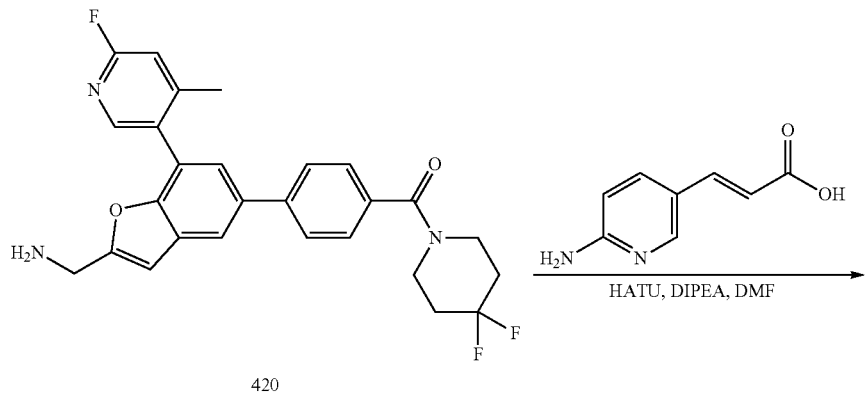

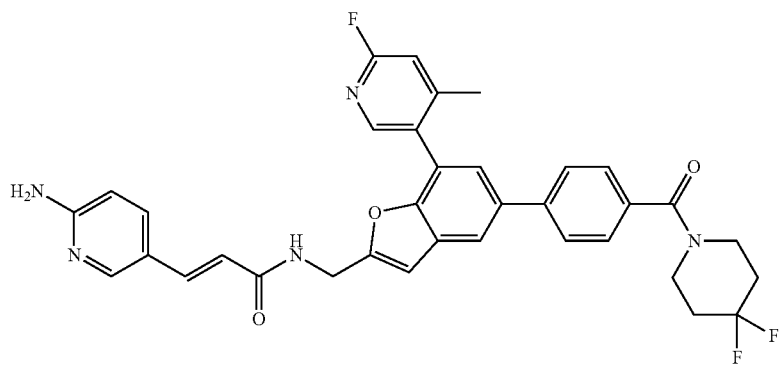

(E)-3-(6-Aminopyridin-3-yl)-N-((5-(4-(4,4-difluoropiperidine-1-carbonyl)phenyl)-7-(6-fluoro-4-methylpyridin-3-yl)benzofuran-2-yl)methyl)acrylamide (743) was synthesized using the indicated reagents in a similar fashion as example (699). $^1$H NMR (400 MHz, DMSO-$d_6$) δ 8.82-8.76 (m, 1H), 8.30-8.00 (m, 5H), 7.84 (d, J=8.2 Hz, 2H), 7.60-7.52 (m, 4H), 7.42 (d, J=16 Hz, 1H), 7.29 (s, 1H), 6.97 (d, J=9 Hz, 1H), 6.89 (s, 1H), 6.56 (d, J=16 Hz, 1H), 4.55 (d, J=5 Hz, 2H), 3.77-3.44 (m, 4H), 2.28 (s, 3H), 2.10-2.00 (m, 4H). LCMS: m/z 626.2 [M+H]$^+$, $t_R$=1.41 min.

Synthesis of (E)-3-(6-aminopyridin-3-yl)-N-((5-(4-(4,4-difluoropiperidine-1-carbonyl)phenyl)-7-(4-methylpyridin-3-yl)benzofuran-2-yl)methyl)acrylamide (744)

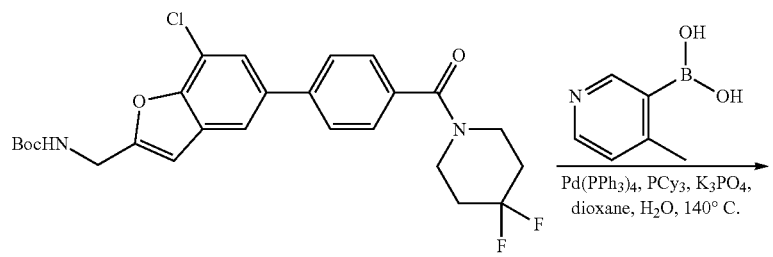

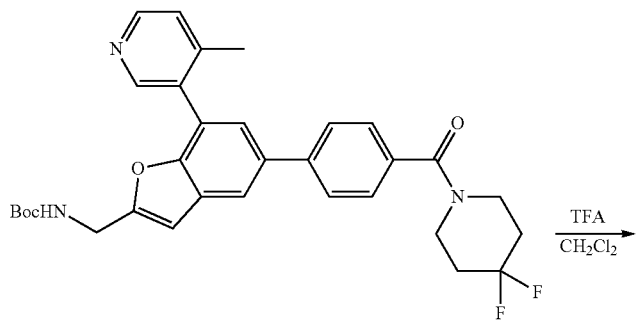

421

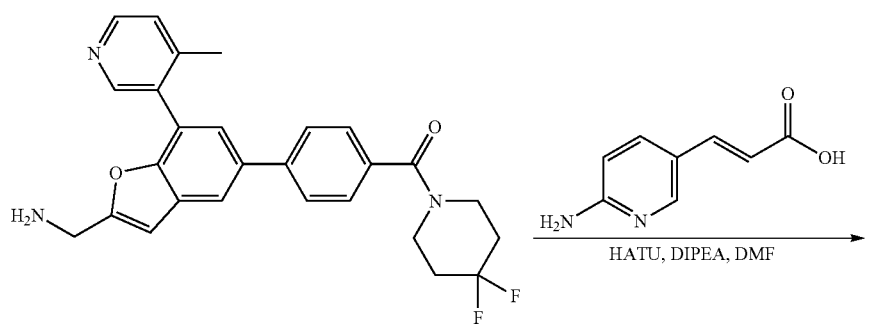

422

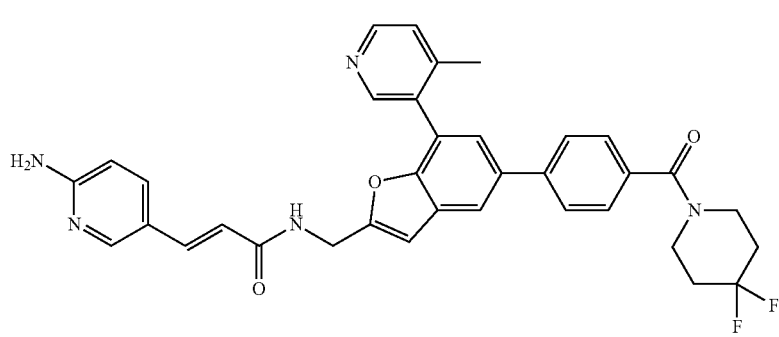

744

(E)-3-(6-aminopyridin-3-yl)-N-((5-(4-(4,4-difluoropiperidine-1-carbonyl)phenyl)-7-(4-methylpyridin-3-yl)benzofuran-2-yl)methyl)acrylamide (744) was synthesized using the indicated reagents in a similar fashion as example (699). Yield: 51%. $^1$H NMR (400 MHz, DMSO-d$_6$) δ 8.84-8.69 (m, 3H), 8.39-8.04 (m, 5H), 7.88-7.54 (m, 6H), 7.42 (d, J=16 Hz, 1H), 7.00 (d, J=9 Hz, 1H), 6.91 (s, 1H), 6.58 (d, J=16 Hz, 1H), 4.56 (s, 2H), 3.84-3.38 (m, 4H), 2.36 (s, 3H), 2.14-1.99 (m, 4H). LCMS: m/z 608.1 [M+H]$^+$, t$_R$=1.30 min.

Synthesis of (E)-3-(6-aminopyridin-3-yl)-N-((5-(5-(4-fluorophenoxy)pyridin-2-yl)-7-(4-fluorophenyl)benzofuran-2-yl)methyl)acrylamide (745)

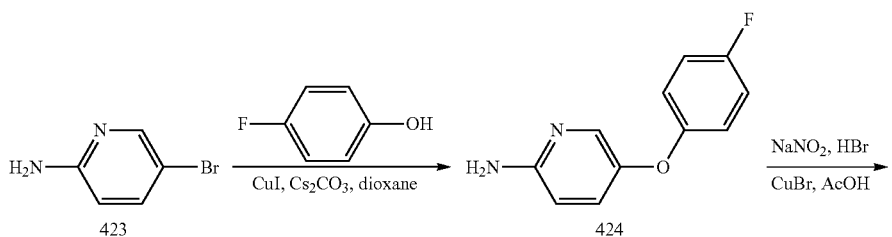

-continued
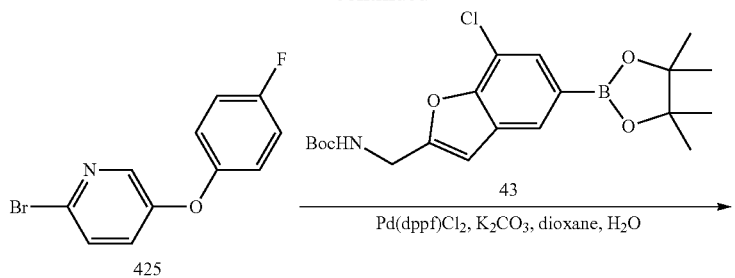
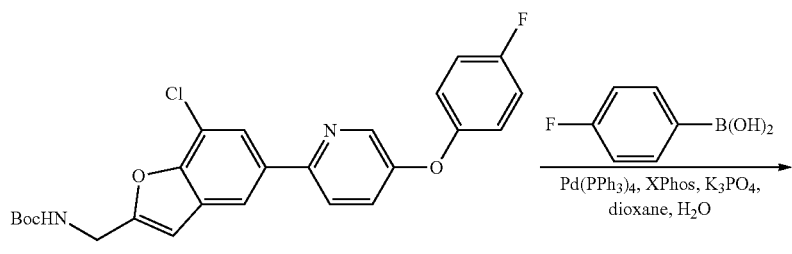
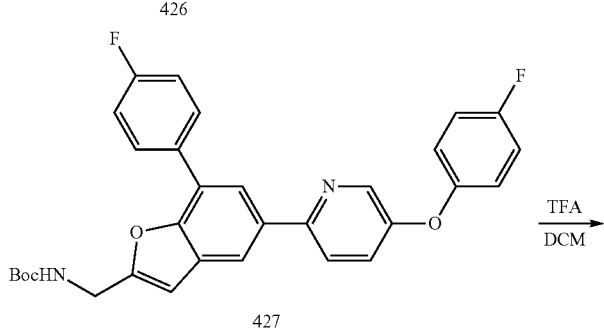
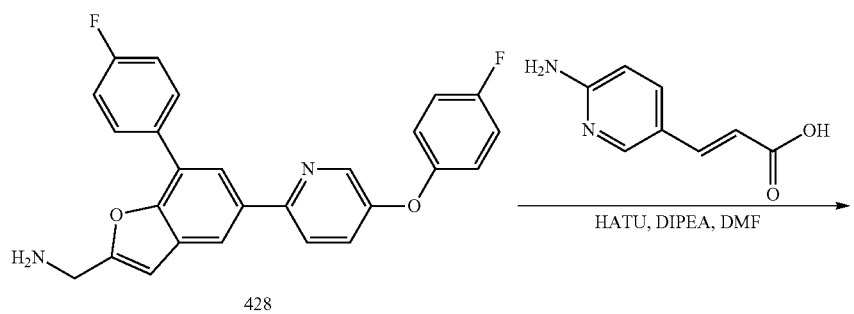
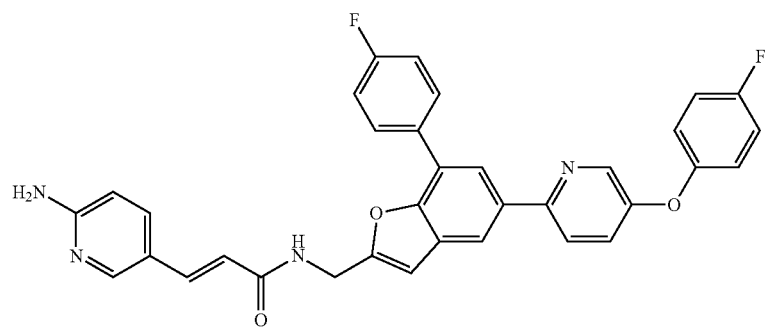

Synthesis of 5-(4-fluorophenoxy)pyridin-2-amine (424)

5-Bromopyridin-2-amine (423; 1 g, 5.8 mmol) was dissolved in dioxane (20 mL). 4-Fluorophenol (0.7 g, 5.8 mmol), CuI (0.1 g, 0.6 mmol) and $Cs_2CO_3$ (3.8 g, 11.6 mmol) were added at 25° C. The reaction mixture was heated at 110° C. for 16 h. After cooling down to room temperature, the reaction mixture was poured into water (20 mL), extracted with EtOAc (50 mL×3). The combined organic layers were washed with brine, dried over anhydrous $Na_2SO_4$, concentrated under reduced pressure to give the crude product, which was purified by silica gel chromatography (20% EtOAc/petroleum ether) to give 150 mg of 5-(4-fluorophenoxy)pyridin-2-amine (424) as white solid (13% yield). LCMS: m/z 205.1 $[M+H]^+$; $t_R$=1.23 min.

Synthesis of 2-bromo-5-(4-fluorophenoxy)pyridine (3)

5-(4-Fluorophenoxy)pyridin-2-amine (424; 200 mg, 1 mmol) was dissolved in 5 mL of AcOH, the mixture was cooled down to 0° C. and degassed. $NaNO_2$ (76 mg, 1.2 mmol) was added. After stirring for 0.5 h, CuBr (170 mg, 1.2 mmol) and HBr aqueous solution (2 mL) was added. The mixture was stirred at 25° C. for 2 h. The reaction mixture was diluted with 20 mL of $H_2O$, extracted with EtOAc (20 mL×3). The combined organic layers were washed with brine (20 mL), dried over $Na_2SO_4$, concentrated and purified by silica gel chromatography (20% EtOAc/petroleum ether) to give 100 mg of 2-bromo-5-(4-fluorophenoxy)pyridine (425) as white solid (37% yield). LCMS: m/z 270.0 $[M+H]^+$; $t_R$=1.73 min.

Synthesis of tert-butyl (7-chloro-5-(5-(4-fluorophenoxy)pyridin-2-yl)benzofuran-2-yl)methylcarbamate (426)

A mixture of 2-bromo-5-(4-fluorophenoxy)pyridine (425; 135 mg, 0.5 mmol), tert-butyl (7-chloro-5-(4,4,5,5-tetramethyl-1,3,2-dioxaborolan-2-yl)benzofuran-2-yl)methylcarbamate (203 mg, 0.5 mmol), $Pd(dppf)Cl_2$ (41 mg, 0.05 mmol) and $K_2CO_3$ (138 mg, 1 mmol) in 5 mL of dioxane and 0.5 mL of $H_2O$ was stirred at 100° C. under nitrogen atmosphere for 2 h. After cooling down to room temperature, the reaction mixture was diluted with water (10 mL), extracted with EtOAc (20 mL×3). The combined organic layers were washed with brine over anhydrous $Na_2SO_4$, and the solvents were removed under reduced pressure to give the crude product, which was purified by silica gel chromatography (20% EtOAc/petroleum ether) to give 170 mg of tert-butyl (7-chloro-5-(5-(4-fluorophenoxy)pyridin-2-yl)benzofuran-2-yl)methylcarbamate (426) as a white solid (71% yield). LCMS: m/z 469.1 $[M+H]^+$, $t_R$=1.89 min.

Synthesis of tert-butyl (5-(5-(4-fluorophenoxy)pyridin-2-yl)-7-(4-fluorophenyl)benzofuran-2-yl)methylcarbamate (427)

tert-Butyl (7-chloro-5-(5-(4-fluorophenoxy)pyridin-2-yl)benzofuran-2-yl)methylcarbamate (426; 180 mg, 0.4 mmol), 4-fluorophenylboronic acid (60 mg, 0.4 mmol), $Pd(PPh_3)_4$ (42 mg, 0.04 mmol), XPhos (36 mg, 0.08 mmol) and $K_3PO_4$ (170 mg, 0.8 mmol) were added to a mixture of dioxane (5 mL) and water (0.5 mL) and degassed. The reaction mixture was heated at 110° C. for 2 h. The reaction mixture was cooled down to room temperature, filtered and the filtrate was concentrated under reduced pressure to give the crude product, which was purified by silica gel chromatography (30% EtOAc/petroleum ether) to give 100 mg of tert-butyl (5-(5-(4-fluorophenoxy)pyridin-2-yl)-7-(4-fluorophenyl)benzofuran-2-yl)methylcarbamate (427) as white solid (47% yield). LCMS: m/z 529.2 $[M+H]^+$; $t_R$=1.92 min.

Synthesis of (5-(5-(4-fluorophenoxy)pyridin-2-yl)-7-(4-fluorophenyl)benzofuran-2-yl)methanamine (428)

tert-Butyl (5-(5-(4-fluorophenoxy)pyridin-2-yl)-7-(4-fluorophenyl)benzofuran-2-yl)methylcarbamate (427; 100 mg, 0.19 mmol) was dissolved in $CH_2Cl_2$ (5 mL). TFA (1 mL) was added dropwise at 0° C. The reaction mixture was allowed to warm to room temperature and stirred for 2 h. The reaction mixture was concentrated under reduced pressure to give (5-(5-(4-fluorophenoxy)pyridin-2-yl)-7-(4-fluorophenyl)benzofuran-2-yl)methanamine (428), which was used without further purification in the next step (80 mg, 100% yield). LCMS: m/z 429.1 $[M+H]^+$; $t_R$=1.49 min.

Synthesis of (E)-3-(6-aminopyridin-3-yl)-N-((5-(5-(4-fluorophenoxy)pyridin-2-yl)-7-(4-fluorophenyl)benzofuran-2-yl)methyl)acrylamide (745)

(5-(5-(4-Fluorophenoxy)pyridin-2-yl)-7-(4-fluorophenyl)benzofuran-2-yl)methanamine (428; 80 mg, 0.19 mmol) was dissolved in DMF (3 mL). (E)-3-(6-aminopyridin-3-yl)acrylic acid (31 mg, 0.19 mmol), HATU (72 mg, 0.19 mmol), and DIPEA (50 mg, 0.38 mmol) were added at room temperature. The reaction mixture was stirred at room temperature for 1 h. The crude mixture was purified by Pre-HPLC without workup to give (E)-3-(6-aminopyridin-3-yl)-N-((5-(5-(4-fluorophenoxy)pyridin-2-yl)-7-(4-fluorophenyl)benzofuran-2-yl)methyl)acrylamide (745) (45 mg, 41% yield) as white solid. $^1$H NMR (400 MHz, $CD_3OD$) δ 8.23 (d, J=3 Hz, 1H), 7.94-7.76 (m, 6H), 7.64-7.57 (m, 1H), 7.40-7.32 (m, 2H), 7.15-6.99 (m, 6H), 6.72 (s, 1H), 6.48 (d, J=9 Hz, 1H), 6.35 (d, J=16 Hz, 1H), 4.57 (s, 2H). LCMS: m/z 575.2 $[M+H]^+$, $t_R$=2.01 min.

Synthesis of (E)-3-(6-aminopyridin-3-yl)-N-((5-(4-(4,4-difluoropiperidine-1-carbonyl)phenyl)-7-(pyridin-2-yl)benzofuran-2-yl)methyl)acrylamide (746)

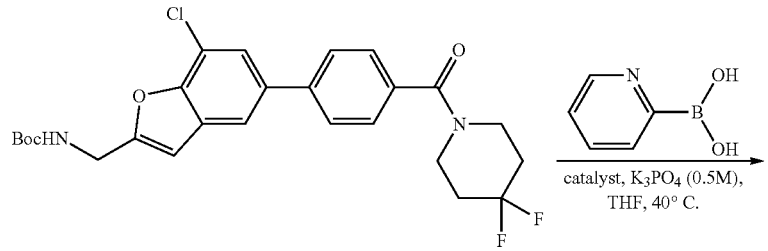

547                                                                                         548

-continued

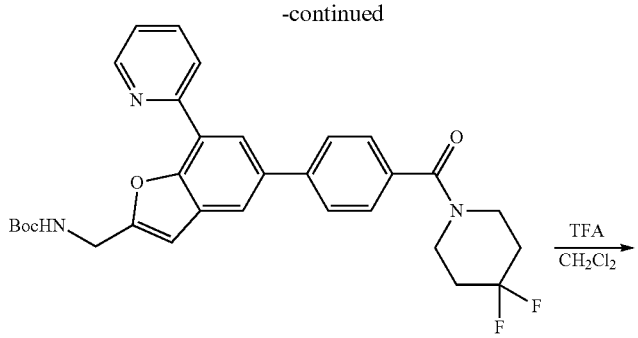

429

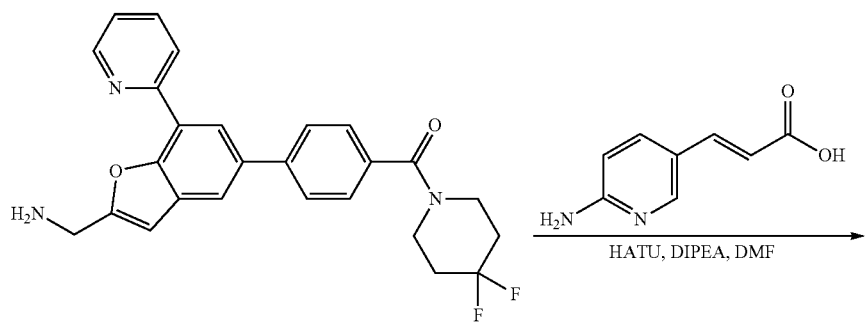

430

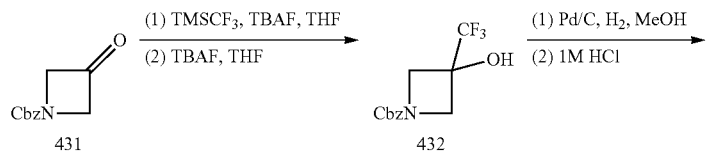

746

(E)-3-(6-Aminopyridin-3-yl)-N-((5-(4-(4,4-difluoropiperidine-1-carbonyl)phenyl)-7-(pyridin-2-yl)benzofuran-2-yl)methyl)acrylamide (746) was synthesized using the indicated reagents in a similar fashion as example (699). $^1$H NMR (400 MHz, CD$_3$OD) δ 8.76-8.69 (m, 1H), 8.40-8.34 (m, 1H), 8.25 (d, J=2 Hz, 1H), 8.09-7.98 (m, 2H), 7.94 (s, 1H), 7.90-7.85 (m, 2H), 7.75 (d, J=9 Hz, 1H), 7.63-7.57 (m, 2H), 7.54-7.42 (m, 2H), 6.92-6.85 (m, 1H), 6.61 (d, J=9 Hz, 1H), 6.49 (d, J=16 Hz, 1H), 4.75 (s, 2H), 3.95-3.61 (m, 4H), 2.18-2.04 (m, 4H). LCMS: m/z 594.2 [M+H]$^+$; t$_R$=1.74 min.

Synthesis of (E)-3-(6-aminopyridin-3-yl)-N-((5-(5-(3-hydroxy-3-(trifluoromethyl)azetidine-1-carbonyl)pyridin-2-yl)-7-(trifluoromethyl)benzofuran-2-yl)methyl)acrylamide (747)

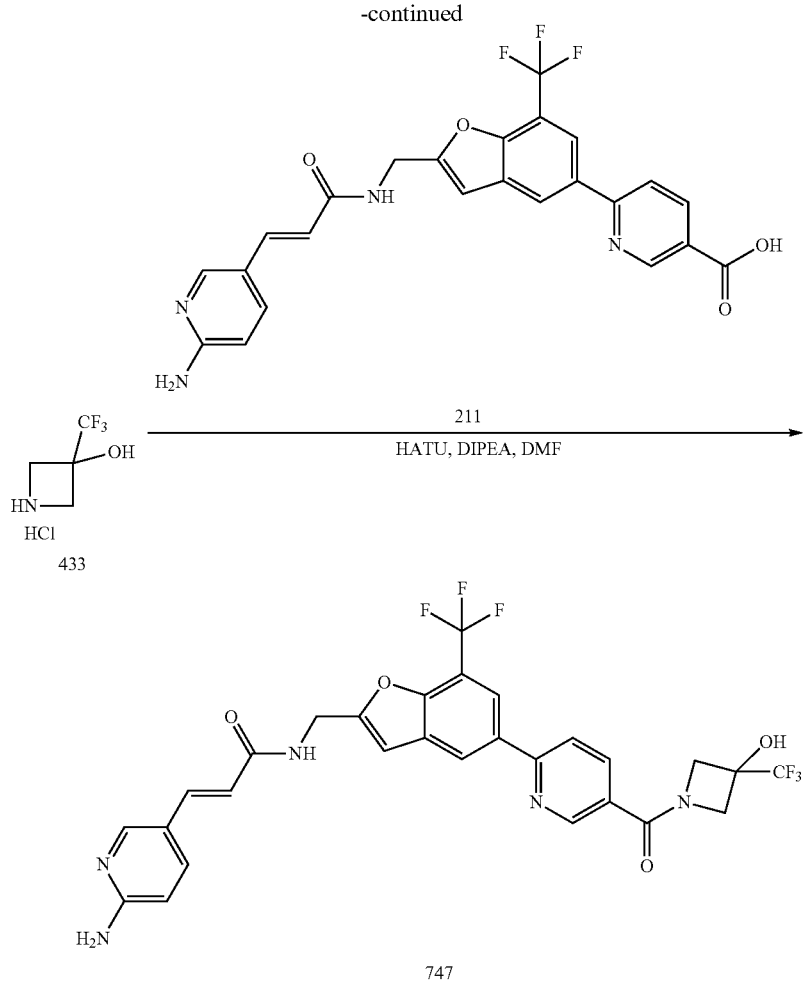

Synthesis of benzyl 3-hydroxy-3-(trifluoromethyl) azetidine-1-carboxylate (432)

Benzyl 3-oxoazetidine-1-carboxylate (431, 1.0 g, 6.1 mmol) was dissolved in THF (20 mL). TMSCF$_3$ (2.2 g, 9.1 mmol) was added dropwise at 0° C. (ice bath) over 5 min followed by TBAF (156 mg, 0.6 mmol). The reaction mixture was stirred at 0° C. for 20 min. A solution of TBAF (1.6 g, 6.1 mmol) in THF (5 mL) was added at 0° C. The reaction mixture was allowed to warm to room temperature and stirred for 15 min. The reaction mixture was diluted with ethyl acetate (20 mL), washed with water (20 mL), brine (30 mL), dried over Na$_2$SO$_4$ and concentrated under reduced pressure to give benzyl 3-hydroxy-3-(trifluoromethyl)azetidine-1-carboxylate (432) (1.1 g, 82% yield) as white solid, which was used in next step without further purification. $^1$H NMR (500 MHz, CD$_3$OD) δ 7.50-7.27 (m, 5H), 5.13 (s, 2H), 4.24 (s, 2H), 3.98 (s, 2H).

Synthesis of 3-(trifluoromethyl)azetidin-3-ol hydrochloride (433)

Benzyl 3-hydroxy-3-(trifluoromethyl)azetidine-1-carboxylate (432, 500 mg, 1.9 mmol) was dissolved in methanol (40 mL). Palladium on carbon (10% Pd, 100 mg) was added. The reaction mixture was stirred under H$_2$ atmosphere at room temperature for 1 h. The reaction mixture was filtered and the filtrated was treated with HCl (2 mL, 1N aqueous solution). The reaction mixture was stirred at room temperature for 1 h and concentrated under reduced pressure to give 3-(trifluoromethyl)azetidin-3-ol hydrochloride (433) (340 mg, 100% yield), which was used in the next step without further purification.

Synthesis of (E)-3-(6-aminopyridin-3-yl)-N-((5-(5-(3-hydroxy-3-(trifluoromethyl)azetidine-1-carbonyl) pyridin-2-yl)-7-(trifluoromethyl)benzofuran-2-yl) methyl)acrylamide (747)

(E)-3-(6-aminopyridin-3-yl)-N-((5-(5-(3-hydroxy-3-(trifluoromethyl)azetidine-1-carbonyl)pyridin-2-yl)-7-(trifluoromethyl)benzofuran-2-yl)methyl)acrylamide (747) was synthesized using the indicated reagents according to General Procedure 4. (50 mg, 22% yield). $^1$H NMR (500 MHz, DMSO-d$_6$) δ 8.97 (s, 1H), 8.92-8.86 (m, 1H), 8.73 (s, 1H), 8.43 (s, 1H), 8.27-8.17 (m, 4H), 8.13 (d, J=9 Hz, 1H), 7.54 (s, 1H), 7.46 (d, J=16 Hz, 1H), 7.05-6.98 (m, 2H), 6.62 (d, J=16 Hz, 1H), 4.71 (d, J=10 Hz, 1H), 4.65 (d, J=5 Hz, 2H), 4.41 (d, J=9 Hz, 1H), 4.34 (d, J=10 Hz, 1H), 4.12 (d, J=11 Hz, 1H), 2.93 (s, 1H). LCMS: m/z 606.2 [M+H]$^+$, t$_R$=1.40 min.

Synthesis of (E)-3-(6-aminopyridin-3-yl)-N-((5-(4-(4,4-difluoropiperidine-1-carbonyl)-2-fluorophenyl)-7-(pyridin-3-yl)benzofuran-2-yl)methyl)acrylamide (748)
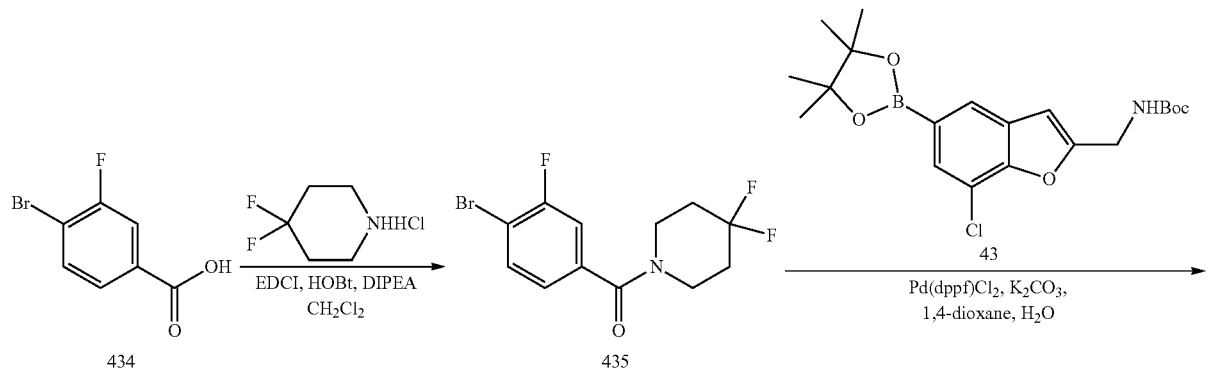
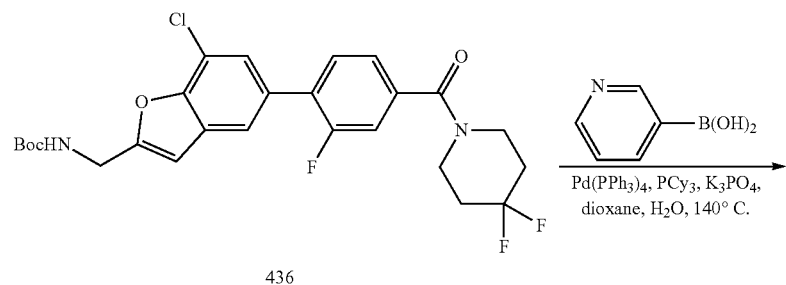
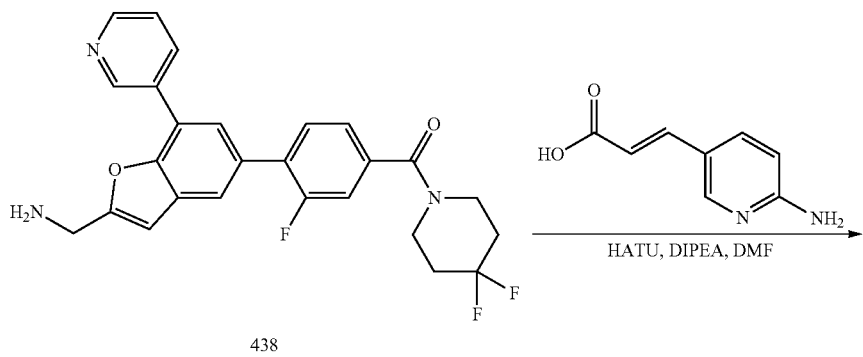

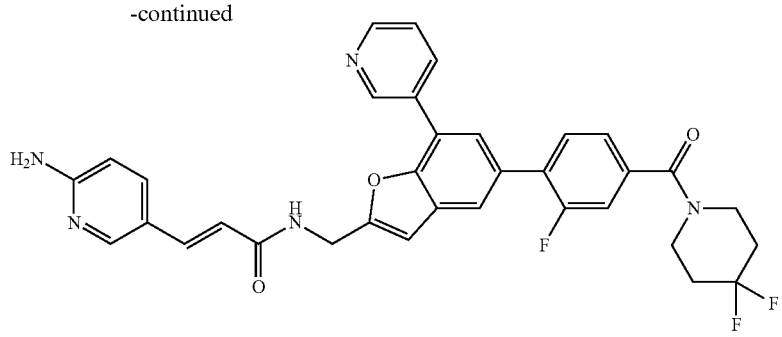

748

Synthesis of (4-bromo-3-fluorophenyl)(4,4-difluoropiperidin-1-yl)methanone (435)

4-Bromo-3-fluorobenzoic acid (434; 2.2 g, 10 mmol) was dissolved in $CH_2Cl_2$ (40 mL) and 4,4-difluoropiperidine hydrochloride (1.6 g, 10 mmol) was added at 0° C. (ice bath). EDCI (2.3 g, 12 mmol) and HOBt hydrate (1.6 g, 12 mmol) were added to this reaction mixture at 0° C. followed by DIPEA (2.6 g, 20 mmol) dropwise. The reaction mixture was allowed to warm to room temperature and stirred further for 2 h. The reaction mixture was diluted with $CH_2Cl_2$ (100 mL), washed with water (50 mL), brine, dried over anhydrous $Na_2SO_4$, concentrated under reduced pressure to give (4-bromo-3-fluorophenyl)(4,4-difluoropiperidin-1-yl)methanone (435), which was used in next step without further purification (3 g, 93% yield). LCMS: m/z 322.1 $[M+H]^+$; $t_R$=1.63 min.

Synthesis of tert-butyl (7-chloro-5-(4-(4,4-difluoropiperidine-1-carbonyl)-2-fluorophenyl)benzofuran-2-yl)methylcarbamate (436)

(4-Bromo-3-fluorophenyl)(4,4-difluoropiperidin-1-yl)methanone (435; 786 mg, 2.45 mmol), tert-butyl (7-chloro-5-(4,4,5,5-tetramethyl-1,3,2-dioxaborolan-2-yl)benzofuran-2-yl)methylcarbamate (43; 1 g, 2.45 mmol), Pd(dppf)Cl$_2$ (204 mg, 0.25 mmol), and $K_2CO_3$ (676 mg, 4.9 mmol) were added in a mixture of dioxane (20 mL) and water (2 mL) and degassed. The reaction mixture was heated at 95° C. under nitrogen atmosphere for 2 h. The reaction mixture was cooled down to room temperature, filtered and the filtrate was concentrated and purified by silica gel chromatography (20% EtOAc/petroleum ether) to yield 1.0 g of tert-butyl (7-chloro-5-(4-(4,4-difluoropiperidine-1-carbonyl)-2-fluorophenyl)benzofuran-2-yl)methylcarbamate (436) as a white solid (78% yield). LCMS: m/z 523.1 $[M+H]^+$, $t_R$=2.06 min.

Synthesis of tert-butyl (5-(4-(4,4-difluoropiperidine-1-carbonyl)-2-fluorophenyl)-7-(pyridin-3-yl)benzofuran-2-yl)methylcarbamate (437)

tert-Butyl (7-chloro-5-(4-(4,4-difluoropiperidine-1-carbonyl)-2-fluorophenyl)benzofuran-2-yl)methylcarbamate (436; 500 mg, 0.96 mmol), pyridin-3-ylboronic acid (177 mg, 1.4 mmol), Pd(PPh$_3$)$_4$ (222 mg, 0.19 mmol), tricyclohexylphosphine (81 mg, 0.29 mmol) and $K_3PO_4$ (248 mg, 1.9 mmol) were added to a mixture of dioxane (10 mL) and water (2 mL) and degassed. The reaction mixture was heated under microwave irradiation at 140° C. for 2 h. The reaction mixture was cooled down to room temperature, poured into 10 mL of water, extracted with EtOAc (20 mL×3). The combined organic layers were washed with brine, dried over anhydrous $Na_2SO_4$, concentrated and purified by silica gel chromatography (50% EtOAc/petroleum ether) to give tert-butyl (5-(4-(4,4-difluoropiperidine-1-carbonyl)-2-fluorophenyl)-7-(pyridin-3-yl)benzofuran-2-yl)methylcarbamate (437) as white solid (240 mg, 44% yield). LCMS: m/z 566.2 $[M+H]^+$; $t_R$=1.59 min.

Synthesis of (4-(2-(aminomethyl)-7-(pyridin-3-yl)benzofuran-5-yl)-3-fluorophenyl)(4,4-difluoropiperidin-1-yl)methanone (438)

tert-Butyl (5-(4-(4,4-difluoropiperidine-1-carbonyl)-2-fluorophenyl)-7-(pyridin-3-yl)benzofuran-2-yl)methylcarbamate (437; 240 mg, 0.43 mmol) was dissolved in $CH_2Cl_2$ (5 mL). TFA (1 mL) was added dropwise at room temperature. The reaction mixture was stirred at room temperature for 1 h. The reaction mixture was concentrated under reduced pressure to give (4-(2-(aminomethyl)-7-(pyridin-3-yl)benzofuran-5-yl)-3-fluorophenyl)(4,4-difluoropiperidin-1-yl)methanone (438), which was used without further purification in the next step (250 mg, 100% yield). LCMS: m/z 466.1 $[M+H]^+$, $t_R$=1.56 min.

Synthesis of (E)-3-(6-aminopyridin-3-yl)-N-((5-(4-(4,4-difluoropiperidine-1-carbonyl)-2-fluorophenyl)-7-(pyridin-3-yl)benzofuran-2-yl)methyl)acrylamide (748)

(4-(2-(Aminomethyl)-7-(pyridin-3-yl)benzofuran-5-yl)-3-fluorophenyl)(4,4-difluoropiperidin-1-yl)methanone (438; 250 mg, 0.43 mmol) was dissolved in DMF (4 mL) and (E)-3-(6-aminopyridin-3-yl)acrylic acid (84 mg, 0.51 mmol) was added at 0° C. HATU (194 mg, 0.51 mmol) was added to this reaction mixture at 0° C. followed by DIPEA (111 mg, 0.86 mmol) dropwise. The reaction mixture was allowed to warm to room temperature and stirred further for 1 h. The reaction mixture was purified Prep-HPLC to afford 38 mg of (E)-3-(6-aminopyridin-3-yl)-N-((5-(4-(4,4-difluoropiperidine-carbonyl)-2-fluorophenyl)-7-(pyridin-3-yl)benzofuran-2-yl)methyl)acrylamide (748) (15% yield). $^1$H NMR (400 MHz, DMSO-d$_6$) δ 9.18 (d, J=2 Hz, 1H), 8.69-8.59 (m, 2H), 8.38-8.30 (m, 1H), 8.08 (d, J=2 Hz, 1H), 7.87 (s, 1H), 7.81-7.71 (m, 2H), 7.64-7.54 (m, 2H), 7.48 (d, J=11 Hz, 1H), 7.41 (d, J=8 Hz, 1H), 7.35 (d, J=16 Hz, 1H), 6.91 (s, 1H), 6.51-6.36 (m, 4H), 4.61 (d, J=6 Hz, 2H), 3.82-3.64 (m, 2H), 3.58-3.40 (m, 2H), 2.14-2.00 (m, 4H). LCMS: m/z 612.2 $[M+H]^+$, $t_R$=1.72 min.

Synthesis of (E)-3-(6-aminopyridin-3-yl)-N-((5-(4-(4,4-difluoropiperidine-1-carbonyl)-2-fluorophenyl)-7-(4-(trifluoromethyl)phenyl)benzofuran-2-yl)methyl)acrylamide (749)
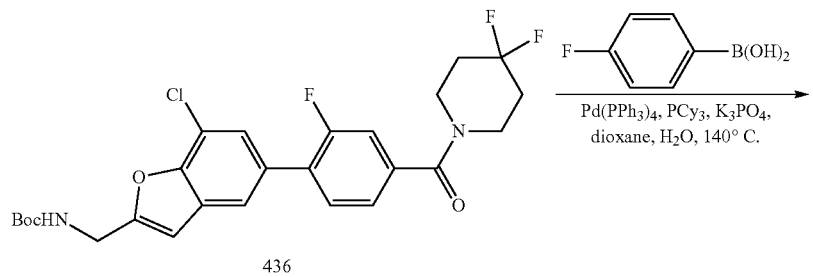
436
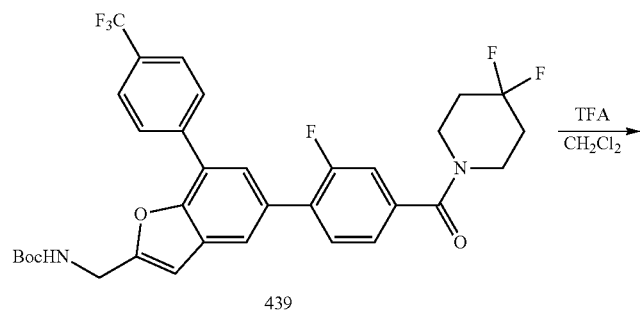
439
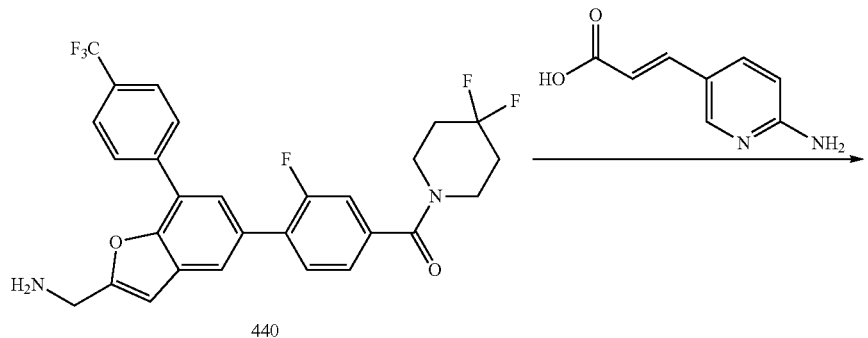
440
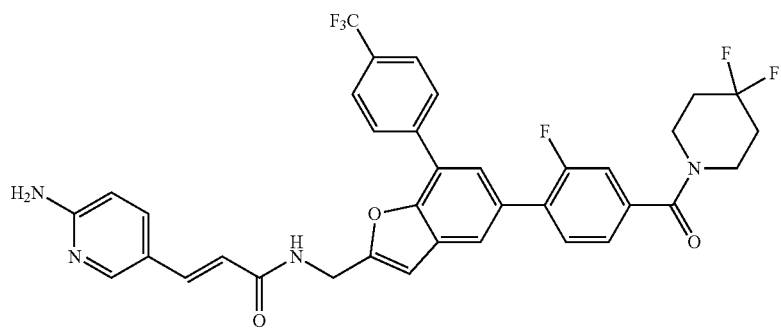
749

(E)-3-(6-aminopyridin-3-yl)-N-((5-(4-(4,4-difluoropiperidine-1-carbonyl)-2-fluorophenyl)-7-(4-(trifluoromethyl)phenyl)benzofuran-2-yl)methyl)acrylamide (749) was synthesized using the indicated reagents in a similar fashion as example (748). Yield: 43%. ¹H NMR (400 MHz, DMSO-$d_6$) δ 8.62 (t, J=5 Hz, 1H), 8.22-8.14 (m, 2H), 8.09 (s, 1H), 7.93-7.85 (m, 3H), 7.80-7.71 (m, 2H), 7.65-7.59 (m, 1H), 7.49 (d, J=11 Hz, 1H), 7.44-7.33 (m, 2H), 6.91 (s, 1H), 6.52-6.38 (m, 4H), 4.61 (d, J=5 Hz, 2H), 3.79-3.43 (m, 4H), 2.16-1.99 (m, 4H). LCMS: m/z 679.2 [M+H]⁺, $t_R$=1.95 min.

Synthesis of (E)-3-(6-aminopyridin-3-yl)-N-((7-(4-chlorophenyl)-5-(4-(4,4-difluoropiperidine-1-carbonyl)-2-fluorophenyl)benzofuran-2-yl)methyl)acrylamide (750)

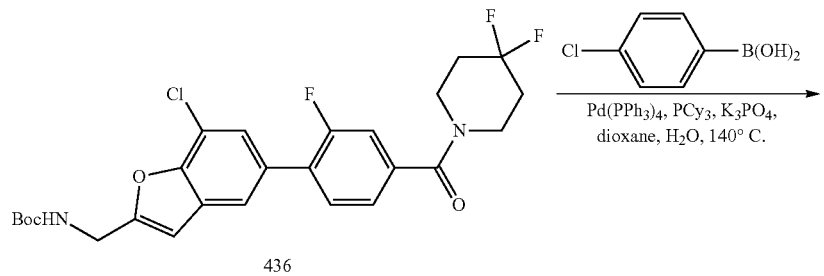

436

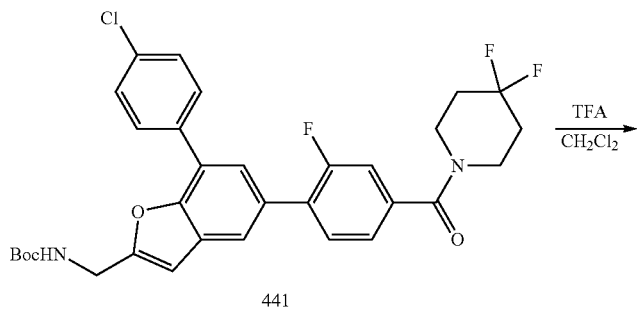

441

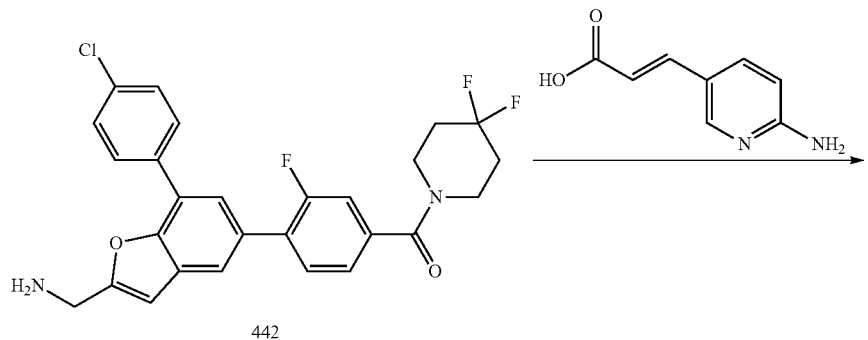

442

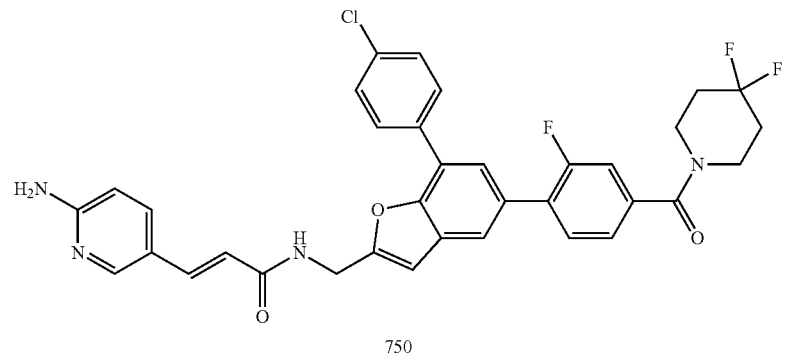

750

(E)-3-(6-aminopyridin-3-yl)-N-((7-(4-chlorophenyl)-5-(4-(4,4-difluoropiperidine-1-carbonyl)-2-fluorophenyl)benzofuran-2-yl)methyl)acrylamide (750) was synthesized using the indicated reagents in a similar fashion as example (748). $^1$H NMR (400 MHz, DMSO-$d_6$) δ 8.63 (t, J=6 Hz, 1H), 8.09 (s, 1H), 8.02-7.95 (m, 2H), 7.83 (s, 1H), 7.75 (t, J=8 Hz, 1H), 7.68-7.56 (m, 4H), 7.48 (d, J=11 Hz, 1H), 7.44-7.32 (m, 2H), 6.89 (s, 1H), 6.51-6.39 (m, 4H), 4.59 (d, J=6 Hz, 2H), 3.79-3.42 (m, 4H), 2.15-2.00 (m, 4H). LCMS: m/z 645.2 [M+H]$^+$, $t_R$=1.51 min.

Synthesis of (E)-3-(6-aminopyridin-3-yl)-N-((5-(4-(4,4-difluoropiperidine-1-carbonyl)-2-fluorophenyl)-7-(4-fluorophenyl)benzofuran-2-yl)methyl)acrylamide (751)

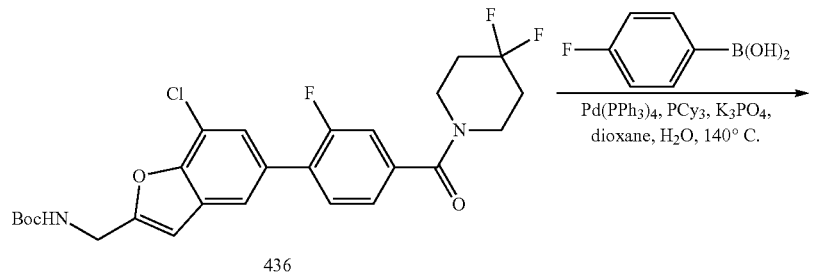

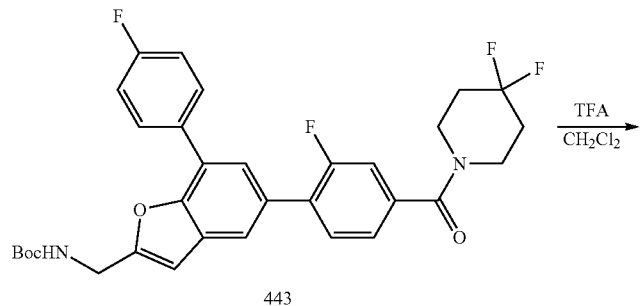

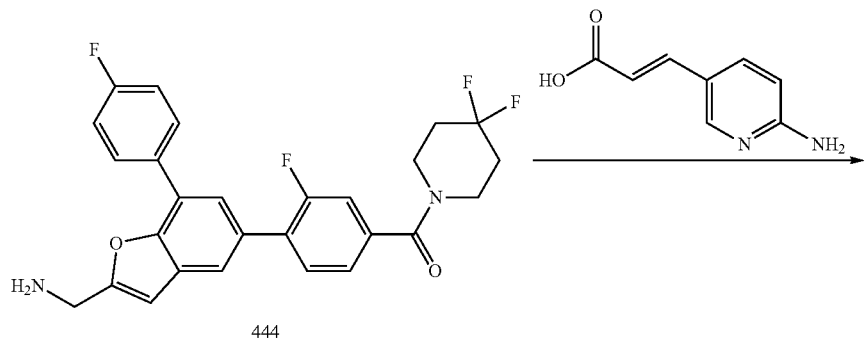

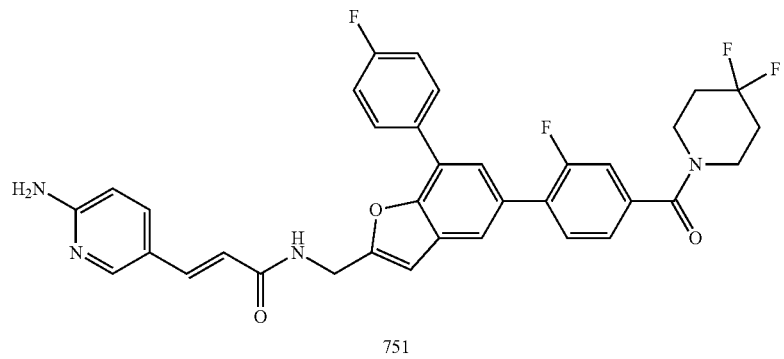

(E)-3-(6-aminopyridin-3-yl)-N-((5-(4(4-(4,4-difluoropiperidine-carbonyl)-2-fluorophenyl)-7-(4-fluorophenyl)benzofuran-2-methyl)methylamide (751) was synthesized using the indicated reagents in a similar fashion as example (748). ¹H NMR (400 MHz, DMSO-d₆) δ 8.63 (t, J=6 Hz, 1H), 8.09 (s, 1H), 8.02-7.95 (m, 2H), 7.83 (s, 1H), 7.75 (t, J=8 Hz, 1H), 7.68-7.56 (m, 4H), 7.48 (d, J=11 Hz, 1H), 7.44-7.32 (m, 2H), 6.89 (s, 1H), 6.51-6.39 (m, 4H), 4.59 (d, J=6 Hz, 2H), 3.79-3.42 (m, 4H), 2.15-2.00 (m, 4H). LCMS: m/z 645.2 [M+H]⁺, t$_R$=1.51 min.

Synthesis of (E)-N-((5-(5-(4,4-difluoropiperidine-1-carbonyl)pyridin-2-yl)-7-(trifluoromethoxy)benzofuran-2-yl)methyl)-3-(pyridin-3-yl)acrylamide (752)

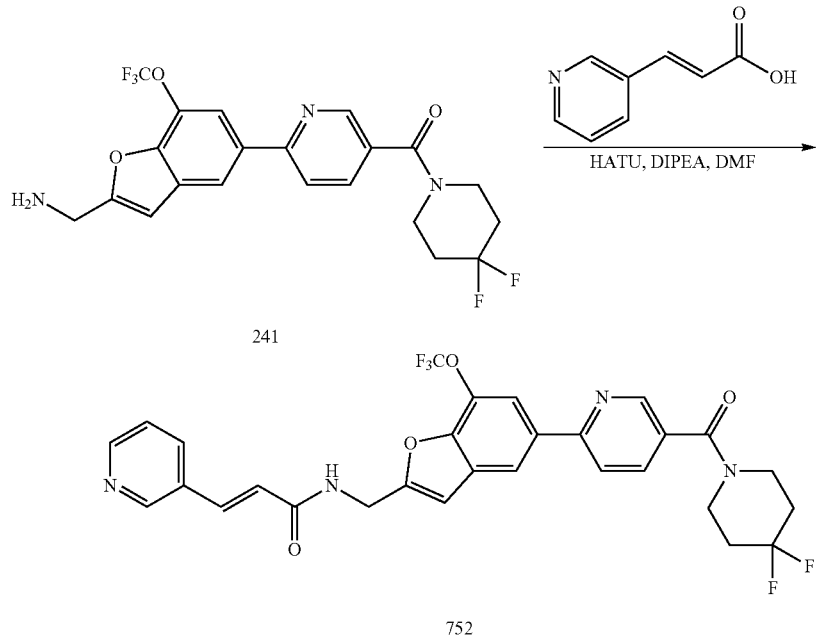

(E)-N-((5-(5-(4,4-difluoropiperidine-1-carbonyl)pyridin-2-yl)-7-(trifluoromethoxy)benzofuran-2-yl)methyl)-3-(pyridin-3-yl)acrylamide (752) was synthesized using the indicated reagents according to General Procedure 4. Yield: 27%. ¹H NMR (400 MHz, DMSO-d₆) δ 8.93 (t, J=6 Hz, 1H), 8.81-8.74 (m, 2H), 8.60-8.54 (m, 1H), 8.45 (d, J=2 Hz, 1H), 8.20-8.11 (m, 2H), 8.05-7.98 (m, 2H), 7.55 (d, J=16 Hz, 1H), 7.49-7.43 (m, 1H), 7.01 (s, 1H), 6.83 (d, J=16 Hz, 1H), 4.65 (d, J=6 Hz, 2H), 3.79-3.44 (m, 4H), 2.15-2.02 (m, 4H). LCMS: m/z 587.2 [M+H]⁺, t$_R$=1.82 min.

Synthesis of (E)-3-(6-aminopyridin-3-yl)-N-((7-(2,4-difluorophenyl)-5-(4-(4,4-difluoropiperidine-1-carbonyl)-2-fluorophenyl)benzofuran-2-yl)methyl) acrylamide (753)

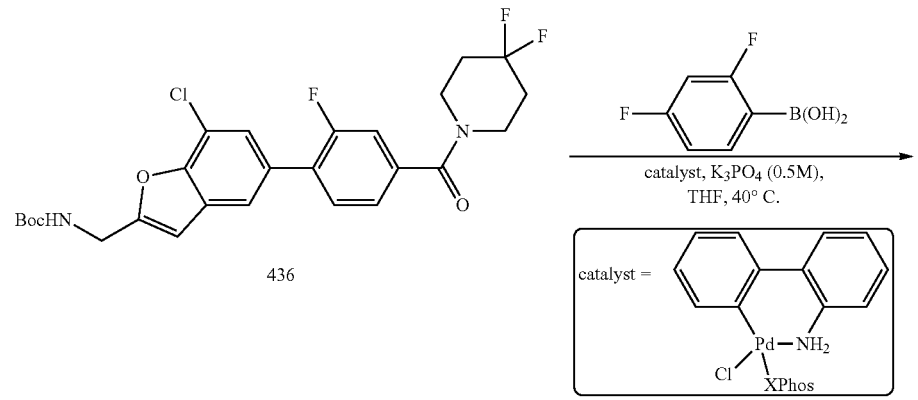

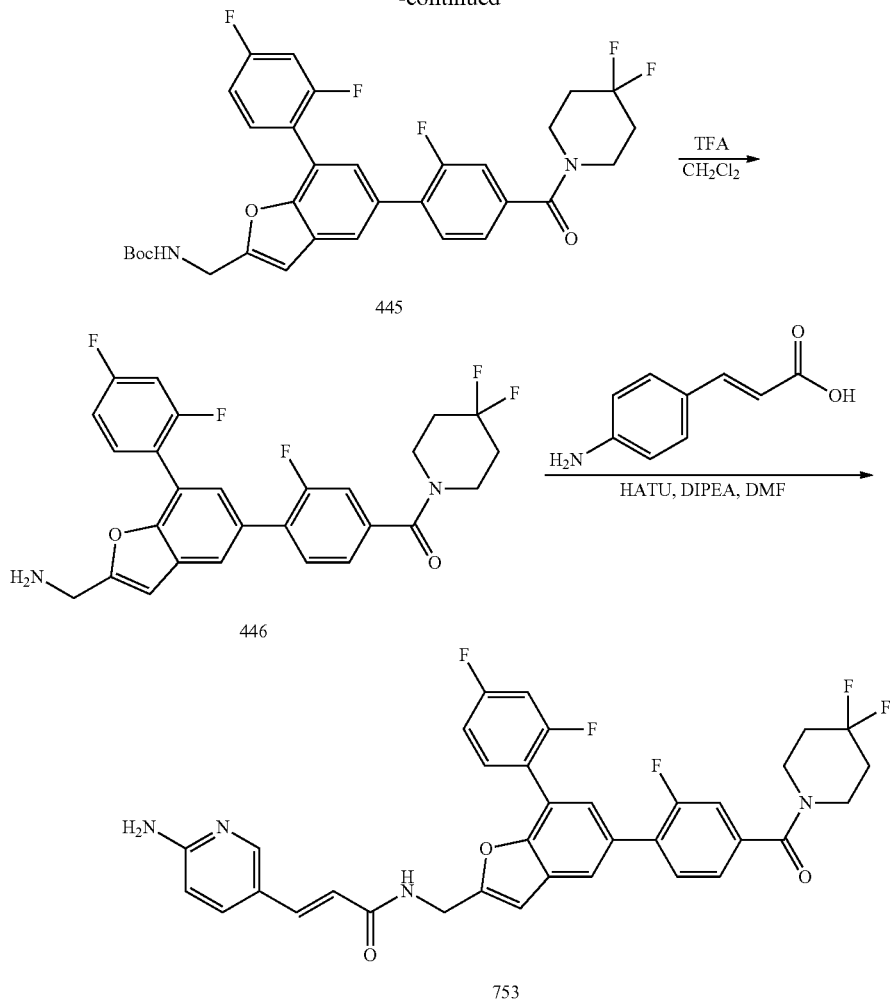

Synthesis of tert-butyl (7-(2,4-difluorophenyl)-5-(4-(4,4-difluoropiperidine-1-carbonyl)-2-fluorophenyl)benzofuran-2-yl)methylcarbamate (445)

tert-Butyl (7-chloro-5-(4-(4,4-difluoropiperidine-1-carbonyl)-2-fluorophenyl)benzofuran-2-yl)methylcarbamate (436; 150 mg, 0.29 mmol), 2,4-difluorophenylboronic acid (68 mg, 0.43 mmol), catalyst (23 mg, 0.03 mmol) and $K_3PO_4$ (1.2 mL, 0.6 mmol, 0.5 M) were added in THF (4 mL) and degassed. The reaction mixture was heated at 40° C. for 2 h. The reaction mixture was concentrated under reduced pressure to give the crude product, which was purified by silica gel chromatography (0-30% EtOAc/petroleum ether) to give tert-butyl (7-(2,4-difluorophenyl)-5-(4-(4,4-difluoropiperidine-1-carbonyl)-2-fluorophenyl)benzofuran-2-yl)methylcarbamate (445) (160 mg, 92% yield). LCMS: m/z 601.2 [M+H]$^+$; $t_R$=1.82 min.

Synthesis of (4-(2-(aminomethyl)-7-(2,4-difluorophenyl)benzofuran-5-yl)-3-fluorophenyl)(4,4-difluoropiperidin-1-yl)methanone (446)

tert-Butyl (7-(2,4-difluorophenyl)-5-(4-(4,4-difluoropiperidine-1-carbonyl)-2-fluorophenyl)benzofuran-2-yl)methylcarbamate (445; 160 mg, 0.27 mmol) was dissolved in $CH_2Cl_2$ (5 mL). TFA (3 mL) was added at 0° C. (ice bath). The reaction mixture was stirred at room temperature for 1 h, and concentrated under reduced pressure to give 133 mg of (4-(2-(aminomethyl)-7-(2,4-difluorophenyl)benzofuran-5-yl)-3-fluorophenyl)(4,4-difluoropiperidin-1-yl)methanone (446), which was used without further purification in next step (100% yield). LCMS: m/z 501.1 [M+H]$^+$; $t_R$=1.27 min.

Synthesis of (E)-3-(6-aminopyridin-3-yl)-N-((7-(2,4-difluorophenyl)-5-(4-(4,4-difluoropiperidine-1-carbonyl)-2-fluorophenyl)benzofuran-2-yl)methyl)acrylamide (753)

(4-(2-(Aminomethyl)-7-(2,4-difluorophenyl)benzofuran-5-yl)-3-fluorophenyl)(4,4-difluoropiperidin-1-yl)methanone (446; 130 mg, 0.25 mmol) was dissolved in DMF (5 mL) and (E)-3-(pyridin-3-yl)acrylic acid (46 mg, 0.28 mmol) was added at 0° C. HATU (148 mg, 0.39 mmol) was added to this reaction mixture at 0° C. followed by DIPEA (100 mg, 0.78 mmol) dropwise. The reaction mixture was allowed to warm to room temperature and stirred further for 1 h. The crude mixture was purified by Prep-HPLC without workup to yield 60 mg of (E)-3-(6-aminopyridin-3-yl)-N-((7-(2,4-difluorophenyl)-5-(4-(4,4-difluoropiperidine-1-carbonyl)-2-fluorophenyl)benzofuran-2-yl)methyl)acrylamide (753). Yield (36%). $^1$H NMR (400 MHz, $CD_3OD$) δ 8.06 (d, J=2 Hz, 1H), 7.82 (s, 1H), 7.77-7.66 (m, 3H), 7.52 (s, 1H), 7.48 (d,

565
J=16 Hz, 1H), 7.42-7.36 (m, 2H), 7.18-7.09 (m, 2H), 6.86 (s, 1H), 6.61 (d, J=9 Hz, 1H), 6.46 (d, J=16 Hz, 1H), 4.67 (s, 2H), 3.95-3.58 (m, 4H), 2.20-1.99 (m, 4H). LCMS: m/z 647.2 [M+H]$^+$, $t_R$=1.88 min.
566
Synthesis of (E)-3-(6-aminopyridin-3-yl)-N-((5-(4-(4,4-difluoropiperidine-1-carbonyl)phenyl)-7-(2,6-difluoropyridin-3-yl)benzofuran-2-yl)methyl)acrylamide (754)
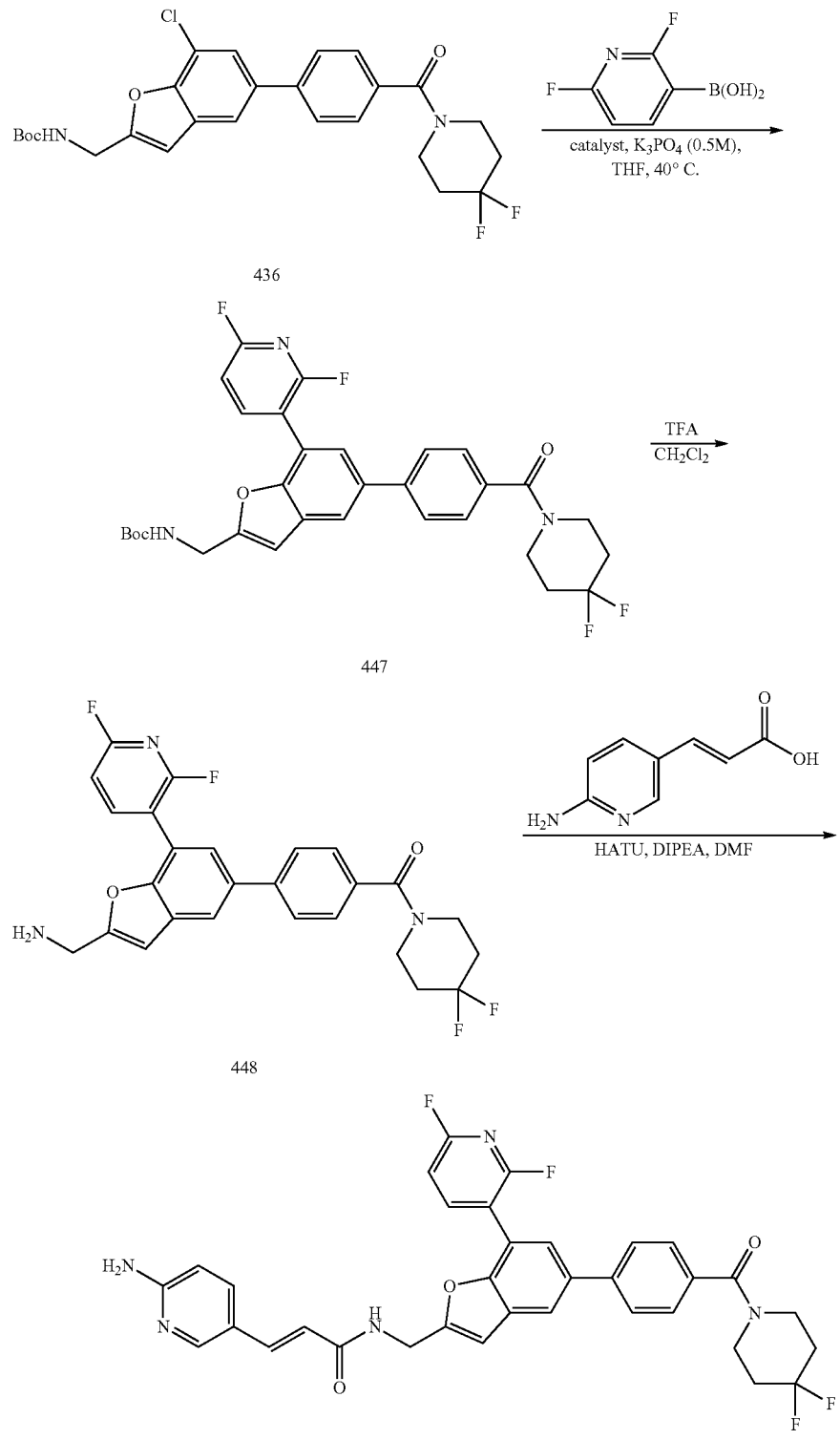

(E)-3-(6-aminopyridin-3-yl)-N-((5-(4-(4,4-difluoropiperidine-1-carbonyl)phenyl)-7-(2,6-difluoropyridin-3-yl)benzofuran-2-yl)methyl)acrylamide (754) was synthesized using the indicated reagents in a similar fashion as example (753). Yield: 28%. $^1$H NMR (400 MHz, DMSO-d$_6$) δ 8.62-8.51 (m, 2H), 8.09-8.00 (m, 2H), 7.87-7.80 (m, 2H), 7.74 (s, 1H), 7.62-7.53 (m, 3H), 7.43-7.38 (m, 1H), 7.34 (d, J=16 Hz, 1H), 6.88 (s, 1H), 6.50-6.36 (m, 4H), 4.55 (d, J=5 Hz, 2H), 3.77-3.41 (m, 4H), 2.14-1.97 (m, 4H). LCMS: m/z 630.3 [M+H]$^+$, t$_R$=1.81 min.

Synthesis of (E)-3-(6-aminopyridin-3-yl)-N-((5-(4-(4,4-difluoropiperidine-1-carbonyl)-2-fluorophenyl)-7-(3-fluorophenyl)benzofuran-2-yl)methyl)acrylamide (755)

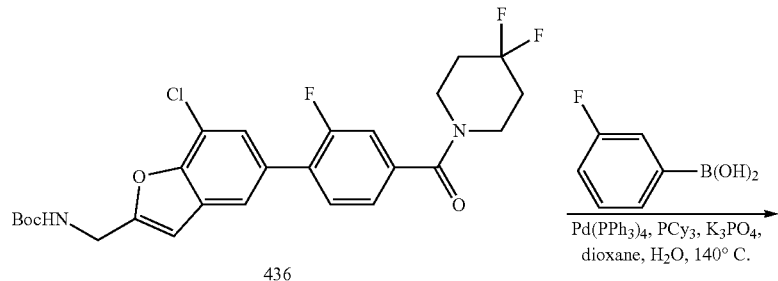

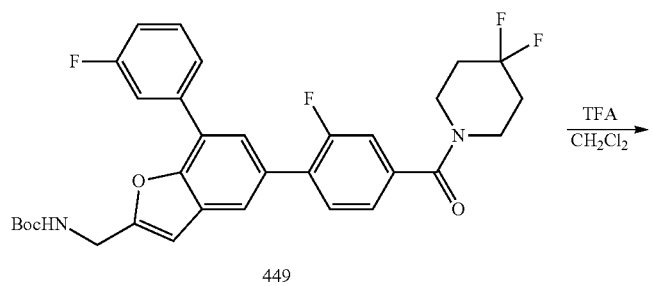

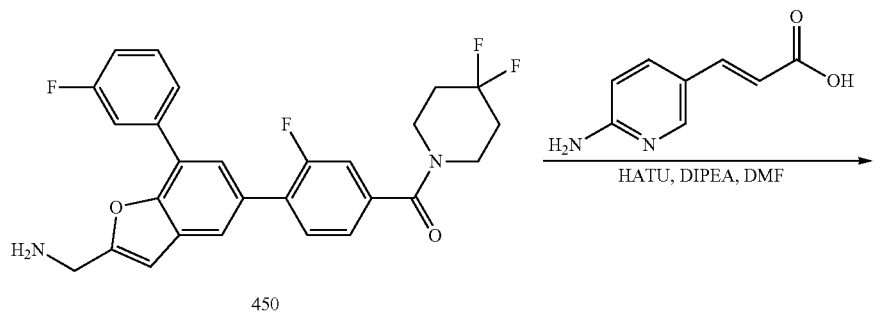

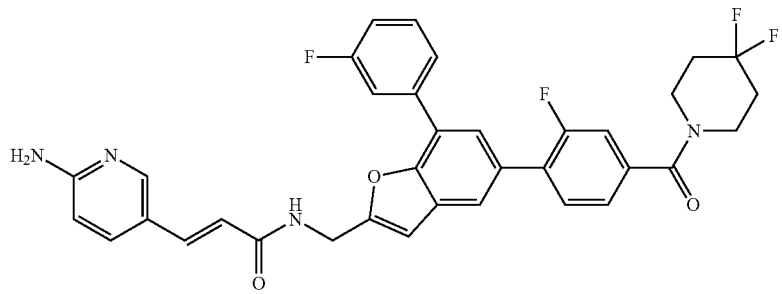

(E)-3-(6-aminopyridin-3-yl)-N-((5-(4-(4,4-difluoropiperidine-1-carbonyl)-2-fluorophenyl)-7-(3-fluorophenyl)benzofuran-2-yl)methyl)acrylamide (755) was synthesized using the indicated reagents in a similar fashion as example (753). Yield: 34%. $^1$H NMR (400 MHz, DMSO-$d_6$) δ 8.83 (t, J=6 Hz, 1H), 8.24-8.03 (m, 4H), 7.86-7.38 (m, 9H), 7.29 (t, J=9 Hz, 1H), 6.96 (d, J=9 Hz, 1H), 6.91 (s, 1H), 6.60 (d, J=16 Hz, 1H), 4.64 (d, J=6 Hz, 2H), 3.77-3.44 (m, 4H), 2.15-2.00 (m, 4H). LCMS: m/z 629.2 [M+H]$^+$, $t_R$=1.47 min.

Synthesis of (E)-3-(6-aminopyridin-3-yl)-N-((7-(3-chlorophenyl)-5-(4-(4,4-difluoropiperidine-1-carbonyl)-2-fluorophenyl)benzofuran-2-yl)methyl)acrylamide (756)

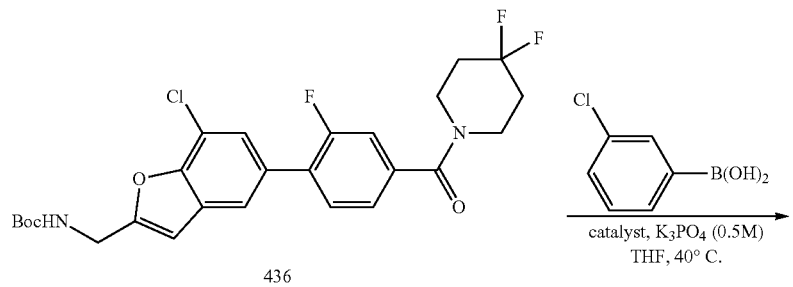

436

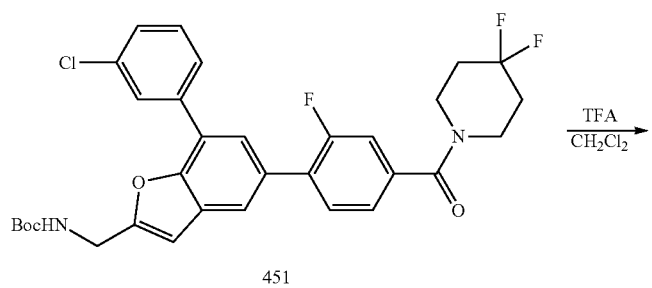

451

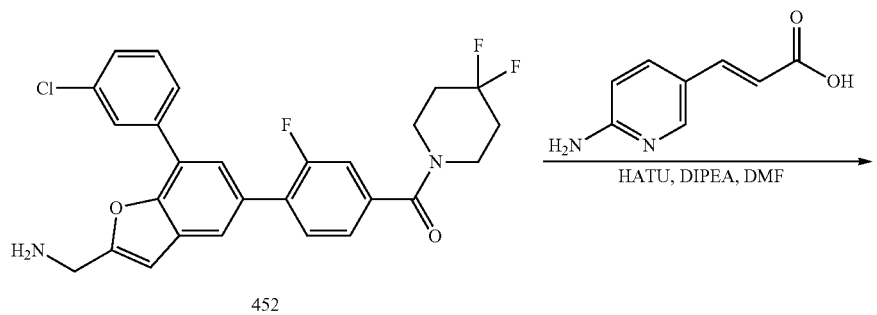

452

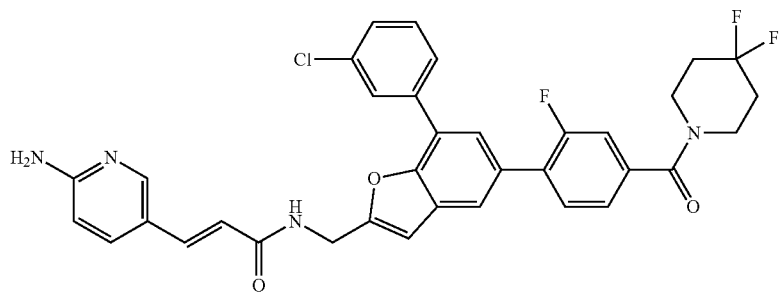

756

(E)-3-(6-aminopyridin-3-yl)-N-((7-(3-chlorophenyl)-5-(4-(4,4-difluoropiperidine-1-carbonyl)-2-fluorophenyl)benzofuran-2-yl)methyl)acrylamide (756) was synthesized using the indicated reagents in a similar fashion as example (753). Yield: 15%. $^1$H NMR (400 MHz, CD$_3$OD) δ 8.08-8.05 (m, 1H), 7.95-7.92 (m, 1H), 7.85 (d, J=8 Hz, 1H), 7.82-7.78 (m, 1H), 7.77-7.69 (m, 2H), 7.66-7.62 (m, 1H), 7.54-7.47 (m, 2H), 7.45-7.37 (m, 3H), 6.87 (s, 1H), 6.61 (d, J=9 Hz, 1H), 6.49 (d, J=16 Hz, 1H), 4.73 (s, 2H), 3.94-3.60 (m, 4H), 2.20-2.03 (m, 4H). LCMS: m z 645.2 [M+H]$^+$, t$_R$=1.93 min.

Synthesis of (E)-3-(6-aminopyridin-3-yl)-N-((7-(3-chloro-4-fluorophenyl)-5-(4-(4,4-difluoropiperidine-1-carbonyl)-2-fluorophenyl)benzofuran-2-yl)methyl)acrylamide (757)

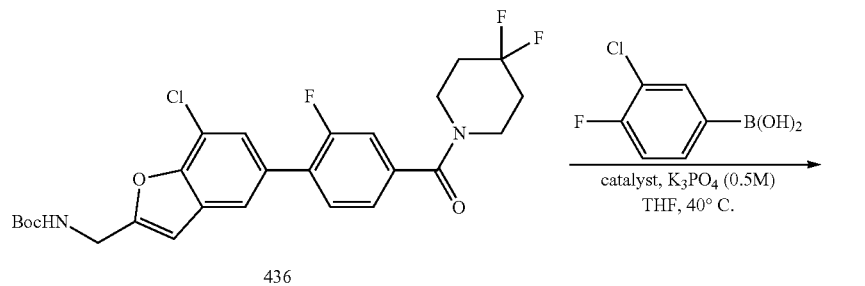

436

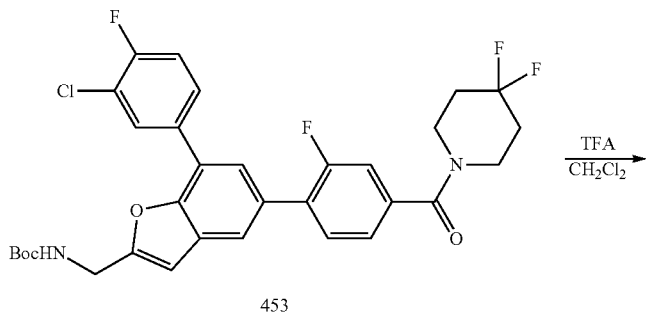

453

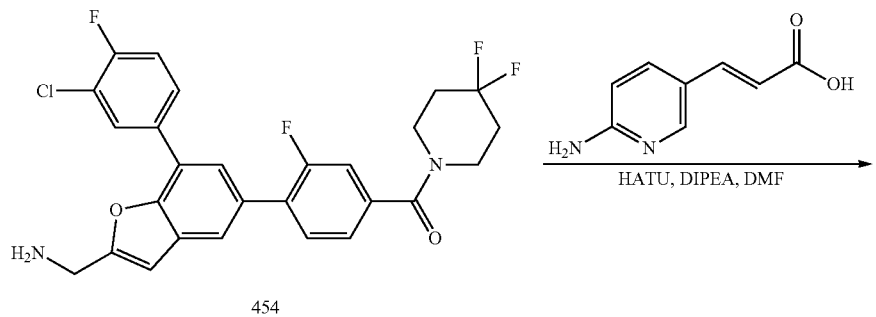

454

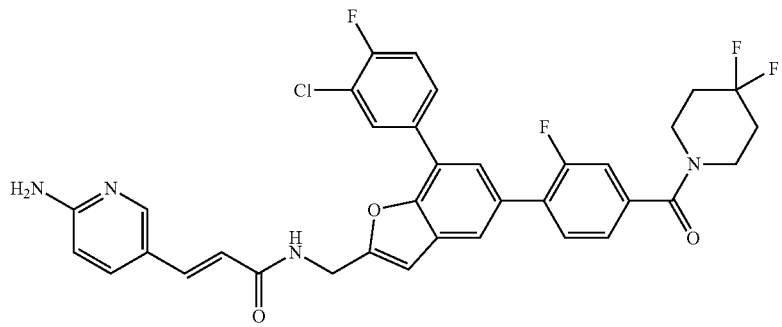

757

573

(E)-3-(6-aminopyridin-3-yl)-N-((7-(3-chloro-4-fluorophenyl)-5-(4-(4,4-difluoropiperidine-1-carbonyl)-2-fluorophenyl)benzofuran-2-yl)methyl)acrylamide (757) was synthesized using the indicated reagents in a similar fashion as example (753). Yield: 8%. $^1$H NMR (400 MHz, DMSO-$d_6$) δ 8.61 (t, J=5 Hz, 1H), 8.20-8.14 (m, 1H), 8.10-8.05 (m, 1H), 8.03-7.96 (m, 1H), 7.84 (s, 1H), 7.77 (t, J=8 Hz, 1H), 7.70 (s, 1H), 7.64-7.56 (m, 2H), 7.47 (d, J=11 Hz, 1H), 7.40 (d, J=8 Hz, 1H), 7.36 (d, J=16 Hz, 1H), 6.89 (s, 1H), 6.49-6.38

574

(m, 4H), 4.61 (d, J=5 Hz, 2H), 3.79-3.43 (m, 4H), 2.15-1.99 (m, 4H). LCMS: m/z 663.2 [M+H]$^+$, $t_R$=1.90 min.

Synthesis of (E)-3-(6-aminopyridin-3-yl)-N-((5-(4-(4,4-difluoropiperidine-1-carbonothioyl)-2-fluorophenyl)-7-(4-fluorophenyl)benzofuran-2-yl)methyl)acrylamide (758)

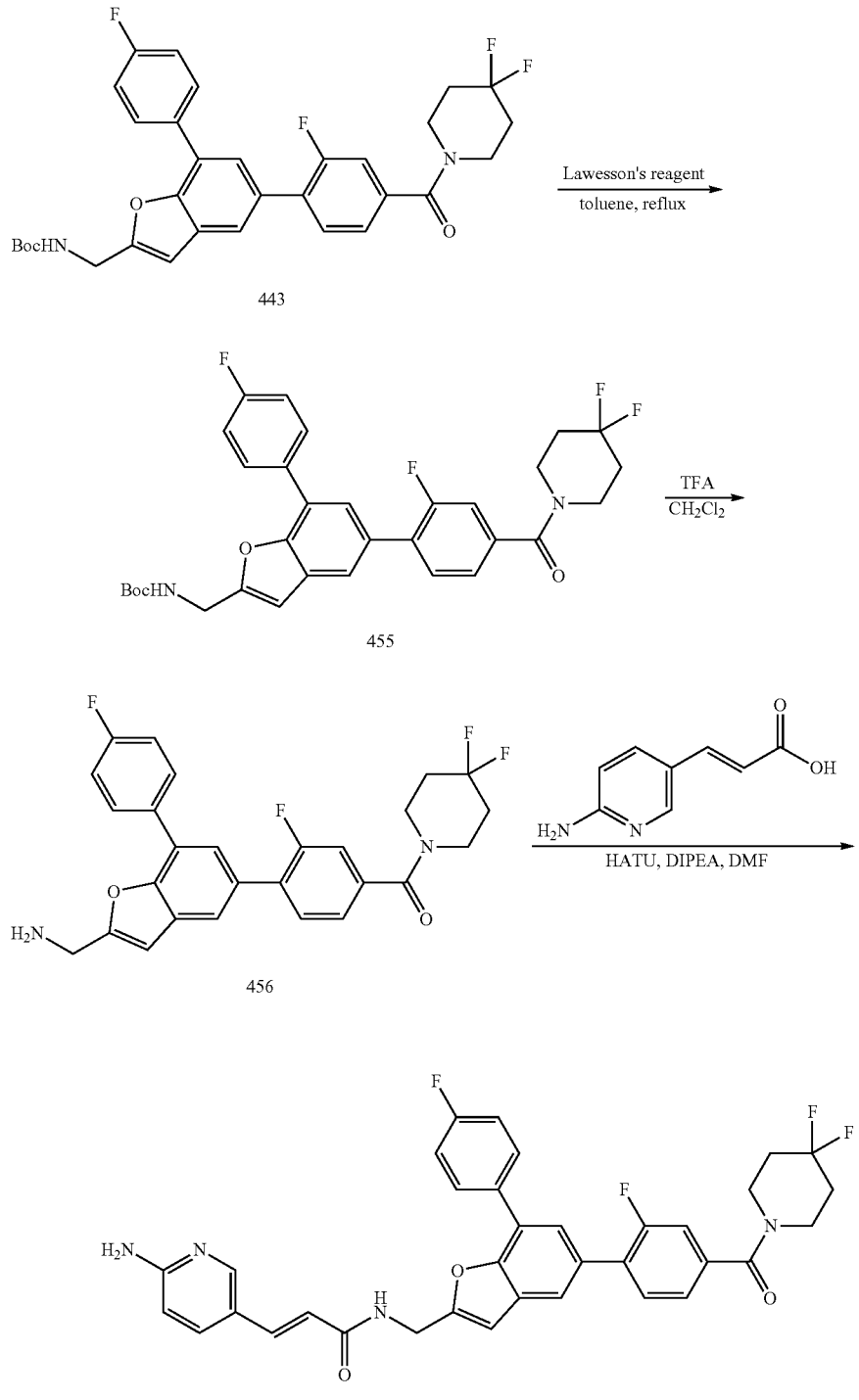

(E)-3-(6-aminopyridin-3-yl)-N-((5-(4-(4,4-difluoropiperidine-1-carbonothioyl)-2-fluorophenyl)-7-(4-fluorophenyl)benzofuran-2-yl)methyl)acrylamide (758) was synthesized using the indicated reagents in a similar fashion as example (705). $^1$H NMR (400 MHz, DMSO-d$_6$) δ 8.61 (t, J=6 Hz, 1H), 8.09 (s, 1H), 8.04-7.96 (m, 2H), 7.80 (s, 1H), 7.69 (t, J=8 Hz, 1H), 7.66-7.58 (m, 2H), 7.42-7.27 (m, 5H), 6.88 (s, 1H), 6.52-6.38 (m, 4H), 4.60 (d, J=6 Hz, 2H), 4.48-4.38 (m, 2H), 3.76-3.66 (m, 2H), 2.33-2.09 (m, 4H). LCMS: m/z 645.3 [M+H]$^+$, t$_R$=1.99 min.

Synthesis of (E)-3-(6-aminopyridin-3-yl)-N-((7-(2,4-difluorophenyl)-5,5'-bibenzofuran-2-yl) methyl) acrylamide (759)

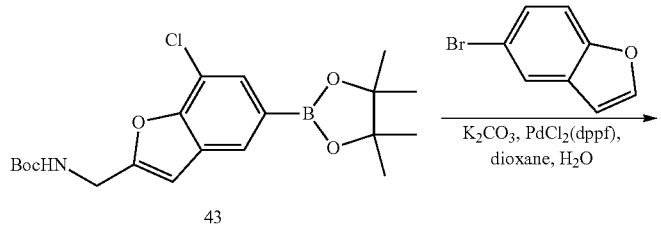

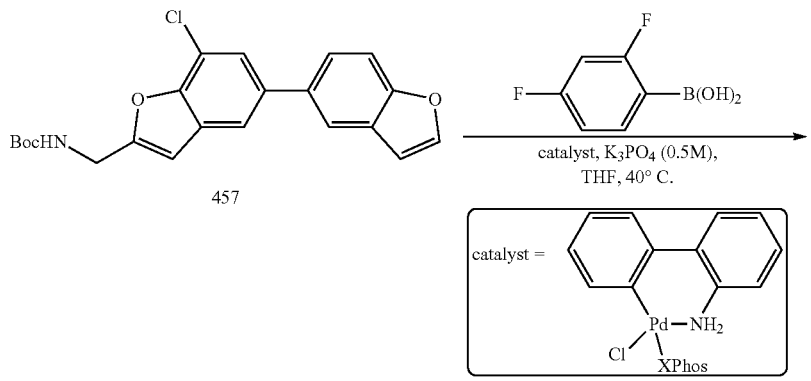

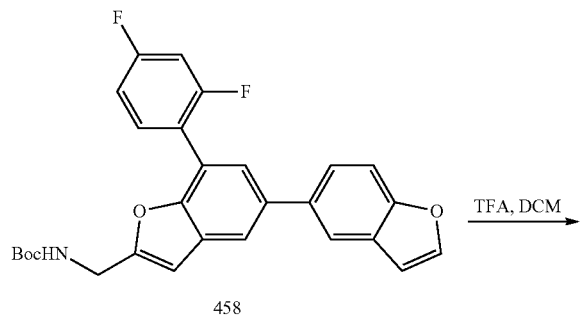

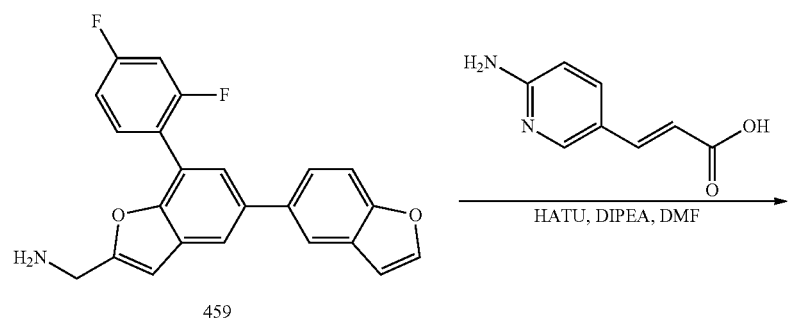

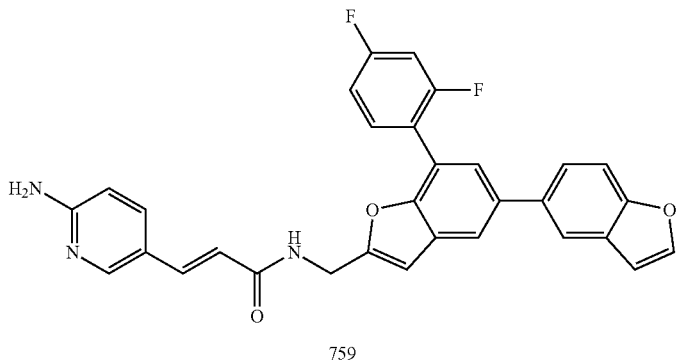

759

Synthesis of tert-butyl (7-chloro-5,5'-bibenzofuran-2-yl)methylcarbamate (457)

tert-Butyl (7-chloro-5-(4,4,5,5-tetramethyl-1,3,2-dioxaborolan-2-yl)benzofuran-2-yl)methylcarbamate (43; 1.2 g, 3 mmol), 5-bromobenzofuran (500 mg, 2.5 mmol), Pd(dppf)Cl$_2$ (200 mg, 0.25 mmol), and K$_2$CO$_3$ (1 g, 7.5 mmol) were added in a mixture of (10:1) dioxane (20 mL) and water (2 mL) and degassed. The reaction mixture was heated at 90° C. under nitrogen atmosphere for 16 h. The reaction mixture was cooled down to room temperature, filtered and the filtrate was concentrated under reduced pressure to give the crude product, which was purified by silica gel chromatography (10% EtOAc/petroleum ether) to yield 720 mg of tert-butyl (7-chloro-5,5'-bibenzofuran-2-yl)methylcarbamate (457) as colorless oil (yield 71%). LCMS: m/z 420.0 [M+Na]$^+$, $t_R$=1.91 min.

Synthesis of tert-butyl (7-(2,4-difluorophenyl)-5,5'-bibenzofuran-2-yl)methylcarbamate (458)

tert-Butyl (7-chloro-5,5'-bibenzofuran-2-yl)methylcarbamate (457; 500 mg, 1.3 mmol), 2,4-difluorophenylboronic acid (300 mg, 1.9 mmol), catalyst (76 mg, 0.13 mmol) and K$_3$PO$_4$ (7.6 mL, 3.8 mmol, 0.5 M) were added in THF (20 mL) and degassed. The reaction mixture was heated at 40° C. for 1 h. The reaction mixture was concentrated under reduced pressure to give the crude product, which was purified by silica gel chromatography (0-10% EtOAc/petroleum ether) to give tert-butyl (7-(2,4-difluorophenyl)-5,5'-bibenzofuran-2-yl)methylcarbamate (458) (470 mg, 56% yield). LCMS: m/z 498.0 [M+Na]$^+$; $t_R$=1.92 min.

Synthesis of (7-(2,4-difluorophenyl)-5,5'-bibenzofuran-2-yl)methanamine (459)

tert-Butyl (7-(2,4-difluorophenyl)-5,5'-bibenzofuran-2-yl)methylcarbamate (458; 150 mg, 0.32 mmol) was dissolved in CH$_2$Cl$_2$ (10 mL). TFA (2 mL) was added at 0° C. (ice bath). The reaction mixture was stirred at room temperature for 1 h, and concentrated under reduced pressure to give 118 mg of (7-(2,4-difluorophenyl)-5,5'-bibenzofuran-2-yl)methanamine (459), which was used without further purification in next step (100% yield). LCMS: m/z 359.0 [M-NH$_2$]$^+$; $t_R$=1.45 min.

Synthesis of (E)-3-(6-aminopyridin-3-yl)-N-((7-(2,4-difluorophenyl)-5,5'-bibenzofuran-2-yl)methyl)acrylamide (759)

(7-(2,4-Difluorophenyl)-5,5'-bibenzofuran-2-yl)methanamine (459; 118 mg, 0.31 mmol) was dissolved in DMF (3 mL) and (E)-3-(pyridin-3-yl)acrylic acid (56 mg, 0.34 mmol) was added at 0° C. HATU (130 mg, 0.34 mmol) was added to this reaction mixture at 0° C. followed by DIPEA (120 mg, 0.93 mmol) dropwise. The reaction mixture was allowed to warm to room temperature and stirred further for 1 h. The crude mixture was purified by Prep-HPLC without workup to yield 45 mg of (E)-3-(6-aminopyridin-3-yl)-N-((7-(2,4-difluorophenyl)-5,5'-bibenzofuran-2-yl)methyl)acrylamide (759). Yield (27%). $^1$H NMR (400 MHz, DMSO-d$_6$) δ 8.56 (t, J=5 Hz, 1H), 8.07 (s, 1H), 8.04 (d, J=2 Hz, 1H), 7.99 (s, 1H), 7.93 (s, 1H), 7.83-7.77 (m, 1H), 7.70-7.57 (m, 4H), 7.49-7.41 (m, 1H), 7.34 (d, J=16 Hz, 1H), 7.31-7.24 (m, 1H), 7.01 (d, J=2 Hz, 1H), 6.85 (s, 1H), 6.49-6.36 (m, 4H), 4.54 (d, J=5 Hz, 2H). LCMS: m/z 522.2 [M+H]$^+$, $t_R$=1.99 min.

Synthesis of (E)-3-(6-aminopyridin-3-yl)-N-((5-(4-(1-(4,4-difluoropiperidin-1-yl)ethyl)phenyl)-7-(4-fluorophenyl)benzofuran-2-yl)methyl)acrylamide (760)

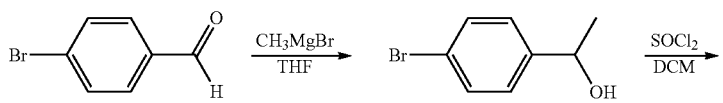

-continued
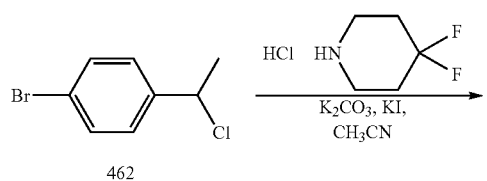
462
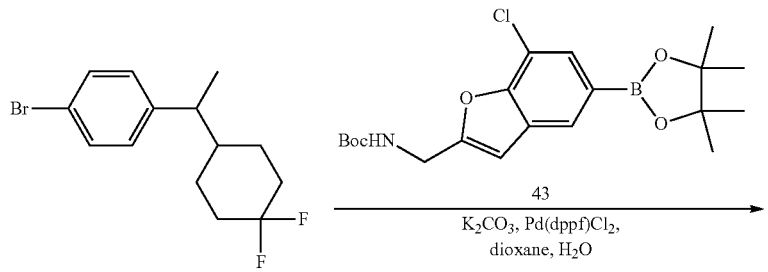
463
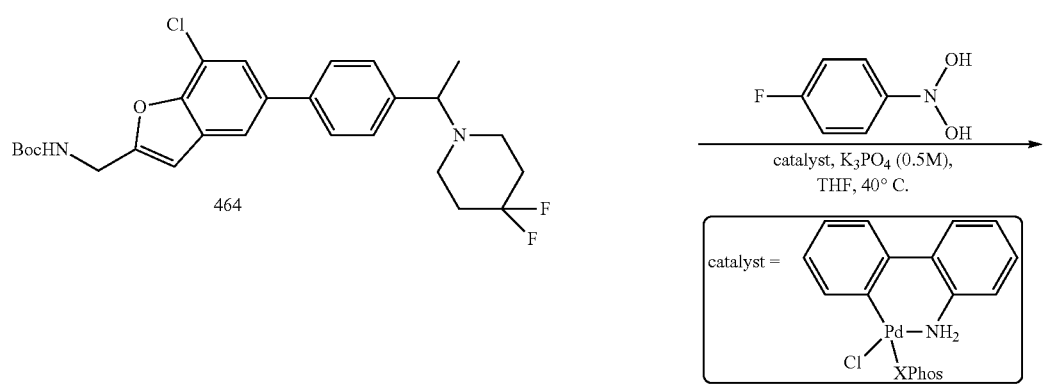
464
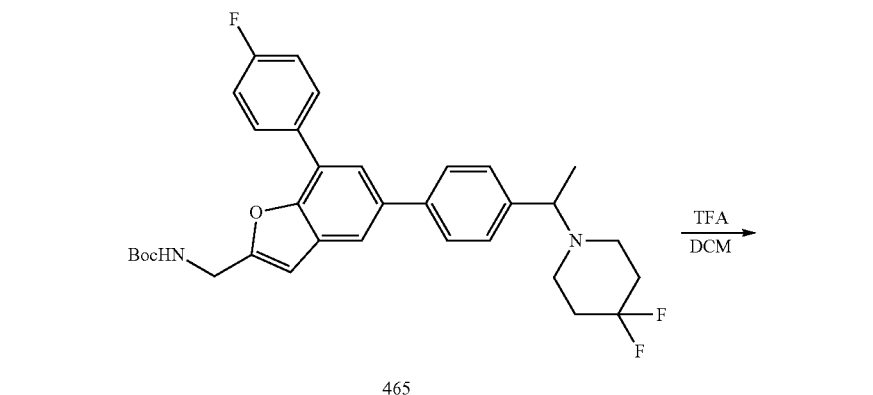
465
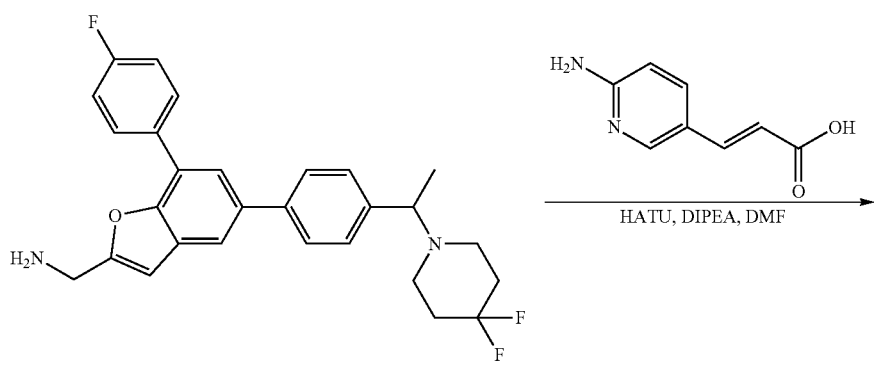
466

-continued

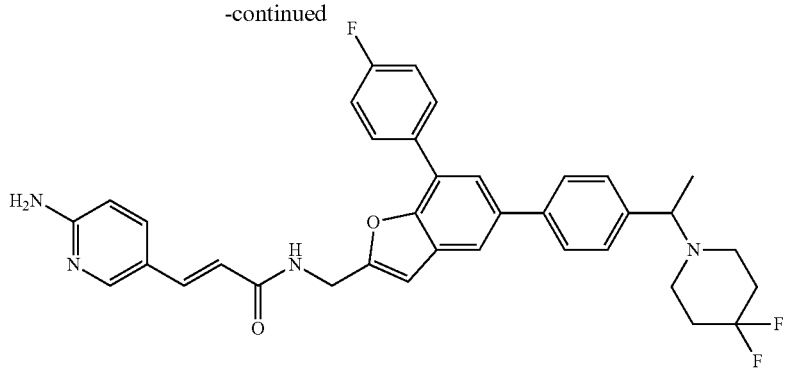

760

Synthesis of 1-(4-bromophenyl)ethanol (461)

4-Bromobenzaldehyde (460; 3 g, 16.2 mmol) was dissolved in THF (100 mL). The mixture was cooled down to 0° C. (ice bath). Methylmagnesium bromide (8.1 mL, 24.3 mmol, 3 M in ether) was added dropwise over 30 min. The reaction mixture was stirred at 0° C. for 2 h, quenched with saturated $NH_4Cl$ aqueous solution (20 mL), extracted with EtOAc (100 mL×3). The combined organic layers were washed with brine, dried over anhydrous $Na_2SO_4$, concentrated under reduced pressure and purified by silica gel chromatography (0-20% EtOAc/petroleum ether) to give 2.6 g of 1-(4-bromophenyl)ethanol (461) as colorless oil (80% yield).

Synthesis of 1-bromo-4-(1-chloroethyl)benzene (462)

1-(4-Bromophenyl)ethanol (461; 1.1 g, 5.5 mmol) was dissolved in $CH_2Cl_2$ (50 mL). The mixture was cooled down to 0° C. (ice bath). $SOCl_2$ (10 mL) was added dropwise over 10 min. The reaction was allowed to warm to room temperature, and then heated at 50° C. for 2 h. The reaction mixture was concentrated under reduced pressure to give a residue, which was dissolved in EtOAc (150 mL). The mixture was washed with saturated $NaHCO_3$ aqueous solution (100 mL), brine, dried over anhydrous $Na_2SO_4$, concentrated to give 940 mg of 1-bromo-4-(1-chloroethyl)benzene (462) as colorless oil (78% yield).

Synthesis of 1-(1-(4-bromophenyl)ethyl)-4,4-difluoropiperidine (463)

1-Bromo-4-(1-chloroethyl)benzene (462; 1.4 g, 6.2 mmol) was dissolved in acetonitrile (80 mL). 4,4-Difluoropiperidine hydrochloride (1.2 g, 7.4 mmol), $K_2CO_3$ (2.6 g, 18.6 mmol) and KI (100 mg, 0.6 mmol) were added at 25° C. The reaction mixture was heated at 80° C. for 6 h. After cooling down to room temperature, the reaction mixture was diluted with water (60 mL), extracted with EtOAc (100 mL×3). The combined organic layers were washed with brine, dried over anhydrous $Na_2SO_4$, concentrated under reduced pressure and purified by silica gel chromatography (0-10% EtOAc/petroleum ether) to give 1.5 g of 1-(1-(4-bromophenyl)ethyl)-4,4-difluoropiperidine (463) as colorless oil (79% yield). LCMS: m/z 304.0 $[M+H]^+$, $t_R$=1.29 min.

Synthesis of tert-butyl (7-chloro-5-(4-(1-(4,4-difluoropiperidin-1-yl)ethyl)phenyl)benzofuran-2-yl)methylcarbamate (464)

A mixture of 1-(1-(4-bromophenyl)ethyl)-4,4-difluoropiperidine (463; 740 mg, 2.4 mmol), tert-butyl (7-chloro-5-(4,4,5,5-tetramethyl-1,3,2-dioxaborolan-2-yl)benzofuran-2-yl)methylcarbamate (43; 1.2 g, 2.9 mmol), $Pd(dppf)Cl_2$ (195 mg, 0.2 mmol) and $K_2CO_3$ (1 g, 7.2 mmol) in 20 mL of dioxane and 2 mL of $H_2O$ was heated at 100° C. under nitrogen atmosphere for 16 h. After cooling down to room temperature, the reaction mixture was filtered. The filtrate was concentrated under reduced pressure to give the crude product, which was purified by silica gel chromatography (0-30% EtOAc/petroleum ether) to give 800 mg of tert-butyl (7-chloro-5-(4-(1-(4,4-difluoropiperidin-1-yl)ethyl)phenyl)benzofuran-2-yl)methylcarbamate (464) as colorless oil (65% yield). LCMS: m/z 505.1 $[M+H]^+$, $t_R$=1.53 min.

Synthesis of tert-butyl (5-(4-(1-(4,4-difluoropiperidin-1-yl)ethyl)phenyl)-7-(4-fluorophenyl)benzofuran-2-yl)methylcarbamate (465)

tert-Butyl (7-chloro-5-(4-(1-(4,4-difluoropiperidin-1-yl)ethyl)phenyl)benzofuran-2-yl)methylcarbamate (464; 320 mg, 0.63 mmol), 4-fluorophenylboronic acid (132 mg, 0.95 mmol), catalyst (35 mg, 0.06 mmol) and $K_3PO_4$ (3.8 mL, 1.9 mmol, 0.5 M) were added in THF (10 mL) and degassed. The reaction mixture was heated at 40° C. for 1 h. The reaction mixture was concentrated under reduced pressure to give the crude product which was purified by silica gel chromatography (0-30% EtOAc/petroleum ether) to give tert-butyl (5-(4-(1-(4,4-difluoropiperidin-1-yl)ethyl)phenyl)-7-(4-fluorophenyl)benzofuran-2-yl)methylcarbamate (465) (350 mg, 98% yield). LCMS: m/z 444.2 $[M-120]^+$; $t_R$=2.37 min.

Synthesis of (5-(4-(1-(4,4-difluoropiperidin-1-yl)ethyl)phenyl)-7-(4-fluorophenyl)benzofuran-2-yl)methanamine (466)

tert-Butyl (5-(4-(1-(4,4-difluoropiperidin-1-yl)ethyl)phenyl)-7-(4-fluorophenyl)benzofuran-2-yl)methylcarbamate (465; 140 mg, 0.25 mmol) was dissolved in $CH_2Cl_2$ (10 mL). TFA (2 mL) was added at 0° C. (ice bath). The reaction mixture was stirred at room temperature for 2 h, and concentrated under reduced pressure to give 115 mg of (5-(4-(1-(4,4-difluoropiperidin-1-yl)ethyl)phenyl)-7-(4-fluorophenyl)benzofuran-2-yl)methanamine (466), which was used without further purification in next step (100% yield). LCMS: m/z 344.1 [M-120]$^+$; $t_R$=1.27 min.

Synthesis of (E)-3-(6-aminopyridin-3-yl)-N-((5-(4-(1-(4,4-difluoropiperidin-1-yl)ethyl)phenyl)-7-(4-fluorophenyl)benzofuran-2-yl)methyl)acrylamide (760)

(5-(4-(1-(4,4-Difluoropiperidin-1-yl)ethyl)phenyl)-7-(4-fluorophenyl)benzofuran-2-yl)methanamine (466; 115 mg, 0.25 mmol) was dissolved in DMF (3 mL) and (E)-3-(pyridin-3-yl)acrylic acid (46 mg, 0.28 mmol) was added at 0° C. HATU (110 mg, 0.28 mmol) was added to this reaction mixture at 0° C. followed by DIPEA (97 mg, 0.75 mmol) dropwise. The reaction mixture was allowed to warm to room temperature and stirred further for 1 h. The crude mixture was purified by Prep-HPLC without workup to yield 12 mg of (E)-3-(6-aminopyridin-3-yl)-N-((5-(4-(1-(4,4-difluoropiperidin-1-yl)ethyl)phenyl)-7-(4-fluorophenyl)benzofuran-2-yl)methyl)acrylamide (760). Yield (7%). $^1$H NMR (400 MHz, CD$_3$OD) δ 8.06 (s, 1H), 8.00-7.93 (m, 2H), 7.80-7.63 (m, 5H), 7.53-7.41 (m, 3H), 7.25 (t, J=8 Hz, 2H), 6.83 (s, 1H), 6.61 (d, J=9 Hz, 1H), 6.48 (d, J=16 Hz, 1H), 4.70 (s, 2H), 3.64 (q, J=6 Hz, 1H), 2.71-2.54 (m, 4H), 2.07-1.91 (m, 4H), 1.47 (d, J=6 Hz, 3H). LCMS: m/z 611.3 [M+H]$^+$, $t_R$=2.11 min.

Synthesis of (E)-3-(6-aminopyridin-3-yl)-N-((4-(5-(4,4-difluoropiperidine-1-carbonyl)pyridin-2-yl)-6-(trifluoromethyl)benzofuran-2-yl)methyl)acrylamide (761)

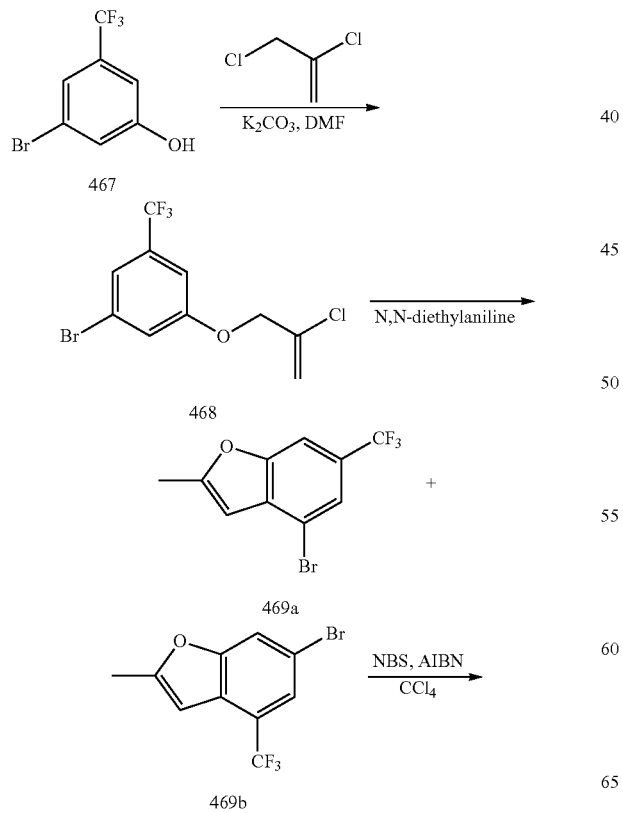

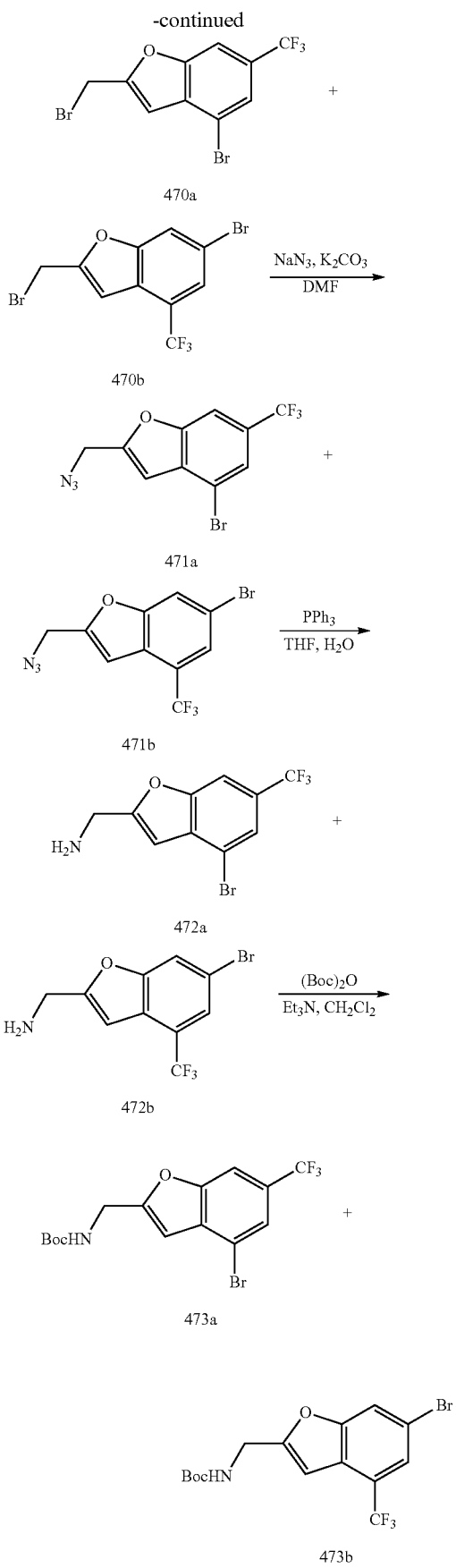

-continued

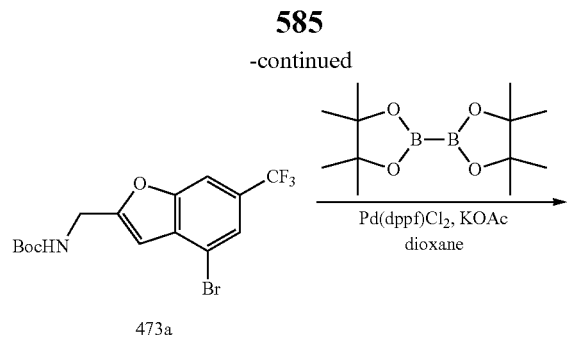
473a

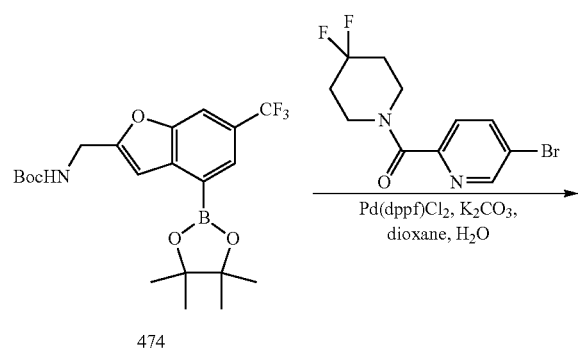
474

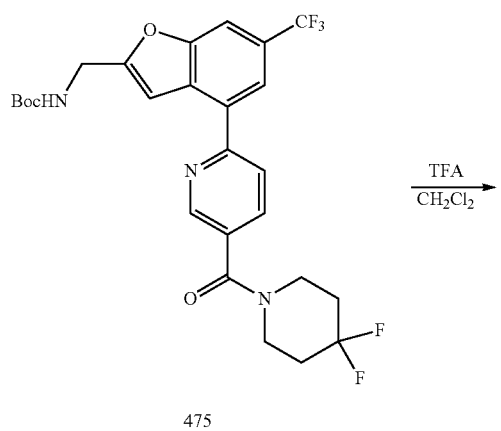
475

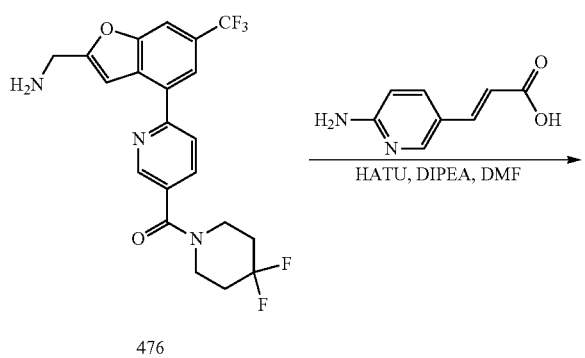
476

-continued

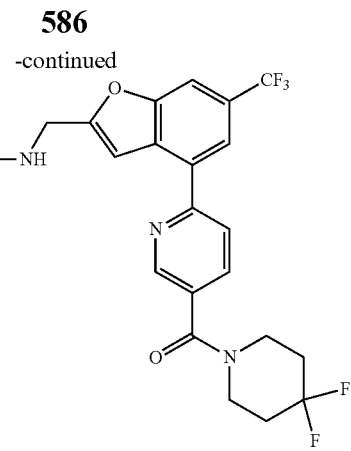
461

Synthesis of 1-bromo-3-(2-chloroallyloxy)-5-(trifluoromethyl)benzene (468)

3-Bromo-5-(trifluoromethyl)phenol (467; 5 g, 20.7 mmol) was dissolved in 50 mL of DMF. 2,3-Dichloroprop-1-ene (4.6 g, 41.4 mmol) and $K_2CO_3$ (5.7 g, 41.4 mmol) were added. The reaction mixture was heated at 100° C. for 2 h. The reaction mixture was cooled down to room temperature, diluted with $H_2O$ (100 mL), extracted with EtOAc (100 mL×3). The combined organic solvents were washed with brine, dried over anhydrous $Na_2SO_4$, concentrated and purified by silica gel chromatography (petroleum ether) to give 6.4 g of 1-bromo-3-(2-chloroallyloxy)-5-(trifluoromethyl)benzene (468) as colorless liquid. Yield (98%). $^1$H NMR (400 MHz, $CDCl_3$): δ 7.42 (s, 1H), 7.28 (s, 1H), 7.12 (s, 1H), 5.58 (s, 1H), 5.52 (s, 1H), 4.63 (s, 2H).

Synthesis of 4-bromo-2-methyl-6-(trifluoromethyl)benzofuran (469a) and 6-bromo-2-methyl-4-(trifluoromethyl)benzofuran (469b)

1-Bromo-3-(2-chloroallyloxy)-5-(trifluoromethyl)benzene (468; 6.4 g, 20.3 mmol) was dissolved in 20 mL of N,N-diethylaniline. The reaction mixture was heated at 220° C. for 15 h. After cooling down to room temperature, 100 mL of EtOAc was added. The mixture was washed with 2 N HCl aqueous solution (100 mL×3), brine (60 mL), dried over anhydrous $Na_2SO_4$, concentrated and purified by silica gel chromatography (petroleum ether) to afford a mixture of 4-bromo-2-methyl-6-(trifluoromethyl)benzofuran (469a) and 6-bromo-2-methyl-4-(trifluoromethyl)benzofuran (469b) as a white solid (2.8 g, 49% yield). LCMS: $t_R$=1.95 min.

Synthesis of 4-bromo-2-(bromomethyl)-6-(trifluoromethyl)benzofuran (470a) and 6-bromo-2-(bromomethyl)-4-(trifluoromethyl)benzofuran (470b)

A mixture of 4-bromo-2-methyl-6-(trifluoromethyl)benzofuran (469a) and 6-bromo-2-methyl-4-(trifluoromethyl)benzofuran (469b) (1 g, 3.6 mmol) were dissolved in 40 mL of $CCl_4$. NBS (770 mg, 4.3 mmol) and AIBN (118 mg, 0.7 mmol) were added. The reaction mixture was degassed and heated at 80° C. for 5 h. The reaction mixture was cooled down to room temperature, filtered and the filtrate was concentrated under reduced pressure to give a mixture of 4-bromo-2-(bromomethyl)-6-(trifluoromethyl)benzofuran (470a) and 6-bromo-2-(bromomethyl)-4-(trifluoromethyl) benzofuran (470b), which was used without further purification in next step (1.2 g, 86% yield). LCMS: $t_R$=1.92 min.

Synthesis of 2-(azidomethyl)-4-bromo-6-(trifluoromethyl)benzofuran (471a) and 2-(azidomethyl)-6-bromo-4-(trifluoromethyl)benzofuran (471b)

A mixture of 4-bromo-2-(bromomethyl)-6-(trifluoromethyl)benzofuran (470a) and 6-bromo-2-(bromomethyl)-4-(trifluoromethyl)benzofuran (470b) (1.2 g, 3.3 mmol) were dissolved in 50 mL of DMF. NaN$_3$ (325 mg, 5 mmol) and K$_2$CO$_3$ (926 mg, 6.7 mmol) were added. The reaction mixture was stirred at room temperature for 5 h, diluted with H$_2$O (100 mL), extracted with EtOAc (50 mL X 3), washed with brine (100 mL), dried over Na$_2$SO$_4$, concentrated under reduced pressure to afford a mixture of 2-(azidomethyl)-4-bromo-6-(trifluoromethyl)benzofuran (471a) and 2-(azidomethyl)-6-bromo-4-(trifluoromethyl)benzofuran (471b) as yellow solid, which was used without further purification in next step (950 mg, 88% yield). LCMS: $t_R$=1.89 min.

Synthesis of (4-bromo-6-(trifluoromethyl)benzofuran-2-yl)methanamine (472a) and (6-bromo-4-(trifluoromethyl)benzofuran-2-yl)methanamine (472b)

2-(Azidomethyl)-4-bromo-6-(trifluoromethyl)benzofuran (471a) and 2-(azidomethyl)-6-bromo-4-(trifluoromethyl) benzofuran (471b) (950 mg, 2.9 mmol) were dissolved in 30 mL of THF. PPh$_3$ (1.1 g, 4.4 mmol) was added. The mixture was stirred at room temperature for 1 h, and H$_2$O (10 mL) was added. The reaction mixture was heated at 60° C. for 2 h. After cooling down to room temperature, the reaction mixture was concentrated under reduced pressure and purified by silica gel chromatography (EtOAc) to afford a mixture of (4-bromo-6-(trifluoromethyl)benzofuran-2-yl) methanamine (472a) and (6-bromo-4-(trifluoromethyl)benzofuran-2-yl)methanamine (472b) (800 mg, 91% yield). LCMS: m/z 277.0 [M-55]$^+$; $t_R$=1.91 min.

Synthesis of tert-butyl (4-bromo-6-(trifluoromethyl)benzofuran-2-yl)methylcarbamate (473a) and tert-butyl (6-bromo-4-(trifluoromethyl)benzofuran-2-yl)methylcarbamate (473b)

(4-Bromo-6-(trifluoromethyl)benzofuran-2-yl)methanamine (472a) and (6-bromo-4-(trifluoromethyl)benzofuran-2-yl)methanamine (472b) (800 mg, 2.7 mmol) were dissolved in dichloromethane (40 mL). Di-tert-butyl dicarbonate (1.2 g, 5.4 mmol) and triethylamine (819 mg, 8.1 mmol) were added at 0° C. The reaction mixture was stirred at room temperature for 18 h. The reaction mixture was concentrated under reduced pressure and purified by silica gel chromatography (20% ethyl acetate/petroleum ether) to give a mixture of tert-butyl (4-bromo-6-(trifluoromethyl) benzofuran-2-yl)methylcarbamate (473a) and tert-butyl (6-bromo-4-(trifluoromethyl)benzofuran-2-yl)methylcarbamate (473b) (900 mg, 84% yield). LCMS: m/z 338.0 [M+Na]$^+$; $t_R$=2.18 min. The two compounds were separated from each other by chiral HPLC ((R,R)-Whelk-O1 column) to give 290 mg of tert-butyl (4-bromo-6-(trifluoromethyl) benzofuran-2-yl)methylcarbamate (473a) and 270 mg of tert-butyl (6-bromo-4-(trifluoromethyl)benzofuran-2-yl) methylcarbamate (473b).

Synthesis of tert-butyl (4-(4,4,5,5-tetramethyl-1,3,2-dioxaborolan-2-yl)-6-(trifluoromethyl)benzofuran-2-yl)methylcarbamate (474)

tert-Butyl (4-bromo-6-(trifluoromethyl)benzofuran-2-yl) methylcarbamate (473a; 200 mg, 0.5 mmol), 4,4,4',4',5,5,5',5'-octamethyl-2,2'-bi(1,3,2-dioxaborolane) (190 mg, 0.7 mmol), Pd(dppf)Cl$_2$ (37 mg, 0.05 mmol), and potassium acetate (98 mg, 1 mmol) were added in 20 mL of dioxane and degassed. The reaction mixture was heated at 100° C. under nitrogen atmosphere for 6 h. After cooling down to room temperature, the reaction mixture was filtered. The filtrate was concentrated under reduced pressure to give the crude product, which was purified by silica gel chromatography (15% EtOAc/petroleum ether) to yield 200 mg of tert-butyl (4-(4,4,5,5-tetramethyl-1,3,2-dioxaborolan-2-yl)-6-(trifluoromethyl)benzofuran-2-yl)methylcarbamate (474) as a yellow solid (85% yield). LCMS: m/z 464.1 [M+Na]$^+$, $t_R$=1.94 min.

Synthesis of tert-butyl (4-(5-(4,4-difluoropiperidine-1-carbonyl)pyridin-2-yl)-6-(trifluoromethyl)benzofuran-2-yl)methylcarbamate (475)

A mixture of tert-butyl (4-(4,4,5,5-tetramethyl-1,3,2-dioxaborolan-2-yl)-6-(trifluoromethyl)benzofuran-2-yl)methylcarbamate (474; 200 mg, 0.45 mmol), (6-bromopyridin-3-yl)(4,4-difluoropiperidin-1-yl)methanone (213 mg, 0.7 mmol), Pd(dppf)Cl$_2$ (37 mg, 0.05 mmol) and K$_2$CO$_3$ (124 mg, 0.9 mmol) in 30 mL of dioxane and 5 mL of H$_2$O was heated at 100° C. under nitrogen atmosphere for 4 h. The reaction mixture was concentrated under reduced pressure and purified by Prep-TLC (33% EtOAc/petroleum ether) to give 110 mg tert-butyl (4-(5-(4,4-difluoropiperidine-1-carbonyl)pyridin-2-yl)-6-(trifluoromethyl)benzofuran-2-yl) methylcarbamate (475) as a white solid. Yield (45%). $^1$H NMR (400 MHz, CD$_3$OD) δ 8.84 (s, 1H), 8.06-8.01 (m, 3H), 7.87 (s, 1H), 7.28 (s, 1H), 4.46 (s, 2H), 3.92-3.61 (m, 4H), 2.11 (s, 4H), 1.20 (s, 9H). LCMS: m/z 540.2 [M+H]$^+$, $t_R$=2.01 min.

Synthesis of (6-(2-(aminomethyl)-6-(trifluoromethyl)benzofuran-4-yl)pyridin-3-yl)(4,4-difluoropiperidine-1-yl)methanone (476)

tert-Butyl (4-(5-(4,4-difluoropiperidine-1-carbonyl)pyridin-2-yl)-6-(trifluoromethyl)benzofuran-2-yl)methylcarbamate (475; 60 mg, 0.15 mmol) was dissolved in CH$_2$Cl$_2$ (10 mL). TFA (2 mL) was added at 0° C. The reaction mixture was stirred at room temperature for 2 h, and concentrated under reduced pressure to give 46 mg of (6-(2-(aminomethyl)-6-(trifluoromethyl)benzofuran-4-yl) pyridin-3-yl)(4,4-difluoropiperidine-1-yl)methanone (476), which was used without further purification in the next step. Yield (94%). LCMS: m/z 440.1 [M+H]$^+$; $t_R$=1.83 min.

Synthesis of (E)-3-(6-aminopyridin-3-yl)-N-((4-(5-(4,4-difluoropiperidine-1-carbonyl)pyridin-2-yl)-6-(trifluoromethyl)benzofuran-2-yl)methyl)acrylamide (761)

(6-(2-(Aminomethyl)-6-(trifluoromethyl)benzofuran-4-yl)pyridin-3-yl)(4,4-difluoropiperidin-1-yl)methanone (476; 46 mg, 0.1 mmol) was dissolved in DMF (2 mL) and (E)-3-(pyridin-3-yl)acrylic acid (25 mg, 0.15 mmol) was added at 0° C. HATU (57 mg, 0.15 mmol) was added to this reaction mixture at 0° C. followed by DIPEA (38 mg, 0.3 mmol) dropwise. The reaction mixture was allowed to warm to room temperature and stirred further for 1 h. The crude mixture was purified by Prep-HPLC without workup to yield 6 mg of (E)-3-(6-aminopyridin-3-yl)-N-((4-(5-(4,4-difluoropiperidine-1-carbonyl)pyridin-2-yl)-6-(trifluoromethyl)benzofuran-2-yl)methyl)acrylamide (761). Yield (10%). $^1$H NMR (400 MHz, DMSO-$d_6$) δ 8.90-8.82 (m, 1H), 8.67 (t, J=6 Hz, 1H), 8.21-8.03 (m, 5H), 7.66-7.58 (m, 1H), 7.43 (s, 1H), 7.35 (d, J=16 Hz, 1H), 6.52-6.38 (m, 4H), 4.66 (d, J=6 Hz, 2H), 3.82-3.48 (m, 4H), 2.18-2.00 (m, 4H). LCMS: m/z 586.2 [M+H]$^+$, $t_R$=1.96 min.

Synthesis of (E)-3-(6-aminopyridin-3-yl)-N-((6-(5-(4,4-difluoropiperidine-1-carbonyl)pyridin-2-yl)-4-(trifluoromethyl)benzofuran-2-yl)methyl)acrylamide (762)

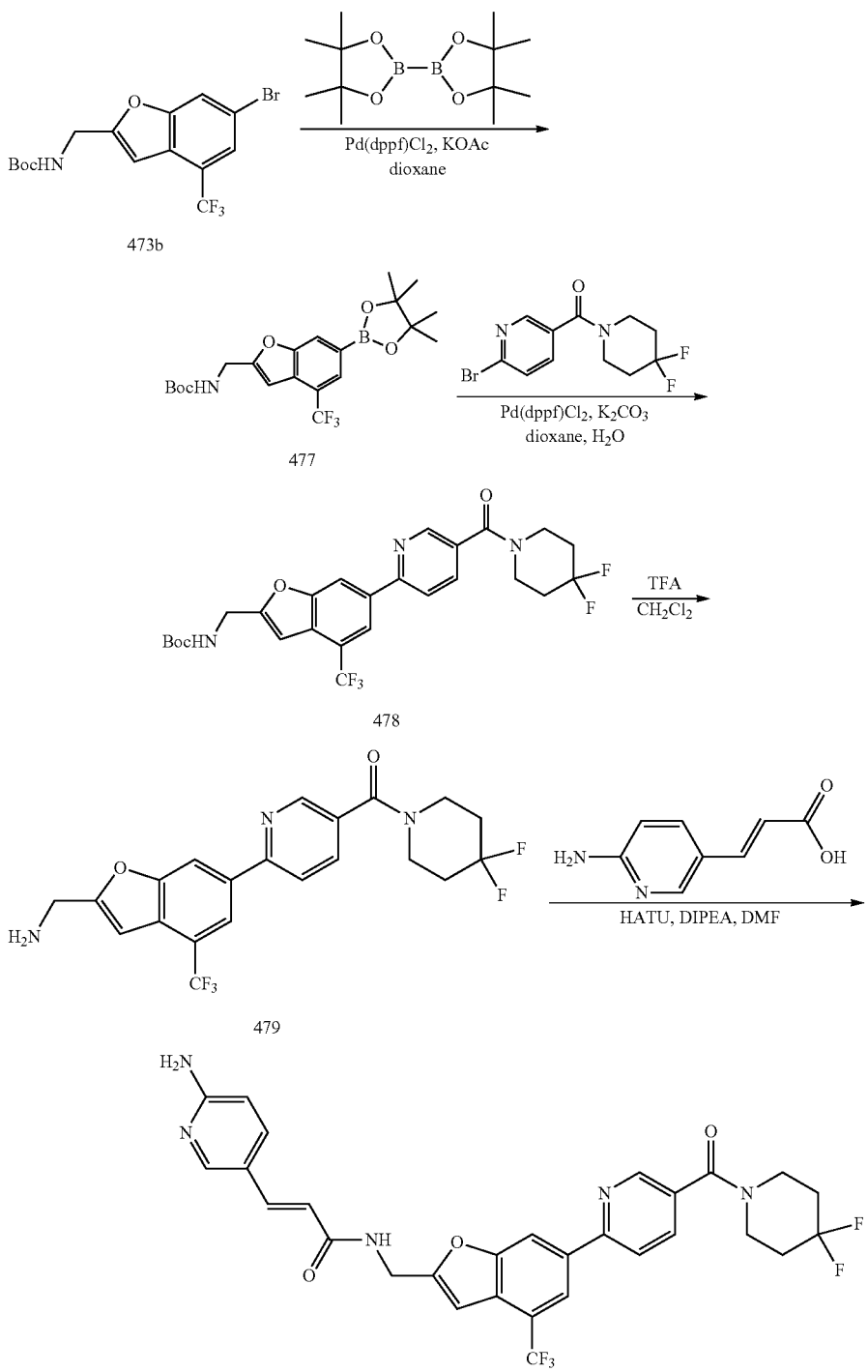

(E)-3-(6-aminopyridin-3-yl)-N-((6-(5-(4,4-difluoropiperidine-1-carbonyl)pyridin-2-yl)-4-(trifluoromethyl)benzofuran-2-yl)methyl)acrylamide (762) was synthesized using the indicated reagents in a similar fashion as example (761). $^1$H NMR (400 MHz, DMSO-$d_6$) δ 8.79 (s, 1H), 8.69-8.61 (m, 2H), 8.45 (s, 1H), 8.29 (d, J=8 Hz, 1H), 8.09 (s, 1H), 8.03 (d, J=8 Hz, 1H), 7.62 (d, J=9 Hz, 1H), 7.37 (d, J=16 Hz, 1H), 6.93 (s, 1H), 6.50-6.38 (m, 4H), 4.66 (d, J=6 Hz, 2H), 3.80-3.45 (m, 4H), 2.16-2.01 (m, 4H). LCMS: m/z 586.2 [M+H]$^+$, $t_R$=1.94 min.

Synthesis of (E)-3-(6-aminopyridin-3-yl)-N-((5-(4-((4,4-difluorocyclohexyl)oxy)phenyl)-7-(4-fluorophenyl)benzofuran-2-yl)methyl)acrylamide (763)

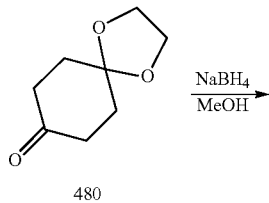

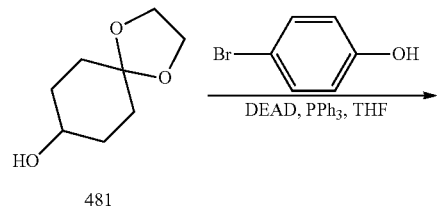

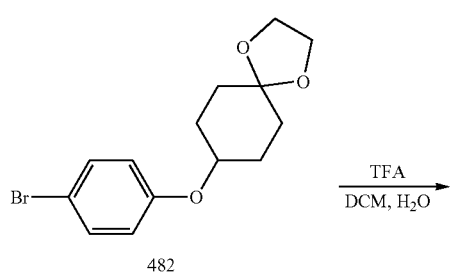

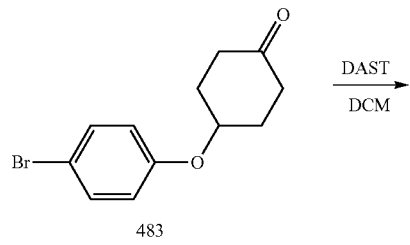

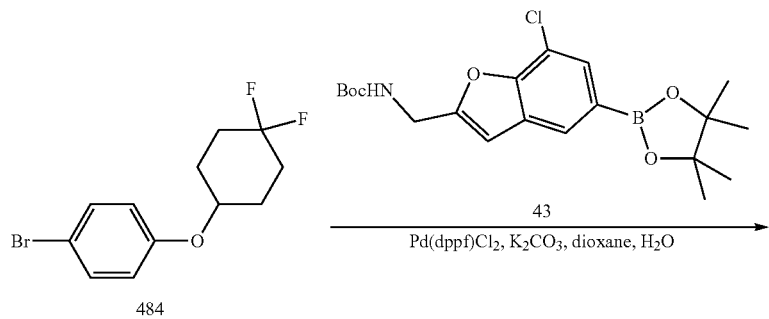

-continued

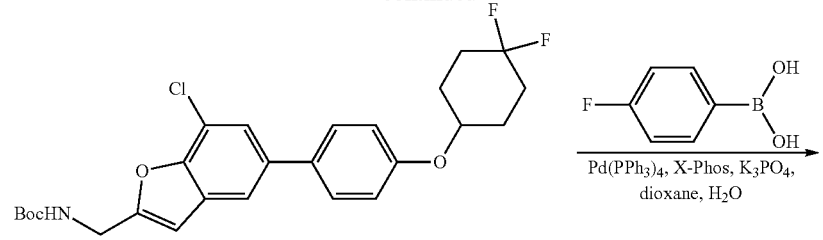
485

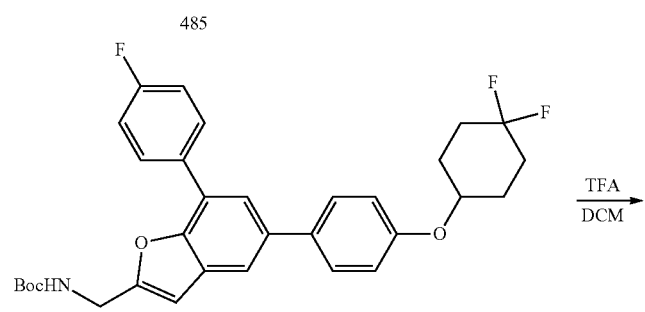
486

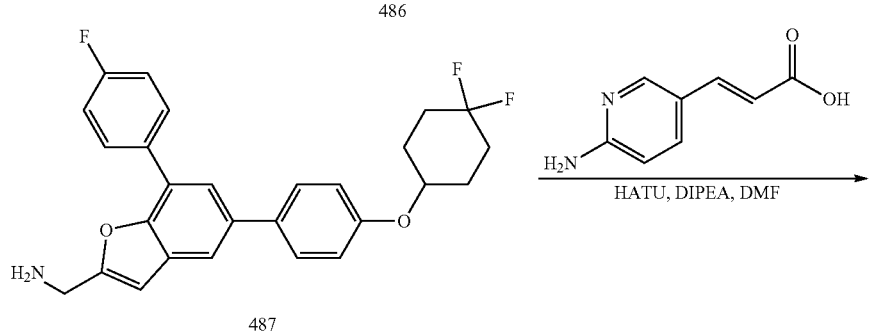
487

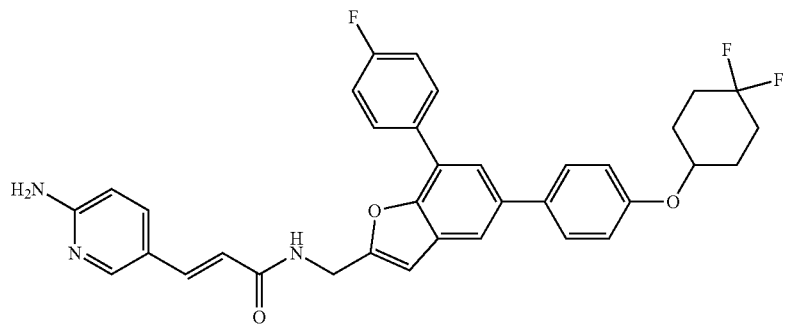
763

Synthesis of 1,4-dioxaspiro[4.5]decan-8-ol (481)

1,4-Dioxaspiro[4.5]decan-8-one (480; 10 g, 64 mmol) was dissolved in MeOH (200 mL). The mixture was cooled down to 0° C. (ice bath). NaBH$_4$ (7.3 g, 192 mmol) was added in portions. The reaction mixture was allowed to warm to 25° C. and stirred for 2 h. The reaction mixture was quenched with water (100 mL), extracted with EtOAc (200 mL×3). The combined organic layers were washed with brine, dried over anhydrous Na$_2$SO$_4$, concentrated under reduced pressure to give 9.2 g of 1,4-dioxaspiro[4.5]decan-8-ol (481) as colorless oil, which was used in next step without further purification (91% yield). LCMS: m/z 159.2 [M+H]$^+$, t$_R$=1.18 min.

Synthesis of 8-(4-bromophenoxy)-1,4-dioxaspiro [4.5]decane (482)

1,4-Dioxaspiro[4.5]decan-8-ol (481; 4 g, 25 mmol) was dissolved in THF (100 mL). 4-Bromophenol (5.3 g, 30 mmol), DEAD (6.1 g, 30 mmol) and PPh$_3$ (7.9 g, 30 mmol) were added at 25° C. and stirred for 2 h. The reaction mixture was quenched with saturated NaHCO$_3$ aqueous solution (100 mL), extracted with EtOAc (100 mL×3). The combined organic layers were washed with brine, dried over anhydrous Na$_2$SO$_4$, concentrated under reduced pressure and purified by silica gel chromatography (5-10% EtOAc/ petroleum ether) to give 4.2 g of 8-(4-bromophenoxy)-1,4-dioxaspiro[4.5]decane (482) as white solid (54% yield). LCMS: m/z 315.0 [M+H]$^+$, t$_R$=1.83 min.

Synthesis of 4-(4-bromophenoxy)cyclohexanone (483)

8-(4-Bromophenoxy)-1,4-dioxaspiro[4.5]decane (482; 1.8 g, 5.8 mmol) was dissolved in DCM (10 mL). TFA (1 mL) and water (1 mL) were added. The reaction mixture was stirred at 25° C. for 3 h. The reaction mixture was concentrated under reduced pressure, diluted with DCM (100 mL), washed with saturated $NaHCO_3$ aqueous solution, brine, dried over anhydrous $Na_2SO_4$, and concentrated under reduced pressure to give 1.4 g of 4-(4-bromophenoxy) cyclohexanone (483) as white solid, which was used in next step without further purification (90% yield). LCMS: m/z 269.0 $[M+H]^+$, $t_R$=1.71 min.

Synthesis of 1-bromo-4-(4,4-difluorocyclohexyloxy)benzene (484)

4-(4-Bromophenoxy)cyclohexanone (483; 1.6 g, 6 mmol) was dissolved in DCM (20 mL). The mixture was cooled down to 0° C. and DAST (1.9 g, 12 mmol) was added. The reaction mixture was allowed to warm to 25° C. and stirred for 1 h. The reaction mixture was diluted with DCM (100 mL), washed with saturated $NaHCO_3$ aqueous solution, brine, dried over anhydrous $Na_2SO_4$, concentrated under reduced pressure and purified by silica gel chromatography (0-5% EtOAc/petroleum ether) to give 1 g of 1-bromo-4-(4,4-difluorocyclohexyloxy)benzene (484) as white solid (60% yield). LCMS: m/z not found, $t_R$=1.87 min.

tert-Butyl (7-chloro-5-(4-(4,4-difluorocyclohexyloxy)phenyl)benzofuran-2-yl)methylcarbamate (485)

(7-chloro-5-(4-(4,4-difluorocyclohexyloxy)phenyl)benzofuran-2-yl)methylcarbamate (485) was synthesized using the indicated reagents according to General Procedure 2. Yield: 45%. LCMS: m/z 514.1 $[M+Na]^+$, $t_R$=1.90 min.

tert-Butyl(5-(4-(4,4-difluorocyclohexyloxy)phenyl)-7-(4-fluorophenyl)benzofuran-2-yl)methylcarbamate (486)

tert-Butyl(5-(4-(4,4-difluorocyclohexyloxy)phenyl)-7-(4-fluorophenyl)benzofuran-2-yl)methylcarbamate (486) was synthesized using the indicated reagents in a similar fashion as Intermediate (445). Yield: 90%. LCMS: m/z 574.1 $[M+Na]^+$, $t_R$=1.96 min.

(5-(4-(4,4-Difluorocyclohexyloxy)phenyl)-7-(4-fluorophenyl)benzofuran-2-yl)methanamine (487)

(5-(4-(4,4-Difluorocyclohexyloxy)phenyl)-7-(4-fluorophenyl)benzofuran-2-yl)methanamine (487) was synthesized using the indicated reagents according to General Procedure 3. Yield: 100%. LCMS: m/z 474.1 $[M+Na]^+$, $t_R$=1.51 min.

(E)-3-(6-aminopyridin-3-yl)-N-((5-(4-((4,4-difluorocyclohexyl)oxy)phenyl)-7-(4-fluorophenyl)benzofuran-2-yl)methyl)acrylamide (763): (E)-3-(6-aminopyridin-3-yl)-N-((5-(4-((4,4-difluorocyclohexyl)oxy)phenyl)-7-(4-fluorophenyl)benzofuran-2-yl)methyl)acrylamide (763) was synthesized using the indicated reagents according to General Procedure 4. Yield: 20%. $^1$H NMR (400 MHz, DMSO-$d_6$) δ 8.58 (t, J=5 Hz, 1H), 8.08 (s, 1H), 8.05-7.98 (m, 2H), 7.79 (s, 1H), 7.73-7.57 (m, 4H), 7.41-7.31 (m, 3H), 7.10 (d, J=9 Hz, 2H), 6.83 (s, 1H), 6.51-6.35 (m, 4H), 4.72-4.62 (m, 1H), 4.58 (d, J=5 Hz, 2H), 2.17-1.79 (m, 8H). LCMS: m/z 598.2 $[M+H]^+$, $t_R$=2.09 min.

Synthesis of (E)-3-(6-aminopyridin-3-yl)-N-((5-(5-(4,4-difluoropiperidine-1-carbonyl)-3-fluoropyridin-2-yl)-7-(4-fluorophenyl)benzofuran-2-yl)methyl) acrylamide (764)

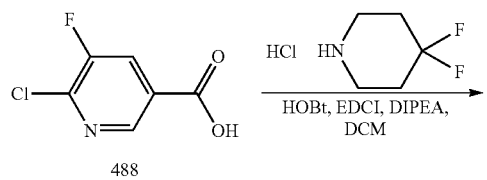

488

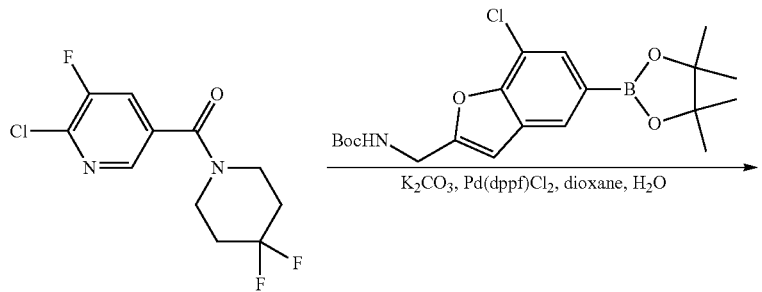

489

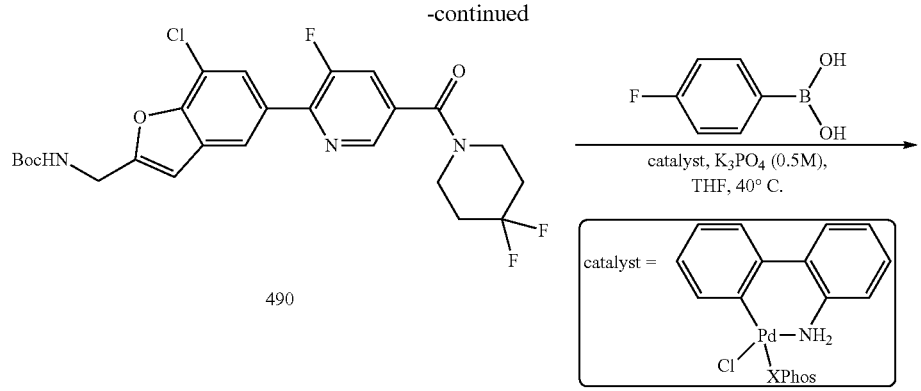
490
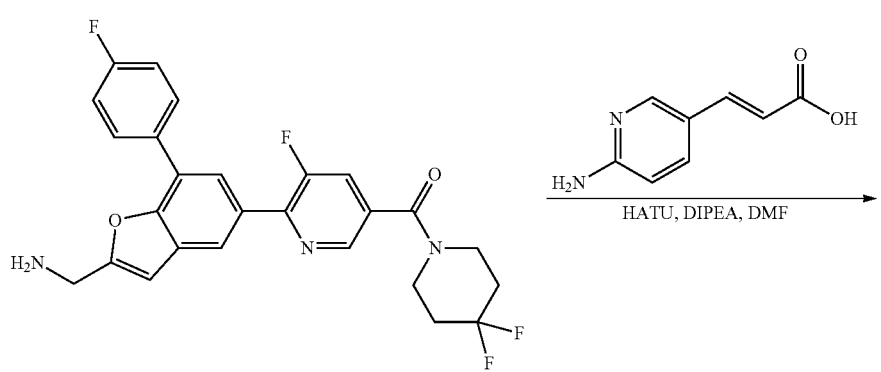
491
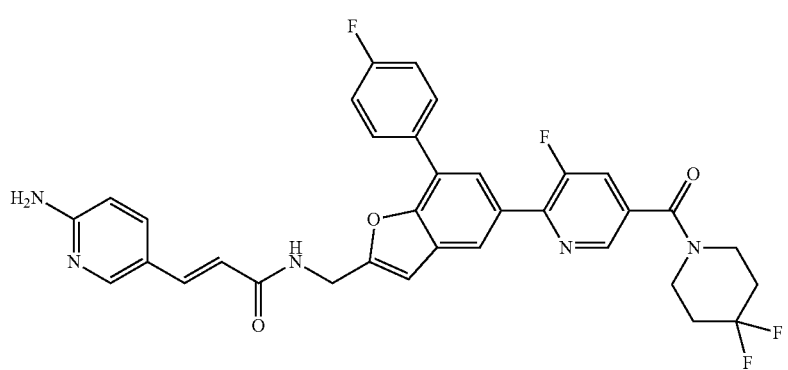
492
764

Synthesis of (6-chloro-5-fluoropyridin-3-yl)(4,4-difluoropiperidin-1-yl)methanone (489)

6-Chloro-5-fluoronicotinic acid (488; 875 mg, 5 mmol) was dissolved in DCM (20 mL) and 4,4-difluoropiperidine hydrochloride (942 mg, 6 mmol) was added. EDCI (1.2 g, 6 mmol), HOBt hydrate (810 mg, 6 mmol) and DIPEA (2 g, 15 mmol) were added. The reaction mixture was stirred at 25° C. for 16 h. The reaction mixture was quenched with water (50 mL), extracted with EtOAc (50 mL×3). The combined organic layers were washed with brine, dried over anhydrous $Na_2SO_4$, concentrated under reduced pressure and purified by silica gel chromatography (0-30% EtOAc/petroleum ether) to give 790 mg of (6-chloro-5-fluoropyridin-3-yl)(4,4-difluoropiperidin-1-yl)methanone (489) as colorless oil (57% yield). LCMS: m/z 279.0 [M+H]$^+$, $t_R$=1.51 min.

Synthesis of tert-butyl (7-chloro-5-(5-(4,4-difluoropiperidine-1-carbonyl)-3-fluoropyridin-2-yl)benzofuran-2-yl)methylcarbamate (490)

A mixture of (6-chloro-5-fluoropyridin-3-yl)(4,4-difluoropiperidin-1-yl)methanone (489; 790 mg, 2.8 mmol), tert-butyl (7-chloro-5-(4,4,5,5-tetramethyl-1,3,2-dioxaborolan-2-yl)benzofuran-2-yl)methylcarbamate (43, 1.4 g, 3.4 mmol), Pd(dppf)Cl$_2$ (245 mg, 0.3 mmol) and K$_2$CO$_3$ (1.2 g, 8.4 mmol) in 20 mL of dioxane and 2 mL of H$_2$O was heated at 100° C. under nitrogen atmosphere for 3 h. After cooling down to room temperature, the reaction mixture was filtered. The filtrate was concentrated under reduced pressure to give the crude product, which was purified by silica gel chromatography (0-50% EtOAc/petroleum ether) to give 1.2 g of tert-butyl (7-chloro-5-(5-(4,4-difluoropiperidine-1-carbonyl)-3-fluoropyridin-2-yl)benzofuran-2-yl)methylcarbamate (490) as white solid (81% yield). LCMS: m/z 524.1 [M+H]$^+$, $t_R$=1.74 min.

Synthesis of tert-butyl (5-(5-(4,4-difluoropiperidine-1-carbonyl)-3-fluoropyridin-2-yl)-7-(4-fluorophenyl)benzofuran-2-yl)methylcarbamate (491)

tert-Butyl (7-chloro-5-(5-(4,4-difluoropiperidine-1-carbonyl)-3-fluoropyridin-2-yl)benzofuran-2-yl)methylcarbamate (490; 320 mg, 0.6 mmol), 4-fluorophenylboronic acid (125 mg, 0.9 mmol), catalyst (48 mg, 0.06 mmol) and K$_3$PO$_4$ (3.6 mL, 1.8 mmol, 0.5 M) were added in THF (10 mL) and degassed. The reaction mixture was heated at 40° C. for 1 h. The reaction mixture was concentrated under reduced pressure to give the crude product which was purified by silica gel chromatography (0-30% EtOAc/petroleum ether) to give tert-butyl (5-(5-(4,4-difluoropiperidine-1-carbonyl)-3-fluoropyridin-2-yl)-7-(4-fluorophenyl)benzofuran-2-yl)methylcarbamate (491) (330 mg, 94% yield). LCMS: m/z 584.2 [M+H]$^+$; $t_R$=1.78 min.

Synthesis of (6-(2-(aminomethyl)-7-(4-fluorophenyl)benzofuran-5-yl)-5-fluoropyridin-3-yl)(4,4-difluoropiperidin-1-yl)methanone (492)

tert-Butyl (5-(5-(4,4-difluoropiperidine-1-carbonyl)-3-fluoropyridin-2-yl)-7-(4-fluorophenyl)benzofuran-2-yl)methylcarbamate (491; 330 mg, 0.57 mmol) was dissolved in CH$_2$Cl$_2$ (20 mL). TFA (3 mL) was added at 0° C. (ice bath). The reaction mixture was stirred at room temperature for 2 h, and concentrated under reduced pressure to give 270 mg of (6-(2-(aminomethyl)-7-(4-fluorophenyl)benzofuran-5-yl)-5-fluoropyridin-3-yl)(4,4-difluoropiperidin-1-yl)methanone (492), which was used without further purification in next step (100% yield). LCMS: m/z 484.1 [M+H]$^+$; $t_R$=1.36 min.

Synthesis of (E)-3-(6-aminopyridin-3-yl)-N-((5-(5-(4,4-difluoropiperidine-1-carbonyl)-3-fluoropyridin-2-yl)-7-(4-fluorophenyl)benzofuran-2-yl)methyl)acrylamide (764)

(6-(2-(Aminomethyl)-7-(4-fluorophenyl)benzofuran-5-yl)-5-fluoropyridin-3-yl)(4,4-difluoropiperidin-1-yl)methanone (492; 270 mg, 0.56 mmol) was dissolved in DMF (3 mL) and (E)-3-(pyridin-3-yl)acrylic acid (102 mg, 0.62 mmol) was added at 0° C. HATU (240 mg, 0.62 mmol) was added to this reaction mixture at 0° C. followed by DIPEA (220 mg, 1.7 mmol) dropwise. The reaction mixture was allowed to warm to room temperature and stirred further for 1 h. The crude mixture was purified by Prep-HPLC without workup to yield 70 mg of (E)-3-(6-aminopyridin-3-yl)-N-((5-(5-(4,4-difluoropiperidine-1-carbonyl)-3-fluoropyridin-2-yl)-7-(4-fluorophenyl)benzofuran-2-yl)methyl)acrylamide (764). Yield (20%). $^1$H NMR (400 MHz, DMSO-d$_6$) δ 8.66 (s, 1H), 8.64-8.59 (m, 1H), 8.19 (s, 1H), 8.11-7.93 (m, 5H), 7.62 (d, J=7 Hz, 1H), 7.44-7.33 (m, 3H), 6.95 (s, 1H), 6.51-6.38 (m, 4H), 4.61 (d, J=5 Hz, 2H), 3.82-3.47 (m, 4H), 2.17-2.04 (m, 4H). LCMS: m/z 630.5 [M+H]$^+$, $t_R$=1.83 min.

Synthesis of (E)-3-(6-aminopyridin-3-yl)-N-((7-chloro-5-(5-(4,4-difluoropiperidine-1-carbonyl) pyridin-2-yl)benzofuran-3-yl)methyl)acrylamide (766)

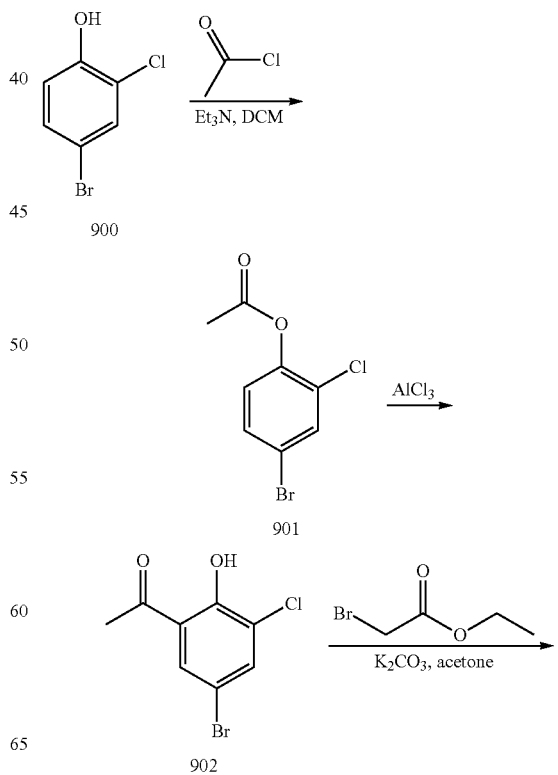

601
-continued
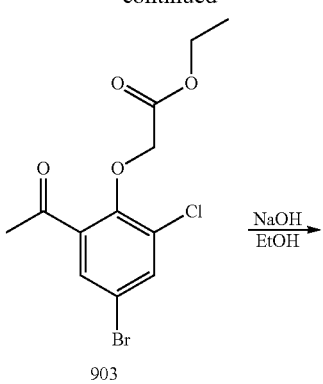
903
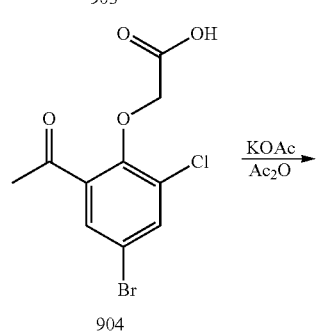
904
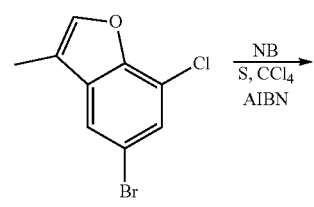
905
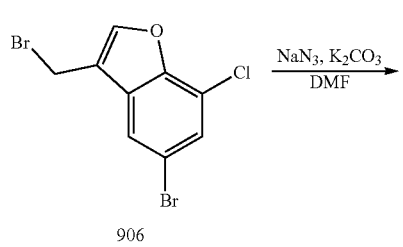
906
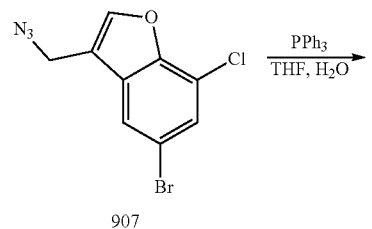
907
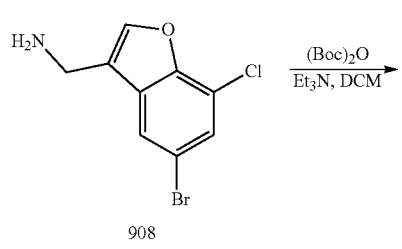
908
602
-continued
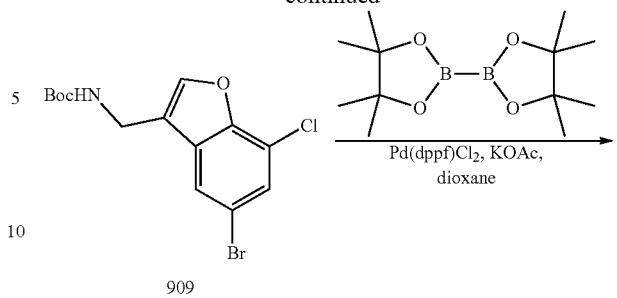
909
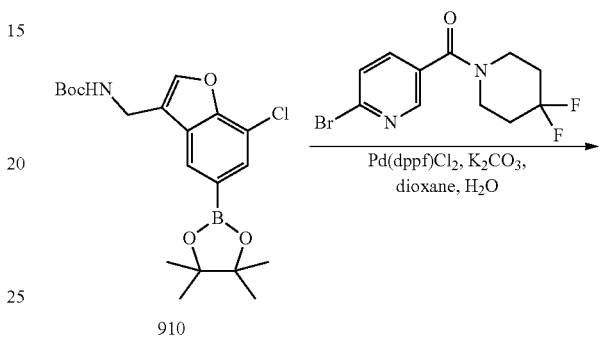
910
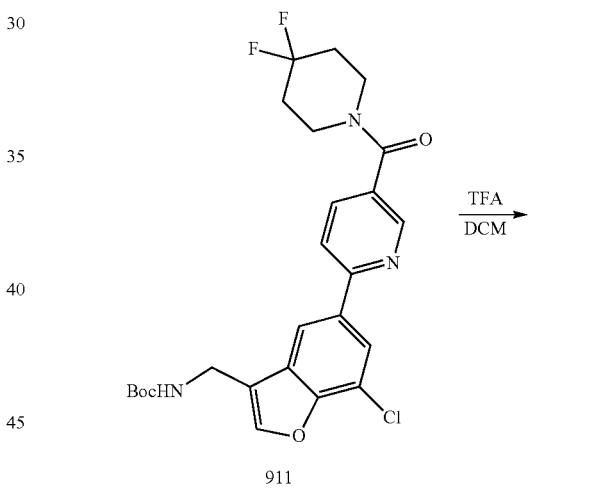
911
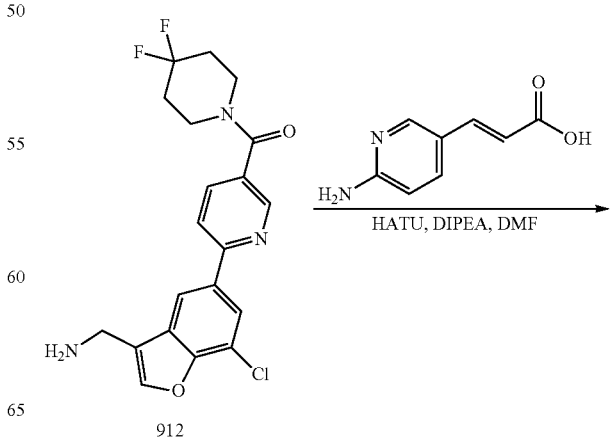
912

603

-continued

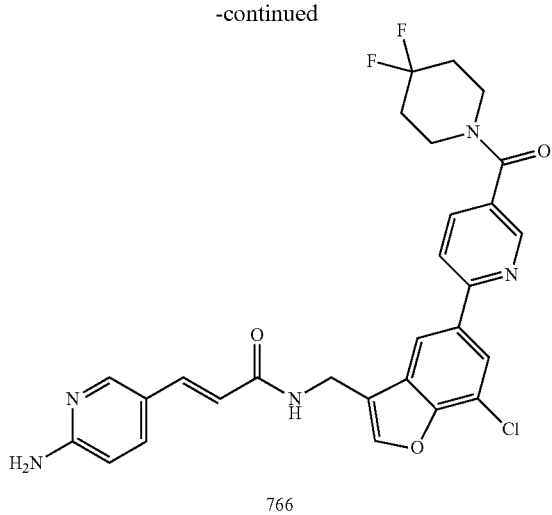

766

Synthesis of 4-bromo-2-chlorophenyl acetate (901)

4-Bromo-2-chlorophenol (900; 15 g, 73 mmol) was dissolved in DCM (300 mL) and triethylamine (15 g, 145 mmol) was added. The mixture was cooled down to 0° C. (ice bath) and acetyl chloride (8.5 g, 109 mmol) was added dropwise. The reaction mixture was stirred at 0° C. for 1 h, then quenched with 1 N HCl (100 mL). The reaction mixture was extracted with DCM (100 mL×3). The combined organic layers were washed with brine, dried over anhydrous $Na_2SO_4$, concnetrated under reduced pressure to give 16.5 g of 4-bromo-2-chlorophenyl acetate (901), which was used in next step without further purification (92% yield). LCMS: $t_R$=1.79 min.

Synthesis of 1-(5-bromo-3-chloro-2-hydroxyphenyl)ethanone (902)

A mixture of 4-bromo-2-chlorophenyl acetate (901; 14.5 g, 58 mmol) and $AlCl_3$ (12 g, 88 mmol) was heated at 160° C. for 1 h. After cooling down to room temperature, the reaction mixture was diluted with DCM (100 mL), poured into diluted HCl aqueous solution (1 N, 100 mL). The mixture was extracted with DCM (100 mL×3). The combined organic layers were washed with brine, dried over anhydrous $Na_2SO_4$, concentrated under reduced pressure to give 5.1 g of 1-(5-bromo-3-chloro-2-hydroxyphenyl)ethanone (902), which was used in next step without further purification (35% yield). LCMS: m/z 250.9 $[M+H]^+$, $t_R$=1.76 min.

Synthesis of ethyl 2-(2-acetyl-4-bromo-6-chlorophenoxy)acetate (903)

1-(5-Bromo-3-chloro-2-hydroxyphenyl)ethanone (902; 6 g, 24 mmol) was dissolved in acetone (150 mL) and $K_2CO_3$ (3.3 g, 24 mmol) was added followed by ethyl 2-bromoacetate (4 g, 24 mmol). The reaction mixture was heated at reflux for 3 h. The reaction mixture was concentrated under reduced pressure and purified by silica gel chromatography (0-10% EtOAc/petroleum ether) to give 5.1 g of ethyl 2-(2-acetyl-4-bromo-6-chlorophenoxy)acetate (903) as white solid (63% yield). LCMS: m/z 337.0 $[M+H]^+$, $t_R$=1.76 min.

604

Synthesis of 2-(2-acetyl-4-bromo-6-chlorophenoxy)acetic acid (904)

Ethyl 2-(2-acetyl-4-bromo-6-chlorophenoxy)acetate (903; 6.2 g, 18.5 mmol) was dissolved in EtOH (150 mL) and a solution of NaOH (1.5 g, 37 mmol) in $H_2O$ (50 mL) was added. The reaction mixture was stirred at 25° C. for 12 h. The reaction mixture was cooled down to 0° C., neutralized with HCl (6 N) to pH=5~6, extracted with EtOAc (100 mL×3). The combined organic layers were washed with brine, dried over anhydrous $Na_2SO_4$, concentrated under reduced pressure to give 5.2 g of 2-(2-acetyl-4-bromo-6-chlorophenoxy)acetic acid (904), which was used in next step without further purification (90% yield). LCMS: m/z 308.9 $[M+H]^+$, $t_R$=1.53 min.

Synthesis of 5-bromo-7-chloro-3-methylbenzofuran (905)

A mixture of 2-(2-acetyl-4-bromo-6-chlorophenoxy)acetic acid (904; 5.1 g, 16.6 mmol) and KOAc (9.8 g, 100 mmol) in 50 mL of $Ac_2O$ was heated at 150° C. for 1 h. After cooling down to room temperature, the reaction mixture was poured into saturated $NaHCO_3$ aqueous solution, extracted with EtOAc (100 mL×3). The combined organic layers were washed with brine, dried over anhydrous $Na_2SO_4$, concentrated under reduced pressure and purified by silica gel chromatography (0-10% EtOAc/petroleum ether) to give 760 mg of 5-bromo-7-chloro-3-methylbenzofuran (905) (19% yield). LCMS: $t_R$=2.24 min.

Synthesis of 5-bromo-3-(bromomethyl)-7-chlorobenzofuran (906)

5-Bromo-7-chloro-3-methylbenzofuran (905; 760 mg, 3.1 mmol) was dissolved in 30 mL of $CCl_4$. NBS (830 mg, 4.6 mmol) and AIBN (50 mg, 0.3 mmol) were added. The reaction mixture was degassed and heated at 80° C. for 3 h. The mixture was cooled down to room temperature and filtered, the filtrate was concentrated to give 600 mg of crude 5-bromo-3-(bromomethyl)-7-chlorobenzofuran (906), which was used directly to next step (60% yield). LCMS: $t_R$=1.88 min.

Synthesis of 3-(azidomethyl)-5-bromo-7-chlorobenzofuran (907)

5-Bromo-3-(bromomethyl)-7-chlorobenzofuran (906; 600 mg, 1.9 mmol) was dissolved in 10 mL of DMF. $NaN_3$ (240 mg, 3.7 mmol) and $K_2CO_3$ (510 mg, 3.7 mmol) were added. The reaction mixture was heated at 80° C. for 2 h, cooled down to room temperature, poured into iced water (50 mL), extracted with EtOAc (50 mL×3). The combined organic phases were washed with brine (50 mL), dried over $Na_2SO_4$, concentrated and purified by silica gel chromatography (10% EtOAc/petroleum ether) to afford 450 mg of 3-(azidomethyl)-5-bromo-7-chlorobenzofuran (907) (85% yield). LCMS: $t_R$=1.74 min.

Synthesis of (5-bromo-7-chlorobenzofuran-3-yl)methanamine (908)

3-(Azidomethyl)-5-bromo-7-chlorobenzofuran (907, 450 mg, 1.6 mmol) was dissolved in THF (10 mL) and $PPh_3$ (825 mg, 3.2 mmol), water (2 mL) was added. The reaction mixture was heated at 60° C. for 2 h. After cooling down to room temperature, the reaction mixture was poured into iced water, extracted with EtOAc (50 mL×3). The combined organic phases were washed with brine (50 mL), dried over $Na_2SO_4$, concentrated and purified by silica gel chromatography (0-100% EtOAc/petroleum ether) to afford 330 mg of (5-bromo-7-chlorobenzofuran-3-yl)methanamine (908) as pale yellow solid (84% yield). LCMS: m/z 262.0 $[M+H]^+$; $t_R$=1.83 min.

Synthesis of tert-butyl (5-bromo-7-chlorobenzofuran-3-yl)methylcarbamate (909)

(5-Bromo-7-chlorobenzofuran-3-yl)methanamine (908; 330 mg, 1.3 mmol) was dissolved in dichloromethane (10 mL). Di-tert-butyl dicarbonate (550 mg, 2.5 mmol) and triethylamine (260 mg, 2.5 mmol) were added at 0° C. (ice bath). The reaction mixture was allowed to warm to room temperature and stirred for 12 h. The reaction mixture was transferred into iced water and extracted with dichloromethane (50 mL×3). The combined organic layers were washed with brine, dried over anhydrous $Na_2SO_4$, concentrated under reduced pressure and purified by silica gel chromatography (0-10% ethyl acetate/petroleum ether) to give 460 mg of tert-butyl (5-bromo-7-chlorobenzofuran-3-yl)methylcarbamate (909) (100% yield). LCMS: m/z 306.0 $[M-55]^+$; $t_R$=2.19 min.

Synthesis of tert-butyl (7-chloro-5-(4,4,5,5-tetramethyl-1,3,2-dioxaborolan-2-yl)benzofuran-3-yl)methylcarbamate (910)

tert-Butyl (5-bromo-7-chlorobenzofuran-3-yl)methylcarbamate (909; 200 mg, 0.55 mmol) was dissolved in dioxane (10 mL) and degassed. $Pd(dppf)Cl_2$ (44 mg, 0.06 mmol), KOAc (108 mg, 1.1 mmol) and 4,4,4',4',5,5,5',5'-octamethyl-2,2'-bi(1,3,2-dioxaborolane) (211 mg, 0.83 mmol) were added at room temperature. The reaction mixture was heated at 100° C. for 5 h. The reaction mixture was filtered, the filtrate was concentrated under reduced pressure to give the crude product, which was purified by silica gel chromatography (0-10% ethyl acetate/petroleum ether) to give 170 mg of tert-butyl (7-chloro-5-(4,4,5,5-tetramethyl-1,3,2-dioxaborolan-2-yl)benzofuran-3-yl)methylcarbamate (910) as white solid (76% yield). LCMS: m/z 352.0 $[M-55]^+$; $t_R$=2.28 min.

Synthesis of tert-butyl (7-chloro-5-(5-(4,4-difluoropiperidine-1-carbonyl)pyridin-2-yl)benzofuran-3-yl)methylcarbamate (911)

tert-Butyl (7-chloro-5-(4,4,5,5-tetramethyl-1,3,2-dioxaborolan-2-yl)benzofuran-3-yl)methylcarbamate (910; 176 mg, 0.43 mmol), (6-bromopyridin-3-yl)(4,4-difluoropiperidin-1-yl)methanone (132 mg, 0.43 mmol), $Pd(dppf)Cl_2$ (13 mg, 0.04 mmol), and $K_2CO_3$ (120 mg, 0.86 mmol) were added in a mixture of (10:1) dioxane (10 mL) and water (1 mL) and degassed. The reaction mixture was heated at 100° C. under nitrogen atmosphere for 4 h. The reaction mixture was cooled down to room temperature. The reaction mixture was filtered and the filtrate was concentrated under reduced pressure to give the crude product, which was purified by silica gel chromatography (0-10% EtOAc/petroleum ether) to yield 120 mg of tert-butyl (7-chloro-5-(5-(4,4-difluoropiperidine-1-carbonyl)pyridin-2-yl)benzofuran-3-yl)methylcarbamate (911) as white solid (55% yield). LCMS: m/z 506.2 $[M+H]^+$, $t_R$=2.03 min.

Synthesis of (6-(3-(aminomethyl)-7-chlorobenzofuran-5-yl)pyridin-3-yl)(4,4-difluoropiperidin-1-yl)methanone (912)

tert-Butyl (7-chloro-5-(5-(4,4-difluoropiperidine-1-carbonyl)pyridin-2-yl)benzofuran-3-yl)methylcarbamate (911; 120 mg, 0.24 mmol) was dissolved in $CH_2Cl_2$ (10 mL). TFA (2 mL) was added dropwise at room temperature. The reaction mixture was stirred at room temperature for 1 h. The reaction mixture was concentrated under reduced pressure to give (6-(3-(aminomethyl)-7-chlorobenzofuran-5-yl)pyridin-3-yl)(4,4-difluoropiperidin-1-yl)methanone (912), which was used without further purification in the next step (90 mg, 93% yield). LCMS: m/z 406.1 $[M+H]^+$, $t_R$=1.32 min.

Synthesis of (E)-3-(6-aminopyridin-3-yl)-N-((7-chloro-5-(5-(4,4-difluoropiperidine-1-carbonyl)pyridin-2-yl)benzofuran-3-yl)methyl)acrylamide (766)

(6-(3-(Aminomethyl)-7-chlorobenzofuran-5-yl)pyridin-3-yl)(4,4-difluoropiperidin-1-yl)methanone (912; 90 mg, 0.22 mmol) was dissolved in DMF (4 mL) and (E)-3-(6-aminopyridin-3-yl)acrylic acid (40 mg, 0.24 mmol) was added at 0° C. HATU (99 mg, 0.26 mmol) was added to this reaction mixture at 0° C. followed by DIPEA (85 mg, 0.66 mmol) dropwise. The reaction mixture was allowed to warm to room temperature and stirred further for 1 h. The reaction mixture was purified by Prep-HPLC to afford 27 mg of (E)-3-(6-aminopyridin-3-yl)-N-((7-chloro-5-(5-(4,4-difluoropiperidine-1-carbonyl)pyridin-2-yl)benzofuran-3-yl)methyl)acrylamide (766) (22% yield). $^1$H NMR (400 MHz, $CD_3OD$) δ 8.80-8.69 (m, 1H), 8.38-8.29 (m, 1H), 8.19-8.11 (m, 1H), 8.09-7.89 (m, 4H), 7.76-7.64 (m, 1H), 7.56-7.43 (m, 1H), 6.63-6.53 (m, 1H), 6.49-6.37 (m, 1H), 4.69 (s, 2H), 3.99-3.57 (m, 4H), 2.24-1.97 (m, 4H). LCMS: m/z 552.2 $[M+H]^+$, $t_R$=1.75 min.

Synthesis of (E)-3-(6-aminopyridin-3-yl)-N-((7-(4-fluorophenyl)-5-(4-(6-fluoropyridin-3-yloxy)phenyl)benzofuran-2-yl)methyl)acrylamide (767)

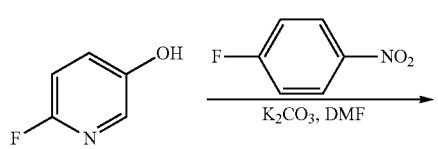

-continued
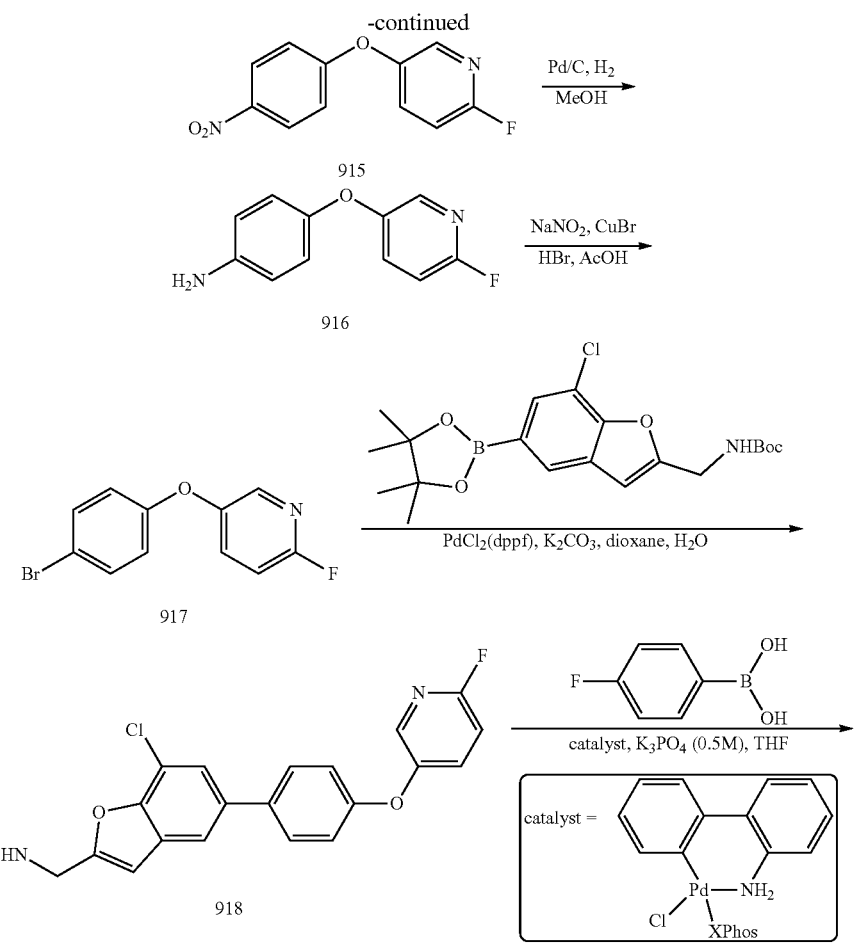
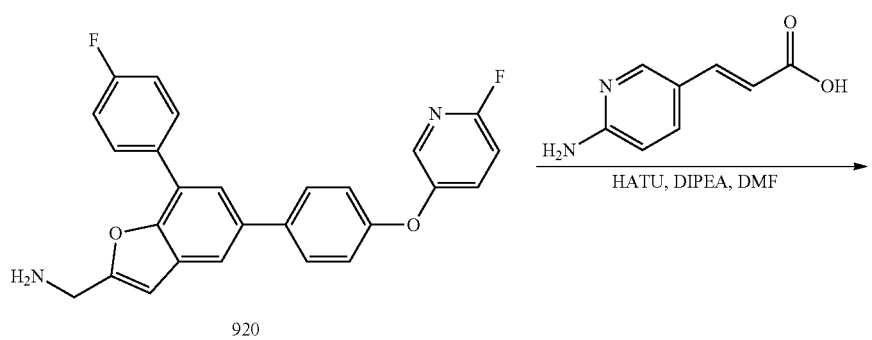

-continued

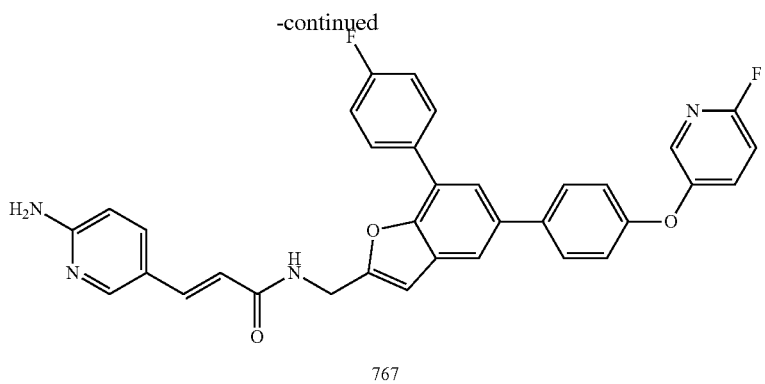

767

Synthesis of 2-fluoro-5-(4-nitrophenoxy)pyridine (915)

6-Fluoropyridin-3-ol (914; 2 g, 17.7 mmol) was dissolved in DMF (20 mL). 1-Fluoro-4-nitrobenzene (2.5 g, 17.7 mmol) and $K_2CO_3$ (4.9 g, 35.4 mmol) were added. The reaction mixture was heated at 80° C. for 2 h. After cooling down to room temperature, the reaction mixture was poured into iced water, extracted with EtOAc (50 mL×3). The combined organic layers were washed with brine, dried over anhydrous $Na_2SO_4$, concentrated under reduced pressure to give 4 g of 2-fluoro-5-(4-nitrophenoxy)pyridine (915) (97% yield), which was used in next step without further purification. LCMS: m/z 235.1 [M+H]$^+$; $t_R$=1.60 min.

Synthesis of 4-(6-fluoropyridin-3-yloxy)aniline (916)

2-Fluoro-5-(4-nitrophenoxy)pyridine (915; 4 g, 17.1 mmol) was dissolved in MeOH (50 mL) and Pd/C (400 mg, 10%) was added. The reaction mixture was stirred under $H_2$ atmosphere for 12 h. The reaction mixture was filtered and the filtrate was concentrated under reduced pressure to give 3.4 g of 4-(6-fluoropyridin-3-yloxy)aniline (916) as white solid, which was used in next step without further purification (98% yield). LCMS: m/z 205.1 [M+H]$^+$; $t_R$=1.33 min.

Synthesis of 5-(4-bromophenoxy)-2-fluoropyridine (917)

4-(6-Fluoropyridin-3-yloxy)aniline (916; 3.4 g, 16.7 mmol) was added to a solution of HBr in AcOH (50 mL, 33% w/w). The mixture was cooled down to 0° C., and $NaNO_2$ (1.7 g, 25 mmol) was added. After stirring at 0° C. for 0.5 h, CuBr (2.9 g, 20 mmol) was added. The reaction mixture was allowed to warm to room temperature and heated at 80° C. for 3 h. The reaction mixture was cooled down to room temperature, diluted with 50 mL of $H_2O$, extracted with EtOAc (100 mL×3). The combined organic layers were washed with brine, dried over anhydrous $Na_2SO_4$, concentrated under reduced pressure and purified by silica gel chromatography (0-30% EtOAc/petroleum ether) to give 2.7 g of 5-(4-bromophenoxy)-2-fluoropyridine (917) as yellow solid (60% yield). LCMS: m/z 268.0 [M+H]$^+$; $t_R$=1.77 min.

Synthesis of tert-butyl (7-chloro-5-(4-(6-fluoropyridin-3-yloxy)phenyl)benzofuran-2-yl)methylcarbamate (918)

A mixture of 5-(4-bromophenoxy)-2-fluoropyridine (917; 500 mg, 1.8 mmol), tert-butyl (7-chloro-5-(4,4,5,5-tetramethyl-1,3,2-dioxaborolan-2-yl)benzofuran-2-yl)methylcarbamate (760 mg, 1.8 mmol), Pd(dppf)Cl$_2$ (150 mg, 0.2 mmol) and $K_2CO_3$ (520 mg, 3.7 mmol) in dioxane (10 mL) and water (1 mL) was degassed and heated at 90° C. for 5 h. After cooling down to room temperature, the reaction mixture was filtered. The filtrate was concentrated under reduced pressure and purified by silica gel chromatography (0-20% EtOAc/petroleum ether) to give 500 mg of tert-butyl (7-chloro-5-(4-(6-fluoropyridin-3-yloxy)phenyl)benzofuran-2-yl)methylcarbamate (918) as white solid (57% yield). LCMS: m/z 469.1 [M+H]$^+$, $t_R$=2.2$^2$ min.

Synthesis of tert-butyl (7-(4-fluorophenyl)-5-(4-(6-fluoropyridin-3-yloxy)phenyl)benzofuran-2-yl)methylcarbamate (919)

tert-Butyl (7-chloro-5-(4-(6-fluoropyridin-3-yloxy)phenyl)benzofuran-2-yl)methylcarbamate (918; 200 mg, 0.43 mmol), 4-fluorophenylboronic acid (90 mg, 0.64 mmol), catalyst (32 mg, 0.04 mmol) and $K_3PO_4$ (1.8 mL, 0.9 mmol, 0.5 M) were added in THF (10 mL) and degassed. The reaction mixture was stirred at room temperature for 5 h. The reaction mixture was concentrated under reduced pressure to give the crude product, which was purified by silica gel chromatography (0-30% EtOAc/petroleum ether) to give tert-butyl (7-(4-fluorophenyl)-5-(4-(6-fluoropyridin-3-yloxy)phenyl)benzofuran-2-yl)methylcarbamate (919) (150 mg, 66% yield). LCMS: m/z 551.2 [M+Na]$^+$; $t_R$=1.93 min.

Synthesis of (7-(4-fluorophenyl)-5-(4-(6-fluoropyridin-3-yloxy)phenyl)benzofuran-2-yl)methanamine (920)

tert-Butyl (7-(4-fluorophenyl)-5-(4-(6-fluoropyridin-3-yloxy)phenyl)benzofuran-2-yl)methylcarbamate (919; 150 mg, 0.28 mmol) was dissolved in $CH_2Cl_2$ (10 mL). TFA (2 mL) was added at 0° C. (ice bath). The reaction mixture was stirred at room temperature for 1 h, and concentrated under reduced pressure to give 120 mg of (7-(4-fluorophenyl)-5-(4-(6-fluoropyridin-3-yloxy)phenyl)benzofuran-2-yl)methanamine (920), which was used without further purification in next step (100% yield). LCMS: m/z 428.1 [M+H]$^+$; $t_R$=1.20 min.

Synthesis of (E)-3-(6-aminopyridin-3-yl)-N-((7-(4-fluorophenyl)-5-(4-(6-fluoropyridin-3-yloxy)phenyl) benzofuran-2-yl)methyl)acrylamide (767)

(7-(4-Fluorophenyl)-5-(4-(6-fluoropyridin-3-yloxy)phenyl)benzofuran-2-yl)methanamine (920; 120 mg, 0.28 mmol) was dissolved in DMF (4 mL) and (E)-3-(pyridin-3-yl)acrylic acid (51 mg, 0.31 mmol) was added at 0° C. HATU (128 mg, 0.34 mmol) was added to this reaction mixture at 0° C. followed by DIPEA (109 mg, 0.84 mmol) dropwise. The reaction mixture was allowed to warm to room temperature and stirred further for 1 h. The crude mixture was purified by Prep-HPLC without workup to yield 40 mg of (E)-3-(6-aminopyridin-3-yl)-N-((7-(4-fluorophenyl)-5-(4-(6-fluoropyridin-3-yloxy)phenyl)benzofuran-2-yl)methyl)acrylamide (767). Yield (25%). $^1$H NMR (400 MHz, CD$_3$OD) δ 8.06 (s, 1H), 8.01-7.92 (m, 3H), 7.78-7.61 (m, 6H), 7.49 (d, J=16 Hz, 1H), 7.24 (t, J=9 Hz, 2H), 7.18-7.09 (m, 3H), 6.83 (s, 1H), 6.61 (d, J=9 Hz, 1H), 6.47 (d, J=16 Hz, 1H), 4.69 (s, 2H). LCMS: m/z 575.2 [M+H]$^+$; $t_R$=2.00 min.

Example 2. MTT Cell Proliferation Assay

The MTT cell proliferation assay was used to study the cytotoxic properties of the compounds. The assay was performed according to the method described by Roche Molecular Biochemicals, with minor modifications. The assay is based on the cleavage of the tetrazolium salt, MTT, in the presence of an electron-coupling reagent. The water-insoluble formazan salt produced must be solubilized in an additional step. Cells grown in a 96-well tissue culture plate were incubated with the MTT solution for approximately 4 hours. After this incubation period, a water-insoluble formazan dye formed. After solubilization, the formazan dye was quantitated using a scanning multi-well spectrophotometer (ELISA reader). The absorbance revealed directly correlates to the cell number. The cells were seeded at 5,000-10,000 cells in each well of 96-well plate in 100 μL of fresh culture medium and were allowed to attach overnight. The stock solutions of the compounds were diluted in 100 L cell culture medium to obtain eight concentrations of each test compound, ranging from 1 nM to 30 μM. After incubation for approximately 64-72 hours, 20 uL of CellTiter 96 Aqueous One Solution Reagent (Promega, G358B) was added to each well and the plate was returned to the incubator (37° C.; 5% CO$_2$) until an absolute OD of 1.5 was reached for the control cells. All optical densities were measured at 490 nm using a Vmax Kinetic Microplate Reader (Molecular Devices). In most cases, the assay was performed in duplicate and the results were presented as a mean percent inhibition to the negative control+SE. The following formula was used to calculate the percent of inhibition: Inhibition (%)=(1-(ODo/OD))×100.

The compounds were tested against MS751, Z138 and 3T3 cells. The MS751 cell line is derived from a metastasis to lymph node of human cervix from a patient diagnosed with squameous cell carcinoma of the cervix. The Z138 cell line is a mature B-cell acute lymphoblastic leukemia cell line derived from a patient with chronic lymphocytic leukemia. 3T3 cells are standard fibroblast cells; they were originally isolated from Swiss mouse embryo tissue.

The results of the MTT assay are reported in Table 1.

TABLE 1

| | | | | | |
|---|---|---|---|---|---|
| | | MTT Assay | | | |
| Cpd No. | Compound Structure | MS-751 | Z138 | 3T3 | Compound Name |
| 500 | | B | B | D | (E)-N-((5-(5-acetylthiophen-2-yl)-7-chlorobenzofuran-2-yl)methyl)-3-(6-aminopyridin-3-yl)acrylamide |
| 501 | | B | B | D | (E)-3-(6-aminopyridin-3-yl)-N-((7-chloro-5-(4-(morpholine-4-carbonyl)phenyl)benzo[d]oxazol-2-yl)methyl)acrylamide |
| 502 | | B | B | D | (E)-3-(6-aminopyridin-3-yl)-N-((7-chloro-5-(4-(morpholine-4-carbonyl)phenyl)benzofuran-2-yl)methyl)acrylamide |
| 503 | | B | D | D | (E)-N-((5-(5-acetylthiophen-2-yl)benzofuran-2-yl)methyl)-3-(6-aminopyridin-3-yl)acrylamide |

TABLE 1-continued

MTT Assay

| Cpd No. | Compound Structure | MS-751 | Z138 | 3T3 | Compound Name |
|---|---|---|---|---|---|
| 504 | 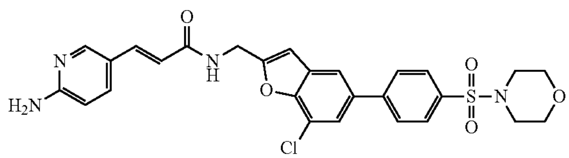 [SMILES: Nc1ccc(/C=C/C(=O)NCc2cc3cc(-c4ccc(S(=O)(=O)N5CCOCC5)cc4)cc(Cl)c3o2)cn1] | A | A | B | (E)-3-(6-aminopyridin-3-yl)-N-((7-chloro-5-(4-(morpholinosulfonyl)phenyl)benzofuran-2-yl)methyl)acrylamide |
| 505 | 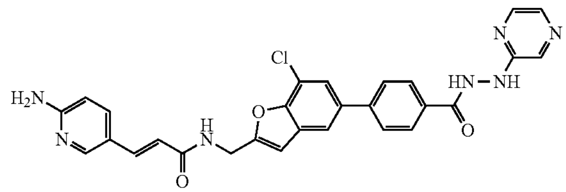 [SMILES: Nc1ccc(/C=C/C(=O)NCc2cc3cc(-c4ccc(C(=O)NNc5cnccn5)cc4)cc(Cl)c3o2)cn1] | B | B | D | (E)-3-(6-aminopyridin-3-yl)-N-((7-chloro-5-(4-(2-(pyrazin-2-yl)hydrazine-1-carbonyl)phenyl)benzofuran-2-yl)methyl)acrylamide |
| 506 | 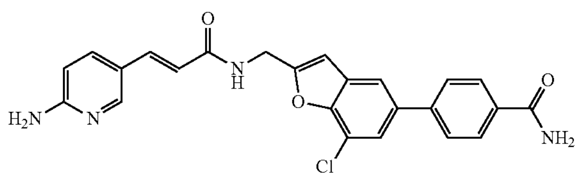 [SMILES: NC(=O)c1ccc(-c2cc(Cl)c3oc(CNC(=O)/C=C/c4ccc(N)nc4)cc3c2)cc1] | C | B | D | (E)-4-(2-((3-(6-aminopyridin-3-yl)acrylamido)methyl)-7-chlorobenzofuran-5-yl)benzamide |
| 507 | 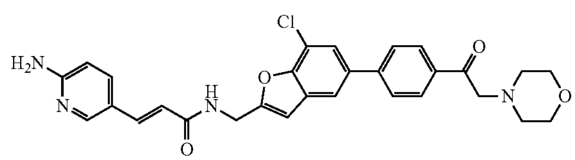 [SMILES: Nc1ccc(/C=C/C(=O)NCc2cc3cc(-c4ccc(C(=O)CN5CCOCC5)cc4)cc(Cl)c3o2)cn1] | B | B | D | (E)-3-(6-aminopyridin-3-yl)-N-((7-chloro-5-(4-(2-morpholinoacetyl)phenyl)benzofuran-2-yl)methyl)acrylamide |
| 508 | 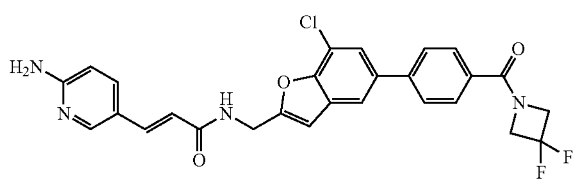 [SMILES: Nc1ccc(/C=C/C(=O)NCc2cc3cc(-c4ccc(C(=O)N5CC(F)(F)C5)cc4)cc(Cl)c3o2)cn1] | B | B | D | (E)-3-(6-aminopyridin-3-yl)-N-((7-chloro-5-(4-(3,3-difluoroazetidine-1-carbonyl)phenyl)benzofuran-2-yl)methyl)acrylamide |
| 509 | 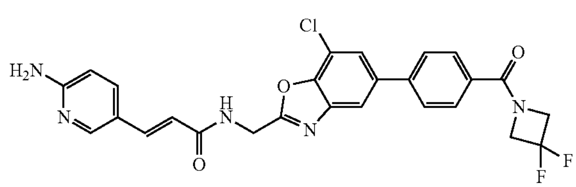 [SMILES: Nc1ccc(/C=C/C(=O)NCc2nc3cc(-c4ccc(C(=O)N5CC(F)(F)C5)cc4)cc(Cl)c3o2)cn1] | B | B | D | (E)-3-(6-aminopyridin-3-yl)-N-((7-chloro-5-(4-(3,3-difluoroazetidine-1-carbonyl)phenyl)benzo[d]oxazol-2-yl)methyl)acrylamide |
| 510 | 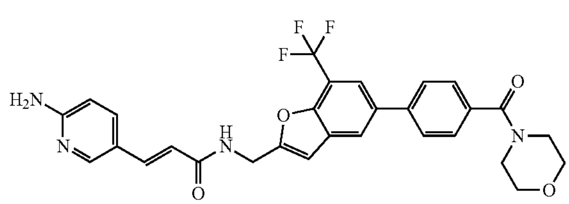 | B | A | D | (E)-3-(6-aminopyridin-3-yl)-N-((5-(4-(morpholine-4-carbonyl)phenyl)-7-(trifluoromethyl)benzofuran-2-yl)methyl)acrylamide |
| 511 | 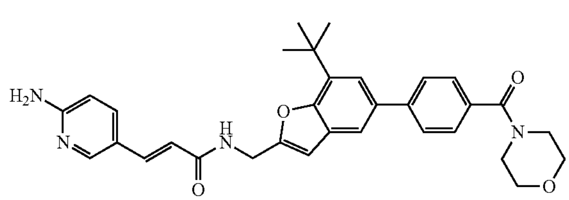 [SMILES: CC(C)(C)c1cc(-c2ccc(C(=O)N3CCOCC3)cc2)cc2cc(CNC(=O)/C=C/c3ccc(N)nc3)oc12] | B | B | D | (E)-3-(6-aminopyridin-3-yl)-N-((7-(tert-butyl)-5-(4-(morpholine-4-carbonyl)phenyl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 512 | 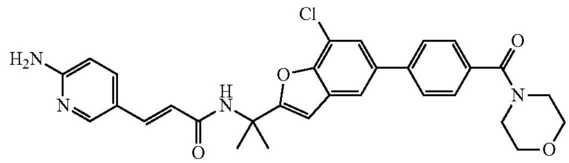 [SMILES: CC(C)(NC(=O)/C=C/c1ccc(N)nc1)c1cc2cc(-c3ccc(C(=O)N4CCOCC4)cc3)cc(Cl)c2o1] | D | D | D | (E)-3-(6-aminopyridin-3-yl)-N-(2-(7-chloro-5-(4-(morpholine-4-carbonyl)phenyl)benzofuran-2-yl)propan-2-yl)acrylamide |
| 513 | 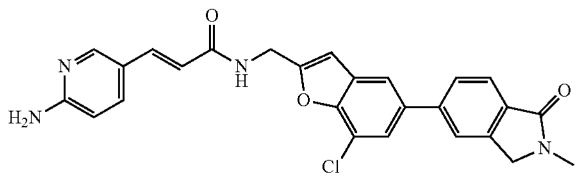 [SMILES: CN1Cc2cc(-c3cc(Cl)c4oc(CNC(=O)/C=C/c5ccc(N)nc5)cc4c3)ccc2C1=O] | D | B | D | (E)-3-(6-aminopyridin-3-yl)-N-((7-chloro-5-(2-methyl-1-oxoisoindolin-5-yl)benzofuran-2-yl)methyl)acrylamide |
| 514 | 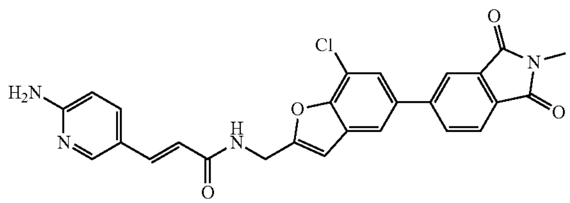 [SMILES: CN1C(=O)c2ccc(-c3cc(Cl)c4oc(CNC(=O)/C=C/c5ccc(N)nc5)cc4c3)cc2C1=O] | C | B | D | (E)-3-(6-aminopyridin-3-yl)-N-((7-chloro-5-(2-methyl-1,3-dioxoisoindolin-5-yl)benzofuran-2-yl)methyl)acrylamide |
| 515 | 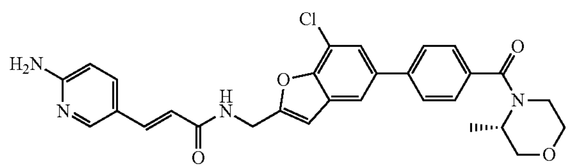 [SMILES: C[C@H]1COCCN1C(=O)c1ccc(-c2cc(Cl)c3oc(CNC(=O)/C=C/c4ccc(N)nc4)cc3c2)cc1] | B | B | D | (S,E)-3-(6-aminopyridin-3-yl)-N-((7-chloro-5-(4-(3-methylmorpholine-4-carbonyl)phenyl)benzofuran-2-yl)methyl)acrylamide |
| 516 | 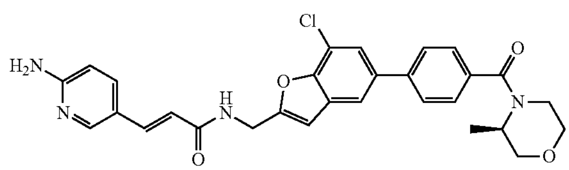 [SMILES: C[C@@H]1COCCN1C(=O)c1ccc(-c2cc(Cl)c3oc(CNC(=O)/C=C/c4ccc(N)nc4)cc3c2)cc1] | B | B | D | (R,E)-3-(6-aminopyridin-3-yl)-N-((7-chloro-5-(4-(3-methylmorpholine-4-carbonyl)phenyl)benzofuran-2-yl)methyl)acrylamide |
| 517 | 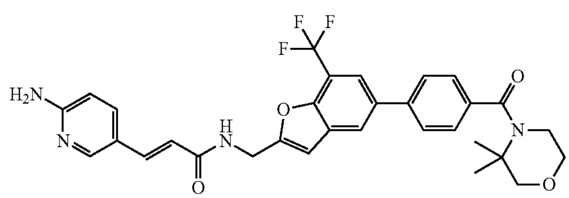 [SMILES: CC1(C)COCCN1C(=O)c1ccc(-c2cc(C(F)(F)F)c3oc(CNC(=O)/C=C/c4ccc(N)nc4)cc3c2)cc1] | B | B | D | (E)-3-(6-aminopyridin-3-yl)-N-((5-(4-(3,3-dimethylmorpholine-4-carbonyl)phenyl)-7-(trifluoromethyl)benzofuran-2-yl)methyl)acrylamide |
| 518 | 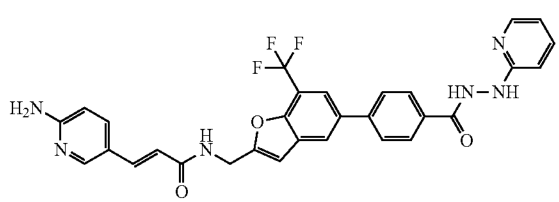 [SMILES: Nc1ccc(/C=C/C(=O)NCc2cc3cc(-c4ccc(C(=O)NNc5ccccn5)cc4)cc(C(F)(F)F)c3o2)cn1] | B | B | D | (E)-3-(6-aminopyridin-3-yl)-N-((5-(4-(2-(pyridin-2-yl)hydrazine-1-carbonyl)phenyl)-7-(trifluoromethyl)benzofuran-2-yl)methyl)acrylamide |
| 519 | 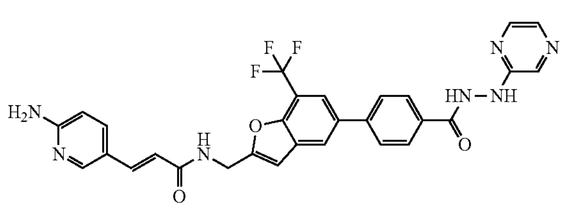 [SMILES: Nc1ccc(/C=C/C(=O)NCc2cc3cc(-c4ccc(C(=O)NNc5cnccn5)cc4)cc(C(F)(F)F)c3o2)cn1] | B | B | D | (E)-3-(6-aminopyridin-3-yl)-N-((5-(4-(2-(pyrazin-2-yl)hydrazine-1-carbonyl)phenyl)-7-(trifluoromethyl)benzofuran-2-yl)methyl)acrylamide |

TABLE 1-continued

| Cpd No. | Compound Structure | MS-751 | Z138 | 3T3 | Compound Name |
|---|---|---|---|---|---|
| 520 | 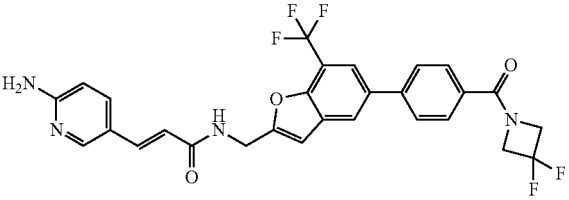 [SMILES: Nc1ccc(/C=C/C(=O)NCc2cc3cc(-c4ccc(C(=O)N5CC(F)(F)C5)cc4)cc(C(F)(F)F)c3o2)cn1] | B | B | D | (E)-3-(6-aminopyridin-3-yl)-N-((5-(4-(3,3-difluoroazetidine-1-carbonyl)phenyl)-7-(trifluoromethyl)benzofuran-2-yl)methyl)acrylamide |
| 521 | 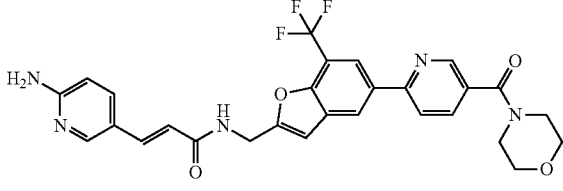 [SMILES: Nc1ccc(/C=C/C(=O)NCc2cc3cc(-c4ccc(C(=O)N5CCOCC5)cn4)cc(C(F)(F)F)c3o2)cn1] | A | A | D | (E)-3-(6-aminopyridin-3-yl)-N-((5-(5-(morpholine-4-carbonyl)pyridin-2-yl)-7-(trifluoromethyl)benzofuran-2-yl)methyl)acrylamide |
| 522 | 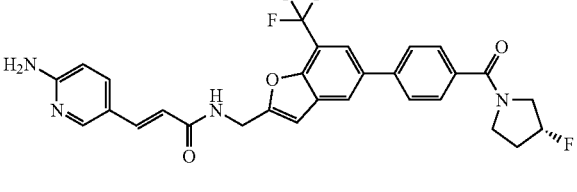 | B | B | D | (R,E)-3-(6-aminopyridin-3-yl)-N-((5-(4-(3-fluoropyrrolidine-1-carbonyl)phenyl)-7-(trifluoromethyl)benzofuran-2-yl)methyl)acrylamide |
| 523 | 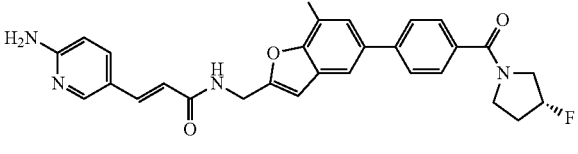 | D | D | D | (R,E)-3-(6-aminopyridin-3-yl)-N-((7-chloro-5-(4-(3-fluoropyrrolidine-1-carbonyl)phenyl)benzofuran-2-yl)methyl)acrylamide |
| 524 | 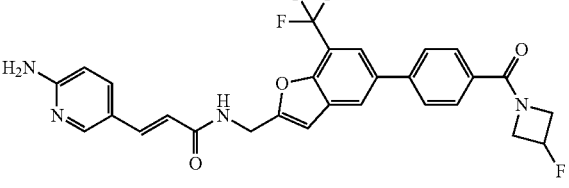 | B | B | D | (E)-3-(6-aminopyridin-3-yl)-N-((5-(4-(3-fluoroazetidine-1-carbonyl)phenyl)-7-(trifluoromethyl)benzofuran-2-yl)methyl)acrylamide |
| 525 | 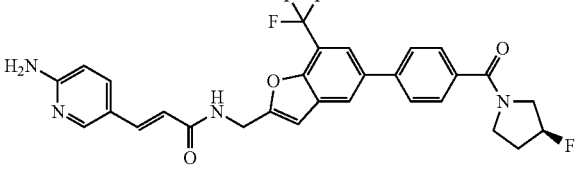 | B | B | D | (S,E)-3-(6-aminopyridin-3-yl)-N-((5-(4-(3-fluoropyrrolidine-1-carbonyl)phenyl)-7-(trifluoromethyl)benzofuran-2-yl)methyl)acrylamide |
| 526 | 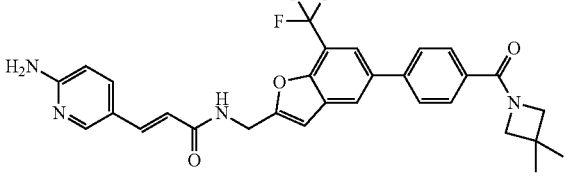 | B | B | D | (E)-3-(6-aminopyridin-3-yl)-N-((5-(4-(3,3-dimethyl-azetidine-1-carbonyl)phenyl)-7-(trifluoromethyl)benzofuran-2-yl)methyl)acrylamide |
| 527 | 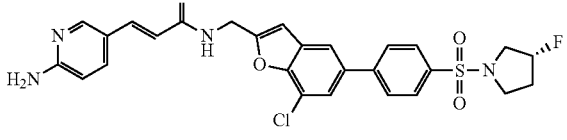 | B | B | D | (R,E)-3-(6-aminopyridin-3-yl)-N-((7-chloro-5-(4-((3-fluoropyrrolidin-1-yl)sulfonyl)phenyl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 528 | 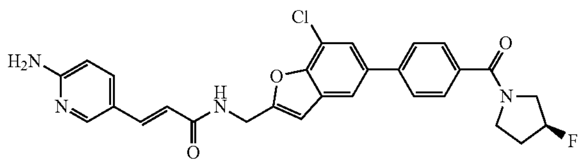 [SMILES: Nc1ccc(/C=C/C(=O)NCc2cc3cc(-c4ccc(C(=O)N5CC[C@H](F)C5)cc4)cc(Cl)c3o2)cn1] | D | D | D | (S,E)-3-(6-aminopyridin-3-yl)-N-((7-chloro-5-(4-(3-fluoropyrrolidine-1-carbonyl)phenyl)benzofuran-2-yl)methyl)acrylamide |
| 529 | 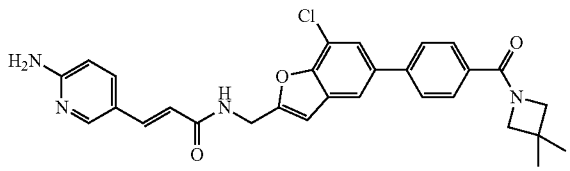 [SMILES: CC1(C)CN(C(=O)c2ccc(-c3cc(Cl)c4oc(CNC(=O)/C=C/c5ccc(N)nc5)cc4c3)cc2)C1] | C | B | D | (E)-3-(6-aminopyridin-3-yl)-N-((7-chloro-5-(4-(3,3-dimethylazetidine-1-carbonyl)phenyl)benzofuran-2-yl)methyl)acrylamide |
| 530 | 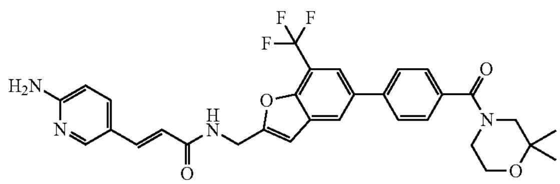 [SMILES: CC1(C)CN(C(=O)c2ccc(-c3cc(C(F)(F)F)c4oc(CNC(=O)/C=C/c5ccc(N)nc5)cc4c3)cc2)CCO1] | B | B | D | (E)-3-(6-aminopyridin-3-yl)-N-((5-(4-(2,2-dimethylmorpholine-4-carbonyl)phenyl)-7-(trifluoromethyl)benzofuran-2-yl)methyl)acrylamide |
| 531 | 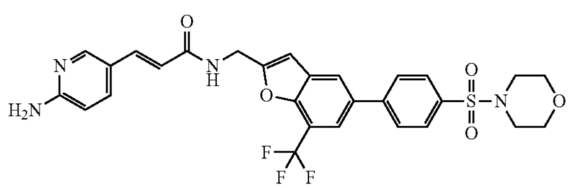 [SMILES: Nc1ccc(/C=C/C(=O)NCc2cc3cc(-c4ccc(S(=O)(=O)N5CCOCC5)cc4)cc(C(F)(F)F)c3o2)cn1] | A | B | B | (E)-3-(6-aminopyridin-3-yl)-N-((5-(4-(morpholinosulfonyl)phenyl)-7-(trifluoromethyl)benzofuran-2-yl)methyl)acrylamide |
| 532 | 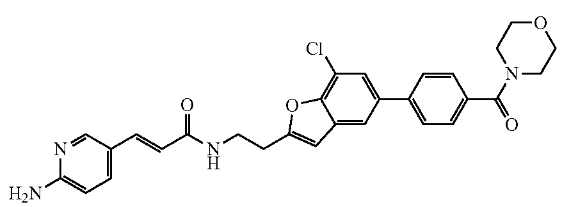 [SMILES: Nc1ccc(/C=C/C(=O)NCCc2cc3cc(-c4ccc(C(=O)N5CCOCC5)cc4)cc(Cl)c3o2)cn1] | A | A | A | (E)-3-(6-aminopyridin-3-yl)-N-(2-(7-chloro-5-(4-(morpholine-4-carbonyl)phenyl)benzofuran-2-yl)ethyl)acrylamide |
| 533 | 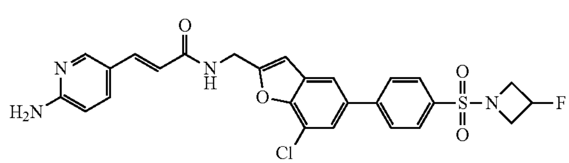 [SMILES: Nc1ccc(/C=C/C(=O)NCc2cc3cc(-c4ccc(S(=O)(=O)N5CC(F)C5)cc4)cc(Cl)c3o2)cn1] | B | B | D | (E)-3-(6-aminopyridin-3-yl)-N-((7-chloro-5-(4-((3-fluoroazetidin-1-yl)sulfonyl)phenyl)benzofuran-2-yl)methyl)acrylamide |
| 534 | 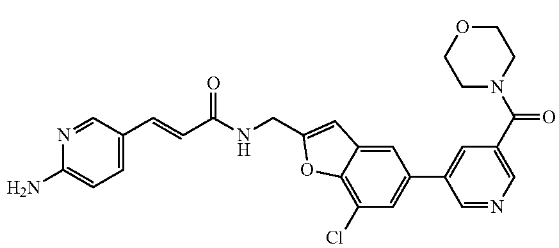 [SMILES: Nc1ccc(/C=C/C(=O)NCc2cc3cc(-c4cncc(C(=O)N5CCOCC5)c4)cc(Cl)c3o2)cn1] | B | B | D | (E)-3-(6-aminopyridin-3-yl)-N-((7-chloro-5-(5-(morpholine-4-carbonyl)pyridin-3-yl)benzofuran-2-yl)methyl)acrylamide |
| 535 | 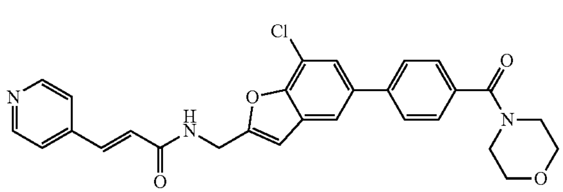 [SMILES: O=C(/C=C/c1ccncc1)NCc1cc2cc(-c3ccc(C(=O)N4CCOCC4)cc3)cc(Cl)c2o1] | D | D | D | (E)-N-((7-chloro-5-(4-(morpholine-4-carbonyl)phenyl)benzofuran-2-yl)methyl)-3-(pyridin-4-yl)acrylamide |

TABLE 1-continued

MTT Assay

| Cpd No. | Compound Structure | MS-751 | Z138 | 3T3 | Compound Name |
|---|---|---|---|---|---|
| 536 | 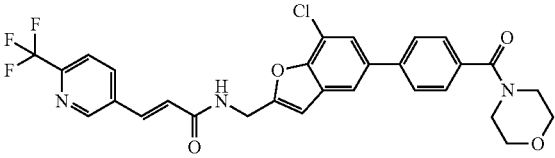 [SMILES: O=C(/C=C/c1ccc(C(F)(F)F)nc1)NCc1cc2cc(-c3ccc(C(=O)N4CCOCC4)cc3)cc(Cl)c2o1] | D | C | D | (E)-N-((7-chloro-5-(4-(morpholine-4-carbonyl)phenyl)benzofuran-2-yl)methyl)-3-(6-(trifluoromethyl)pyridin-3-yl)acrylamide |
| 537 | 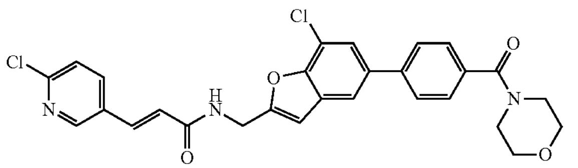 [SMILES: O=C(/C=C/c1ccc(Cl)nc1)NCc1cc2cc(-c3ccc(C(=O)N4CCOCC4)cc3)cc(Cl)c2o1] | D | D | D | (E)-N-((7-chloro-5-(4-(morpholine-4-carbonyl)phenyl)benzofuran-2-yl)methyl)-3-(6-chloropyridin-3-yl)acrylamide |
| 538 | 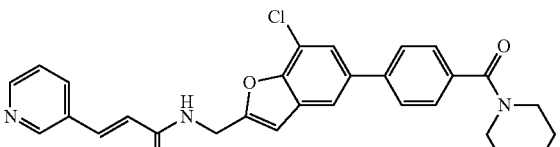 | B | B | B | (E)-N-((7-chloro-5-(4-(morpholine-4-carbonyl)phenyl)benzofuran-2-yl)methyl)-3-(pyridin-3-yl)acrylamide |
| 539 | 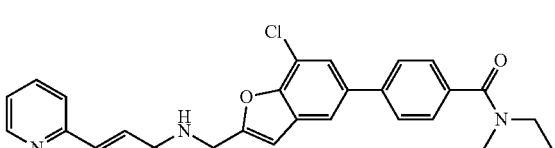 | B | B | D | (E)-N-((7-chloro-5-(4-(morpholine-4-carbonyl)phenyl)benzofuran-2-yl)methyl)-3-(pyridin-2-yl)acrylamide |
| 540 | 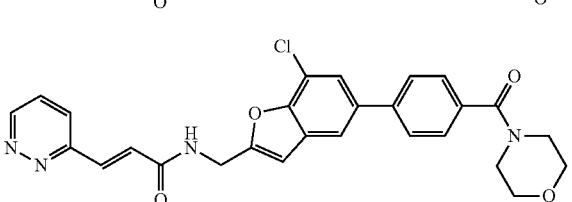 | C | C | C | (E)-N-((7-chloro-5-(4-(morpholine-4-carbonyl)phenyl)benzofuran-2-yl)methyl)-3-(pyridazin-3-yl)acrylamide |
| 541 | 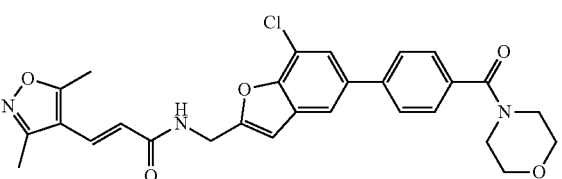 [SMILES: Cc1noc(C)c1/C=C/C(=O)NCc1cc2cc(-c3ccc(C(=O)N4CCOCC4)cc3)cc(Cl)c2o1] | B | B | D | (E)-N-((7-chloro-5-(4-(morpholine-4-carbonyl)phenyl)benzofuran-2-yl)methyl)-3-(3,5-dimethylisoxazol-4-yl)acrylamide |
| 542 | 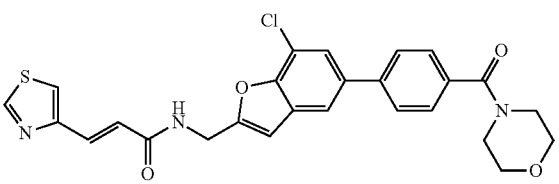 [SMILES: O=C(/C=C/c1cscn1)NCc1cc2cc(-c3ccc(C(=O)N4CCOCC4)cc3)cc(Cl)c2o1] | B | B | D | (E)-N-((7-chloro-5-(4-(morpholine-4-carbonyl)phenyl)benzofuran-2-yl)methyl)-3-(thiazol-4-yl)acrylamide |
| 543 | 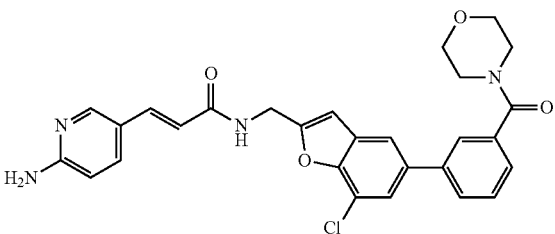 [SMILES: Nc1ccc(/C=C/C(=O)NCc2cc3cc(-c4cccc(C(=O)N5CCOCC5)c4)cc(Cl)c3o2)cn1] | A | A | B | (E)-3-(6-aminopyridin-3-yl)-N-((7-chloro-5-(3-(morpholine-4-carbonyl)phenyl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 544 | 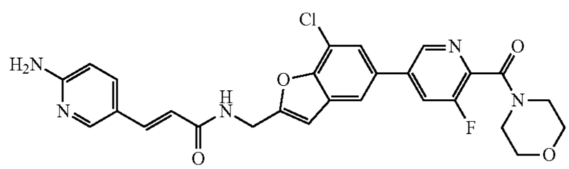 | B | B | D | (E)-3-(6-aminopyridin-3-yl)-N-((7-chloro-5-(5-fluoro-6-(morpholine-4-carbonyl)pyridin-3-yl)benzofuran-2-yl)methyl)acrylamide |
| 545 | 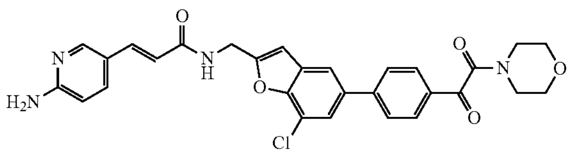 [SMILES: Nc1ccc(/C=C/C(=O)NCc2cc3cc(-c4ccc(C(=O)C(=O)N5CCOCC5)cc4)cc(Cl)c3o2)cn1] | B | B | C | (E)-3-(6-aminopyridin-3-yl)-N-((7-chloro-5-(4-(2-morpholino-2-oxoacetyl)phenyl)benzofuran-2-yl)methyl)acrylamide |
| 546 | 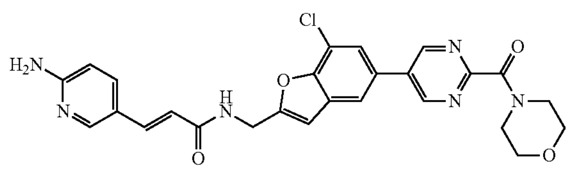 [SMILES: Nc1ccc(/C=C/C(=O)NCc2cc3cc(-c4cnc(C(=O)N5CCOCC5)nc4)cc(Cl)c3o2)cn1] | B | B | D | (E)-3-(6-aminopyridin-3-yl)-N-((7-chloro-5-(2-(morpholine-4-carbonyl)pyrimidin-5-yl)benzofuran-2-yl)methyl)acrylamide |
| 547 | 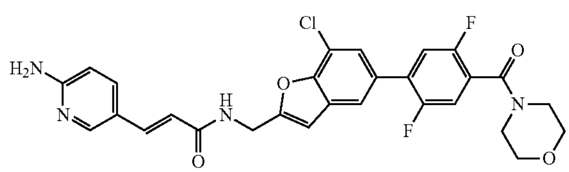 [SMILES: Nc1ccc(/C=C/C(=O)NCc2cc3cc(-c4cc(F)c(C(=O)N5CCOCC5)cc4F)cc(Cl)c3o2)cn1] | B | B | D | (E)-3-(6-aminopyridin-3-yl)-N-((7-chloro-5-(2,5-difluoro-4-(morpholine-4-carbonyl)phenyl)benzofuran-2-yl)methyl)acrylamide |
| 548 | 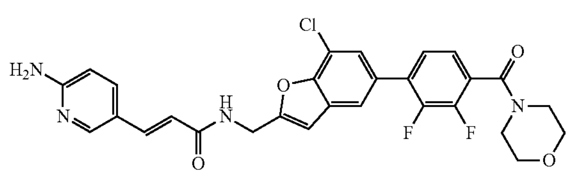 [SMILES: Nc1ccc(/C=C/C(=O)NCc2cc3cc(-c4ccc(C(=O)N5CCOCC5)c(F)c4F)cc(Cl)c3o2)cn1] | B | B | D | (E)-3-(6-aminopyridin-3-yl)-N-((7-chloro-5-(2,3-difluoro-4-(morpholine-4-carbonyl)phenyl)benzofuran-2-yl)methyl)acrylamide |
| 549 | 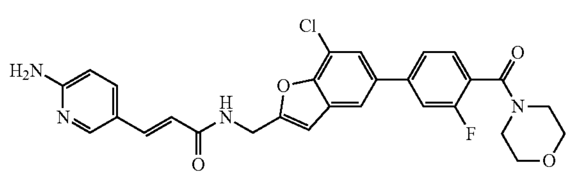 | B | B | D | (E)-3-(6-aminopyridin-3-yl)-N-((7-chloro-5-(3-fluoro-4-(morpholine-4-carbonyl)phenyl)benzofuran-2-yl)methyl)acrylamide |
| 550 | 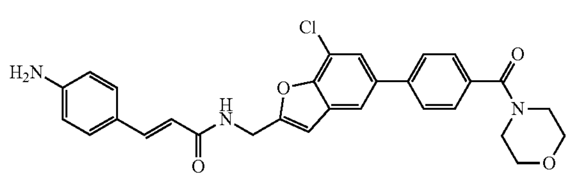 [SMILES: Nc1ccc(/C=C/C(=O)NCc2cc3cc(-c4ccc(C(=O)N5CCOCC5)cc4)cc(Cl)c3o2)cc1] | D | D | D | (E)-3-(4-aminophenyl)-N-((7-chloro-5-(4-(morpholine-4-carbonyl)phenyl)benzofuran-2-yl)methyl)acrylamide |
| 551 | 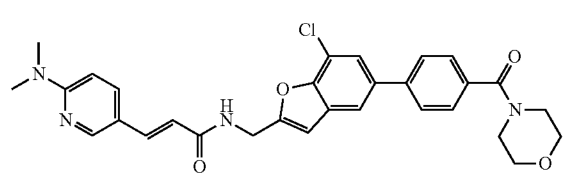 [SMILES: CN(C)c1ccc(/C=C/C(=O)NCc2cc3cc(-c4ccc(C(=O)N5CCOCC5)cc4)cc(Cl)c3o2)cn1] | D | D | D | (E)-N-((7-chloro-5-(4-(morpholine-4-carbonyl)phenyl)benzofuran-2-yl)methyl)-3-(6-(dimethylamino)pyridin-3-yl)acrylamide |

TABLE 1-continued

MTT Assay

| Cpd No. | Compound Structure | MS-751 | Z138 | 3T3 | Compound Name |
|---|---|---|---|---|---|
| 552 | 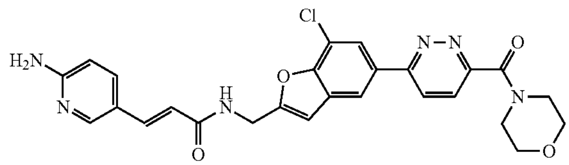 | B | B | D | (E)-3-(6-aminopyridin-3-yl)-N-((7-chloro-5-(6-(morpholine-4-carbonyl)pyridazin-3-yl)benzofuran-2-yl)methyl)acrylamide |
| 553 | 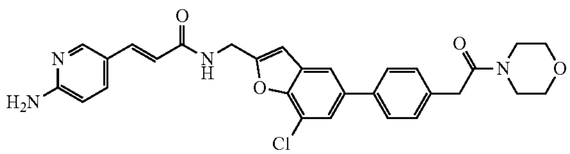 [SMILES: Nc1ccc(/C=C/C(=O)NCc2cc3cc(-c4ccc(CC(=O)N5CCOCC5)cc4)cc(Cl)c3o2)cn1] | B | B | D | (E)-3-(6-aminopyridin-3-yl)-N-((7-chloro-5-(4-(2-morpholino-2-oxoethyl)phenyl)benzofuran-2-yl)methyl)acrylamide |
| 554 | 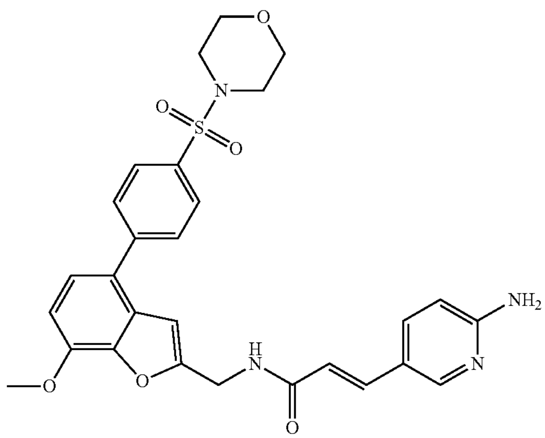 [SMILES: COc1ccc(-c2ccc(S(=O)(=O)N3CCOCC3)cc2)c2cc(CNC(=O)/C=C/c3ccc(N)nc3)oc12] | B | A | D | (E)-3-(6-aminopyridin-3-yl)-N-((7-methoxy-4-(4-(morpholinosulfonyl)phenyl)benzofuran-2-yl)methyl)acrylamide |
| 555 | 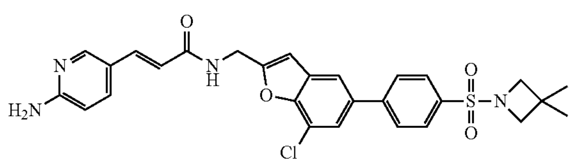 [SMILES: CC1(C)CN(S(=O)(=O)c2ccc(-c3cc(Cl)c4oc(CNC(=O)/C=C/c5ccc(N)nc5)cc4c3)cc2)C1] | B | B | D | (E)-3-(6-aminopyridin-3-yl)-N-((7-chloro-5-(4-((3,3-dimethylazetidin-1-yl)sulfonyl)phenyl)benzofuran-2-yl)methyl)acrylamide |
| 556 | 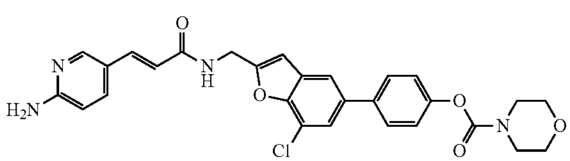 [SMILES: Nc1ccc(/C=C/C(=O)NCc2cc3cc(-c4ccc(OC(=O)N5CCOCC5)cc4)cc(Cl)c3o2)cn1] | B | B | D | (E)-4-(2-((3-(6-aminopyridin-3-yl)acrylamido)methyl)-7-chlorobenzofuran-5-yl)phenyl morpholine-4-carboxylate |
| 557 | 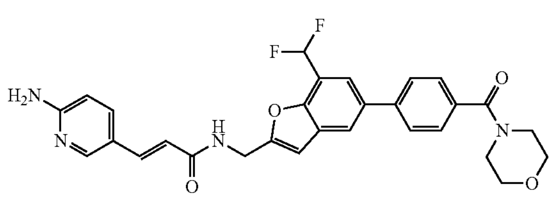 [SMILES: Nc1ccc(/C=C/C(=O)NCc2cc3cc(-c4ccc(C(=O)N5CCOCC5)cc4)cc(C(F)F)c3o2)cn1] | B | B | D | (E)-3-(6-aminopyridin-3-yl)-N-((7-(difluoromethyl)-5-(4-(morpholine-4-carbonyl)phenyl)benzofuran-2-yl)methyl)acrylamide |
| 558 | 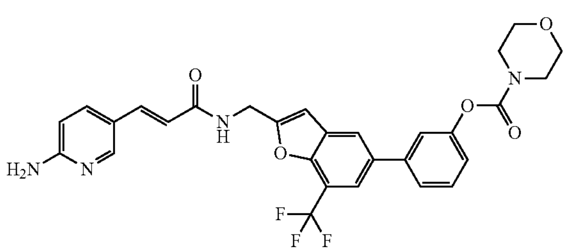 [SMILES: Nc1ccc(/C=C/C(=O)NCc2cc3cc(-c4cccc(OC(=O)N5CCOCC5)c4)cc(C(F)(F)F)c3o2)cn1] | D | D | D | (E)-3-(2-((3-(6-aminopyridin-3-yl)acrylamido)methyl)-7-(trifluoromethyl)benzofuran-5-yl)phenyl morpholine-4-carboxylate |

TABLE 1-continued

| Cpd No. | Compound Structure | MS-751 | Z138 | 3T3 | Compound Name |
|---|---|---|---|---|---|
| 559 | 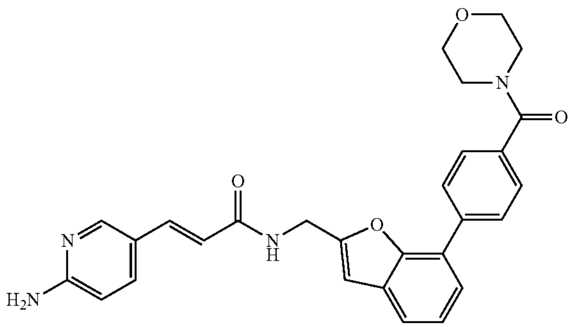 [SMILES: Nc1ccc(/C=C/C(=O)NCc2cc3cccc(-c4ccc(C(=O)N5CCOCC5)cc4)c3o2)cn1] | A | A | B | (E)-3-(6-aminopyridin-3-yl)-N-((7-(4-(morpholine-4-carbonyl)phenyl)benzofuran-2-yl)methyl)acrylamide |
| 560 | 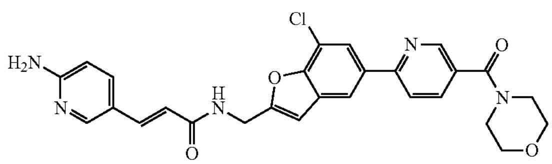 | B | B | D | (E)-3-(6-aminopyridin-3-yl)-N-((7-chloro-5-(5-(morpholine-4-carbonyl)pyridin-2-yl)benzofuran-2-yl)methyl)acrylamide |
| 561 | 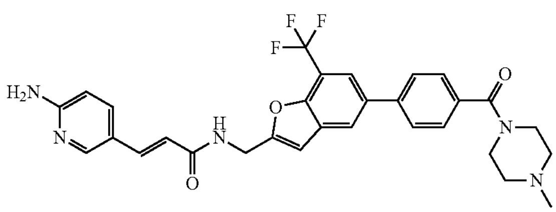 | A | A | C | (E)-3-(6-aminopyridin-3-yl)-N-((5-(4-(4-methylpiperazine-1-carbonyl)phenyl)-7-(trifluoromethyl)benzofuran-2-yl)methyl)acrylamide |
| 562 | 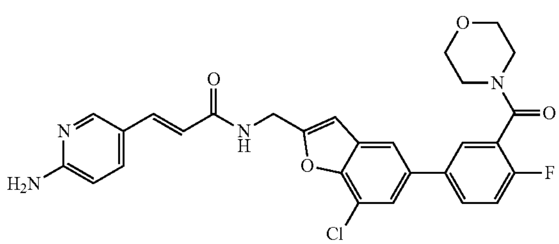 [SMILES: Nc1ccc(/C=C/C(=O)NCc2cc3cc(-c4ccc(F)c(C(=O)N5CCOCC5)c4)cc(Cl)c3o2)cn1] | A | A | D | (E)-3-(6-aminopyridin-3-yl)-N-((7-chloro-5-(4-fluoro-3-(morpholine-4-carbonyl)phenyl)benzofuran-2-yl)methyl)acrylamide |
| 563 | 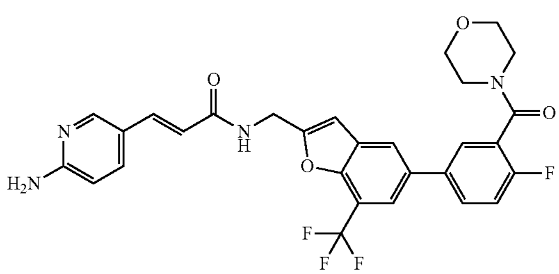 [SMILES: Nc1ccc(/C=C/C(=O)NCc2cc3cc(-c4ccc(F)c(C(=O)N5CCOCC5)c4)cc(C(F)(F)F)c3o2)cn1] | B | A | D | (E)-3-(6-aminopyridin-3-yl)-N-((5-(4-fluoro-3-(morpholine-4-carbonyl)phenyl)-7-(trifluoromethyl)benzofuran-2-yl)methyl)acrylamide |
| 564 | 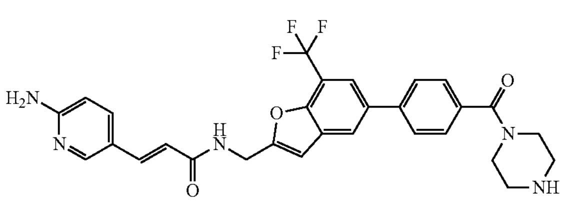 [SMILES: Nc1ccc(/C=C/C(=O)NCc2cc3cc(-c4ccc(C(=O)N5CCNCC5)cc4)cc(C(F)(F)F)c3o2)cn1] | A | A | D | (E)-3-(6-aminopyridin-3-yl)-N-((5-(4-(piperazine-1-carbonyl)phenyl)-7-(trifluoromethyl)benzofuran-2-yl)methyl)acrylamide |

TABLE 1-continued

| Cpd No. | Compound Structure | MS-751 | Z138 | 3T3 | Compound Name |
|---|---|---|---|---|---|
| 565 | 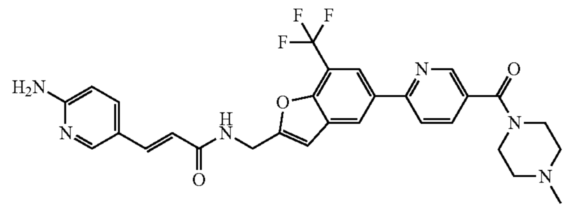 | A | A | B | (E)-3-(6-aminopyridin-3-yl)-N-((5-(5-(4-methyl-piperazine-1-carbonyl)pyridin-2-yl)-7-(trifluoromethyl)benzofuran-2-yl)methyl)acrylamide |
| 566 | 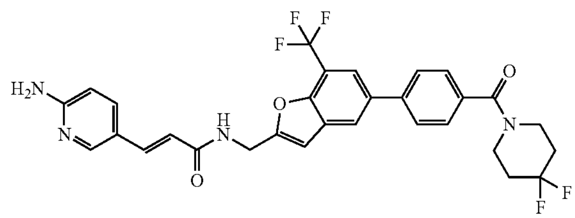 | B | B | D | (E)-3-(6-aminopyridin-3-yl)-N-((5-(4-(4,4-difluoro-piperidine-1-carbonyl)phenyl)-7-(trifluoromethyl)benzofuran-2-yl)methyl)acrylamide |
| 567 | 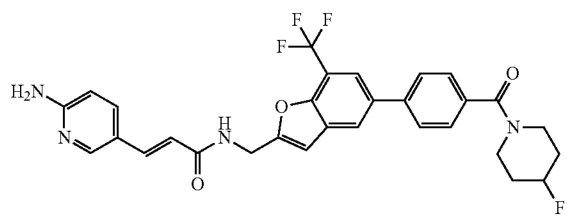 [SMILES: Nc1ccc(/C=C/C(=O)NCc2cc3cc(-c4ccc(C(=O)N5CCC(F)CC5)cc4)cc(C(F)(F)F)c3o2)cn1] | B | B | D | (E)-3-(6-aminopyridin-3-yl)-N-((5-(4-(4-fluoropiperidine-1-carbonyl)phenyl)-7-(trifluoromethyl)benzofuran-2-yl)methyl)acrylamide |
| 568 | 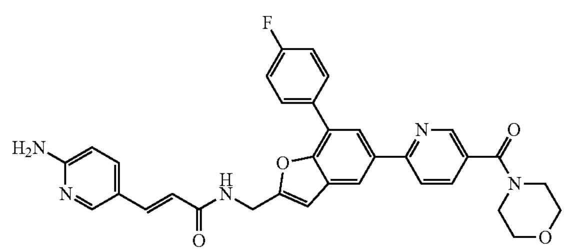 [SMILES: Nc1ccc(/C=C/C(=O)NCc2cc3cc(-c4ccc(C(=O)N5CCOCC5)cn4)cc(-c4ccc(F)cc4)c3o2)cn1] | A | A | B | (E)-3-(6-aminopyridin-3-yl)-N-((7-(4-fluorophenyl)-5-(5-(morpholine-4-carbonyl)pyridin-2-yl)benzofuran-2-yl)methyl)acrylamide |
| 569 | 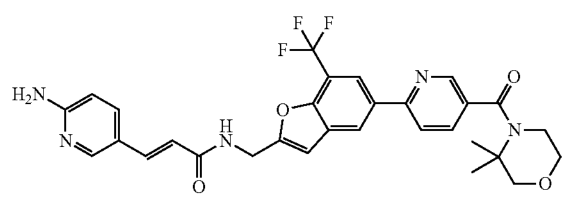 [SMILES: CC1(C)COCCN1C(=O)c1ccc(-c2cc(C(F)(F)F)c3oc(CNC(=O)/C=C/c4ccc(N)nc4)cc3c2)nc1] | A | A | D | (E)-3-(6-aminopyridin-3-yl)-N-((5-(5-(3,3-dimethylmorpholine-4-carbonyl)pyridin-2-yl)-7-(trifluoromethyl)benzofuran-2-yl)methyl)acrylamide |
| 570 | 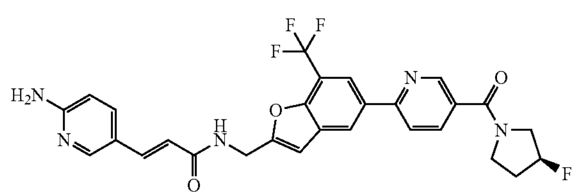 | B | A | D | (S,E)-3-(6-aminopyridin-3-yl)-N-((5-(5-(3-fluoro-pyrrolidine-1-carbonyl)pyridin-2-yl)-7-(trifluoromethyl)benzofuran-2-yl)methyl)acrylamide |
| 571 | 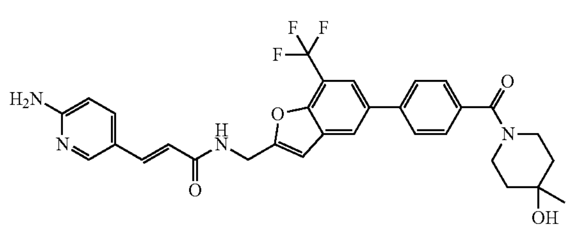 | B | A | D | (E)-3-(6-aminopyridin-3-yl)-N-((5-(4-(4-hydroxy-4-methylpiperidine-1-carbonyl)phenyl)-7-(trifluoromethyl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 572 | 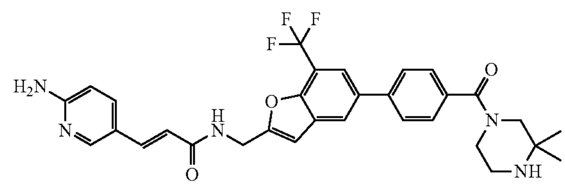 [SMILES: CC1(C)CN(C(=O)c2ccc(-c3cc(C(F)(F)F)c4oc(CNC(=O)/C=C/c5ccc(N)nc5)cc4c3)cc2)CCN1] | A | A | B | (E)-3-(6-aminopyridin-3-yl)-N-((5-(4-(3,3-dimethylpiperazine-1-carbonyl)phenyl)-7-(trifluoromethyl)benzofuran-2-yl)methyl)acrylamide |
| 573 | 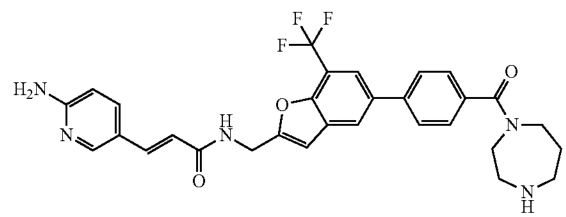 [SMILES: Nc1ccc(/C=C/C(=O)NCc2cc3cc(-c4ccc(C(=O)N5CCCNCC5)cc4)cc(C(F)(F)F)c3o2)cn1] | A | A | D | (E)-N-((5-(4-(1,4-diazepane-1-carbonyl)phenyl)-7-(trifluoromethyl)benzofuran-2-yl)methyl)-3-(6-aminopyridin-3-yl)acrylamide |
| 574 | 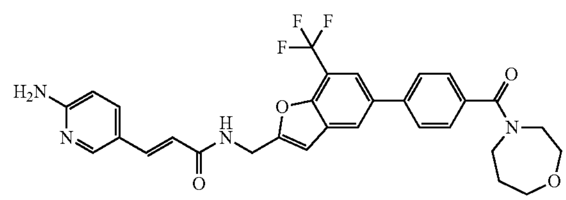 [SMILES: Nc1ccc(/C=C/C(=O)NCc2cc3cc(-c4ccc(C(=O)N5CCCOCC5)cc4)cc(C(F)(F)F)c3o2)cn1] | B | B | D | (E)-N-((5-(4-(1,4-oxazepane-4-carbonyl)phenyl)-7-(trifluoromethyl)benzofuran-2-yl)methyl)-3-(6-aminopyridin-3-yl)acrylamide |
| 575 | 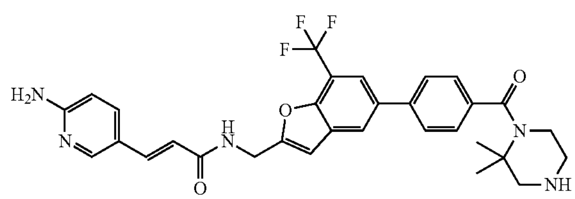 [SMILES: CC1(C)CNCCN1C(=O)c1ccc(-c2cc(C(F)(F)F)c3oc(CNC(=O)/C=C/c4ccc(N)nc4)cc3c2)cc1] | B | B | D | (E)-3-(6-aminopyridin-3-yl)-N-((5-(4-(2,2-dimethylpiperazine-1-carbonyl)phenyl)-7-(trifluoromethyl)benzofuran-2-yl)methyl)acrylamide |
| 576 | 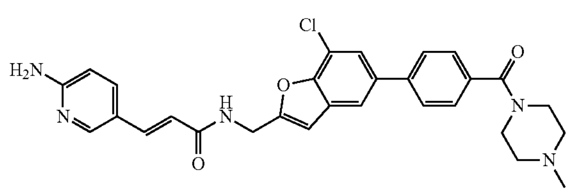 [SMILES: CN1CCN(C(=O)c2ccc(-c3cc(Cl)c4oc(CNC(=O)/C=C/c5ccc(N)nc5)cc4c3)cc2)CC1] | B | B | D | (E)-3-(6-aminopyridin-3-yl)-N-((7-chloro-5-(4-(4-methylpiperazine-1-carbonyl)phenyl)benzofuran-2-yl)methyl)acrylamide |
| 577 | 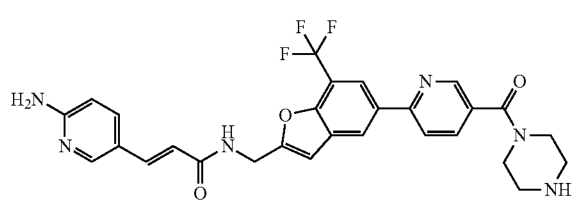 [SMILES: Nc1ccc(/C=C/C(=O)NCc2cc3cc(-c4ccc(C(=O)N5CCNCC5)cn4)cc(C(F)(F)F)c3o2)cn1] | A | A | D | (E)-3-(6-aminopyridin-3-yl)-N-((5-(5-(piperazine-1-carbonyl)pyridin-2-yl)-7-(trifluoromethyl)benzofuran-2-yl)methyl)acrylamide |
| 578 | 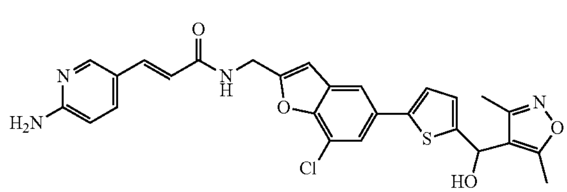 [SMILES: Cc1noc(C)c1C(O)c1ccc(-c2cc(Cl)c3oc(CNC(=O)/C=C/c4ccc(N)nc4)cc3c2)s1] | C | C | D | (E)-3-(6-aminopyridin-3-yl)-N-((7-chloro-5-(5-((3,5-dimethylisoxazol-4-yl)(hydroxy)methyl)thiophen-2-yl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 579 | 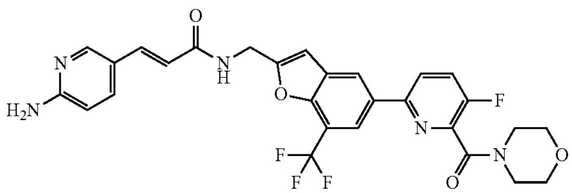 [SMILES: Nc1ccc(/C=C/C(=O)NCc2cc3cc(-c4ccc(F)c(C(=O)N5CCOCC5)n4)cc(C(F)(F)F)c3o2)cn1] | A | A | D | (E)-3-(6-aminopyridin-3-yl)-N-((5-(5-fluoro-6-(morpholine-4-carbonyl)pyridin-2-yl)-7-(trifluoromethyl)benzofuran-2-yl)methyl)acrylamide |
| 580 | 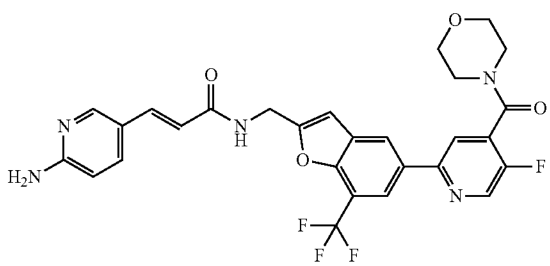 [SMILES: Nc1ccc(/C=C/C(=O)NCc2cc3cc(-c4cc(C(=O)N5CCOCC5)c(F)cn4)cc(C(F)(F)F)c3o2)cn1] | A | A | C | (E)-3-(6-aminopyridin-3-yl)-N-((5-(5-fluoro-4-(morpholine-4-carbonyl)pyridin-2-yl)-7-(trifluoromethyl)benzofuran-2-yl)methyl)acrylamide |
| 581 | 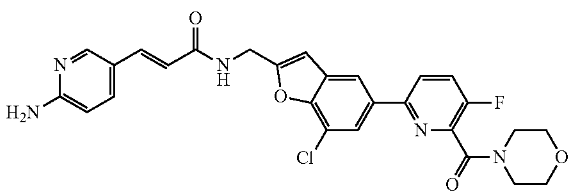 [SMILES: Nc1ccc(/C=C/C(=O)NCc2cc3cc(-c4ccc(F)c(C(=O)N5CCOCC5)n4)cc(Cl)c3o2)cn1] | A | A | D | (E)-3-(6-aminopyridin-3-yl)-N-((7-chloro-5-(5-fluoro-6-(morpholine-4-carbonyl)pyridin-2-yl)benzofuran-2-yl)methyl)acrylamide |
| 582 | 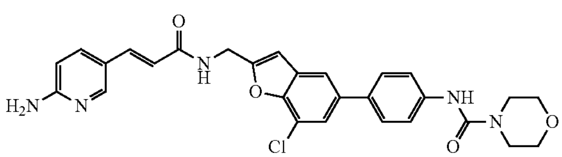 [SMILES: Nc1ccc(/C=C/C(=O)NCc2cc3cc(-c4ccc(NC(=O)N5CCOCC5)cc4)cc(Cl)c3o2)cn1] | C | C | D | (E)-N-(4-(2-((3-(6-aminopyridin-3-yl)acrylamido)methyl)-7-chlorobenzofuran-5-yl)phenyl)morpholine-4-carboxamide |
| 583 | 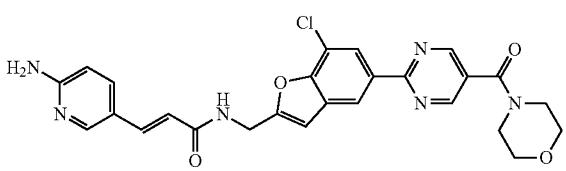 [SMILES: Nc1ccc(/C=C/C(=O)NCc2cc3cc(-c4ncc(C(=O)N5CCOCC5)cn4)cc(Cl)c3o2)cn1] | B | B | D | (E)-3-(6-aminopyridin-3-yl)-N-((7-chloro-5-(5-(morpholine-4-carbonyl)pyrimidin-2-yl)benzofuran-2-yl)methyl)acrylamide |
| 584 | 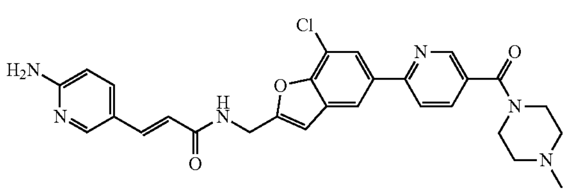 [SMILES: CN1CCN(C(=O)c2ccc(-c3cc(Cl)c4oc(CNC(=O)/C=C/c5ccc(N)nc5)cc4c3)nc2)CC1] | A | A | C | (E)-3-(6-aminopyridin-3-yl)-N-((7-chloro-5-(5-(4-methylpiperazine-1-carbonyl)pyridin-2-yl)benzofuran-2-yl)methyl)acrylamide |
| 585 | 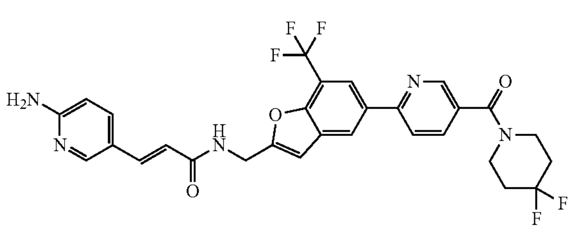 | A | A | D | (E)-3-(6-aminopyridin-3-yl)-N-((5-(5-(4,4-difluoropiperidine-1-carbonyl)pyridin-2-yl)-7-(trifluoromethyl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 586 | 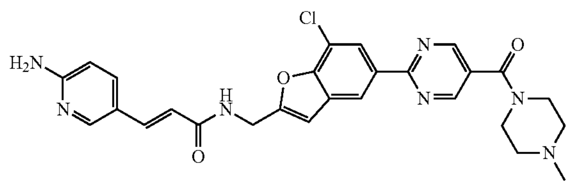 [SMILES: CN1CCN(C(=O)c2cnc(-c3cc(Cl)c4oc(CNC(=O)/C=C/c5ccc(N)nc5)cc4c3)nc2)CC1] | B | B | D | (E)-3-(6-aminopyridin-3-yl)-N-((7-chloro-5-(5-(4-methylpiperazine-1-carbonyl)pyrimidin-2-yl)benzofuran-2-yl)methyl)acrylamide |
| 587 | 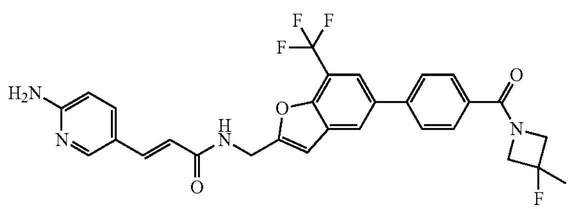 [SMILES: CC1(F)CN(C(=O)c2ccc(-c3cc(C(F)(F)F)c4oc(CNC(=O)/C=C/c5ccc(N)nc5)cc4c3)cc2)C1] | B | B | D | (E)-3-(6-aminopyridin-3-yl)-N-((5-(4-(3-fluoro-3-methylazetidine-1-carbonyl)phenyl)-7-(trifluoromethyl)benzofuran-2-yl)methyl)acrylamide |
| 588 | 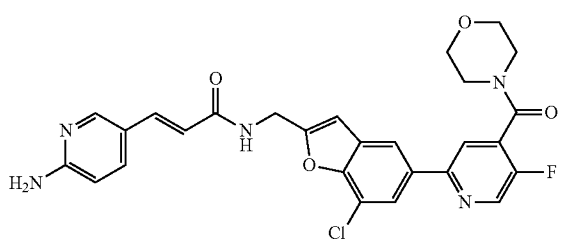 [SMILES: Nc1ccc(/C=C/C(=O)NCc2cc3cc(-c4cc(C(=O)N5CCOCC5)c(F)cn4)cc(Cl)c3o2)cn1] | A | A | B | (E)-3-(6-aminopyridin-3-yl)-N-((7-chloro-5-(5-fluoro-4-(morpholine-4-carbonyl)pyridin-2-yl)benzofuran-2-yl)methyl)acrylamide |
| 589 | 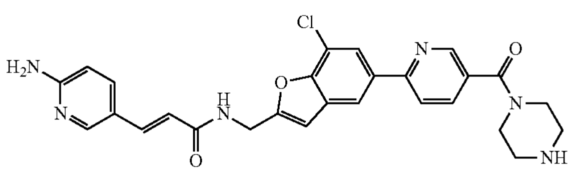 | B | A | D | (E)-3-(6-aminopyridin-3-yl)-N-((7-chloro-5-(5-(piperazine-1-carbonyl)pyridin-2-yl)benzofuran-2-yl)methyl)acrylamide |
| 590 | 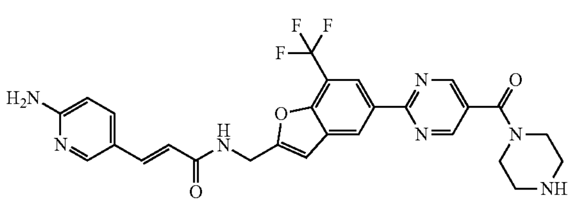 [SMILES: Nc1ccc(/C=C/C(=O)NCc2cc3cc(-c4ncc(C(=O)N5CCNCC5)cn4)cc(C(F)(F)F)c3o2)cn1] | B | B | D | (E)-3-(6-aminopyridin-3-yl)-N-((5-(5-(piperazine-1-carbonyl)pyrimidin-2-yl)-7-(trifluoromethyl)benzofuran-2-yl)methyl)acrylamide |
| 591 | 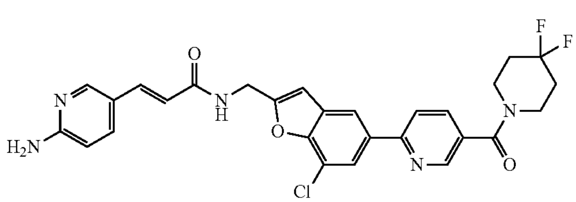 [SMILES: Nc1ccc(/C=C/C(=O)NCc2cc3cc(-c4ccc(C(=O)N5CCC(F)(F)CC5)cn4)cc(Cl)c3o2)cn1] | B | B | D | (E)-3-(6-aminopyridin-3-yl)-N-((7-chloro-5-(5-(4,4-difluoropiperidine-1-carbonyl)pyridin-2-yl)benzofuran-2-yl)methyl)acrylamide |
| 592 | 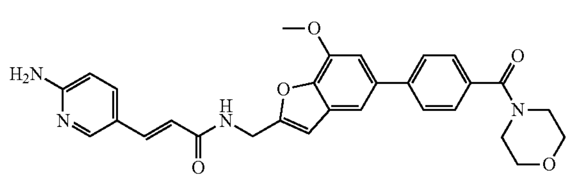 [SMILES: COc1cc(-c2ccc(C(=O)N3CCOCC3)cc2)cc2cc(CNC(=O)/C=C/c3ccc(N)nc3)oc12] | B | A | D | (E)-3-(6-aminopyridin-3-yl)-N-((7-methoxy-5-(4-(morpholine-4-carbonyl)phenyl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 593 | 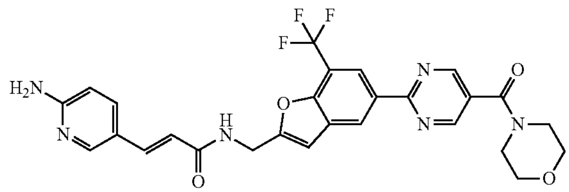 | B | B | D | (E)-3-(6-aminopyridin-3-yl)-N-((5-(5-(morpholine-4-carbonyl)pyrimidin-2-yl)-7-(trifluoromethyl)benzofuran-2-yl)methyl)acrylamide |
| 594 | 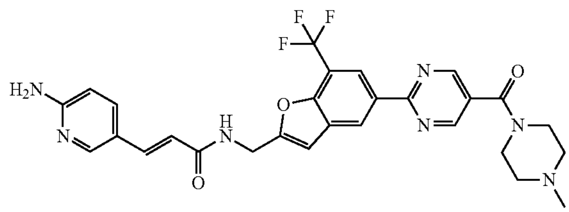 [SMILES: CN1CCN(C(=O)c2cnc(-c3cc(C(F)(F)F)c4oc(CNC(=O)/C=C/c5ccc(N)nc5)cc4c3)nc2)CC1] | B | B | D | (E)-3-(6-aminopyridin-3-yl)-N-((5-(5-(4-methyl-piperazine-1-carbonyl)pyrimidin-2-yl)-7-(trifluoromethyl)benzofuran-2-yl)methyl)acrylamide |
| 595 | 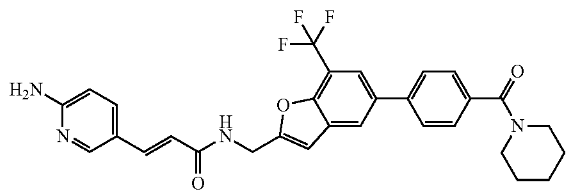 [SMILES: Nc1ccc(/C=C/C(=O)NCc2cc3cc(-c4ccc(C(=O)N5CCCCC5)cc4)cc(C(F)(F)F)c3o2)cn1] | B | B | D | (E)-3-(6-aminopyridin-3-yl)-N-((5-(4-(piperidine-1-carbonyl)phenyl)-7-(trifluoromethyl)benzofuran-2-yl)methyl)acrylamide |
| 596 | 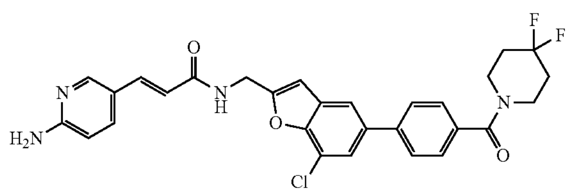 | B | B | D | (E)-3-(6-aminopyridin-3-yl)-N-((7-chloro-5-(4-(4,4-difluoropiperidine-1-carbonyl)phenyl)benzofuran-2-yl)methyl)acrylamide |
| 598 | 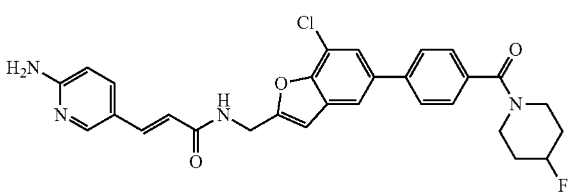 [SMILES: Nc1ccc(/C=C/C(=O)NCc2cc3cc(-c4ccc(C(=O)N5CCC(F)CC5)cc4)cc(Cl)c3o2)cn1] | B | B | D | (E)-3-(6-aminopyridin-3-yl)-N-((7-chloro-5-(4-(4-fluoropiperidine-1-carbonyl)phenyl)benzofuran-2-yl)methyl)acrylamide |
| 599 | 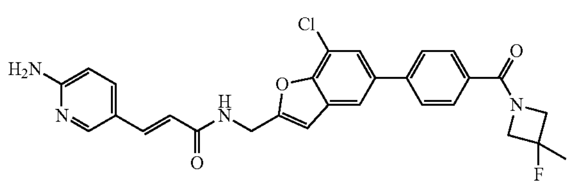 [SMILES: CC1(F)CN(C(=O)c2ccc(-c3cc(Cl)c4oc(CNC(=O)/C=C/c5ccc(N)nc5)cc4c3)cc2)C1] | B | B | C | (E)-3-(6-aminopyridin-3-yl)-N-((7-chloro-5-(4-(3-fluoro-3-methylazetidine-1-carbonyl)phenyl)benzofuran-2-yl)methyl)acrylamide |
| 600 | 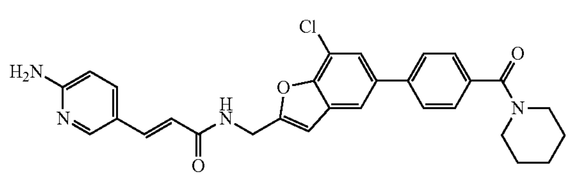 [SMILES: Nc1ccc(/C=C/C(=O)NCc2cc3cc(-c4ccc(C(=O)N5CCCCC5)cc4)cc(Cl)c3o2)cn1] | C | B | D | (E)-3-(6-aminopyridin-3-yl)-N-((7-chloro-5-(4-(piperidine-1-carbonyl)phenyl)benzofuran-2-yl)methyl)acrylamide |
| 601 | 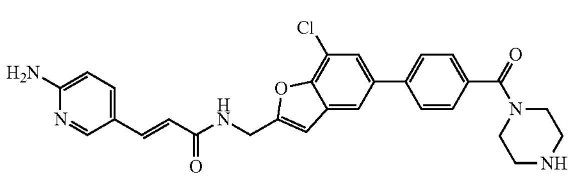 | B | B | D | (E)-3-(6-aminopyridin-3-yl)-N-((7-chloro-5-(4-(piperazine-1-carbonyl)phenyl)benzofuran-2-yl)methyl)acrylamide |

TABLE 1-continued

| Cpd No. | Compound Structure | MS-751 | Z138 | 3T3 | Compound Name |
|---|---|---|---|---|---|
| 602 | 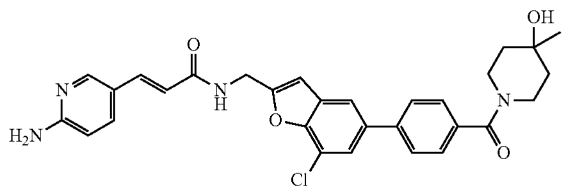 [SMILES: CC1(O)CCN(C(=O)c2ccc(-c3cc(Cl)c4oc(CNC(=O)/C=C/c5ccc(N)nc5)cc4c3)cc2)CC1] | B | B | D | (E)-3-(6-aminopyridin-3-yl)-N-((7-chloro-5-(4-(4-hydroxy-4-methylpiperidine-1-carbonyl)phenyl)benzofuran-2-yl)methyl)acrylamide |
| 603 | 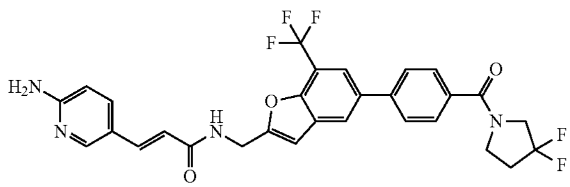 [SMILES: Nc1ccc(/C=C/C(=O)NCc2cc3cc(-c4ccc(C(=O)N5CCC(F)(F)C5)cc4)cc(C(F)(F)F)c3o2)cn1] | B | B | D | (E)-3-(6-aminopyridin-3-yl)-N-((5-(4-(3,3-difluoropyrrolidine-1-carbonyl)phenyl)-7-(trifluoromethyl)benzofuran-2-yl)methyl)acrylamide |
| 604 | 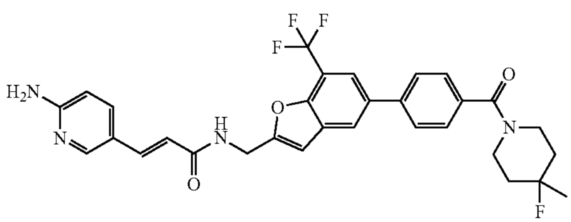 [SMILES: CC1(F)CCN(C(=O)c2ccc(-c3cc(C(F)(F)F)c4oc(CNC(=O)/C=C/c5ccc(N)nc5)cc4c3)cc2)CC1] | B | B | D | (E)-3-(6-aminopyridin-3-yl)-N-((5-(4-(4-fluoro-4-methylpiperidine-1-carbonyl)phenyl)-7-(trifluoromethyl)benzofuran-2-yl)methyl)acrylamide |
| 605 | 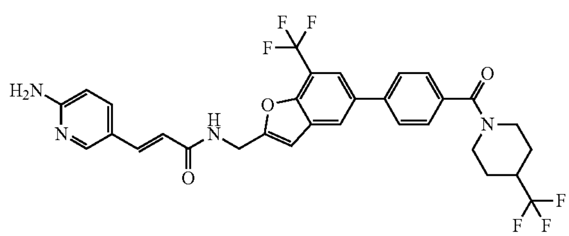 [SMILES: Nc1ccc(/C=C/C(=O)NCc2cc3cc(-c4ccc(C(=O)N5CCC(C(F)(F)F)CC5)cc4)cc(C(F)(F)F)c3o2)cn1] | B | B | D | (E)-3-(6-aminopyridin-3-yl)-N-((7-(trifluoromethyl)-5-(4-(4-(trifluoromethyl)piperidine-1-carbonyl)phenyl)benzofuran-2-yl)methyl)acrylamide |
| 606 | 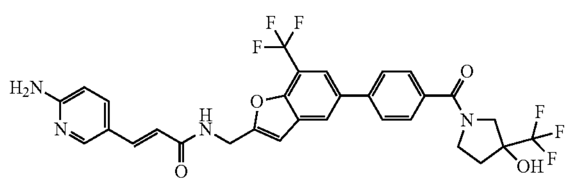 [SMILES: Nc1ccc(/C=C/C(=O)NCc2cc3cc(-c4ccc(C(=O)N5CCC(O)(C(F)(F)F)C5)cc4)cc(C(F)(F)F)c3o2)cn1] | B | B | D | (E)-3-(6-aminopyridin-3-yl)-N-((5-(4-(3-hydroxy-3-(trifluoromethyl)pyrrolidine-1-carbonyl)phenyl)-7-(trifluoromethyl)benzofuran-2-yl)methyl)acrylamide |
| 607 | 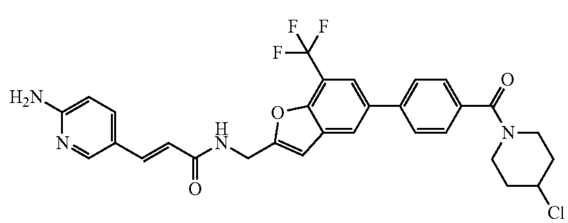 [SMILES: Nc1ccc(/C=C/C(=O)NCc2cc3cc(-c4ccc(C(=O)N5CCC(Cl)CC5)cc4)cc(C(F)(F)F)c3o2)cn1] | B | B | D | (E)-3-(6-aminopyridin-3-yl)-N-((5-(4-(4-chloro-piperidine-1-carbonyl)phenyl)-7-(trifluoromethyl)benzofuran-2-yl)methyl)acrylamide |
| 608 | 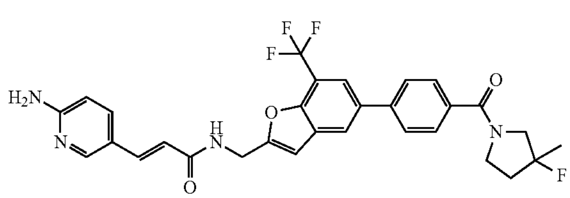 [SMILES: CC1(F)CCN(C(=O)c2ccc(-c3cc(C(F)(F)F)c4oc(CNC(=O)/C=C/c5ccc(N)nc5)cc4c3)cc2)C1] | B | B | D | (E)-3-(6-aminopyridin-3-yl)-N-((5-(4-(3-fluoro-3-methylpyrrolidine-1-carbonyl)phenyl)-7-(trifluoromethyl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 609 | 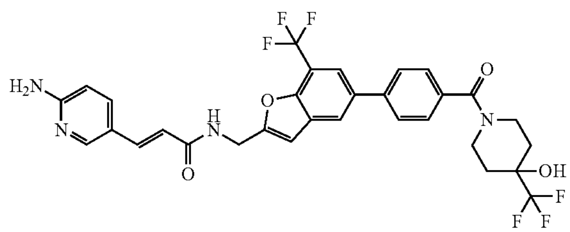 [SMILES: Nc1ccc(/C=C/C(=O)NCc2cc3cc(-c4ccc(C(=O)N5CCC(O)(C(F)(F)F)CC5)cc4)cc(C(F)(F)F)c3o2)cn1] | B | B | D | (E)-3-(6-aminopyridin-3-yl)-N-((5-(4-(4-hydroxy-4-(trifluoromethyl)piperidine-1-carbonyl)phenyl)-7-(trifluoromethyl)benzofuran-2-yl)methyl)acrylamide |
| 610 | 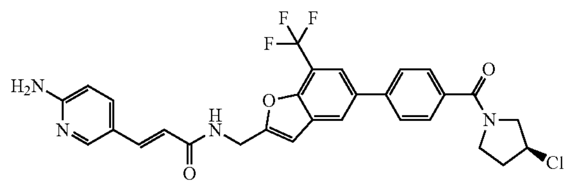 [SMILES: Nc1ccc(/C=C/C(=O)NCc2cc3cc(-c4ccc(C(=O)N5CC[C@H](Cl)C5)cc4)cc(C(F)(F)F)c3o2)cn1] | B | B | D | (S,E)-3-(6-aminopyridin-3-yl)-N-((5-(4-(3-chloropyrrolidine-1-carbonyl)phenyl)-7-(trifluoromethyl)benzofuran-2-yl)methyl)acrylamide |
| 611 | 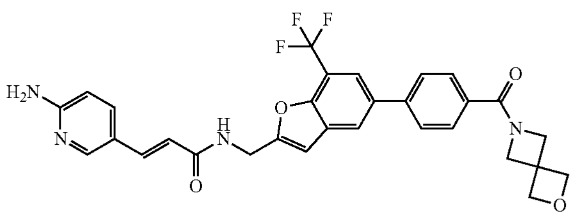 [SMILES: Nc1ccc(/C=C/C(=O)NCc2cc3cc(-c4ccc(C(=O)N5CC6(COC6)C5)cc4)cc(C(F)(F)F)c3o2)cn1] | A | A | D | (E)-N-((5-(4-(2-oxa-6-azaspiro[3.3]heptane-6-carbonyl)phenyl)-7-(trifluoromethyl)benzofuran-2-yl)methyl)-3-(6-aminopyridin-3-yl)acrylamide |
| 612 | 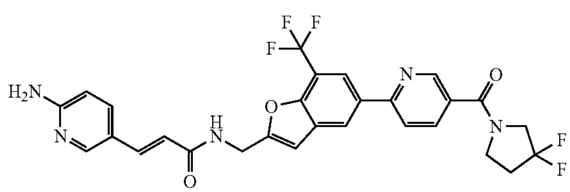 | B | A | D | (E)-3-(6-aminopyridin-3-yl)-N-((5-(5-(3,3-difluoropyrrolidine-1-carbonyl)pyridin-2-yl)-7-(trifluoromethyl)benzofuran-2-yl)methyl)acrylamide |
| 613 | 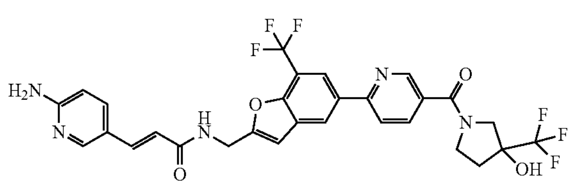 [SMILES: Nc1ccc(/C=C/C(=O)NCc2cc3cc(-c4ccc(C(=O)N5CCC(O)(C(F)(F)F)C5)cn4)cc(C(F)(F)F)c3o2)cn1] | B | A | D | (E)-3-(6-aminopyridin-3-yl)-N-((5-(5-(3-hydroxy-3-(trifluoromethyl)pyrrolidine-1-carbonyl)pyridin-2-yl)-7-(trifluoromethyl)benzofuran-2-yl)methyl)acrylamide |
| 614 | 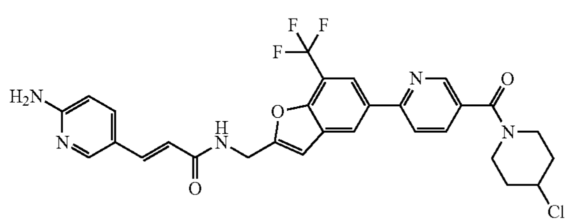 [SMILES: Nc1ccc(/C=C/C(=O)NCc2cc3cc(-c4ccc(C(=O)N5CCC(Cl)CC5)cn4)cc(C(F)(F)F)c3o2)cn1] | B | B | D | (E)-3-(6-aminopyridin-3-yl)-N-((5-(5-(4-chloropiperidine-1-carbonyl)pyridin-2-yl)-7-(trifluoromethyl)benzofuran-2-yl)methyl)acrylamide |
| 615 | 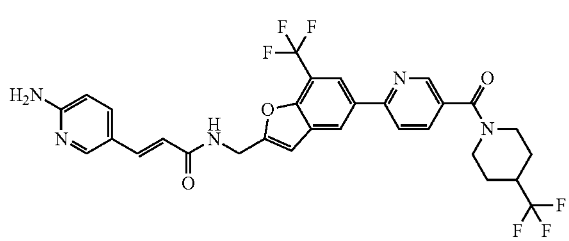 [SMILES: Nc1ccc(/C=C/C(=O)NCc2cc3cc(-c4ccc(C(=O)N5CCC(C(F)(F)F)CC5)cn4)cc(C(F)(F)F)c3o2)cn1] | B | B | D | (E)-3-(6-aminopyridin-3-yl)-N-((7-(trifluoromethyl)-5-(5-(4-(trifluoromethyl)piperidine-1-carbonyl)pyridin-2-yl)benzofuran-2-yl)methyl)acrylamide |

TABLE 1-continued

| Cpd No. | Compound Structure | MS-751 | Z138 | 3T3 | Compound Name |
|---|---|---|---|---|---|
| 616 | 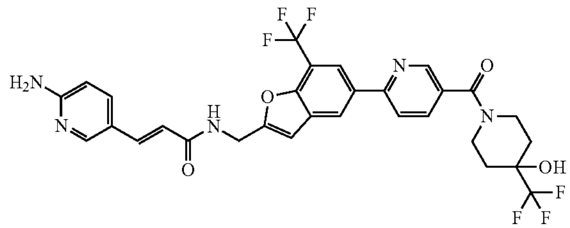 [SMILES: Nc1ccc(/C=C/C(=O)NCc2cc3cc(-c4ccc(C(=O)N5CCC(O)(C(F)(F)F)CC5)cn4)cc(C(F)(F)F)c3o2)cn1] | A | A | D | (E)-3-(6-aminopyridin-3-yl)-N-((5-(5-(4-hydroxy-4-(trifluoromethyl)piperidine-1-carbonyl)pyridin-2-yl)-7-(trifluoromethyl)benzofuran-2-yl)methyl)acrylamide |
| 617 | 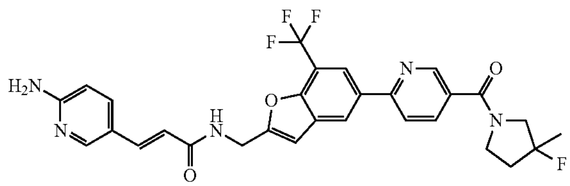 [SMILES: CC1(F)CCN(C(=O)c2ccc(-c3cc(C(F)(F)F)c4oc(CNC(=O)/C=C/c5ccc(N)nc5)cc4c3)nc2)C1] | B | A | D | (E)-3-(6-aminopyridin-3-yl)-N-((5-(5-(3-fluoro-3-methylpyrrolidine-1-carbonyl)pyridin-2-yl)-7-(trifluoromethyl)benzofuran-2-yl)methyl)acrylamide |
| 618 | 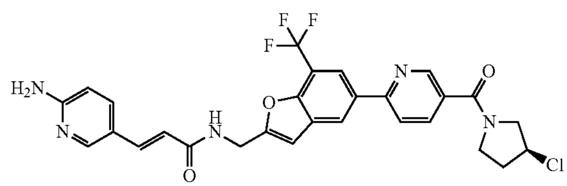 [SMILES: Nc1ccc(/C=C/C(=O)NCc2cc3cc(-c4ccc(C(=O)N5CC[C@H](Cl)C5)cn4)cc(C(F)(F)F)c3o2)cn1] | B | B | D | (S,E)-3-(6-aminopyridin-3-yl)-N-((5-(5-(3-chloropyrrolidine-1-carbonyl)pyridin-2-yl)-7-(trifluoromethyl)benzofuran-2-yl)methyl)acrylamide |
| 619 | 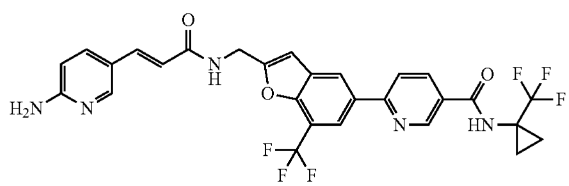 [SMILES: Nc1ccc(/C=C/C(=O)NCc2cc3cc(-c4ccc(C(=O)NC5(C(F)(F)F)CC5)cn4)cc(C(F)(F)F)c3o2)cn1] | B | B | D | (E)-6-(2-((3-(6-aminopyridin-3-yl)acrylamido)methyl)-7-(trifluoromethyl)benzofuran-5-yl)-N-(1-(trifluoromethyl)cyclopropyl)nicotinamide |
| 620 | 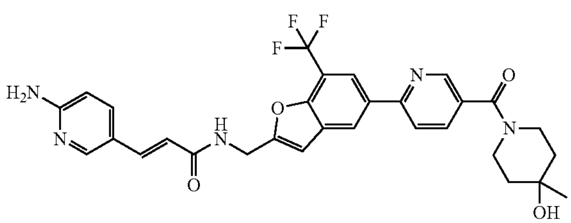 [SMILES: CC1(O)CCN(C(=O)c2ccc(-c3cc(C(F)(F)F)c4oc(CNC(=O)/C=C/c5ccc(N)nc5)cc4c3)nc2)CC1] | A | A | D | (E)-3-(6-aminopyridin-3-yl)-N-((5-(5-(4-hydroxy-4-methylpiperidine-1-carbonyl)pyridin-2-yl)-7-(trifluoromethyl)benzofuran-2-yl)methyl)acrylamide |
| 621 | 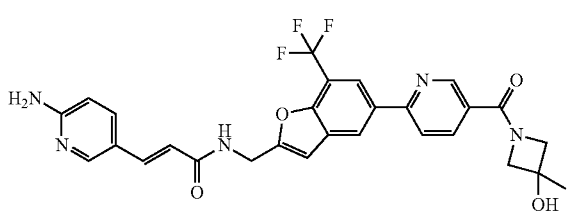 [SMILES: CC1(O)CN(C(=O)c2ccc(-c3cc(C(F)(F)F)c4oc(CNC(=O)/C=C/c5ccc(N)nc5)cc4c3)nc2)C1] | B | B | D | (E)-3-(6-aminopyridin-3-yl)-N-((5-(5-(3-hydroxy-3-methylazetidine-1-carbonyl)pyridin-2-yl)-7-(trifluoromethyl)benzofuran-2-yl)methyl)acrylamide |
| 622 | 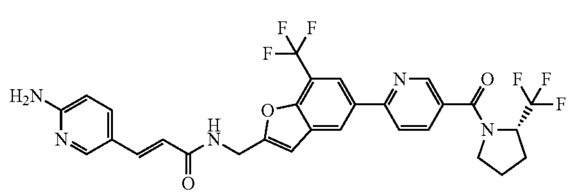 [SMILES: Nc1ccc(/C=C/C(=O)NCc2cc3cc(-c4ccc(C(=O)N5CCC[C@H]5C(F)(F)F)cn4)cc(C(F)(F)F)c3o2)cn1] | D | C | D | (S,E)-3-(6-aminopyridin-3-yl)-N-((7-(trifluoromethyl)-5-(5-(2-(trifluoromethyl)pyrrolidine-1-carbonyl)pyridin-2-yl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 623 | 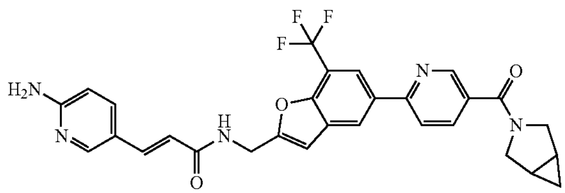 [SMILES: Nc1ccc(/C=C/C(=O)NCc2cc3cc(-c4ccc(C(=O)N5CC6CC6C5)cn4)cc(C(F)(F)F)c3o2)cn1] | B | B | D | (E)-N-((5-(5-(3-azabicyclo[3.1.0]hexane-3-carbonyl)pyridin-2-yl)-7-(trifluoromethyl)benzofuran-2-yl)methyl)-3-(6-aminopyridin-3-yl)acrylamide |
| 624 | 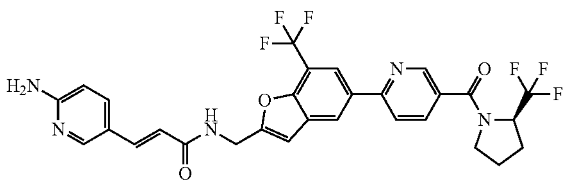 [SMILES: Nc1ccc(/C=C/C(=O)NCc2cc3cc(-c4ccc(C(=O)N5CCC[C@@H]5C(F)(F)F)cn4)cc(C(F)(F)F)c3o2)cn1] | B | B | D | (R,E)-3-(6-aminopyridin-3-yl)-N-((7-(trifluoromethyl)-5-(5-(2-(trifluoromethyl)pyrrolidine-1-carbonyl)pyridin-2-yl)benzofuran-2-yl)methyl)acrylamide |
| 625 | 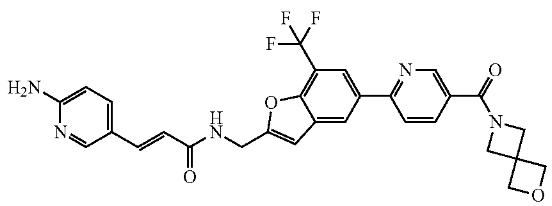 [SMILES: Nc1ccc(/C=C/C(=O)NCc2cc3cc(-c4ccc(C(=O)N5CC6(COC6)C5)cn4)cc(C(F)(F)F)c3o2)cn1] | A | A | B | (E)-N-((5-(5-(2-oxa-6-azaspiro[3.3]heptane-6-carbonyl)pyridin-2-yl)-7-(trifluoromethyl)benzofuran-2-yl)methyl)-3-(6-aminopyridin-3-yl)acrylamide |
| 626 | 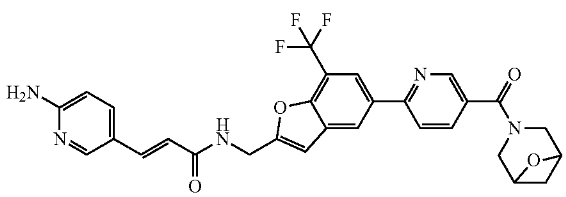 [SMILES: Nc1ccc(/C=C/C(=O)NCc2cc3cc(-c4ccc(C(=O)N5CC6CC(C5)O6)cn4)cc(C(F)(F)F)c3o2)cn1] | B | B | D | (E)-N-((5-(5-(6-oxa-3-azabicyclo[3.1.1]heptane-3-carbonyl)pyridin-2-yl)-7-(trifluoromethyl)benzofuran-2-yl)methyl)-3-(6-aminopyridin-3-yl)acrylamide |
| 627 | 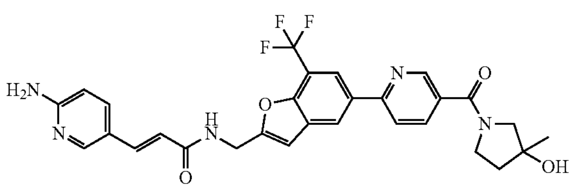 [SMILES: CC1(O)CCN(C(=O)c2ccc(-c3cc(C(F)(F)F)c4oc(CNC(=O)/C=C/c5ccc(N)nc5)cc4c3)nc2)C1] | A | A | D | (E)-3-(6-aminopyridin-3-yl)-N-((5-(5-(3-hydroxy-3-methylpyrrolidine-1-carbonyl)pyridin-2-yl)-7-(trifluoromethyl)benzofuran-2-yl)methyl)acrylamide |
| 628 | 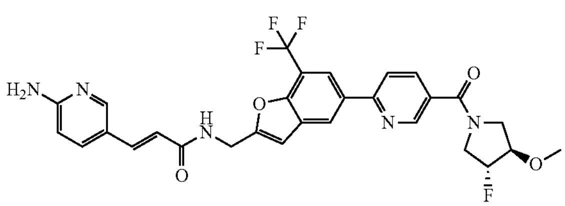 [SMILES: CO[C@@H]1CN(C(=O)c2ccc(-c3cc(C(F)(F)F)c4oc(CNC(=O)/C=C/c5ccc(N)nc5)cc4c3)nc2)C[C@H]1F] | B | B | D | (E)-3-(6-aminopyridin-3-yl)-N-((5-(5-((3R,4R)-3-fluoro-4-methoxypyrrolidine-1-carbonyl)pyridin-2-yl)-7-(trifluoromethyl)benzofuran-2-yl)methyl)acrylamide |
| 629 | 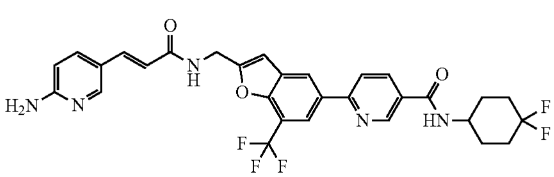 [SMILES: Nc1ccc(/C=C/C(=O)NCc2cc3cc(-c4ccc(C(=O)NC5CCC(F)(F)CC5)cn4)cc(C(F)(F)F)c3o2)cn1] | B | B | D | (E)-6-(2-((3-(6-aminopyridin-3-yl)acrylamido)methyl)-7-(trifluoromethyl)benzofuran-5-yl)-N-(4,4-difluorocyclohexyl)nicotinamide |

TABLE 1-continued

MTT Assay

| Cpd No. | Compound Structure | MS-751 | Z138 | 3T3 | Compound Name |
|---|---|---|---|---|---|
| 630 | 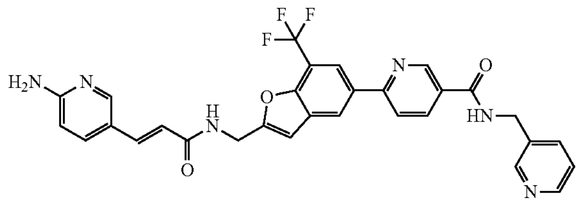 [SMILES: Nc1ccc(/C=C/C(=O)NCc2cc3cc(-c4ccc(C(=O)NCc5cccnc5)cn4)cc(C(F)(F)F)c3o2)cn1] | A | A | B | (E)-6-(2-((3-(6-aminopyridin-3-yl)acrylamido)methyl)-7-(trifluoromethyl)benzofuran-5-yl)-N-(pyridin-3-ylmethyl)nicotinamide |
| 631 | 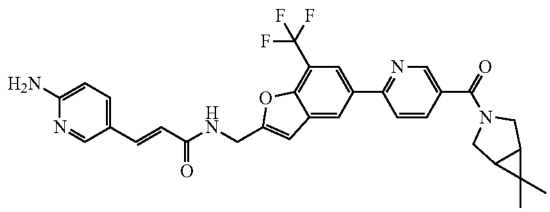 [SMILES: CC1(C)C2CN(C(=O)c3ccc(-c4cc(C(F)(F)F)c5oc(CNC(=O)/C=C/c6ccc(N)nc6)cc5c4)nc3)CC21] | B | B | D | (E)-3-(6-aminopyridin-3-yl)-N-((5-(5-(6,6-dimethyl-3-azabicyclo[3.1.0]hexane-3-carbonyl)pyridin-2-yl)-7-(trifluoromethyl)benzofuran-2-yl)methyl)acrylamide |
| 632 | 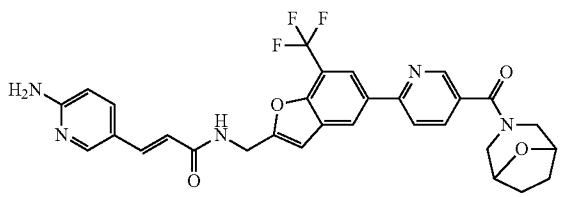 [SMILES: Nc1ccc(/C=C/C(=O)NCc2cc3cc(-c4ccc(C(=O)N5CC6CCC(C5)O6)cn4)cc(C(F)(F)F)c3o2)cn1] | B | B | D | (E)-N-((5-(5-(8-oxa-3-azabicyclo[3.2.1]octane-3-carbonyl)pyridin-2-yl)-7-(trifluoromethyl)benzofuran-2-yl)methyl)-3-(6-aminopyridin-3-yl)acrylamide |
| 633 | 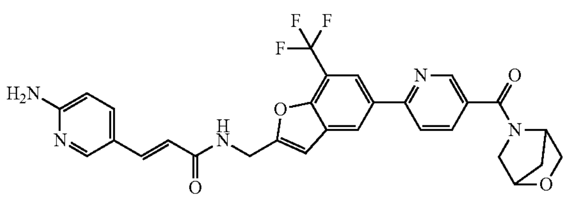 [SMILES: Nc1ccc(/C=C/C(=O)NCc2cc3cc(-c4ccc(C(=O)N5CC6CC5CO6)cn4)cc(C(F)(F)F)c3o2)cn1] | B | B | D | (E)-N-((5-(5-(2-oxa-5-azabicyclo[2.2.1]heptane-5-carbonyl)pyridin-2-yl)-7-(trifluoromethyl)benzofuran-2-yl)methyl)-3-(6-aminopyridin-3-yl)acrylamide |
| 634 | 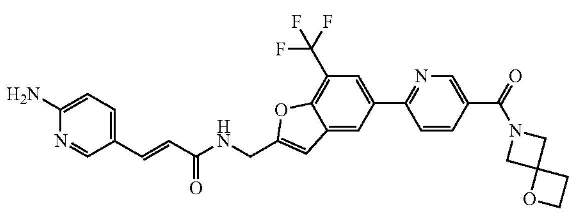 [SMILES: Nc1ccc(/C=C/C(=O)NCc2cc3cc(-c4ccc(C(=O)N5CC6(CCO6)C5)cn4)cc(C(F)(F)F)c3o2)cn1] | B | B | D | (E)-N-((5-(5-(1-oxa-6-azaspiro[3.3]heptane-6-carbonyl)pyridin-2-yl)-7-(trifluoromethyl)benzofuran-2-yl)methyl)-3-(6-aminopyridin-3-yl)acrylamide |
| 635 | 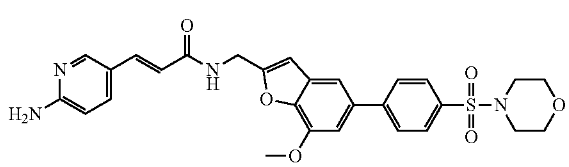 [SMILES: COc1cc(-c2ccc(S(=O)(=O)N3CCOCC3)cc2)cc2cc(CNC(=O)/C=C/c3ccc(N)nc3)oc12] | A | A | B | (E)-3-(6-aminopyridin-3-yl)-N-((7-methoxy-5-(4-(morpholinosulfonyl)phenyl)benzofuran-2-yl)methyl)acrylamide |
| 636 | 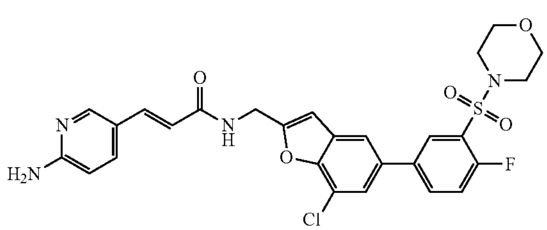 [SMILES: Nc1ccc(/C=C/C(=O)NCc2cc3cc(-c4ccc(F)c(S(=O)(=O)N5CCOCC5)c4)cc(Cl)c3o2)cn1] | B | B | D | (E)-3-(6-aminopyridin-3-yl)-N-((7-chloro-5-(4-fluoro-3-(morpholinosulfonyl)phenyl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 637 | 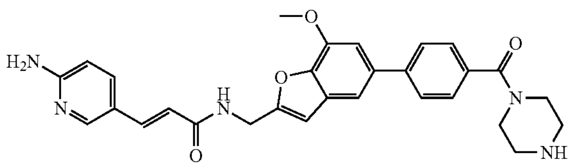 [SMILES: COc1cc(-c2ccc(C(=O)N3CCNCC3)cc2)cc2cc(CNC(=O)/C=C/c3ccc(N)nc3)oc12] | B | B | D | (E)-3-(6-aminopyridin-3-yl)-N-((7-methoxy-5-(4-(piperazine-1-carbonyl)phenyl)benzofuran-2-yl)methyl)acrylamide |
| 638 | 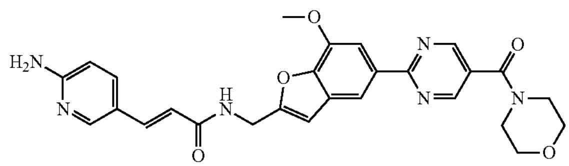 [SMILES: COc1cc(-c2ncc(C(=O)N3CCOCC3)cn2)cc2cc(CNC(=O)/C=C/c3ccc(N)nc3)oc12] | B | A | D | (E)-3-(6-aminopyridin-3-yl)-N-((7-methoxy-5-(5-(morpholine-4-carbonyl)pyrimidin-2-yl)benzofuran-2-yl)methyl)acrylamide |
| 639 | 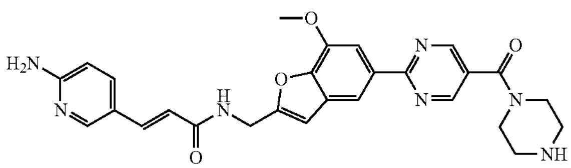 [SMILES: COc1cc(-c2ncc(C(=O)N3CCNCC3)cn2)cc2cc(CNC(=O)/C=C/c3ccc(N)nc3)oc12] | B | B | D | (E)-3-(6-aminopyridin-3-yl)-N-((7-methoxy-5-(5-(piperazine-1-carbonyl)pyrimidin-2-yl)benzofuran-2-yl)methyl)acrylamide |
| 640 | 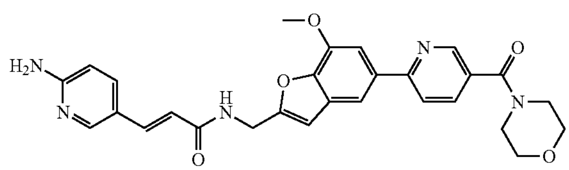 [SMILES: COc1cc(-c2ccc(C(=O)N3CCOCC3)cn2)cc2cc(CNC(=O)/C=C/c3ccc(N)nc3)oc12] | A | A | D | (E)-3-(6-aminopyridin-3-yl)-N-((7-methoxy-5-(5-(morpholine-4-carbonyl)pyridin-2-yl)benzofuran-2-yl)methyl)acrylamide |
| 641 | 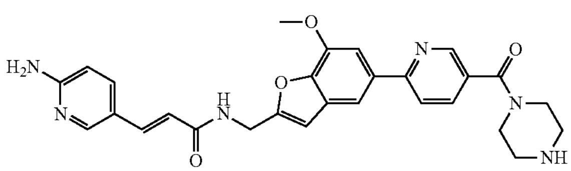 | A | A | D | (E)-3-(6-aminopyridin-3-yl)-N-((7-methoxy-5-(5-(piperazine-1-carbonyl)pyridin-2-yl)benzofuran-2-yl)methyl)acrylamide |
| 642 | 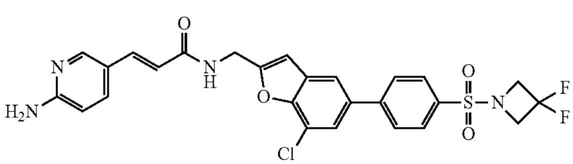 [SMILES: Nc1ccc(/C=C/C(=O)NCc2cc3cc(-c4ccc(S(=O)(=O)N5CC(F)(F)C5)cc4)cc(Cl)c3o2)cn1] | B | B | D | (E)-3-(6-aminopyridin-3-yl)-N-((7-chloro-5-(4-((3,3-difluoroazetidin-1-yl)sulfonyl)phenyl)benzofuran-2-yl)methyl)acrylamide |
| 643 | 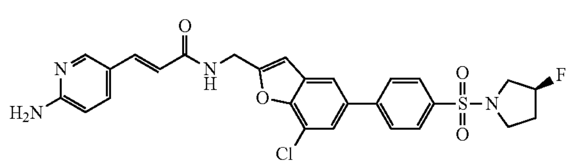 [SMILES: Nc1ccc(/C=C/C(=O)NCc2cc3cc(-c4ccc(S(=O)(=O)N5CC[C@H](F)C5)cc4)cc(Cl)c3o2)cn1] | B | B | D | (S,E)-3-(6-aminopyridin-3-yl)-N-((7-chloro-5-(4-((3-fluoropyrrolidin-1-yl)sulfonyl)phenyl)benzofuran-2-yl)methyl)acrylamide |
| 644 | 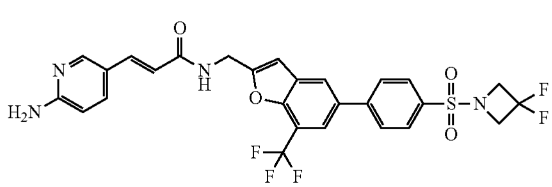 [SMILES: Nc1ccc(/C=C/C(=O)NCc2cc3cc(-c4ccc(S(=O)(=O)N5CC(F)(F)C5)cc4)cc(C(F)(F)F)c3o2)cn1] | C | B | D | (E)-3-(6-aminopyridin-3-yl)-N-((5-(4-((3,3-difluoroazetidin-1-yl)sulfonyl)phenyl)-7-(trifluoromethyl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 645 | 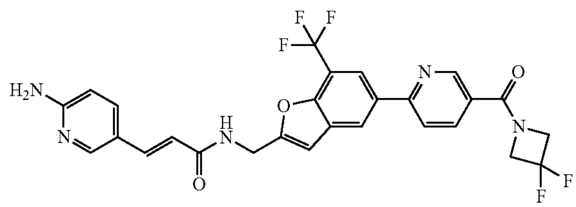 [SMILES: Nc1ccc(/C=C/C(=O)NCc2cc3cc(-c4ccc(C(=O)N5CC(F)(F)C5)cn4)cc(C(F)(F)F)c3o2)cn1] | B | A | D | (E)-3-(6-aminopyridin-3-yl)-N-((5-(5-(3,3-difluoroazetidine-1-carbonyl)pyridin-2-yl)-7-(trifluoromethyl)benzofuran-2-yl)methyl)acrylamide |
| 646 | 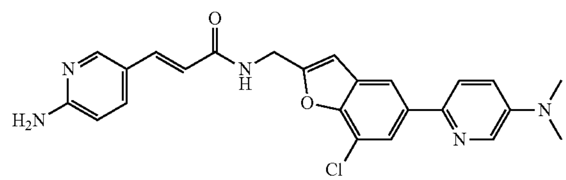 [SMILES: CN(C)c1ccc(-c2cc(Cl)c3oc(CNC(=O)/C=C/c4ccc(N)nc4)cc3c2)nc1] | D | D | D | (E)-3-(6-aminopyridin-3-yl)-N-((7-chloro-5-(5-(dimethylamino)pyridin-2-yl)benzofuran-2-yl)methyl)acrylamide |
| 648 | 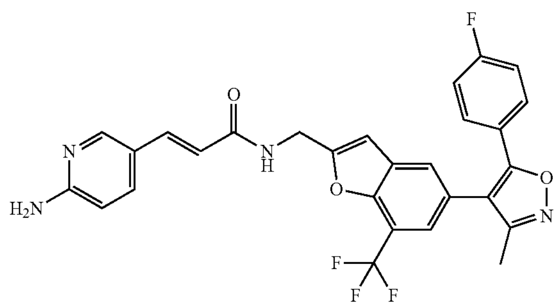 [SMILES: Cc1noc(-c2ccc(F)cc2)c1-c1cc(C(F)(F)F)c2oc(CNC(=O)/C=C/c3ccc(N)nc3)cc2c1] | B | B | D | (E)-3-(6-aminopyridin-3-yl)-N-((5-(5-(4-fluorophenyl)-3-methylisoxazol-4-yl)-7-(trifluoromethyl)benzofuran-2-yl)methyl)acrylamide |
| 649 | 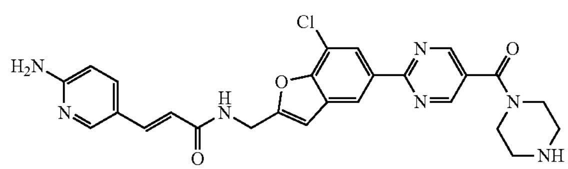 | B | B | D | (E)-3-(6-aminopyridin-3-yl)-N-((7-chloro-5-(5-(piperazine-1-carbonyl)pyrimidin-2-yl)benzofuran-2-yl)methyl)acrylamide |
| 650 | 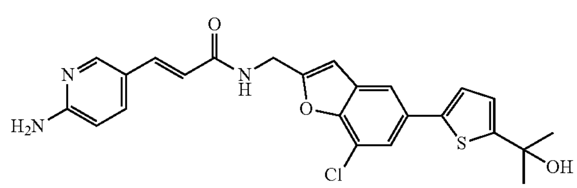 [SMILES: CC(C)(O)c1ccc(-c2cc(Cl)c3oc(CNC(=O)/C=C/c4ccc(N)nc4)cc3c2)s1] | B | B | D | (E)-3-(6-aminopyridin-3-yl)-N-((7-chloro-5-(5-(2-hydroxypropan-2-yl)thiophen-2-yl)benzofuran-2-yl)methyl)acrylamide |
| 651 | 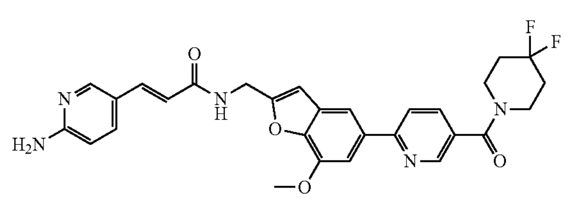 [SMILES: COc1cc(-c2ccc(C(=O)N3CCC(F)(F)CC3)cn2)cc2cc(CNC(=O)/C=C/c3ccc(N)nc3)oc12] | A | A | D | (E)-3-(6-aminopyridin-3-yl)-N-((5-(5-(4,4-difluoropiperidine-1-carbonyl)pyridin-2-yl)-7-methoxybenzofuran-2-yl)methyl)acrylamide |
| 652 | 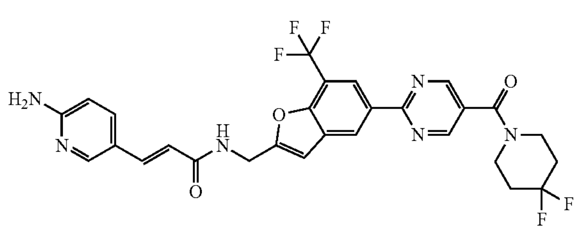 [SMILES: Nc1ccc(/C=C/C(=O)NCc2cc3cc(-c4ncc(C(=O)N5CCC(F)(F)CC5)cn4)cc(C(F)(F)F)c3o2)cn1] | B | B | D | (E)-3-(6-aminopyridin-3-yl)-N-((5-(5-(4,4-difluoropiperidine-1-carbonyl)pyrimidin-2-yl)-7-(trifluoromethyl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 653 | (structure) | B | B | D | (E)-3-(6-aminopyridin-3-yl)-N-((5-(5-(3,3-difluoropyrrolidine-1-carbonyl)pyrimidin-2-yl)-7-(trifluoromethyl)benzofuran-2-yl)methyl)acrylamide |
| 654 | (structure) Enantiomer 1 $t_R$ = 19.46 minutes (chiral HPLC) | A | A | D | (E)-3-(6-aminopyridin-3-yl)-N-((5-(5-(3-fluoro-3-methylpyrrolidine-1-carbonyl)pyridin-2-yl)-7-(trifluoromethyl)benzofuran-2-yl)methyl)acrylamide |
| 655 | (structure) Enantiomer 2 $t_R$ = 30.74 minutes (chiral HPLC) | B | B | D | (E)-3-(6-aminopyridin-3-yl)-N-((5-(5-(3-fluoro-3-methylpyrrolidine-1-carbonyl)pyridin-2-yl)-7-(trifluoromethyl)benzofuran-2-yl)methyl)acrylamide |
| 656 | (structure) Enantiomer 1 $t_R$ = 8.16 minutes (chiral HPLC) | C | B | D | (Z)-3-(6-aminopyridin-3-yl)-N-((5-(5-(3-fluoro-3-methylpyrrolidine-1-carbonyl)pyridin-2-yl)-7-(trifluoromethyl)benzofuran-2-yl)methyl)acrylamide |

TABLE 1-continued

| Cpd No. | Compound Structure | MS-751 | Z138 | 3T3 | Compound Name |
|---|---|---|---|---|---|
| 657 | Enantiomer 2 $t_R$ = 7.51 minutes (chiral HPLC) | B | B | D | (Z)-3-(6-aminopyridin-3-yl)-N-((5-(5-(3-fluoro-3-methylpyrrolidine-1-carbonyl)pyridin-2-yl)-7-(trifluoromethyl)benzofuran-2-yl)methyl)acrylamide |
| 658 | 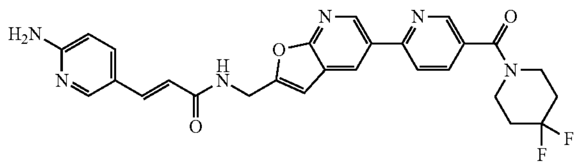 [SMILES: Nc1ccc(/C=C/C(=O)NCc2cc3cc(-c4ccc(C(=O)N5CCC(F)(F)CC5)cn4)cnc3o2)cn1] | B | B | D | (E)-3-(6-aminopyridin-3-yl)-N-((5-(5-(4,4-difluoropiperidine-1-carbonyl)pyridin-2-yl)furo[2,3-b]pyridin-2-yl)methyl)acrylamide |
| 659 | 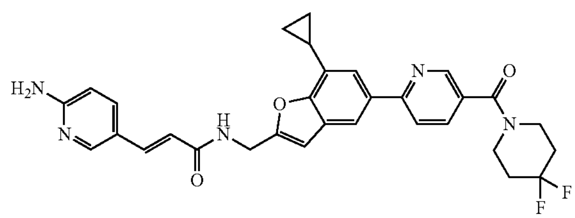 [SMILES: Nc1ccc(/C=C/C(=O)NCc2cc3cc(-c4ccc(C(=O)N5CCC(F)(F)CC5)cn4)cc(C4CC4)c3o2)cn1] | B | B | D | (E)-3-(6-aminopyridin-3-yl)-N-((7-cyclopropyl-5-(5-(4,4-difluoropiperidine-1-carbonyl)pyridin-2-yl)benzofuran-2-yl)methyl)acrylamide |
| 660 | 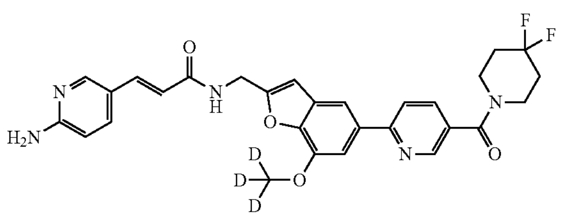 [SMILES: [2H]C([2H])([2H])Oc1cc(-c2ccc(C(=O)N3CCC(F)(F)CC3)cn2)cc2cc(CNC(=O)/C=C/c3ccc(N)nc3)oc12] | A | A | D | (E)-3-(6-aminopyridin-3-yl)-N-((5-(5-(4,4-difluoropiperidine-1-carbonyl)pyridin-2-yl)-7-(methoxy-d3)benzofuran-2-yl)methyl)acrylamide |
| 661 | 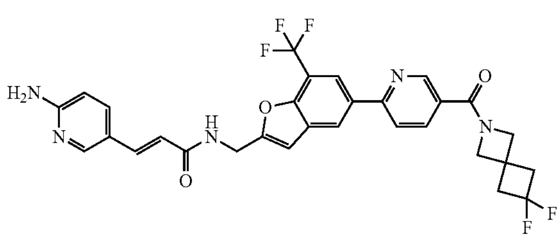 [SMILES: Nc1ccc(/C=C/C(=O)NCc2cc3cc(-c4ccc(C(=O)N5CC6(C5)CC(F)(F)C6)cn4)cc(C(F)(F)F)c3o2)cn1] | B | B | D | (E)-3-(6-aminopyridin-3-yl)-N-((5-(5-(6,6-difluoro-2-azaspiro[3.3]heptane-2-carbonyl)pyridin-2-yl)-7-(trifluoromethyl)benzofuran-2-yl)methyl)acrylamide |
| 662 | 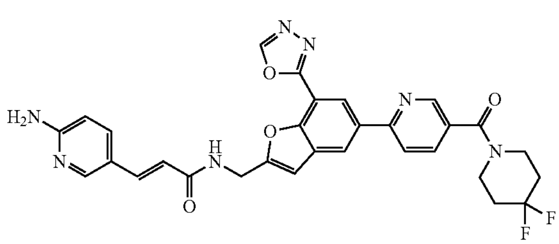 [SMILES: Nc1ccc(/C=C/C(=O)NCc2cc3cc(-c4ccc(C(=O)N5CCC(F)(F)CC5)cn4)cc(-c4nnco4)c3o2)cn1] | B | B | D | (E)-3-(6-aminopyridin-3-yl)-N-((5-(5-(4,4-difluoropiperidine-1-carbonyl)pyridin-2-yl)-7-(1,3,4-oxadiazol-2-yl)benzofuran-2-yl)methyl)acrylamide |

TABLE 1-continued

| Cpd No. | Compound Structure | MS-751 | Z138 | 3T3 | Compound Name |
|---|---|---|---|---|---|
| 663 | 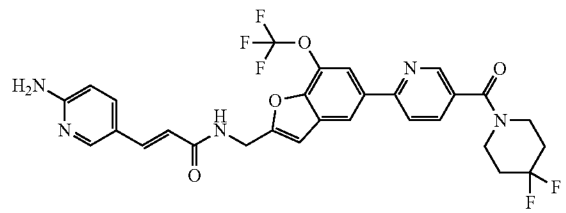 [SMILES: Nc1ccc(/C=C/C(=O)NCc2cc3cc(-c4ccc(C(=O)N5CCC(F)(F)CC5)cn4)cc(OC(F)(F)F)c3o2)cn1] | A | A | B | (E)-3-(6-aminopyridin-3-yl)-N-((5-(5-(4,4-difluoropiperidine-1-carbonyl)pyridin-2-yl)-7-(trifluoromethoxy)benzofuran-2-yl)methyl)acrylamide |
| 664 | 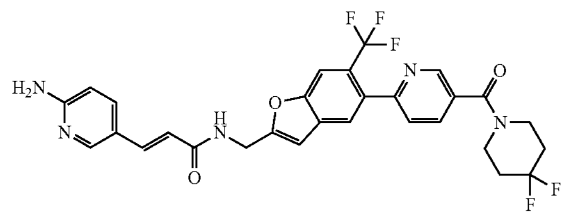 [SMILES: Nc1ccc(/C=C/C(=O)NCc2cc3cc(-c4ccc(C(=O)N5CCC(F)(F)CC5)cn4)c(C(F)(F)F)cc3o2)cn1] | D | D | D | (E)-3-(6-aminopyridin-3-yl)-N-((5-(5-(4,4-difluoropiperidine-1-carbonyl)pyridin-2-yl)-6-(trifluoromethyl)benzofuran-2-yl)methyl)acrylamide |
| 665 | 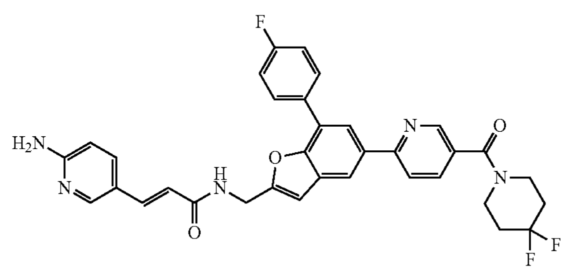 [SMILES: Nc1ccc(/C=C/C(=O)NCc2cc3cc(-c4ccc(C(=O)N5CCC(F)(F)CC5)cn4)cc(-c4ccc(F)cc4)c3o2)cn1] | A | A | B | (E)-3-(6-aminopyridin-3-yl)-N-((5-(5-(4,4-difluoropiperidine-1-carbonyl)pyridin-2-yl)-7-(4-fluorophenyl)benzofuran-2-yl)methyl)acrylamide |
| 666 | 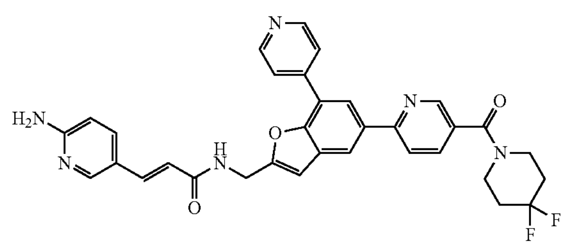 [SMILES: Nc1ccc(/C=C/C(=O)NCc2cc3cc(-c4ccc(C(=O)N5CCC(F)(F)CC5)cn4)cc(-c4ccncc4)c3o2)cn1] | A | A | B | (E)-3-(6-aminopyridin-3-yl)-N-((5-(5-(4,4-difluoropiperidine-1-carbonyl)pyridin-2-yl)-7-(pyridin-4-yl)benzofuran-2-yl)methyl)acrylamide |
| 667 | 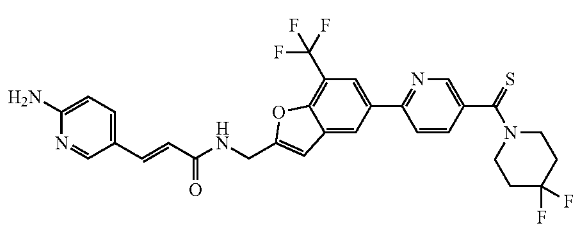 [SMILES: Nc1ccc(/C=C/C(=O)NCc2cc3cc(-c4ccc(C(=S)N5CCC(F)(F)CC5)cn4)cc(C(F)(F)F)c3o2)cn1] | A | A | D | (E)-3-(6-aminopyridin-3-yl)-N-((5-(5-(4,4-difluoropiperidine-1-carbonothioyl)pyridin-2-yl)-7-(trifluoromethyl)benzofuran-2-yl)methyl)acrylamide |
| 668 | 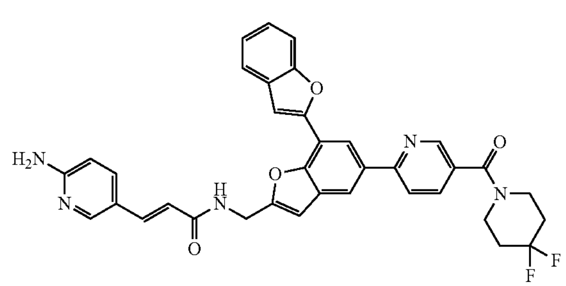 [SMILES: Nc1ccc(/C=C/C(=O)NCc2cc3cc(-c4ccc(C(=O)N5CCC(F)(F)CC5)cn4)cc(-c4cc5ccccc5o4)c3o2)cn1] | A | A | B | (E)-3-(6-aminopyridin-3-yl)-N-((5'-(5-(4,4-difluoropiperidine-1-carbonyl)pyridin-2-yl)-[2,7'-bibenzofuran]-2'-yl)methyl)acrylamide |

TABLE 1-continued

MTT Assay

| Cpd No. | Compound Structure | MS-751 | Z138 | 3T3 | Compound Name |
|---|---|---|---|---|---|
| 669 | 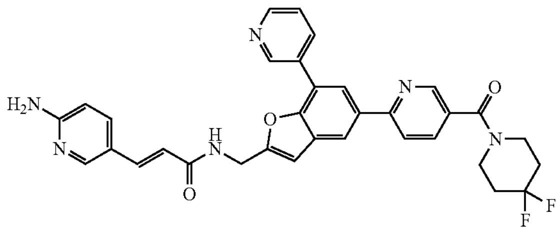 [SMILES: Nc1ccc(/C=C/C(=O)NCc2cc3cc(-c4ccc(C(=O)N5CCC(F)(F)CC5)cn4)cc(-c4cccnc4)c3o2)cn1] | A | A | B | (E)-3-(6-aminopyridin-3-yl)-N-((5-(5-(4,4-difluoropiperidine-1-carbonyl)pyridin-2-yl)-7-(pyridin-3-yl)benzofuran-2-yl)methyl)acrylamide |
| 670 | 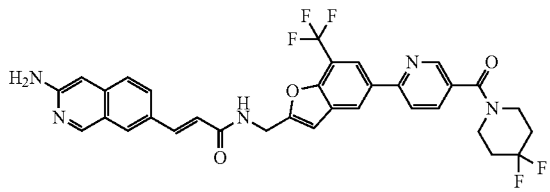 [SMILES: Nc1cc2ccc(/C=C/C(=O)NCc3cc4cc(-c5ccc(C(=O)N6CCC(F)(F)CC6)cn5)cc(C(F)(F)F)c4o3)cc2cn1] | D | D | D | (E)-3-(3-aminoisoquinolin-7-yl)-N-((5-(5-(4,4-difluoropiperidine-1-carbonyl)pyridin-2-yl)-7-(trifluoromethyl)benzofuran-2-yl)methyl)acrylamide |
| 671 | 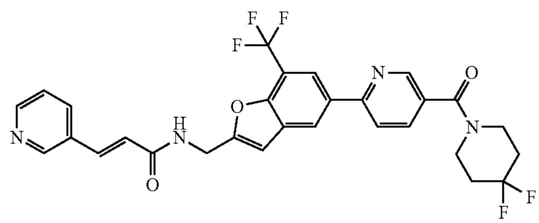 [SMILES: O=C(/C=C/c1cccnc1)NCc1cc2cc(-c3ccc(C(=O)N4CCC(F)(F)CC4)cn3)cc(C(F)(F)F)c2o1] | B | B | B | (E)-N-((5-(5-(4,4-difluoropiperidine-1-carbonyl)pyridin-2-yl)-7-(trifluoromethyl)benzofuran-2-yl)methyl)-3-(pyridin-3-yl)acrylamide |
| 672 | 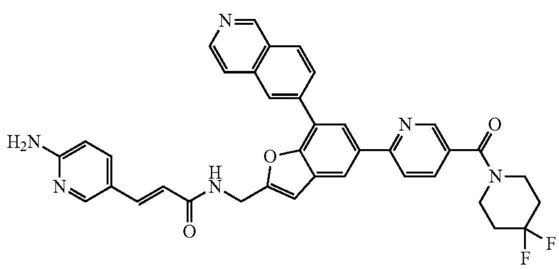 [SMILES: Nc1ccc(/C=C/C(=O)NCc2cc3cc(-c4ccc(C(=O)N5CCC(F)(F)CC5)cn4)cc(-c4ccc5cnccc5c4)c3o2)cn1] | B | B | D | (E)-3-(6-aminopyridin-3-yl)-N-((5-(5-(4,4-difluoropiperidine-1-carbonyl)pyridin-2-yl)-7-(isoquinolin-6-yl)benzofuran-2-yl)methyl)acrylamide |
| 673 | 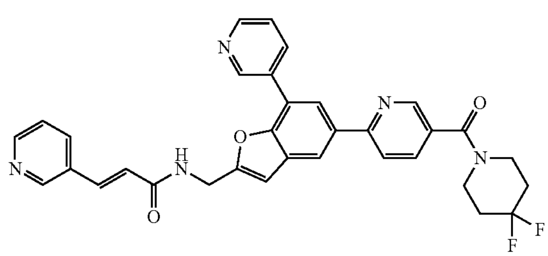 | A | A | A | (E)-N-((5-(5-(4,4-difluoropiperidine-1-carbonyl)pyridin-2-yl)-7-(pyridin-3-yl)benzofuran-2-yl)methyl)-3-(pyridin-3-yl)acrylamide |
| 674 | 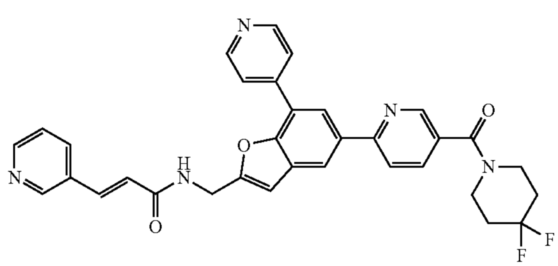 [SMILES: O=C(/C=C/c1cccnc1)NCc1cc2cc(-c3ccc(C(=O)N4CCC(F)(F)CC4)cn3)cc(-c3ccncc3)c2o1] | A | A | A | (E)-N-((5-(5-(4,4-difluoropiperidine-1-carbonyl)pyridin-2-yl)-7-(pyridin-4-yl)benzofuran-2-yl)methyl)-3-(pyridin-3-yl)acrylamide |

TABLE 1-continued

MTT Assay

| Cpd No. | Compound Structure | MS-751 | Z138 | 3T3 | Compound Name |
|---|---|---|---|---|---|
| 675 | 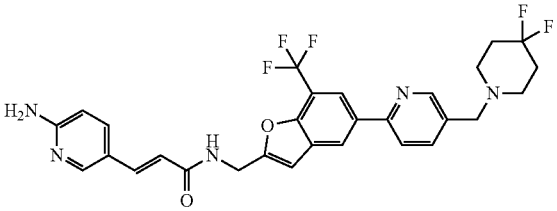 [SMILES: Nc1ccc(/C=C/C(=O)NCc2cc3cc(-c4ccc(CN5CCC(F)(F)CC5)cn4)cc(C(F)(F)F)c3o2)cn1] | D | D | D | (E)-3-(6-aminopyridin-3-yl)-N-((5-(5-((4,4-difluoropiperidin-1-yl)methyl)pyridin-2-yl)-7-(trifluoromethyl)benzofuran-2-yl)methyl)acrylamide |
| 676 | 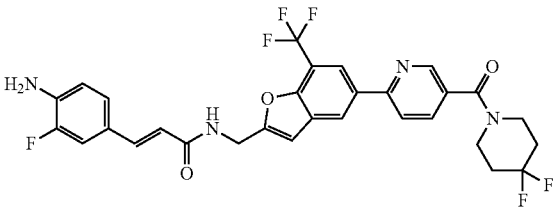 [SMILES: Nc1ccc(/C=C/C(=O)NCc2cc3cc(-c4ccc(C(=O)N5CCC(F)(F)CC5)cn4)cc(C(F)(F)F)c3o2)cc1F] | D | D | D | (E)-3-(4-amino-3-fluorophenyl)-N-((5-(5-(4,4-difluoropiperidine-1-carbonyl)pyridin-2-yl)-7-(trifluoromethyl)benzofuran-2-yl)methyl)acrylamide |
| 677 | 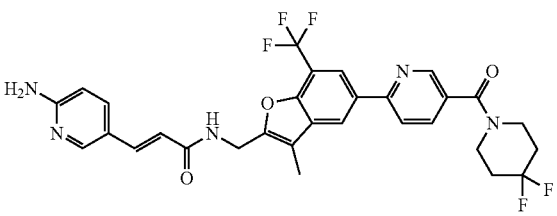 [SMILES: Cc1c(CNC(=O)/C=C/c2ccc(N)nc2)oc2c(C(F)(F)F)cc(-c3ccc(C(=O)N4CCC(F)(F)CC4)cn3)cc12] | D | D | D | (E)-3-(6-aminopyridin-3-yl)-N-((5-(5-(4,4-difluoropiperidine-1-carbonyl)pyridin-2-yl)-3-methyl-7-(trifluoromethyl)benzofuran-2-yl)methyl)acrylamide |
| 678 | 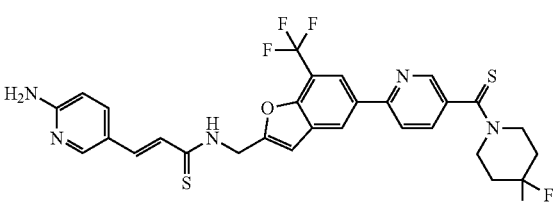 | B | B | D | (E)-3-(6-aminopyridin-3-yl)-N-((5-(5-(4,4-difluoropiperidine-1-carbonothioyl)pyridin-2-yl)-7-(trifluoromethyl)benzofuran-2-yl)methyl)prop-2-enethioamide |
| 679 | 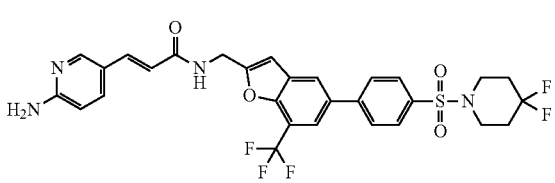 [SMILES: Nc1ccc(/C=C/C(=O)NCc2cc3cc(-c4ccc(S(=O)(=O)N5CCC(F)(F)CC5)cc4)cc(C(F)(F)F)c3o2)cn1] | B | B | B | (E)-3-(6-aminopyridin-3-yl)-N-((5-(4-((4,4-difluoropiperidin-1-yl)sulfonyl)phenyl)-7-(trifluoromethyl)benzofuran-2-yl)methyl)acrylamide |
| 680 | 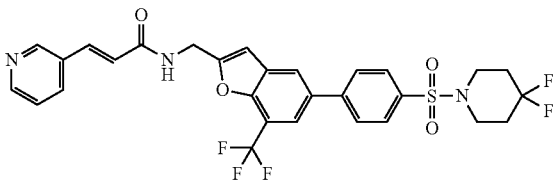 [SMILES: O=C(/C=C/c1cccnc1)NCc1cc2cc(-c3ccc(S(=O)(=O)N4CCC(F)(F)CC4)cc3)cc(C(F)(F)F)c2o1] | B | B | D | (E)-N-((5-(4-((4,4-difluoropiperidin-1-yl)sulfonyl)phenyl)-7-(trifluoromethyl)benzofuran-2-yl)methyl)-3-(pyridin-3-yl)acrylamide |
| 681 | 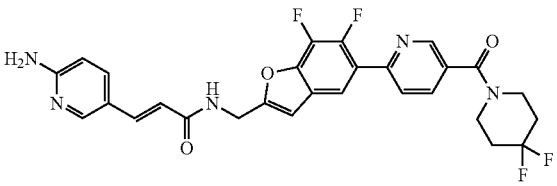 [SMILES: Nc1ccc(/C=C/C(=O)NCc2cc3cc(-c4ccc(C(=O)N5CCC(F)(F)CC5)cn4)c(F)c(F)c3o2)cn1] | D | C | D | (E)-3-(6-aminopyridin-3-yl)-N-((5-(5-(4,4-difluoropiperidine-1-carbonyl)pyridin-2-yl)-6,7-difluorobenzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 682 | | | B | B | B | (E)-N-((5-(4-(4,4-difluoropiperidine-1-carbonyl)phenyl)-7-(trifluoromethyl)benzofuran-2-yl)methyl)-3-(pyridin-3-yl)acrylamide |
| 683 | | | B | B | D | (E)-3-(6-aminopyridin-3-yl)-N-((5-(4-(4,4-difluoropiperidine-1-carbonyl)-2-fluorophenyl)-7-(trifluoromethyl)benzofuran-2-yl)methyl)acrylamide |
| 684 | | | B | B | D | (E)-N-((5-(4-(4,4-difluoropiperidine-1-carbonyl)-2-fluorophenyl)-7-(trifluoromethyl)benzofuran-2-yl)methyl)-3-(pyridin-3-yl)acrylamide |
| 685 | | | B | B | D | (E)-3-(6-aminopyridin-3-yl)-N-((5-(5-(4,4-difluoropiperidine-1-carbonyl)thiophen-2-yl)-7-(trifluoromethyl)benzofuran-2-yl)methyl)acrylamide |
| 686 | | | B | B | D | (E)-3-(6-aminopyridin-3-yl)-N-((5-(4-(4,4-difluoropiperidine-1-carbonyl)phenyl)-7-(trifluoromethoxy)benzofuran-2-yl)methyl)acrylamide |
| 687 | | | A | A | B | (E)-N-((5-(4-(4,4-difluoropiperidine-1-carbonyl)phenyl)-7-(trifluoromethoxy)benzofuran-2-yl)methyl)-3-(pyridin-3-yl)acrylamide |

TABLE 1-continued

MTT Assay

| Cpd No. | Compound Structure | MS-751 | Z138 | 3T3 | Compound Name |
| --- | --- | --- | --- | --- | --- |
| 688 | 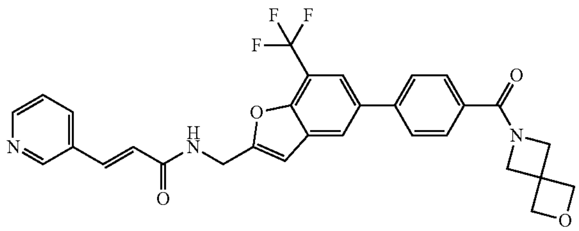 [SMILES: O=C(/C=C/c1cccnc1)NCc1cc2cc(-c3ccc(C(=O)N4CC5(COC5)C4)cc3)cc(C(F)(F)F)c2o1] | B | B | B | (E)-N-((5-(4-(2-oxa-6-azaspiro[3.3]heptane-6-carbonyl)phenyl)-7-(trifluoromethyl)benzofuran-2-yl)methyl)-3-(pyridin-3-yl)acrylamide |
| 689 | 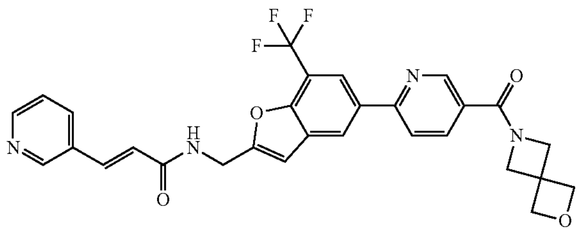 [SMILES: O=C(/C=C/c1cccnc1)NCc1cc2cc(-c3ccc(C(=O)N4CC5(COC5)C4)cn3)cc(C(F)(F)F)c2o1] | A | A | B | (E)-N-((5-(5-(2-oxa-6-azaspiro[3.3]heptane-6-carbonyl)pyridin-2-yl)-7-(trifluoromethyl)benzofuran-2-yl)methyl)-3-(pyridin-3-yl)acrylamide |
| 690 | 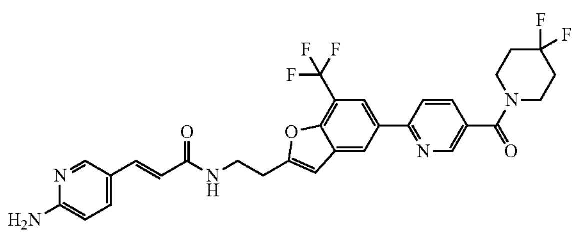 [SMILES: Nc1ccc(/C=C/C(=O)NCCc2cc3cc(-c4ccc(C(=O)N5CCC(F)(F)CC5)cn4)cc(C(F)(F)F)c3o2)cn1] | A | A | B | (E)-3-(6-aminopyridin-3-yl)-N-(2-(5-(5-(4,4-difluoropiperidine-1-carbonyl)pyridin-2-yl)-7-(trifluoromethyl)benzofuran-2-yl)ethyl)acrylamide |
| 691 | 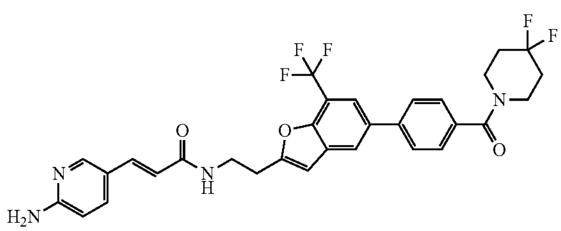 | B | A | B | (E)-3-(6-aminopyridin-3-yl)-N-(2-(5-(4-(4,4-difluoropiperidine-1-carbonyl)phenyl)-7-(trifluoromethyl)benzofuran-2-yl)ethyl)acrylamide |
| 692 | 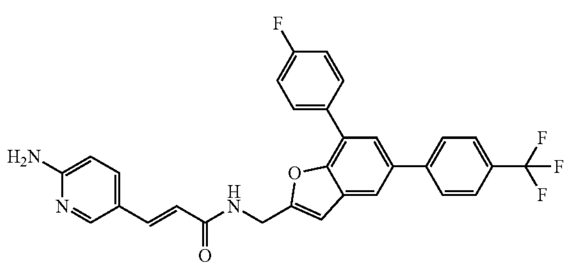 [SMILES: Nc1ccc(/C=C/C(=O)NCc2cc3cc(-c4ccc(C(F)(F)F)cc4)cc(-c4ccc(F)cc4)c3o2)cn1] | B | B | D | (E)-3-(6-aminopyridin-3-yl)-N-((7-(4-fluorophenyl)-5-(4-(trifluoromethyl)phenyl)benzofuran-2-yl)methyl)acrylamide |
| 693 | 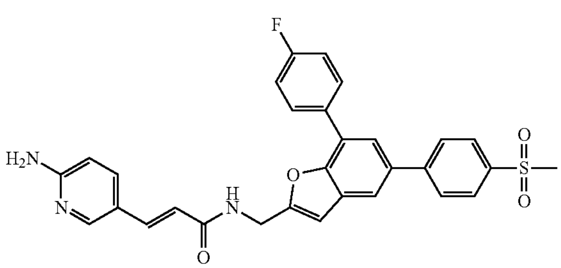 [SMILES: CS(=O)(=O)c1ccc(-c2cc(-c3ccc(F)cc3)c3oc(CNC(=O)/C=C/c4ccc(N)nc4)cc3c2)cc1] | A | A | B | (E)-3-(6-aminopyridin-3-yl)-N-((7-(4-fluorophenyl)-5-(4-(methylsulfonyl)phenyl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 694 | 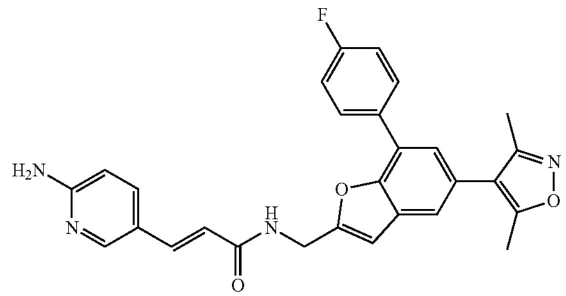 [SMILES: Cc1noc(C)c1-c1cc(-c2ccc(F)cc2)c2oc(CNC(=O)/C=C/c3ccc(N)nc3)cc2c1] | B | A | D | (E)-3-(6-aminopyridin-3-yl)-N-((5-(3,5-dimethylisoxazol-4-yl)-7-(4-fluorophenyl)benzofuran-2-yl)methyl)acrylamide |
| 695 | 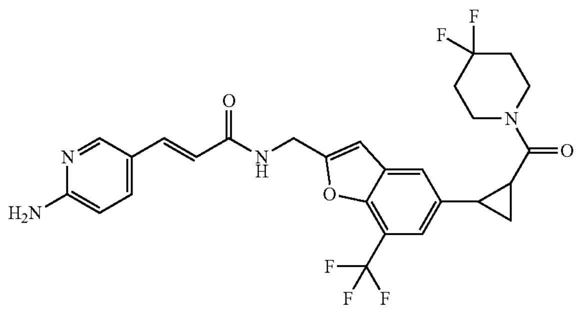 [SMILES: Nc1ccc(/C=C/C(=O)NCc2cc3cc(C4CC4C(=O)N4CCC(F)(F)CC4)cc(C(F)(F)F)c3o2)cn1] | B | B | D | (E)-3-(6-aminopyridin-3-yl)-N-((5-(2-(4,4-difluoropiperidine-1-carbonyl)cyclopropyl)-7-(trifluoromethyl)benzofuran-2-yl)methyl)acrylamide |
| 696 | 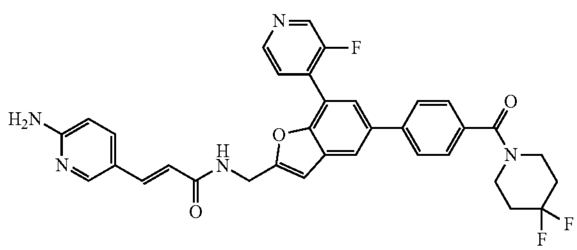 [SMILES: Nc1ccc(/C=C/C(=O)NCc2cc3cc(-c4ccc(C(=O)N5CCC(F)(F)CC5)cc4)cc(-c4ccncc4F)c3o2)cn1] | A | A | B | (E)-3-(6-aminopyridin-3-yl)-N-((5-(4-(4,4-difluoropiperidine-1-carbonyl)phenyl)-7-(3-fluoropyridin-4-yl)benzofuran-2-yl)methyl)acrylamide |
| 697 | 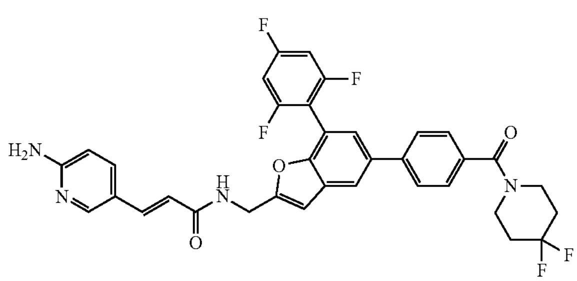 [SMILES: Nc1ccc(/C=C/C(=O)NCc2cc3cc(-c4ccc(C(=O)N5CCC(F)(F)CC5)cc4)cc(-c4c(F)cc(F)cc4F)c3o2)cn1] | A | A | B | (E)-3-(6-aminopyridin-3-yl)-N-((5-(4-(4,4-difluoropiperidine-1-carbonyl)phenyl)-7-(2,4,6-trifluorophenyl)benzofuran-2-yl)methyl)acrylamide |
| 698 | 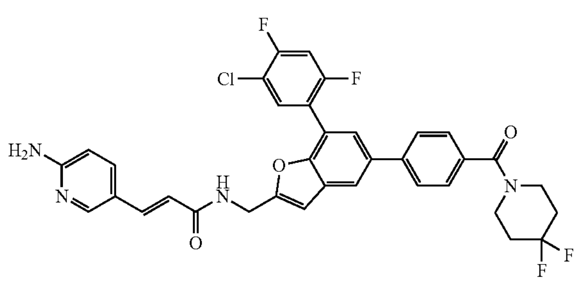 [SMILES: Nc1ccc(/C=C/C(=O)NCc2cc3cc(-c4ccc(C(=O)N5CCC(F)(F)CC5)cc4)cc(-c4cc(Cl)c(F)cc4F)c3o2)cn1] | A | A | B | (E)-3-(6-aminopyridin-3-yl)-N-((7-(5-chloro-2,4-difluorophenyl)-5-(4-(4,4-difluoropiperidine-1-carbonyl)phenyl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 699 | 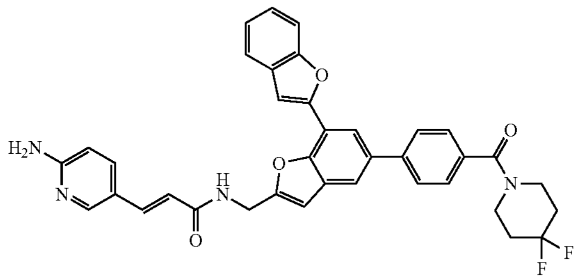 [SMILES: Nc1ccc(/C=C/C(=O)NCc2cc3cc(-c4ccc(C(=O)N5CCC(F)(F)CC5)cc4)cc(-c4cc5ccccc5o4)c3o2)cn1] | A | A | C | (E)-3-(6-aminopyridin-3-yl)-N-((5'-(4-(4,4-difluoropiperidine-1-carbonyl)phenyl)-[2,7'-bibenzofuran]-2'-yl)methyl)acrylamide |
| 700 | 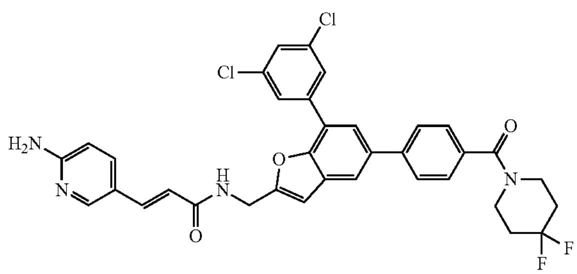 [SMILES: Nc1ccc(/C=C/C(=O)NCc2cc3cc(-c4ccc(C(=O)N5CCC(F)(F)CC5)cc4)cc(-c4cc(Cl)cc(Cl)c4)c3o2)cn1] | A | A | B | (E)-3-(6-aminopyridin-3-yl)-N-((7-(3,5-dichlorophenyl)-5-(4-(4,4-difluoropiperidine-1-carbonyl)phenyl)benzofuran-2-yl)methyl)acrylamide |
| 701 | 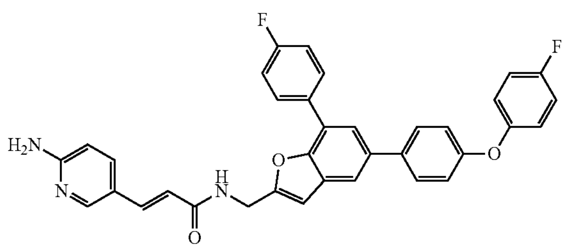 [SMILES: Nc1ccc(/C=C/C(=O)NCc2cc3cc(-c4ccc(Oc5ccc(F)cc5)cc4)cc(-c4ccc(F)cc4)c3o2)cn1] | B | B | D | (E)-3-(6-aminopyridin-3-yl)-N-((5-(4-(4-fluorophenoxy)phenyl)-7-(4-fluorophenyl)benzofuran-2-yl)methyl)acrylamide |
| 702 | 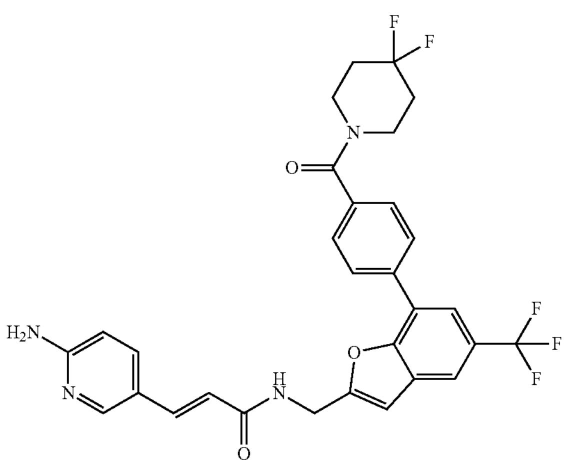 [SMILES: Nc1ccc(/C=C/C(=O)NCc2cc3cc(C(F)(F)F)cc(-c4ccc(C(=O)N5CCC(F)(F)CC5)cc4)c3o2)cn1] | C | B | D | (E)-3-(6-aminopyridin-3-yl)-N-((7-(4-(4,4-difluoropiperidine-1-carbonyl)phenyl)-5-(trifluoromethyl)benzofuran-2-yl)methyl)acrylamide |
| 703 | 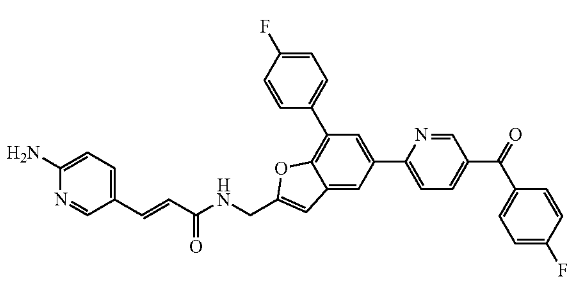 [SMILES: Nc1ccc(/C=C/C(=O)NCc2cc3cc(-c4ccc(C(=O)c5ccc(F)cc5)cn4)cc(-c4ccc(F)cc4)c3o2)cn1] | B | A | C | (E)-3-(6-aminopyridin-3-yl)-N-((5-(5-(4-fluorobenzoyl)pyridin-2-yl)-7-(4-fluorophenyl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 704 | 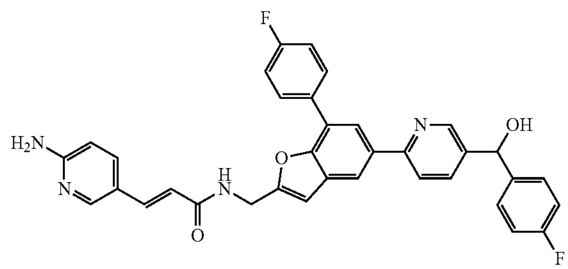 [SMILES: Nc1ccc(/C=C/C(=O)NCc2cc3cc(-c4ccc(C(O)c5ccc(F)cc5)cn4)cc(-c4ccc(F)cc4)c3o2)cn1] | B | B | D | (E)-3-(6-aminopyridin-3-yl)-N-((7-(4-fluorophenyl)-5-(5-((4-fluorophenyl)(hydroxy)methyl)pyridin-2-yl)benzofuran-2-yl)methyl)acrylamide |
| 705 | 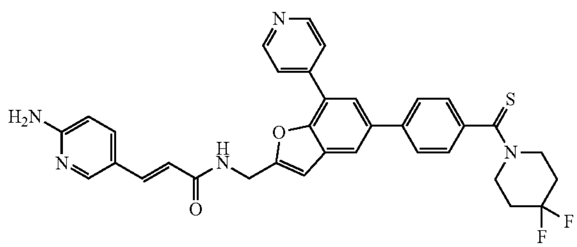 [SMILES: Nc1ccc(/C=C/C(=O)NCc2cc3cc(-c4ccc(C(=S)N5CCC(F)(F)CC5)cc4)cc(-c4ccncc4)c3o2)cn1] | A | A | B | (E)-3-(6-aminopyridin-3-yl)-N-((5-(4-(4,4-difluoropiperidine-1-carbonothioyl)phenyl)-7-(pyridin-4-yl)benzofuran-2-yl)methyl)acrylamide |
| 706 | 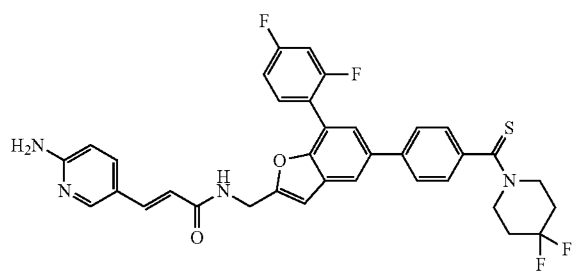 [SMILES: Nc1ccc(/C=C/C(=O)NCc2cc3cc(-c4ccc(C(=S)N5CCC(F)(F)CC5)cc4)cc(-c4ccc(F)cc4F)c3o2)cn1] | A | A | B | (E)-3-(6-aminopyridin-3-yl)-N-((7-(2,4-difluorophenyl)-5-(4-(4,4-difluoropiperidine-1-carbonothioyl)phenyl)benzofuran-2-yl)methyl)acrylamide |
| 707 | 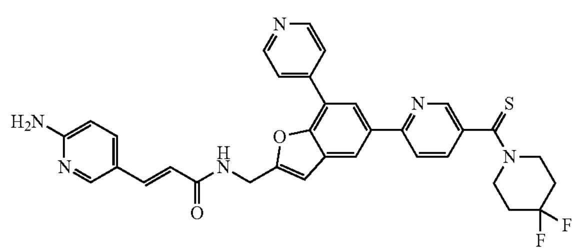 | A | A | B | (E)-3-(6-aminopyridin-3-yl)-N-((5-(5-(4,4-difluoropiperidine-1-carbonothioyl)pyridin-2-yl)-7-(pyridin-4-yl)benzofuran-2-yl)methyl)acrylamide |
| 708 | 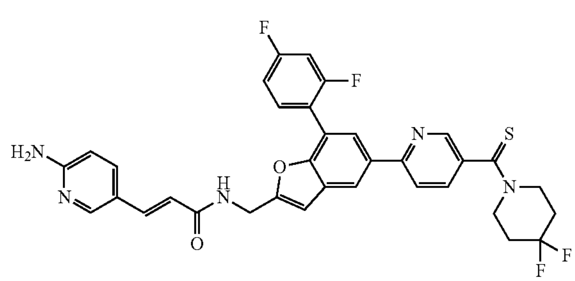 [SMILES: Nc1ccc(/C=C/C(=O)NCc2cc3cc(-c4ccc(C(=S)N5CCC(F)(F)CC5)cn4)cc(-c4ccc(F)cc4F)c3o2)cn1] | A | A | B | (E)-3-(6-aminopyridin-3-yl)-N-((7-(2,4-difluorophenyl)-5-(5-(4,4-difluoropiperidine-1-carbonothioyl)pyridin-2-yl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 709 | 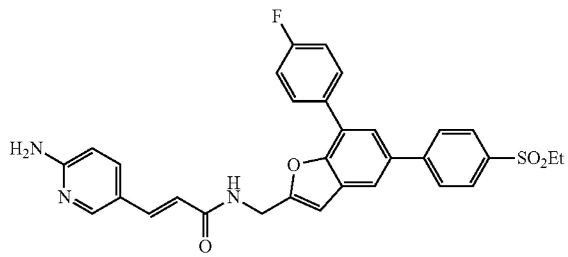 | A | A | D | (E)-3-(6-aminopyridin-3-yl)-N-((5-(4-(ethylsulfonyl)phenyl)-7-(4-fluorophenyl)benzofuran-2-yl)methyl)acrylamide |
| 710 | 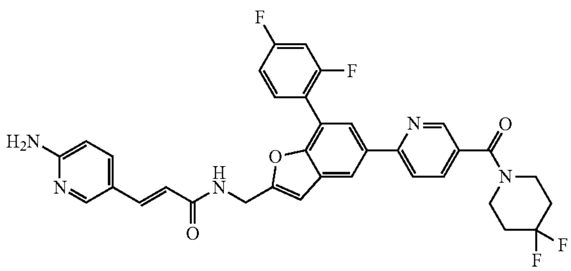 [SMILES: Nc1ccc(/C=C/C(=O)NCc2cc3cc(-c4ccc(C(=O)N5CCC(F)(F)CC5)cn4)cc(-c4ccc(F)cc4F)c3o2)cn1] | A | A | B | (E)-3-(6-aminopyridin-3-yl)-N-((7-(2,4-difluorophenyl)-5-(5-(4,4-difluoropiperidine-1-carbonyl)pyridin-2-yl)benzofuran-2-yl)methyl)acrylamide |
| 711 | 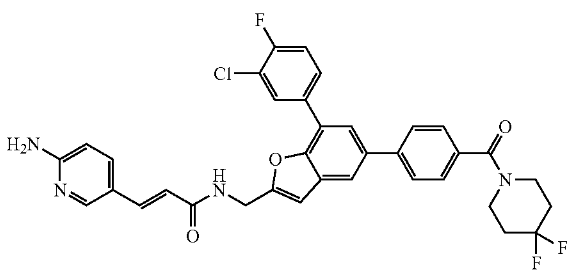 [SMILES: Nc1ccc(/C=C/C(=O)NCc2cc3cc(-c4ccc(C(=O)N5CCC(F)(F)CC5)cc4)cc(-c4ccc(F)c(Cl)c4)c3o2)cn1] | A | A | B | (E)-3-(6-aminopyridin-3-yl)-N-((7-(3-chloro-4-fluoro-phenyl)-5-(4-(4,4-difluoropiperidine-1-carbonyl)phenyl)benzofuran-2-yl)methyl)acrylamide |
| 713 | 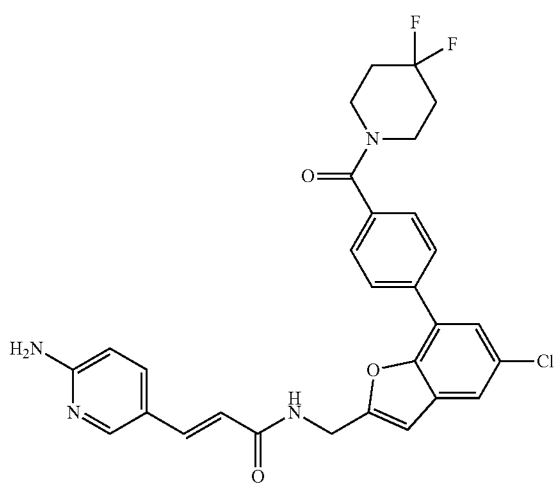 [SMILES: Nc1ccc(/C=C/C(=O)NCc2cc3cc(Cl)cc(-c4ccc(C(=O)N5CCC(F)(F)CC5)cc4)c3o2)cn1] | B | B | C | (E)-3-(6-aminopyridin-3-yl)-N-((6-chloro-4-(4-(4,4-difluoropiperidine-1-carbonyl)phenyl)benzofuran-2-yl)methyl)acrylamide |
| 714 | 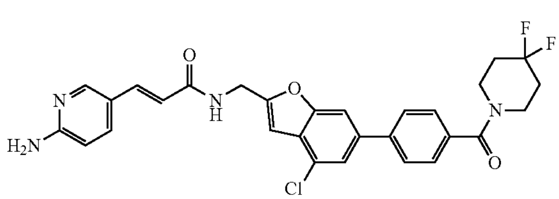 [SMILES: Nc1ccc(/C=C/C(=O)NCc2cc3c(Cl)cc(-c4ccc(C(=O)N5CCC(F)(F)CC5)cc4)cc3o2)cn1] | B | B | D | (E)-3-(6-aminopyridin-3-yl)-N-((4-chloro-6-(4-(4,4-difluoropiperidine-1-carbonyl)phenyl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 715 | Enantiomer 1, t_R = 5.09 minutes (chiral HPLC) | B | B | D | (E)-3-(6-aminopyridin-3-yl)-N-((5-(4-(3-fluoro-3-methylpyrrolidine-1-carbonyl)phenyl)-7-(trifluoromethyl)benzofuran-2-yl)methyl)acrylamide |
| 716 | Enantiomer 2, t_R = 5.99 minutes (chiral HPLC) | B | B | D | (E)-3-(6-aminopyridin-3-yl)-N-((5-(4-(3-fluoro-3-methylpyrrolidine-1-carbonyl)phenyl)-7-(trifluoromethyl)benzofuran-2-yl)methyl)acrylamide |
| 717 | 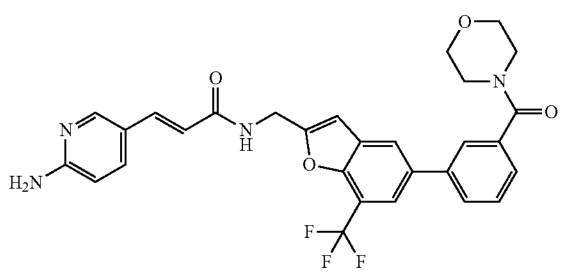 [SMILES: Nc1ccc(/C=C/C(=O)NCc2cc3cc(-c4cccc(C(=O)N5CCOCC5)c4)cc(C(F)(F)F)c3o2)cn1] | B | A | D | (E)-3-(6-aminopyridin-3-yl)-N-((5-(3-(morpholine-4-carbonyl)phenyl)-7-(trifluoromethyl)benzofuran-2-yl)methyl)acrylamide |
| 718 | 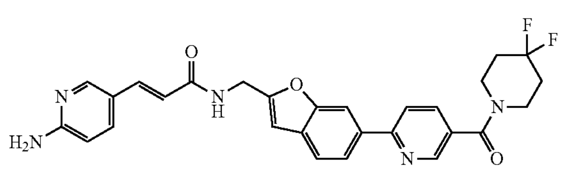 [SMILES: Nc1ccc(/C=C/C(=O)NCc2cc3ccc(-c4ccc(C(=O)N5CCC(F)(F)CC5)cn4)cc3o2)cn1] | B | B | D | (E)-3-(6-aminopyridin-3-yl)-N-((6-(5-(4,4-difluoropiperidine-1-carbonyl)pyridin-2-yl)benzofuran-2-yl)methyl)acrylamide |
| 719 | 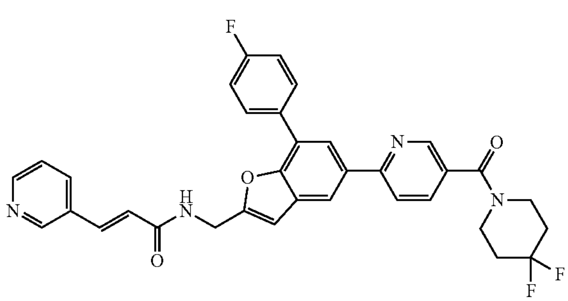 [SMILES: O=C(/C=C/c1cccnc1)NCc1cc2cc(-c3ccc(C(=O)N4CCC(F)(F)CC4)cn3)cc(-c3ccc(F)cc3)c2o1] | A | A | A | (E)-N-((5-(5-(4,4-difluoropiperidine-1-carbonyl)pyridin-2-yl)-7-(4-fluorophenyl)benzofuran-2-yl)methyl)-3-(pyridin-3-yl)acrylamide |

TABLE 1-continued

MTT Assay

| Cpd No. | Compound Structure | MS-751 | Z138 | 3T3 | Compound Name |
|---|---|---|---|---|---|
| 720 | 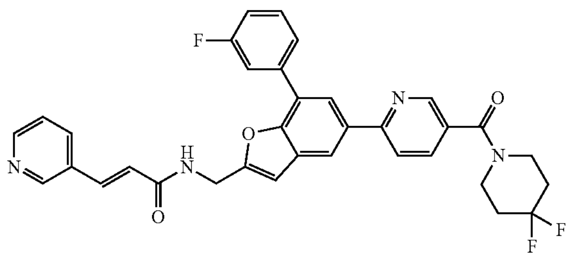 [SMILES: O=C(/C=C/c1cccnc1)NCc1cc2cc(-c3ccc(C(=O)N4CCC(F)(F)CC4)cn3)cc(-c3cccc(F)c3)c2o1] | A | A | A | (E)-N-((5-(5-(4,4-difluoropiperidine-1-carbonyl)pyridin-2-yl)-7-(3-fluorophenyl)benzofuran-2-yl)methyl)-3-(pyridin-3-yl)acrylamide |
| 721 | 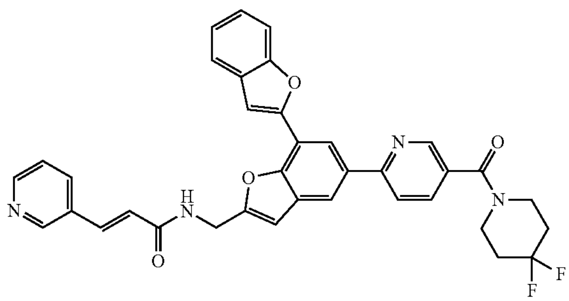 [SMILES: O=C(/C=C/c1cccnc1)NCc1cc2cc(-c3ccc(C(=O)N4CCC(F)(F)CC4)cn3)cc(-c3cc4ccccc4o3)c2o1] | A | A | A | (E)-N-((5'-(5-(4,4-difluoropiperidine-1-carbonyl)pyridin-2-yl)-[2,7'-bibenzofuran]-2'-yl)methyl)-3-(pyridin-3-yl)acrylamide |
| 722 | 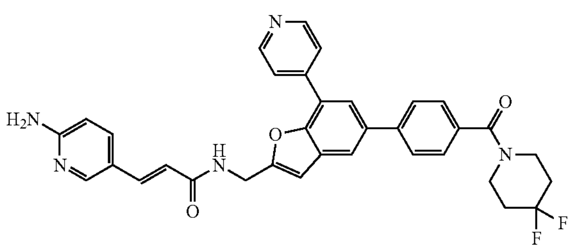 | A | A | B | (E)-3-(6-aminopyridin-3-yl)-N-((5-(4-(4,4-difluoropiperidine-1-carbonyl)phenyl)-7-(pyridin-4-yl)benzofuran-2-yl)methyl)acrylamide |
| 723 | 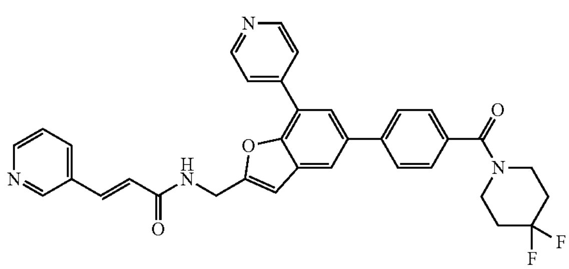 [SMILES: O=C(/C=C/c1cccnc1)NCc1cc2cc(-c3ccc(C(=O)N4CCC(F)(F)CC4)cc3)cc(-c3ccncc3)c2o1] | A | A | A | (E)-N-((5-(4-(4,4-difluoropiperidine-1-carbonyl)phenyl)-7-(pyridin-4-yl)benzofuran-2-yl)methyl)-3-(pyridin-3-yl)acrylamide |
| 724 | 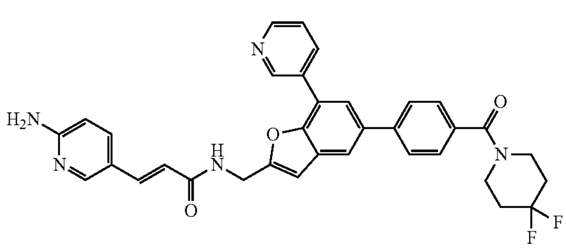 | A | A | B | (E)-3-(6-aminopyridin-3-yl)-N-((5-(4-(4,4-difluoropiperidine-1-carbonyl)phenyl)-7-(pyridin-3-yl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 725 | 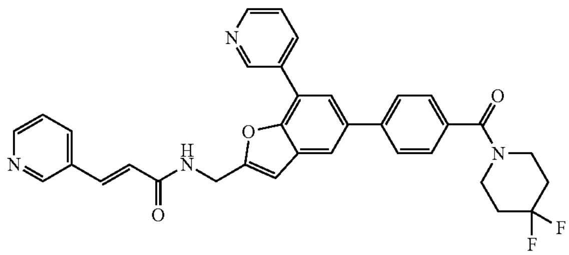 [SMILES: O=C(/C=C/c1cccnc1)NCc1cc2cc(-c3ccc(C(=O)N4CCC(F)(F)CC4)cc3)cc(-c3cccnc3)c2o1] | A | A | A | (E)-N-((5-(4-(4,4-difluoropiperidine-1-carbonyl)phenyl)-7-(pyridin-3-yl)benzofuran-2-yl)methyl)-3-(pyridin-3-yl)acrylamide |
| 726 | 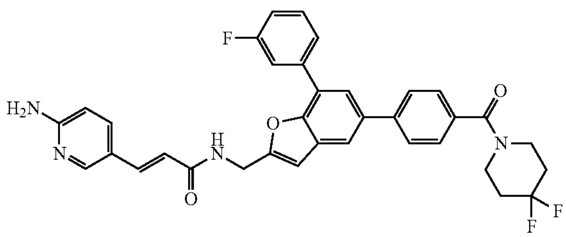 [SMILES: Nc1ccc(/C=C/C(=O)NCc2cc3cc(-c4ccc(C(=O)N5CCC(F)(F)CC5)cc4)cc(-c4cccc(F)c4)c3o2)cn1] | A | A | B | (E)-3-(6-aminopyridin-3-yl)-N-((5-(4-(4,4-difluoropiperidine-1-carbonyl)phenyl)-7-(3-fluorophenyl)benzofuran-2-yl)methyl)acrylamide |
| 727 | 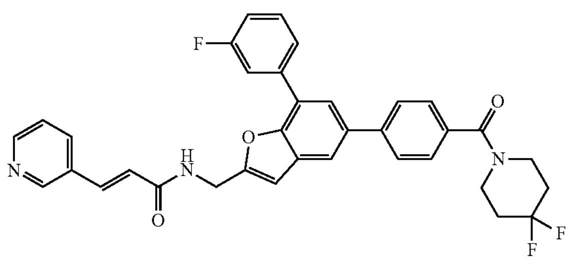 | A | A | A | (E)-N-((5-(4-(4,4-difluoropiperidine-1-carbonyl)phenyl)-7-(3-fluorophenyl)benzofuran-2-yl)methyl)-3-(pyridin-3-yl)acrylamide |
| 728 | 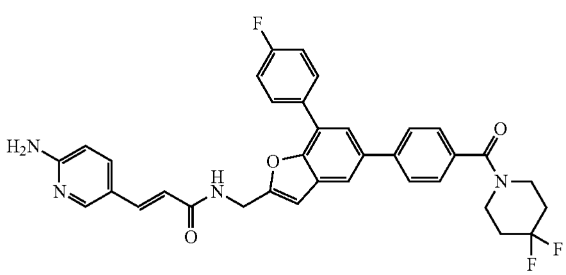 [SMILES: Nc1ccc(/C=C/C(=O)NCc2cc3cc(-c4ccc(C(=O)N5CCC(F)(F)CC5)cc4)cc(-c4ccc(F)cc4)c3o2)cn1] | A | A | B | (E)-3-(6-aminopyridin-3-yl)-N-((5-(4-(4,4-difluoropiperidine-1-carbonyl)phenyl)-7-(4-fluorophenyl)benzofuran-2-yl)methyl)acrylamide |
| 729 | 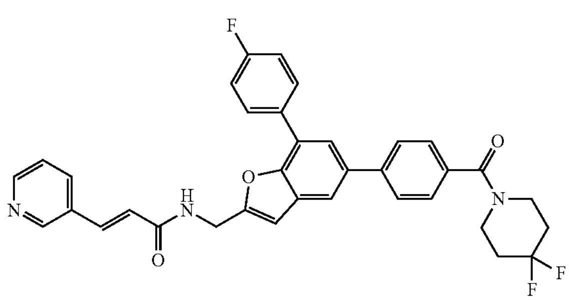 [SMILES: O=C(/C=C/c1cccnc1)NCc1cc2cc(-c3ccc(C(=O)N4CCC(F)(F)CC4)cc3)cc(-c3ccc(F)cc3)c2o1] | A | A | A | (E)-N-((5-(4-(4,4-difluoropiperidine-1-carbonyl)phenyl)-7-(4-fluorophenyl)benzofuran-2-yl)methyl)-3-(pyridin-3-yl)acrylamide |

TABLE 1-continued

MTT Assay

| Cpd No. | Compound Structure | MS-751 | Z138 | 3T3 | Compound Name |
|---|---|---|---|---|---|
| 730 | 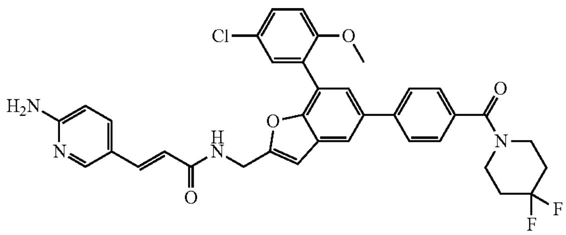 [SMILES: COc1ccc(Cl)cc1-c1cc(-c2ccc(C(=O)N3CCC(F)(F)CC3)cc2)cc2cc(CNC(=O)/C=C/c3ccc(N)nc3)oc12] | A | A | A | (E)-3-(6-aminopyridin-3-yl)-N-((7-(5-chloro-2-methoxyphenyl)-5-(4-(4,4-difluoropiperidine-1-carbonyl)phenyl)benzofuran-2-yl)methyl)acrylamide |
| 731 | 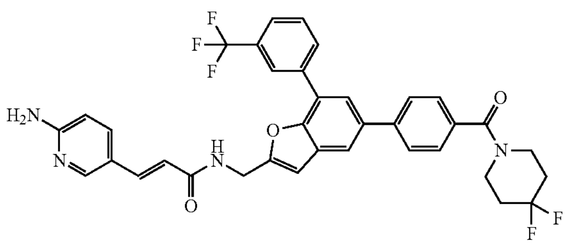 [SMILES: Nc1ccc(/C=C/C(=O)NCc2cc3cc(-c4ccc(C(=O)N5CCC(F)(F)CC5)cc4)cc(-c4cccc(C(F)(F)F)c4)c3o2)cn1] | B | A | B | (E)-3-(6-aminopyridin-3-yl)-N-((5-(4-(4,4-difluoropiperidine-1-carbonyl)phenyl)-7-(3-(trifluoromethyl)phenyl)benzofuran-2-yl)methyl)acrylamide |
| 732 | 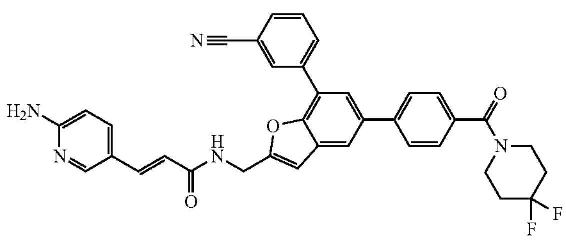 [SMILES: N#Cc1cccc(-c2cc(-c3ccc(C(=O)N4CCC(F)(F)CC4)cc3)cc3cc(CNC(=O)/C=C/c4ccc(N)nc4)oc23)c1] | A | A | B | (E)-3-(6-aminopyridin-3-yl)-N-((7-(3-cyanophenyl)-5-(4-(4,4-difluoropiperidine-1-carbonyl)phenyl)benzofuran-2-yl)methyl)acrylamide |
| 733 | 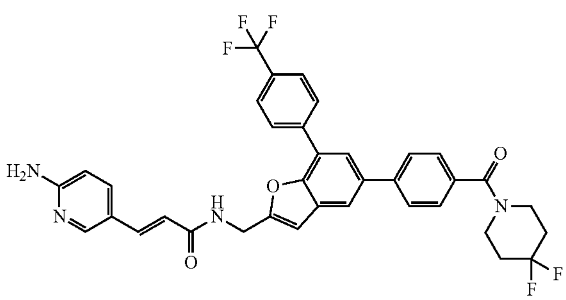 [SMILES: Nc1ccc(/C=C/C(=O)NCc2cc3cc(-c4ccc(C(=O)N5CCC(F)(F)CC5)cc4)cc(-c4ccc(C(F)(F)F)cc4)c3o2)cn1] | B | B | D | (E)-3-(6-aminopyridin-3-yl)-N-((5-(4-(4,4-difluoropiperidine-1-carbonyl)phenyl)-7-(4-(trifluoromethyl)phenyl)benzofuran-2-yl)methyl)acrylamide |
| 734 | 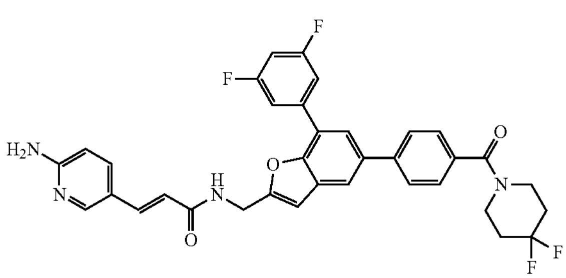 [SMILES: Nc1ccc(/C=C/C(=O)NCc2cc3cc(-c4ccc(C(=O)N5CCC(F)(F)CC5)cc4)cc(-c4cc(F)cc(F)c4)c3o2)cn1] | A | A | B | (E)-3-(6-aminopyridin-3-yl)-N-((7-(3,5-difluorophenyl)-5-(4-(4,4-difluoropiperidine-1-carbonyl)phenyl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 735 | 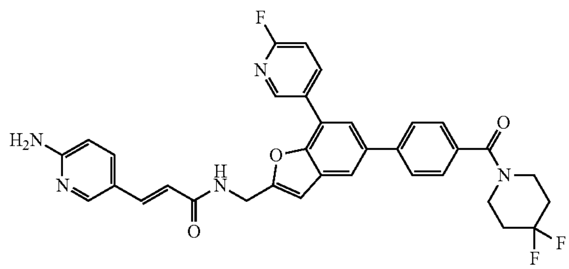 [SMILES: Nc1ccc(/C=C/C(=O)NCc2cc3cc(-c4ccc(C(=O)N5CCC(F)(F)CC5)cc4)cc(-c4ccc(F)nc4)c3o2)cn1] | A | A | B | (E)-3-(6-aminopyridin-3-yl)-N-((5-(4-(4,4-difluoropiperidine-1-carbonyl)phenyl)-7-(6-fluoropyridin-3-yl)benzofuran-2-yl)methyl)acrylamide |
| 736 | 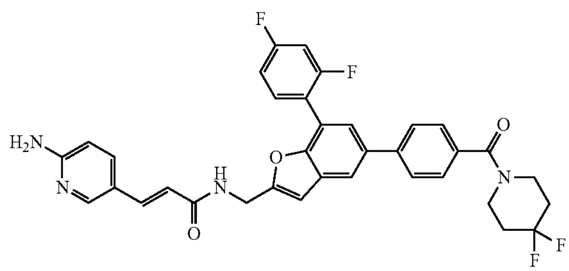 [SMILES: Nc1ccc(/C=C/C(=O)NCc2cc3cc(-c4ccc(C(=O)N5CCC(F)(F)CC5)cc4)cc(-c4ccc(F)cc4F)c3o2)cn1] | A | A | B | (E)-3-(6-aminopyridin-3-yl)-N-((7-(2,4-difluorophenyl)-5-(4-(4,4-difluoropiperidine-1-carbonyl)phenyl)benzofuran-2-yl)methyl)acrylamide |
| 737 | 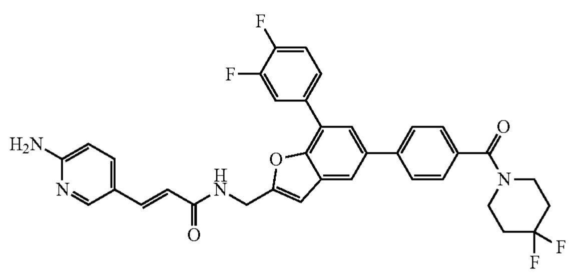 [SMILES: Nc1ccc(/C=C/C(=O)NCc2cc3cc(-c4ccc(C(=O)N5CCC(F)(F)CC5)cc4)cc(-c4ccc(F)c(F)c4)c3o2)cn1] | A | A | B | (E)-3-(6-aminopyridin-3-yl)-N-((7-(3,4-difluorophenyl)-5-(4-(4,4-difluoropiperidine-1-carbonyl)phenyl)benzofuran-2-yl)methyl)acrylamide |
| 738 | 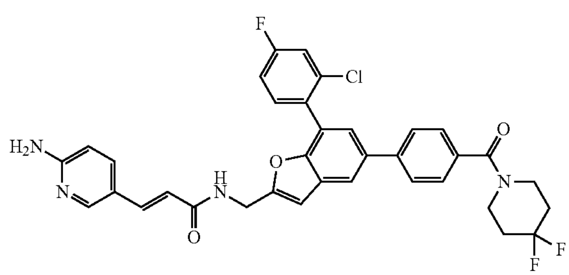 [SMILES: Nc1ccc(/C=C/C(=O)NCc2cc3cc(-c4ccc(C(=O)N5CCC(F)(F)CC5)cc4)cc(-c4ccc(F)cc4Cl)c3o2)cn1] | A | A | B | (E)-3-(6-aminopyridin-3-yl)-N-((7-(2-chloro-4-fluorophenyl)-5-(4-(4,4-difluoropiperidine-1-carbonyl)phenyl)benzofuran-2-yl)methyl)acrylamide |
| 739 | 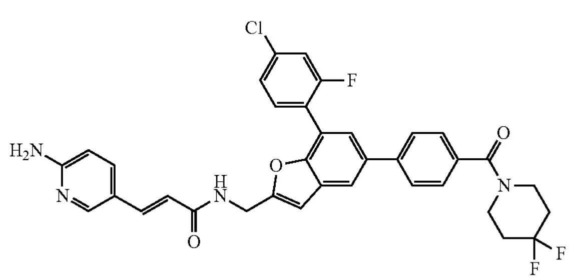 | B | B | D | (E)-3-(6-aminopyridin-3-yl)-N-((7-(4-chloro-2-fluorophenyl)-5-(4-(4,4-difluoropiperidine-1-carbonyl)phenyl)benzofuran-2-yl)methyl)acrylamide |

TABLE 1-continued

| Cpd No. | Compound Structure | MS-751 | Z138 | 3T3 | Compound Name |
|---|---|---|---|---|---|
| 740 | 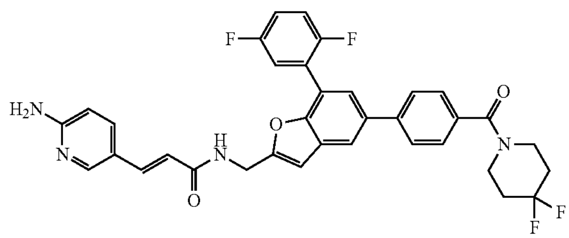 [SMILES: Nc1ccc(/C=C/C(=O)NCc2cc3cc(-c4ccc(C(=O)N5CCC(F)(F)CC5)cc4)cc(-c4cc(F)ccc4F)c3o2)cn1] | A | A | B | (E)-3-(6-aminopyridin-3-yl)-N-((7-(2,5-difluorophenyl)-5-(4-(4,4-difluoropiperidine-1-carbonyl)phenyl)benzofuran-2-yl)methyl)acrylamide |
| 741 | 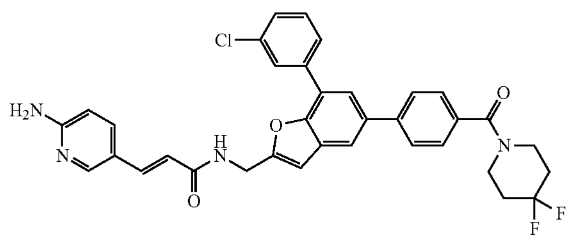 | A | A | B | (E)-3-(6-aminopyridin-3-yl)-N-((7-(3-chlorophenyl)-5-(4-(4,4-difluoropiperidine-1-carbonyl)phenyl)benzofuran-2-yl)methyl)acrylamide |
| 742 | 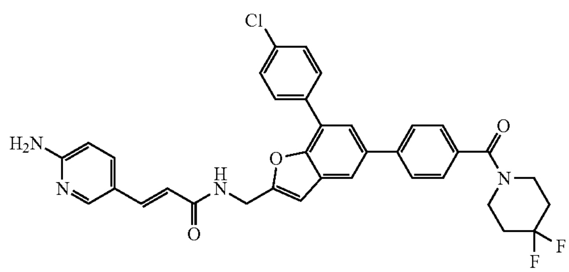 | B | B | D | (E)-3-(6-aminopyridin-3-yl)-N-((7-(4-chlorophenyl)-5-(4-(4,4-difluoropiperidine-1-carbonyl)phenyl)benzofuran-2-yl)methyl)acrylamide |
| 743 | 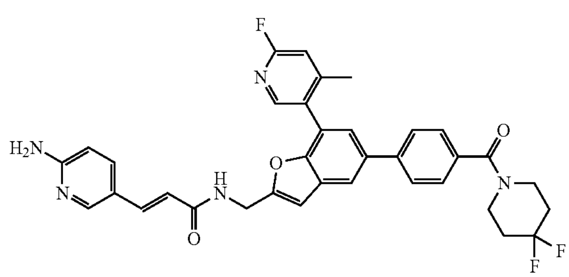 [SMILES: Cc1cc(F)ncc1-c1cc(-c2ccc(C(=O)N3CCC(F)(F)CC3)cc2)cc2cc(CNC(=O)/C=C/c3ccc(N)nc3)oc12] | A | A | B | (E)-3-(6-aminopyridin-3-yl)-N-((5-(4-(4,4-difluoropiperidine-1-carbonyl)phenyl)-7-(6-fluoro-4-methylpyridin-3-yl)benzofuran-2-yl)methyl)acrylamide |
| 744 | 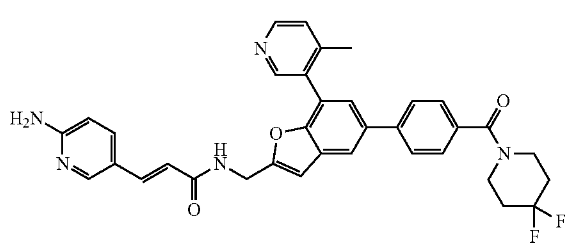 [SMILES: Cc1ccncc1-c1cc(-c2ccc(C(=O)N3CCC(F)(F)CC3)cc2)cc2cc(CNC(=O)/C=C/c3ccc(N)nc3)oc12] | A | A | B | (E)-3-(6-aminopyridin-3-yl)-N-((5-(4-(4,4-difluoropiperidine-1-carbonyl)phenyl)-7-(4-methylpyridin-3-yl)benzofuran-2-yl)methyl)acrylamide |
| 745 | 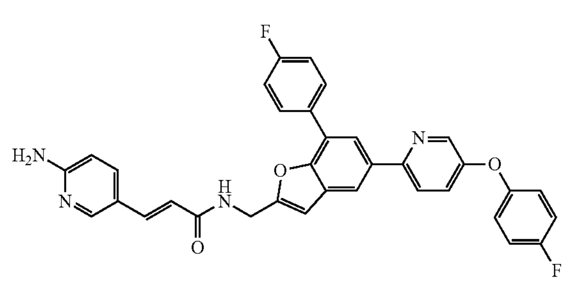 [SMILES: Nc1ccc(/C=C/C(=O)NCc2cc3cc(-c4ccc(Oc5ccc(F)cc5)cn4)cc(-c4ccc(F)cc4)c3o2)cn1] | B | B | D | (E)-3-(6-aminopyridin-3-yl)-N-((5-(5-(4-fluorophenoxy)pyridin-2-yl)-7-(4-fluorophenyl)benzofuran-2-yl)methyl)acrylamide |

TABLE 1-continued

| Cpd No. | Compound Structure | MS-751 | Z138 | 3T3 | Compound Name |
|---|---|---|---|---|---|
| 746 | 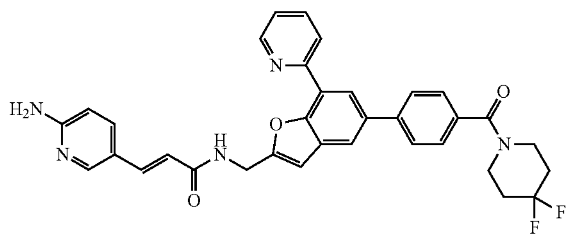 [SMILES: Nc1ccc(/C=C/C(=O)NCc2cc3cc(-c4ccc(C(=O)N5CCC(F)(F)CC5)cc4)cc(-c4ccccn4)c3o2)cn1] | A | A | B | (E)-3-(6-aminopyridin-3-yl)-N-((5-(4-(4,4-difluoropiperidine-1-carbonyl)phenyl)-7-(pyridin-2-yl)benzofuran-2-yl)methyl)acrylamide |
| 747 | 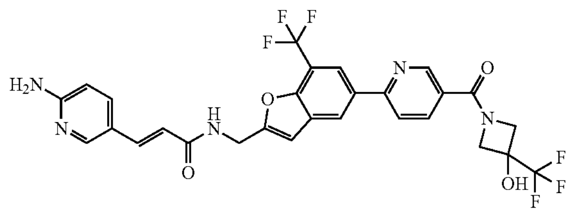 [SMILES: Nc1ccc(/C=C/C(=O)NCc2cc3cc(-c4ccc(C(=O)N5CC(O)(C(F)(F)F)C5)cn4)cc(C(F)(F)F)c3o2)cn1] | B | B | D | (E)-3-(6-aminopyridin-3-yl)-N-((5-(5-(3-hydroxy-3-(trifluoromethyl)azetidine-1-carbonyl)pyridin-2-yl)-7-(trifluoromethyl)benzofuran-2-yl)methyl)acrylamide |
| 748 | 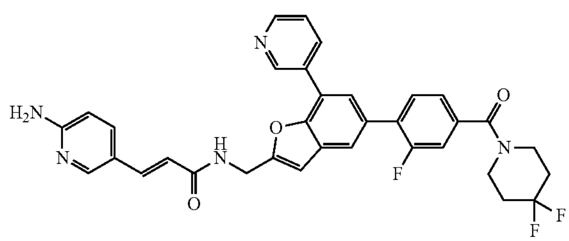 | A | A | B | (E)-3-(6-aminopyridin-3-yl)-N-((5-(4-(4,4-difluoropiperidine-1-carbonyl)-2-fluorophenyl)-7-(pyridin-3-yl)benzofuran-2-yl)methyl)acrylamide |
| 749 | 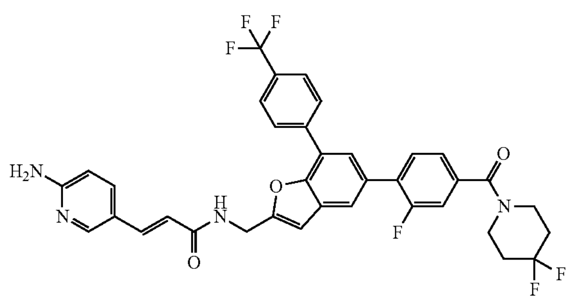 [SMILES: Nc1ccc(/C=C/C(=O)NCc2cc3cc(-c4ccc(C(=O)N5CCC(F)(F)CC5)cc4F)cc(-c4ccc(C(F)(F)F)cc4)c3o2)cn1] | D | B | D | (E)-3-(6-aminopyridin-3-yl)-N-((5-(4-(4,4-difluoropiperidine-1-carbonyl)-2-fluorophenyl)-7-(4-(trifluoromethyl)phenyl)benzofuran-2-yl)methyl)acrylamide |
| 750 | 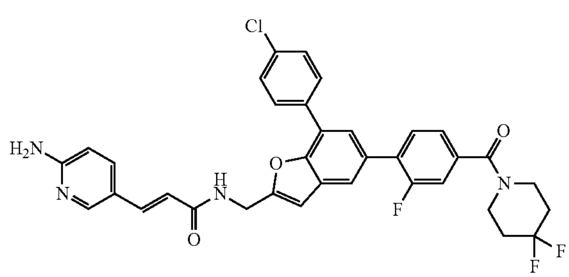 [SMILES: Nc1ccc(/C=C/C(=O)NCc2cc3cc(-c4ccc(C(=O)N5CCC(F)(F)CC5)cc4F)cc(-c4ccc(F)cc4)c3o2)cn1] | B | B | D | (E)-3-(6-aminopyridin-3-yl)-N-((7-(4-chlorophenyl)-5-(4-(4,4-difluoropiperidine-1-carbonyl)-2-fluorophenyl)benzofuran-2-yl)methyl)acrylamide |
| 751 | 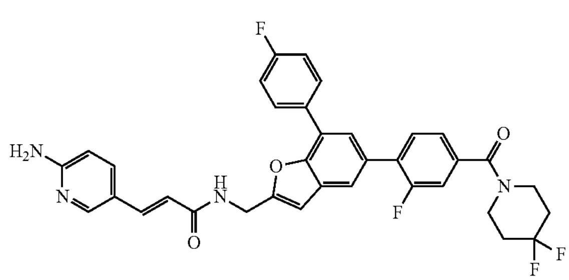 | A | A | B | (E)-3-(6-aminopyridin-3-yl)-N-((5-(4-(4,4-difluoropiperidine-1-carbonyl)-2-fluorophenyl)-7-(4-fluorophenyl)benzofuran-2-yl)methyl)acrylamide |

TABLE 1-continued

| Cpd No. | Compound Structure | MS-751 | Z138 | 3T3 | Compound Name |
|---|---|---|---|---|---|
| 752 | 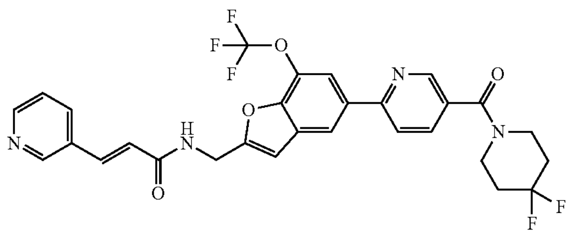 [SMILES: O=C(/C=C/c1cccnc1)NCc1cc2cc(-c3ccc(C(=O)N4CCC(F)(F)CC4)cn3)cc(OC(F)(F)F)c2o1] | A | A | A | (E)-N-((5-(5-(4,4-difluoropiperidine-1-carbonyl)pyridin-2-yl)-7-(trifluoromethoxy)benzofuran-2-yl)methyl)-3-(pyridin-3-yl)acrylamide |
| 753 | 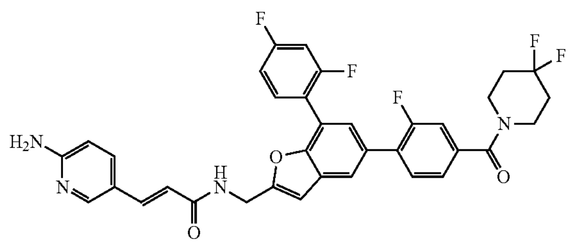 [SMILES: Nc1ccc(/C=C/C(=O)NCc2cc3cc(-c4ccc(C(=O)N5CCC(F)(F)CC5)cc4F)cc(-c4ccc(F)cc4F)c3o2)cn1] | A | A | B | (E)-3-(6-aminopyridin-3-yl)-N-((7-(2,4-difluorophenyl)-5-(4-(4,4-difluoropiperidine-1-carbonyl)-2-fluorophenyl)benzofuran-2-yl)methyl)acrylamide |
| 754 | 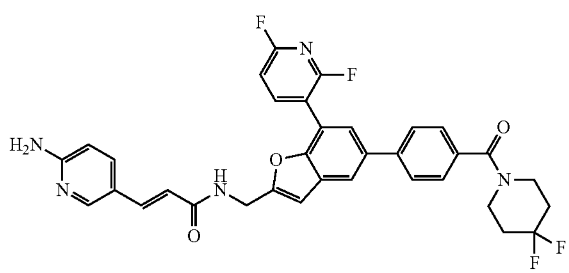 [SMILES: Nc1ccc(/C=C/C(=O)NCc2cc3cc(-c4ccc(C(=O)N5CCC(F)(F)CC5)cc4)cc(-c4ccc(F)nc4F)c3o2)cn1] | A | A | B | (E)-3-(6-aminopyridin-3-yl)-N-((5-(4-(4,4-difluoropiperidine-1-carbonyl)phenyl)-7-(2,6-difluoropyridin-3-yl)benzofuran-2-yl)methyl)acrylamide |
| 755 | 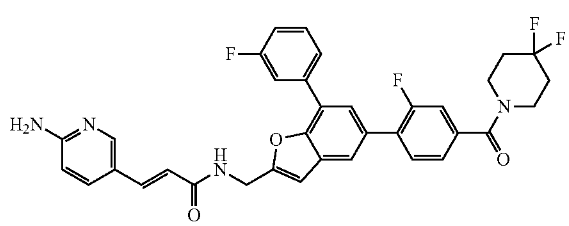 [SMILES: Nc1ccc(/C=C/C(=O)NCc2cc3cc(-c4ccc(C(=O)N5CCC(F)(F)CC5)cc4F)cc(-c4cccc(F)c4)c3o2)cn1] | B | A | B | (E)-3-(6-aminopyridin-3-yl)-N-((5-(4-(4,4-difluoropiperidine-1-carbonyl)-2-fluorophenyl)-7-(3-fluorophenyl)benzofuran-2-yl)methyl)acrylamide |
| 756 | 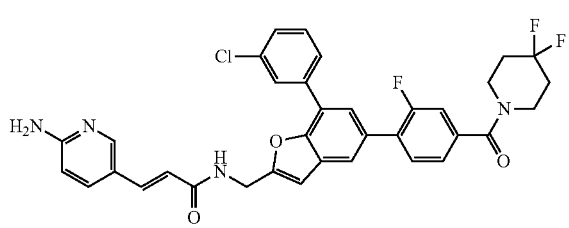 [SMILES: Nc1ccc(/C=C/C(=O)NCc2cc3cc(-c4ccc(C(=O)N5CCC(F)(F)CC5)cc4F)cc(-c4cccc(Cl)c4)c3o2)cn1] | A | A | D | (E)-3-(6-aminopyridin-3-yl)-N-((7-(3-chlorophenyl)-5-(4-(4,4-difluoropiperidine-1-carbonyl)-2-fluorophenyl)benzofuran-2-yl)methyl)acrylamide |
| 757 | 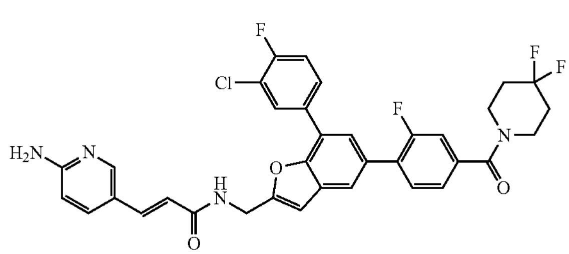 [SMILES: Nc1ccc(/C=C/C(=O)NCc2cc3cc(-c4ccc(C(=O)N5CCC(F)(F)CC5)cc4F)cc(-c4ccc(F)c(Cl)c4)c3o2)cn1] | A | A | D | (E)-3-(6-aminopyridin-3-yl)-N-((7-(3-chloro-4-fluorophenyl)-5-(4-(4,4-difluoropiperidine-1-carbonyl)-2-fluorophenyl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 758 | 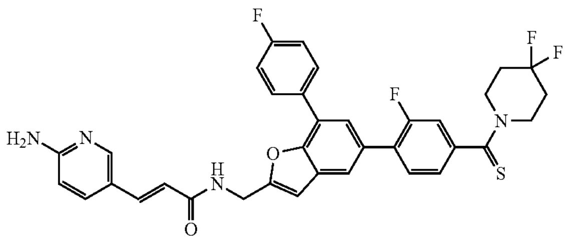 [SMILES: Nc1ccc(/C=C/C(=O)NCc2cc3cc(-c4ccc(C(=S)N5CCC(F)(F)CC5)cc4F)cc(-c4ccc(F)cc4)c3o2)cn1] | A | A | D | (E)-3-(6-aminopyridin-3-yl)-N-((5-(4-(4,4-difluoropiperidine-1-carbonothioyl)-2-fluorophenyl)-7-(4-fluorophenyl)benzofuran-2-yl)methyl)acrylamide |
| 759 | 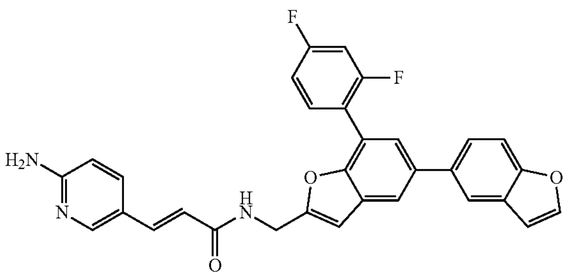 [SMILES: Nc1ccc(/C=C/C(=O)NCc2cc3cc(-c4ccc5occc5c4)cc(-c4ccc(F)cc4F)c3o2)cn1] | B | A | D | (E)-3-(6-aminopyridin-3-yl)-N-((7-(2,4-difluorophenyl)-[5,5'-bibenzofuran]-2-yl)methyl)acrylamide |
| 760 | 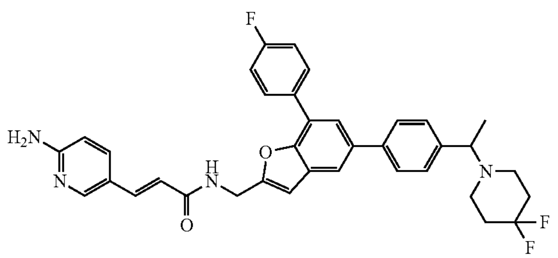 [SMILES: CC(c1ccc(-c2cc(-c3ccc(F)cc3)c3oc(CNC(=O)/C=C/c4ccc(N)nc4)cc3c2)cc1)N1CCC(F)(F)CC1] | B | B | D | (E)-3-(6-aminopyridin-3-yl)-N-((5-(4-(1-(4,4-difluoropiperidin-1-yl)ethyl)phenyl)-7-(4-fluorophenyl)benzofuran-2-yl)methyl)acrylamide |
| 761 | 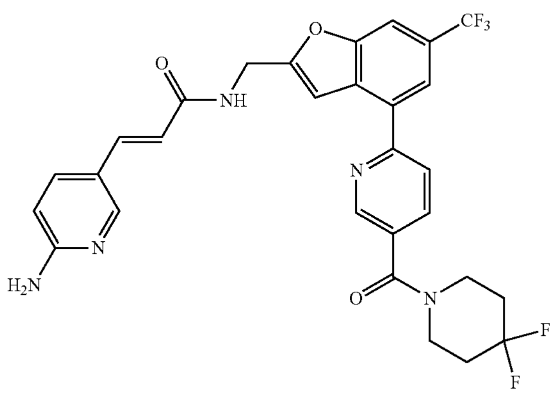 [SMILES: Nc1ccc(/C=C/C(=O)NCc2cc3c(-c4ccc(C(=O)N5CCC(F)(F)CC5)cn4)cc(C(F)(F)F)cc3o2)cn1] | D | D | D | (E)-3-(6-aminopyridin-3-yl)-N-((4-(5-(4,4-difluoropiperidine-1-carbonyl)pyridin-2-yl)-6-(trifluoromethyl)benzofuran-2-yl)methyl)acrylamide |
| 762 | 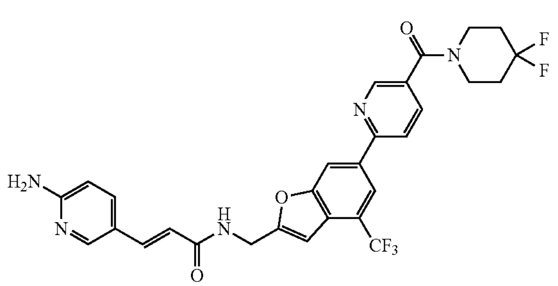 [SMILES: Nc1ccc(/C=C/C(=O)NCc2cc3c(C(F)(F)F)cc(-c4ccc(C(=O)N5CCC(F)(F)CC5)cn4)cc3o2)cn1] | C | B | D | (E)-3-(6-aminopyridin-3-yl)-N-((6-(5-(4,4-difluoropiperidine-1-carbonyl)pyridin-2-yl)-4-(trifluoromethyl)benzofuran-2-yl)methyl)acrylamide |

TABLE 1-continued

MTT Assay

| Cpd No. | Compound Structure | MS-751 | Z138 | 3T3 | Compound Name |
|---|---|---|---|---|---|
| 763 | 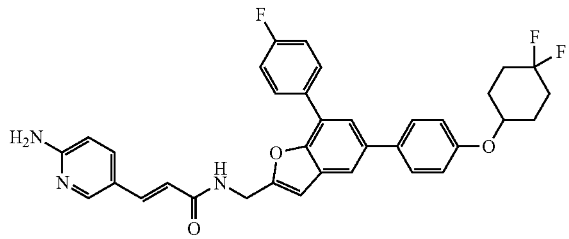 [SMILES: Nc1ccc(/C=C/C(=O)NCc2cc3cc(-c4ccc(OC5CCC(F)(F)CC5)cc4)cc(-c4ccc(F)cc4)c3o2)cn1] | B | B | D | (E)-3-(6-aminopyridin-3-yl)-N-((5-(4-((4,4-difluorocyclohexyl)oxy)phenyl)-7-(4-fluorophenyl)benzofuran-2-yl)methyl)acrylamide |
| 764 | 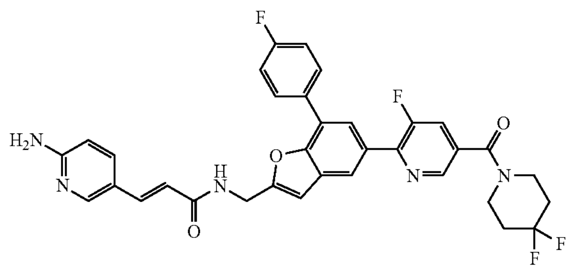 [SMILES: Nc1ccc(/C=C/C(=O)NCc2cc3cc(-c4ncc(C(=O)N5CCC(F)(F)CC5)cc4F)cc(-c4ccc(F)cc4)c3o2)cn1] | A | A | B | (E)-3-(6-aminopyridin-3-yl)-N-((5-(5-(4,4-difluoropiperidine-1-carbonyl)-3-fluoropyridin-2-yl)-7-(4-fluorophenyl)benzofuran-2-yl)methyl)acrylamide |
| 766 | 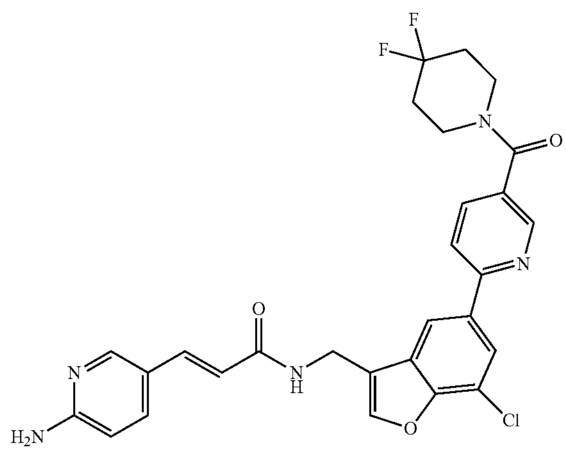 [SMILES: Nc1ccc(/C=C/C(=O)NCc2coc3c(Cl)cc(-c4ccc(C(=O)N5CCC(F)(F)CC5)cn4)cc23)cn1] | B | B | C | (E)-3-(6-aminopyridin-3-yl)-N-((7-chloro-5-(5-(4,4-difluoropiperidine-1-carbonyl)pyridin-2-yl)benzofuran-3-yl)methyl)acrylamide |
| 767 | 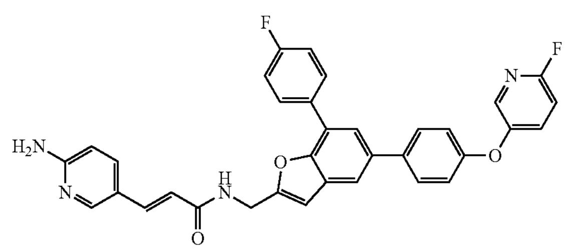 [SMILES: Nc1ccc(/C=C/C(=O)NCc2cc3cc(-c4ccc(Oc5ccc(F)nc5)cc4)cc(-c4ccc(F)cc4)c3o2)cn1] | B | A | D | (E)-3-(6-aminopyridin-3-yl)-N-((7-(4-fluorophenyl)-5-(4-((6-fluoropyridin-3-yl)oxy)phenyl)benzofuran-2-yl)methyl)acrylamide |

(IC$_{50}$: A = <100 nM; B = 100 nM to <5 μM; C = 5 μM to 10 μM; D = >10 μM)

Selected compounds were further tested in the MTT cell proliferation assay against the cell lines listed in Table 2. The M24 cell line is derived from human melanoma cells. The U2OS cell line is a human osteosarcoma cell line expressing wild type p53 and Rb, but lacking p16. The MM1S cell line is a multiple myeloma cell line; the parent cell line, MM. 1, was established from peripheral blood of a multiple myeloma patient who had become resistant to steroid-based therapy. The RPMI8226 cell line is derived from human B lymphocyte cells. NHDF cells are normal human dermal fibroblasts. The MRC-5 cell line is derived from normal lung tissue of a male fetus. The PC3 cell line is a human prostate cancer cell line. The DU-145 cell line is a human prostate cancer cell line. The MDA-MB-231 cell line is a human breast adenocarcinoma cell line. The MDA-MB-468 cell line is a human breast carcinoma cell line. HL-60 cells are human promyelocytic leukemia cells. Hep G2 cells are human hepatocellular carcinoma cells. HEP 3B cells are human hepatocellular carcinoma cells. The DLD-1 cell line is a colorectal adenocarcinoma cell line. The HCT-15 cell line is a human colon carcinoma cell line. The Colo-205 cell line is derived from a human adenocarcinoma of the colon. The LoVo cell line is a human colon adenocarcinoma cell line.

Further results of the MTT assay are reported in Table 2.

TABLE 2

MTT Assay

| Cell Line | Compound Number | | | | | |
|---|---|---|---|---|---|---|
| | 502 | 504 | 510 | 517 | 521 | 525 |
| M24 | NT | B | B | NT | NT | NT |
| U2OS | NT | A | A | NT | NT | NT |
| MM1S | NT | B | A | NT | NT | B |
| RPMI8226 | NT | NT | NT | NT | NT | B |
| NHDF | NT | A | A | NT | NT | NT |
| MRC-5 | B | A | A | NT | NT | NT |
| PC3 | NT | A | NT | NT | NT | NT |
| DU-145 | NT | A | B | NT | NT | NT |
| MDA-MB-231 | NT | B | B | B | B | NT |
| MDA-MB-468 | NT | B | A | NT | NT | NT |
| HL-60 | NT | NT | NT | NT | NT | B |
| Hep G2 | B | NT | NT | NT | NT | NT |
| HEP 3B | B | NT | NT | NT | NT | NT |
| DLD-1 | NT | B | B | NT | NT | NT |
| HCT-15 | NT | A | B | NT | NT | NT |
| Colo-205 | NT | A | B | NT | NT | NT |
| LoVo | NT | B | B | NT | NT | NT |

($IC_{50}$: A = <100 nM; B = 100 nM to <5 μM; C = 5 μM to 30 μM; D = >30 μM; NT = Not tested)

Compounds 504, 510, 525 and 585 were further tested against selected solid and hematological cancer cell lines and selected normal cell lines in a 72-hour MTT cell proliferation assay. Further results of the MTT assay for Compounds 504 and 510 are reported in Table 3. Further results of the MTT assay for Compound 525 are reported in Table 4. Further results of the MTT assay for Compound 585 are reported in Table 5.

TABLE 3

MTT Assay of Compounds 504 and 510

| Cell line | Cmpd 504 (uM) | Cell line | Cmpd 510 (uM) |
|---|---|---|---|
| Z-138 MTT | 0.01 | U2OS MTT | 0.008 |
| MRC-5 MTT | 0.02 | PC3 MTT | 0.02 |
| MS761 MTT | 0.03 | MDA-MB-468 MTT | 0.03 |
| U2OS MTT | 0.04 | MRC-5 MTT | 0.05 |
| M24 MTT | 0.05 | NHDF MTT | 0.08 |
| PC3 MTT | 0.05 | MM1S MTT | 0.09 |
| NHDF MTT | 0.06 | MS761 MTT | 0.1 |
| DU-145 MTT | 0.08 | Z-138 MTT | 0.1 |
| HCT-16 MTT | 0.08 | Colo-205 MTT | 0.16 |
| Colo-206 MTT | 0.08 | LoVo MTT | 0.23 |
| DLD-1 MTT | 0.11 | M24 MTT | 0.29 |
| LoVo MTT | 0.18 | DLD-1 MTT | 0.95 |
| MDA-MB-231 MTT | 0.22 | HCT-15 MTT | 1.27 |
| MM1S MTT | 0.29 | MDA-MB-231 MTT | 1.41 |
| 3T3 MTT | 0.35 | DU-145 MTT | 1.47 |
| HT-29 MTT | 0.48 | HT-29 MTT | 9.31 |
| MDA-MB-468 MTT | 1 | 3T3 MTT | >10 |

TABLE 4

MTT Assay of Compound 525

| Cell line | Cmpd 525 (uM) |
|---|---|
| Z-138 MTT | 0.1 |
| MS751 MTT | 0.3 |
| MM1S MTT | 0.31 |
| RPMI8226 MTT | 0.43 |
| HL-60 MTT | 1.06 |
| 3T3 MTT | >10 |

TABLE 5

MTT Assay of Compound 585

| Cell line | Cmpd 585 (uM) |
|---|---|
| RWPE-1 MTT | 0.004 |
| Z-138 MTT | 0.02 |
| NCI-H520 MTT | 0.02 |
| THP1 MTT | 0.02 |
| MO7e MTT | 0.02 |
| AML-193 MTT | 0.03 |
| MOLT4 MTT | 0.04 |
| Jurkat MTT | 0.04 |
| T47D MTT | 0.04 |
| Daudi MTT | 0.04 |
| U118MG MTT | 0.05 |
| OCIAMLS MTT | 0.05 |
| Toledo MTT | 0.05 |
| RKO MTT | 0.05 |
| HeLa MTT | 0.06 |
| U2OS MTT | 0.06 |
| NCI-H889 MTT | 0.06 |
| TF-1 MTT | 0.06 |
| HuCCT-1 MTT | 0.06 |
| NCI-H187 MTT | 0.07 |
| Farage MTT | 0.07 |
| HEP 3B MTT | 0.07 |
| L3.6pl MTT | 0.07 |
| NCI-H65 MTT | 0.08 |
| Pfieffer MTT | 0.08 |
| MM1S MTT | 0.09 |
| DoHH-2 MTT | 0.09 |
| MV-4-11 MTT | 0.09 |
| HH MTT | 0.09 |
| Raji MTT | 0.09 |
| DU-4475 MTT | 0.09 |
| CAPAN-1 MTT | 0.09 |
| MS751 MTT | 0.1 |
| MINO MTT | 0.11 |
| Tera-1 MTT | 0.12 |
| SHSY5Y MTT | 0.12 |
| HEL.52.1.7 MTT | 0.12 |
| MRC-5 MTT | 0.13 |
| PCS MTT | 0.14 |
| AU-666 MTT | 0.14 |
| MCF-10A MTT | 0.14 |
| SW-420 MTT | 0.14 |
| RPMI8226 MTT | 0.15 |
| KOG1 MTT | 0.15 |
| LS-180 MTT | 0.15 |
| Hep G2 MTT | 0.16 |
| Celo-206 MTT | 0.17 |
| SW-48 MTT | 0.17 |
| BL-2 MTT | 0.18 |
| MM1R MTT | 0.19 |
| NCI-H1299 MTT | 0.19 |
| NCI-H29 MTT | 0.2 |
| HS-Sultan MTT | 0.2 |
| MDA-MS-488 MTT | 0.2 |
| HT9280 MTT | 0.21 |
| SHP-77 MTT | 0.21 |
| RL MTT | 0.21 |
| HCC-1143 MTT | 0.21 |
| HL-60 MTT | 0.21 |
| WI-03 MTT | 0.22 |
| MSTO-211H MTT | 0.25 |
| Hs878T MTT | 0.25 |
| U-937 MTT | 0.26 |

TABLE 5-continued

MTT Assay of Compound 585

| Cell line | Cmpd 585 (uM) |
|---|---|
| LoVo MTT | 0.26 |
| HCT-16 MTT | 0.27 |
| D8 MTT | 0.29 |
| NCI-H2030 MTT | 0.3 |
| BL-40 MTT | 0.3 |
| U-266 MTT | 0.31 |
| Calu-S MTT | 0.33 |
| Calu-S MTT | 0.35 |
| MCF-12A MTT | 0.38 |
| SW-400 MTT | 0.38 |
| HPAC MTT | 0.38 |
| NCI-H1660 MTT | 0.39 |
| Hs738-st MTT | 0.45 |
| PATU-89888 MTT | 0.47 |
| SW-460 MTT | 0.48 |
| PATU-8902 MTT | 0.51 |
| NCI-H1680 MTT | 0.53 |
| BT-20 MTT | 0.54 |
| PATU-9988T MTT | 0.54 |
| HPAF-II MTT | 0.55 |
| Colo-201 MTT | 0.56 |
| A549 MTT | 0.57 |
| NCI-H747 MTT | 0.59 |
| SW-837 MTT | 0.6 |
| MCF7 MTT | 0.7 |
| HCC-4006 MTT | 0.74 |
| HCC-827 MTT | 0.78 |
| ARPE-19 MTT | 0.78 |
| NCI-H368 MTT | 0.8 |
| Panc-1 MTT | 0.84 |
| PANC-10.05 MTT | 0.87 |
| MIaPaCa-2 MTT | 0.88 |
| SW-348 MTT | 0.91 |
| NCI-H929 MTT | 0.93 |
| DLD-1 MTT | 0.94 |
| SW-1116 MTT | 0.97 |
| ANBL-6 MTT | 1.01 |
| PL-46 MTT | 1.01 |
| MDA-MB-416 MTT | 1.02 |
| TFK-1 MTT | 1.03 |
| CAMA-1 MTT | 1.06 |
| K562 MTT | 1.09 |
| MDA-MB-231 MTT | 1.12 |
| SK-CO-1 MTT | 1.19 |
| NCI-H2170 MTT | 1.26 |
| SW-1417 MTT | 1.27 |
| NCI-H609 MTT | 1.46 |
| ST-649 MTT | 1.53 |
| LN 18 MTT | 1.66 |
| HCC-202 MTT | 1.69 |
| PaMC MTT | 2.2 |
| CaOVa MTT | 2.22 |
| NCI-H820 MTT | 2.84 |
| IMR-90 MTT | 4 |
| HCC-2935 MTT | 4.39 |
| HCC-1428 MTT | 4.4 |
| SNU-398 MTT | 4.42 |
| DU-146 MTT | 4.9 |
| NCI-H2122 MTT | 5.81 |
| NHDF MTT | 5.82 |
| BT-474 MTT | 6.47 |
| NCI-H226 MTT | 6.78 |
| LS-174T MTT | 8.8 |
| HCT116 MTT | 9.82 |
| NHEK MTT | 10.36 |
| 3T3 MTT | >10 |
| SW-800 MTT | >10 |
| NCI-H1990 MTT | >10 |
| HCT118.1 MTT | >10 |
| C8 MTT | >10 |
| MDA-MB-176 MTT | >10 |
| MDA-MB-381 MTT | >10 |
| MHCC97H MTT | >10 |
| SKOVS MTT | >10 |
| HTB-SS MTT | >10 |

Table 5 shows that Compound 585 had an $IC_{50}$ of less than 1 µM in 72% (91/126) of the cancer cell lines tested. Compound 585 had an $IC_{50}$ of less than 500 nM in 91% (30/33) of the hematological cancer cell lines tested, and an $IC_{50}$ of less than 500 nM in 45% (42/93) of the solid cancer cell lines tested. Hematological cancer cell lines tested included MOLT-4, Z-138, THP-1, MO7E, AML-193, Jurkat, Daudi, Toledo, AML-5, TF-1, Farage, DOHH-2, Pfieffer, HH, MV-4-11, MM1S, Raji, MINO, HEL.92.1.7, KG-1, RPMI 8226, BL-2, MM1R, HS-Sultan, HL-60, RL, U-937, DB, BL-40, U-266, NCI-H929, ANBL-6 and K562. Solid cancer cell lines tested included NCI-H520, RKO, U118 MG, HeLa, HuCCT-1, CAPAN-1, U2OS, NCI-H889, NCI-H187, L3.6pl, HEP 3B, MS751, NCI-H69, DU-4475, AU-565, SHSY 5Y, Tera-1, SW-620, PC3, LS-180, HepG2, SW-48, NCI-H1299, Colo-205, NCI-H28, HCC-1143, HT1080, SHP-77, MDA-MB-468, MSTO-211H, LoVo, HCT-15, NCI-H2030, Calu-6, SW-403, HPAC, NCI-H1563, PATU-8988S, A549, HPAF-II, Colo-201, NCI-H747, SW-837, HCC-4006, NCI-H358, HCC-827, Panc-1, PANC-10.05, MiaPaCa-2, SW-948, DLD-1, SW-1116, MDA-MB-231, NCI-H508, BT-549, MCF7, LN-18, HCC-202, CaOV3, NCI-H820, HCC-2935, SNU-398, DU145, NCI-H2122, BT-474, NCI-H226, LS-174T, NCT116, MDA-MB-175, MDA-MB-361, SW-900, NCI-H1993, HCT116.1, C6, HTB-38, MHCC97H and SKOV3.

Table 6 also shows that Compound 585 did not inhibit normal cells (n=10). Normal cell lines tested included NHDF, 3T3, NHEK, IMR-90, PBMC, ARPE-19, HS738.st, WI-38, MRC-5 and RWPE-1.

Example 3. Target Identification

Without being bound by a particular theory, it is believed that the compounds described herein can modulate (e.g., inhibit) one or more p21-activated kinases (PAK), for example, one or more of PAKs 1-6. More specifically, and without being bound by a particular theory, it is believed that the compounds described herein can bind to one or more PAKs and function as allosteric modulators of one or more PAKs. For example, the compounds described herein may exert their modulatory effect(s) on one or more PAKs by binding to and destabilizing one or more PAKs or contributing to the degradation of one or more PAKs, thereby modulating (e.g., inhibiting) the effect of one or more PAKs on one or more proteins downstream of the one or more PAKs, for example, growth signaling proteins such as Akt, ERK1/2, p90RSK, β-catenin, cofilin, p21 and cyclin D1.

In a particular embodiment, one or more of the Group I PAKs (e.g., PAK1, PAK2, PAK3) is modulated. For example, PAK1 is modulated, PAK2 is modulated, PAK3 is modulated or a combination of PAK1, PAK2 and PAK3, such as PAK1 and PAK2, PAK1 and PAK3, PAK2 and PAK3, or PAK1, PAK2 and PAK3 is modulated. In a particular embodiment, one or more of the group II PAKs (e.g., PAK4, PAK5, PAK6) is modulated. For example, PAK4 is modulated, PAK5 is modulated, PAK6 is modulated or a combination of PAK4, PAK5 and PAK6, such as PAK4 and PAK5, PAK4 and PAK6, PAK5 and PAK6 or PAK4, PAK5 and PAK6 is modulated. Therefore, the compounds described herein can be useful for treating PAK-mediated disorders.

In another particular embodiment, one or more of the Group I PAKs (e.g., PAK1, PAK2, PAK3) is inhibited. For example, PAK1 is inhibited, PAK2 is inhibited, PAK3 is inhibited or a combination of PAK1, PAK2 and PAK3, such as PAK1 and PAK2, PAK1 and PAK3, PAK2 and PAK3, or PAK1, PAK2 and PAK3 is inhibited. In a particular embodiment, one or more of the group II PAKs (e.g., PAK4, PAK5, PAK6) is inhibited. For example, PAK4 is inhibited, PAK5 is inhibited, PAK6 is inhibited or a combination of PAK4, PAK5 and PAK6, such as PAK4 and PAK5, PAK4 and PAK6, PAK5 and PAK6 or PAK4, PAK5 and PAK6 is inhibited. Therefore, the compounds described herein can be useful for treating PAK-mediated disorders.

PAKs are a family of serine/threonine kinases that are involved in multiple intracellular signaling pathways. Six human PAKs have been identified to date (PAKs 1-6). The PAKs can be classified into two subfamilies based on domain structure, sequence homology, and regulation: Group 1, which includes PAKs 1-3, and Group 2, which includes PAKs 4-6 (1).

Group I PAKs are characterized by an N-terminal region that includes a conserved p21 binding domain (PBD) that overlaps with an autoinhibitory domain (AID), and a C-terminal kinase domain. Group I PAKs are known to be involved in regulating normal cellular activities and can play a role in disease progression. For example, PAK1 plays an important role in cytoskeleton dynamics, cell adhesion, migration, proliferation, apoptosis, mitosis and vesicle-mediated transport processes, and has been shown to be up-regulated in breast, ovary and thyroid cancer. PAK1 activity has also been shown to be suppressed in brain lysates from Alzheimer's disease patients. PAK2 plays a role in a variety of different signaling pathways including cytoskeleton regulation, cell motility, cell cycle progression, apoptosis and proliferation. PAK3 plays a role in cytoskeleton regulation, cell migration, and cell cycle regulation.

Group II PAKs are characterized by an N-terminal PBD and a C-terminal kinase domain, but lack other motifs found in the group I PAKs. PAK4 is a pluripotent kinase known to mediate cell motility and morphology, proliferation, embryonic development, cell survival, immune defense, and oncogenic transformation (2), and is a key effector for Cdc42, a subset of the Rho GTPase family, which has been shown to be required for Ras driven tumorigenesis (3). PAK5 is unique amongst the PAK family, as it is constitutively localized to the mitochondria, and its localization is independent of kinase activity and Cdc42 binding. The mitochondrial localization of PAK5 is required for it to exert its anti-apoptotic effects and to promote cell survival. One report suggests that PAK5 is overexpressed in colorectal cancer and promotes cancer cell invasion. Both PAK4 and PAK5 have been linked to the regulation of neurite outgrowth; whereas PAK5 induces neurite outgrowth, PAK4 inhibits neurite outgrowth. The link of PAK4 and PAK5 to neuronal development suggests that PAK4 and PAK5 may be involved in the progression of neurological disorders, such as Parkinson's disease, dementia and brain atrophy. PAK6 has been found to specifically bind to androgen receptor (AR) and estrogen receptor a (ERa), and co-translocates into the nucleus with AR in response to androgen. PAK6 expression in adult tissue is mainly restricted to the prostrate and testis. However, PAK6 has been found to be overexpressed in many cancer cell lines, particularly breast and prostate cancers.

Since the PAKs and, in particular, PAK4, are critical hubs of signaling cascades, inhibiting their function can be beneficial for the treatment of cancers, neurodegenerative diseases, and immune system diseases as described herein.

Target Identification Using SILAC (Stable Isotope Labeling of Amino Acids in Cells)

MS751 cellular proteins are labeled with non-radioactive heavy lysine (L-Lysine-2HCl, $^{13}C_6$, $^{15}N_2$) and arginine (L-Arginine-HCl, $^{13}C_6$, $^{15}N_4$) for 7 to 8 doublings. The heavy isotopes are incorporated efficiently with greater than 95% heavy proteins identified by LC-MS. Separate plates of cells are maintained in light amino acids. FIG. 1 is a schematic representation of a SILAC experiment, and shows the experimental design.

After successful isotope labeling, heavy and light plates of MS751 cells are collected and lysed in ModRIPA buffer (50 mM Tris-HCl, pH 7.8, 150 mM NaCl, 1% NP-40, 0.1% sodium deoxycholate, 1 mM EDTA), and the protein quantified using Pierce 660 reagent. Two milligrams of light total protein are mixed with a 50-fold excess of soluble competitor (for example, a compound of the invention or a PEGylated compound of the invention) while two milligrams of heavy protein lysate are mixed with an equal amount of vehicle (DMSO). In the second replicate, the heavy and light proteins are flipped. The mixture is incubated at 4° C. for 1 h with constant rotation. 30 µL of slurry (for example, 15 µL of 12.5% PEGylated compound of the invention immobilized on resin in 15 µL of PBS) is added to separate tubes with the protein mixtures of DMSO or soluble competitor, and incubated for 16 to 24 h with constant rotation.

The following day, the beads are collected by quick centrifugation and the supernatant removed. The resin is washed separately twice in ModRIPA buffer with spins after washes. The light (PEGylated compound of the invention) and heavy (DMSO) resins are mixed together then washed twice with ModRIPA, with spins after washes, and prepared for SDS-PAGE.

The lysates are run on a gradient SDS-PAGE gel and stained with Coomassie blue. Six bands from each replicate are cut from the gel, digested with trypsin, desalted, and prepared for LC-MS proteomics.

Samples are run on a Q-Exactive, and the heavy and light peptides are identified using MaxQuan and R Moderated T Test for statistical analysis. The statistical analysis shows the enrichment of PAK4 in DMSO samples compared to the soluble competitor samples.

Pull-Down of Proteins Using Immobilized Inhibitor

MS751, U2OS, or HeLa cells are collected and lysed in ModRIPA buffer, and the protein content quantified using Pierce 660 reagent. Two milligrams of total protein is mixed with a 50-fold excess of soluble competitor (for example, a compound of the invention or a PEGylated compound of the invention) or an equal amount of DMSO in three separate tubes. The mixture is incubated at 4° C. for 1 h with constant rotation. 30 µL of slurry (for example, 15 µL of 12.5% PEGylated compound of the invention immobilized on resin in 15 µL of PBS) is added to separate tubes with the protein mixtures of DMSO or soluble competitor and incubated for 16 to 24 h with constant rotation.

The following day, the beads are collected by quick centrifugation and the supernatant removed. The resin is washed separately three times in ModRIPA buffer with spins after each wash. Each sample along with input lysate is prepared for SDS-PAGE.

Samples are boiled, run on a 4-20% SDS-PAGE gel and transferred to nitrocellulose membranes for Western blotting. Anti-PAK4 primary antibody is incubated on the membrane overnight and detected with fluorescent secondary antibody. The Western blot shows that PAK4 binds to the resin pre-treated with DMSO but not the resin corresponding to samples pre-treated with soluble competitor.

Example 4. Compound 585 Induces Autophagy

U2OS cells were plated in a 6-well plate overnight. The next day, the cells were treated with 1 µM or 10 µM Compound 585 for 48 hours, then collected and lysed in RIPA buffer. The lysate was run on SDS-PAGE and Western blots of PAK4, PUMA, CHOP, p21, cyclin D, MLH1, p-AMPK, AMPK and LC3 were performed.

Figure 2:
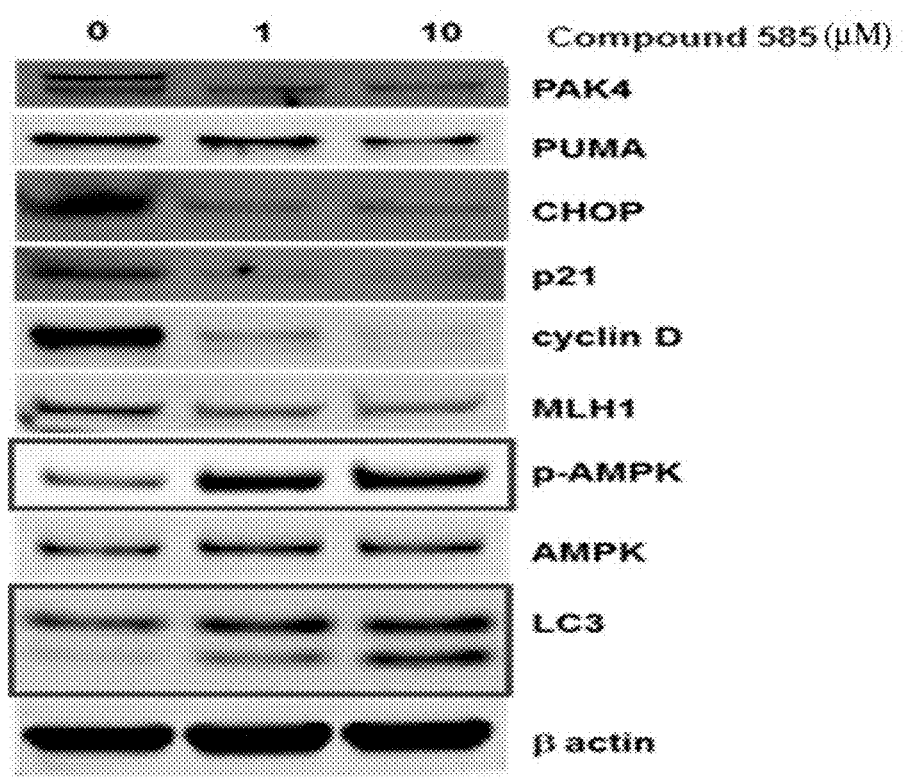
FIG. 2 is images of Western blots, and shows the effect of 48-hour treatment with increasing concentrations of Compound 585 on the levels of markers of autophagy, such as pAMPK, AMPK and LC3, in U2OS cells.

FIG. 2 is images of Western blots, and shows the effect of 48-hour treatment with increasing concentrations of Compound 585 on the levels of markers of autophagy, such as pAMPK, AMPK and LC3, in U2OS cells. Treatment for 48 hours with Compound 585 induced markers of stress response and autophagy, as evidenced by increased AMPK phosphorylation and the presence of the short form of LC3 lysosome marker. Treatment with Compound 585 also reduced cell cycle proteins, p21 and cyclin D1.

Example 5. PAK4 Signalling is Unchanges in Normal Cell Lines

Normal human dermal fibroblasts (NHDF) and normal lung cells (IMR-90) were treated with Compound 585 for 72 hours, at which time the cells were lysed in RIPA buffer. The lysates were run on SDS-PAGE and Western blots of phospho-PAK4, PAK4, phospho-cofilin, cofilin, phospho-β-catenin, β-catenin, PARP and caspase-3 were performed.

Figure 3:
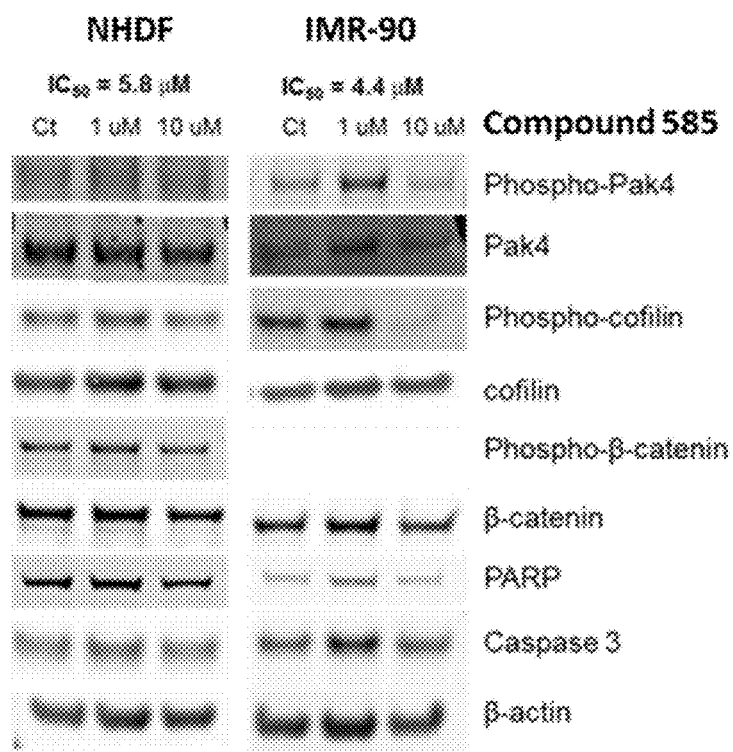
FIG. 3 is images of Western blots, and shows that 72-hour treatment with increasing concentrations of Compound 585 had little to no effect on PAK4 signalling in two normal cell lines, NHDF and IMR-90, as indicated by the levels of phospho-PAK4, PAK4, phospho-cofilin, cofilin, phospho-β-catenin, β-catenin, PARP and caspase 3.

FIG. 3 is images of Western blots, and shows that 72-hour treatment with increasing concentrations of Compound 585 had little to no effect on PAK4 signalling in two normal cell lines, NHDF and IMR-90, as indicated by the levels of phospho-PAK4, PAK4, phospho-cofilin, cofilin, phospho-β-catenin, β-catenin, PARP and caspase 3.

Example 6. Compound 585 Reduces β-Catenin and Cofilin Signals and Increases Stress Fibers U2OS cells were grown on coverslips and treated with DMSO or 1 μM Compound 585 for 48 hours, at which time the cells were fixed and stained. The cells were labeled with phospho- or total β-catenin antibodies; phospho- or total cofilin antibodies; or ALEXA-FLUOR® 488 phalloidin. Both phospho- and total β-catenin were reduced by treatment with Compound 585. Both phospho- and total cofilin were reduced by treatment with Compound 585. ALEXA-FLUOR® 488 phalloidin was used to stain F-actin. Compound 585 caused an increase in stress fiber formation.

Example 7. Compound 585 Causes Cell Cycle Changes

U2OS cells were treated with DMSO or 1 μM Compound 585 for one, two or three days. At each time point, cells were treated with 10 μM BrdU for 2 hours, and then collected by trypsinization. Cells were subsequently washed, fixed and stained for BrdU and total DNA (7-AAD). BrdU incorporation and cell cycle analysis was performed using flow cytometry on a BD Fortessa Analyzer. Data was then analyzed using FCS Express 4 software.

Figure 4:
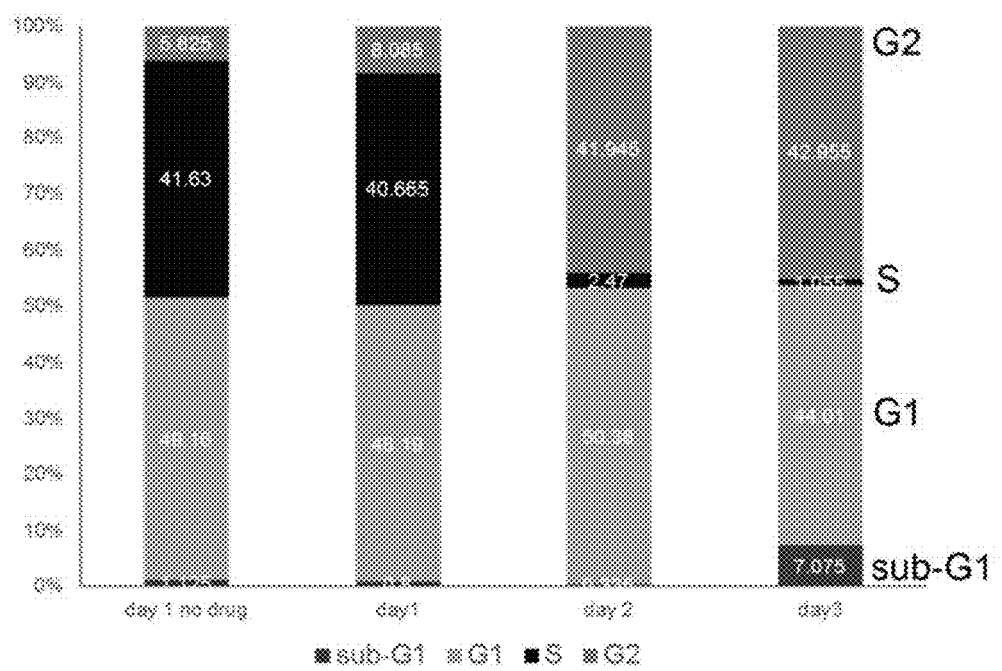
FIG. 4 is a graphical representation of cell cycle changes observed upon treatment of U2OS cells with 1 μM Compound 585 for one, two or three days.

FIG. 4 is a graphical representation of cell cycle changes observed upon treatment of U2OS cells with 1 μM Compound 585 for one, two or three days. Treatment with Compound 585 caused loss of S phase and increase in G2 phase at 48-72 hours. Sub-G1 phase started to appear around 48-72 hours.

Example 8. MDA-MB-468 Xenograft in SCID Mice

The oncological impact of Compound 504 and Compound 510 were tested using a MDA-MB-468 (triple negative breast cancer) xenograft model in CB-17 SCID mice. MDA-MB-468 (ATCC #HTB-102) breast adenocarcinoma cells were obtained from ATCC. The cells were grown in high glucose DMEM supplemented with 10% fetal bovine serum, 1% penicillin and streptomycin, and 2 mM L-glutamine. Cells were sub-cultured by dilution at a ratio of 1:4. MDA-MB-468 cells were harvested by trypsinization and counted using a hemocytometer. Cells were resuspended in PBS at a $4 \times 10^8$ cells per mL. Cells were placed on ice and mixed with an equal volume of Matrigel (BD Biosciences CB-40234). Thirty-two (32) CB-17 SCID mice were inoculated sub-cutaneously in the left flank with $4 \times 10^7$ MDA-MB-468 cells. Treatment was initiated when the tumors reached a mean volume of about 100 mm$^3$. Mice were allocated to four (4) groups of eight (8) mice such that mean tumor volume was about 100 mm$^3$ in each group. Mice were treated with vehicle, standard of care/positive control drug (paclitaxel), Compound 504 or Compound 510. Compound 504 (15 mg/kg) and Compound 510 (15 mg/kg) were given orally (PO) once daily on Monday through Friday each week. Animals' weights and condition were recorded daily, and tumors were measured on Mondays, Wednesdays, and Fridays.

Figure 5:
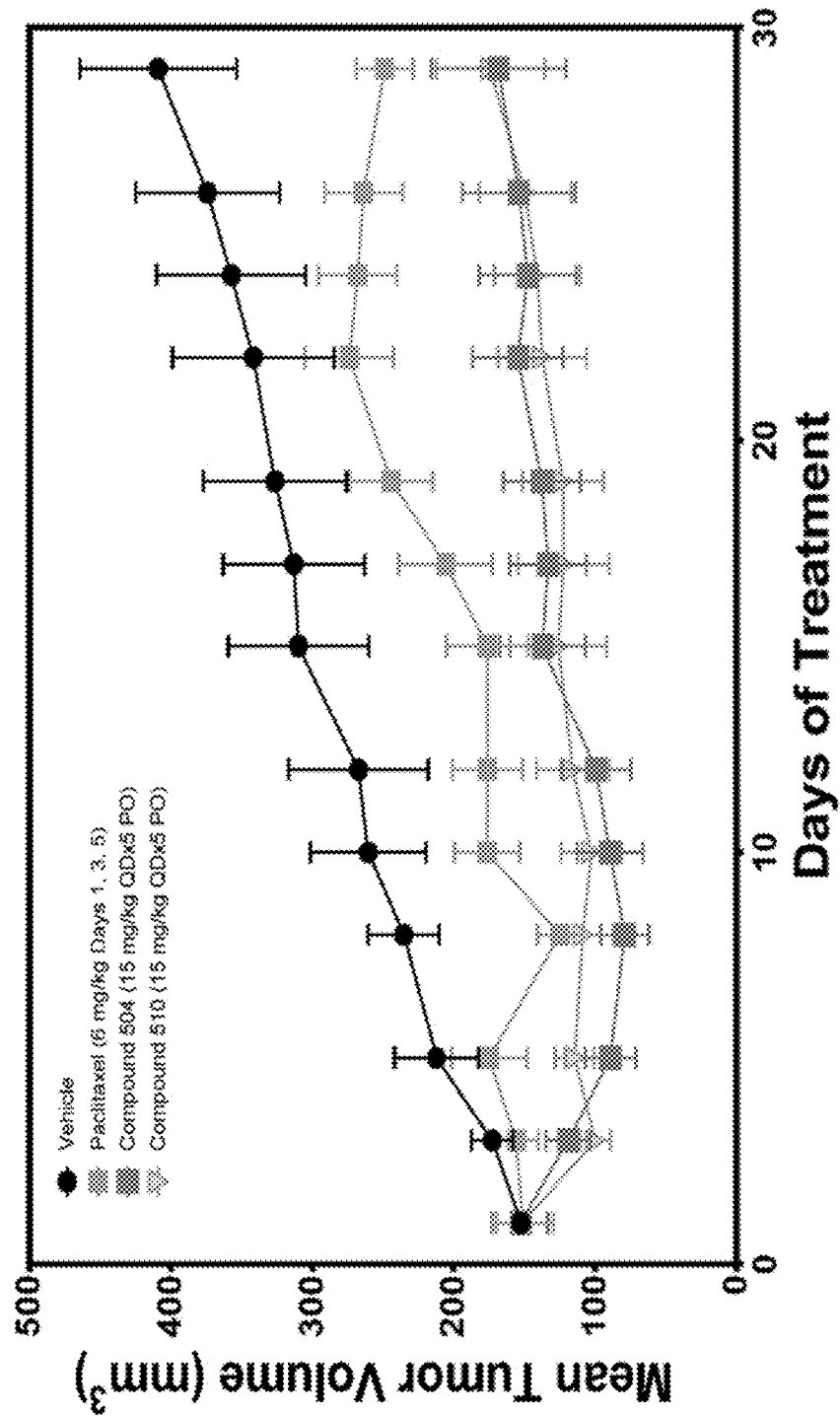
FIG. 5 is a graph of mean tumor volume as a function of time, and shows the effect of Compounds 504 and 510 on the volume of MDA-MB-468 xenografts in CB-17 SCID mice.

FIG. 5 is a graph of mean tumor volume as a function of time, and shows the effect of Compounds 504 and 510 on the volume of MDA-MB-468 xenografts in CB-17 SCID mice. The model demonstrated tumor growth inhibition without major toxicity (minimal or no side effects or weight loss up to 200 mg/kg daily dose).

Mice bearing MDA-MB-468 tumors were treated for three weeks with 30 mg/kg Compound 525 orally every day. Tumors were resected from the mice and fixed in buffered formalin and put into paraffin blocks. The blocks were sectioned and stained with antibodies against Ki67, Apotag, c-Myc, p-S473-Akt1 or p-S450-Akt1. The cells were imaged with a Nikon microscope.

There was a reduction in proliferation (Ki67) and an increase in apoptosis (Apotag) upon treatment with Compound 525. There were also overall reductions in c-Myc and PAK4 pathway signaling through Akt (phospho-Akt1).

Example 9. Z-138 Xenograft in SCID Mice

The impact of Compound 585 on tumor growth was tested using a Z-138 mantle cell lymphoma cancer xenograft model in SCID mice. Z-138 (ATCC #CRL-3001) mantle cell lymphoma cells were obtained from ATCC. These cells were grown in IMEM medium supplemented with 10% horse serum, 1% penicillin and streptomycin, and 2 mM L-glutamine. Cells were sub-cultured by dilution at a ratio of 1:5 to 1:10. Z-138 cells were harvested by centrifugation and counted using a hemocytometer. Cells were resuspended in PBS at a 2×108 cells per mL. Cells were placed on ice and mixed with an equal volume of Matrigel (BD Biosciences CB-40234). This mixture was kept on ice and injected into the left flank of mice in a volume of 0.2 mL, equivalent to $2 \times 10^7$ cells per mouse. Forty (40) CB-17 SCID mice were inoculated subcutaneously in the left flank with $2 \times 10^7$ Z-138 cells. Treatment was initiated when the tumors reached a mean volume of 125.2 mm$^3$. Mice were allocated to five (5) groups of eight (8) mice such that mean tumor volume in each group was within the range of 106.5 to 138.8 mm$^3$. Mice were treated with vehicle, standard of care/positive control drug (cyclophosphamide), or Compound 585. Compound 585 (10, 30, or 60 mg/kg) was given orally (PO) daily beginning on Day 1. Animal weights and conditions were recorded daily, and tumors were measured on Mondays, Wednesdays and Fridays.

Figure 6:
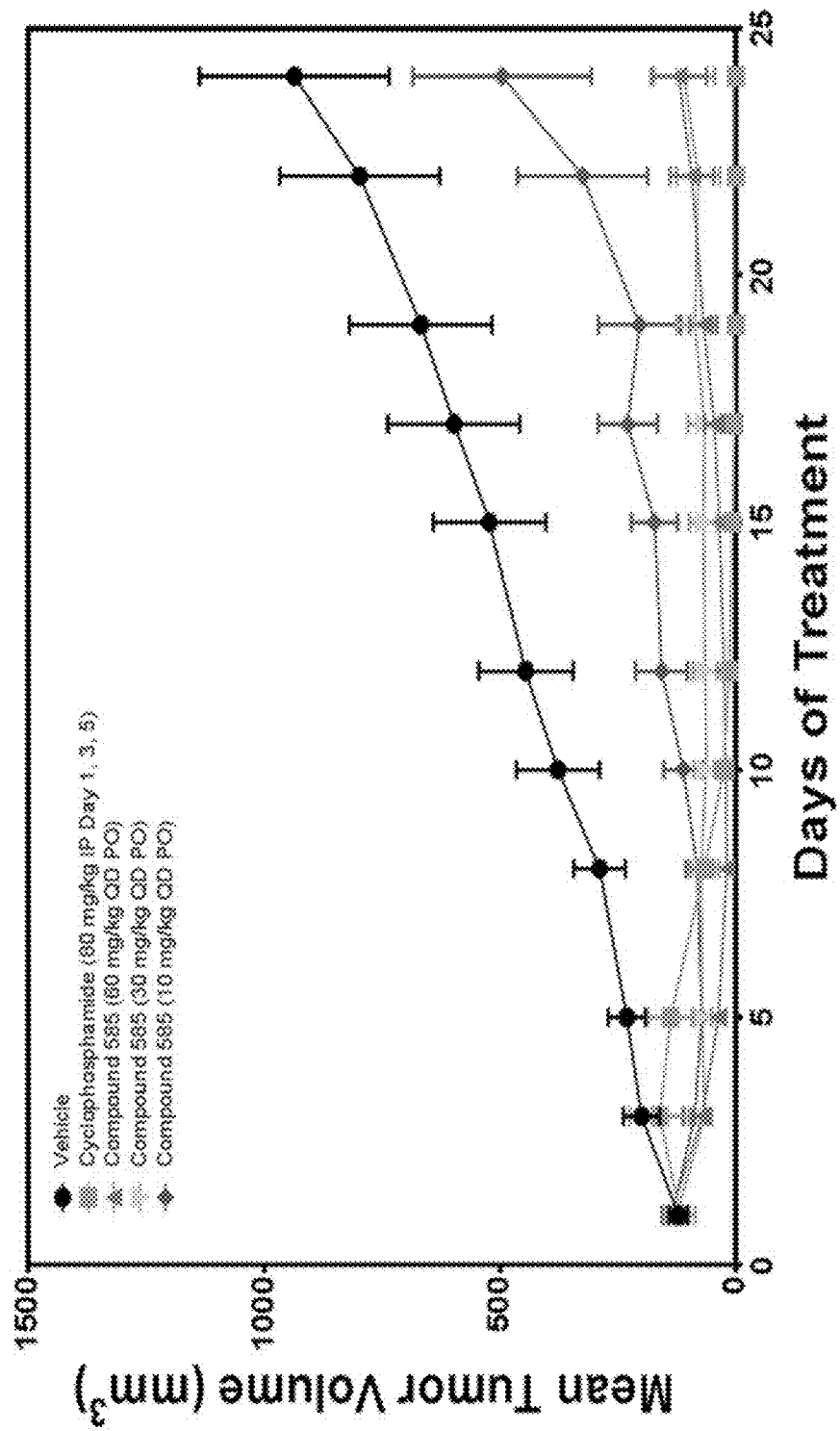
FIG. 6 is a graph of mean tumor volume as a function of time, and shows the effect of varying concentrations of Compound 585 on the volume of Z-138 xenografts in SCID mice.

FIG. 6 is a graph of mean tumor volume as a function of time, and shows the effect of varying concentrations of Compound 585 on the volume of Z-138 xenografts in SCID mice. The model demonstrated tumor growth inhibition and even tumor regression without major toxicity (minimal or no side effects or weight loss up to 200 mg/kg daily dose).

Example 10. Hep3B Xenograft in SCID Mice

The effects of Compound 585 were evaluated on tumor growth using a Hep3B hepatocellular carcinoma xenograft model in SCID mice. Hep 3B (ATCC #HTB-8064) hepatocellular carcinoma cells were obtained from ATCC. These cells were grown in DMEM medium supplemented with 10% fetal bovine serum and 1% penicillin and streptomycin. Cells were sub-cultured by dilution at a ratio of 1:4. Hep3B cells were harvested by centrifugation and counted using a hemocytometer. Cells were resuspended in PBS at a $5 \times 10^7$ cells per mL. Cells were placed on ice, then mixed with an equal volume of Matrigel™ (BD Biosciences CB-40234). This mixture was kept on ice and injected into the left flank of mice in a volume of 0.2 mL, equivalent to $5 \times 10^6$ cells per mouse. Thirty-two (32) SCID mice were inoculated subcutaneously in the left flank with $5 \times 10^6$ Hep 3B cells. Treatment was initiated when the tumors reached a mean volume of 103.7 mm3 (standard deviation±30 mm$^3$, range 17-183 mm$^3$). Mice were allocated to four (4) groups of eight (8) mice such that mean tumor volume in each group was within the range of 95 to 104 mm$^3$. Mice were treated with vehicle, standard of care control (doxorubicin), or Compound 585. With the exception of doxorubicin (which was given IP), all compounds were given by oral gavage. Compound 585 (20 or 60 mg/kg) was given orally (PO) daily. Animal weights and conditions were recorded daily, and tumors were measured on Mondays, Wednesdays and Fridays.

Figure 7:
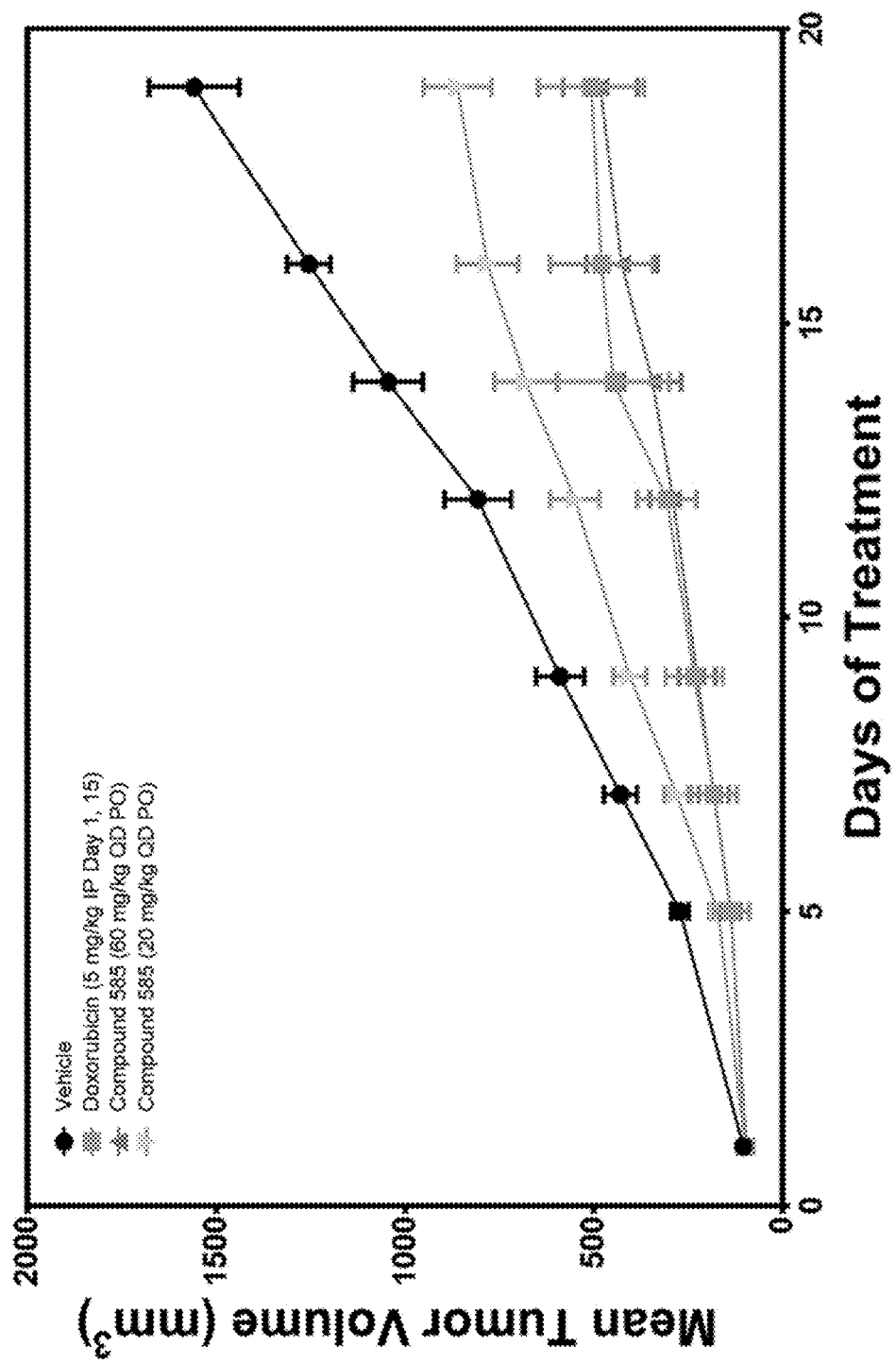
FIG. 7 is a graph of mean tumor volume as a function of time, and shows the effect of varying concentrations of Compound 585 on the volume of Hep 3B xenografts in SCID mice.

FIG. 7 is a graph of mean tumor volume as a function of time, and shows the effect of varying concentrations of Compound 585 on the volume of Hep 3B xenografts in SCID mice. The model demonstrated tumor growth inhibition without major toxicity (minimal or no side effects or weight loss up to 200 mg/kg daily dose).

Example 11. MOLT-4 Xenograft in SCID Mice

In this study, the impact of Compounds 667 and 728 on tumor growth was tested using the Molt-4 T-ALL cancer xenograft model in SCID mice. MOLT-4 (CRL-1582) acute lymphoblastic leukemia cells were obtained from ATCC. These cells were grown in RPMI-1640 medium supplemented with 10% fetal bovine serum, 1% penicillin and streptomycin. Cells were sub-cultured by transferring floating cells to a new flask and trypsinizing adherent cells before subculturing at a ratio of 1:4. Molt-4 cells were harvested by centrifugation and counted using a hemocytometer. Cells were resuspended in PBS at a $5 \times 10^7$ cells per mL. Cells were placed on ice and mixed with an equal volume of Matrigel (BD Biosciences CB-40234). This mixture was kept on ice and injected into the left flank of mice in a volume of 0.2 mL, equivalent to $5 \times 10^6$ cells per mouse. Twenty-four (24) CB-17 SCID mice were inoculated subcutaneously in the left flank with the Molt-4 cells. Treatment was initiated when the tumors reached a mean volume of approximately 100 mm$^3$. Mice were allocated to three (3) groups of eight (8) mice. Mice were treated with vehicle, Compound 667 or Compound 728. Compounds 667 and 728 (100 mg/kg) were given orally (PO) twice daily (BID) beginning on Day 1. Animal weights and conditions were recorded daily, and tumors were measured on Mondays, Wednesdays and Fridays.

Figure 8:
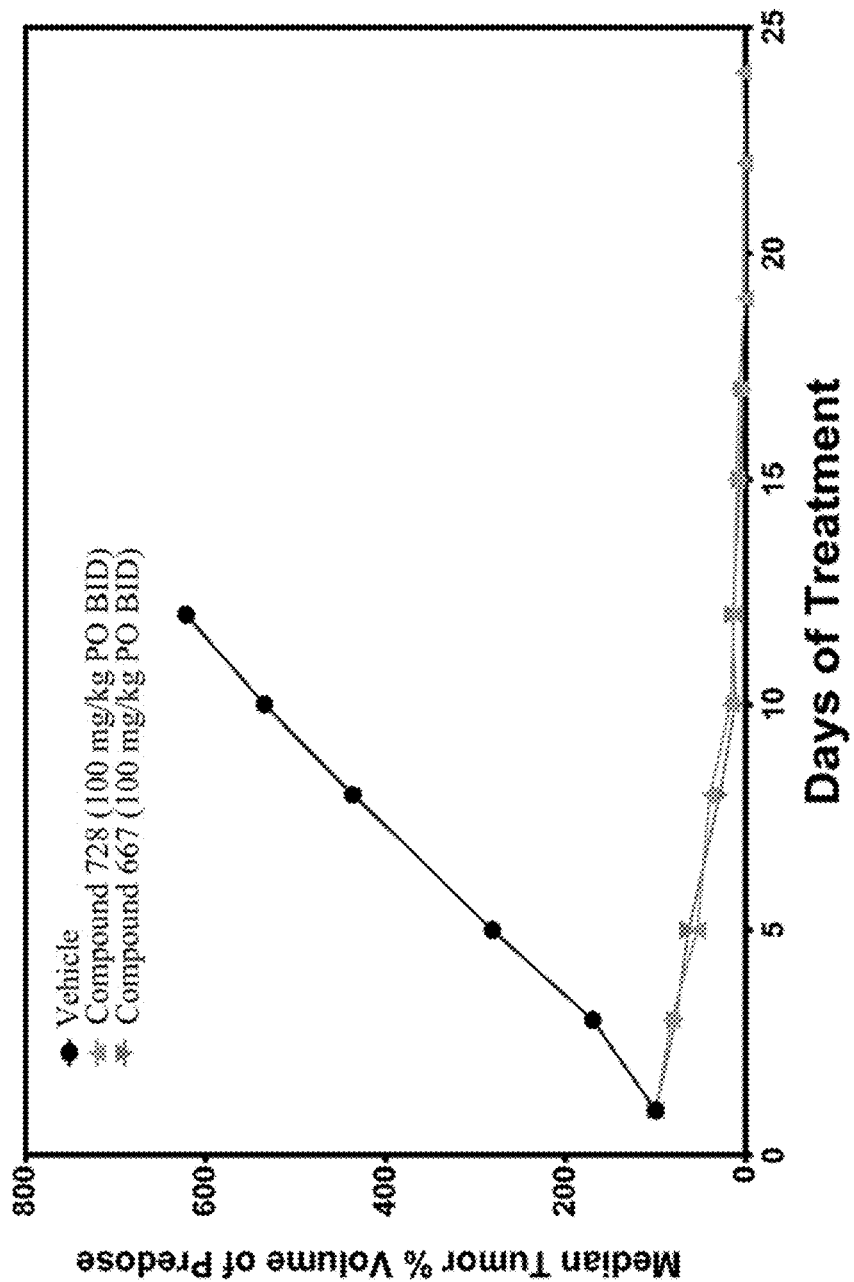
FIG. 8 is a graph of median tumor volume (as a percentage of pre-dose tumor volume) as a function of time, and shows the effect of Compound 667 and Compound 728 on the volume of Molt-4 xenografts in SCID mice.

FIG. 8 is a graph of median tumor volume (as a percentage of pre-dose tumor volume) as a function of time, and shows the effect of Compound 667 and Compound 728 on the volume of Molt-4 xenografts in SCID mice. The model demonstrated tumor growth inhibition.

REFERENCES

1. Arias-Romano, L. E.; Chernoff, *J. Biol. Cell*, 2008, 100, 97-108.
2. a) Dart, A. E.; Wells, C. M. *European Journal of Cell Biology*, 2013, 92, 129-138. b) Clairvoyant, F.; Zhu. S. et al. *J Biol Chem*, 2002, 277, 550-8. c) Cammarano, M. S. et al. *Mol Cell Biol.*, 2005, 21, 9532-42. d) Wells, C. M. et al, *J Cell Sci.*, 2010, 123, 1663-73. d) Siu, M. K. et al. *Proc. Natl. Acad. Sci. USA*, 2010, 107(43), 18622-7.
3. a) Guo, C. et al.; *J Med. Chem.*, 2012, 55, 4728-4739 b) Deacon, S. W. et al. *Chemistry & Biology*, 2008, 15, 322-331c) Wells, C. M.; Jones, G. E. *Biochem. J*, 2010, 425, 465-473.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:
1. A compound represented by Structural Formula IX:

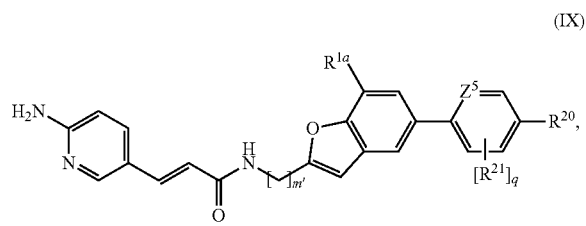

(IX)

or a pharmaceutically acceptable salt thereof, wherein:
m" is 1 or 2;
$R^{1a}$ is halogen, halo($C_1$-$C_4$)alkyl, ($C_1$-$C_4$)alkyl, —O—($C_1$-$C_4$)alkyl, —O-halo($C_1$-$C_4$)alkyl, optionally substituted ($C_5$-$C_{15}$)aryl or optionally substituted ($C_5$-$C_{15}$) heteroaryl;
$Z^5$ is —N— or —C(H)—;
$R^{20}$ is ($C_1$-$C_4$)alkyl, ($C_1$-$C_4$)haloalkyl, —O—($C_0$-$C_4$ alkylene)carbocyclyl, —O—($C_0$-$C_4$ alkylene)heterocyclyl, —C(H)(OH)-carbocyclyl, —C(H)(OH)-heterocyclyl, —C(H)($CH_3$)-carbocyclyl, —C(H)($CH_3$)-heterocyclyl, —C(O)($C_1$-$C_4$)alkyl, —C(S)($C_1$-$C_4$)alkyl, —C(O)($C_0$-$C_4$ alkylene)$NR^{11}R^{12}$, —C(S)($C_0$-$C_4$ alkylene)$NR^{11}R^{12}$, —S(O)$_2$($C_1$-$C_4$)alkyl, —S(O)$_2NR^{11}R^{12}$ or —C(O)$NR^{13}NR^{11}R^{12}$, wherein:
$R^{11}$ and $R^{12}$ are each independently hydrogen, optionally substituted $C_1$-$C_4$ alkyl, optionally substituted carbocyclyl, or optionally substituted heterocyclyl; or $R^{11}$ and $R^{12}$ are taken together with the nitrogen atom to which they are commonly attached to form an optionally substituted heterocyclyl; and $R^{13}$ is hydrogen or optionally substituted $(C_1-C_4)$alkyl;

each $R^{21}$, if present, is independently halo; and q is 0, 1, 2, 3 or 4.

2. The compound of claim 1, represented by Structural Formula XII:

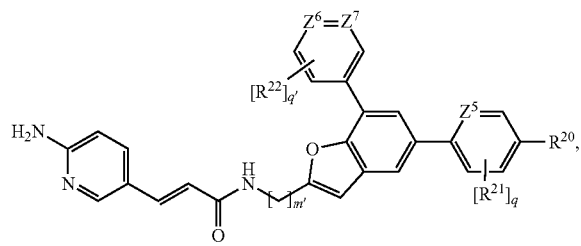

(XII)

or a pharmaceutically acceptable salt thereof, wherein:

each of $Z^6$ and $Z^7$ is independently —N— or —C(H)—, wherein no more than one of $Z^6$ and $Z^7$ is nitrogen;

each $R^{22}$, if present, is independently halo, cyano, $(C_1-C_3)$alkyl, halo$(C_1-C_3)$alkyl, hydroxy, $(C_1-C_3)$alkoxy or halo$(C_1-C_3)$alkoxy; and q' is 0, 1, 2 or 3.

3. The compound of claim 1, wherein q is 0, 1 or 2.

4. The compound of claim 1, wherein $R^{21}$, for each occurrence and if present, is fluoro.

5. The compound of claim 1, wherein $R^{20}$ is —C(O)(C$_0$-C$_4$ alkylene)NR$^{11}$R$^{12}$ or —C(S)(C$_0$-C$_4$ alkylene)NR$^{11}$R$^{12}$, wherein $R^{11}$ and $R^{12}$ are taken together with the nitrogen atom to which they are commonly attached to form an optionally substituted $(C_3-C_7)$heterocyclyl having 1 or 2 heteroatoms independently selected from nitrogen, oxygen and sulfur.

6. The compound of claim 1, wherein the heterocyclyl formed by $R^{11}$ and $R^{12}$ taken together with the nitrogen atom to which they are commonly attached is optionally substituted with 1, 2, 3 or 4 substituents independently selected from halo, hydroxyl, halo$(C_1-C_3)$alkyl, $(C_1-C_3)$alkyl and $(C_1-C_3)$alkoxy.

7. The compound of claim 1, wherein $Z^5$ is —C(H)—.

8. The compound of claim 1, wherein $Z^5$ is —N—.

9. The compound of claim 1, represented by Structural Formula X:

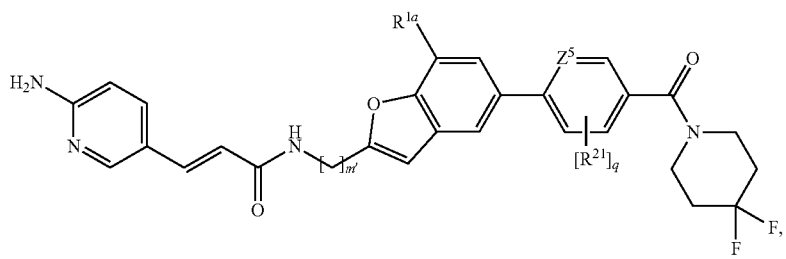

(X)

or a pharmaceutically acceptable salt thereof.

10. The compound of claim 1, wherein the heterocyclyl formed by $R^{11}$ and $R^{12}$ taken together with the nitrogen atom to which they are commonly attached is optionally substituted with 1 or 2 substituents independently selected from halo, $(C_1-C_3)$alkyl, halo$(C_1-C_3)$alkyl, hydroxy, $(C_1-C_3)$alkoxy and halo$(C_1-C_3)$alkoxy.

11. The compound of claim 1, wherein the carbocyclyl or heterocyclyl of $R^{1a}$ is optionally substituted with 1, 2 or 3 substituents independently selected from halo, cyano, $(C_1-C_3)$alkyl, halo$(C_1-C_3)$alkyl, hydroxy, $(C_1-C_3)$alkoxy and halo$(C_1-C_3)$alkoxy.

12. The compound of claim 9, represented by Structural Formula XI:

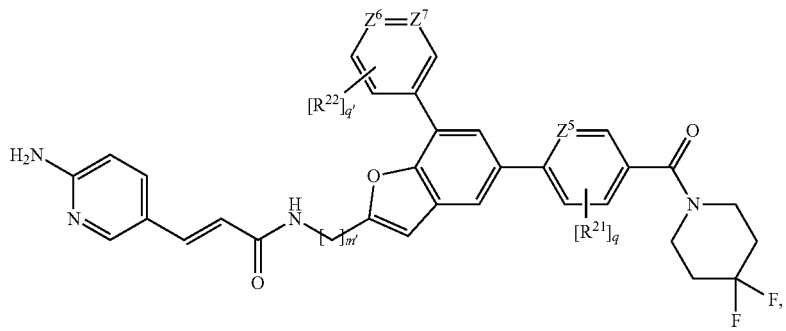

(XI)

or a pharmaceutically acceptable salt thereof, wherein:
each of $Z^6$ and $Z^7$ is independently —N— or —C(H)—, wherein no more than one of $Z^6$ and $Z^7$ is nitrogen;
each $R^{22}$, if present, is independently halo, cyano, $(C_1-C_3)$alkyl, halo$(C_1-C_3)$alkyl, hydroxy, $(C_1-C_3)$alkoxy or halo$(C_1-C_3)$alkoxy; and
q' is 0, 1, 2 or 3.
13. A compound, represented by any one of the following structural formulas:
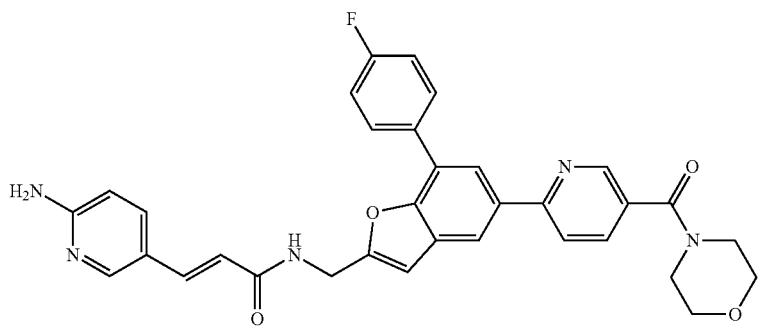
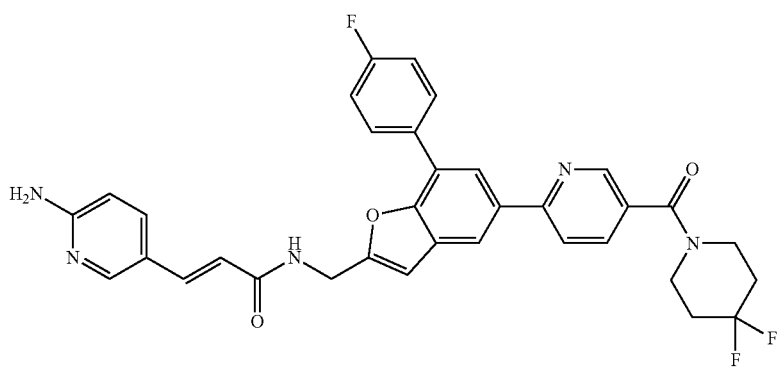
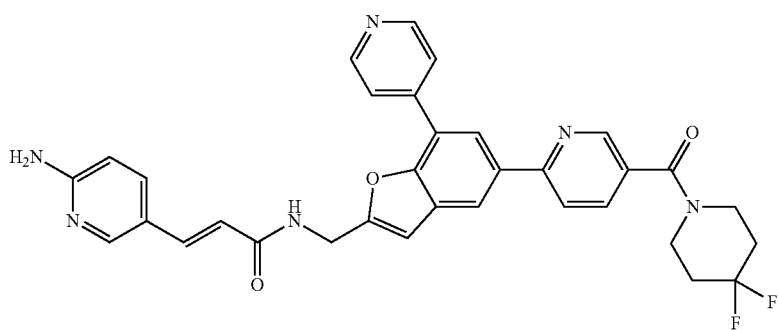
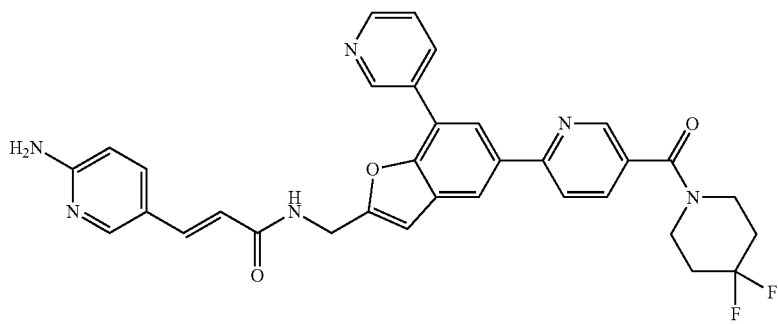

-continued
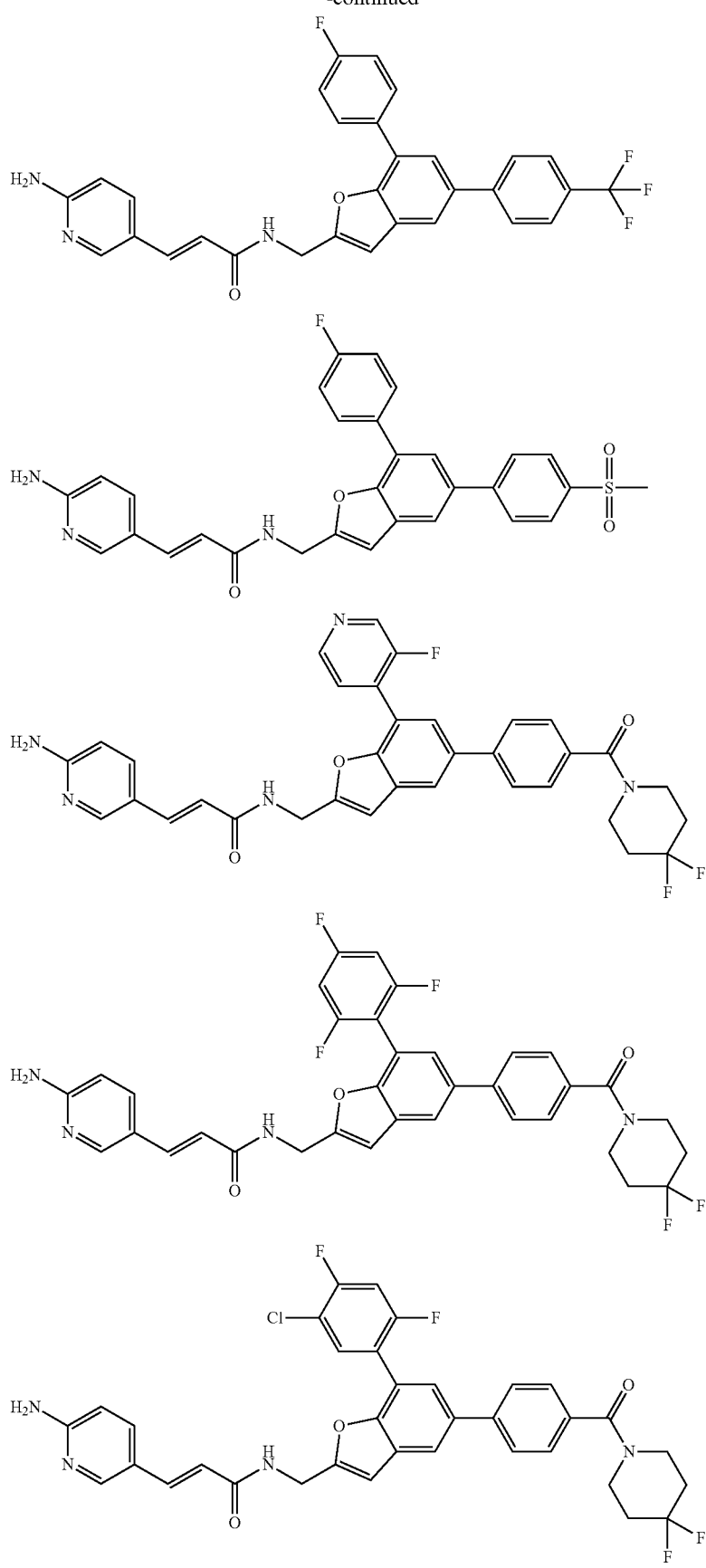

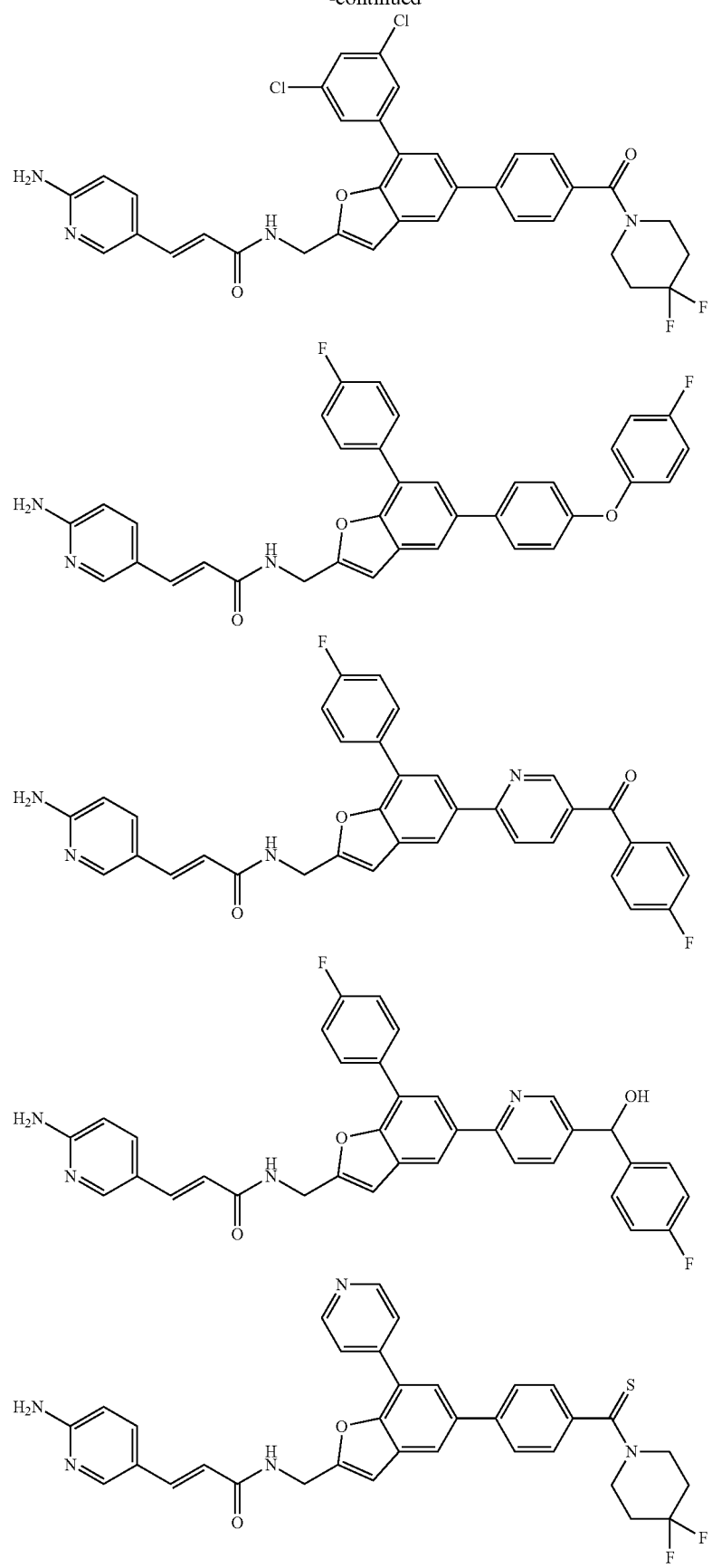

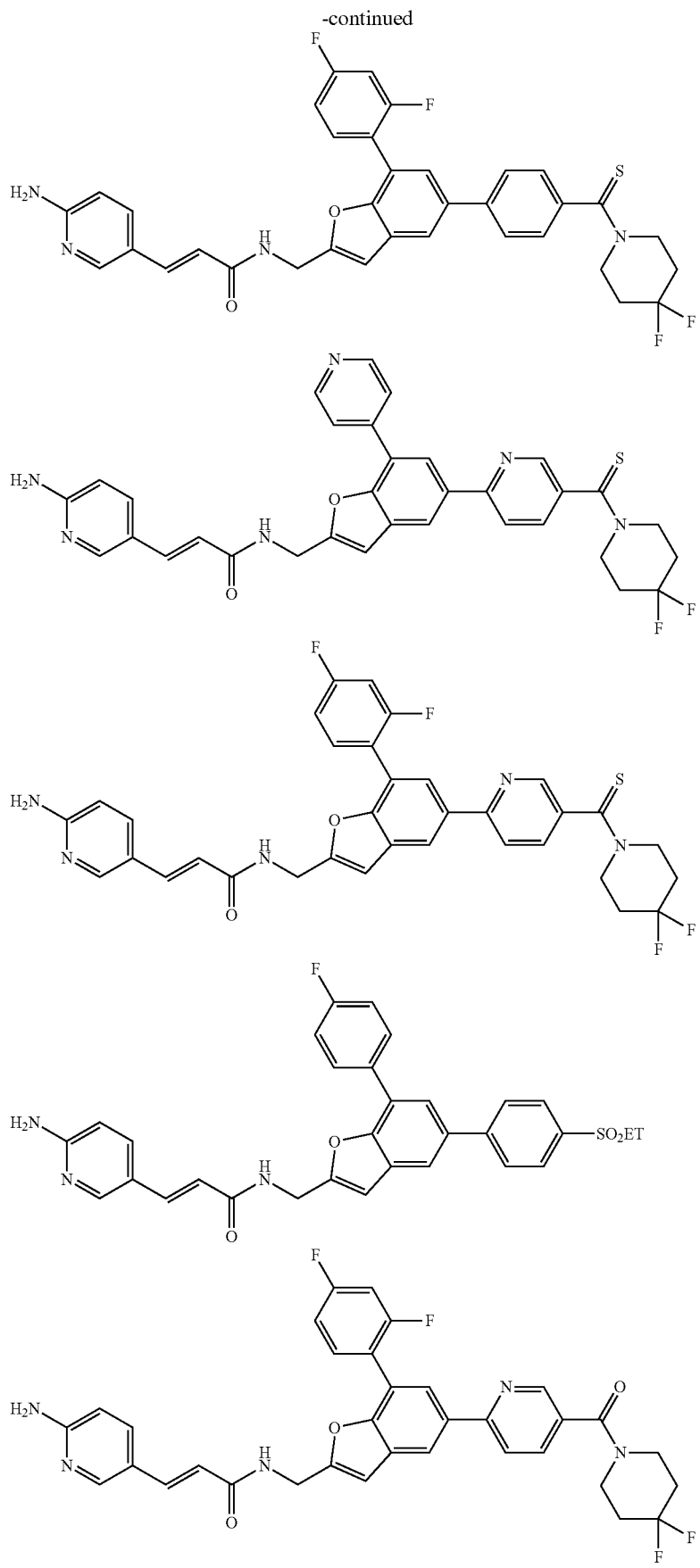
-continued

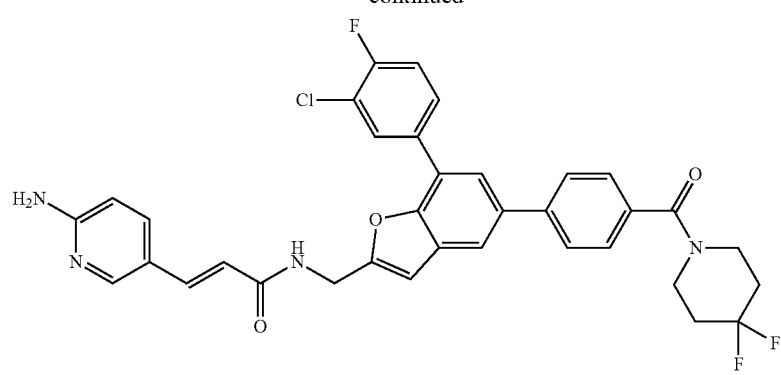
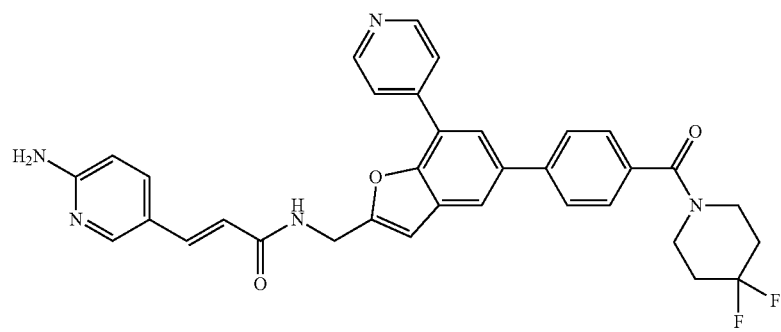
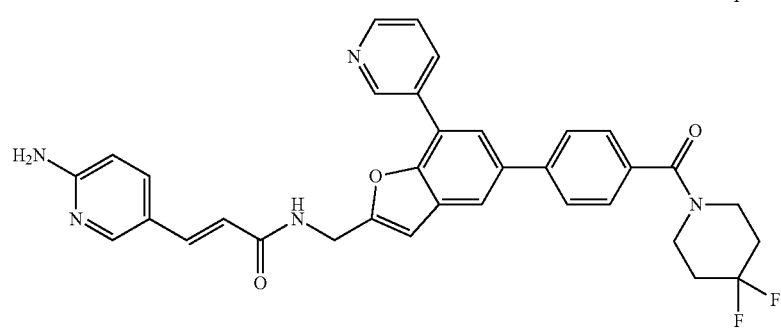
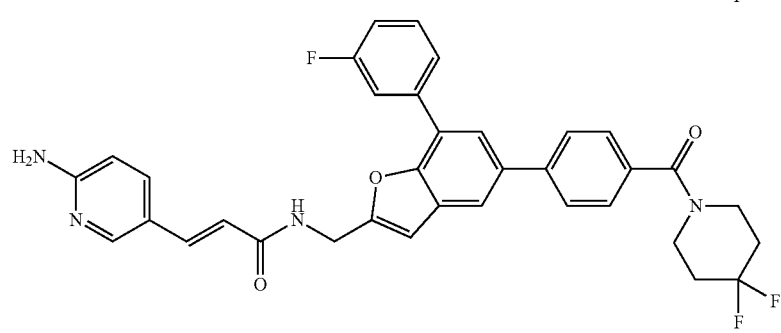
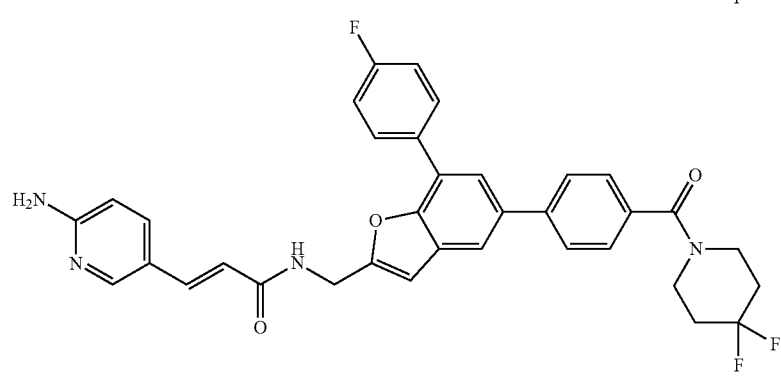

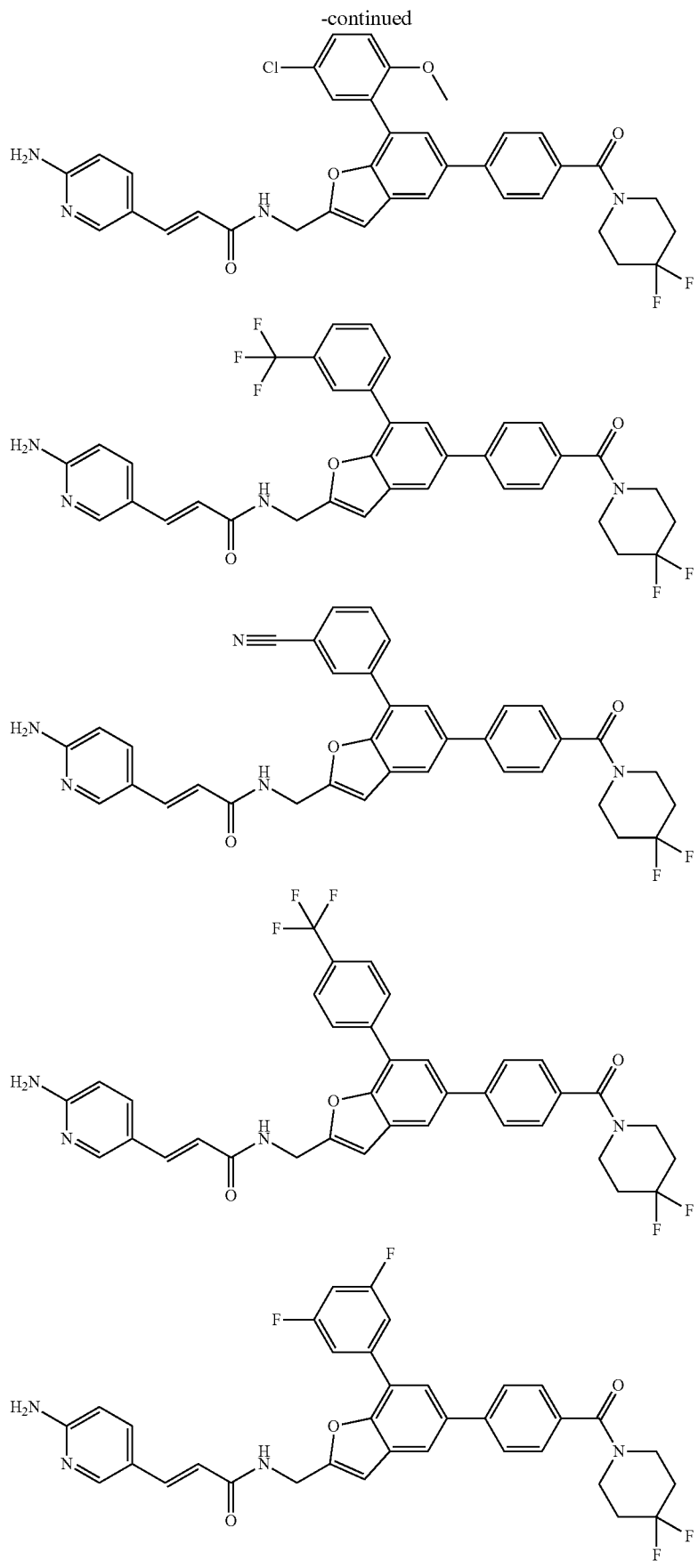

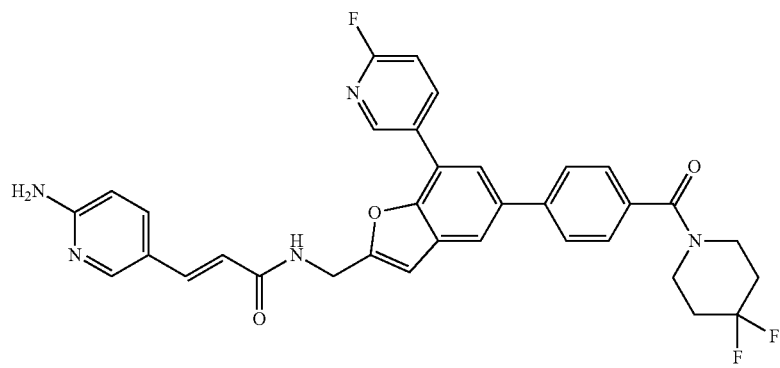
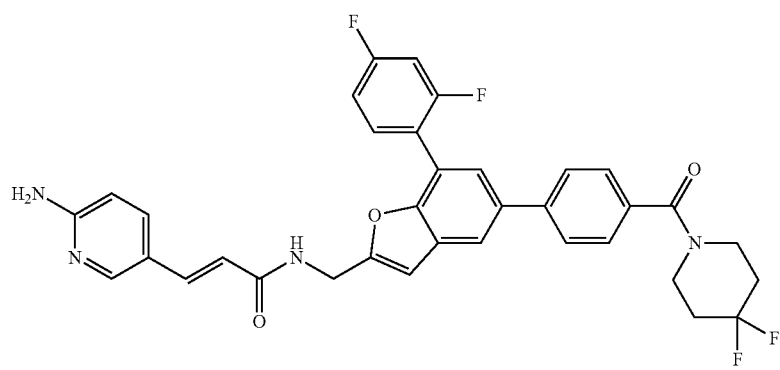
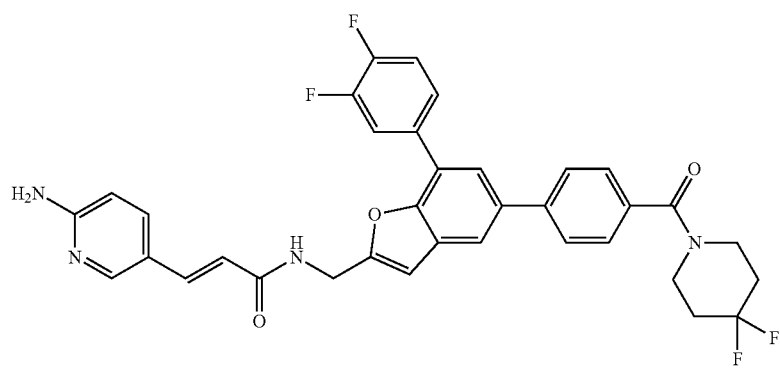
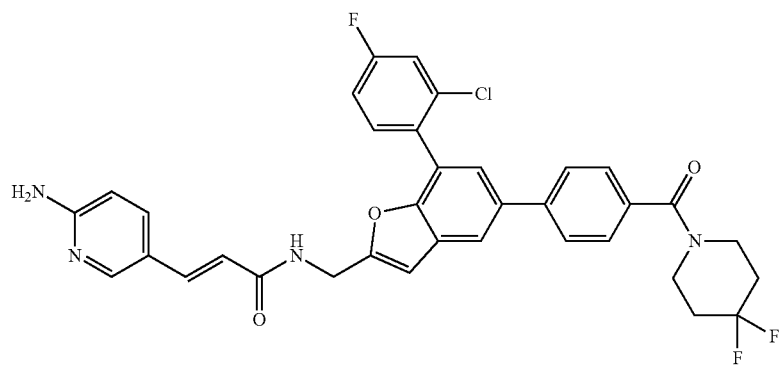

-continued
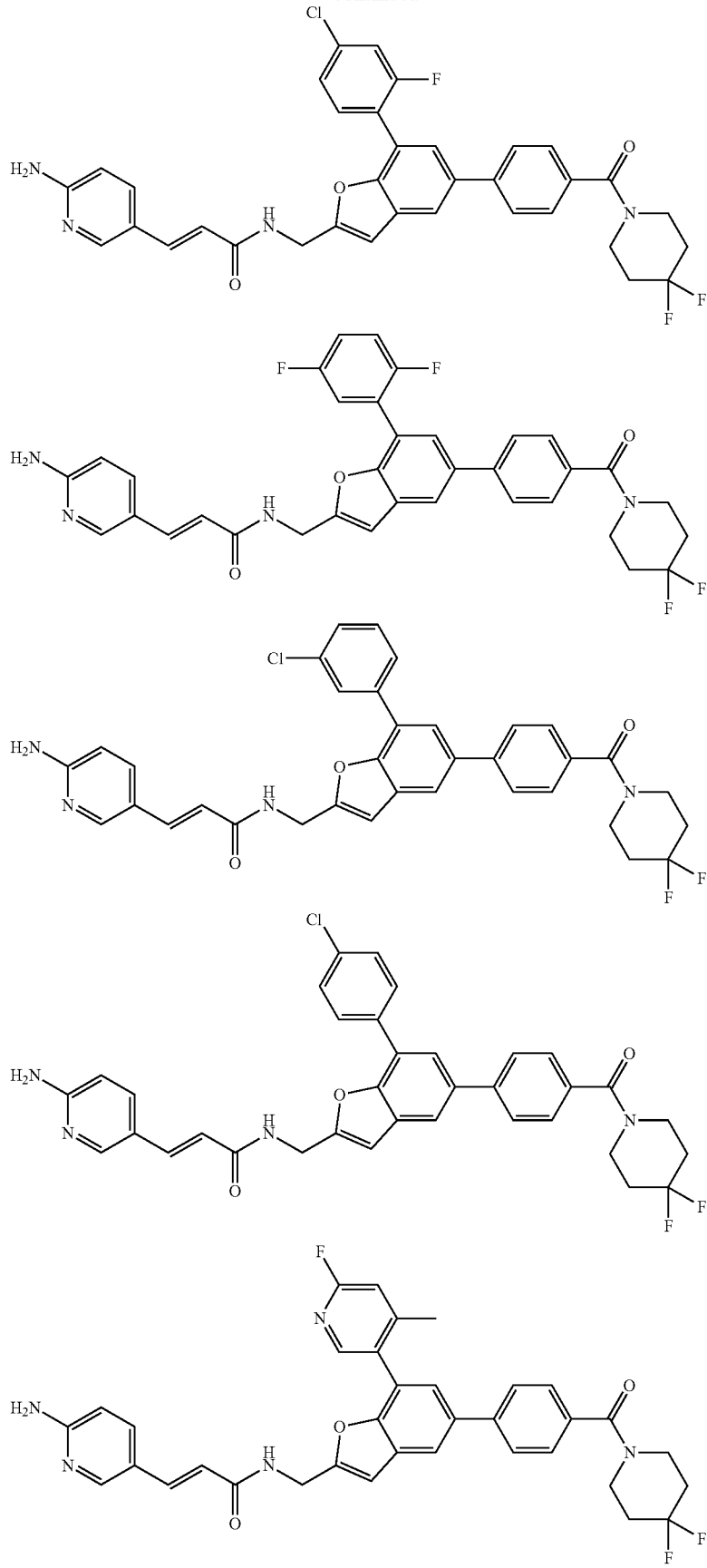

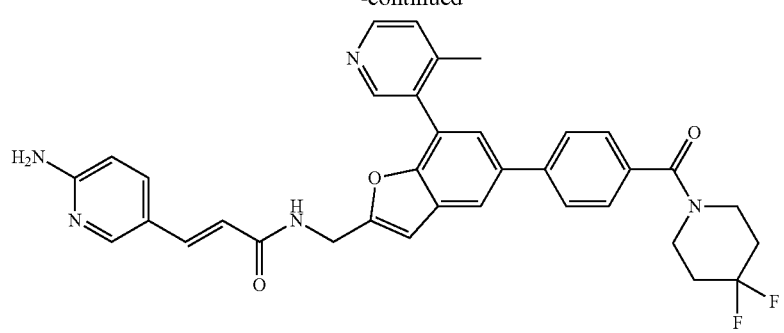
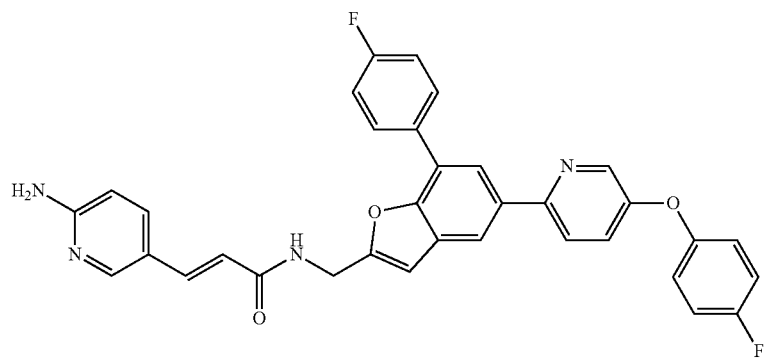
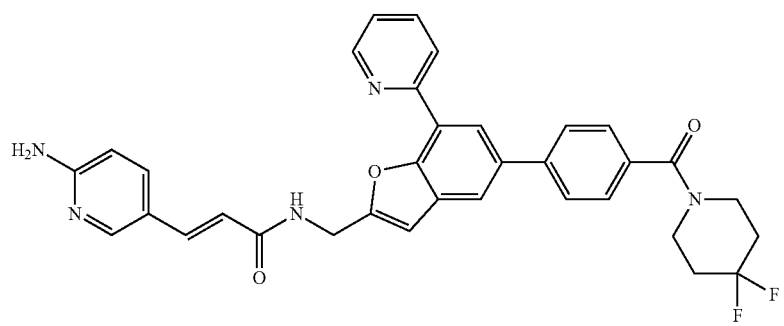
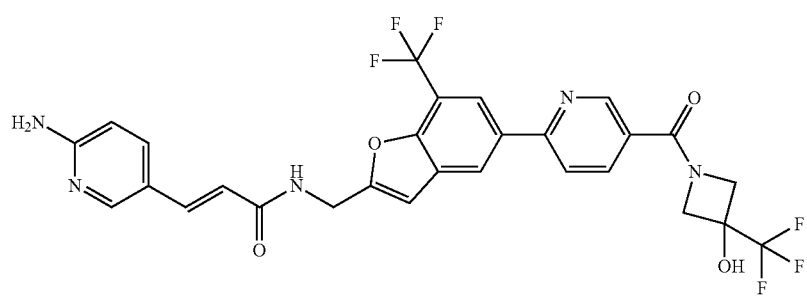
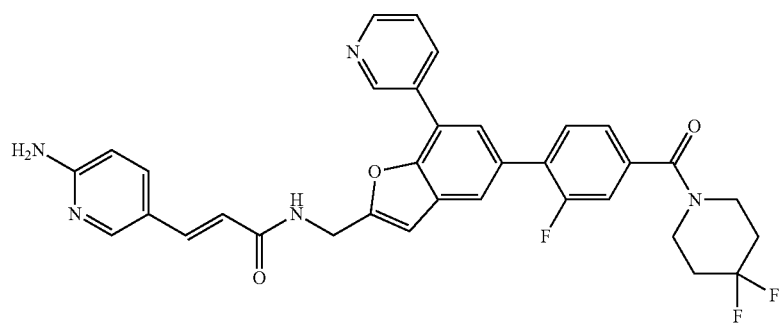

-continued
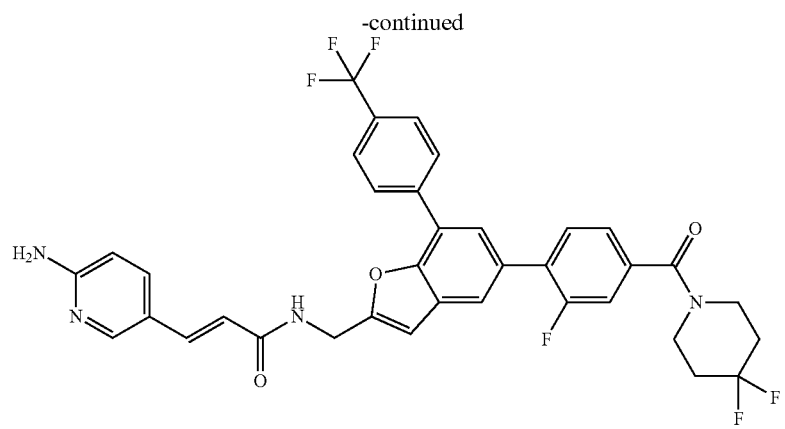
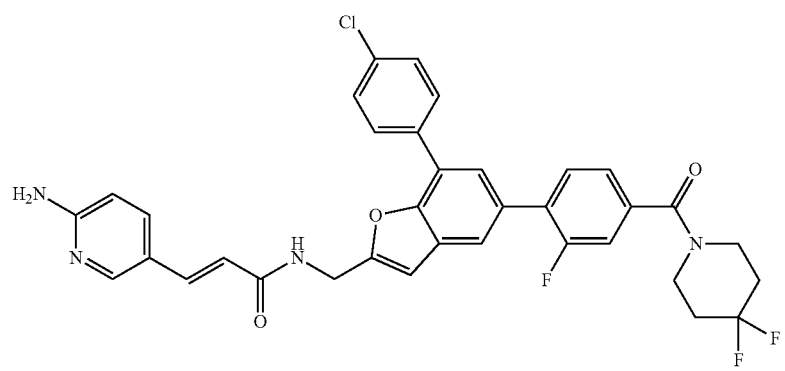
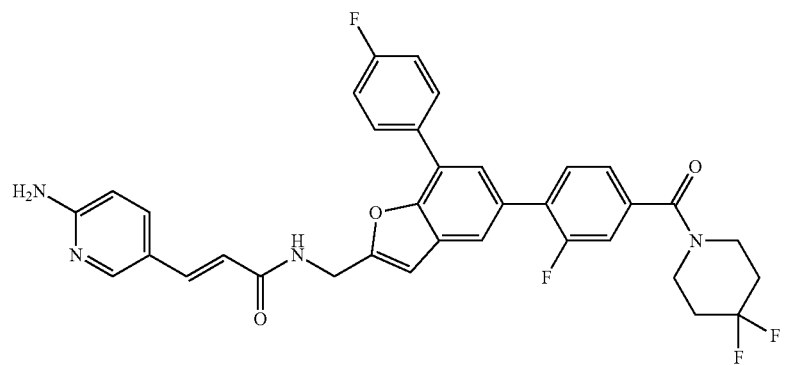
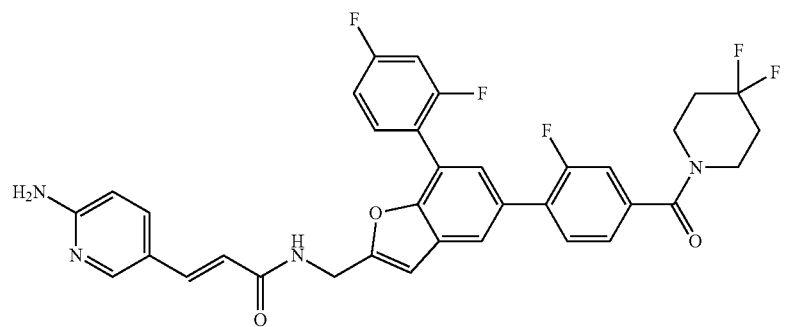

-continued
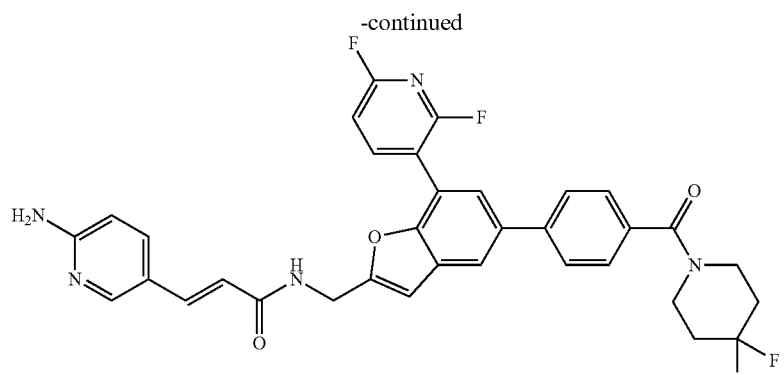
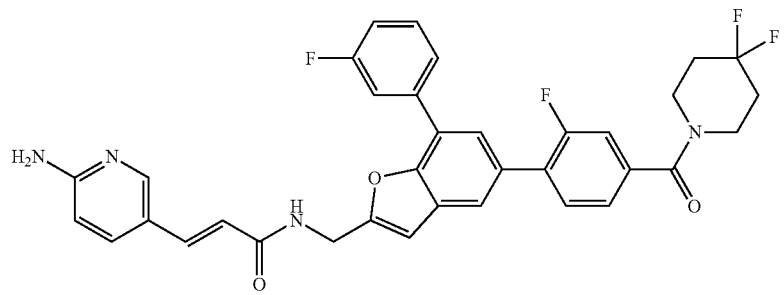
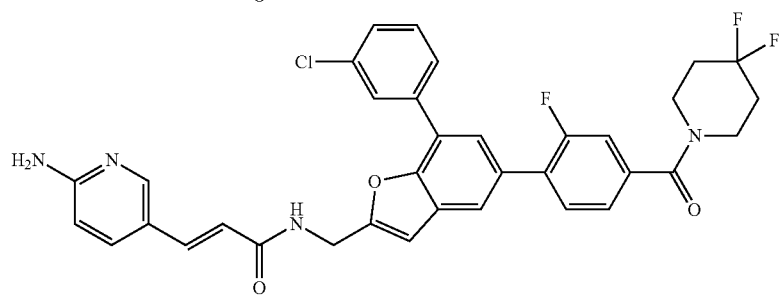
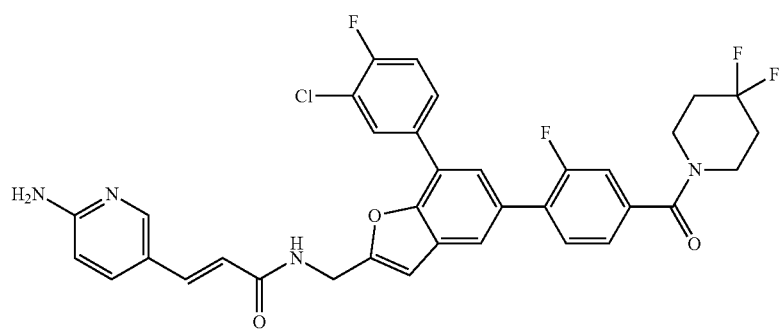
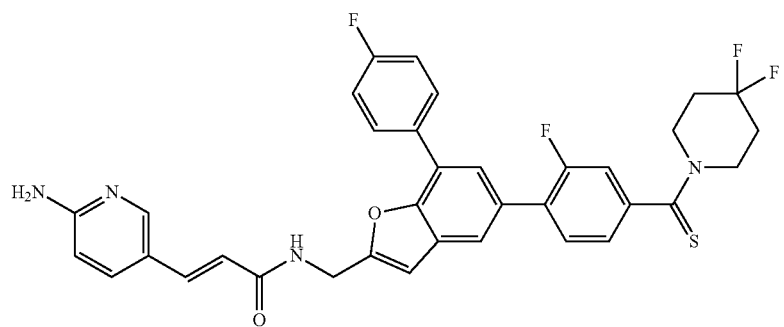

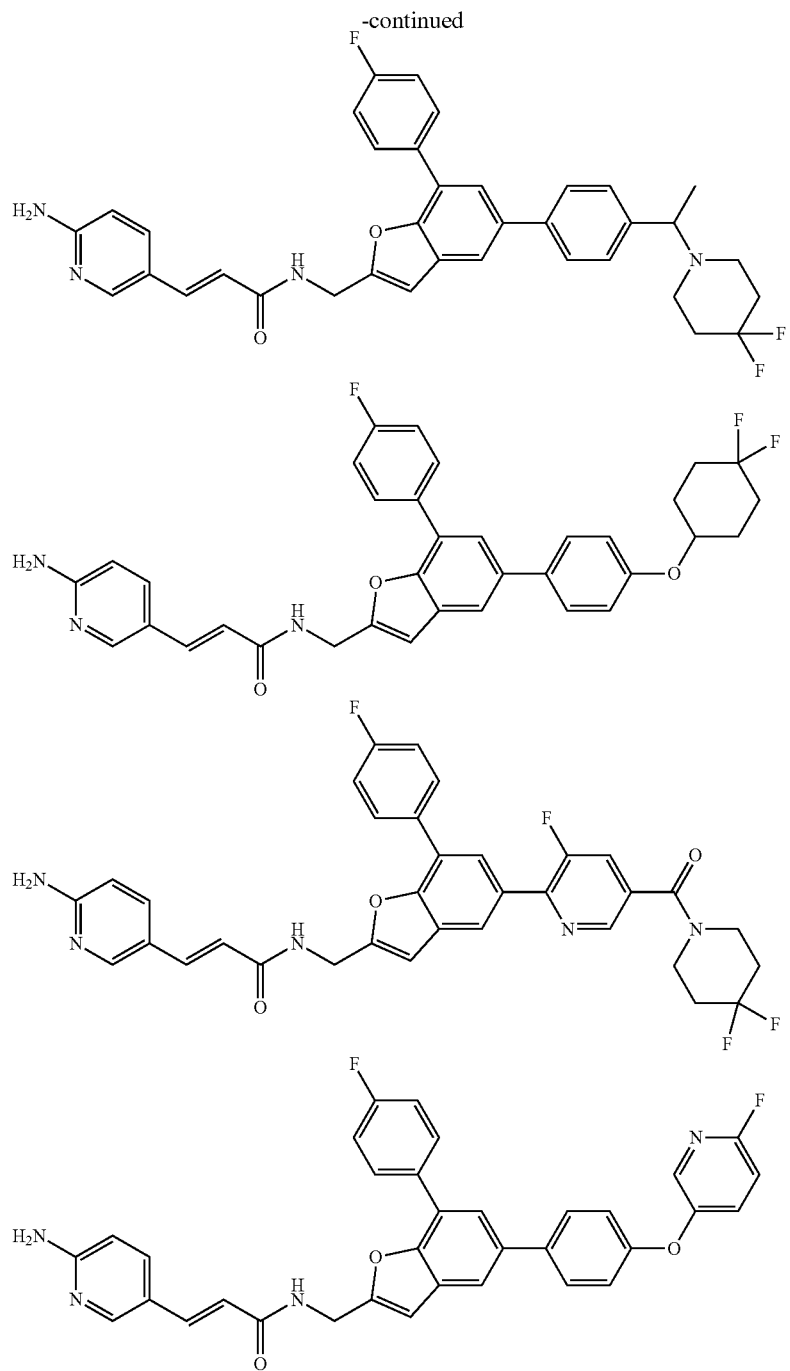

or a pharmaceutically acceptable salt thereof.

14. A pharmaceutical composition comprising:
(a) a compound of claim 1, or a pharmaceutically acceptable salt thereof; and
(b) a pharmaceutically acceptable carrier.

15. A method of treating cancer in a subject in need thereof, comprising administering to the subject a therapeutically effective amount of a compound of claim 1, or a pharmaceutically acceptable salt thereof, or a pharmaceutical composition of claim 14.

16. The method of claim 15, wherein the cancer is lymphoma.

17. The method of claim 15, wherein the cancer is cervical cancer.

18. The method of claim 15, wherein the cancer is mantle cell lymphoma.

19. A method of treating a PAK-mediated disorder in a subject in need thereof, comprising administering to the subject in need thereof a therapeutically effective amount of a compound of claim 1, wherein the PAK-mediated disorder is cancer, a neurodegenerative disease or an immune system disease.

20. A compound represented by any one of the following structural formulas:
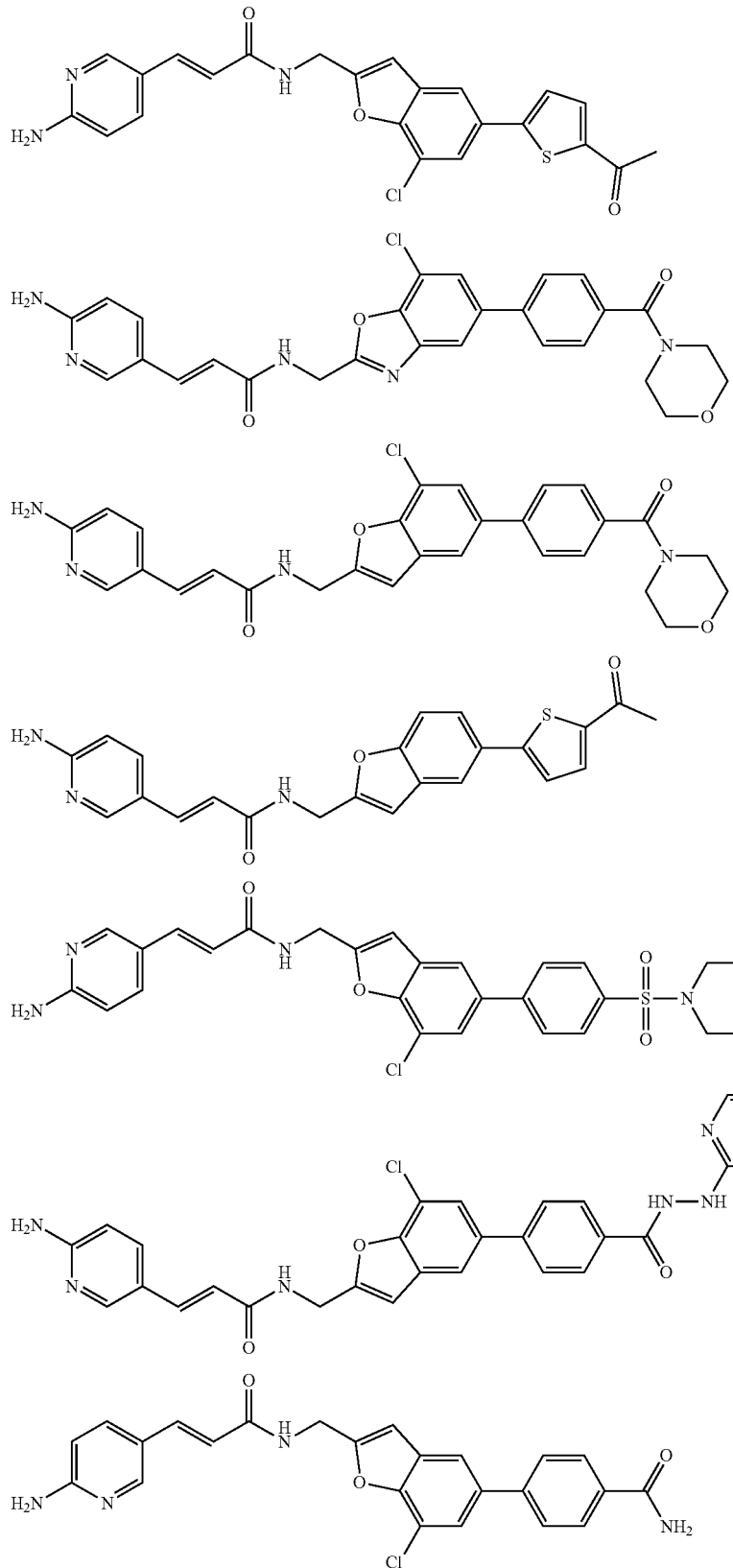

-continued
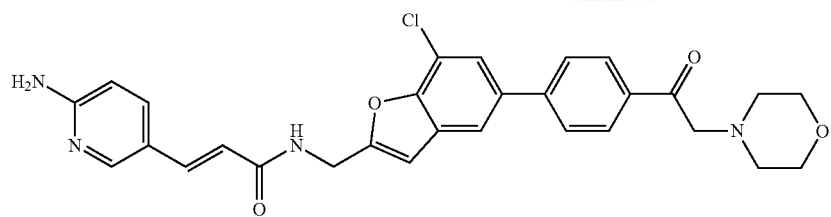
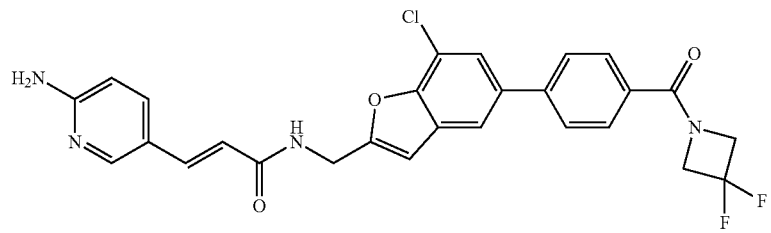
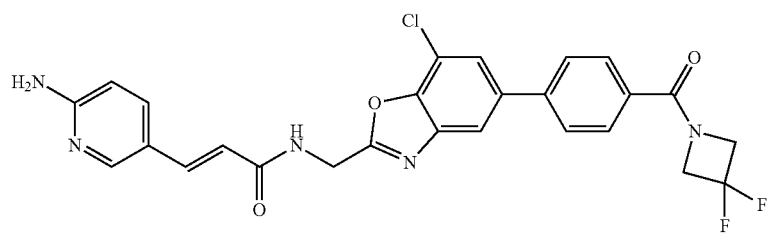
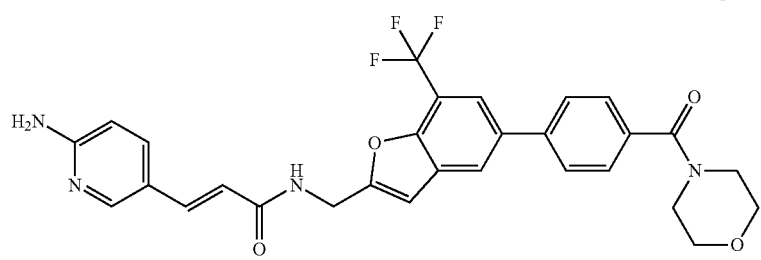
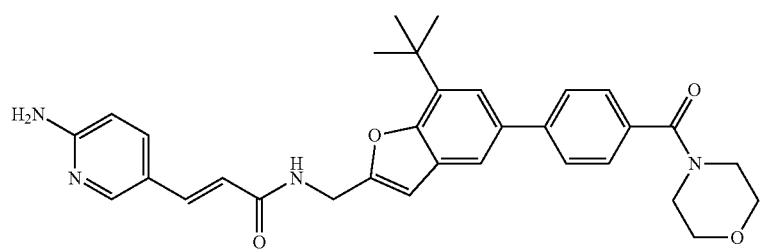
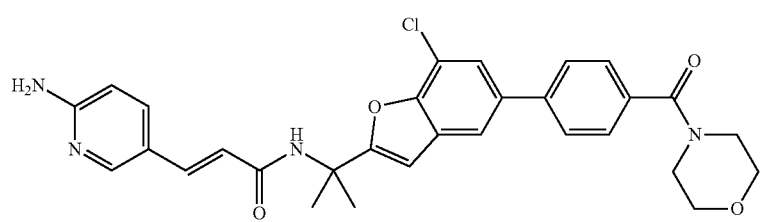
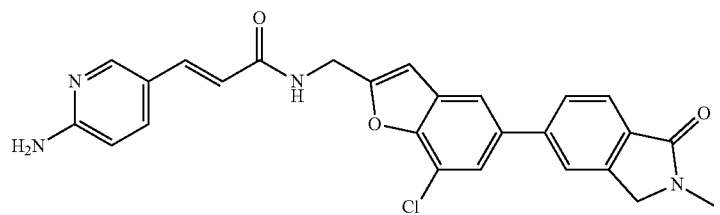

-continued
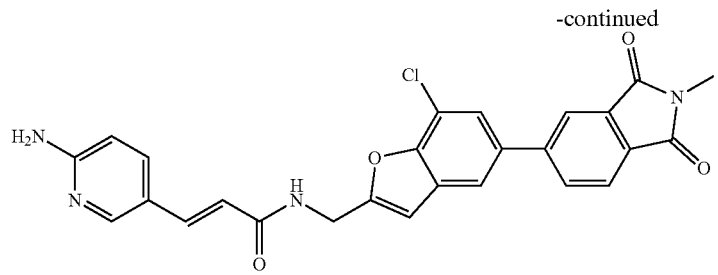
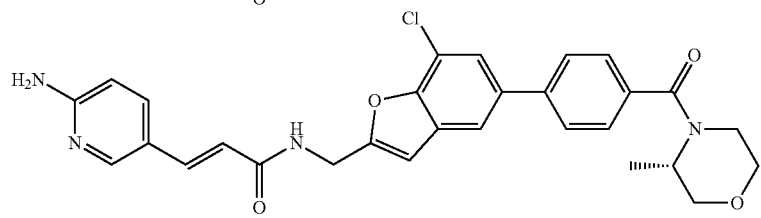
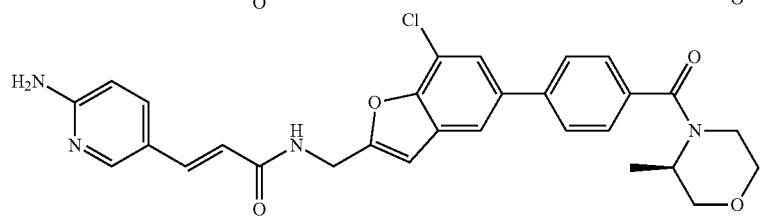
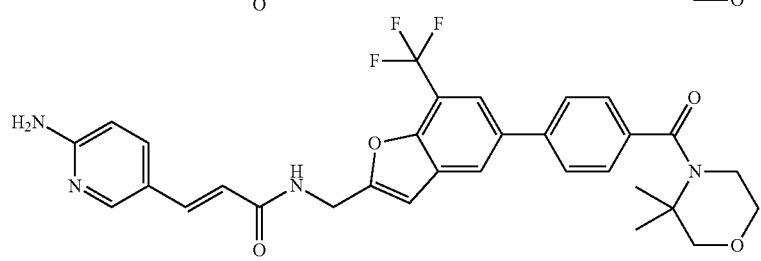
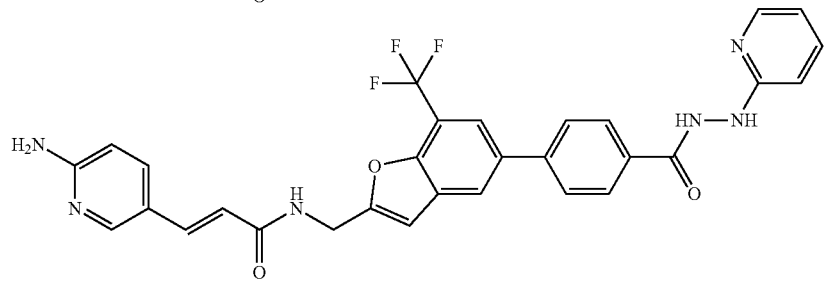
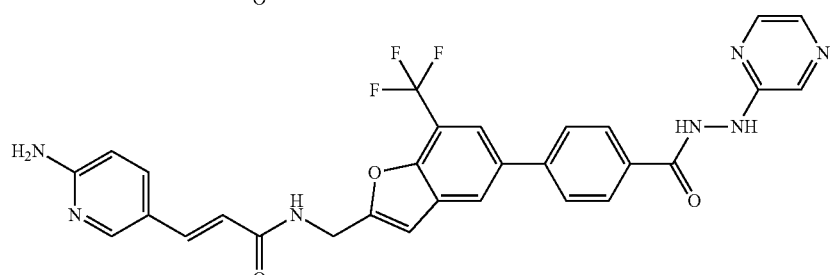
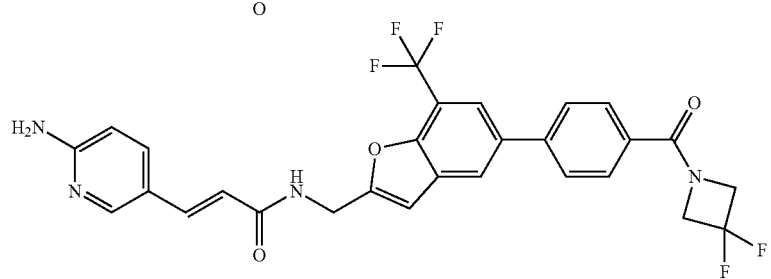

-continued
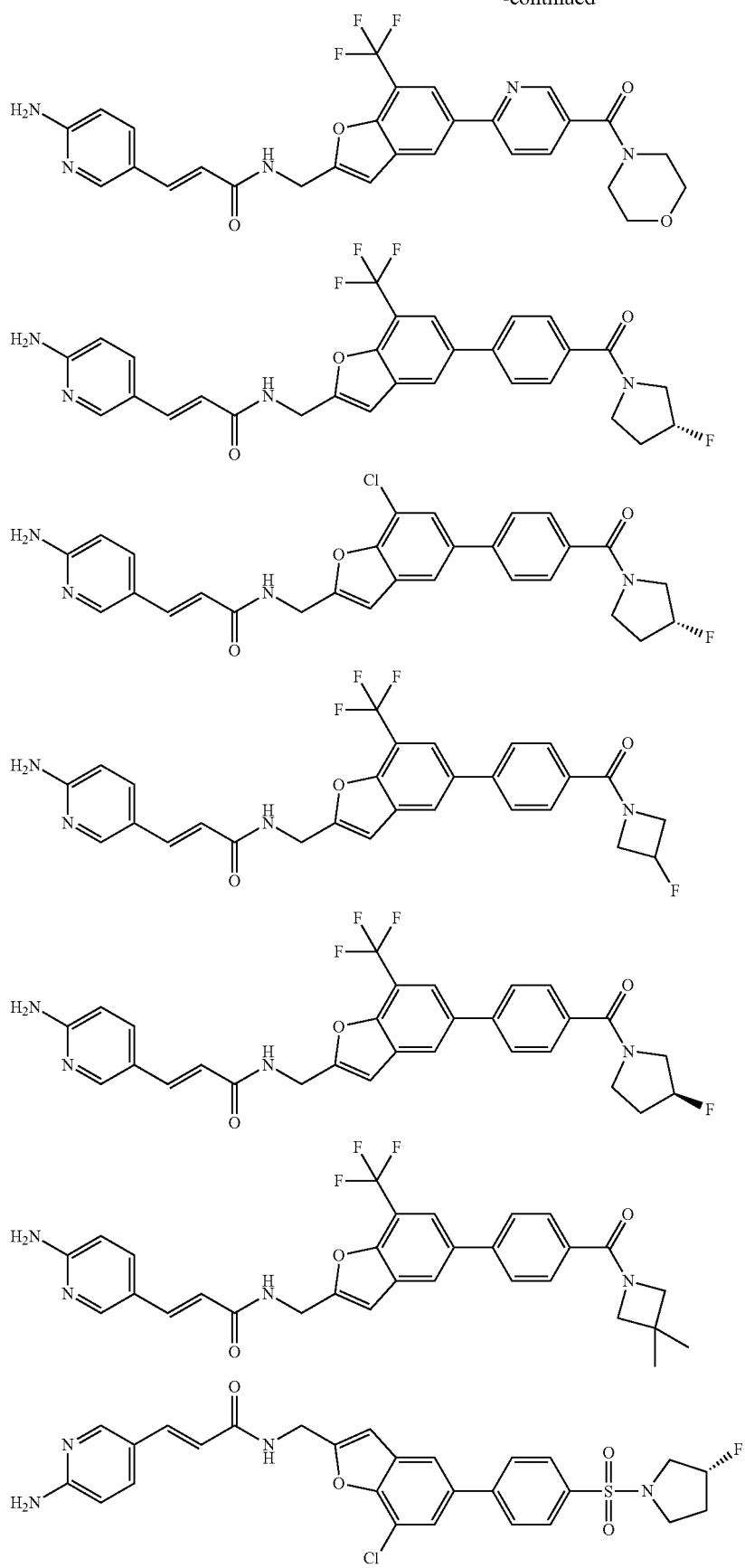

-continued
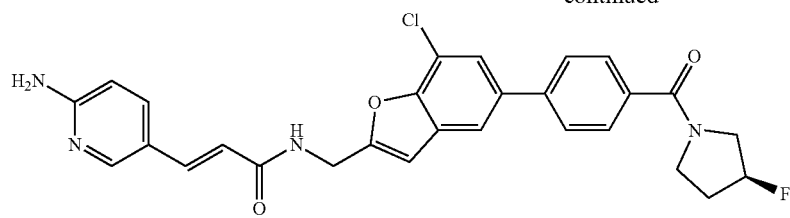
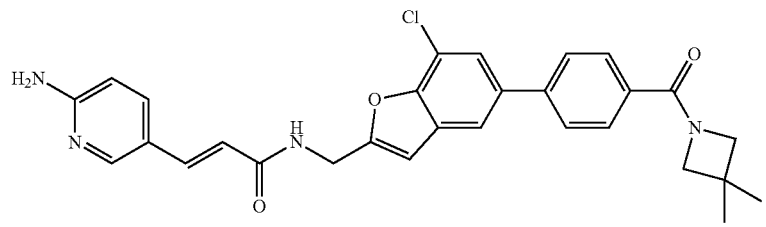
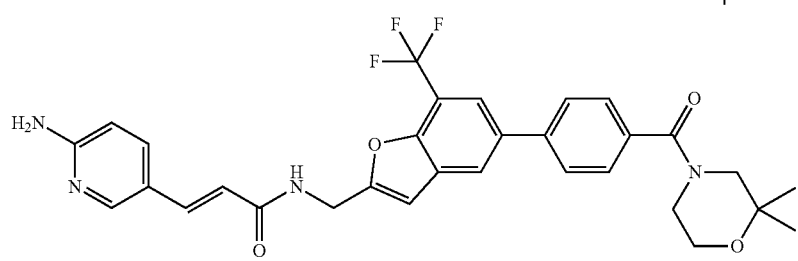
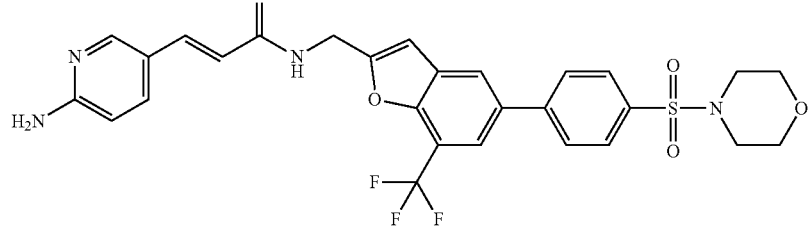
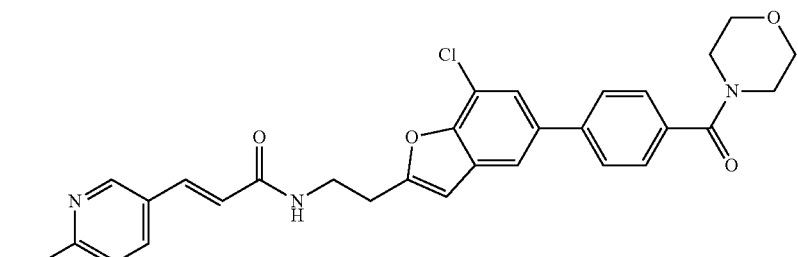
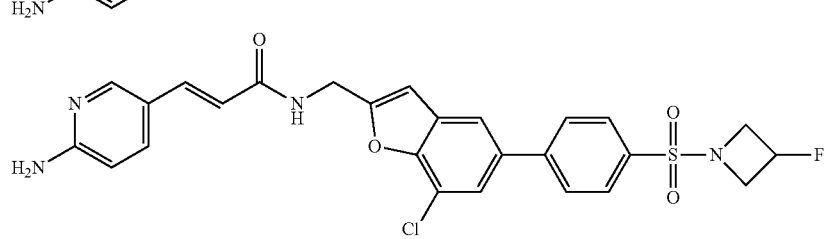
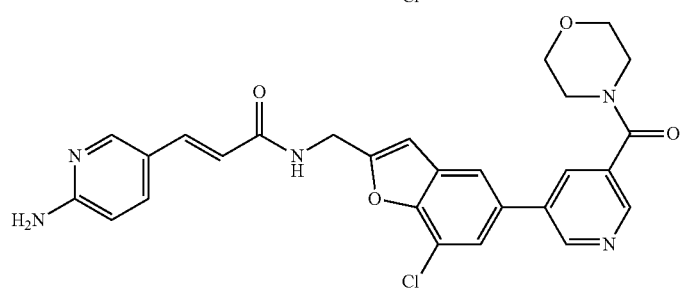

-continued
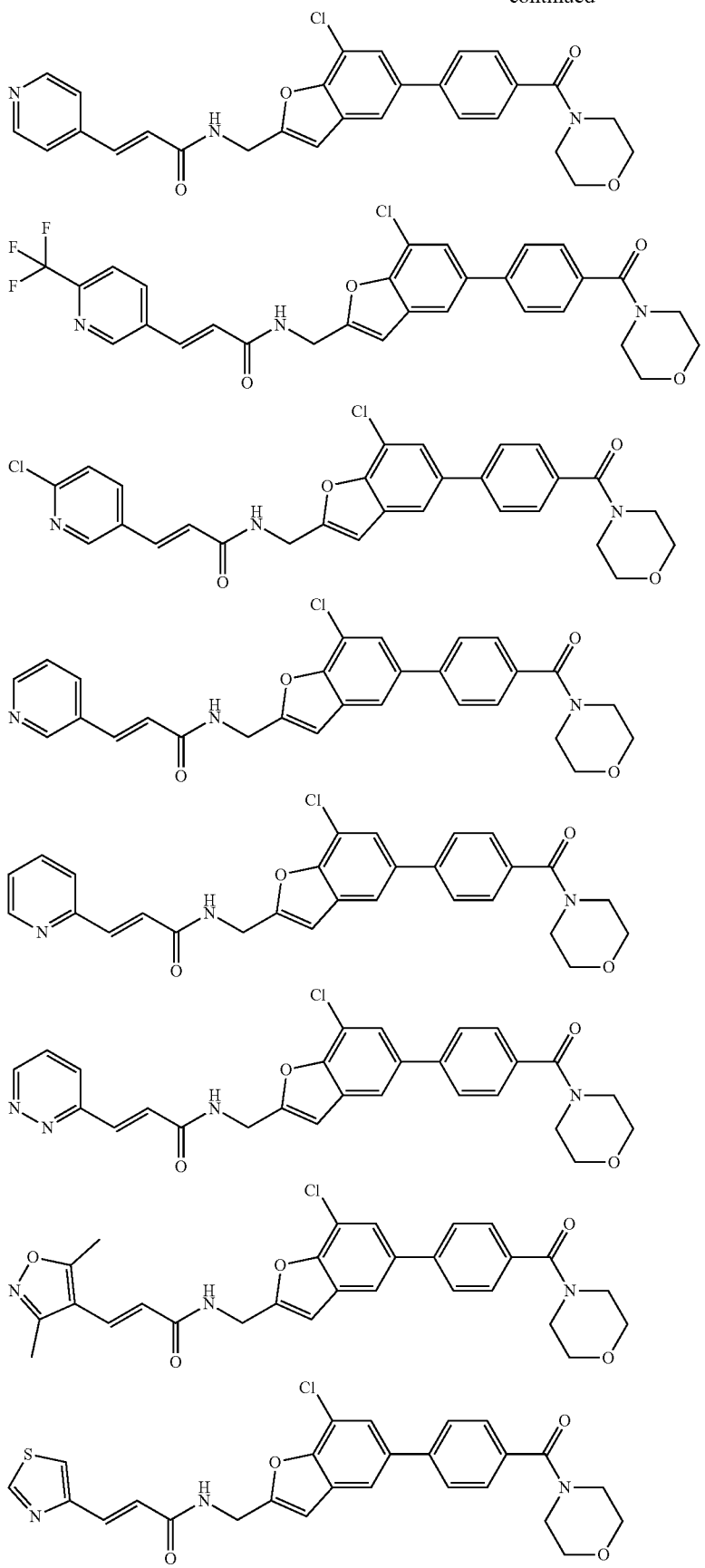

-continued
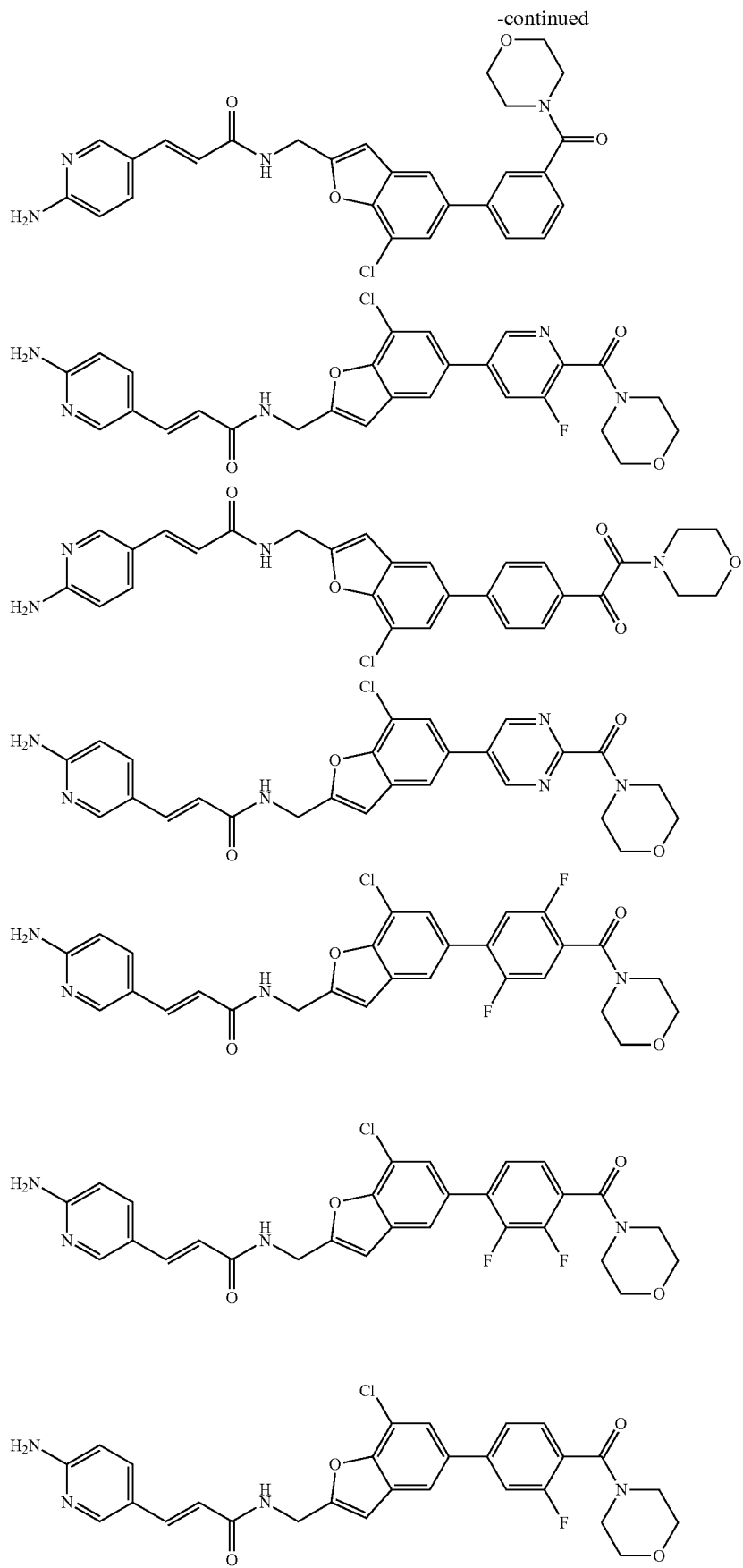

-continued
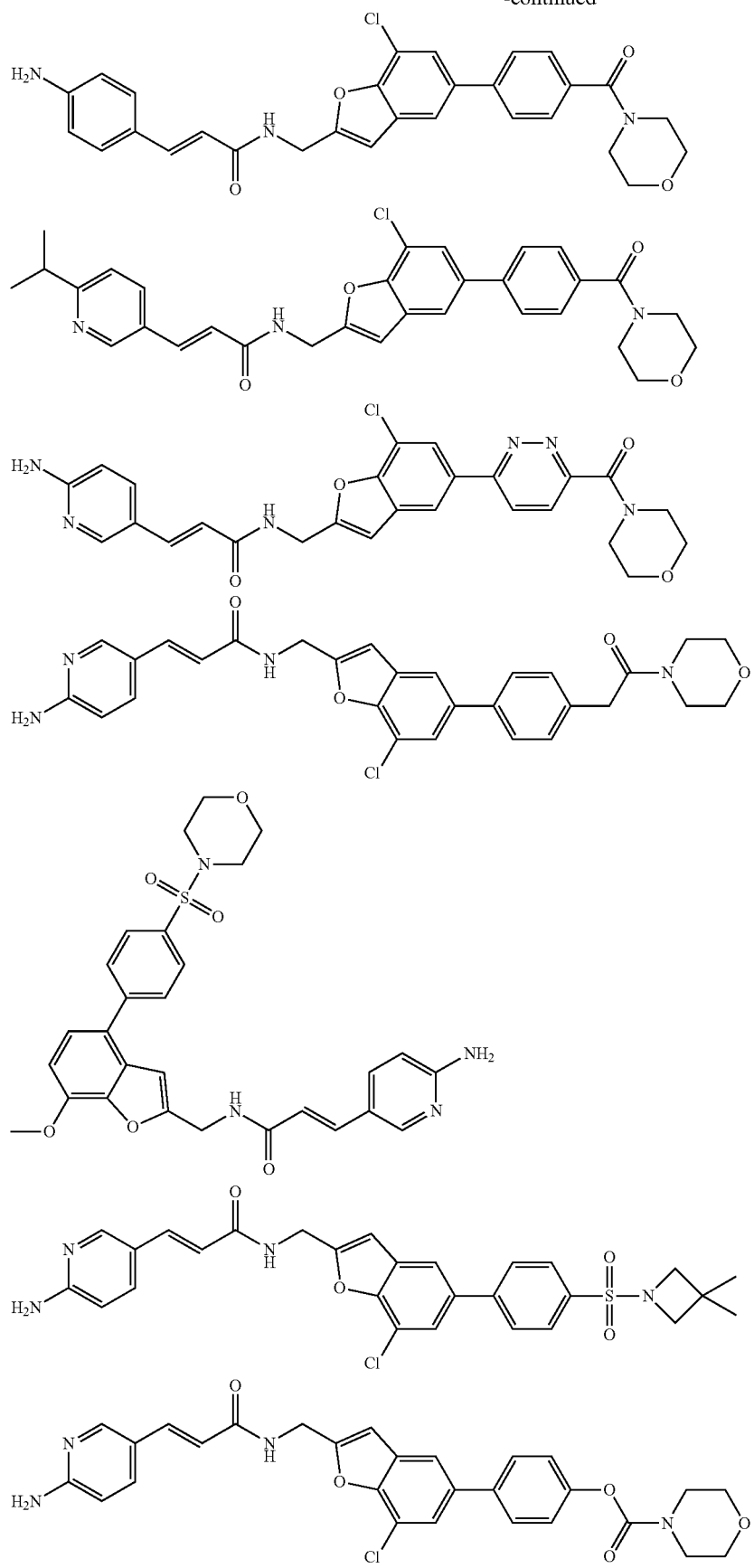

-continued
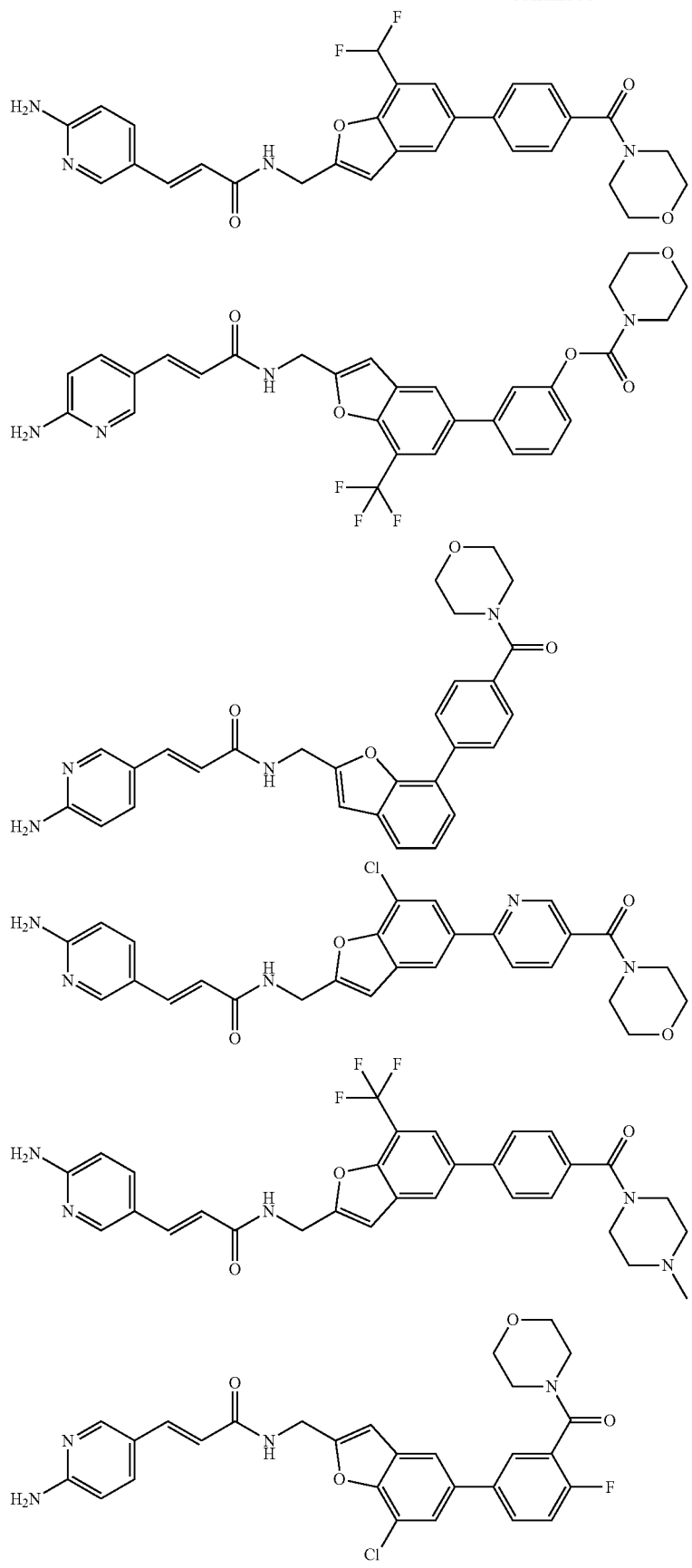

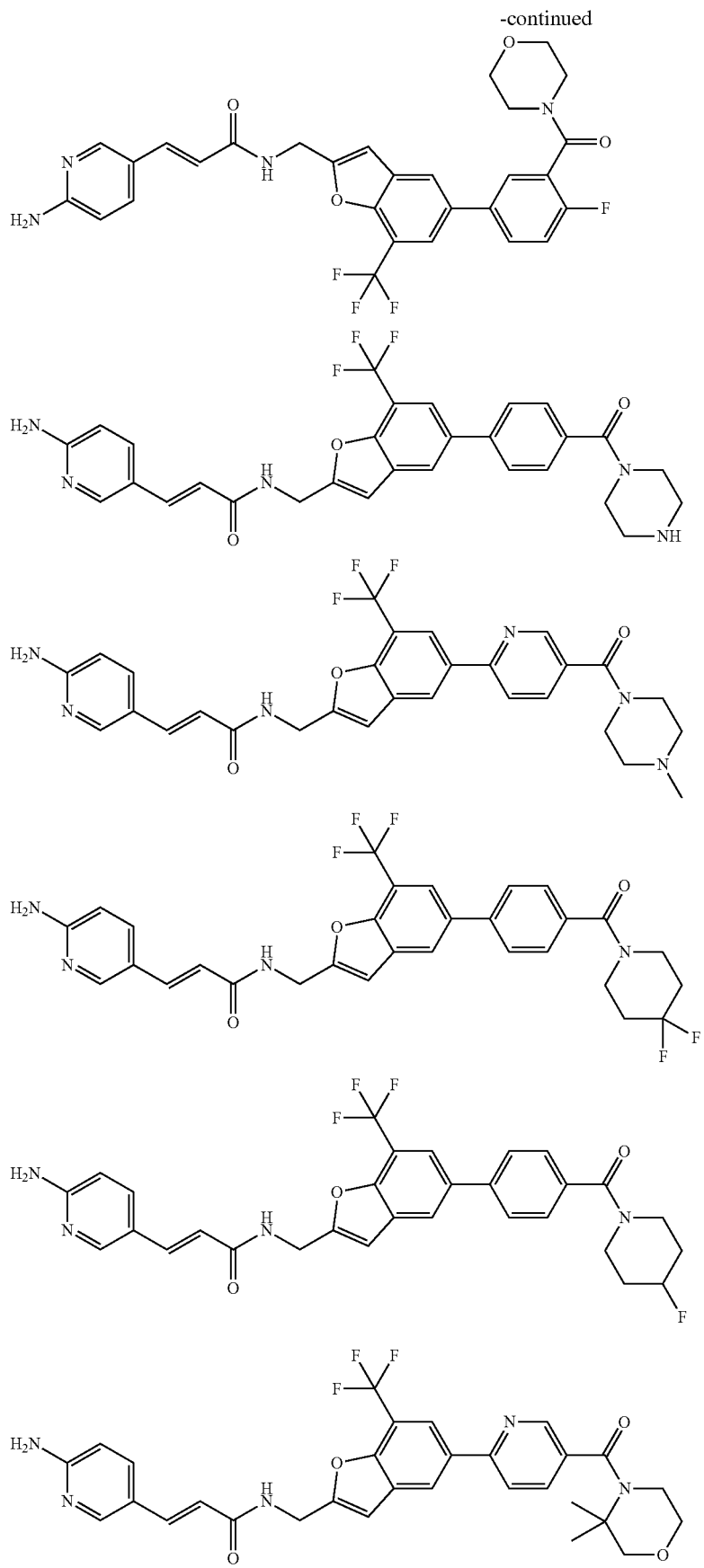

-continued
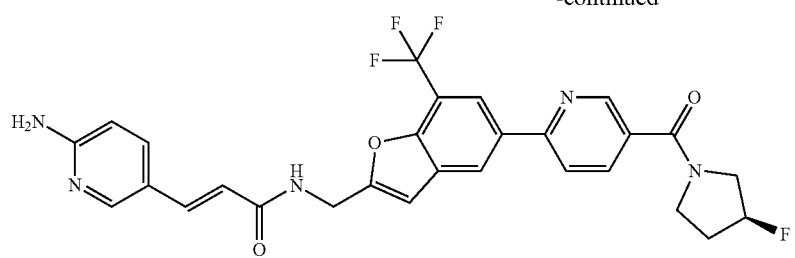
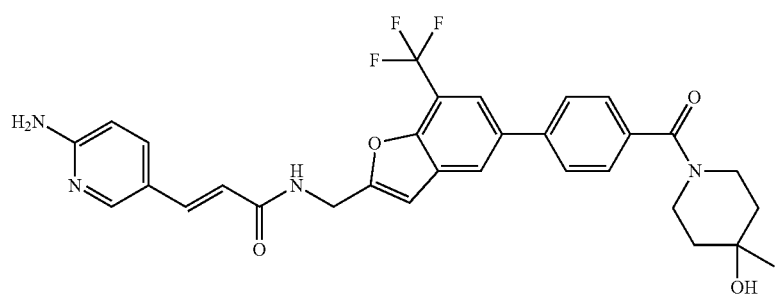
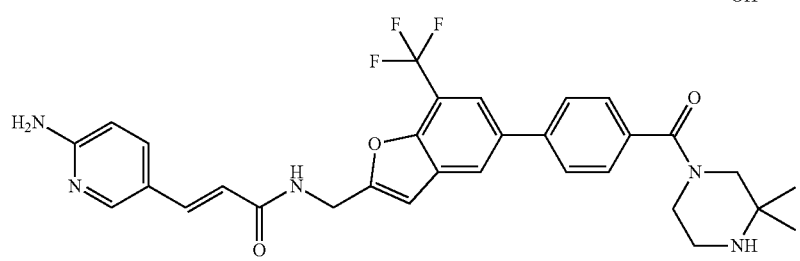
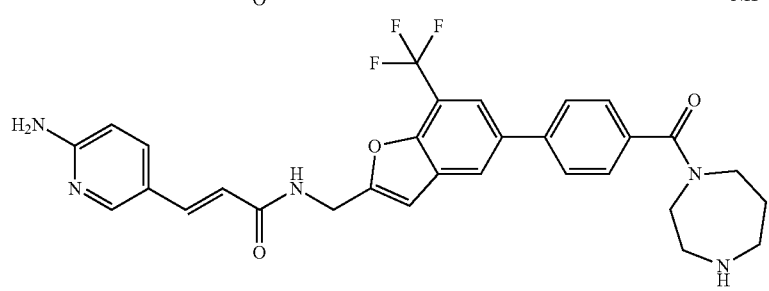
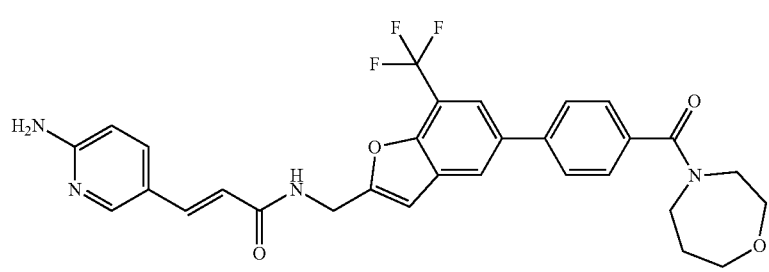
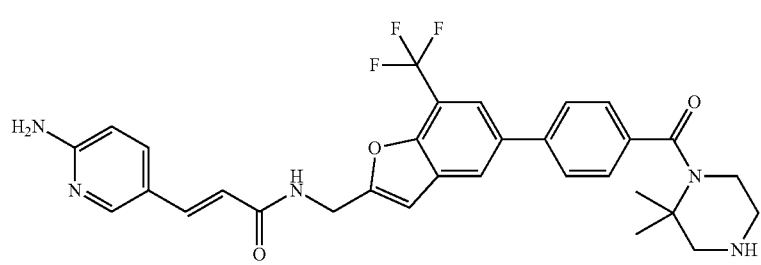

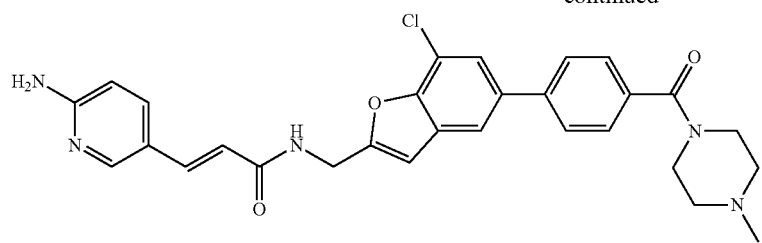
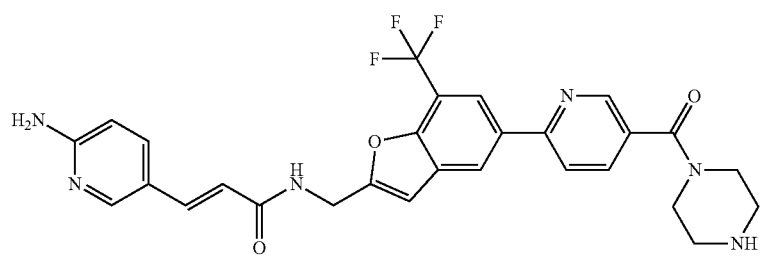
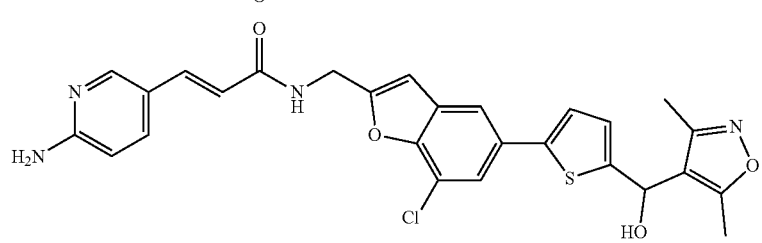
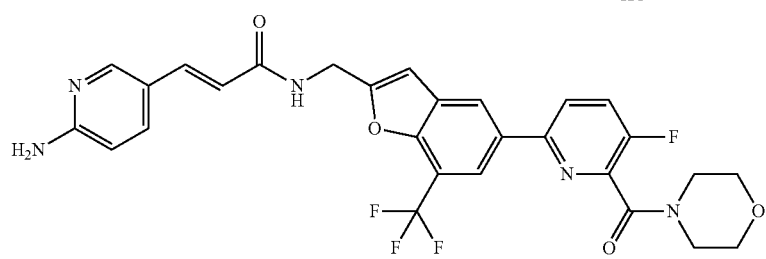
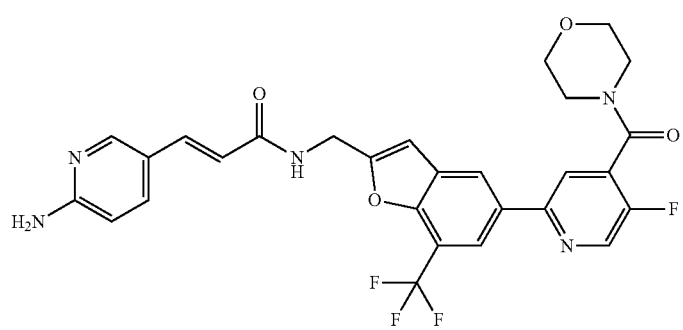
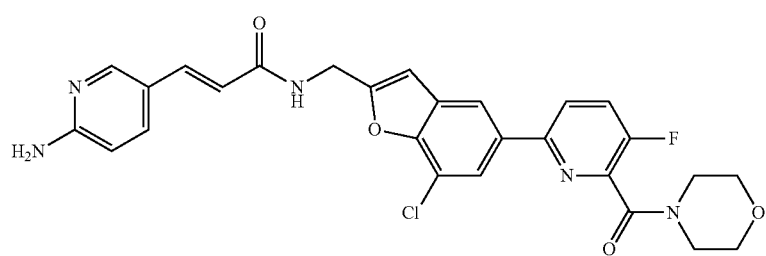

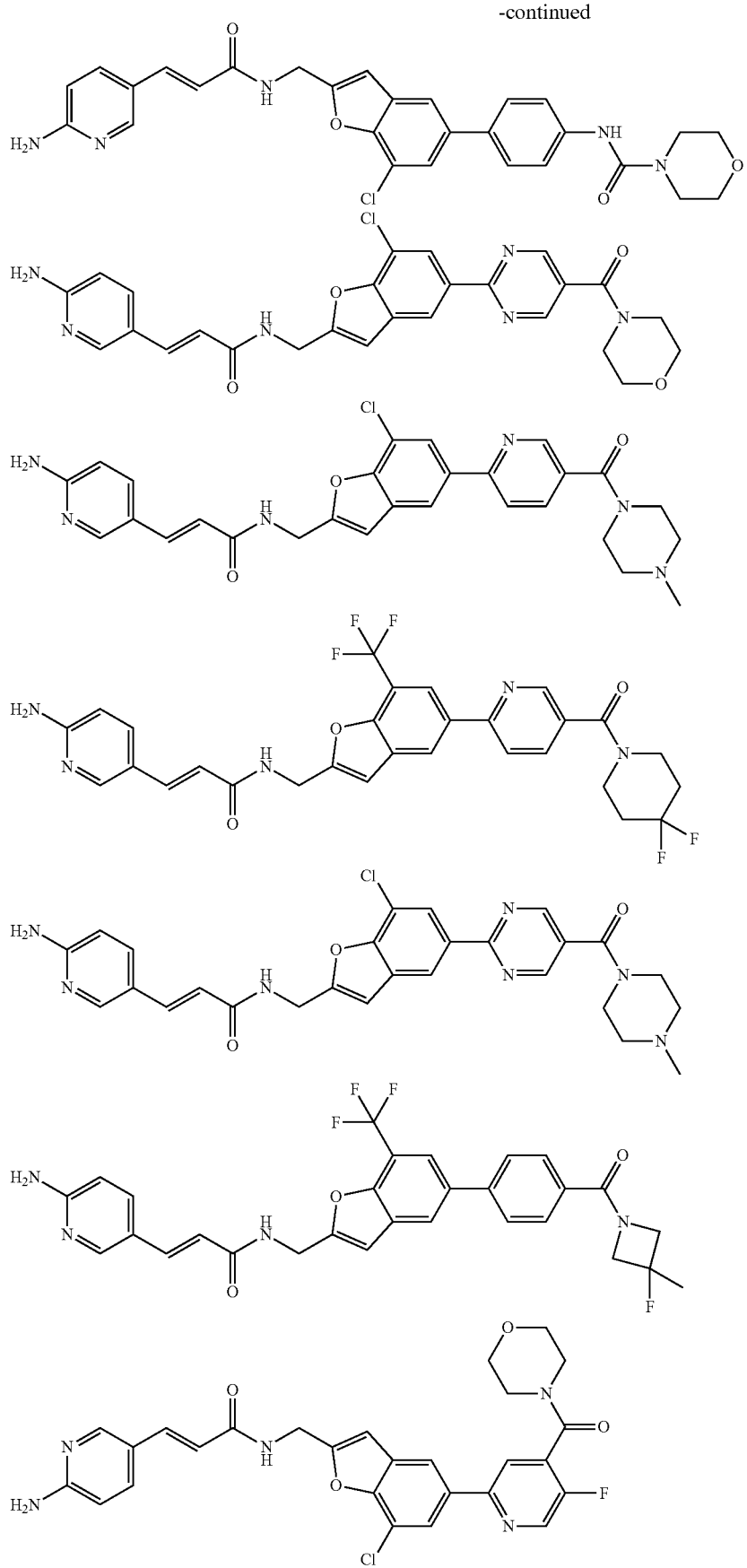

-continued
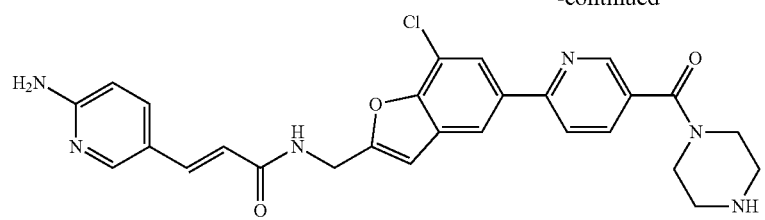
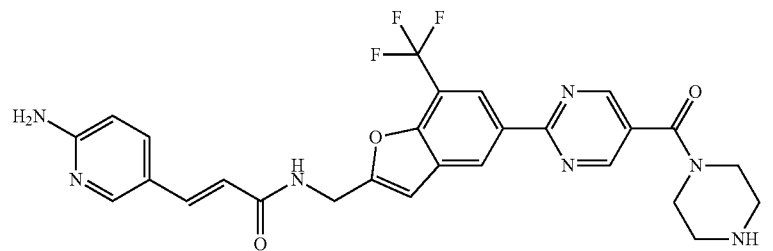
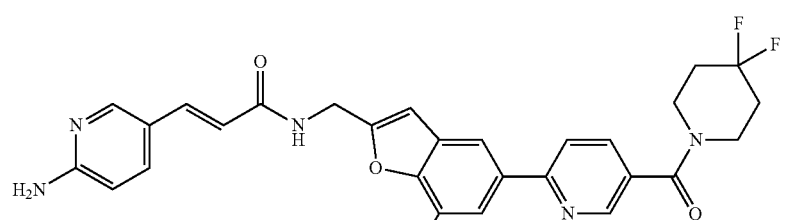
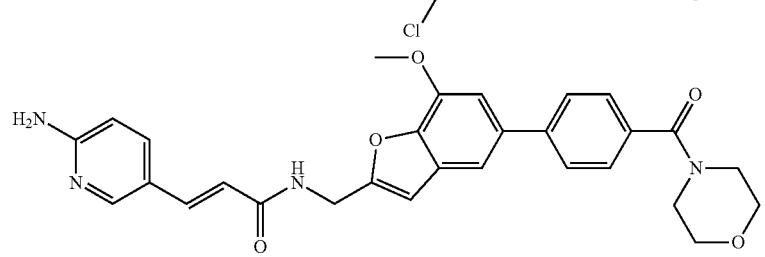
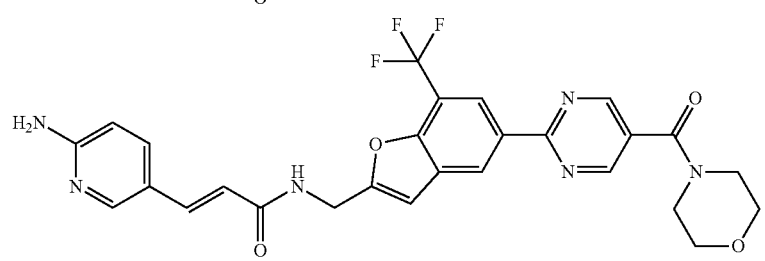
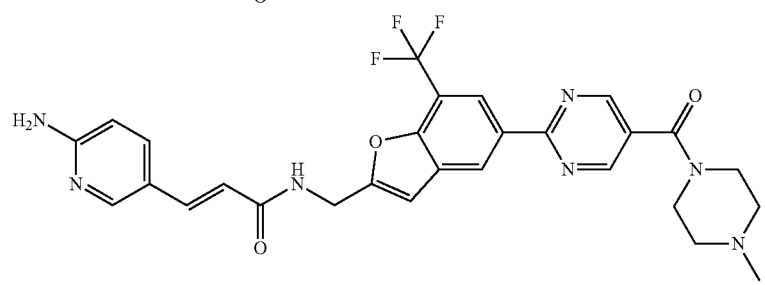
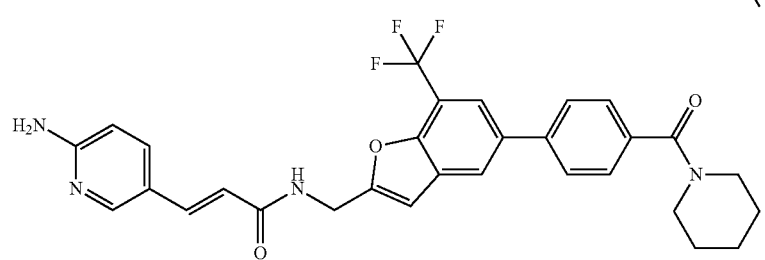

-continued
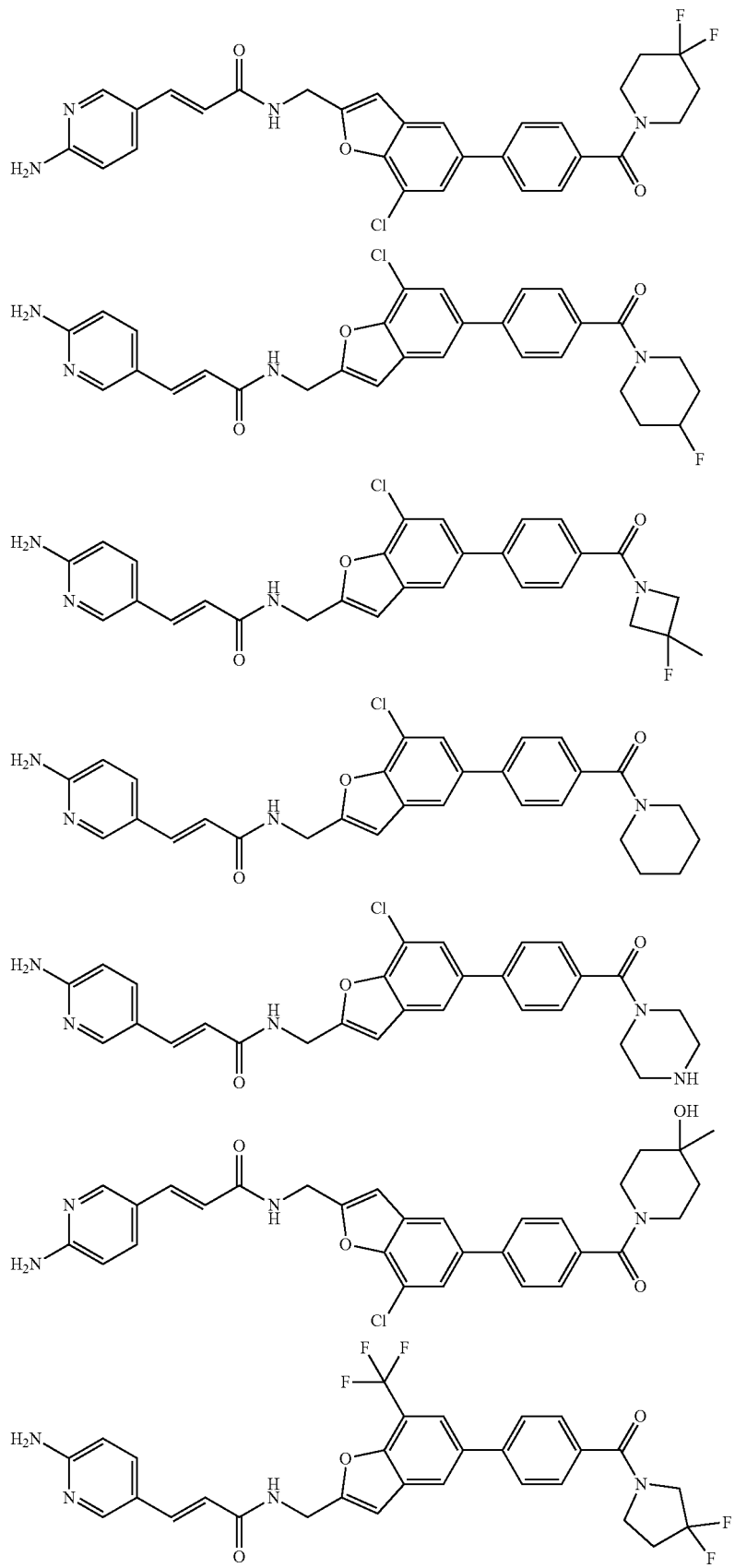

-continued
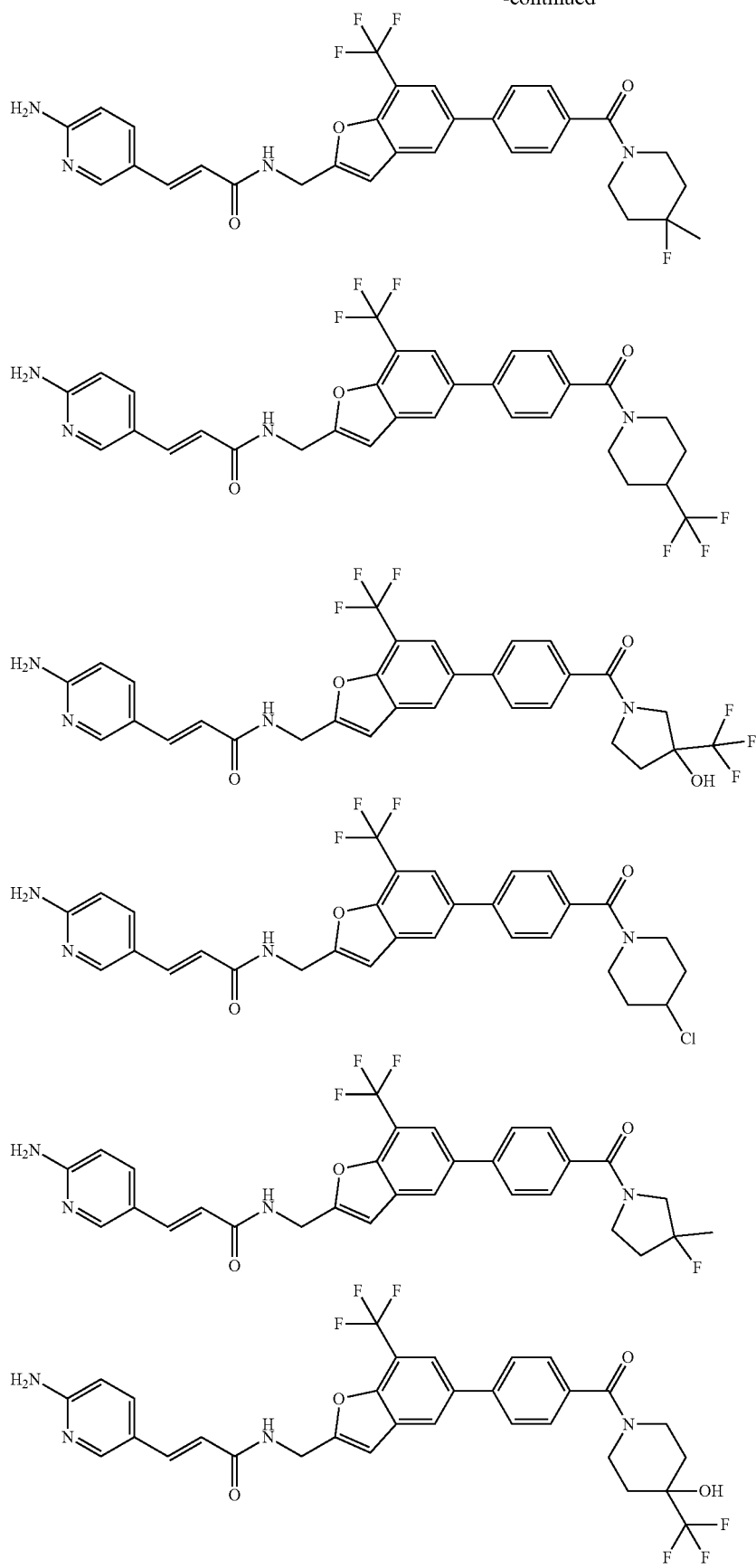

-continued
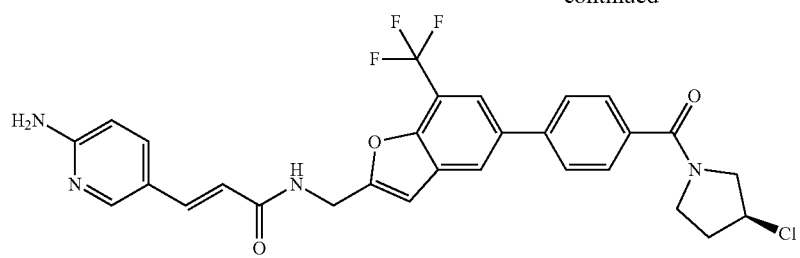
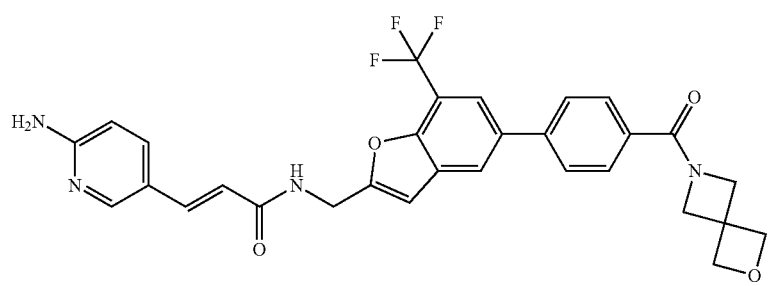
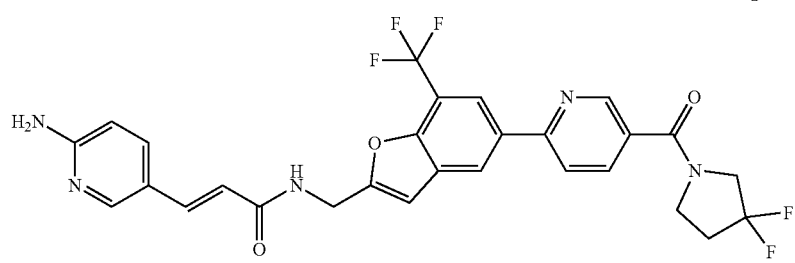
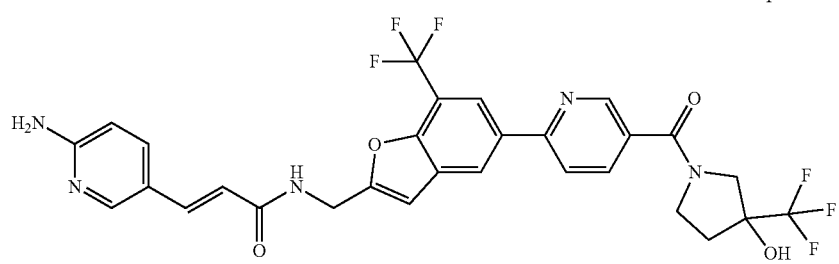
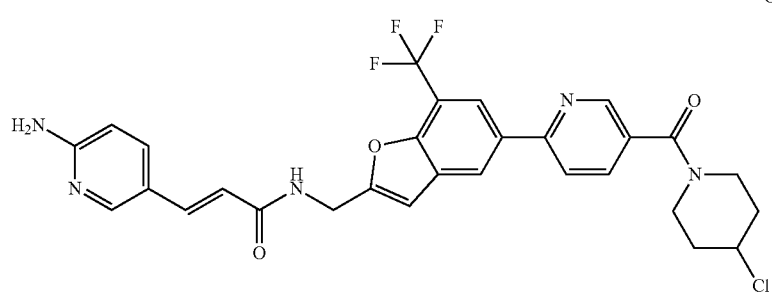
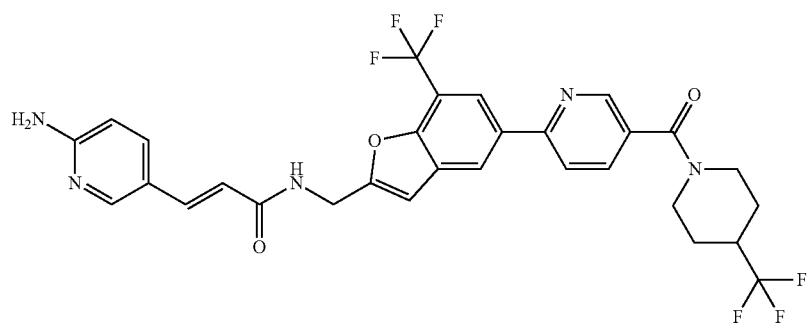

-continued
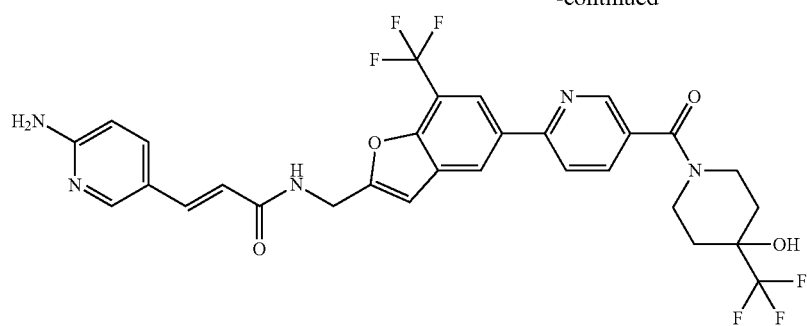
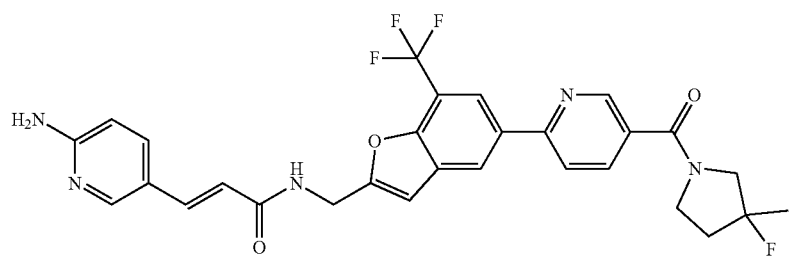
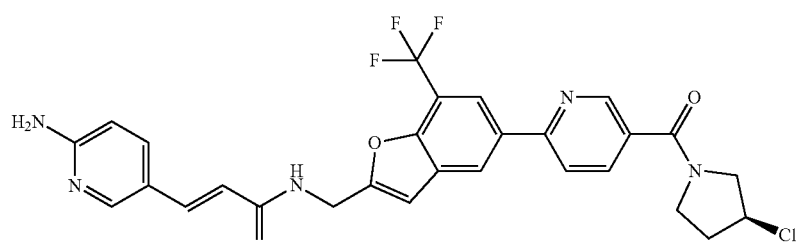
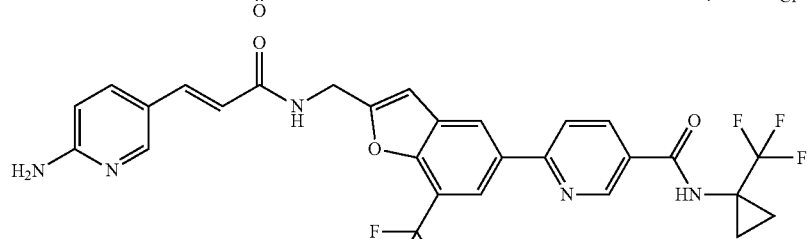
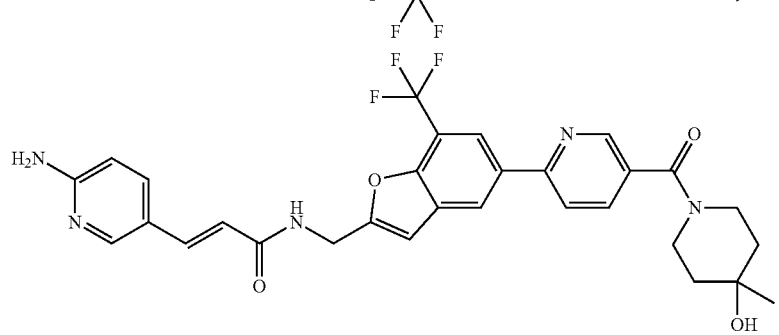
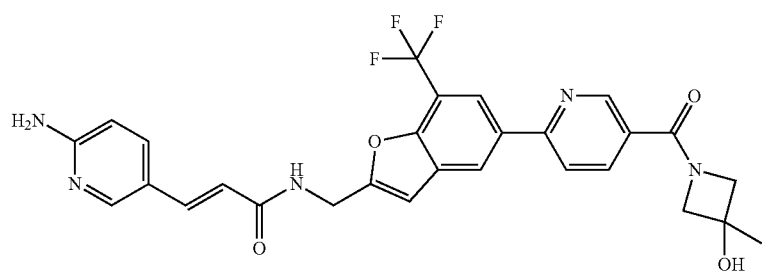

-continued
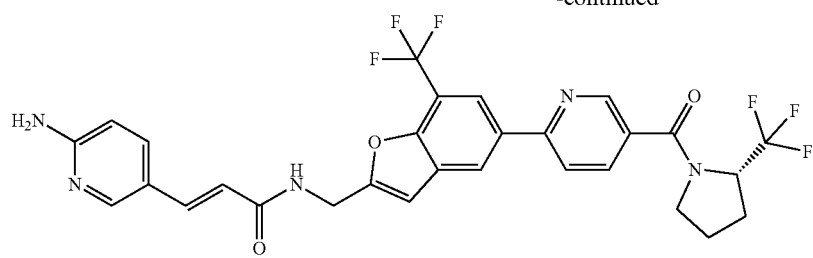
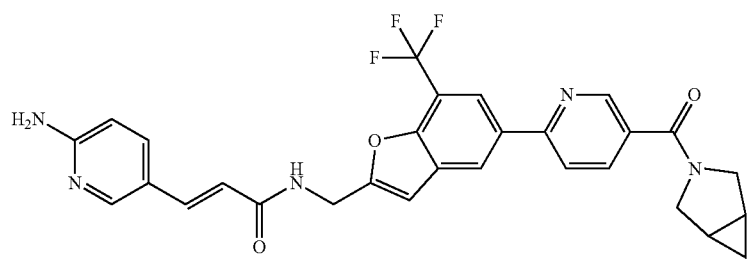
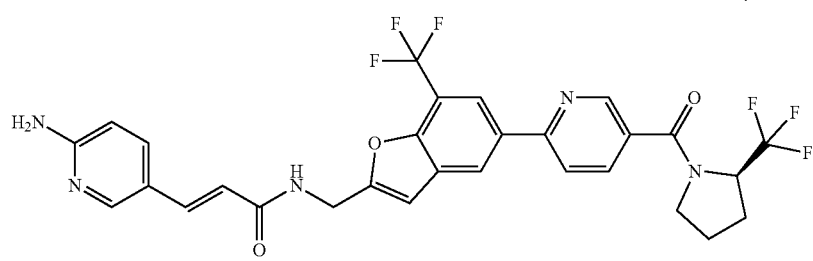
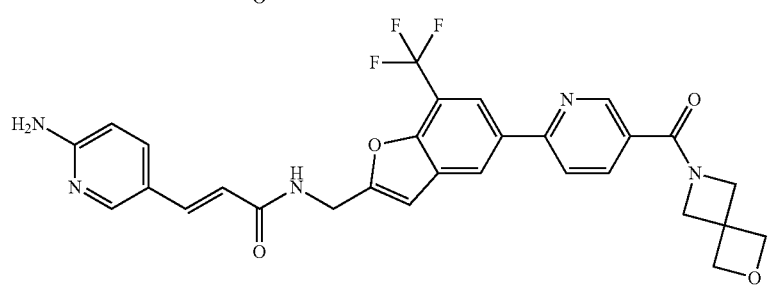
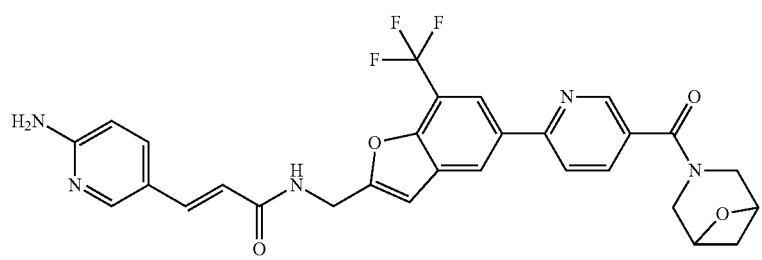
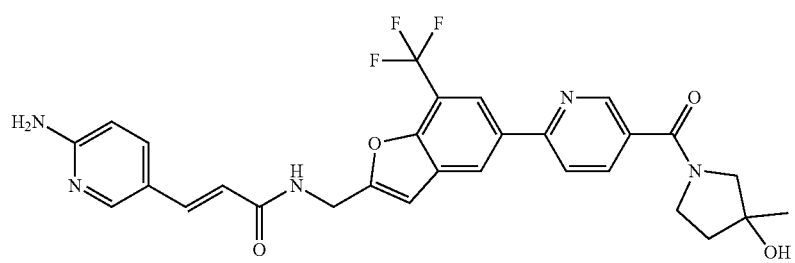

-continued
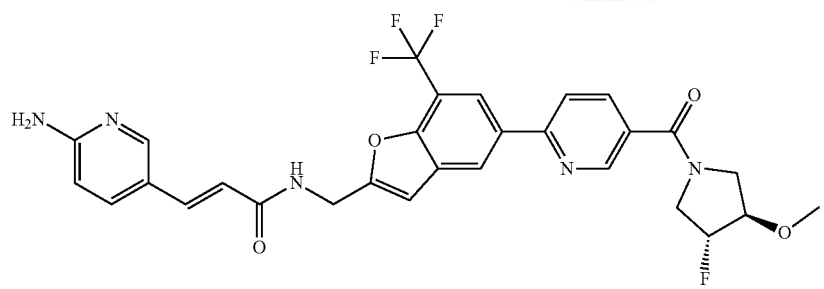
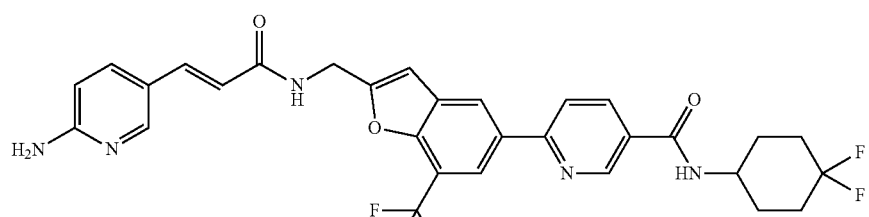
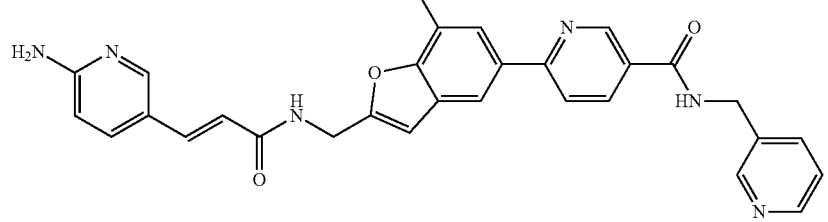
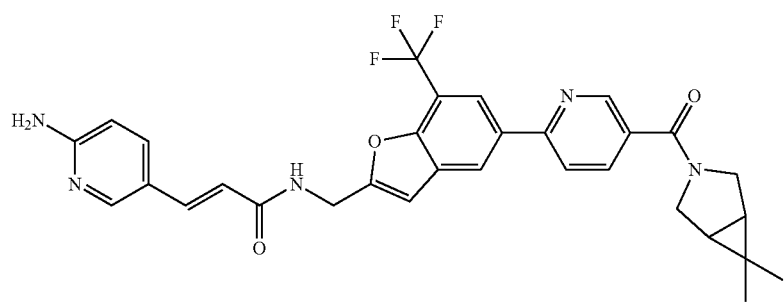
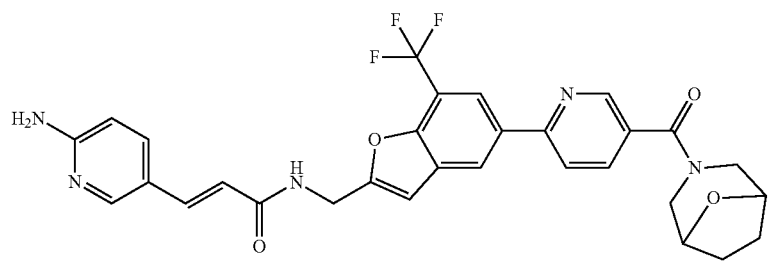
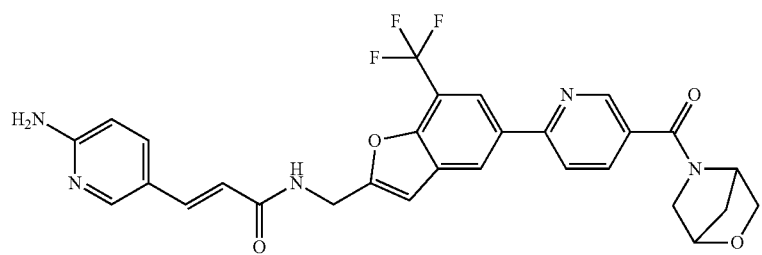

-continued
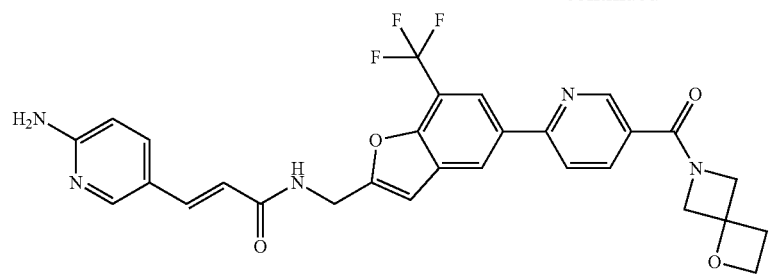
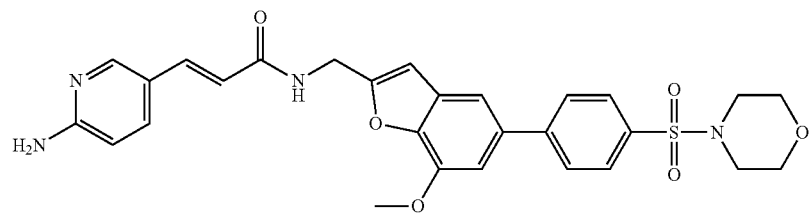
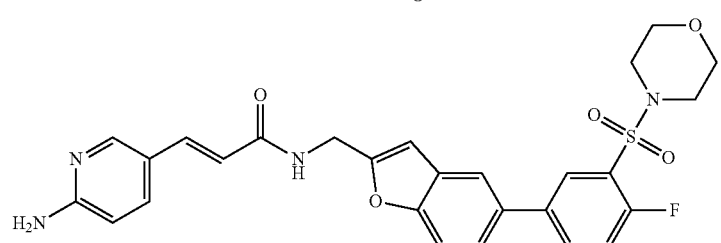
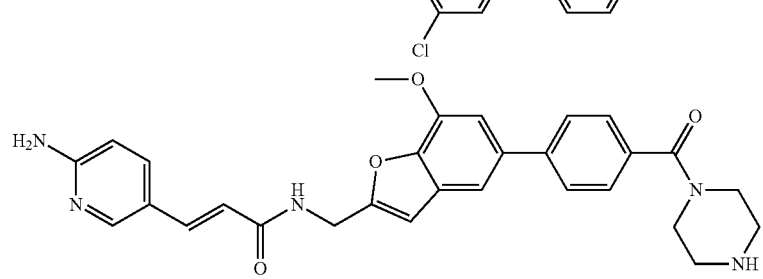
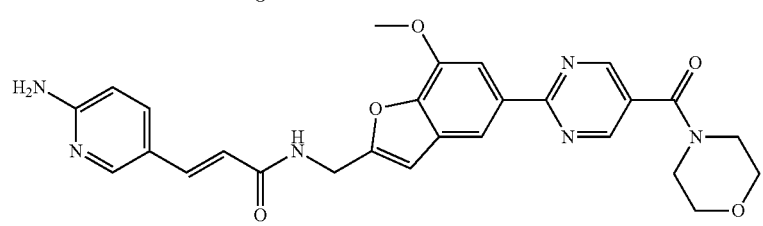
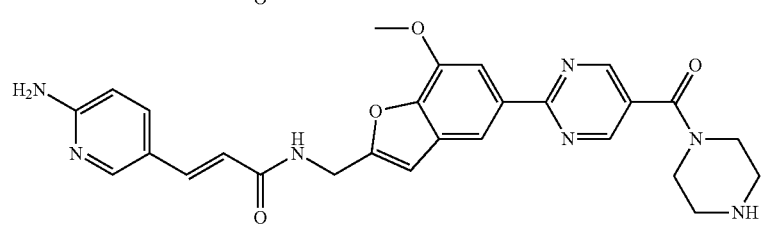
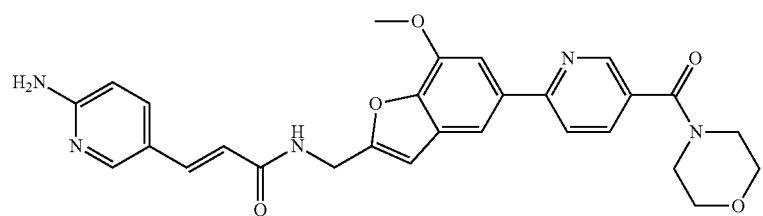

-continued
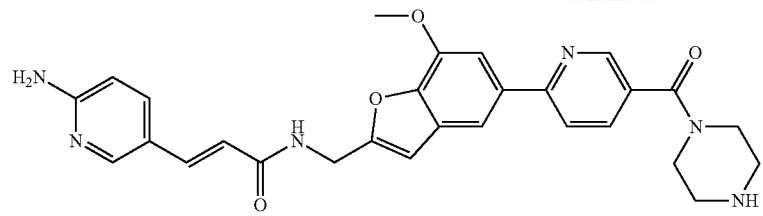
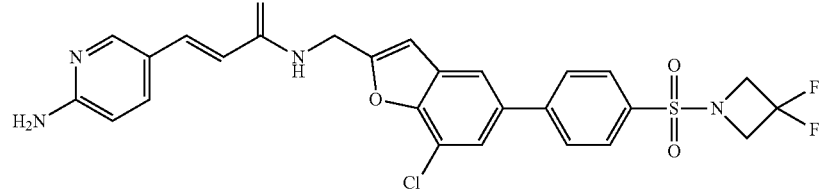
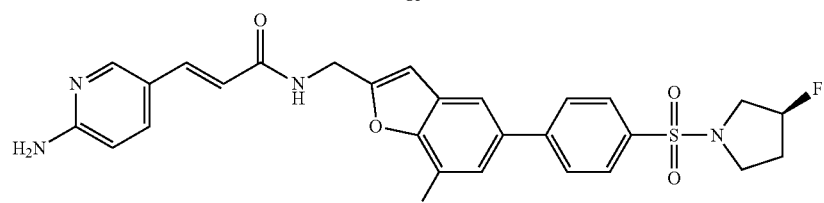
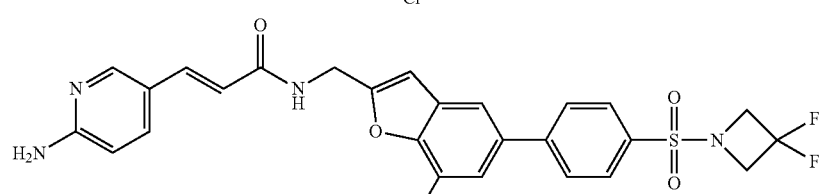
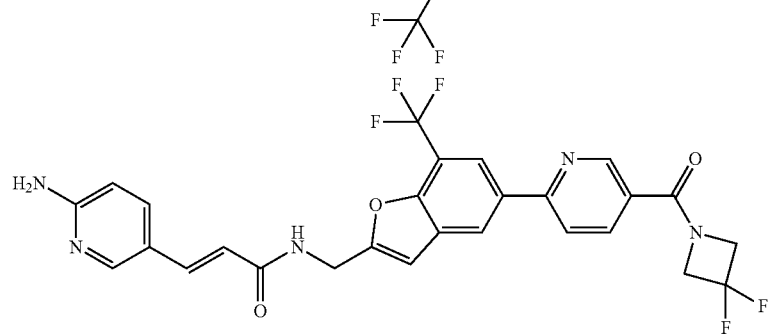
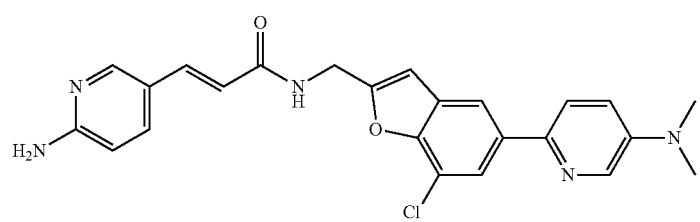
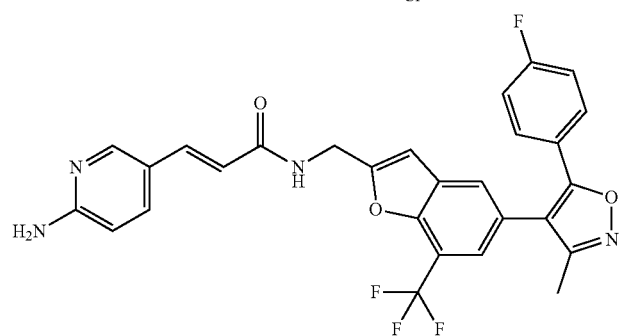

-continued
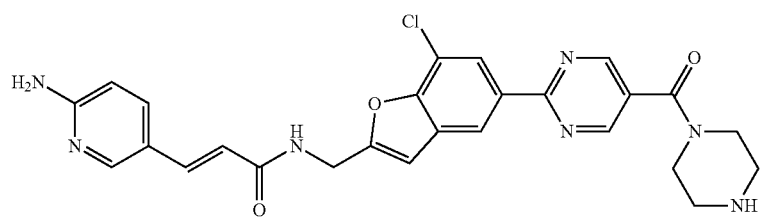
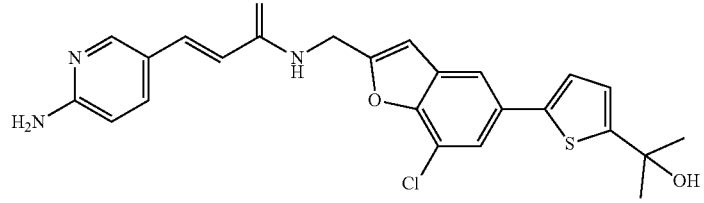
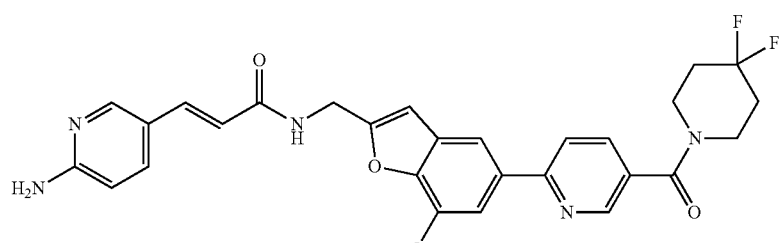
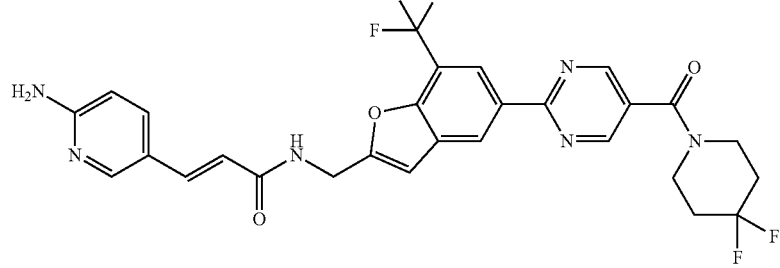
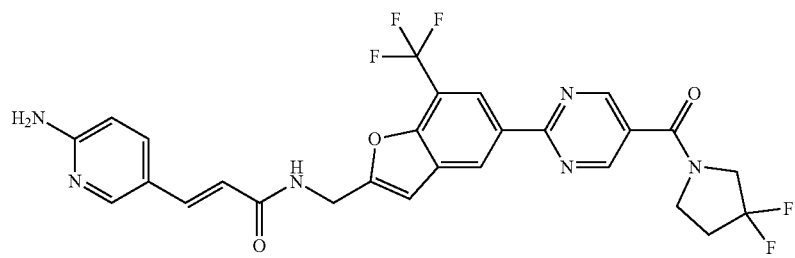
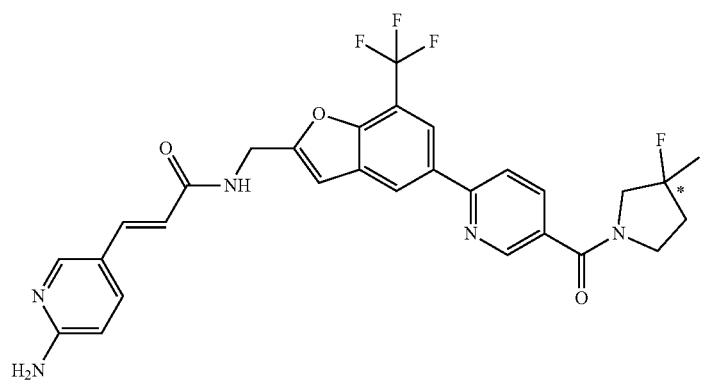
Enantiomer 1
$t_R$ = 19.46 minutes (chiral HPLC)

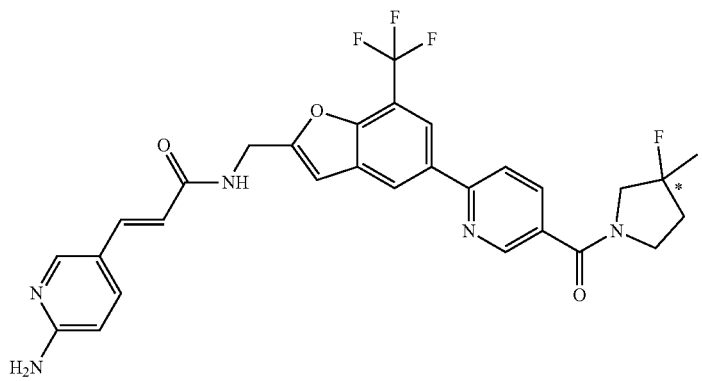
Enantiomer 2
$t_R$ = 30.74 minutes (chiral HPLC)
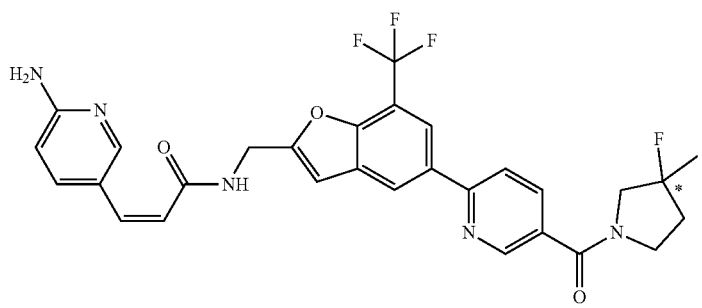
Enantiomer 1
$t_R$ = 8.16 minutes (chiral HPLC)
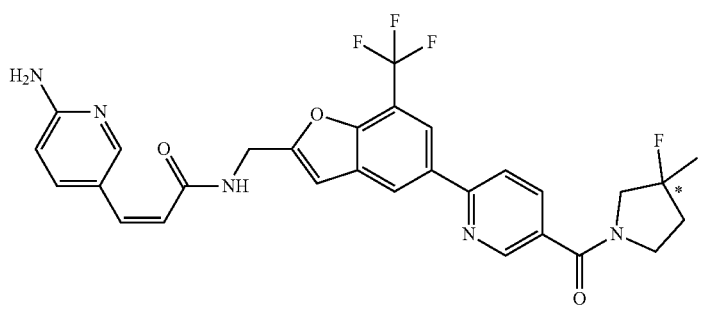
Enantiomer 2
$t_R$ = 7.51 minutes (chiral HPLC)
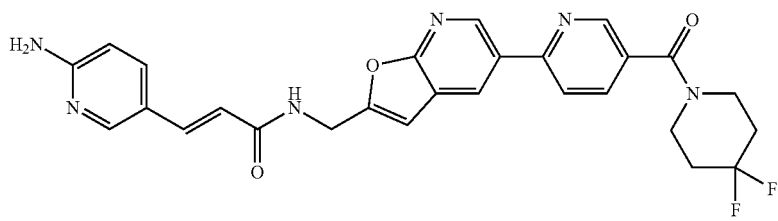
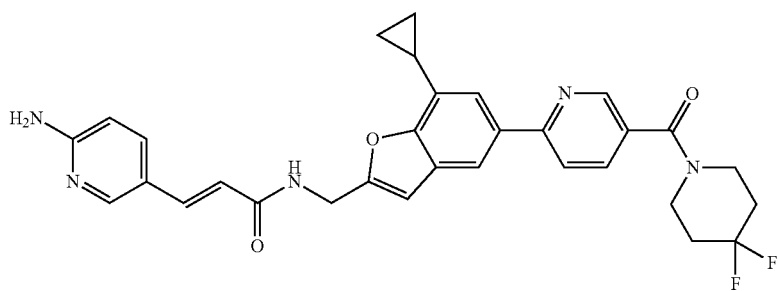

-continued
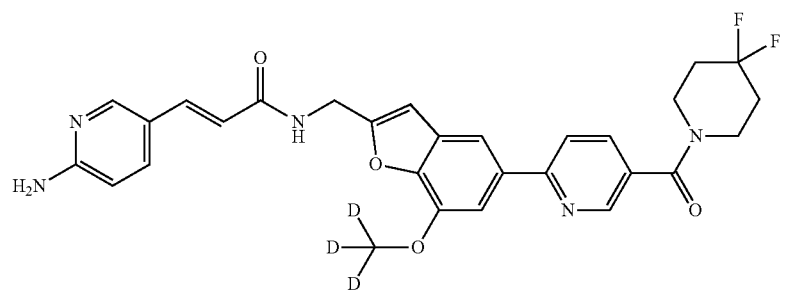
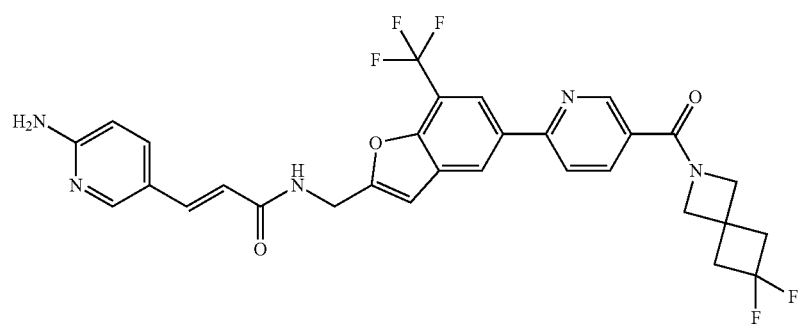
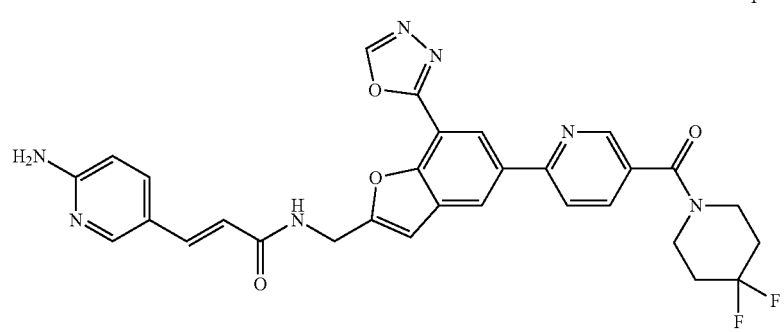
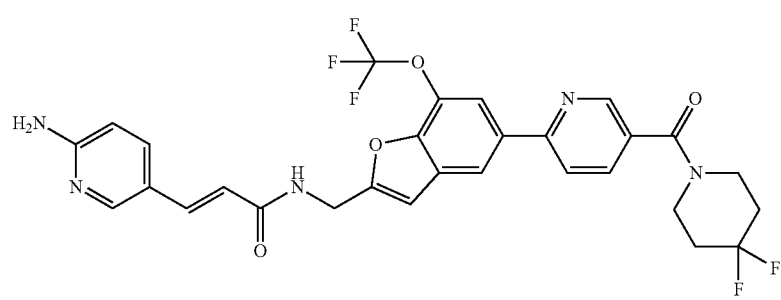
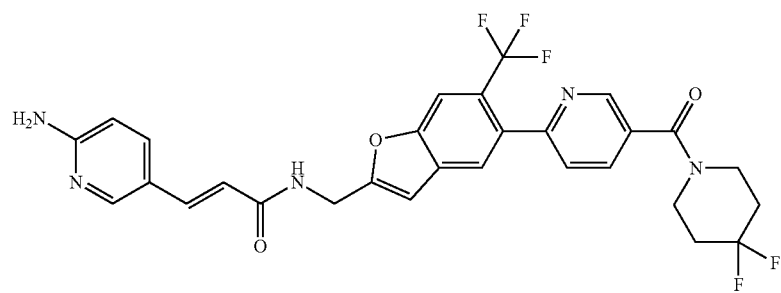

-continued
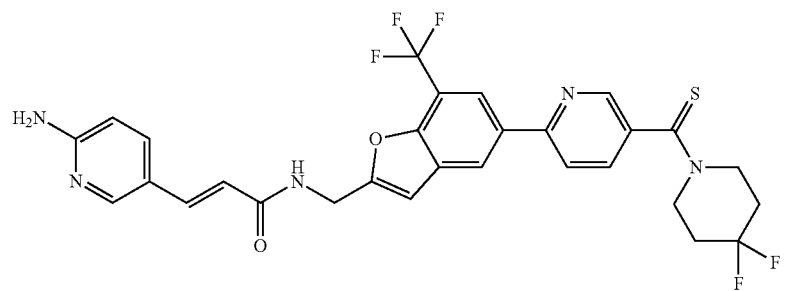
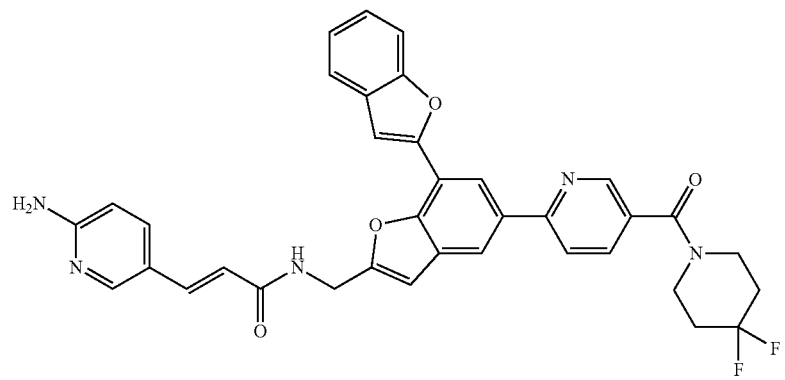
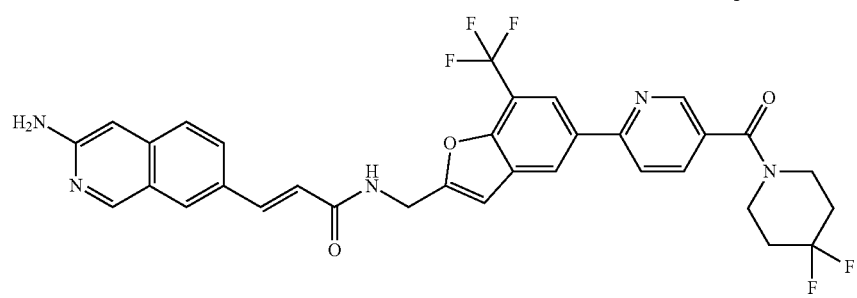
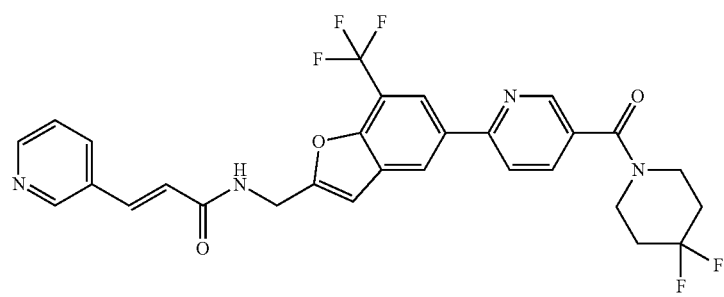
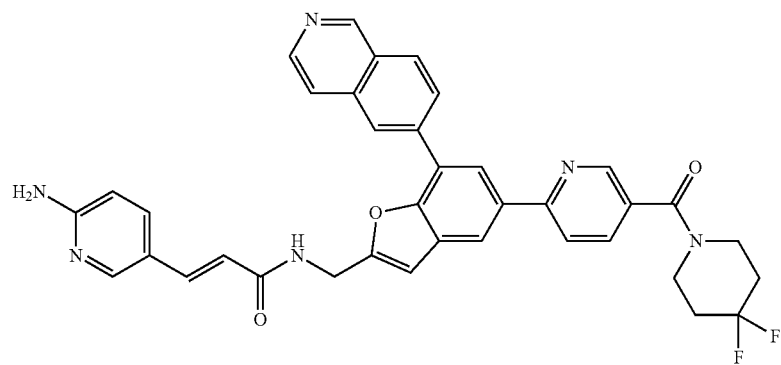

-continued
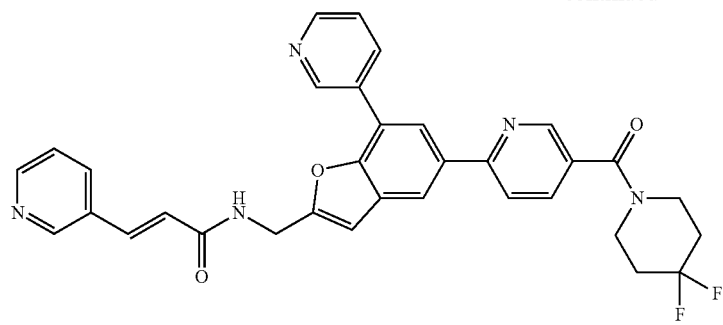
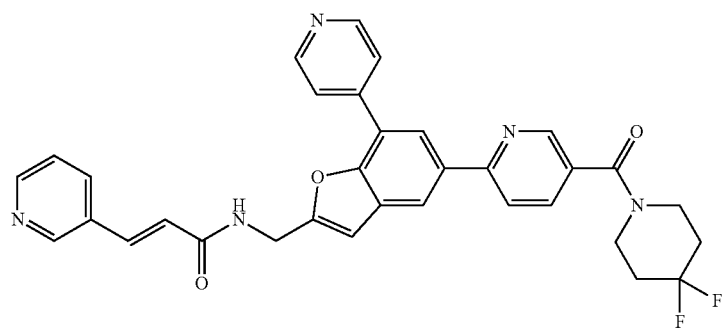
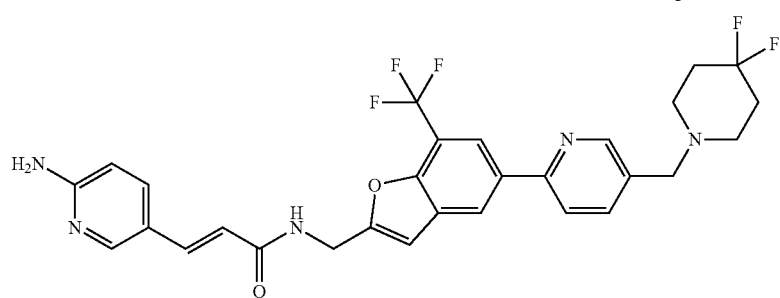
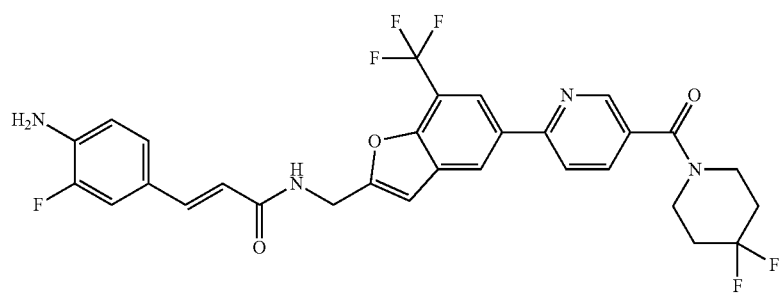
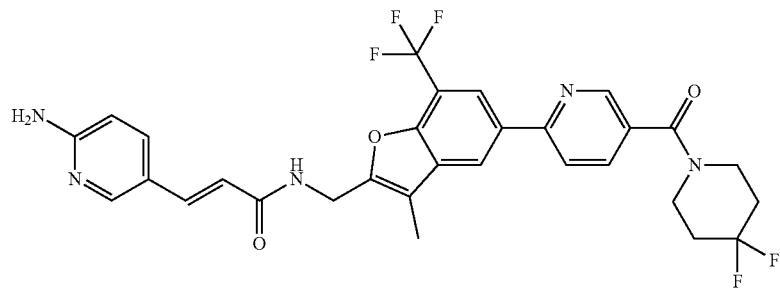

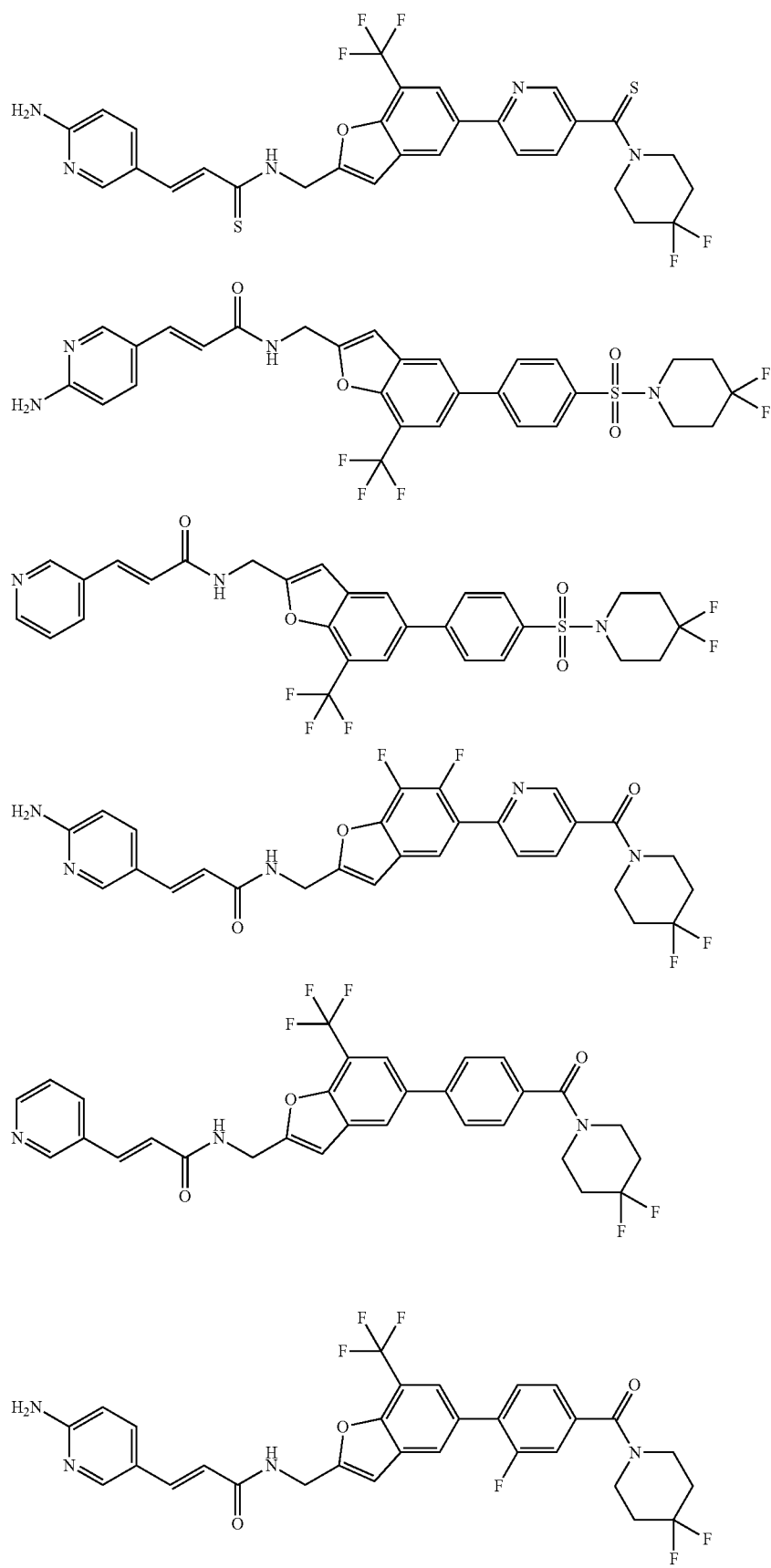

-continued
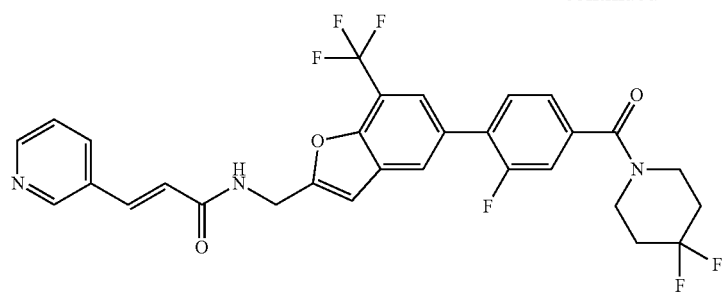
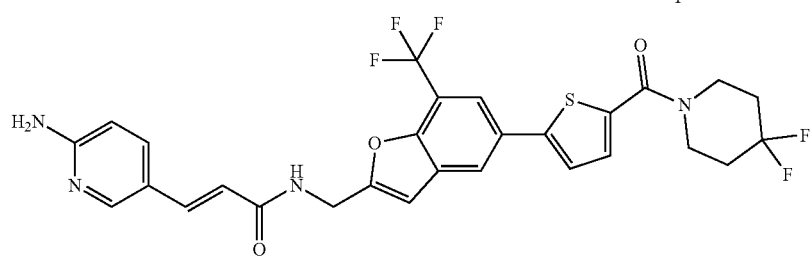
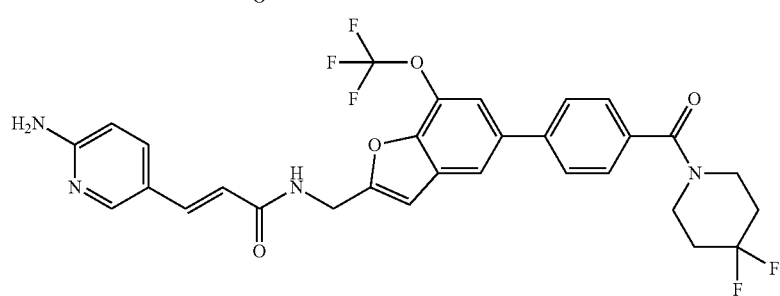
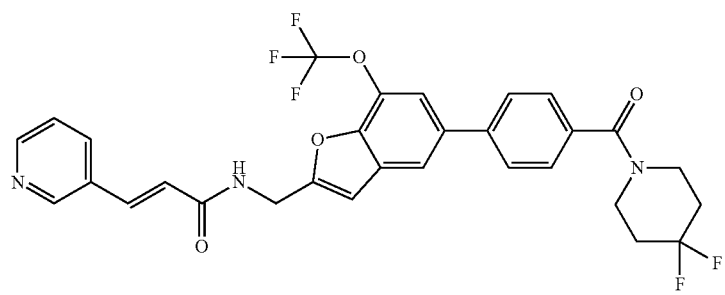
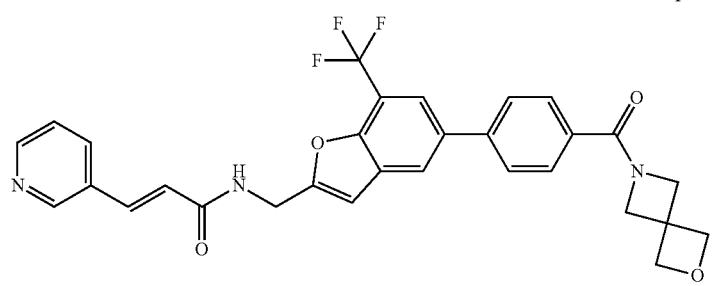
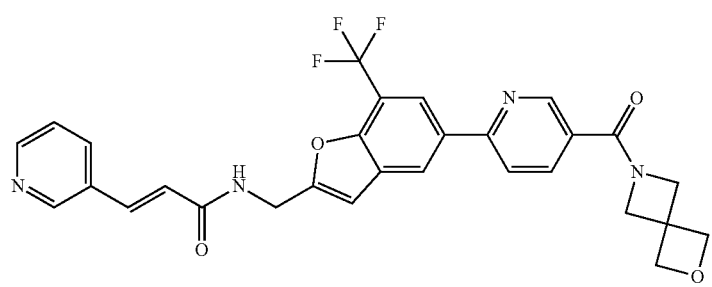

-continued
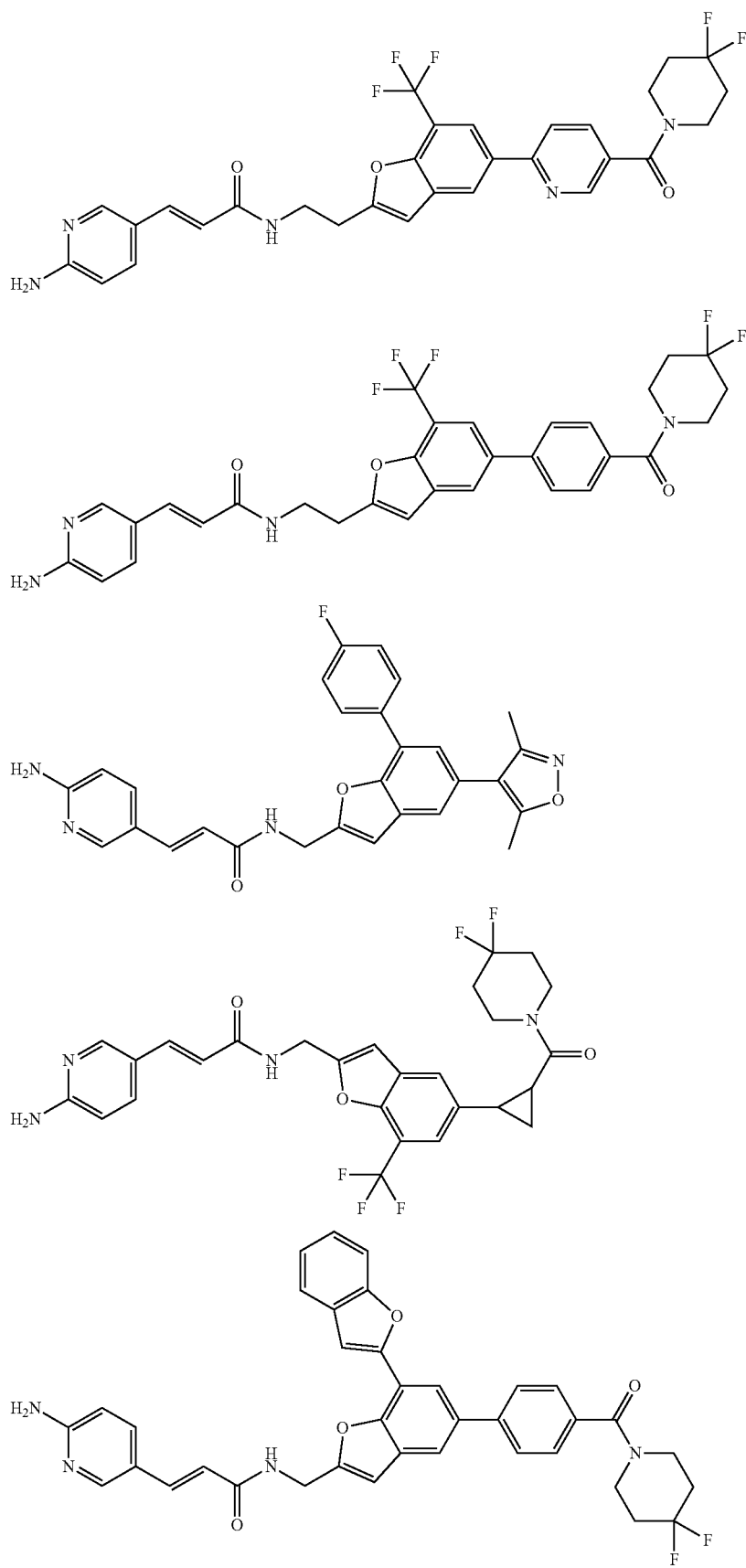

791 792
-continued
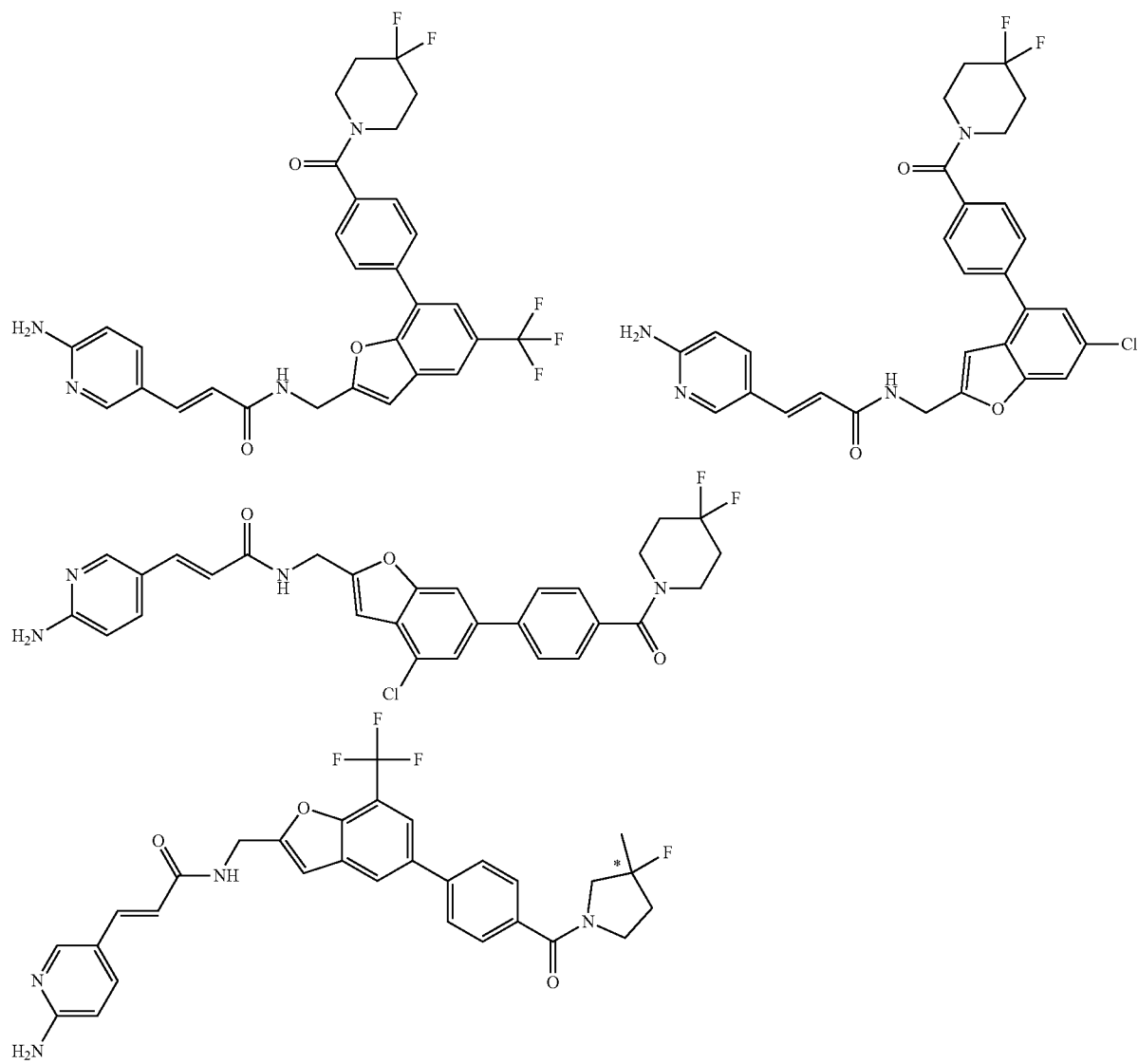
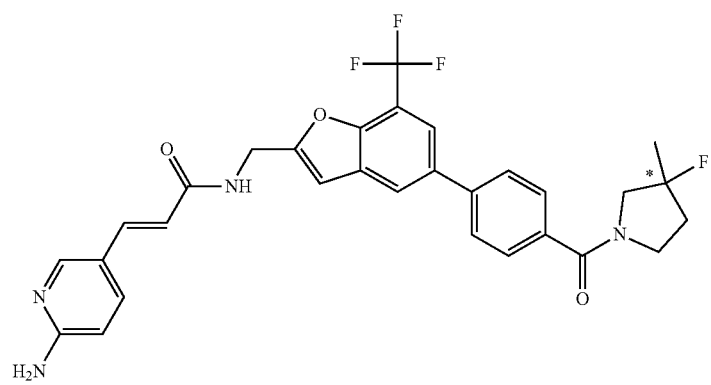
Enantiomer 1
$t_R$ = 5.09 minutes (chiral HPLC)
Enantiomer 2
$t_R$ = 5.99 minutes (chiral HPLC)

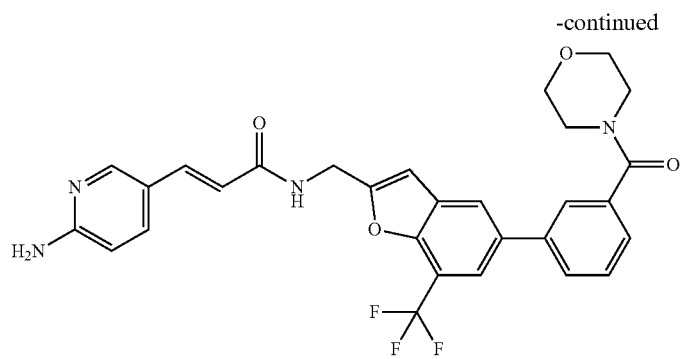
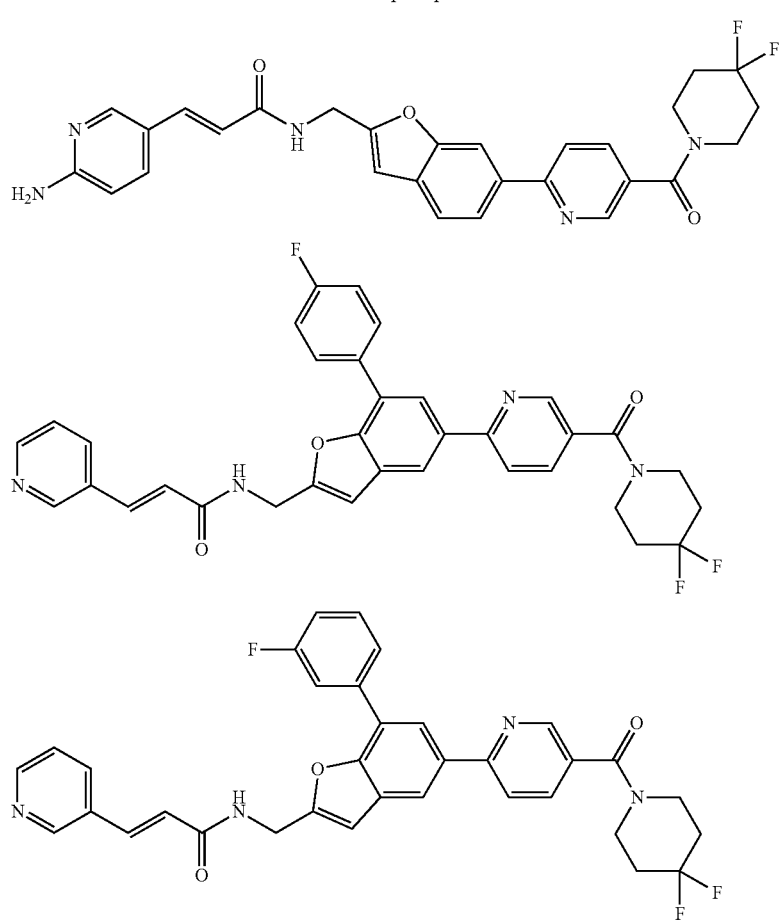
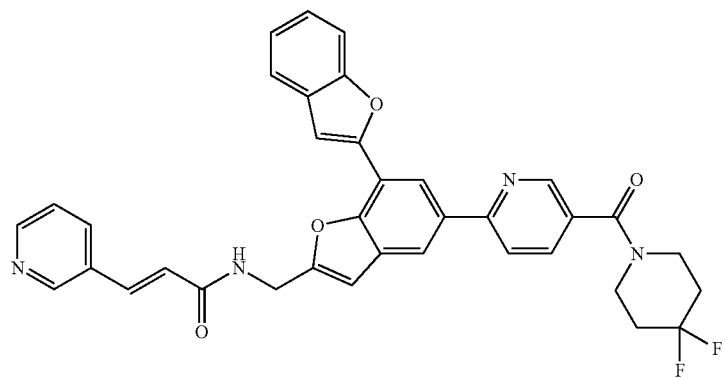

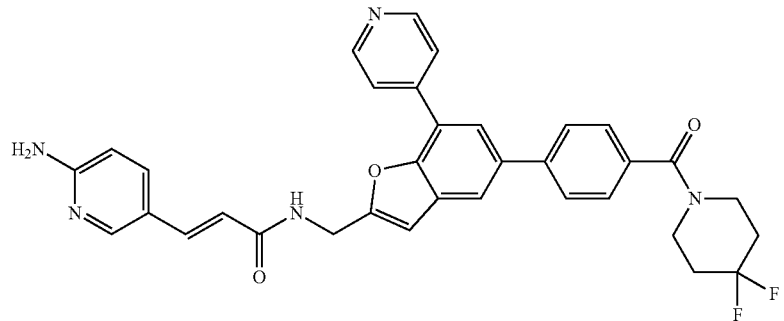
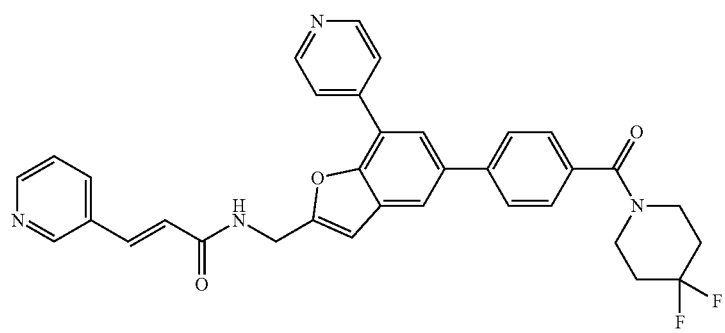
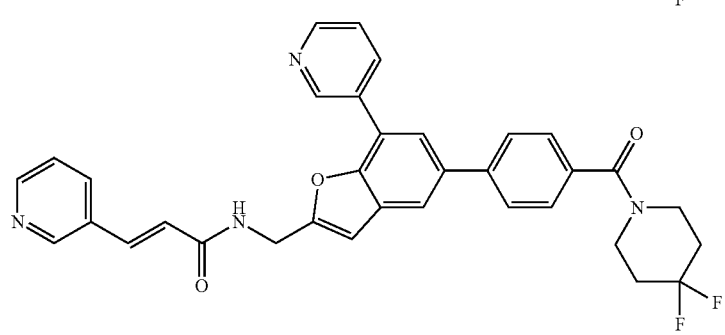
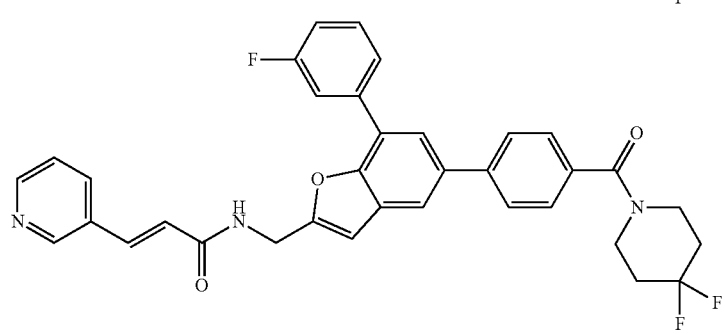
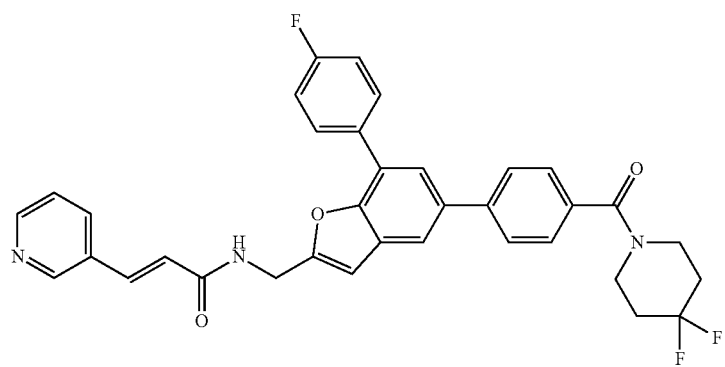

-continued
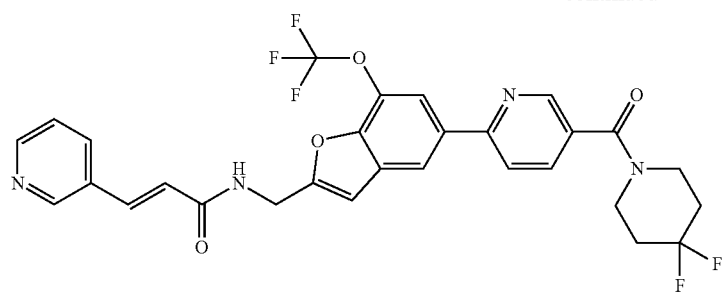
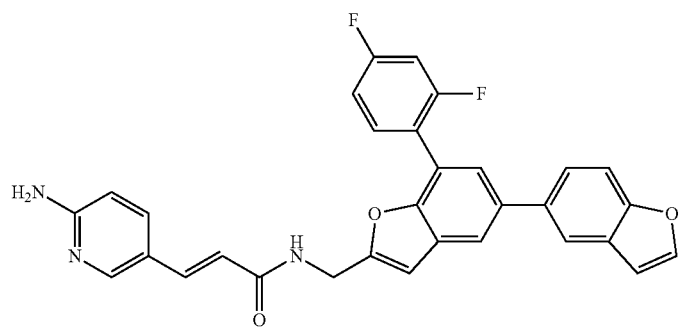
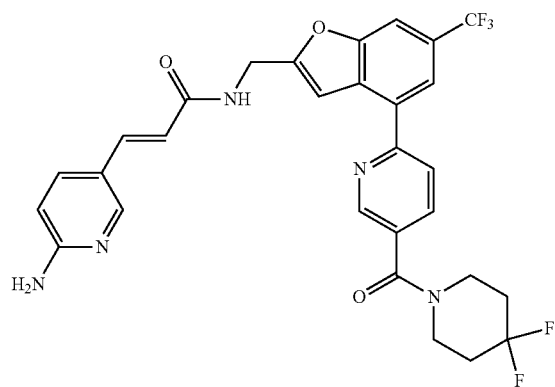
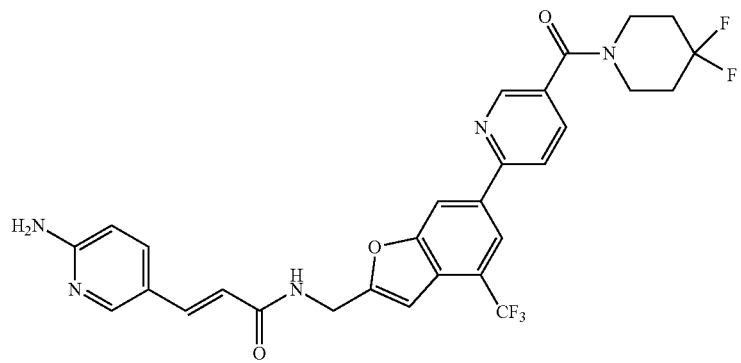

-continued
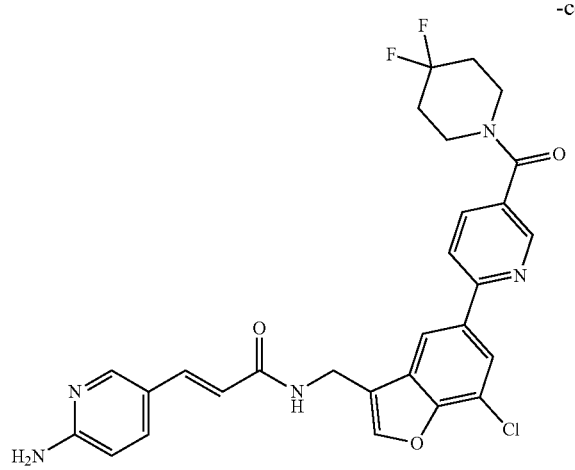
or a pharmaceutically acceptable salt thereof.
* * * * *